US008063015B2

(12) United States Patent
DeFrees et al.

(10) Patent No.: US 8,063,015 B2
(45) Date of Patent: *Nov. 22, 2011

(54) GLYCOPEGYLATION METHODS AND PROTEINS/PEPTIDES PRODUCED BY THE METHODS

(75) Inventors: Shawn DeFrees, North Wales, PA (US); David A. Zopf, Wayne, PA (US); Robert J. Bayer, San Diego, CA (US); David James Hakes, Willow Grove, PA (US); Caryn L. Bowe, Doylestown, PA (US); Xi Chen, Lansdale, PA (US)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

This patent is subject to a terminal disclaimer.

(21) Appl. No.: 12/496,595

(22) Filed: Jul. 1, 2009

(65) Prior Publication Data

US 2010/0048456 A1 Feb. 25, 2010

Related U.S. Application Data

(63) Continuation of application No. 10/552,896, filed as application No. PCT/US2004/011494 on Apr. 9, 2004, now abandoned.

(51) Int. Cl.
*A01N 37/18* (2006.01)

(52) U.S. Cl. ........................................................ 514/3.1

(58) Field of Classification Search ........................ None
See application file for complete search history.

(56) References Cited

U.S. PATENT DOCUMENTS

| | | | |
|---|---|---|---|
| 4,055,635 | A | 10/1977 | Green et al. |
| 4,088,538 | A | 5/1978 | Schneider |
| 4,179,337 | A | 12/1979 | Davis et al. |
| 4,385,260 | A | 5/1983 | Watts |
| 4,412,989 | A | 11/1983 | Iwashita et al. |
| 4,414,147 | A | 11/1983 | Klibanov et al. |
| 4,438,253 | A | 3/1984 | Casey et al. |
| 4,496,689 | A | 1/1985 | Mitra |
| 4,565,653 | A | 1/1986 | Ives et al. |
| 4,806,595 | A | 2/1989 | Noishiki et al. |
| 4,826,945 | A | 5/1989 | Cohn et al. |
| 4,847,325 | A | 7/1989 | Shadle et al. |
| 4,879,236 | A | 11/1989 | Smith et al. |
| 4,925,796 | A | 5/1990 | Bergh et al. |
| 5,032,519 | A | 7/1991 | Paulson et al. |
| 5,104,651 | A | 4/1992 | Boone et al. |
| 5,122,614 | A | 6/1992 | Zalipsky |

(Continued)

FOREIGN PATENT DOCUMENTS

EP 0474313 A2 3/1992

(Continued)

OTHER PUBLICATIONS

Abeijon et al., *J. Biol. Chem.*, 261(24): 11374-11377 (1986).

(Continued)

*Primary Examiner* — Cecilia J Tsang
*Assistant Examiner* — Thomas Heard
(74) *Attorney, Agent, or Firm* — Leydig, Voit & Mayer, Ltd.

(57) ABSTRACT

The invention includes methods and compositions for remodeling a peptide molecule, including the addition or deletion of one or more glycosyl groups to a peptide, and/or the addition of a modifying group to a peptide.

19 Claims, 497 Drawing Sheets

Trimannosyl core

Trimannosyl core with Bisecting GlcNAc

U.S. PATENT DOCUMENTS

| | | | | |
|---|---|---|---|---|
| 5,147,788 | A | 9/1992 | Page et al. | |
| 5,153,265 | A | 10/1992 | Shadle et al. | |
| 5,154,924 | A | 10/1992 | Friden | |
| 5,169,933 | A | 12/1992 | Anderson et al. | |
| 5,182,107 | A | 1/1993 | Friden | |
| 5,194,376 | A | 3/1993 | Kang | |
| 5,202,413 | A | 4/1993 | Spinu | |
| 5,219,564 | A | 6/1993 | Zalipsky et al. | |
| 5,281,698 | A | 1/1994 | Nitecki | |
| 5,324,663 | A | 6/1994 | Lowe | |
| 5,324,844 | A | 6/1994 | Zalipsky | |
| 5,342,940 | A | 8/1994 | Ono et al. | |
| 5,346,696 | A | 9/1994 | Kim et al. | |
| 5,352,670 | A | 10/1994 | Venot et al. | |
| 5,369,017 | A | 11/1994 | Wong et al. | |
| 5,374,541 | A | 12/1994 | Wong et al. | |
| 5,374,655 | A | 12/1994 | Kashem et al. | |
| 5,405,753 | A | 4/1995 | Brossmer et al. | |
| 5,410,016 | A | 4/1995 | Hubbell et al. | |
| 5,432,059 | A | 7/1995 | Bean et al. | |
| 5,446,090 | A | 8/1995 | Harris | |
| 5,492,841 | A | 2/1996 | Craig | |
| 5,527,527 | A | 6/1996 | Friden | |
| 5,529,914 | A | 6/1996 | Hubbell et al. | |
| 5,545,553 | A | 8/1996 | Gotschlich | |
| 5,583,042 | A | 12/1996 | Roth | |
| 5,605,793 | A | 2/1997 | Stemmer | |
| 5,614,184 | A | 3/1997 | Sytkowski et al. | |
| 5,621,039 | A | 4/1997 | Hallahan et al. | |
| 5,629,384 | A | 5/1997 | Veronese et al. | |
| 5,635,603 | A | 6/1997 | Hansen et al. | |
| 5,643,575 | A | 7/1997 | Martinez et al. | |
| 5,646,113 | A | 7/1997 | Attie et al. | |
| 5,672,662 | A | 9/1997 | Harris et al. | |
| 5,672,683 | A | 9/1997 | Friden et al. | |
| 5,705,367 | A | 1/1998 | Gotschlich | |
| 5,716,812 | A | 2/1998 | Withers et al. | |
| 5,728,554 | A | 3/1998 | Bayer et al. | |
| 5,770,420 | A | 6/1998 | Lowe et al. | |
| 5,798,233 | A | 8/1998 | Gotschlich | |
| 5,811,238 | A | 9/1998 | Stemmer et al. | |
| 5,824,778 | A | 10/1998 | Ishikawa et al. | |
| 5,824,864 | A | 10/1998 | Fox et al. | |
| 5,830,721 | A | 11/1998 | Stemmer et al. | |
| 5,833,988 | A | 11/1998 | Friden | |
| 5,834,251 | A | 11/1998 | Maras et al. | |
| 5,837,458 | A | 11/1998 | Minshull et al. | |
| 5,849,535 | A | 12/1998 | Cunningham et al. | |
| 5,858,751 | A | 1/1999 | Paulson et al. | |
| 5,858,752 | A | 1/1999 | Seed et al. | |
| 5,876,980 | A | 3/1999 | DeFrees et al. | |
| 5,922,577 | A | 7/1999 | Defrees et al. | |
| 5,932,462 | A | 8/1999 | Harris et al. | |
| 5,945,314 | A | 8/1999 | Prieto et al. | |
| 5,945,322 | A | 8/1999 | Gotschlich | |
| 5,955,347 | A | 9/1999 | Lowe | |
| 5,962,294 | A | 10/1999 | Paulson et al. | |
| 5,969,040 | A | 10/1999 | Hallahan et al. | |
| 5,977,307 | A | 11/1999 | Friden et al. | |
| 6,010,999 | A | 1/2000 | Daley et al. | |
| 6,015,555 | A | 1/2000 | Friden | |
| 6,030,815 | A | 2/2000 | DeFrees et al. | |
| 6,037,452 | A | 3/2000 | Minamino et al. | |
| 6,057,292 | A | 5/2000 | Cunningham et al. | |
| 6,087,325 | A | 7/2000 | Meers et al. | |
| 6,096,512 | A | 8/2000 | Elhammer et al. | |
| 6,113,906 | A | 9/2000 | Greenwald et al. | |
| 6,117,651 | A | 9/2000 | Schultz et al. | |
| 6,166,183 | A | 12/2000 | Ishikawa et al. | |
| 6,183,738 | B1 * | 2/2001 | Clark | 424/94.4 |
| 6,261,805 | B1 | 7/2001 | Wood | |
| 6,268,193 | B1 | 7/2001 | Lowe | |
| 6,342,382 | B1 | 1/2002 | Gotschlich | |
| 6,348,558 | B1 | 2/2002 | Harris et al. | |
| 6,362,254 | B2 | 3/2002 | Harris et al. | |
| 6,376,604 | B2 | 4/2002 | Kozlowski | |
| 6,399,336 | B1 | 6/2002 | Paulson et al. | |
| 6,399,337 | B1 | 6/2002 | Taylor et al. | |
| 6,440,703 | B1 | 8/2002 | DeFrees | |
| 6,465,220 | B1 | 10/2002 | Hassan et al. | |
| 6,531,121 | B2 | 3/2003 | Brines et al. | |
| 6,555,346 | B1 | 4/2003 | Kretzdorn et al. | |
| 6,555,660 | B2 | 4/2003 | Nissen et al. | |
| 6,586,398 | B1 | 7/2003 | Kinstler et al. | |
| 6,692,931 | B1 | 2/2004 | Reutter et al. | |
| 6,693,183 | B2 | 2/2004 | Natsuka et al. | |
| 6,716,626 | B1 | 4/2004 | Itoh et al. | |
| 6,743,896 | B2 | 6/2004 | Filpula et al. | |
| 6,780,624 | B2 | 8/2004 | Gotschlich | |
| 6,800,740 | B1 | 10/2004 | Cunningham et al. | |
| 6,949,372 | B2 | 9/2005 | Betenbaugh et al. | |
| 7,094,530 | B1 | 8/2006 | Sasaki et al. | |
| 7,125,843 | B2 | 10/2006 | DeFrees et al. | |
| 7,138,371 | B2 * | 11/2006 | DeFrees et al. | 514/8 |
| 7,157,277 | B2 | 1/2007 | DeFrees et al. | |
| 7,173,003 | B2 | 2/2007 | DeFrees et al. | |
| 7,179,617 | B2 | 2/2007 | DeFrees et al. | |
| 7,202,208 | B2 | 4/2007 | Papadimitriou | |
| 7,214,660 | B2 * | 5/2007 | DeFrees et al. | 514/8 |
| 7,226,903 | B2 | 6/2007 | DeFrees et al. | |
| 7,229,962 | B2 | 6/2007 | Chung et al. | |
| 7,235,638 | B2 | 6/2007 | Persson | |
| 7,265,084 | B2 * | 9/2007 | DeFrees et al. | 514/6 |
| 7,265,085 | B2 | 9/2007 | DeFrees et al. | |
| 7,276,475 | B2 * | 10/2007 | DeFrees et al. | 514/8 |
| 7,297,511 | B2 | 11/2007 | DeFrees et al. | |
| 7,304,150 | B1 | 12/2007 | Egrie et al. | |
| 7,338,933 | B2 | 3/2008 | DeFrees et al. | |
| 7,368,108 | B2 | 5/2008 | DeFrees et al. | |
| 7,399,613 | B2 | 7/2008 | DeFrees et al. | |
| 7,405,198 | B2 | 7/2008 | DeFrees et al. | |
| 7,416,858 | B2 | 8/2008 | DeFrees et al. | |
| 7,439,043 | B2 | 10/2008 | DeFrees et al. | |
| 7,473,680 | B2 | 1/2009 | DeFrees et al. | |
| 7,691,603 | B2 | 4/2010 | DeFrees | |
| 7,696,163 | B2 | 4/2010 | DeFrees et al. | |
| 7,795,210 | B2 | 9/2010 | DeFrees et al. | |
| 7,803,777 | B2 | 9/2010 | DeFrees | |
| 7,842,661 | B2 | 11/2010 | DeFrees et al. | |
| 2002/0016003 | A1 | 2/2002 | Saxon et al. | |
| 2002/0019342 | A1 | 2/2002 | Bayer | |
| 2002/0037841 | A1 | 3/2002 | Papadimitriou | |
| 2002/0115833 | A1 | 8/2002 | Burg et al. | |
| 2002/0137134 | A1 | 9/2002 | Gerngross | |
| 2002/0142370 | A1 | 10/2002 | Paulson et al. | |
| 2002/0150981 | A1 | 10/2002 | Canfield | |
| 2002/0168323 | A1 | 11/2002 | Gonda | |
| 2002/0182586 | A1 | 12/2002 | Morris et al. | |
| 2003/0027257 | A1 | 2/2003 | Iatrou et al. | |
| 2003/0040037 | A1 | 2/2003 | Bayer | |
| 2003/0124645 | A1 | 7/2003 | Paulson et al. | |
| 2003/0166212 | A1 | 9/2003 | Taylor et al. | |
| 2003/0166525 | A1 | 9/2003 | Hoffmann et al. | |
| 2003/0180835 | A1 | 9/2003 | Bayer | |
| 2003/0186580 | A1 | 10/2003 | Dambach et al. | |
| 2003/0195338 | A1 | 10/2003 | Chung et al. | |
| 2003/0207406 | A1 | 11/2003 | Johnson et al. | |
| 2004/0043446 | A1 | 3/2004 | DeFrees et al. | |
| 2004/0063911 | A1 | 4/2004 | DeFrees et al. | |
| 2004/0077836 | A1 | 4/2004 | DeFrees et al. | |
| 2004/0082026 | A1 | 4/2004 | DeFrees et al. | |
| 2004/0102607 | A1 | 5/2004 | Danishefsky et al. | |
| 2004/0115168 | A1 | 6/2004 | DeFrees et al. | |
| 2004/0126838 | A1 | 7/2004 | DeFrees et al. | |
| 2004/0132640 | A1 | 7/2004 | DeFrees et al. | |
| 2004/0136955 | A1 | 7/2004 | Barker et al. | |
| 2004/0137557 | A1 | 7/2004 | DeFrees et al. | |
| 2004/0197875 | A1 | 10/2004 | Hauser et al. | |
| 2005/0026266 | A1 | 2/2005 | Clausen et al. | |
| 2005/0031584 | A1 | 2/2005 | DeFrees et al. | |
| 2005/0064540 | A1 | 3/2005 | Defrees et al. | |
| 2005/0100982 | A1 | 5/2005 | DeFrees et al. | |
| 2005/0106658 | A1 | 5/2005 | DeFrees et al. | |
| 2005/0118672 | A1 | 6/2005 | DeFrees et al. | |
| 2005/0143292 | A1 | 6/2005 | DeFrees et al. | |
| 2005/0250678 | A1 | 11/2005 | DeFrees et al. | |
| 2005/0269265 | A1 | 12/2005 | DeFrees | |

| | | | |
|---|---|---|---|
| 2005/0271690 | A1 | 12/2005 | Gotschlich |
| 2005/0288490 | A1 | 12/2005 | Nakamoto et al. |
| 2006/0024286 | A1 | 2/2006 | Glidden |
| 2006/0030521 | A1 | 2/2006 | DeFrees et al. |
| 2006/0035224 | A1 | 2/2006 | Johansen |
| 2006/0111279 | A1 | 5/2006 | DeFrees et al. |
| 2006/0177892 | A1 | 8/2006 | De Frees |
| 2006/0246544 | A1 | 11/2006 | Kang et al. |
| 2006/0276618 | A1 | 12/2006 | DeFrees et al. |
| 2006/0287224 | A1 | 12/2006 | DeFrees et al. |
| 2007/0014759 | A1 | 1/2007 | DeFrees et al. |
| 2007/0026485 | A1 | 2/2007 | DeFrees et al. |
| 2007/0027068 | A1 | 2/2007 | DeFrees et al. |
| 2007/0032405 | A1 | 2/2007 | DeFrees et al. |
| 2007/0059275 | A1 | 3/2007 | DeFrees et al. |
| 2007/0105755 | A1 | 5/2007 | DeFrees et al. |
| 2007/0154992 | A1 | 7/2007 | DeFrees |
| 2007/0254834 | A1 | 11/2007 | DeFrees et al. |
| 2007/0254836 | A1 | 11/2007 | Defrees et al. |
| 2008/0015142 | A1 | 1/2008 | DeFrees et al. |
| 2008/0050772 | A1 | 2/2008 | DeFrees et al. |
| 2008/0102083 | A1 | 5/2008 | DeFrees et al. |
| 2008/0108557 | A1 | 5/2008 | Behrens et al. |
| 2008/0146494 | A1 | 6/2008 | DeFrees et al. |
| 2008/0146782 | A1 | 6/2008 | DeFrees et al. |
| 2008/0176790 | A1 | 7/2008 | DeFrees |
| 2008/0187955 | A1 | 8/2008 | DeFrees et al. |
| 2008/0200651 | A1 | 8/2008 | Ostergaard et al. |
| 2008/0206808 | A1 | 8/2008 | DeFrees et al. |
| 2008/0206810 | A1 | 8/2008 | Johnson et al. |
| 2008/0207487 | A1 | 8/2008 | DeFrees et al. |
| 2008/0242607 | A1 | 10/2008 | DeFrees |
| 2008/0242846 | A1 | 10/2008 | DeFrees et al. |
| 2008/0248959 | A1 | 10/2008 | DeFrees |
| 2008/0253992 | A1 | 10/2008 | DeFrees et al. |
| 2008/0255026 | A1 | 10/2008 | DeFrees et al. |
| 2008/0255040 | A1 | 10/2008 | DeFrees |
| 2008/0274958 | A1 | 11/2008 | DeFrees |
| 2008/0280818 | A1 | 11/2008 | DeFrees |
| 2008/0300173 | A1 | 12/2008 | DeFrees |
| 2008/0300175 | A1 | 12/2008 | DeFrees et al. |
| 2008/0305991 | A1 | 12/2008 | DeFrees et al. |
| 2008/0305992 | A1 | 12/2008 | DeFrees et al. |
| 2008/0318850 | A1 | 12/2008 | DeFrees et al. |
| 2008/0319183 | A1 | 12/2008 | DeFrees et al. |
| 2009/0028822 | A1 | 1/2009 | DeFrees et al. |
| 2009/0048440 | A1 | 2/2009 | Felo et al. |
| 2009/0053167 | A1 | 2/2009 | DeFrees |
| 2009/0054623 | A1 | 2/2009 | DeFrees |
| 2009/0055942 | A1 | 2/2009 | Ostergaard et al. |
| 2009/0093399 | A1 | 4/2009 | DeFrees et al. |
| 2009/0124544 | A1 | 5/2009 | DeFrees |
| 2009/0137763 | A1 | 5/2009 | DeFrees et al. |
| 2009/0143292 | A1 | 6/2009 | Hinderer et al. |
| 2009/0169509 | A1 | 7/2009 | DeFrees et al. |
| 2009/0176967 | A1 | 7/2009 | Stennicke |
| 2009/0203579 | A1 | 8/2009 | Defrees et al. |
| 2009/0227504 | A1 | 9/2009 | Klausen et al. |
| 2009/0252720 | A1 | 10/2009 | Ostergaard et al. |
| 2009/0292110 | A1 | 11/2009 | Defrees |
| 2009/0305967 | A1 | 12/2009 | Defrees et al. |
| 2010/0009902 | A1 | 1/2010 | Defrees |
| 2010/0015684 | A1 | 1/2010 | Defrees et al. |
| 2010/0028939 | A1 | 2/2010 | Behrens et al. |
| 2010/0029555 | A1 | 2/2010 | Tonon et al. |
| 2010/0035299 | A1 | 2/2010 | Defrees et al. |
| 2010/0041872 | A1 | 2/2010 | Defrees et al. |
| 2010/0048456 | A1 | 2/2010 | Defrees et al. |
| 2010/0056428 | A1 | 3/2010 | Behrens |
| 2010/0075375 | A1 | 3/2010 | Defrees et al. |
| 2010/0081791 | A1 | 4/2010 | Defrees et al. |
| 2010/0120666 | A1 | 5/2010 | Zopf et al. |
| 2010/0174059 | A1 | 7/2010 | Defrees et al. |
| 2010/0210507 | A9 | 8/2010 | DeFrees et al. |
| 2010/0286067 | A1 | 11/2010 | Defrees |

FOREIGN PATENT DOCUMENTS

| | | | |
|---|---|---|---|
| EP | 0585109 | A2 | 3/1994 |
| EP | 0605963 | A2 | 7/1994 |
| EP | 1428878 | A1 | 6/2004 |
| JP | H03-503759 | A | 8/1991 |
| WO | WO 87/00056 | A1 | 1/1987 |
| WO | WO 87/05330 | A1 | 9/1987 |
| WO | WO 89/06546 | A1 | 7/1989 |
| WO | WO 89/10134 | A1 | 11/1989 |
| WO | WO 90/07572 | A1 | 7/1990 |
| WO | WO 90/08164 | A1 | 7/1990 |
| WO | WO 90/08823 | A1 | 8/1990 |
| WO | WO 90/13540 | A1 | 11/1990 |
| WO | WO 91/14697 | A1 | 10/1991 |
| WO | WO 92/18135 | A1 | 10/1992 |
| WO | WO 93/15189 | A1 | 8/1993 |
| WO | WO 94/04193 | A1 | 3/1994 |
| WO | WO 94/05332 | A2 | 3/1994 |
| WO | WO 94/09027 | A1 | 4/1994 |
| WO | WO 94/15625 | A1 | 7/1994 |
| WO | WO 94/17039 | A1 | 8/1994 |
| WO | WO 94/18247 | A1 | 8/1994 |
| WO | WO 94/28024 | A1 | 12/1994 |
| WO | WO 95/02421 | A1 | 1/1995 |
| WO | WO 96/21469 | A1 | 7/1996 |
| WO | WO 96/32491 | A1 | 10/1996 |
| WO | WO 96/40731 | A1 | 12/1996 |
| WO | WO 96/40881 | A1 | 12/1996 |
| WO | WO 97/05330 | A1 | 2/1997 |
| WO | WO 98/05363 | A2 | 2/1998 |
| WO | WO 98/31826 | A1 | 7/1998 |
| WO | WO 98/51784 | A1 | 11/1998 |
| WO | WO 98/58964 | A1 | 12/1998 |
| WO | WO 99/00150 | A2 | 1/1999 |
| WO | WO 99/14259 | A1 | 3/1999 |
| WO | WO 99/22764 | A1 | 5/1999 |
| WO | WO 99/34833 | A1 | 7/1999 |
| WO | WO 99/45964 | A1 | 9/1999 |
| WO | WO 99/48515 | A1 | 9/1999 |
| WO | WO 99/55376 | A1 | 11/1999 |
| WO | WO 00/23114 | A2 | 4/2000 |
| WO | WO 00/26354 | A1 | 5/2000 |
| WO | WO 00/65087 | A1 | 11/2000 |
| WO | WO 01/02017 | A2 | 1/2001 |
| WO | WO 01/49830 | A2 | 7/2001 |
| WO | WO 01/58493 | A1 | 8/2001 |
| WO | WO 01/58935 | A2 | 8/2001 |
| WO | WO 01/60411 | A1 | 8/2001 |
| WO | WO 01/76640 | A2 | 10/2001 |
| WO | WO 01/88117 | A2 | 11/2001 |
| WO | WO 02/02597 | A2 | 1/2002 |
| WO | WO 02/02764 | A2 | 1/2002 |
| WO | WO 02/13843 | A2 | 2/2002 |
| WO | WO 02/13873 | A2 | 2/2002 |
| WO | WO 02/053580 | A2 | 7/2002 |
| WO | WO 02/074806 | A2 | 9/2002 |
| WO | WO 02/092619 | A2 | 11/2002 |
| WO | WO 03/017949 | A2 | 3/2003 |
| WO | WO 03/031464 | A2 | 4/2003 |
| WO | WO 03/045980 | A2 | 6/2003 |
| WO | WO 03/046150 | A2 | 6/2003 |
| WO | WO 03/093448 | A2 | 11/2003 |
| WO | WO 2004/009838 | A2 | 1/2004 |
| WO | WO 2004/010327 | A2 | 1/2004 |
| WO | WO 2004/022004 | A2 | 3/2004 |
| WO | WO 2004/033651 | A2 | 4/2004 |
| WO | WO 2004/046222 | A1 | 6/2004 |
| WO | WO 2004/083258 | A2 | 9/2004 |
| WO | WO 2004/083259 | A2 | 9/2004 |
| WO | WO 2004/091499 | A2 | 10/2004 |
| WO | WO 2004/096148 | A2 | 11/2004 |
| WO | WO 2004/099231 | A2 | 11/2004 |
| WO | WO 2004/103275 | A2 | 12/2004 |
| WO | WO 2005/012484 | A2 | 2/2005 |
| WO | WO 2005/025606 | A1 | 3/2005 |
| WO | WO 2005/051327 | A2 | 6/2005 |
| WO | WO 2005/055946 | A2 | 6/2005 |
| WO | WO 2005/056760 | A2 | 6/2005 |
| WO | WO 2005/067601 | A2 | 7/2005 |
| WO | WO 2005/070138 | A2 | 8/2005 |
| WO | WO 2005/072371 | A2 | 8/2005 |
| WO | WO 2005/091944 | A2 | 10/2005 |

| | | | |
|---|---|---|---|
| WO | WO 2005/121331 | A2 | 12/2005 |
| WO | WO 2006/010143 | A2 | 1/2006 |
| WO | WO 2006/014349 | A2 | 2/2006 |
| WO | WO 2006/014466 | A2 | 2/2006 |
| WO | WO 2006/020372 | A2 | 2/2006 |
| WO | WO 2006/031811 | A2 | 3/2006 |
| WO | WO 2006/050247 | A2 | 5/2006 |
| WO | WO 2006/074279 | A1 | 7/2006 |
| WO | WO 2006/074467 | A2 | 7/2006 |
| WO | WO 2006/078645 | A2 | 7/2006 |
| WO | WO 2006/105426 | A2 | 10/2006 |
| WO | WO 2006/121569 | A2 | 11/2006 |
| WO | WO 2006/127910 | A2 | 11/2006 |
| WO | WO 2007/022512 | A2 | 2/2007 |
| WO | WO 2007/056191 | A2 | 5/2007 |
| WO | WO 2008/011633 | A2 | 1/2008 |
| WO | WO 2008/057683 | A2 | 5/2008 |
| WO | WO 2008/060780 | A2 | 5/2008 |
| WO | WO 2008/073620 | A2 | 6/2008 |
| WO | WO 2008/124406 | A2 | 10/2008 |
| WO | WO 2008/151258 | A2 | 12/2008 |
| WO | WO 2008/154639 | A2 | 12/2008 |
| WO | WO 2009/089396 | A2 | 7/2009 |

OTHER PUBLICATIONS

Abuchowski et al., *J. Biol. Chem.*, 252(11): 3578-3581 (1977).
Abuchowski et al., *J. Biol. Chem.*, 252(11): 3582-3586 (1977).
Abuchowski et al., *Cancer Biochem. Biophys.*, 7(2): 175-186 (1984).
Ailor et al., *Glycobiology,* 10(8): 837-847 (2000).
Alam et al., *J. Biotechnol,* 65(2-3): 183-190 (1998).
Allegre et al., *J. Memb. Sci,* 269(1-2): 109-117 (2006).
Altmann et al., *Glycoconj. J.,* 16(2): 109-123 (1999).
Amersham Pharmacia Biotech, "Hydrophobic Interaction Chromatography: Principles and Methods," 104 pp. (2000).
Aplin et al., *CRC Crit. Rev. Biochem.,* 10(4): 259-306 (1981).
Barrios et al., *J. Mol. Recognit.,* 17(4):332-338 (2004).
Beauchamp et al., *Anal. Biochem.,* 131(1): 25-33 (1983).
Bedard et al., *Cytotechnology,* 15(1-3):129-138 (1994).
Bennett et al., *J. Biol. Chem.,* 273(46): 30472-30481 (1998).
Bennett et al., *FEBS Lett.,* 460(2): 226-230 (1999).
Berger et al., *Blood,* 71(6): 1641-1647 (1988).
Berg-Fussman et al., *J. Biol. Chem.,* 268(20): 14861-14866 (1993).
Bhadra et al., *Pharmazie,* 57(1): 5-29 (2002).
Bhatia et al., *Anal. Biochem.,* 178(2): 408-413 (1989).
Bickel et al., *Adv. Drug Deify. Rev.,* 46(1-3): 247-279 (2001).
Bijsterbosch et al., *Eur. J. Biochem.,* 237(2): 344-349 (1996).
Bjoern et al., *J. Biol. Chem.,* 266(17): 11051-11057 (1991).
Boccu et al., *Z. Naturforsch.,* 38c: 94-99 (1983).
Boime et al., *Recent Prog. Horm. Res.,* 54: 271-289 (1999).
Boissel et al., *J. Biol. Chem.,* 268(21): 15983-15993 (1993).
Bork et al., *Trends Genet.,* 12(10): 425-427 (1996).
Bork, *Genome Res.,* 10(4): 398-400 (2000).
Bouizar et al., *Eur. J. Biochem.,* 155(1): 141-147 (1986).
Boyd et al., *Mol. Immunol.,* 32(17-18): 1311-1318 (1995).
Brenner, *Trends Genet.,* 15(4): 132-133 (1999).
Brockhausen et al., *Acta Anatomica,* 161: 36-78 (1998).
Browning et al., *J. Immunol.,* 143(6): 1859-1867 (1989).
Bückmann et al., *Makromol. Chem.,* 182(5): 1379-1384 (1981).
Burns et al., *Blood,* 99(12): 4400-4405 (2002).
Butnev et al., *Biol. Reprod.,* 58(2): 458-469 (1998).
Byun et al., *ASAIO J.,* 38(3): M649-M653 (1992).
Cantin et al., *Am. J. Respir. Cell Mol. Biol.,* 27(6): 659-665 (2002).
Casares et al., *Nat. Biotechnol.,* 19(2): 142-147 (2001).
Chaffee et al., *J. Clin. Invest.,* 89(5): 1643-1651 (1992).
Charter et al., *Glycobiology,* 10(10): 1049-1056 (2000).
Chern et al., *Eur. J. Biochem.,* 202(2): 225-229 (1991).
Chiba et al., *Biochem. J.,* 308(2): 405-409 (1995).
Chrisey et al., *Nucleic Acids Res.,* 24(15): 3031-3039 (1996).
Clark et al., *J. Biol. Chem.,* 271(36): 21969-21977 (1996).
Cohn et al., *J. Biomed. Mater. Res.,* 22(11): 993-1009 (1988).
Cointe et al., *Glycobiology,* 10(5): 511-519 (2000).
Conradt et al., *J. Biol. Chem.,* 262(30): 14600-14605 (1987).
Cope et al., *Mol. Microbiol.,* 5(5): 1113-1124 (1991).
Copeland, "Enzymes: A Practical Introduction to Structure, Mechanism and Data Analysis" 2nd ed., Wiley-VCH, New York, pp. 146-150 (2000).
Crout et al., *Curr. Opin. Chem. Biol,* 2(1): 98-111 (1998).
Defrees et al., *Glycobiology,* 16(9): 833-843 (2006).
Delgado et al., *Biotechnol. Appl. Biochem.,* 12(2): 119-128 (1990).
Delgado et al., *Crit. Rev. Ther. Drug Carrier Syst.,* 9(3-4): 249-304 (1992).
Doerks et al., *Trends Genet.,* 14(6): 248-250 (1998).
Douglas et al., *J. Am. Chem. Soc.,* 113(13): 5095-5097 (1991).
Dunn, 1991, "Polymeric Drugs and Drug Delivery Systems" Dunn et al. (eds.), Chapter 2 "Polymeric Matrices", pp. 11-23, ACS Symposium Series vol. 469, American Chemical Society, Washington D.C.
Durieux et al., *Tetrahedron Lett.,* 42(12): 2297-2299 (2001).
Dwek et al., *J. Anat.,* 187(Pt. 2): 279-292 (1995).
Eavarone et al., *J. Biomed. Mater. Res.,* 51(1): 10-14 (2000).
Edge et al., *Anal. Biochem.,* 118(1): 131-137 (1981).
Fan et al., *J. Biol. Chem.,* 272(43): 27058-27064 (1997).
Felix et al., *J. Peptide Res.,* 63: 85-90 (2004).
Fibi et al., *Blood,* 85(5): 1229-1236 (1995).
Fischer et al., *Thromb. Res.,* 89(3): 147-150 (1998).
Flynn et al., *Curr. Opin. Oncol,* 12(6): 574-581 (2000).
Fritz et al., *Proc. Natl. Acad. Sci. USA,* 101(43): 1 5307-15312 (2004).
Fritz et al., *J. Biol. Chem.,* 281(13): 8613-8619 (2006).
Garnett et al., *Adv. Drug Deliv. Rev.,* 53(2): 171-216 (2002).
Gatot et al., *J. Biol. Chem.,* 273(21): 12870-12880 (1998).
Ge et al., *J. Biol. Chem.,* 272(34): 21357-21363 (1997).
Gervais et al., *Glycobiology,* 13(3): 179-189 (2003).
Gilbert et al., *Cytotechnology,* 22(1-3): 211-216 (1996).
Gillis et al., *Behring Inst. Mitt.,* 83:1-7 (1988).
Ginns, Peg Glucocerebrosidase, Internet page from www.gaucher.org.uk/peg2.prg, Nov. 1994, printed Jun. 21, 2002.
Gombotz et al., "PEGylation: A Tool for Enhanced Protein Delivery," in Controlled Drug Delivery, Park et al. (eds.), Chapter 12, pp. 110-123, ACS Symposium Series, American Chemical Society, Washington D.C. (2000).
Gotschlich, *J. Exp. Med.,* 180(6): 2181-2190 (1994).
Grabenhorst et al., *Eur. J. Biochem.,* 215(1): 189-197 (1993).
Grabenhorst et al., *J. Biol. Chem.,* 274(51): 36107-36116 (1999).
Grodberg et al., *Eur. J. Biochem.,* 218(2): 597-601 (1993).
Gross et al., *Biochemistry,* 28(18): 7386-7392 (1989).
Gross, Eur. *J. Biochem.,* 203(1-2): 269-275 (1992).
Hagen et al., *J. Biol. Chem.,* 274(10): 6797-6803 (1999).
Hagen et al., *J. Biol. Chem.,* 276(20): 17395-17404 (2001).
Hall, *Methods Mol. Biol.,* 166: 139-154 (2001).
Haneda et al., *Carbohydr. Res.,* 292: 61-70 (1996).
Hang et al., *J. Am. Chem. Soc.,* 123(6): 1242-1243 (2001).
Harris et al., *Nat. Rev. Drug Discov.,* 2(3): 214-221 (2003).
Harris et al., Abstracts of Papers of the American Chemical Society, V 201, APR, P 64-POLY, pp. 154-155 (1991).
Harris, *J. Macromol. Science, Rev. Macromol. Chem. Phys.,* C25(3): 325-373 (1985).
Harris (ed.), "Poly(Ethylene Glycol) Chemistry: Biotechnical and Biomedical Applications", Plenum Press, New York (1992).
Harris et al. (eds.), "Poly(ethylene glycol): Chemistry and Biological Applications," ACS Symposium Series, vol. 680, American Chemical Society (1997).
Hassan et al., *J. Biol. Chem.,* 275(49): 38197-38205 (2000).
Hassan et al., *Carbohydrates in Chemistry and Biology,* Part II, 3: 273-292 (2000).
Hayes et al., *J. Biol. Chem.,* 268(22): 16170-16178 (1993).
Hellstrom et al., *Methods Mol. Biol,* 166: 3-16 (2001).
Hermanson et al., *Immobilized Affinity Ligand Techniques,* Academic Press (1992).
Hermanson, *Bioconjugate Techniques,* Academic Press, San Diego (1996).
Hermentin, et al., *Glycobiology,* 6(2): 217-230 (1996).
Herscovics et al., *FASEB J.,* 7(6): 540-550 (1993).
Hills et al., *Am. Biotechnol. Lab.,* 20(11): 30 (2002).
Hink et al., *Biotechnol. Prog.,* 7(1): 9-14 (1991).
Hollister et al., *Glycobiology,* 11(1): 1-9 (2001).
Hounsell et al., *Glycoconj J.,* 13(1): 19-26 (1996).

Ichikawa et al., *J. Am. Chem. Soc.*, 114(24): 9283-9298 (1992).
Ikonomou et al., *In Vitro Cell. Dev. Biol. Anim.*, 37(9): 549-559 (2001).
Inlow et al., *J. Tissue Cult. Methods*, 12(1): 13-16 (1989).
Inoue et al., *Biotechnol. Annu. Rev.*, 1: 297-313 (1995).
Ito et al., *Pure Appl. Chem.*, 65(4): 753-762 (1993).
Jackson et al., *Anal. Biochem.*, 165(1): 114-127 (1987).
Jarvis et al., *Curr. Opin. Biotechnol.*, 9(5): 528-533 (1998).
Joppich et al., *Makromol. Chem.*, 180: 1381-1384 (1979).
Joshi et al., *J. Biol. Chem.*, 265(24): 14518-14525 (1990).
Jung et al., *Biochim. Biophys. Acta*, 761(2): 152-162 (1983).
Kajihara et al., *Carbohydrate Research*, 315: 137-141 (1999).
Kalsner et al., *Glycoconj. J.*, 12(3): 360-370 (1995).
Kasina et al., *Bioconjug. Chem.*, 9(1): 108-117 (1998).
Katre et al., *Proc. Natl. Acad. Sci. USA*, 84(6): 1487-1491 (1987).
Kawasaki et al., *Anal. Biochem.*, 285: 82-91 (2000).
Keana et al., *J. Org. Chem.*, 55(11): 3640-3647 (1990).
Keene et al., *J. Biol. Chem.*, 264(9): 4769-4775 (1989).
Keppler et al., *Glycobiology*, 11(2): 11R-18R (2001).
Kitamura et al., *Biochem. Biophys. Res. Commun.*, 171(3): 1387-1394 (1990).
Kitamura et al., *Cancer Res.*, 51(16): 4310-4315 (1991).
Kobayashi et al., *Eur. J. Nucl. Med.*, 27(9):1334-1339 (2000).
Kodama et al., *Tetrahedron Lett.*, 34(40): 6419-6422 (1993).
Koeller et al., *Nat. Biotechnol*, 18(8): 835-841 (2000).
Koeller et al., *Nature*, 409(6817): 232-240 (2001).
Koide et al., *Biochem. Biophys. Res. Commun.*, 111(2): 659-667 (1983).
Kornfeld et al., *Ann. Rev. Biochem.*, 54: 631-664 (1985).
Kreitman, *Curr Pharm Biotechnol.*, 2(4): 313-325 (2001).
Kuhn et al., *J. Biol. Chem.*, 270(49): 29493-29497 (1995).
Kukuruzinska et al., *Proc. Natl. Acad. Sci. USA*, 84(8): 2145-2149 (1987).
Lai et al, *J. Biol. Chem.*, 261(7): 3116-3121 (1986).
Langer, *Science*, 249(4976): 1527-1533 (1990).
Lau et al., *J. Biotechnol.*, 75(2-3): 105-115 (1999).
Lee et al., *Biochemistry*, 28(4): 1856-1861 (1989).
Lee-Huang et al., *Proc. Natl. Acad. Sci. USA*, 81(9): 2708-2712 (1984).
Legault et al., *J. Biol. Chem.*, 270(36): 20987-20996 (1995).
Leung, *J Immunol.* 154(11): 5919-5926 (1995).
Li et al., *Trends Pharmacol. Sci.*, 23(5): 206-209 (2002).
Li et al., *Med. Res. Rev.*, 22(3): 225-250 (2002).
Licari et al., *Biotechnol. Bioeng.*, 39(4): 432-441 (1992).
Licari et al., *BiotechnoL Bioeng.*, 39(9): 932-944 (1992).
Lin et al., *Proc. Natl. Acad. Sci. USA*, 82: 7580-7584 (1985).
Liu et al., *Chem. Eur. J.*, 2(11): 1359-1362 (1996).
Long et al., *Exp. Hematol.*, 34(6): 697-704 (2006).
Lord et al., *Clin. Cancer Res.*, 7(7): 2085-2090 (2001).
Lougheed et al., *J. Biol. Chem.*, 274(53): 37717-37722 (1999).
Luckow et al., *Curr. Opin. Biotechnol.*, 4(5): 564-572 (1993).
Lund et al., *FASEB J.*, 9(1): 115-119 (1995).
Lund et al., *J. Immunol.*, 157(11): 4963-4969 (1996).
Mahal et al., *Science*, 276(5315): 1125-1128 (1997).
Maranga et al., *Biotechnol. Bioeng.*, 84(2): 245-253 (2003).
Maras et al., *J Biotechnol.*, 77(2-3): 255-263 (2000).
Meynial-Salles et al., *J. Biotechnol.*, 46(1): 1-14 (1996).
Miller, *Curr. Opin. Genet. Dev.*, 3(1): 97-101 (1993).
Min et al., *Endocr. J.*, 43(5): 585-593 (1996).
Mistry et al., *Lancet*, 348(9041): 1555-1559 (1996).
Morimoto et al., *Glycoconj. J.*, 13(6): 1013-1020 (1996).
Muller et al., *J. Biol. Chem.*, 272(40): 24780-24793 (1997).
Muller et al., *J. Biol. Chem.*, 274(26): 18165-18172 (1999).
NCBI—Accession No. NCAA26095 (2 pgs.) (2006).
NCBI—Accession No. NP_058697 (3 pgs.) (2007).
NCBI—Accession No. NP_999299 (2 pgs.) (2007).
NCBI Database hits for erythropoietin protein sequences (3 pgs.) (2007).
Ngo et al., "The Protein Folding Problem and Tertiary Structure Prediction, Chapter 14: Computational Complexity Protein Structure Prediction, and the Levinthal Paradox," pp. 433-440 and 492-495 (1994).
Nilsson et al., *Methods Enzymol.*, 104: 56-69 (1984).
O'Connell et al., *J. Biol. Chem.*, 267(35): 25010-25018 (1992).
Oetke et al., *J. Biol. Chem.*, 277(8): 6688-6695 (2002).
Olson et al., *J. Biol. Chem.*, 274(42): 29889-29896 (1999).
Orlean, "vol. III: The Molecular and Cellular Biology of the Yeast *Saccharomyces*: Cell Cycle and Cell Biology", in *Biogenesis of Yeast Wall and Surface Components*, Chapter 3, pp. 229-362, Cold Spring Harbor Laboratory Press (1997).
Palacpac et al., *Proc. Natl. Acad. Sci. USA*, 96(8): 4692-4697 (1999).
Park et al., *J. Biol. Chem.*, 261(1): 205-210 (1986).
Paulson et al., *J. Biol. Chem.*, 252(23): 8624-8628 (1977).
Plummer et al., *J. Biol. Chem.*, 270(22): 13192-13196 (1995).
PNGase-F Amidase Sequence from F. Meningosepticum (RN 128688-70-0) (2007).
PNGase-F Amidase Sequence from F. Meningosepticum (RN 128688-71-1) (2007).
Pyatak et al., *Res. Commun. Chem. Pathol. Pharmacol.*, 29(1): 113-127 (1980).
Rabouille et al., *J Cell Sci.*, 112(Pt. 19): 3319-3330 (1999).
Reff et al., *Cancer Control*, 9(2): 152-166 (2002).
Rosenthal et al., *Methods Enzymol.*, 235: 253-285 (1994).
Rotondaro et al., *Mol. Biotech.*, 11: 117-128 (1999).
Rudikoff et al., *Proc. Natl. Acad. Sci. USA*, 79(6):1979-1983 (1982).
Sadler et al., *Methods Enzymol.*, 83: 458-514 (1982).
Sandberg et al., *Semin. Hematol.*, 38(2 Suppl. 4): 4-12 (2001).
Saneyoshi et al., *Biol. Reprod.*, 65(6): 1686-1690 (2001).
Sasaki et al., *J. Biol. Chem.*, 262(25): 12059-12076 (1987).
Sasaki et al., *J.Biol. Chem.*, 269: 14730-14737 (1994).
Saxon et al., *Science*, 287(5460): 2007-2010 (2000).
Schlaeger, *Cytotechnology*, 20(1-3): 57-70 (1996).
Schwientek et al., *Gene*, 145(2): 299-303 (1994).
Schwientek et al., *J. Biol. Chem.*, 277(25): 22623-22638 (2002).
Scouten, *Methods Enzymol.*, 135: 30-65 (1987).
Seely et al., *J. Chromatog.*, 908: 235-241 (2001).
Seitz, *Chembiochem.*, 1(4): 214-246 (2000).
Shah et al., *J. Pharm. Sci.*, 85(12): 1306-1311 (1996).
Shapiro et al., *Blood*, 105(2): 518-525 (2005).
Shen et al., *Biochem. Biophys. Res. Commun.*, 102(3): 1048-1054 (1981).
Shinkai et al., *Prot. Exp. Purif.*, 10: 379-385 (1997).
Singh et al., *Chem. Commun.*, 1996(8): 993-994 (1996).
Sinha et al., *Infect. lmmun.*, 29(3): 914-925 (1980).
Skolnick et al., *Trends Biotechnol.*, 18(1): 34-39 (2000).
Smith et al., *Nat. Biotechnol.*, 15(12): 1222-1223 (1997).
Snider et al., *J. Chromatogr.*, A 599(1-2): 141-155 (1992).
Sojar et al., *Arch. Biochem. Biophys.*, 259(1): 52-57 (1987).
Song et al., *J. Pharmacol. Exp. Ther.*, 301(2): 605-610 (2002).
Srinivasachar et al., *Biochemistry*, 28(6): 2501-2509 (1989).
Stemmer, *Nature*, 370(6488): 389-391 (1994).
Stemmer, *Proc. Natl. Acad. Sci. USA*, 91(22): 10747-10751 (1994).
Stephens et al., *Eur. J. Biochem.*, 133(1): 155-162 (1983).
Stephens et al., *Eur. J. Biochem.*, 133(3): 481-489 (1983).
Stephens et al., *Eur. J. Biochem.*, 135(3): 519-527 (1983).
Strausberg et al., *Proc Natl Acad Sci USA*, 99(26): 16899-16903 (2002).
Takane et al., *J Pharmacol Exp Ther.*, 294(2): 746-752 (2000).
Takeda et al., *Trends Biochem. Sci.*, 20(9): 367-371 (1995).
Takeuchi et al., *J. Biol. Chem.*, 265(21): 12127-12130 (1990).
Taniguchi et al., *Proteomics*, 1(2): 239-247 (2001).
Tanner et al., *Biochim. Biophys. Acta*, 906(1): 81-99. (1987).
Taylor et al., *Protein Immobilization Fundamentals and Applications*, Manual (1991).
Ten Hagen et al., *J. Biol. Chem.*, 274(39): 27867-27874 (1999).
Tenno et al., *J. Biol. Chem.*, 277(49): 47088-47096 (2002).
Thotakura et al., *Meth. Enzym.*, 138: 350-9 (1987).
Tsuboi et al., *Arch. Biochem. Biophys.*, 374(1): 100-106 (2000).
Tsunoda et al., *J. Pharmacol. Exp. Ther.*, 209(1): 368-372 (1999).
Tuddenham, *Nature*, 419(6902): 23-24 (2002).
Udenfriend et al., *Annu. Rev. Biochem.*, 64: 563-591 (1995).
Ulloa-Aguirre et al., *Endocrine*, 11(3): 205-215 (1999).
Uludag et al., *Biotechnol. Prog.*, 18(3): 604-611 (2002).
Urdal et al, *J. Chromatogr.*, 296: 171-179 (1984).
Van Berkel et al., *Biochem. J.*, 319(Pt. 1): 117-122 (1996).
Van Reis et al., *Biotechnol. Bioeng.*, 38(4): 413-422 (1991).

Veronese et al., *Appl. Biochem. Biotechnol.*, 11(2): 141-152 (1985).
Vitetta et al., *Science*, 313: 308-309 (2006).
Vocadlo et al., "Glycosidase-Catalysed Oligosaccharide Synthesis" in *Carbohydrate Chemistry and Biology*, vol. 2, Chapter 29, pp. 723-844 (2000).
Vyas et al., *Crit. Rev. Ther. Drug Carrier Syst.*, 18(1): 1-76 (2001).
Wang et al., *Tetrahedron Lett.*, 37(12): 1975-1978 (1996).
Wang et al., *Protein Eng.*, 11(12): 1277-1283 (1998).
Wellhoner et al., *J. Biol. Chem.*, 266(7): 4309-4314 (1991).
Wells, *Biochemistry*, 29(37): 8509-8517 (1990).
White et al., *J. Biol. Chem.*, 270(41): 24156-24165 (1995).
Witte et al., *J. Am. Chem. Soc.*, 119(9): 2114-2118 (1997).
Witte et al., *Cancer and Metastasis Rev.*, 17: 155-161 (1998).
Woghiren et al., *Bioconjug. Chem.*, 4(5): 314-318 (1993).
Wong et al., *J. Org. Chem.*, 47(27): 5416-5418 (1982).
Wong et al., *Enzyme Microb Technol.*, 14(11): 866-874 (1992).
Wong et al., Biotechnol. Bioeng., 49(6): 659-666 (1996).
Woods et al., *Eur. J. Cell Biol.*, 50(1): 132-143 (1989).
Wright et al., *J. Immunol.*, 160(7): 3393-3402 (1998).
Wu et al., *J. Drug Target.*, 10(3): 239-245 (2002).
Xing et al., *Biochem. J.*, 336(Pt. 3): 667-673 (1998).
Yamada et al., *Biochemistry*, 20(17): 4836-4842 (1981).
Yamamoto et al., *Carbohydr. Res.*, 305(3-4): 415-422 (1998).
Yarema et al., *J. Biol. Chem.*, 273(47): 31168-31179 (1998).
Yoshida et al., *Glycobiology*, 9(1): 53-58 (1999).
Yoshitake et al., *Biochemistry*, 24(14): 3736-3750 (1985).
Younes et al., *J. Biomed. Mater. Res.*, 21(11): 1301-1316 (1987).
Zalipsky et al., "Use of Functionalized Poly(Ethylene Glycol)s for Modification of Polypeptides" in *Poly(Ethylene Glycol) Chemistry: Biotechnical and Biomedical Applications*, Harris (ed.), Chapter 21, pp. 347-370 (Plenum Press, New York, 1992).
Zalipsky, *Bioconjug. Chem.*, 6(2): 150-165 (1995).
Zarling et al., *J. Immunol.*, 124(2): 913-920 (1980).
Zheng et al., *Biotechnol. Bioeng.*, 65(5): 600-604 (1999).
Zhou et al., 1994, *Mol. Microbiol.*, 14(4): 609-618 (1994).
Adelhorst et al., *J. Biol. Chem.*, 269(9): 6275-6278 (1994).
Brockhausen et al., *Glycoconj. J.*, 15: 595-603 (1998).
Broun et al., *Science*, 282(5392): 1315-1317 (1998).
Costa et al., *J. Biol. Chem.*, 272(17): 11613-11621 (1997).
Culajay et al., *Biochem.*, 39: 7153-7158 (2000).
De Vries et al, *J. Biol. Chem.*, 270(15): 8712-8722 (1995).
Dinter et al., *Biotechnol. Lett.*, 22(1): 25-30 (2000).
Dubé et al., *J. Biol. Chem.*, 263(33): 17516-17521 (1988).
Dumas et al., *Bioorg. Med. Chem. Lett.*, 1(8): 425-428 (1991).
Fairhall et al., *Endocrinology*, 131(4): 1963-1969 (1992).
Feldman et al., *Proc. Natl. Acad. Sci. USA*, 102(8): 3016-3021 (2005).
Francis et al., *Intl. J. Hematol.*, 68(1): 1-18 (1998).
Hansen et al., *Biochem J.*, 308: 801-813 (1995).
Haro et al., *Biochem. Biophys. Res. Comm.*, 228(2): 549-556 (1996).
Höglund, *Med. Oncol.*, 15(4): 229-233 (1998).
Jezek et al., *J. Peptide Sci.*, 5: 46-55 (1999).
Kaneko et al., *Cytogenet. Cell Genet.*, 86(3-4): 329-330 (1999).
Kaneko et al., *FEBS Lett.*, 452(3): 237-242 (1999).
Kimura et al., *Proc. Natl. Acad. Sci. USA*, 96(8): 4530-4535 (1999).
Kisselev, *Structure*, 10(1): 8-9 (2002).
Kukowska-Latallo et al., *Genes Dev.*, 4(8): 1288-1303 (1990).
Leist et al., *Science*, 305: 239-242 (2004).
Leiter et al., *J. Biol. Chem.*, 274(31): 21830-21839 (1999).
Lewis et al., *Endocr. J.*, 47(Suppl.): S1-S8 (2000).
Lönnberg, *Curr. Org. Synth.*, 6(4): 400-425 (2009).
Malissard et al., *Biochem. Biophys. Res. Commun.*, 267(1): 169-173 (2000).
Mollicone et al., *Eur. J. Biochem.*, 191(1): 169-176 (1990).
Monaco et al., *Gene*, 180: 145-150 (1996).
Nagata et al., *EMBO J.*, 5(3): 575-581 (1986).
Nunez et al., *Can. J. Chem.*, 59(14): 2086-2095 (1981).
Oh-Eda et al., *J. Biol. Chem.*, 265: 11432-11435 (1990).
Palcic et al., *Carbohydr. Res.*, 190(1): 1-11 (1989).
Prati et al., *Biotech and Bioeng.*, 79(5): 580-585 (2002).
Prieels et al., *J. Biol. Chem.*, 256(20): 10456-10463 (1981).
Rasko et al., *J. Biol. Chem.*, 275(7): 4988-4994 (2000).
Seffernick et al., *J. Bacteriol.*, 183(8): 2405-2410 (2001).
Sinclair et al., *J. Pharm. Sci.*, 94: 1626-1635 (2005).
Staudacher, *Trends Glycosci. Glycotechnol.*, 8(44): 391-408 (1996).
Trottein et al., *Mol. Biochem. Parasitol.*, 107(2): 279-287 (2000).
Van Tetering et al., *FEBS Lett.*, 461(3): 311-314 (1999).
Wang et al., *Glycobiology*, 6(8): 837-842 (1996).
Wang et al., *Microbiol.*, 145(Pt. 11): 3245-3253 (1999).
Weston et al., *J. Biol. Chem.*, 267(34): 24575-24584 (1992).
Wishart et al., *J. Biol. Chem.*, 270(45): 26782-26785 (1995).
Witkowski et al., *Biochemistry*, 38(36): 11643-11650 (1999).
Office Action dated Sep. 20, 1994 in U.S. Appl. No. 08/215,727.
Office Action dated May 4, 1995 in U.S. Appl. No. 08/102,385.
Office Action dated Jun. 7, 1995 in U.S. Appl. No. 08/215,727.
Office Action dated Apr. 5, 1996 in U.S. Appl. No. 08/102,385.
Office Action dated Jun. 23, 1996 in U.S. Appl. No. 08/447,435.
Office Action dated Jun. 28, 1996 in U.S. Appl. No. 08/447,783.
Office Action dated Aug. 28, 1996 in U.S. Appl. No. 08/478,140.
Office Action dated Oct. 15, 1996 in U.S. Appl. No. 08/102,385.
Office Action dated Feb. 24, 1997 in U.S. Appl. No. 08/447,435.
Office Action dated Feb. 24, 1997 in U.S. Appl. No. 08/447,783.
Office Action dated Apr. 12, 1997 in U.S. Appl. No. 08/215,727.
Office Action dated Jul. 23, 1997 in U.S. Appl. No. 08/102,385.
Office Action dated Aug. 8, 1997 in U.S. Appl. No. 08/745,840.
Office Action dated Oct. 9, 1997 in U.S. Appl. No.. 08/478,140.
Office Action dated Dec. 1, 1997 in U.S. Appl. No. 08/446,875.
Office Action dated Jan. 2, 1998 in U.S. Appl. No. 08/878,360.
Office Action dated Mar. 30, 1998 in U.S. Appl. No. 08/745,840.
Office Action dated Jun. 19, 1998 in U.S. Appl. No. 08/478,140.
Office Action dated Oct. 29, 1998 in U.S. Appl. No. 08/745,840.
Office Action dated Feb. 4, 1999 in U.S. Appl. No. 08/478,140.
Office Action dated Apr. 1, 1999 in U.S. Appl. No. 08/745,840.
Office Action dated Oct. 23, 1999 in U.S. Appl. No. 08/102,385.
Office Action dated Oct. 4, 2000 in U.S. Appl. No. 09/333,412.
Office Action dated Jan. 30, 2001 in U.S. Appl. No. 09/338,943.
Office Action dated Jun. 4, 2002 in U.S. Appl. No. 09/855,320.
Office Action dated Sep. 27, 2002 in U.S. Appl. No. 09/855,320.
Office Action dated Dec. 9, 2002 in U.S. Appl. No. 10/007,267.
Office Action dated Jun. 2, 2003 in U.S. Appl. No. 10/007,267.
Office Action dated Aug. 26, 2003 in U.S. Appl. No. 10/109,498.
Office Action dated Nov. 5, 2003 in U.S. Appl. No. 10/007,267.
Office Action dated Nov. 17, 2003 in U.S. Appl. No. 09/855,320.
Office Action dated Dec. 16, 2003 in U.S. Appl. No. 10/109,498.
Office Action dated Jun. 9, 2004 in U.S. Appl. No. 09/855,320.
Office Action dated Oct. 20, 2004 in U.S. Appl. No. 10/198,806.
Office Action dated Nov. 12, 2004 in U.S. Appl. No. 10/219,197.
Office Action dated Jan. 12, 2005 in U.S. Appl. No. 10/198,806.
Office Action dated Mar. 4, 2005 in U.S. Appl. No. 10/410,945.
Office Action dated Mar. 7, 2005 in U.S. Appl. No. 10/287,994.
Office Action dated Mar. 14, 2005 in U.S. Appl. No. 09/855,320.
Office Action dated Jun. 2, 2005 in U.S. Appl. No. 10/654,528.
Office Action dated Jun. 9, 2005 in U.S. Appl. No. 10/109,498.
Office Action dated Jun. 29, 2005 in U.S. Appl. No. 10/287,994.
Office Action dated Jul. 21, 2005 in U.S. Appl. No. 10/198,806.
Office Action dated Aug. 10, 2005 in U.S. Appl. No. 10/410,945.
Office Action dated Sep. 21, 2005 in U.S. Appl. No. 10/391,035.
Office Action dated Sep. 28, 2005 in U.S. Appl. No. 10/410,962.
Office Action dated Sep. 28, 2005 in U.S. Appl. No. 10/411,049.
Office Action dated Sep. 28, 2005 in U.S. Appl. No. 10/410,930.
Office Action dated Sep. 28, 2005 in U.S. Appl. No. 10/411,012.
Office Action dated Sep. 28, 2005 in U.S. Appl. No. 10/410,980.
Office Action dated Sep. 28, 2005 in U.S. Appl. No. 10/411,043.
Office Action dated Sep. 28, 2005 in U.S. Appl. No. 10/411,037.
Office Action dated Sep. 28, 2005 in U.S. Appl. No. 10/410,913.
Office Action dated Sep. 28, 2005 in U.S. Appl. No. 10/410,897.
Office Action dated Sep. 28, 2005 in U.S. Appl. No. 10/410,997.
Office Action dated Sep. 28, 2005 in U.S. Appl. No. 10/411,044.
Office Action dated Oct. 6, 2005 in U.S. Appl. No. 10/411,026.
Office Action dated Oct. 19, 2005 in U.S. Appl. No. 10/997,405.
Office Action dated Nov. 14, 2005 in U.S. Appl. No.10/410,897.
Office Action dated Nov. 14, 2005 in U.S. Appl. No. 10/410,997.
Office Action dated Nov. 15, 2005 in U.S. Appl. No. 10/287,994.
Office Action dated Nov. 30, 2005 in U.S. Appl. No. 10/654,528.
Office Action dated Dec. 7, 2005 in U.S. Appl. No. 10/609,701.
Office Action dated Dec. 8, 2005 in U.S. Appl. No. 10/391,035.

Office Action dated Dec. 13, 2005 in U.S. Appl. No. 11/033,365.
Office Action dated Dec. 29, 2005 in U.S. Appl. No. 09/855,320.
Office Action dated Jan. 24, 2006 in U.S. Appl. No. 10/410,930.
Office Action dated Jan. 26, 2006 in U.S. Appl. No. 10/411,012.
Office Action dated Jan. 26, 2006 in U.S. Appl. No. 10/410,913.
Office Action dated Jan. 27, 2006 in U.S. Appl. No. 10/410,945.
Office Action dated Jan. 31, 2006 in U.S. Appl. No. 10/410,962.
Office Action dated Feb. 7, 2006 in U.S. Appl. No. 10/997,405.
Office Action dated Feb. 7, 2006 in U.S. Appl. No. 10/410,980.
Office Action dated Feb. 7, 2006 in U.S. Appl. No. 10/411,043.
Office Action dated Mar. 3, 2006 in U.S. Appl. No. 10/391,035.
Office Action dated Mar. 15, 2006 in U.S. Appl. No. 10/198,806.
Office Action dated Mar. 22, 2006 in U.S. Appl. No. 10/411,049.
Office Action dated Apr. 4, 2006 in U.S. Appl. No. 10/411,026.
Office Action dated Apr. 4, 2006 in U.S. Appl. No. 10/410,897.
Office Action dated Apr. 4, 2006 in U.S. Appl. No. 10/410,997.
Office Action dated Apr. 6, 2006 in U.S. Appl. No. 11/102,497.
Office Action dated May 2, 2006 in U.S. Appl. No. 11/144,223.
Office Action dated Jul. 28, 2006 in U.S. Appl. No. 10/109,498.
Office Action dated Aug. 24, 2006 in U.S. Appl. No. 10/492,261.
Office Action dated Aug. 30, 2006 in U.S. Appl. No. 11/102,497.
Office Action dated Oct. 6, 2006 in U.S. Appl. No. 10/497,284.
Office Action dated Oct. 17, 2006 in U.S. Appl. No. 11/339,752.
Office Action dated Nov. 1, 2006 in U.S. Appl. No. 11/183,205.
Office Action dated Nov. 1, 2006 in U.S. Appl. No. 11/183,218.
Office Action dated Nov. 15, 2006 in U.S. Appl. No. 10/411,026.
Office Action dated Nov. 28, 2006 in U.S. Appl. No. 11/144,223.
Office Action dated Dec. 8, 2006 in U.S. Appl. No. 10/997,405.
Office Action dated Dec. 13, 2006 in U.S. Appl. No. 10/410,980.
Office Action dated Dec. 13, 2006 in U.S. Appl. No. 10/411,043.
Office Action dated Dec. 13, 2006 in U.S. Appl. No. 10/497,284.
Office Action dated Dec. 18, 2006 in UU.S. Appl. No. 09/855,320.
Office Action dated Dec. 21, 2006 in U.S. Appl. No. 11/183,205.
Office Action dated Dec. 21, 2006 in U.S. Appl. No. 11/183,218.
Office Action dated Dec. 29, 2006 in U.S. Appl. No. 11/033,365.
Office Action dated Jan. 22, 2007 in U.S. Appl. No. 10/198,806.
Office Action dated Jan. 24, 2007 in U.S. Appl. No. 11/404,266.
Office Action dated Jan. 31, 2007 in U.S. Appl. No. 10/497,283.
Office Action dated Feb. 27, 2007 in U.S. Appl. No. 10/609,701.
Office Action dated Feb. 28, 2007 in U.S. Appl. No. 10/492,261.
Office Action dated Apr. 5, 2007 in U.S. Appl. No. 10/485,892.
Office Action dated Apr. 6, 2007 in U.S. Appl. No. 11/339,752.
Office Action dated Apr. 12, 2007 in U.S. Appl. No. 10/497,283.
Office Action dated Apr. 16, 2007 in U.S. Appl. No. 10/410,980.
Office Action dated Apr. 26, 2007 in U.S. Appl. No. 11/033,365.
Office Action dated Apr. 27, 2007 in U.S. Appl. No. 11/183,205.
Office Action dated Apr. 30, 2007 in U.S. Appl. No. 11/183,218.
Office Action dated May 15, 2007 in U.S. Appl. No. 11/144,223.
Office Action dated May 31, 2007 in U.S. Appl. No. 11/395,784.
Office Action dated Jun. 1, 2007 in U.S. Appl. No. 11/102,497.
Office Action dated Jun. 11, 2007 in U.S. Appl. No. 11/514,484.
Office Action dated Jun. 25, 2007 in U.S. Appl. No. 10/411,043.
Office Action dated Jun. 26, 2007 in U.S. Appl. No. 10/411,026.
Office Action dated Jul. 13, 2007 in U.S. Appl. No. 11/440,839.
Office Action dated Jul. 26, 2007 in U.S. Appl. No. 11/395,784.
Office Action dated Aug. 16, 2007 in U.S. Appl. No. 10/497,283.
Office Action dated Aug. 17, 2007 in U.S. Appl. No. 10/492,261.
Office Action dated Aug. 30, 2007 in U.S. Appl. No. 10/497,284.
Office Action dated Sep. 4, 2007 in U.S. Appl. No. 11/144,223.
Office Action dated Sep. 18, 2007 in U.S. Appl. No. 09/855,320.
Office Action dated Oct. 1, 2007 in U.S. Appl. No. 10/411,043.
Office Action dated Oct. 2, 2007 in U.S. Appl. No. 11/166,028.
Office Action dated Oct. 3, 2007 in U.S. Appl. No. 11/514,484.
Office Action dated Oct. 16, 2007 in U.S. Appl. No. 11/183,205.
Office Action dated Oct. 16, 2007 in U.S. Appl. No. 11/183,218.
Office Action dated Oct. 30, 2007 in U.S. Appl. No. 11/580,669.
Office Action dated Nov. 1, 2007 in U.S. Appl. No. 11/339,752.
Office Action dated Nov. 15, 2007 in U.S. Appl. No. 11/166,404.
Office Action dated Nov. 28, 2007 in U.S. Appl. No. 11/102,497.
Office Action dated Dec. 7, 2007 in U.S. Appl. No. 10/530,972.
Office Action dated Dec. 11, 2007 in U.S. Appl. No. 11/440,839.
Office Action dated Dec. 17, 2007 in U.S. Appl. No. 10/497,284.
Office Action dated Dec. 27, 2007 in U.S. Appl. No. 11/396,215.
Office Action dated Dec. 28, 2007 in U.S. Appl. No. 10/565,331.
Office Action dated Dec. 28, 2007 in U.S. Appl. No. 11/402,105.
Office Action dated Jan. 3, 2008 in U.S. Appl. No. 10/549,528.
Office Action dated Jan. 9, 2008 in U.S. Appl. No. 11/144,223.
Office Action dated Jan. 11, 2008 in U.S. Appl. No. 10/485,892.
Office Action dated Jan. 30, 2008 in U.S. Appl. No. 10/411,043.
Office Action dated Feb. 6, 2008 in U.S. Appl. No. 11/395,784.
Office Action dated Mar. 3, 2008 in U.S. Appl. No. 11/166,404.
Office Action dated Mar. 3, 2008 in U.S. Appl. No. 10/497,284.
Office Action dated Mar. 4, 2008 in U.S. Appl. No. 09/855,320.
Office Action dated Mar. 7, 2008 in U.S. Appl. No. 11/580,669.
Office Action dated Mar. 13, 2008 in U.S. Appl. No. 10/411,026.
Office Action dated Mar. 20, 2008 in U.S. Appl. No. 10/411,044.
Office Action dated Mar. 31, 2008 in U.S. Appl. No. 10/549,528.
Office Action dated Apr. 3, 2008 in U.S. Appl. No. 11/166,028.
Office Action dated Apr. 7, 2008 in U.S. Appl. No. 11/344,767.
Office Action dated Apr. 28, 2008 in U.S. Appl. No. 11/402,105.
Office Action dated Apr. 29, 2008 in U.S. Appl. No. 10/565,331.
Office Action dated May 12, 2008 in U.S. Appl. No. 10/485,892.
Office Action dated Jun. 9, 2008 in U.S. Appl. No. 09/855,320.
Office Action dated Jun. 30, 2008 in U.S. Appl. No. 11/396,215.
Office Action dated Jul. 10, 2008 in U.S. Appl. No. 11/514,484.
Office Action dated Jul. 22, 2008 in U.S. Appl. No. 11/102,497.
Office Action dated Jul. 24, 2008 in U.S. Appl. No. 11/344,767.
Office Action dated Aug. 15, 2008 in U.S. Appl. No. 11/845,175.
Office Action dated Aug. 21, 2008 in U.S. Appl. No. 10/411,044.
Office Action dated Aug. 26, 2008 in U.S. Appl. No. 11/580,669.
Office Action dated Sep. 16, 2008 in U.S. Appl. No. 11/440,839.
Office Action dated Sep. 22, 2008 in U.S. Appl. No. 10/556,094.
Office Action dated Oct. 21, 2008 in U.S. Appl. No. 10/530,972.
Office Action dated Oct. 30, 2008 in U.S. Appl. No. 10/411,026.
Office Action dated Oct. 31, 2008 in U.S. Appl. No. 11/166,404.
Office Action dated Nov. 12, 2008 in U.S. Appl. No. 11/144,223.
Office Action dated Nov. 18, 2008 in U.S. Appl. No. 10/497,284.
Office Action dated Dec. 24, 2008 in U.S. Appl. No. 11/396,215.
Office Action dated Jan. 6, 2009 in U.S. Appl. No. 10/549,528.
Office Action dated Jan. 21, 2009 in U.S. Appl. No. 10/565,331.
Office Action dated Feb. 9, 2009 in U.S. Appl. No. 09/855,320.
Office Action dated Feb. 10, 2009 in U.S. Appl. No. 11/166,404.
Office Action dated Mar. 4, 2009 in U.S. Appl. No. 11/580,669.
Office Action dated Mar. 12, 2009 in U.S. Appl. No. 11/102,497.
Office Action dated Mar. 12, 2009 in U.S. Appl. No. 11/514,484.
Office Action dated Mar. 17, 2009 in U.S. Appl. No. 10/411,026.
Office Action dated Apr. 1, 2009 in U.S. Appl. No. 10/552,896.
Office Action dated Apr. 16, 2009 in U.S. Appl. No. 10/576,506.
Office Action dated May 11, 2009 in U.S. Appl. No. 10/411,044.
Office Action dated May 14, 2009 in U.S. Appl. No. 11/910,958.
Office Action dated May 22, 2009 in U.S. Appl. No. 11/166,404.
Office Action dated Jun. 1, 2009 in U.S. Appl. No. 12/201,705.
Office Action dated Jun. 3, 2009 in U.S. Appl. No. 10/549,520.
Office Action dated Jun. 17, 2009 in U.S. Appl. No. 11/934,700.
Office Action dated Jul. 2, 2009 in U.S. Appl. No. 10/497,284.
Office Action dated Jul. 21, 2009 in U.S. Appl. No. 11/440,839.
Office Action dated Jul. 21, 2009 in U.S. Appl. No. 10/549,528.
Office Action dated Aug. 7, 2009 in U.S. Appl. No. 10/556,094.
Office Action dated Aug. 7, 2009 in U.S. Appl. No. 10/579,621.
Office Action dated Aug. 11, 2009 in U.S. Appl. No. 10/549,445.
Office Action dated Aug. 13, 2009 in U.S. Appl. No. 09/855,320.
Office Action dated Aug. 17, 2009 in U.S. Appl. No. 10/581,538.
Office Action dated Sep. 18, 2009 in U.S. Appl. No. 11/652,467.
Office Action dated Sep. 23 2009 in U.S. Appl. No. 12/201,705.
Office Action dated Sep. 28, 2009 in U.S. Appl. No. 11/910,958.
Office Action dated Sep. 29, 2009 in U.S. Appl. No. 11/714,874.
Office Action dated Sep. 29, 2009 in U.S. Appl. No. 11/645,839.
Office Action dated Oct. 29, 2009 in U.S. Appl. No. 11/781,900.
Office Action dated Oct. 2, 2009 in U.S. Appl. No. 11/781,902.
Office Action dated Oct. 14, 2009 in U.S. Appl. No. 10/565,331.
Office Action dated Oct. 14, 2009 in U.S. Appl. No. 10/549,528.
Office Action dated Oct. 23, 2009 in U.S. Appl. No. 11/396,215.
Office Action dated Oct. 27, 2009 in U.S. Appl. No. 11/402,105.
Office Action dated Nov. 2, 2009 in U.S. Appl. No. 11/659,942.
Office Action dated Nov. 2, 2009 in U.S. Appl. No. 11/866,969.
Office Action dated Nov. 4, 2009 in U.S. Appl. No.. 10/549,445.

Office Action dated Nov. 20, 2009 in U.S. Appl. No. 11/580,669.
Office Action dated Nov. 24, 2009 in U.S. Appl. No. 11/781,888.
Office Action dated Nov. 27, 2009 in U.S. Appl. No. 11/781,885.
Office Action dated Dec. 10, 2009 in U.S. Appl. No. 11/144,223.
Office Action dated Dec. 12, 2009 in U.S. Appl. No. 12/418,530.
Office Action dated Dec. 14, 2009 in U.S. Appl. No. 11/102,497.
Office Action dated Dec. 17, 2009 in U.S. Appl. No. 10/581,538.
Office Action dated Dec. 17, 2009 in U.S. Appl. No. 11/781,896.
Office Action dated Dec. 22, 2009 in U.S. Appl. No. 09/855,320.
Office Action dated Dec. 28, 2009 in U.S. Appl. No. 12/371,156.
Office Action dated Jan. 6, 2010 in U.S. Appl. No. 11/656,643.
Office Action dated Jan. 19, 2010 in U.S. Appl. No. 11/597,258.
Office Action dated Jan. 26, 2010 in U.S. Appl. No. 11/166,404.
Office Action dated Jan. 27, 2010 in U.S. Appl. No. 11/440,839.
Office Action dated Feb. 4, 2010 in U.S. Appl. No. 12/201,705.
Office Action dated Feb. 5, 2010 in U.S. Appl. No. 11/657,441.
Office Action dated Feb. 5, 2010 in U.S. Appl. No. 11/584,743.
Office Action dated Feb. 8, 2010 in U.S. Appl. No. 12/184,956.
Office Action dated Feb. 19, 2010 in U.S. Appl. No. 11/981,483.
Office Action dated Feb. 19, 2010 in U.S. Appl. No. 11/982,273.
Office Action dated Mar. 3, 2010 in U.S. Appl. No. 10/579,620.
Office Action dated Mar. 3, 2010 in U.S. Appl. No. 11/917,772.
Office Action dated Mar. 4, 2010 in U.S. Appl. No. 09/855,320.
Office Action dated Mar. 8, 2010 in U.S. Appl. No. 11/652,467.
Office Action dated Mar. 11, 2010 in U.S. Appl. No. 12/101,389.
Office Action dated Mar. 15, 2010 in U.S. Appl. No. 10/497,284.
Office Action dated Mar. 29, 2010 in U.S. Appl. No. 11/514,484.
Office Action dated Mar. 30, 2010 in U.S. Appl. No. 12/496,595.
Office Action dated Apr. 2, 2010 in U.S. Appl. No. 11/701,949.
Office Action dated Apr. 5, 2010 in U.S. Appl. No. 10/556,094.
Office Action dated Apr. 5, 2010 in U.S. Appl. No. 10/579,621.
Office Action dated May 3, 2010 in U.S. Appl. No. 12/276,885.
Office Action dated May 13, 2010 in U.S. Appl. No. 11/781,888.
Office Action dated May 14, 2010 in U.S. Appl. No. 11/781,885.
Office Action dated May 24, 2010 in U.S. Appl. No. 10/581,538.
Office Action dated May 26, 2010 in U.S. Appl. No. 11/144,223.
Office Action dated May 26, 2010 in U.S. Appl. No. 11/659,942.
Office Action dated May 26, 2010 in U.S. Appl. No. 11/866,969.
Office Action dated May 27, 2010 in U.S. Appl. No. 10/565,331.
Office Action dated Jun. 16, 2010 in U.S. Appl. No. 11/843,588.
Office Action dated Jul. 1, 2010 in U.S. Appl. No. 11/981,483.
Office Action dated Jul. 2, 2010 in U.S. Appl. No. 11/632,005.
Office Action dated Jul. 6, 2010 in U.S. Appl. No. 10/579,620.
Office Action dated Jul. 6, 2010 in U.S. Appl. No. 11/917,772.
Office Action dated Jul. 8, 2010 in U.S. Appl. No. 11/867,553.
Office Action dated Jul. 15, 2010 in U.S. Appl. No. 11/701,949.
Office Action dated Jul. 15, 2010 in U.S. Appl. No. 11/664,199.
Office Action dated Jul. 20, 2010 in U.S. Appl. No. 11/652,467.
Office Action dated Jul. 22, 2010 in U.S. Appl. No. 12/201,705.
Office Action dated Jul. 27, 2010 in U.S. Appl. No. 11/656,643.
Office Action dated Aug. 5, 2010 in U.S. Appl. No. 12/496,595.
Office Action dated Aug. 17, 2010 in U.S. Appl. No. 11/632,005.
Office Action dated Aug. 19, 2010 in U.S. Appl. No. 11/665,908.
Office Action dated Aug. 20, 2010 in U.S. Appl. No. 11/144,223.
Office Action dated Sep. 10, 2010 in U.S. Appl. No. 11/867,553.
Office Action dated Sep. 14, 2010 in U.S. Appl. No. 12/371,156.
Office Action dated Sep. 22, 2010 in U.S. Appl. No. 11/982,273.
Office Action dated Oct. 1, 2010 in U.S. Appl. No. 11/166,404.
Office Action dated Oct. 1, 2010 in U.S. Appl. No. 11/910,958.
Office Action dated Oct. 1, 2010 in U.S. Appl. No. 11/644,014.
Office Action dated Oct. 1, 2010 in U.S. Appl. No. 11/597,258.
Office Action dated Oct. 4, 2010 in U.S. Appl. No. 12/302,167.
Office Action dated Oct. 5, 2010 in U.S. Appl. No. 11/579,401.
Office Action dated Oct. 12, 2010 in U.S. Appl. No. 12/066,619.
Office Action dated Oct. 13, 2010 in U.S. Appl. No. 11/792,610.
Office Action dated Oct. 14, 2010 in U.S. Appl. No. 11/781,885.
Office Action dated Oct. 15, 2010 in U.S. Appl. No. 11/664,199.
Office Action dated Oct. 15, 2010 in U.S. Appl. No. 11/781,888.
Office Action dated Nov. 24, 2010 in U.S. Appl. No. 11/866,969.
Office Action dated Nov. 26, 2010 in U.S. Appl. No. 11/981,483.

* cited by examiner

BisP =Linker-HN-CH$(PO_3)_2$

12AP1/E5 -- Viventia Biotech
1964 -- Aventis
20K growth hormone -- AMUR
28P6/E6 -- Viventia Biotech
3-Hydroxyphthaloyl-beta-lactoglobulin –
4-IBB ligand gene therapy –
64-Cu MAb conjugate TETA-1A3 -- Mallinckrodt Institute of Radiology
64-Cu MAb conjugate TETA-cT84.66
64-Cu Trastuzumab TETA conjugate – Genentech
A 200 -- Amgen
A10255 – Eli Liliy
A1PDX – Hedral Therapeutics
A6 -- Angstrom
aaAT-III -- Genzyme
Abciximab -- Centocor
ABI.001 – Atlantic BioPharmaceuticals
ABT-828 – Abbott
Accutin
Actinohivin
activin -- Biotech Australia, Human Therapeutics, Curis
AD 439 – Tanox
AD 519 – Tanox
Adalimumab -- Cambridge Antibody Tech.
Adenocarcinoma vaccine – Biomira -- NIS
Adenosine deanimase -- Enzond
Adenosine A2B receptor antagonists -- Adenosine Therapeutics
ADP-001 – Axis Genetics
AF 13948 – Affymax
Afelimomab – Knoll
AFP-SCAN – Immunomedics
AG 2195 – Corixa
agalsidase alfa -- Transkaryotic Therapies
agalsidase beta -- Genzyme
AGENT– Antisoma
AI 300 – AutoImmune
AI-101 – Teva
AI-102 – Teva
AI-201 – AutoImmune
AI-301 – AutoImmune
AIDS vaccine – ANRS, CIBG, Hesed Biomed, Hollis-Eden, Rome, United Biomedical, American Home Products, Maxygen
airway receptor ligand -- IC Innovations
AJvW 2 – Ajinomoto
AK 30 NGF -- Alkermes
Albuferon -- Human Genome Sciences
albumin – Biogen, DSM Anti-Infectives, Genzyme Transgenics, PPL Therapeutics, TranXenoGen, Welfide Corp.
aldesleukin -- Chiron
alefacept -- Biogen
Alemtuzumab
Allergy therapy -- ALK-Abello/Maxygen, ALK-Abello/RP Scherer
allergy vaccines -- Allergy Therapeutics
Alnidofibatide -- Aventis Pasteur
Alnorine -- SRC VB VECTOR
ALP 242 -- Gruenenthal
Alpha antitrypsin -- Arriva/Hyland Immuno/ProMetic/Protease Sciences
Alpha-1 antitrypsin – Cutter, Bayer, PPL Therapeutics, Profile, ZymoGenetics, Arriva
Alpha-1 protease inhibitor -- Genzyme Transgenics, Welfide Corp.
Alpha-galactose fusion protein – Immunomedics
Alpha-galactosidase A -- Research Corporation Technologies, Genzyme
Alpha-glucosidase – Genzyme, Novazyme
Alpha-lactalbumin
Alpha-L-iduronidase -- Transkaryotic Therapies, BioMarin
alteplase -- Genentech
alvircept sudotox -- NIH
ALX1-11 –sNPS Pharmaceuticals
Alzheimer's disease gene therapy

FIG. 28A

AM-133 -- AMRAD
Amb a 1 immunostim conj. -- Dynavax
AMD 3100 – AnorMED -- NIS
AMD 3465 – AnorMED -- NIS
AMD 3465 – AnorMED -- NIS
AMD Fab -- Genentech
Amediplase – Menarini, Novartis
AM-F9
Amoebiasis vaccine
Amphiregulin -- Octagene
anakinra -- Amgen
analgesic -- Nobex
ancestim -- Amgen
AnergiX.RA -- Corixa, Organon
Angiocidin -- InKine
angiogenesis inhibitors -- ILEX
AngioMab – Antisoma
Angiopoietins -- Regeneron/Procter & Gamble
angiostatin -- EntreMed
Angiostatin/endostatin gene therapy -- Genetix Pharmaceuticals
angiotensin-II, topical -- Maret
Anthrax -- EluSys Therapeutics/US Army Medical Research Institute
Anthrax vaccine
Anti platelet-derived growth factor D human monoclonal antibodies -- CuraGen
Anti-17-1A MAb 3622W94 -- GlaxoSmithKline
Anti-2C4 MAb -- Genentech
anti-4-1BB monoclonal antibodies -- Bristol-Myers Squibb
Anti-Adhesion Platform Tech. -- Cytovax
Anti-adipocyte MAb -- Cambridge Antibody Tech./ObeSys
antiallergics -- Maxygen
antiallergy vaccine -- Acambis
Anti-alpha-4-integrin MAb
Anti-alphav$\beta$3 integrin MAb – Applied Molecular Evolution
Anti-angiogenesis monoclonal antibodies -- KS Biomedix/Schering AG
Anti-B4 MAb-DC1 conjugate -- ImmunoGen
Anti-B7 antibody PRIMATIZED -- IDEC
Anti-B7-1 MAb 16-10A1
Anti-B7-1 MAb 1G10
Anti-B7-2 MAb GL-1
Anti-B7-2-gelonin immunotoxin --
Antibacterials/antifungals -- Diversa/IntraBiotics
Anti-beta-amyloid monoclonal antibodies -- Cambridge Antibody Tech., Wyeth-Ayerst
Anti-BLyS antibodies -- Cambridge Antibody Tech. /Human Genome Sciences
Antibody-drug conjugates -- Seattle Genetics/Eos
Anti-C5 MAb BB5-1 -- Alexion
Anti-C5 MAb N19-8 -- Alexion
Anti-C8 MAb
anticancer cytokines -- BioPulse
anticancer matrix – Telios Integra
Anticancer monoclonal antibodies – ARIUS, Immunex
anticancer peptides – Maxygen, Micrologix
Anticancer prodrug Tech. -- Alexion Antibody Technologies
anticancer Troy-Bodies -- Affite -- Affitech
anticancer vaccine -- NIH
anticancers -- Epimmune
Anti-CCR5/CXCR4 sheep MAb -- KS Biomedix Holdings
Anti-CD11a MAb KBA --
Anti-CD11a MAb M17
Anti-CD11a MAb TA-3 –
Anti-CD11a MAb WT.1 –
Anti-CD11b MAb -- Pharmacia
Anti-CD11b MAb LM2
Anti-CD154 MAb -- Biogen
Anti-CD16-anti-CD30 MAb -- Biotest
Anti-CD18 MAb -- Pharmacia
Anti-CD19 MAb B43 –

FIG. 28B

Anti-CD19 MAb -liposomal sodium butyrate conjugate –
Anti-CD147
Anti-CD19 MAb-saporin conjugate –
Anti-CD19-dsFv-PE38-immunotoxin –
Anti-CD2 MAb 12-15 –
Anti-CD2 MAb B-E2 – Diaclone
Anti-CD2 MAb OX34 –
Anti-CD2 MAb OX54 –
Anti-CD2 MAb OX55 –
Anti-CD2 MAb RM2-1
Anti-CD2 MAb RM2-2
Anti-CD2 MAb RM2-4
Anti-CD20 MAb BCA B20
Anti-CD20-anti-Fc alpha RI bispecific MAb – Medarex, Tenovus
Anti-CD22 MAb-saporin-6 complex –
Anti-CD3 immunotoxin –
Anti-CD3 MAb 145-2C11 – Pharming
Anti-CD3 MAb CD4IgG conjugate – Genentech
Anti-CD3 MAb humanised – Protein Design, RW Johnson
Anti-CD3 MAb WT32
Anti-CD3 MAb-ricin-chain-A conjugate –
Anti-CD3 MAb-xanthine-oxidase conjugate –
Anti-CD30 MAb BerH2 – Medac
Anti-CD30 MAb-saporin conjugate
Anti-CD30-scFv-ETA'-immunotoxin
Anti-CD38 MAb AT13/5
Anti-CD38 MAb-saporin conjugate
Anti-CD3-anti-CD19 bispecific MAb
Anti-CD3-anti-EGFR MAb
Anti-CD3-anti-interleukin-2-receptor MAb
Anti-CD3-anti-MOv18 MAb – Centocor
Anti-CD3-anti-SCLC bispecific MAb
Anti-CD4 idiotype vaccine
Anti-CD4 MAb – Centocor, IDEC Pharmaceuticals, Xenova Group
Anti-CD4 MAb 16H5
Anti-CD4 MAb 4162W94 – GlaxoSmithKline
Anti-CD4 MAb B-F5 -- Diaclone
Anti-CD4 MAb GK1-5
Anti-CD4 MAb KT6
Anti-CD4 MAb OX38
Anti-CD4 MAb PAP conjugate – Bristol-Myers Squibb
Anti-CD4 MAb RIB 5-2
Anti-CD4 MAb W3/25
Anti-CD4 MAb YTA 3.1.2
Anti-CD4 MAb YTS 177-9
Anti-CD40 ligand MAb 5c8 -- Biogen
Anti-CD40 MAb
Anti-CD40 MAb 5D12 – Tanox
Anti-CD44 MAb A3D8
Anti-CD44 MAb GKWA3
Anti-CD44 MAb IM7
Anti-CD44 MAb KM81
Anti-CD44 variant monoclonal antibodies – Corixa/Hebrew University
Anti-CD45 MAb BC8-I-131
Anti-CD45RB MAb
Anti-CD48 MAb HuLy-m3
Anti-CD48 MAb WM-63
Anti-CD5 MAb – Becton Dickinson
Anti-CD5 MAb OX19
Anti-CD6 MAb
Anti-CD7 MAb-PAP conjugate
Anti-CD7 MAb-ricin-chain-A conjugate
Anti-CD8 MAb – Amerimmune, Cytodyn, Becton Dickinson
Anti-CD8 MAb 2-43
Anti-CD8 MAb OX8
Anti-CD80 MAb P16C10 – IDEC
Anti-CD80 MAb P7C10 – ID Vaccine
Anti-CD8-idarubicin conjugate
Anti-CEA MAb CE-25
Anti-CEA MAb MN 14 – Immunomedics
Anti-CEA MAb MN14-PE40 conjugate – Immunomedics

FIG. 28C

Anti-CEA MAb T84.66-interleukin-2 conjugate
Anti-CEA sheep MAb -- KS Biomedix Holdings
Anti-cell surface monoclonal antibodies -- Cambridge Antibody Tech. /Pharmacia
Anti-c-erbB2-anti-CD3 bifunctional MAb -- Otsuka
Anti-CMV MAb -- Scotgen
Anti-complement
Anti-CTLA-4 MAb
Anti-EGFR catalytic antibody -- Hesed Biomed
anti-EGFR immunotoxin -- IVAX
Anti-EGFR MAb -- Abgenix
Anti-EGFR MAb 528
Anti-EGFR MAb KSB 107 -- KS Biomedix
Anti-EGFR MAb-DM1 conjugate -- ImmunoGen
Anti-EGFR MAb-LA1 --
Anti-EGFR sheep MAb -- KS Biomedix
Anti-FAP MAb F19-I-131
Anti-Fas IgM MAb CH11
Anti-Fas MAb Jo2
Anti-Fas MAb RK-8
Anti-Flt-1 monoclonal antibodies -- ImClone
Anti-fungal peptides -- State University of New York
antifungal tripeptides -- BTG
Anti-ganglioside GD2 antibody-interleukin-2 fusion protein -- Lexigen
Anti-GM2 MAb -- Kyowa
Anti-GM-CSF receptor monoclonal antibodies -- AMRAD
Anti-gp130 MAb -- Tosoh
Anti-HCA monoclonal antibodies -- AltaRex/Epigen
Anti-hCG antibodies -- Abgenix/AVI BioPharma
Anti-heparanase human monoclonal antibodies -- Oxford Glycosciences/Medarex
Anti-hepatitis C virus human monoclonal antibodies -- XTL Biopharmaceuticals
Anti-HER-2 antibody gene therapy
Anti-herpes antibody -- Epicyte
Anti-HIV antibody -- Epicyte
anti-HIV catalytic antibody -- Hesed Biomed
anti-HIV fusion protein -- Idun
anti-HIV proteins -- Cangene
Anti-HM1-24 MAb -- Chugai
Anti-hR3 MAb
Anti-Human-Carcinoma-Antigen MAb -- Epicyte
Anti-ICAM-1 MAb -- Boehringer Ingelheim
Anti-ICAM-1 MAb 1A-29 -- Pharmacia
Anti-ICAM-1 MAb HA58
Anti-ICAM-1 MAb YN1/1.7.4
Anti-ICAM-3 MAb ICM3 -- ICOS
Anti-idiotype breast cancer vaccine 11D10
Anti-idiotype breast cancer vaccine ACA14C5 --
Anti-idiotype cancer vaccine -- ImClone Systems/Merck KGaA ImClone, Viventia Biotech
Anti-idiotype cancer vaccine 1A7 -- Titan
Anti-idiotype cancer vaccine 3H1 -- Titan
Anti-idiotype cancer vaccine TriAb -- Titan
Anti-idiotype Chlamydia trachomatis vaccine
Anti-idiotype colorectal cancer vaccine -- Novartis
Anti-idiotype colorectal cancer vaccine -- Onyvax
Anti-idiotype melanoma vaccine -- IDEC Pharmaceuticals
Anti-idiotype ovarian cancer vaccine ACA 125
Anti-idiotype ovarian cancer vaccine AR54 -- AltaRex

FIG. 28D

Anti-idiotype ovarian cancer vaccine CA-125 – AltaRex, Biomira
Anti-IgE catalytic antibody -- Hesed Biomed
Anti-IgE MAb E26 -- Genentech
Anti-IGF-1 MAb
anti-inflammatory -- GeneMax
anti-inflammatory peptide -- BTG
anti-integrin peptides -- Burnha
Anti-interferon-alpha-receptor MAb 64G12 – Pharma Pacific Management
Anti-interferon-gamma MAb -- Protein Design Labs
Anti-interferon-gamma polyclonal antibody -- Advanced Biotherapy
Anti-interleukin-10 MAb –
Anti-interleukin-12 MAb –
Anti-interleukin-1-beta polyclonal antibody -- R&D Systems
Anti-interleukin-2 receptor MAb 2A3
Anti-interleukin-2 receptor MAb 33B3-1 -- Immunotech
Anti-interleukin-2 receptor MAb ART-18
Anti-interleukin-2 receptor MAb LO-Tact-1
Anti-interleukin-2 receptor MAb Mikbeta1
Anti-interleukin-2 receptor MAb NDS61
Anti-interleukin-4 MAb 11B11
Anti-interleukin-5 MAb -- Wallace Laboratories
Anti-interleukin-6 MAb – Centocor, Diaclone, Pharmadigm
Anti-interleukin-8 MAb -- Abgenix
Anti-interleukin-8 MAb – Xenotech
Anti-JL1 MAb
Anti-Klebsiella sheep MAb -- KS Biomedix Holdings
Anti-Laminin receptor MAb-liposomal doxorubicin conjugate
Anti-LCG MAb -- Cytoclonal
Anti-lipopolysaccharide MAb -- VitaResc
Anti-L-selectin monoclonal antibodies -- Protein Design Labs, Abgenix, Stanford University
Anti-MBL monoclonal antibodies -- Alexion/Brigham and Women's Hospital
Anti-MHC monoclonal antibodies
Anti-MIF antibody humanised – IDEC, Cytokine PharmaSciences
Anti-MRSA/VRSA sheep MAb -- KS Biomedix Holdings
Anti-mu MAb -- Novartis
Anti-MUC-1 MAb
Anti-MUC 18
Anti-Nogo-A MAb IN1
Anti-nuclear autoantibodies -- Procyon
Anti-ovarian cancer monoclonal antibodies -- Dompe
Anti-p185 monoclonal antibodies
Anti-p43 MAb
Antiparasitic vaccines
Anti-PDGF/bFGF sheep MAb -- KS Biomedix
Anti-properdin monoclonal antibodies -- Abgenix/Gliatech
Anti-PSMA (prostrate specific membrane antigen)
Anti-PSMA MAb J591 -- BZL Biologics
Anti-Rev MAb gene therapy –
Anti-RSV antibodies – Epicyte, Intracell
Anti-RSV monoclonal antibodies -- Medarex/MedImmune, Applied Molecular Evolution/MedImmune
Anti-RSV MAb, inhalation -- Alkermes/MedImmune
Anti-RT gene therapy
Antisense K-ras RNA gene therapy
Anti-SF-25 MAb
Anti-sperm antibody -- Epicyte
Anti-Tac(Fv)-PE38 conjugate
Anti-TAPA/CD81 MAb AMP1
Anti-tat gene therapy

FIG. 28E

Anti-TCR-alphabeta MAb H57-597
Anti-TCR-alphabeta MAb R73
Anti-tenascin MAb BC-4-I-131
Anti-TGF-beta human monoclonal antibodies -- Cambridge Antibody Tech., Genzyme
Anti-TGF-beta MAb 2G7 – Genentech
Antithrombin III – Genzyme Transgenics, Aventis, Bayer, Behringwerke, CSL, Myriad
Anti-Thy1 MAb
Anti-Thy1.1 MAb
Anti-tissue factor/factor VIIA sheep MAb – KS Biomedix
Anti-TNF monoclonal antibodies – Centocor, Chiron, Peptech, Pharacia, Serono
Anti-TNF sheep MAb -- KS Biomedix Holdings
Anti-TNFalpha MAb – Genzyme
Anti-TNFalpha MAb B-C7 -- Diaclone
Anti-tooth decay MAb – Planet BioTech.
Anti-TRAIL receptor-1 MAb -- Takeda
Antitumour RNases – NIH
Anti-VCAM MAb 2A2 – Alexion
Anti-VCAM MAb 3F4 – Alexion
Anti-VCAM-1 MAb
Anti-VEC MAb -- ImClone
Anti-VEGF MAb -- Genentech
Anti-VEGF MAb 2C3
Anti-VEGF sheep MAb -- KS Biomedix Holdings
Anti-VLA-4 MAb HP1/2 – Biogen
Anti-VLA-4 MAb PS/2
Anti-VLA-4 MAb R1-2
Anti-VLA-4 MAb TA-2
Anti-VAP-1 human MAb
Anti-VRE sheep MAb – KS Biomedix Holdings
ANUP – TranXenoGen
ANUP-1 – Pharis
AOP-RANTES -- Senetek
Apan-CH – Praecis Pharmaceuticals
APC-8024 -- Demegen
ApoA-1 – Milano, Pharmacia
Apogen -- Alexion
apolipoprotein A1 – Avanir
Apolipoprotein E -- Bio-Tech. General
Applaggin – Biogen
aprotinin -- ProdiGene
APT-070C – AdProTech
AR 177 – Aronex Pharmaceuticals
AR 209 -- Aronex Pharmaceuticals, Antigenics
AR545C
ARGENT gene delivery systems – ARIAD
Arresten
ART-123 -- Asahi Kasei
arylsulfatase B -- BioMarin
Arylsulfatase B, Recombinant human -- BioMarin
AS 1051 – Ajinomoto
ASI-BCL – Intracell
Asparaginase - Merck
ATL-101 -- Alizyme
Atrial natriuretic peptide – Pharis
Aurintricarboxylic acid-high molecular weight
Autoimmune disorders -- GPC Biotech/MorphoSys
Autoimmune disorders and transplant rejection -- Bristol-Myers Squibb/Genzyme Tra
Autoimmune disorders/cancer – Abgenix/Chiron, CuraGen
Autotaxin
Avicidin – NeoRx
axogenesis factor-1 -- Boston Life Sciences
Axokine -- Regeneron
B cell lymphoma vaccine – Biomira
B7-1 gene therapy –
BABS proteins – Chiron

FIG. 28F

BAM-002 -- Novelos Therapeutics
Basiliximab (anti CD25 MAb) -- Novartis
Bay-16-9996 -- Bayer
Bay-39-9437 -- Bayer
Bay-50-4798 -- Bayer
BB-10153 -- British Biotech
BBT-001 -- Bolder BioTech.
BBT-002 -- Bolder BioTech.
BBT-003 -- Bolder BioTech.
BBT-004 -- Bolder BioTech.
BBT-005 -- Bolder BioTech.
BBT-006 -- Bolder BioTech.
BBT-007 -- Bolder BioTech.
BCH-2763 -- Shire
BCSF -- Millenium Biologix
BDNF -- Regeneron -- Amgen
Becaplermin -- Johnson & Johnson, Chiron
Bectumomab -- Immunomedics
Beriplast -- Aventis
Beta-adrenergic receptor gene therapy -- University of Arkansas
bFGF -- Scios
BI 51013 -- Behringwerke AG
BIBH 1 -- Boehringer Ingelheim
BIM-23190 -- Beaufour-Ipsen
birch pollen immunotherapy -- Pharmacia
bispecific fusion proteins -- NIH
Bispecific MAb 2B1 -- Chiron
Bitistatin
BIWA 4 -- Boehringer Ingelheim
blood substitute -- Northfield, Baxter Intl.
BLP-25 -- Biomira
BLS-0597 -- Boston Life Sciences
BLyS -- Human Genome Sciences
BLyS radiolabelled -- Human Genome Sciences
BM 06021 -- Boehringer Mannheim
BM-202 -- BioMarin
BM-301 -- BioMarin
BM-301 -- BioMarin
BM-302 -- BioMarin
BMP 2 -- Genetics Institute/Medtronic-Sofamor Danek, Genetics Institute/Collagenesis, Genetics Institute/Yamanouch
BMP 2 gene therapy
BMP 52 -- Aventis Pasteur, Biopharm
BMP-2 -- Genetics Institute
BMS 182248 -- Bristol-Myers Squibb
BMS 202448 -- Bristol-Myers Squibb
bone growth factors -- IsoTis
BPC-15 -- Pfizer
brain natriuretic peptide --
Breast cancer -- Oxford GlycoSciences/Medarex
Breast cancer vaccine -- Therion Biologics, Oregon
BSSL -- PPL Therapeutics
BST-2001 -- BioStratum
BST-3002 -- BioStratum
BTI 322 --
butyrylcholinesterase -- Shire
C 6822 -- COR Therapeutics
C1 esterase inhibitor -- Pharming
C3d adjuvant -- AdProTech
CAB-2.1 -- Millennium
calcitonin -- Inhale Therapeutics Systems, Aventis, Genetronics, TranXenoGen, Unigene, Rhone Poulenc Rohrer
calcitonin -- oral -- Nobex, Emisphere, Pharmaceutical Discovery
Calcitonin gene-related peptide -- Asahi Kasei -- Unigene
calcitonin, human -- Suntory
calcitonin, nasal -- Novartis, Unigene
calcitonin, Panoderm -- Elan
calcitonin, Peptitrol -- Shire
calcitonin, salmon -- Therapicon
calin -- Biopharm
Calphobindin I
calphobindin I -- Kowa
calreticulin -- NYU

FIG. 28G

Campath-1G
Campath-1M
cancer therapy -- Cangene
cancer vaccine -- Aixlie, Aventis Pasteur, Center of Molecular Immunology ,YM BioSciences, Cytos, Genzyme, Transgenics, GlobeImmune, Igeneon, ImClone, Virogenetics, InterCell, Iomai, Jenner Biotherapies, Memorial Sloan-Kettering Cancer Center, Sydney Kimmel Cancer Center, Novavax, Protein Sciences, Argonex, SIGA
Cancer vaccine ALVAC-CEA B7.1 -- Aventis Pasteur/Therion Biologics
Cancer vaccine CEA-TRICOM -- Aventis Pasteur/Therion Biologics
Cancer vaccine gene therapy -- Cantab Pharmaceuticals
Cancer vaccine HER-2/neu -- Corixa
Cancer vaccine THERATOPE -- Biomira
cancer vaccine, PolyMASC -- Valentis
Candida vaccine -- Corixa, Inhibitex
Canstatin -- ILEX
CAP-18 -- Panorama
Cardiovascular gene therapy -- Collateral Therapeutics
carperitide -- Suntory
Casocidin-1 -- Pharis
CAT 152 -- Cambridge Antibody Tech.
CAT 192 -- Cambridge Antibody Tech.
CAT 213 -- Cambridge Antibody Tech.
Catalase-- Enzon
Cat-PAD -- Circassia
CB 0006 -- Celltech
CCK(27-32)-- Akzo Nobel
CCR2-64I -- NIH
CD, Procept -- Paligent
CD154 gene therapy
CD39 -- Immunex
CD39-L2 -- Hyseq
CD39-L4 -- Hyseq CD4 fusion toxin -- Senetek
CD4 IgG -- Genentech
CD4 receptor antagonists -- Pharmacopeia/Progenics
CD4 soluble -- Progenics
CD4, soluble -- Genzyme Transgenics
CD40 ligand -- Immunex
CD4-ricin chain A -- Genentech
CD59 gene therapy -- Alexion
CD8 TIL cell therapy -- Aventis Pasteur
CD8, soluble -- Avidex
CD95 ligand -- Roche
CDP 571 -- Celltech
CDP 850 -- Celltech
CDP-860 (PEG-PDGF MAb) -- Celltech
CDP 870 -- Celltech
CDS-1 -- Ernest Orlando
Cedelizumab -- Ortho-McNeil
Cetermin -- Insmed
CETP vaccine -- Avant
Cetrorelix
Cetuximab
CGH 400 -- Novartis
CGP 42934 -- Novartis
CGP 51901 -- Tanox
CGRP -- Unigene
CGS 27913 -- Novartis
CGS 32359 -- Novartis
Chagas disease vaccine -- Corixa
chemokines -- Immune Response
CHH 380 -- Novartis
chitinase -- Genzyme, ICOS
Chlamydia pneumoniae vaccine -- Antex Biologics
Chlamydia trachomatis vaccine -- Antex Biologics
Chlamydia vaccine -- GlaxoSmithKline
Cholera vaccine CVD 103-HgR -- Swiss Serum and Vaccine Institute Berne
Cholera vaccine CVD 112 -- Swiss Serum and Vaccine Institute Berne

FIG. 28H

Cholera vaccine inactivated oral -- SBL Vaccin
Chrysalin -- Chrysalis BioTech.
CI-782 -- Hitachi Kase
Ciliary neurotrophic factor -- Fidia, Roche
CIM project -- Active Biotech
CL 329753 -- Wyeth-Ayerst
CL22, Cobra -- ML Laboratories
Clenoliximab -- IDEC
Clostridium difficile antibodies -- Epicyte
clotting factors -- Octagene
CMB 401 -- Celltech
CNTF -- Sigma-Tau
Cocaine abuse vaccine -- Cantab, ImmuLogic, Scripps
coccidiomycosis vaccine -- Arizo
collagen -- Type I -- Pharming
Collagen formation inhibitors -- FibroGen
Collagen/hydroxyapatite/bone growth factor -- Aventis Pasteur, Biopharm, Orquest
collagenase -- BioSpecifics
Colorectal cancer vaccine -- Wistar Institute
Component B, Recombinant -- Serono
Connective tissue growth factor inhibitors -- FibroGen/Taisho
Contortrostatin
contraceptive vaccine -- Zonagen
Contraceptive vaccine hCG
Contraceptive vaccine male reversible -- IMMUCON
Contraceptive vaccine zona pellucida -- Zonagen
Copper-64 labelled MAb TETA-1A3 -- NCI
Coralyne
Corsevin M
C-peptide analogues -- Schwarz
CPI-1500 -- Consensus
CRF -- Neurobiological Tech.
cRGDfV pentapeptide --
CRL 1095 -- CytRx
CRL 1336 -- CytRx
CRL 1605 -- CytRx
CS-560 -- Sankyo
CSF -- ZymoGenetics
CSF-G -- Hangzhou, Dong-A, Hanmi
CSF-GM -- Cangene, Hunan, LG Chem
CSF-M -- Zarix
CT 1579 -- Merck Frosst
CT 1786 -- Merck Frosst
CT-112^ -- BTG
CTB-134L -- Xenova
CTC-111 -- Kaketsuken
CTGF -- FibroGen
CTLA4-Ig -- Bristol-Myers Squibb
CTLA4-Ig gene therapy --
CTP-37 -- AVI BioPharma
C-type natriuretic peptide -- Suntory
CVS 995 -- Corvas Intl.
CX 397 -- Nikko Kyodo
CY 1747 -- Epimmune
CY 1748 -- Epimmune
Cyanovirin-N
Cystic fibrosis therapy -- CBR/IVAX
CYT 351
cytokine Traps -- Regeneron
cytokines -- Enzon, Cytoclonal
Cytomegalovirus glycoprotein vaccine -- Chiron, Aquila Biopharmaceuticals, Aventis Pasteur, Virogenetics
Cytomegalovirus vaccine live -- Aventis Pasteur
Cytosine deaminase gene therapy -- GlaxoSmithKline
DA-3003 -- Dong-A
DAB389interleukin-6 -- Senetek
DAB389interleukin-7
Daclizumab (anti-IL2R MAb) -- Protein Design Labs
DAMP^ -- Incyte Genomics
Daniplestim -- Pharmacia
darbepoetin alfa -- Amgen
DBI-3019 -- Diabetogen

FIG. 28I

DCC -- Genzyme
DDF -- Hyseq
decorin -- Integra, Telios
defensins -- Large Scale Biology
DEGR-VIIa
DeImmunised antibody 3B6/22 AGEN
Deimmunised anti-cancer antibodies -- Biovation/Viragen
Dendroamide A
Dengue vaccine -- Bavarian Nordic, Merck
denileukin diftitox -- Ligand
DES-1101 -- Desmos
desirudin -- Novartis
desmopressin -- Unigene
Desmoteplase -- Merck, Schering AG
Destabilase
Diabetes gene therapy -- DeveloGen, Pfizer
Diabetes therapy -- Crucell
Diabetes type 1 vaccine -- Diamyd Therapeutics
DiaCIM -- YM BioSciences
dialytic oligopeptides -- Research Corp
Diamyd -- Diamyd Therapeutics
DiaPep227-- Pepgen
DiavaX -- Corixa
Digoxin MAb -- Glaxo
Diphtheria tetanus pertussis-hepatitis B vaccine -- GlaxoSmithKline
DIR therapy -- Solis Therapeutics --
DNase -- Genentech
Dornase alfa -- Genentech
Dornase alfa, inhalation -- Genentech
Doxorubicin-anti-CEA MAb conjugate -- Immunomedics
DP-107 -- Trimeris
drotrecogin alfa -- Eli Lilly
DTctGMCSF
DTP-polio vaccine -- Aventis Pasteur
DU 257-KM231 antibody conjugate -- Kyowa
dural graft matrix -- Integra
Duteplase -- Baxter Intl.
DWP-401 -- Daewoong
DWP-404 -- Daewoong
DWP-408 -- Daewoong
Dx 88 (Epi-KAL2) -- Dyax
Dx 890 (elastin inhibitors) -- Dyax
E coli O157 vaccine -- NIH
E21-R -- BresaGen
Eastern equine encephalitis virus vaccine --
Echicetin --
Echinhibin 1 --
Echistatin -- Merck
Echitamine --
Ecromeximab -- Kyowa Hakko
EC-SOD -- PPL Therapeutics
Eculizumab (5G1.1) -- Alexion
EDF -- Ajinomoto
EDN derivative -- NIH
EDNA -- NIH
Edobacomab -- XOMA
Edrecolomab -- Centocor
EF 5077
Efalizumab -- Genentech
EGF fusion toxin -- Seragen, Ligand
EGF-P64k vaccine -- Center of Molecular Immunology
EL 246 -- LigoCyte
elastase inhibitor -- Synergen
elcatonin -- Therapicon
EMD 72000 -- Merck KGaA
Emdogain -- BIORA
emfilermin -- AMRAD
Emoctakin -- Novartis
enamel matrix protein -- BIORA
Endo III -- NYU
endostatin -- EntreMed, Pharis
Enhancins -- Micrologix
Enlimomab -- Isis Pharm.
Enoxaparin sodium -- Pharmuka
enzyme linked antibody nutrient depletion therapy -- KS Biomedix Holdings

FIG. 28J

Eosinophil-derived neutralizing agent --
EP-51216 -- Asta Medica
EP-51389 -- Asta Medica
EPH family ligands -- Regeneron
Epidermal growth factor -- Hitachi Kasei, Johnson & Johnson
Epidermal growth factor fusion toxin -- Senetek
Epidermal growth factor-genistein --
EPI-HNE-4 -- Dyax
EPI-KAL2 -- Dyax
Epoetin-alfa -- Amgen, Dragon Pharmaceuticals, Nanjing Huaxin
Epratuzumab -- Immunomedics
Epstein-Barr virus vaccine -- Aviron/SmithKline Beecham, Bioresearch
Eptacog alfa -- Novo Nordisk
Eptifibatide -- COR Therapeutics
erb-38 --
Erlizumab -- Genentech
erythropoietin -- Alkermes, ProLease, Dong-A, Elanex, Genetics Institute, LG Chem, Protein Sciences, Serono, Snow Brand, SRC VB VECTOR, Transkaryotic Therapies
Erythropoietin Beta -- Hoffman La Roche
Erythropoietin/Epoetin alfa -- Chugai
Escherichia coli vaccine -- North American Vaccine, SBL Vaccin, Swiss Serum and Vaccine Institute Berne
etanercept -- Immunex
examorelin -- Mediolanum
Exendin 4 -- Amylin
exonuclease VII
F 105 -- Centocor
F-992 -- Fomix
Factor IX -- Alpha Therapeutics, Welfide Corp., CSL, enetics Institute/AHP, Pharmacia, PPL Therapeutics
Factor IX gene therapy -- Cell Genesys
Factor VII -- Novo Nordisk, Bayer, Baxter Intl.
Factor VIIa -- PPL Therapeutics, ZymoGenetics
Factor VIII -- Bayer Genentech, Beaufour-Ipsen, CLB, Inex, Octagen, Pharmacia, Pharming
Factor VIII -- PEGylated -- Bayer
Factor VIII fragments -- Pharmacia
Factor VIII gene therapy -- Targeted Genetics
Factor VIII sucrose formulation -- Bayer, Genentech
Factor VIII-2 -- Bayer
Factor VIII-3 -- Bayer
Factor Xa inhibitors -- Merck, Novo Nordisk, Mochida
Factor XIII -- ZymoGenetics
Factors VIII and IX gene therapy -- Genetics Institute/Targeted Genetics
Famoxin -- Genset
Fas (delta) TM protein -- LXR BioTech.
Fas TR -- Human Genome Sciences
Felvizumab -- Scotgen
FFR-VIIa -- Novo Nordisk
FG-001 -- F-Gene
FG-002 -- F-Gene
FG-004 -- F-Gene
FG-005 -- F-Gene
FGF + fibrin -- Repair
Fibrimage -- Bio-Tech. General
fibrin-binding peptides -- ISIS Innovation
fibrinogen -- PPL Therapeutics, Pharming
fibroblast growth factor -- Chiron, NYU, Ramot, ZymoGenetics
fibrolase conjugate -- Schering AG
Filgrastim -- Amgen
filgrastim -- PDA modified -- Xencor
FLT-3 ligand -- Immunex
FN18 CRM9 --

FIG. 28K follistatin -- Biotech Australia, Human Therapeutics
follitropin alfa -- Alkermes, ProLease, PowderJect, Serono, Akzo Nobel
Follitropin Beta -- Bayer, Organon
FP 59
FSH -- Ferring
FSH + LH -- Ferring
F-spondin -- CeNeS
fusion protein delivery system -- UAB Research Foundation
fusion toxins -- Boston Life Sciences
G 5598 -- Genentech
GA-II -- Transkaryotic Therapies
Gamma-interferon analogues -- SRC VB VECTOR
Ganirelix -- Roche
gastric lipase -- Meristem
Gavilimomab --
G-CSF -- Amgen, SRC VB VECTOR
GDF-1 -- CeNeS
GDF-5 -- Biopharm
GDNF (glial derived neurotrophic factor) -- Amgen
gelsolin -- Biogen
Gemtuzumab ozogamicin -- Celltech
Gene-activated epoetin-alfa -- Aventis Pharma -- Transkaryotic Therapies
Glanzmann thrombasthenia gene therapy --
Glatiramer acetate -- Yeda
glial growth factor 2 -- CeNeS
GLP-1 -- Amylin, Suntory, TheraTech, Watson
GLP-1 peptide analogues -- Zealand Pharaceuticals
glucagon -- Eli Lilly, ZymoGenetics
Glucagon-like peptide-1 7-36 amide -- Suntory
Glucogen-like peptide -- Amylin
Glucocerebrosidase -- Genzyme
glutamate decarboxylase -- Genzyme Transgenics
Glycoprotein S3 -- Kureha
GM-CSF -- Immunex
GM-CSF tumour vaccine -- PowderJect
GnRH immunotherapeutic -- Protherics
Goserelin (LhRH antagonist) -- AstraZeneca
gp75 antigen -- ImClone
gp96 -- Antigenics
GPI 0100 -- Galenica
GR 4991W93 -- GlaxoSmithKline
Granulocyte colony-stimulating factor -- Dong-A
Granulocyte colony-stimulating factor conjugate
grass allergy therapy -- Dynavax
GRF1-44 -- ICN
Growth Factor -- Chiron, Atrigel, Atrix, Innogenetics, ZymoGenetics, Novo
growth factor peptides -- Biotherapeutics
growth hormone -- LG Chem
growth hormone, Recombinant human -- Serono
GT 4086 -- Gliatech
GW 353430 -- GlaxoSmithKline
GW-278884 -- GlaxoSmithKline
H 11 -- Viventia Biotech
H5N1 influenza A virus vaccine -- Protein Sciences
haemoglobin -- Biopure
haemoglobin 3011, Recombinant -- Baxter Healthcare
haemoglobin crosfumaril -- Baxter Intl.
haemoglobin stabilized -- Ajinomoto
haemoglobin, recombinant -- Apex
HAF -- Immune Response
Hantavirus vaccine
HB 19
HBNF -- Regeneron
HCC-1 -- Pharis
hCG -- Milkhaus

FIG. 28L hCG vaccine -- Zonagen
HE-317 -- Hollis-Eden Pharmaceuticals
Heat shock protein cancer and influenza vaccines -- StressGen
Helicobacter pylori vaccine -- Acambis, AstraZeneca/CSL, Chiron, Provalis
Helistat-G -- GalaGen
Hemolink -- Hemosol
hepapoietin -- Snow Brand
heparanase -- InSight
heparinase I -- Ibex
heparinase III -- Ibex
Hepatitis A vaccine -- American Biogenetic Sciences
Hepatitis A vaccine inactivated
Hepatitis A vaccine Nothav -- Chiron
Hepatitis A-hepatitis B vaccine -- GlaxoSmithKline
hepatitis B therapy -- Tripep
Hepatitis B vaccine -- Amgen, Chiron SpA, Meiji Milk, NIS, Prodeva, PowderJect, Rhein Biotech
Hepatitis B vaccine recombinant -- Evans Vaccines, Epitec Combiotech, Genentech, MedImmune, Merck Sharp & Dohme, Rhein Biotech, Shantha Biotechnics, Vector, Yeda
Hepatitis B vaccine recombinant TGP 943 -- Takeda
Hepatitis C vaccine -- Bavarian Nordic, Chiron, Innogenetics Acambis,
Hepatitis D vaccine -- Chiron Vaccines
Hepatitis E vaccine recombinant -- Genelabs/GlaxoSmithKline, Novavax
hepatocyte growth factor -- Panorama, Sosei
hepatocyte growth factor kringle fragments -- EntreMed
Her-2/Neu peptides -- Corixa
Herpes simplex glycoprotein DNA vaccine -- Merck, Wyeth-Lederle Vaccines-Malvern, Genentech, GlaxoSmithKline, Chiron, Takeda
Herpes simplex vaccine -- Cantab Pharmaceuticals, CEL-SCI, Henderson Morley
Herpes simplex vaccine live -- ImClone Systems/Wyeth-Lederle, Aventis Pasteur
HGF derivatives -- Dompe
hIAPP vaccine -- Crucell
Hib-hepatitis B vaccine -- Aventis Pasteur
HIC 1
HIP-- Altachem
Hirudins -- Biopharma, Cangene, Dongkook, Japan Energy Corporation, Pharmacia Corporation, SIR International, Sanofi-Synthelabo, Sotragene, Rhein Biotech
HIV edible vaccine -- ProdiGene
HIV gp120 vaccine -- Chiron, Ajinomoto, GlaxoSmithKline, ID Vaccine, Progenics, VaxGen
HIV gp120 vaccine gene therapy --
HIV gp160 DNA vaccine -- PowderJect, Aventis Pasteur, Oncogen, Hyland Immuno, Protein Sciences
HIV gp41 vaccine -- Panacos
HIV HGP-30W vaccine -- CEL-SCI
HIV immune globulin -- Abbott, Chiron
HIV peptides -- American Home Products
HIV vaccine -- Applied bioTech., Axis Genetics, Biogen, Bristol-Myers Squibb, Genentech, Korea Green Cross, NIS, Oncogen, Protein Sciences Corporation, Terumo, Tonen Corporation, Wyeth-Ayerst, Wyeth-Lederle Vaccines-Malvern, Advanced BioScience Laboratories, Bavarian Nordic, Bavarian Nordic/Statens Serum Institute, GeneCure, Immune Response, Progenics, Therion Biologics, United Biomedical, Chiron

FIG. 28M

HIV vaccine vCP1433 -- Aventis Pasteur
HIV vaccine vCP1452 -- Aventis Pasteur
HIV vaccine vCP205 -- Aventis Pasteur
HL-9 -- American BioScience
HM-9239 -- Cytran
HML-103 -- Hemosol
HML-104 -- Hemosol
HML-105 -- Hemosol
HML-109 -- Hemosol
HML-110 -- Hemosol
HML-121 -- Hemosol
hNLP -- Pharis
Hookworm vaccine
host-vector vaccines -- Henogen
HPM 1 -- Chugai
HPV vaccine -- MediGene
HSA -- Meristem
HSF -- StressGen
HSP carriers –Weizmann, Yeda, Peptor
HSPPC-70 -- Antigenics
HSPPC-96, pathogen-derived -- Antigenics
HSV 863 -- Novartis
HTLV-I DNA vaccine
HTLV-I vaccine
HTLV-II vaccine -- Access
HU 901 -- Tanox
Hu23F2G -- ICOS
HuHMFG1
HumaLYM -- Intracell
Human krebs statika -- Yamanouchi
human monoclonal antibodies -- Abgenix/Biogen, Abgenix/ Corixa, Abgenix/Immunex, Abgenix/Lexicon, Abgenix/ Pfizer, Athersys/Medarex, Biogen/MorphoSys, CAT/Searle, Centocor/Medarex, Corixa/Kirin Brewery, Corixa/Medarex, Eos BioTech./Medarex, Eos/Xenerex, Exelixis/Protein Design Labs, ImmunoGen/ Raven, Medarex/ B.Twelve, MorphoSys/ImmunoGen, XTL Biopharmaceuticals/Dyax,
Human monoclonal antibodies -- Medarex/Northwest Biotherapeutics, Medarex/Seattle Genetics
human netrin-1 -- Exelixis
human papillomavirus antibodies -- Epicyte
Human papillomavirus vaccine -- Biotech Australia, IDEC, StressGen
Human papillomavirus vaccine MEDI 501 -- MedImmune/GlaxoSmithKline
Human papillomavirus vaccine MEDI 503/MEDI 504 -- MedImmune/GlaxoSmithKline
Human papillomavirus vaccine TA-CIN -- Cantab Pharmaceuticals
Human papillomavirus vaccine TA-HPV -- Cantab Pharmaceuticals
Human papillomavirus vaccine TH-GW -- Cantab/GlaxoSmithKline
human polyclonal antibodies -- Biosite/Eos BioTech./ Medarex
human type II anti factor VIII monoclonal antibodies -- ThromboGenics
humanised anti glycoprotein Ib murine monoclonal antibodies -- ThromboGenics
HumaRAD -- Intracell
HuMax EGFR -- Genmab
HuMax-CD4 -- Medarex
HuMax-IL15 -- Genmab
HYB 190 -- Hybridon
HYB 676 -- Hybridon
I-125 MAb A33 -- Celltech
Ibritumomab tiuxetan -- IDEC
IBT-9401 -- Ibex
IBT-9402 -- Ibex
IC 14 -- ICOS
Idarubicin anti-Ly-2.1 --
IDEC 114 -- IDEC
IDEC 131 -- IDEC
IDEC 152 -- IDEC
IDM 1 -- IDM
IDPS -- Hollis-Eden Pharmaceuticals

FIG. 28N iduronate-2-sulfatase -- Transkaryotic Therapies
IGF/IBP-2-13 – Pharis
IGN-101 -- Igeneon
IK HIR02 – Iketon
IL-11 – Genetics Institute/AHP
IL-13-PE38 – NeoPharm
IL-17 receptor -- Immunex
IL-18BP – Yeda
IL-1Hy1 – Hyseq
IL-1ß -- Celltech
IL-1ß adjuvant – Celltech
IL-2 -- Chiron
IL-2 + IL-12 -- Hoffman La-Roche
IL-6/sIL-6R fusion -- Hadasit
IL-6R derivative – Tosoh
IL-7-Dap 389 fusion toxin – Ligand
IM-862 – Cytran
IMC-1C11 -- ImClone
imiglucerase -- Genzyme
Immune globulin intravenous (human) – Hoffman La Roche
immune privilege factor -- Proneuron
Immunocal -- Immunotec
Immunogene therapy – Briana Bio-Tech
Immunoliposomal 5-fluorodeoxyuridine-dipalmitate --
immunosuppressant vaccine -- Aixlie
immunotoxin – Antisoma, NIH
ImmuRAIT-Re-188 – Immunomedics
imreg-1 -- Imreg
infertility -- Johnson & Johnson, E-TRANS
Infliximab -- Centocor
Influenza virus vaccine -- Aventis Pasteur, Protein Sciences
inhibin -- Biotech Australia, Human Therapeutics
Inhibitory G protein gene therapy
INKP-2001 – InKine
Inolimomab – Diaclone
insulin -- AutoImmune, Altea, Biobras, BioSante, Bio-Tech. General, Chong Kun Dang, Emisphere, Flamel, Provalis, Rhein Biotech, TranXenoGen
insulin (bovine) -- Novartis
insulin analogue -- Eli Lilly
Insulin Aspart -- Novo Nordisk
insulin detemir – Novo Nordisk
insulin glargine -- Aventis
insulin inhaled – Inhale Therapeutics Systems, Alkermes
insulin oral -- Inovax
insulin, AeroDose -- AeroGen
insulin, AERx -- Aradigm
insulin, BEODAS -- Elan
insulin, Biphasix -- Helix
insulin, buccal – Generex
insulin, I2R -- Flemington
insulin, intranasal -- Bentley
insulin, oral -- Nobex, Unigene
insulin, Orasome – Endorex
insulin, ProMaxx -- Epic
insulin, Quadrant -- Elan
insulin, recombinant -- Aventis
insulin, Spiros -- Elan
insulin, Transfersome -- IDEA
insulin, Zymo, recombinant -- Novo Nordisk
insulinotropin -- Scios
Insulysin gene therapy --
integrin antagonists -- Merck
interferon (Alpha2) -- SRC VB VECTOR, Viragen, Dong-A, Hoffman La-Roche, Genentech
interferon -- BioMedicines, Human Genome Sciences
interferon (Alfa-n3)—Interferon Sciences Intl.
interferon (Alpha), Biphasix -- Helix

FIG. 28O interferon (Alpha)—Amgen, BioNative, Novartis, Genzyme Transgenics, Hayashibara, Inhale Therapeutics Systems, Medusa, Flamel, Dong-A, GeneTrol, Nastech, Shantha, Wassermann, LG Chem, Sumitomo, Aventis, Behring EGIS, Pepgen, Servier, Rhein Biotech,
interferon (Alpha2A)
interferon (Alpha2B) – Enzon, Schering-Plough, Biogen, IDEA
interferon (Alpha-N1) -- GlaxoSmithKline
interferon (beta) – Rentschler, GeneTrol, Meristem, Rhein Biotech, Toray, Yeda, Daiichi, Mochida
interferon (Beta1A) – Serono, Biogen
interferon (beta1A),inhale -- Biogen
interferon (ß1b)-- Chiron
interferon (tau)-- Pepgen
Interferon alfacon-1 -- Amgen
Interferon alpha-2a vaccine
Interferon Beta 1b -- Schering/Chiron, InterMune
Interferon Gamma -- Boehringer Ingelheim, Sheffield, Rentschler, Hayashibara
interferon receptor , Type I -- Serono
interferon(Gamma1B) -- Genentech
Interferon-alpha-2b + ribavirin – Biogen, ICN
Interferon-alpha-2b gene therapy -- Schering-Plough
Interferon-con1 gene therapy –
interleukin-1 antagonists -- Dompe
Interleukin-1 receptor antagonist – Abbott Bioresearch, Pharmacia
Interleukin-1 receptor type I -- Immunex
interleukin-1 receptor Type II -- Immunex
Interleukin-1 trap -- Regeneron
Interleukin-1-alpha -- Immunex/Roche
interleukin-2 -- SRC VB VECTOR, Ajinomoto, Biomira, Chiron
IL-2/ diphtheria toxin -- Ligand
Interleukin-3 -- Cangene
Interleukin-4 -- Immunology Ventures, Sanofi Winthrop, Schering-Plough, Immunex/ Sanofi Winthrop, Bayer, Ono
interleukin-4 + TNF-Alpha -- NIH
interleukin-4 agonist -- Bayer
interleukin-4 fusion toxin -- Ligand
Interleukin-4 receptor – Immunex, Immun
Interleukin-6 – Ajinomoto, Cangene, Yeda, Genetics Institute, Novartis
interleukin-6 fusion protein
interleukin-6 fusion toxin – Ligand, Serono
interleukin-7 -- IC Innovations
interleukin-7 receptor -- Immunex
interleukin-8 antagonists -- Kyowa Hakko/Millennium/Pfizer
interleukin-9 antagonists -- Genaera
Interleukin-10 – DNAX, Schering-Plough
Interleukin-10 gene therapy –
interleukin-12 -- Genetics Institute, Hoffman La-Roche
interleukin-13 -- Sanofi
interleukin-13 antagonists -- AMRAD
Interleukin-13-PE38QQR
interleukin-15 -- Immunex
interleukin-16 -- Research Corp
interleukin-18 -- GlaxoSmithKline
Interleukin-18 binding protein -- Serono
Ior-P3 -- Center of Molecular Immunology
IP-10 – NIH
IPF -- Metabolex
IR-501 -- Immune Response
ISIS 9125 -- Isis Pharmaceuticals
ISURF No. 1554 -- Millennium
ISURF No. 1866 – Iowa State Univer.
ITF-1697 -- Italfarmaco
IxC 162 -- Ixion
J 695 -- Cambridge Antibody Tech., Genetics Inst., Knoll
Jagged + FGF -- Repair

FIG. 28P

JKC-362 -- Phoenix Pharmaceuticals
JTP-2942 -- Japan Tobacce
Juman monoclonal antibodies -- Medarex/Raven
K02 -- Axys Pharmaceuticals
Keliximab -- IDEC
Keyhole limpet haemocyanin
KGF -- Amgen
KM 871 -- Kyowa
KPI 135 -- Scios
KPI-022 -- Scios
Kringle 5
KSB 304
KSB-201 -- KS Biomedix
L 696418 -- Merck
L 703801 -- Merck
L1 -- Acorda
L-761191 -- Merck
lactoferrin -- Meristem, Pharming, Agennix
lactoferrin cardio -- Pharming
LAG-3 -- Serono
LAIT -- GEMMA
LAK cell cytotoxin -- Arizona
lamellarins -- PharmaMar/University of Malaga
laminin A peptides -- NIH
lanoteplase -- Genetics Institute
laronidase -- BioMarin
Lassa fever vaccine
LCAT -- NIH
LDP 01 -- Millennium
LDP 02 -- Millennium
Lecithinized superoxide dismutase -- Seikagaku
LeIF adjuvant -- Corixa
leishmaniasis vaccine -- Corixa
lenercept -- Hoffman La-Roche
Lenograstim -- Aventis, Chugai
lepirudin -- Aventis
leptin -- Amgen, IC Innovations
Leptin gene therapy -- Chiron Corporation
leptin, 2nd-generation -- Amgen
leridistim -- Pharmacia
leuprolide, ProMaxx -- Epic
leuprorelin, oral -- Unigene
LeuTech -- Papatin
LEX 032 -- SuperGen
LiDEPT -- Novartis
Lintuzumab (anti-CD33 MAb) -- Protein Design Labs
lipase -- Altus Biologics
lipid A vaccine -- EntreMed
lipid-linked anchor Tech. -- ICRT, ID Biomedical
liposome-CD4 Tech. -- Sheffield
Listeria monocytogenes vaccine
LMB 1
LMB 7
LMB 9 -- Battelle Memorial Institute, NIH
LM-CD45 -- Cantab Pharmaceuticals
lovastatin -- Merck
LSA-3
LT-ß receptor -- Biogen
lung cancer vaccine -- Corixa
lusupultide -- Scios
L-Vax -- AVAX
LY 355455 -- Eli Lilly
LY 366405 -- Eli Lilly
LY-355101 -- Eli Lilly
Lyme disease DNA vaccine -- Vical/Aventis Pasteur
Lyme disease vaccine -- Aquila Biopharmaceuticals, Aventis, Pasteur, Symbicom, GlaxoSmithKline, Hyland Immuno, MedImmune
Lymphocytic choriomeningitis virus vaccine
lymphoma vaccine -- Biomira, Genitope
LYP18
lys plasminogen, recombinant
Lysosomal storage disease gene therapy -- Avigen
lysostaphin -- Nutrition 21

FIG. 28Q

M 23 -- Gruenenthal
M1 monoclonal antibodies -- Acorda Therapeutics
MA 16N7C2 -- Corvas Intl.
malaria vaccine -- GlaxoSmithKline, AdProTech, Antigenics, Apovia, Aventis Pasteur, Axis Genetics, Behringwerke, CDCP, Chiron Vaccines, Genzyme Transgenics, Hawaii, MedImmune, NIH, NYU, Oxxon, Roche/Saramane, Biotech Australia, Rx Tech
Malaria vaccine CDC/NIIMALVAC-1
malaria vaccine,multicomponent
mammaglobin -- Corixa
mammastatin -- Biotherapeutics
mannan-binding lectin -- NatImmu
mannan-MUC1 -- Psiron
MAP 30
Marinovir -- Phytera
MARstem -- Maret
MB-015 -- Mochida
MBP -- ImmuLogic
MCI-028 -- Mitsubishi-Tokyo
MCIF -- Human Genome Sciences
MDC -- Advanced BioScience -- Akzo Nobel, ICOS
MDX 11 -- Medarex
MDX 210 -- Medarex
MDX 22 -- Medarex
MDX 22
MDX 240 -- Medarex
MDX 33
MDX 44 -- Medarex
MDX 447 -- Medarex
MDX H210 -- Medarex
MDX RA -- Houston BioTech., Medarex
ME-104 -- Pharmexa
Measles vaccine
Mecasermin -- Cephalon/Chiron, Chiron
MEDI 488 -- MedImmune
MEDI 500
MEDI 507 -- BioTransplant
melanin concentrating hormone -- Neurocrine Biosciences
melanocortins -- OMRF
Melanoma monoclonal antibodies -- Viragen
melanoma vaccine -- GlaxoSmithKline, Akzo Nobel, Avant, Aventis Pasteur, Bavarian Nordic, Biovector, CancerVax, Genzyme Molecular Oncology, Humbolt, ImClone Systems, Memorial, NYU, Oxxon
Melanoma vaccine Magevac -- Therion
memory enhancers -- Scios
meningococcal B vaccine -- Chiron
meningococcal vaccine -- CAMR
Meningococcal vaccine group B conjugate -- North American Vaccine
Meningococcal vaccine group B recombinant -- BioChem Vaccines, Microscience
Meningococcal vaccine group Y conjugate -- North American Vaccine
Meningococcal vaccine groups A B and C conjugate -- North American Vaccine
Mepolizumab -- GlaxoSmithKline
Metastatin -- EntreMed, Takeda
Met-CkB7 -- Human Genome Sciences
met-enkephalin -- TNI
METH-1 -- Human Genome Sciences
methioninase -- AntiCancer
Methionine lyase gene therapy -- AntiCancer
Met-RANTES -- Genexa Biomedical, Serono
Metreleptin
Microtubule inhibitor MAb Immunogen/Abgenix
MGDF -- Kirin
MGV -- Progenics
micrin -- Endocrine
microplasmin -- ThromboGenics
MIF -- Genetics Institute

FIG. 28R migration inhibitory factor -- NIH
Mim CD4.1 – Xycte Therapies
mirostipen -- Human Genome Sciences
Mitumomab (BEC-2) – ImClone Systems, Merck KGaA
MK 852 – Merck
MLN 1202 (Anti-CCR2 monoclonal antibody) – Millenium Pharmaceuticals
Mobenakin -- NIS
molgramostim -- Genetics Institute, Novartis
monoclonal antibodies -- Abgenix/Celltech, Immusol/ Medarex, Viragen/ Roslin Institute, Cambridge Antibody Tech./Elan
MAb 108 –
MAb 10D5 –
MAb 14.18-interleukin-2 immunocytokine -- Lexigen
MAb 14G2a –
MAb 15A10 –
MAb 170 -- Biomira
MAb 177Lu CC49 --
MAb 17F9
MAb 1D7
MAb 1F7 – Immune Network
MAb 1H10-doxorubicin conjugate
MAb 26-2F
MAb 2A11
MAb 2E1 -- RW Johnson
MAb 2F5
MAb 31.1 -- International BioImmune Systems
MAb 32 -- Cambridge Antibody Tech., Peptech
MAb 323A3 -- Centocor
MAb 3C5
MAb 3F12
MAb 3F8
MAb 42/6
MAb 425 – Merck KGaA
MAb 447-52D -- Merck Sharp & Dohme
MAb 45-2D9- -  haematoporphyrin conjugate
MAb 4B4
MAb 4E3-CPA conjugate -- BCM Oncologia
MAb 4E3-daunorubicin conjugate
MAb 50-6
MAb 50-61A – Institut Pasteur
MAb 5A8 -- Biogen
MAb 791T/36-methotrexate conjugate
MAb 7c11.e8
MAb 7E11 C5-selenocystamine conjugate
MAb 93KA9 – Novartis
MAb A5B7-cisplatin conjugate -- Biodynamics Research, Pharmacia
MAb A5B7-I-131
MAb A7
MAb A717 -- Exocell
MAb A7-zinostatin conjugate
MAb ABX-RB2 -- Abgenix
MAb ACA 11
MAb AFP-I-131 – Immunomedics
MAb AP1
MAb AZ1
MAb B3-LysPE40 conjugate
MAb B4 – United Biomedical
MAb B43 Genistein-conjugate
MAb B43.13-Tc-99m -- Biomira
MAb B43-PAP conjugate
MAb B4G7-gelonin conjugate
MAb BCM 43-daunorubicin conjugate -- BCM Oncologia
MAb BIS-1
MAb BMS 181170 -- Bristol-Myers Squibb
MAb BR55-2
MAb BW494
MAb C 242-DM1 conjugate -- ImmunoGen
MAb C242-PE conjugate
MAb c30-6
MAb CA208-cytorhodin-S conjugate -- Hoechst Japan
MAb CC49 -- Enzon

FIG. 28S

MAb ch14.18 –
MAb CH14.18-GM-CSF fusion protein -- Lexigen
MAb chCE7
MAb CI-137 -- AMRAD
MAb cisplatin conjugate
MAb CLB-CD19
MAb CLB-CD19v
MAb CLL-1 -- Peregrine
MAb CLL-1-GM-CSF conjugate
MAb CLL-1-IL-2 conjugate -- Peregrine
MAb CLN IgG -- doxorubicin conjugates
MAb conjugates – Tanox
MAb D612
MAb Dal B02
MAb DC101 -- ImClone
MAb EA 1 –
MAb EC708 -- Biovation
MAb EP-5C7 -- Protein Design Labs
MAb ERIC-1 -- ICRT
MAb F105 gene therapy
MAb FC 2.15
MAb G250 -- Centocor
MAb GA6
MAb GA733
MAb Gliomab-H -- Viventia Biotech
MAb HB2-saporin conjugate
MAb HD 37 –
MAb HD37-ricin chain-A conjugate
MAb HNK20 -- Acambis
MAb huN901-DM1 conjugate -- ImmunoGen
MAb I-131 CC49 -- Corixa
MAb ICO25
MAb ICR12-CPG2 conjugate
MAb ICR-62
MAb IRac-ricin A conjugate
MAb K1
MAb KS1-4-methotrexate conjugate
MAb L6 -- Bristol-Myers Squibb, Oncogen
MAb LiCO 16-88
MAb LL2-I-131 – Immunomedics
MAb LL2-Y-90
MAb LS2D617 -- Hybritech
MAb LYM-1-gelonin conjugate
MAb LYM-1-I-131
MAb LYM-1-Y-90
MAb LYM-2 -- Peregrine
MAb M195
MAb M195-bismuth 213 conjugate -- Protein Design Labs
MAb M195-gelonin conjugate
MAb M195-I-131
MAb M195-Y-90
MAb MA 33H1 -- Sanofi
MAb MAD11
MAb MGb2
MAb MINT5
MAb MK2-23
MAb MOC31 ETA(252-613) conjugate
MAb MOC-31-In-111
MAb MOC-31-PE conjugate
MAb MR6 –
MAb MRK-16 -- Aventis Pasteur
MAb MS11G6
MAb MX-DTPA BrE-3
MAb MY9
MAb Nd2 -- Tosoh
MAb NG-1 -- Hygeia
MAb NM01 – Nissin Food
MAb OC 125
MAb OC 125-CMA conjugate
MAb OKI-1 -- Ortho-McNeil
MAb OX52 -- Bioproducts for Science
MAb PMA5
MAb PR1
MAb prost 30
MAb R-24
MAb R-24 α Human GD3 -- Celltech
MAb RFB4-ricin chain A conjugate
MAb RFT5-ricin chain A conjugate
MAb SC 1

FIG. 28T

MAb SM-3 -- ICRT
MAb SMART 1D10 -- Protein Design Labs
MAb SMART ABL 364 -- Novartis
MAb SN6f
MAb SN6f-deglycosylated ricin A chain conjugate --
MAb SN6j
MAb SN7-ricin chain A conjugate
MAb T101-Y-90 conjugate -- Hybritech
MAb T-88 -- Chiron
MAb TB94 -- Cancer ImmunoBiology
MAb TEC 11
MAb TES-23 -- Chugai
MAb TM31 -- Avant
MAb TNT-1 -- Cambridge Antibody Tech., Peregrine
MAb TNT-3
MAb TNT-3 -- IL2 fusion protein --
MAb TP3-At-211
MAb TP3-PAP conjugate --
MAb UJ13A -- ICRT
MAb UN3
MAb ZME-018-gelonin conjugate
MAb-BC2 -- GlaxoSmithKline
MAb-DM1 conjugate -- ImmunoGen
MAb-ricin-chain-A conjugate -- XOMA
MAb-temoporfin conjugates
Monopharm C -- Viventia Biotech
monteplase -- Eisai
montirelin hydrate -- Gruenenthal
moroctocog alfa -- Genetics Institute
Moroctocog-alfa -- Pharmacia
MP 4
MP-121 -- Biopharm
MP-52 -- Biopharm
MRA -- Chugai
MS 28168 -- Mitsui Chemicals, Nihon Schering
MSH fusion toxin -- Ligand
MSI-99 -- Genaera
MT 201 -- Micromet
Muc-1 vaccine -- Corixa
mucosal tolerance -- Aberdeen
mullerian inhibiting subst
muplestim -- Genetics Institute, Novartis, DSM Anti-Infectives
murine MAb -- KS Biomedix
Mutant somatropin -- JCR Pharmaceutical
MV 833 -- Toagosei
Mycoplasma pulmonis vaccine
Mycoprex -- XOMA
myeloperoxidase -- Henogen
myostatin -- Genetics Institute
Nacolomab tafenatox -- Pharmacia
Nagrecor -- Scios
nagrestipen -- British Biotech
NAP-5 -- Corvas Intl.
NAPc2 -- Corvas Intl.
nartograstim -- Kyowa
Natalizumab -- Protein Design Labs
Nateplase -- NIH, Nihon Schering
nateplase -- Schering AG
NBI-3001 -- Neurocrine Biosci.
NBI-5788 -- Neurocrine Biosci.
NBI-6024 -- Neurocrine Biosci.
Nef inhibitors -- BRI
Neisseria gonorrhoea vaccine -- Antex Biologics
Neomycin B-arginine conjugate
Nerelimomab -- Chiron
Nerve growth factor -- Amgen -- Chiron, Genentech
Nerve growth factor gene therapy
nesiritide citrate -- Scios
neuregulin-2 -- CeNeS
neurocan -- NYU
neuronal delivery system -- CAMR
Neurophil inhibitory Factor -- Corvas
Neuroprotective vaccine -- University of Auckland
neurotrophic chimaeras -- Regeneron
neurotrophic factor -- NsGene, CereMedix

FIG. 28U

NeuroVax -- Immune Response
neurturin -- Genentech
neutral endopeptidase -- Genentech
NGF enhancers -- NeuroSearch
NHL vaccine -- Large Scale Biology
NIP45 -- Boston Life Sciences
NKI-B20
NM 01 -- Nissin Food
NMI-139 -- NitroMed
NMMP -- Genetics Institute
NN-2211 -- Novo Nordisk
Noggin -- Regeneron
Nonacog alfa
Norelin -- Biostar
Norwalk virus vaccine
NRLU 10 -- NeoRx
NRLU 10 PE -- NeoRx
NT-3 -- Regeneron
NT-4/5 -- Genentech
NU 3056
NU 3076
NX 1838 -- Gilead Sciences
NY ESO-1/CAG-3 antigen -- NIH
NYVAC-7 -- Aventis Pasteur
NZ-1002 -- Novazyme
obesity therapy -- Nobex
OC 10426 -- Ontogen
OC 144093 -- Ontogen
OCIF -- Sankyo
Oct-43 -- Otsuka
Odulimomab -- Immunotech
OK PSA - liposomal
OKT3-gamma-1-ala-ala
OM 991
OM 992
Omalizumab -- Genentech
oncoimmunin-L -- NIH
Oncolysin B -- ImmunoGen
Oncolysin CD6 -- ImmunoGen
Oncolysin M -- ImmunoGen
Oncolysin S -- ImmunoGen
Oncophage -- Antigenics
Oncostatin M -- Bristol-Myers Squibb
OncoVax-CL -- Jenner Biotherapies
OncoVax-P -- Jenner Biotherapies
onercept -- Yeda
onychomycosis vaccine -- Boehringer Ingelheim
opebecan -- XOMA
opioids -- Arizona
Oprelvekin -- Genetics Institute
Oregovomab -- AltaRex
Org-33408 b-- Akzo Nobel
Orolip DP -- EpiCept
oryzacystatin
OSA peptides -- GenSci Regeneration
osteoblast-cadherin GF -- Pharis
Osteocalcin-thymidine kinase gene therapy
osteogenic protein -- Curis
osteopontin -- OraPharma
osteoporosis peptides -- Integra, Telios
osteoprotegerin -- Amgen, SnowBrand
otitis media vaccines -- Antex Biologics
ovarian cancer -- University of Alabama
OX40-IgG fusion protein -- Cantab, Xenova
P 246 -- Diatide
P 30 -- Alfacell
p1025 -- Active Biotech
P-113^ -- Demegen
P-16 peptide -- Transition Therapeutics
p43 -- Ramot
P-50 peptide -- Transition Therapeutics
p53 + RAS vaccine -- NIH, NCI
PACAP(1-27) analogue
paediatric vaccines -- Chiron
Pafase -- ICOS
PAGE-4 plasmid DNA -- IDEC
PAI-2 -- Biotech Australia, Human Therapeutics
Palifermin (keratinocyte growth factor) -- Amgen
Palivizumab -- MedImmune

FIG. 28V

PAM 4 – Merck
pamiteplase – Yamanouchi
pancreatin, Minitabs – Eurand
Pangen – Fournier
Pantarin – Selective Genetics
Parainfluenza virus vaccine – Pharmacia, Pierre Fabre
paraoxanase – Esperion
parathyroid hormone – Abiogen, Korea Green Cross
Parathyroid hormone (1-34) – Chugai/Suntory
Parkinson's disease gene therapy -- Cell Genesys/ Ceregene
Parvovirus vaccine – MedImmune
PCP-Scan – Immunomedics
PDGF – Chiron
PDGF cocktail – Theratechnologies
peanut allergy therapy – Dynavax
PEG anti-ICAM MAb – Boehringer Ingelheim
PEG asparaginase -- Enzon
PEG glucocerebrosidase
PEG hirudin – Knoll
PEG interferon-alpha-2a – Roche
PEG interferon-alpha-2b + ribavirin – Biogen, Enzon, ICN Pharmaceuticals, Schering-Plough
PEG MAb A5B7 –
Pegacaristim – Amgen – Kirin Brewery – ZymoGenetics
Pegaldesleukin – Research Corp
pegaspargase – Enzon
pegfilgrastim – Amgen
PEG-interferon Alpha – Viragen
PEG-interferon Alpha 2A – Hoffman La-Roche
PEG-interferon Alpha 2B – Schering-Plough
PEG-r-hirudin – Abbott
PEG-rHuMGDF – Amgen
PEG-uricase – Mountain View
Pegvisomant – Genentech
PEGylated proteins, PolyMASC – Valentis
PEGylated recombinant native human leptin – Roche
Pemtumomab
Penetratin – Cyclacel
Pepscan – Antisoma
peptide G – Peptech, ICRT
peptide vaccine – NIH ,NCI
Pexelizumab
pexiganan acetate – Genaera
Pharmaprojects No. 3179 – NYU
Pharmaprojects No. 3390 – Emest Orlando
Pharmaprojects No. 3417 – Sumitomo
Pharmaprojects No. 3777 -- Acambis
Pharmaprojects No. 4209 – XOMA
Pharmaprojects No. 4349 – Baxter Intl.
Pharmaprojects No. 4651
Pharmaprojects No. 4915 -- Avanir
Pharmaprojects No. 5156 – Rhizogenics
Pharmaprojects No. 5200 – Pfizer
Pharmaprojects No. 5215 – Origene
Pharmaprojects No. 5216 – Origene
Pharmaprojects No. 5218 – Origene
Pharmaprojects No. 5267 – ML Laboratories
Pharmaprojects No. 5373 – MorphoSys
Pharmaprojects No. 5493 – Metabolex
Pharmaprojects No. 5707 – Genentech
Pharmaprojects No. 5728 – Autogen
Pharmaprojects No. 5733 – BioMarin
Pharmaprojects No. 5757 – NIH
Pharmaprojects No. 5765 -- Gryphon
Pharmaprojects No. 5830 – AntiCancer
Pharmaprojects No. 5839 – Dyax
Pharmaprojects No. 5849 – Johnson & Johnson
Pharmaprojects No. 5860 – Mitsubishi-Tokyo

FIG. 28W

Pharmaprojects No. 5869 -- Oxford GlycoSciences
Pharmaprojects No. 5883 -- Asahi Brewery
Pharmaprojects No. 5947 -- StressGen
Pharmaprojects No. 5961 -- Theratechnologies
Pharmaprojects No. 5962 -- NIH
Pharmaprojects No. 5966 -- NIH
Pharmaprojects No. 5994 -- Pharming
Pharmaprojects No. 5995 -- Pharming
Pharmaprojects No. 6023 -- IMMUCON
Pharmaprojects No. 6063 -- Cytoclonal
Pharmaprojects No. 6073 -- SIDDCO
Pharmaprojects No. 6115 -- Genzyme
Pharmaprojects No. 6227 -- NIH
Pharmaprojects No. 6230 -- NIH
Pharmaprojects No. 6236 -- NIH
Pharmaprojects No. 6243 -- NIH
Pharmaprojects No. 6244 -- NIH
Pharmaprojects No. 6281 -- Senetek
Pharmaprojects No. 6365 -- NIH
Pharmaprojects No. 6368 -- NIH
Pharmaprojects No. 6373 -- NIH
Pharmaprojects No. 6408 -- Pan Pacific
Pharmaprojects No. 6410 -- Athersys
Pharmaprojects No. 6421 -- Oxford GlycoSciences
Pharmaprojects No. 6522 -- Maxygen
Pharmaprojects No. 6523 -- Pharis
Pharmaprojects No. 6538 -- Maxygen
Pharmaprojects No. 6554 -- APALEXO
Pharmaprojects No. 6560 -- Ardana
Pharmaprojects No. 6562 -- Bayer
Pharmaprojects No. 6569 -- Eos
Phenoxazine
Phenylase -- Ibex
Pigment epithelium derived factor --
plasminogen activator inhibitor-1, recombinant -- DuPont Pharmaceuticals
Plasminogen activators -- Abbott Laboratories, American Home Products, Boehringer Mannheim, Chiron Corporation, DuPont Pharmaceuticals, Eli Lilly, Shionogi, Genentech, Genetics Institute, GlaxoSmithKline, Hemispherx Biopharma, Merck & Co, Novartis, Pharmacia Corporation, Wakamoto, Yeda
plasminogen-related peptides -- Bio-Tech. General/MGH
platelet factor 4 -- RepliGen
Platelet-derived growth factor -- Amgen -- ZymoGenetics
plusonermin-- Hayashibara
PMD-2850 -- Protherics
Pneumococcal vaccine -- Antex Biologics, Aventis Pasteur
Pneumococcal vaccine intranasal -- BioChem Vaccines/Biovector
PR1A3
PR-39
pralmorelin -- Kaken
Pretarget-Lymphoma -- NeoRx
Priliximab -- Centocor
PRO 140 -- Progenics
PRO 2000 -- Procept
PRO 367 -- Progenics
PRO 542 -- Progenics
pro-Apo A-I -- Esperion
prolactin -- Genzyme
Prosaptide TX14(A) -- Bio-Tech. General
prostate cancer antbodies -- Immunex, UroCor
prostate cancer antibody therapy -- Genentech/UroGenesys, Genotherapeutics
prostate cancer immunotherapeutics -- The PSMA Development Company
prostate cancer vaccine -- Aventis Pasteur, Zonagen, Corixa, Dendreon, Jenner Biotherapies, Therion Biologics

FIG. 28X prostate-specific antigen -- EntreMed
protein A -- RepliGen
protein adhesives -- Enzon
protein C -- Baxter Intl., PPL Therapeutics, ZymoGenetics
protein C activator -- Gilead Sciences
protein kinase R antags -- NIH
protirelin -- Takeda
protocadherin 2 -- Caprion
Pro-urokinase -- Abbott, Bristol-Myers Squibb, Dainippon, Tosoh -- Welfide
P-selectin glycoprotein ligand-1 -- Genetics Institute
pseudomonal infections -- InterMune
Pseudomonas vaccine -- Cytovax
PSGL-Ig -- American Home Products
PSP-94 -- Procyon
PTH 1-34 -- Nobex
Quilimmune-M -- Antigenics
R 744 -- Roche
R 101933
R 125224 -- Sankyo
RA therapy -- Cardion
Rabies vaccine recombinant -- Aventis Pasteur, BioChem Vaccines, Kaketsuken Pharmaceuticals
RadioTheraCIM -- YM BioSciences
Ramot project No. 1315 -- Ramot
Ramot project No. K-734A -- Ramot
Ramot project No. K-734B -- Ramot
Ranibizumab (Anti-VEGF fragment) -- Genentech
RANK -- Immunex
ranpirnase -- Alfacell
ranpirnase-anti-CD22 MAb -- Alfacell
RANTES inhibitor -- Milan
RAPID drug delivery systems -- ARIAD
rasburicase -- Sanofi
rBPI-21, topical -- XOMA
RC 529 -- Corixa
rCFTR -- Genzyme Transgenics
RD 62198
rDnase -- Genentech
RDP-58 -- SangStat
RecepTox-Fce -- Keryx
RecepTox-GnRH -- Keryx, MTR Technologies
RecepTox-MBP -- Keryx, MTR Technologies
recFSH -- Akzo Nobel, Organon
REGA 3G12
Regavirumab -- Teijin
relaxin -- Connetics Corp
Renal cancer vaccine -- Macropharm
repifermin -- Human Genome Sciences
Respiratory syncytial virus PFP-2 vaccine -- Wyeth-Lederle
Respiratory syncytial virus vaccine -- GlaxoSmithKline, Pharmacia, Pierre Fabre
Respiratory syncytial virus vaccine inactivated
Respiratory syncytial virus-parainfluenza virus vaccine -- Aventis Pasteur, Pharmacia
Reteplase -- Boehringer Mannheim, Hoffman La-Roche
Retropep -- Retroscreen
RFB4 (dsFv) PE38
RFI 641 -- American Home Products
RFTS -- UAB Research Foundation
RG 12986 -- Aventis Pasteur
RG 83852 -- Aventis Pasteur
RG-1059 -- RepliGen
rGCR -- NIH
rGLP-1 -- Restoragen
rGRF -- Restoragen
rh Insulin -- Eli Lilly
RHAMM targeting peptides -- Cangene
rHb1.1 -- Baxter Intl.
rhCC10 -- Claragen
rhCG -- Serono
Rheumatoid arthritis gene therapy

FIG. 28Y

Rheumatoid arthritis vaccine -- Veterans Affairs Medical Center
rhLH -- Serono
Ribozyme gene therapy -- Genset
Rickettsial vaccine recombinant
RIGScan CR -- Neoprobe
RIP-3 -- Rigel
Rituximab -- Genentech
RK-0202 -- RxKinetix
RLT peptide -- Esperion
rM/NEI -- IVAX
rmCRP -- Immtech
RN-1001 -- Renovo
RN-3 -- Renovo
RNAse conjugate -- Immunomedics
RO 631908 -- Roche
Rotavirus vaccine -- Merck
RP 431 -- DuPont Pharmaceuticals
RP-128 -- Resolution
RPE65 gene therapy --
RPR 110173 -- Aventis Pasteur
RPR 115135 -- Aventis Pasteur
RPR 116258A -- Aventis Pasteur
rPSGL-Ig -- American Home Products
r-SPC surfactant -- Byk Gulden
RSV antibody -- Medimmune
Ruplizumab -- Biogen
rV-HER-2/neu -- Therion Biologics
SA 1042 -- Sankyo
sacrosidase -- Orphan Medical
Sant 7
Sargramostim -- Immunex
saruplase -- Gruenenthal
Satumomab -- Cytogen
SB 1 -- COR Therapeutics
SB 207448 -- GlaxoSmithKline
SB 208651 -- GlaxoSmithKline
SB 240683 -- GlaxoSmithKline
SB 249415 -- GlaxoSmithKline
SB 249417 -- GlaxoSmithKline
SB 6 -- COR Therapeutics
SB RA 31012 --
SC 56929 -- Pharmacia
SCA binding proteins -- Curis, Enzon
scFv(14E1)-ETA Berlex Laboratories, Schering AG
ScFv(FRP5)-ETA --
ScFv6C6-PE40 --
SCH 55700 -- Celltech
Schistosomiasis vaccine -- Glaxo Wellcome/Medeva, Brazil
SCPF -- Advanced Tissue Sciences
scuPA-suPAR complex -- Hadasit
SD-9427 -- Pharmacia
SDF-1 -- Ono
SDZ 215918 -- Novartis
SDZ 280125 -- Novartis
SDZ 89104 -- Novartis
SDZ ABL 364 -- Novartis
SDZ MMA 383 -- Novartis
Secretin -- Ferring, Repligen
serine protease inhibs -- Pharis
sermorelin acetate -- Serono
SERP-1 -- Viron
sertenef -- Dainippon
serum albumin, Recombinant human -- Aventis Behring
serum-derived factor -- Hadasit
Sevirumab -- Novartis
SGN 14 -- Seatle Genetics
SGN 15 -- Seatle Genetics
SGN 17/19 -- Seatle Genetics
SGN 30 -- Seatle Genetics
SGN-10 -- Seatle Genetics
SGN-11 -- Seatle Genetics
SH 306 -- DuPont Pharmaceuticals
Shanvac-B -- Shantha
Shigella flexneri vaccine -- Avant, Acambis, Novavax
Shigella sonnei vaccine --
sICAM-1 -- Boehringer Ingelheim
Silteplase -- Genzyme

FIG. 28Z

SIV vaccine – Endocon, Institut Pasteur
SK 896 – Sanwa Kagaku Kenkyusho
SK-827 -- Sanwa Kagaku Kenkyusho
Skeletex – CellFactors
SKF 106160 – GlaxoSmithKline
S-nitroso-AR545C –
SNTP – Active Biotech
somatomedin-1 – GroPep, Mitsubishi-Tokyo, NIH
somatomedin-1 carrier protein -- Insmed
somatostatin – Ferring
Somatotropin/
Human Growth Hormone – Bio-Tech. General, Eli Lilly
somatropin – Bio-Tech. General, Alkermes, ProLease, Aventis Behring, Biovector, Cangene, Dong-A, Eli Lilly, Emisphere, Enact, Genentech, Genzyme Transgenics, Grandis/InfiMed, CSL, InfiMed, MacroMed, Novartis, Novo Nordisk, Pharmacia Serono, TranXenoGen
somatropin derivative – Schering AG
somatropin, AIR – Eli Lilly
Somatropin, inhaled – Eli Lilly/Alkermes
somatropin, Kabi – Pharmacia
somatropin, Orasome – Novo Nordisk
Sonermin -- Dainippon Pharmaceutical
SP(V5.2)C – Supertek
SPf66
sphingomyelinase – Genzyme
SR 29001 – Sanofi
SR 41476 – Sanofi
SR-29001 – Sanofi
SS1(dsFV)-PE38 – NeoPharm
ß2 microglobulin – Avidex
ß2-microglobulin fusion proteins – NIH
ß-amyloid peptides – CeNeS
ß-defensin – Pharis
Staphylococcus aureus infections – Inhibitex/ZLB
Staphylococcus aureus vaccine conjugate – Nabi
Staphylococcus therapy – Tripep
Staphylokinase – Biovation, Prothera, Thrombogenetics
Streptococcal A vaccine – M6 Pharmaceuticals, North American Vaccine
Streptococcal B vaccine – Microscience
Streptococcal B vaccine recombinant – Biochem Vaccines
Streptococcus pyogenes vaccine
STRL-33 – NIH
Subalin – SRC VB VECTOR
SUIS – United Biomedical
SUIS-LHRH – United Biomedical
SUN-E3001 – Suntory
super high affinity monoclonal antibodies – YM BioSciences
Superoxide dismutase – Chiron, Enzon, Ube Industries, Bio-Tech, Yeda
superoxide dismutase-2 – OXIS
suppressin – UAB Research Foundation
SY-161-P5 – ThromboGenics
SY-162 – ThromboGenics
Systemic lupus erythematosus vaccine – MedClone/VivoRx
T cell receptor peptides – Xoma
T cell receptor peptide vaccine
T4N5 liposomes -- AGI Dermatics
TACI, soluble – ZymoGenetics
targeted apoptosis – Antisoma
tasonermin – Boehringer Ingelheim
TASP
TASP-V
Tat peptide analogues – NIH
TBP I – Yeda
TBP II
TBV25H – NIH
Tc 99m ior cea1 – Center of Molecular Immunology
Tc 99m P 748 – Diatide

FIG. 28AA

Tc 99m votumumab -- Intracell
Tc-99m rh-Annexin V -- Theseus Imaging
teceleukin -- Biogen
tenecteplase -- Genentech
Teriparatide -- Armour Pharmaceuticals, Asahi Kasei, Eli Lilly
terlipressin -- Ferring
testisin -- AMRAD
Tetrafibricin -- Roche
TFPI -- EntreMed
tgD-IL-2 -- Takeda
TGF-Alpha -- ZymoGenetics
TGF-ß -- Kolon
TGF-ß2 -- Insmed
TGF-ß3 -- OSI
Thalassaemia gene therapy -- Crucell
TheraCIM-h-R3 -- Center of Molecular Immunology, YM BioSciences
Theradigm-HBV -- Epimmune
Theradigm-HPV -- Epimmune
Theradigm-malaria -- Epimmune
Theradigm-melanoma -- Epimmune
TheraFab -- Antisoma
ThGRF 1-29 -- Theratechnologies
ThGRF 1-44 -- Theratechnologies
Thrombin receptor activating peptide -- Abbott
thrombomodulin -- Iowa, Novocastra
Thrombopoietin -- Dragon Pharmaceuticals, Genentech
thrombopoietin, Pliva -- Receptron
Thrombospondin 2 --
thrombostatin -- Thromgen
thymalfasin -- SciClone
thymocartin -- Gedeon Richter
thymosin Alpha1 -- NIH
thyroid stimulating hormone -- Genzyme
tICAM-1 -- Bayer
Tick anticoagulant peptide -- Merck
TIF -- Xoma
Tifacogin -- Chiron, NIS, Pharmacia
Tissue factor -- Genentech
Tissue factor pathway inhibitor
TJN-135 -- Tsumura
TM 27 -- Avant
TM 29 -- Avant
TMC-151 -- Tanabe Seiyaku
TNF tumour necrosis factor -- Asahi Kasei
TNF Alpha -- CytImmune
TNF antibody -- Johnson & Johnson
TNF binding protein -- Amgen
TNF degradation product -- Oncotech
TNF receptor -- Immunex
TNF receptor 1, soluble -- Amgen
TNF Tumour necrosis factor-alpha -- Asahi Kasei, Genetech, Mochida
TNF-Alpha inhibitor -- Tripep
TNFR:Fc gene therapy -- Targeted Genetics
TNF-SAM2
ToleriMab -- Innogenetics
Toxoplasma gondii vaccine -- GlaxoSmithKline
TP 9201 -- Telios
TP10 -- Avant
TP20 -- Avant
tPA -- Centocor
trafermin -- Scios
TRAIL/Apo2L -- Immunex
TRAIL-R1 MAb -- Cambridge Antibody Technologies
transferrin-binding proteins -- CAMR
Transforming growth factor-beta-1 -- Genentech
transport protein -- Genesis
Trastuzumab -- Genetech
TRH -- Ferring
Triabin -- Schering AG
Triconal
Triflavin
troponin I -- Boston Life Sciences
TRP-2^ -- NIH
trypsin inhibitor -- Mochida

FIG. 28BB

TSP-1 gene therapy –
TT-232
TTS-CD2 -- Active Biotech
Tuberculosis vaccine -- Aventis Pasteur, Genesis
Tumor Targeted Superantigens -- Active Biotech -- Pharmacia
tumour vaccines -- PhotoCure
tumour-activated prodrug antibody conjugates -- Millennium/ImmunoGen
tumstatin – ILEX
Tuvirumab -- Novartis
TV-4710 – Teva
TWEAK receptor -- Immunex
TXU-PAP
TY-10721 – TOA Eiyo
Type I diabetes vaccine -- Research Corp
Typhoid vaccine CVD 908
U 143677 -- Pharmacia
U 81749 -- Pharmacia
UA 1248 -- Arizona
UGIF -- Sheffield
UIC 2
UK 101
UK-279276 – Corvas Intl.
urodilatin -- Pharis
urofollitrophin -- Serono
Urokinase -- Abbott
uteroferrin-- Pepgen
V 20 -- GLYCODesign
V2 vasopressin receptor gene therapy
vaccines -- Active Biotech
Varicella zoster glycoprotein vaccine -- Research Corporation Technologies
Varicella zoster virus vaccine live -- Cantab Pharmaceuticals
Vascular endothelial growth factor – Genentech, University of California
Vascular endothelial growth factors – R&D Systems
vascular targeting agents -- Peregrine
vasopermeation enhancement agents -- Peregrine
vasostatin -- NIH
VCL – Bio-Tech. General
VEGF – Genentech, Scios
VEGF inhibitor -- Chugai
VEGF-2 -- Human Genome Sciences
VEGF-Trap -- Regeneron
viscumin, recombinant -- Madaus
Vitaxin
Vitrase – ISTA Pharmaceuticals
West Nile virus vaccine -- Bavarian Nordic
WP 652
WT1 vaccine -- Corixa
WX-293 – Wilex BioTech.
WX-360 -- Wilex BioTech.
WX-UK1 -- Wilex BioTech.
XMP-500 -- XOMA
XomaZyme-791 -- XOMA
XTL 001 -- XTL Biopharmaceuticals
XTL 002 -- XTL Biopharmaceuticals
yeast delivery system -- GlobeImmune
Yersinia pestis vaccine
YIGSR-Stealth -- Johnson & Johnson
Yissum Project No. D-0460 -- Yissum
YM 207 -- Yamanouchi
YM 337 -- Protein Design Labs
Yttrium-90 labelled biotin
Yttrium-90-labeled anti-CEA MAb T84.66 –
ZD 0490 – AstraZeneca
ziconotide -- Elan
ZK 157138 -- Berlex Laboratories
Zolimomab aritox
Zorcell -- Immune Response
ZRXL peptides -- Novartis

FIG. 28CC

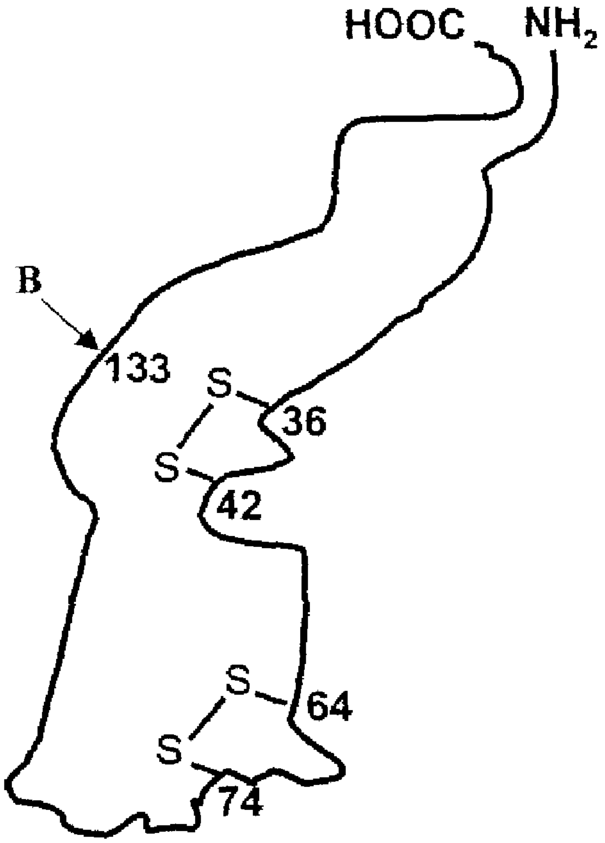
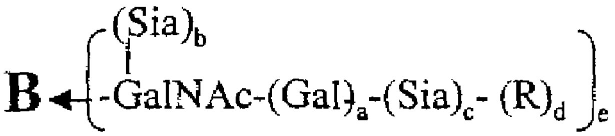
a-c, e (independently selected) = 0 or 1;
d = 0;
R = modifying group, sialyl or oligosialyl
FIG. 29A E. coli expressed G-CSF
a-e = 0.

1. GalNAc Transferase, UDP-GalNAc
2. CMP-SA-PEG, sialyltransferase c, d, e (independently selected) = 0 or 1;
a, b = 0; R = PEG.

FIG. 29D

NSO expressed G-CSF
a, e (independently selected) = 0 or 1;
b, c, d = 0

1. CMP-SA-levulinate, ST3Gal1
2. $H_4N_2$-PEG a, c, d, e (independently selected) = 0 or 1;
b = 0; R = PEG.

FIG. 29E

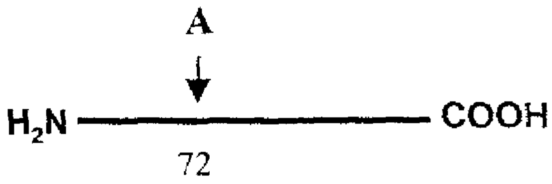
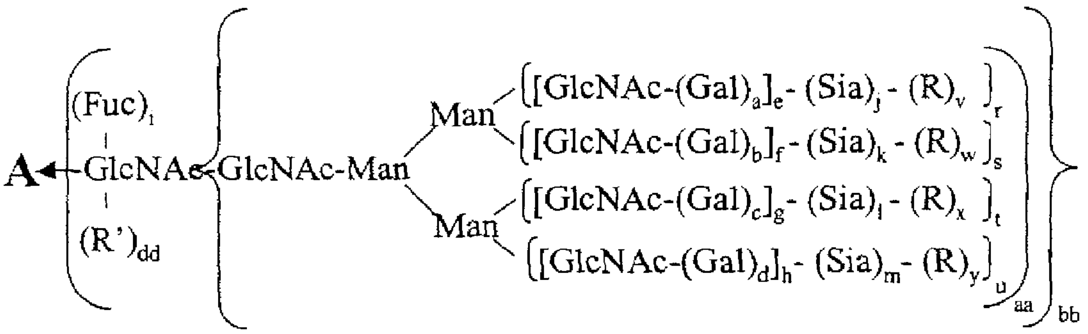
a-d, i, n-u (independently selected) = 0 or 1.
aa, bb, cc, dd, ee (independently selected) = 0 or 1.
e-h (independently selected) = 0 to 6.
j-m (independently selected) = 0 to 20.
v-z = 0; R = modifying group, mannose, oligo-mannose.
R' = H, glycosyl residue, modifying group, glycoconjugate.
FIG. 30A CHO, BHK, 293 cells, Vero expressed interferon alpha 14C.
a-d, aa, bb = 1; e-h = 1 to 4;
cc, j-m, i, r-u (independently selected) = 0 or 1;
q, n-p, v-z, cc, dd, ee = 0.

1. Sialidase
2. CMP-SA-PEG, ST3Gal3 a-d, aa, bb = 1; e-h = 1 to 4;
bb, cc, i, r-u (independently selected) = 0 or 1;
q, n-p, v-z, cc, dd, ee = 0;
v-y (independently selected) = 1,
when j-m (independently selected) = 1;
R = PEG.

FIG. 30B

Insect cell or fungi expressed interferon alpha-14C.
a-d, f, h, j-q, s, u, v-z, cc, dd, ee = 0;
e, g, i, r, t (independently selected) = 0 or 1;
aa, bb = 1.

1. GNT's 1&2, UDP-GlcNAc
2. Galactosyltransferase, UDP-Gal-PEG b, d, f, h, j-q, s, u, w, y, z, cc, dd, ee = 0;
a, c, e, g, i, r, t, v, x (independently selected) = 0 or 1;
v, x (independently selected) = 1,
when a, c, (independently selected) = 1;
aa, bb = 1; R = PEG.

FIG. 30C

Yeast expressed interferon alpha-14C.
a-q, cc, dd, ee, v-z = 0;
r-y (independently selected) = 0 to 1;
aa, bb = 1;
R (branched or linear) = Man, oligomannose or polysaccharide.

1. Endo-H
2. Galactosyltransferase, UDP-Gal
3.. CMP-SA-PEG, ST3Gal3 a-z, bb = 0; aa = 1; R' = -Gal-Sia-PEG.

FIG. 30D a-d, i, r-u (independently selected) = 0 or 1.
e-h (independently selected) = 0 to 4.
j-m (independently selected) = 0 or 1.
n, v-y = 0; z = 0 or 1.
R = polymer; R' = sugar, glycoconjugate.

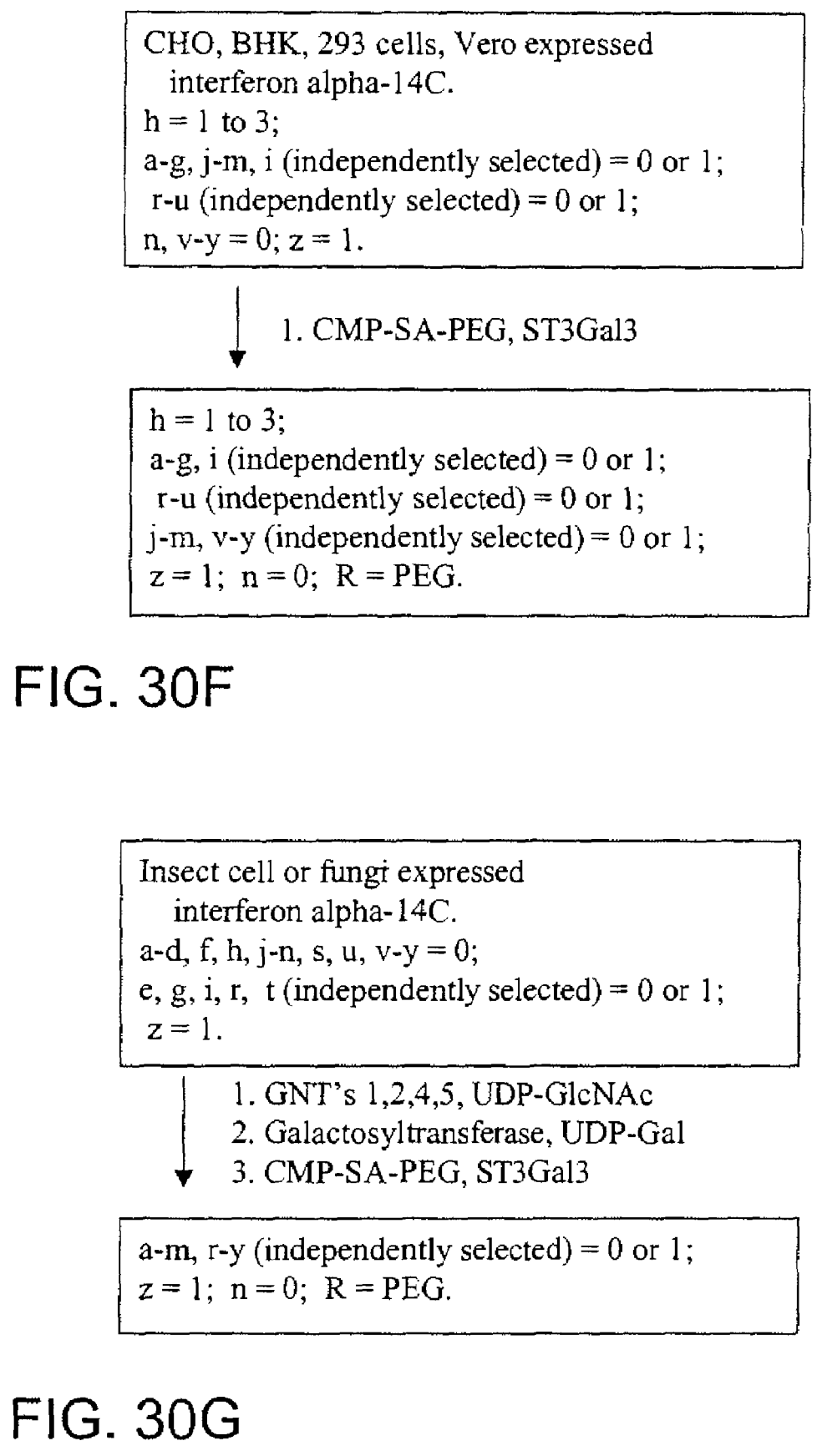

CHO, BHK, 293 cells, Vero expressed
interferon alpha-14C.
h = 1 to 3;
a-g, j-m, i (independently selected) = 0 or 1;
r-u (independently selected) = 0 or 1;
n, v-y = 0; z = 1.

1. CMP-SA-PEG, ST3Gal3 h = 1 to 3;
a-g, i (independently selected) = 0 or 1;
r-u (independently selected) = 0 or 1;
j-m, v-y (independently selected) = 0 or 1;
z = 1; n = 0; R = PEG.

FIG. 30F

Insect cell or fungi expressed
interferon alpha-14C.
a-d, f, h, j-n, s, u, v-y = 0;
e, g, i, r, t (independently selected) = 0 or 1;
z = 1.

1. GNT's 1,2,4,5, UDP-GlcNAc
2. Galactosyltransferase, UDP-Gal
3. CMP-SA-PEG, ST3Gal3 a-m, r-y (independently selected) = 0 or 1;
z = 1; n = 0; R = PEG.

FIG. 30G

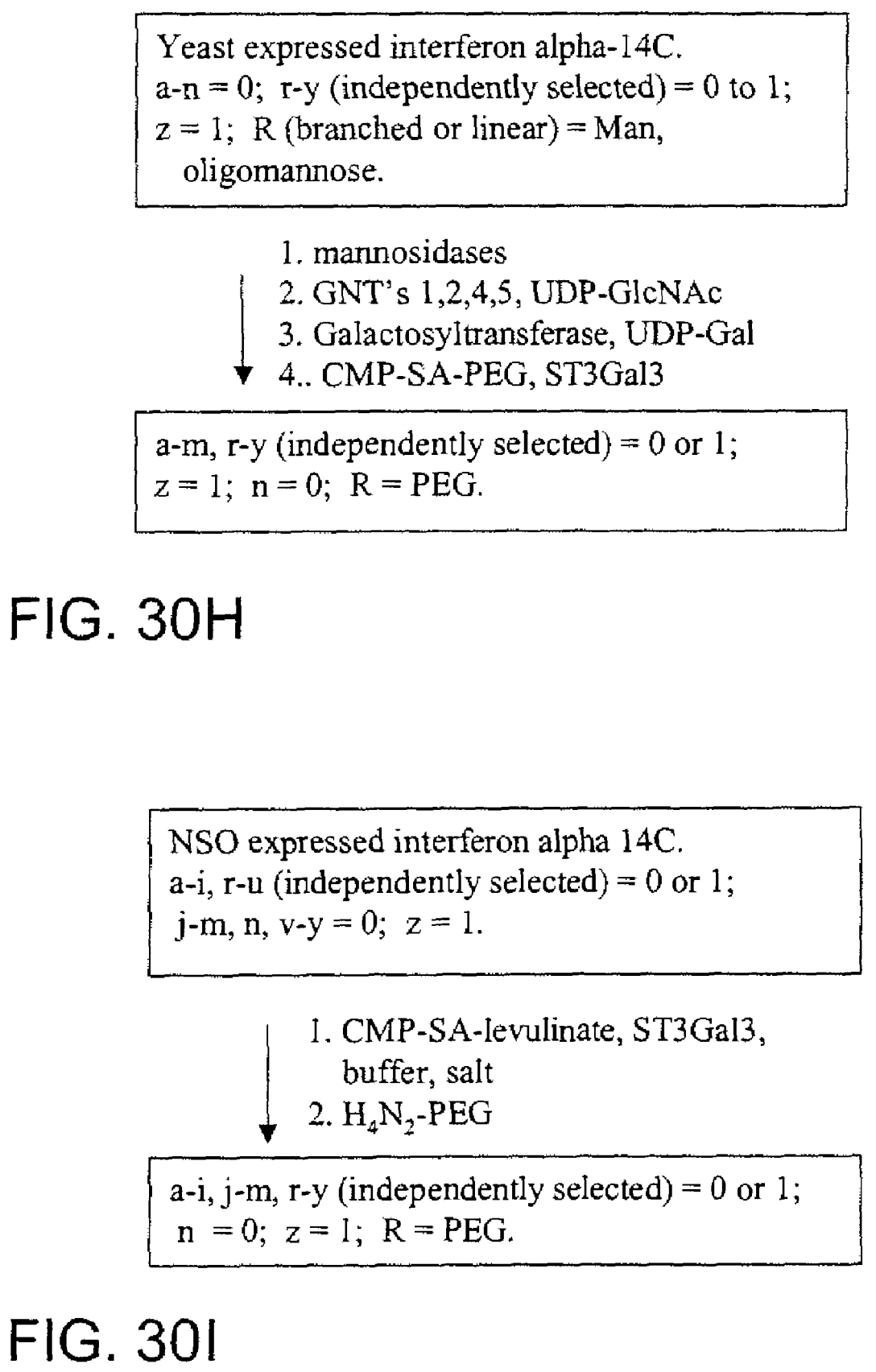

Yeast expressed interferon alpha-14C.
a-n = 0; r-y (independently selected) = 0 to 1;
z = 1; R (branched or linear) = Man, oligomannose.

1. mannosidases
2. GNT's 1,2,4,5, UDP-GlcNAc
3. Galactosyltransferase, UDP-Gal
4.. CMP-SA-PEG, ST3Gal3 a-m, r-y (independently selected) = 0 or 1;
z = 1; n = 0; R = PEG.

FIG. 30H

NSO expressed interferon alpha 14C.
a-i, r-u (independently selected) = 0 or 1;
j-m, n, v-y = 0; z = 1.

1. CMP-SA-levulinate, ST3Gal3, buffer, salt
2. $H_4N_2$-PEG a-i, j-m, r-y (independently selected) = 0 or 1;
n = 0; z = 1; R = PEG.

FIG. 30I

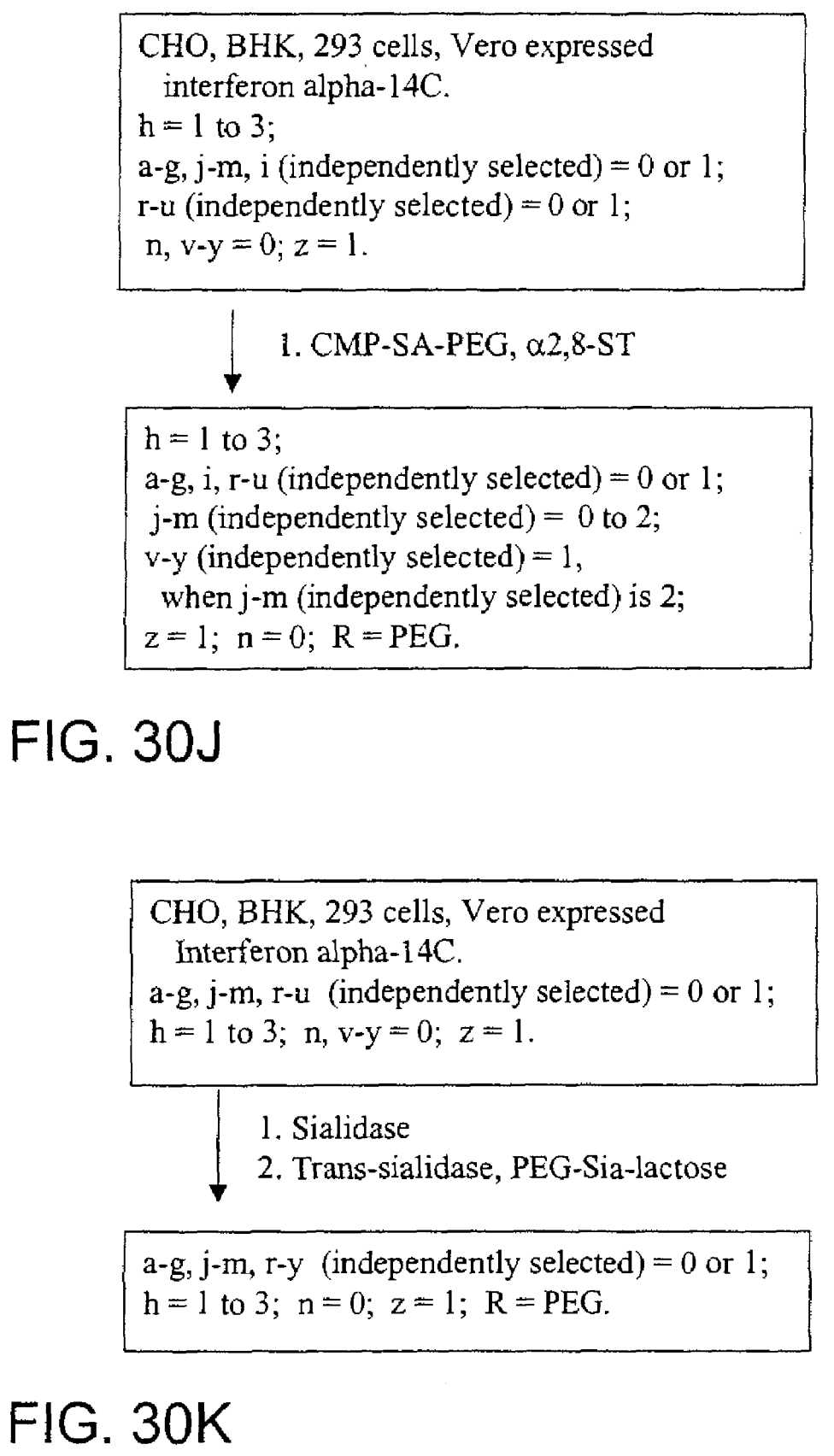

CHO, BHK, 293 cells, Vero expressed interferon alpha-14C.
h = 1 to 3;
a-g, j-m, i (independently selected) = 0 or 1;
r-u (independently selected) = 0 or 1;
n, v-y = 0; z = 1.

↓ 1. CMP-SA-PEG, α2,8-ST h = 1 to 3;
a-g, i, r-u (independently selected) = 0 or 1;
j-m (independently selected) = 0 to 2;
v-y (independently selected) = 1, when j-m (independently selected) is 2;
z = 1; n = 0; R = PEG.

FIG. 30J

CHO, BHK, 293 cells, Vero expressed Interferon alpha-14C.
a-g, j-m, r-u (independently selected) = 0 or 1;
h = 1 to 3; n, v-y = 0; z = 1.

↓ 1. Sialidase
2. Trans-sialidase, PEG-Sia-lactose a-g, j-m, r-y (independently selected) = 0 or 1;
h = 1 to 3; n = 0; z = 1; R = PEG.

FIG. 30K

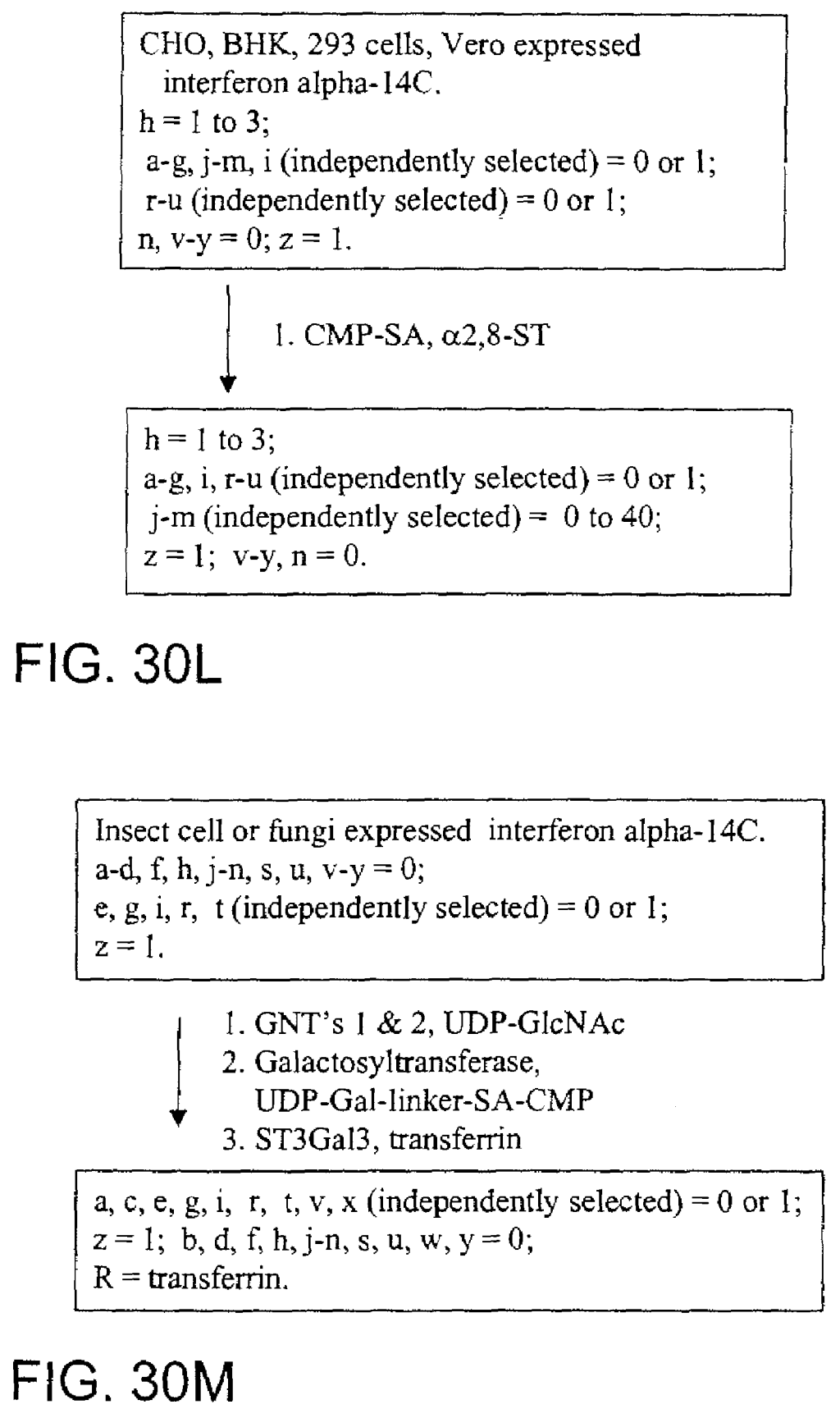

CHO, BHK, 293 cells, Vero expressed interferon alpha-14C.
h = 1 to 3;
a-g, j-m, i (independently selected) = 0 or 1;
r-u (independently selected) = 0 or 1;
n, v-y = 0; z = 1.

1. CMP-SA, α2,8-ST h = 1 to 3;
a-g, i, r-u (independently selected) = 0 or 1;
j-m (independently selected) = 0 to 40;
z = 1; v-y, n = 0.

FIG. 30L

Insect cell or fungi expressed interferon alpha-14C.
a-d, f, h, j-n, s, u, v-y = 0;
e, g, i, r, t (independently selected) = 0 or 1;
z = 1.

1. GNT's 1 & 2, UDP-GlcNAc
2. Galactosyltransferase, UDP-Gal-linker-SA-CMP
3. ST3Gal3, transferrin a, c, e, g, i, r, t, v, x (independently selected) = 0 or 1;
z = 1; b, d, f, h, j-n, s, u, w, y = 0;
R = transferrin.

FIG. 30M

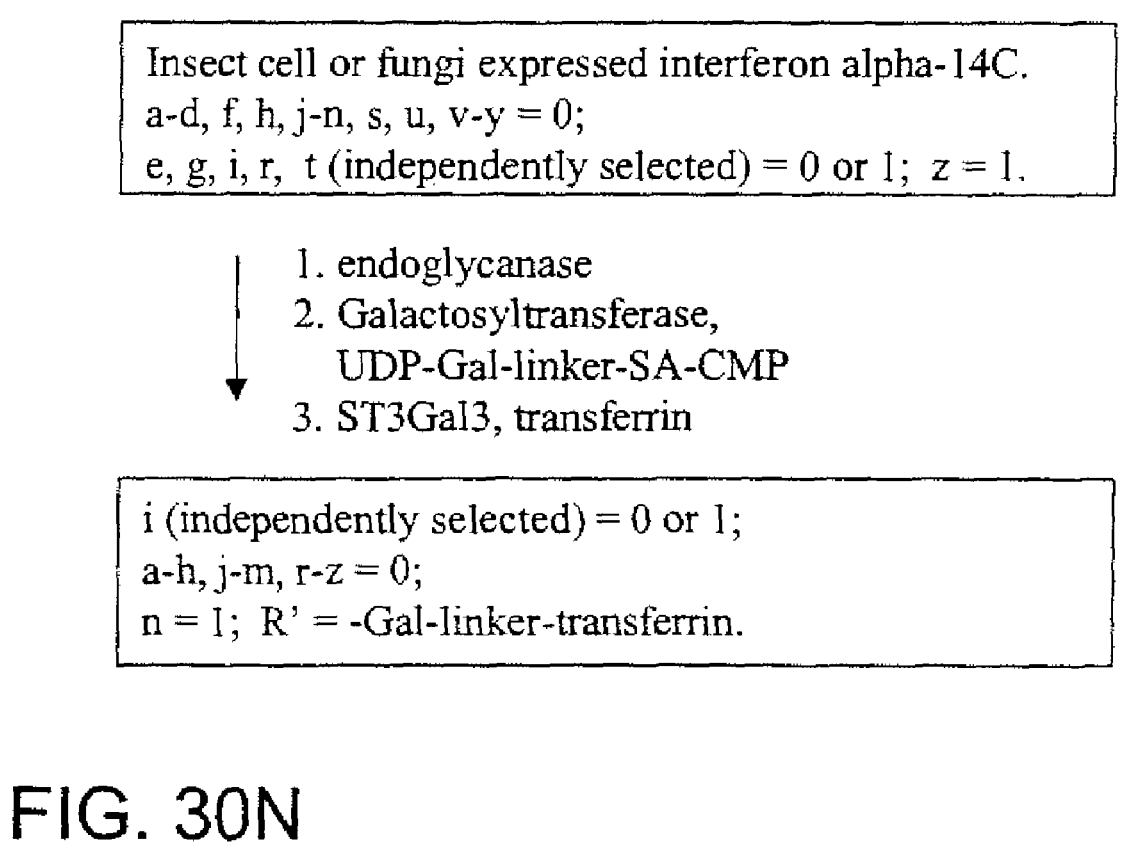

Insect cell or fungi expressed interferon alpha-14C.
a-d, f, h, j-n, s, u, v-y = 0;
e, g, i, r, t (independently selected) = 0 or 1; z = 1.

1. endoglycanase
2. Galactosyltransferase, UDP-Gal-linker-SA-CMP
3. ST3Gal3, transferrin i (independently selected) = 0 or 1;
a-h, j-m, r-z = 0;
n = 1; R' = -Gal-linker-transferrin.

FIG. 30N

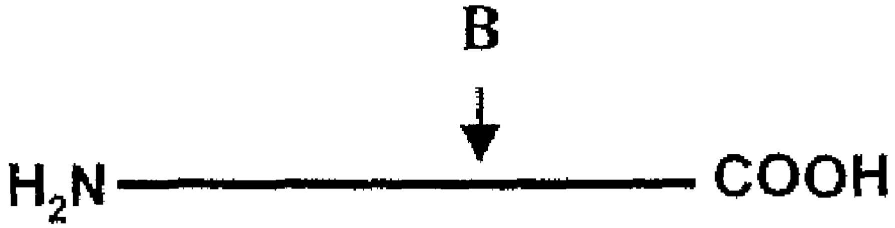
106
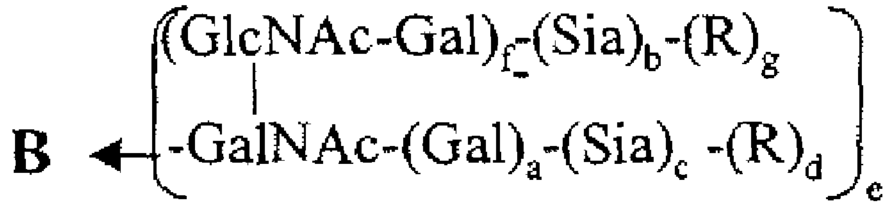
a-c, e, f (independently selected) = 0 or 1;
d, g = 0; R = polymer, glycoconjugate.
FIG. 30O CHO, BHK, 293 cells, Vero expressed IF-alpha (2a or 2b).
a-c (independently selected) = 0 or 1;
e = 1; d, f, g = 0

1. Sialidase
2. CMP-SA-PEG, ST3Gal1 a-d (independently selected) = 0 or 1;
e = 1; b, f, g = 0; R = PEG.

FIG. 30P

Insect cell expressed interferon alpha (2a or 2b).
a, e (independently selected) = 0 or 1;
b, c, d, f, g = 0.

1. Galactosyltransferase, UDP-Gal
2. CMP-SA-PEG, ST3Gal1 a, c, d, e (independently selected) = 0 or 1;
b, f, g = 0; R = PEG.

FIG. 30Q

CHO, BHK, 293 cells, Vero expressed IF-alpha (2a or 2b).
a-c, f (independently selected) = 0 or 1;
e = 1; d, g = 0

1. Sialidase
2. CMP-SA-PEG, ST3Gal1 and ST3Gal3 a-d, f, g (independently selected) = 0 or 1;
e = 1; R = PEG.

CHO, BHK, 293 cells, Vero expressed IF-alpha (2a or 2b).
a-c, f (independently selected) = 0 or 1;
e = 1; d, g = 0

1. Sialidase
2. CMP-SA-linker-SA-CMP, ,ST3Gal1
3. ST3Gal3, transferrin a-d, f (independently selected) = 0 or 1;
e = 1; R = transferrin; g = 0.

a-c, e (independently selected) = 0 or 1;
d = 0; R = polymer, glycoconjugate.

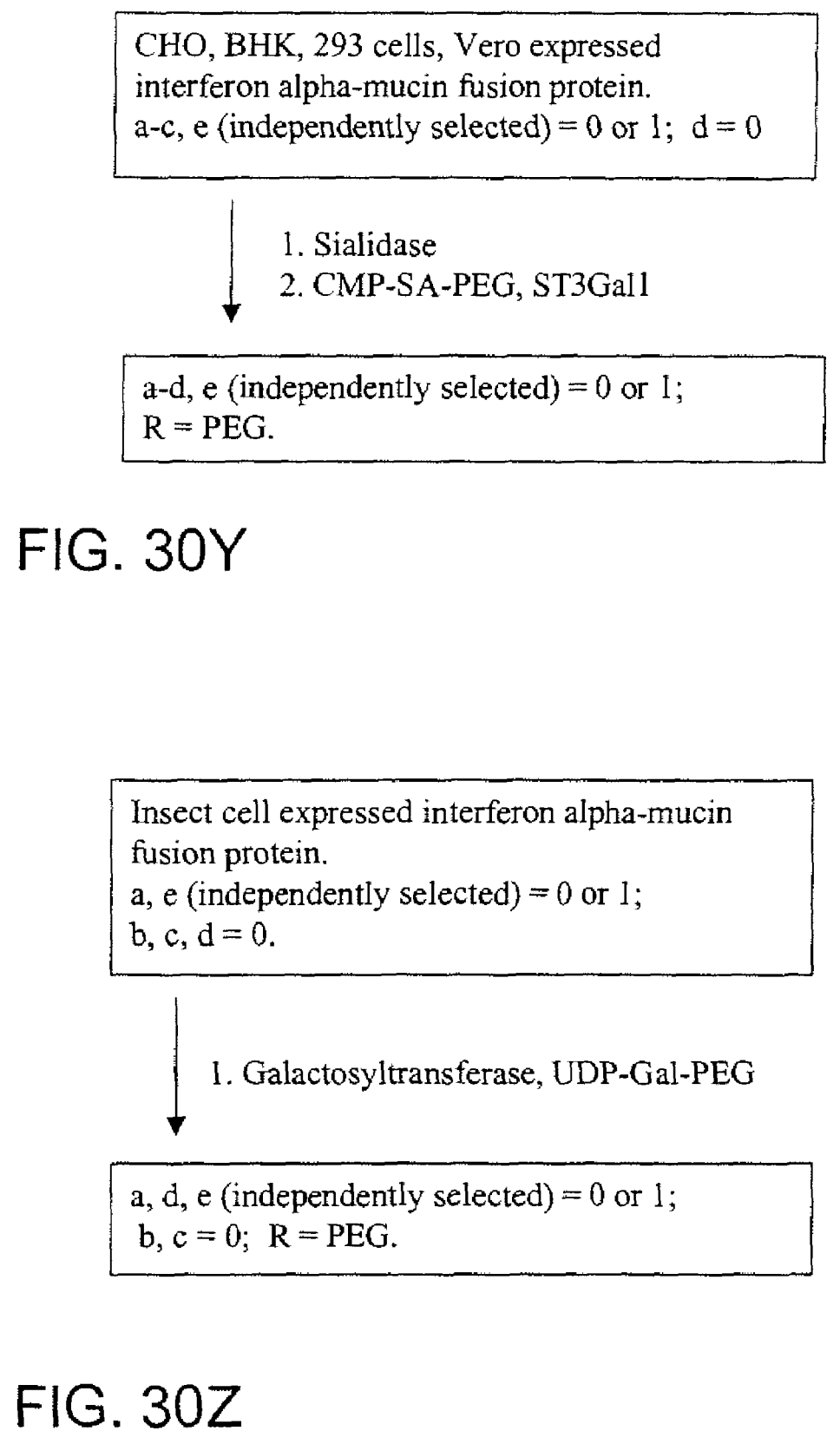

CHO, BHK, 293 cells, Vero expressed interferon alpha-mucin fusion protein.
a-c, e (independently selected) = 0 or 1; d = 0

1. Sialidase
2. CMP-SA-PEG, ST3Gal1 a-d, e (independently selected) = 0 or 1;
R = PEG.

FIG. 30Y

Insect cell expressed interferon alpha-mucin fusion protein.
a, e (independently selected) = 0 or 1;
b, c, d = 0.

1. Galactosyltransferase, UDP-Gal-PEG a, d, e (independently selected) = 0 or 1;
b, c = 0; R = PEG.

FIG. 30Z

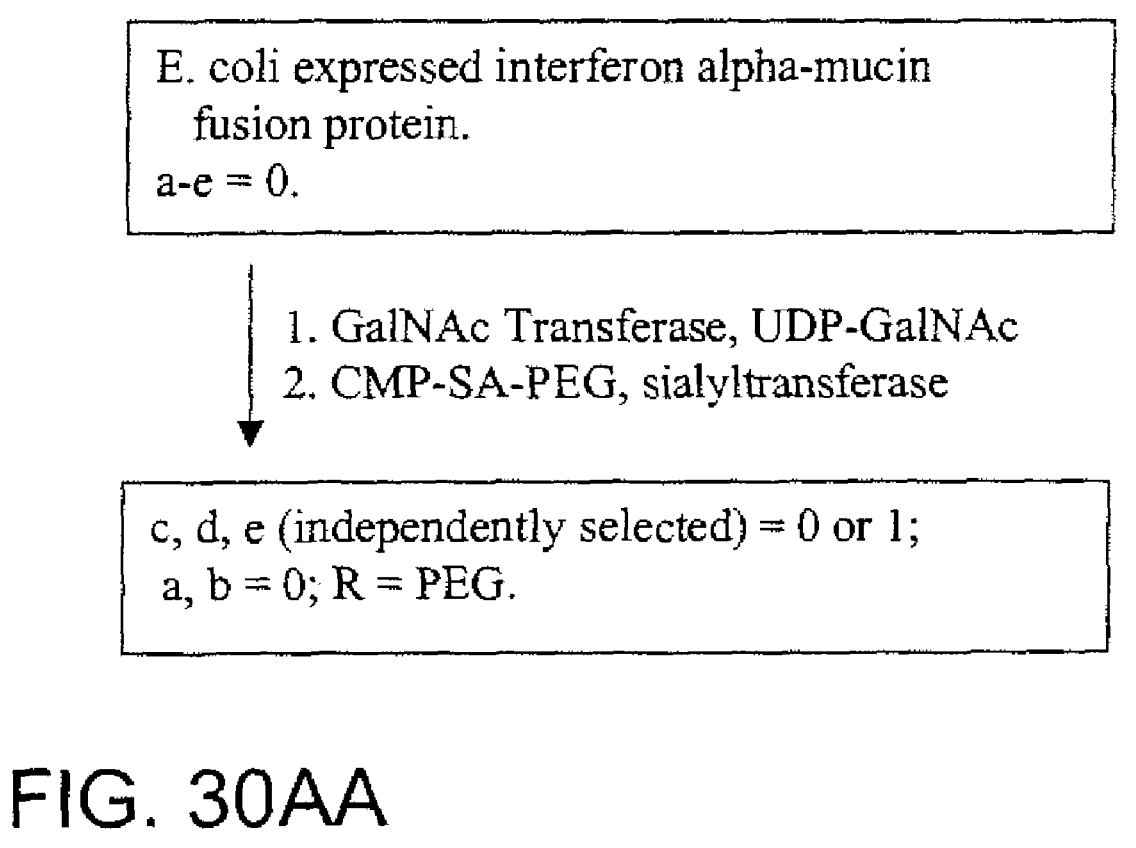

E. coli expressed interferon alpha-mucin fusion protein.
a-e = 0.

1. GalNAc Transferase, UDP-GalNAc
2. CMP-SA-PEG, sialyltransferase c, d, e (independently selected) = 0 or 1;
a, b = 0; R = PEG.

FIG. 30AA

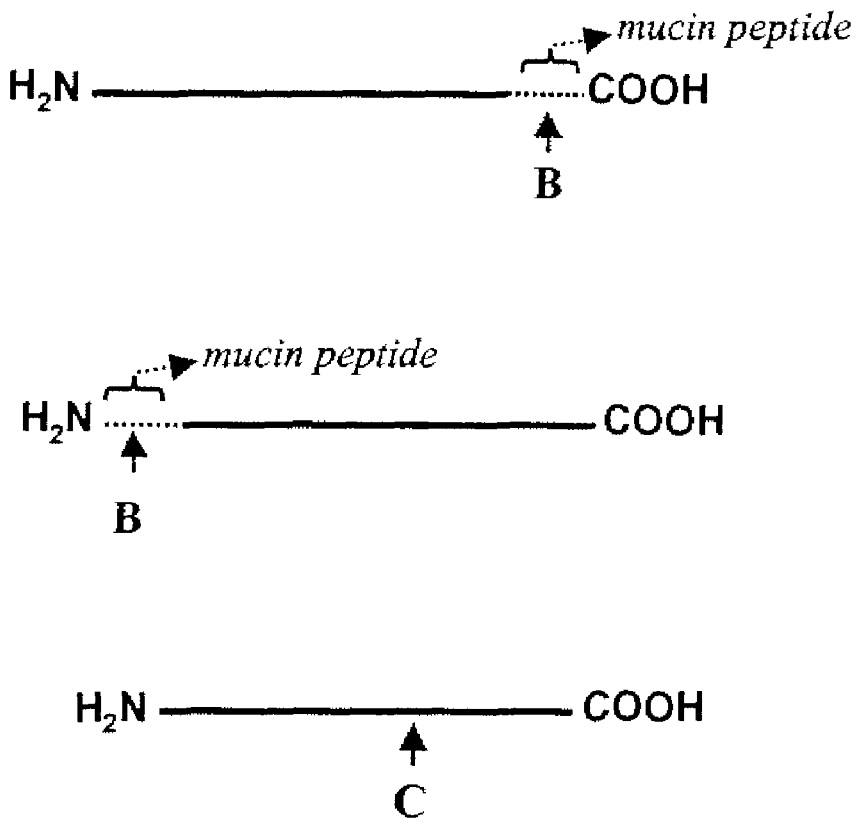
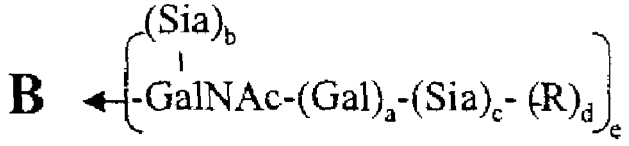
C ← $(R')_n$
a-c, e (independently selected) = 0 or 1;
d = 0; R = polymer, linker.
FIG. 30BB E. coli expressed interferon alpha-mucin fusion protein.
a-e, n = 0.

1. GalNAc Transferase, UDP-GalNAc-PEG d, e (independently selected) = 0 or 1;
a-c, n = 0; R = PEG.

FIG. 30CC

E. coli expressed interferon alpha-mucin fusion protein.
a-e, n = 0.

1. GalNAc Transferase, UDP-GalNAc-linker-SA-CMP
2. ST3Gal3, asialo-transferrin
3. CMP-SA, ST3Gal3 d, e (independently selected) = 0 or 1;
a-c, n = 0; R = linker-transferrin.

FIG. 30DD

E. coli expressed Interferon alpha (no fusion).
a-e, n = 0.

1. NHS-CO-linker-SA-CMP
2. ST3Gal3, transferrin a-e = 0; n = 1; R' = linker-transferrin.

FIG. 30EE

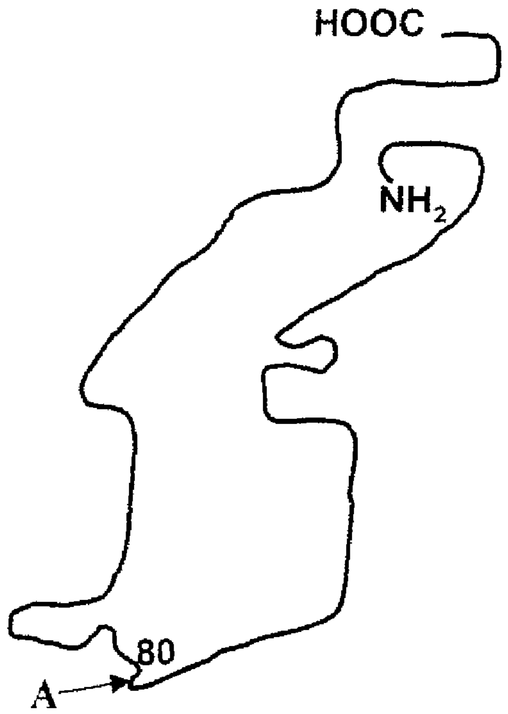
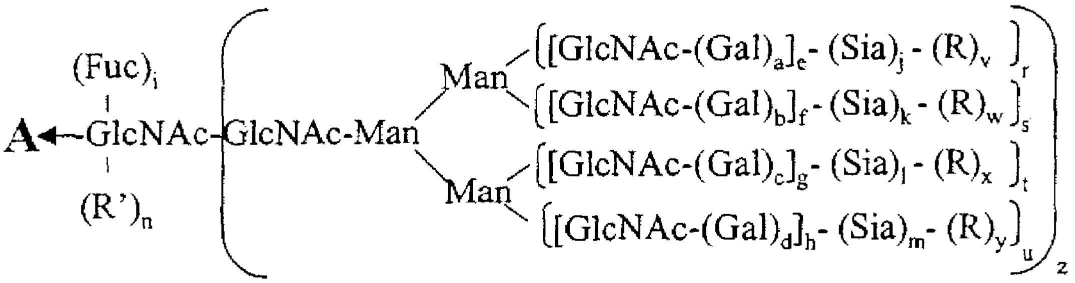
a-d, i, r-u (independently selected) = 0 or 1.
e-h (independently selected) = 0 to 4.
j-m (independently selected) = 0 or 1.
n, v-y = 0; z = 0 or 1; R = polymer
FIG. 31A CHO, BHK, 293 cells, Vero expressed IF-beta
h = 1 to 3;
a-g, j-m, i (independently selected) = 0 or 1;
r-u (independently selected) = 0 or 1;
n, v-y = 0; z = 1.

1. Sialidase
2. CMP-SA-PEG, ST3Gal3 h = 1 to 3;
a-g, i (independently selected) = 0 or 1;
r-u (independently selected) = 0 or 1;
j-m, v-y (independently selected) = 0 or 1;
z = 1; n = 0; R = PEG.

FIG. 31B

Insect cell expressed IF-beta
a-d, f, h, j-n, s, u, v-y = 0;
e, g, i, r, t (independently selected) = 0 or 1;
z = 1.

1. GNT's 1&2, UDP-GlcNAc
2. Galactosyltransferase, UDP-Gal
2. CMP-SA-PEG, ST3Gal3, buffer, salt b, d, f, h, k, m, n, s, u, w, y = 0;
a, c, e, g, i, r, t (independently selected) = 0 or 1;
j, l, v, x (independently selected) = 0 or 1;
z = 1; R = PEG.

FIG. 31C

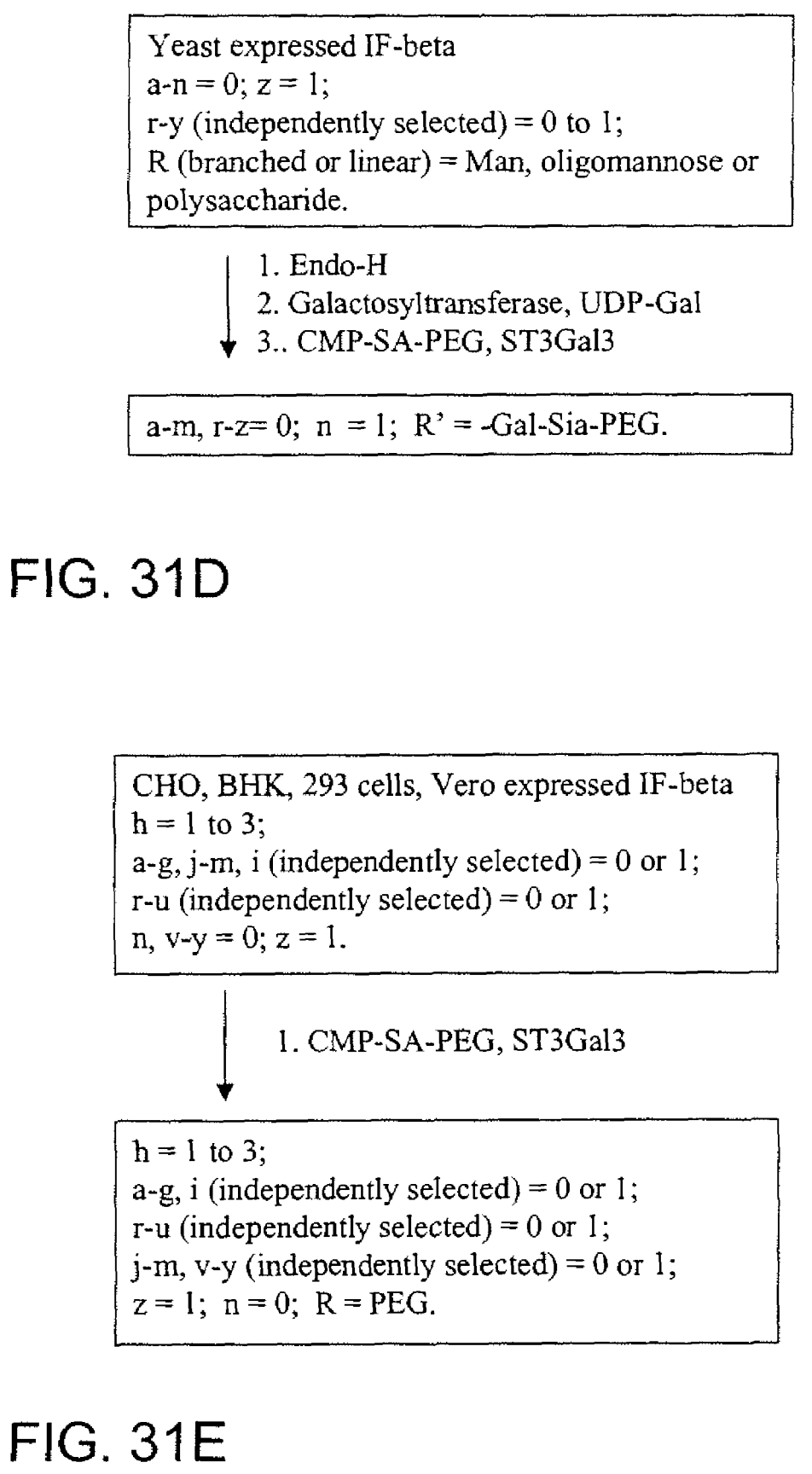

Yeast expressed IF-beta
a-n = 0; z = 1;
r-y (independently selected) = 0 to 1;
R (branched or linear) = Man, oligomannose or polysaccharide.

1. Endo-H
2. Galactosyltransferase, UDP-Gal
3.. CMP-SA-PEG, ST3Gal3 a-m, r-z= 0; n = 1; R' = -Gal-Sia-PEG.

FIG. 31D

CHO, BHK, 293 cells, Vero expressed IF-beta
h = 1 to 3;
a-g, j-m, i (independently selected) = 0 or 1;
r-u (independently selected) = 0 or 1;
n, v-y = 0; z = 1.

1. CMP-SA-PEG, ST3Gal3 h = 1 to 3;
a-g, i (independently selected) = 0 or 1;
r-u (independently selected) = 0 or 1;
j-m, v-y (independently selected) = 0 or 1;
z = 1; n = 0; R = PEG.

FIG. 31E

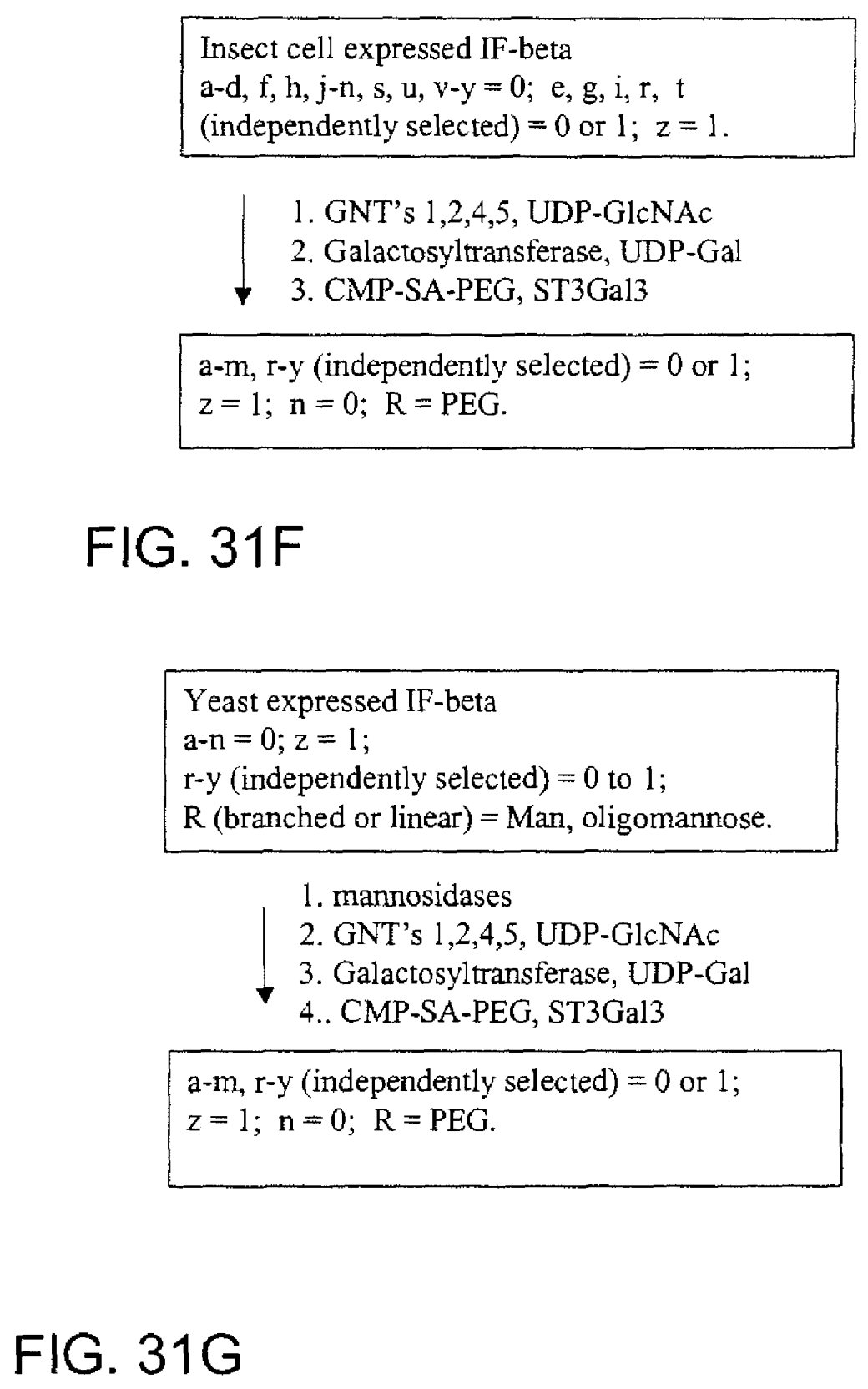

Insect cell expressed IF-beta
a-d, f, h, j-n, s, u, v-y = 0; e, g, i, r, t
(independently selected) = 0 or 1; z = 1.

1. GNT's 1,2,4,5, UDP-GlcNAc
2. Galactosyltransferase, UDP-Gal
3. CMP-SA-PEG, ST3Gal3 a-m, r-y (independently selected) = 0 or 1;
z = 1; n = 0; R = PEG.

FIG. 31F

Yeast expressed IF-beta
a-n = 0; z = 1;
r-y (independently selected) = 0 to 1;
R (branched or linear) = Man, oligomannose.

1. mannosidases
2. GNT's 1,2,4,5, UDP-GlcNAc
3. Galactosyltransferase, UDP-Gal
4.. CMP-SA-PEG, ST3Gal3 a-m, r-y (independently selected) = 0 or 1;
z = 1; n = 0; R = PEG.

FIG. 31G

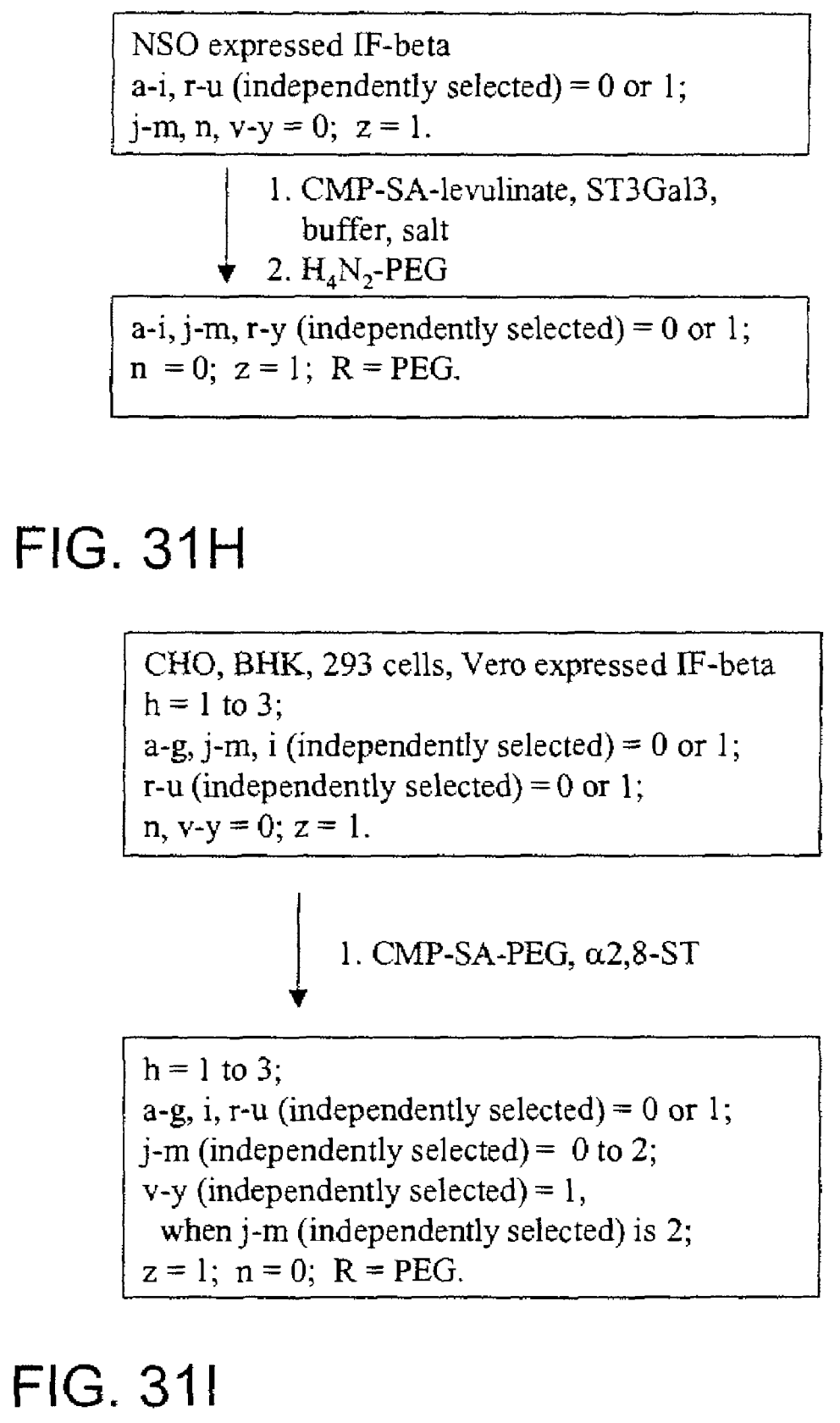

NSO expressed IF-beta
a-i, r-u (independently selected) = 0 or 1;
j-m, n, v-y = 0; z = 1.

1. CMP-SA-levulinate, ST3Gal3, buffer, salt
2. $H_4N_2$-PEG a-i, j-m, r-y (independently selected) = 0 or 1;
n = 0; z = 1; R = PEG.

FIG. 31H

CHO, BHK, 293 cells, Vero expressed IF-beta
h = 1 to 3;
a-g, j-m, i (independently selected) = 0 or 1;
r-u (independently selected) = 0 or 1;
n, v-y = 0; z = 1.

1. CMP-SA-PEG, α2,8-ST h = 1 to 3;
a-g, i, r-u (independently selected) = 0 or 1;
j-m (independently selected) = 0 to 2;
v-y (independently selected) = 1,
when j-m (independently selected) is 2;
z = 1; n = 0; R = PEG.

FIG. 31I

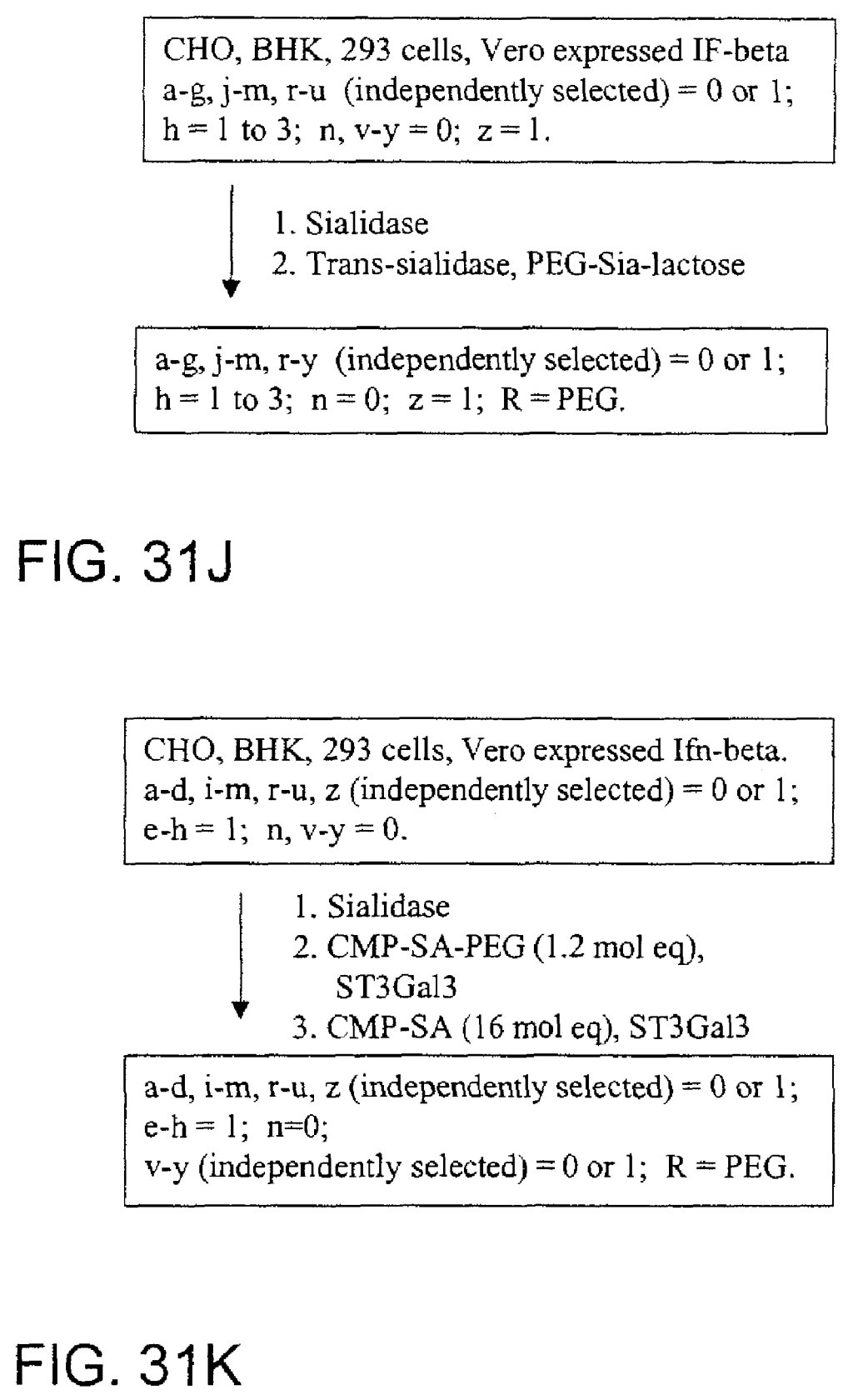

CHO, BHK, 293 cells, Vero expressed IF-beta
a-g, j-m, r-u (independently selected) = 0 or 1;
h = 1 to 3; n, v-y = 0; z = 1.

1. Sialidase
2. Trans-sialidase, PEG-Sia-lactose a-g, j-m, r-y (independently selected) = 0 or 1;
h = 1 to 3; n = 0; z = 1; R = PEG.

FIG. 31J

CHO, BHK, 293 cells, Vero expressed Ifn-beta.
a-d, i-m, r-u, z (independently selected) = 0 or 1;
e-h = 1; n, v-y = 0.

1. Sialidase
2. CMP-SA-PEG (1.2 mol eq), ST3Gal3
3. CMP-SA (16 mol eq), ST3Gal3 a-d, i-m, r-u, z (independently selected) = 0 or 1;
e-h = 1; n=0;
v-y (independently selected) = 0 or 1; R = PEG.

FIG. 31K

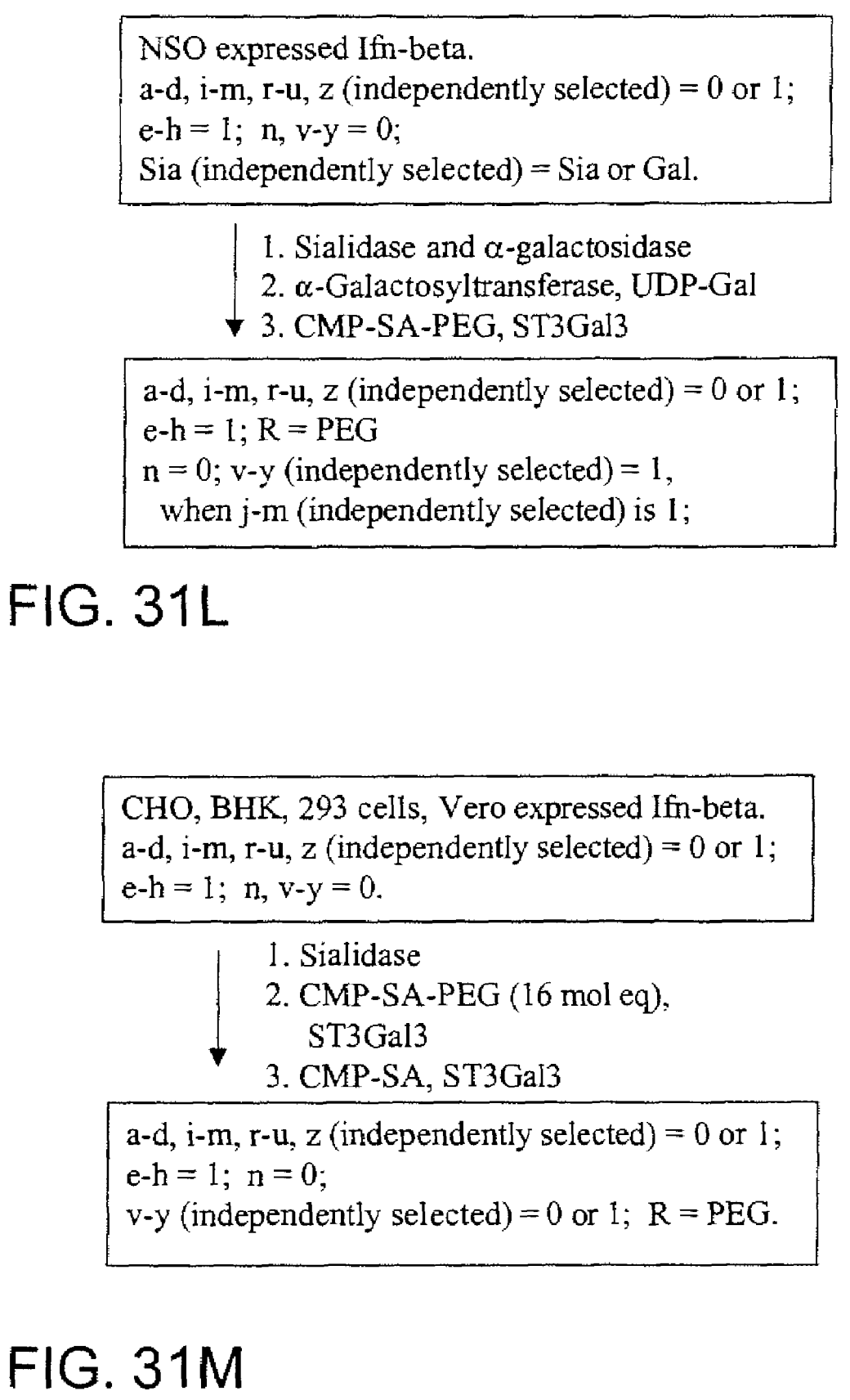

NSO expressed Ifn-beta.
a-d, i-m, r-u, z (independently selected) = 0 or 1;
e-h = 1; n, v-y = 0;
Sia (independently selected) = Sia or Gal.

1. Sialidase and α-galactosidase
2. α-Galactosyltransferase, UDP-Gal
3. CMP-SA-PEG, ST3Gal3 a-d, i-m, r-u, z (independently selected) = 0 or 1;
e-h = 1; R = PEG
n = 0; v-y (independently selected) = 1,
when j-m (independently selected) is 1;

FIG. 31L

CHO, BHK, 293 cells, Vero expressed Ifn-beta.
a-d, i-m, r-u, z (independently selected) = 0 or 1;
e-h = 1; n, v-y = 0.

1. Sialidase
2. CMP-SA-PEG (16 mol eq), ST3Gal3
3. CMP-SA, ST3Gal3 a-d, i-m, r-u, z (independently selected) = 0 or 1;
e-h = 1; n = 0;
v-y (independently selected) = 0 or 1; R = PEG.

FIG. 31M

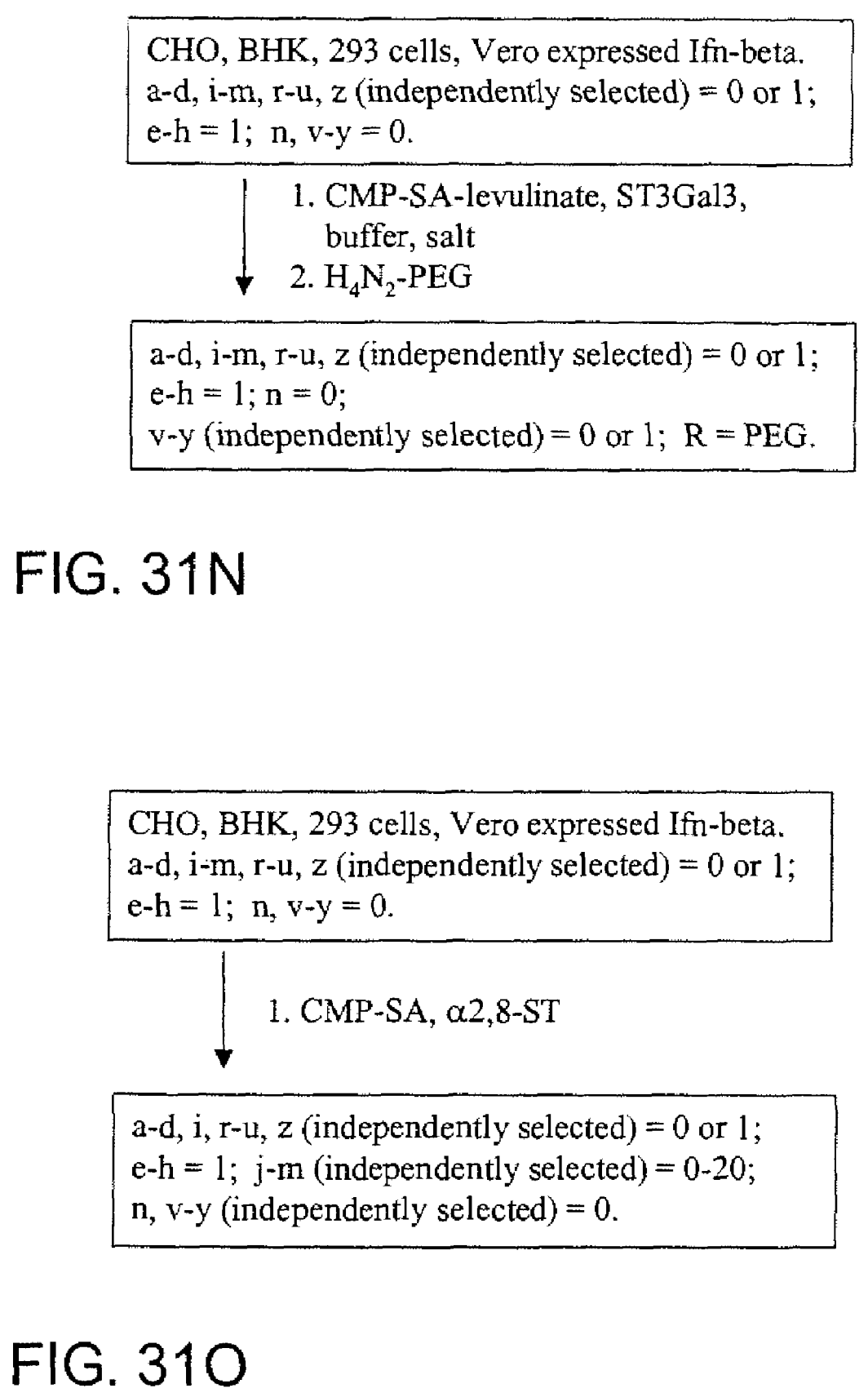

CHO, BHK, 293 cells, Vero expressed Ifn-beta.
a-d, i-m, r-u, z (independently selected) = 0 or 1;
e-h = 1; n, v-y = 0.

1. CMP-SA-levulinate, ST3Gal3, buffer, salt
2. $H_4N_2$-PEG a-d, i-m, r-u, z (independently selected) = 0 or 1;
e-h = 1; n = 0;
v-y (independently selected) = 0 or 1; R = PEG.

FIG. 31N

CHO, BHK, 293 cells, Vero expressed Ifn-beta.
a-d, i-m, r-u, z (independently selected) = 0 or 1;
e-h = 1; n, v-y = 0.

1. CMP-SA, α2,8-ST a-d, i, r-u, z (independently selected) = 0 or 1;
e-h = 1; j-m (independently selected) = 0-20;
n, v-y (independently selected) = 0.

FIG. 31O

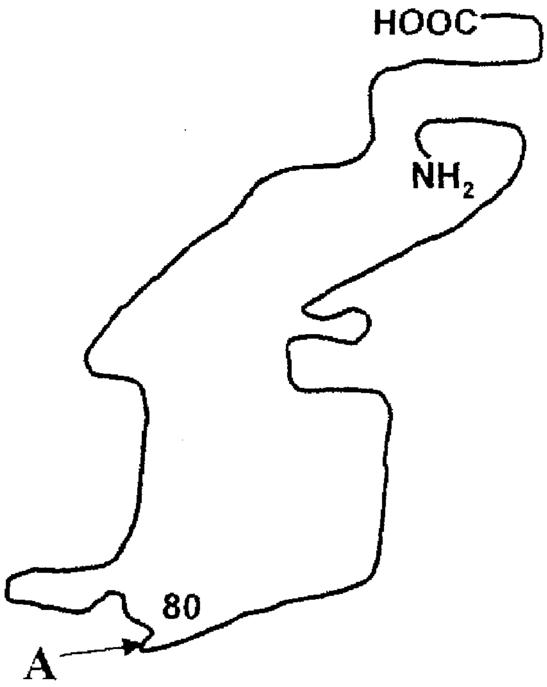
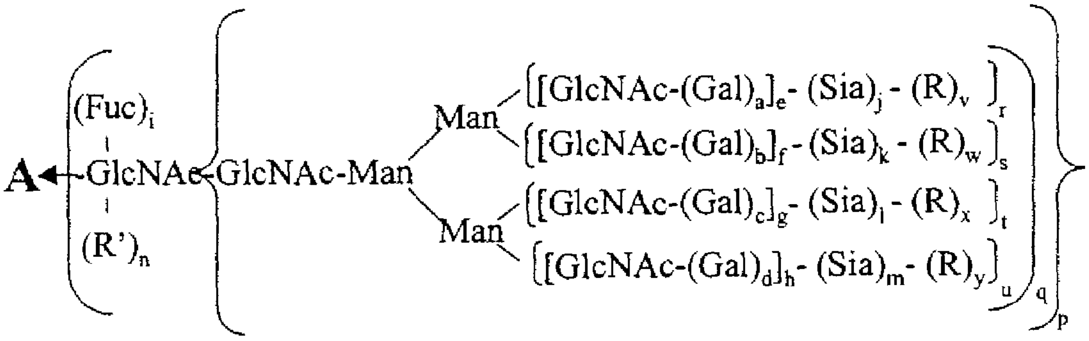
a-d, i, p-u (independently selected) = 0 or 1.
e-h (independently selected) = 0 to 6.
j-m (independently selected) = 0 to 100.
v-y = 0; R = modifying group;
R' = H, glycosyl group, modifying group, glycoconjugate.
FIG. 31P Insect cell expressed Ifn-beta.
a-d, f, h, j-m, s, u, v-y = 0;
e, g, i, q, r, t (independently selected) = 0 or 1.

1. GNT's 1,2,4,5, UDP-GlcNAc
2. Galactosyltransferase, UDP-Gal-PEG a-i, q-u (independently selected) = 0 or 1;
j-m = 0; v-y (independently selected) = 1, when e-h (independently selected) is 1;
R = PEG.

FIG. 31Q

Yeast expressed Ifn-beta.
a-m = 0; q-y (independently selected) = 0 to 1;
p = 1;
R (branched or linear) = Man, oligomannose.

1. Endoglycanase
2. Galactosyltransferase, UDP-Gal
3. CMP-SA-PEG, ST3Gal3 a-m, p-y = 0;
n (independently selected) = 0 or 1;
R' = -Gal-Sia-PEG.

FIG. 31R

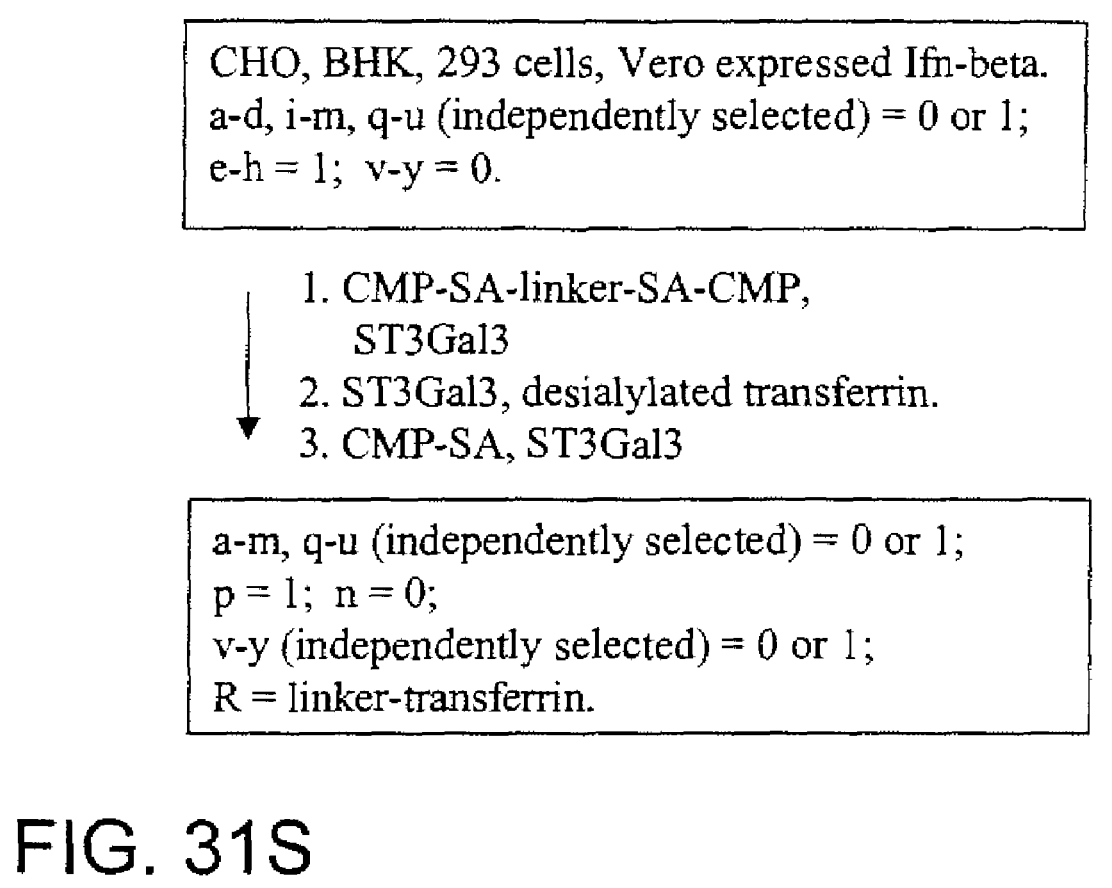

CHO, BHK, 293 cells, Vero expressed Ifn-beta.
a-d, i-m, q-u (independently selected) = 0 or 1;
e-h = 1; v-y = 0.

1. CMP-SA-linker-SA-CMP, ST3Gal3
2. ST3Gal3, desialylated transferrin.
3. CMP-SA, ST3Gal3 a-m, q-u (independently selected) = 0 or 1;
p = 1; n = 0;
v-y (independently selected) = 0 or 1;
R = linker-transferrin.

FIG. 31S

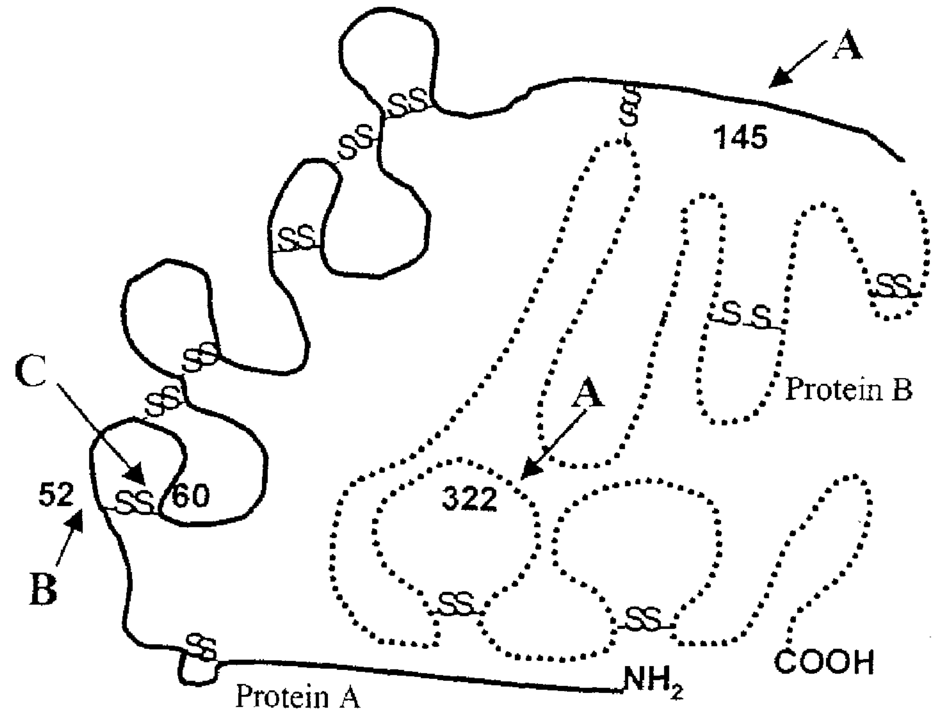
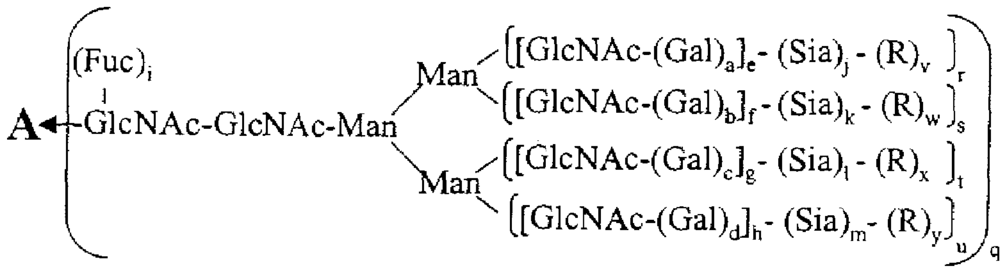
$B \leftarrow [Glc\text{-}(Xyl)_n]_o$
$C \leftarrow [\text{-}Fuc]_p$
a-d, i, q-u (independently selected) = 0 or 1.
o, p (independently selected) = 0 or 1.
e-h, n (independently selected) = 0 to 6.
j-m (independently selected) = 0 to 20.
v-y = 0;
R = modifying group, mannose, oligo-mannose, Sia-Lewis X, Sia-Lewis A..
FIG. 32A BHK expressed Factor VII or VIIa
a-d, e, i, g, q, j, l, o, p (independently selected) = 0 or 1;
r, t = 1; f, h, k, m, s, u, v-y = 0; n = 0-4.

1. Sialidase
2. CMP-SA-PEG (16 mole eq), ST3Gal3 a-d, e, g, i, q, j, l, o, p (independently selected) = 0 or 1;
r, t = 1; f, h, k, m, s, u, w, y = 0; n = 0-4;
v, x, (independently selected) = 1,
when j, l (respectively, independently selected) is 1;
R = PEG.

FIG. 32B

CHO, BHK, 293 cells, Vero expressed Factor VII or VIIa
a-d, e, i, g, q, j, l, o, p (independently selected) = 0 or 1;
r, t = 1; f, h, k, m, s, u, v-y = 0; n = 0-4.

1. Sialidase
2. CMP-SA-PEG (1.2 mole eq), ST3Gal3
3. CMP-SA (8 mol eq), ST3Gal3 a-d, e, g, i, q, j, l, o, p (independently selected) = 0 or 1;
r, t = 1; f, h, k, m, s, u, w, y = 0; n = 0-4;
v or x, (independently selected) = 1,
when j or l, (respectively, independently selected) is 1;
R = PEG.

FIG. 32C

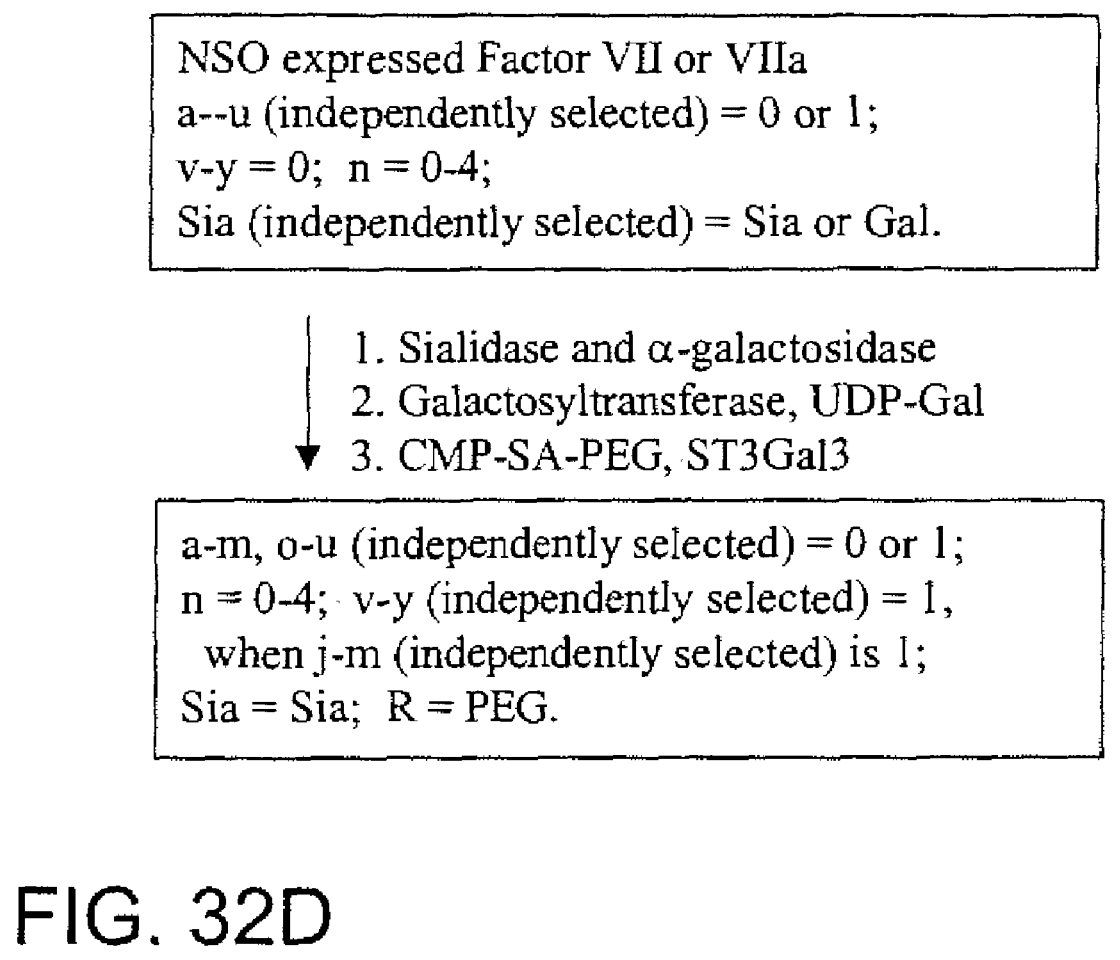

NSO expressed Factor VII or VIIa
a--u (independently selected) = 0 or 1;
v-y = 0; n = 0-4;
Sia (independently selected) = Sia or Gal.

1. Sialidase and α-galactosidase
2. Galactosyltransferase, UDP-Gal
3. CMP-SA-PEG, ST3Gal3 a-m, o-u (independently selected) = 0 or 1;
n = 0-4; v-y (independently selected) = 1,
when j-m (independently selected) is 1;
Sia = Sia; R = PEG.

FIG. 32D

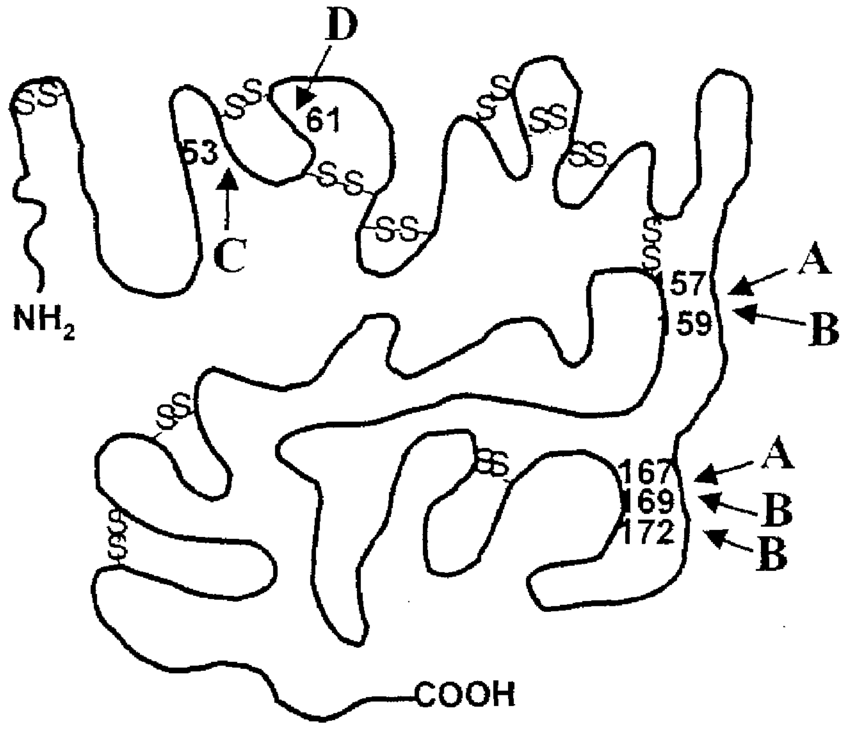
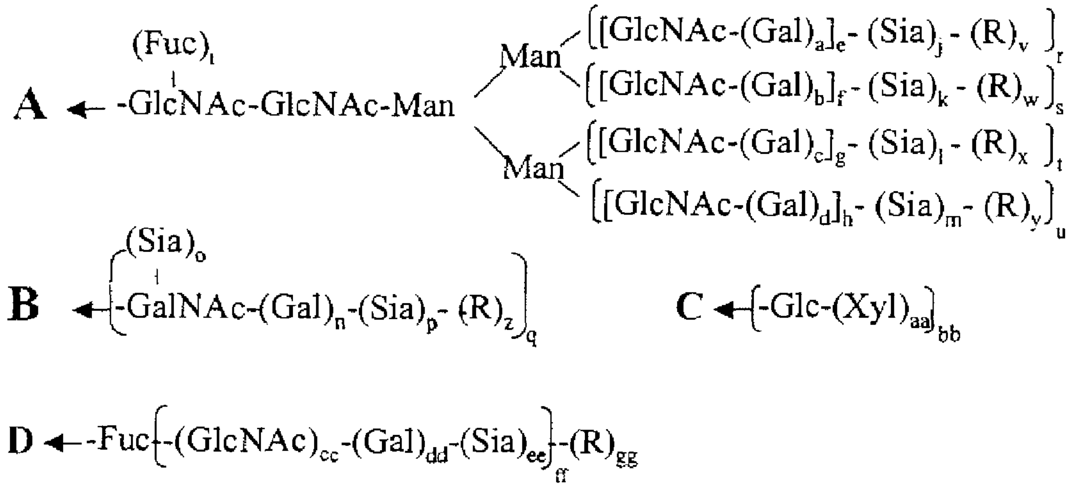
a-d, i, n-u (independently selected) = 0 or 1.
bb, cc, dd, ee, ff, gg (independently selected) = 0 or 1.
e-h, aa (independently selected) = 0 to 6.
j-m (independently selected) = 0 to 20.
v-z = 0; R = modifying group, mannose, oligo-mannose.
FIG. 33A CHO, BHK, 293 cells, Vero expressed Factor IX
a-d, q = 1; e-h = 1 to 4;
aa, bb, cc, dd, ee, ff, j-m, i, n, o, p, r-u (independently selected) = 0 or 1;
v-z, gg = 0.

1. Sialidase
2. CMP-SA-PEG, ST3Gal3 a-d, q = 1; e-h = 1 to 4;
aa, bb, cc, dd, ee, ff, i, n, r-u (independently selected) = 0 or 1;
o, p, z = 0;
j-m, ee, v-y, gg (independently selected) = 0 or 1;
R = PEG.

FIG. 33B

CHO, BHK, 293 cells, Vero expressed Factor IX
a-d, n, q = 1; e-h = 1 to 4;
aa, bb, cc, dd, ee, ff, j-m, i, o, p, r-u (independently selected) = 0 or 1;
v-z, gg = 0.

1. Sialidase
2. CMP-SA-PEG, ST3Gal3
3. ST3Gal1, CMP-SA a-d, n, p, q = 1; e-h = 1 to 4;
aa, bb, cc, dd, ee, ff, i, r-u (independently selected) = 0 or 1;
j-m, ee, v-y, gg (independently selected) = 0 or 1;
o, z = 0; R = PEG.

FIG. 33C

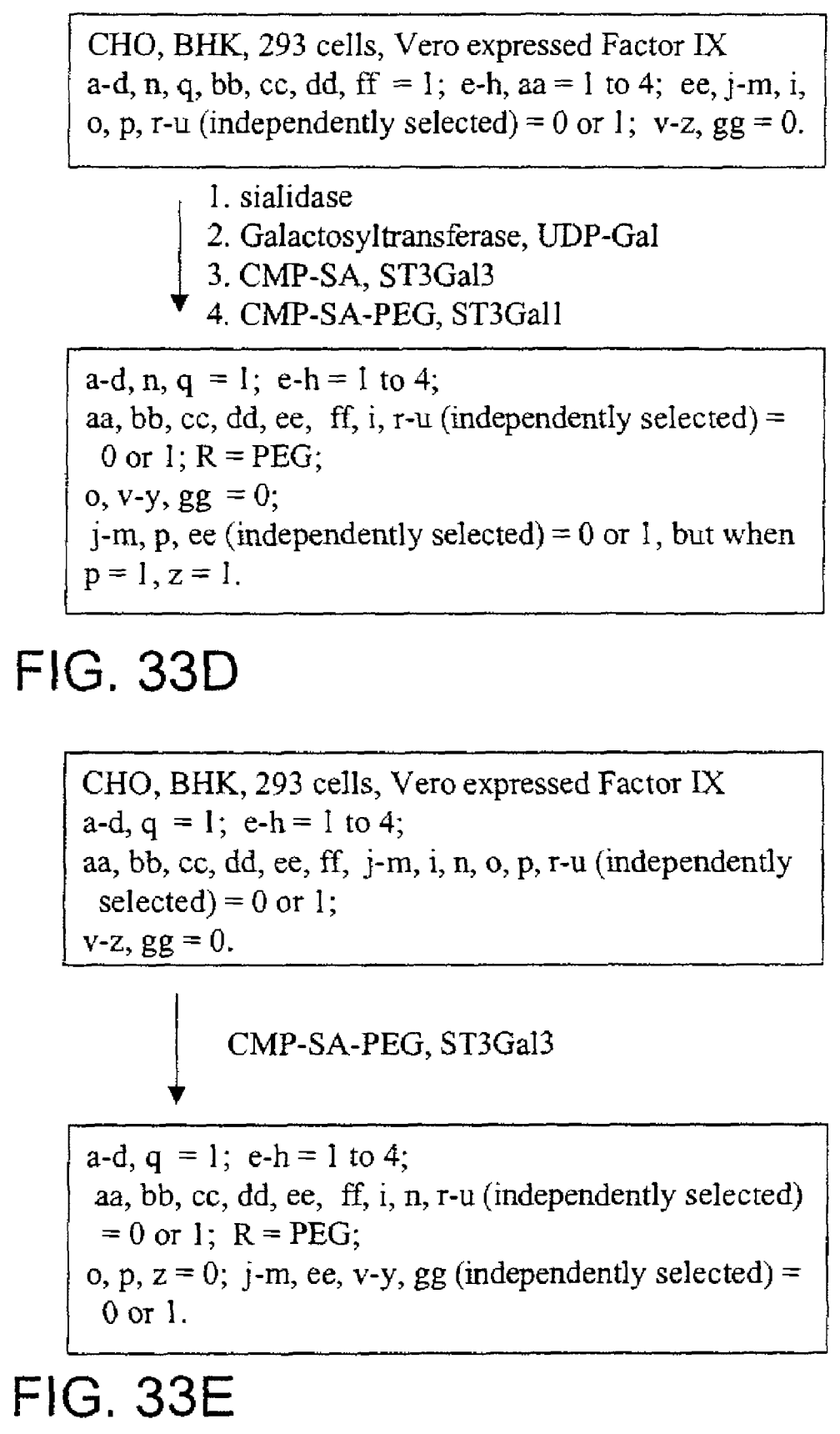

CHO, BHK, 293 cells, Vero expressed Factor IX
a-d, n, q, bb, cc, dd, ff = 1; e-h, aa = 1 to 4; ee, j-m, i, o, p, r-u (independently selected) = 0 or 1; v-z, gg = 0.

1. sialidase
2. Galactosyltransferase, UDP-Gal
3. CMP-SA, ST3Gal3
4. CMP-SA-PEG, ST3Gal1 a-d, n, q = 1; e-h = 1 to 4;
aa, bb, cc, dd, ee, ff, i, r-u (independently selected) = 0 or 1; R = PEG;
o, v-y, gg = 0;
j-m, p, ee (independently selected) = 0 or 1, but when p = 1, z = 1.

FIG. 33D

CHO, BHK, 293 cells, Vero expressed Factor IX
a-d, q = 1; e-h = 1 to 4;
aa, bb, cc, dd, ee, ff, j-m, i, n, o, p, r-u (independently selected) = 0 or 1;
v-z, gg = 0.

CMP-SA-PEG, ST3Gal3 a-d, q = 1; e-h = 1 to 4;
aa, bb, cc, dd, ee, ff, i, n, r-u (independently selected) = 0 or 1; R = PEG;
o, p, z = 0; j-m, ee, v-y, gg (independently selected) = 0 or 1.

FIG. 33E

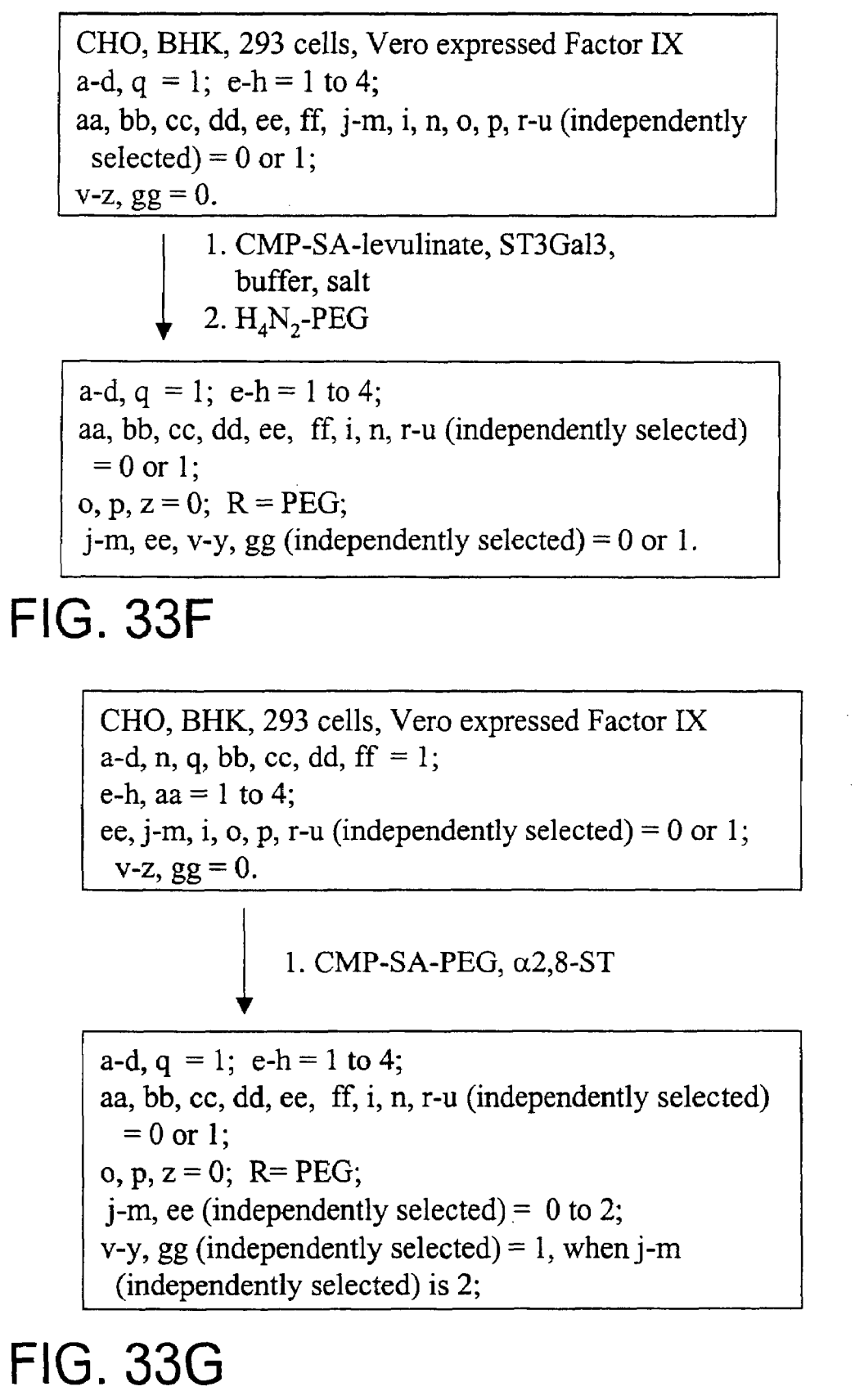

CHO, BHK, 293 cells, Vero expressed Factor IX
a-d, q = 1; e-h = 1 to 4;
aa, bb, cc, dd, ee, ff, j-m, i, n, o, p, r-u (independently selected) = 0 or 1;
v-z, gg = 0.

1. CMP-SA-levulinate, ST3Gal3, buffer, salt
2. $H_4N_2$-PEG a-d, q = 1; e-h = 1 to 4;
aa, bb, cc, dd, ee, ff, i, n, r-u (independently selected) = 0 or 1;
o, p, z = 0; R = PEG;
j-m, ee, v-y, gg (independently selected) = 0 or 1.

FIG. 33F

CHO, BHK, 293 cells, Vero expressed Factor IX
a-d, n, q, bb, cc, dd, ff = 1;
e-h, aa = 1 to 4;
ee, j-m, i, o, p, r-u (independently selected) = 0 or 1;
v-z, gg = 0.

1. CMP-SA-PEG, α2,8-ST a-d, q = 1; e-h = 1 to 4;
aa, bb, cc, dd, ee, ff, i, n, r-u (independently selected) = 0 or 1;
o, p, z = 0; R= PEG;
j-m, ee (independently selected) = 0 to 2;
v-y, gg (independently selected) = 1, when j-m (independently selected) is 2;

FIG. 33G

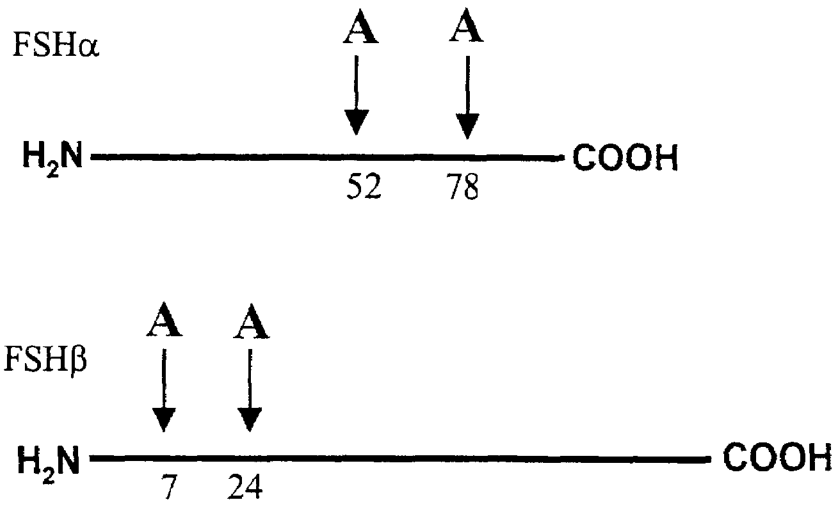
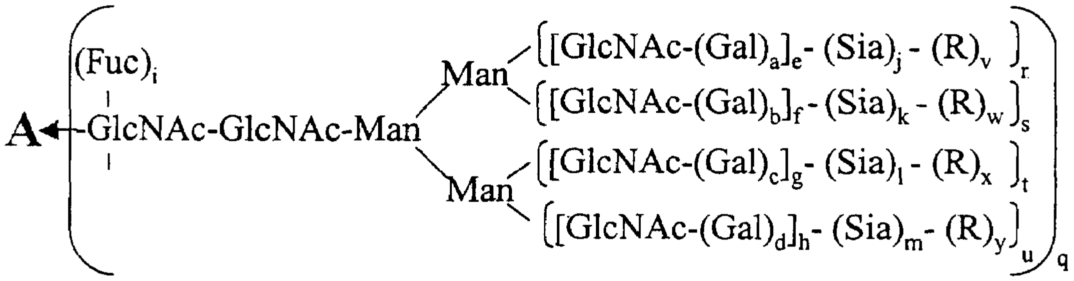
a-d, i, q-u (independently selected) = 0 or 1.
e-h (independently selected) = 0 to 6.
j-m (independently selected) = 0 to 100.
v-y = 0;
R = modifying group, mannose, oligo-mannose.
FIG. 34A CHO, BHK, 293 cells, Vero expressed FSH.
a-d, i-m, q-u (independently selected) = 0 or 1;
e-h = 1; v-y = 0.

1. Sialidase
2. CMP-SA-PEG (16 mol eq), ST3Gal3 a-d, i-m, q-u (independently selected) = 0 or 1;
e-h = 1; v-y (independently selected) = 1, when j-m (independently selected) is 1;
R = PEG.

FIG. 34B

CHO, BHK, 293 cells, Vero expressed FSH.
a-d, i-m, q-u (independently selected) = 0 or 1;
e-h = 1; v-y = 0.

1. Sialidase
2. CMP-SA-PEG (1.2 mol eq), ST3Gal3
3. CMP-SA (16 mol eq), ST3Gal3 a-d, i-m, q-u (independently selected) = 0 or 1;
e-h = 1; v-y (independently selected) = 0 or 1;
R = PEG.

FIG. 34C

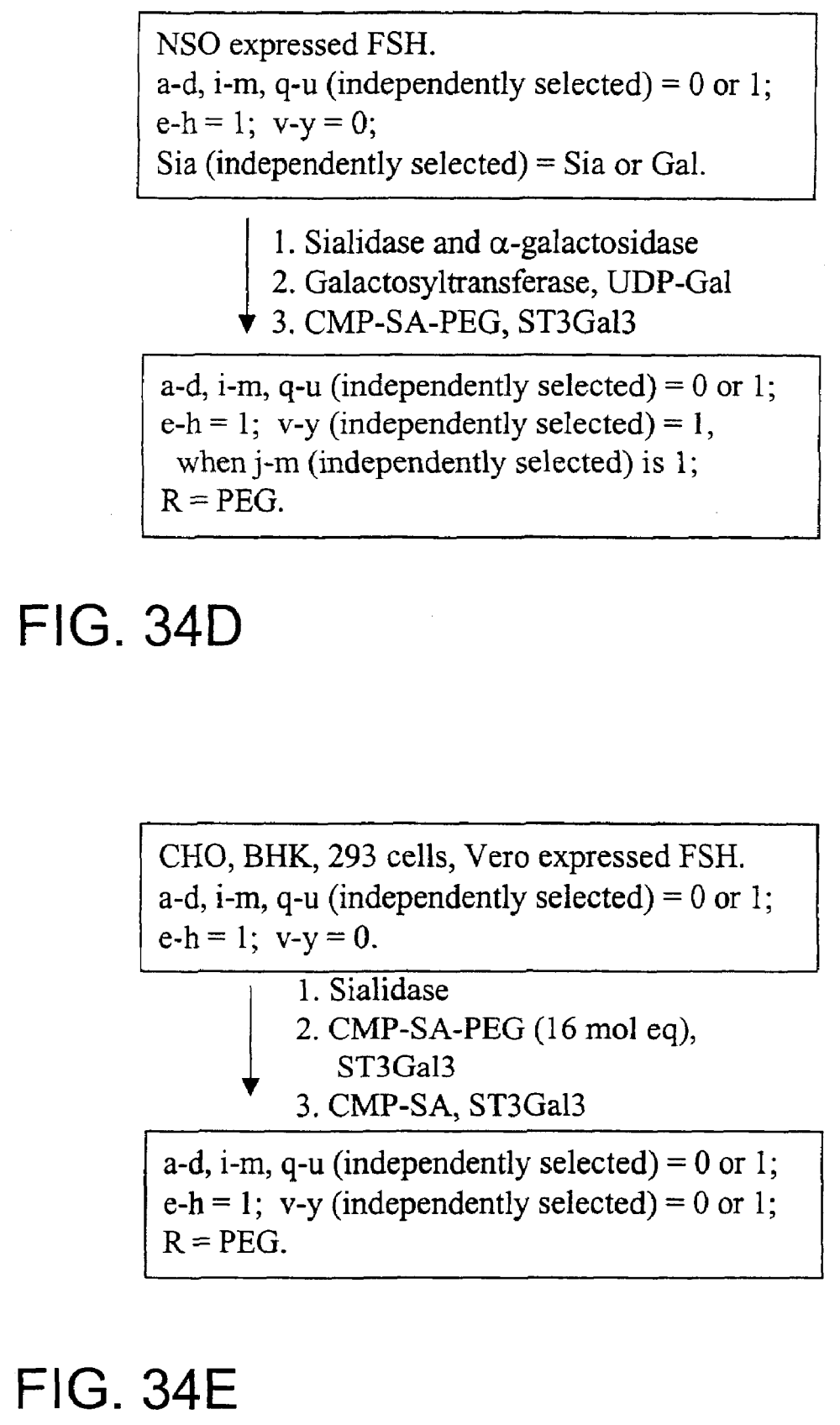

NSO expressed FSH.
a-d, i-m, q-u (independently selected) = 0 or 1;
e-h = 1; v-y = 0;
Sia (independently selected) = Sia or Gal.

1. Sialidase and α-galactosidase
2. Galactosyltransferase, UDP-Gal
3. CMP-SA-PEG, ST3Gal3 a-d, i-m, q-u (independently selected) = 0 or 1;
e-h = 1; v-y (independently selected) = 1,
when j-m (independently selected) is 1;
R = PEG.

FIG. 34D

CHO, BHK, 293 cells, Vero expressed FSH.
a-d, i-m, q-u (independently selected) = 0 or 1;
e-h = 1; v-y = 0.

1. Sialidase
2. CMP-SA-PEG (16 mol eq), ST3Gal3
3. CMP-SA, ST3Gal3 a-d, i-m, q-u (independently selected) = 0 or 1;
e-h = 1; v-y (independently selected) = 0 or 1;
R = PEG.

FIG. 34E

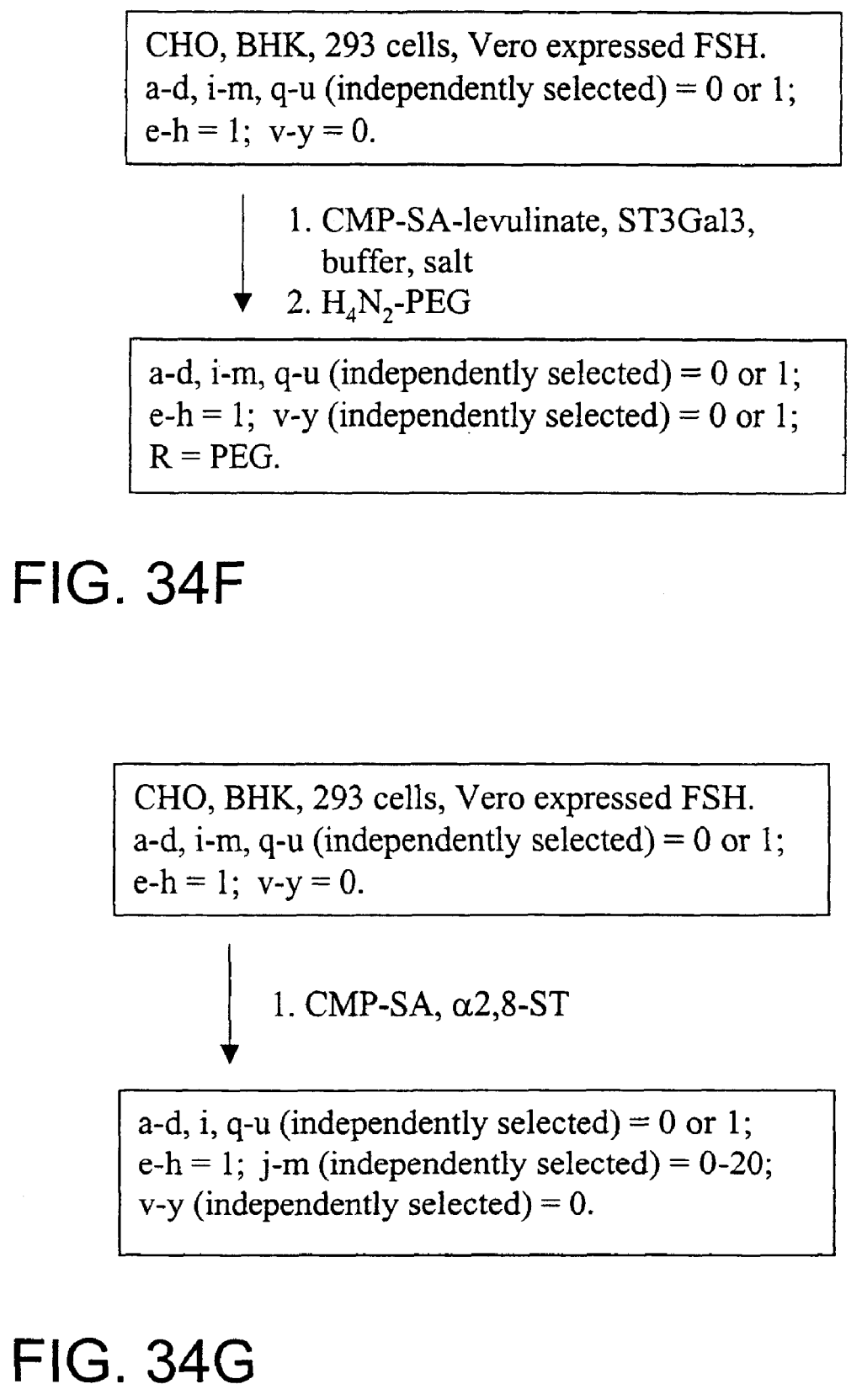

CHO, BHK, 293 cells, Vero expressed FSH.
a-d, i-m, q-u (independently selected) = 0 or 1;
e-h = 1; v-y = 0.

1. CMP-SA-levulinate, ST3Gal3, buffer, salt
2. $H_4N_2$-PEG a-d, i-m, q-u (independently selected) = 0 or 1;
e-h = 1; v-y (independently selected) = 0 or 1;
R = PEG.

FIG. 34F

CHO, BHK, 293 cells, Vero expressed FSH.
a-d, i-m, q-u (independently selected) = 0 or 1;
e-h = 1; v-y = 0.

1. CMP-SA, α2,8-ST a-d, i, q-u (independently selected) = 0 or 1;
e-h = 1; j-m (independently selected) = 0-20;
v-y (independently selected) = 0.

FIG. 34G

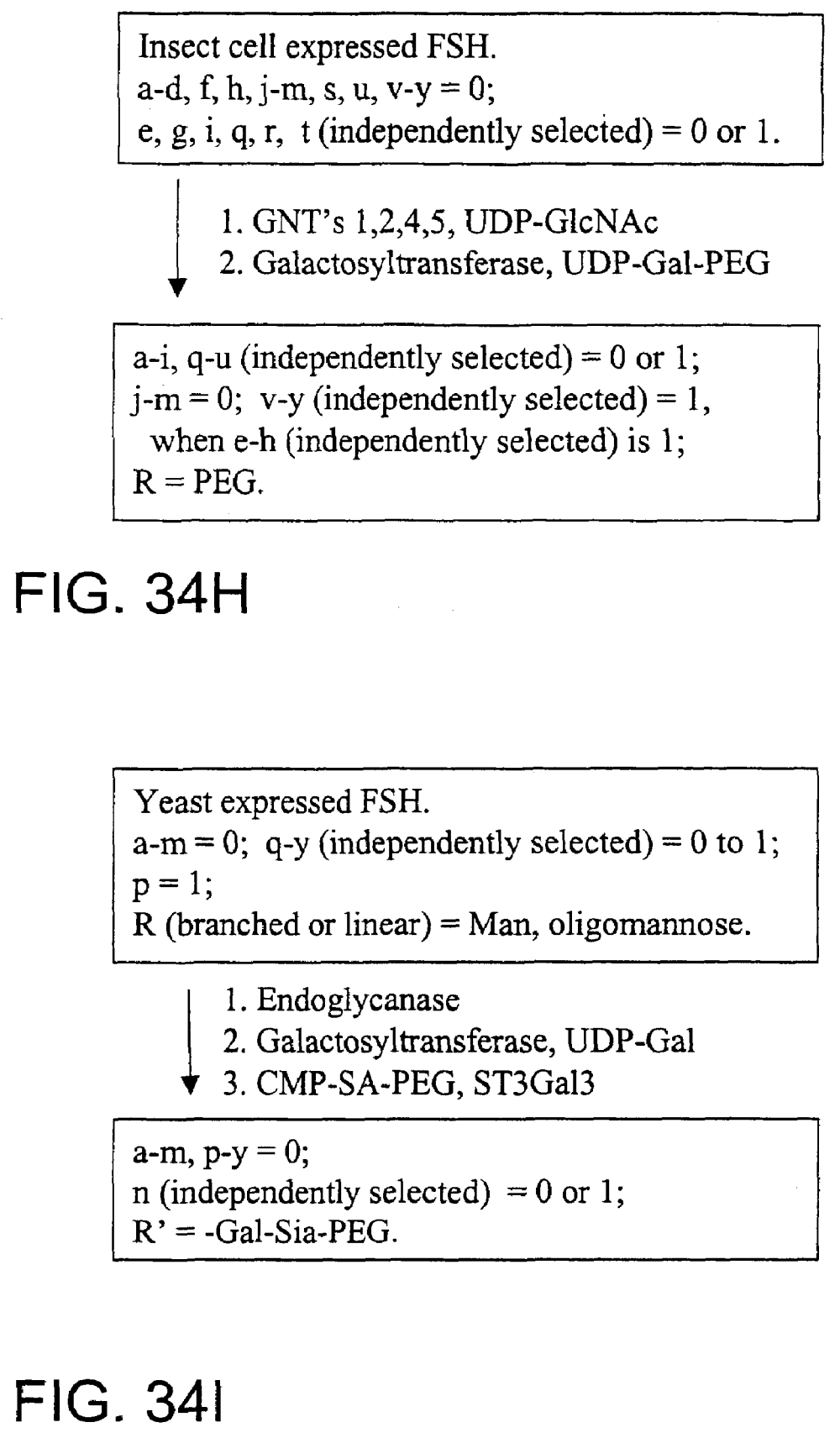

Insect cell expressed FSH.
a-d, f, h, j-m, s, u, v-y = 0;
e, g, i, q, r, t (independently selected) = 0 or 1.

↓
1. GNT's 1,2,4,5, UDP-GlcNAc
2. Galactosyltransferase, UDP-Gal-PEG a-i, q-u (independently selected) = 0 or 1;
j-m = 0; v-y (independently selected) = 1,
when e-h (independently selected) is 1;
R = PEG.

FIG. 34H

Yeast expressed FSH.
a-m = 0; q-y (independently selected) = 0 to 1;
p = 1;
R (branched or linear) = Man, oligomannose.

↓
1. Endoglycanase
2. Galactosyltransferase, UDP-Gal
3. CMP-SA-PEG, ST3Gal3 a-m, p-y = 0;
n (independently selected) = 0 or 1;
R' = -Gal-Sia-PEG.

FIG. 34I

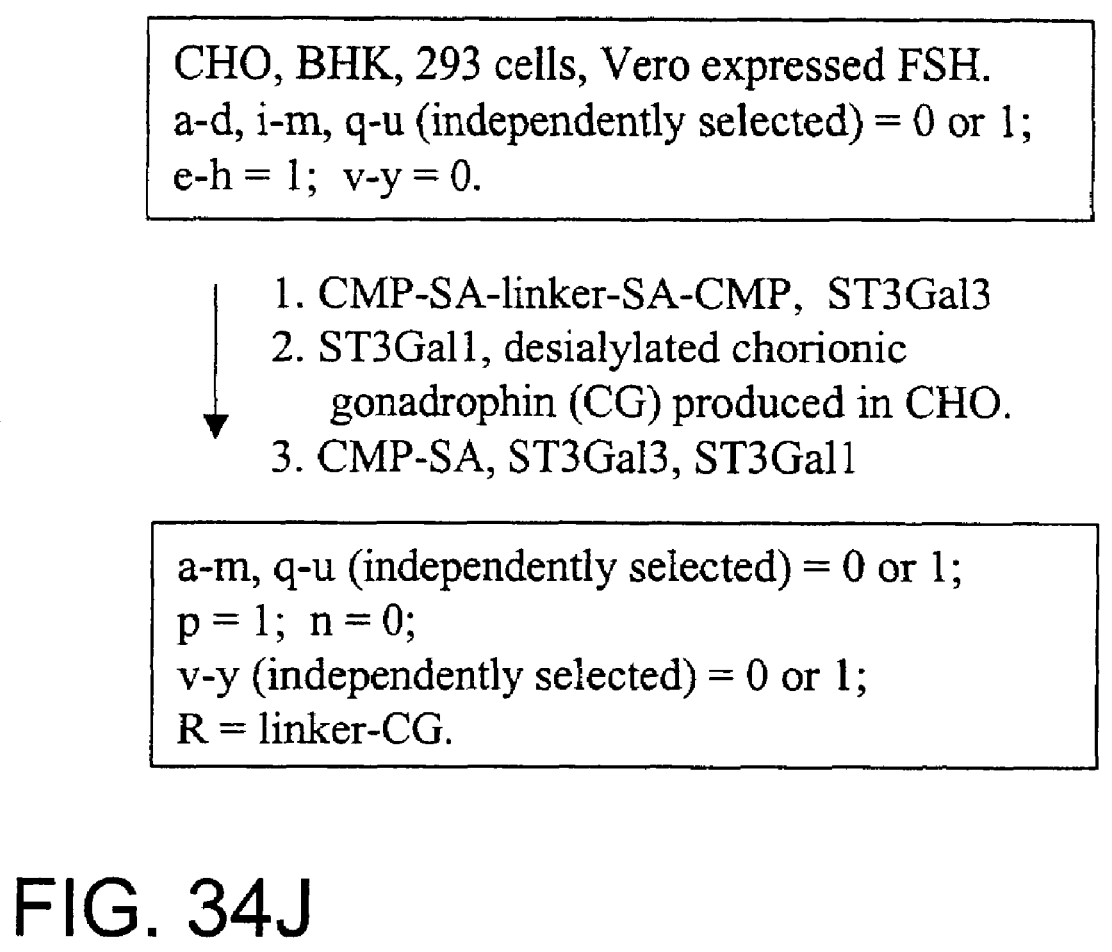

CHO, BHK, 293 cells, Vero expressed FSH.
a-d, i-m, q-u (independently selected) = 0 or 1;
e-h = 1; v-y = 0.

1. CMP-SA-linker-SA-CMP, ST3Gal3
2. ST3Gal1, desialylated chorionic gonadrophin (CG) produced in CHO.
3. CMP-SA, ST3Gal3, ST3Gal1 a-m, q-u (independently selected) = 0 or 1;
p = 1; n = 0;
v-y (independently selected) = 0 or 1;
R = linker-CG.

FIG. 34J

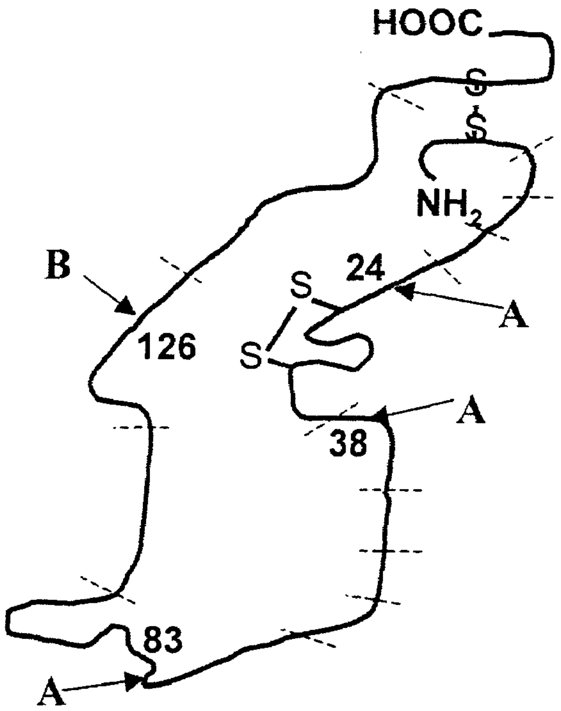
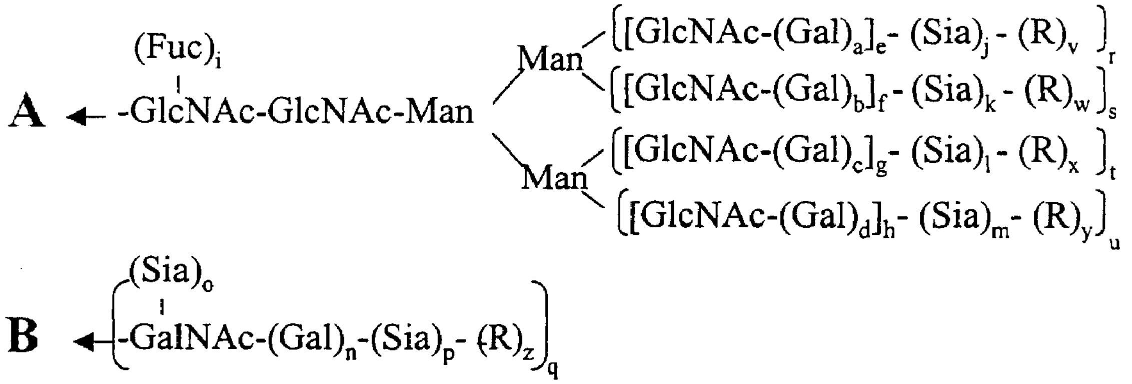
a-d, i, n-u (independently selected) = 0 or 1.
e-h (independently selected) = 0 to 4.
j-m (independently selected) = 0 to 20.
v-z = 0;
R = polymer.
FIG. 35A CHO, BHK, 293 cells, Vero expressed EPO
a-g, n, q = 1; h = 1 to 3;
j-m, i, o, p (independently selected) = 0 or 1;
r-u (independently selected) = 0 to1; v-z = 0

1. Sialidase
2. CMP-SA-PEG, ST3Gal3 a-g, n, q = 1; h = 1 to 3;
i, o, p (independently selected) = 0 or 1;
r-u (independently selected) = 0 or 1;
j-m, v-y (independently selected) = 0 or 1;
R = PEG; z = 0.

FIG. 35B

Insect cell expressed EPO
a-d, f, h, j-q, s, u, v-z = 0;
e, g, i, r, t (independently selected) = 0 or 1.

1. GNT's 1&2, UDP-GlcNAc
2. Galactosyltransferase, UDP-Gal
2. CMP-SA-PEG, ST3Gal3 b, d, f, h, k, m-q, s, u, w, y, z = 0;
a, c, e, g, i, r, t (independently selected)= 0 or 1;
j, l, v, x (independently selected) = 0 or 1;
R = PEG.

FIG. 35C

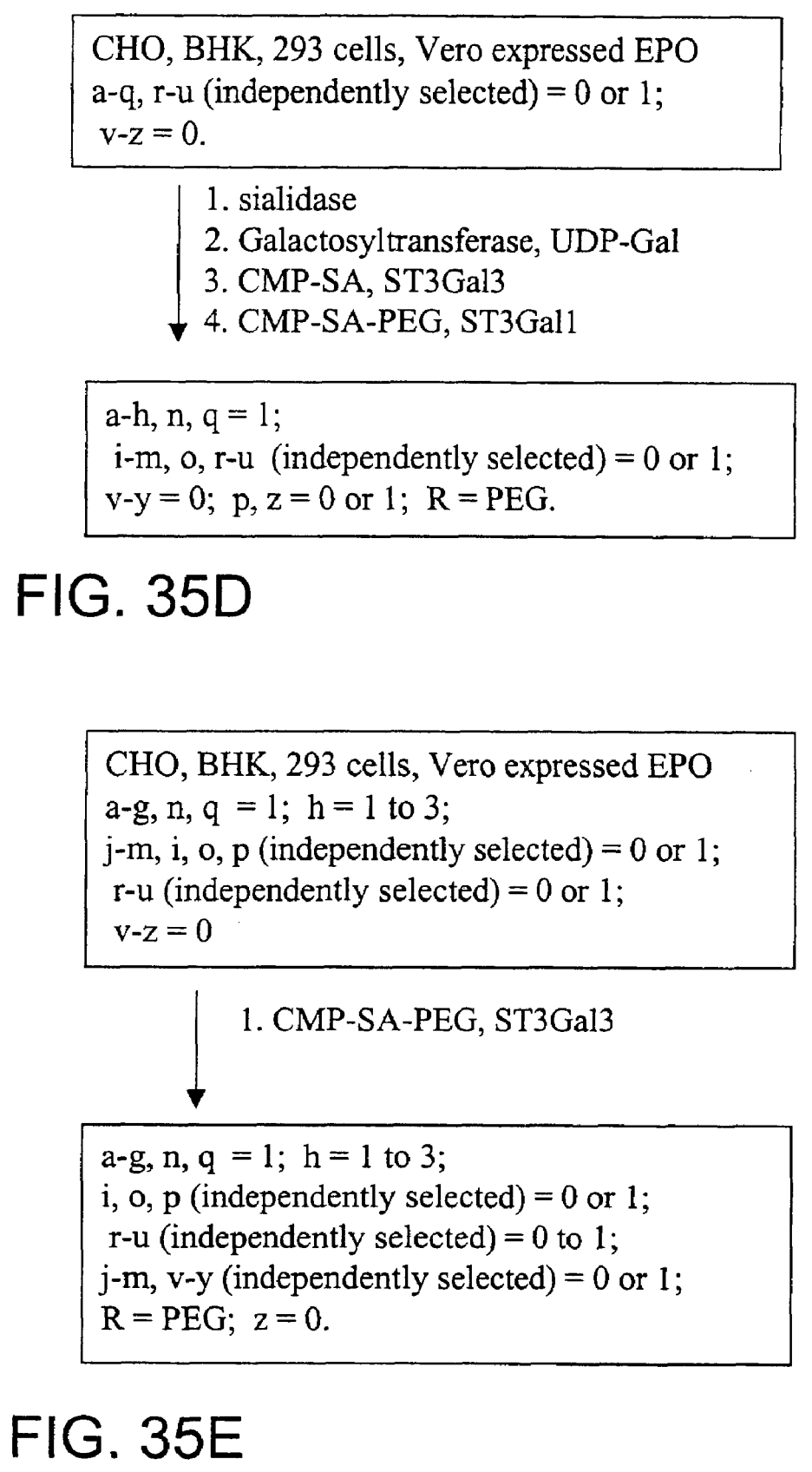

CHO, BHK, 293 cells, Vero expressed EPO
a-q, r-u (independently selected) = 0 or 1;
v-z = 0.

1. sialidase
2. Galactosyltransferase, UDP-Gal
3. CMP-SA, ST3Gal3
4. CMP-SA-PEG, ST3Gal1 a-h, n, q = 1;
i-m, o, r-u (independently selected) = 0 or 1;
v-y = 0; p, z = 0 or 1; R = PEG.

FIG. 35D

CHO, BHK, 293 cells, Vero expressed EPO
a-g, n, q = 1; h = 1 to 3;
j-m, i, o, p (independently selected) = 0 or 1;
r-u (independently selected) = 0 or 1;
v-z = 0

1. CMP-SA-PEG, ST3Gal3 a-g, n, q = 1; h = 1 to 3;
i, o, p (independently selected) = 0 or 1;
r-u (independently selected) = 0 to 1;
j-m, v-y (independently selected) = 0 or 1;
R = PEG; z = 0.

FIG. 35E

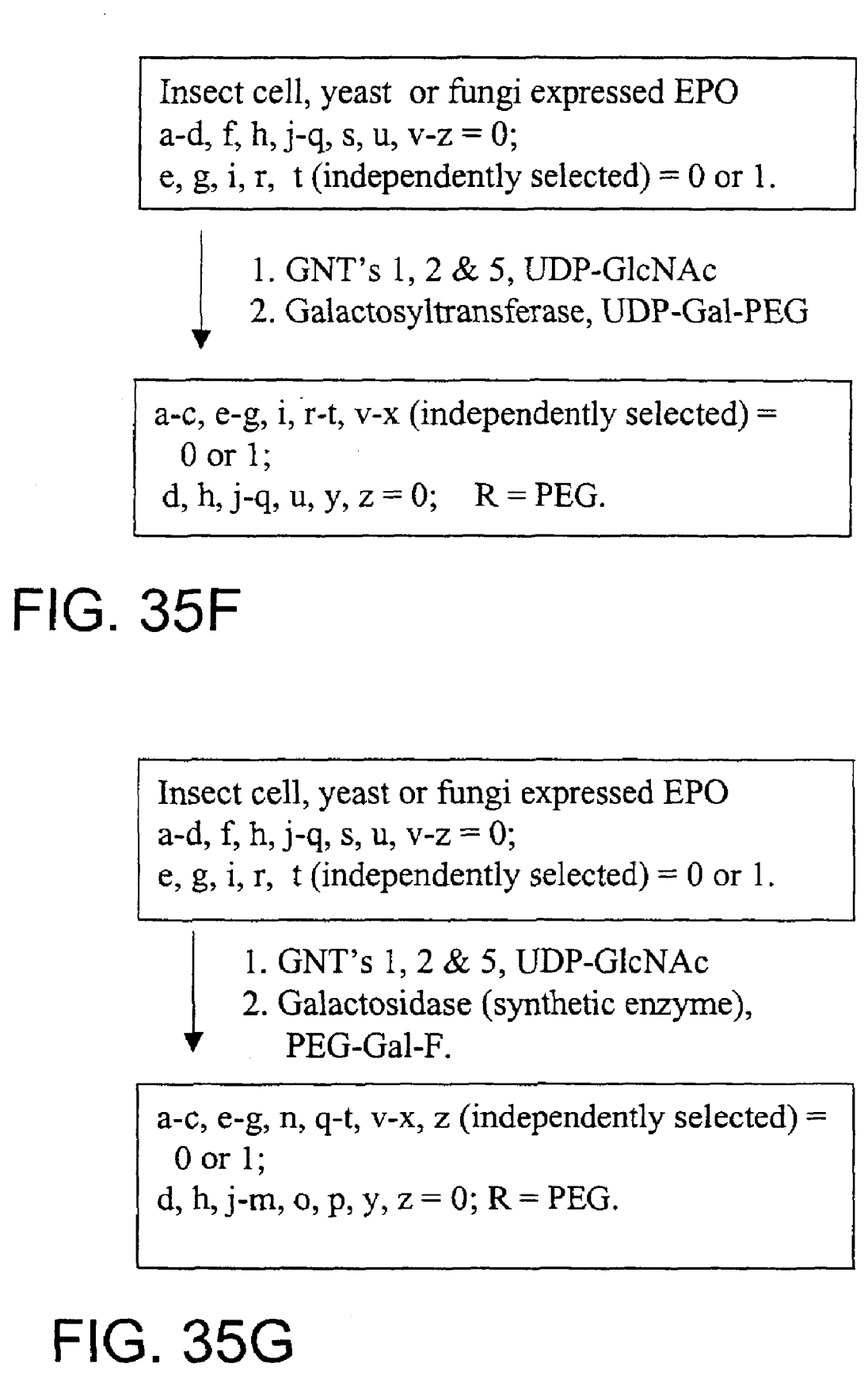

Insect cell, yeast or fungi expressed EPO
a-d, f, h, j-q, s, u, v-z = 0;
e, g, i, r, t (independently selected) = 0 or 1.

1. GNT's 1, 2 & 5, UDP-GlcNAc
2. Galactosyltransferase, UDP-Gal-PEG a-c, e-g, i, r-t, v-x (independently selected) = 0 or 1;
d, h, j-q, u, y, z = 0; R = PEG.

FIG. 35F

Insect cell, yeast or fungi expressed EPO
a-d, f, h, j-q, s, u, v-z = 0;
e, g, i, r, t (independently selected) = 0 or 1.

1. GNT's 1, 2 & 5, UDP-GlcNAc
2. Galactosidase (synthetic enzyme), PEG-Gal-F.

a-c, e-g, n, q-t, v-x, z (independently selected) = 0 or 1;
d, h, j-m, o, p, y, z = 0; R = PEG.

FIG. 35G

Insect cell, yeast or fungi expressed EPO
a-d, f, h, j-m, n-q, s, u, v-z = 0;
e, g, i, r, t (independently selected) = 0 or 1.

1. GNT-1, UDP-GlcNAc-PEG e, i, r, v (independently selected) = 0 or 1;
a-h, j-q, s-u, w-z = 0; R = PEG.

FIG. 35H

Insect cell, yeast or fungi expressed EPO
a-d, f, h, j-m, n-q, s, u, v-z = 0;
e, g, i, r, t (independently selected) = 0 or 1.

1. GNT-1, UDP-GlcNAc
2. Galactosyltransferase, UDP-Gal-PEG a, e, i, r, v (independently selected) = 0 or 1;
b-d, f-h, j-q, s-u, w-z = 0; R = PEG.

FIG. 35I

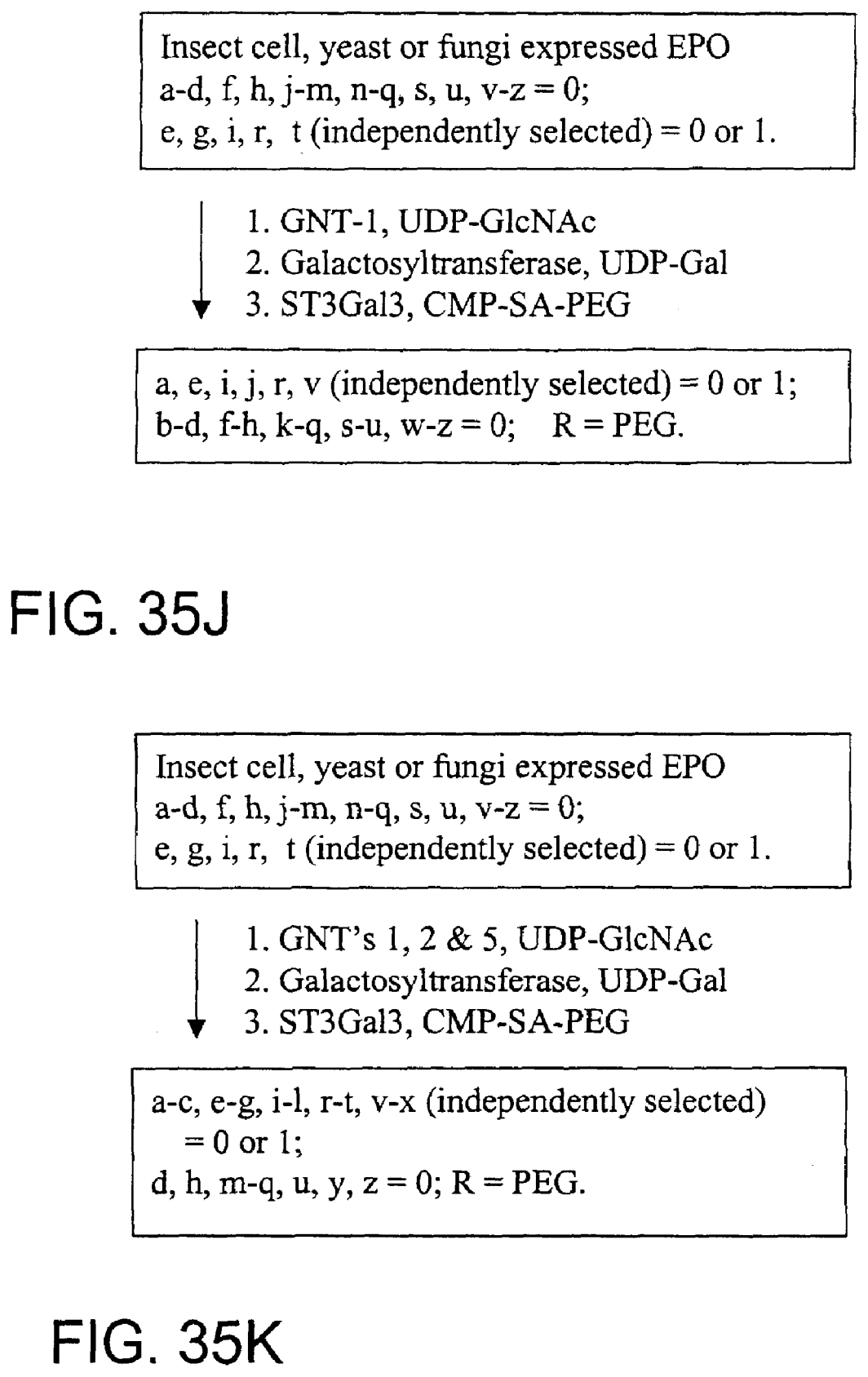

Insect cell, yeast or fungi expressed EPO
a-d, f, h, j-m, n-q, s, u, v-z = 0;
e, g, i, r, t (independently selected) = 0 or 1.

1. GNT-1, UDP-GlcNAc
2. Galactosyltransferase, UDP-Gal
3. ST3Gal3, CMP-SA-PEG a, e, i, j, r, v (independently selected) = 0 or 1;
b-d, f-h, k-q, s-u, w-z = 0; R = PEG.

FIG. 35J

Insect cell, yeast or fungi expressed EPO
a-d, f, h, j-m, n-q, s, u, v-z = 0;
e, g, i, r, t (independently selected) = 0 or 1.

1. GNT's 1, 2 & 5, UDP-GlcNAc
2. Galactosyltransferase, UDP-Gal
3. ST3Gal3, CMP-SA-PEG a-c, e-g, i-l, r-t, v-x (independently selected) = 0 or 1;
d, h, m-q, u, y, z = 0; R = PEG.

FIG. 35K

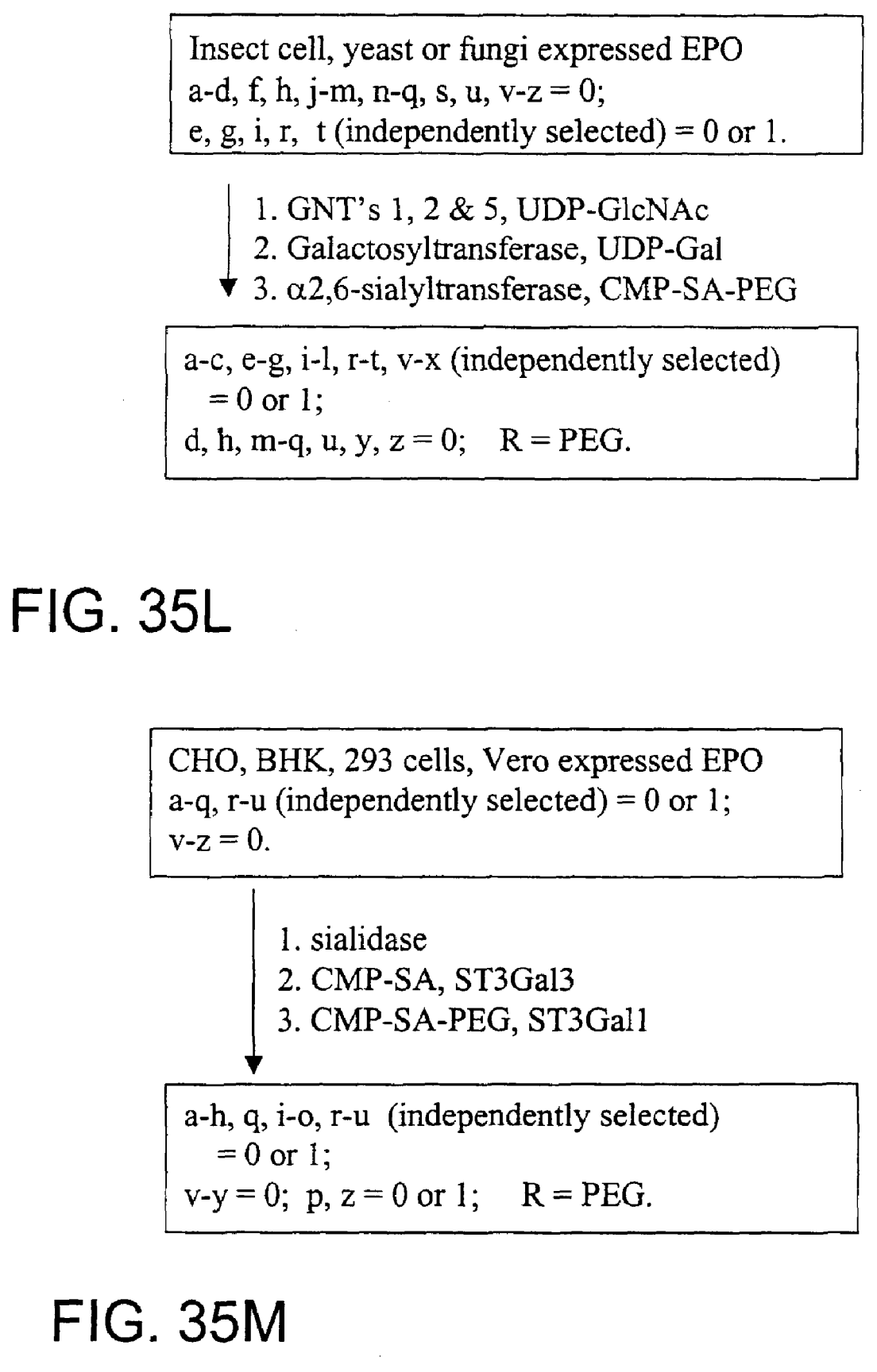

Insect cell, yeast or fungi expressed EPO
a-d, f, h, j-m, n-q, s, u, v-z = 0;
e, g, i, r, t (independently selected) = 0 or 1.

1. GNT's 1, 2 & 5, UDP-GlcNAc
2. Galactosyltransferase, UDP-Gal
3. α2,6-sialyltransferase, CMP-SA-PEG a-c, e-g, i-l, r-t, v-x (independently selected) = 0 or 1;
d, h, m-q, u, y, z = 0; R = PEG.

FIG. 35L

CHO, BHK, 293 cells, Vero expressed EPO
a-q, r-u (independently selected) = 0 or 1;
v-z = 0.

1. sialidase
2. CMP-SA, ST3Gal3
3. CMP-SA-PEG, ST3Gal1 a-h, q, i-o, r-u (independently selected) = 0 or 1;
v-y = 0; p, z = 0 or 1; R = PEG.

FIG. 35M

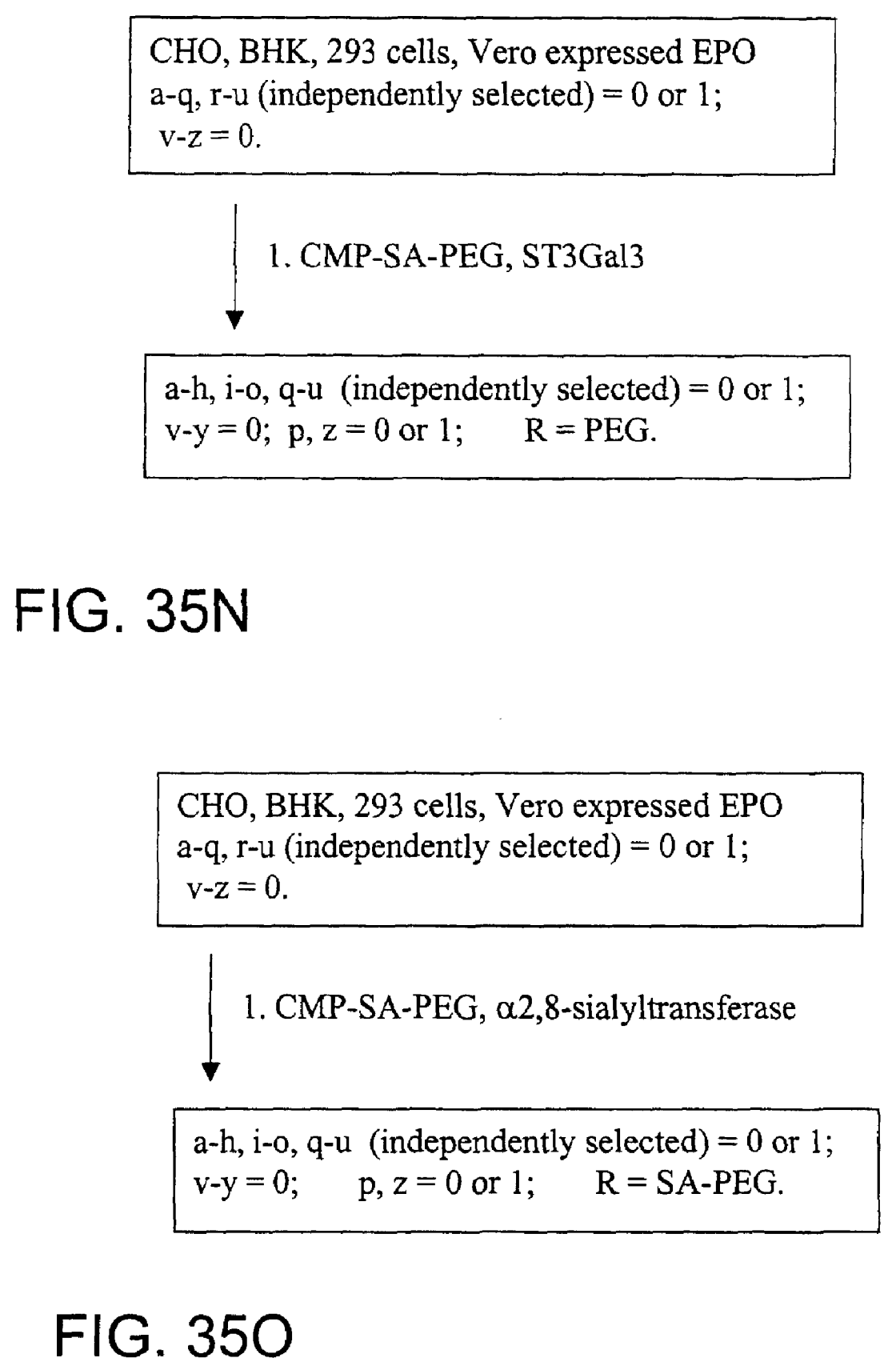

CHO, BHK, 293 cells, Vero expressed EPO
a-q, r-u (independently selected) = 0 or 1;
v-z = 0.

1. CMP-SA-PEG, ST3Gal3 a-h, i-o, q-u (independently selected) = 0 or 1;
v-y = 0; p, z = 0 or 1; R = PEG.

FIG. 35N

CHO, BHK, 293 cells, Vero expressed EPO
a-q, r-u (independently selected) = 0 or 1;
v-z = 0.

1. CMP-SA-PEG, α2,8-sialyltransferase a-h, i-o, q-u (independently selected) = 0 or 1;
v-y = 0; p, z = 0 or 1; R = SA-PEG.

FIG. 35O

Figures 35P, 35Q:
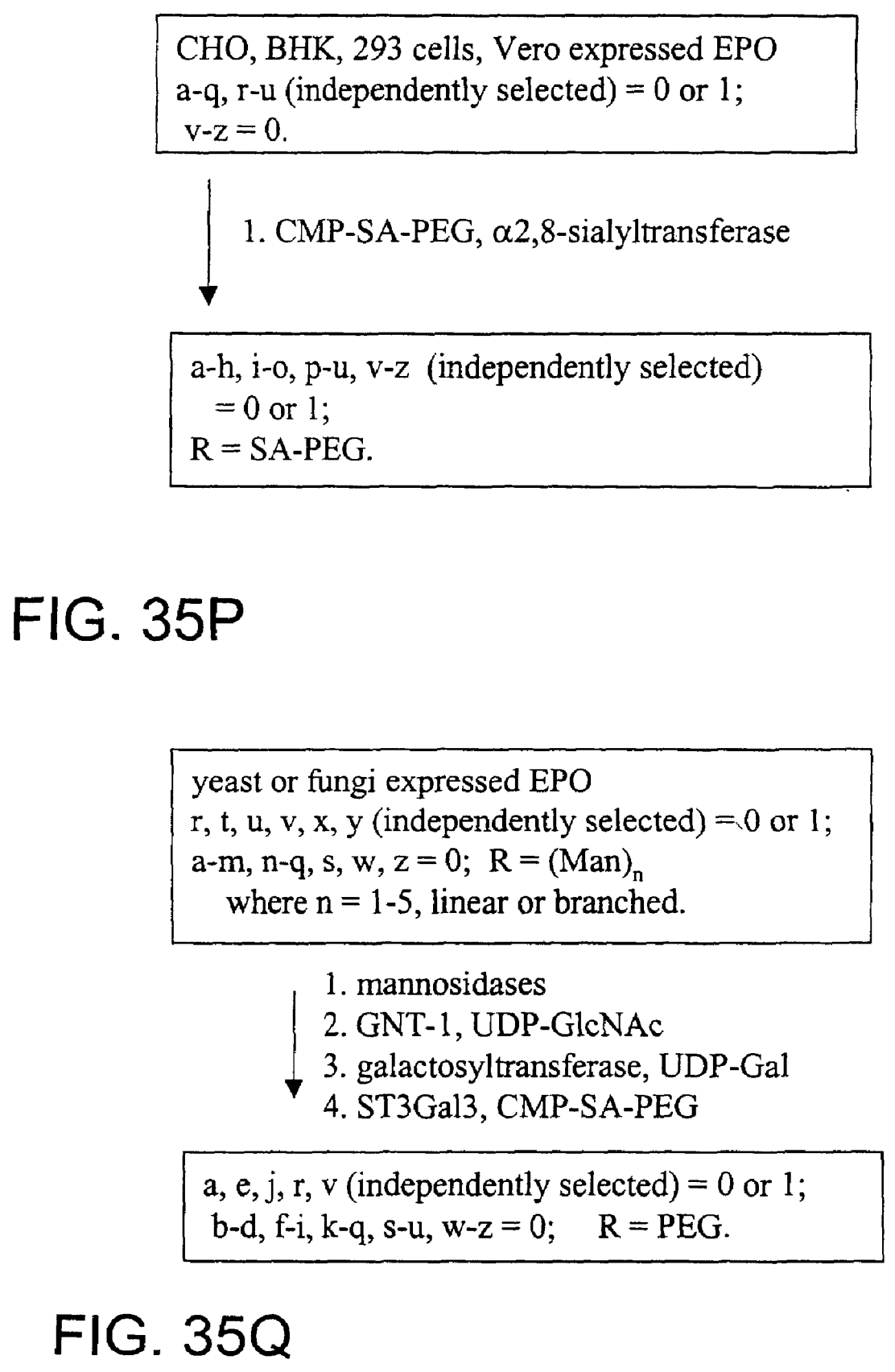

CHO, BHK, 293 cells, Vero expressed EPO
a-q, r-u (independently selected) = 0 or 1;
v-z = 0.

1. CMP-SA-PEG, α2,8-sialyltransferase a-h, i-o, p-u, v-z (independently selected) = 0 or 1;
R = SA-PEG.

FIG. 35P yeast or fungi expressed EPO
r, t, u, v, x, y (independently selected) = 0 or 1;
a-m, n-q, s, w, z = 0; R = $(Man)_n$ where n = 1-5, linear or branched.

1. mannosidases
2. GNT-1, UDP-GlcNAc
3. galactosyltransferase, UDP-Gal
4. ST3Gal3, CMP-SA-PEG a, e, j, r, v (independently selected) = 0 or 1;
b-d, f-i, k-q, s-u, w-z = 0; R = PEG.

FIG. 35Q yeast or fungi expressed EPO
r, t, u, v, x, y (independently selected) = 0 or 1;
a-m, n-q, s, w, z = 0; R = $(Man)_n$
where n = 1-5, linear or branched.

1. mannosidases
2. GNT-1, UDP-GlcNAc-PEG e, r, v (independently selected) = 0 or 1;
a-h, i-q, s-u, w-z = 0; R = PEG.

FIG. 35R yeast or fungi expressed EPO
r, t, u, v, x, y (independently selected) = 0 or 1;
a-m, n-q, s, w, z = 0; R = $(Man)_n$
where n = 1-5, linear or branched.

1. mannosidase-I
2. GNT-1, UDP-GlcNAc
3. galactosyltransferase, UDP-Gal
4. ST3Gal3, CMP-SA-PEG a, e, j, r, t-u, v, x, y (independently selected)
= 0 or 1;
b-d, f-i, k-q, s, w, z = 0;
$(R)_v$ = PEG; $(R)_x$ and $(R)_y$ = Man.

FIG. 35S a-d, i, n-u (independently selected) = 0 or 1.
e-h (independently selected) = 0 to 4.
j-m (independently selected) = 0 to 20.
v-z = 0; aa, bb = 1; cc = 0;
R = polymer; R'' and R' = sugar-polymer or Fuc.

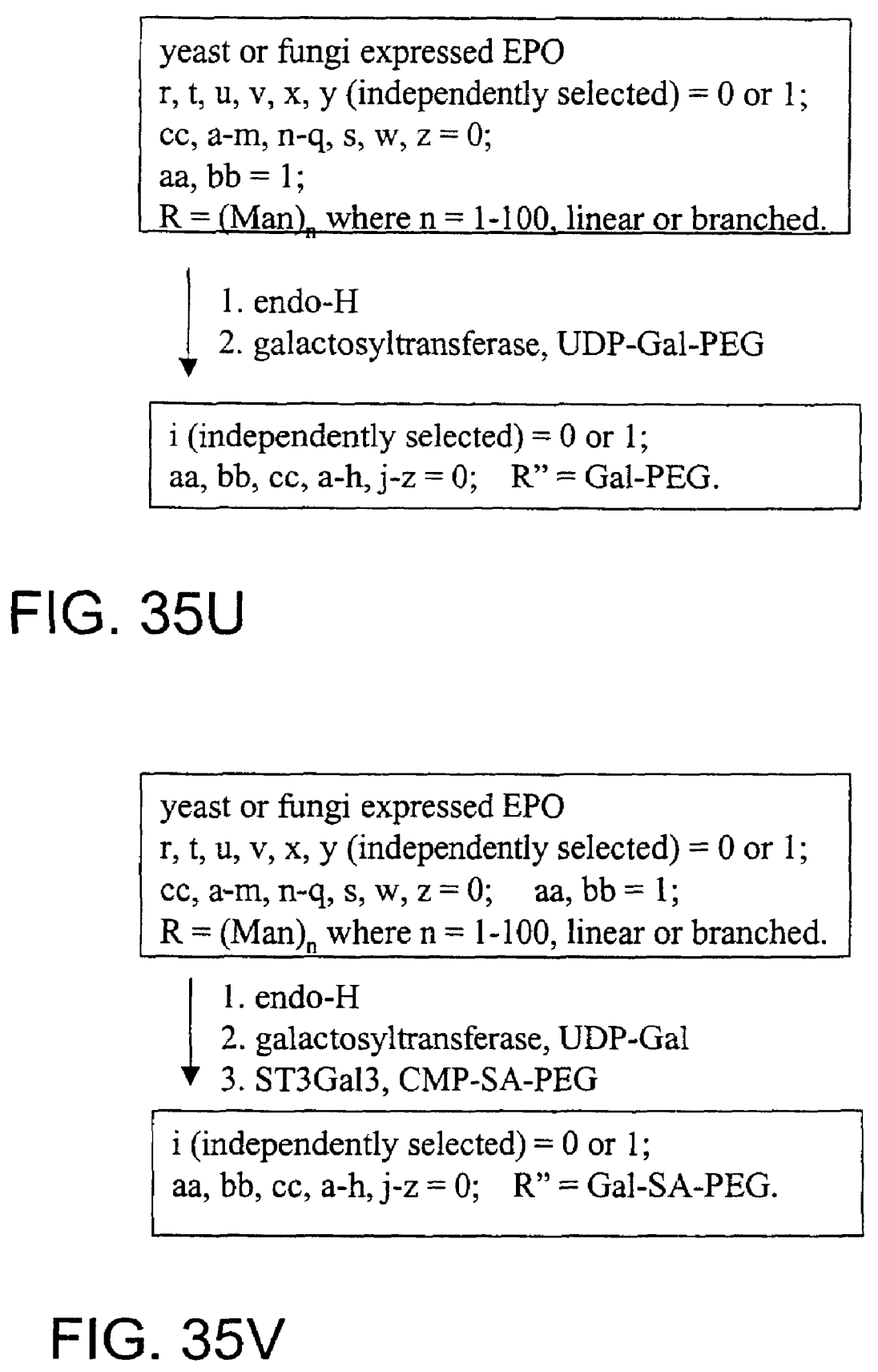

yeast or fungi expressed EPO
r, t, u, v, x, y (independently selected) = 0 or 1;
cc, a-m, n-q, s, w, z = 0;
aa, bb = 1;
R = $(Man)_n$ where n = 1-100, linear or branched.

1. endo-H
2. galactosyltransferase, UDP-Gal-PEG i (independently selected) = 0 or 1;
aa, bb, cc, a-h, j-z = 0; R" = Gal-PEG.

FIG. 35U yeast or fungi expressed EPO
r, t, u, v, x, y (independently selected) = 0 or 1;
cc, a-m, n-q, s, w, z = 0; aa, bb = 1;
R = $(Man)_n$ where n = 1-100, linear or branched.

1. endo-H
2. galactosyltransferase, UDP-Gal
3. ST3Gal3, CMP-SA-PEG i (independently selected) = 0 or 1;
aa, bb, cc, a-h, j-z = 0; R" = Gal-SA-PEG.

FIG. 35V

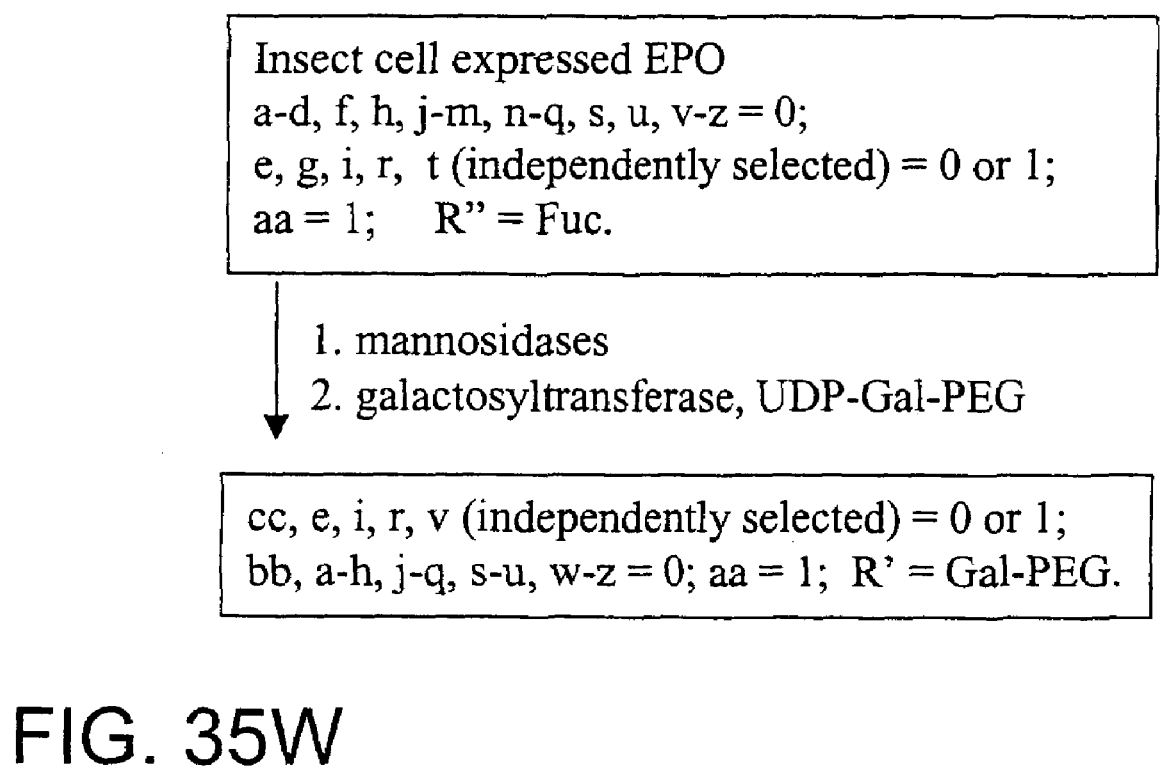

Insect cell expressed EPO
a-d, f, h, j-m, n-q, s, u, v-z = 0;
e, g, i, r, t (independently selected) = 0 or 1;
aa = 1; R" = Fuc.

1. mannosidases
2. galactosyltransferase, UDP-Gal-PEG cc, e, i, r, v (independently selected) = 0 or 1;
bb, a-h, j-q, s-u, w-z = 0; aa = 1; R' = Gal-PEG.

FIG. 35W

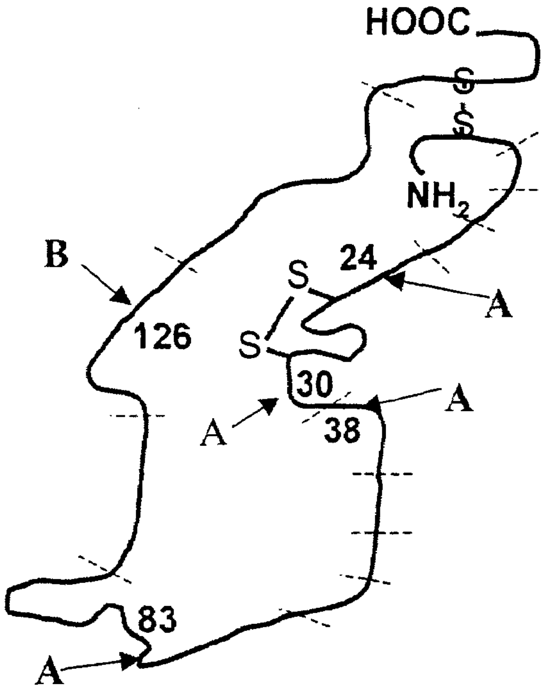
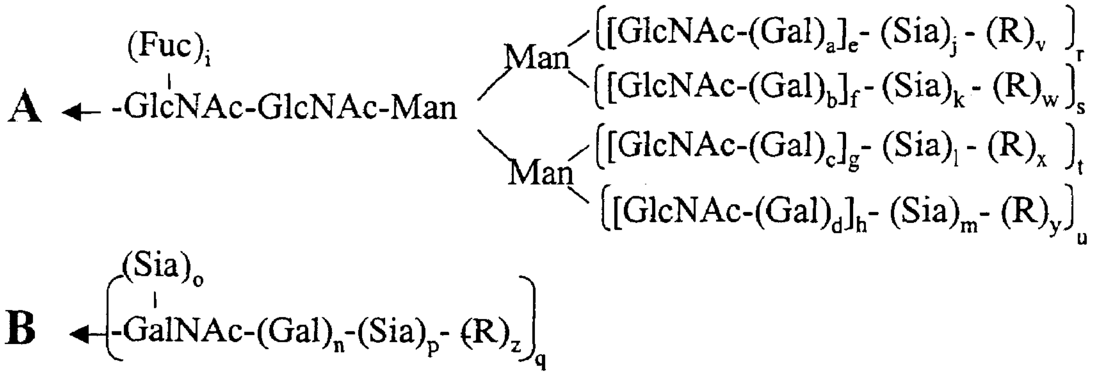
a-d, i, n-u (independently selected) = 0 or 1.
e-h (independently selected) = 0 to 4.
j-m (independently selected) = 0 to 20.
v-z = 0;
R = polymer.
FIG. 35X NSO expressed NESP
q = 1; a-i, n, r-u (independently selected) = 0 or 1; j-m, o, p, v-z = 0

1. CMP-SA-levulinate, ST3Gal3, buffer, salt
2. $H_4N_2$-PEG q = 1; a-i, j-n, r-y (independently selected) = 0 or 1;
o, p, z = 0; R = PEG.

FIG. 35Y

CHO, BHK, 293 cells, Vero expressed NESP
a-g, n, q = 1; h = 1 to 3;
j-m, i, o, p (independently selected) = 0 or 1;
r-u (independently selected) = 0 or 1;
v-z = 0

1. CMP-SA-PEG, α2,8-ST a-g, n, q = 1; h = 1 to 3;
i, o, p (independently selected) = 0 or 1;
r-u (independently selected) = 0 to 1;
j-m (independently selected) = 0 to 2;
v-y (independently selected) = 1, when j-m (independently selected) is 2;
R = PEG; z = 0.

FIG. 35Z

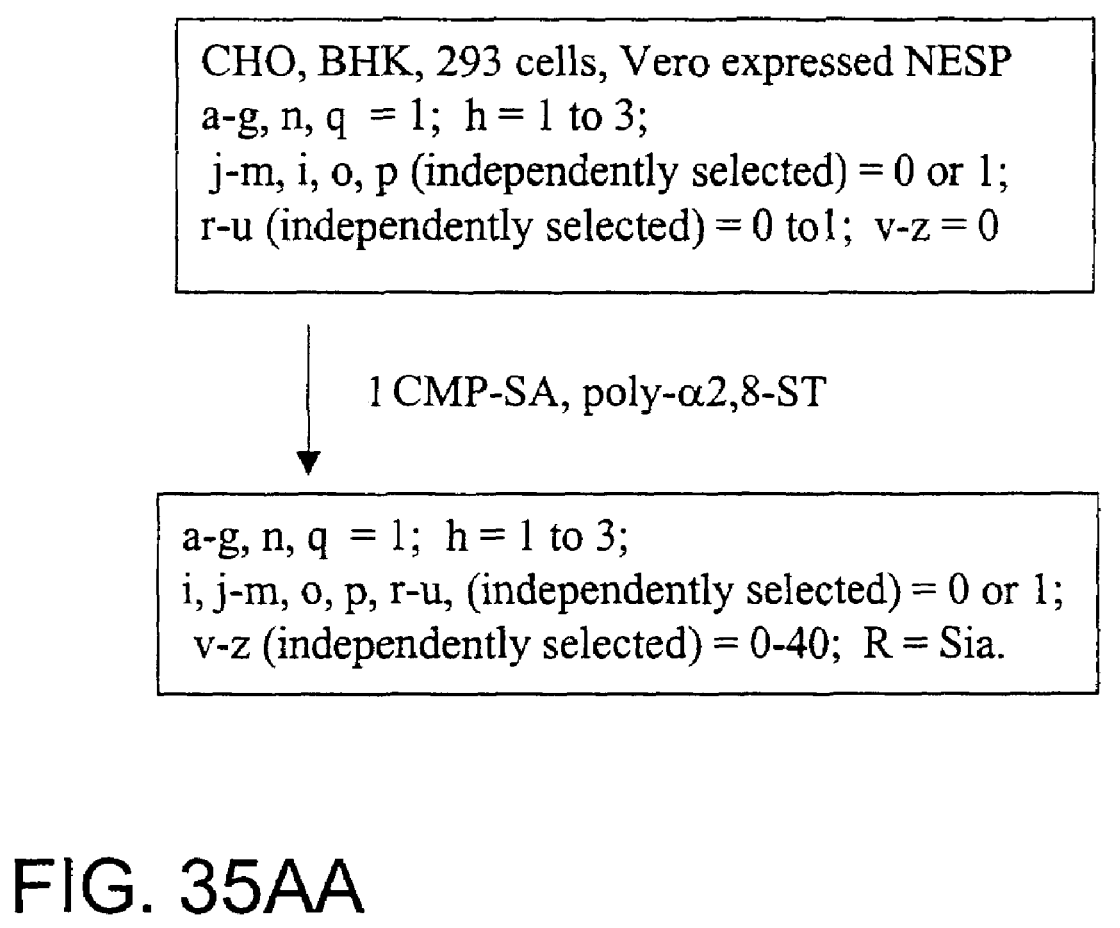

CHO, BHK, 293 cells, Vero expressed NESP
a-g, n, q = 1; h = 1 to 3;
j-m, i, o, p (independently selected) = 0 or 1;
r-u (independently selected) = 0 to1; v-z = 0

1 CMP-SA, poly-α2,8-ST a-g, n, q = 1; h = 1 to 3;
i, j-m, o, p, r-u, (independently selected) = 0 or 1;
v-z (independently selected) = 0-40; R = Sia.

FIG. 35AA

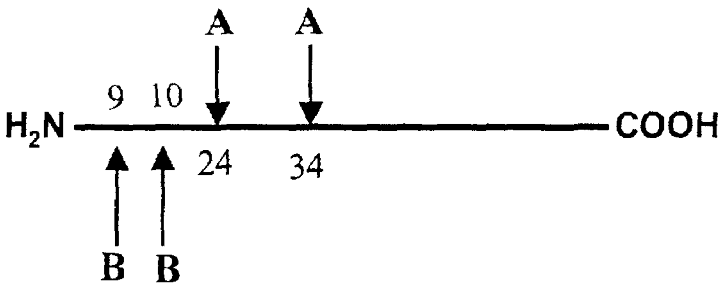
A 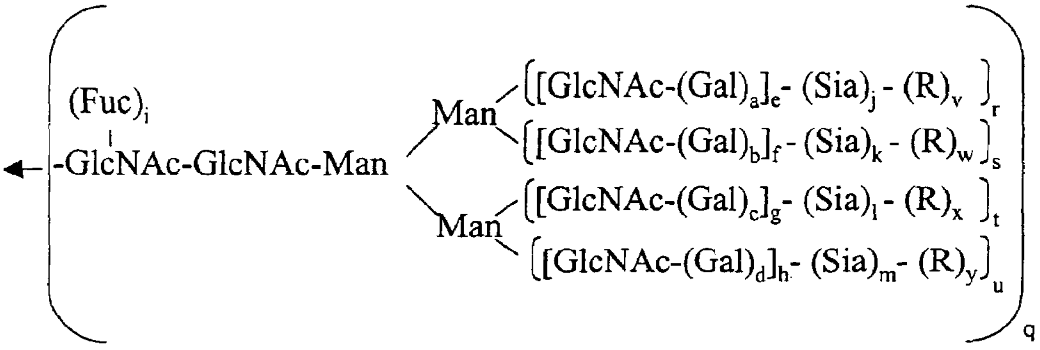
B 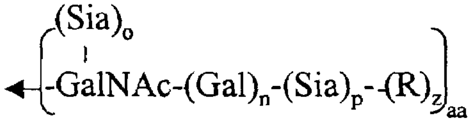
a-d, i, n-u, aa (independently selected) = 0 or 1.
e-h (independently selected) = 0 to 6.
j-m (independently selected) = 0 to 100.
v-y = 0; R = polymer, glycoconjugate.
FIG. 36A CHO, BHK, 293 cells, Vero expressed GM-CSF.
a-d, i-m, o-u, aa (independently selected) = 0 or 1;
n, e-h = 1; v-z = 0.

1. Sialidase
2. CMP-SA-PEG (16 mol eq), ST3Gal3 a-d, i-m, q-u, aa (independently selected) = 0 or 1;
o, p, z = 0; n, e-h = 1;
v-y (independently selected) = 1, when j-m (independently selected) is 1;
R = PEG.

FIG. 36B

CHO, BHK, 293 cells, Vero expressed GM-CSF.
a-d, i-m, o-u, aa (independently selected) = 0 or 1;
n, e-h = 1; v-z = 0.

1. Sialidase
2. CMP-SA-PEG (1.2 mol eq), ST3Gal3
3. CMP-SA (16 mol eq), ST3Gal3 & ST3Gal1 a-d, i-m, p-u, aa (independently selected) = 0 or 1;
o, z = 0; n, e-h = 1;
v-y (independently selected) = 0 or 1; R = PEG.

FIG. 36C

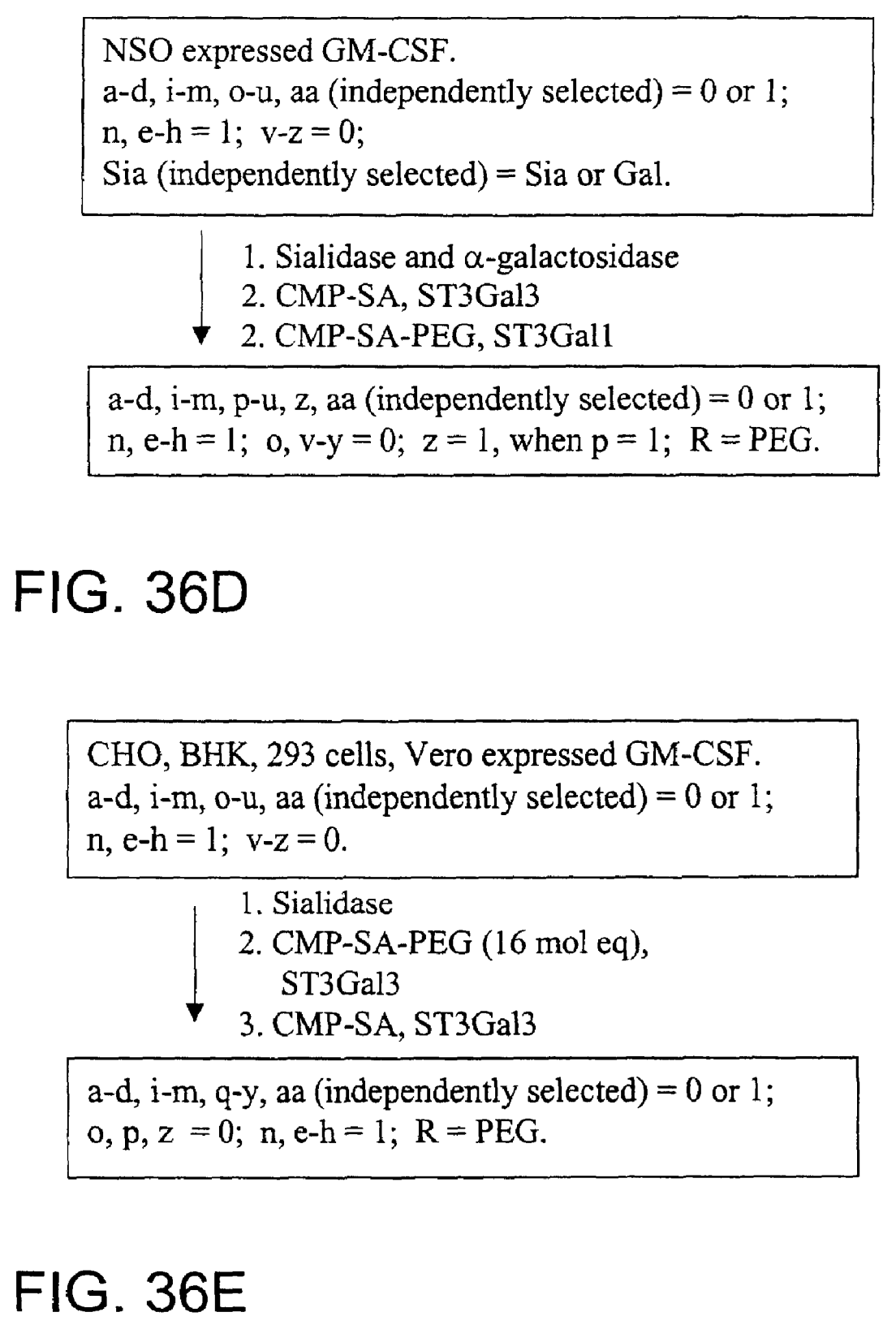

NSO expressed GM-CSF.
a-d, i-m, o-u, aa (independently selected) = 0 or 1;
n, e-h = 1; v-z = 0;
Sia (independently selected) = Sia or Gal.

1. Sialidase and α-galactosidase
2. CMP-SA, ST3Gal3
2. CMP-SA-PEG, ST3Gal1 a-d, i-m, p-u, z, aa (independently selected) = 0 or 1;
n, e-h = 1; o, v-y = 0; z = 1, when p = 1; R = PEG.

FIG. 36D

CHO, BHK, 293 cells, Vero expressed GM-CSF.
a-d, i-m, o-u, aa (independently selected) = 0 or 1;
n, e-h = 1; v-z = 0.

1. Sialidase
2. CMP-SA-PEG (16 mol eq), ST3Gal3
3. CMP-SA, ST3Gal3 a-d, i-m, q-y, aa (independently selected) = 0 or 1;
o, p, z = 0; n, e-h = 1; R = PEG.

FIG. 36E

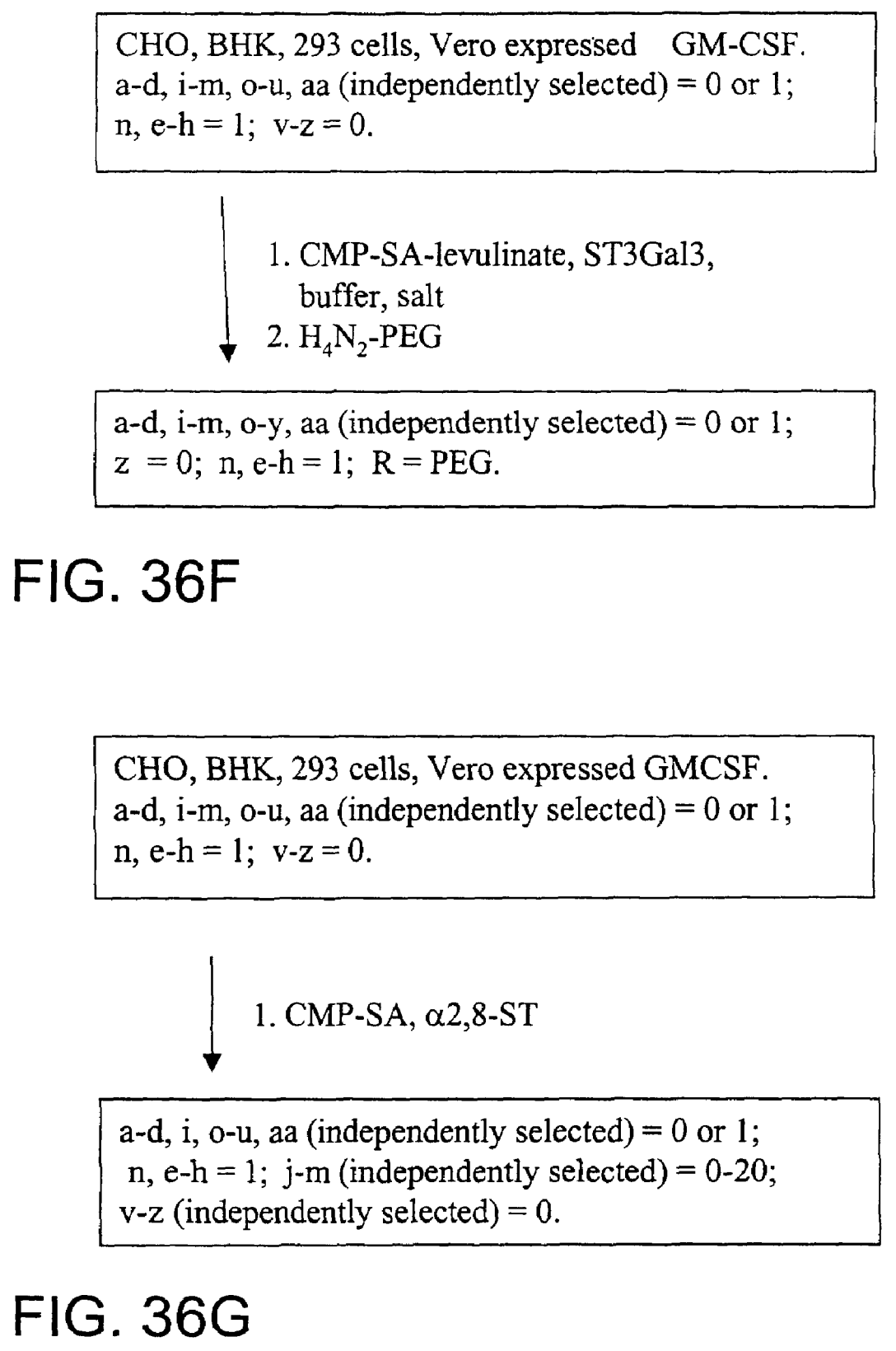

CHO, BHK, 293 cells, Vero expressed GM-CSF.
a-d, i-m, o-u, aa (independently selected) = 0 or 1;
n, e-h = 1; v-z = 0.

1. CMP-SA-levulinate, ST3Gal3, buffer, salt
2. $H_4N_2$-PEG a-d, i-m, o-y, aa (independently selected) = 0 or 1;
z = 0; n, e-h = 1; R = PEG.

FIG. 36F

CHO, BHK, 293 cells, Vero expressed GMCSF.
a-d, i-m, o-u, aa (independently selected) = 0 or 1;
n, e-h = 1; v-z = 0.

1. CMP-SA, α2,8-ST a-d, i, o-u, aa (independently selected) = 0 or 1;
n, e-h = 1; j-m (independently selected) = 0-20;
v-z (independently selected) = 0.

FIG. 36G

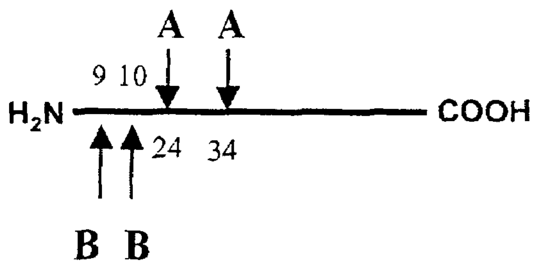
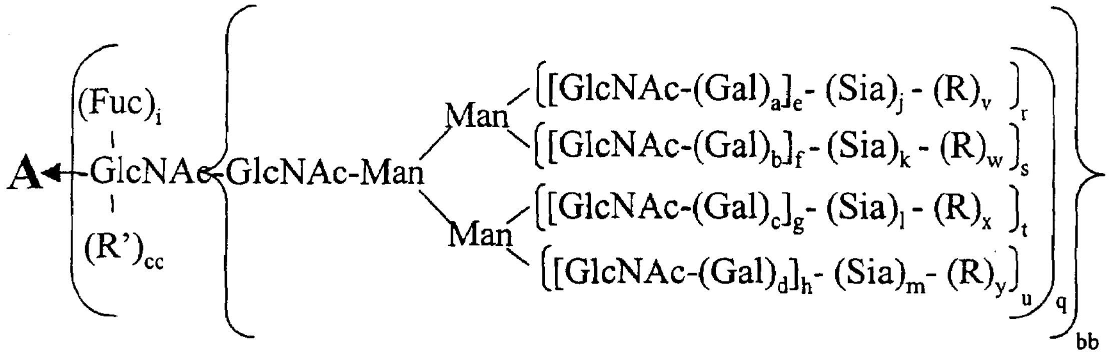
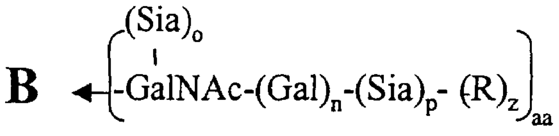
a-d, i, n-u, aa, bb, cc (independently selected) = 0 or 1.
e-h (independently selected) = 0 to 6.
j-m (independently selected) = 0 to 100.
v-y = 0; R = modifying group, mannose, oligo-mannose.
R'= H, glycosyl residue, modifying group. glycoconjugate.
FIG. 36H Insect cell expressed GM-CSF.
a-d, f, h, j-m, o, p, s, u, v-z = 0;
e, g, i, n, q, r, t, aa (independently selected) = 0 or 1.

↓
1. GNT's 1,2,4,5, UDP-GlcNAc
2. Galactosyltransferase, UDP-Gal-PEG a-i, n, q-u (independently selected) = 0 or 1;
j-m = 0; v-y (independently selected) = 1,
when e-h (independently selected) is 1;
R = PEG.

FIG. 36I

Yeast expressed GM-CSF.
a-p, z, cc = 0;
q-y, aa (independently selected) = 0 to 1;
bb = 1; R (branched or linear) = Man, oligomannose;
GalNAc = Man.

↓
1. Endoglycanase
2. mannosidase (if aa = 1).
3. Galactosyltransferase, UDP-Gal-PEG a-p, r-z, aa, bb = 0;
q, cc (independently selected) = 0 or 1;
R' = -Gal-PEG.

FIG. 36J

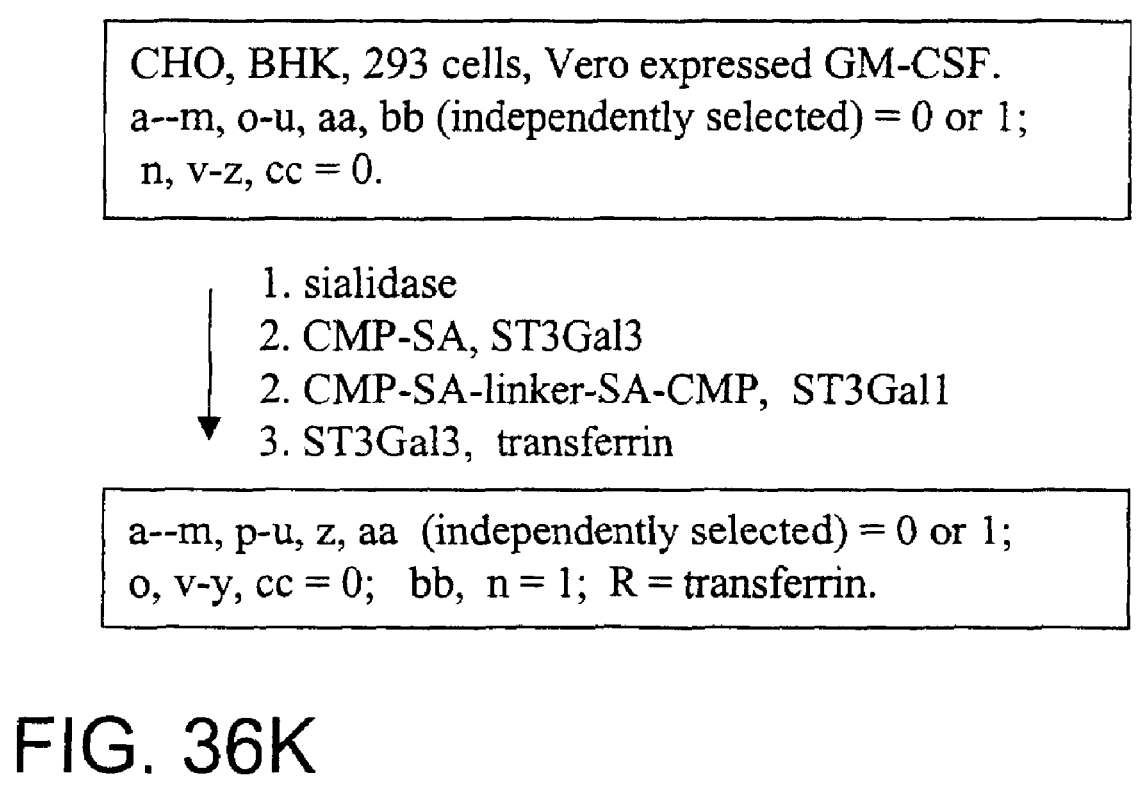

CHO, BHK, 293 cells, Vero expressed GM-CSF.
a--m, o-u, aa, bb (independently selected) = 0 or 1;
n, v-z, cc = 0.

1. sialidase
2. CMP-SA, ST3Gal3
2. CMP-SA-linker-SA-CMP, ST3Gal1
3. ST3Gal3, transferrin a--m, p-u, z, aa (independently selected) = 0 or 1;
o, v-y, cc = 0; bb, n = 1; R = transferrin.

FIG. 36K

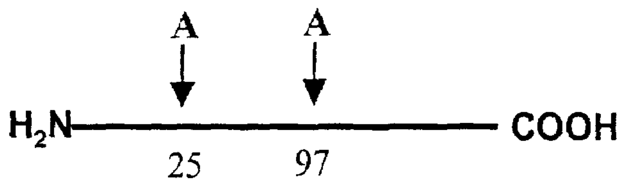
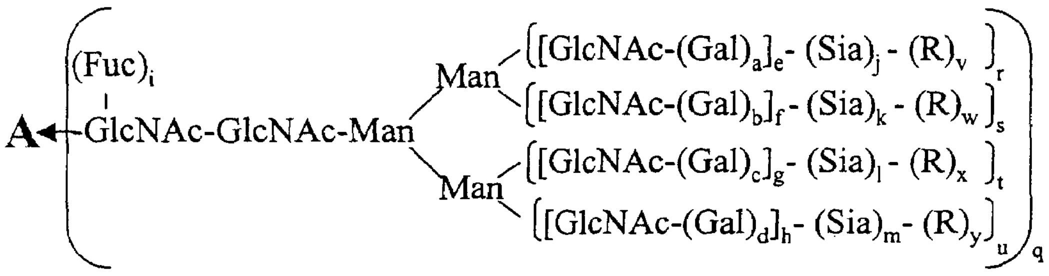
a-d, i, q-u (independently selected) = 0 or 1.
e-h (independently selected) = 0 to 6.
j-m (independently selected) = 0 to 100.
v-y = 0; R = polymer.
FIG. 37A CHO, BHK, 293 cells, Vero expressed IF-gamma.
a-d, i-m, q-u (independently selected) = 0 or 1;
e-h = 1; v-y = 0.

1. Sialidase
2. CMP-SA-PEG (16 mol eq), ST3Gal3 a-d, i-m, q-u (independently selected) = 0 or 1;
e-h = 1; v-y (independently selected) = 1, when j-m (independently selected) is 1;
R = PEG.

FIG. 37B

CHO, BHK, 293 cells, Vero expressed IF-gamma.
a-d, i-m, q-u (independently selected) = 0 or 1;
e-h = 1; v-y = 0.

1. Sialidase
2. CMP-SA-PEG (1.2 mol eq), ST3Gal3
3. CMP-SA (16 mol eq), ST3Gal3 a-d, i-m, q-u (independently selected) = 0 or 1;
e-h = 1; v-y (independently selected) = 0 or 1;
R = PEG.

FIG. 37C

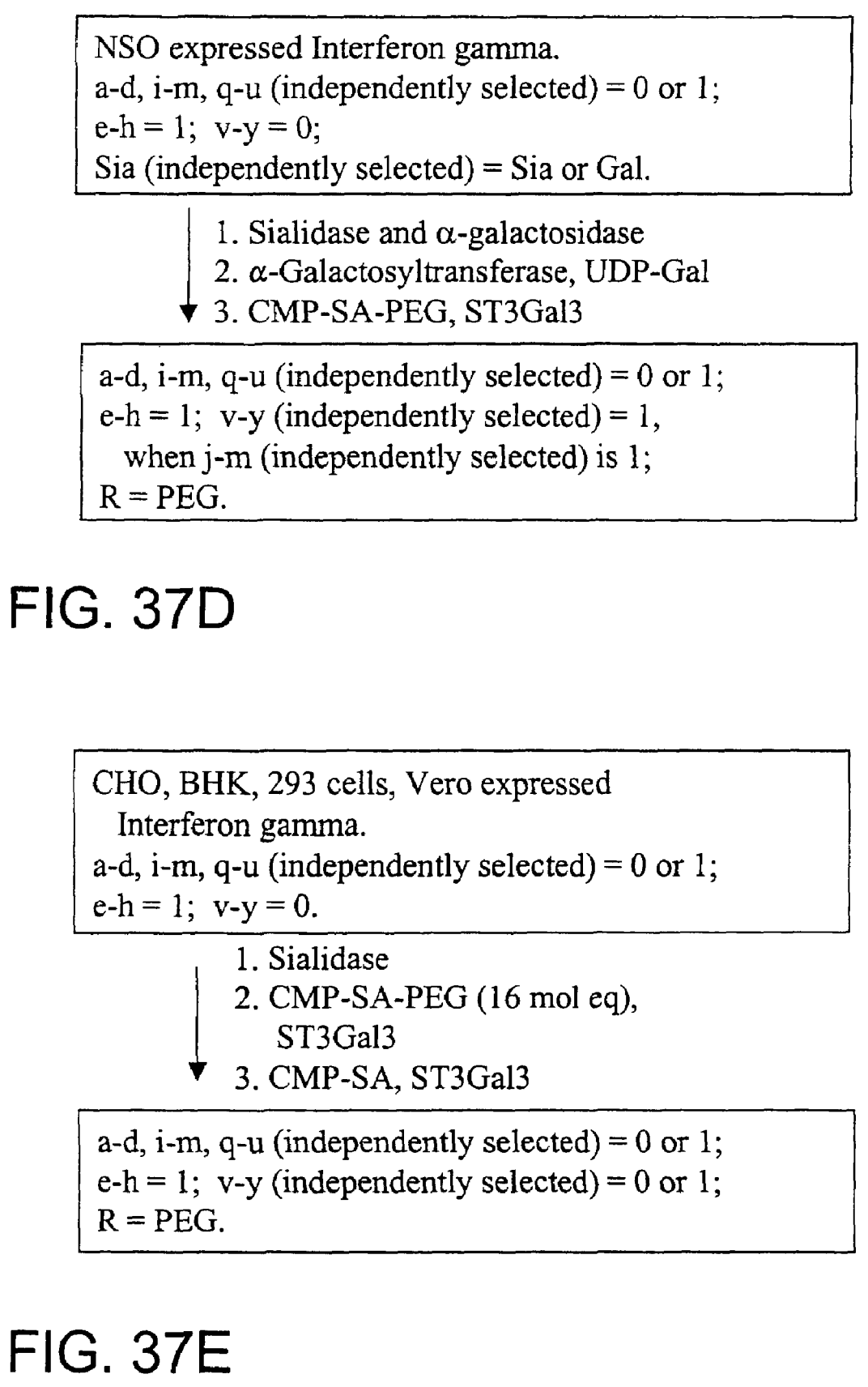

NSO expressed Interferon gamma.
a-d, i-m, q-u (independently selected) = 0 or 1;
e-h = 1; v-y = 0;
Sia (independently selected) = Sia or Gal.

1. Sialidase and α-galactosidase
2. α-Galactosyltransferase, UDP-Gal
3. CMP-SA-PEG, ST3Gal3 a-d, i-m, q-u (independently selected) = 0 or 1;
e-h = 1; v-y (independently selected) = 1,
when j-m (independently selected) is 1;
R = PEG.

FIG. 37D

CHO, BHK, 293 cells, Vero expressed
Interferon gamma.
a-d, i-m, q-u (independently selected) = 0 or 1;
e-h = 1; v-y = 0.

1. Sialidase
2. CMP-SA-PEG (16 mol eq),
ST3Gal3
3. CMP-SA, ST3Gal3 a-d, i-m, q-u (independently selected) = 0 or 1;
e-h = 1; v-y (independently selected) = 0 or 1;
R = PEG.

FIG. 37E

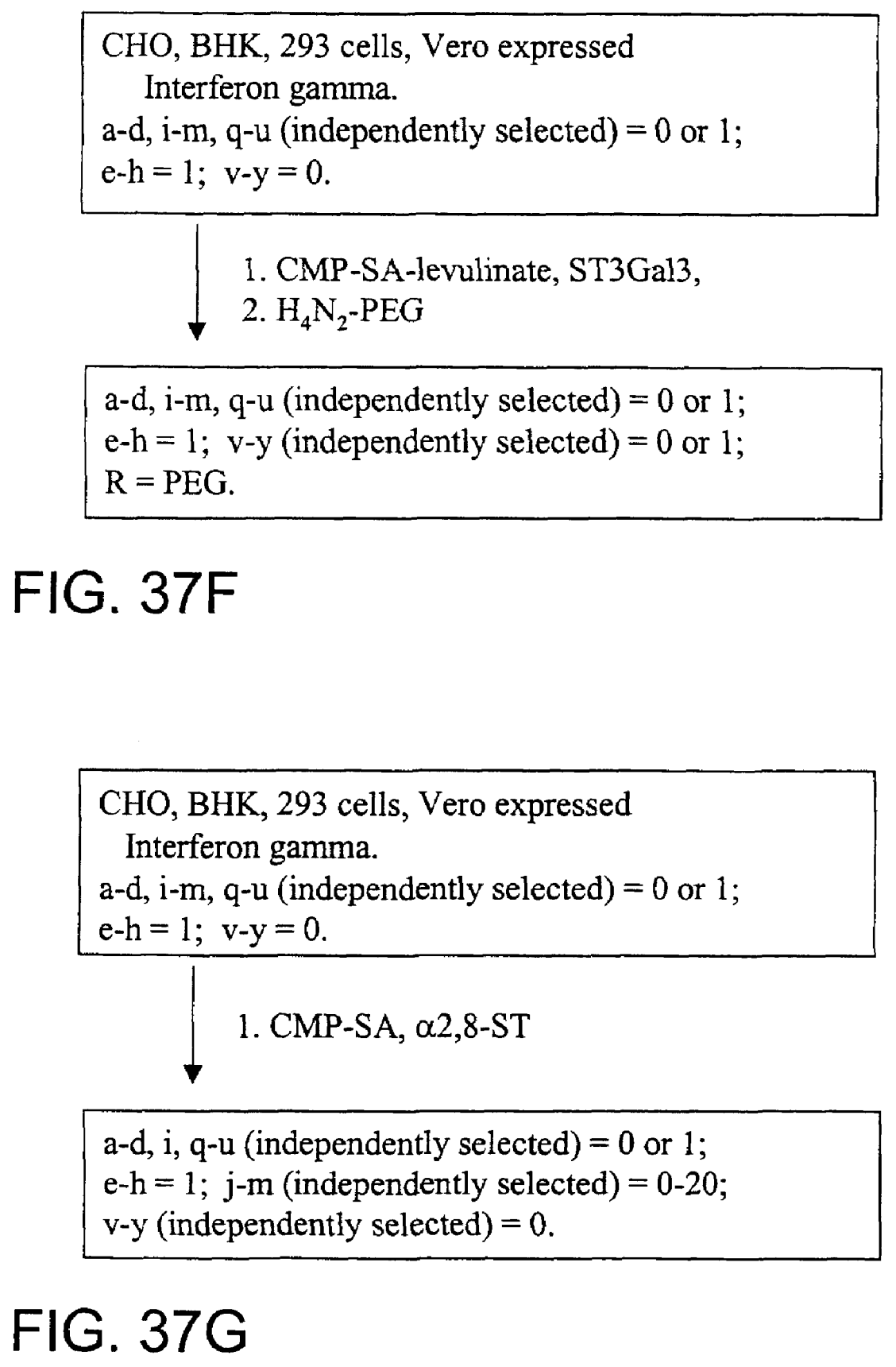

CHO, BHK, 293 cells, Vero expressed
Interferon gamma.
a-d, i-m, q-u (independently selected) = 0 or 1;
e-h = 1; v-y = 0.

1. CMP-SA-levulinate, ST3Gal3,
2. $H_4N_2$-PEG a-d, i-m, q-u (independently selected) = 0 or 1;
e-h = 1; v-y (independently selected) = 0 or 1;
R = PEG.

FIG. 37F

CHO, BHK, 293 cells, Vero expressed
Interferon gamma.
a-d, i-m, q-u (independently selected) = 0 or 1;
e-h = 1; v-y = 0.

1. CMP-SA, α2,8-ST a-d, i, q-u (independently selected) = 0 or 1;
e-h = 1; j-m (independently selected) = 0-20;
v-y (independently selected) = 0.

FIG. 37G

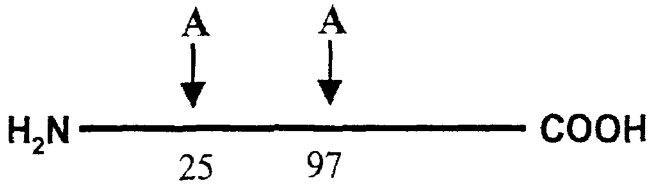
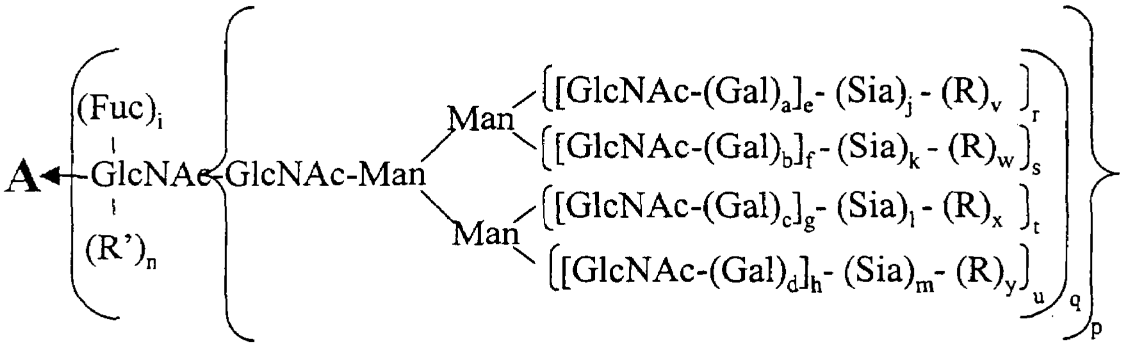
a-d, i, n, p-u (independently selected) = 0 or 1.
e-h (independently selected) = 0 to 6.
j-m (independently selected) = 0 to 100.
v-y = 0;
R = modifying group, mannose, oligo-mannose;
R' = H, glycosyl residue, modifying group, glycoconjugate.
FIG. 37H Insect or fungi cell expressed IF-gamma.
a-d, f, h, j-m, s, u, v-y = 0;
e, g, i, q, r, t (independently selected) = 0 or 1.

1. GNT's 1,2,4,5, UDP-GlcNAc
2. Galactosyltransferase, UDP-Gal-PEG a-i, q-u (independently selected) = 0 or 1;
j-m = 0; v-y (independently selected) = 1,
when e-h (independently selected) is 1;
R = PEG.

FIG. 37I

Yeast expressed IF-gamma.
a-m = 0; q-y (independently selected) = 0 to 1; p = 1;
R (branched or linear) = Man, oligomannose.

1. Endoglycanase
2. Galactosyltransferase, UDP-Gal
3. CMP-SA-PEG, ST3Gal3 a-m, p-y = 0; n (independently selected) = 0 or 1;
R' = -Gal-Sia-PEG.

FIG. 37J

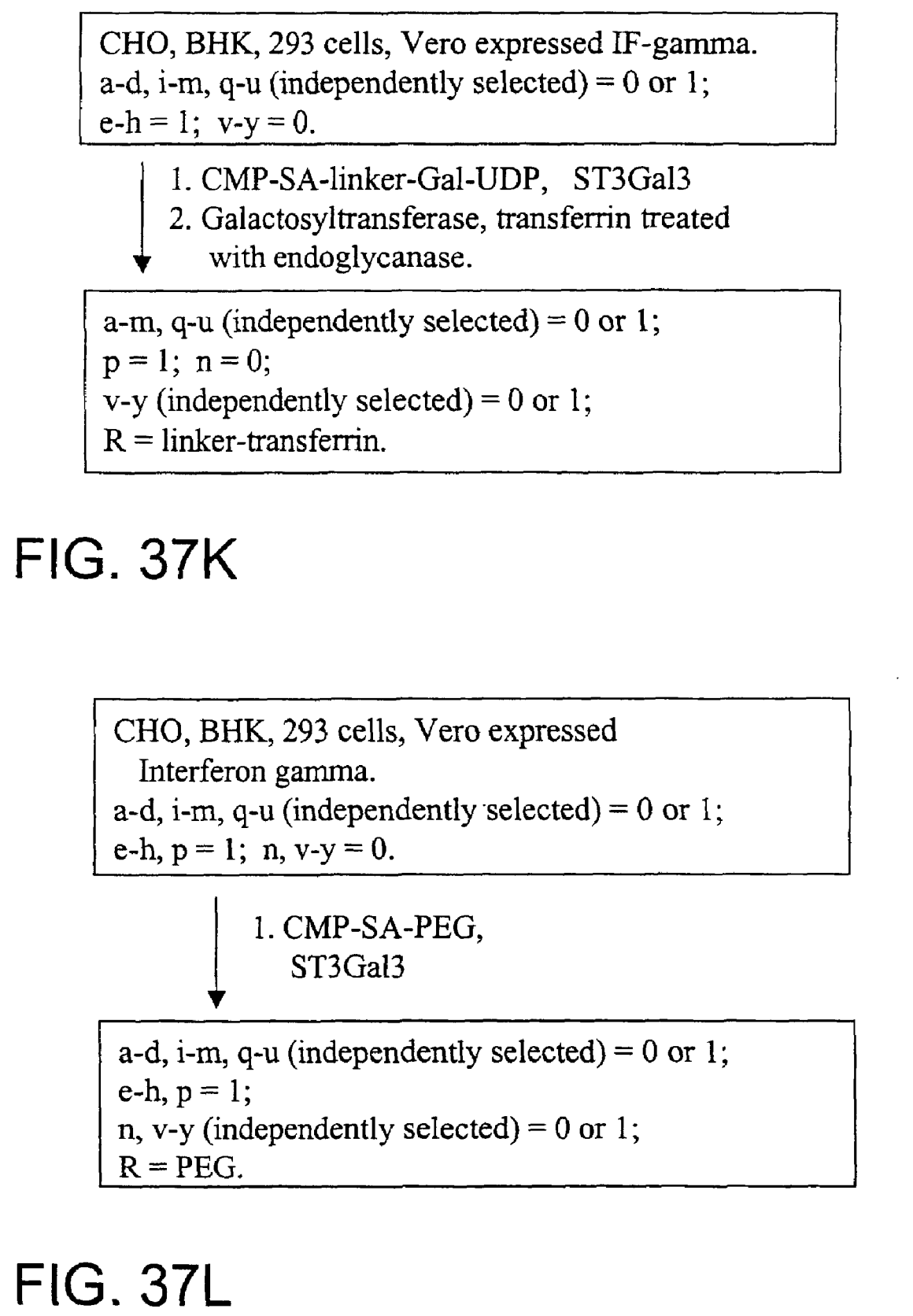

CHO, BHK, 293 cells, Vero expressed IF-gamma.
a-d, i-m, q-u (independently selected) = 0 or 1;
e-h = 1; v-y = 0.

1. CMP-SA-linker-Gal-UDP, ST3Gal3
2. Galactosyltransferase, transferrin treated with endoglycanase.

a-m, q-u (independently selected) = 0 or 1;
p = 1; n = 0;
v-y (independently selected) = 0 or 1;
R = linker-transferrin.

FIG. 37K

CHO, BHK, 293 cells, Vero expressed Interferon gamma.
a-d, i-m, q-u (independently selected) = 0 or 1;
e-h, p = 1; n, v-y = 0.

1. CMP-SA-PEG, ST3Gal3 a-d, i-m, q-u (independently selected) = 0 or 1;
e-h, p = 1;
n, v-y (independently selected) = 0 or 1;
R = PEG.

FIG. 37L

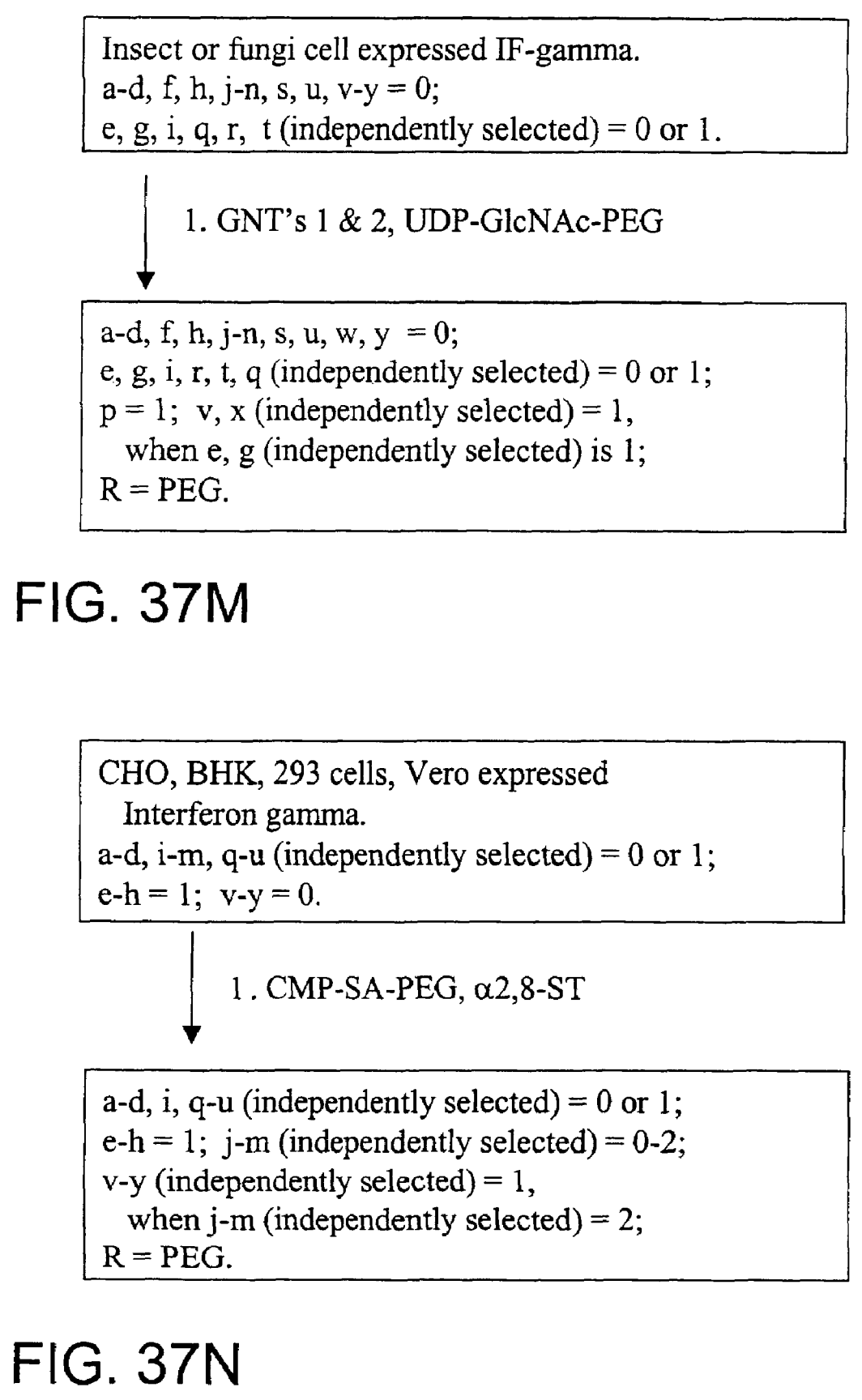

Insect or fungi cell expressed IF-gamma.
a-d, f, h, j-n, s, u, v-y = 0;
e, g, i, q, r, t (independently selected) = 0 or 1.

1. GNT's 1 & 2, UDP-GlcNAc-PEG a-d, f, h, j-n, s, u, w, y = 0;
e, g, i, r, t, q (independently selected) = 0 or 1;
p = 1; v, x (independently selected) = 1,
when e, g (independently selected) is 1;
R = PEG.

FIG. 37M

CHO, BHK, 293 cells, Vero expressed
Interferon gamma.
a-d, i-m, q-u (independently selected) = 0 or 1;
e-h = 1; v-y = 0.

1. CMP-SA-PEG, α2,8-ST a-d, i, q-u (independently selected) = 0 or 1;
e-h = 1; j-m (independently selected) = 0-2;
v-y (independently selected) = 1,
when j-m (independently selected) = 2;
R = PEG.

FIG. 37N

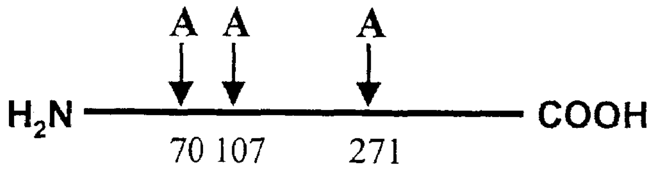
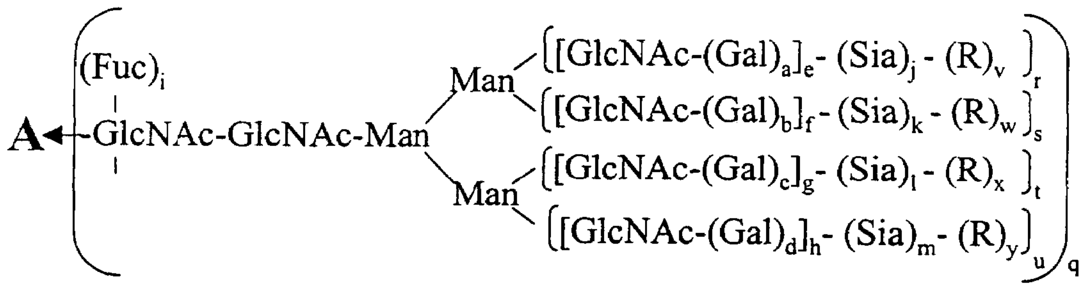
a-d, i, q-u (independently selected) = 0 or 1.
e-h (independently selected) = 0 to 6.
j-m (independently selected) = 0 to 100.
v-y = 0; R = polymer.
FIG. 38A CHO, BHK, 293 cells, Vero or transgenic animal expressed $\alpha_1$ antitrypsin.
a-d, i-m, q-u (independently selected) = 0 or 1;
e-h = 1; v-y = 0.

↓
1. Sialidase
2. CMP-SA-PEG (16 mol eq), ST3Gal3 a-d, i-m, q-u (independently selected) = 0 or 1;
e-h = 1; v-y (independently selected) = 1, when j-m (independently selected) is 1;
R = PEG.

FIG. 38B

CHO, BHK, 293 cells, Vero or transgenic animal expressed $\alpha_1$ antitrypsin.
a-d, i-m, q-u (independently selected) = 0 or 1;
e-h = 1; v-y = 0.

↓
1. Sialidase
2. CMP-SA-PEG (1.2 mol eq), ST3Gal3
3. CMP-SA (16 mol eq), ST3Gal3 a-d, i-m, q-u (independently selected) = 0 or 1;
e-h = 1; v-y (independently selected) = 0 or 1;
R = PEG.

FIG. 38C

CHO, BHK, 293 cells, Vero or transgenic animal expressed alpha-1 antitrypsin.
a-d, i-m, q-u (independently selected) = 0 or 1;
e-h = 1; v-y = 0.

1. Sialidase
2. CMP-SA-PEG (16 mol eq), ST3Gal3
3. CMP-SA, ST3Gal3 a-d, i-m, q-u (independently selected) = 0 or 1;
e-h = 1; v-y (independently selected) = 0 or 1;
R = PEG.

FIG. 38D

CHO, BHK, 293 cells, Vero or transgenic animal expressed $\alpha_1$-antitrypsin.
a-d, i-m, q-u (independently selected) = 0 or 1;
e-h = 1; v-y = 0.

1. CMP-SA-levulinate, ST3Gal3, buffer, salt
2. $H_4N_2$-PEG a-d, i-m, q-u (independently selected) = 0 or 1;
e-h = 1; v-y (independently selected) = 0 or 1;
R = PEG.

FIG. 38E

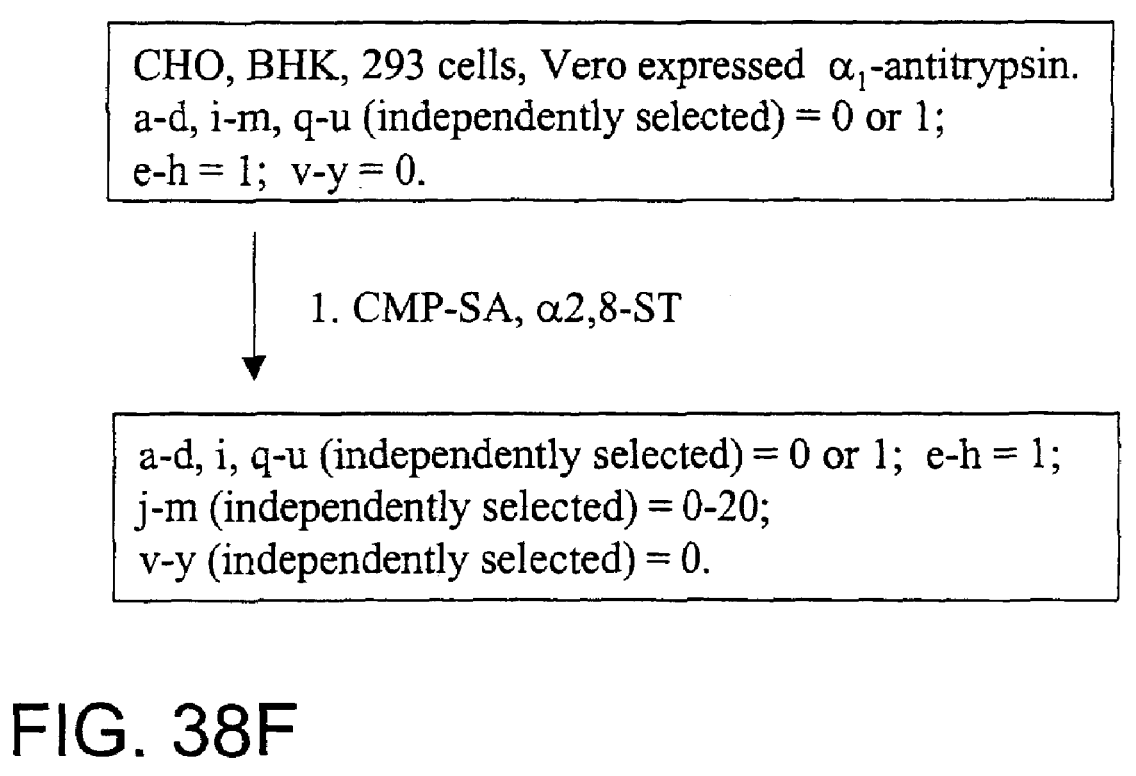

CHO, BHK, 293 cells, Vero expressed $\alpha_1$-antitrypsin.
a-d, i-m, q-u (independently selected) = 0 or 1;
e-h = 1; v-y = 0.

1. CMP-SA, α2,8-ST a-d, i, q-u (independently selected) = 0 or 1; e-h = 1;
j-m (independently selected) = 0-20;
v-y (independently selected) = 0.

FIG. 38F

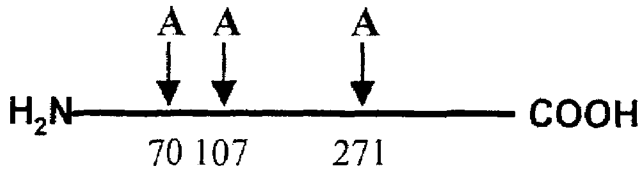
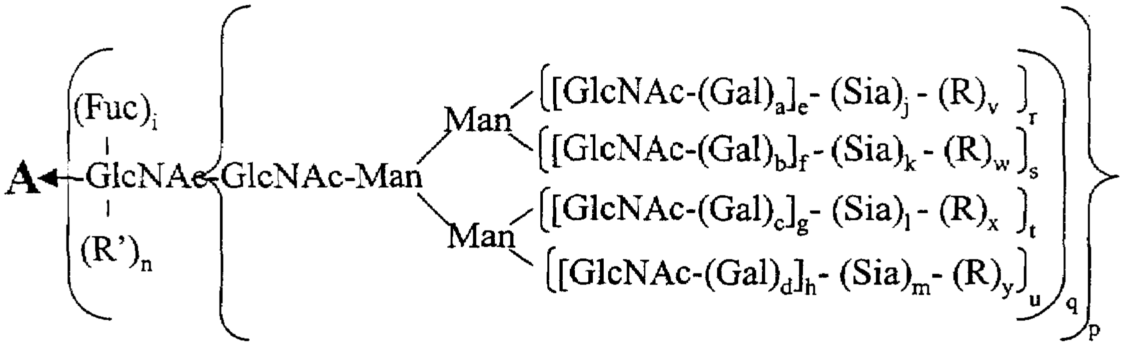
a-d, i, n, p-u (independently selected) = 0 or 1.
e-h (independently selected) = 0 to 6.
j-m (independently selected) = 0 to 100.
v-y = 0;
R = modifying group, mannose, oligo-mannose;
R' = H, glycosyl residue, modifying group, glycoconjugate.
FIG. 38G Insect or fungi cell expressed $\alpha_1$-antitrypsin.
a-d, f, h, j-m, s, u, v-y = 0;
e, g, i, q, r, t (independently selected) = 0 or 1.

1. GNT's 1,2,4,5, UDP-GlcNAc
2. Galactosyltransferase, UDP-Gal-PEG a-i, q-u (independently selected) = 0 or 1; j-m = 0;
v-y (independently selected) = 1,
when e-h (independently selected) is 1;
R = PEG.

FIG. 38H

Yeast expressed $\alpha_1$-antitrypsin.
a-m = 0; q-y (independently selected) = 0 to 1;
p = 1; R (branched or linear) = Man, oligomannose.

1. Endoglycanase
2. Galactosyltransferase, UDP-Gal
3. CMP-SA-PEG, ST3Gal3 a-m, p-y = 0; n (independently selected) = 0 or 1;
R' = -Gal-Sia-PEG.

FIG. 38I

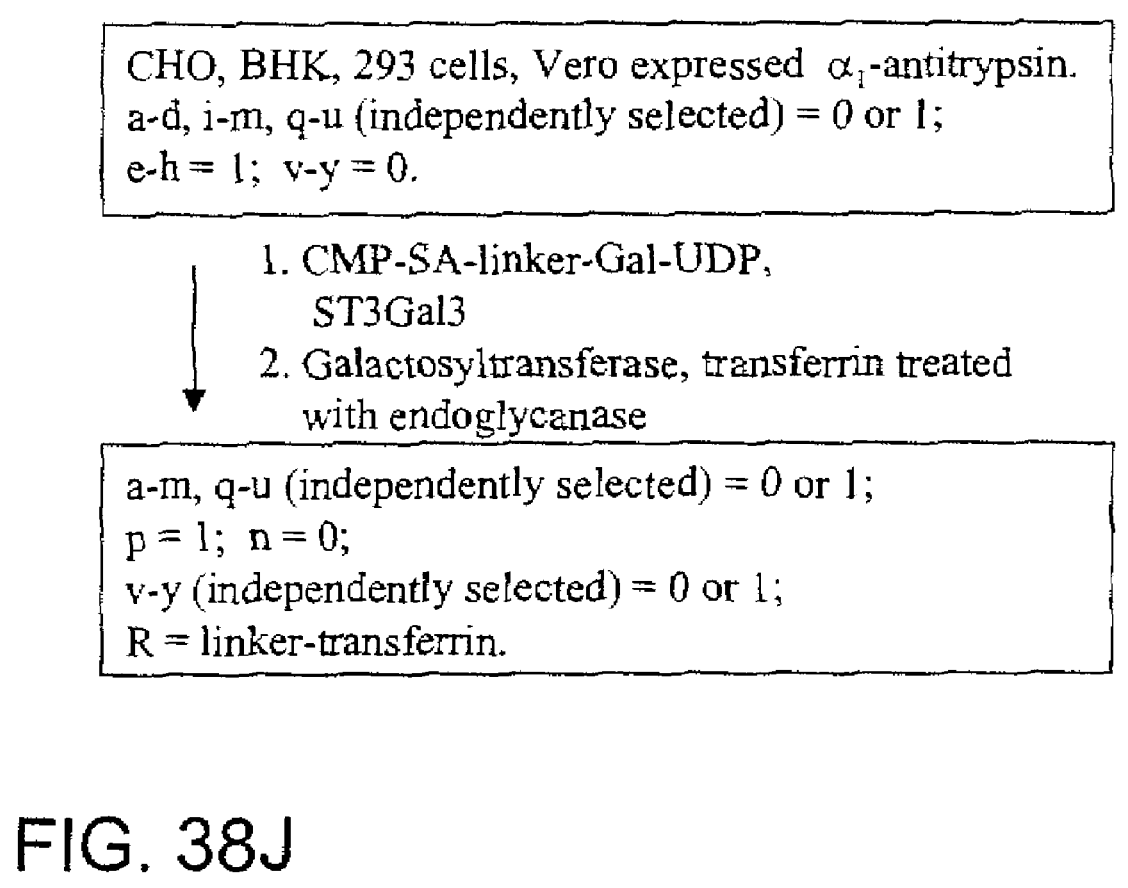

CHO, BHK, 293 cells, Vero expressed $\alpha_1$-antitrypsin.
a-d, i-m, q-u (independently selected) = 0 or 1;
e-h = 1; v-y = 0.

1. CMP-SA-linker-Gal-UDP, ST3Gal3
2. Galactosyltransferase, transferrin treated with endoglycanase a-m, q-u (independently selected) = 0 or 1;
p = 1; n = 0;
v-y (independently selected) = 0 or 1;
R = linker-transferrin.

FIG. 38J

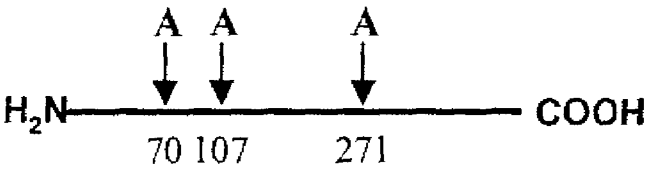
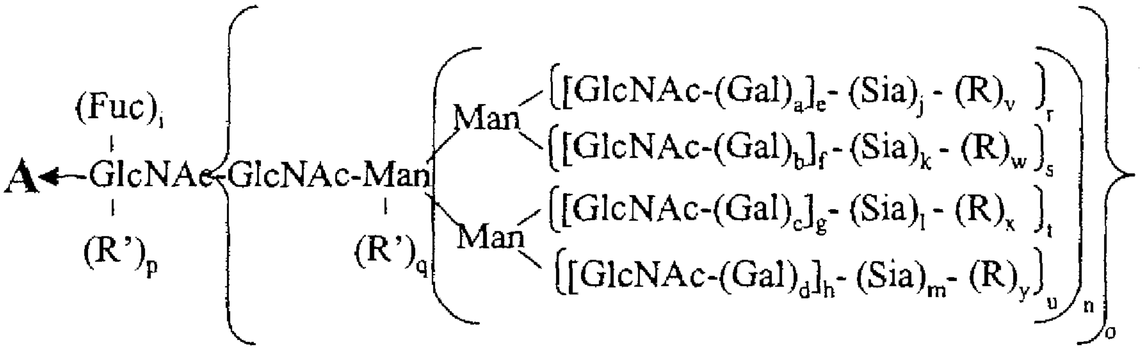
a-d, i, n-u (independently selected) = 0 or 1.
e-h (independently selected) = 0 to 4.
j-m (independently selected) = 0 to 20.
R = polymer;
R', R" (independently selected) = sugar, glycoconjugate.
FIG. 38K Yeast expressed alpha-1 antitrypsin.
a-h, i-m, p, q = 0;
R (independently selected) = mannose, oligomannose, polymannose;
r-u, v-y (independently selected) = 0 or 1; n, o = 1.

1. endoglycanase
2. Galactosyltransferase, UDP-Gal-PEG a-h, i-o, q, r-u, v-y = 0; p = 1.
R" = Gal-PEG.

FIG. 38L

Plant expressed alpha-1 antitrypsin.
a-d, f, h, j- m, s, u , v-y = 0;
e, g, i, q, r, t (independently selected) = 0 or 1;
n = 1; R' = xylose 1. hexosaminidase,
2. alpha mannosidase and xylosidase
3. GlcNAc transferase, UDP-GlcNAc-PEG a-d, f, h, j-n, s, u , v-y = 0;
e, g, i, r, t (independently selected) = 0;
q = 1; R' = GlcNAc-PEG.

FIG. 38M

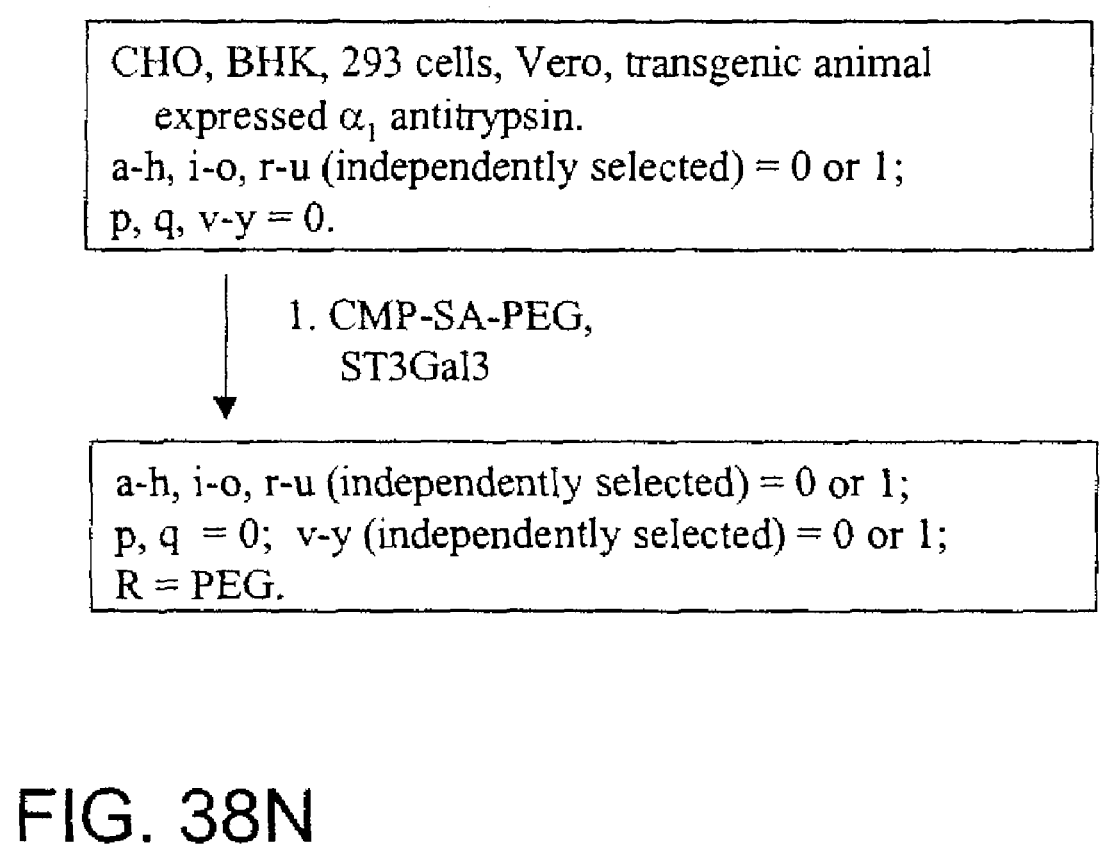

CHO, BHK, 293 cells, Vero, transgenic animal expressed $\alpha_1$ antitrypsin.
a-h, i-o, r-u (independently selected) = 0 or 1;
p, q, v-y = 0.

1. CMP-SA-PEG, ST3Gal3 a-h, i-o, r-u (independently selected) = 0 or 1;
p, q = 0; v-y (independently selected) = 0 or 1;
R = PEG.

FIG. 38N

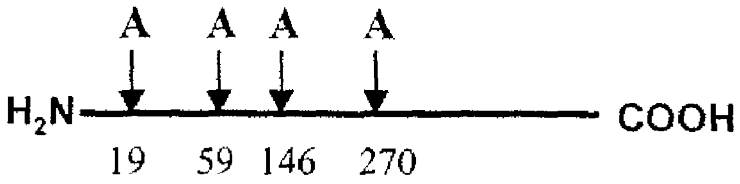
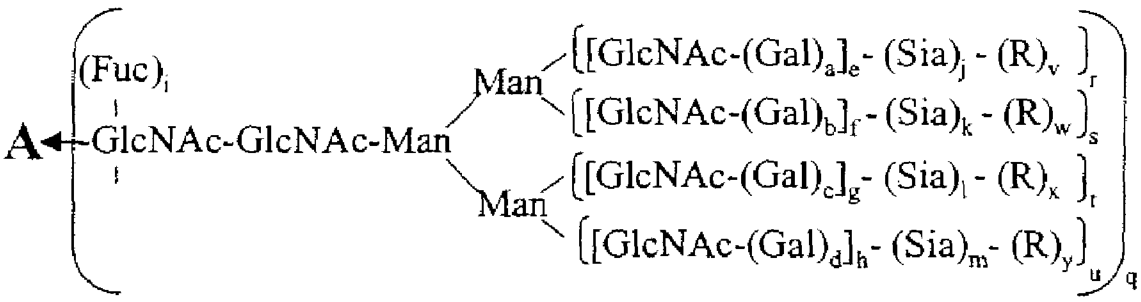
a-d, i, q-u (independently selected) = 0 or 1.
e-h (independently selected) = 0 to 6.
j-m (independently selected) = 0 to 100.
v-y = 0; R = polymer.
FIG. 39A CHO, BHK, 293 cells, Vero expressed Cerezyme
a-d, i-m, q-u (independently selected) = 0 or 1;
e-h = 1; v-y = 0.

1. Sialidase
2. CMP-SA-PEG (16 mol eq), ST3Gal3 a-d, i-m, q-u (independently selected) = 0 or 1;
e-h = 1; v-y (independently selected) = 1, when j-m (independently selected) is 1;
R = PEG.

FIG. 39B

CHO, BHK, 293 cells, Vero expressed Cerezyme.
a-d, i-m, q-u (independently selected) = 0 or 1;
e-h = 1; v-y = 0.

1. Sialidase
2. CMP-SA-M-6-P (1.2 mol eq), ST3Gal3
3. CMP-SA (16 mol eq), ST3Gal3 a-d, i-m, q-u (independently selected) = 0 or 1;
e-h = 1; v-y (independently selected) = 0 or 1;
R = mannose-6-phosphate

FIG. 39C

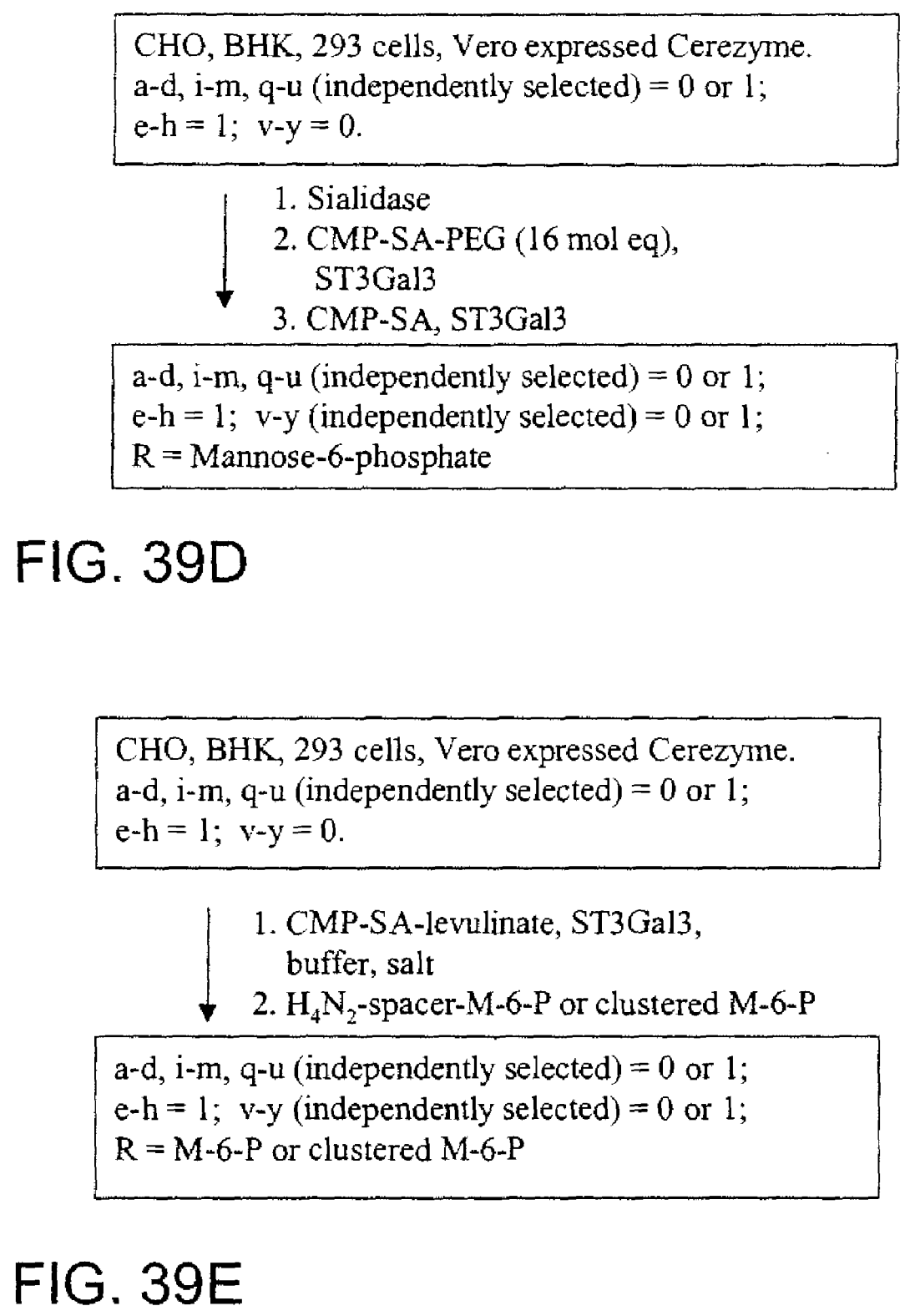

CHO, BHK, 293 cells, Vero expressed Cerezyme.
a-d, i-m, q-u (independently selected) = 0 or 1;
e-h = 1; v-y = 0.

↓
1. Sialidase
2. CMP-SA-PEG (16 mol eq), ST3Gal3
3. CMP-SA, ST3Gal3 a-d, i-m, q-u (independently selected) = 0 or 1;
e-h = 1; v-y (independently selected) = 0 or 1;
R = Mannose-6-phosphate

FIG. 39D

CHO, BHK, 293 cells, Vero expressed Cerezyme.
a-d, i-m, q-u (independently selected) = 0 or 1;
e-h = 1; v-y = 0.

↓
1. CMP-SA-levulinate, ST3Gal3, buffer, salt
2. $H_4N_2$-spacer-M-6-P or clustered M-6-P a-d, i-m, q-u (independently selected) = 0 or 1;
e-h = 1; v-y (independently selected) = 0 or 1;
R = M-6-P or clustered M-6-P

FIG. 39E

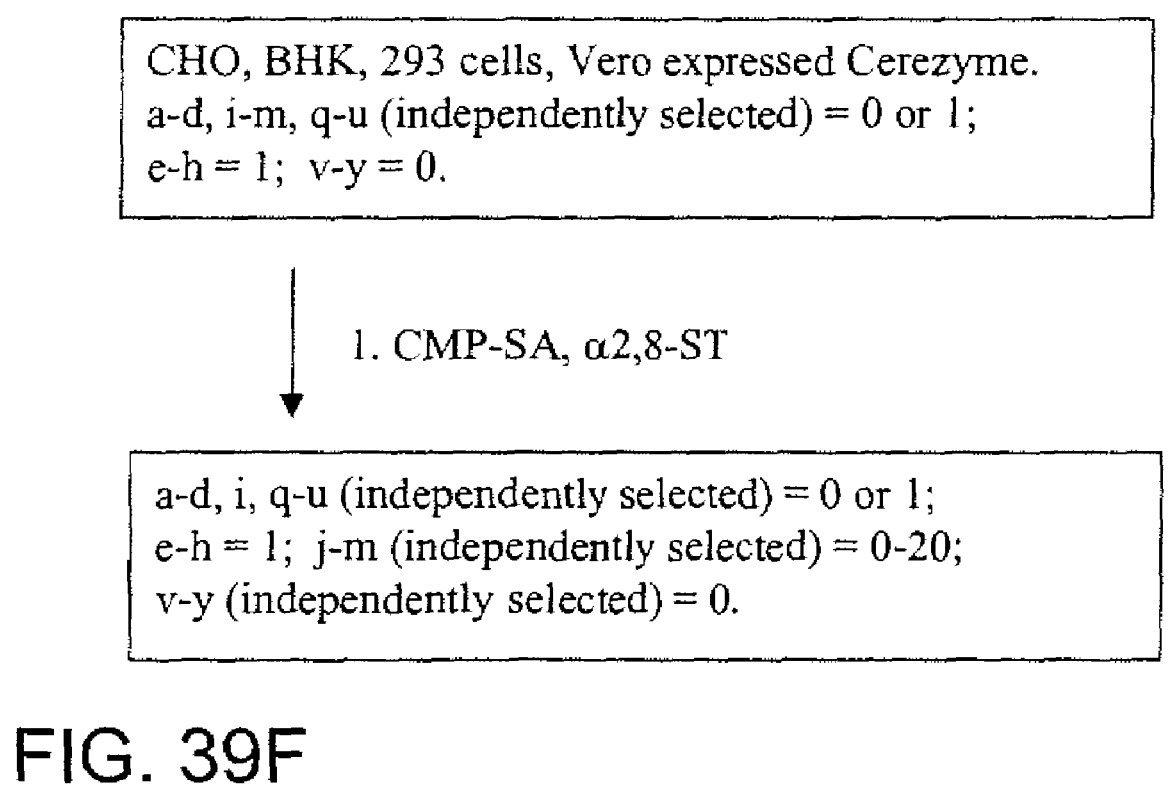

CHO, BHK, 293 cells, Vero expressed Cerezyme.
a-d, i-m, q-u (independently selected) = 0 or 1;
e-h = 1; v-y = 0.

↓ 1. CMP-SA, α2,8-ST a-d, i, q-u (independently selected) = 0 or 1;
e-h = 1; j-m (independently selected) = 0-20;
v-y (independently selected) = 0.

FIG. 39F

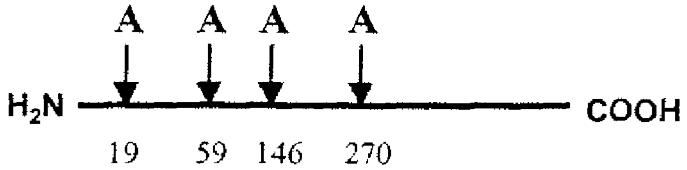
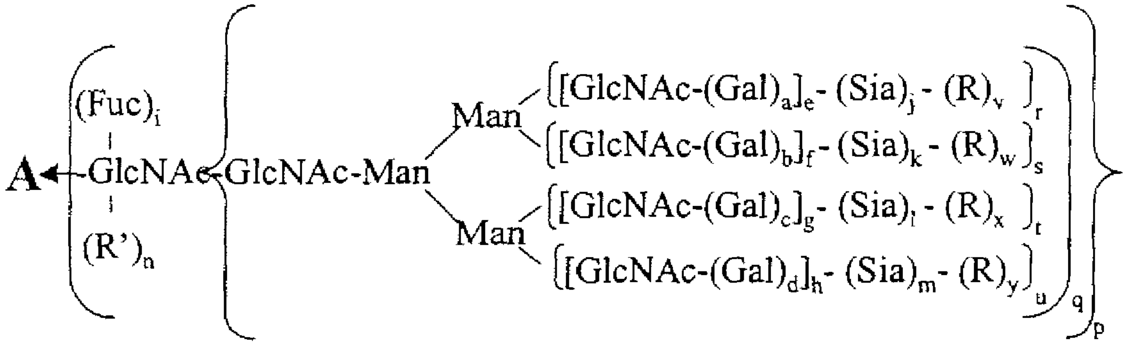
a-d, i, n, p-u (independently selected) = 0 or 1.
e-h (independently selected) = 0 to 6.
j-m (independently selected) = 0 to 100.
v-y = 0;
R = modifying group, mannose, oligo-mannose;
R' = H, glycosyl residue, modifying group, glycoconjugate.
FIG. 39G Insect cell expressed Cerezyme.
a-d, f, h, j-m, s, u, v-y = 0;
e, g, i, q, r, t (independently selected) = 0 or 1.

↓
1. GNT's 1,2,4,5, UDP-GlcNAc
2. Galactosyltransferase, UDP-Gal-PEG a-i, q-u (independently selected) = 0 or 1;
j-m = 0;
v-y (independently selected) = 1,
when e-h (independently selected) is 1;
R = PEG.

FIG. 39H

Yeast expressed Cerezyme.
a-m = 0; q-y (independently selected) = 0 to 1;
p = 1; R (branched or linear) = Man, oligomannose.

↓
1. Endoglycanase
2. Galactosyltransferase, UDP-Gal
3. CMP-SA-PEG, ST3Gal3 a-m, p-y = 0; n (independently selected) = 0 or 1;
R' = -Gal-Sia-PEG.

FIG. 39I

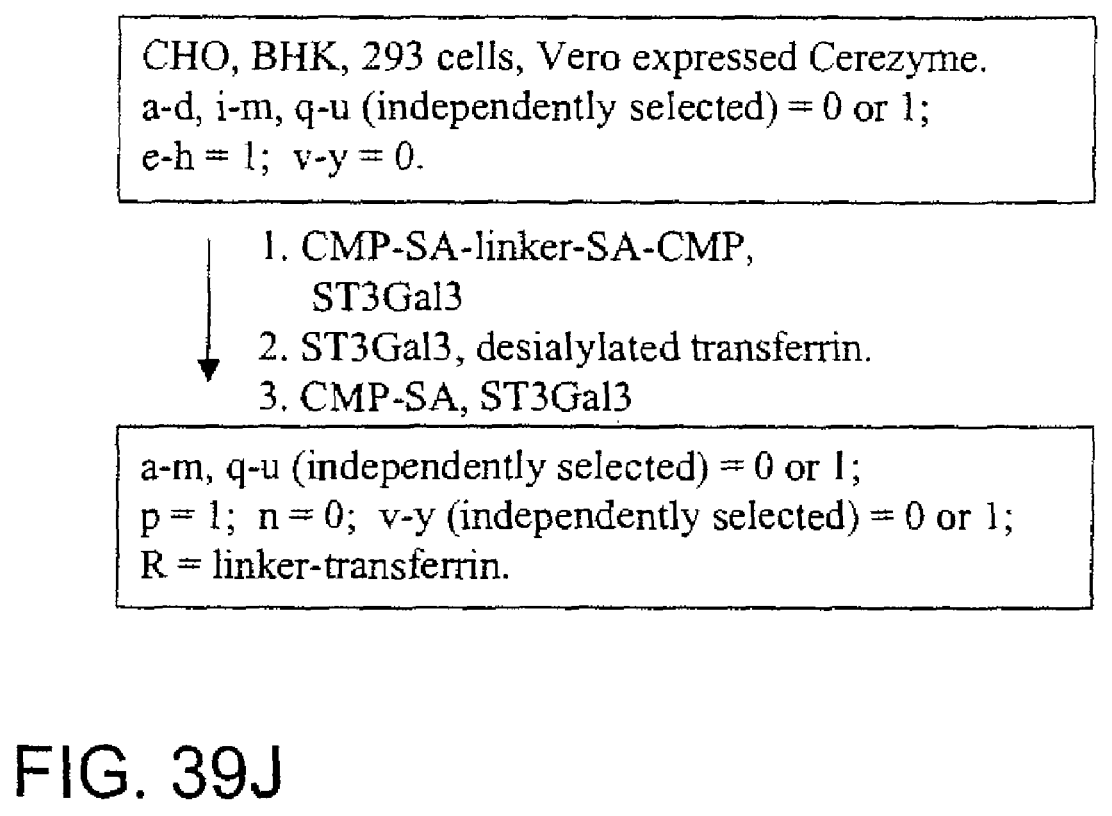

CHO, BHK, 293 cells, Vero expressed Cerezyme.
a-d, i-m, q-u (independently selected) = 0 or 1;
e-h = 1; v-y = 0.

1. CMP-SA-linker-SA-CMP,
   ST3Gal3
2. ST3Gal3, desialylated transferrin.
3. CMP-SA, ST3Gal3 a-m, q-u (independently selected) = 0 or 1;
p = 1; n = 0; v-y (independently selected) = 0 or 1;
R = linker-transferrin.

FIG. 39J

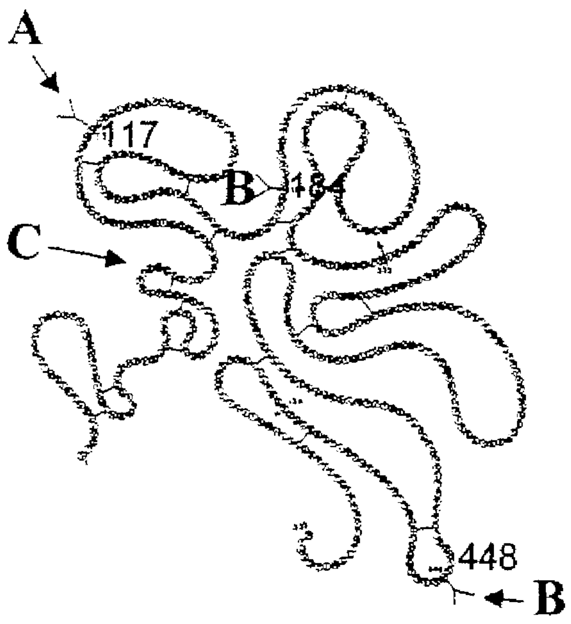
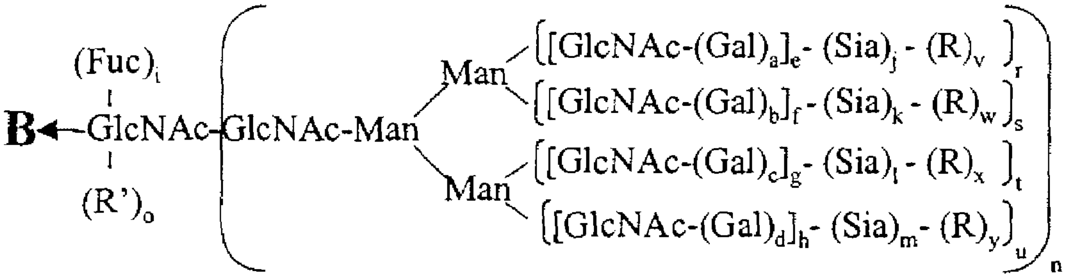
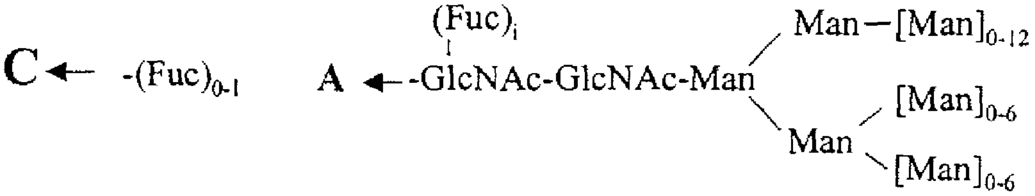
a-d, i, n-u (independently selected) = 0 or 1.
e-h (independently selected) = 0 to 4.
j-m (independently selected) = 0 to 20.
R = polymer; R' = sugar, glycoconjugate.
FIG. 40A CHO, BHK, 293 cells, Vero expressed tPA
a-g, n = 1; h = 1 to 3;
j-m, i, (independently selected) = 0 or 1;
r-u (independently selected) = 0 to 1; o, v-y = 0.

1. Mannosidase(s), sialidase
2. GNT1,2 (4 and/or 5) UDP-GlcNAc
3. Gal transferase, UDP-Gal
4. CMP-SA-PEG, ST3Gal3

A = B; a-g, n = 1; h = 1 to 3;
i, r-u (independently selected) = 0 or 1;
o = 0; j-m, v-y (independently selected) = 0 or 1;
R = PEG

FIG. 40B

Insect or fungi cell expressed tPA
A = B; a-d, f, h, j-o, s, u, v-y = 0;
e, g, i, n, r, t (independently selected) = 0 or 1.

1. GNT's 1&2, UDP-GlcNAc
2. Galactosyltransferase, UDP-Gal
3. CMP-SA-PEG, ST3Gal3

A = B; b, d, f, h, k, m, o, s, u, w, y = 0;
a, c, e, g, i, r, t (independently selected) = 0 or 1;
n = 1; j, l, v, x (independently selected) = 0 or 1;
R = PEG.

FIG. 40C

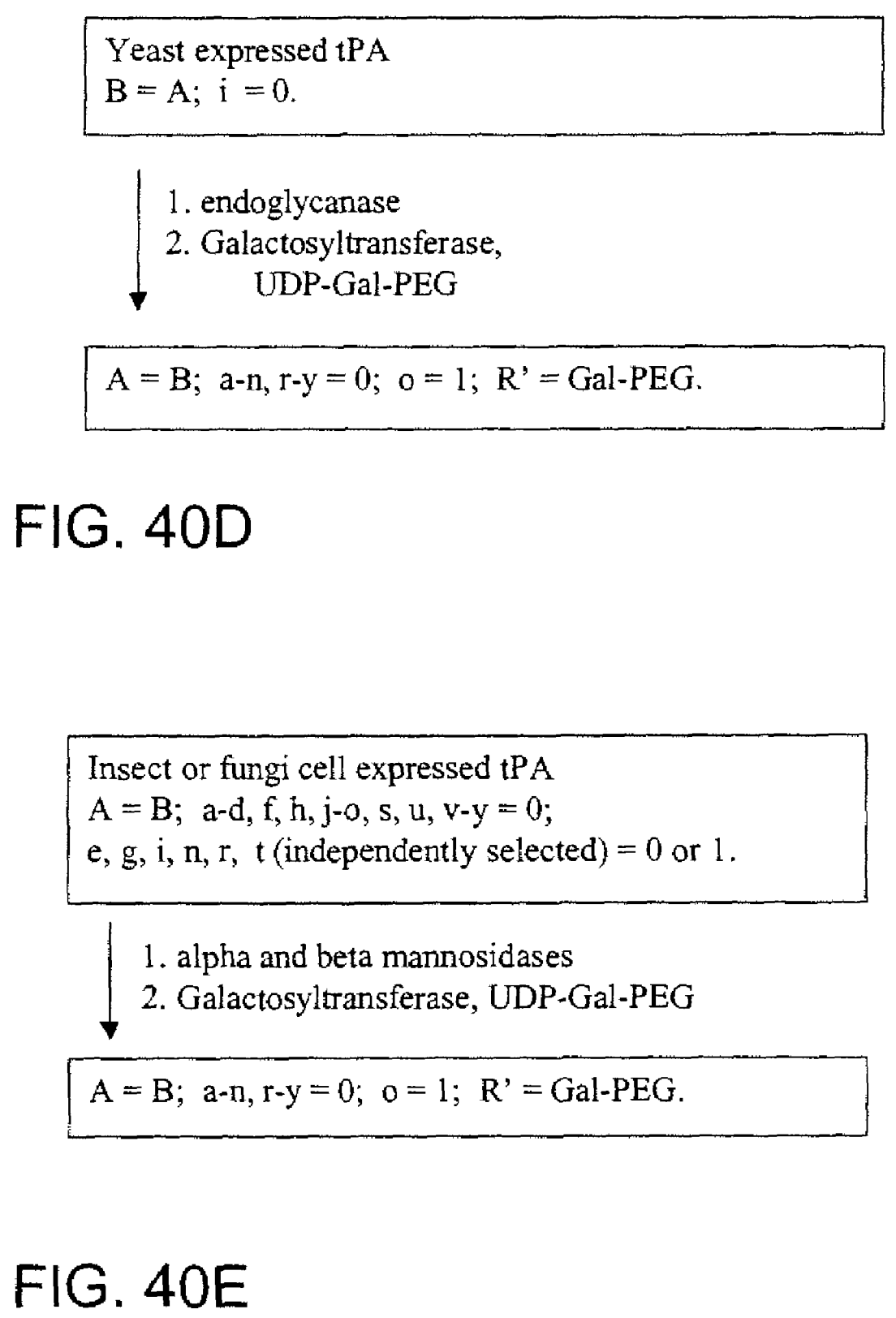

Yeast expressed tPA
B = A; i = 0.

1. endoglycanase
2. Galactosyltransferase,
UDP-Gal-PEG

A = B; a-n, r-y = 0; o = 1; R' = Gal-PEG.

FIG. 40D

Insect or fungi cell expressed tPA
A = B; a-d, f, h, j-o, s, u, v-y = 0;
e, g, i, n, r, t (independently selected) = 0 or 1.

1. alpha and beta mannosidases
2. Galactosyltransferase, UDP-Gal-PEG

A = B; a-n, r-y = 0; o = 1; R' = Gal-PEG.

FIG. 40E

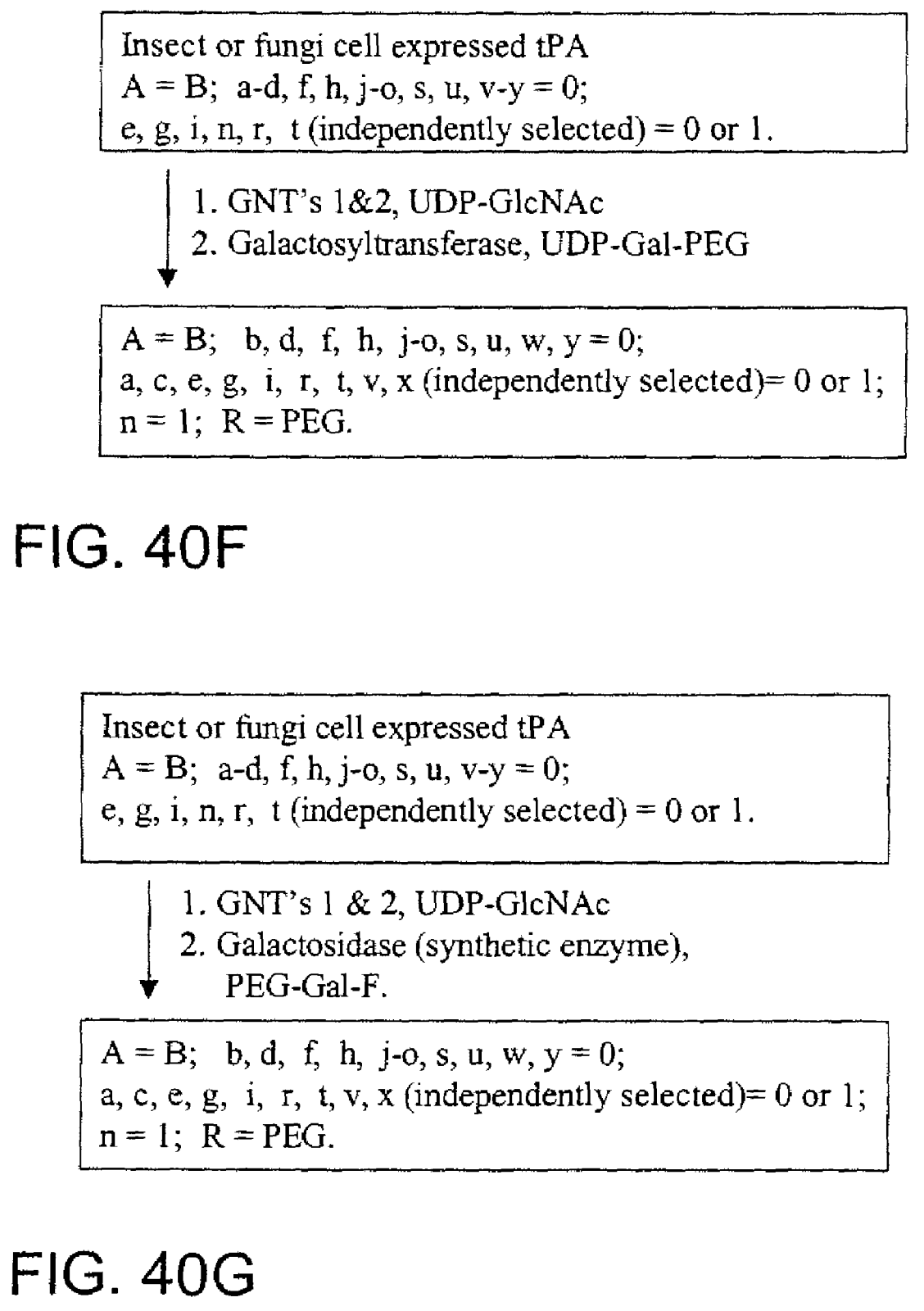

Insect or fungi cell expressed tPA
A = B; a-d, f, h, j-o, s, u, v-y = 0;
e, g, i, n, r, t (independently selected) = 0 or 1.

1. GNT's 1&2, UDP-GlcNAc
2. Galactosyltransferase, UDP-Gal-PEG

A = B; b, d, f, h, j-o, s, u, w, y = 0;
a, c, e, g, i, r, t, v, x (independently selected)= 0 or 1;
n = 1; R = PEG.

FIG. 40F

Insect or fungi cell expressed tPA
A = B; a-d, f, h, j-o, s, u, v-y = 0;
e, g, i, n, r, t (independently selected) = 0 or 1.

1. GNT's 1 & 2, UDP-GlcNAc
2. Galactosidase (synthetic enzyme), PEG-Gal-F.

A = B; b, d, f, h, j-o, s, u, w, y = 0;
a, c, e, g, i, r, t, v, x (independently selected)= 0 or 1;
n = 1; R = PEG.

FIG. 40G

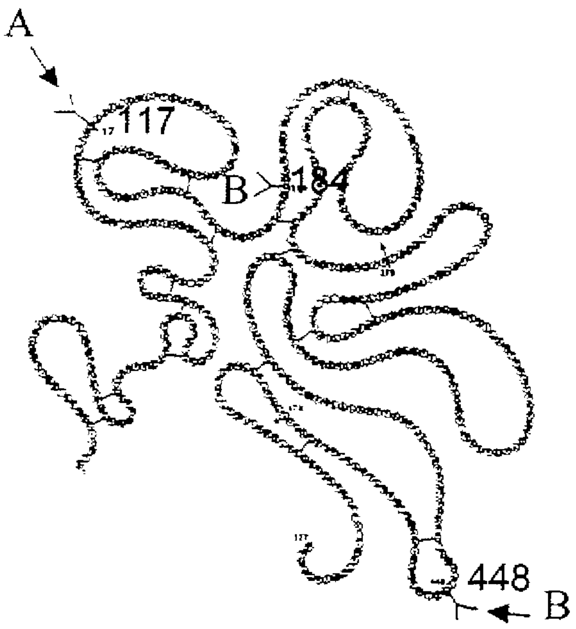
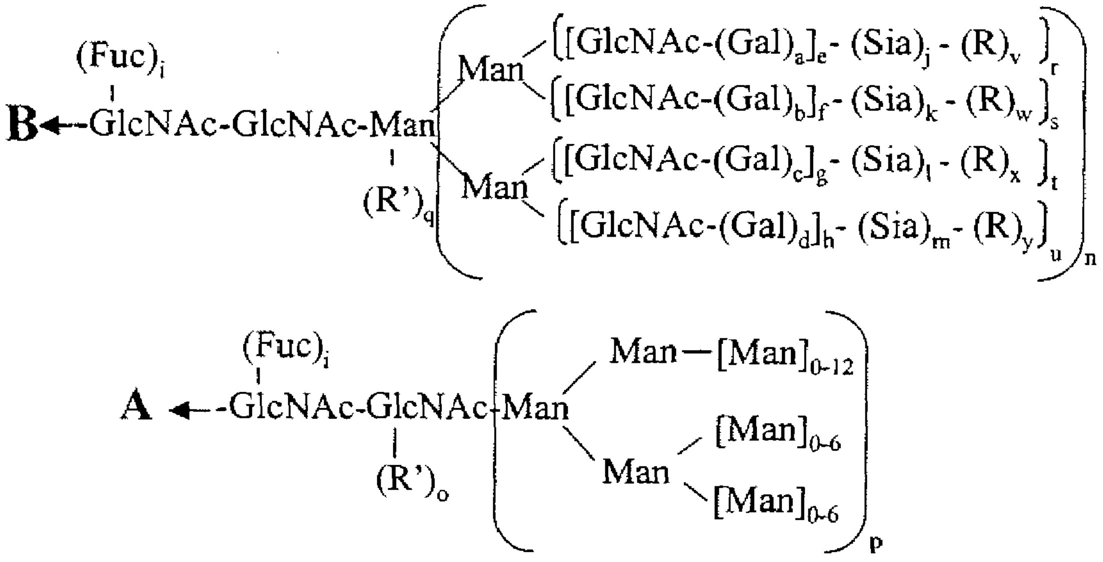
a-d, i, n-u (independently selected) = 0 or 1.
e-h (independently selected) = 0 to 4.
j-m (independently selected) = 0 to 20.
R = polymer; R' = sugar, glycoconjugate.
FIG. 40H NSO expressed tPA
A = B; a-m, r-u (independently selected) = 0 or 1;
n = 1; o, p, q, v-y = 0

1. sialidase, alpha-galactosidase
2. CMP-SA-levulinate, ST3Gal3,
3. $H_4N_2$-PEG A = B; a-m, r-y (independently selected) = 0 or 1;
n = 1; o, p, q = 0;
v-y (independently selected) = 1,
when j-m (independently selected) is 1;
R = PEG.

FIG. 40I

CHO, BHK, 293 cells, Vero expressed tPA
a-g, n, p = 1; h = 1 to 3;
j-m, i, (independently selected) = 0 or 1;
r-u (independently selected) = 0 to 1; q, o, v-y = 0.

1. alpha and beta Mannosidases
2. CMP-SA, ST3Gal3
3. Galactosyltransferase, UDP-Gal-PEG a-g, n = 1; h = 1 to 3;
i, r-u (independently selected) = 0 or 1; o = 1;
q, p, v-y = 0; j-m (independently selected) = 0 or 1;
R' = Gal-PEG

FIG. 40J

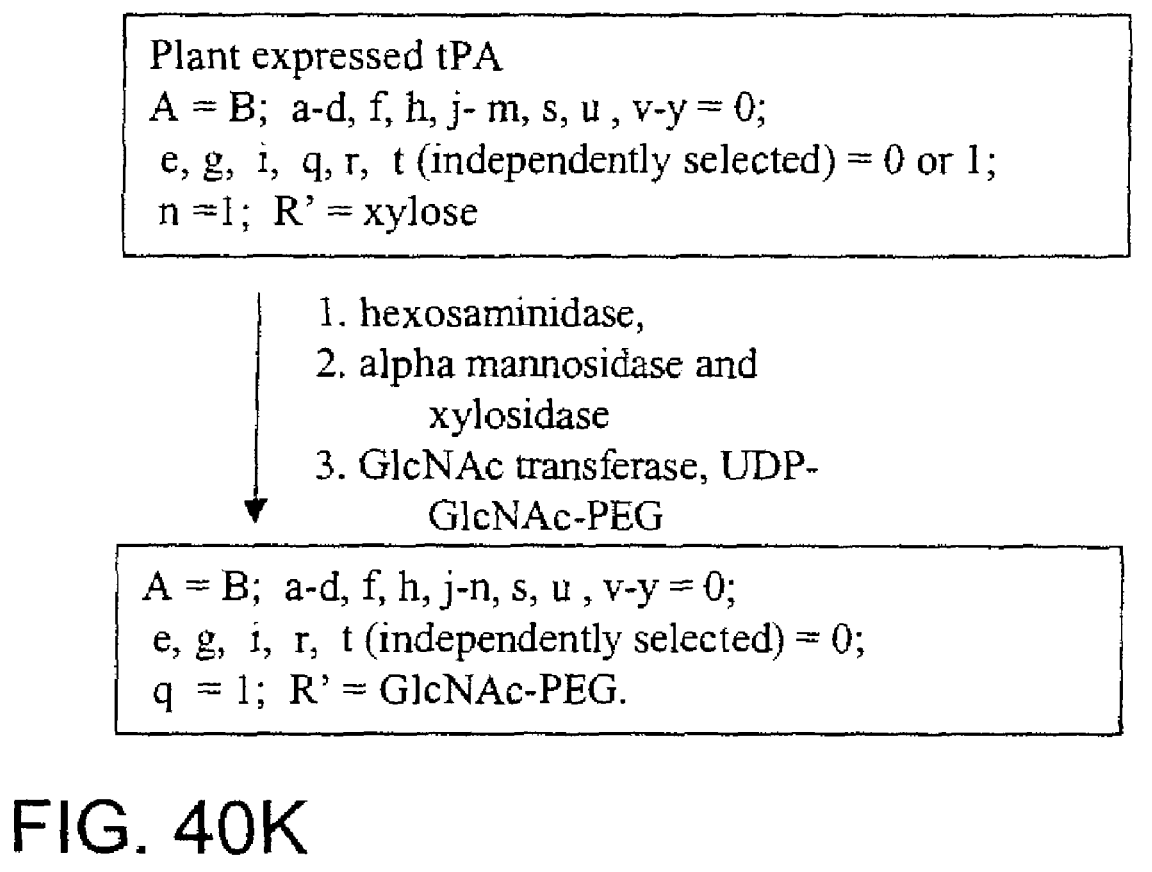

Plant expressed tPA
A = B; a-d, f, h, j- m, s, u , v-y = 0;
e, g, i, q, r, t (independently selected) = 0 or 1;
n =1; R' = xylose 1. hexosaminidase,
2. alpha mannosidase and xylosidase
3. GlcNAc transferase, UDP-GlcNAc-PEG A = B; a-d, f, h, j-n, s, u , v-y = 0;
e, g, i, r, t (independently selected) = 0;
q = 1; R' = GlcNAc-PEG.

FIG. 40K

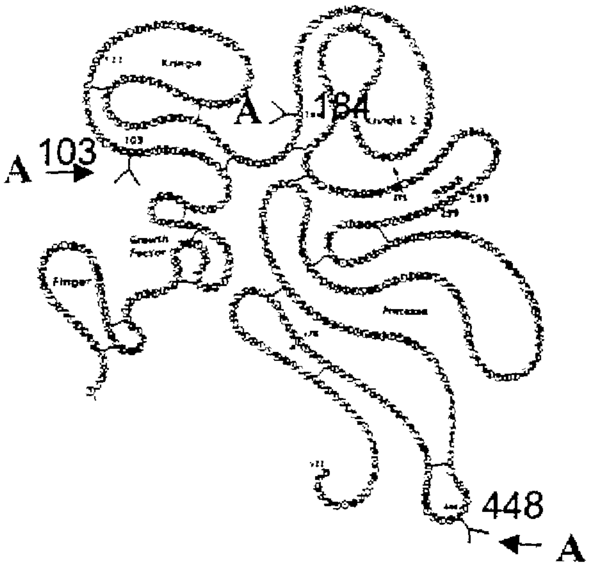
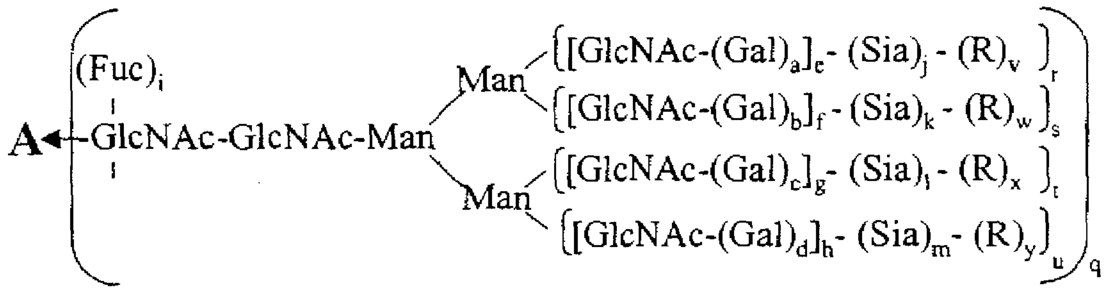
a-d, i, q-u (independently selected) = 0 or 1.
e-h (independently selected) = 0 to 6.
j-m (independently selected) = 0 to 100.
v-y = 0; R = polymer.
FIG. 40L CHO, BHK, 293 cells, Vero expressed TNK tPA
a-d, i-m, q-u (independently selected) = 0 or 1;
e-h = 1; v-y = 0.

1. Sialidase
2. CMP-SA-PEG (16 mol eq),
ST3Gal3 a-d, i-m, q-u (independently selected) = 0 or 1;
e-h = 1; v-y (independently selected) = 1,
when j-m (independently selected) is 1;
R = PEG.

FIG. 40M

CHO, BHK, 293 cells, Vero expressed TNK tPA
a-d, i-m, q-u (independently selected) = 0 or 1;
e-h = 1; v-y = 0.

1. Sialidase
2. CMP-SA-PEG (1.2 mol eq),
ST3Gal3
3. CMP-SA (16 mol eq), ST3Gal3 a-d, i-m, q-u (independently selected) = 0 or 1;
e-h = 1; v-y (independently selected) = 0 or 1;
R = PEG.

FIG. 40N

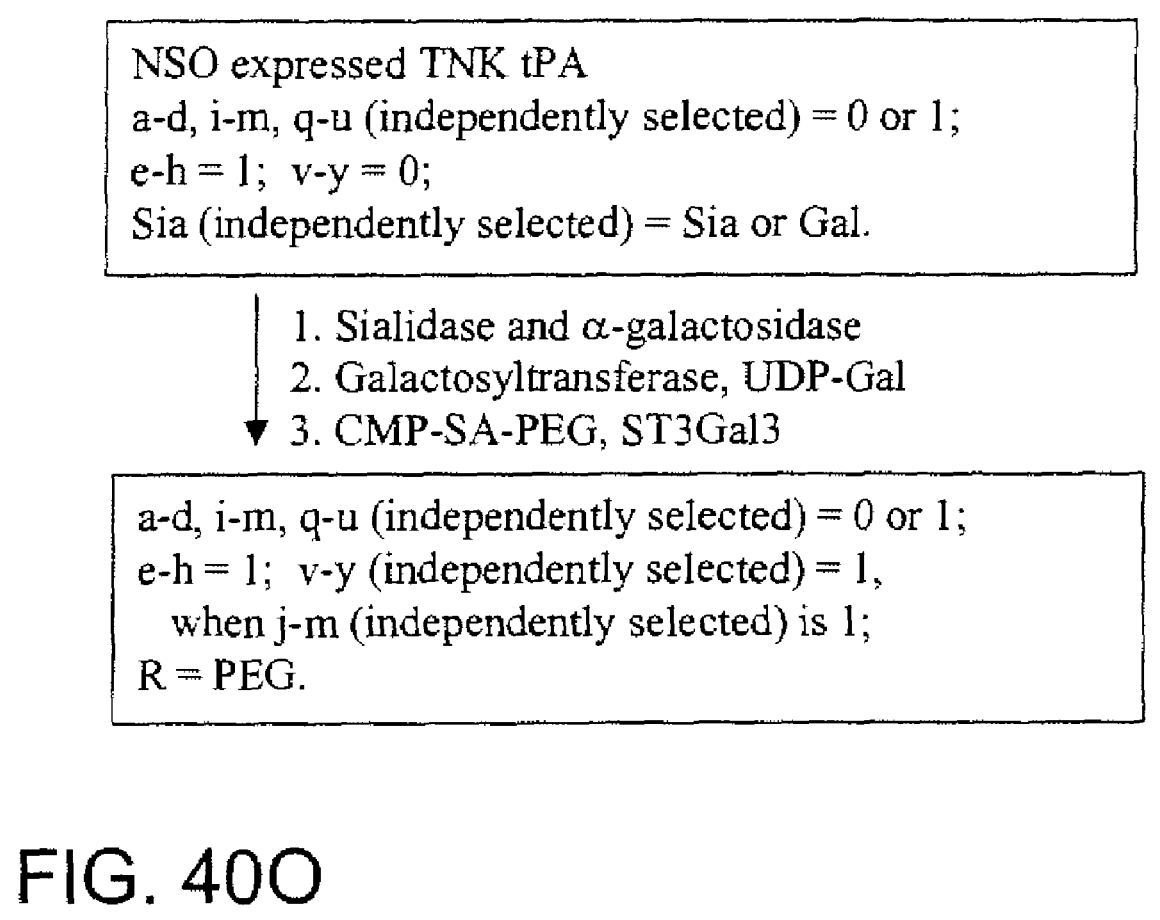

NSO expressed TNK tPA
a-d, i-m, q-u (independently selected) = 0 or 1;
e-h = 1; v-y = 0;
Sia (independently selected) = Sia or Gal.

1. Sialidase and α-galactosidase
2. Galactosyltransferase, UDP-Gal
3. CMP-SA-PEG, ST3Gal3 a-d, i-m, q-u (independently selected) = 0 or 1;
e-h = 1; v-y (independently selected) = 1,
when j-m (independently selected) is 1;
R = PEG.

FIG. 40O

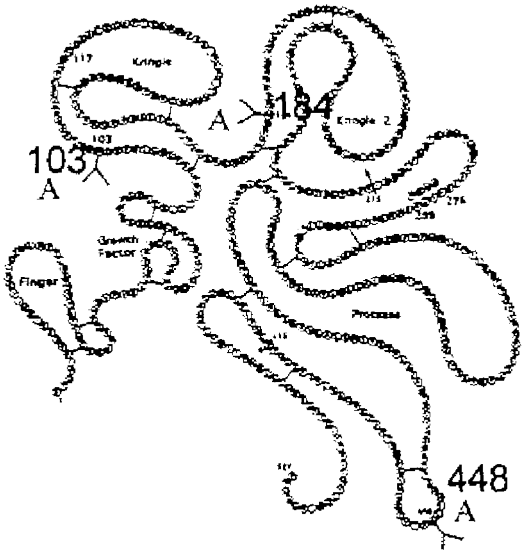
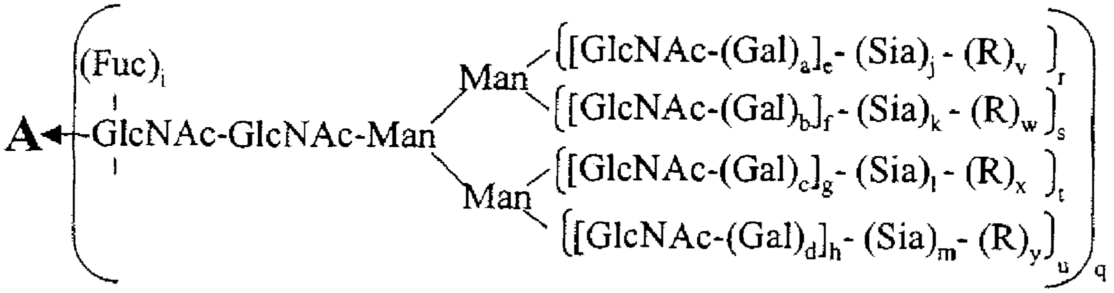
a-d, i, q-u (independently selected) = 0 or 1.
e-h (independently selected) = 0 to 6.
j-m (independently selected) = 0 to 100.
v-y = 0; R = polymer.
FIG. 40P CHO, BHK, 293 cells, Vero expressed TNK tPA
a-d, i-m, q-u (independently selected) = 0 or 1;
e-h = 1; v-y = 0.

1. Sialidase
2. CMP-SA-PEG (16 mol eq), ST3Gal3
3. CMP-SA, ST3Gal3 a-d, i-m, q-u (independently selected) = 0 or 1;
e-h = 1; v-y (independently selected) = 0 or 1;
R = PEG.

FIG. 40Q

CHO, BHK, 293 cells, Vero expressed TNK tPA
a-d, i-m, q-u (independently selected) = 0 or 1;
e-h = 1; v-y = 0.

1. CMP-SA-levulinate, ST3Gal3, buffer, salt
2. $H_4N_2$-PEG a-d, i-m, q-u (independently selected) = 0 or 1;
e-h = 1; v-y (independently selected) = 0 or 1;
R = PEG.

FIG. 40R

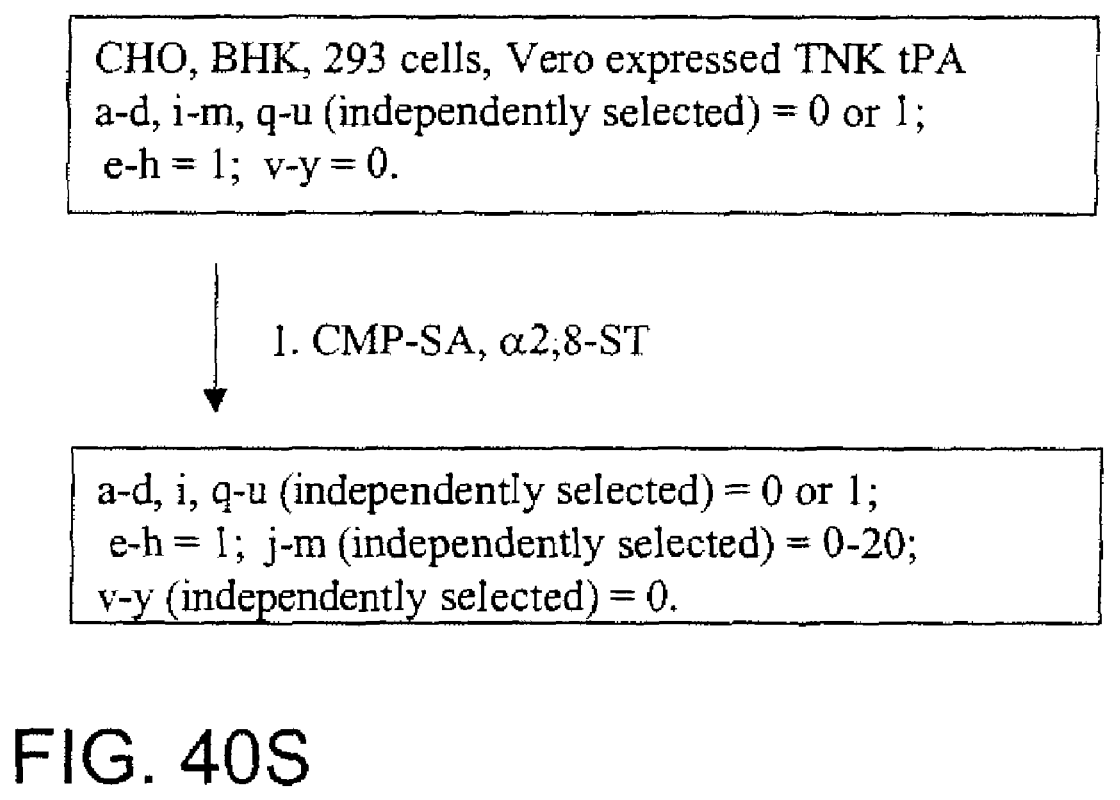

CHO, BHK, 293 cells, Vero expressed TNK tPA
a-d, i-m, q-u (independently selected) = 0 or 1;
e-h = 1; v-y = 0.

1. CMP-SA, α2;8-ST a-d, i, q-u (independently selected) = 0 or 1;
e-h = 1; j-m (independently selected) = 0-20;
v-y (independently selected) = 0.

FIG. 40S

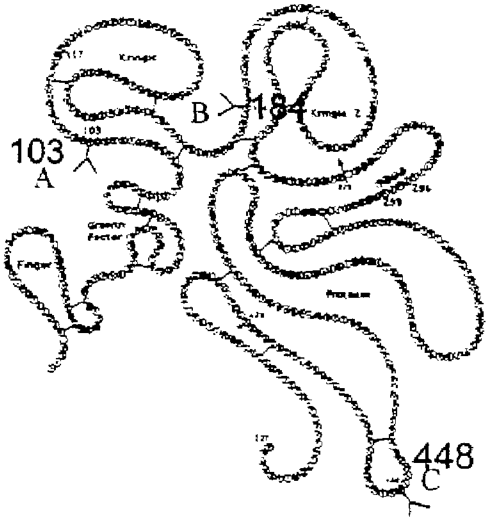
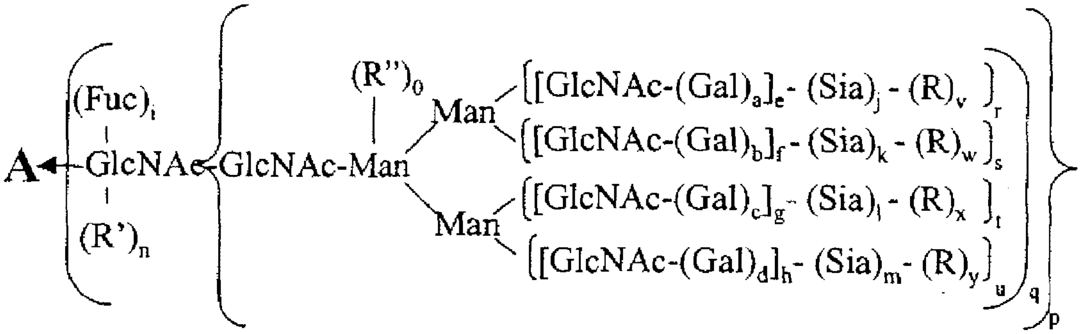
a-d, i, n-y (independently selected) = 0 or 1.
e-h (independently selected) = 0 to 6.
j-m (independently selected) = 0 to 100.
R = modifying group, mannose, oligo-mannose;
R' = H, glycosyl residue, modifying group, glycoconjugate.
R" = glycosyl residue.
FIG. 40T Insect cell expressed TNK tPA
a-d, f, h, j-m, s, u, v-y = 0;
e, g, i, q, r, t (independently selected) = 0 or 1.

1. GNT's 1,2,4,5, UDP-GlcNAc
2. Galactosyltransferase, UDP-Gal-PEG a-i, q-u (independently selected) = 0 or 1;
j-m = 0; v-y (independently selected) = 1,
when e-h (independently selected) is 1;
R = PEG.

FIG. 40U

Yeast expressed TNK tPA
a-m = 0; q-y (independently selected) = 0 to 1; p = 1;
R (branched or linear) = Man, oligomannose.

1. Endoglycanase
2. Galactosyltransferase, UDP-Gal-PEG a-m, p-y = 0; n (independently selected) = 0 or 1;
R' = -Gal-PEG.

FIG. 40V

Figure 40W:
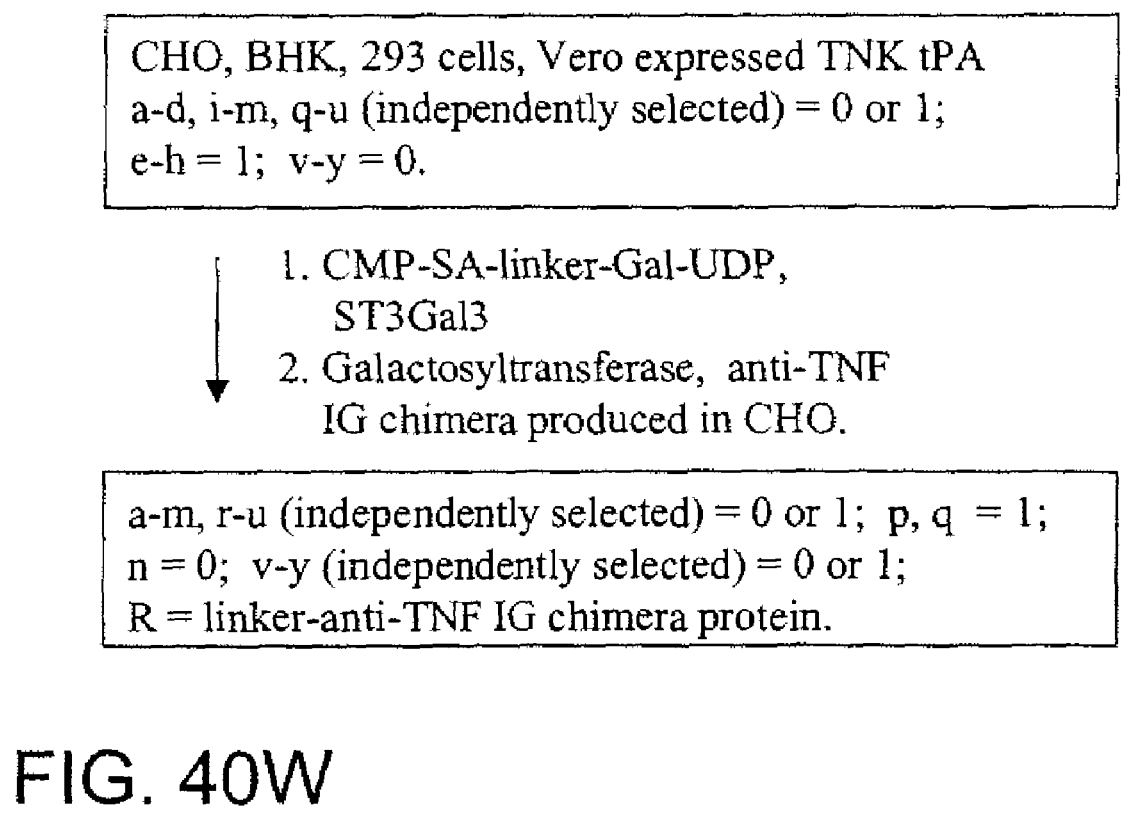

CHO, BHK, 293 cells, Vero expressed TNK tPA
a-d, i-m, q-u (independently selected) = 0 or 1;
e-h = 1; v-y = 0.

1. CMP-SA-linker-Gal-UDP, ST3Gal3
2. Galactosyltransferase, anti-TNF IG chimera produced in CHO.

a-m, r-u (independently selected) = 0 or 1; p, q = 1;
n = 0; v-y (independently selected) = 0 or 1;
R = linker-anti-TNF IG chimera protein.

FIG. 40W a-c, e (independently selected) = 0 or 1;
d = 0;
R = modifying group, mannose, oligo-mannose.

CHO, BHK, 293 cells, Vero expressed IL-2
a-c, e (independently selected) = 0 or 1; d = 0

↓ 1. Sialidase
2. CMP-SA-PEG, ST3Gal1 a-d, e (independently selected) = 0 or 1;
R = PEG.

Insect cell expressed IL-2
a, e (independently selected) = 0 or 1;
b, c, d = 0.

↓ 1. Galactosyltransferase, UDP-Gal
2. CMP-SA-PEG, ST3Gal1 a, c, d, e (independently selected) = 0 or 1;
R = PEG.

2 peptides
A and A' - N-linked sites
B - O-linked sites
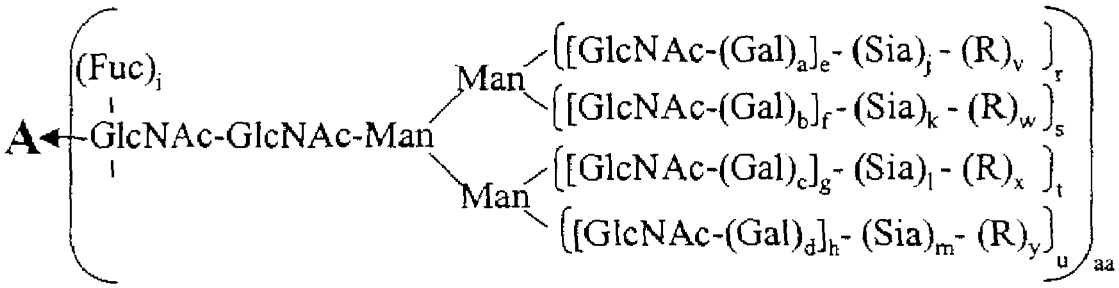
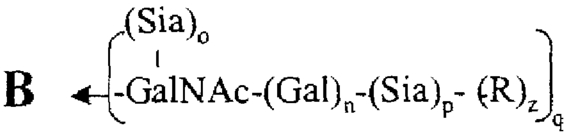
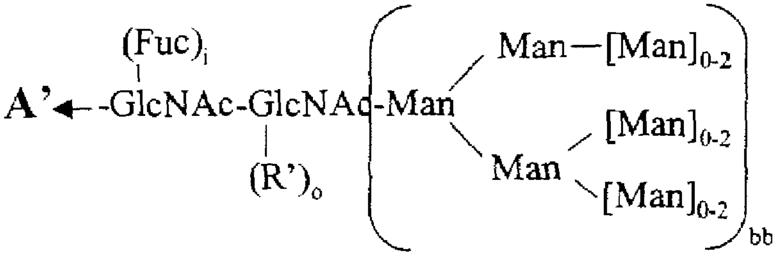
Alternate structure for some N-linked structures of A.
a-d, i, n-u (independently selected) = 0 or 1.
aa, bb (independently selected) = 0 or 1.
e-h (independently selected) = 0 to 6.
j-m (independently selected) = 0 to 20.
v-z = 0; R = polymer, glycoconjugate.
FIG. 42A CHO, BHK, 293s cells, Vero, MDCK, HEKC expressed Factor VIII.
e-h = 1 to 4;
aa, bb, a-d, j-m, i, n-u (independently selected) = 0 or 1;
v-z = 0.

1. Sialidase
2. CMP-SA-PEG, ST3Gal3 e-h = 1 to 4;
aa, bb, a-d, i, n, q-u (independently selected) = 0 or 1;
o, p, z = 0; j-m, v-y (independently selected) = 0 or 1;
R = PEG.

FIG. 42B

CHO, BHK, 293S cells, Vero, MDCK, 293S, HEKC expressed Factor VIII.
e-h = 1 to 4;
aa, bb, a-d, j-m, i, n-u (independently selected) = 0 or 1;
v-z = 0.

1. Sialidase
2. CMP-SA-PEG, ST3Gal3
3. ST3Gal1, CMP-SA e-h = 1 to 4;
aa, bb, a-d, i, n, p-u (independently selected) = 0 or 1;
o, z = 0; j-m, v-y (independently selected) = 0 or 1;
R = PEG.

FIG. 42C

CHO, BHK, 293s cells, Vero, MDCK, HEKC expressed Factor VIII.
e-h = 1 to 4;
aa, bb, a-d, j-m, i, n-u (independently selected)=0 or 1;
v-z = 0.

1. CMP-SA-PEG, ST3Gal3 e-h = 1 to 4;
aa, bb, a-d, i, n-u (independently selected) = 0 or 1;
z = 0; j-m, v-y (independently selected) = 0 or 1;
R = PEG.

FIG. 42D

CHO, BHK, 293S cells, Vero, MDCK, HEKC expressed Factor VIII.
e-h = 1 to 4;
aa, bb, a-d, j-m, i, n-u (independently selected) 0 or 1;
v-z = 0.

1. CMP-SA-PEG, ST3Gal1 e-h = 1 to 4;
aa, bb, a-d, i, n-u (independently selected) = 0 or 1;
z = 0; j-m, v-y (independently selected) = 0 or 1;
R = PEG.

FIG. 42E

Figure 42F:
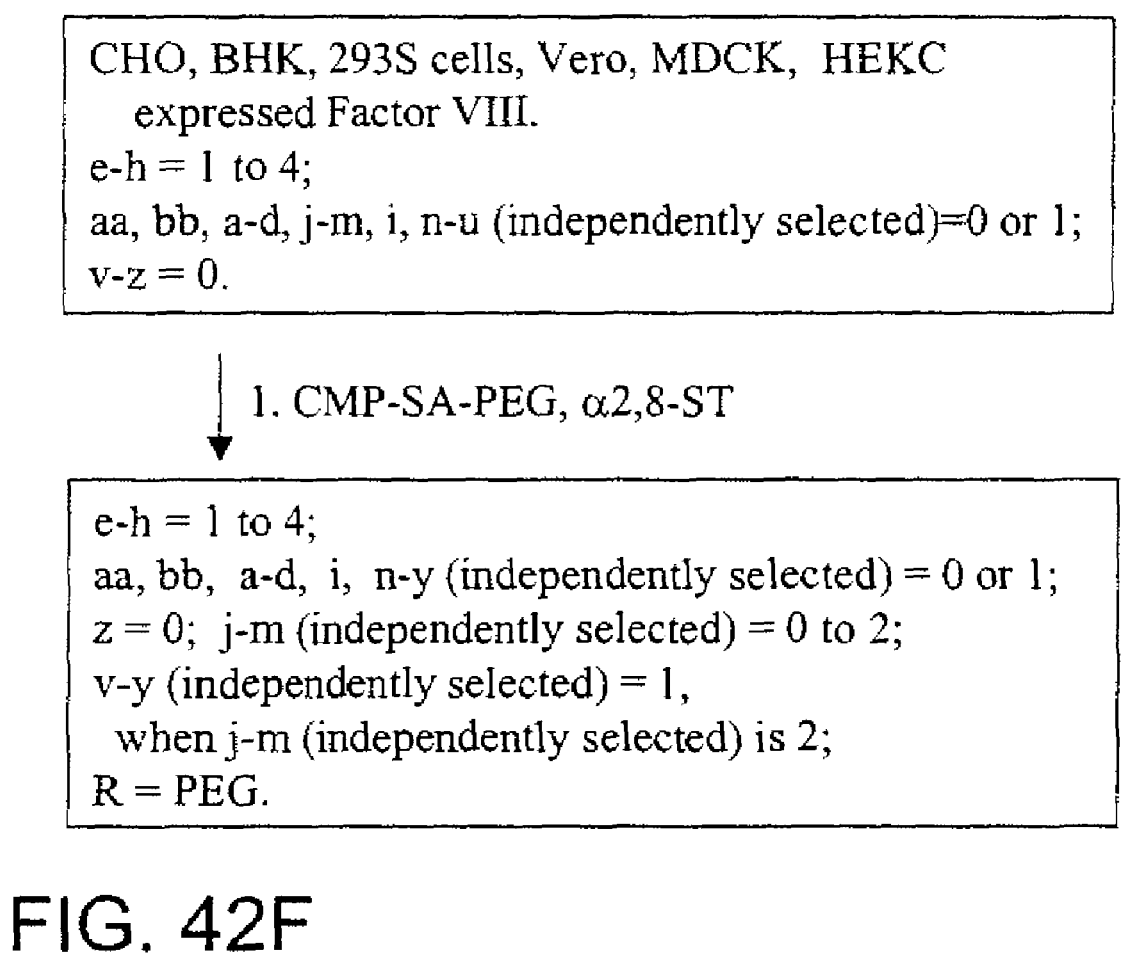

CHO, BHK, 293S cells, Vero, MDCK, HEKC expressed Factor VIII.
e-h = 1 to 4;
aa, bb, a-d, j-m, i, n-u (independently selected)=0 or 1;
v-z = 0.

↓ 1. CMP-SA-PEG, α2,8-ST e-h = 1 to 4;
aa, bb, a-d, i, n-y (independently selected) = 0 or 1;
z = 0; j-m (independently selected) = 0 to 2;
v-y (independently selected) = 1,
when j-m (independently selected) is 2;
R = PEG.

FIG. 42F 2 peptides
A or A' - N-linked sites
B - O-linked sites
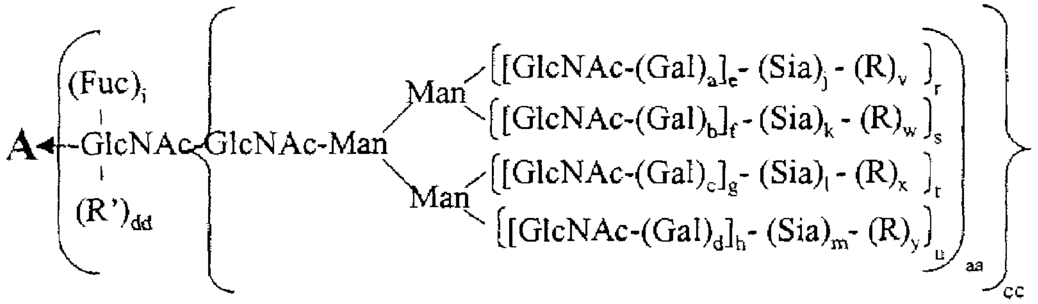
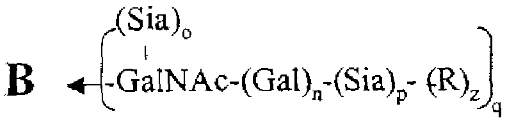
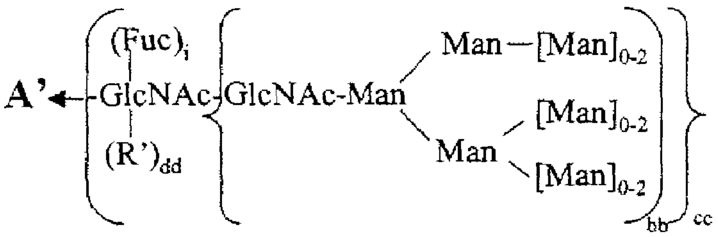
Alternate structure for some N-linked structures of A.
a-d, i, n-u, (independently selected) = 0 or 1.
aa, bb, cc, dd (independently selected) = 0 or 1.
e-h (independently selected) = 0 to 6.
j-m (independently selected) = 0 to 20.
v-z = 0;
R = modifying group, mannose, oligo-mannose.
R' = H, glycosyl residue, modifying group, glycoconjugate.
FIG. 42G CHO, BHK, 293S cells, Vero, MDCK, HEKC expressed Factor VIII.
e-h = 1 to 4;
aa, bb, cc, a-d, j-m, i, n-u (independently selected) = 0 or 1;
dd, v-z = 0.

1. CMP-SA-levulinate, ST3Gal3,
2. $H_4N_2$-PEG e-h = 1 to 4;
aa, bb, cc, a-d, i, n-u (independently selected) = 0 or 1;
dd, z = 0; j-m, v-y (independently selected) = 0 or 1;
R = PEG.

FIG. 42H

CHO, BHK, 293S cells, Vero, MDCK, HEKC expressed Factor VIII.
e-h = 1 to 4;
aa, bb, cc, a-d, j-m, i, n-u (independently selected) = 0 or 1;
dd, v-z = 0.

1. endo-H
2. galactosyltransferase, UDP-Gal-PEG e-h = 1 to 4;
aa, bb, dd, a-d, i, j-u (independently selected) = 0 or 1;
cc, v-z = 0; R' = -Gal-PEG.

FIG. 42I

CHO, BHK, 293S cells, Vero, MDCK, HEKC expressed Factor VIII.
e-h = 1 to 4;
aa, bb, cc, a-d, j-m, i, n-u (independently selected) = 0 or 1;
dd, v-z = 0.

1. ST3Gal3, CMP-SA
2. endo-H
3. galactosyltransferase, UDP-Gal-PEG e-h = 1 to 4;
aa, bb, dd, a-d, i, j-u (independently selected) = 0 or 1;
cc, v-z = 0; R' = -Gal-PEG.

FIG. 42J

CHO, BHK, 293S cells, Vero, MDCK, HEKC expressed Factor VIII.
e-h = 1 to 4;
aa, bb, cc, a-d, j-m, i, n-u (independently selected) = 0 or 1;
dd, v-z = 0.

1. mannosidases
2. GNT 1 & 2, UDP-GlcNAc
3. galactosyltransferase, UDP-Gal-PEG e-h = 1 to 4;
aa, a-d, i, j-y (independently selected) = 0 or 1;
bb, cc, dd, z = 0; R = PEG.

FIG. 42K

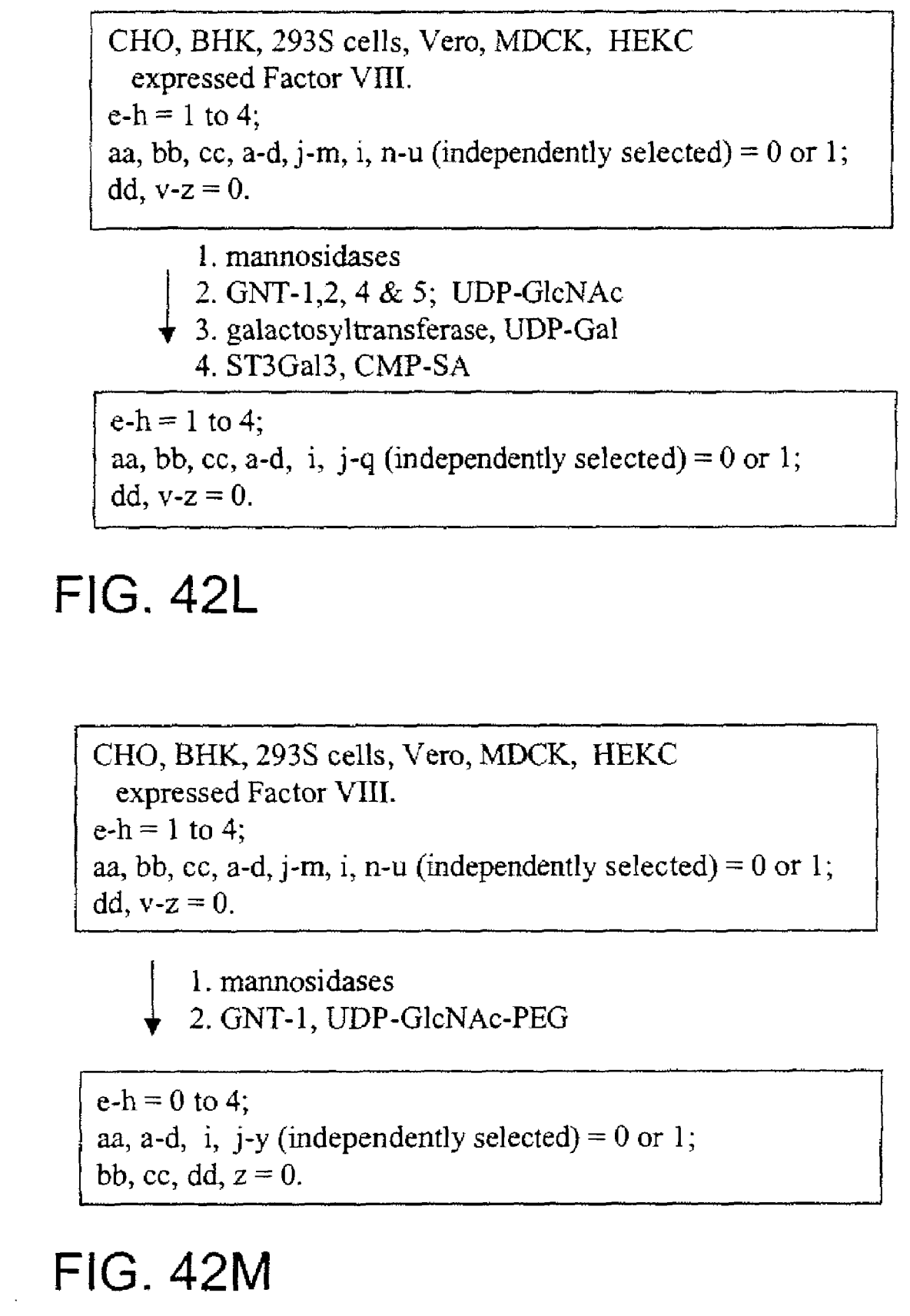

CHO, BHK, 293S cells, Vero, MDCK, HEKC expressed Factor VIII.
e-h = 1 to 4;
aa, bb, cc, a-d, j-m, i, n-u (independently selected) = 0 or 1;
dd, v-z = 0.

1. mannosidases
2. GNT-1,2, 4 & 5; UDP-GlcNAc
3. galactosyltransferase, UDP-Gal
4. ST3Gal3, CMP-SA e-h = 1 to 4;
aa, bb, cc, a-d, i, j-q (independently selected) = 0 or 1;
dd, v-z = 0.

FIG. 42L

CHO, BHK, 293S cells, Vero, MDCK, HEKC expressed Factor VIII.
e-h = 1 to 4;
aa, bb, cc, a-d, j-m, i, n-u (independently selected) = 0 or 1;
dd, v-z = 0.

1. mannosidases
2. GNT-1, UDP-GlcNAc-PEG e-h = 0 to 4;
aa, a-d, i, j-y (independently selected) = 0 or 1;
bb, cc, dd, z = 0.

FIG. 42M a-d, i, q-u (independently selected) = 0 or 1.
e-h (independently selected) = 0 to 6.
j-m (independently selected) = 0 to 100.
v-y = 0; R = polymer.

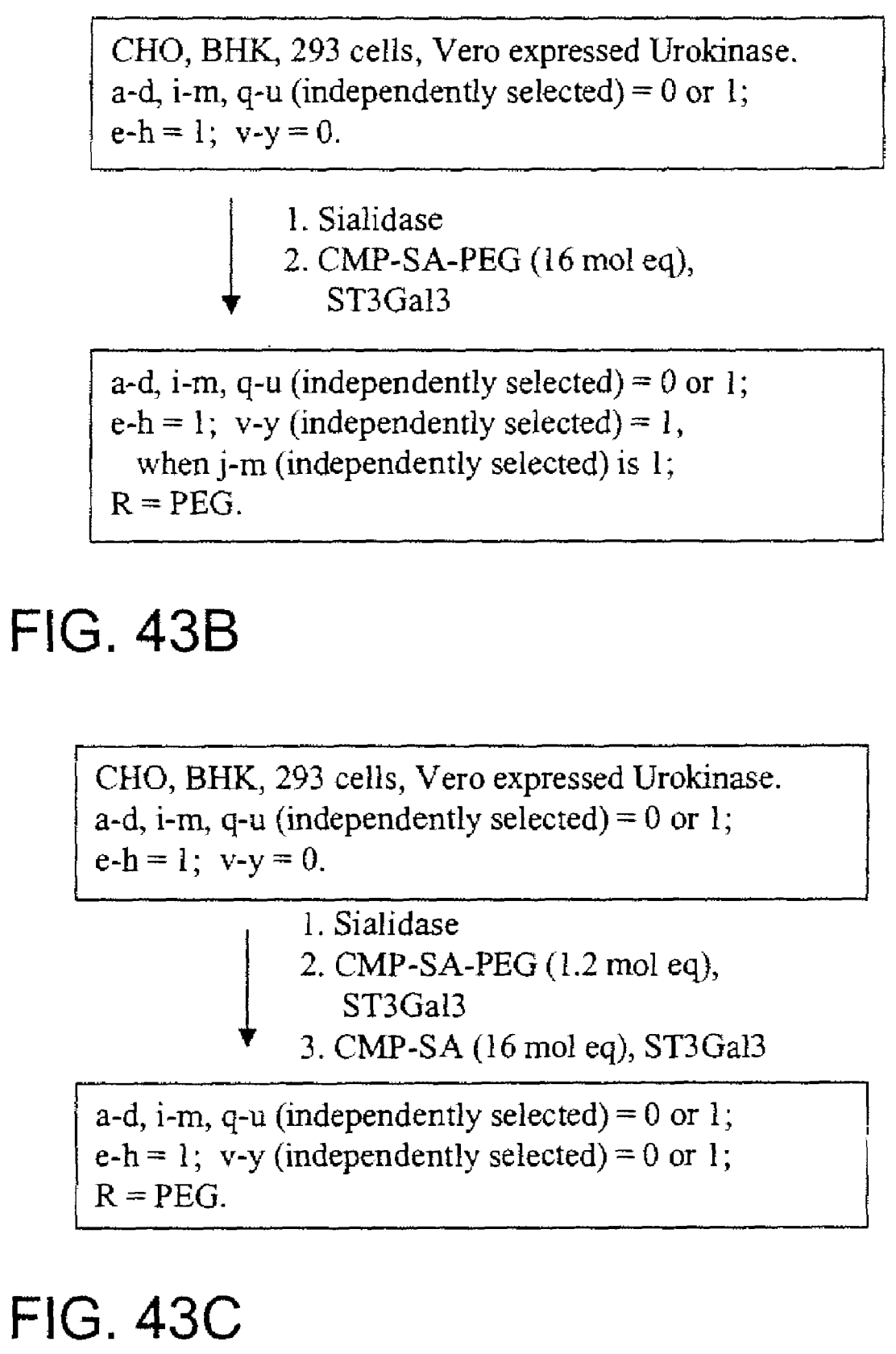

CHO, BHK, 293 cells, Vero expressed Urokinase.
a-d, i-m, q-u (independently selected) = 0 or 1;
e-h = 1; v-y = 0.

1. Sialidase
2. CMP-SA-PEG (16 mol eq), ST3Gal3 a-d, i-m, q-u (independently selected) = 0 or 1;
e-h = 1; v-y (independently selected) = 1, when j-m (independently selected) is 1;
R = PEG.

FIG. 43B

CHO, BHK, 293 cells, Vero expressed Urokinase.
a-d, i-m, q-u (independently selected) = 0 or 1;
e-h = 1; v-y = 0.

1. Sialidase
2. CMP-SA-PEG (1.2 mol eq), ST3Gal3
3. CMP-SA (16 mol eq), ST3Gal3 a-d, i-m, q-u (independently selected) = 0 or 1;
e-h = 1; v-y (independently selected) = 0 or 1;
R = PEG.

FIG. 43C

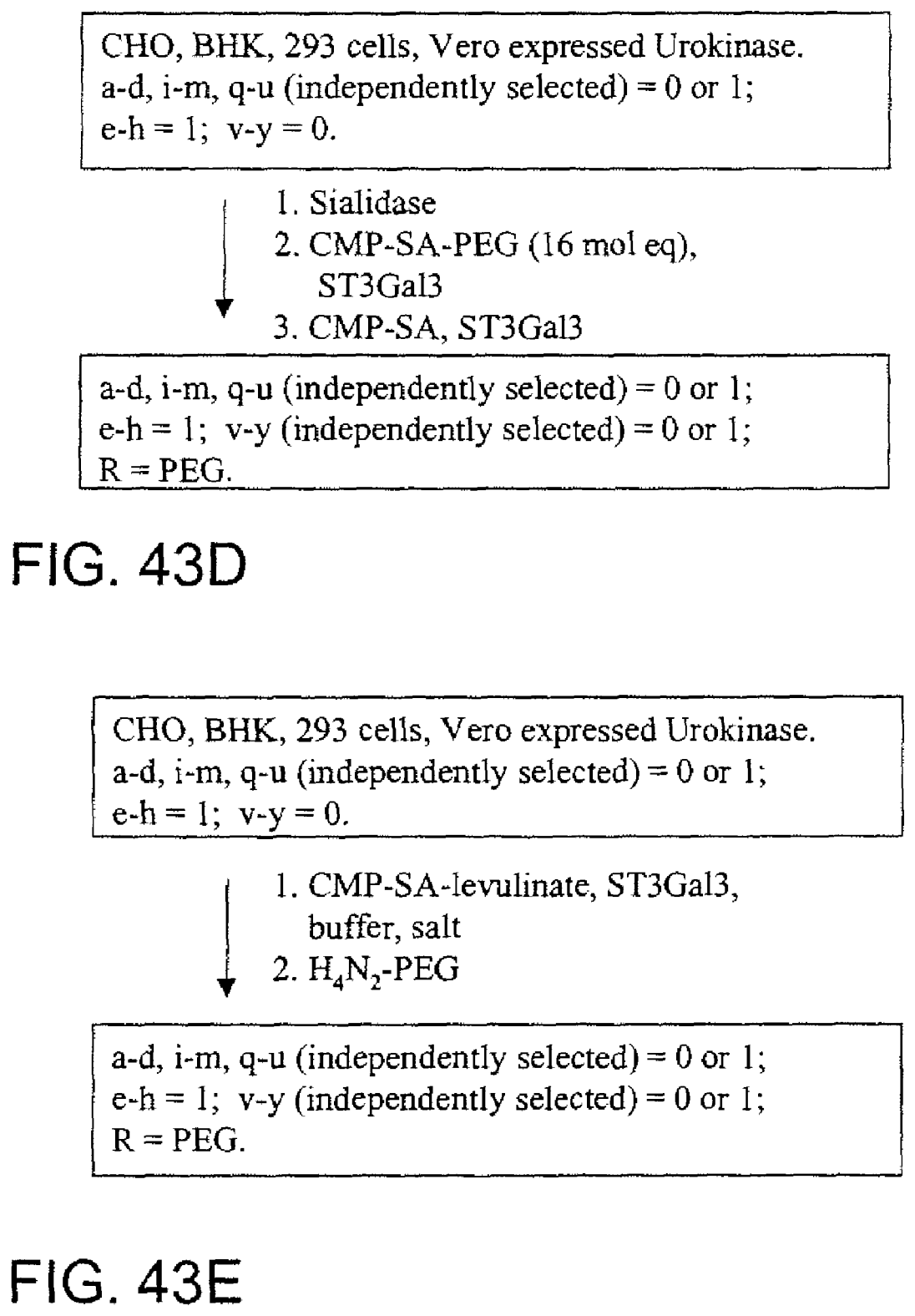

CHO, BHK, 293 cells, Vero expressed Urokinase.
a-d, i-m, q-u (independently selected) = 0 or 1;
e-h = 1; v-y = 0.

↓
1. Sialidase
2. CMP-SA-PEG (16 mol eq), ST3Gal3
3. CMP-SA, ST3Gal3 a-d, i-m, q-u (independently selected) = 0 or 1;
e-h = 1; v-y (independently selected) = 0 or 1;
R = PEG.

FIG. 43D

CHO, BHK, 293 cells, Vero expressed Urokinase.
a-d, i-m, q-u (independently selected) = 0 or 1;
e-h = 1; v-y = 0.

↓
1. CMP-SA-levulinate, ST3Gal3, buffer, salt
2. $H_4N_2$-PEG a-d, i-m, q-u (independently selected) = 0 or 1;
e-h = 1; v-y (independently selected) = 0 or 1;
R = PEG.

FIG. 43E

CHO, BHK, 293 cells, Vero expressed Urokinase.
a-d, i-m, q-u (independently selected) = 0 or 1;
e-h = 1; v-y = 0.

1. CMP-SA, α2,8-ST a-d, i, q-u (independently selected) = 0 or 1;
e-h = 1;
j-m (independently selected) = 0-20;
v-y (independently selected) = 0.

302
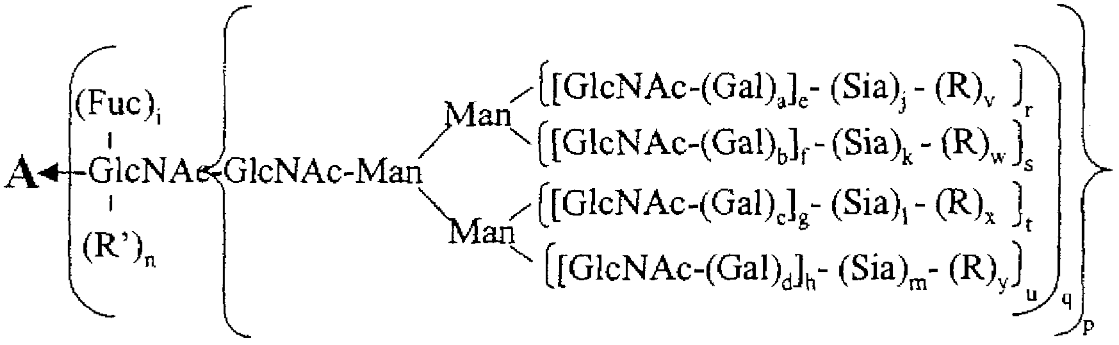
a-d, i, n, p-u (independently selected) = 0 or 1.
e-h (independently selected) = 0 to 6.
j-m (independently selected) = 0 to 100.
v-y = 0;
R = modifying group, mannose, oligo-mannose;
R' = H, glycosyl residue, modifying group, glycoconjugate.
FIG. 43G Insect cell expressed Urokinase.
a-d, f, h, j-n, s, u, v-y = 0;
e, g, i, q, r, t (independently selected) = 0 or 1.

↓
1. GNT's 1,2,4,5, UDP-GlcNAc
2. Galactosyltransferase, UDP-Gal-PEG a-i, q-u (independently selected) = 0 or 1;
j-n = 0; v-y (independently selected) = 1,
when e-h (independently selected) is 1;
R = PEG.

FIG. 43H

Yeast expressed Urokinase.
a-n = 0;
q-y (independently selected) = 0 to 1;
p = 1; R (branched or linear) = Man, oligomannose.

↓
1. Endoglycanase
2. Galactosyltransferase, UDP-Gal
3. CMP-SA-PEG, ST3Gal3 a-m, p-y = 0; n (independently selected) = 0 or 1;
R' = -Gal-Sia-PEG.

FIG. 43I

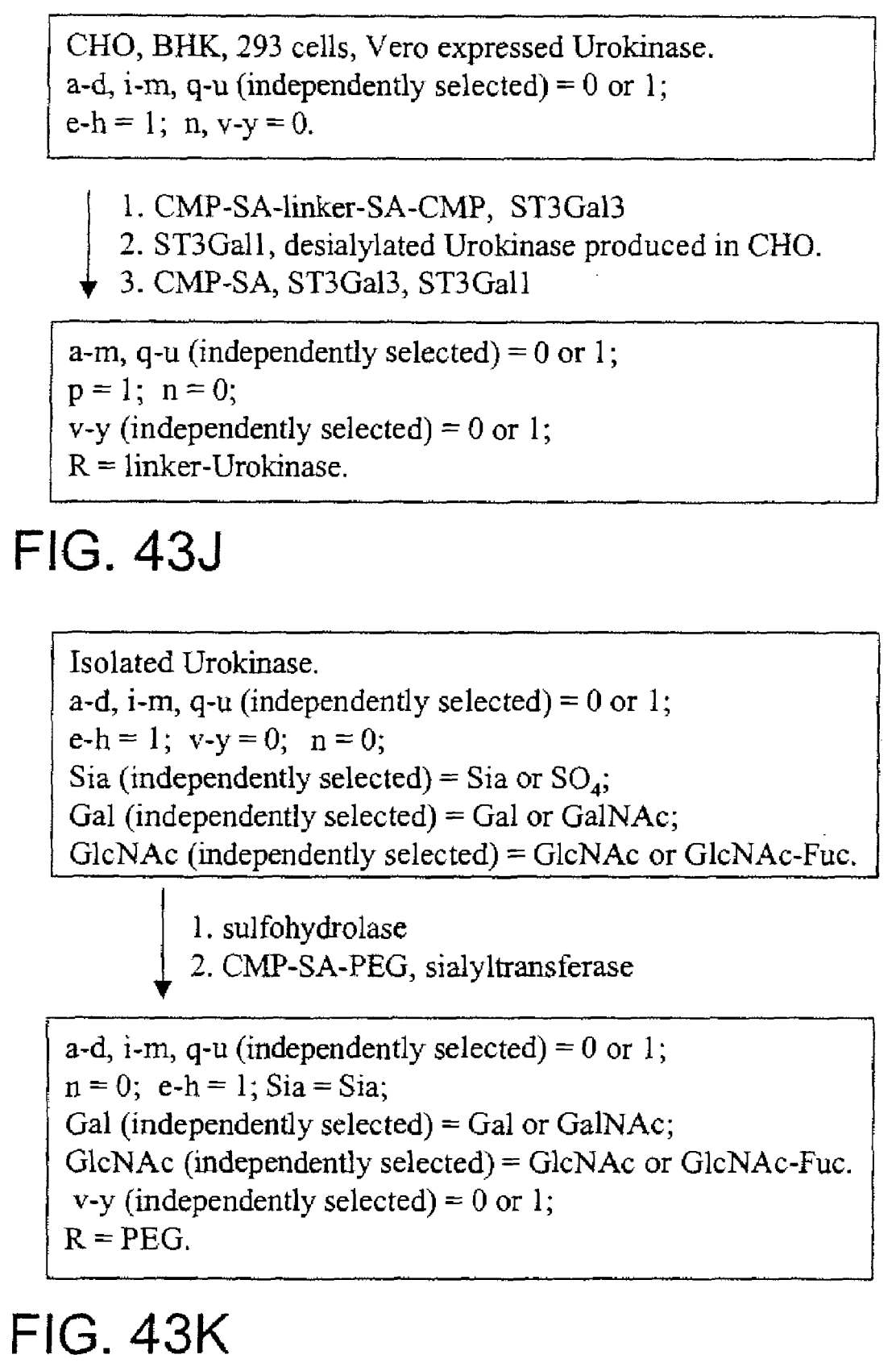

CHO, BHK, 293 cells, Vero expressed Urokinase.
a-d, i-m, q-u (independently selected) = 0 or 1;
e-h = 1; n, v-y = 0.

1. CMP-SA-linker-SA-CMP, ST3Gal3
2. ST3Gal1, desialylated Urokinase produced in CHO.
3. CMP-SA, ST3Gal3, ST3Gal1 a-m, q-u (independently selected) = 0 or 1;
p = 1; n = 0;
v-y (independently selected) = 0 or 1;
R = linker-Urokinase.

FIG. 43J

Isolated Urokinase.
a-d, i-m, q-u (independently selected) = 0 or 1;
e-h = 1; v-y = 0; n = 0;
Sia (independently selected) = Sia or $SO_4$;
Gal (independently selected) = Gal or GalNAc;
GlcNAc (independently selected) = GlcNAc or GlcNAc-Fuc.

1. sulfohydrolase
2. CMP-SA-PEG, sialyltransferase a-d, i-m, q-u (independently selected) = 0 or 1;
n = 0; e-h = 1; Sia = Sia;
Gal (independently selected) = Gal or GalNAc;
GlcNAc (independently selected) = GlcNAc or GlcNAc-Fuc.
v-y (independently selected) = 0 or 1;
R = PEG.

FIG. 43K

Figure 43L:
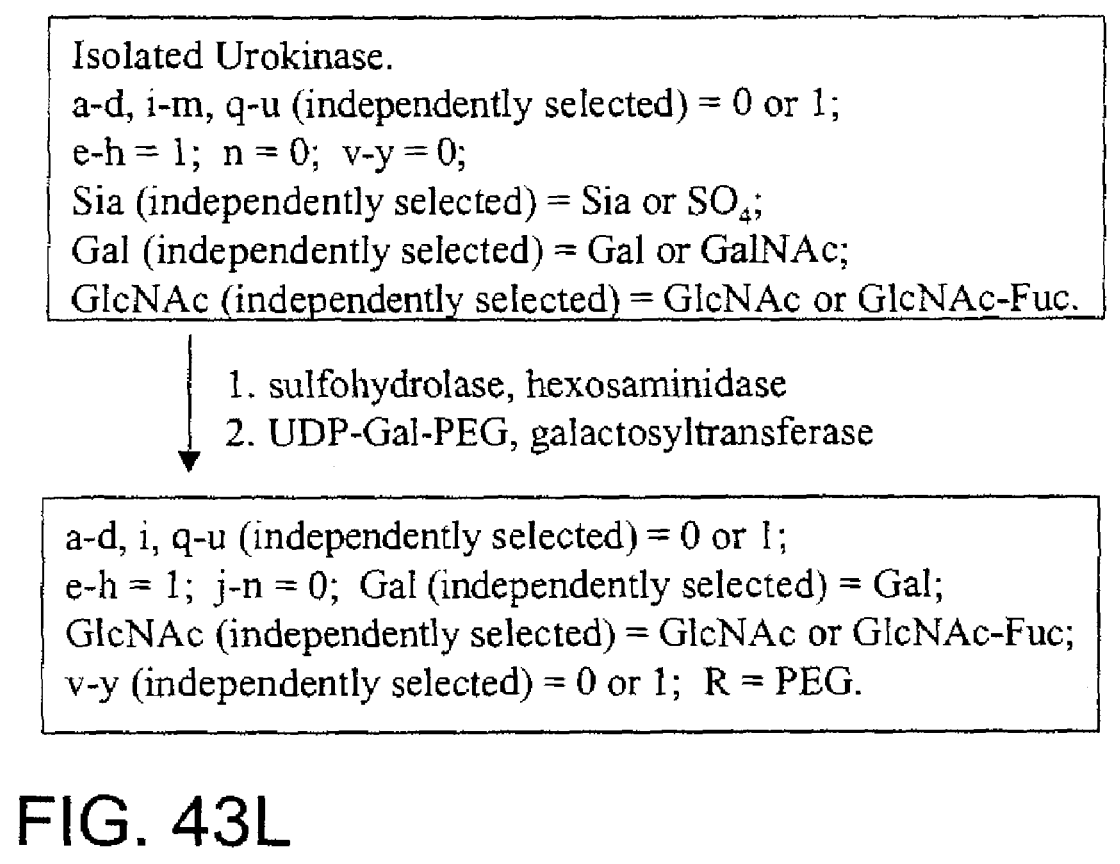

Isolated Urokinase.
a-d, i-m, q-u (independently selected) = 0 or 1;
e-h = 1; n = 0; v-y = 0;
Sia (independently selected) = Sia or $SO_4$;
Gal (independently selected) = Gal or GalNAc;
GlcNAc (independently selected) = GlcNAc or GlcNAc-Fuc.

1. sulfohydrolase, hexosaminidase
2. UDP-Gal-PEG, galactosyltransferase a-d, i, q-u (independently selected) = 0 or 1;
e-h = 1; j-n = 0; Gal (independently selected) = Gal;
GlcNAc (independently selected) = GlcNAc or GlcNAc-Fuc;
v-y (independently selected) = 0 or 1; R = PEG.

FIG. 43L a-d, i, q-u (independently selected) = 0 or 1.
e-h (independently selected) = 0 to 6.
j-m (independently selected) = 0 to 100.
v-y = 0; R = polymer, glycoconjugate.

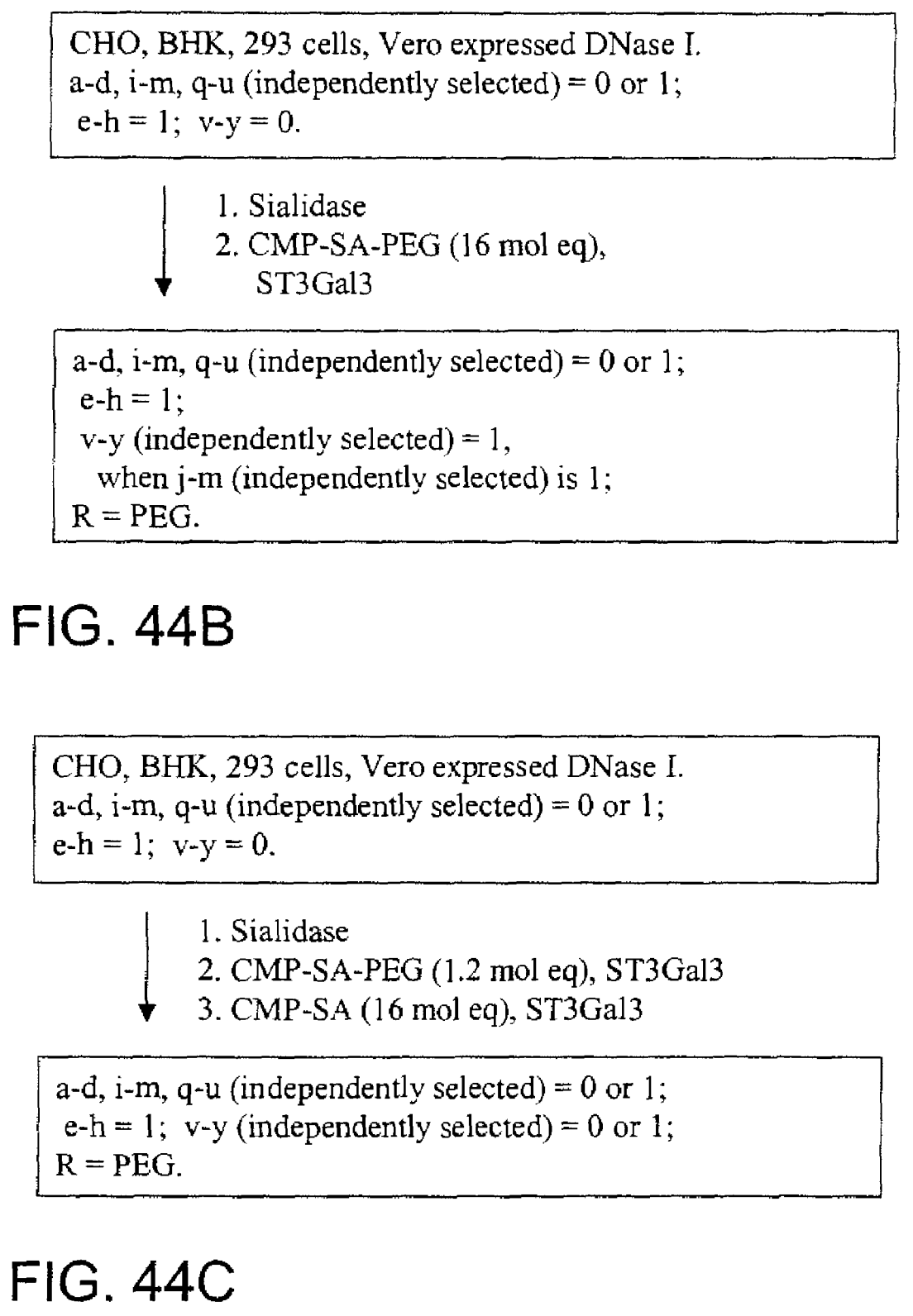

CHO, BHK, 293 cells, Vero expressed DNase I.
a-d, i-m, q-u (independently selected) = 0 or 1;
e-h = 1; v-y = 0.

1. Sialidase
2. CMP-SA-PEG (16 mol eq), ST3Gal3 a-d, i-m, q-u (independently selected) = 0 or 1;
e-h = 1;
v-y (independently selected) = 1, when j-m (independently selected) is 1;
R = PEG.

FIG. 44B

CHO, BHK, 293 cells, Vero expressed DNase I.
a-d, i-m, q-u (independently selected) = 0 or 1;
e-h = 1; v-y = 0.

1. Sialidase
2. CMP-SA-PEG (1.2 mol eq), ST3Gal3
3. CMP-SA (16 mol eq), ST3Gal3 a-d, i-m, q-u (independently selected) = 0 or 1;
e-h = 1; v-y (independently selected) = 0 or 1;
R = PEG.

FIG. 44C

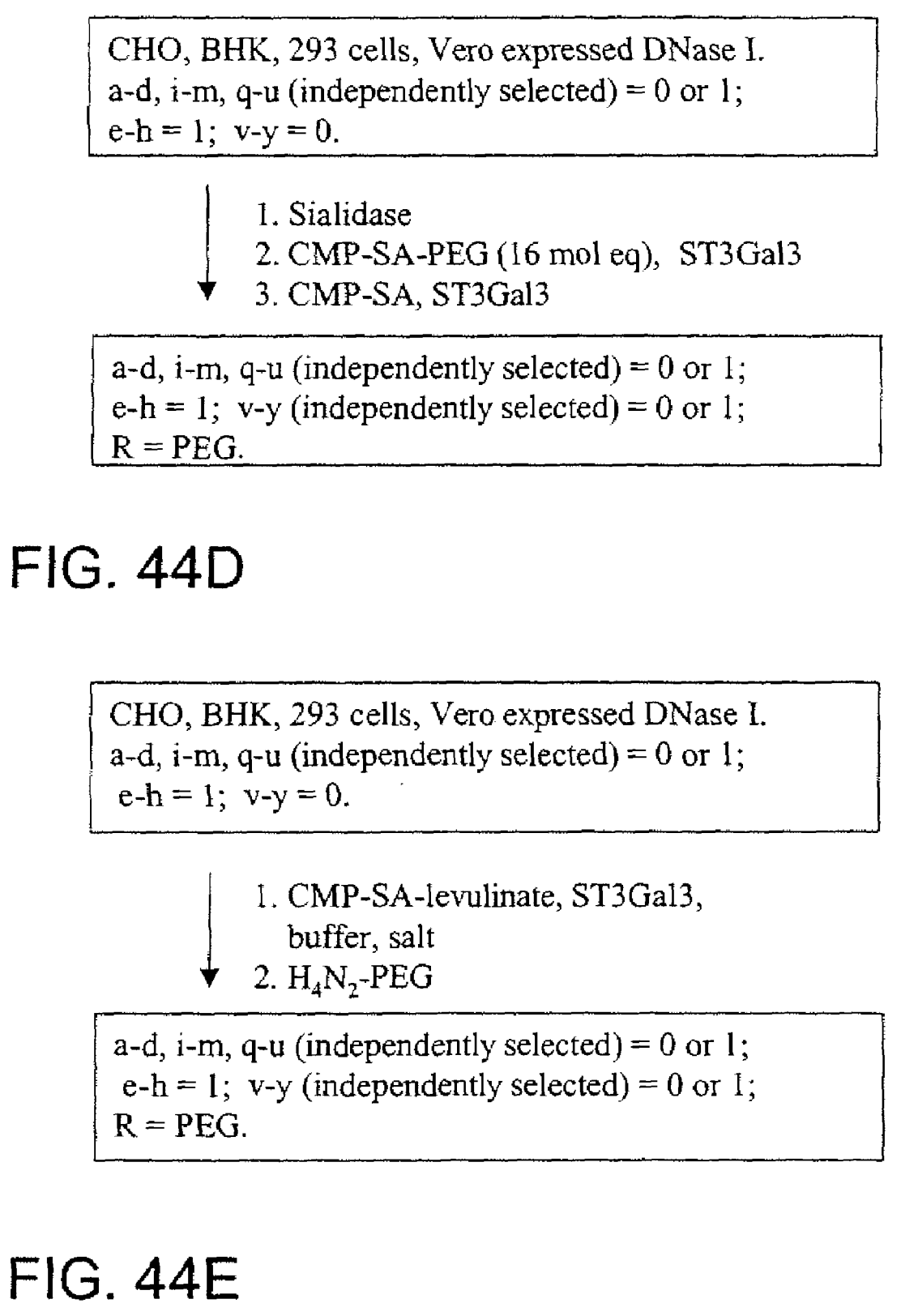

CHO, BHK, 293 cells, Vero expressed DNase I.
a-d, i-m, q-u (independently selected) = 0 or 1;
e-h = 1; v-y = 0.

↓

1. Sialidase
2. CMP-SA-PEG (16 mol eq), ST3Gal3
3. CMP-SA, ST3Gal3 a-d, i-m, q-u (independently selected) = 0 or 1;
e-h = 1; v-y (independently selected) = 0 or 1;
R = PEG.

FIG. 44D

CHO, BHK, 293 cells, Vero expressed DNase I.
a-d, i-m, q-u (independently selected) = 0 or 1;
e-h = 1; v-y = 0.

↓

1. CMP-SA-levulinate, ST3Gal3, buffer, salt
2. $H_4N_2$-PEG a-d, i-m, q-u (independently selected) = 0 or 1;
e-h = 1; v-y (independently selected) = 0 or 1;
R = PEG.

FIG. 44E

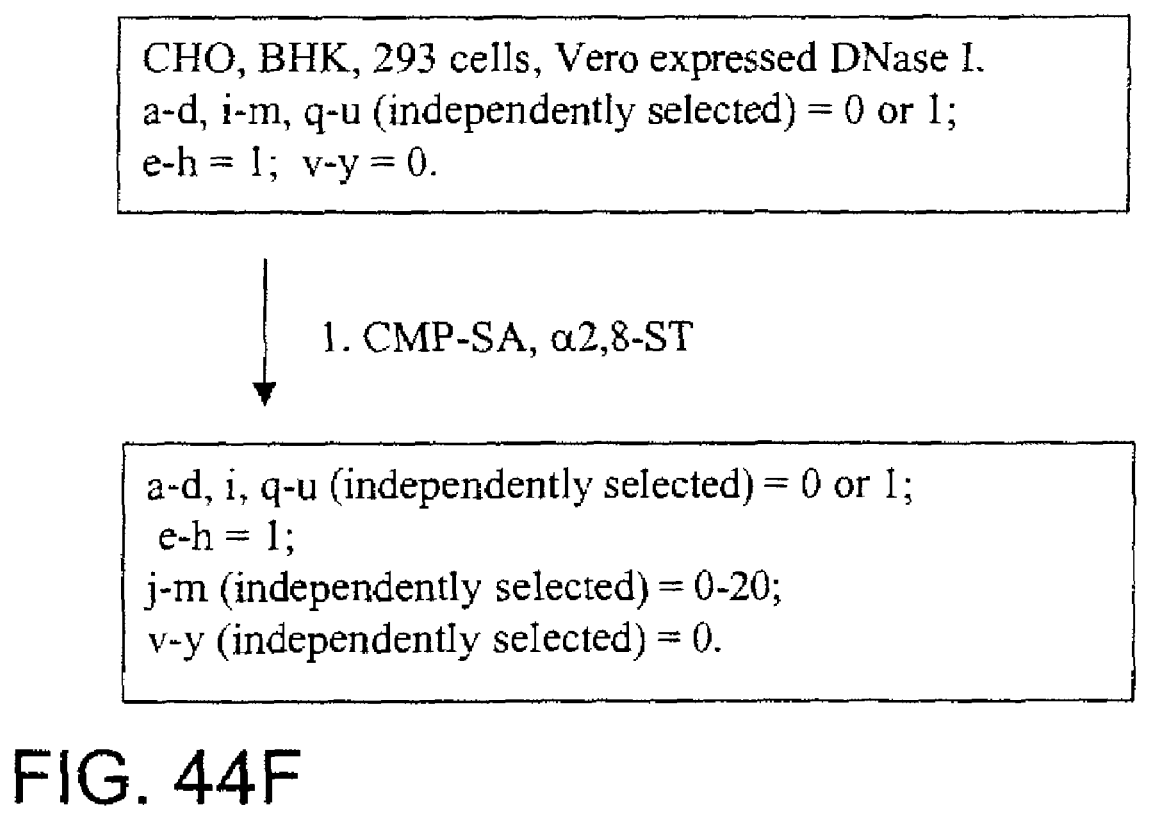

CHO, BHK, 293 cells, Vero expressed DNase I.
a-d, i-m, q-u (independently selected) = 0 or 1;
e-h = 1; v-y = 0.

1. CMP-SA, α2,8-ST a-d, i, q-u (independently selected) = 0 or 1;
e-h = 1;
j-m (independently selected) = 0-20;
v-y (independently selected) = 0.

FIG. 44F

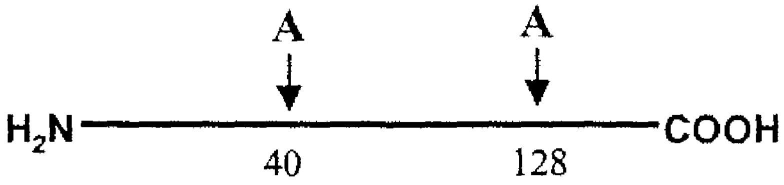
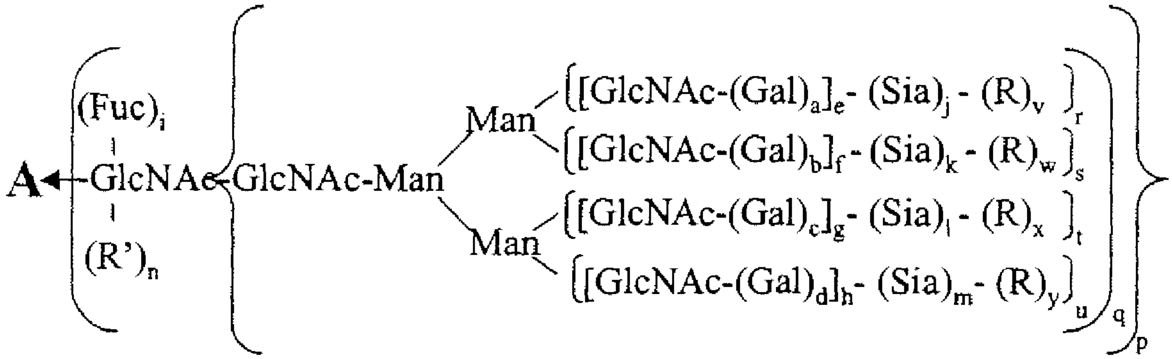
a-d, i, n, p-u (independently selected) = 0 or 1.
e-h (independently selected) = 0 to 6.
j-m (independently selected) = 0 to 100.
v-y = 0;
R = modifying group, mannose, oligo-mannose;
R' = H, glycosyl residue, modifying group, glycoconjugate.
FIG. 44G Insect cell expressed DNase I.
a-d, f, h, j-n, s, u, v-y = 0;
e, g, i, q, r, t (independently selected) = 0 or 1.

↓
1. GNT's 1,2,4,5, UDP-GlcNAc
2. Galactosyltransferase, UDP-Gal-PEG a-i, q-u (independently selected) = 0 or 1; j-n = 0;
v-y (independently selected) = 1,
when e-h (independently selected) is 1;
R = PEG.

FIG. 44H

Yeast expressed DNase I.
a-n = 0;
q-y (independently selected) = 0 to 1;
p = 1; R (branched or linear) = Man, oligomannose.

↓
1. Endoglycanase
2. Galactosyltransferase, UDP-Gal
3. CMP-SA-PEG, ST3Gal3 a-n, p-y = 0; n (independently selected) = 0 or 1;
R' = -Gal-Sia-PEG.

FIG. 44I

Figure 44J:
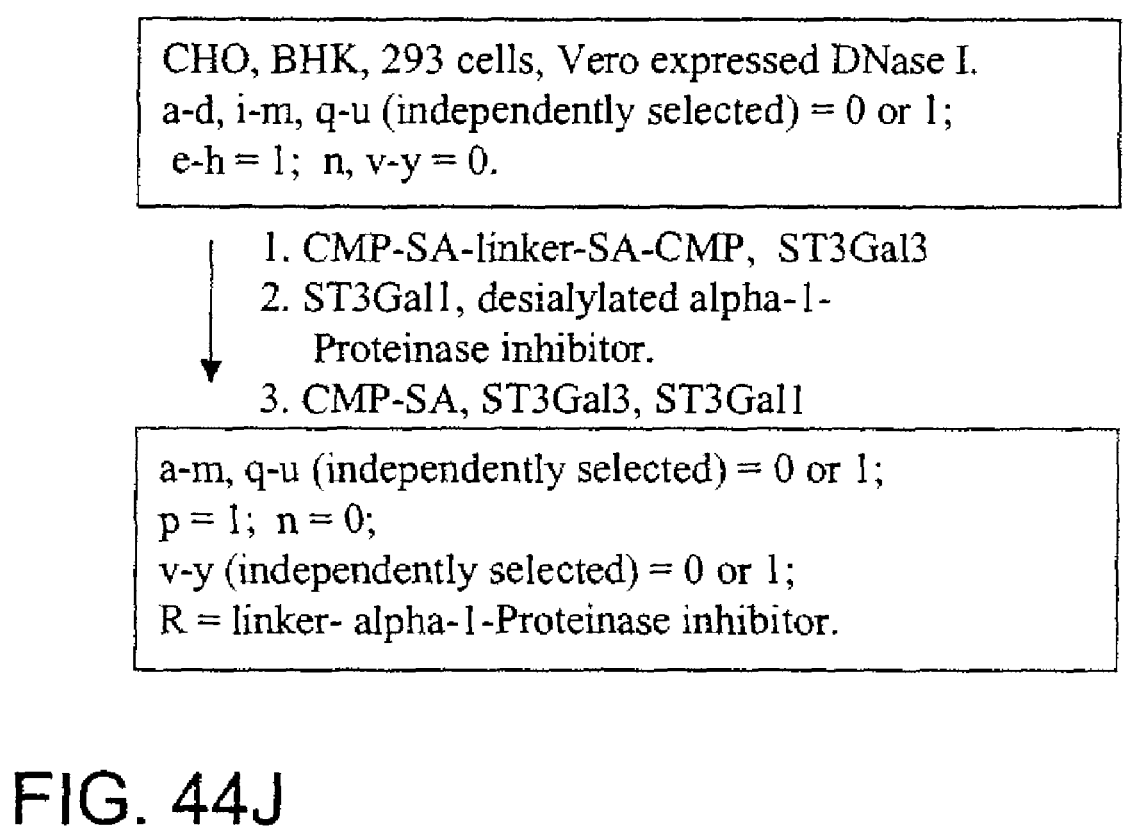

CHO, BHK, 293 cells, Vero expressed DNase I.
a-d, i-m, q-u (independently selected) = 0 or 1;
e-h = 1; n, v-y = 0.

1. CMP-SA-linker-SA-CMP, ST3Gal3
2. ST3Gal1, desialylated alpha-1-Proteinase inhibitor.
3. CMP-SA, ST3Gal3, ST3Gal1 a-m, q-u (independently selected) = 0 or 1;
p = 1; n = 0;
v-y (independently selected) = 0 or 1;
R = linker- alpha-1-Proteinase inhibitor.

FIG. 44J a-d, i, r-u (independently selected) = 0 or 1.
e-h (independently selected) = 0 to 4.
j-m (independently selected) = 0 or 1.
n, v-y = 0; z = 0 or 1;
R = modifying group, mannose, oligo-mannose;
R' = H, glycosyl residue, modifying group, glycoconjugate.

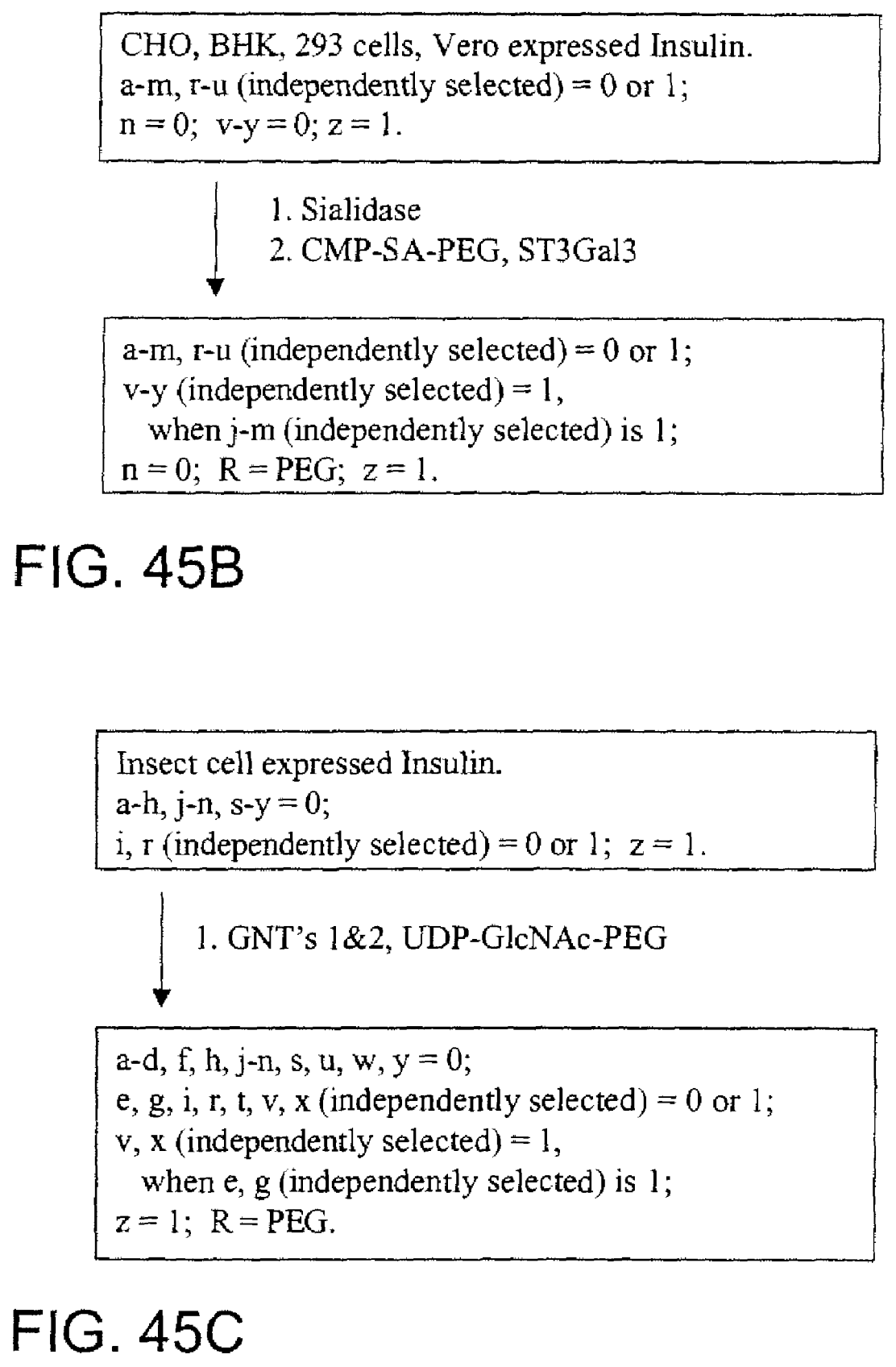

CHO, BHK, 293 cells, Vero expressed Insulin.
a-m, r-u (independently selected) = 0 or 1;
n = 0; v-y = 0; z = 1.

↓

1. Sialidase
2. CMP-SA-PEG, ST3Gal3 a-m, r-u (independently selected) = 0 or 1;
v-y (independently selected) = 1,
when j-m (independently selected) is 1;
n = 0; R = PEG; z = 1.

FIG. 45B

Insect cell expressed Insulin.
a-h, j-n, s-y = 0;
i, r (independently selected) = 0 or 1; z = 1.

↓

1. GNT's 1&2, UDP-GlcNAc-PEG a-d, f, h, j-n, s, u, w, y = 0;
e, g, i, r, t, v, x (independently selected) = 0 or 1;
v, x (independently selected) = 1,
when e, g (independently selected) is 1;
z = 1; R = PEG.

FIG. 45C

Figure 45D:
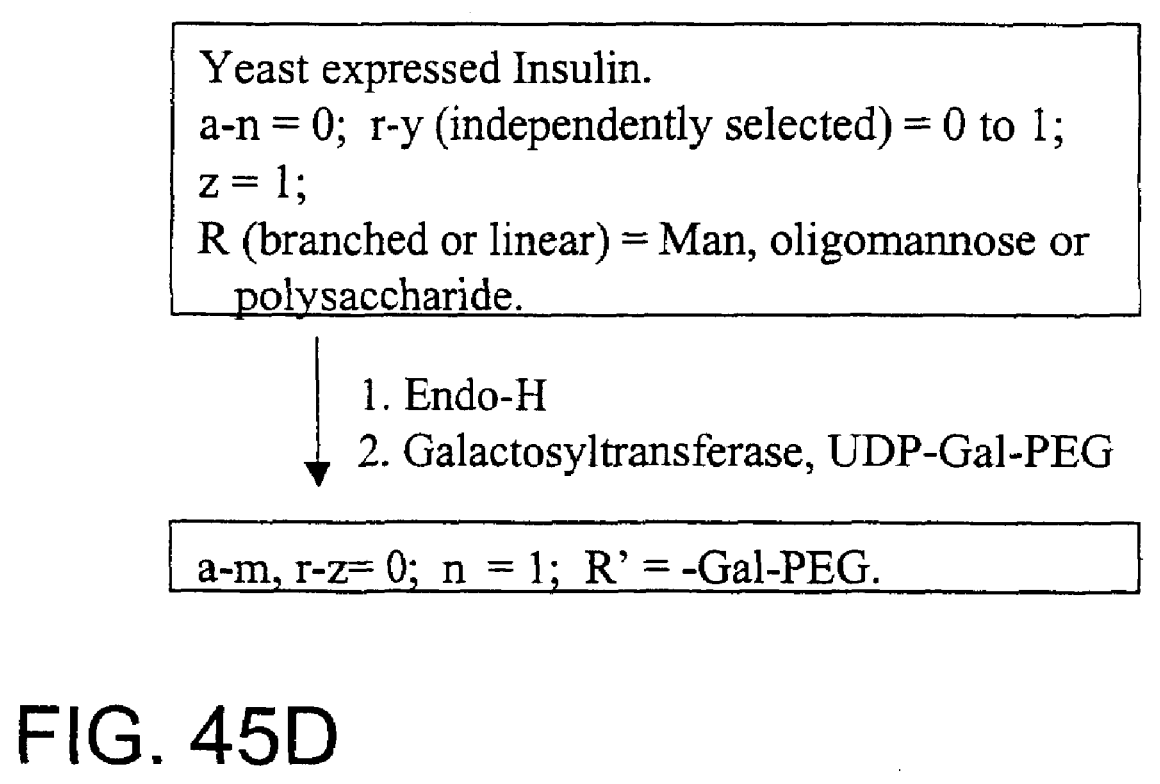

Yeast expressed Insulin.
a-n = 0; r-y (independently selected) = 0 to 1;
z = 1;
R (branched or linear) = Man, oligomannose or polysaccharide.

1. Endo-H
2. Galactosyltransferase, UDP-Gal-PEG a-m, r-z= 0; n = 1; R' = -Gal-PEG.

FIG. 45D a-c, e (independently selected) = 0 or 1;
d = 0; R = polymer

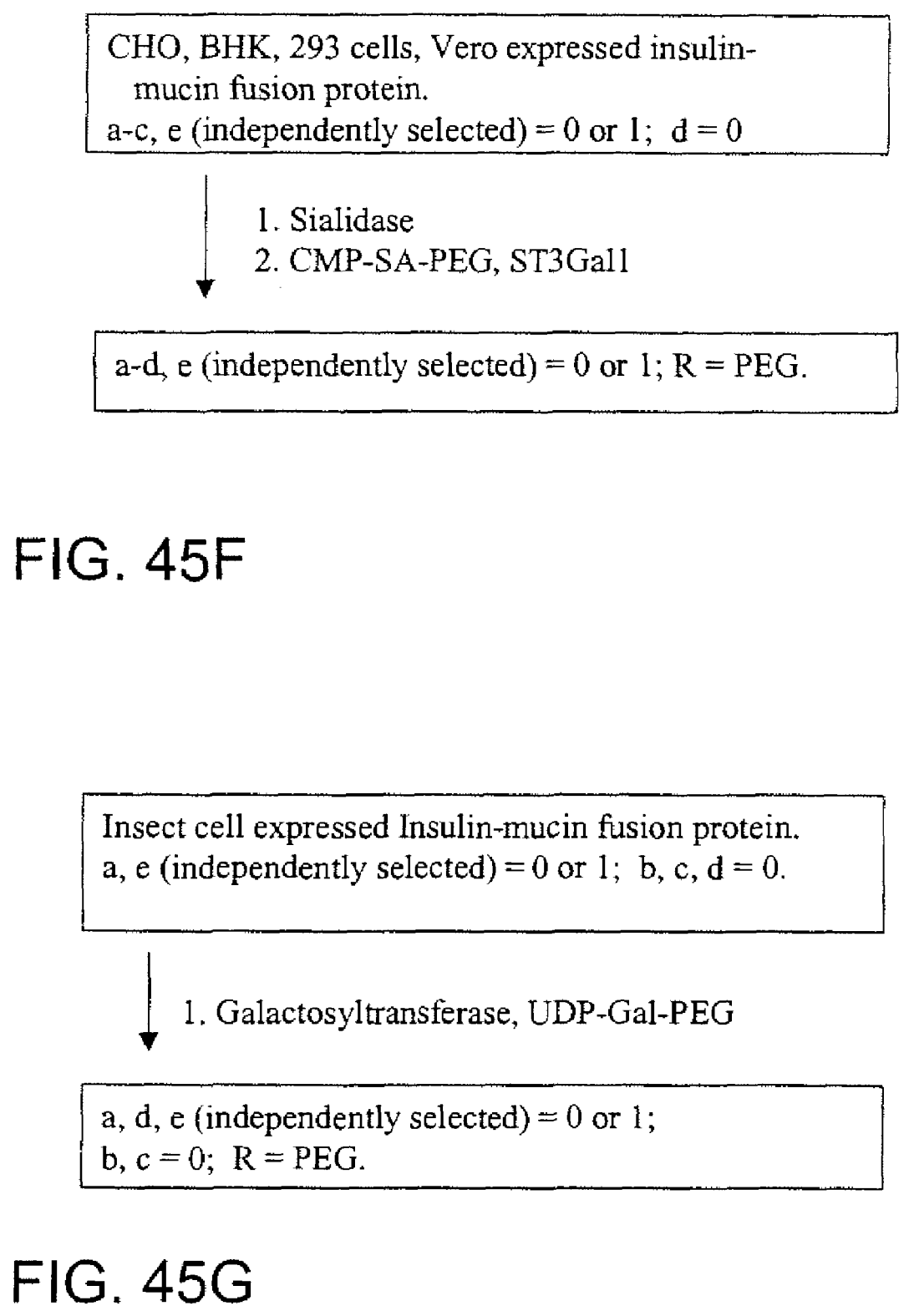

CHO, BHK, 293 cells, Vero expressed insulin-mucin fusion protein.
a-c, e (independently selected) = 0 or 1; d = 0

1. Sialidase
2. CMP-SA-PEG, ST3Gal1 a-d, e (independently selected) = 0 or 1; R = PEG.

FIG. 45F

Insect cell expressed Insulin-mucin fusion protein.
a, e (independently selected) = 0 or 1; b, c, d = 0.

1. Galactosyltransferase, UDP-Gal-PEG a, d, e (independently selected) = 0 or 1;
b, c = 0; R = PEG.

FIG. 45G

E. coli expressed Insulin-mucin fusion protein.
a-e = 0.

1. GalNAc Transferase, UDP-GalNAc
2. CMP-SA-PEG, sialyltransferase c, d, e (independently selected) = 0 or 1;
a, b = 0; R = PEG.

$$\mathbf{B} \leftarrow \left[ \underset{}{\overset{(Sia)_b}{|}}\text{-GalNAc-}(Gal)_a\text{-}(Sia)_c\text{-}(R)_d \right]_e$$

$$\mathbf{C} \leftarrow (R')_n$$

a-c, e (independently selected) = 0 or 1;
d = 0; R = modifying group, mannose, oligo-mannose.

E. coli expressed Insulin-mucin fusion protein.
a-e, n = 0.

↓ 1. GalNAc Transferase,
UDP-GalNAc-PEG d, e (independently selected) = 0 or 1;
a-c, n = 0; R = PEG.

E. coli expressed Insulin-mucin fusion protein.
a-e, n = 0.

↓ 1. GalNAc Transferase,
UDP-GalNAc-linker-SA-CMP
2. ST3Gal3, asialo-transferrin
3. CMP-SA, ST3Gal3 d, e (independently selected) = 0 or 1;
a-c, n = 0; R = linker-transferrin.

Figure 45L:
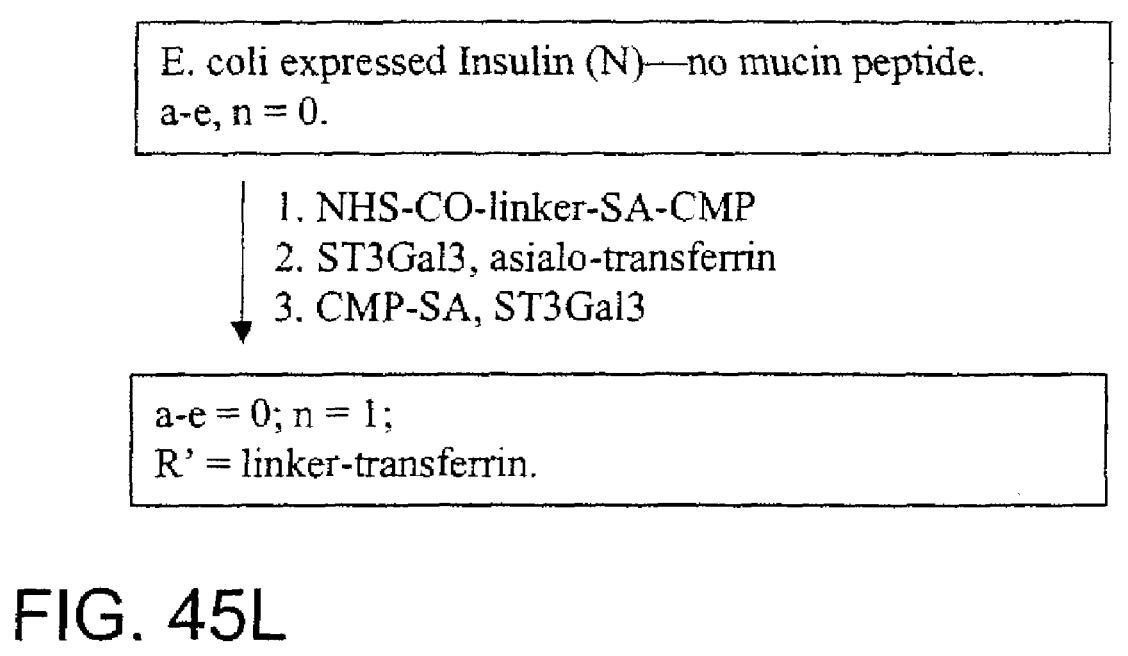

E. coli expressed Insulin (N)—no mucin peptide.
a-e, n = 0.

1. NHS-CO-linker-SA-CMP
2. ST3Gal3, asialo-transferrin
3. CMP-SA, ST3Gal3 a-e = 0; n = 1;
R' = linker-transferrin.

FIG. 45L a-d, i, n-u, aa (independently selected) = 0 or 1.
e-h (independently selected) = 0 to 6.
j-m (independently selected) = 0 to 100.
v-y = 0; R = polymer, glycoconjugate.

CHO, BHK, 293 cells, Vero expressed M-antigen.
a-d, i-m, o-u, aa (independently selected) = 0 or 1;
n, e-h = 1; v-z = 0.

1. Sialidase
2. CMP-SA-linker-lipid-A, ST3Gal3 a-d, i-m, q-u, aa (independently selected) = 0 or 1;
o, p, z = 0; n, e-h = 1;
v-y (independently selected) = 1,
when j-m (independently selected) is 1;
R = linker-lipid-A.

FIG. 46B

CHO, BHK, 293 cells, Vero expressed M-antigen.
a-d, i-m, o-u, aa (independently selected) = 0 or 1;
n, e-h = 1; v-z = 0.

1. sialidase
2. CMP-SA-linker-tetanus toxin, ST3Gal1
3. CMP-SA, ST3Gal3 a-d, i-m, p-u, z, aa (independently selected) = 0 or 1;
o, v-y = 0; n, e-h = 1; R = tetanus toxin.

FIG. 46C

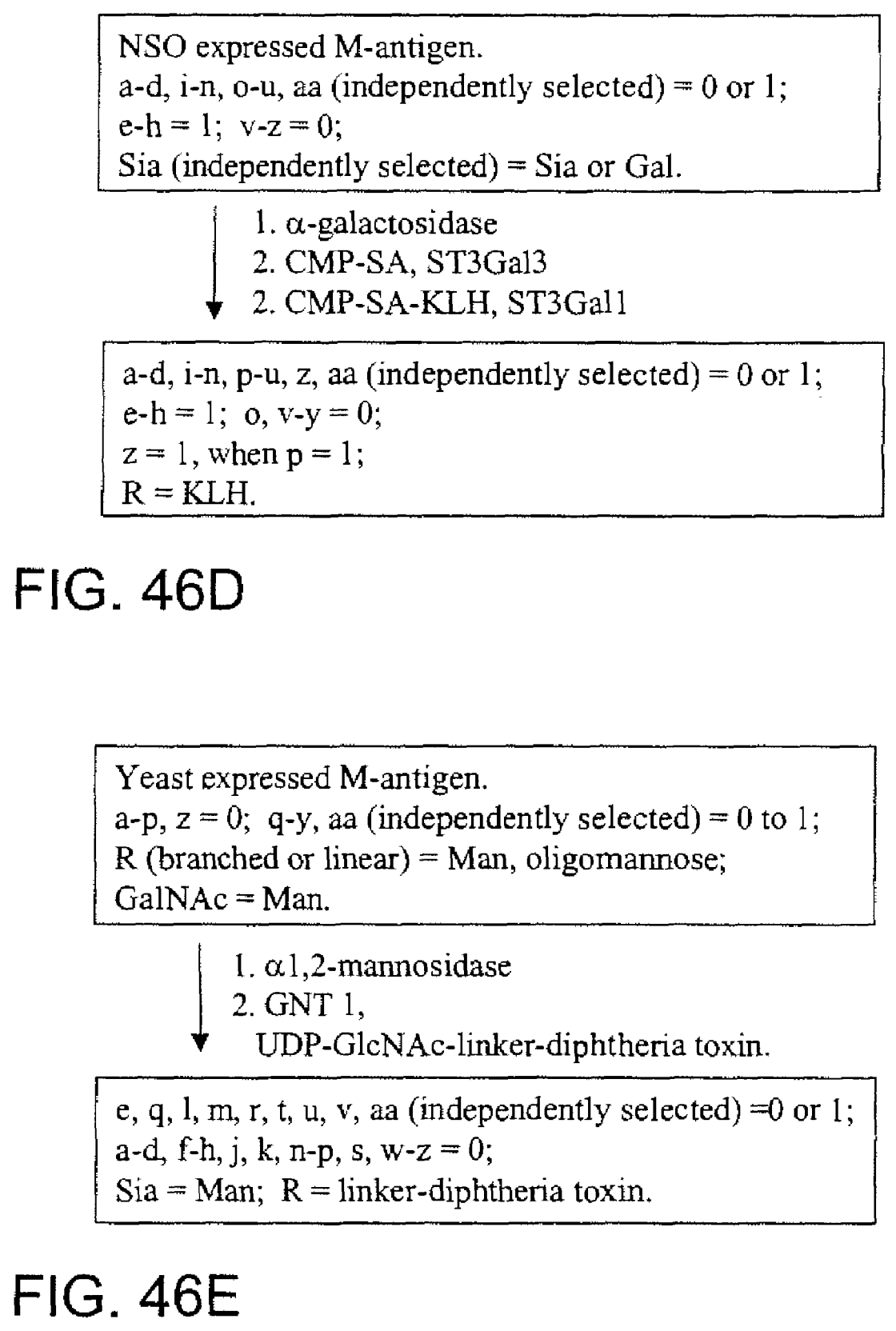

NSO expressed M-antigen.
a-d, i-n, o-u, aa (independently selected) = 0 or 1;
e-h = 1; v-z = 0;
Sia (independently selected) = Sia or Gal.

1. α-galactosidase
2. CMP-SA, ST3Gal3
2. CMP-SA-KLH, ST3Gal1 a-d, i-n, p-u, z, aa (independently selected) = 0 or 1;
e-h = 1; o, v-y = 0;
z = 1, when p = 1;
R = KLH.

FIG. 46D

Yeast expressed M-antigen.
a-p, z = 0; q-y, aa (independently selected) = 0 to 1;
R (branched or linear) = Man, oligomannose;
GalNAc = Man.

1. α1,2-mannosidase
2. GNT 1,
UDP-GlcNAc-linker-diphtheria toxin.

e, q, l, m, r, t, u, v, aa (independently selected) =0 or 1;
a-d, f-h, j, k, n-p, s, w-z = 0;
Sia = Man; R = linker-diphtheria toxin.

FIG. 46E

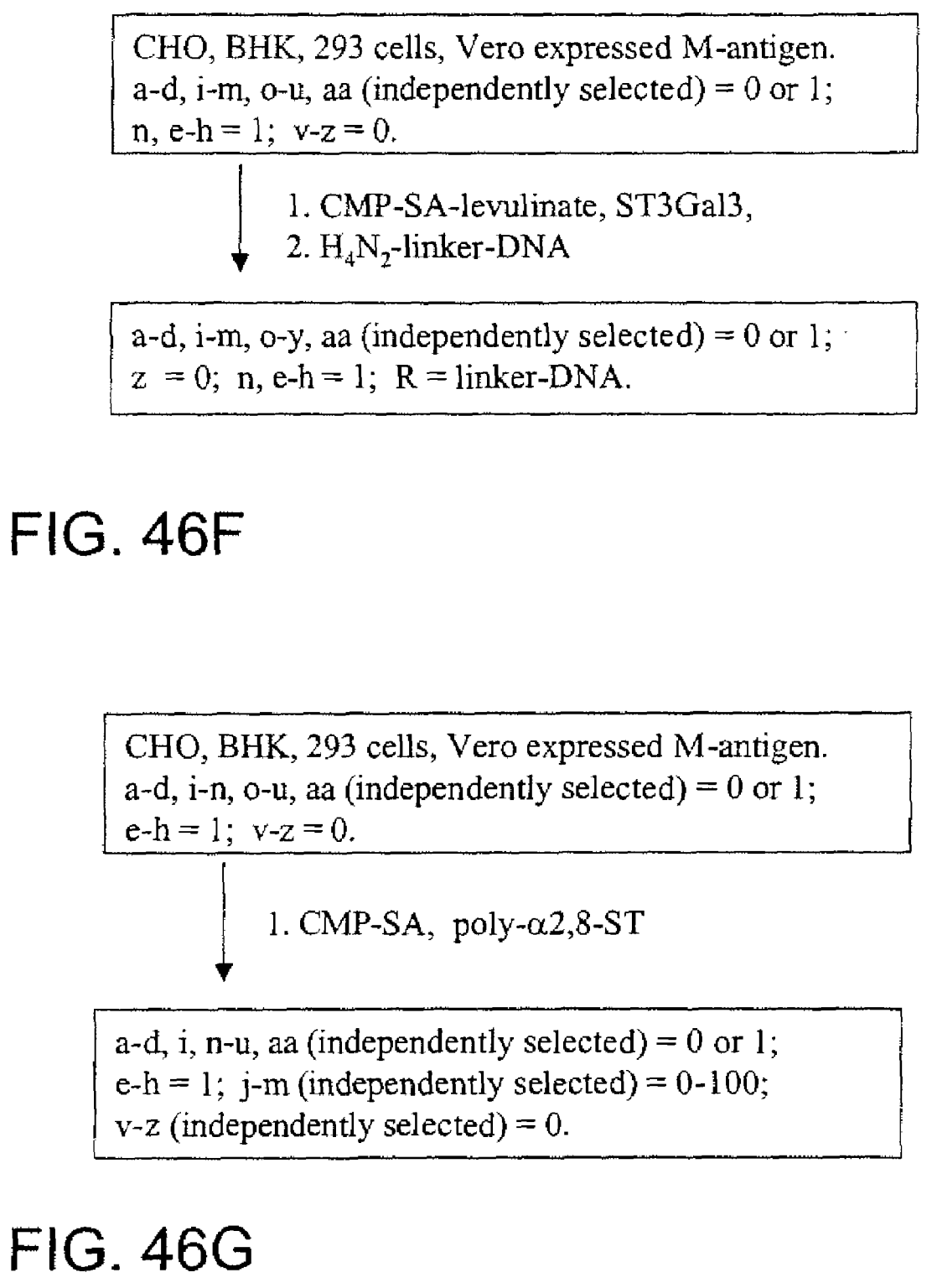

CHO, BHK, 293 cells, Vero expressed M-antigen.
a-d, i-m, o-u, aa (independently selected) = 0 or 1;
n, e-h = 1; v-z = 0.

1. CMP-SA-levulinate, ST3Gal3,
2. $H_4N_2$-linker-DNA a-d, i-m, o-y, aa (independently selected) = 0 or 1;
z = 0; n, e-h = 1; R = linker-DNA.

FIG. 46F

CHO, BHK, 293 cells, Vero expressed M-antigen.
a-d, i-n, o-u, aa (independently selected) = 0 or 1;
e-h = 1; v-z = 0.

1. CMP-SA, poly-α2,8-ST a-d, i, n-u, aa (independently selected) = 0 or 1;
e-h = 1; j-m (independently selected) = 0-100;
v-z (independently selected) = 0.

FIG. 46G a-d, i, n, q-u, aa, bb, (independently selected) = 0 or 1.
e-h (independently selected) = 0 to 6.
j-p (independently selected) = 0 to 100.
Cc, v-y = 0;
R = modifying group, mannose, oligo-mannose.
R'= H, glycosyl residue, modifying group, glycoconjugate.

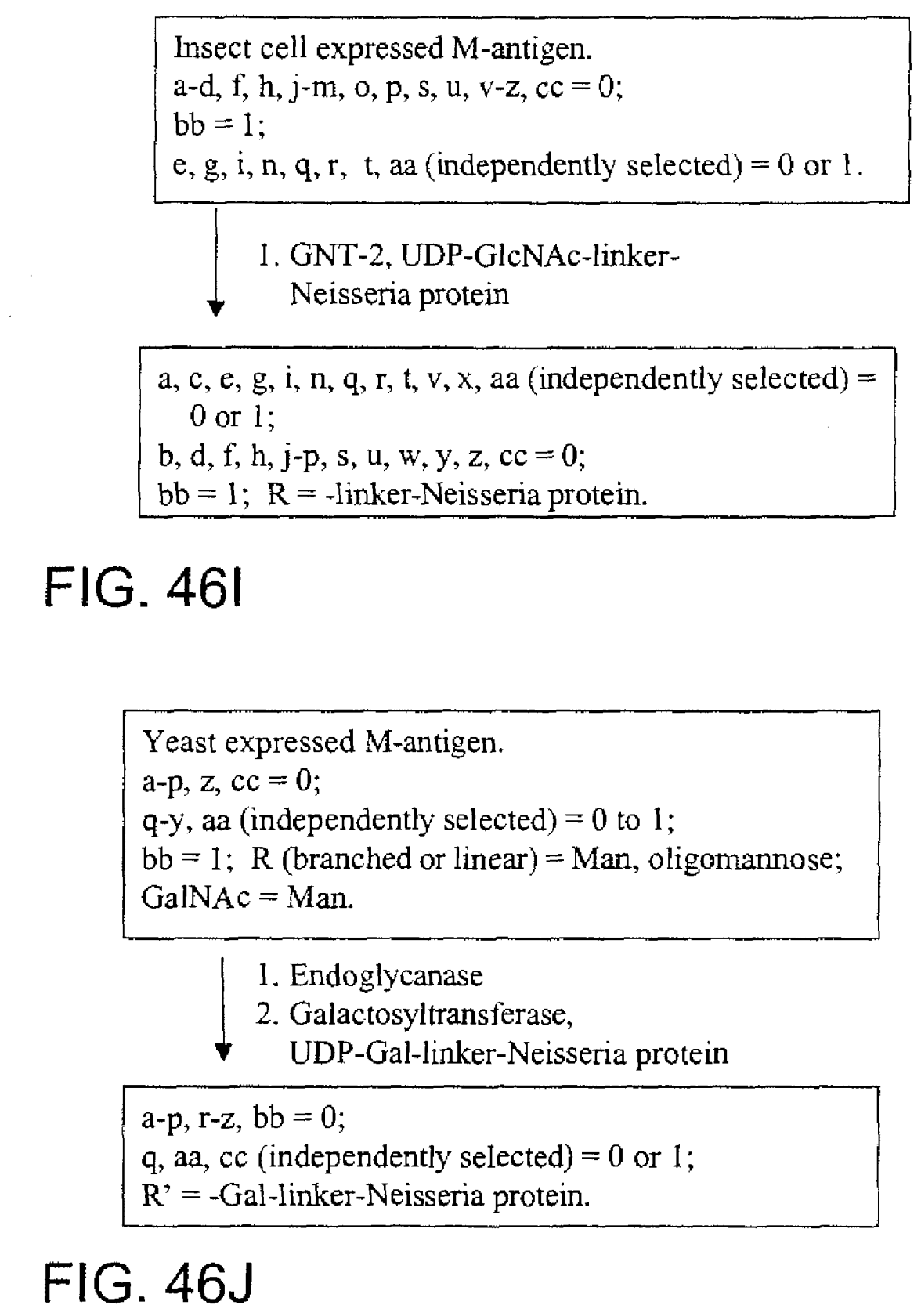

Insect cell expressed M-antigen.
a-d, f, h, j-m, o, p, s, u, v-z, cc = 0;
bb = 1;
e, g, i, n, q, r, t, aa (independently selected) = 0 or 1.

1. GNT-2, UDP-GlcNAc-linker-Neisseria protein a, c, e, g, i, n, q, r, t, v, x, aa (independently selected) = 0 or 1;
b, d, f, h, j-p, s, u, w, y, z, cc = 0;
bb = 1; R = -linker-Neisseria protein.

FIG. 46I

Yeast expressed M-antigen.
a-p, z, cc = 0;
q-y, aa (independently selected) = 0 to 1;
bb = 1; R (branched or linear) = Man, oligomannose;
GalNAc = Man.

1. Endoglycanase
2. Galactosyltransferase, UDP-Gal-linker-Neisseria protein a-p, r-z, bb = 0;
q, aa, cc (independently selected) = 0 or 1;
R' = -Gal-linker-Neisseria protein.

FIG. 46J

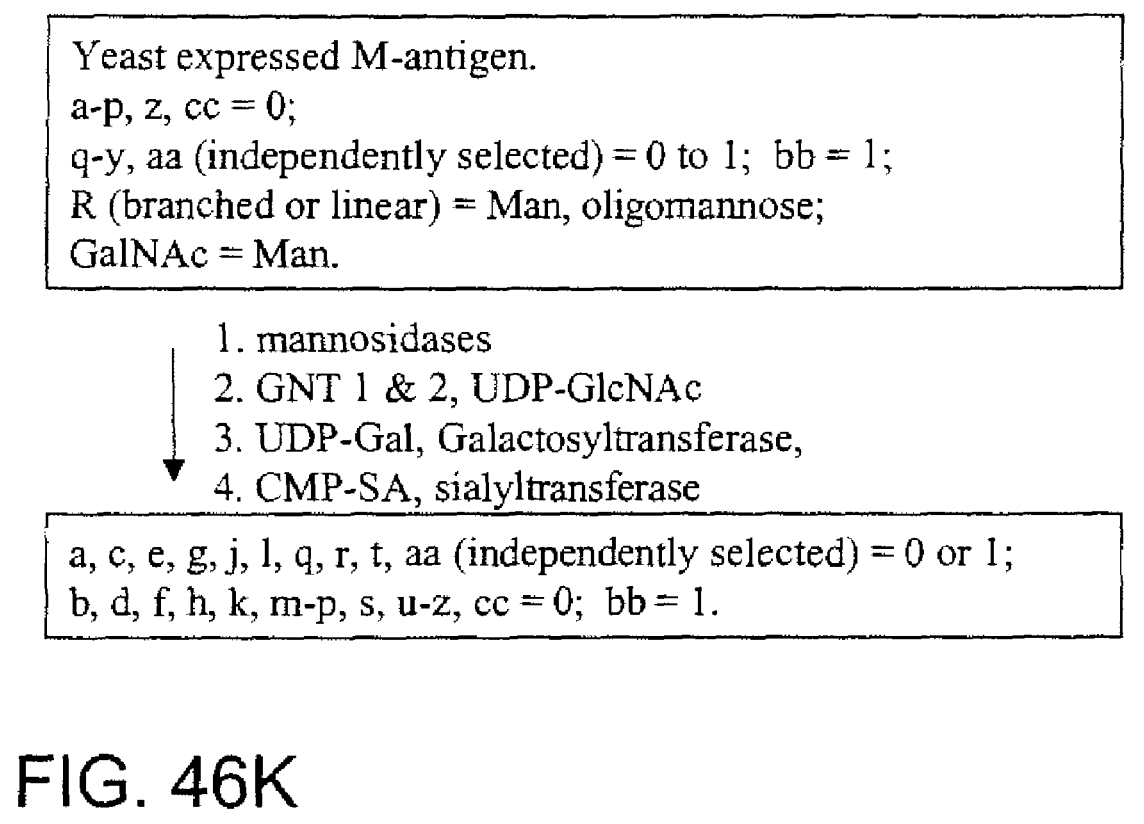

Yeast expressed M-antigen.
a-p, z, cc = 0;
q-y, aa (independently selected) = 0 to 1; bb = 1;
R (branched or linear) = Man, oligomannose;
GalNAc = Man.

1. mannosidases
2. GNT 1 & 2, UDP-GlcNAc
3. UDP-Gal, Galactosyltransferase,
4. CMP-SA, sialyltransferase a, c, e, g, j, l, q, r, t, aa (independently selected) = 0 or 1;
b, d, f, h, k, m-p, s, u-z, cc = 0; bb = 1.

FIG. 46K

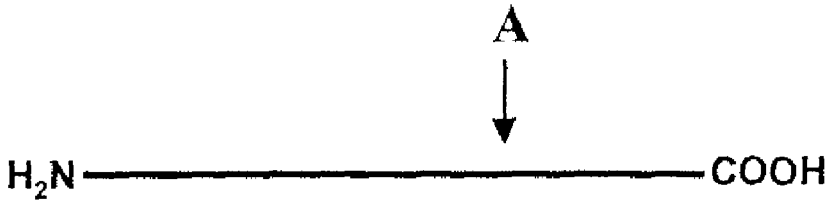
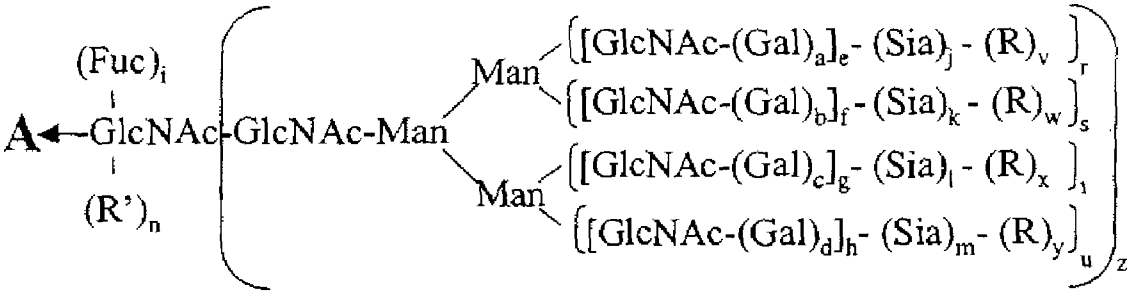
a-d, i, r-u (independently selected) = 0 or 1.
e-h (independently selected) = 0 to 4.
j-m (independently selected) = 0 or 1.
n, v-y = 0; z = 0 or 1;
R = modifying group, mannose, oligo-mannose;
R' = H, glycosyl residue, modifying group, glycoconjugate.
FIG. 47A CHO, BHK, 293 cells, Vero expressed Growth Hormone.
a-m, r-u (independently selected) = 0 or 1;
n = 0; v-y = 0; z = 1.

1. Sialidase
2. CMP-SA-PEG, ST3Gal3 a-m, r-u (independently selected) = 0 or 1;
v-y (independently selected) = 1,
when j-m (independently selected) is 1;
n = 0; R = PEG; z = 1.

FIG. 47B

Insect cell expressed growth hormone.
a-h, j-n, s-y = 0;
i, r (independently selected) = 0 or 1; z = 1.

1. GNT's 1&2, UDP-GlcNAc-PEG a-d, f, h, j-n, s, u, w, y = 0;
e, g, i, r, t, v, x (independently selected)= 0 or 1;
v, x (independently selected) = 1,
when e, g (independently selected) is 1;
z = 1; R = PEG.

FIG. 47C

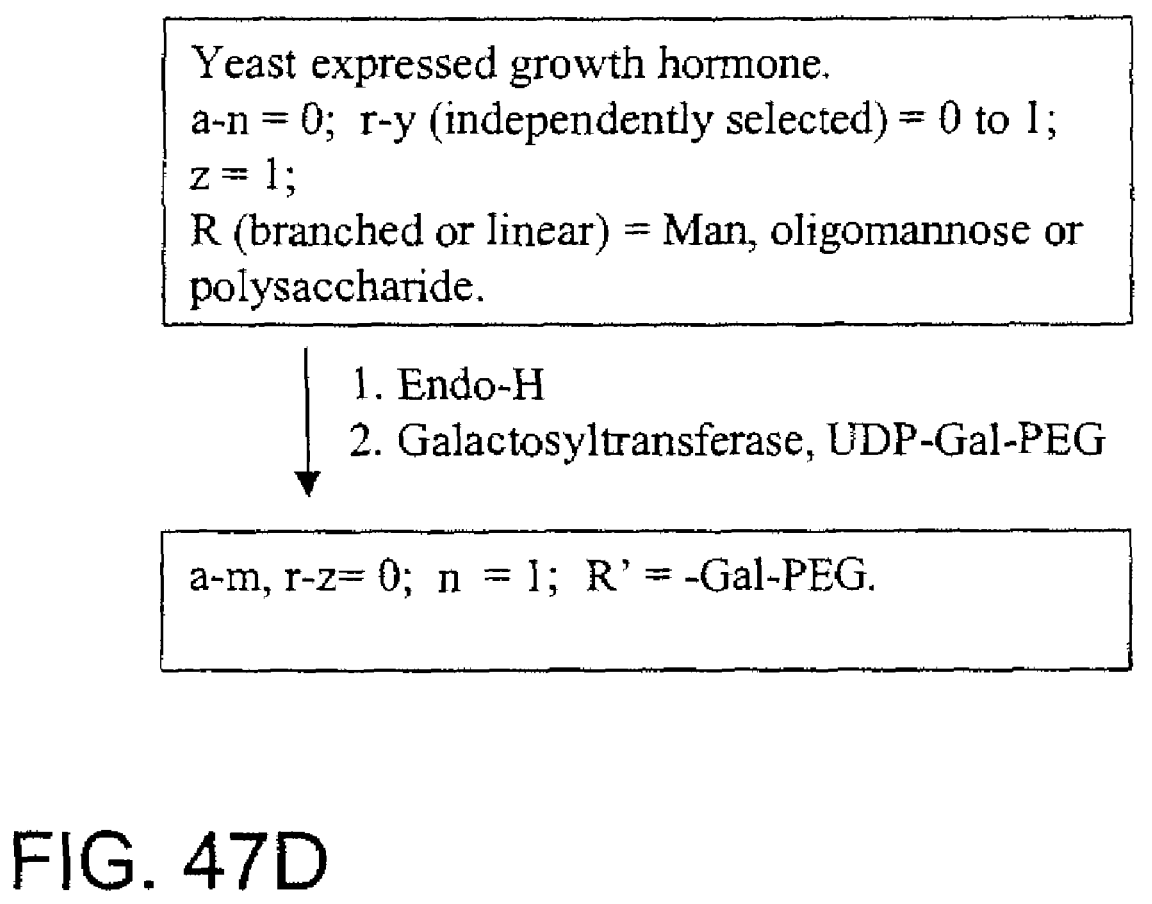

Yeast expressed growth hormone.
a-n = 0; r-y (independently selected) = 0 to 1;
z = 1;
R (branched or linear) = Man, oligomannose or polysaccharide.

1. Endo-H
2. Galactosyltransferase, UDP-Gal-PEG a-m, r-z= 0; n = 1; R' = -Gal-PEG.

FIG. 47D

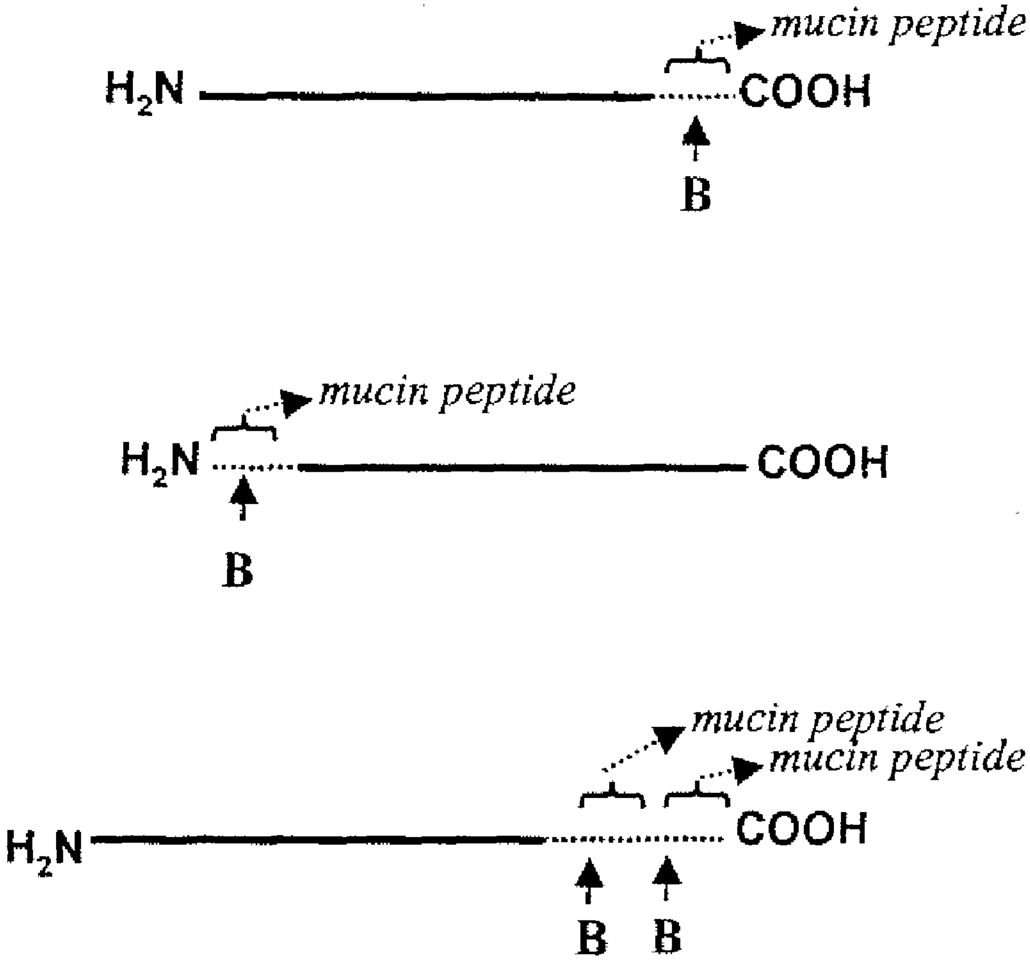
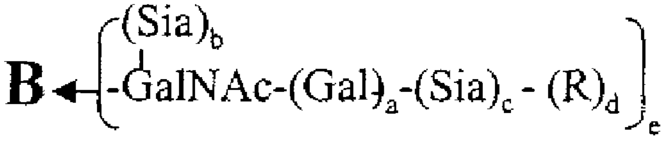
a-c, e (independently selected) = 0 or 1;
d = 0;
R = modifying group, mannose, oligo-mannose.
FIG. 47E CHO, BHK, 293 cells, Vero expressed growth hormone-mucin fusion protein.
a-c, e (independently selected) = 0 or 1; d = 0

1. Sialidase
2. CMP-SA-PEG, ST3Gal1 a-d, e (independently selected) = 0 or 1;
R = PEG.

FIG. 47F

Insect cell expressed Growth Hormone-mucin fusion protein.
a, e (independently selected) = 0 or 1;
b, c, d = 0.

1. Galactosyltransferase, UDP-Gal-PEG a, d, e (independently selected) = 0 or 1;
b, c = 0; R = PEG.

FIG. 47G

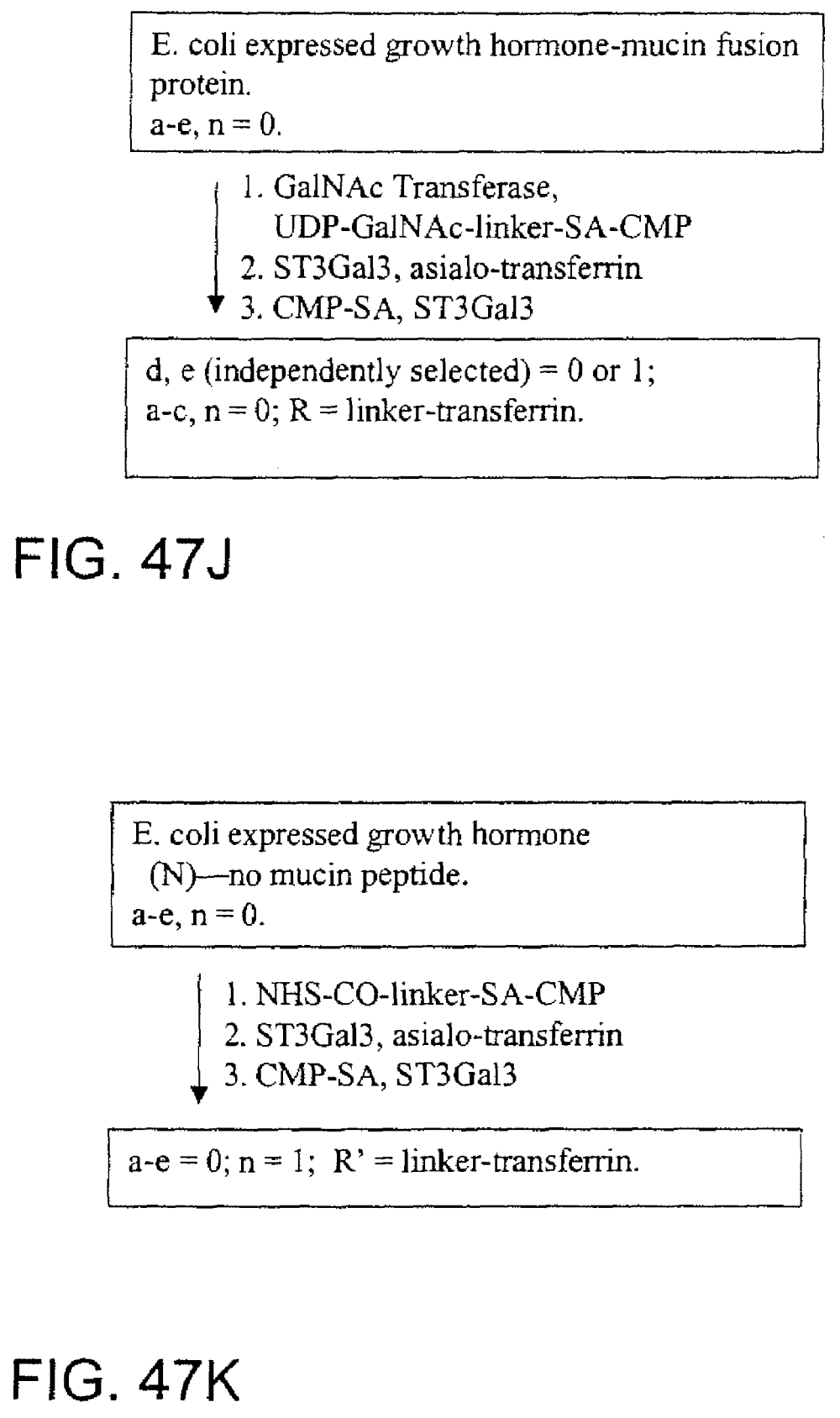

E. coli expressed growth hormone-mucin fusion protein.
a-e, n = 0.

1. GalNAc Transferase, UDP-GalNAc-linker-SA-CMP
2. ST3Gal3, asialo-transferrin
3. CMP-SA, ST3Gal3 d, e (independently selected) = 0 or 1;
a-c, n = 0; R = linker-transferrin.

FIG. 47J

E. coli expressed growth hormone (N)—no mucin peptide.
a-e, n = 0.

1. NHS-CO-linker-SA-CMP
2. ST3Gal3, asialo-transferrin
3. CMP-SA, ST3Gal3 a-e = 0; n = 1; R' = linker-transferrin.

FIG. 47K

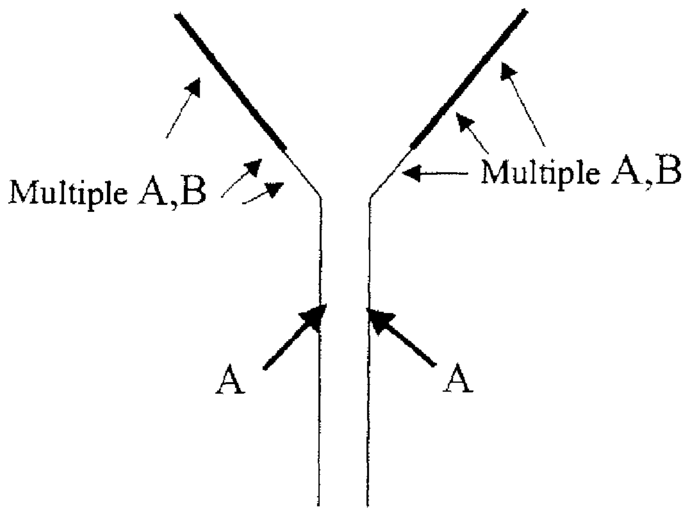
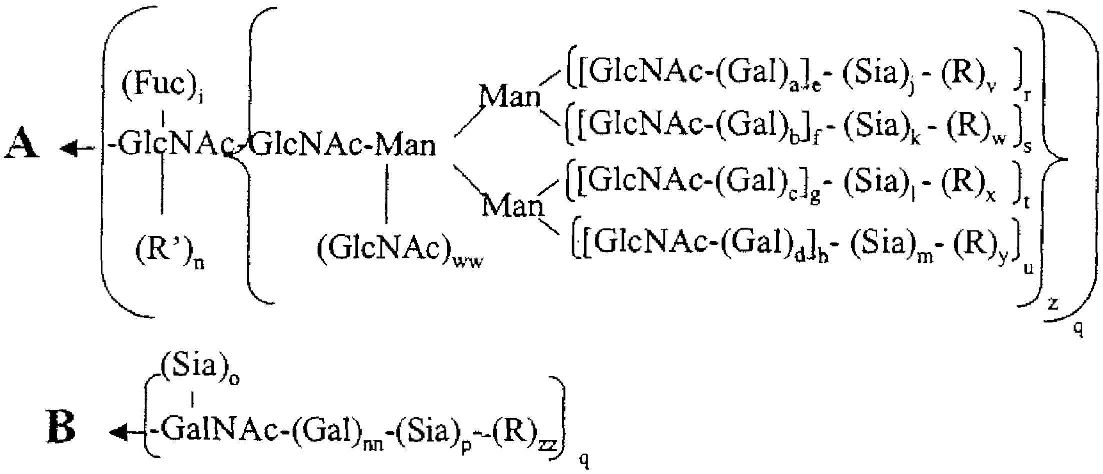
a-d, i-m, q-u, w, z, nn, ww, zz (independently selected) = 0 or 1.
e-h (independently selected) = 0 to 4.
n, v-y = 0;
R = modifying group, mannose, oligo-mannose;
R' = H, glycosyl residue, modifying group, glycoconjugate.
FIG. 48A CHO, BHK, 293 cells, Vero or transgenic animals expressed TNF Receptor IgG Fusion.
a-m, o-u, aa (independently selected) = 0 or 1;
n = 1; v-z = 0.

1. CMP-SA, ST3Gal1
2. galactosyltransferase, UPD-Gal
3. CMP-SA-PEG, ST3Gal3 a-m, o-u, v-y, aa (independently selected) = 0 or 1;
n = 1; z = 0; R = PEG.

FIG. 48B

CHO, BHK, 293 cells, Vero expressed TNF Receptor IgG Fusion.
a-m, o-u, aa (independently selected) = 0 or 1;
n = 1; v-z = 0.

1. sialidase
2. CMP-SA-PEG, ST3Gal1 a-i, p-u, z, aa (independently selected) = 0 or 1;
n = 1; o, j-m, v-y = 0; R = PEG.

FIG. 48C

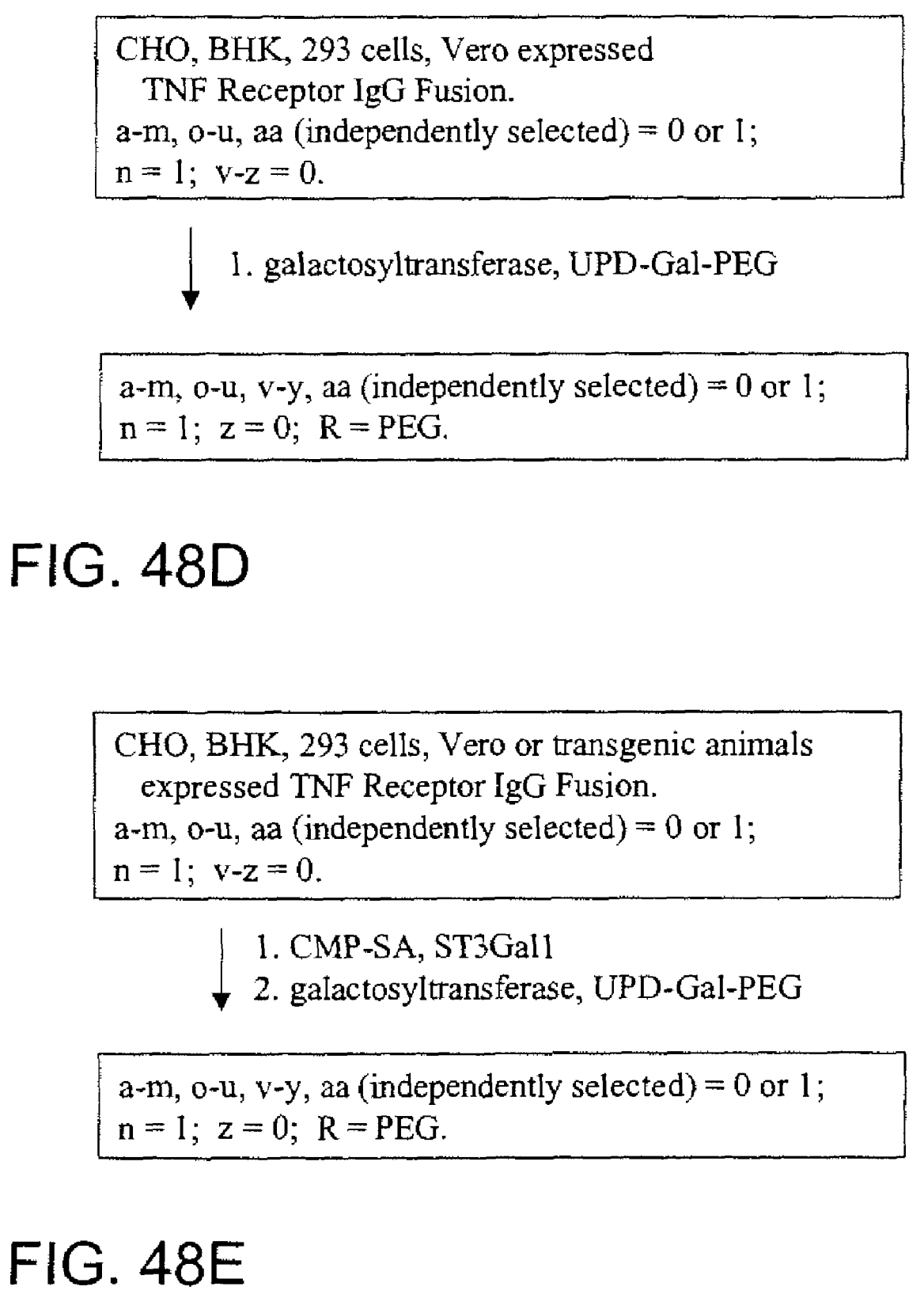

CHO, BHK, 293 cells, Vero expressed TNF Receptor IgG Fusion.
a-m, o-u, aa (independently selected) = 0 or 1;
n = 1; v-z = 0.

1. galactosyltransferase, UPD-Gal-PEG a-m, o-u, v-y, aa (independently selected) = 0 or 1;
n = 1; z = 0; R = PEG.

FIG. 48D

CHO, BHK, 293 cells, Vero or transgenic animals expressed TNF Receptor IgG Fusion.
a-m, o-u, aa (independently selected) = 0 or 1;
n = 1; v-z = 0.

1. CMP-SA, ST3Gal1
2. galactosyltransferase, UPD-Gal-PEG a-m, o-u, v-y, aa (independently selected) = 0 or 1;
n = 1; z = 0; R = PEG.

FIG. 48E

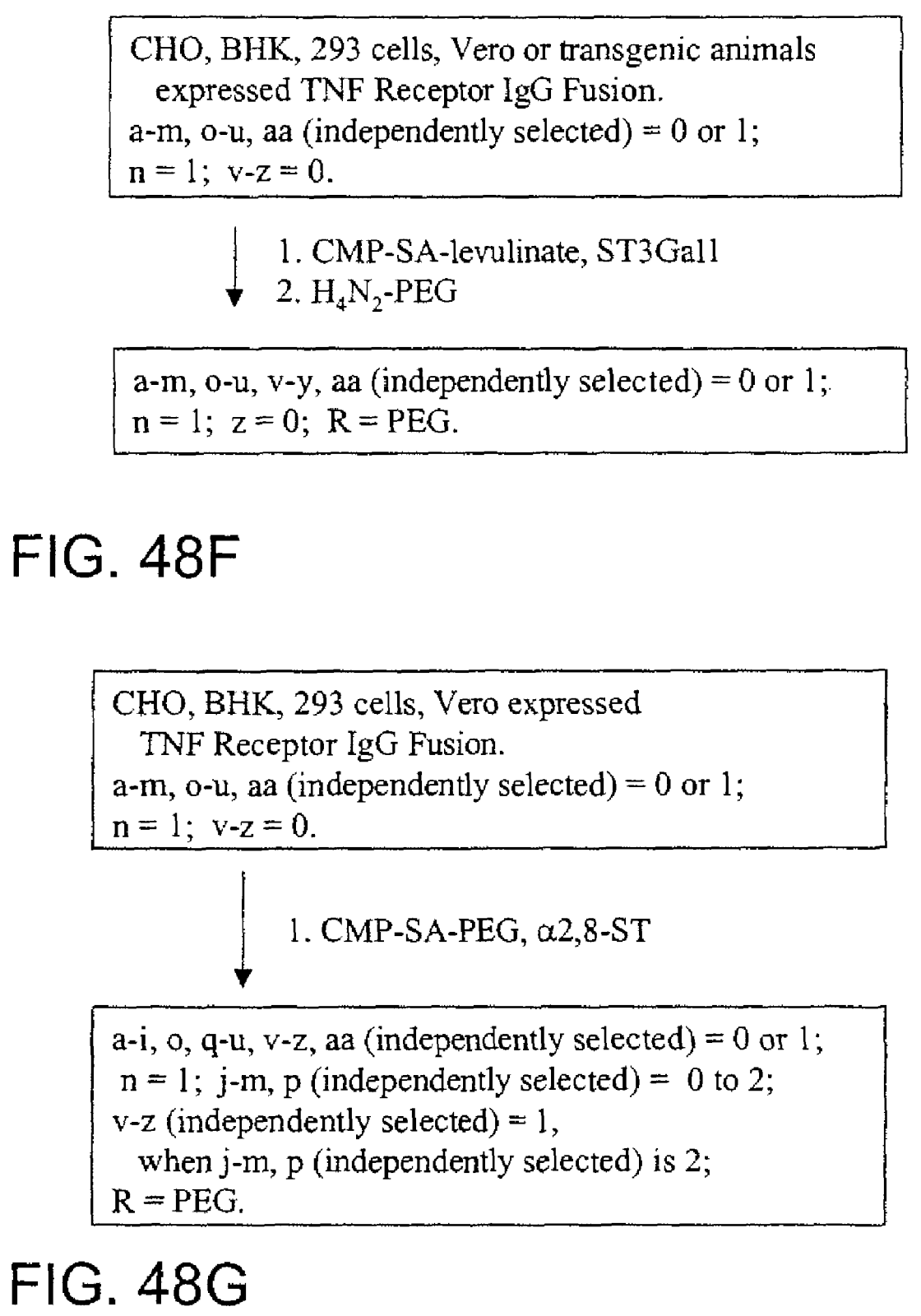

CHO, BHK, 293 cells, Vero or transgenic animals expressed TNF Receptor IgG Fusion.
a-m, o-u, aa (independently selected) = 0 or 1;
n = 1; v-z = 0.

1. CMP-SA-levulinate, ST3Gal1
2. $H_4N_2$-PEG a-m, o-u, v-y, aa (independently selected) = 0 or 1;
n = 1; z = 0; R = PEG.

FIG. 48F

CHO, BHK, 293 cells, Vero expressed TNF Receptor IgG Fusion.
a-m, o-u, aa (independently selected) = 0 or 1;
n = 1; v-z = 0.

1. CMP-SA-PEG, α2,8-ST a-i, o, q-u, v-z, aa (independently selected) = 0 or 1;
n = 1; j-m, p (independently selected) = 0 to 2;
v-z (independently selected) = 1,
when j-m, p (independently selected) is 2;
R = PEG.

FIG. 48G a-d, i, l, q-u (independently selected) = 0 or 1.
e-h (independently selected) = 0 to 4.
j-k (independently selected) = 0 or 1.
M = 0 to 20.
n, v-y = 0; z = 0 or 1;
R = polymer, toxin, radioisotope-complex, drug, mannose, oligo-mannose.
R' = H, glycosyl residue, modifying group, glycoconjugate.

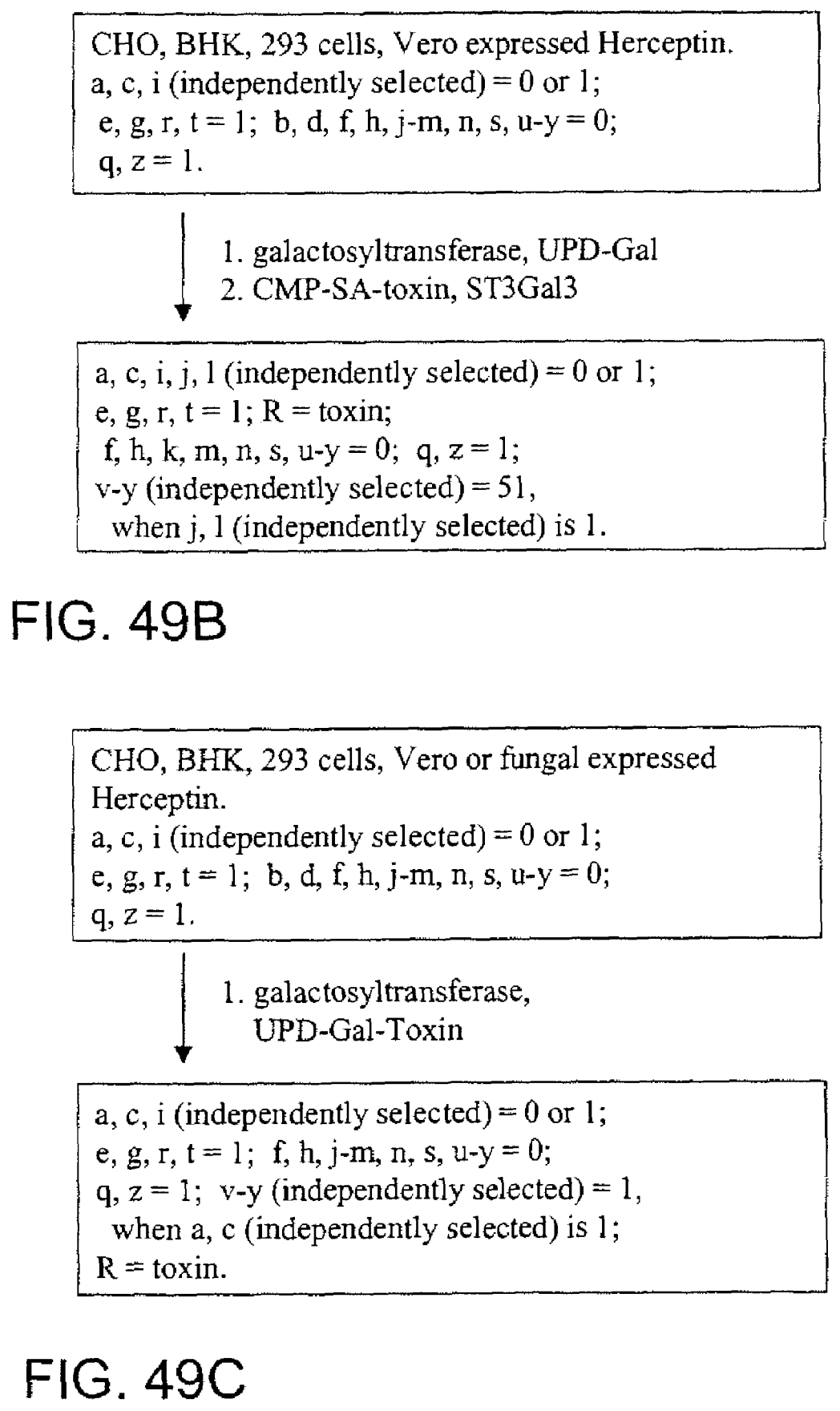

CHO, BHK, 293 cells, Vero expressed Herceptin.
a, c, i (independently selected) = 0 or 1;
e, g, r, t = 1; b, d, f, h, j-m, n, s, u-y = 0;
q, z = 1.

1. galactosyltransferase, UPD-Gal
2. CMP-SA-toxin, ST3Gal3 a, c, i, j, l (independently selected) = 0 or 1;
e, g, r, t = 1; R = toxin;
f, h, k, m, n, s, u-y = 0; q, z = 1;
v-y (independently selected) = 51,
when j, l (independently selected) is 1.

FIG. 49B

CHO, BHK, 293 cells, Vero or fungal expressed Herceptin.
a, c, i (independently selected) = 0 or 1;
e, g, r, t = 1; b, d, f, h, j-m, n, s, u-y = 0;
q, z = 1.

1. galactosyltransferase, UPD-Gal-Toxin a, c, i (independently selected) = 0 or 1;
e, g, r, t = 1; f, h, j-m, n, s, u-y = 0;
q, z = 1; v-y (independently selected) = 1,
when a, c (independently selected) is 1;
R = toxin.

FIG. 49C

Figure 49D:
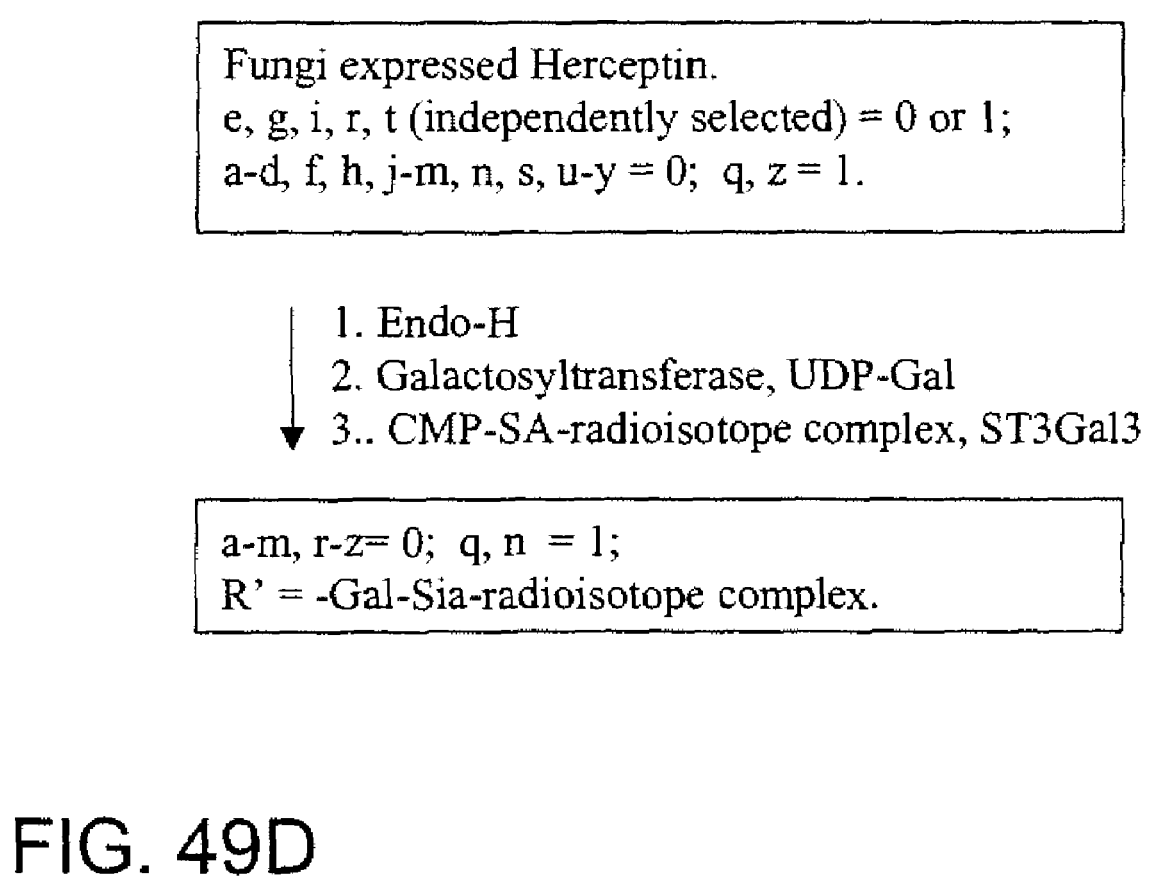

Fungi expressed Herceptin.
e, g, i, r, t (independently selected) = 0 or 1;
a-d, f, h, j-m, n, s, u-y = 0; q, z = 1.

1. Endo-H
2. Galactosyltransferase, UDP-Gal
3.. CMP-SA-radioisotope complex, ST3Gal3 a-m, r-z= 0; q, n = 1;
R' = -Gal-Sia-radioisotope complex.

FIG. 49D a-d, i, p-u, (independently selected) = 0 or 1.
e-h (independently selected) = 0 to 4.
j-m (independently selected) = 0 or 1.
n, v-y = 0; z = 0 or 1;
R = polymer, toxin, radioisotope-complex, drug, mannose, oligo-mannose.
R' = H, glycosyl residue, modifying group, glycoconjugate.

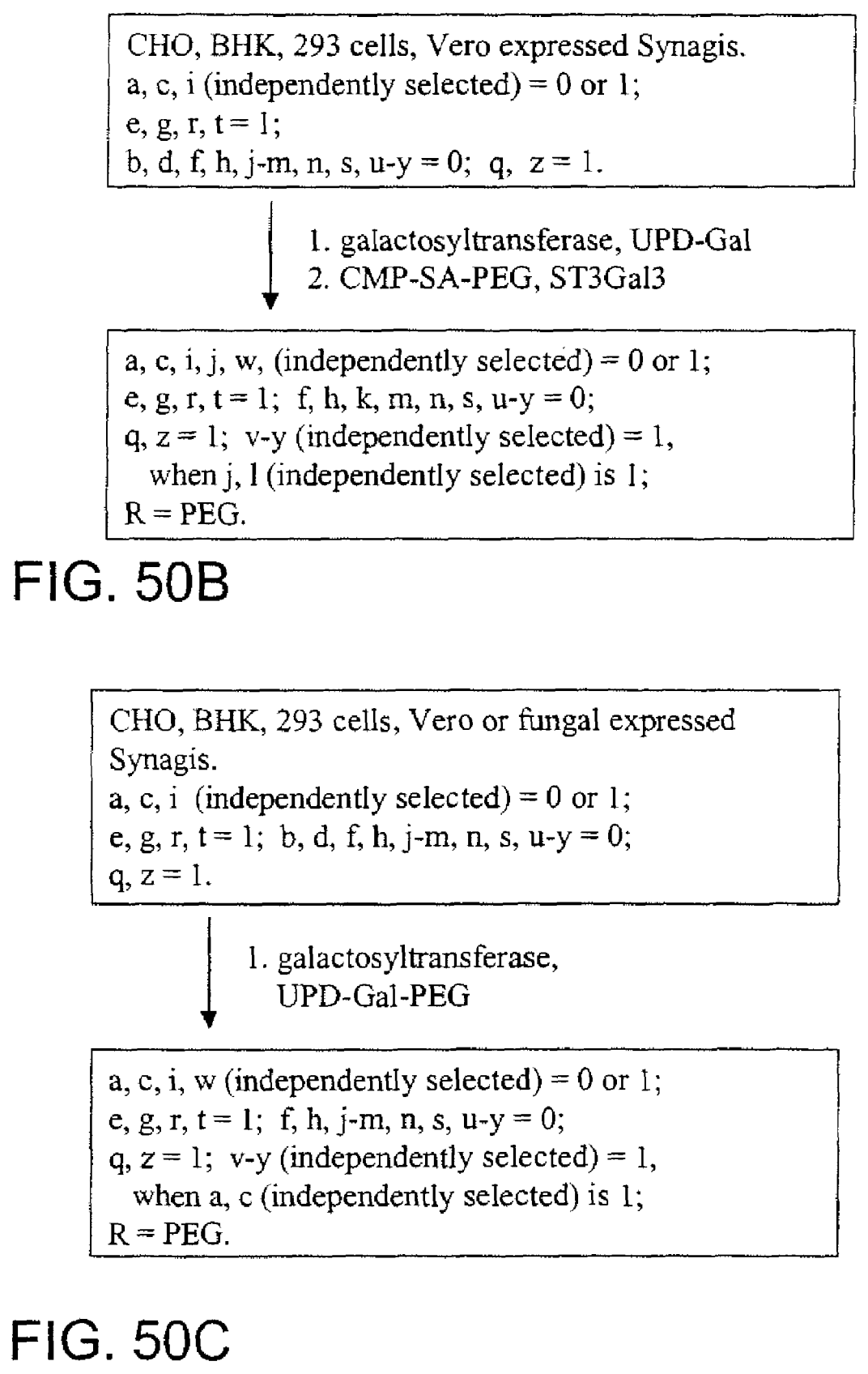

CHO, BHK, 293 cells, Vero expressed Synagis.
a, c, i (independently selected) = 0 or 1;
e, g, r, t = 1;
b, d, f, h, j-m, n, s, u-y = 0; q, z = 1.

1. galactosyltransferase, UPD-Gal
2. CMP-SA-PEG, ST3Gal3 a, c, i, j, w, (independently selected) = 0 or 1;
e, g, r, t = 1; f, h, k, m, n, s, u-y = 0;
q, z = 1; v-y (independently selected) = 1,
when j, l (independently selected) is 1;
R = PEG.

FIG. 50B

CHO, BHK, 293 cells, Vero or fungal expressed Synagis.
a, c, i (independently selected) = 0 or 1;
e, g, r, t = 1; b, d, f, h, j-m, n, s, u-y = 0;
q, z = 1.

1. galactosyltransferase, UPD-Gal-PEG a, c, i, w (independently selected) = 0 or 1;
e, g, r, t = 1; f, h, j-m, n, s, u-y = 0;
q, z = 1; v-y (independently selected) = 1,
when a, c (independently selected) is 1;
R = PEG.

FIG. 50C

Figure 50D:
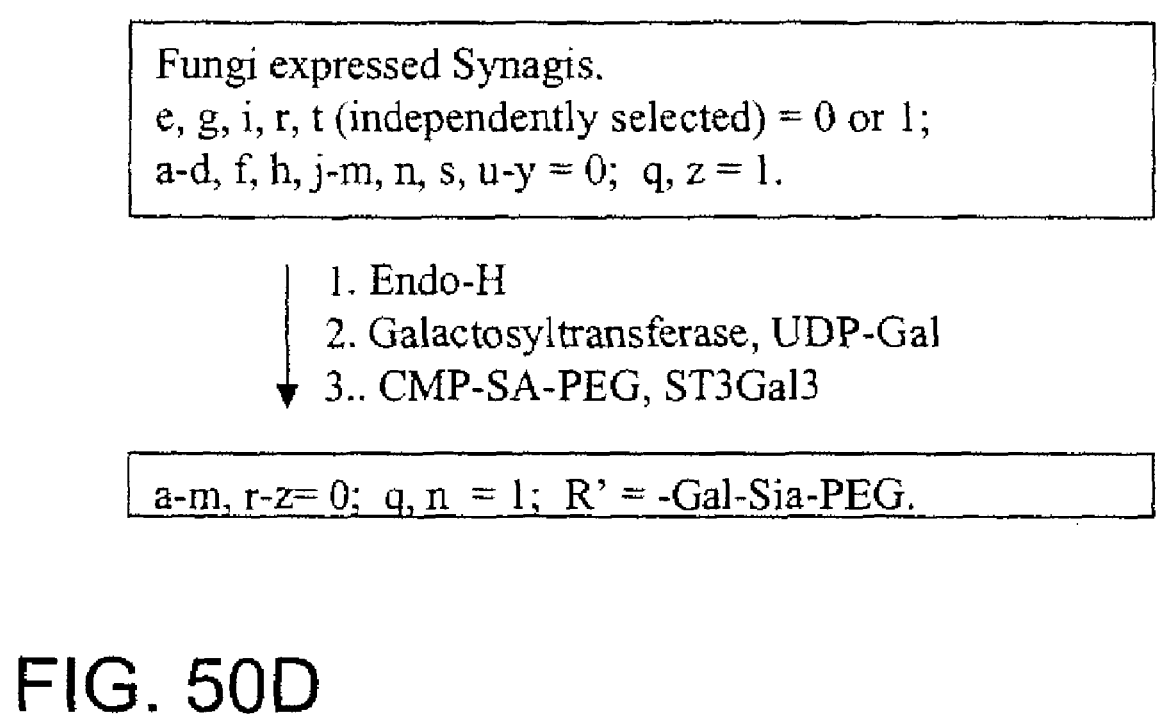

Fungi expressed Synagis.
e, g, i, r, t (independently selected) = 0 or 1;
a-d, f, h, j-m, n, s, u-y = 0; q, z = 1.

1. Endo-H
2. Galactosyltransferase, UDP-Gal
3.. CMP-SA-PEG, ST3Gal3 a-m, r-z= 0; q, n = 1; R' = -Gal-Sia-PEG.

FIG. 50D a-d, i, q-u, w (independently selected) = 0 or 1.
e-h (independently selected) = 0 to 6.
j-m (independently selected) = 0 to 20.
n, v-y = 0; z = 0 or 1;
R = polymer, toxin, radioisotope-complex, drug, mannose, oligo-mannose.
R' = H, glycosyl residue, modifying group, glycoconjugate.

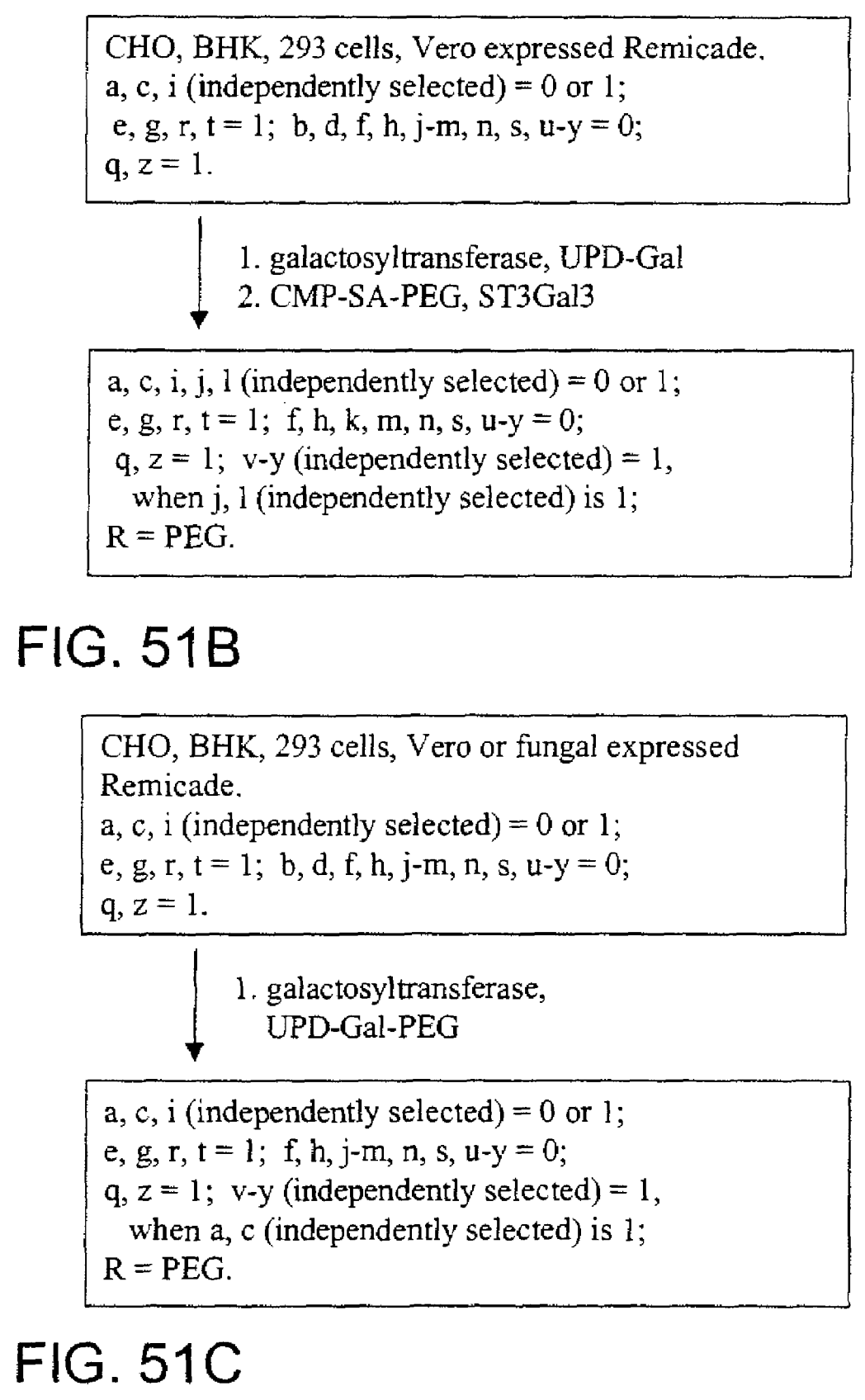

CHO, BHK, 293 cells, Vero expressed Remicade.
a, c, i (independently selected) = 0 or 1;
e, g, r, t = 1; b, d, f, h, j-m, n, s, u-y = 0;
q, z = 1.

1. galactosyltransferase, UPD-Gal
2. CMP-SA-PEG, ST3Gal3 a, c, i, j, l (independently selected) = 0 or 1;
e, g, r, t = 1; f, h, k, m, n, s, u-y = 0;
q, z = 1; v-y (independently selected) = 1,
when j, l (independently selected) is 1;
R = PEG.

FIG. 51B

CHO, BHK, 293 cells, Vero or fungal expressed Remicade.
a, c, i (independently selected) = 0 or 1;
e, g, r, t = 1; b, d, f, h, j-m, n, s, u-y = 0;
q, z = 1.

1. galactosyltransferase, UPD-Gal-PEG a, c, i (independently selected) = 0 or 1;
e, g, r, t = 1; f, h, j-m, n, s, u-y = 0;
q, z = 1; v-y (independently selected) = 1,
when a, c (independently selected) is 1;
R = PEG.

FIG. 51C

Fungi expressed Remicade.
e, g, i, r, t (independently selected) = 0 or 1;
a-d, f, h, j-m, n, s, u-y = 0; q, z = 1.

| 1. Endo-H
| 2. Galactosyltransferase, UDP-Gal
↓ 3.. CMP-SA-radioisotope complex, ST3Gal3 a-m, r-z = 0; q, n = 1;
R' = -Gal-Sia-radioisotope complex.

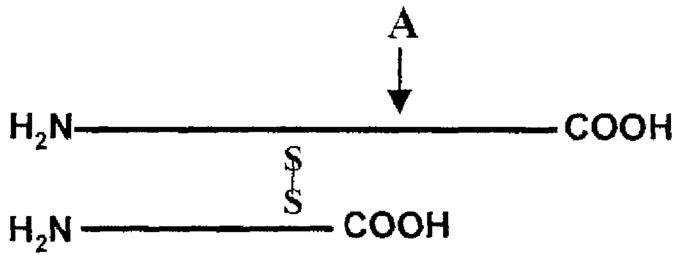
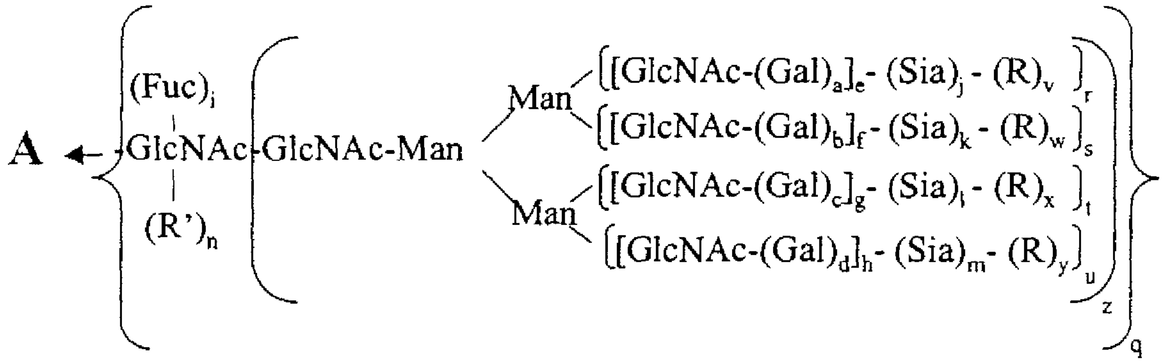
a-d, i, q-u (independently selected) = 0 or 1.
e-h (independently selected) = 0 to 4.
j-m (independently selected) = 0 or 1.
n, v-y = 0; z = 0 or 1;
R = modifying group, mannose, oligo-mannose;
R' = H, glycosyl residue, modifying group, glycoconjugate.
FIG. 52A CHO, BHK, 293 cells, Vero expressed Reopro.
a-m, r-u (independently selected) = 0 or 1;
n = 0; v-y = 0; z = 1.

1. Sialidase
2. CMP-SA-PEG, ST3Gal3 a-m, r-u (independently selected) = 0 or 1;
v-y (independently selected) = 1,
when j-m (independently selected) is 1;
n = 0; R = PEG; z = 1.

FIG. 52B

Insect cell expressed Reopro.
a-h, j-n, s-y = 0; i, r (independently selected) = 0 or 1;
z = 1.

1. GNT's 1&2, UDP-GlcNAc-PEG a-d, f, h, j-n, s, u, w, y = 0;
e, g, i, r, t, v, x (independently selected) = 0 or 1;
v, x (independently selected) = 1,
when e, g (independently selected) is 1;
z = 1; R = PEG.

FIG. 52C

Figure 52D:
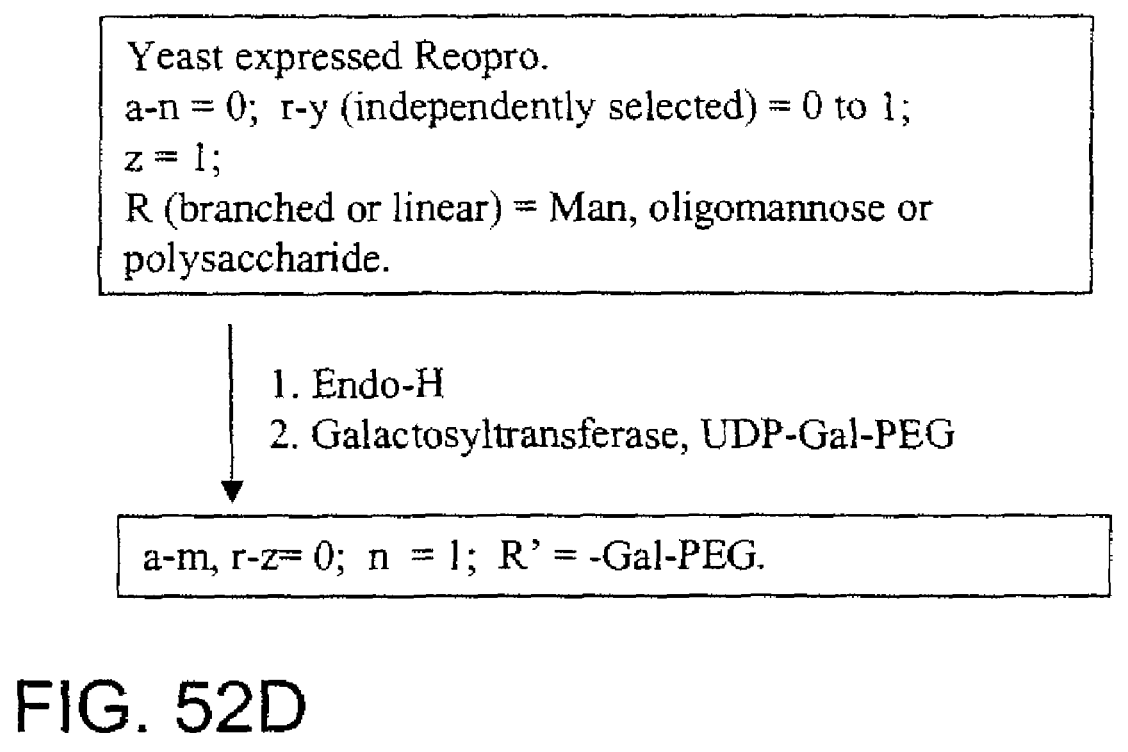

Yeast expressed Reopro.
a-n = 0; r-y (independently selected) = 0 to 1;
z = 1;
R (branched or linear) = Man, oligomannose or polysaccharide.

1. Endo-H
2. Galactosyltransferase, UDP-Gal-PEG a-m, r-z= 0; n = 1; R' = -Gal-PEG.

FIG. 52D a-c, e (independently selected) = 0 or 1;
d = 0; R = polymer

CHO, BHK, 293 cells, Vero expressed
Reopro-mucin fusion protein.
a-c, e (independently selected) = 0 or 1; d = 0

1. Sialidase
2. CMP-SA-PEG, ST3Gal1 a-d, e (independently selected) = 0 or 1; R = PEG.

FIG. 52F

Insect cell expressed Reopro-mucin fusion protein.
a, e (independently selected) = 0 or 1; b, c, d = 0.

1. Galactosyltransferase, UDP-Gal-PEG a, d, e (independently selected) = 0 or 1;
b, c = 0; R = PEG.

FIG. 52G

Figure 52H:
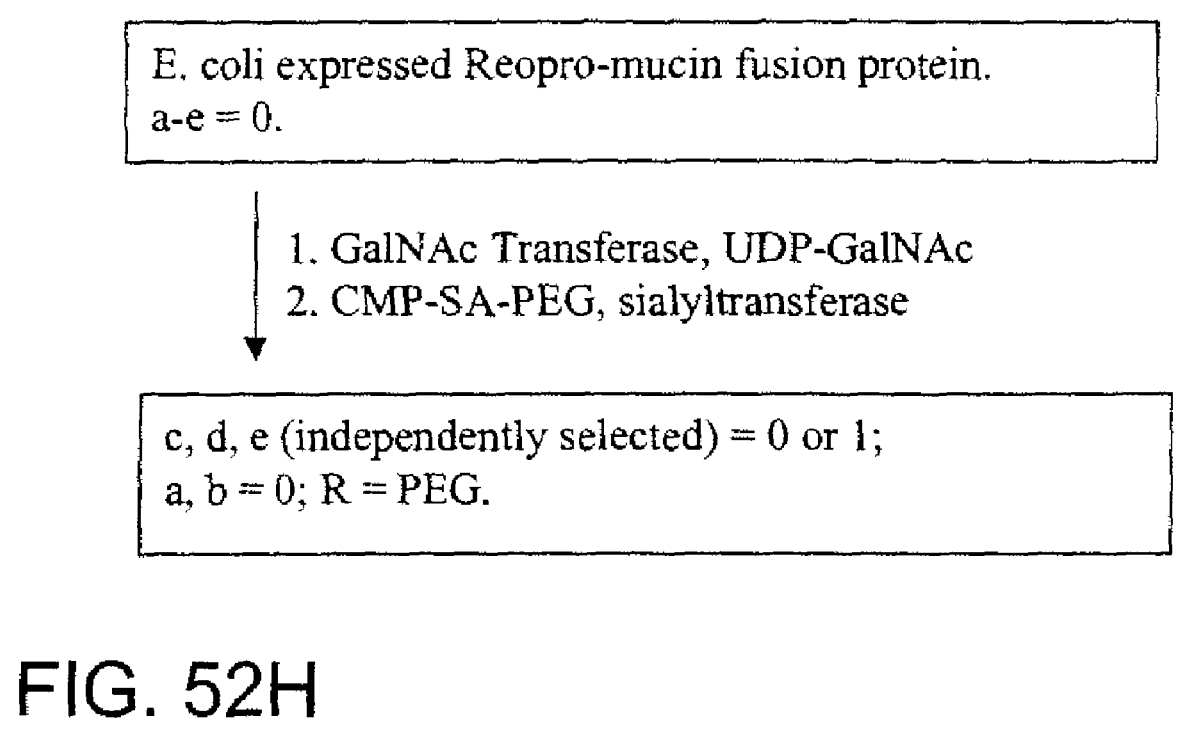

E. coli expressed Reopro-mucin fusion protein.
a-e = 0.

1. GalNAc Transferase, UDP-GalNAc
2. CMP-SA-PEG, sialyltransferase c, d, e (independently selected) = 0 or 1;
a, b = 0; R = PEG.

FIG. 52H a-c, e (independently selected) = 0 or 1;
d = 0; R = polymer, linker.

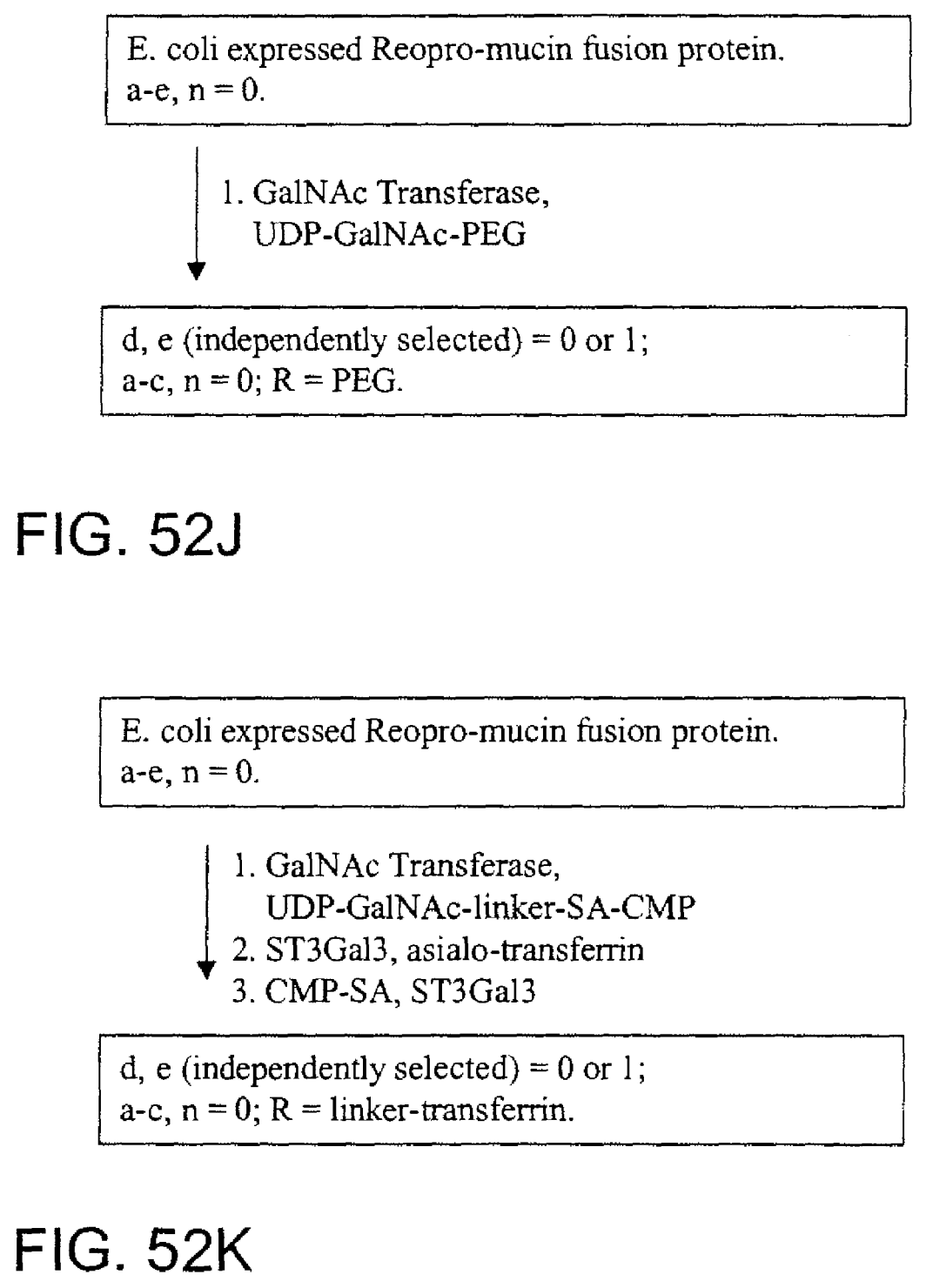

E. coli expressed Reopro-mucin fusion protein.
a-e, n = 0.

1. GalNAc Transferase,
UDP-GalNAc-PEG d, e (independently selected) = 0 or 1;
a-c, n = 0; R = PEG.

FIG. 52J

E. coli expressed Reopro-mucin fusion protein.
a-e, n = 0.

1. GalNAc Transferase,
UDP-GalNAc-linker-SA-CMP
2. ST3Gal3, asialo-transferrin
3. CMP-SA, ST3Gal3 d, e (independently selected) = 0 or 1;
a-c, n = 0; R = linker-transferrin.

FIG. 52K

Figure 52L:
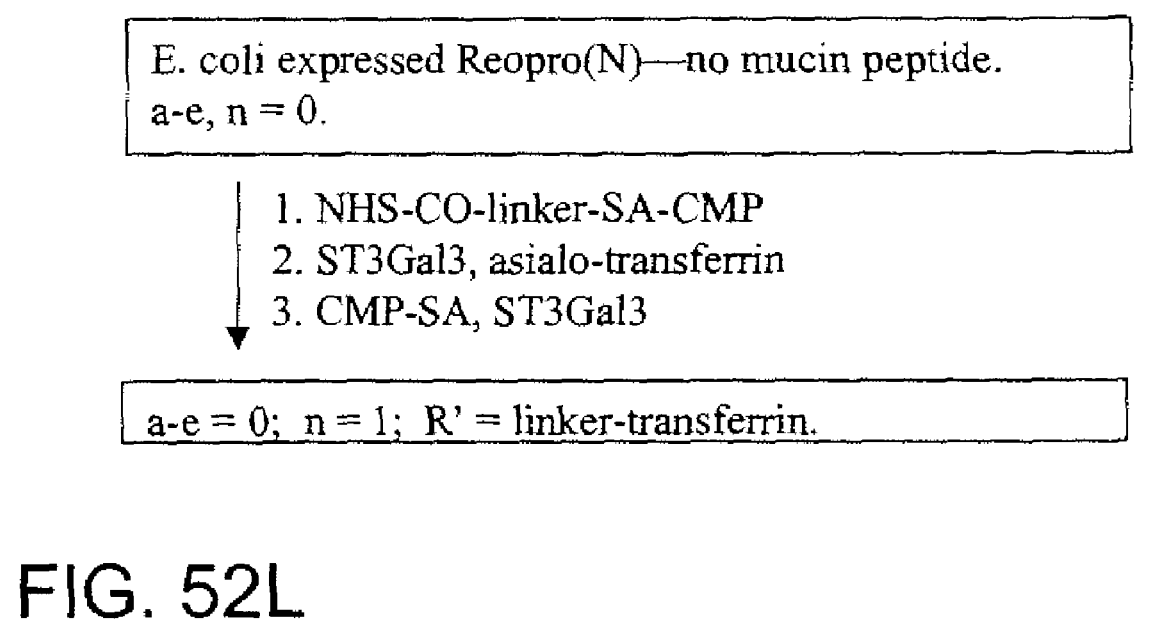

E. coli expressed Reopro(N)—no mucin peptide.
a-e, n = 0.

1. NHS-CO-linker-SA-CMP
2. ST3Gal3, asialo-transferrin
3. CMP-SA, ST3Gal3 a-e = 0; n = 1; R' = linker-transferrin.

FIG. 52L a-d, i, q-u (independently selected) = 0 or 1.
e-h (independently selected) = 0 to 4.
j-m (independently selected) = 0 or 1.
n, v-y = 0; z = 0 or 1; R = polymer, toxin, radioisotope-complex, drug, glycoconjugate.
R' = H, sugar, glycoconjugate.

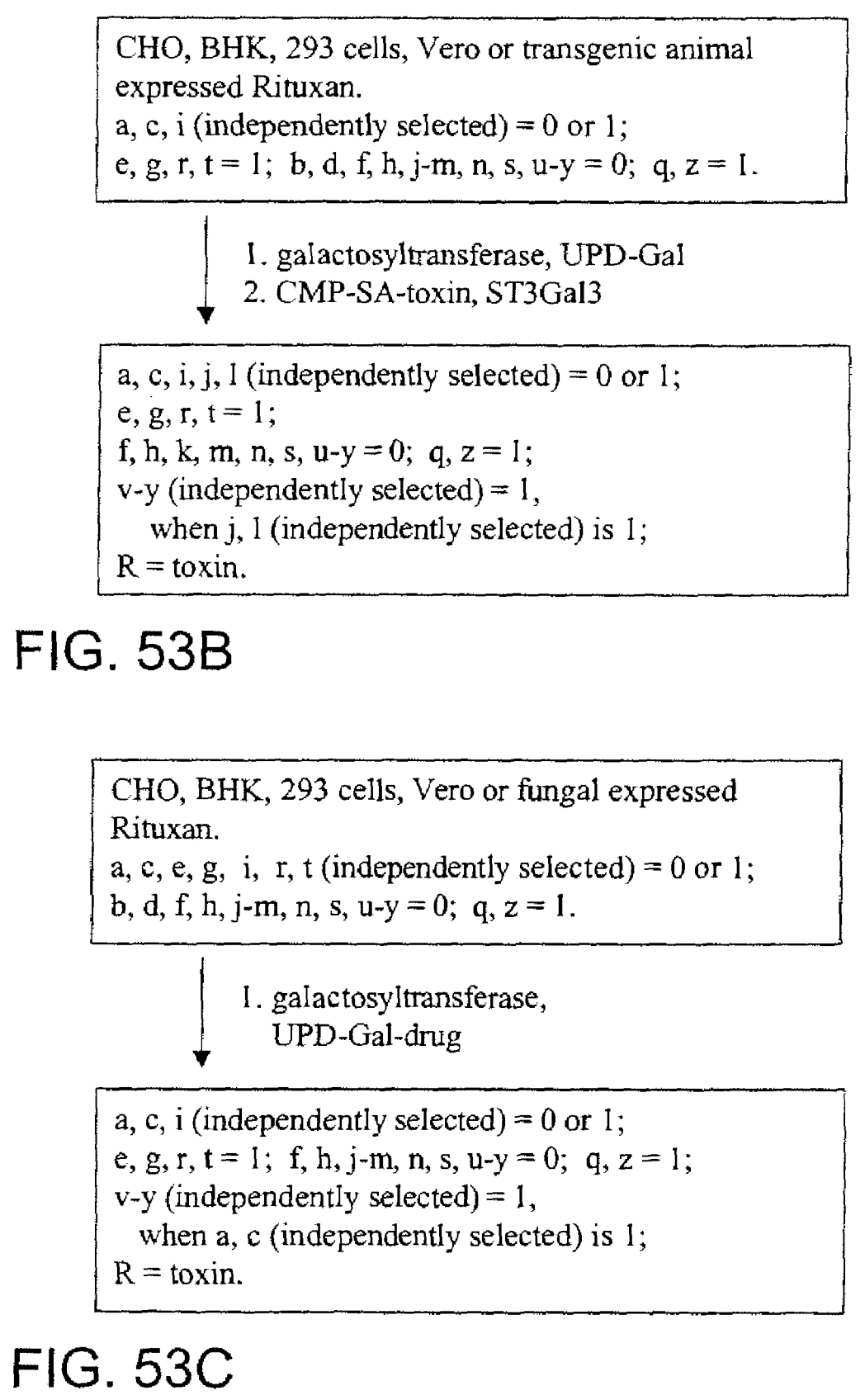

CHO, BHK, 293 cells, Vero or transgenic animal expressed Rituxan.
a, c, i (independently selected) = 0 or 1;
e, g, r, t = 1; b, d, f, h, j-m, n, s, u-y = 0; q, z = 1.

1. galactosyltransferase, UPD-Gal
2. CMP-SA-toxin, ST3Gal3 a, c, i, j, l (independently selected) = 0 or 1;
e, g, r, t = 1;
f, h, k, m, n, s, u-y = 0; q, z = 1;
v-y (independently selected) = 1,
when j, l (independently selected) is 1;
R = toxin.

FIG. 53B

CHO, BHK, 293 cells, Vero or fungal expressed Rituxan.
a, c, e, g, i, r, t (independently selected) = 0 or 1;
b, d, f, h, j-m, n, s, u-y = 0; q, z = 1.

1. galactosyltransferase, UPD-Gal-drug a, c, i (independently selected) = 0 or 1;
e, g, r, t = 1; f, h, j-m, n, s, u-y = 0; q, z = 1;
v-y (independently selected) = 1,
when a, c (independently selected) is 1;
R = toxin.

FIG. 53C

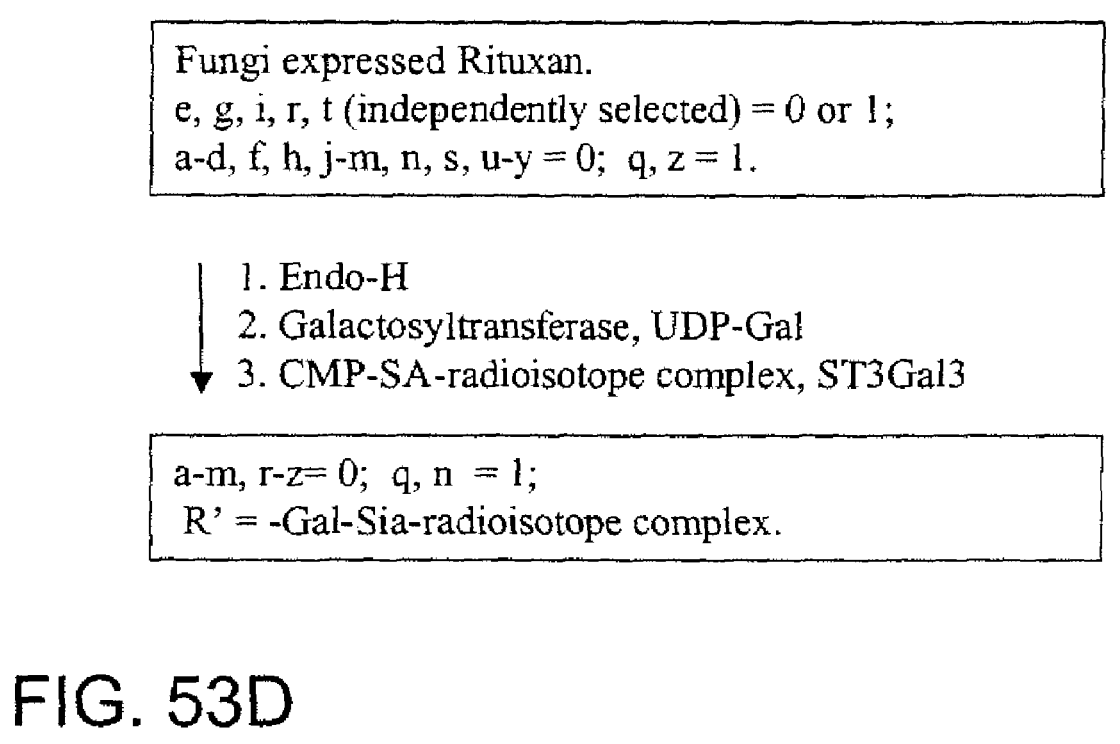

Fungi expressed Rituxan.
e, g, i, r, t (independently selected) = 0 or 1;
a-d, f, h, j-m, n, s, u-y = 0; q, z = 1.

1. Endo-H
2. Galactosyltransferase, UDP-Gal
3. CMP-SA-radioisotope complex, ST3Gal3 a-m, r-z= 0; q, n = 1;
R' = -Gal-Sia-radioisotope complex.

FIG. 53D

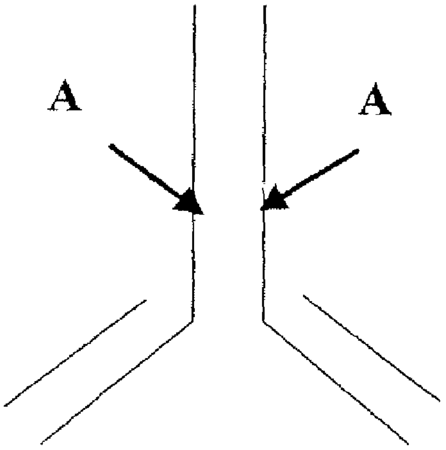
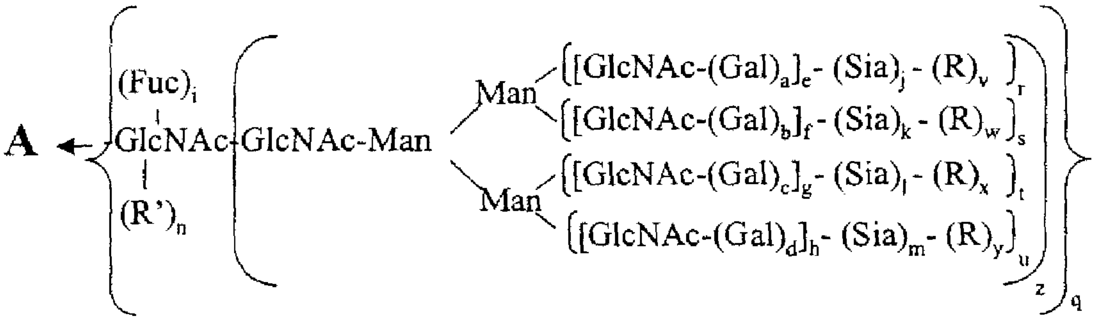
a-d, i, q-u (independently selected) = 0 or 1.
e-h (independently selected) = 0 to 4.
j-m (independently selected) = 0 or 1.
n, v-y = 0; z = 0 or 1;
R = polymer, toxin, radioisotope-complex, drug, glycoconjugate, mannose, oligo-mannose.
R' = H, glycosyl residue, modifying group, glycoconjugate.
FIG. 53E CHO, BHK, 293 cells, Vero or transgenic animal expressed Rituxan.
a, c, i (independently selected) = 0 or 1;
e, g, r, t = 1; b, d, f, h, j-m, n, s, u-y = 0;
q, z = 1.

1. galactosyltransferase, UPD-Gal
2. CMP-SA-PEG, ST3Gal3 a, c, i, j, l (independently selected) = 0 or 1;
e, g, r, t = 1; f, h, k, m, n, s, u-y = 0;
q, z = 1; v-y (independently selected) = 1,
when j, l (independently selected) is 1;
R = PEG.

FIG. 53F

Fungi, yeast or CHO expressed Rituxan.
e, g, i, r, t, v, x (independently selected) = 0 or 1;
a-d, f, h, j-m, n, s, u, w, y = 0; q, z = 1;
R (independently selected) = mannose, oligomannose, polymannose.

1. mannosidases (alpha and beta)
2. GNT-I,II, UDP-GlcNAc
3. Galactosyltransferase, UDP-Gal-radioisotope a-m, r-z= 0; q, n = 1;
R' = -Gal-radioisotope complex.

FIG. 53G

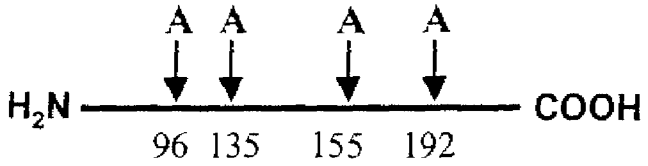
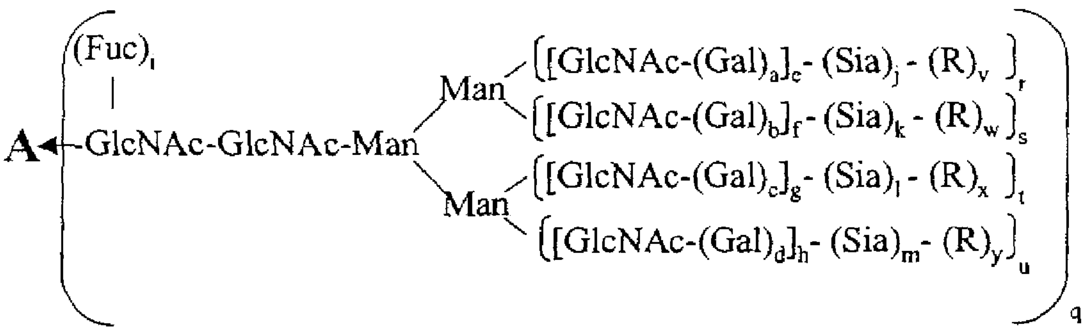
a-d, i, q-u (independently selected) = 0 or 1.
e-h (independently selected) = 0 to 6.
j-m (independently selected) = 0 to 100.
v-y = 0; R = mannose, polymer.
FIG. 54A CHO, BHK, 293 cells, Vero or
transgenic animal expressed AT III.
a-d, i-m, q-u (independently selected) = 0 or 1;
e-h = 1; v-y = 0.

1. Sialidase
2. CMP-SA-PEG (16 mol eq),
ST3Gal3 a-d, i-m, q-u (independently selected) = 0 or 1;
e-h = 1;
v-y (independently selected) = 1,
when j-m (independently selected) is 1;
R = PEG.

FIG. 54B

CHO, BHK, 293 cells, Vero or
transgenic animal expressed AT III.
a-d, i-m, q-u (independently selected) = 0 or 1;
e-h = 1; v-y = 0.

1. Sialidase
2. CMP-SA-PEG (1.2 mol eq),
ST3Gal3
3. CMP-SA (16 mol eq), ST3Gal3 a-d, i-m, q-u (independently selected) = 0 or 1;
e-h = 1;
v-y (independently selected) = 0 or 1;
R = PEG.

FIG. 54C

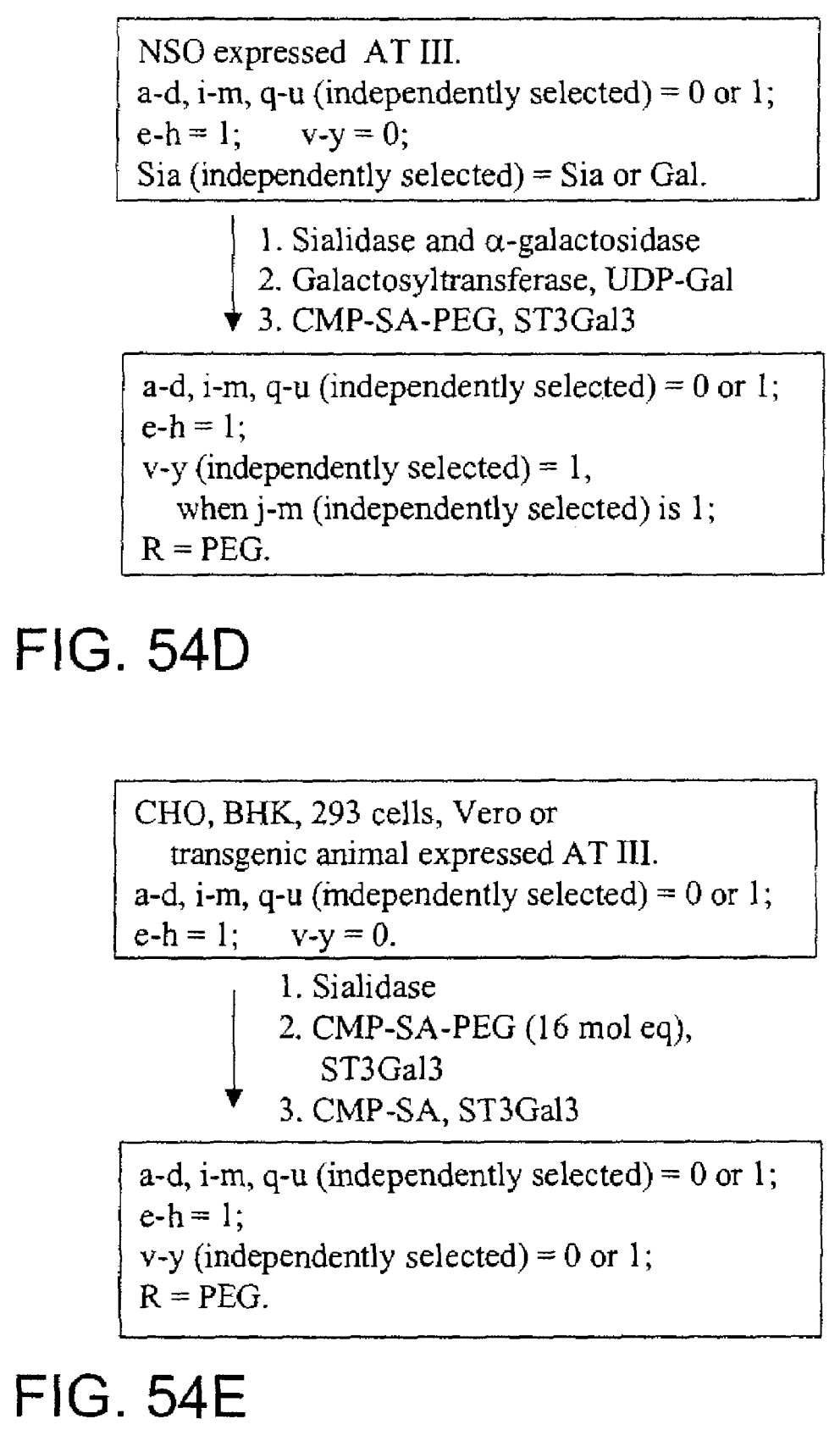

NSO expressed AT III.
a-d, i-m, q-u (independently selected) = 0 or 1;
e-h = 1; v-y = 0;
Sia (independently selected) = Sia or Gal.

1. Sialidase and α-galactosidase
2. Galactosyltransferase, UDP-Gal
3. CMP-SA-PEG, ST3Gal3 a-d, i-m, q-u (independently selected) = 0 or 1;
e-h = 1;
v-y (independently selected) = 1,
when j-m (independently selected) is 1;
R = PEG.

FIG. 54D

CHO, BHK, 293 cells, Vero or
transgenic animal expressed AT III.
a-d, i-m, q-u (independently selected) = 0 or 1;
e-h = 1; v-y = 0.

1. Sialidase
2. CMP-SA-PEG (16 mol eq), ST3Gal3
3. CMP-SA, ST3Gal3 a-d, i-m, q-u (independently selected) = 0 or 1;
e-h = 1;
v-y (independently selected) = 0 or 1;
R = PEG.

FIG. 54E

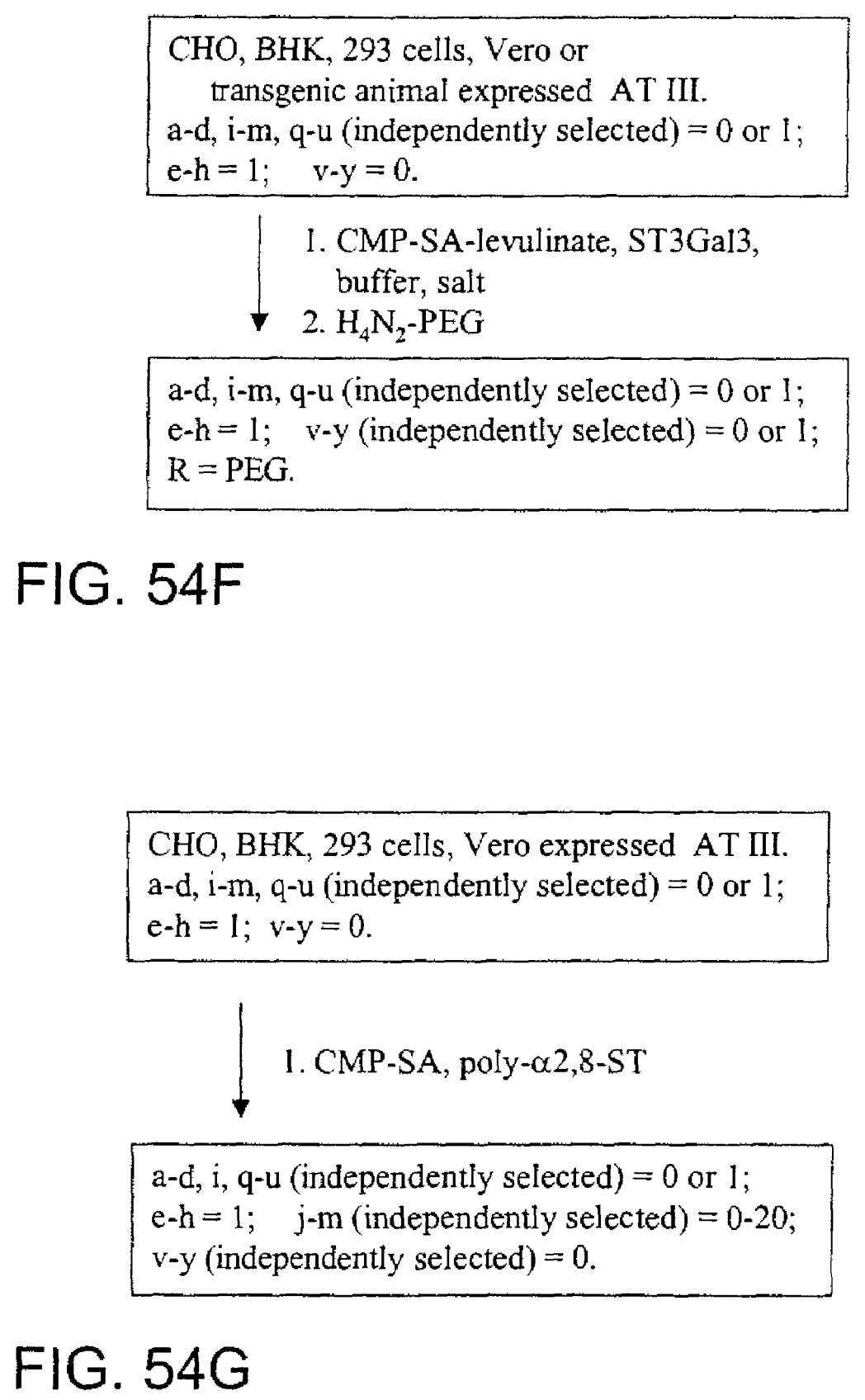

CHO, BHK, 293 cells, Vero or transgenic animal expressed AT III.
a-d, i-m, q-u (independently selected) = 0 or 1;
e-h = 1; v-y = 0.

1. CMP-SA-levulinate, ST3Gal3, buffer, salt
2. $H_4N_2$-PEG a-d, i-m, q-u (independently selected) = 0 or 1;
e-h = 1; v-y (independently selected) = 0 or 1;
R = PEG.

FIG. 54F

CHO, BHK, 293 cells, Vero expressed AT III.
a-d, i-m, q-u (independently selected) = 0 or 1;
e-h = 1; v-y = 0.

1. CMP-SA, poly-α2,8-ST a-d, i, q-u (independently selected) = 0 or 1;
e-h = 1; j-m (independently selected) = 0-20;
v-y (independently selected) = 0.

FIG. 54G a-d, i, p-u (independently selected) = 0 or 1.
e-h (independently selected) = 0 to 6.
j-m (independently selected) = 0 to 100.
v-y = 0 to 100.
R = polymer, linker, mannose.
R' = H, sugar, glycoconjugate.

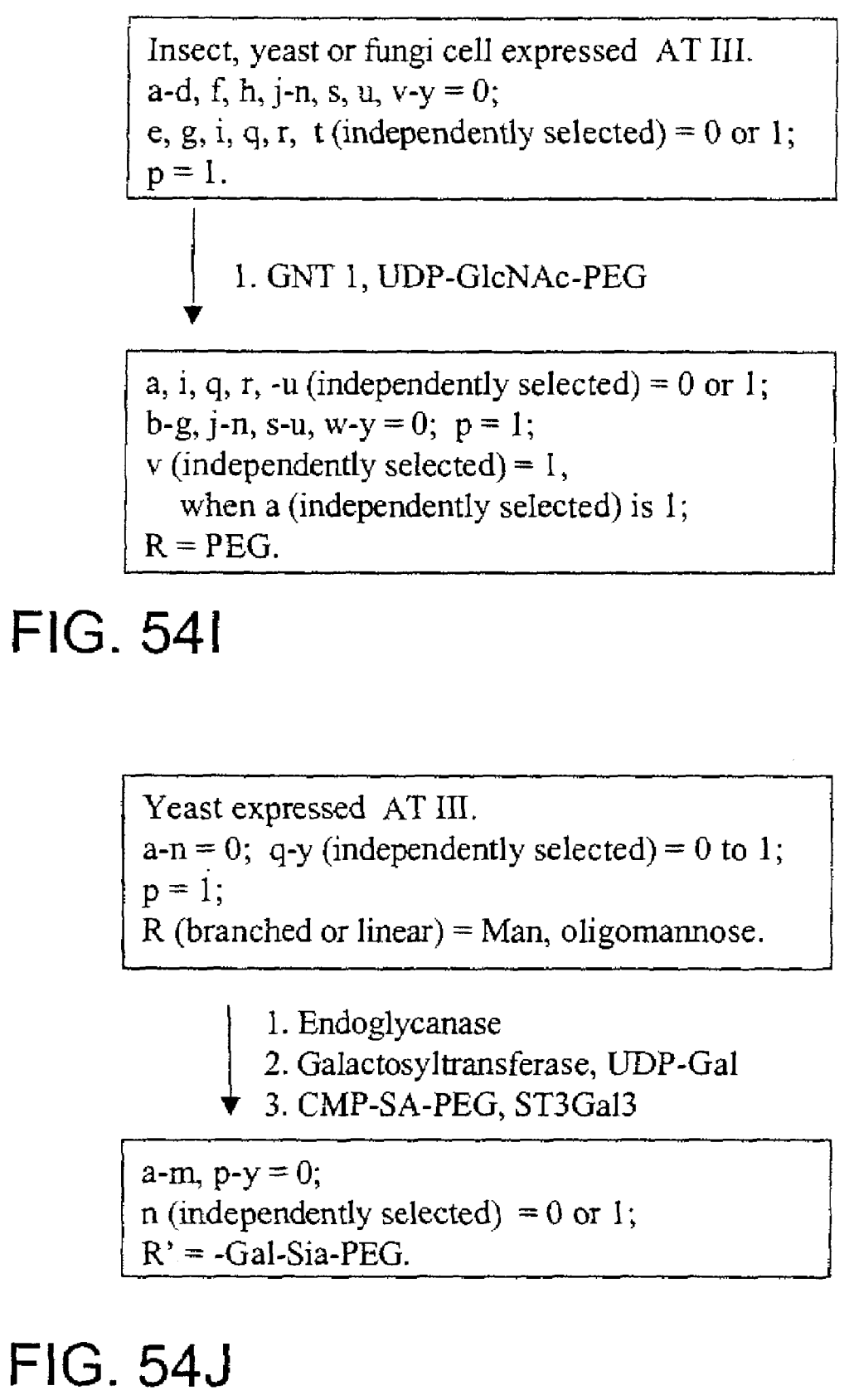

Insect, yeast or fungi cell expressed AT III.
a-d, f, h, j-n, s, u, v-y = 0;
e, g, i, q, r, t (independently selected) = 0 or 1;
p = 1.

1. GNT 1, UDP-GlcNAc-PEG a, i, q, r, -u (independently selected) = 0 or 1;
b-g, j-n, s-u, w-y = 0; p = 1;
v (independently selected) = 1,
when a (independently selected) is 1;
R = PEG.

FIG. 54I

Yeast expressed AT III.
a-n = 0; q-y (independently selected) = 0 to 1;
p = 1;
R (branched or linear) = Man, oligomannose.

1. Endoglycanase
2. Galactosyltransferase, UDP-Gal
3. CMP-SA-PEG, ST3Gal3 a-m, p-y = 0;
n (independently selected) = 0 or 1;
R' = -Gal-Sia-PEG.

FIG. 54J

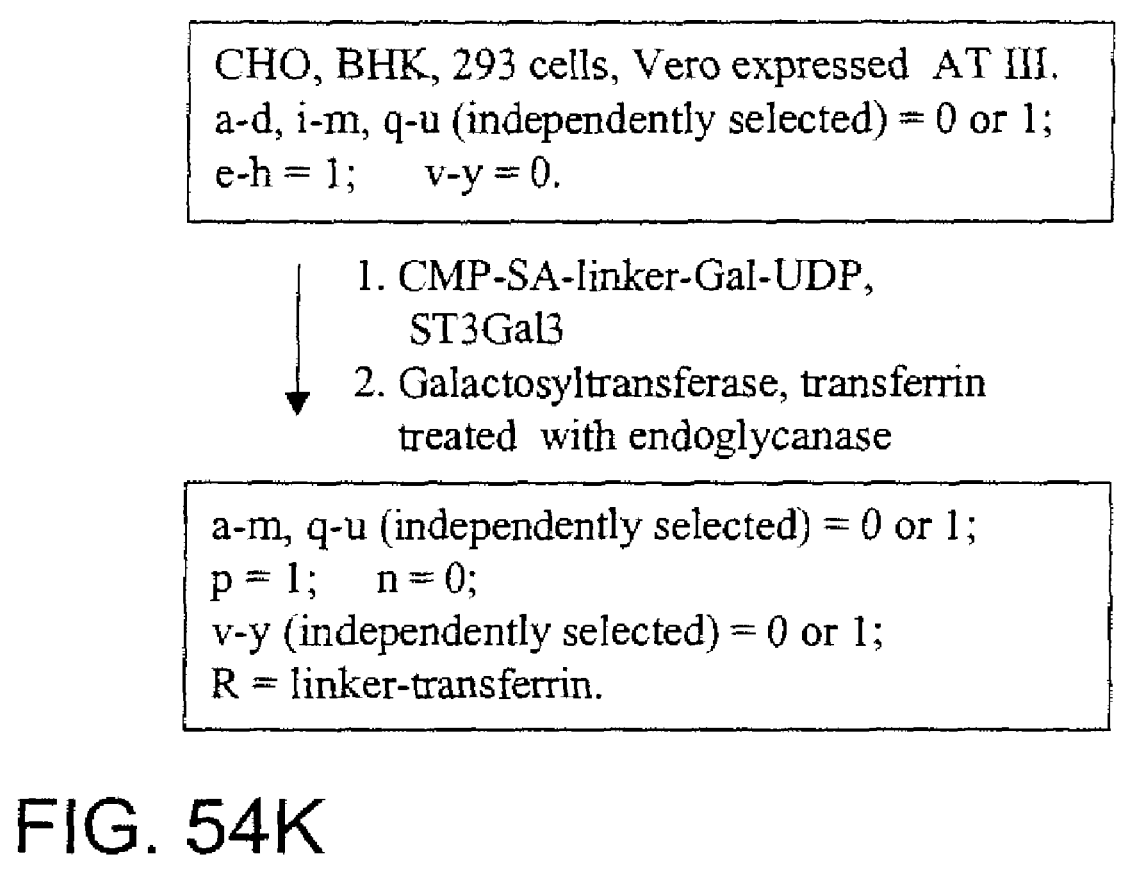

CHO, BHK, 293 cells, Vero expressed AT III.
a-d, i-m, q-u (independently selected) = 0 or 1;
e-h = 1; v-y = 0.

1. CMP-SA-linker-Gal-UDP, ST3Gal3
2. Galactosyltransferase, transferrin treated with endoglycanase a-m, q-u (independently selected) = 0 or 1;
p = 1; n = 0;
v-y (independently selected) = 0 or 1;
R = linker-transferrin.

FIG. 54K

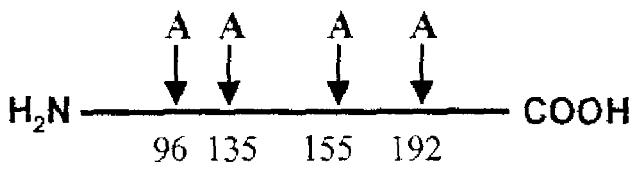
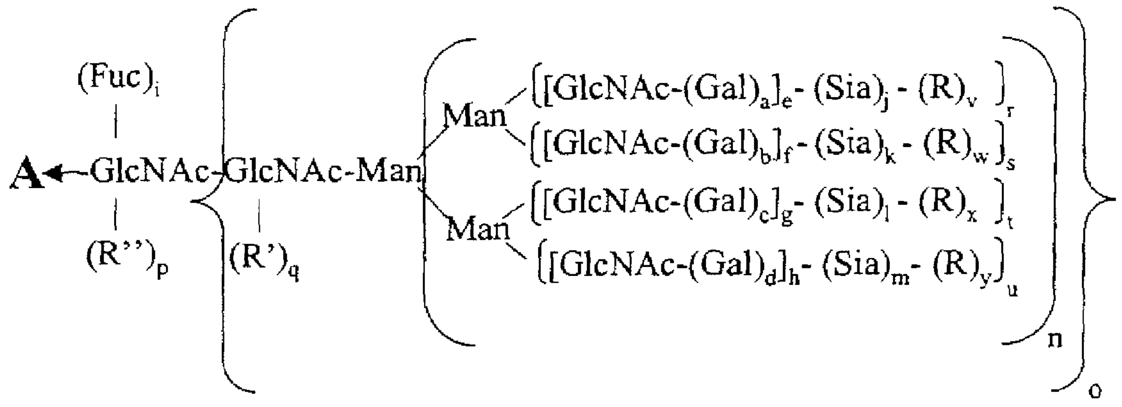
a-d, i, n-u (independently selected) = 0 or 1.
e-h (independently selected) = 0 to 4.
j-m (independently selected) = 0 to 20.
R = polymer.
R', R" (independently selected) = sugar, glycoconjugate.
FIG. 54L Yeast expressed AT III.
a-h, i-m, p, q = 0;
R (independently selected) = mannose, oligomannose, polymannose;
r-u, v-y (independently selected) = 0 or 1;
n, o = 1.

1. endoglycanase
2. Galactosyltransferase, UDP-Gal-PEG a-h, i-o, q, r-u, v-y = 0; p = 1.
R" = Gal-PEG.

FIG. 54M

Plant expressed AT III.
a-d, f-h, j-m, p, s-u, v-y = 0;
e, i, q, r (independently selected) = 0 or 1;
n, o =1; R' = xylose.

1. xylosidase
3. Galactosyl transferase, UDP-Gal-PEG b-d, f-h, j-m, p, q, s-u, w-y = 0;
a, e, i, r (independently selected) = 0 or 1;
n, o = 1; R = PEG.

FIG. 54N

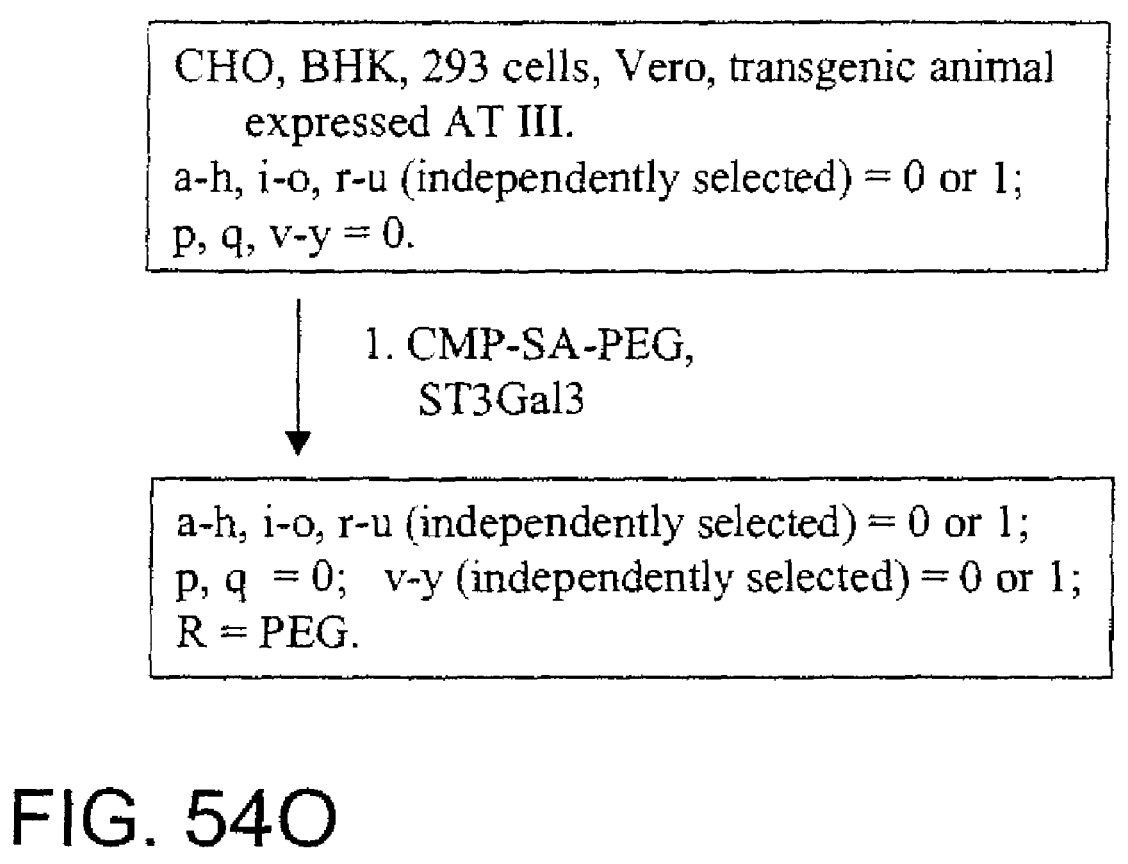

CHO, BHK, 293 cells, Vero, transgenic animal expressed AT III.
a-h, i-o, r-u (independently selected) = 0 or 1;
p, q, v-y = 0.

1. CMP-SA-PEG, ST3Gal3 a-h, i-o, r-u (independently selected) = 0 or 1;
p, q = 0; v-y (independently selected) = 0 or 1;
R = PEG.

FIG. 54O

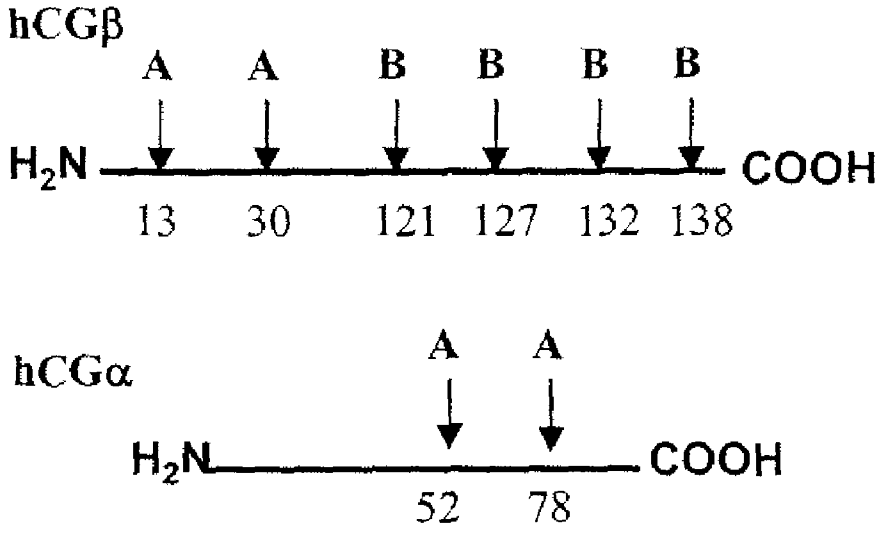
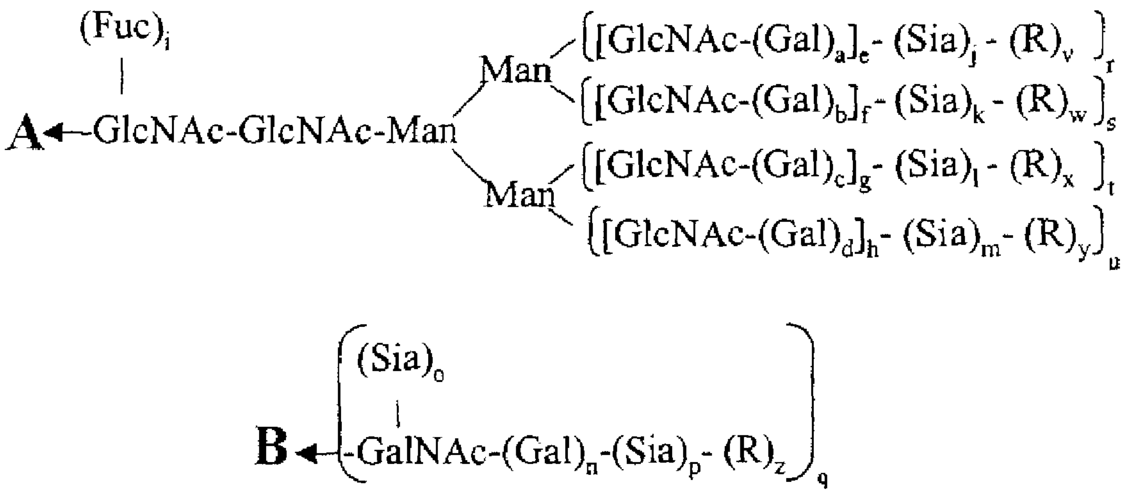
a-d, i, n-u (independently selected) = 0 or 1.
e-h (independently selected) = 0 to 4.
j-m (independently selected) = 0 to 20.
v-z = 0; R = polymer
FIG. 55A CHO, BHK, 293 cells, insect cell, Vero expressed hCG
a-g, n, q = 1; h = 1 to 3; j-m, i, o, p (independently selected) = 0 or 1; r-u (independently selected) = 0 to1; v-z = 0

1. Sialidase
2. CMP-SA-PEG, ST3Gal3 a-g, n, q = 1; h = 1 to 3; i, o, p (independently selected) = 0 or 1; r-u (independently selected) = 0 or 1; j-m, v-y (independently selected) = 0 or 1; R = PEG; z = 0.

FIG. 55B

Insect cell, yeast, fungi expressed hCG
a-d, f, h, j-m, o, p, s, u, v-z = 0;
e, g, i, n, q, r, t (independently selected) = 0 or 1.

1. GNT's 1&2, UDP-GlcNAc
2. Galactosyltransferase, UDP-Gal
2. CMP-SA-PEG, ST3Gal3 b, d, f, h, k, m, o, p, s, u, w, y, z = 0;
a, c, e, g, i, n, q, r, t (independently selected) = 0 or 1;
j, l, v, x (independently selected) = 0 or 1;
R = PEG.

FIG. 55C

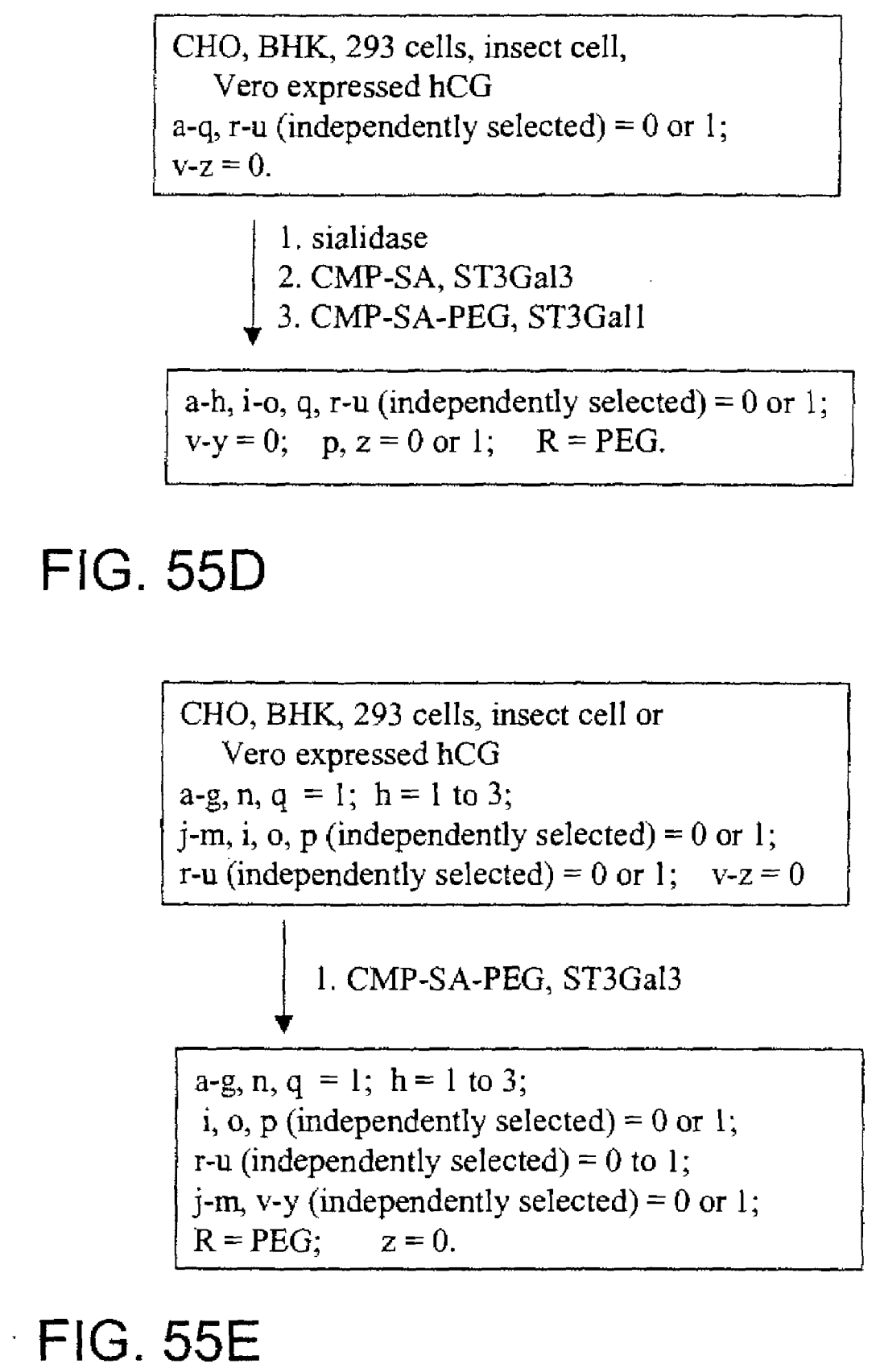

CHO, BHK, 293 cells, insect cell,
Vero expressed hCG
a-q, r-u (independently selected) = 0 or 1;
v-z = 0.

1. sialidase
2. CMP-SA, ST3Gal3
3. CMP-SA-PEG, ST3Gal1 a-h, i-o, q, r-u (independently selected) = 0 or 1;
v-y = 0; p, z = 0 or 1; R = PEG.

FIG. 55D

CHO, BHK, 293 cells, insect cell or
Vero expressed hCG
a-g, n, q = 1; h = 1 to 3;
j-m, i, o, p (independently selected) = 0 or 1;
r-u (independently selected) = 0 or 1; v-z = 0

1. CMP-SA-PEG, ST3Gal3 a-g, n, q = 1; h = 1 to 3;
i, o, p (independently selected) = 0 or 1;
r-u (independently selected) = 0 to 1;
j-m, v-y (independently selected) = 0 or 1;
R = PEG; z = 0.

FIG. 55E

CHO, BHK, 293 cells, insect cell or Vero expressed hCG
a-g, n, q = 1; h = 1 to 3;
j-m, i, o, p (independently selected) = 0 or 1;
r-u (independently selected) = 0 or 1; v-z = 0

1. CMP-SA-PEG, ST3Gal3 a-g, n, q = 1; h = 1 to 3;
i, o (independently selected) = 0 or 1;
r-u (independently selected) = 0 to 1;
j-m, p, z (independently selected) = 0 or 1;
R = PEG; v-y = 0.

FIG. 55H

CHO, BHK, 293 cells, Vero expressed hCG
a-g, n, q = 1; h = 1 to 3;
j-m, i, o, p (independently selected) = 0 or 1;
r-u (independently selected) = 0 or 1; v-z = 0

1. CMP-SA-PEG, α2,8-ST a-g, n, q = 1; h = 1 to 3;
i, o, p (independently selected) = 0 or 1;
r-u (independently selected) = 0 to 1;
j-m (independently selected) = 0 to 2;
v-y (independently selected) = 1, when j-m (independently selected) is 2; R = PEG; z = 0.

FIG. 55I

CHO, BHK, 293 cells, Vero expressed hCG
a-g, n, q = 1;   h = 1 to 3;
j-m, i, o, p (independently selected) = 0 or 1;
r-u (independently selected) = 0 to 1;   v-z = 0

↓ 1. CMP-SA, poly-α2,8-ST a-i, j-q, r-u, (independently selected) = 0 or 1;
v-z (independently selected) = 0-100;   R = Sia.

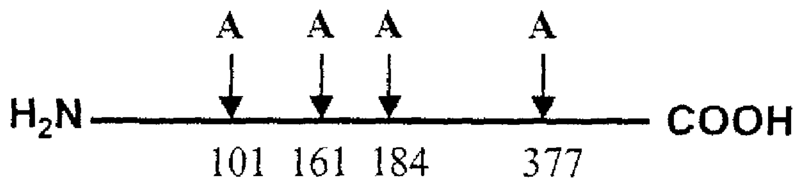
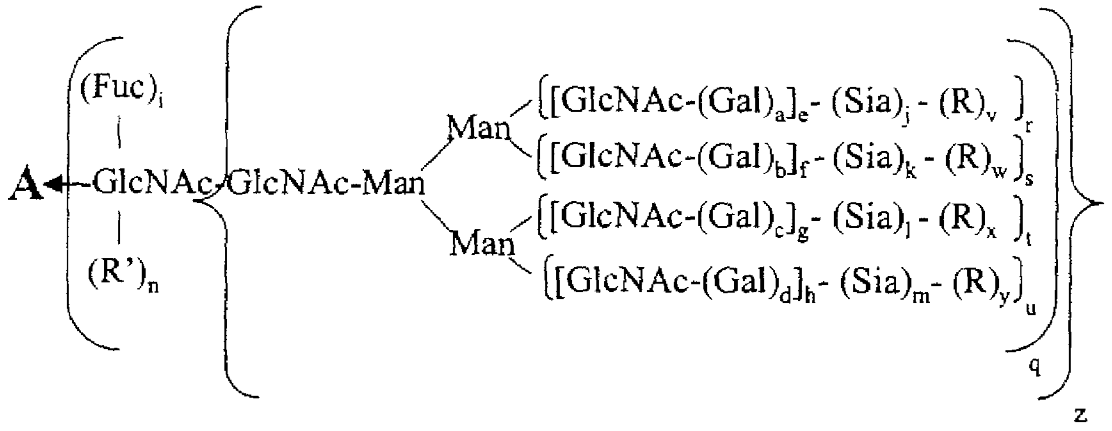
a-d, i, n, q-u, z (independently selected) = 0 or 1.
e-h (independently selected) = 0 to 6.
j-m (independently selected) = 0 to 100.
v-y = 0 to 100;
R = mannose, mannose-6-phosphate and mannose, polymer.
FIG. 56A CHO, BHK, 293 cells, insect cells, Vero expressed and secreted alpha-galactosidase
a-h, i-m, q-u (independently selected) = 0 or 1;
z = 1; n, v-y = 0; and when a-n = 0, then r-u (independently selected) = 0 or 1; v-y (independently selected) = 0-100;
R = mannose or mannose with mannose-6-phosphate.

1. Endo-H
2. Galactosyltransferase, UDP-Gal-PEG-transferrin a-h, i-m, q-u (independently selected) = 0 or 1;
n, v-y = 0; z = 1; and when z = 0 and q = 1,
then n (independently selected) = 0 or 1;
R' = Gal-PEG-transferrin.

FIG. 56B

CHO, BHK, 293 cells, Insect cells, Vero expressed and secreted alpha-galactosidase
a-h, i-m, q-u (independently selected) = 0 or 1; z = 1; n, v-y = 0; and when a-n = 0, then r-u (independently selected) = 0 or 1; v-y (independently selected) = 0-100;
R = mannose or mannose with mannose-6-phosphate.

1. Sialidase
2. CMP-SA-linker-Mannose-6-phosphate ST3Gal3 a-h, i-m, q-u, v-y (independently selected) = 0 or 1;
n = 0; z =1; R = mannose-6-phosphate; and when a-n = 0, then r-u (independently selected) = 0 or 1;
v-y (independently selected) = 0-100;
R = mannose or mannose with mannose-6-phosphate.

FIG. 56C

NSO expressed alpha-galactosidase.
a-d, i-m, q-u (independently selected) = 0 or 1;
e-h = 1; v-y = 0;
Sia (independently selected) = Sia or Gal.

1. Sialidase and α-galactosidase
2. Galactosyltransferase, UDP-Gal
3. CMP-SA-linker-mannose-6-phosphate sialyltransferase a-d, i-m, q-u (independently selected) = 0 or 1; e-h = 1;
v-y (independently selected) = 1, when j-m (independently selected) is 1; R = mannose-6 phosphate

FIG. 56D

CHO, BHK, 293 cells, Insect cells, Vero expressed and secreted alpha-galactosidase
a-h, i-m, q-u (independently selected) = 0 or 1; z = 1;
n, v-y = 0; and when a-n = 0, then r-u (independently selected) = 0 or 1; v-y (independently selected) = 0-100;
R = mannose or mannose with mannose-6-phosphate.

1. Sialidase
2. CMP-SA-PEG, sialyltransferase a-h, i-m, q-u, v-y (independently selected) = 0 or 1; n = 0; z = 1; R = PEG; and when a-n = 0, then r-u (independently selected) = 0 or 1; v-y = 0-100; R = mannose or mannose with mannose-6-phosphate.

FIG. 56E

CHO, BHK, 293 cells, Insect cells, Vero, yeast, fungi expressed alpha-galactosidase.
a-i, v-y = 0; q (independently selected) = 0 or 1; z = 1;
r-u (independently selected) = 0 or 1;
j-m (independently selected) = 0-100;
Sia = mannose or mannose with mannose-6-phosphate.

↓ 1. mannosyltransferase, GDP-mannose-linker-ApoE a-i = 0; q (independently selected) = 0 or 1; z = 1;
r-u (independently selected) = 0 or 1;
j-m (independently selected) = 0-100;
Sia = mannose or mannose with mannose-6-phosphate;
v-y (independently selected) = 0 or 1;
R = mannose-linker-ApoE.

FIG. 56F

CHO, BHK, 293 cells, Insect cells, Vero, yeast, fungi expressed alpha-galactosidase.
a-i, v-y = 0; q (independently selected) = 0 or 1; z = 1;
r-u (independently selected) = 0 or 1;
j-m (independently selected) = 0-100;
Sia = mannose or mannose with mannose-6-phosphate.

↓ 1. endo-H
2. galactosyltransferase, UDP-Gal-linker-alpha2-macroglobulin a-m, r-z = 0; n, q (independently selected) = 0 or 1;
R' = galacotose-linker-alpha2-macroglobulin.

FIG. 56G

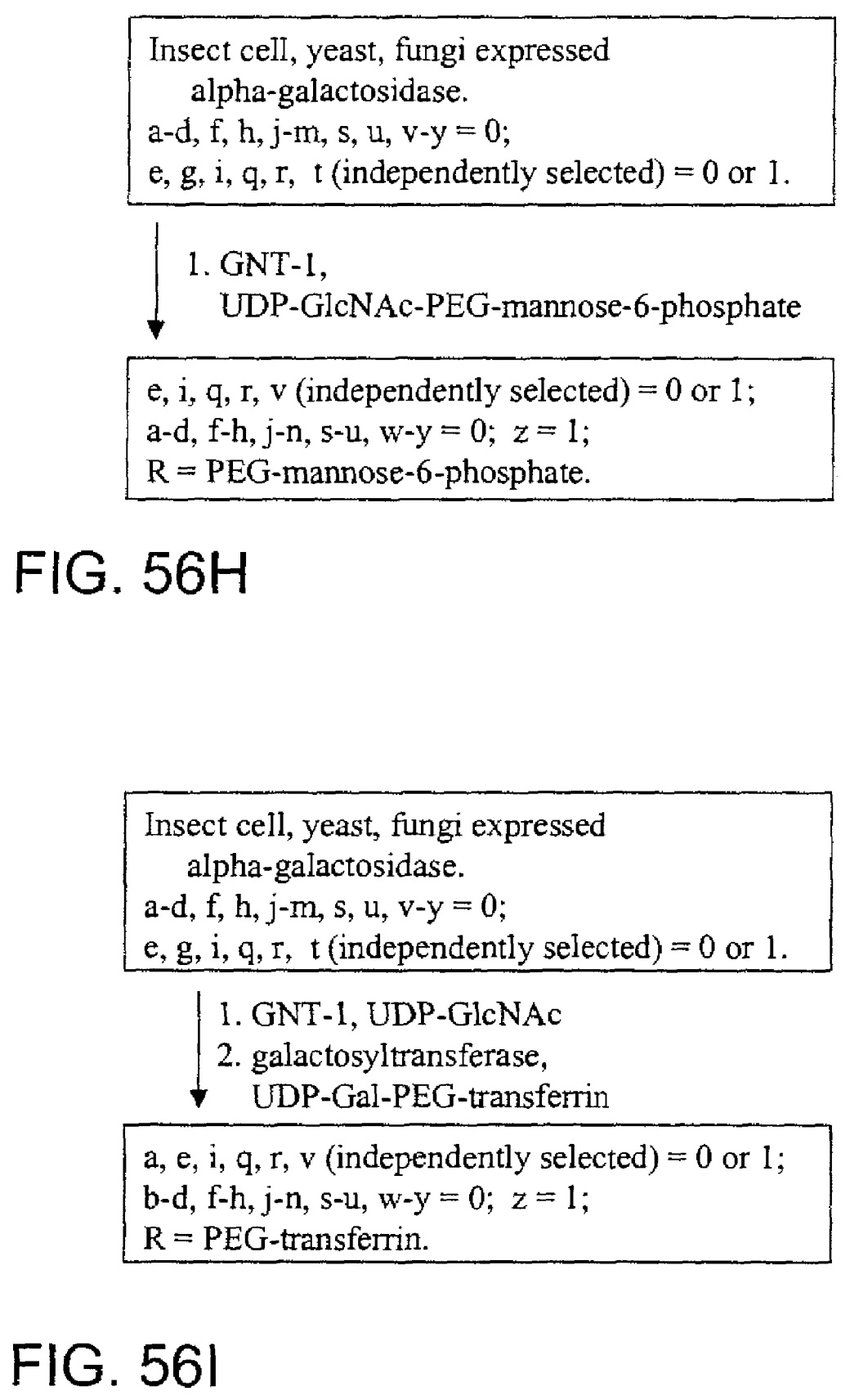

Insect cell, yeast, fungi expressed alpha-galactosidase.
a-d, f, h, j-m, s, u, v-y = 0;
e, g, i, q, r, t (independently selected) = 0 or 1.

1. GNT-1, UDP-GlcNAc-PEG-mannose-6-phosphate e, i, q, r, v (independently selected) = 0 or 1;
a-d, f-h, j-n, s-u, w-y = 0; z = 1;
R = PEG-mannose-6-phosphate.

FIG. 56H

Insect cell, yeast, fungi expressed alpha-galactosidase.
a-d, f, h, j-m, s, u, v-y = 0;
e, g, i, q, r, t (independently selected) = 0 or 1.

1. GNT-1, UDP-GlcNAc
2. galactosyltransferase, UDP-Gal-PEG-transferrin a, e, i, q, r, v (independently selected) = 0 or 1;
b-d, f-h, j-n, s-u, w-y = 0; z = 1;
R = PEG-transferrin.

FIG. 56I

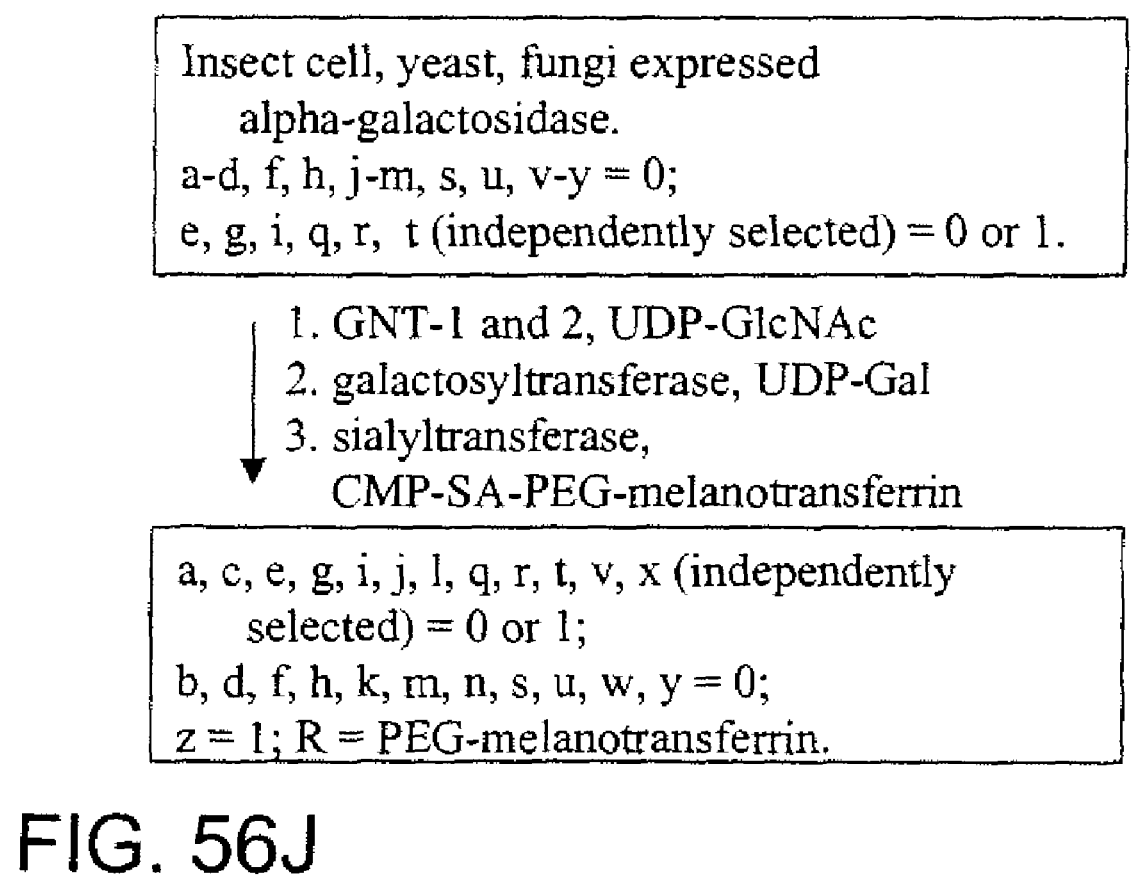

Insect cell, yeast, fungi expressed alpha-galactosidase.
a-d, f, h, j-m, s, u, v-y = 0;
e, g, i, q, r, t (independently selected) = 0 or 1.

1. GNT-1 and 2, UDP-GlcNAc
2. galactosyltransferase, UDP-Gal
3. sialyltransferase, CMP-SA-PEG-melanotransferrin a, c, e, g, i, j, l, q, r, t, v, x (independently selected) = 0 or 1;
b, d, f, h, k, m, n, s, u, w, y = 0;
z = 1; R = PEG-melanotransferrin.

FIG. 56J

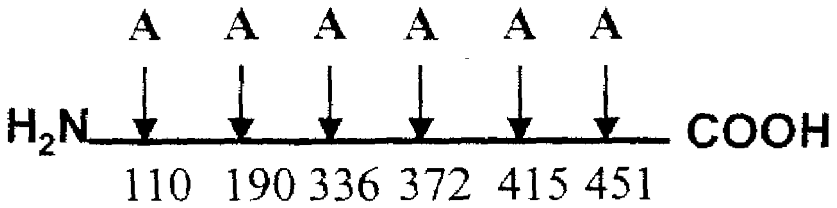
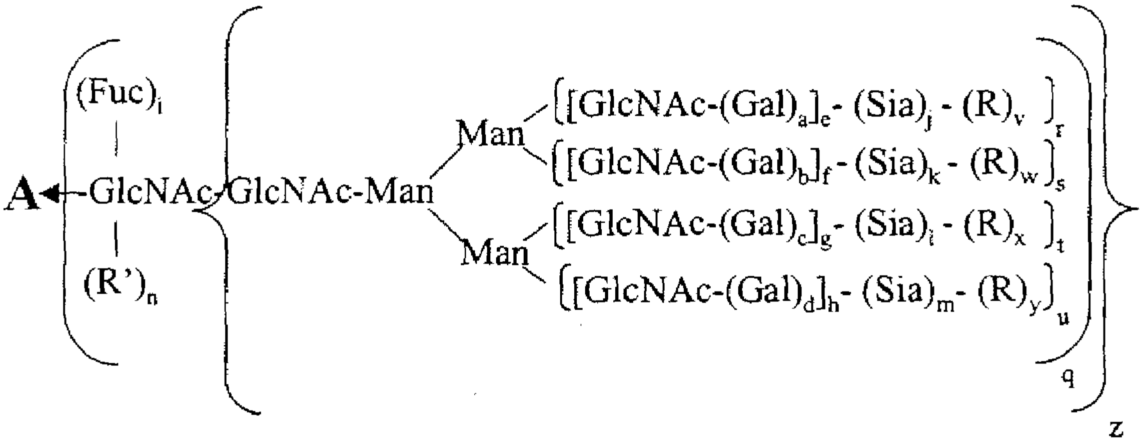
a-d, i, n, q-u, z (independently selected) = 0 or 1.
e-h (independently selected) = 0 to 6.
j-m (independently selected) = 0 to 100.
v-y = 0 to 100;
R = mannose, mannose-6-phosphate and mannose, polymer.
FIG. 57A CHO, BHK, 293 cells, Insect cells, Vero expressed
and secreted alpha-iduronidase
a-h, i-m, q-u (independently selected) = 0 or 1; z = 1;
n, v-y = 0; and when a-n = 0, then r-u (independently
selected) = 0 or 1; v-y (independently selected) = 0-100;
R = mannose or mannose with mannose-6-phosphate.

1. Endo-H
2. Galactosyltransferase, UDP-Gal-PEG-transferrin a-h, i-m, q-u (independently selected) = 0 or 1;
n, v-y = 0; z = 1; and when z = 0 and q = 1, then n
(independently selected) = 0 or 1; R' = Gal-PEG-transferrin.

FIG. 57B

CHO, BHK, 293 cells, Insect cells, Vero expressed
and secreted alpha-iduronidase
a-h, i-m, q-u (independently selected) = 0 or 1; z = 1;
n, v-y = 0; and when a-n = 0, then r-u (independently
selected) = 0 or 1; v-y (independently selected) = 0-100;
R = mannose or mannose with mannose-6-phosphate.

1. Sialidase
2. CMP-SA-linker-Mannose-6-phosphate ST3Gal3 a-h, i-m, q-u, v-y (independently selected) = 0 or 1; n = 0;
z =1; R = mannose-6-phosphate; and when a-n = 0,
then r-u (independently selected) = 0 or 1;
v-y (independently selected) = 0-100;
R = mannose or mannose with mannose-6-phosphate.

FIG. 57C

NSO expressed alpha-iduronidase.
a-d, i-m, q-u (independently selected) = 0 or 1; e-h = 1;
v-y = 0; Sia (independently selected) = Sia or Gal.

1. Sialidase and α-galactosidase
2. Galactosyltransferase, UDP-Gal
3. CMP-SA-linker-mannose-6-phosphate sialyltransferase a-d, i-m, q-u (independently selected) = 0 or 1;
e-h = 1; v-y (independently selected) = 1,
when j-m (independently selected) is 1;
R = mannose-6 phosphate

FIG. 57D

CHO, BHK, 293 cells, Insect cells, Vero expressed
and secreted alpha-iduronidase
a-h, i-m, q-u (independently selected) = 0 or 1; z = 1;
n, v-y = 0; and when a-n = 0, then r-u (independently
selected) = 0 or 1; v-y (independently selected) = 0-100;
R = mannose or mannose with mannose-6-phosphate.

1. Sialidase
2. CMP-SA-PEG, sialyltransferase a-h, i-m, q-u, v-y (independently selected) = 0 or 1; n = 0;
z = 1; R = PEG; and when a-n = 0, then r-u
(independently selected) = 0 or 1; v-y = 0-100;
R = mannose or mannose with mannose-6-phosphate.

FIG. 57E

CHO, BHK, 293 cells, Insect cells, Vero, yeast, fungi expressed alpha-iduronidase.
a-i, v-y = 0; q (independently selected) = 0 or 1; z = 1;
r-u (independently selected) = 0 or 1;
j-m (independently selected) = 0-100;
Sia = mannose or mannose with mannose-6-phosphate.

1. mannosyltransferase, GDP-mannose-linker-ApoE a-i = 0; q (independently selected) = 0 or 1; z = 1;
r-u (independently selected) = 0 or 1; j-m (independently selected) = 0-100;
Sia = mannose or mannose with mannose-6-phosphate;
v-y (independently selected) = 0 or 1;
R = mannose-linker-ApoE.

FIG. 57F

CHO, BHK, 293 cells, Insect cells, Vero, yeast, fungi expressed alpha-iduronidase.
a-i, v-y = 0; q (independently selected) = 0 or 1;
z = 1; r-u (independently selected) = 0 or 1;
j-m (independently selected) = 0-100;
Sia = mannose or mannose with mannose-6-phosphate.

1. endo-H
2. galactosyltransferase, UDP-Gal-linker-alpha2-macroglobulin a-m, r-z = 0; n, q (independently selected) = 0 or 1;
R' = galacotose-linker-alpha2-macroglobulin.

FIG. 57G

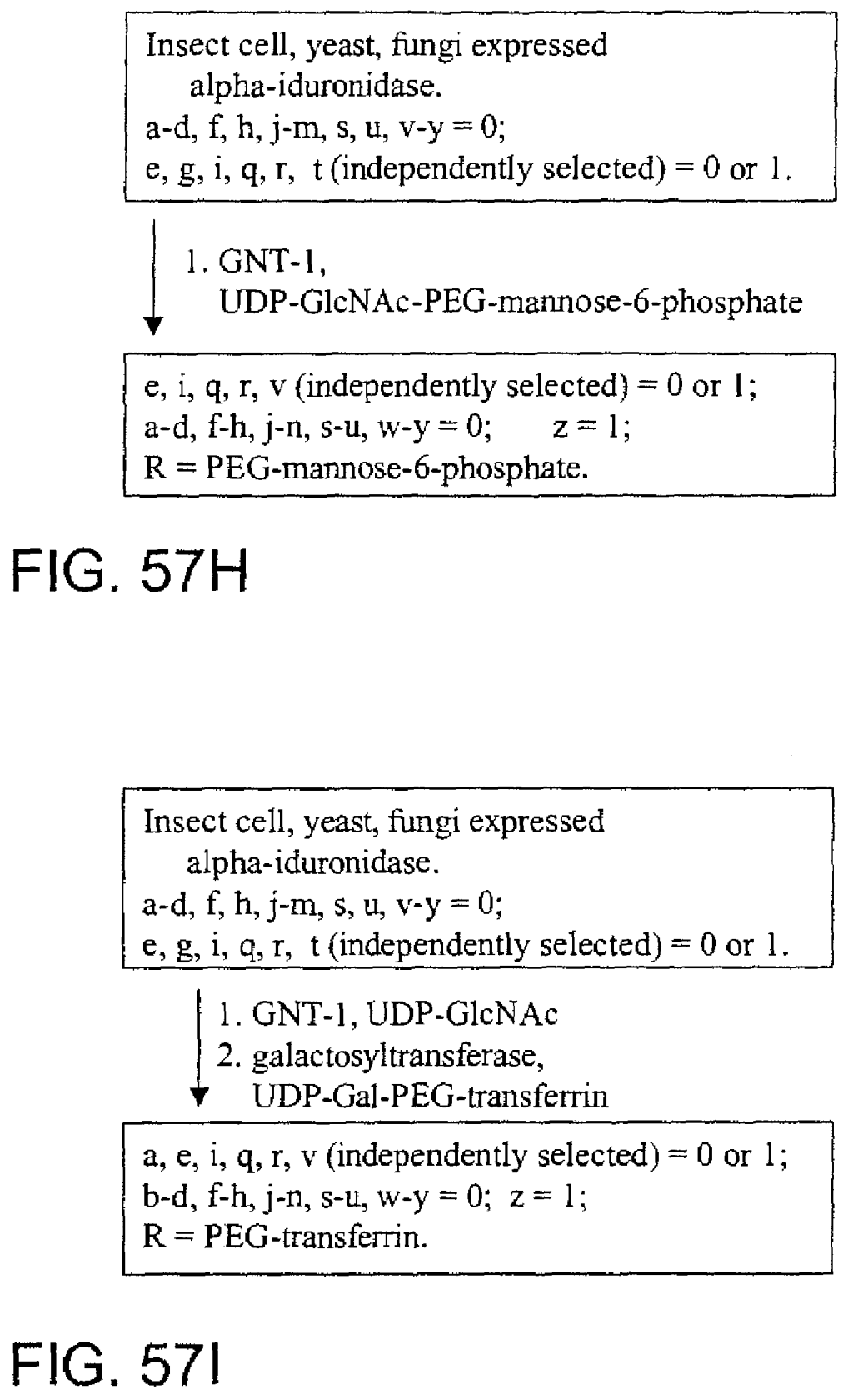

Insect cell, yeast, fungi expressed alpha-iduronidase.
a-d, f, h, j-m, s, u, v-y = 0;
e, g, i, q, r, t (independently selected) = 0 or 1.

1. GNT-1, UDP-GlcNAc-PEG-mannose-6-phosphate e, i, q, r, v (independently selected) = 0 or 1;
a-d, f-h, j-n, s-u, w-y = 0; z = 1;
R = PEG-mannose-6-phosphate.

FIG. 57H

Insect cell, yeast, fungi expressed alpha-iduronidase.
a-d, f, h, j-m, s, u, v-y = 0;
e, g, i, q, r, t (independently selected) = 0 or 1.

1. GNT-1, UDP-GlcNAc
2. galactosyltransferase, UDP-Gal-PEG-transferrin a, e, i, q, r, v (independently selected) = 0 or 1;
b-d, f-h, j-n, s-u, w-y = 0; z = 1;
R = PEG-transferrin.

FIG. 57I

Figure 57J:
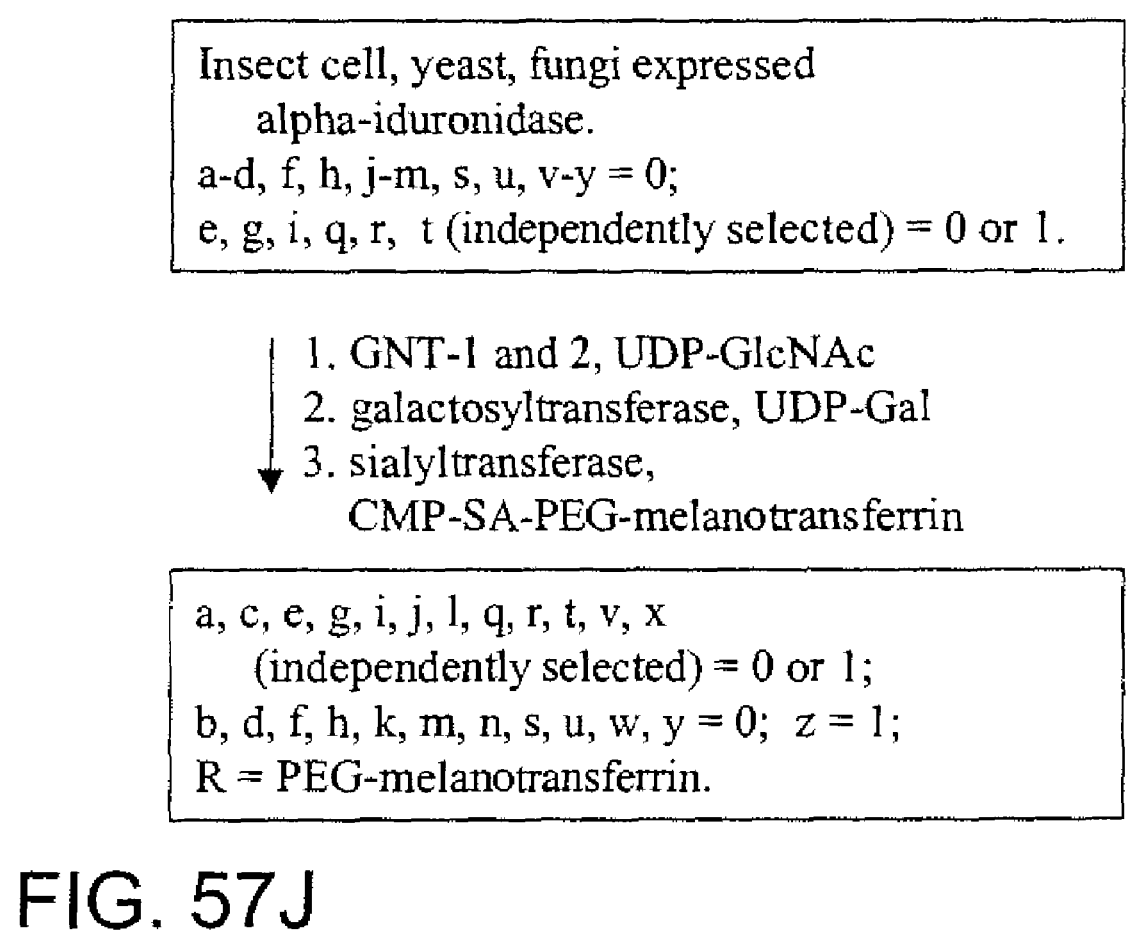

Insect cell, yeast, fungi expressed alpha-iduronidase.
a-d, f, h, j-m, s, u, v-y = 0;
e, g, i, q, r, t (independently selected) = 0 or 1.

1. GNT-1 and 2, UDP-GlcNAc
2. galactosyltransferase, UDP-Gal
3. sialyltransferase, CMP-SA-PEG-melanotransferrin a, c, e, g, i, j, l, q, r, t, v, x (independently selected) = 0 or 1;
b, d, f, h, k, m, n, s, u, w, y = 0; z = 1;
R = PEG-melanotransferrin.

ACCCCCCTGGGCCCTGCCAGCTCCCTGCCCCAGAGCTTCCTGCTCAAT
GCTTAGAGCAAGTGAGGAAGATCCAGGGCGATGGCGCAGCGCTCCAG
GAGAAGCTGTGTGCCACCTACAAGCTGTGCCACCCCGAGGAGCTGGT
GCTGCTCGGACACTCTCTGGGCATCCCCTGGGCTCCCCTGAGCAGCTG
CCCCAGCCAGGCCCTGCAGCTGGCAGGCTGCTTGAGCCAACTCCATA
GCGGCCTTTTCCTCTACCAGGGGCTCCTGCAGGCCCTGGAAGGGATCT
CCCCCGAGTTGGGTCCCACCTTGGACACACTGCAGCTGGACGTCGCCG
ACTTTGCCACCACCATCTGGCAGCAGATGGAAGAACTGGGAATGGCC
CCTGCCCTGCAGCCCACCCAGGGTGCCATGCCGGCCTTCGCCTCTGCT
TTCCAGCGCCGGGCAGGAGGGGTCCTGGTTGCCTCCCATCTGCAGAG
CTTCCTGGAGGTGTCGTACCGCGTTCTACGCCACCTTGCCCAGCCCTG
A

FIG. 58B

Thr Pro Leu Gly Pro Ala Ser Ser Leu Pro Gln Ser Phe Leu Leu Lys Cys Leu Glu
Gln Val Arg Lys Ile Gln Gly Asp Gly Ala Ala Leu Gln Glu Lys Leu Cys Ala Thr
Tyr Lys Leu Cys His Pro Glu Glu Leu Val Leu Leu Gly His Ser Leu Gly Ile Pro
Trp Ala Pro Leu Ser Ser Cys Pro Ser Gln Ala Leu Gln Leu Ala Gly Cys Leu Ser
Gln Leu His Ser Gly Leu Phe Leu Tyr Gln Gly Leu Leu Gln Ala Leu Glu Gly Ile
Ser Pro Glu Leu Gly Pro Thr Leu Asp Thr Leu Gln Leu Asp Val Ala Asp Phe
Ala Thr Thr Ile Trp Gln Gln Met Glu Glu Leu Gly Met Ala Pro Ala Leu Gln Pro
Thr Gln Gly Ala Met Pro Ala Phe Ala Ser Ala Phe Gln Arg Arg Ala Gly Gly Val
Leu Val Ala Ser His Leu Gln Ser Phe Leu Glu Val Ser Tyr Arg Val Leu Arg His
Leu Ala Gln Pro

FIG. 59A

GCGCCTCTTATGTACCCACAAAAATCTATTTTCAAAAAAGTTGCTCTA
AGAATATAGTTATCAAGTTAAGTAAAATGTCAATAGCCTTTTAATTTA
ATTTTTAATTGTTTTATCATTCTTTGCAATAATAAAACATTAACTTTAT
ACTTTTTAATTTAATGTATAGAATAGAGATATACATAGGATATGTAAA
TAGATACACAGTGTATATGTGATTAAAATATAATGGGAGATTCAATC
AGAAAAAAGTTTCTAAAAAGGCTCTGGGGTAAAAGAGGAAGGAAAC
AATAATGAAAAAAATGTGGTGAGAAAAACAGCTGAAAACCCATGTA
AAGAGTGTATAAAGAAAGCAAAAAGAGAAGTAGAAAGTAACACAGG
GGCATTTGGAAAATGTAAACGAGTATGTTCCCTATTTAAGGCTAGGC
ACAAAGCAAGGTCTTCAGAGAACCTGGAGCCTAAGGTTTAGGCTCAC
CCATTTCAACCAGTCTAGCAGCATCTGCAACATCTACAATGGCCTTGA
CCTTTGCTTTACTGGTGGCCCTCCTGGTGCTCAGCTGCAAGTCAAGCT
GCTCTGTGGGCTGTGATCTGCCTCAAACCCACAGCCTGGGTAGCAGG
AGGACCTTGATGCTCCTGGCACAGATGAGGAGAATCTCTCTTTTCTCC
TGCTTGAAGGACAGACATGACTTTGGATTTCCCCAGGAGGAGTTTGG
CAACCAGTTCCAAAAGGCTGAAACCATCCCTGTCCTCCATGAGATGA
TCCAGCAGATCTTCAATCTCTTCAGCACAAAGGACTCATCTGCTGCTT
GGGATGAGACCCTCCTAGACAAATTCTACACTGAACTCTACCAGCAG
CTGAATGACCTGGAAGCCTGTGTGATACAGGGGGTGGGGGTGACAGA
GACTCCCCTGATGAAGGAGGACTCCATTCTGGCTGTGAGGAAATACT
TCCAAAGAATCACTCTCTATCTGAAAGAGAAGAAATACAGCCCTTGT
GCCTGGGAGGTTGTCAGAGCAGAAATCATGAGATCTTTTTCTTTGTCA
ACAAACTTGCAAGAAAGTTTAAGAAGTAAGGAATGAAAACTGGTTCA
ACATGGAAATGATTTTCATTGATTCGTATGCCAGCTCACCTTTTTATG
ATCTGCCATTTCAAAGACTCATGTTTCTGCTATGACCATGACACGATT
TAAATCTTTTCAAATGTTTTTAGGAGTATTAATCAACATTGTATTCAG
CTCTTAAGGCACTAGTCCCTTACAGAGGACCATGCTGACTGATCCATT
ATCTATTTAAATATTTTTAAAATATTATTTATTTAACTATTTATAAAAC
AACTTATTTTTGTTCATATTATGTCATGTGCACCTTTGCACAGTGGTTA
ATGTAATAAAATGTGTTCTTTGTATTTGGTAAATTTATTTTGTGTTGTT
CATTGAACTTTTGCTATGGAACTTTTGTACTTGTTTATTCTTTAAAATG
AAATTCCAAGCCTAATTGTGCAACCTGATTACAGAATAACTGGTACA
CTTCATTTGTCCATCAATATTATATTCAAGATATAAGTAAAAATAAAC
TTTCTGTAAACCAAGTTGTATGTTGTACTCAAGATAACAGGGTGAACC
TAACAAATACAATTCTGCTCTCTTGTGTATTTGATTTTTGTATGAAAA
AAACTAAAAATGGTAATCATACTTAATTATCAGTTATGGTAAATGGT
ATGAAGAGAAGAAGGAACG

FIG. 59B

Met Ala Leu Thr Phe Ala Leu Leu Val Ala Leu Leu Val Leu Ser Cys Lys Ser
Ser Cys Ser Val Gly Cys Asp Leu Pro Gln Thr His Ser Leu Gly Ser Arg Arg Thr
Leu Met Leu Leu Ala Gln Met Arg Arg Ile Ser Leu Phe Ser Cys Leu Lys Asp
Arg His Asp Phe Gly Phe Pro Gln Glu Glu Phe Gly Asn Gln Phe Gln Lys Ala
Glu Thr Ile Pro Val Leu His Glu Met Ile Gln Gln Ile Phe Asn Leu Phe Ser Thr
Lys Asp Ser Ser Ala Ala Trp Asp Glu Thr Leu Leu Asp Lys Phe Tyr Thr Glu
Leu Tyr Gln Gln Leu Asn Asp Leu Glu Ala Cys Val Ile Gln Gly Val Gly Val
Thr Glu Thr Pro Leu Met Lys Glu Asp Ser Ile Leu Ala Val Arg Lys Tyr Phe
Gln Arg Ile Thr Leu Tyr Leu Lys Glu Lys Lys Tyr Ser Pro Cys Ala Trp Glu Val
Val Arg Ala Glu Ile Met Arg Ser Phe Ser Leu Ser Thr Asn Leu Gln Glu Ser Leu
Arg Ser Lys Glu

FIG. 59C

ATGGCCCTCCTGTTCCCTCTACTGGCAGCCCTAGTGATGACCAGCTAT
AGCCCTGTTGGATCTCTGGGCTGTGATCTGCCTCAGAACCATGGCCTA
CTTAGCAGGAACACCTTGGTGCTTCTGCACCAAATGAGGAGAATCTCC
CCTTTCTTGTGTCTCAAGGACAGAAGAGACTTCAGGTTCCCCCAGGAG
ATGGTAAAAGGGAGCCAGTTGCAGAAGGCCCATGTCATGTCTGTCCT
CCATGAGATGCTGCAGCAGATCTTCAGCCTCTTCCACACAGAGCGCTC
CTCTGCTGCCTGGAACATGACCCTCCTAGACCAACTCCACACTGGACT
TCATCAGCAACTGCAACACCTGGAGACCTGCTTGCTGCAGGTAGTGG
GAGAAGGAGAATCTGCTGGGGCAATTAGCAGCCCTGCACTGACCTTG
AGGAGGTACTTCCAGGGAATCCGTGTCTACCTGAAAGAGAAGAAATA
CAGCGACTGTGCCTGGGAAGTTGTCAGAATGGAAATCATGAAATCCT
TGTTCTTATCAACAAACATGCAAGAAAGACTGAGAAGTAAAGATAGA
GACCTGGGCTCATCTTGA

FIG. 59D

Met Ala Leu Leu Phe Pro Leu Leu Ala Ala Leu Val Met Thr Ser Tyr Ser Pro Val
Gly Ser Leu Gly Cys Asp Leu Pro Gln Asn His Gly Leu Leu Ser Arg Asn Thr
Leu Val Leu Leu His Gln Met Arg Arg Ile Ser Pro Phe Leu Cys Leu Lys Asp
Arg Arg Asp Phe Arg Phe Pro Gln Glu Met Val Lys Gly Ser Gln Leu Gln Lys
Ala His Val Met Ser Val Leu His Glu Met Leu Gln Gln Ile Phe Ser Leu Phe His
Thr Glu Arg Ser Ser Ala Ala Trp Asn Met Thr Leu Leu Asp Gln Leu His Thr
Gly Leu

FIG. 60A

ATGACCAACAAGTGTCTCCTCCAAATTGCTCTCCTGTTGTGCTTCTCC
ACTACAGCTCTTTCCATGAGCTACAACTTGCTTGGATTCCTACAAAGA
AGCAGCAATTTTCAGTGTCAGAAGCTCCTGTGGCAATTGAATGGGAG
GCTTGAATATTGCCTCAAGGACAGGATGAACTTTGACATCCCTGAGG
AGATTAAGCAGCTGCAGCAGTTCCAGAAGGAGGACGCCGCATTGACC
ATCTATGAGATGCTCCAGAACATCTTTGCTATTTTCAGACAAGATTCA
TCTAGCACTGGCTGGAATGAGACTATTGTTGAGAACCTCCTGGCTAA
TGTCTATCATCAGATAAACCATCTGAAGACAGTCCTGGAAGAAAAAC
TGGAGAAAGAAGATTTTACCAGGGGAAAACTCATGAGCAGTCTGCAC
CTGAAAAGATATTATGGGAGGATTCTGCATTACCTGAAGGCCAAGGA
GTACAGTCACTGTGCCTGGACCATAGTCAGAGTGGAAATCCTAAGGA
ACTTTTACTTCATTAACAGACTTACAGGTTACCTCCGAAACTGAAGAT
CTCCTAGCCTGTCCCTCTGGGACTGGACAATTGCTTCAAGCATTCTTC
AACCAGCAGATGCTGTTTAAGTGACTGATGGCTAATGTACTGCAAAT
GAAAGGACACTAGAAGATTTTGAAATTTTTATTAAATTATGAGTTATT
TTTATTTAT TTAAATTTTATTTTGGAAAATAAATTATTTTTGGTGC

FIG. 60B

Met Thr Asn Lys Cys Leu Leu Gln Ile Ala Leu Leu Leu Cys Phe Ser Thr Thr Ala
Leu Ser Met Ser Tyr Asn Leu Leu Gly Phe Leu Gln Arg Ser Ser Asn Phe Gln
Cys Gln Lys Leu Leu Trp Gln Leu Asn Gly ArgLeu Glu Tyr Cys Leu Lys Asp
Arg Met Asn Phe Asp Ile Pro Glu Glu Ile Lys Gln Leu Gln Gln Phe Gln Lys Glu
Asp Ala Ala Leu Thr Ile Tyr Glu Met Leu Gln Asn Ile Phe Ala Ile Phe Arg Gln
Asp Ser Ser Ser Thr Gly Trp Asn Glu Thr Ile Val Glu Asn Leu Leu Ala Asn Val
Tyr His Gln Ile Asn His Leu Lys Thr Val Leu Glu Glu Lys Leu Glu Lys Glu Asp
Phe Thr Arg Gly Lys Leu Met Ser Ser Leu His Leu Lys Arg Tyr Tyr Gly Arg Ile
Leu His Tyr Leu Lys Ala Lys Glu Tyr Ser His Cys Ala Trp Thr Ile Val Arg Val
Glu Ile Leu Arg Asn Phe Tyr Phe Ile Asn Arg Leu Thr Gly Tyr Leu Arg Asn

FIG. 61A

ATGGTCTCCCAGGCCCTCAGGCTCCTCTGCCTTCTGCTTGGGCTTCAG
GGCTGCCTGGCTGCAGTCTTCGTAACCCAGGAGGAAGCCCACGGCGT
CCTGCACCGGCGCCGGCGCGCCAACGCGTTCCTGGAGGAGCTGCGGC
CGGGCTCCCTGGAGAGGGAGTGCAAGGAGGAGCAGTGCTCCTTCGA
GGAGGCCCGGGAGATCTTCAAGGACGCGGAGAGGACGAAGCTGTTC
TGGATTTCTTACAGTGATGGGGACCAGTGTGCCTCAAGTCCATGCCA
GAATGGGGGCTCCTGCAAGGACCAGCTCCAGTCCTATATCTGCTTCT
GCCTCCCTGCCTTCGAGGGCCGGAACTGTGAGACGCACAAGGATGAC
CAGCTGATCTGTGTGAACGAGAACGGCGGCTGTGAGCAGTACTGCAG
TGACCACACGGGCACCAAGCGCTCCTGTCGGTGCCACGAGGGGTACT
CTCTGCTGGCAGACGGGGTGTCCTGCACACCCACAGTTGAATATCCA
TGTGGAAAAATACCTATTCTAGAAAAAAGAAATGCCAGCAAACCCCA
AGGCCGAATTGTGGGGGGCAAGGTGTGCCCCAAAGGGGAGTGTCCA
TGGCAGGTCCTGTTGTTGGTGAATGGAGCTCAGTTGTGTGGGGGGAC
CCTGATCAACACCATCTGGGTGGTCTCCGCGGCCCACTGTTTCGACAA
AATCAAGAACTGGAGGAACCTGATCGCGGTGCTGGGCGAGCACGAC
CTCAGCGAGCACGACGGGGATGAGCAGAGCCGGCGGGTGGCGCAGG
TCATCATCCCCAGCACGTACGTCCCGGGCACCACCAACCACGACATC
GCGCTGCTCCGCCTGCACCAGCCCGTGGTCCTCACTGACCATGTGGTG
CCCCTCTGCCTGCCCGAACGGACGTTCTCTGAGAGGACGCTGGCCTTC
GTGCGCTTCTCATTGGTCAGCGGCTGGGGCCAGCTGCTGGACCGTGG
CGCCACGGCCCTGGAGCTCATGGTGCTCAACGTGCCCCGGCTGATGA
CCCAGGACTGCCTGCAGCAGTCACGGAAGGTGGGAGACTCCCCAAAT
ATCACGGAGTACATGTTCTGTGCCGGCTACTCGGATGGCAGCAAGGA
CTCCTGCAAGGGGGACAGTGGAGGCCCACATGCCACCCACTACCGGG
GCACGTGGTACCTGACGGGCATCGTCAGCTGGGGCCAGGGCTGCGCA
ACCGTGGGCCACTTTGGGGTGTACACCAGGGTCTCCCAGTACATCGA
GTGGCTGCAAAAGCTCATGCGCTCAGAGCCACGCCCAGGAGTCCTCC
TGCGAGCCCCATTTCCC

FIG. 61B

Met Val Ser Gln Ala Leu Arg Leu Leu Cys Leu Leu Leu Gly Leu Gln Gly Cys
Leu Ala Ala Val Phe Val Thr Gln Glu Glu Ala His Gly Val Leu His Arg Arg Arg
Arg Ala Asn Ala Phe Leu Glu Glu Leu Arg Pro Gly Ser Leu Glu Arg Glu Cys
Lys Glu Glu Gln Cys Ser Phe Glu Glu Ala Arg Glu Ile Phe Lys Asp Ala Glu Arg
Thr Lys Leu Phe Trp Ile Ser Tyr Ser Asp Gly Asp Gln Cys Ala Ser Ser Pro Cys
Gln Asn Gly Gly Ser Cys Lys Asp Gln Leu Gln Ser Tyr Ile Cys Phe Cys Leu Pro
Ala Phe Glu Gly Arg Asn Cys Glu Thr His Lys Asp Asp Gln Leu Ile Cys Val
Asn Glu Asn Gly Gly Cys Glu Gln Tyr Cys Ser Asp His Thr Gly Thr Lys Arg
Ser Cys Arg Cys His Glu Gly Tyr Ser Leu Leu Ala Asp Gly Val Ser Cys Thr Pro
Thr Val Glu Tyr Pro Cys Gly Lys Ile Pro Ile Leu Glu Lys Arg Asn Ala Ser Lys
Pro Gln Gly Arg Ile Val Gly Gly Lys Val Cys Pro Lys Gly Glu Cys Pro Trp Gln
Val Leu Leu Leu Val Asn Gly Ala Gln Leu Cys Gly Gly Thr Leu Ile Asn Thr Ile
Trp Val Val Ser Ala Ala His Cys Phe Asp Lys Ile Lys Asn Trp Arg Asn Leu Ile
Ala Val Leu Gly Glu His Asp Leu Ser Glu His Asp Gly Asp Glu Gln Ser Arg
Arg Val Ala Gln Val Ile Ile Pro Ser Thr Tyr Val Pro Gly Thr Thr Asn His Asp
Ile Ala Leu Leu Arg Leu His Gln Pro Val Val Leu Thr Asp His Val Val Pro Leu
Cys Leu Pro Glu Arg Thr Phe Ser Glu Arg Thr Leu Ala Phe Val Arg Phe Ser
Leu Val Ser Gly Trp Gly Gln Leu Leu Asp Arg Gly Ala Thr Ala Leu Glu Leu
Met Val Leu Asn Val Pro Arg Leu Met Thr Gln Asp Cys Leu Gln Gln Ser Arg
Lys Val Gly Asp Ser Pro Asn Ile Thr Glu Tyr Met Phe Cys Ala Gly Tyr Ser Asp
Gly Ser Lys Asp Ser Cys Lys Gly Asp Ser Gly Gly Pro His Ala Thr His Tyr Arg
Gly Thr Trp Tyr Leu Thr Gly Ile Val Ser Trp Gly Gln Gly Cys Ala Thr Val Gly
His Phe Gly Val Tyr Thr Arg Val Ser Gln Tyr Ile Glu Trp Leu Gln Lys Leu Met
Arg Ser Glu Pro Arg Pro Gly Val Leu Leu Arg Ala Pro Phe Pro

FIG. 62A

ATGCAGCGCGTGAACATGATCATGGCAGAATCACCAAGCCTCATCAC
CATCTGCCTTTTAGGATATCTACTCAGTGCTGAATGTACAGTTTTTCTT
GATCATGAAAACGCCAACAAAATTCTGAATCGGCCAAAGAGGTATAA
TTCAGGTAAATTGGAAGAGTTTGTTCAAGGGAACCTTGAGAGAGAAT
GTATGGAAGAAAAGTGTAGTTTTGAAGAACCACGAGAAGTTTTTGAA
AACACTGAAAAGACAACTGAATTTTGGAAGCAGTATGTTGATGGAGA
TCAGTGTGAGTCCAATCCATGTTTAAATGGCGGCAGTTGCAAGGATG
ACATTAATTCCTATGAATGTTGGTGTCCCTTTGGATTTGAAGGAAAGA
ACTGTGAATTAGATGTAACATGTAACATTAAGAATGGCAGATGCGAG
CAGTTTTGTAAAAATAGTGCTGATAACAAGGTGGTTTGCTCCTGTACT
GAGGGATATCGACTTGCAGAAAACCAGAAGTCCTGTGAACCAGCAGT
GCCATTTCCATGTGGAAGAGTTTCTGTTTCACAAACTTCTAAGCTCAC
CCGTGCTGAGGCTGTTTTTCCTGATGTGGACTATGTAAATCCTACTGA
AGCTGAAACCATTTTGGATAACATCACTCAAGGCACCCAATCATTTA
ATGACTTCACTCGGGTTGTTGGTGGAGAAGATGCCAAACCAGGTCAA
TTCCCTTGGCAGGTTGTTTTGAATGGTAAAGTTGATGCATTCTGTGGA
GGCTCTATCGTTAATGAAAAATGGATTGTAACTGCTGCCCACTGTGTT
GAAACTGGTGTTAAAATTACAGTTGTCGCAGGTGAACATAATATTGA
GGAGACAGAACATACAGAGCAAAAGCGAAATGTGATTCGAGCAATT
ATTCCTCACCACAACTACAATGCAGCTATTAATAAGTACAACCATGA
CATTGCCCTTCTGGAACTGGACGAACCCTTAGTGCTAAACAGCTACG
TTACACCTATTTGCATTGCTGACAAGGAATACACGAACATCTTCCTCA
AATTTGGATCTGGCTATGTAAGTGGCTGGGCAAGAGTCTTCCACAAA
GGGAGATCAGCTTTAGTTCTTCAGTACCTTAGAGTTCCACTTGTTGAC
CGAGCCACATGTCTTCGATCTACAAAGTTCACCATCTATAACAACAT
GTTCTGTGCTGGCTTCCATGAAGGAGGTAGAGATTCATGTCAAGGAG
ATAGTGGGGGACCCCATGTTACTGAAGTGGAAGGGACCAGTTTCTTA
ACTGGAATTATTAGCTGGGGTGAAGAGTGTGCAATGAAAGGCAAATA
TGGAATATATACCAAGGTATCCCGGTATGTCAACTGGATTAAGGAAA
AAACAAAGCTCACTTAATGAAAGATGGATTTCCAAGGTTAATTCATT
GGAATTGAAAATTAACAG

FIG. 62B

Met Gln Arg Val Asn Met Ile Met Ala Glu Ser Pro Ser Leu Ile Thr Ile Cys Leu
Leu Gly Tyr Leu Leu Ser Ala Glu Cys Thr Val Phe LeuAsp His Glu Asn Ala
Asn Lys Ile Leu Asn Arg Pro Lys Arg Tyr Asn Ser Gly Lys Leu Glu Glu Phe
Val Gln Gly Asn Leu Glu Arg Glu Cys Met Glu Glu Lys Cys Ser Phe Glu Glu
Pro Arg Glu Val Phe Glu Asn Thr Glu Lys Thr Thr Glu Phe Trp Lys Gln Tyr
Val Asp Gly Asp Gln Cys Glu Ser Asn Pro Cys Leu Asn Gly Gly Ser Cys Lys
Asp Asp Ile Asn Ser Tyr Glu Cys Trp Cys Pro Phe Gly Phe Glu Gly Lys Asn
Cys Glu Leu Asp Val Thr Cys Asn Ile Lys Asn Gly Arg Cys Glu Gln Phe Cys
Lys Asn Ser Ala Asp Asn Lys Val Val Cys Ser Cys Thr Glu Gly Tyr Arg Leu
Ala Glu Asn Gln Lys Ser Cys Glu Pro Ala Val Pro Phe Pro Cys Gly Arg Val Ser
Val Ser Gln Thr Ser Lys Leu Thr Arg Ala Glu Ala Val Phe Pro Asp Val Asp Tyr
Val Asn Pro Thr Glu Ala Glu Thr Ile Leu Asp Asn Ile Thr Gln Gly Thr Gln Ser
Phe Asn Asp Phe Thr Arg Val Val Gly Gly Glu Asp Ala Lys Pro Gly Gln Phe
Pro Trp Gln Val Val Leu Asn Gly Lys Val Asp Ala Phe Cys Gly Gly Ser Ile Val
Asn Glu Lys Trp Ile Val Thr Ala Ala His Cys Val Glu Thr Gly Val Lys Ile Thr
Val Val Ala Gly Glu His Asn Ile Glu Glu Thr Glu His Thr Glu Gln Lys Arg Asn
Val Ile Arg Ala Ile Ile Pro His His Asn Tyr Asn Ala Ala Ile Asn Lys Tyr Asn
His Asp Ile Ala Leu Leu Glu Leu Asp Glu Pro Leu Val Leu Asn Ser Tyr Val Thr
Pro Ile Cys Ile Ala Asp Lys Glu Tyr Thr Asn Ile Phe Leu Lys Phe Gly Ser Gly
Tyr Val Ser Gly Trp Ala Arg Val Phe His Lys Gly Arg Ser Ala Leu Val Leu Gln
Tyr Leu Arg Val Pro Leu Val Asp Arg Ala Thr Cys Leu Arg Ser Thr Lys Phe
Thr Ile Tyr Asn Asn Met Phe Cys Ala Gly Phe His Glu Gly Gly Arg Asp Ser
Cys Gln Gly Asp Ser Gly Gly Pro His Val Thr Glu Val Glu Gly Thr Ser Phe Leu
Thr Gly Ile Ile Ser Trp Gly Glu Glu Cys Ala Met Lys Gly Lys Tyr Gly Ile Tyr
Thr Lys Val Ser Arg Tyr Val Asn Trp Ile Lys Glu Lys Thr Lys Leu Thr

FIG. 63A

ATGGATTACTACAGAAAATATGCAGCTATCTTTCTGGTCACATTGTCG
GTGTTTCTGCATGTTCTCCATTCCGCTCCTGATGTGCAGGATTGCCCA
GAATGCACGCTACAGGAAAACCCATTCTTCTCCCAGCCGGGTGCCCC
AATACTTCAGTGCATGGGCTGCTGCTTCTCTAGAGCATATCCCACTCC
ACTAAGGTCCAAGAAGACGATGTTGGTCCAAAAGAACGTCACCTCAG
AGTCCACTTGCTGTGTAGCTAAATCATATAACAGGGTCACAGTAATG
GGGGGTTTCAAAGTGGAGAACCACACGGCGTGCCACTGCAGTACTTG
TTATTATCACAAATCTTAAATGTTTTACCAAGTGCTGTCTTGATGACT
GCTGATTTTCTGGAATGGAAAATTAAGTTGTTTAGTGTTTATGGCTTT
GTGAGATAAAACTCTCCTTTTCCTTACCATACCACTTTGACACGCTTC
AAGGATATACTGCAGCTTTACTGCCTTCCTCCTTATCCTACAGTACAA
TCAGCAGTCTAGTTCTTTTCATTTGGAATGAATACAGCATTAAGCTTG
TTCCACTGCAAATAAAGCCTTTTAAATCATC

FIG. 63B

Met Asp Tyr Tyr Arg Lys Tyr Ala Ala Ile Phe Leu Val Thr Leu Ser Val Phe Leu
His Val Leu His Ser Ala Pro Asp Val Gln Asp Cys Pro Glu Cys Thr Leu Gln Glu
Asn Pro Phe Phe Ser Gln Pro Gly Ala Pro Ile Leu Gln Cys Met Gly Cys Cys Phe
Ser Arg Ala Tyr Pro Thr Pro Leu Arg Ser Lys Lys Thr Met Leu Val Gln Lys Asn
Val Thr Ser Glu Ser Thr Cys Cys Val Ala Lys Ser Tyr Asn Arg Val Thr Val Met
Gly Gly Phe Lys Val Glu Asn His Thr Ala Cys His Cys Ser Thr Cys Tyr Tyr His
Lys Ser

FIG. 63C

ATGAAGACACTCCAGTTTTTCTTCCTTTTCTGTTGCTGGAAAGCAATC
TGCTGCAATAGCTGTGAGCTGACCAACATCACCATTGCAATAGAGAA
AGAAGAATGTCGTTTCTGCATAAGCATCAACACCACTTGGTGTGCTG
GCTACTGCTACACCAGGGATCTGGTGTATAAGGACCCAGCCAGGCCC
AAAATCCAGAAAACATGTACCTTCAAGGAACTGGTATATGAAACAGT
GAGAGTGCCCGGCTGTGCTCACCATGCAGATTCCTTGTATACATACCC
AGTGGCCACCCAGTGTCACTGTGGCAAGTGTGACAGCGACAGCACTG
ATTGTACTGTGCGAGGCCTGGGGCCCAGCTACTGCTCCTTTGGTGAAA
TGAAAGAATAA

FIG. 63D

Met Lys Thr Leu Gln Phe Phe Phe Leu Phe Cys Cys Trp Lys Ala Ile Cys Cys
Asn Ser Cys Glu Leu Thr Asn Ile Thr Ile Ala Ile Glu Lys Glu Glu Cys Arg Phe
Cys Ile Ser Ile Asn Thr Thr Trp Cys Ala Gly Tyr Cys Tyr Thr Arg Asp Leu Val
Tyr Lys Asp Pro Ala Arg Pro Lys Ile Gln Lys Thr Cys Thr Phe Lys Glu Leu Val
Tyr Glu Thr Val Arg Val Pro Gly Cys Ala His His Ala Asp Ser Leu Tyr Thr Tyr
Pro Val Ala Thr Gln Cys His Cys Gly Lys Cys Asp Ser Asp Ser Thr Asp Cys
Thr Val Arg Gly Leu Gly Pro Ser Tyr Cys Ser Phe Gly Glu Met Lys Glu

FIG. 64A

CCCGGAGCCGGACCGGGGCCACCGCGCCCGCTCTGCTCCGACACCGC
GCCCCCTGGACAGCCGCCCTCTCCTCCAGGCCCGTGGGGCTGGCCCT
GCACCGCCGAGCTTCCCGGGATGAGGGCCCCCGGTGTGGTCACCCGG
CGCGCCCCAGGTCGCTGAGGGACCCCGGCCAGGCGCGGAGATGGGG
GTGCACGAATGTCCTGCCTGGCTGTGGCTTCTCCTGTCCCTGCTGTCG
CTCCCTCTGGGCCTCCCAGTCCTGGGCGCCCCACCACGCCTCATCTGT
GACAGCCGAGTCCTGGAGAGGTACCTCTTGGAGGCCAAGGAGGCCG
AGAATATCACGACGGGCTGTGCTGAACACTGCAGCTTGAATGAGAAT
ATCACTGTCCCAGACACCAAAGTTAATTTCTATGCCTGGAAGAGGAT
GGAGGTCGGGCAGCAGGCCGTAGAAGTCTGGCAGGGCCTGGCCCTG
CTGTCGGAAGCTGTCCTGCGGGGCCAGGCCCTGTTGGTCAACTCTTCC
CAGCCGTGGGAGCCCCTGCAGCTGCATGTGGATAAAGCCGTCAGTGG
CCTTCGCAGCCTCACCACTCTGCTTCGGGCTCTGCGAGCCCAGAAGG
AAGCCATCTCCCCTCCAGATGCGGCCTCAGCTGCTCCACTCCGAACA
ATCACTGCTGACACTTTCCGCAAACTCTTCCGAGTCTACTCCAATTTC
CTCCGGGGAAAGCTGAAGCTGTACACAGGGGAGGCCTGCAGGACAG
GGGACAGATGACCAGGTGTGTCCACCTGGGCATATCCACCACCTCCC
TCACCAACATTGCTTGTGCCACACCCTCCCCCGCCACTCCTGAACCCC
GTCGAGGGGCTCTCAGCTCAGCGCCAGCCTGTCCCATGGACACTCCA
GTGCCAGCAATGACATCTCAGGGGCCAGAGGAACTGTCCAGAGAGC
AACTCTGAGATCTAAGGATGTCACAGGGCCAACTTGAGGGCCCAGAG
CAGGAAGCATTCAGAGAGCAGCTTTAAACTCAGGGACAGAGCCATG
CTGGGAAGACGCCTGAGCTCACTCGGCACCCTGCAAAATTTGATGCC
AGGACACGCTTTGGAGGCGATTTACCTGTTTTCGCACCTACCATCAGG
GACAGGATGACCTGGAGAACTTAGGTGGCAAGCTGTGACTTCTCCAG
GTCTCACGGGCATGGGCACTCCCTTGGTGGCAAGAGCCCCCTTGACA
CCGGGGTGGTGGGAACCATGAAGACAGGATGGGGGCTGGCCTCTGG
CTCTCATGGGGTCCAAGTTTTGTGTATTCTTCAACCTCATTGACAAGA
ACTGAAACCACCAAAAAAAAAAAAAA

FIG. 64B

Met Gly Val His Glu Cys Pro Ala Trp Leu Trp Leu Leu Leu Ser Leu Leu Ser
Leu Pro Leu Gly Leu Pro Val Leu Gly Ala Pro Pro Arg Leu Ile Cys Asp Ser
Arg Val Leu Glu Arg Tyr Leu Leu Glu Ala Lys Glu Ala Glu Asn Ile Thr Thr
Gly Cys Ala Glu His Cys Ser Leu Asn Glu Asn Ile Thr Val Pro Asp Thr Lys
Val Asn Phe Tyr Ala Trp Lys Arg Met Glu Val Gly Gln Gln Ala Val Glu Val
Trp Gln Gly Leu Ala Leu Leu Ser Glu Ala Val Leu Arg Gly Gln Ala Leu Leu
Val Asn Ser Ser Gln Pro Trp Glu Pro Leu Gln Leu His Val Asp Lys Ala Val Ser
Gly Leu Arg Ser Leu Thr Thr Leu Leu Arg Ala Leu Arg Ala Gln Lys Glu Ala Ile
Ser Pro Pro Asp Ala Ala Ser Ala Ala Pro Leu Arg Thr Ile Thr Ala Asp Thr Phe
Arg Lys Leu Phe Arg Val Tyr Ser Asn Phe Leu Arg Gly Lys Leu Lys Leu Tyr
Thr Gly Glu Ala Cys Arg Thr Gly Asp Arg

FIG. 65

Ala Pro Pro Arg Leu Ile Cys Asp Ser Arg Val Leu Glu Arg Tyr Leu Leu Glu Ala
Lys Glu Ala Glu Asn Ile Thr Thr Gly Cys Ala Glu His Cys Ser Leu Asn Glu Asn
Ile Thr Val Pro Asp Thr Lys Val Asn Phe Tyr Ala Trp Lys Arg Met Glu Val Gly
Gln Gln Ala Val Glu Val Trp Gln Gly Leu Ala Leu Leu Ser Glu Ala Val Leu Arg
Gly Gln Ala Leu Leu Val Asn Ser Ser Gln Pro Trp Glu Pro Leu Gln Leu His Val
Asp Lys Ala Val Ser Gly Leu Arg Ser Leu Thr Thr Leu Leu Arg Ala Leu Gly
Ala Gln Lys Glu Ala Ile Ser Pro Pro Asp Ala Ala Ser Ala Ala Pro Leu Arg Thr
Ile Thr Ala Asp Thr Phe Arg Lys Leu Phe Arg Val Tyr Ser Asn Phe Leu Arg Gly
Lys Leu Lys Leu Tyr Thr Gly Glu Ala Cys Arg Thr Gly Asp

FIG. 66A

ATGTGGCTGCAGAGCCTGCTGCTCTTGGGCACTGTGGCCTGCAGCAT
CTCTGCACCCGCCCGCTCGCCCAGCCCCAGCACGCAGCCCTGGGAGC
ATGTGAATGCCATCCAGGAGGCCCGGCGTCTCCTGAACCTGAGTAGA
GACACTGCTGCTGAGATGAATGAAACAGTAGAAGTCATCTCAGAAAT
GTTTGACCTCCAGGAGCCGACCTGCCTACAGACCCGCCTGGAGCTGT
ACAAGCAGGGCCTGCGGGGCAGCCTCACCAAGCTCAAGGGCCCCTTG
ACCATGATGGCCAGCCACTACAAGCAGCACTGCCCTCCAACCCCGGA
AACTTCCTGTGCAACCCAGATTATCACCTTTGAAAGTTTCAAAGAGA
ACCTGAAGGACTTTCTGCTTGTCATCCCCTTTGACTGCTGGGAGCCAG
TCCAGGAGTGA

FIG. 66B

Met Trp Leu Gln Ser Leu Leu Leu Leu Gly Thr Val Ala Cys Ser Ile Ser Ala Pro
Ala Arg Ser Pro Ser Pro Ser Thr Gln Pro Trp Glu His Val Asn Ala Ile Gln Glu
Ala Arg Arg Leu Leu Asn Leu Ser Arg Asp Thr Ala Ala Glu Met Asn Glu Thr
Val Glu Val Ile Ser Glu Met Phe Asp Leu Gln Glu Pro Thr Cys Leu Gln Thr Arg
Leu Glu Leu Tyr Lys Gln Gly Leu Arg Gly Ser Leu Thr Lys Leu Lys Gly Pro
Leu Thr Met Met Ala Ser His Tyr Lys Gln His Cys Pro Pro Thr Pro Glu Thr Ser
Cys Ala Thr Gln Ile Ile Thr Phe Glu Ser Phe Lys Glu Asn Leu Lys Asp Phe Leu
Leu Val Ile Pro Phe Asp Cys Trp Glu Pro Val Gln Glu

FIG. 67A

ATGAAATATACAAGTTATATCTTGGCTTTTCAGCTCTGCATCGTTTTG
GGTTCTCTTGGCTGTTACTGCCAGGACCCATATGTAAAAGAAGCAGA
AAACCTTAAGAAATATTTTAATGCAGGTCATTCAGATGTAGCGGATA
ATGGAACTCTTTTCTTAGGCATTTTGAAGAATTGGAAAGAGGAGAGT
GACAGAAAAATAATGCAGAGCCAAATTGTCTCCTTTTACTTCAAACT
TTTTAAAAACTTTAAAGATGACCAGAGCATCCAAAAGAGTGTGGAGA
CCATCAAGGAAGACATGAATGTCAAGTTTTTCAATAGCAACAAAAAG
AAACGAGATGACTTCGAAAAGCTGACTAATTATTCGGTAACTGACTT
GAATGTCCAACGCAAAGCAATACATGAACTCATCCAAGTGATGGCTG
AACTGTCGCCAGCAGCTAAAACAGGGAAGCGAAAAAGGAGTCAGAT
GCTGTTTCGAGGTCGAAGAGCATCCCAGTAA

FIG. 67B

Met Lys Tyr Thr Ser Tyr Ile Leu Ala Phe Gln Leu Cys Ile Val Leu Gly Ser Leu
Gly Cys Tyr Cys Gln Asp Pro Tyr Val Lys Glu Ala Glu Asn Leu Lys Lys Tyr
Phe Asn Ala Gly His Ser Asp Val Ala Asp Asn Gly Thr Leu Phe Leu Gly Ile
Leu Lys Asn Trp Lys Glu Glu Ser Asp Arg Lys Ile Met Gln Ser Gln Ile Val Ser
Phe Tyr Phe Lys Leu Phe Lys Asn Phe Lys Asp Asp Gln Ser Ile Gln Lys Ser Val
Glu Thr Ile Lys Glu Asp Met Asn Val Lys Phe Phe Asn Ser Asn Lys Lys Lys
Arg Asp Asp Phe Glu Lys Leu Thr Asn Tyr Ser Val Thr Asp Leu Asn Val Gln
Arg Lys Ala Ile His Glu Leu Ile Gln Val Met Ala Glu Leu Ser Pro Ala Ala Lys
Thr Gly Lys Arg Lys Arg Ser Gln Met Leu Phe Arg Gly Arg Arg Ala Ser Gln

FIG. 68A

CTGGGACAGTGAATCGACAATGCCGTCTTCTGTCTCGTGGGGCATCCT
CCTGCTGGCAGGCCTGTGCTGCCTGGTCCCTGTCTCCCTGGCTGAGGA
TCCCCAGGGAGATGCTGCCCAGAAGACAGATACATCCCACCATGATC
AGGATCACCCAACCTTCAACAAGATCACCCCCAACCTGGCTGAGTTC
GCCTTCAGCCTATACCGCCAGCTGGCACACCAGTCCAACAGCACCAA
TATCTTCTTCTCCCCAGTGAGCATCGCTACAGCCTTTGCAATGCTCTC
CCTGGGGACCAAGGCTGACACTCACGATGAAATCCTGGAGGGCCTGA
ATTTCAACCTCACGGAGATTCCGGAGGCTCAGATCCATGAAGGCTTC
CAGGAACTCCTCCGTACCCTCAACCAGCCAGACAGCCAGCTCCAGCT
GACCACCGGCAATGGCCTGTTCCTCAGCGAGGGCCTGAAGCTAGTGG
ATAAGTTTTTGGAGGATGTTAAAAAGTTGTACCACTCAGAAGCCTTC
ACTGTCAACTTCGGGGACACCGAAGAGGCCAAGAAACAGATCAACG
ATTACGTGGAGAAGGGTACTCAAGGGAAAATTGTGGATTTGGTCAAG
GAGCTTGACAGAGACACAGTTTTGCTCTGGTGAATTACATCTTCTTT
AAAGGCAAATGGGAGAGACCCTTTGAAGTCAAGGACACCGAGGAAG
AGGACTTCCACGTGGACCAGGTGACCACCGTGAAGGTGCCTATGATG
AAGCGTTTAGGCATGTTTAACATCCAGCACTGTAAGAAGCTGTCCAG
CTGGGTGCTGCTGATGAAATACCTGGGCAATGCCACCGCCATCTTCT
TCCTGCCTGATGAGGGGAAACTACAGCACCTGGAAAATGAACTCACC
CACGATATCATCACCAAGTTCCTGGAAAATGAAGACAGAAGGTCTGC
CAGCTTACATTTACCCAAACTGTCCATTACTGGAACCTATGATCTGAA
GAGCGTCCTGGGTCAACTGGGCATCACTAAGGTCTTCAGCAATGGGG
CTGACCTCTCCGGGGTCACAGAGGAGGCACCCCTGAAGCTCTCCAAG
GCCGTGCATAAGGCTGTGCTGACCATCGACGAGAAAGGGACTGAAGC
TGCTGGGGCCATGTTTTTAGAGGCCATACCCATGTCTATCCCCCCCGA
GGTCAAGTTCAACAAACCCTTTGTCTTCTTAATGATTGAACAAAATAC
CAAGTCTCCCCTCTTCATGGGAAAAGTGGTGAATCCCACCCAAAAAT
AACTGCCTCTCGCTCCTCAACCCCTCCCCTCCATCCCTGGCCCCCTCC
CTGGATGACATTAAAGAAGGGTTGAGCTGG

FIG. 68B

Met Pro Ser Ser Val Ser Trp Gly Ile Leu Leu Leu Ala Gly Leu Cys Cys Leu Val
Pro Val Ser Leu Ala Glu Asp Pro Gln Gly Asp Ala Ala Gln Lys Thr Asp Thr Ser
His His Asp Gln Asp His Pro Thr Phe Asn Lys Ile Thr Pro Asn Leu Ala Glu Phe
Ala Phe Ser Leu Tyr Arg Gln Leu Ala His Gln Ser Asn Ser Thr Asn Ile Phe Phe
Ser Pro Val Ser Ile Ala Thr Ala Phe Ala Met Leu Ser Leu Gly Thr Lys Ala Asp
Thr His Asp Glu Ile Leu Glu Gly Leu Asn Phe Asn Leu Thr Glu Ile Pro Glu Ala
Gln Ile His Glu Gly Phe Gln Glu Leu Leu Arg Thr Leu Asn Gln Pro Asp Ser Gln
Leu Gln Leu Thr Thr Gly Asn Gly Leu Phe Leu Ser Glu Gly Leu Lys Leu Val
Asp Lys Phe Leu Glu Asp Val Lys Lys Leu Tyr His Ser Glu Ala Phe Thr Val
Asn Phe Gly Asp Thr Glu Glu Ala Lys Lys Gln Ile Asn Asp Tyr Val Glu Lys
Gly Thr Gln Gly Lys Ile Val Asp Leu Val Lys Glu Leu Asp Arg Asp Thr Val
Phe Ala LeuVal Asn Tyr Ile Phe Phe Lys Gly Lys Trp Glu Arg Pro Phe Glu Val
Lys Asp Thr Glu Glu Glu Asp Phe His Val Asp Gln Val Thr Thr Val Lys Val
Pro Met Met Lys Arg Leu Gly Met Phe Asn Ile Gln His Cys Lys Lys Leu Ser
Ser Trp Val Leu Leu Met Lys Tyr Leu Gly Asn Ala Thr Ala Ile Phe Phe Leu Pro
Asp Glu Gly Lys Leu Gln His Leu Glu Asn Glu Leu Thr His Asp Ile Ile Thr Lys
Phe Leu Glu Asn Glu AspArg Arg Ser Ala Ser Leu His Leu Pro Lys Leu Ser Ile
Thr Gly Thr Tyr Asp Leu Lys Ser Val Leu Gly Gln Leu Gly Ile Thr Lys Val Phe
Ser Asn Gly Ala Asp Leu Ser Gly Val Thr Glu Glu Ala Pro Leu Lys Leu Ser Lys
Ala Val His Lys Ala Val Leu Thr Ile Asp Glu Lys Gly Thr Glu Ala Ala Gly Ala
Met Phe Leu Glu Ala Ile Pro Met Ser Ile Pro Pro Glu Val Lys Phe Asn Lys Pro
Phe Val Phe Leu Met Ile Glu Gln Asn Thr Lys Ser Pro Leu Phe Met Gly Lys Val
Val Asn Pro Thr Gln Lys

FIG. 69A-1

GCTAACCTAGTGCCTATAGCTAAGGCAGGTACCTGCATCCTTGTTTTT
GTTTAGTGGATCCTCTATCCTTCAGAGACTCTGGAACCCCTGTGGTCT
TCTCTTCATCTAATGACCCTGAGGGGATGGAGTTTTCAAGTCCTTCCA
GAGAGGAATGTCCCAAGCCTTTGAGTAGGGTAAGCATCATGGCTGGC
AGCCTCACAGGTTTGCTTCTACTTCAGGCAGTGTCGTGGGCATCAGGT
GCCCGCCCCTGCATCCCTAAAAGCTTCGGCTACAGCTCGGTGGTGTGT
GTCTGCAATGCCACATACTGTGACTCCTTTGACCCCCCGACCTTTCCT
GCCCTTGGTACCTTCAGCCGCTATGAGAGTACACGCAGTGGGCGACG
GATGGAGCTGAGTATGGGGCCCATCCAGGCTAATCACACGGGCACAG
GCCTGCTACTGACCCTGCAGCCAGAACAGAAGTTCCAGAAAGTGAAG
GGATTTGGAGGGGCCATGACAGATGCTGCTGCTCTCAACATCCTTGCC
CTGTCACCCCCTGCCCAAAATTTGCTACTTAAATCGTACTTCTCTGAA
GAAGGAATCGGATATAACATCATCCGGGTACCCATGGCCAGCTGTGA
CTTCTCCATCCGCACCTACACCTATGCAGACACCCCTGATGATTTCCA
GTTGCACAACTTCAGCCTCCCAGAGGAAGATACCAAGCTCAAGATAC
CCCTGATTCACCGAGCCCTGCAGTTGGCCCAGCGTCCCGTTTCACTCC
TTGCCAGCCCCTGGACATCACCCACTTGGCTCAAGACCAATGGAGCG
GTGAATGGGAAGGGGTCACTCAAGGGACAGCCCGGAGACATCTACC
ACCAGACCTGGGCCAGATACTTTGTGAAGTTCCTGGATGCCTATGCTG
AGCACAAGTTACAGTTCTGGGCAGTGACAGCTGAAAATGAGCCTTCT
GCTGGGCTGTTGAGTGGATACCCCTTCCAGTGCCTGGGCTTCACCCCT
GAACATCAGCGAGACTTCATTGCCCGTGACCTAGGTCCTACCCTCGCC
AACAGTACTCACCACAATGTCCGCCTACTCATGCTGGATGACCAACGC
TTGCTGCTGCCCCACTGGGCAAAGGTGGTACTGACAGACCCAGAAGC
AGCTAAATATGTTCATGGCATTGCTGTACATTGGTACCTGGACTTTCT
GGCTCCAGCCAAAGCCACCCTAGGGGAGACACACCGCCTGTTCCCCA
ACACCATGCTCTTTGCCTCAGAGGCCTGTGTGGGCTCCAAGTTCTGGG
AGCAGAGTGTGCGGCTAGGCTCCTGGGATCGAGGGATGCAGTACAGC
CACAGCATCATCACGAACCTCCTGTACCATGTGGTCGGCTGGACCGAC
TGGAACCTTGCCCTGAACCCCGAAGGAGGACCCAATTGGGTGCGTAA
CTTTGTCGACAGTCCCATCATTGTAGACATCACCAAGGACACGTTTTA
CAAACAGCCCATGTTCTACCACCTTGGCCACTTCAGCAAGTTCATTCC
TGAGGGCTCCCAGAGAGTGGGGCTGGTTGCCAGTCAGAAGAACGACC
TGGACGCAGTGGCACTGATGCATCCCGATGGCTCTGCTGTTGTGGTCG
TGCTAAACCGCTCCTCTAAGGATGTGCCTCTTACCATCAAGGATCCTG
CTGTGGGCTTCCTGGAGACAATCTCACCTGGCTACTCCATTCACACCT
ACCTGTGGCATCGCCAGTGATGGAGCAGATACTCAAGGAGGCACTGG
GCTCAGCCTGGGCATTAAAGGACAGAGTCAGCTCACACGCTGTCTG
TGACTAAAGAGGGCACAGCAGGGCCAGTGTGAGCTTACAGCGACGT

FIG. 69A-2

AAGCCCAGGGGCAATGGTTTGGGTGACTCACTTTCCCCTCTAGGTGGT
GCCCAGGGCTGGAGGCCCCTAGAAAAAGATCAGTAAGCCCCAGTGTC
CCCCCAGCCCCCATGCTTATGTGAACATGCGCTGTGTGCTGCTTGCTT
TGGAAACT

FIG. 69B

Met Glu Phe Ser Ser Pro Ser Arg Glu Glu Cys Pro Lys Pro Leu Ser Arg Val Ser
Ile Met Ala Gly Ser Leu Thr Gly Leu Leu Leu Leu Gln Ala Val Ser Trp Ala Ser
Gly Ala Arg Pro Cys Ile Pro Lys Ser Phe Gly Tyr Ser Ser Val Val Cys Val Cys
Asn Ala Thr Tyr Cys Asp Ser Phe Asp Pro Pro Thr Phe Pro Ala Leu Gly Thr
Phe Ser Arg Tyr Glu Ser Thr Arg Ser Gly Arg Arg Met Glu Leu Ser Met Gly
Pro Ile Gln Ala Asn His Thr Gly Thr Gly Leu Leu Leu Thr Leu Gln Pro Glu Gln
Lys Phe Gln Lys Val Lys Gly Phe Gly Gly Ala Met Thr Asp Ala Ala Ala Leu
Asn Ile Leu Ala Leu Ser Pro Pro Ala Gln Asn Leu Leu Leu Lys Ser Tyr Phe Ser
Glu Glu Gly Ile Gly Tyr Asn Ile Ile Arg Val Pro Met Ala Ser Cys Asp Phe Ser
Ile Arg Thr Tyr Thr Tyr Ala Asp Thr Pro Asp Asp Phe Gln Leu His Asn Phe Ser
Leu Pro Glu Glu Asp Thr Lys Leu Lys Ile Pro Leu Ile His Arg Ala Leu Gln Leu
Ala Gln Arg Pro Val Ser Leu Leu Ala Ser Pro Trp Thr Ser Pro Thr Trp Leu Lys
Thr Asn Gly Ala Val Asn Gly Lys Gly Ser Leu Lys Gly Gln Pro Gly Asp Ile
Tyr His Gln Thr Trp Ala Arg Tyr Phe Val Lys Phe Leu Asp Ala Tyr Ala Glu
His Lys Leu Gln Phe Trp Ala Val Thr Ala Glu Asn Glu Pro Ser Ala Gly Leu
Leu Ser Gly Tyr Pro Phe Gln Cys Leu Gly Phe Thr Pro Glu His Gln Arg Asp
Phe Ile Ala Arg Asp Leu Gly Pro Thr Leu Ala Asn Ser Thr His His Asn Val Arg
Leu Leu Met Leu Asp Asp Gln Arg Leu Leu Leu Pro His Trp Ala Lys Val Val
Leu Thr Asp Pro Glu Ala Ala Lys Tyr Val His Gly Ile Ala Val His Trp Tyr Leu
Asp Phe Leu Ala Pro Ala Lys Ala Thr Leu Gly Glu Thr His Arg Leu Phe Pro
Asn Thr Met Leu Phe Ala Ser Glu Ala Cys Val Gly Ser Lys Phe Trp Glu Gln Ser
Val Arg Leu Gly Ser Trp Asp Arg Gly Met Gln Tyr Ser His Ser Ile Ile Thr Asn
Leu Leu Tyr His Val Val Gly Trp Thr Asp Trp Asn Leu Ala Leu Asn Pro Glu
Gly Gly Pro Asn Trp Val Arg Asn Phe Val Asp Ser Pro Ile Ile Val Asp Ile Thr
Lys Asp Thr Phe Tyr Lys Gln Pro Met Phe Tyr His Leu Gly His Phe Ser Lys
Phe Ile Pro Glu Gly Ser Gln Arg Val Gly Leu Val Ala Ser Gln Lys Asn Asp Leu
Asp Ala Val Ala Leu Met His Pro Asp Gly Ser Ala Val Val Val Val Leu Asn
Arg Ser Ser Lys Asp Val Pro Leu Thr Ile Lys Asp Pro Ala Val Gly Phe Leu Glu
Thr Ile Ser Pro Gly Tyr Ser Ile His Thr Tyr Leu Trp His Arg Gln

FIG. 70A

ATGGATGCAATGAAGAGAGGGCTCTGCTGTGTGCTGCTGCTGTGTGG
AGCAGTCTTCGTTTCGCCCAGCCAGGAAATCCATGCCCGATTCAGAA
GAGGAGCCAGATCTTACCAAGTGATCTGCAGAGATGAAAAAACGCA
GATGATATACCAGCAACATCAGTCATGGCTGCGCCCTGTGCTCAGAA
GCAACCGGGTGGAATATTGCTGGTGCAACAGTGGCAGGGCACAGTGC
CACTCAGTGCCTGTCAAAAGTTGCAGCGAGCCAAGGTGTTTCAACGG
GGGCACCTGCCAGCAGGCCCTGTACTTCTCAGATTTCGTGTGCCAGTG
CCCCGAAGGATTTGCTGGGAAGTGCTGTGAAATAGATACCAGGGCCA
CGTGCTACGAGGACCAGGGCATCAGCTACAGGGGCACGTGGAGCAC
AGCGGAGAGTGGCGCCGAGTGCACCAACTGGAACAGCAGCGCGTTG
GCCCAGAAGCCCTACAGCGGGCGGAGGCCAGACGCCATCAGGCTGG
GCCTGGGGAACCACAACTACTGCAGAAACCCAGATCGAGACTCAAA
GCCCTGGTGCTACGTCTTTAAGGCGGGGAAGTACAGCTCAGAGTTCT
GCAGCACCCCTGCCTGCTCTGAGGGAAACAGTGACTGCTACTTTGGG
AATGGGTCAGCCTACCGTGGCACGCACAGCCTCACCGAGTCGGGTGC
CTCCTGCCTCCCGTGGAATTCCATGATCCTGATAGGCAAGGTTTACAC
AGCACAGAACCCCAGTGCCCAGGCACTGGGCCTGGGCAAACATAATT
ACTGCCGGAATCCTGATGGGGATGCCAAGCCCTGGTGCCACGTGCTG
AAGAACCGCAGGCTGACGTGGGAGTACTGTGATGTGCCCTCCTGCTC
CACCTGCGGCCTGAGACAGTACAGCCAGCCTCAGTTTCGCATCAAAG
GAGGGCTCTTCGCCGACATCGCCTCCCACCCCTGGCAGGCTGCCATCT
TTGCCAAGCACAGGAGGTCGCCGGGAGAGCGGTTCCTGTGCGGGGGC
ATACTCATCAGCTCCTGCTGGATTCTCTCTGCCGCCCACTGCTTCCAG
GAGAGGTTTCCGCCCCACCACCTGACGGTGATCTTGGGCAGAACATA
CCGGGTGGTCCCTGGCGAGGAGGAGCAGAAATTTGAAGTCGAAAAA
TACATTGTCCATAAGGAATTCGATGATGACACTTACGACAATGACAT
TGCGCTGCTGCAGCTGAAATCGGATTCGTCCCGCTGTGCCCAGGAGA
GCAGCGTGGTCCGCACTGTGTGCCTTCCCCCGGCGGACCTGCAGCTG
CCGGACTGGACGGAGTGTGAGCTCTCCGGCTACGGCAAGCATGAGGC
CTTGTCTCCTTTCTATTCGGAGCGGCTGAAGGAGGCTCATGTCAGACT
GTACCCATCCAGCCGCTGCACATCACAACATTTACTTAACAGAACAG
TCACCGACAACATGCTGTGTGCTGGAGACACTCGGAGCGGCGGGCCC
CAGGCAAACTTGCACGACGCCTGCCAGGGCGATTCGGGAGGCCCCCT
GGTGTGTCTGAACGATGGCCGCATGACTTTGGTGGGCATCATCAGCT
GGGGCCTGGGCTGTGGACAGAAGGATGTCCCGGGTGTGTACACCAAG
GTTACCAACTACCTAGACTGGATTCGTGACAACATGCGACCGTGACC
AGGAACACCCGACTCCTCAAAAGCAAATGAGATCC

FIG. 70B

Met Asp Ala Met Lys Arg Gly Leu Cys Cys Val Leu Leu Leu Cys Gly Ala Val
Phe Val Ser Pro Ser Gln Glu Ile His Ala Arg Phe Arg Arg Gly Ala Arg Ser Tyr
Gln Val Ile Cys Arg Asp Glu Lys Thr Gln Met Ile Tyr Gln Gln His Gln Ser Trp
Leu Arg Pro Val Leu Arg Ser Asn Arg Val Glu Tyr Cys Trp Cys Asn Ser Gly
Arg Ala Gln Cys His Ser Val Pro Val Lys Ser Cys Ser Glu Pro Arg Cys Phe Asn
Gly Gly Thr Cys Gln Gln Ala Leu Tyr Phe Ser Asp Phe Val Cys Gln Cys Pro
Glu Gly Phe Ala Gly Lys Cys Cys Glu Ile Asp Thr Arg Ala Thr Cys Tyr Glu
Asp Gln Gly Ile Ser Tyr Arg Gly Thr Trp Ser Thr Ala Glu Ser Gly Ala Glu Cys
Thr Asn Trp Asn Ser Ser Ala Leu Ala Gln Lys Pro Tyr Ser Gly Arg Arg Pro Asp
Ala Ile Arg Leu Gly Leu Gly Asn His Asn Tyr Cys Arg Asn Pro Asp Arg Asp
Ser Lys Pro Trp Cys Tyr Val Phe Lys Ala Gly Lys Tyr Ser Ser Glu Phe Cys Ser
Thr Pro Ala Cys Ser Glu Gly Asn Ser Asp Cys Tyr Phe Gly Asn Gly Ser Ala Tyr
Arg Gly Thr His Ser Leu Thr Glu Ser Gly Ala Ser Cys Leu Pro Trp Asn Ser Met
Ile Leu Ile Gly Lys Val Tyr Thr Ala Gln Asn Pro Ser Ala Gln Ala Leu Gly Leu
Gly Lys His Asn Tyr Cys Arg Asn Pro Asp Gly Asp Ala Lys Pro Trp Cys His
Val Leu Lys Asn Arg Arg Leu Thr Trp Glu Tyr Cys Asp Val Pro Ser Cys Ser
Thr Cys Gly Leu Arg Gln Tyr Ser Gln Pro Gln Phe Arg Ile Lys Gly Gly Leu Phe
Ala Asp Ile Ala Ser His Pro Trp Gln Ala Ala Ile Phe Ala Lys His Arg Arg Ser
Pro Gly Glu Arg Phe Leu Cys Gly Gly Ile Leu Ile Ser Ser Cys Trp Ile Leu Ser
Ala Ala His Cys Phe Gln Glu Arg Phe Pro Pro His His Leu Thr Val Ile Leu Gly
Arg Thr Tyr Arg Val Val Pro Gly Glu Glu Glu Gln Lys Phe Glu Val Glu Lys
Tyr Ile Val His Lys Glu Phe Asp Asp Asp Thr Tyr Asp Asn Asp Ile Ala Leu
Leu Gln Leu Lys Ser Asp Ser Ser Arg Cys Ala Gln Glu Ser Ser Val Val Arg
Thr Val Cys Leu Pro Pro Ala Asp Leu Gln Leu Pro Asp Trp Thr Glu Cys Glu
Leu Ser Gly Tyr Gly Lys His Glu Ala Leu Ser Pro Phe Tyr Ser Glu Arg Leu Lys
Glu Ala His Val Arg Leu Tyr Pro Ser Ser Arg Cys Thr Ser Gln His Leu Leu Asn
Arg Thr Val Thr Asp Asn Met Leu Cys Ala Gly Asp Thr Arg Ser Gly Gly Pro
Gln Ala Asn Leu His Asp Ala Cys Gln Gly Asp Ser Gly Gly Pro Leu Val Cys
Leu Asn Asp Gly Arg Met Thr Leu Val Gly Ile Ile Ser Trp Gly Leu Gly Cys Gly
Gln Lys Asp Val Pro Gly Val Tyr Thr Lys Val Thr Asn Tyr Leu Asp Trp Ile Arg
Asp Asn Met Arg Pro

FIG. 71A

ATCACTCTCTTTAATCACTACTCACATTAACCTCAACTCCTGCCACAA
TGTACAGGATGCAACTCCTGTCTTGCATTGCACTAATTCTTGCACTTG
TCACAAACAGTGCACCTACTTCAAGTTCGACAAAGAAAACAAAGAAA
ACACAGCTACAACTGGAGCATTTACTGCTGGATTTACAGATGATTTTG
AATGGAATTAATAATTACAAGAATCCCAAACTCACCAGGATGCTCAC
ATTTAAGTTTTACATGCCCAAGAAGGCCACAGAACTGAAACAGCTTC
AGTGTCTAGAAGAAGAACTCAAACCTCTGGAGGAAGTGCTGAATTTA
GCTCAAAGCAAAAACTTTCACTTAAGACCCAGGGACTTAATCAGCAA
TATCAACGTAATAGTTCTGGAACTAAAGGGATCTGAAACAACATTCA
TGTGTGAATATGCAGATGAGACAGCAACCATTGTAGAATTTCTGAAC
AGATGGATTACCTTTTGTCAAAGCATCATCTCAACACTAACTTGATAA
TTAAGTGCTTCCCACTTAAAACATATCAGGCCTTCTATTTATTTATTTA
AATATTTAAATTTTATATTTATTGTTGAATGTATGGTTGCTACCTATTG
TAACTATTATTCTTAATCTTAAAACTATAAATATGGATCTTTTATGAT
TCTTTTTGTAAGCCCTAGGGGCTCTAAAATGGTTTACCTTATTTATCC
CAAAAATATTTATTATTATGTTGAATGTTAAATATAGTATCTATGTAG
ATTGGTTAGTAAAACTATTTAATAAATTTGATAAATATAAAAAAAAA
AAACAAAAAAAAAAAA

FIG. 71B

Met Tyr Arg Met Gln Leu Leu Ser Cys Ile Ala Leu Ile Leu Ala Leu Val Thr Asn
Ser Ala Pro Thr Ser Ser Ser Thr Lys Lys Thr Lys Lys Thr Gln Leu Gln Leu Glu
His Leu Leu Leu Asp Leu Gln Met Ile Leu Asn Gly Ile Asn Asn Tyr Lys Asn
Pro Lys Leu Thr Arg Met Leu Thr Phe Lys Phe Tyr Met Pro Lys Lys Ala Thr
Glu Leu Lys Gln Leu Gln Cys Leu Glu Glu Glu Leu Lys Pro Leu Glu Glu Val
Leu Asn Leu Ala Gln Ser Lys Asn Phe His Leu Arg Pro Arg Asp Leu Ile Ser
Asn Ile Asn Val Ile Val Leu Glu Leu Lys Gly Ser Glu Thr Thr Phe Met Cys Glu
Tyr Ala Asp Glu Thr Ala Thr Ile Val Glu Phe Leu Asn Arg Trp Ile Thr Phe Cys
Gln Ser Ile Ile Ser Thr Leu Thr

FIG. 72A-1

ATGCAAATAGAGCTCTCCACCTGCTTCTTTCTGTGCCTTTTGCGATTCT
GCTTTAGTGCCACCAGAAGATACTACCTGGGTGCAGTGGAACTGTCA
TGGGACTATATGCAAAGTGATCTCGGTGAGCTGCCTGTGGACGCAAG
ATTTCCTCCTAGAGTGCCAAAATCTTTTCCATTCAACACCTCAGTCGT
GTACAAAAAGACTCTGTTTGTAGAATTCACGGATCACCTTTTCAACAT
CGCTAAGCCAAGGCCACCCTGGATGGGTCTGCTAGGTCCTACCATCC
AGGCTGAGGTTTATGATACAGTGGTCATTACACTTAAGAACATGGCT
TCCCATCCTGTCAGTCTTCATGCTGTTGGTGTATCCTACTGGAAAGCT
TCTGAGGGAGCTGAATATGATGATCAGACCAGTCAAAGGGAGAAAG
AAGATGATAAAGTCTTCCCTGGTGGAAGCCATACATATGTCTGGCAG
GTCCTGAAAGAGAATGGTCCAATGGCCTCTGACCCACTGTGCCTTAC
CTACTCATATCTTTCTCATGTGGACCTGGTAAAAGACTTGAATTCAGG
CCTCATTGGAGCCCTACTAGTATGTAGAGAAGGGAGTCTGGCCAAGG
AAAAGACACAGACCTTGCACAAATTTATACTACTTTTTGCTGTATTTG
ATGAAGGGAAAAGTTGGCACTCAGAAACAAAGAACTCCTTGATGCA
GGATAGGGATGCTGCATCTGCTCGGGCCTGGCCTAAAATGCACACAG
TCAATGGTTATGTAAACAGGTCTCTGCCAGGTCTGATTGGATGCCACA
GGAAATCAGTCTATTGGCATGTGATTGGAATGGGCACCACTCCTGAA
GTGCACTCAATATTCCTCGAAGGTCACACATTTCTTGTGAGGAACCAT
CGCCAGGCGTCCTTGGAAATCTCGCCAATAACTTTCCTTACTGCTCAA
ACACTCTTGATGGACCTTGGACAGTTTCTACTGTTTTGTCATATCTCTT
CCCACCAACATGATGGCATGGAAGCTTATGTCAAAGTAGACAGCTGT
CCAGAGGAACCCCAACTACGAATGAAAAATAATGAAGAAGCGGAAG
ACTATGATGATGATCTTACTGATTCTGAAATGGATGTGGTCAGGTTTG
ATGATGACAACTCTCCTTCCTTTATCCAAATTCGCTCAGTTGCCAAGA
AGCATCCTAAAACTTGGGTACATTACATTGCTGCTGAAGAGGAGGAC
TGGGACTATGCTCCCTTAGTCCTCGCCCCCGATGACAGAAGTTATAAA
AGTCAATATTTGAACAATGGCCCTCAGCGGATTGGTAGGAAGTACAA
AAAAGTCCGATTTATGGCATACACAGATGAAACCTTTAAGACTCGTG
AAGCTATTCAGCATGAATCAGGAATCTTGGGACCTTTACTTTATGGGG
AAGTTGGAGACACACTGTTGATTATATTTAAGAATCAAGCAAGCAGA
CCATATAACATCTACCCTCACGGAATCACTGATGTCCGTCCTTTGTAT
TCAAGGAGATTACCAAAAGGTGTAAAACATTTGAAGGATTTTCCAAT
TCTGCCAGGAGAAATATTCAAATATAAATGGACAGTGACTGTAGAAG
ATGGGCCAACTAAATCAGATCCTCGGTGCCTGACCCGCTATTACTCTA
GTTTCGTTAATATGGAGAGAGATCTAGCTTCAGGACTCATTGGCCCTC
TCCTCATCTGCTACAAAGAATCTGTAGATCAAAGAGGAAACCAGATA
ATGTCAGACAAGAGGAATGTCATCCTGTTTTCTGTATTTGATGAGAAC
CGAAGCTGGTACCTCACAGAGAATATACAACGCTTTCTCCCCAATCCA
GCTGGAGTGCAGCTTGAGGATCCAGAGTTCCAAGCCTCCAACATCAT
GCACAGCATCAATGGCTATGTTTTTGATAGTTTGCAGTTGTCAGTTTG
TTTGCATGAGGTGGCATACTGGTACATTCTAAGCATTGGAGCACAGA
CTGACTTCCTTTCTGTCTTCTTCTCTGGATATACCTTCAAACACAAAAT

FIG. 72A-2

GGTCTATGAAGACACACTCACCCTATTCCCATTCTCAGGAGAAACTGT
CTTCATGTCGATGGAAAACCCAGGTCTATGGATTCTGGGGTGCCACA
ACTCAGACTTTCGGAACAGAGGCATGACCGCCTTACTGAAGGTTTCT
AGTTGTGACAAGAACACTGGTGATTATTACGAGGACAGTTATGAAGA
TATTTCAGCATACTTGCTGAGTAAAAACAATGCCATTGAACCAAGAA
GCTTCTCCCAGAATTCAAGACACCGTAGCACTAGGCAAAAGCAATTT
AATGCCACCACAATTCCAGAAAATGACATAGAGAAGACTGACCCTTG
GTTTGCACACAGAACACCTATGCCTAAAATACAAAATGTCTCCTCTA
GTGATTTGTTGATGCTCTTGCGACAGAGTCCTACTCCACATGGGCTAT
CCTTATCTGATCTCCAAGAAGCCAAATATGAGACTTTTTCTGATGATC
CATCACCTGGAGCAATAGACAGTAATAACAGCCTGTCTGAAATGACA
CACTTCAGGCCACAGCTCCATCACAGTGGGGACATGGTATTTACCCC
TGAGTCAGGCCTCCAATTAAGATTAAATGAGAAACTGGGGACAACTG
CAGCAACAGAGTTGAAGAAACTTGATTTCAAAGTTTCTAGTACATCA
AATAATCTGATTTCAACAATTCCATCAGACAATTTGGCAGCAGGTACT
GATAATACAAGTTCCTTAGGACCCCCAAGTATGCCAGTTCATTATGAT
AGTCAATTAGATACCACTCTATTTGGCAAAAAGTCATCTCCCCTTACT
GAGTCTGGTGGACCTCTGAGCTTGAGTGAAGAAAATAATGATTCAAA
GTTGTTAGAATCAGGTTTAATGAATAGCCAAGAAAGTTCATGGGGAA
AAAATGTATCGTCAACAGAGAGTGGTAGGTTATTTAAAGGGAAAAGA
GCTCATGGACCTGCTTTGTTGACTAAAGATAATGCCTTATTCAAAGTT
AGCATCTCTTTGTTAAAGACAAACAAAACTTCCAATAATTCAGCAACT
AATAGAAAGACTCACATTGATGGCCCATCATTATTAATTGAGAATAG
TCCATCAGTCTGGCAAAATATATTAGAAAGTGACACTGAGTTTAAAA
AAGTGACACCTTTGATTCATGACAGAATGCTTATGGACAAAAATGCT
ACAGCTTTGAGGCTAAATCATATGTCAAATAAAACTACTTCATCAAA
AAACATGGAAATGGTCCAACAGAAAAAAGAGGGCCCCATTCCACCA
GATGCACAAAATCCAGATATGTCGTTCTTTAAGATGCTATTCTTGCCA
GAATCAGCAAGGTGGATACAAAGGACTCATGGAAAGAACTCTCTGAA
CTCTGGGCAAGGCCCCAGTCCAAAGCAATTAGTATCCTTAGGACCAG
AAAAATCTGTGGAAGGTCAGAATTTCTTGTCTGAGAAAAACAAAGTG
GTAGTAGGAAAGGGTGAATTTACAAAGGACGTAGGACTCAAAGAGA
TGGTTTTTCCAAGCAGCAGAAACCTATTTCTTACTAACTTGGATAATT
TACATGAAAATAATACACACAATCAAGAAAAAAAAATTCAGGAAGA
AATAGAAAAGAAGGAAACATTAATCCAAGAGAATGTAGTTTTGCCTC
AGATACATACAGTGACTGGCACTAAGAATTTCATGAAGAACCTTTTC
TTACTGAGCACTAGGCAAAATGTAGAAGGTTCATATGACGGGGCATA
TGCTCCAGTACTTCAAGATTTTAGGTCATTAAATGATTCAACAAATAG
AACAAAGAAACACACAGCTCATTTCTCAAAAAAAGGGGAGGAAGAA
AACTTGGAAGGCTTGGGAAATCAAACCAGCAAATTGTAGAGAAATAT
GCATGCACCACAAGGAATATCTCCTAATACAAGCCAGCAGAATTTTG
TCACGCAACGTAGTAAGAGAGCTTTGAAACAATTCAGACTCCCACTA

FIG. 72A-3

GAAGAAACAGAACTTGAAAAAAGGATAATTGTGGATGACACCTCAAC
CCAGTGGTCCAAAAACATGAAACATTTGACCCCGAGCACCCTCACAC
AGATAGACTACAATGAGAAGGAGAAAGGGGCCATTACTCAGTCTCCC
TTATCAGATTGCCTTACGAGGAGTCATAGCATCCCTCAAGCAAATAGA
TCTCCATTACCCATTGCAAAGGTATCATCATTTCCATCTATTAGACCTA
TATATCTGACCAGGGTCCTATTCCAAGACAACTCTTCTCATCTTCCAG
CAGCATCTTATAGAAAGAAAGATTCTGGGGTCCAAGAAAGCAGTCAT
TTCTTACAAGGAGCCAAAAAAAAATAACCTTTCTTTAGCCATTCTAACC
TTGGAGATGACTGGTGATCAAAGAGAGGTTGGCTCCCTGGGGACAAG
TGCCACAAATTCAGTCACATACAAGAAAGTTGAGAACACTGTTCTCCC
GAAACCAGACTTGCCCAAAACATCTGGCAAAGTTGAATTGCTTCCAA
AAGTTCACATTTATCAGAAGGACCTATTCCCTACGGAAACTAGCAATG
GGTCTCCTGGCCATCTGGATCTCGTGGAAGGGAGCCTTCTTCAGGGAA
CAGAGGGAGCGATTAAGTGGAATGAAGCAAACAGACCTGGAAAAGT
TCCCTTTCTGAGAGTAGCAACAGAAAGCTCTGCAAAGACTCCCTCCAA
GCTATTGGATCCTCTTGCTTGGGATAACCACTATGGTACTCAGATACC
AAAAGAAGAGTGGAAATCCCAAGAGAAGTCACCAGAAAAAACAGCT
TTTAAGAAAAAGGATACCATTTTGTCCCTGAACGCTTGTGAAAGCAAT
CATGCAATAGCAGCAATAAATGAGGGACAAAATAAGCCCGAAATAG
AAGTCACCTGGGCAAAGCAAGGTAGGACTGAAAGGCTGTGCTCTCAA
AACCCACCAGTCTTGAAACGCCATCAACGGGAAATAACTCGTACTAC
TCTTCAGTCAGATCAAGAGGAAATTGACTATGATGATACCATATCAGT
TGAAATGAAGAAGGAAGATTTTGACATTTATGATGAGGATGAAAATC
AGAGCCCCCGCAGCTTTCAAAAGAAAACACGACACTATTTTATTGCTG
CAGTGGAGAGGCTCTGGGATTATGGGATGAGTAGCTCCCCACATGTT
CTAAGAAACAGGGCTCAGAGTGGCAGTGTCCCTCAGTTCAAGAAAGT
TGTTTTCCAGGAATTTACTGATGGCTCCTTTACTCAGCCCTTATACCGT
GGAGAACTAAATGAACATTTGGGACTCCTGGGGCCATATATAAGAGC
AGAAGTTGAAGATAATATCATGGTAACTTTCAGAAATCAGGCCTCTC
GTCCCTATTCCTTCTATTCTAGCCTTATTTCTTATGAGGAAGATCAGAG
GCAAGGAGCAGAACCTAGAAAAAACTTTGTCAAGCCTAATGAAACCA
AAACTTACTTTTGGAAAGTGCAACATCATATGGCACCCACTAAAGAT
GAGTTTGACTGCAAAGCCTGGGCTTATTTCTCTGATGTTGACCTGGAA
AAAGATGTGCACTCAGGCCTGATTGGACCCCTTCTGGTCTGCCACACT
AACACACTGAACCCTGCTCATGGGAGACAAGTGACAGTACAGGAATT
TGCTCTGTTTTTCACCATCTTTGATGAGACCAAAAGCTGGTACTTCACT
GAAAATATGGAAAGAAACTGCAGGGCTCCCTGCAATATCCAGATGGA
AGATCCCACTTTTAAAGAGAATTATCGCTTCCATGCAATCAATGGCTA
CATAATGGATACACTACCTGGCTTAGTAATGGCTCAGGATCAAAGGA
TTCGATGGTATCTGCTCAGCATGGGCAGCAATGAAAACATCCATTCT
ATTCATTTCAGTGGACATGTGTTCACTGTACGAAAAAAAGAGGAGTA
TAAAATGGCACTGTACAATCTCTATCCAGGTGTTTTTGAGACAGTGGA

FIG. 72A-4

AATGTTACCATCCAAAGCTGGAATTTGGCGGGTGGAATGCCTTATTGG
CGAGCATCTACATGCTGGGATGAGCACACTTTTTCTGGTGTACAGCAA
TAAGTGTCAGACTCCCCTGGGAATGGCTTCTGGACACATTAGAGATTT
TCAGATTACAGCTTCAGGACAATATGGACAGTGGGCCCCAAAGCTGG
CCAGACTTCATTATTCCGGATCAATCAATGCCTGGAGCACCAAGGAG
CCCTTTTCTTGGATCAAGGTGGATCTGTTGGCACCAATGATTATTCAC
GGCATCAAGACCCAGGGTGCCCGTCAGAAGTTCTCCAGCCTCTACAT
CTCTCAGTTTATCATCATGTATAGTCTTGATGGGAAGAAGTGGCAGA
CTTATCGAGGAAATTCCACTGGAACCTTAATGGTCTTCTTTGGCAATG
TGGATTCATCTGGGATAAAACACAATATTTTTAACCCTCCAATTATTG
CTCGATACATCCGTTTGCACCCAACTCATTATAGCATTCGCAGCACTC
TTCGCATGGAGTTGATGGGCTGTGATTTAAATAGTTGCAGCATGCCAT
TGGGAATGGAGAGTAAAGCAATATCAGATGCACAGATTACTGCTTCA
TCCTACTTTACCAATATGTTTGCCACCTGGTCTCCTTCAAAAGCTCGA
CTTCACCTCCAAGGGAGGAGTAATGCCTGGAGACCTCAGGTGAATAA
TCCAAAAGAGTGGCTGCAAGTGGACTTCCAGAAGACAATGAAAGTCA
CAGGAGTAACTACTCAGGGAGTAAAATCTCTGCTTACCAGCATGTAT
GTGAAGGAGTTCCTCATCTCCAGCAGTCAAGATGGCCATCAGTGGAC
TCTCTTTTTTCAGAATGGCAAAGTAAAGGTTTTTCAGGGAAATCAAGA
CTCCTTCACACCTGTGGTGAACTCTCTAGACCCACCGTTACTGACTCG
CTACCTTCGAATTCACCCCCAGAGTTGGGTGCACCAGATTGCCCTGAG
GATGGAGGTTCTGGGCTGCGAGGCACAGGACCTCTACTGAGGGTGGC
CACTGCAGCACCTGCCACTGCCGTCACCTCTCCCTCCTCAGCTCCAGG
GCAGTGTCCCTCCCTGGCTTGCCTTCTACCTTTGTGCTAAATCCTAGC
AGACACTGCCTTGAAGCCTCCTGAATTAACTATCATCAGTCCTGCATT
TCTTTGGTGGGGGGCCAGGAGGGTGCATCCAATTTAACTTAACTCTTA
CCTATTTTCTGCAGCTGCTCCCAGATTACTCCTTCCTTCCAATATAACT
AGGCAAAAAGAAGTGAGGAGAAACCTGCATGAAAGCATTCTTCCCTG
AAAAGTTAGGCCTCTCAGAGTCACCACTTCCTCTGTTGTAGAAAAACT
ATGTGATGAAACTTTGAAAAAGATATTTATGATGTTAACATTTCAGGT
TAAGCCTCATACGTTTAAAATAAAACTCTCAGTTGTTTATTATCCTGA
TCAAGCATGGAACAAAGCATGTTTCAGGATCAGATCAATACAATCTT
GGAGTCAAAAGGCAAATCATTTGGACAATCTGCAAAATGGAGAGAA
TACAATAACTACTACAGTAAAGTCTGTTTCTGCTTCCTTACACATAGA
TATAATTATGTTATTTAGTCATTATGAGGGGCACATTCTTATCTCCAA
AACTAGCATTCTTAAACTGAGAATTATAGATGGGGTTCAAGAATCCC
TAAGTCCCCTGAAATTATATAAGGCATTCTGTATAAATGCAAATGTGC
ATTTTTCTGACGAGTGTCCATAGATATAAAGCCATTTGGTCTTAATTCT
GACCAATAAAAAAATAAGTCAGGAGGATGCAATTGTTGAAAGCTTTG
AAATAAAATAACAATGTCTTCTTGAAATTTGTGATGGCCAAGAAAGA
AAATGATGA

FIG. 72B-1

Met Gln Ile Glu Leu Ser Thr Cys Phe Phe Leu Cys Leu Leu Arg Phe Cys Phe Ser
Ala Thr Arg Arg Tyr Tyr Leu Gly Ala Val Glu Leu Ser Trp Asp Tyr Met Gln Ser
Asp Leu Gly Glu Leu Pro Val Asp Ala Arg Phe Pro Pro Arg Val Pro Lys Ser Phe
Pro Phe Asn Thr Ser Val Val Tyr Lys Lys Thr Leu Phe Val Glu Phe Thr Asp His
Leu Phe Asn Ile Ala Lys Pro Arg Pro Pro Trp Met Gly Leu Leu Gly Pro Thr Ile
Gln Ala Glu Val Tyr Asp Thr Val Val Ile Thr Leu Lys Asn Met Ala Ser His Pro
Val Ser Leu His Ala Val Gly Val Ser Tyr Trp Lys Ala Ser Glu Gly Ala Glu Tyr
Asp Asp Gln Thr Ser Gln Arg Glu Lys Glu Asp Asp Lys Val Phe Pro Gly Gly
Ser His Thr Tyr Val Trp Gln Val Leu Lys Glu Asn Gly Pro Met Ala Ser Asp Pro
Leu Cys Leu Thr Tyr Ser Tyr Leu Ser His Val Asp Leu Val Lys Asp Leu Asn
Ser Gly Leu Ile Gly Ala Leu Leu Val Cys Arg Glu Gly Ser Leu Ala Lys Glu Lys
Thr Gln Thr Leu His Lys Phe Ile Leu Leu Phe Ala Val Phe Asp Glu Gly Lys Ser
Trp His Ser Glu Thr Lys Asn Ser Leu Met Gln Asp Arg Asp Ala Ala Ser Ala Arg
Ala Trp Pro Lys Met His Thr Val Asn Gly Tyr Val Asn Arg Ser Leu Pro Gly Leu
Ile Gly Cys His Arg Lys Ser Val Tyr Trp His Val Ile Gly Met Gly Thr Thr Pro
Glu Val His Ser Ile Phe Leu Glu Gly His Thr Phe Leu Val Arg Asn His Arg Gln
Ala Ser Leu Glu Ile Ser Pro Ile Thr Phe Leu Thr Ala Gln Thr Leu Leu Met Asp
Leu Gly Gln Phe Leu Leu Phe Cys His Ile Ser Ser His Gln His Asp Gly Met Glu
Ala Tyr Val Lys Val Asp Ser Cys Pro Glu Glu Pro Gln Leu Arg Met Lys Asn
Asn Glu Glu Ala Glu Asp Tyr Asp Asp Asp Leu Thr Asp Ser Glu Met Asp Val
Val Arg Phe Asp Asp Asp Asn Ser Pro Ser Phe Ile Gln Ile Arg Ser Val Ala Lys
Lys His Pro Lys Thr Trp Val His Tyr Ile Ala Ala Glu Glu Glu Asp Trp Asp Tyr
Ala Pro Leu Val Leu Ala Pro Asp Asp Arg Ser Tyr Lys Ser Gln Tyr Leu Asn
Asn Gly Pro Gln Arg Ile Gly Arg Lys Tyr Lys Lys Val Arg Phe Met Ala Tyr Thr
Asp Glu Thr Phe Lys Thr Arg Glu Ala Ile Gln His Glu Ser Gly Ile Leu Gly Pro
Leu Leu Tyr Gly Glu Val Gly Asp Thr Leu Leu Ile Ile Phe Lys Asn Gln Ala Ser
Arg Pro Tyr Asn Ile Tyr Pro His Gly Ile Thr Asp Val Arg Pro Leu Tyr Ser Arg
Arg Leu Pro Lys Gly Val Lys His Leu Lys Asp Phe Pro Ile Leu Pro Gly Glu Ile
Phe Lys Tyr Lys Trp Thr Val Thr Val Glu Asp Gly Pro Thr Lys Ser Asp Pro Arg
Cys Leu Thr Arg Tyr Tyr Ser Ser Phe Val Asn Met Glu Arg Asp Leu Ala Ser
Gly Leu Ile Gly Pro Leu Leu Ile Cys Tyr Lys Glu Ser Val Asp Gln Arg Gly Asn
Gln Ile Met Ser Asp Lys Arg Asn Val Ile Leu Phe Ser Val Phe Asp Glu Asn Arg
Ser Trp Tyr Leu Thr Glu Asn Ile Gln Arg Phe Leu Pro Asn Pro Ala Gly Val Gln
Leu Glu Asp Pro Glu Phe Gln Ala Ser Asn Ile Met His Ser Ile Asn Gly Tyr Val
Phe Asp Ser Leu Gln Leu Ser Val Cys Leu His Glu Val Ala Tyr Trp Tyr Ile Leu
Ser Ile Gly Ala Gln Thr Asp Phe Leu Ser Val Phe Phe Ser Gly Tyr Thr Phe Lys
His Lys Met Val Tyr Glu Asp Thr Leu Thr Leu Phe Pro Phe Ser Gly Glu Thr Val
Phe Met Ser Met Glu Asn Pro Gly Leu Trp Ile Leu Gly Cys His Asn Ser Asp Phe

FIG. 72B-2

Arg Asn Arg Gly Met Thr Ala Leu Leu Lys Val Ser Ser Cys Asp Lys Asn Thr
Gly Asp Tyr Tyr Glu Asp Ser Tyr Glu Asp Ile Ser Ala Tyr Leu Leu Ser Lys Asn
Asn Ala Ile Glu Pro Arg Ser Phe Ser Gln Asn Ser Arg His Arg Ser Thr Arg Gln
Lys Gln Phe Asn Ala Thr Thr Ile Pro Glu Asn Asp Ile Glu Lys Thr Asp Pro Trp
Phe Ala His Arg Thr Pro Met Pro Lys Ile Gln Asn Val Ser Ser Ser Asp Leu Leu
Met Leu Leu Arg Gln Ser Pro Thr Pro His Gly Leu Ser Leu Ser Asp Leu Gln Glu
Ala Lys Tyr Glu Thr Phe Ser Asp Asp Pro Ser Pro Gly Ala Ile Asp Ser Asn Asn
Ser Leu Ser Glu Met Thr His Phe Arg Pro Gln Leu His His Ser Gly Asp Met Val
Phe Thr Pro Glu Ser Gly Leu Gln Leu Arg Leu Asn Glu Lys Leu Gly Thr Thr
Ala Ala Thr Glu Leu Lys Lys Leu Asp Phe Lys Val Ser Ser Thr Ser Asn Asn Leu
Ile Ser Thr Ile Pro Ser Asp Asn Leu Ala Ala Gly Thr Asp Asn Thr Ser Ser Leu
Gly Pro Pro Ser Met Pro Val His Tyr Asp Ser Gln Leu Asp Thr Thr Leu Phe Gly
Lys Lys Ser Ser Pro Leu Thr Glu Ser Gly Gly Pro Leu Ser Leu Ser Glu Glu Asn
Asn Asp Ser Lys Leu Leu Glu Ser Gly Leu Met Asn Ser Gln Glu Ser Ser Trp Gly
Lys Asn Val Ser Ser Thr Glu Ser Gly Arg Leu Phe Lys Gly Lys Arg Ala His Gly
Pro Ala Leu Leu Thr Lys Asp Asn Ala Leu Phe Lys Val Ser Ile Ser Leu Leu
Lys Thr Asn Lys Thr Ser Asn Asn Ser Ala Thr Asn Arg Lys Thr His Ile Asp
Gly Pro Ser Leu Leu Ile Glu Asn Ser Pro Ser Val Trp Gln Asn Ile Leu Glu Ser
Asp Thr Glu Phe Lys Lys Val Thr Pro Leu Ile His Asp Arg Met Leu Met Asp
Lys Asn Ala Thr Ala Leu Arg Leu Asn His Met Ser Asn Lys Thr Thr Ser Ser
Lys Asn Met Glu Met Val Gln Gln Lys Lys Glu Gly Pro Ile Pro Pro Asp Ala
Gln Asn Pro Asp Met Ser Phe Phe Lys Met Leu Phe Leu Pro Glu Ser Ala Arg
Trp Ile Gln Arg Thr His Gly Lys Asn Ser Leu Asn Ser Gly Gln Gly Pro Ser Pro
Lys Gln Leu Val Ser Leu Gly Pro Glu Lys Ser Val Glu Gly Gln Asn Phe Leu
Ser Glu Lys Asn Lys Val Val Val Gly Lys Gly Glu Phe Thr Lys Asp Val Gly
Leu Lys Glu Met Val Phe Pro Ser Ser Arg Asn Leu Phe Leu Thr Asn Leu Asp
Asn Leu His Glu Asn Asn Thr His Asn Gln Glu Lys Lys Ile Gln Glu Glu Ile
Glu Lys Lys Glu Thr Leu Ile Gln Glu Asn Val Val Leu Pro Gln Ile His Thr
Val Thr Gly Thr Lys Asn Phe Met Lys Asn Leu Phe Leu Leu Ser Thr Arg Gln
Asn Val Glu Gly Ser Tyr Asp Gly Ala Tyr Ala Pro Val Leu Gln Asp Phe Arg
Ser Leu Asn Asp Ser Thr Asn Arg Thr Lys Lys His Thr Ala His Phe Ser Lys
Lys Gly Glu Glu Glu Asn Leu Glu Gly Leu Gly Asn Gln Thr Lys Gln Ile Val
Glu Lys Tyr Ala Cys Thr Thr Arg Ile Ser Pro Asn Thr Ser Gln Gln Asn Phe
Val Thr Gln Arg Ser Lys Arg Ala Leu Lys Gln Phe Arg Leu Pro Leu Glu Glu
Thr Glu Leu Glu Lys Arg Ile Ile Val Asp Asp Thr Ser Thr Gln Trp Ser Lys Asn
Met Lys His Leu Thr Pro Ser Thr Leu Thr Gln Ile Asp Tyr Asn Glu Lys Glu
Lys Gly Ala Ile Thr Gln Ser Pro Leu Ser Asp Cys Leu Thr Arg Ser His Ser Ile
Pro Gln Ala Asn Arg Ser Pro Leu Pro Ile Ala Lys Val Ser Ser Phe Pro Ser Ile
Arg Pro Ile Tyr Leu Thr Arg Val Leu Phe Gln Asp Asn Ser Ser His Leu Pro

FIG. 72B-3

Ala Ala Ser Tyr Arg Lys Lys Asp Ser Gly Val Gln Glu Ser Ser His Phe Leu
Gln Gly Ala Lys Lys Asn Asn Leu Ser Leu Ala Ile Leu Thr Leu Glu Met Thr
Gly Asp Gln Arg Glu Val Gly Ser Leu Gly Thr Ser Ala Thr Asn Ser Val Thr
Tyr Lys Lys Val Glu Asn Thr Val Leu Pro Lys Pro Asp Leu Pro Lys Thr Ser
Gly Lys Val Glu Leu Leu Pro Lys Val His Ile Tyr Gln Lys Asp Leu Phe Pro
Thr Glu Thr Ser Asn Gly Ser Pro Gly His Leu Asp Leu Val Glu Gly Ser Leu
Leu Gln Gly Thr Glu Gly Ala Ile Lys Trp Asn Glu Ala Asn Arg Pro Gly Lys
Val Pro Phe Leu Arg Val Ala Thr Glu Ser Ser Ala Lys Thr Pro Ser Lys Leu
Leu Asp Pro Leu Ala Trp Asp Asn His Tyr Gly Thr Gln Ile Pro Lys Glu Glu
Trp Lys Ser Gln Glu Lys Ser Pro Glu Lys Thr Ala Phe Lys Lys Lys Asp Thr Ile
Leu Ser Leu Asn Ala Cys Glu Ser Asn His Ala Ile Ala Ala Ile Asn Glu Gly
Gln Asn Lys Pro Glu Ile Glu Val Thr Trp Ala Lys Gln Gly Arg Thr Glu Arg
Leu Cys Ser Gln Asn Pro Pro Val Leu Lys Arg His Gln Arg Glu Ile Thr Arg
Thr Thr Leu Gln Ser Asp Gln Glu Glu Ile Asp Tyr Asp Asp Thr Ile Ser Val Glu
Met Lys Lys Glu Asp Phe Asp Ile Tyr Asp Glu Asp Glu Asn Gln Ser Pro Arg
Ser Phe Gln Lys Lys Thr Arg His Tyr Phe Ile Ala Ala Val Glu Arg Leu Trp Asp
Tyr Gly Met Ser Ser Ser Pro His Val Leu Arg Asn Arg Ala Gln Ser Gly Ser Val
Pro Gln Phe Lys Lys Val Val Phe Gln Glu Phe Thr Asp Gly Ser Phe Thr Gln Pro
Leu Tyr Arg Gly Glu Leu Asn Glu His Leu Gly Leu Leu Gly Pro Tyr Ile Arg
Ala Glu Val Glu Asp Asn Ile Met Val Thr Phe Arg Asn Gln Ala Ser Arg Pro
Tyr Ser Phe Tyr Ser Ser Leu Ile Ser Tyr Glu Glu Asp Gln Arg Gln Gly Ala Glu
Pro Arg Lys Asn Phe Val Lys Pro Asn Glu Thr Lys Thr Tyr Phe Trp Lys Val
Gln His His Met Ala Pro Thr Lys Asp Glu Phe Asp Cys Lys Ala Trp Ala Tyr
Phe Ser Asp Val Asp Leu Glu Lys Asp Val His Ser Gly Leu Ile Gly Pro Leu
Leu Val Cys His Thr Asn Thr Leu Asn Pro Ala His Gly Arg Gln Val Thr Val Gln
Glu Phe Ala Leu Phe Phe Thr Ile Phe Asp Glu Thr Lys Ser Trp Tyr Phe Thr Glu
Asn Met Glu Arg Asn Cys Arg Ala Pro Cys Asn Ile Gln Met Glu Asp Pro Thr
Phe Lys Glu Asn Tyr Arg Phe His Ala Ile Asn Gly Tyr Ile Met Asp Thr Leu Pro
Gly Leu Val Met Ala Gln Asp Gln Arg Ile Arg Trp Tyr Leu Leu Ser Met Gly
Ser Asn Glu Asn Ile His Ser Ile His Phe Ser Gly His Val Phe Thr Val Arg Lys
Lys Glu Glu Tyr Lys Met Ala Leu Tyr Asn Leu Tyr Pro Gly Val Phe Glu Thr
Val Glu Met Leu Pro Ser Lys Ala Gly Ile Trp Arg Val Glu Cys Leu Ile Gly Glu
His Leu His Ala Gly Met Ser Thr Leu Phe Leu Val Tyr Ser Asn Lys Cys Gln Thr
Pro Leu Gly Met Ala Ser Gly His Ile Arg Asp Phe Gln Ile Thr Ala Ser Gly Gln
Tyr Gly Gln Trp Ala Pro Lys Leu Ala Arg Leu His Tyr Ser Gly Ser Ile Asn Ala
Trp Ser Thr Lys Glu Pro Phe Ser Trp Ile Lys Val Asp Leu Leu Ala Pro Met Ile
Ile His Gly Ile Lys Thr Gln Gly Ala Arg Gln Lys Phe Ser Ser Leu Tyr Ile Ser
Gln Phe Ile Ile Met Tyr Ser Leu Asp Gly Lys Lys Trp Gln Thr Tyr Arg Gly
Asn Ser Thr Gly Thr Leu Met Val Phe Phe Gly Asn Val Asp Ser Ser Gly Ile

FIG. 72B-4

Lys His Asn Ile Phe Asn Pro Pro Ile Ile Ala Arg Tyr Ile Arg Leu His Pro Thr
His Tyr Ser Ile Arg Ser Thr Leu Arg Met Glu Leu Met Gly Cys Asp Leu Asn
Ser Cys Ser Met Pro Leu Gly Met Glu Ser Lys Ala Ile Ser Asp Ala Gln Ile Thr
Ala Ser Ser Tyr Phe Thr Asn Met Phe Ala Thr Trp Ser Pro Ser Lys Ala Arg Leu
His Leu Gln Gly Arg Ser Asn Ala Trp Arg Pro Gln Val Asn Asn Pro Lys Glu
Trp Leu Gln Val Asp Phe Gln Lys Thr Met Lys Val Thr Gly Val Thr Thr Gln
Gly Val Lys Ser Leu Leu Thr Ser Met Tyr Val Lys Glu Phe Leu Ile Ser Ser Ser
Gln Asp Gly His Gln Trp Thr Leu Phe Phe Gln Asn Gly Lys Val Lys Val Phe
Gln Gly Asn Gln Asp Ser Phe Thr Pro Val Val Asn Ser Leu Asp Pro Pro Leu
Leu Thr Arg Tyr Leu Arg Ile His Pro Gln Ser Trp Val His Gln Ile Ala Leu Arg
Met Glu Val Leu Gly Cys Glu Ala Gln Asp Leu Tyr

FIG. 73A

TCCACCTGTCCCCGCAGCGCCGGCTCGCGCCCTCCTGCCGCAGCCACC
GAGCCGCCGTCTAGCGCCCCGACCTCGCCACCATGAGAGCCCTGCTG
GCGCGCCTGCTTCTCTGCGTCCTGGTCGTGAGCGACTCCAAAGGCAGC
AATGAACTTCATCAAGTTCCATCGAACTGTGACTGTCTAAATGGAGGA
ACATGTGTGTCCAACAAGTACTTCTCCAACATTCACTGGTGCAACTGC
CCAAAGAAATTCGGAGGGCAGCACTGTGAAATAGATAAGTCAAAAAC
CTGCTATGAGGGGAATGGTCACTTTTACCGAGGAAAGGCCAGCACTG
ACACCATGGGCCGGCCCTGCCTGCCCTGGAACTCTGCCACTGTCCTTC
AGCAAACGTACCATGCCCACAGATCTGATGCTCTTCAGCTGGGCCTGG
GGAAACATAATTACTGCAGGAACCCAGACAACCGGAGGCGACCCTGG
TGCTATGTGCAGGTGGGCCTAAAGCCGCTTGTCCAAGAGTGCATGGT
GCATGACTGCGCAGATGGAAAAAAGCCCTCCTCTCCTCCAGAAGAAT
TAAAATTTCAGTGTGGCCAAAAGACTCTGAGGCCCCGCTTTAAGATTA
TTGGGGGAGAATTCACCACCATCGAGAACCAGCCCTGGTTTGCGGCC
ATCTACAGGAGGCACCGGGGGGGCTCTGTCACCTACGTGTGTGGAGG
CAGCCTCATCAGCCCTTGCTGGGTGATCAGCGCCACACACTGCTTCAT
TGATTACCCAAAGAAGGAGGACTACATCGTCTACCTGGGTCGCTCAA
GGCTTAACTCCAACACGCAAGGGGAGATGAAGTTTGAGGTGGAAAAC
CTCATCCTACACAAGGACTACAGCGCTGACACGCTTGCTCACCACAAC
GACATTGCCTTGCTGAAGATCCGTTCCAAGGAGGGCAGGTGTGCGCA
GCCATCCCGGACTATACAGACCATCTGCCTGCCCTCGATGTATAACGA
TCCCCAGTTTGGCACAAGCTGTGAGATCACTGGCTTTGGAAAAGAGA
ATTCTACCGACTATCTCTATCCGGAGCAGCTGAAGATGACTGTTGTGA
AGCTGATTTCCCACCGGGAGTGTCAGCAGCCCCACTACTACGGCTCTG
AAGTCACCACCAAAATGCTGTGTGCTGCTGACCCACAGTGGAAAACA
GATTCCTGCCAGGGAGACTCAGGGGGACCCCTCGTCTGTTCCCTCCAA
GGCCGCATGACTTTGACTGGAATTGTGAGCTGGGGCCGTGGATGTGC
CCTGAAGGACAAGCCAGGCGTCTACACGAGAGTCTCACACTTCTTAC
CCTGGATCCGCAGTCACACCAAGGAAGAGAATGGCCTGGCCCTCTGA
GGGTCCCCAGGGAGGAAACGGGCACCACCCGCTTTCTTGCTGGTTGTC
ATTTTTGCAGTAGAGTCATCTCCATCAGCTGTAAGAAGAGACTGGGA
AGAT

FIG. 73B

Met Arg Ala Leu Leu Ala Arg Leu Leu Leu Cys Val Leu Val Val Ser Asp Ser
Lys Gly Ser Asn Glu Leu His Gln Val Pro Ser Asn Cys Asp Cys Leu Asn Gly
Gly Thr Cys Val Ser Asn Lys Tyr Phe Ser Asn Ile His Trp Cys Asn Cys Pro Lys
Lys Phe Gly Gly Gln His Cys Glu Ile Asp Lys Ser Lys Thr Cys Tyr Glu Gly Asn
Gly His Phe Tyr Arg Gly Lys Ala Ser Thr Asp Thr Met Gly Arg Pro Cys Leu Pro
Trp Asn Ser Ala Thr Val Leu Gln Gln Thr Tyr His Ala His Arg Ser Asp Ala Leu
Gln Leu Gly Leu Gly Lys His Asn Tyr Cys Arg Asn Pro Asp Asn Arg Arg Arg
Pro Trp Cys Tyr Val Gln Val Gly Leu Lys Pro Leu Val Gln Glu Cys Met Val His
Asp Cys Ala Asp Gly Lys Lys Pro Ser Ser Pro Pro Glu Glu Leu Lys Phe Gln Cys
Gly Gln Lys Thr Leu Arg Pro Arg Phe Lys Ile Ile Gly Gly Glu Phe Thr Thr Ile
Glu Asn Gln Pro Trp Phe Ala Ala Ile Tyr Arg Arg His Arg Gly Gly Ser Val Thr
Tyr Val Cys Gly Gly Ser Leu Ile Ser Pro Cys Trp Val Ile Ser Ala Thr His Cys
Phe Ile Asp Tyr Pro Lys Lys Glu Asp Tyr Ile Val Tyr Leu Gly Arg Ser Arg Leu
Asn Ser Asn Thr Gln Gly Glu Met Lys Phe Glu Val Glu Asn Leu Ile Leu His Lys
Asp Tyr Ser Ala Asp Thr Leu Ala His His Asn Asp Ile Ala Leu Leu Lys Ile Arg
Ser Lys Glu Gly Arg Cys Ala Gln Pro Ser Arg Thr Ile Gln Thr Ile Cys Leu Pro
Ser Met Tyr Asn Asp Pro Gln Phe Gly Thr Ser Cys Glu Ile Thr Gly Phe Gly Lys
Glu Asn Ser Thr Asp Tyr Leu Tyr Pro Glu Gln Leu Lys Met Thr Val Val Lys
Leu Ile Ser His Arg Glu Cys Gln Gln Pro His Tyr Tyr Gly Ser Glu Val Thr Thr
Lys Met Leu Cys Ala Ala Asp Pro Gln Trp Lys Thr Asp Ser Cys Gln Gly Asp
Ser Gly Gly Pro Leu Val Cys Ser Leu Gln Gly Arg Met Thr Leu Thr Gly Ile Val
Ser Trp Gly Arg Gly Cys Ala Leu Lys Asp Lys Pro Gly Val Tyr Thr Arg Val Ser
His Phe Leu Pro Trp Ile Arg Ser His Thr Lys Glu Glu Asn Gly Leu Ala Leu

FIG.74A

TCCTGCACAGGCAGTGCCTTGAAGTGCTTCTTCAGAGACCTTTCTTCA
TAGACTACTTTTTTTTCTTTAAGCAGCAAAAGGAGAAAATTGTCATCA
AGGATATTCCAGATTCTTGACAGCATTCTCGTCATCTCTGAGGACATC
ACCATCATCTCAGGATGAGGGGCATGAAGCTGCTGGGGGCGCTGCTG
GCACTGGCGGCCCTACTGCAGGGGGCCGTGTCCCTGAAGATCGCAGC
CTTCAACATCCAGACATTTGGGGAGACCAAGATGTCCAATGCCACCCT
CGTCAGCTACATTGTGCAGATCCTGAGCCGCTATGACATCGCCCTGGT
CCAGGAGGTCAGAGACAGCCACCTGACTGCCGTGGGGAAGCTGCTGG
ACAACCTCAATCAGGATGCACCAGACACCTATCACTACGTGGTCAGT
GAGCCACTGGGACGGAACAGCTATAAGGAGCGCTACCTGTTCGTGTA
CAGGCCTGACCAGGTGTCTGCGGTGGACAGCTACTACTACGATGATG
GCTGCGAGCCCTGCGGGAACGACACCTTCAACCGAGAGCCAGCCATT
GTCAGGTTCTTCTCCCGGTTCACAGAGGTCAGGGAGTTTGCCATTGTT
CCCCTGCATGCGGCCCCGGGGGACGCAGTAGCCGAGATCGACGCTCT
CTATGACGTCTACCTGGATGTCCAAGAGAAATGGGGCTTGGAGGACG
TCATGTTGATGGGCGACTTCAATGCGGGCTGCAGCTATGTGAGACCCT
CCCAGTGGTCATCCATCCGCCTGTGGACAAGCCCCACCTTCCAGTGGC
TGATCCCCGACAGCGCTGACACCACAGCTACACCCACGCACTGTGCCT
ATGACAGGATCGTGGTTGCAGGGATGCTGCTCCGAGGCGCCGTTGTTC
CCGACTCGGCTCTTCCCTTTAACTTCCAGGCTGCCTATGGCCTGAGTG
ACCAACTGGCCCAAGCCATCAGTGACCACTATCCAGTGGAGGTGATG
CTGAAGTGAGCAGCCCCTCCCCACACCAGTTGAACTGCAG

FIG. 74B

Met Arg Gly Met Lys Leu Leu Gly Ala Leu Leu Ala Leu Ala Ala Leu Leu Gln
Gly Ala Val Ser Leu Lys Ile Ala Ala Phe Asn Ile Gln Thr Phe Gly Glu Thr Lys
Met Ser Asn Ala Thr Leu Val Ser Tyr Ile Val Gln Ile Leu Ser Arg Tyr Asp Ile
Ala Leu Val Gln Glu Val Arg Asp Ser His Leu Thr Ala Val Gly Lys Leu Leu
Asp Asn Leu Asn Gln Asp Ala Pro Asp Thr Tyr His Tyr Val Val Ser Glu Pro
Leu Gly Arg Asn Ser Tyr Lys Glu Arg Tyr Leu Phe Val Tyr Arg Pro Asp Gln
Val Ser Ala Val Asp Ser Tyr Tyr Tyr Asp Asp Gly Cys Glu Pro Cys Gly Asn
Asp Thr Phe Asn Arg Glu Pro Ala Ile Val Arg Phe Phe Ser Arg Phe Thr Glu Val
Arg Glu Phe Ala Ile Val Pro Leu His Ala Ala Pro Gly Asp Ala Val Ala Glu Ile
Asp Ala Leu Tyr Asp Val Tyr Leu Asp Val Gln Glu Lys Trp Gly Leu Glu Asp
Val Met Leu Met Gly Asp Phe Asn Ala Gly Cys Ser Tyr Val Arg Pro Ser Gln
Trp Ser Ser Ile Arg Leu Trp Thr Ser Pro Thr Phe Gln Trp Leu Ile Pro Asp Ser
Ala Asp Thr Thr Ala Thr Pro Thr His Cys Ala Tyr Asp Arg Ile Val Val Ala Gly
Met Leu Leu Arg Gly Ala Val Val Pro Asp Ser Ala Leu Pro Phe Asn Phe Gln
Ala Ala Tyr Gly Leu Ser Asp Gln Leu Ala Gln Ala Ile Ser Asp His Tyr Pro Val
Glu Val Met Leu Lys

FIG. 75A

GCTGCATCAGAAGAGGCCATCAAGCACATCACTGTCCTTCTGCCATGG
CCCTGTGGATGCGCCTCCTGCCCCTGCTGGCGCTGCTGGCCCTCTGGG
GACCTGACCCAGCCGCAGCCTTTGTGAACCAACACCTGTGCGGCTCAC
ACCTGGTGGAAGCTCTCTACCTAGTGTGCGGGGAACGAGGCTTCTTCT
ACACACCCAAGACCCGCCGGGAGGCAGAGGACCTGCAGGTGGGGCA
GGTGGAGCTGGGCGGGGGCCCTGGTGCAGGCAGCCTGCAGCCCTTGG
CCCTGGAGGGGTCCCTGCAGAAGCGTGGCATTGTGGAACAATGCTGT
ACCAGCATCTGCTCCCTCTACCAGCTGGAGAACTACTGCAACTAGACG
CAGCCCGCAGGCAGCCCCCCACCCGCCGCCTCCTGCACCGAGAGAGA
TGGAATAAAGCCCTTGAACCAGC

FIG. 75B

Met Ala Leu Trp Met Arg Leu Leu Pro Leu Leu Ala Leu Leu Ala Leu Trp Gly
Pro Asp Pro Ala Ala Ala Phe Val Asn Gln His Leu Cys Gly Ser His Leu Val
Glu Ala Leu Tyr Leu Val Cys Gly Glu Arg Gly Phe Phe Tyr Thr Pro Lys Thr
Arg Arg Glu Ala Glu Asp Leu Gln Val Gly Gln Val Glu Leu Gly Gly Gly Pro
Gly Ala Gly Ser Leu Gln Pro Leu Ala Leu Glu Gly Ser Leu Gln Lys Arg Gly Ile
Val Glu Gln Cys Cys Thr Ser Ile Cys Ser Leu Tyr Gln Leu Glu Asn Tyr Cys Asn

FIG. 76A

ATGGGAGGTTGGTCTTCCAAACCTCGACAAGGCATGGGGACGAATCT
TTCTGTTCCCAATCCTCTGGGATTCTTTCCCGATCACCAGTTGGACCCT
GCGTTCGGAGCCAACTCAAACAATCCAGATTGGGACTTCAACCCCAA
CAAGGATCACTGGCCAGAGGCAATCAAGGTAGGAGCGGGAGACTTC
GGGCCAGGGTTCACCCCACCACACGGCGGTCTTTTGGGGTGGAGCCC
TCAGGCTCAGGGCATATTGACAACAGTGCCAGCAGCGCCTCCTCCTG
TTTCCACCAATCGGCAGTCAGGAAGACAGCCTACTCCCATCTCTCCAC
CTCTAAGAGACAGTCATCCTCAGGCCATGCAGTGGAACTCCACAACA
TTCCACCAAGCTCTGCTAGATCCCAGAGTGAGGGGCCTATATTTTCCT
GCTGGTGGCTCCAGTTCCGGAACAGTAAACCCTGTTCCGACTACTGTC
TCACCCATATCGTCAATCTTCTCGAGGACTGGGGACCCTGCACCGAAC
ATGGAGAGCACAACATCAGGATTCCTAGGACCCCTGCTCGTGTTACA
GGCGGGGTTTTTCTTGTTGACAAGAATCCTCACAATACCACAGAGTCT
AGACTCGTGGTGGACTTCTCTCAATTTTCTAGGGGGAGCACCCACGTG
TCCTGGCCAAAATTCGCAGTCCCCAACCTCCAATCACTCACCAACCTC
TTGTCCTCCAATTTGTCCTGGTTATCGCTGGATGTGTCTGCGGCGTTTT
ATCATATTCCTCTTCATCCTGCTGCTATGCCTCATCTTCTTGTTGGTTC
TTCTGGACTACCAAGGTATGTTGCCCGTTTGTCCTCTACTTCCAGGAA
CATCAACTACCAGCACGGGACCATGCAAGACCTGCACGATTCCTGCT
CAAGGAACCTCTATGTTTCCCTCTTGTTGCTGTACAAAACCTTCGGAC
GGAAACTGCACTTGTATTCCCATCCCATCATCCTGGGCTTTCGCAAGA
TTCCTATGGGAGTGGGCCTCAGTCCGTTTCTCCTGGCTCAGTTTACTA
GTGCCATTTGTTCAGTGGTTCGCAGGGCTTTCCCCCACTGTTTGGCTTT
CAGTTATATGGATGATGTGGTATTGGGGGCCAAGTCTGTACAACATCT
TGAGTCCCTTTTTACCTCTATTACCAATTTTCTTTTGTCTTTGGGTATAC
ATTTGA

FIG. 76B

Met Gly Gly Trp Ser Ser Lys Pro Arg Gln Gly Met Gly Thr Asn Leu Ser Val Pro
Asn Pro Leu Gly Phe Phe Pro Asp His Gln Leu Asp Pro Ala Phe Gly Ala Asn
Ser Asn Asn Pro Asp Trp Asp Phe Asn Pro Asn Lys Asp His Trp Pro Glu Ala Ile
Lys Val Gly Ala Gly Asp Phe Gly Pro Gly Phe Thr Pro Pro His Gly Gly Leu Leu
Gly Trp Ser Pro Gln Ala Gln Gly Ile Leu Thr Thr Val Pro Ala Ala Pro Pro Pro
Val Ser Thr Asn Arg Gln Ser Gly Arg Gln Pro Thr Pro Ile Ser Pro Pro Leu Arg
Asp Ser His Pro Gln Ala Met Gln Trp Asn Ser Thr Thr Phe His Gln Ala Leu Leu
Asp Pro Arg Val Arg Gly Leu Tyr Phe Pro Ala Gly Gly Ser Ser Ser Gly Thr Val
Asn Pro Val Pro Thr Thr Val Ser Pro Ile Ser Ser Ile Phe Ser Arg Thr Gly Asp
Pro Ala Pro Asn Met Glu Ser Thr Thr Ser Gly Phe Leu Gly Pro Leu Leu Val Leu
Gln Ala Gly Phe Phe Leu Leu Thr Arg Ile Leu Thr Ile Pro Gln Ser Leu Asp Ser
Trp Trp Thr Ser Leu Asn Phe Leu Gly Gly Ala Pro Thr Cys Pro Gly Gln Asn Ser
Gln Ser Pro Thr Ser Asn His Ser Pro Thr Ser Cys Pro Pro Ile Cys Pro Gly Tyr
Arg Trp Met Cys Leu Arg Arg Phe Ile Ile Phe Leu Phe Ile Leu Leu Leu Cys Leu
Ile Phe Leu Leu Val Leu Leu Asp Tyr Gln Gly Met Leu Pro Val Cys Pro Leu
Leu Pro Gly Thr Ser Thr Thr Ser Thr Gly Pro Cys Lys Thr Cys Thr Ile Pro Ala
Gln Gly Thr Ser Met Phe Pro Ser Cys Cys Cys Thr Lys Pro Ser Asp Gly Asn
Cys Thr Cys Ile Pro Ile Pro Ser Ser Trp Ala Phe Ala Arg Phe Leu Trp Glu Trp
Ala Ser Val Arg Phe Ser Trp Leu Ser Leu Leu Val Pro Phe Val Gln Trp Phe Ala
Gly Leu Ser Pro Thr Val Trp Leu Ser Val Ile Trp Met Met Trp Tyr Trp Gly Pro
Ser Leu Tyr Asn Ile Leu Ser Pro Phe Leu Pro Leu Leu Pro Ile Phe Phe Cys Leu
Trp Val Tyr Ile

FIG. 77A

CGAACCACTCAGGGTCCTGTGGACAGCTCACCTAGCTGCAATGGCTA
CAGGCTCCCGGACGTCCCTGCTCCTGGCTTTGGCCTGCTCTGCCTGC
CCTGGCTTCAAGAGGGCAGTGCCTTCCCAACCATTCCCTTATCCAGGC
CTTTTGACAACGCTATGCTCCGCGCCCATCGTCTGCACCAGCTGGCCT
TTGACACCTACCAGGAGTTTGAAGAAGCCTATATCCCAAAGGAACAG
AAGTATTCATTCCTGCAGAACCCCCAGACCTCCCTCTGTTTCTCAGAG
TCTATTCCGACACCCTCCAACAGGGAGGAAACACAACAGAAATCCAA
CCTAGAGCTGCTCCGCATCTCCCTGCTGCTCATCCAGTCGTGGCTGGA
GCCCGTGCAGTTCCTCAGGAGTGTCTTCGCCAACAGCCTGGTGTACGG
CGCCTCTGACAGCAACGTCTATGACCTCCTAAAGGACCTAGAGGAAG
GCATCCAAACGCTGATGGGGAGGCTGGAAGATGGCAGCCCCCGGACT
GGGCAGATCTTCAAGCAGACCTACAGCAAGTTCGACACAAACTCACA
CAACGATGACGCACTACTCAAGAACTACGGGCTGCTCTACTGCTTCAG
GAAGGACATGGCAAGGTCGAGACATTCCTGCGCATCGTGCAGTGCCG
CTCTGTGGAGGGCAGCTGTGGCTTCTAGCTGCCCGGGTGGCATCCCTG
TGACCCCTCCCCAGTGCCTCTCCTGGCCCTGGAAGTTGCCACTCCAGT
GCCCACCAGCCTTGTCCTAATAAAATTAAGTTGCATC

FIG. 77B

Met Ala Thr Gly Ser Arg Thr Ser Leu Leu Leu Ala Phe Gly Leu Leu Cys Leu
Pro Trp Leu Gln Glu Gly Ser Ala Phe Pro Thr Ile Pro Leu Ser Arg Pro Phe Asp
Asn Ala Met Leu Arg Ala His Arg Leu His Gln Leu Ala Phe Asp Thr Tyr Gln
Glu Phe Glu Glu Ala Tyr Ile Pro Lys Glu Gln Lys Tyr Ser Phe Leu Gln Asn Pro
Gln Thr Ser Leu Cys Phe Ser Glu Ser Ile Pro Thr Pro Ser Asn Arg Glu Glu Thr
Gln Gln Lys Ser Asn Leu Glu Leu Leu Arg Ile Ser Leu Leu Leu Ile Gln Ser Trp
Leu Glu Pro Val Gln Phe Leu Arg Ser Val Phe Ala Asn Ser Leu Val Tyr Gly Ala
Ser Asp Ser Asn Val Tyr Asp Leu Leu Lys Asp Leu Glu Glu Gly Ile Gln Thr Leu
Met Gly Arg Leu Glu Asp Gly Ser Pro Arg Thr Gly Gln Ile Phe Lys Gln Thr Tyr
Ser Lys Phe Asp Thr Asn Ser His Asn Asp Asp Ala Leu Leu Lys Asn Tyr Gly
Leu Leu Tyr Cys Phe Arg Lys Asp Met Asp Lys Val Glu Thr Phe Leu Arg Ile
Val Gln CysArg Ser Val Glu Gly Ser Cys Gly Phe

FIG. 78A

ATGTATTCCAATGTGATAGGAACTGTAACCTCTGGAAAAAGGAAGGT
TTATCTTTTGTCCTTGCTGCTCATTGGCTTCTGGGACTGCGTGACCTGT
CACGGGAGCCCTGTGGACATCTGCACAGCCAAGCCGCGGGACATTCC
CATGAATCCCATGTGCATTTACCGCTCCCCGGAGAAGAAGGCAACTG
AGGATGAGGGCTCAGAACAGAAGATCCCGGAGGCCACCAACCGGCG
TGTCTGGGAACTGTCCAAGGCCAATTCCCGCTTTGCTACCACTTTCTA
TCAGCACCTGGCAGATTCCAAGAATGACAATGATAACATTTTCCTGTC
ACCCCTGAGTATCTCCACGGCTTTTGCTATGACCAAGCTGGGTGCCTG
TAATGACACCCTCCAGCAACTGATGGAGGTATTTAAGTTTGACACCAT
ATCTGAGAAAACATCTGATCAGATCCACTTCTTCTTTGCCAAACTGAA
CTGCCGACTCTATCGAAAAGCCAACAAATCCTCCAAGTTAGTATCAGC
CAATCGCCTTTTTGGAGACAAATCCCTTACCTTCAATGAGACCTACCA
GGACATCAGTGAGTTGGTATATGGAGCCAAGCTCCAGCCCCTGGACT
TCAAGGAAAATGCAGAGCAATCCAGAGCGGCCATCAACAAATGGGTG
TCCAATAAGACCGAAGGCCGAATCACCGATGTCATTCCCTCGGAAGC
CATCAATGAGCTCACTGTTCTGGTGCTGGTTAACACCATTTACTTCAA
GGGCCTGTGGAAGTCAAAGTTCAGCCCTGAGAACACAAGGAAGGAAC
TGTTCTACAAGGCTGATGGAGAGTCGTGTTCAGCATCTATGATGTACC
AGGAAGGCAAGTTCCGTTATCGGCGCGTGGCTGAAGGCACCCAGGTG
CTTGAGTTGCCCTTCAAAGGTGATGACATCACCATGGTCCTCATCTTG
CCCAAGCCTGAGAAGAGCCTGGCCAAGGTGGAGAAGGAACTCACCCC
AGAGGTGCTGCAGGAGTGGCTGGATGAATTGGAGGAGATGATGCTGG
TGGTCCACATGCCCCGCTTCCGCATTGAGGACGGCTTCAGTTTGAAGG
AGCAGCTGCAAGACATGGGCCTTGTCGATCTGTTCAGCCCTGAAAAG
TCCAAACTCCCAGGTATTGTTGCAGAAGGCCGAGATGACCTCTATGTC
TCAGATGCATTCCATAAGGCATTTCTTGAGGTAAATGAAGAAGGCAG
TGAAGCAGCTGCAAGTACCGCTGTTGTGATTGCTGGCCGTTCGCTAAA
CCCCAACAGGGTGACTTTCAAGGCCAACAGGCCTTTCCTGGTTTTTAT
AAGAGAAGTTCCTCTGAACACTATTATCTTCATGGGCAGAGTAGCCA
ACCCTTGTGTTAAGTAA

FIG. 78B

Met Tyr Ser Asn Val Ile Gly Thr Val Thr Ser Gly Lys Arg Lys Val Tyr Leu Leu
Ser Leu Leu Leu Ile Gly Phe Trp Asp Cys Val Thr Cys His Gly Ser Pro Val Asp
Ile Cys Thr Ala Lys Pro Arg Asp Ile Pro Met Asn Pro Met Cys Ile Tyr Arg Ser
Pro Glu Lys Lys Ala Thr Glu Asp Glu Gly Ser Glu Gln Lys Ile Pro Glu Ala Thr
Asn Arg Arg Val Trp Glu Leu Ser Lys Ala Asn Ser Arg Phe Ala Thr Thr Phe Tyr
Gln His Leu Ala Asp Ser Lys Asn Asp Asn Asp Asn Ile Phe Leu Ser Pro Leu Ser
Ile Ser Thr Ala Phe Ala Met Thr Lys Leu Gly Ala Cys Asn Asp Thr Leu Gln Gln
Leu Met Glu Val Phe Lys Phe Asp Thr Ile Ser Glu Lys Thr Ser Asp Gln Ile His
Phe Phe Phe Ala Lys Leu Asn Cys Arg Leu Tyr Arg Lys Ala Asn Lys Ser Ser
Lys Leu Val Ser Ala Asn Arg Leu Phe Gly Asp Lys Ser Leu Thr Phe Asn Glu
Thr Tyr Gln Asp Ile Ser Glu Leu Val Tyr Gly Ala Lys Leu Gln Pro Leu Asp Phe
Lys Glu Asn Ala Glu Gln Ser Arg Ala Ala Ile Asn Lys Trp Val Ser Asn Lys Thr
Glu Gly Arg Ile Thr Asp Val Ile Pro Ser Glu Ala Ile Asn Glu Leu Thr Val Leu
Val Leu Val Asn Thr Ile Tyr Phe Lys Gly Leu Trp Lys Ser Lys Phe Ser Pro Glu
Asn Thr Arg Lys Glu Leu Phe Tyr Lys Ala Asp Gly Glu Ser Cys Ser Ala Ser
Met Met Tyr Gln Glu Gly Lys Phe Arg Tyr Arg Arg Val Ala Glu Gly Thr Gln
Val Leu Glu Leu Pro Phe Lys Gly Asp Asp Ile Thr Met Val Leu Ile Leu Pro Lys
Pro Glu Lys Ser Leu Ala Lys Val Glu Lys Glu Leu Thr Pro Glu Val Leu Gln Glu
Trp Leu Asp Glu Leu Glu Glu Met Met Leu Val Val His Met Pro Arg Phe Arg
Ile Glu Asp Gly Phe Ser Leu Lys Glu Gln Leu Gln Asp Met Gly Leu Val Asp
Leu Phe Ser Pro Glu Lys Ser Lys Leu Pro Gly Ile Val Ala Glu Gly Arg Asp Asp
Leu Tyr Val Ser Asp Ala Phe His Lys Ala Phe Leu Glu Val Asn Glu Glu Gly Ser
Glu Ala Ala Ala Ser Thr Ala Val Val Ile Ala Gly Arg Ser Leu Asn Pro Asn Arg
Val Thr Phe Lys Ala Asn Arg Pro Phe Leu Val Phe Ile Arg Glu Val Pro Leu Asn
Thr Ile Ile Phe Met Gly Arg Val Ala Asn Pro Cys Val Lys

FIG. 79A

ATGGATTACTACAGAAAATATGCAGCTATCTTTCTGGTCACATTGTCG
GTGTTTCTGCATGTTCTCCATTCCGCTCCTGATGTGCAGGATTGCCCAG
AATGCACGCTACAGGAAAACCCATTCTTCTCCCAGCCGGGTGCCCCA
ATACTTCAGTGCATGGGCTGCTGCTTCTCTAGAGCATATCCCACTCCA
CTAAGGTCCAAGAAGACGATGTTGGTCCAAAAGAACGTCACCTCAGA
GTCCACTTGCTGTGTAGCTAAATCATATAACAGGGTCACAGTAATGGG
GGGTTTCAAAGTGGAGAACCACACGGCGTGCCACTGCAGTACTTGTT
ATTATCACAAATCTTAA

FIG. 79B

Met Asp Tyr Tyr Arg Lys Tyr Ala Ala Ile Phe Leu Val Thr Leu Ser Val Phe Leu
His Val Leu His Ser Ala Pro Asp Val Gln Asp Cys Pro Glu Cys Thr Leu Gln Glu
Asn Pro Phe Phe Ser Gln Pro Gly Ala Pro Ile Leu Gln Cys Met Gly Cys Cys Phe
Ser Arg Ala Tyr Pro Thr Pro Leu Arg Ser Lys Lys Thr Met Leu Val Gln Lys Asn
Val Thr Ser Glu Ser Thr Cys Cys Val Ala Lys Ser Tyr Asn Arg Val Thr Val Met
Gly Gly Phe Lys Val Glu Asn His Thr Ala Cys His Cys Ser Thr Cys Tyr Tyr His
Lys Ser

FIG. 79C

ATGGAGATGTTCCAGGGGCTGCTGCTGTTGCTGCTGCTGAGCATGGGC
GGGACATGGGCATCCAAGGAGCCGCTTCGGCCACGGTGCCGCCCCAT
CAATGCCACCCTGGCTGTGGAGAAGGAGGGCTGCCCCGTGTGCATCA
CCGTCAACACCACCATCTGTGCCGGCTACTGCCCCACCATGACCCGCG
TGCTGCAGGGGGTCCTGCCGGCCCTGCCTCAGGTGGTGTGCAACTACC
GCGATGTGCGCTTCGAGTCCATCCGGCTCCCTGGCTGCCCGCGCGGCG
TGAACCCCGTGGTCTCCTACGCCGTGGCTCTCAGCTGTCAATGTGCAC
TCTGCCGCCGCAGCACCACTGACTGCGGGGGTCCCAAGGACCACCCC
TTGACCTGTGATGACCCCCGCTTCCAGGACTCCTCTTCCTCAAAGGCC
CCTCCCCCCAGCCTTCCAAGCCCATCCCGACTCCCGGGGCCCTCGGAC
ACCCCGATCCTCC CACAATAA

FIG. 79D

Met Glu Met Phe Gln Gly Leu Leu Leu Leu Leu Leu Leu Ser Met Gly Gly Thr
Trp Ala Ser Lys Glu Pro Leu Arg Pro Arg Cys Arg Pro Ile Asn Ala Thr Leu Ala
Val Glu Lys Glu Gly Cys Pro Val Cys Ile Thr Val Asn Thr Thr Ile Cys Ala Gly
Tyr Cys Pro Thr Met Thr Arg Val Leu Gln Gly Val Leu Pro Ala Leu Pro Gln Val
Val Cys Asn Tyr Arg Asp Val Arg Phe Glu Ser Ile Arg Leu Pro Gly Cys Pro Arg
Gly Val Asn Pro Val Val Ser Tyr Ala Val Ala Leu Ser Cys Gln Cys Ala Leu Cys
Arg Arg Ser Thr Thr Asp Cys Gly Gly Pro Lys Asp His Pro Leu Thr Cys Asp
Asp Pro Arg Phe Gln Asp Ser Ser Ser Ser Lys Ala Pro Pro Pro Ser Leu Pro Ser
Pro Ser Arg Leu Pro Gly Pro Ser Asp Thr Pro Ile Leu Pro Gln

FIG. 80A

ATGCGTCCCCTGCGCCCCCGCGCCGCGCTGCTGGCGCTCCTGGCCTCG
CTCCTGGCCGCGCCCCCGGTGGCCCCGGCCGAGGCCCCGCACCTGGT
GCAGGTGGACGCGGCCCGCGCGCTGTGGCCCCTGCGGCGCTTCTGGA
GGAGCACAGGCTTCTGCCCCCCGCTGCCACACAGCCAGGCTGACCAG
TACGTCCTCAGCTGGGACCAGCAGCTCAACCTCGCCTATGTGGGCGCC
GTCCCTCACCGCGGCATCAAGCAGGTCCGGACCCACTGGCTGCTGGA
GCTTGTCACCACCAGGGGGTCCACTGGACGGGGCCTGAGCTACAACT
TCACCCACCTGGACGGGTACTTGGACCTTCTCAGGGAGAACCAGCTCC
TCCCAGGGTTTGAGCTGATGGGCAGCGCCTCGGGCCACTTCACTGACT
TTGAGGACAAGCAGCAGGTGTTTGAGTGGAAGGACTTGGTCTCCAGC
CTGGCCAGGAGATACATCGGTAGGTACGGACTGGCGCATGTTTCCAA
GTGGAACTTCGAGACGTGGAATGAGCCAGACCACCACGACTTTGACA
ACGTCTCCATGACCATGCAAGGCTTCCTGAACTACTACGATGCCTGCT
CGGAGGGTCTGCGCGCCGCCAGCCCCGCCCTGCGGCTGGGAGGCCCC
GGCGACTCCTTCCACACCCCACCGCGATCCCCGCTGAGCTGGGGCCTC
CTGCGCCACTGCCACGACGGTACCAACTTCTTCACTGGGGAGGCGGG
CGTGCGGCTGGACTACATCTCCCTCCACAGGAAGGGTGCGCGCAGCT
CCATCTCCATCCTGGAGCAGGAGAAGGTCGTCGCGCAGCAGATCCGG
CAGCTCTTCCCCAAGTTCGCGGACACCCCCATTTACAACGACGAGGCG
GACCCGCTGGTGGGCTGGTCCCTGCCACAGCCGTGGAGGGCGGACGT
GACCTACGCGGCCATGGTGGTGAAGGTCATCGCGCAGCATCAGAACC
TGCTACTGGCCAACACCACCTCCGCCTTCCCCTACGCGCTCCTGAGCA
ACGACAATGCCTTCCTGAGCTACCACCCGCACCCCTTCGCGCAGCGCA
CGCTCACCGCGCGCTTCCAGGTCAACAACACCCGCCCGCCGCACGTG
CAGCTGTTGCGCAAGCCGGTGCTCACGGCCATGGGGCTGCTGGCGCT
GCTGGATGAGGAGCAGCTCTGGGCCGAAGTGTCGCAGGCCGGGACCG
TCCTGGACAGCAACCACACGGTGGGCGTCCTGGCCAGCGCCCACCGC
CCCCAGGGCCCGGCCGACGCCTGGCGCGCCGCGGTGCTGATCTACGC
GAGCGACGACACCCGCGCCCACCCCAACCGCAGCGTCGCGGTGACCC
TGCGGCTGCGCGGGGTGCCCCCCGGCCCGGGCCTGGTCTACGTCACG
CGCTACCTGGACAACGGGCTCTGCAGCCCCGACGGCGAGTGGCGGCG
CCTGGGCCGGCCCGTCTTCCCCACGGCAGAGCAGTTCCGGCGCATGC
GCGCGGCTGAGGACCCGGTGGCCGCGGCGCCCCGCCCCTTACCCGCC
GGCGGCCGCCTGACCCTGCGCCCCGCGCTGCGGCTGCCGTCGCTTTTG
CTGGTGCACGTGTGTGCGCGCCCCGAGAAGCCGCCCGGGCAGGTCAC
GCGGCTCCGCGCCCTGCCCCTGACCCAAGGGCAGCTGGTTCTGGTCTG
GTCGGATGAACACGTGGGCTCCAAGTGCCTGTGGACATACGAGATCC
AGTTCTCTCAGGACGGTAAGGCGTACACCCCGGTCAGCAGGAAGCCA
TCGACCTTCAACCTCTTTGTGTTCAGCCCAGACACAGGTGCTGTCTCT
GGCTCCTACCGAGTTCGAGCCCTGGACTACTGGGCCCGACCAGGCCC
CTTCTCGGACCCTGTGCCGTACCTGGAGGTCCCTGTGCCAAGAGGGCC
CCCATCCCCGGGCAATCCATGA

FIG. 80B

Met Arg Pro Leu Arg Pro Arg Ala Ala Leu Leu Ala Leu Leu Ala Ser Leu Leu
Ala Ala Pro Pro Val Ala Pro Ala Glu Ala Pro His Leu Val Gln Val Asp Ala Ala
Arg Ala Leu Trp Pro Leu Arg Arg Phe Trp Arg Ser Thr Gly Phe Cys Pro Pro Leu
Pro His Ser Gln Ala Asp Gln Tyr Val Leu Ser Trp Asp Gln Gln Leu Asn Leu Ala
Tyr Val Gly Ala Val Pro His Arg Gly Ile Lys Gln Val Arg Thr His Trp Leu Leu
Glu Leu Val Thr Thr Arg Gly Ser Thr Gly Arg Gly Leu Ser Tyr Asn Phe Thr His
Leu Asp Gly Tyr Leu Asp Leu Leu Arg Glu Asn Gln Leu Leu Pro Gly Phe Glu
Leu Met Gly Ser Ala Ser Gly His Phe Thr Asp Phe Glu Asp Lys Gln Gln Val
Phe Glu Trp Lys Asp Leu Val Ser Ser Leu Ala Arg Arg Tyr Ile Gly Arg Tyr Gly
Leu Ala His Val Ser Lys Trp Asn Phe Glu Thr Trp Asn Glu Pro Asp His His Asp
Phe Asp Asn Val Ser Met Thr Met Gln Gly Phe Leu Asn Tyr Tyr Asp Ala Cys
Ser Glu Gly Leu Arg Ala Ala Ser Pro Ala Leu Arg Leu Gly Gly Pro Gly Asp Ser
Phe His Thr Pro Pro Arg Ser Pro Leu Ser Trp Gly Leu Leu Arg His Cys His Asp
Gly Thr Asn Phe Phe Thr Gly Glu Ala Gly Val Arg Leu Asp Tyr Ile Ser Leu His
Arg Lys Gly Ala Arg Ser Ser Ile Ser Ile Leu Glu Gln Glu Lys Val Val Ala Gln
Gln Ile Arg Gln Leu Phe Pro Lys Phe Ala Asp Thr Pro Ile Tyr Asn Asp Glu Ala
Asp Pro Leu Val Gly Trp Ser Leu Pro Gln Pro Trp Arg Ala Asp Val Thr Tyr Ala
Ala Met Val Val Lys Val Ile Ala Gln His Gln Asn Leu Leu Leu Ala Asn Thr Thr
Ser Ala Phe Pro Tyr Ala Leu Leu Ser Asn Asp Asn Ala Phe Leu Ser Tyr His Pro
His Pro Phe Ala Gln Arg Thr Leu Thr Ala Arg Phe Gln Val Asn Asn Thr Arg
Pro Pro His Val Gln Leu Leu Arg Lys Pro Val Leu Thr Ala Met Gly Leu Leu Ala
Leu Leu Asp Glu Glu Gln Leu Trp Ala Glu Val Ser Gln Ala Gly Thr Val Leu
Asp Ser Asn His Thr Val Gly Val Leu Ala Ser Ala His Arg Pro Gln Gly Pro Ala
Asp Ala Trp Arg Ala Ala Val Leu Ile Tyr Ala Ser Asp Asp Thr Arg Ala His Pro
Asn Arg Ser Val Ala Val Thr Leu Arg Leu Arg Gly Val Pro Pro Gly Pro Gly Leu
Val Tyr Val Thr Arg Tyr Leu Asp Asn Gly Leu Cys Ser Pro Asp Gly Glu Trp
Arg Arg Leu Gly Arg Pro Val Phe Pro Thr Ala Glu Gln Phe Arg Arg Met Arg
Ala Ala Glu Asp Pro Val Ala Ala Ala Pro Arg Pro Leu Pro Ala Gly Gly Arg Leu
Thr Leu Arg Pro Ala Leu Arg Leu Pro Ser Leu Leu Leu Val His Val Cys Ala
Arg Pro Glu Lys Pro Pro Gly Gln Val Thr Arg Leu Arg Ala Leu Pro Leu Thr Gln
Gly Gln Leu Val Leu Val Trp Ser Asp Glu His Val Gly Ser Lys Cys Leu Trp Thr
Tyr Glu Ile Gln Phe Ser Gln Asp Gly Lys Ala Tyr Thr Pro Val Ser Arg Lys Pro
Ser Thr Phe Asn Leu Phe Val Phe Ser Pro Asp Thr Gly Ala Val Ser Gly Ser Tyr
Arg Val Arg Ala Leu Asp Tyr Trp Ala Arg Pro Gly Pro Phe Ser Asp Pro Val Pro
Tyr Leu Glu Val Pro Val Pro Arg Gly Pro Pro Ser Pro Gly Asn Pro

FIG. 81A

ATGCAGCTGAGGAACCCAGAACTACATCTGGGCTGCGCGCTTGCGCT
TCGCTTCCTGGCCCTCGTTTCCTGGGACATCCCTGGGGCTAGAGCACT
GGACAATGGATTGGCAAGGACGCCTACCATGGGCTGGCTGCACTGGG
AGCGCTTCATGTGCAACCTTGACTGCCAGGAAGAGCCAGATTCCTGC
ATCAGTGAGAAGCTCTTCATGGAGATGGCAGAGCTCATGGTCTCAGA
AGGCTGGAAGGATGCAGGTTATGAGTACCTCTGCATTGATGACTGTTG
GATGGCTCCCCAAAGAGATTCAGAAGGCAGACTTCAGGCAGACCCTC
AGCGCTTTCCTCATGGGATTCGCCAGCTAGCTAATTATGTTCACAGCA
AAGGACTGAAGCTAGGGATTTATGCAGATGTTGGAAATAAAACCTGC
GCAGGCTTCCCTGGGAGTTTTGGATACTACGACATTGATGCCCAGACC
TTTGCTGACTGGGGAGTAGATCTGCTAAAATTTGATGGTTGTTACTGT
GACAGTTTGGAAAATTTGGCAGATGGTTATAAGCACATGTCCTTGGCC
CTGAATAGGACTGGCAGAAGCATTGTGTACTCCTGTGAGTGGCCTCTT
TATATGTGGCCCTTTCAAAAGCCCAATTATACAGAAATCCGACAGTAC
TGCAATCACTGGCGAAATTTTGCTGACATTGATGATTCCTGGAAAAGT
ATAAAGAGTATCTTGGACTGGACATCTTTTAACCAGGAGAGAATTGTT
GATGTTGCTGGACCAGGGGGTTGGAATGACCCAGATATGTTAGTGAT
TGGCAACTTTGGCCTCAGCTGGAATCAGCAAGTAACTCAGATGGCCCT
CTGGGCTATCATGGCTGCTCCTTTATTCATGTCTAATGACCTCCGACA
CATCAGCCCTCAAGCCAAAGCTCTCCTTCAGGATAAGGACGTAATTGC
CATCAATCAGGACCCCTTGGGCAAGCAAGGGTACCAGCTTAGACAGG
GAGACAACTTTGAAGTGTGGGAACGACCTCTCTCAGGCTTAGCCTGG
GCTGTAGCTATGATAAACCGGCAGGAGATTGGTGGACCTCGCTCTTAT
ACCATCGCAGTTGCTTCCCTGGGTAAAGGAGTGGCCTGTAATCCTGCC
TGCTTCATCACACAGCTCCTCCCTGTGAAAAGGAAGCTAGGGTTCTAT
GAATGGACTTCAAGGTTAAGAAGTCACATAAATCCCACAGGCACTGT
TTTGCTTCAGCTAGAAAATACAATGCAGATGTCATTAAAAGACTTACT
TTAA

FIG. 81B

Met Gln Leu Arg Asn Pro Glu Leu His Leu Gly Cys Ala Leu Ala Leu Arg Phe
Leu Ala Leu Val Ser Trp Asp Ile Pro Gly Ala Arg Ala Leu Asp Asn Gly Leu Ala
Arg Thr Pro Thr Met Gly Trp Leu His Trp Glu Arg Phe Met Cys Asn Leu Asp
Cys Gln Glu Glu Pro Asp Ser Cys Ile Ser Glu Lys Leu Phe Met Glu Met Ala Glu
Leu Met Val Ser Glu Gly Trp Lys Asp Ala Gly Tyr Glu Tyr Leu Cys Ile Asp Asp
Cys Trp Met Ala Pro Gln Arg Asp Ser Glu Gly Arg Leu Gln Ala Asp Pro Gln
Arg Phe Pro His Gly Ile Arg Gln Leu Ala Asn Tyr Val His Ser Lys Gly Leu Lys
Leu Gly Ile Tyr Ala Asp Val Gly Asn Lys Thr Cys Ala Gly Phe Pro Gly Ser Phe
Gly Tyr Tyr Asp Ile Asp Ala Gln Thr Phe Ala Asp Trp Gly Val Asp Leu Leu Lys
Phe Asp Gly Cys Tyr Cys Asp Ser Leu Glu Asn Leu Ala Asp Gly Tyr Lys His
Met Ser Leu Ala Leu Asn Arg Thr Gly Arg Ser Ile Val Tyr Ser Cys Glu Trp Pro
Leu Tyr Met Trp Pro Phe Gln Lys Pro Asn Tyr Thr Glu Ile Arg Gln Tyr Cys Asn
His Trp Arg Asn Phe Ala Asp Ile Asp Asp Ser Trp Lys Ser Ile Lys Ser Ile Leu
Asp Trp Thr Ser Phe Asn Gln Glu Arg Ile Val Asp Val Ala Gly Pro Gly Gly Trp
Asn Asp Pro Asp Met Leu Val Ile Gly Asn Phe Gly Leu Ser Trp Asn Gln Gln
Val Thr Gln Met Ala Leu Trp Ala Ile Met Ala Ala Pro Leu Phe Met Ser Asn Asp
Leu Arg His Ile Ser Pro Gln Ala Lys Ala Leu Leu Gln Asp Lys Asp Val Ile Ala
Ile Asn Gln Asp Pro Leu Gly Lys Gln Gly Tyr Gln Leu Arg Gln Gly Asp Asn
Phe Glu Val Trp Glu Arg Pro Leu Ser Gly Leu Ala Trp Ala Val Ala Met Ile Asn
Arg Gln Glu Ile Gly Gly Pro Arg Ser Tyr Thr Ile Ala Val Ala Ser Leu Gly Lys
Gly Val Ala Cys Asn Pro Ala Cys Phe Ile Thr Gln Leu Leu Pro Val Lys Arg Lys
Leu Gly Phe Tyr Glu Trp Thr Ser Arg Leu Arg Ser His Ile Asn Pro Thr Gly Thr
Val Leu Leu Gln Leu Glu Asn Thr Met Gln Met Ser Leu Lys Asp Leu Leu

FIG. 82A

ATGGCGCCCGTCGCCGTCTGGGCCGCGCTGGCCGTCGGACTGGAGCT
CTGGGCTGCGGCGCACGCCTTGCCCGCCCAGGTGGCATTTACACCCTA
CGCCCCGGAGCCCGGGAGCACATGCCGGCTCAGAGAATACTATGACC
AGACAGCTCAGATGTGCTGCAGCAAATGCTCGCCGGGCCAACATGCA
AAAGTCTTCTGTACCAAGACCTCGGACACCGTGTGTGACTCCTGTGAG
GACAGCACATACACCCAGCTCTGGAACTGGGTTCCCGAGTGCTTGAG
CTGTGGCTCCCGCTGTAGCTCTGACCAGGTGGAAACTCAAGCCTGCAC
TCGGGAACAGAACCGCATCTGCACCTGCAGGCCCGGCTGGTACTGCG
CGCTGAGCAAGCAGGAGGGGTGCCGGCTGTGCGCGCCGCTGCGCAAG
TGCCGCCCGGGCTTCGGCGTGGCCAGACCAGGAACTGAAACATCAGA
CGTGGTGTGCAAGCCCTGTGCCCCGGGGACGTTCTCCAACACGACTTC
ATCCACGGATATTTGCAGGCCCCACCAGATCTGTAACGTGGTGGCCAT
CCCTGGGAATGCAAGCATGGATGCAGTCTGCACGTCCACGTCCCCCA
CCCGGAGTATGGCCCCAGGGGCAGTACACTTACCCCAGCCAGTGTCC
ACACGATCCCAACACACGCAGCCAACTCCAGAACCCAGCACTGCTCC
AAGCACCTCCTTCCTGCTCCCAATGGGCCCCAGCCCCCCAGCTGAAGG
GAGCACTGGCGACTTCGCTCTTCCAGTTGGACTGATTGTGGGTGTGAC
AGCCTTGGGTCTACTAATAATAGGAGTGGTGAACTGTGTCATCATGAC
CCAGGTGAAAAAGAAGCCCTTGTGCCTGCAGAGAGAAGCCAAGGTGC
CTCACTTGCCTGCCGATAAGGCCCGGGGTACACAGGGCCCCGAGCAG
CAGCACCTGCTGATCACAGCGCCGAGCTCCAGCAGCAGCTCCCTGGA
GAGCTCGGCCAGTGCGTTGGACAGAAGGGCGCCCACTCGGAACCAGC
CACAGGCACCAGGCGTGGAGGCCAGTGGGGCCGGGGAGGCCCGGGC
CAGCACCGGGAGCTCAGATTCTTCCCCTGGTGGCCATGGGACCCAGG
TCAATGTCACCTGCATCGTGAACGTCTGTAGCAGCTCTGACCACAGCT
CACAGTGCTCCTCCCAAGCCAGCTCCACAATGGGAGACACAGATTCC
AGCCCCTCGGAGTCCCCGAAGGACGAGCAGGTCCCCTTCTCCAAGGA
GGAATGTGCCTTTCGGTCACAGCTGGAGACGCCAGAGACCCTGCTGG
GGAGCACCGAAGAGAAGCCCCTGCCCCTTGGAGTGCCTGATGCTGGG
ATGAAGCCCAGTTAACCAGGCCGGTGTGGGCTGTGTCGTAGCCAAGG
TGGGCTGAGCCCTGGCAGGATGACCCTGCGAAGGGGCCCTGGTCCTT
CCAGGC

FIG. 82B

Met Ala Pro Val Ala Val Trp Ala Ala Leu Ala Val Gly Leu Glu Leu Trp Ala Ala
Ala His Ala Leu Pro Ala Gln Val Ala Phe Thr Pro Tyr Ala Pro Glu Pro Gly Ser
Thr Cys Arg Leu Arg Glu Tyr Tyr Asp Gln Thr Ala Gln Met Cys Cys Ser Lys
Cys Ser Pro Gly Gln His Ala Lys Val Phe Cys Thr Lys Thr Ser Asp Thr Val Cys
Asp Ser Cys Glu Asp Ser Thr Tyr Thr Gln Leu Trp Asn Trp Val Pro Glu Cys
Leu Ser Cys Gly Ser Arg Cys Ser Ser Asp Gln Val Glu Thr Gln Ala Cys Thr Arg
Glu Gln Asn Arg Ile Cys Thr Cys Arg Pro Gly Trp Tyr Cys Ala Leu Ser Lys Gln
Glu Gly Cys Arg Leu Cys Ala Pro Leu Arg Lys Cys Arg Pro Gly Phe Gly Val
Ala Arg Pro Gly Thr Glu Thr Ser Asp Val Val Cys Lys Pro Cys Ala Pro Gly Thr
Phe Ser Asn Thr Thr Ser Ser Thr Asp Ile Cys Arg Pro His Gln Ile Cys Asn Val
Val Ala Ile Pro Gly Asn Ala Ser Met Asp Ala Val Cys Thr Ser Thr Ser Pro Thr
Arg Ser Met Ala Pro Gly Ala Val His Leu Pro Gln Pro Val Ser Thr Arg Ser Gln
His Thr Gln Pro Thr Pro Glu Pro Ser Thr Ala Pro Ser Thr Ser Phe Leu Leu Pro
Met Gly Pro Ser Pro Pro Ala Glu Gly Ser Thr Gly Asp Phe Ala Leu Pro Val Gly
Leu Ile Val Gly Val Thr Ala Leu Gly Leu Leu Ile Ile Gly Val Val Asn Cys Val
Ile Met Thr Gln Val Lys Lys Lys Pro Leu Cys Leu Gln Arg Glu Ala Lys Val Pro
His Leu Pro Ala Asp Lys Ala Arg Gly Thr Gln Gly Pro Glu Gln Gln His Leu Leu
Ile Thr Ala Pro Ser Ser Ser Ser Ser Ser Leu Glu Ser Ser Ala Ser Ala Leu Asp Arg
Arg Ala Pro Thr Arg Asn Gln Pro Gln Ala Pro Gly Val Glu Ala Ser Gly Ala Gly
Glu Ala Arg Ala Ser Thr Gly Ser Ser Asp Ser Ser Pro Gly Gly His Gly Thr Gln
Val Asn Val Thr Cys Ile Val Asn Val Cys Ser Ser Ser Asp His Ser Ser Gln Cys
Ser Ser Gln Ala Ser Ser Thr Met Gly Asp Thr Asp Ser Ser Pro Ser Glu Ser Pro
Lys Asp Glu Gln Val Pro Phe Ser Lys Glu Glu Cys Ala Phe Arg Ser Gln Leu Glu
Thr Pro Glu Thr Leu Leu Gly Ser Thr Glu Glu Lys Pro Leu Pro Leu Gly Val Pro
Asp Ala Gly Met Lys Pro Ser

FIG. 83A

Asp Ile Gln Met Thr Gln Ser Pro Ser Ser Leu Ser Ala Ser Val Gly Asp Arg Val
Thr Ile Thr Cys Arg Ala Ser Gln Asp Val Asn Thr Ala Val Ala Trp Tyr Gln Gln
Lys Pro Gly Lys Ala Pro Lys Leu Leu Ile Tyr Ser Ala Ser Phe Leu Tyr Ser Gly
Val Pro Ser Arg Phe Ser Gly Ser Arg Ser Gly Thr Asp Phe Thr Leu Thr Ile Ser
Ser Leu Gln Pro Glu Asp Phe Ala Thr Tyr Tyr Cys Gln Gln His Tyr Thr Thr Pro
Pro Thr Phe Gly Gln Gly Thr Lys Val Glu Ile Lys

FIG. 83B

Glu Val Gln Leu Val Glu Ser Gly Gly Gly Leu Val Gln Pro Gly Gly Ser Leu Arg
Leu Ser Cys Ala Ala Ser Gly Phe Asn Ile Lys Asp Thr Tyr Ile His Trp Val Arg
Gln Ala Pro Gly Lys Gly Leu Glu Trp Val Ala Arg Ile Tyr Pro Thr Asn Gly Tyr
Thr Arg Tyr Ala Asp Ser Val Lys Gly Arg Phe Thr Ile Ser Ala Asp Thr Ser Lys
Asn Thr Ala Tyr Leu Gln Met Asn Ser Leu Arg Ala Glu Asp Thr Ala Val Tyr
Tyr Cys Ser Arg Trp Gly Gly Asp Gly Phe Tyr Ala Met Asp Tyr Trp Gly Gln
Gly Thr Leu Val Thr Val Ser Ser

FIG. 84A

Gln Val Thr Leu Arg Glu Ser Gly Pro Ala Leu Val Lys Pro Thr Gln Thr Leu Thr Leu Thr Cys Thr Phe Ser Gly Phe Ser Leu Ser Thr Ser Gly Met Ser Val Gly Trp Ile Arg Gln Pro Ser Gly Lys Ala Leu Glu Trp Leu Ala Asp Ile Trp Trp Asp Asp Lys Lys Asp Tyr Asn Pro Ser Leu Lys Ser Arg Leu Thr Ile Ser Lys Asp Thr Ser Lys Asn Gln Val Val Leu Lys Val Thr Asn Met Asp Pro Ala Asp Thr Ala Thr Tyr Tyr Cys Ala Arg Ser Met Ile Thr Asn Trp Tyr Phe Asp Val Trp Gly Ala Gly Thr Thr Val Thr Val Ser Ser

FIG. 84B

Asp Ile Gln Met Thr Gln Ser Pro Ser Thr Leu Ser Ala Ser Val Gly Asp Arg Val Thr Ile Thr Cys Lys Cys Gln Leu Ser Val Gly Tyr Met His Trp Tyr Gln Gln Lys Pro Gly Lys Ala Pro Lys Leu Trp Ile Tyr Asp Thr Ser Lys Leu Ala Ser Gly Val Pro Ser Arg Phe Ser Gly Ser Gly Ser Gly Thr Glu Phe Thr Leu Thr Ile Ser Ser Leu Gln Pro Asp Asp Phe Ala Thr Tyr Tyr Cys Phe Gln Gly Ser Gly Tyr Pro Phe Thr Phe Gly Gly Gly Thr Lys Leu Glu Ile Lys

FIG. 85A

GACATCTTGCTGACTCAGTCTCCAGCCATCCTGTCTGTGAGTCCAGGA
GAAAGAGTCAGTTTCTCCTGCAGGGCCAGTCAGTTCGTTGGCTCAAGC
ATCCACTGGTATCAGCAAAGAACAAATGGTTCTCCAAGGCTTCTCATA
AAGTATGCTTCTGAGTCTATGTCTGGGATCCCTTCCAGGTTTAGTGGC
AGTGGATCAGGGACAGATTTTACTCTTAGCATCAACACTGTGGAGTCT
GAAGATATTGCAGATTATTACTGTCAACAAAGTCATAGCTGGCCATTC
ACGTTCGGCTCGGGGACAAATTTGGAAGTAAAAGAAGTGAAGCTTGA
GGAGTCTGGAGGAGGCTTGGTGCAACCTGGAGGATCCATGAAACTCT
CCTGTGTTGCCTCTGGATTCATTTTCAGTAACCACTGGATGAACTGGG
TCCGCCAGTCTCCAGAGAAGGGGCTTGAGTGGGTTGCTGAAATTAGA
TCAAAATCTATTAATTCTGCAACACATTATGCGGAGTCTGTGAAAGGG
AGGTTCACCATCTCAAGAGATGATTCCAAAAGTGCTGTCTACCTGCAA
ATGACCGACTTAAGAACTGAAGACACTGGCGTTTATTACTGTTCCAGG
AATTACTACGGTAGTACCTACGACTACTGGGGCCAAGGCACCACTCTC
ACAGTCTCC

FIG. 85B

Asp Ile Leu Leu Thr Gln Ser Pro Ala Ile Leu Ser Val Ser Pro Gly Glu Arg Val
Ser Phe Ser Cys Arg Ala Ser Gln Phe Val Gly Ser Ser Ile His Trp Tyr Gln Gln
Arg Thr Asn Gly Ser Pro Arg Leu Leu Ile Lys Tyr Ala Ser Glu Ser Met Ser Gly
Ile Pro Ser Arg Phe Ser Gly Ser Gly Ser Gly Thr Asp Phe Thr Leu Ser Ile Asn
Thr Val Glu Ser Glu Asp Ile Ala Asp Tyr Tyr Cys Gln Gln Ser His Ser Trp Pro
Phe Thr Phe Gly Ser Gly Thr Asn Leu Glu Val Lys Glu Val Lys Leu Glu Glu Ser
Gly Gly Gly Leu Val Gln Pro Gly Gly Ser Met Lys Leu Ser Cys Val Ala Ser Gly
Phe Ile Phe Ser Asn His Trp Met Asn Trp Val Arg Gln Ser Pro Glu Lys Gly Leu
Glu Trp Val Ala Glu Ile Arg Ser Lys Ser Ile Asn Ser Ala Thr His Tyr Ala Glu
Ser Val Lys Gly Arg Phe Thr Ile Ser Arg Asp Asp Ser Lys Ser Ala Val Tyr
LeuGln Met Thr Asp Leu Arg Thr Glu Asp Thr Gly Val Tyr Tyr Cys Ser Arg
Asn Tyr Tyr Gly Ser Thr Tyr Asp Tyr Trp Gly Gln Gly Thr Thr Leu Thr Val Ser

FIG. 86A

ATGGAGACAGACACACTCCTGTTATGGGTGCTGCTGCTCTGGGTTCCA
GGTTCCACTGGTGACGTCAGGCGAGGGCCCCGGAGCCTGCGGGGCAG
GGACGCGCCAGCCCCCACGCCCTGCGTCCCGGCCGAGTGCTTCGACC
TGCTGGTCCGCCACTGCGTGGCCTGCGGGCTCCTGCGCACGCCGCGGC
CGAAACCGGCCGGGGCCAGCAGCCCTGCGCCCAGGACGGCGCTGCAG
CCGCAGGAGTCGGTGGGCGCGGGGGCCGGCGAGGCGGCGGTCGACA
AAACTCACACATGCCCACCGTGCCCAGCACCTGAACTCCTGGGGGGA
CCGTCAGTCTTCCTCTTCCCCCCAAAACCCAAGGACACCCTCATGATC
TCCCGGACCCCTGAGGTCACATGCGTGGTGGTGGACGTGAGCCACGA
AGACCCTGAGGTCAAGTTCAACTGGTACGTGGACGGCGTGGAGGTGC
ATAATGCCAAGACAAAGCCGCGGGAGGAGCAGTACAACAGCACGTA
CCGTGTGGTCAGCGTCCTCACCGTCCTGCACCAGGACTGGCTGAATGG
CAAGGAGTACAAGTGCAAGGTCTCCAACAAAGCCCTCCCAGCCCCCA
TCGAGAAAACCATCTCCAAAGCCAAAGGGCAGCCCCGAGAACCACAG
GTGTACACCCTGCCCCCATCCCGGGATGAGCTGACCAAGAACCAGGT
CAGCCTGACCTGCCTGGTCAAAGGCTTCTATCCCAGCGACATCGCCGT
GGAGTGGGAGAGCAATGGGCAGCCGGAGAACAACTACAAGACCACG
CCTCCCGTGTTGGACTCCGACGGCTCCTTCTTCCTCTACAGCAAGCTC
ACCGTGGACAAGAGCAGGTGGCAGCAGGGGAACGTCTTCTCATGCTC
CGTGATGCATGAGGCTCTGCACAACCACTACACGCAGAAGAGCCTCT
CCCTGTCTCCGGGAAATGA

FIG. 86B

Met Glu Thr Asp Thr Leu Leu Leu Trp Val Leu Leu Leu Trp Val Pro Gly Ser
Thr Gly Asp Val Arg Arg Gly Pro Arg Ser Leu Arg Gly Arg Asp Ala Pro Ala
Pro Thr Pro Cys Val Pro Ala Glu Cys Phe Asp Leu Leu Val Arg His Cys Val Ala
Cys Gly Leu Leu Arg Thr Pro Arg Pro Lys Pro Ala Gly Ala Ser Ser Pro Ala Pro
Arg Thr Ala Leu Gln Pro Gln Glu Ser Val Gly Ala Gly Ala Gly Glu Ala Ala Val
Asp Lys Thr His Thr Cys Pro Pro Cys Pro Ala Pro Glu Leu Leu Gly Gly Pro Ser
Val Phe Leu Phe Pro Pro Lys Pro Lys Asp Thr Leu Met Ile Ser Arg Thr Pro Glu
Val Thr Cys Val Val Val Asp Val Ser His Glu Asp Pro Glu Val Lys Phe Asn Trp
Tyr Val Asp Gly Val Glu Val His Asn Ala Lys Thr Lys Pro Arg Glu Glu Gln Tyr
Asn Ser Thr Tyr Arg Val Val Ser Val Leu Thr Val Leu His Gln Asp Trp Leu Asn
Gly Lys Glu Tyr Lys Cys Lys Val Ser Asn Lys Ala Leu Pro Ala Pro Ile Glu Lys
Thr Ile Ser Lys Ala Lys Gly Gln Pro Arg Glu Pro Gln Val Tyr Thr Leu Pro Pro
Ser Arg Asp Glu Leu Thr Lys Asn Gln Val Ser Leu Thr Cys Leu Val Lys Gly
Phe Tyr Pro Ser Asp Ile Ala Val Glu Trp Glu Ser Asn Gly Gln Pro Glu Asn Asn
Tyr Lys Thr Thr Pro Pro Val Leu Asp Ser Asp Gly Ser Phe Phe Leu Tyr Ser Lys
Leu Thr Val Asp Lys Ser Arg Trp Gln Gln Gly Asn Val Phe Ser Cys Ser Val Met
His Glu Ala Leu His Asn His Tyr Thr Gln Lys Ser Leu Ser Leu Ser Pro Gly Lys

FIG. 87

Asp Ile Gln Met Thr Gln Thr Thr Ser Ser Leu Ser Ala Ser Leu Gly Asp Arg Val Thr Ile Ser Cys Arg Ala Ser Gln Asp Ile Asn Asn Tyr Leu Asn Trp Tyr Gln Gln Lys Pro Asp Gly Ile Val Lys Leu Leu Ile Tyr Tyr Thr Ser Thr Leu His Ser Gly Val Pro Ser Arg Phe Ser Gly Ser Gly Ser Gly Thr Asp Tyr Ser Leu Thr Ile Ser Asn Leu Glu Gln Glu Asp Ile Ala Thr Tyr Phe Cys Gln Gln Gly Asn Thr Leu Pro Trp Thr Phe Gly Gly Gly Thr Lys Leu Glu Ile Lys

FIG. 88

Gln Val Gln Leu Gln Gln Ser Gly Ala Glu Leu Val Gly Pro Gly Thr Ser Val Arg Val Ser Cys Lys Ala Ser Gly Tyr Ala Phe Thr Asn Tyr Leu Ile Glu Trp Val Lys Gln Arg Pro Gly Gln Gly Leu Glu Trp Ile Gly Val Ile Tyr Pro Gly Ser Gly Gly Thr Asn Tyr Asn Glu Lys Phe Lys Gly Lys Ala Thr Leu Thr Val Asp Lys Ser Ser Thr Thr Ala Tyr Met Gln Leu Ser Ser Leu Thr Ser Asp Asp Ser Ala Val Tyr Phe Cys Ala Arg Arg Asp Gly Asn Tyr Gly Trp Phe Ala Tyr Trp Gly Arg Gly Thr Leu Val Thr Val Ser Ala

FIG. 89

Asp Ile Gln Met Thr Gln Thr Pro Ser Thr Leu Ser Ala Ser Val Gly Asp Arg Val Thr Ile Ser Cys Arg Ala Ser Gln Asp Ile Asn Asn Tyr Leu Asn Trp Tyr Gln Gln Lys Pro Gly Lys Ala Pro Lys Leu Leu Ile Tyr Tyr Thr Ser Thr Leu His Ser Gly Val Pro Ser Arg Phe Ser Gly Ser Gly Ser Gly Thr Asp Tyr Thr Leu Thr Ile Ser Ser Leu Gln Pro Asp Asp Phe Ala Thr Tyr Phe Cys Gln Gln Gly Asn Thr Leu Pro Trp Thr Phe Gly Gln Gly Thr Lys Val Glu Val Lys

FIG. 90

Gln Val Gln Leu Val Gln Ser Gly Ala Glu Val Lys Lys Pro Gly Ser Ser Val Lys Val Ser Cys Lys Ala Ser Gly Tyr Ala Phe Thr Asn Tyr Leu Ile Glu Trp Val Arg Gln Ala Pro Gly Gln Gly Leu Glu Trp Ile Gly Val Ile Tyr Pro Gly Ser Gly Gly Thr Asn Tyr Asn Glu Lys Phe Lys Gly Arg Val Thr Leu Thr Val Asp Glu Ser Thr Asn Thr Ala Tyr Met Glu Leu Ser Ser Leu Arg Ser Glu Asp Thr Ala Val Tyr Phe Cys Ala Arg Arg Asp Gly Asn Tyr Gly Trp Phe Ala Tyr Trp Gly Gln Gly Thr Leu Val Thr Val Ser Ser

FIG. 91

Asp Ile Gln Met Thr Gln Thr Pro Ser Thr Leu Ser Ala Ser Val Gly Asp Arg Val
Thr Ile Ser Cys Arg Ala Ser Gln Asp Ile Asn Asn Tyr Leu Asn Trp Tyr Gln Gln
Lys Pro Gly Lys Ala Pro Lys Leu Leu Ile Tyr Tyr Thr Ser Thr Leu His Ser Gly
Val Pro Ser Arg Phe Ser Gly Ser Gly Ser Gly Thr Asp Tyr Thr Leu Thr Ile Ser
Ser Leu Gln Pro Asp Asp Phe Ala Thr Tyr Phe Cys Gln Gln Gly Asn Thr Leu
Pro Trp Thr Phe Gly Gln Gly Thr Lys Val Glu Val Lys Arg Thr Val Ala Ala Pro
Ser Val Phe Ile Phe Pro Pro Ser Asp Glu Gln Leu Lys Ser Gly Thr Ala Ser Val
Val Cys Leu Leu Asn Asn Phe Tyr Pro Arg Glu Ala Lys Val Gln Trp Lys Val
Asp Asn Ala Leu Gln Ser Gly Asn Ser Gln Glu Ser Val Thr Glu Gln Asp Ser Lys
Asp Ser Thr Tyr Ser Leu Ser Ser Thr Leu Thr Leu Ser Lys Ala Asp Tyr Glu Lys
His Lys Val Tyr Ala Cys Glu Val Thr His Gln Gly Leu Ser Ser Pro Val Thr Lys
Ser Phe Asn Arg Gly Glu Cys

FIG. 92

Gln Val Gln Leu Val Gln Ser Gly Ala Glu Val Lys Lys Pro Gly Ser Ser Val Lys
Val Ser Cys Lys Ala Ser Gly Tyr Ala Phe Thr Asn Tyr Leu Ile Glu Trp Val Arg
Gln Ala Pro Gly Gln Gly Leu Glu Trp Ile Gly Val Ile Tyr Pro Gly Ser Gly Gly
Thr Asn Tyr Asn Glu Lys Phe Lys Gly Arg Val Thr Leu Thr Val Asp Glu Ser
Thr Asn Thr Ala Tyr Met Glu Leu Ser Ser Leu Arg Ser Glu Asp Thr Ala Val Tyr
Phe Cys Ala Arg Arg Asp Gly Asn Tyr Gly Trp Phe Ala Tyr Trp Gly Gln Gly
Thr Leu Val Thr Val Ser Ser Ala Ser Thr Lys Gly Pro Ser Val Phe Pro Leu Ala
Pro Ser Ser Lys Ser Thr Ser Gly Gly Thr Ala Ala Leu Gly Cys Leu Val Lys Asp
Tyr Phe Pro Glu Pro Val Thr Val Ser Trp Asn Ser Gly Ala Leu Thr Ser Gly Val
His Thr Phe Pro Ala Val Leu Gln Ser Ser Gly Leu Tyr Ser Leu Ser Ser Val Val
Thr Val Pro Ser Ser Ser Leu Gly Thr Gln Thr Tyr Ile Cys Asn Val Asn His Lys
Pro Ser Asn Thr Lys Val Asp Lys Lys Val Glu Pro Lys Ser Cys Asp Lys Thr His
Thr Cys Pro Pro Cys Pro Ala Pro Glu Leu Leu Gly Gly Pro Ser Val Phe Leu Phe
Pro Pro Lys Pro Lys Asp Thr Leu Met Ile Ser Arg Thr Pro Glu Val Thr Cys Val
Val Val Asp Val Ser His Glu Asp Pro Glu Val Lys Phe Asn Trp Tyr Val Asp Gly
Val Glu Val His Asn Ala Lys Thr Lys Pro Arg Glu Glu Gln Tyr Asn Ser Thr Tyr
Arg Val Val Ser Val Leu Thr Val Leu His Gln Asp Trp Leu Asn Gly Lys Glu
Tyr Lys Cys Lys Val Ser Asn Lys Ala Leu Pro Ala Pro Ile Glu Lys Thr Ile Ser
Lys Ala Lys Gly Gln Pro Arg Glu Pro Gln Val Tyr Thr Leu Pro Pro Ser Arg Asp
Glu Leu Thr Lys Asn Gln Val Ser Leu Thr Cys Leu Val Lys Gly Phe Tyr Pro Ser
Asp Ile Ala Val Glu Trp Glu Ser Asn Gly Gln Pro Glu Asn Asn Tyr Lys Thr Thr
Pro Pro Val Leu Asp Ser Asp Gly Ser Phe Phe Leu Tyr Ser Lys Leu Thr Val Asp
Lys Ser Arg Trp Gln Gln Gly Asn Val Phe Ser Cys Ser Val Met His Glu Ala Leu
His Asn His Tyr Thr Gln Lys Ser Leu Ser Leu Ser Pro Gly

FIG. 93A

ATGGATTTTCAGGTGCAGATTATCAGCTTCCTGCTAATCAGTGCTTCA
GTCATAATGTCCAGAGGGCAAATTGTTCTCTCCCAGTCTCCAGCAATC
CTGTCTGCATCTCCAGGGGAGAAGGTCACAATGACTTGCAGGGCCAG
CTCAAGTGTAAGTTACATCCACTGGTTCCAGCAGAAGCCAGGATCCTC
CCCCAAACCCTGGATTTATGCCACATCCAACCTGGCTTCTGGAGTCCC
TGTTCGCTTCAGTGGCAGTGGGTCTGGGACTTCTTACTCTCTCACAAT
CAGCAGAGTGGAGGCTGAAGATGCTGCCACTTATTACTGCCAGCAGT
GGACTAGTAACCCACCCACGTTCGGAGGGGGGACCAAGCTGGAAATC
AAA

FIG. 93B

Met Asp Phe Gln Val Gln Ile Ile Ser Phe Leu Leu Ile Ser Ala Ser Val Ile Met Ser
Arg Gly Gln Ile Val Leu Ser Gln Ser Pro Ala Ile Leu Ser Ala Ser Pro Gly Glu
Lys Val Thr Met Thr Cys Arg Ala Ser Ser Ser Val Ser Tyr Ile His Trp Phe Gln
Gln Lys Pro Gly Ser Ser Pro Lys Pro Trp Ile Tyr Ala Thr Ser Asn Leu Ala Ser
Gly Val Pro Val Arg Phe Ser Gly Ser Gly Ser Gly Thr Ser Tyr Ser Leu Thr Ile
Ser Arg Val Glu Ala Glu Asp Ala Ala Thr Tyr Tyr Cys Gln Gln Trp Thr Ser Asn
Pro Pro Thr Phe Gly Gly Gly Thr Lys Leu Glu Ile Lys

FIG. 94A

ATGGGTTGGAGCCTCATCTTGCTCTTCCTTGTCGCTGTTGCTACGCGTG
TCCTGTCCCAGGTACAACTGCAGCAGCCTGGGGCTGAGCTGGTGAAG
CCTGGGGCCTCAGTGAAGATGTCCTGCAAGGCTTCTGGCTACACATTT
ACCAGTTACAATATGCACTGGGTAAAACAGACACCTGGTCGGGGCCT
GGAATGGATTGGAGCTATTTATCCCGGAAATGGTGATACTTCCTACAA
TCAGAAGTTCAAAGGCAAGGCCACATTGACTGCAGACAAATCCTCCA
GCACAGCCTACATGCAGCTCAGCAGCCTGACATCTGAGGACTCTGCG
GTCTATTACTGTGCAAGATCGACTTACTACGGCGGTGACTGGTACTTC
AATGTCTGGGGCGCAGGGACCACGGTCACCGTCTCTGCA

FIG. 94B

Met Gly Trp Ser Leu Ile Leu Leu Phe Leu Val Ala Val Ala Thr Arg Val Leu Ser
Gln Val Gln Leu Gln Gln Pro Gly Ala Glu Leu Val Lys Pro Gly Ala Ser Val Lys
Met Ser Cys Lys Ala Ser Gly Tyr Thr Phe Thr Ser Tyr Asn Met His Trp Val Lys
Gln Thr Pro Gly Arg Gly Leu Glu Trp Ile Gly Ala Ile Tyr Pro Gly Asn Gly Asp
Thr Ser Tyr Asn Gln Lys Phe Lys Gly Lys Ala Thr Leu Thr Ala Asp Lys Ser Ser
Ser Thr Ala Tyr Met Gln Leu Ser Ser Leu Thr Ser Glu Asp Ser Ala Val Tyr Tyr
Cys Ala Arg Ser Thr Tyr Tyr Gly Gly Asp Trp Tyr Phe Asn Val Trp Gly Ala Gly
Thr Thr Val Thr Val Ser Ala

FIG. 95A

GACGTCGCGGCCGCTCTAGGCCTCCAAAAAAGCCTCCTCACTACTTCT
GGAATAGCTCAGAGGCCGAGGCGGCCTCGGCCTCTGCATAAATAAAA
AAAATTAGTCAGCCATGCATGGGGCGGAGAATGGGCGGAACTGGGCG
GAGTTAGGGGCGGGATGGGCGGAGTTAGGGGCGGGACTATGGTTGCT
GACTAATTGAGATGCATGCTTTGCATACTTCTGCCTGCTGGGGAGCCT
GGGGACTTTCCACACCTGGTTGCTGACTAATTGAGATGCATGCTTTGC
ATACTTCTGCCTGCTGGGGAGCCTGGGGACTTTCCACACCCTAACTGA
CACACATTCCACAGAATTAATTCCCCTAGTTATTAATAGTAATCAATT
ACGGGGTCATTAGTTCATAGCCCATATATGGAGTTCCGCGTTACATAA
CTTACGGTAAATGGCCCGCCTGGCTGACCGCCCAACGACCCCCGCCC
ATTGACGTCAATAATGACGTATGTTCCCATAGTAACGCCAATAGGGA
CTTTCCATTGACGTCAATGGGTGGACTATTTACGGTAAACTGCCCACT
TGGCAGTACATCAAGTGTATCATATGCCAAGTACGCCCCCTATTGACG
TCAATGACGGTAAATGGCCCGCCTGGCATTATGCCCAGTACATGACCT
TATGGGACTTTCCTACTTGGCAGTACATCTACGTATTAGTCATCGCTA
TTACCATGGTGATGCGGTTTTGGCAGTACATCAATGGGCGTGGATAGC
GGTTTGACTCACGGGGATTTCCAAGTCTCCACCCCATTGACGTCAATG
GGAGTTTGTTTTGGCACCAAAATCAACGGGACTTTCCAAAATGTCGTA
ACAACTCCGCCCCATTGACGCAAATGGGCGGTAGGCGTGTACGGTGG
GAGGTCTATATAAGCAGAGCTGGGTACGTGAACCGTCAGATCGCCTG
GAGACGCCATCACAGATCTCTCACCATGAGGGTCCCCGCTCAGCTCCT
GGGGCTCCTGCTGCTCTGGCTCCCAGGTGCACGATGTGATGGTACCAA
GGTGGAAATCAAACGTACGGTGGCTGCACCATCTGTCTTCATCTTCCC
GCCATCTGATGAGCAGTTGAAATCTGGAACTGCCTCTGTTGTGTGCCT
GCTGAATAACTTCTATCCCAGAGAGGCCAAAGTACAGTGGAAGGTGG
ATAACGCCCTCCAATCGGGTAACTCCCAGGAGAGTGTCACAGAGCAG
GACAGCAAGGACAGCACCTACAGCCTCAGCAGCACCCTGACGCTGAG
CAAAGCAGACTACGAGAAACACAAAGTCTACGCCTGCGAAGTCACCC
ATCAGGGCCTGAGCTCGCCCGTCACAAAGAGCTTCAACAGGGGAGAG
TGTTGAATTCAGATCCGTTAACGGTTACCAACTACCTAGACTGGATTC
GTGACAACATGCGGCCGTGATATCTACGTATGATCAGCCTCGACTGTG
CCTTCTAGTTGCCAGCCATCTGTTGTTTGCCCCTCCCCCGTGCCTTCCT
TGACCCTGGAAGGTGCCACTCCCACTGTCCTTTCCTAATAAAATGAGG
AAATTGCATCGCATTGTCTGAGTAGGTGTCATTCTATTCTGGGGGGTG
GGGTGGGGCAGGACAGCAAGGGGGAGGATTGGGAAGACAATAGCAG
GCATGCTGGGGATGCGGTGGGCTCTATGGAACCAGCTGGGGCTCGAC
AGCTATGCCAAGTACGCCCCCTATTGACGTCAATGACGGTAAATGGC
CCGCCTGGCATTATGCCCAGTACATGACCTTATGGGACTTTCCTACTT
GGCAGTACATCTACGTATTAGTCATCGCTATTACCATGGTGATGCGGT
TTTGGCAGTACATCAATGGGCGTGGATAGCGGTTTGACTCACGGGGA
TTTCCAAGTCTCCACCCCATTGACGTCAATGGGAGTTTGTTTTGGCAC

FIG. 95B

CAAAATCAACGGGACTTTCCAAAATGTCGTAACAACTCCGCCCCATTG
ACGCAAATGGGCGGTAGGCGTGTACGGTGGGAGGTCTATATAAGCAG
AGCTGGGTACGTCCTCACATTCAGTGATCAGCACTGAACACAGACCC
GTCGACATGGGTTGGAGCCTCATCTTGCTCTTCCTTGTCGCTGTTGCTA
CGCGTGTCGCTAGCACCAAGGGCCCATCGGTCTTCCCCCTGGCACCCT
CCTCCAAGAGCACCTCTGGGGGCACAGCGGCCCTGGGCTGCCTGGTC
AAGGACTACTTCCCCGAACCGGTGACGGTGTCGTGGAACTCAGGCGC
CCTGACCAGCGGCGTGCACACCTTCCCGGCTGTCCTACAGTCCTCAGG
ACTCTACTCCCTCAGCAGCGTGGTGACCGTGCCCTCCAGCAGCTTGGG
CACCCAGACCTACATCTGCAACGTGAATCACAAGCCCAGCAACACCA
AGGTGGACAAGAAAGCAGAGCCCAAATCTTGTGACAAAACTCACACA
TGCCCACCGTGCCCAGCACCTGAACTCCTGGGGGGACCGTCAGTCTTC
CTCTTCCCCCCAAAACCCAAGGACACCCTCATGATCTCCCGGACCCCT
GAGGTCACATGCGTGGTGGTGGACGTGAGCCACGAAGACCCTGAGGT
CAAGTTCAACTGGTACGTGGACGGCGTGGAGGTGCATAATGCCAAGA
CAAAGCCGCGGGAGGAGCAGTACAACAGCACGTACCGTGTGGTCAGC
GTCCTCACCGTCCTGCACCAGGACTGGCTGAATGGCAAGGACTACAA
GTGCAAGGTCTCCAACAAAGCCCTCCCAGCCCCCATCGAGAAAACCA
TCTCCAAAGCCAAAGGGCAGCCCCGAGAACCACAGGTGTACACCCTG
CCCCCATCCCGGGATGAGCTGACCAGGAACCAGGTCAGCCTGACCTG
CCTGGTCAAAGGCTTCTATCCCAGCGACATCGCCGTGGAGTGGGAGA
GCAATGGGCAGCCGGAGAACAACTACAAGACCACGCCTCCCGTGCTG
GACTCCGACGGCTCCTTCTTCCTCTACAGCAAGCTCACCGTGGACAAG
AGCAGGTGGCAGCAGGGGAACGTCTTCTCATGCTCCGTGATGCATGA
GGCTCTGCACAACCACTACACGCAGAAGAGCCTCTCCCTGTCTCCGGG
TAAATGAGGATCCGTTAACGGTTACCAACTACCTAGACTGGATTCGTG
ACAACATGCGGCCGTGATATCTACGTATGATCAGCCTCGACTGTGCCT
TCTAGTTGCCAGCCATCTGTTGTTTGCCCCTCCCCCGTGCCTTCCTTGA
CCCTGGAAGGTGCCACTCCCACTGTCCTTTCCTAATAAAATGAGGAAA
TTGCATCGCATTGTCTGAGTAGGTGTCATTCTATTCTGGGGGGTGGGG
TGGGGCAGGACAGCAAGGGGGAGGATTGGGAAGACAATAGCAGGCA
TGCTGGGGATGCGGTGGGCTCTATGGAACCAGCTGGGGCTCGACAGC
GCTGGATCTCCCGATCCCCAGCTTTGCTTCTCAATTTCTTATTTGCATA
ATGAGAAAAAAAGGAAAATTAATTTTAACACCAATTCAGTAGTTGAT
TGAGCAAATGCGTTGCCAAAAAGGATGCTTTAGAGACAGTGTTCTCT
GCACAGATAAGGACAAACATTATTCAGAGGGAGTACCCAGAGCTGAG
ACTCCTAAGCCAGTGAGTGGCACAGCATTCTAGGGAGAAATATGCTT
GTCATCACCGAAGCCTGATTCCGTAGAGCCACACCTTGGTAAGGGCC
AATCTGCTCACACAGGATAGAGAGGGCAGGAGCCAGGGCAGAGCAT
ATAAGGTGAGGTAGGATCAGTTGCTCCTCACATTTGCTTCTGACATAG
TTGTGTTGGGAGCTTGGATAGCTTGGACAGCTCAGG

FIG. 95C

GCTGCGATTTCGCGCCAAACTTGACGGCAATCCTAGCGTGAAGGCTG
GTAGGATTTTATCCCCGCTGCCATCATGGTTCGACCATTGAACTGCAT
CGTCGCCGTGTCCCAAAATATGGGGATTGGCAAGAACGGAGACCTAC
CCTGGCCTCCGCTCAGGAACGAGTTCAAGTACTTCCAAAGAATGACC
ACAACCTCTTCAGTGGAAGGTAAACAGAATCTGGTGATTATGGGTAG
GAAAACCTGGTTCTCCATTCCTGAGAACAATCGACCTTTAAAGGACA
GAATTAATATAGTTCTCAGTAGAGAACTCAAAGAACCACCACGAGGA
GCTCATTTTCTTGCCAAAAGTTTGGATGATGCCTTAAGACTTATTGAA
CAACCGGAATTGGCAAGTAAAGTAGACATGGTTTGGATAGTCGGAGG
CAGTTCTGTTTACCAGGAAGCCATGAATCAACCAGGCCACCTTAGACT
CTTTGTGACAAGGATCATGCAGGAATTTGAAAGTGACACGTTTTTCCC
AGAAATTGATTTGGGGAAATATAAACTTCTCCCAGAATACCCAGGCG
TCCTCTCTGAGGTCCAGGAGGAAAAAGGCATCAAGTATAAGTTTGAA
GTCTACGAGAAGAAAGACTAACAGGAAGATGCTTTCAAGTTCTCTGC
TCCCCTCCTAAAGTCATGCATTTTTATAAGACCATGGGACTTTTGCTG
GCTTTAGATCAGCCTCGACTGTGCCTTCTAGTTGCCAGCCATCTGTTGT
TTGCCCCTCCCCCGTGCCTTCCTTGACCCTGGAAGGTGCCACTCCCAC
TGTCCTTTCCTAATAAAATGAGGAAATTGCATCGCATTGTCTGAGTAG
GTGTCATTCTATTCTGGGGGGTGGGGTGGGGCAGGACAGCAAGGGGG
AGGATTGGGAAGACAATAGCAGGCATGCTGGGGATGCGGTGGGCTCT
ATGGAACCAGCTGGGGCTCGAGCTACTAGCTTTGCTTCTCAATTTCTT
ATTTGCATAATGAGAAAAAAAGGAAAATTAATTTTAACACCAATTCA
GTAGTTGATTGAGCAAATGCGTTGCCAAAAAGGATGCTTTAGAGACA
GTGTTCTCTGCACAGATAAGGACAAACATTATTCAGAGGGAGTACCC
AGAGCTGAGACTCCTAAGCCAGTGAGTGGCACAGCATTCTAGGGAGA
AATATGCTTGTCATCACCGAAGCCTGATTCCGTAGAGCCACACCTTGG
TAAGGGCCAATCTGCTCACACAGGATAGAGAGGGCAGGAGCCAGGG
CAGAGCATATAAGGTGAGGTAGGATCAGTTGCTCCTCACATTTGCTTC
TGACATAGTTGTGTTGGGAGCTTGGATCGATCCTCTATGGTTGAACAA
GATGGATTGCACGCAGGTTCTCCGGCCGCTTGGGTGGAGAGGCTATTC
GGCTATGACTGGGCACAACAGACAATCGGCTGCTCTGATGCCGCCGT
GTTCCGGCTGTCAGCGCAGGGGCGCCCGGTTCTTTTTGTCAAGACCGA
CCTGTCCGGTGCCCTGAATGAACTGCAGGACGAGGCAGCGCGGCTAT
CGTGGCTGGCCACGACGGGCGTTCCTTGCGCAGCTGTGCTCGACGTTG
TCACTGAAGCGGGAAGGGACTGGCTGCTATTGGGCGAAGTGCCGGGG
CAGGATCTCCTGTCATCTCACCTTGCTCCTGCCGAGAAAGTATCCATC
ATGGCTGATGCAATGCGGCGGCTGCATACGCTTGATCCGGCTACCTGC
CCATTCGACCACCAAGCGAAACATCGCATCGAGCGAGCACGTACTCG
GATGGAAGCCGGTCTTGTCGATCAGGATGATCTGGACGAAGAGCATC
AGGGGCTCGCGCCAGCCGAACTGTTCGCCAGGCTCAAGGCGCGCATG
CCCGACGGCGAGGATCTCGTCGTGACCCATGGCGATGCCTGCTTGCCG

FIG. 95D

AATATCATGGTGGAAAATGGCCGCTTTTCTGGATTCATCGACTGTGGC
CGGCTGGGTGTGGCGGACCGCTATCAGGACATAGCGTTGGCTACCCG
TGATATTGCTGAAGAGCTTGGCGGCGAATGGGCTGACCGCTTCCTCGT
GCTTTACGGTATCGCCGCTTCCCGATTCGCAGCGCATCGCCTTCTATC
GCCTTCTTGACGAGTTCTTCTGAGCGGGACTCTGGGGTTCGAAATGAC
CGACCAAGCGACGCCCAACCTGCCATCACGAGATTTCGATTCCACCG
CCGCCTTCTATGAAAGGTTGGGCTTCGGAATCGTTTTCCGGGACGCCG
GCTGGATGATCCTCCAGCGCGGGGATCTCATGCTGGAGTTCTTCGCCC
ACCCCAACTTGTTTATTGCAGCTTATAATGGTTACAAATAAAGCAATA
GCATCACAAATTTCACAAATAAAGCATTTTTTTCACTGCATTCTAGTT
GTGGTTTGTCCAAACTCATCAATCTATCTTATCATGTCTGGATCGCGG
CCGCGATCCCGTCGAGAGCTTGGCGTAATCATGGTCATAGCTGTTTCC
TGTGTGAAATTGTTATCCGCTCACAATTCCACACAACATACGAGCCGG
AGCATAAAGTGTAAAGCCTGGGGTGCCTAATGAGTGAGCTAACTCAC
ATTAATTGCGTTGCGCTCACTGCCCGCTTTCCAGTCGGGAAACCTGTC
GTGCCAGCTGCATTAATGAATCGGCCAACGCGCGGGGAGAGGCGGTT
TGCGTATTGGGCGCTCTTCCGCTTCCTCGCTCACTGACTCGCTGCGCTC
GGTCGTTCGGCTGCGGCGAGCGGTATCAGCTCACTCAAAGGCGGTAA
TACGGTTATCCACAGAATCAGGGGATAACGCAGGAAAGAACATGTGA
GCAAAAGGCCAGCAAAAGGCCAGGAACCGTAAAAAGGCCGCGTTGC
TGGCGTTTTTCCATAGGCTCCGCCCCCCTGACGAGCATCACAAAAATC
GACGCTCAAGTCAGAGGTGGCGAAACCCGACAGGACTATAAAGATAC
CAGGCGTTTCCCCCTGGAAGCTCCCTCGTGCGCTCTCCTGTTCCGACC
CTGCCGCTTACCGGATACCTGTCCGCCTTTCTCCCTTCGGGAAGCGTG
GCGCTTTCTCAATGCTCACGCTGTAGGTATCTCAGTTCGGTGTAGGTC
GTTCGCTCCAAGCTGGGCTGTGTGCACGAACCCCCCGTTCAGCCCGAC
CGCTGCGCCTTATCCGGTAACTATCGTCTTGAGTCCAACCCGGTAAGA
CACGACTTATCGCCACTGGCAGCAGCCACTGGTAACAGGATTAGCAG
AGCGAGGTATGTAGGCGGTGCTACAGAGTTCTTGAAGTGGTGGCCTA
ACTACGGCTACACTAGAAGGACAGTATTTGGTATCTGCGCTCTGCTGA
AGCCAGTTACCTTCGGAAAAAGAGTTGGTAGCTCTTGATCCGGCAAA
CAAACCACCGCTGGTAGCGGTGGTTTTTTTGTTTGCAAGCAGCAGATT
ACGCGCAGAAAAAAAGGATCTCAAGAAGATCCTTTGATCTTTTCTAC
GGGGTCTGACGCTCAGTGGAACGAAAACTCACGTTAAGGGATTTTGG
TCATGAGATTATCAAAAAGGATCTTCACCTAGATCCTTTTAAATTAAA
AATGAAGTTTTAAATCAATCTAAAGTATATATGAGTAAACTTGGTCTG
ACAGTTACCAATGCTTAATCAGTGAGGCACCTATCTCAGCGATCTGTC
TATTTCGTTCATCCATAGTTGCCTGACTCCCCGTCGTGTAGATAACTAC
GATACGGGAGGGCTTACCATCTGGCCCCAGTGCTGCAATGATACCGC
GAGACCCACGCTCACCGGCTCCAGATTTATCAGCAATAAACCAGCCA
GCCGGAAGGGCCGAGCGCAGAAGTGGTCCTGCAACTTTATCCGCCTC
CATCCAGTCTATTAATTGTTGCCGGGAAGCTAGAGTAAGTAGTTCGC

FIG. 95E

CAGTTAATAGTTTGCGCAACGTTGTTGCCATTGCTACAGGCATCGTGG
TGTCACGCTCGTCGTTTGGTATGGCTTCATTCAGCTCCGGTTCCCAAC
GATCAAGGCGAGTTACATGATCCCCCATGTTGTGCAAAAAAGCGGTT
AGCTCCTTCGGTCCTCCGATCGTTGTCAGAAGTAAGTTGGCCGCAGTG
TTATCACTCATGGTTATGGCAGCACTGCATAATTCTCTTACTGTCATGC
CATCCGTAAGATGCTTTTCTGTGACTGGTGAGTACTCAACCAAGTCAT
TCTGAGAATAGTGTATGCGGCGACCGAGTTGCTCTTGCCCGGCGTCAA
TACGGGATAATACCGCGCCACATAGCAGAACTTTAAAAGTGCTCATC
ATTGGAAAACGTTCTTCGGGGCGAAAACTCTCAAGGATCTTACCGCTG
TTGAGATCCAGTTCGATGTAACCCACTCGTGCACCCAACTGATCTTCA
GCATCTTTTACTTTCACCAGCGTTTCTGGGTGAGCAAAAACAGGAAGG
CAAAATGCCGCAAAAAAGGGAATAAGGGCGACACGGAAATGTTGAA
TACTCATACTCTTCCTTTTTCAATATTATTGAAGCATTTATCAGGGTTA
TTGTCTCATGAGCGGATACATATTTGAATGTATTTAGAAAAATAAACA
AATAGGGGTTCCGCGCACATTTCCCCGAAAAGTGCCACCT

FIG. 96A

GACGTCGCGGCCGCTCTAGGCCTCCAAAAAAGCCTCCTCACTACTTCT
GGAATAGCTCAGAGGCCGAGGCGGCCTCGGCCTCTGCATAAATAAAA
AAAATTAGTCAGCCATGCATGGGGCGGAGAATGGGCGGAACTGGGCG
GAGTTAGGGGCGGGATGGGCGGAGTTAGGGGCGGGACTATGGTTGCT
GACTAATTGAGATGCATGCTTTGCATACTTCTGCCTGCTGGGGAGCCT
GGGGACTTTCCACACCTGGTTGCTGACTAATTGAGATGCATGCTTTGC
ATACTTCTGCCTGCTGGGGAGCCTGGGGACTTTCCACACCCTAACTGA
CACACATTCCACAGAATTAATTCCCCTAGTTATTAATAGTAATCAATT
ACGGGGTCATTAGTTCATAGCCCATATATGGAGTTCCGCGTTACATAA
CTTACGGTAAATGGCCCGCCTGGCTGACCGCCCAACGACCCCCGCCC
ATTGACGTCAATAATGACGTATGTTCCCATAGTAACGCCAATAGGGA
CTTTCCATTGACGTCAATGGGTGGACTATTTACGGTAAACTGCCCACT
TGGCAGTACATCAAGTGTATCATATGCCAAGTACGCCCCCTATTGACG
TCAATGACGGTAAATGGCCCGCCTGGCATTATGCCCAGTACATGACCT
TATGGGACTTTCCTACTTGGCAGTACATCTACGTATTAGTCATCGCTA
TTACCATGGTGATGCGGTTTTGGCAGTACATCAATGGGCGTGGATACC
GGTTTGACTCACGCGGATTTCCAAGTCTCCACCCCATTGACGTCAATG
GGAGTTTGTTTTGGCACCAAAATCAACGGGACTTTCCAAAATGTCGTA
ACAACTCCGCCCCATTGACGCAAATGGGCGGTAGGCGTGTACGGTGG
GAGGTCTATATAAGCAGAGCTGGGTACGTGAACCGTCAGATCGCCTG
GAGACGCCATCACAGATCTCTCACTATGGATTTTCAGGTGCAGATTAT
CAGCTTCCTGCTAATCAGTGCTTCAGTCATAATGTCCAGAGGACAAAT
TGTTCTCTCCCAGTCTCCAGCAATCCTGTCTGCATCTCCAGGGGAGAA
GGTCACAATGACTTGCAGGGCCAGCTCAAGTGTAAGTTACATCCACT
GGTTCCAGCAGAAGCCAGGATCCTCCCCCAAACCCTGGATTTATGCCA
CATCCAACCTGGCTTCTGGAGTCCCTGTTCGCTTCAGTGGCAGTGGGT
CTGGGACTTCTTACTCTCTCACAATCAGCAGAGTGGAGGCTGAAGATG
CTGCCACTTATTACTGCCAGCAGTGGACTAGTAACCCACCCACGTTCG
GAGGGGGGACCAAGCTGGAAATCAAACGTACGGTGGCTGCACCATCT
GTCTTCATCTTCCCGCCATCTGATGAGCAGTTGAAATCTGGAACTGCC
TCTGTTGTGTGCCTGCTGAATAACTTCTATCCCAGAGAGGCCAAAGTA
CAGTGGAAGGTGGATAACGCCCTCCAATCGGGTAACTCCCAGGAGAG
TGTCACAGAGCAGGACAGCAAGGACAGCACCTACAGCCTCAGCAGCA
CCCTGACGCTGAGCAAAGCAGACTACGAGAAACACAAAGTCTACGCC
TGCGAAGTCACCCATCAGGGCCTGAGCTCGCCCGTCACAAAGAGCTT
CAACAGGGGAGAGTGTTGAATTCAGATCCGTTAACGGTTACCAACTA
CCTAGACTGGATTCGTGACAACATGCGGCCGTGATATCTACGTATGAT
CAGCCTCGACTGTGCCTTCTAGTTGCCAGCCATCTGTTGTTTGCCCCTC
CCCCGTGCCTTCCTTGACCCTGGAAGGTGCCACTCCCACTGTCCTTTCC

FIG. 96B

TAATAAAATGAGGAAATTGCATCGCATTGTCTGAGTAGGTGTCATTCT
ATTCTGGGGGGTGGGGTGGGGCAGGACAGCAAGGGGGAGGATTGGG
AAGACAATAGCAGGCATGCTGGGGATGCGGTGGGCTCTATGGAACCA
GCTGGGGCTCGACAGCTATGCCAAGTACGCCCCCTATTGACGTCAATG
ACGGTAAATGGCCCGCCTGGCATTATGCCCAGTACATGACCTTATGGG
ACTTTCCTACTTGGCAGTACATCTACGTATTAGTCATCGCTATTACCAT
GGTGATGCGGTTTTGGCAGTACATCAATGGGCGTGGATAGCGGTTTG
ACTCACGGGGATTTCCAAGTCTCCACCCCATTGACGTCAATGGGAGTT
TGTTTTGGCACCAAAATCAACGGGACTTTCCAAAATGTCGTAACAACT
CCGCCCCATTGACGCAAATGGGCGGTAGGCGTGTACGGTGGGAGGTC
TATATAAGCAGAGCTGGGTACGTCCTCACATTCAGTGATCAGCACTGA
ACACAGACCCGTCGACATGGGTTGGAGCCTCATCTTGCTCTTCCTTGT
CGCTGTTGCTACGCGTGTCCTGTCCCAGGTACAACTGCAGCAGCCTGG
GGCTGAGCTGGTGAAGCCTGGGGCCTCAGTGAAGATGTCCTGCAAGG
CTTCTGGCTACACATTTACCAGTTACAATATGCACTGGGTAAAACAGA
CACCTGGTCGGGGCCTGGAATGGATTGGAGCTATTTATCCCGGAAAT
GGTGATACTTCCTACAATCAGAAGTTCAAAGGCAAGGCCACATTGAC
TGCAGACAAATCCTCCAGCACAGCCTACATGCAGCTCAGCAGCCTGA
CATCTGAGGACTCTGCGGTCTATTACTGTGCAAGATCGACTTACTACG
GCGGTGACTGGTACTTCAATGTCTGGGGCGCAGGGACCACGGTCACC
GTCTCTGCAGCTAGCACCAAGGGCCCATCGGTCTTCCCCCTGGCACCC
TCCTCCAAGAGCACCTCTGGGGGCACAGCGGCCCTGGGCTGCCTGGT
CAAGGACTACTTCCCCGAACCGGTGACGGTGTCGTGGAACTCAGGCG
CCCTGACCAGCGGCGTGCACACCTTCCCGGCTGTCCTACAGTCCTCAG
GACTCTACTCCCTCAGCAGCGTGGTGACCGTGCCCTCCAGCAGCTTGG
GCACCCAGACCTACATCTGCAACGTGAATCACAAGCCCAGCAACACC
AAGGTGGACAAGAAAGCAGAGCCCAAATCTTGTGACAAAACTCACAC
ATGCCCACCGTGCCCAGCACCTGAACTCCTGGGGGGACCGTCAGTCTT
CCTCTTCCCCCCAAAACCCAAGGACACCCTCATGATCTCCCGGACCCC
TGAGGTCACATGCGTGGTGGTGGACGTGAGCCACGAAGACCCTGAGG
TCAAGTTCAACTGGTACGTGGACGGCGTGGAGGTGCATAATGCCAAG
ACAAAGCCGCGGGAGGAGCAGTACAACAGCACGTACCGTGTGGTCAG
CGTCCTCACCGTCCTGCACCAGGACTGGCTGAATGGCAAGGAGTACA
AGTGCAAGGTCTCCAACAAAGCCCTCCCAGCCCCCATCGAGAAAACC
ATCTCCAAAGCCAAAGGGCAGCCCCGAGAACCACAGGTGTACACCCT
GCCCCCATCCCGGGATGAGCTGACCAAGAACCAGGTCAGCCTGACCT
GCCTGGTCAAAGGCTTCTATCCCAGCGACATCGCCGTGGAGTGGGAG
AGCAATGGGCAGCCGGAGAACAACTACAAGACCACGCCTCCCGTGCT
GGACTCCGACGGCTCCTTCTTCCTCTACAGCAAGCTCACCGTGGACAA
GAGCAGGTGGCAGCAGGGGAACGTCTTCTCATGCTCCGTGATGCATG
AGGCTCTGCACAACCACTACACGCAGAAGAGCCTCTCCCTGTCTCCGG
GTAAATGAGGATCCGTTAACGGTTACCAACTACCTAGACTGGATTCGT

FIG. 96C

GACAACATGCGGCCGTGATATCTACGTATGATCAGCCTCGACTGTGCC
TTCTAGTTGCCAGCCATCTGTTGTTTGCCCCTCCCCCGTGCCTTCCTTG
ACCCTGGAAGGTGCCACTCCCACTGTCCTTTCCTAATAAAATGAGGAA
ATTGCATCGCATTGTCTGAGTAGGTGTCATTCTATTCTGGGGGGTGGG
GTGGGGCAGGACAGCAAGGGGGAGGATTGGGAAGACAATAGCAGGC
ATGCTGGGGATGCGGTGGGCTCTATGGAACCAGCTGGGGCTCGACAG
CGCTGGATCTCCCGATCCCCAGCTTTGCTTCTCAATTTCTTATTTGCAT
AATGAGAAAAAAAGGAAAATTAATTTTAACACCAATTCAGTAGTTGA
TTGAGCAAATGCGTTGCCAAAAAGGATGCTTTAGAGACAGTGTTCTCT
GCACAGATAAGGACAAACATTATTCAGAGGGAGTACCCAGAGCTGAG
ACTCCTAAGCCAGTGAGTGGCACAGCATTCTAGGGAGAAATATGCTT
GTCATCACCGAAGCCTGATTCCGTAGAGCCACACCTTGGTAAGGGCC
AATCTGCTCACACAGGATAGAGAGGGCAGGAGCCAGGGCAGAGCAT
ATAAGGTGAGGTAGGATCAGTTGCTCCTCACATTTGCTTCTGACATAG
TTGTGTTGGGAGCTTGGATAGCTTGGACAGCTCAGGGCTGCGATTTCG
CGCCAAACTTGACGGCAATCCTAGCGTGAAGGCTGGTAGGATTTTATC
CCCGCTGCCATCATGGTTCGACCATTGAACTGCATCGTCGCCGTGTCC
CAAAATATGGGGATTGGCAAGAACGGAGACCTACCCTGGCCTCCGCT
CAGGAACGAGTTCAAGTACTTCCAAAGAATGACCACAACCTCTTCAG
TGGAAGGTAAACAGAATCTGGTGATTATGGGTAGGAAAACCTGGTTC
TCCATTCCTGAGAAGAATCGACCTTTAAAGGACAGAATTAATATAGTT
CTCAGTAGAGAACTCAAAGAACCACCACGAGGAGCTCATTTTCTTGC
CAAAAGTTTGGATGATGCCTTAAGACTTATTGAACAACCGGAATTGG
CAAGTAAAGTAGACATGGTTTGGATAGTCGGAGGCAGTTCTGTTTACC
AGGAAGCCATGAATCAACCAGGCCACCTTAGACTCTTTGTGACAAGG
ATCATGCAGGAATTTGAAAGTGACACGTTTTTCCCAGAAATTGATTTG
GGGAAATATAAACTTCTCCCAGAATACCCAGGCGTCCTCTCTGA
GGTCCAGGAGGAAAAAGGCATCAAGTATAAGTTTGAAGTCTACGAGA
AGAAAGACTAACAGGAAGATGCTTTCAAGTTCTCTGCTCCCCTCCTAA
AGCTATGCATTTTTATAAGACCATGGGACTTTTGCTGGCTTTAGATCA
GCCTCGACTGTGCCTTCTAGTTGCCAGCCATCTGTTGTTTGCCCCTCCC
CCGTGCCTTCCTTGACCCTGGAAGGTGCCACTCCCACTGTCCTTTCCTA
ATAAAATGAGGAAATTGCATCGCATTGTCTGAGTAGGTGTCATTCTAT
TCTGGGGGGTGGGGTGGGGCAGGACAGCAAGGGGGAGGATTGGGAA
GACAATAGCAGGCATGCTGGGGATGCGGTGGGCTCTATGGAACCAGC
TGGGGCTCGAGCTACTAGCTTTGCTTCTCAATTTCTTATTTGCATAATG
AGAAAAAAAGGAAAATTAATTTTAACACCAATTCAGTAGTTGATTGA
GCAAATGCGTTGCCAAAAAGGATGCTTTAGAGACAGTGTTCTCTGCA
CAGATAAGGACAAACATTATTCAGAGGGAGTACCCAGAGCTGAGACT
CCTAAGCCAGTGAGTGGCACAGCATTCTAGGGAGAAATATGCTTGTC
ATCACCGAAGCCTGATTCCGTAGAGCCACACCTTGGTAAGGGCCAAT
CTGCTCACACAGGATAGAGAGGGCAGGAGCCAGGGCAGAGCATATA
AGGTGAGGTAGGATCAGTTGCTCCTCACATTTGCTTCTGACATAGTTG

FIG. 96D

TGTTGGGAGCTTGGATCGATCCTCTATGGTTGAACAAGATGGATTGCA
CGCAGGTTCTCCGGCCGCTTGGGTGGAGAGGCTATTCGGCTATGACTG
GGCACAACAGACAATCGGCTGCTCTGATGCCGCCGTGTTCCGGCTGTC
AGCGCAGGGGCGCCCGGTTCTTTTTGTCAAGACCGACCTGTCCGGTGC
CCTGAATGAACTGCAGGACGAGGCAGCGCGGCTATCGTGGCTGGCCA
CGACGGGCGTTCCTTGCGCAGCTGTGCTCGACGTTGTCACTGAAGCGG
GAAGGGACTGGCTGCTATTGGGCGAAGTGCCGGGGCAGGATCTCCTG
TCATCTCACCTTGCTCCTGCCGAGAAAGTATCCATCATGGCTGATGCA
ATGCGGCGGCTGCATACGCTTGATCCGGCTACCTGCCCATTCGACCAC
CAAGCGAAACATCGCATCGAGCGAGCACGTACTCGGATGGAAGCCGG
TCTTGTCGATCAGGATGATCTGGACGAAGAGCATCAGGGGCTCGCGC
CAGCCGAACTGTTCGCCAGGCTCAAGGCGCGCATGCCCGACGGCGAG
GATCTCGTCGTGACCCATGGCGATGCCTGCTTGCCGAATATCATGGTG
GAAAATGGCCGCTTTTCTGGATTCATCGACTGTGGCCGGCTGGGTGTG
GCGGACCGCTATCAGGACATAGCGTTGGCTACCCGTGATATTGCTGA
AGAGCTTGGCGGCGAATGGGCTGACCGCTTCCTCGTGCTTTACGGTAT
CGCCGCTCCCGATTCGCAGCGCATCGCCTTCTATCGCCTTCTTGACGA
GTTCTTCTGAGCGGGACTCTGGGGTTCGAAATGACCGACCAAGCGAC
GCCCAACCTGCCATCACGAGATTTCGATTCCACCGCCGCCTTCTATGA
AAGGTTGGGCTTCGGAATCGTTTTCCGGGACGCCGGCTGGATGATCCT
CCAGCGCGGGGATCTCATGCTGGAGTTCTTCGCCCACCCCAACTTGTT
TATTGCAGCTTATAATGGTTACAAATAAAGCAATAGCATCACAAATTT
CACAAATAAAGCATTTTTTTCACTGCATTCTAGTTGTGGTTTGTCCAA
ACTCATCAATCTATCTTATCATGTCTGGATCGCGGCCGCGATCCCGTC
GAGAGCTTGGCGTAATCATGGTCATAGCTGTTTCCTGTGTGAAATTGT
TATCCGCTCACAATTCCACACAACATACGAGCCGGAAGCATAAAGTG
TAAAGCCTGGGGTGCCTAATGAGTGAGCTAACTCACATTAATTGCGTT
GCGCTCACTGCCCGCTTTCCAGTCGGGAAACCTGTCGTGCCAGCTGCA
TTAATGAATCGGCCAACGCGCGGGGAGAGGCGGTTTGCGTATTGGGC
GCTCTTCCGCTTCCTCGCTCACTGACTCGCTGCGCTCGGTCGTTCGGCT
GCGGCGAGCGGTATCAGCTCACTCAAAGGCGGTAATACGGTTATCCA
CAGAATCAGGGGATAACGCAGGAAAGAACATGTGAGCAAAAGGCCA
GCAAAAGGCCAGGAACCGTAAAAAGGCCGCGTTGCTGGCGTTTTTCC
ATAGGCTCCGCCCCCCTGACGAGCATCACAAAAATCGACGCTCAAGT
CAGAGGTGGCGAAACCCGACAGGACTATAAAGATACCAGGCGTTTCC
CCCTGGAAGCTCCCTCGTGCGCTCTCCTGTTCCGACCCTGCCGCTTAC
CGGATACCTGTCCGCCTTTCTCCCTTCGGGAAGCGTGGCGCTTTCTCA
ATGCTCACGCTGTAGGTATCTCAGTTCGGTGTAGGTCGTTCGCTCCAA
GCTGGGCTGTGTGCACGAACCCCCCGTTCAGCCCGACCGCTGCGCCTT
ATCCGGTAACTATCGTCTTGAGTCCAACCCGGTAAGACACGACTTATC

FIG. 96E

GCCACTGGCAGCAGCCACTGGTAACAGGATTAGCAGAGCGAGGTATG
TAGGCGGTGCTACAGAGTTCTTGAAGTGGTGGCCTAACTACGGCTAC
ACTAGAAGGACAGTATTTGGTATCTGCGCTCTGCTGAAGCCAGTTACC
TTCGGAAAAAGAGTTGGTAGCTCTTGATCCGGCAAACAAACCACCGC
TGGTAGCGGTGGTTTTTTTGTTTGCAAGCAGCAGATTACGCGCAGAAA
AAAAGGATCTCAAGAAGATCCTTTGATCTTTTCTACGGGGTCTGACGC
TCAGTGGAACGAAAACTCACGTTAAGGGATTTTGGTCATGAGATTATC
AAAAAGGATCTTCACCTAGATCCTTTTAAATTAAAAATGAAGTTTTAA
ATCAATCTAAAGTATATATGAGTAAACTTGGTCTGACAGTTACCAATG
CTTAATCAGTGAGGCACCTATCTCAGCGATCTGTCTATTTCGTTCATCC
ATAGTTGCCTGACTCCCCGTCGTGTAGATAACTACGATACGGGAGGG
CTTACCATCTGGCCCCAGTGCTGCAATGATACCGCGAGACCCACGCTC
ACCGGCTCCAGATTTATCAGCAATAAACCAGCCAGCCGGAAGGGCCG
AGCGCAGAAGTGGTCCTGCAACTTTATCCGCCTCCATCCAGTCTATTA
ATTGTTGCCGGGAAGCTAGAGTAAGTAGTTCGCCAGTTAATAGTTTGC
GCAACGTTGTTGCCATTGCTACAGGCATCGTGGTGTCACGCTCGTCGT
TTGGTATGGCTTCATTCAGCTCCGGTTCCCAACGATCAAGGCGAGTTA
CATGATCCCCCATGTTGTGCAAAAAAGCGGTTAGCTCCTTCGGTCCTC
CGATCGTTGTCAGAAGTAAGTTGGCCGCAGTGTTATCACTCATGGTTA
TGGCAGCACTGCATAATTCTCTTACTGTCATGCCATCCGTAAGATGCT
TTTCTGTGACTGGTGAGTACTCAACCAAGTCATTCTGAGAATAGTGTA
TGCGGCGACCGAGTTGCTCTTGCCCGGCGTCAATACGGGATAATACC
GCGCCACATAGCAGAACTTTAAAAGTGCTCATCATTGGAAAACGTTCT
TCGGGGCGAAAACTCTCAAGGATCTTACCGCTGTTGAGATCCAGTTCG
ATGTAACCCACTCGTGCACCCAACTGATCTTCAGCATCTTTTACTTTCA
CCAGCGTTTCTGGGTGAGCAAAAACAGGAAGGCAAAATGCCGCAAAA
AAGGGAATAAGGGCGACACGGAAATGTTGAATACTCATACTCTTCCT
TTTTCAATATTATTGAAGCATTTATCAGGGTTATTGTCTCATGAGCGG
ATACATATTTGAATGTATTTAGAAAAATAAACAAATAGGGGTTCCGC
GCACATTTCCCCGAAAAGTGCCACCT

GLYCOPEGYLATION METHODS AND PROTEINS/PEPTIDES PRODUCED BY THE METHODS

CROSS REFERENCE TO RELATED APPLICATIONS

This application is a Continuation of U.S. application Ser. No. 10/552,896 filed Jun. 8, 2006, now abandoned, which is a U.S. National Phase of PCT Application No. PCT/US2004/011494 filed Apr. 9, 2004, which application claims priority under 35 USC §120 to U.S. application Ser. No. 10/411,012 filed Apr. 9, 2003, issued as U.S. Pat. No. 7,265,084, U.S. application Ser. No. 10/411,026 filed Apr. 9, 2003, issued as U.S. Pat. No. 7,795,210, U.S. application Ser. No. 10/410,962 filed Apr. 9, 2003, issued as U.S. Pat. No. 7,173,003, U.S. application Ser. No. 10/411,049 filed Apr. 9, 2003, issued as U.S. Pat. No. 7,297,511, U.S. application Ser. No. 10/410,930 filed Apr. 9, 2003, issued as U.S. Pat. No. 7,226,903, U.S. application Ser. No. 10/410,897 filed Apr. 9, 2003, issued as U.S. Pat. No. 7,179,617, U.S. application Ser. No. 10/410,997 filed Apr. 9, 2003, issued as U.S. Pat. No. 7,157,277, U.S. application Ser. No. 10/411,044 filed Apr. 9, 2003, U.S. application Ser. No. 10/410,980 filed Apr. 9, 2003, issued as U.S. Pat. No. 7,399,613, U.S. application Ser. No. 10/410,945 filed Apr. 9, 2003, issued as U.S. Pat. No. 7,214,660, U.S. application Ser. No. 10/410,913 filed Apr. 9, 2003, issued as U.S. Pat. No. 7,265,085, U.S. application Ser. No. 10/411,037 filed Apr. 9, 2003, issued as U.S. Pat. No. 7,125,843, and U.S. application Ser. No. 10/411,043 filed Apr. 9, 2003, issued as U.S. Pat. No. 7,439,043, each of which is incorporated herein by reference in its entirety for all purposes.

BACKGROUND OF THE INVENTION

Most naturally occurring peptides contain carbohydrate moieties attached to the peptide via specific linkages to a select number of amino acids along the length of the primary peptide chain. Thus, many naturally occurring peptides are termed "glycopeptides." The variability of the glycosylation pattern on any given peptide has enormous implications for the function of that peptide. For example, the structure of the N-linked glycans on a peptide can impact various characteristics of the peptide, including the protease susceptibility, intracellular trafficking, secretion, tissue targeting, biological half-life and antigenicity of the peptide in a cell or organism. The alteration of one or more of these characteristics greatly affects the efficacy of a peptide in its natural setting, and also affects the efficacy of the peptide as a therapeutic agent in situations where the peptide has been generated for that purpose.

The carbohydrate structure attached to the peptide chain is known as a "glycan" molecule. The specific glycan structure present on a peptide affects the solubility and aggregation characteristics of the peptide, the folding of the primary peptide chain and therefore its functional or enzymatic activity, the resistance of the peptide to proteolytic attack and the control of proteolysis leading to the conversion of inactive forms of the peptide to active forms. Importantly, terminal sialic acid residues present on the glycan molecule affect the length of the half life of the peptide in the mammalian circulatory system. Peptides whose glycans do not contain terminal sialic acid residues are rapidly removed from the circulation by the liver, an event which negates any potential therapeutic benefit of the peptide.

The glycan structures found in naturally occurring glycopeptides are typically divided into two classes, N-linked and O-linked glycans.

Peptides expressed in eukaryotic cells are typically N-glycosylated on asparagine residues at sites in the peptide primary structure containing the sequence asparagine-X-serine/threonine where X can be any amino acid except proline and aspartic acid. The carbohydrate portion of such peptides is known as an N-linked glycan. The early events of N-glycosylation occur in the endoplasmic reticulum (ER) and are identical in mammals, plants, insects and other higher eukaryotes. First, an oligosaccharide chain comprising fourteen sugar residues is constructed on a lipid carrier molecule. As the nascent peptide is translated and translocated into the ER, the entire oligosaccharide chain is transferred to the amide group of the asparagine residue in a reaction catalyzed by a membrane bound glycosyltransferase enzyme. The N-linked glycan is further processed both in the ER and in the Golgi apparatus. The further processing generally entails removal of some of the sugar residues and addition of other sugar residues in reactions catalyzed by glycosidases and glycosyltransferases specific for the sugar residues removed and added.

Typically, the final structures of the N-linked glycans are dependent upon the organism in which the peptide is produced. For example, in general, peptides produced in bacteria are completely unglycosylated. Peptides expressed in insect cells contain high mannose and paunci-mannose N-linked oligosaccharide chains, among others. Peptides produced in mammalian cell culture are usually glycosylated differently depending, e.g., upon the species and cell culture conditions. Even in the same species and under the same conditions, a certain amount of heterogeneity in the glycosyl chains is sometimes encountered. Further, peptides produced in plant cells comprise glycan structures that differ significantly from those produced in animal cells. The dilemma in the art of the production of recombinant peptides, particularly when the peptides are to be used as therapeutic agents, is to be able to generate peptides that are correctly glycosylated, i.e., to be able to generate a peptide having a glycan structure that resembles, or is identical to that present on the naturally occurring form of the peptide. Most peptides produced by recombinant means comprise glycan structures that are different from the naturally occurring glycans.

A variety of methods have been proposed in the art to customize the glycosylation pattern of a peptide including those described in WO 99/22764, WO 98/58964, WO 99/54342 and U.S. Pat. No. 5,047,335, among others. Essentially, many of the enzymes required for the in vitro glycosylation of peptides have been cloned and sequenced. In some instances, these enzymes have been used in vitro to add specific sugars to an incomplete glycan molecule on a peptide. In other instances, cells have been genetically engineered to express a combination of enzymes and desired peptides such that addition of a desired sugar moiety to an expressed peptide occurs within the cell.

Peptides may also be modified by addition of O-linked glycans, also called mucin-type glycans because of their prevalence on mucinous glycopeptide. Unlike N-glycans that are linked to asparagine residues and are formed by en bloc transfer of oligosaccharide from lipid-bound intermediates, O-glycans are linked primarily to serine and threonine residues and are formed by the stepwise addition'of sugars from nucleotide sugars (Tanner et al., *Biochim. Biophys. Acta.* 906:81-91 (1987); and Hounsell et al., *Glycoconj. J* 13:19-26 (1996)). Peptide function can be affected by the structure of the O-linked glycans present thereon. For example, the activity of P-selectin ligand is affected by the O-linked glycan structure present thereon. For a review of O-linked glycan structures, see Schachter and Brockhausen, The Biosynthesis of Branched O-Linked Glycans, 1989, Society for Experimental Biology, pp. 1-26 (Great Britain). Other glycosylation patterns are formed by linking glycosylphosphatidylinositol to the carboxyl-terminal carboxyl group of the protein (Takeda et al., *Trends Biochem. Sci.* 20:367-371 (1995); and Udenfriend et al., *Ann. Rev. Biochem.* 64:593-591 (1995).

Although various techniques currently exist to modify the N-linked glycans of peptides, there exists in the art the need for a generally applicable method of producing peptides having a desired, i.e., a customized glycosylation pattern. There is a particular need in the art for the customized in vitro glycosylation of peptides, where the resulting peptide can be produced at industrial scale. This and other needs are met by the present invention.

The administration of glycosylated and non-glycosylated peptides for engendering a particular physiological response is well known in the medicinal arts. Among the best known peptides utilized for this purpose is insulin, which is used to treat diabetes. Enzymes have also been used for their therapeutic benefits. A major factor, which has limited the use of therapeutic peptides is the immunogenic nature of most peptides. In a patient, an immunogenic response to an administered peptide can neutralize the peptide and/or lead to the development of an allergic response in the patient. Other deficiencies of therapeutic peptides include suboptimal potency and rapid clearance rates. The problems inherent in peptide therapeutics are recognized in the art, and various methods of eliminating the problems have been investigated. To provide soluble peptide therapeutics, synthetic polymers have been attached to the peptide backbone.

Poly(ethylene glycol) ("PEG") is an exemplary polymer that has been conjugated to peptides. The use of PEG to derivatize peptide therapeutics has been demonstrated to reduce the immunogenicity of the peptides and prolong the clearance time from the circulation. For example, U.S. Pat. No. 4,179,337 (Davis et al.) concerns non-immunogenic peptides, such as enzymes and peptide hormones coupled to polyethylene glycol (PEG) or polypropylene glycol. Between 10 and 100 moles of polymer are used per mole peptide and at least 15% of the physiological activity is maintained.

WO 93/15189 (Veronese et al.) concerns a method to maintain the activity of polyethylene glycol-modified proteolytic enzymes by linking the proteolytic enzyme to a macromolecularized inhibitor. The conjugates are intended for medical applications.

The principal mode of attachment of PEG, and its derivatives, to peptides is a non-specific bonding through a peptide amino acid residue. For example, U.S. Pat. No. 4,088,538 discloses an enzymatically active polymer-enzyme conjugate of an enzyme covalently linked to PEG. Similarly, U.S. Pat. No. 4,496,689 discloses a covalently attached complex of α-1 protease inhibitor with a polymer such as PEG or methoxypoly(ethylene glycol) ("mPEG"). Abuchowski et al. (*J. Biol. Chem.* 252: 3578 (1977) discloses the covalent attachment of mPEG to an amine group of bovine serum albumin. U.S. Pat. No. 4,414,147 discloses a method of rendering interferon less hydrophobic by conjugating it to an anhydride of a dicarboxylic acid, such as poly(ethylene succinic anhydride). PCT WO 87/00056 discloses conjugation of PEG and poly(oxyethylated) polyols to such proteins as interferon-β, interleukin-2 and immunotoxins. EP 154,316 discloses and claims chemically modified lymphokines, such as IL-2 containing PEG bonded directly to at least one primary amino group of the lymphokine. U.S. Pat. No. 4,055,635 discloses pharmaceutical compositions of a water-soluble complex of a proteolytic enzyme linked covalently to a polymeric substance such as a polysaccharide.

Another mode of attaching PEG to peptides is through the non-specific oxidation of glycosyl residues on a peptide. The oxidized sugar is utilized as a locus for attaching a PEG moiety to the peptide. For example, M'Timkulu (WO 94/05332) discloses the use of a hydrazine- or amino-PEG to add PEG to a glycoprotein. The glycosyl moieties are randomly oxidized to the corresponding aldehydes, which are subsequently coupled to the amino-PEG. See also, Bona et al. (WO 96/40731), where a PEG is added to an immunoglobulin molecule by enzymatically oxidizing a glycan on the immunoglobulin and then contacting the glycan with an amino-PEG molecule.

In each of the methods described above, poly(ethylene glycol) is added in a random, non-specific manner to reactive residues on a peptide backbone. For the production of therapeutic peptides, it is clearly desirable to utilize a derivatization strategy that results in the formation of a specifically labeled, readily characterizable, essentially homogeneous product.

Two principal classes of enzymes are used in the synthesis of carbohydrates, glycosyltransferases (e.g., sialyltransferases, oligosaccharyltransferases, N-acetylglucosaminyltransferases), and glycosidases. The glycosidases are further classified as exoglycosidases (e.g., β-mannosidase, β-glucosidase), and endoglycosidases (e.g., Endo-A, Endo-M). Each of these classes of enzymes has been successfully used synthetically to prepare carbohydrates. For a general review, see, Crout et al., *Curr. Opin. Chem. Biol.* 2: 98-111 (1998).

Glycosyltransferases modify the oligosaccharide structures on peptides. Glycosyltransferases are effective for producing specific products with good stereochemical and regiochemical control. Glycosyltransferases have been used to prepare oligosaccharides and to modify terminal N- and O-linked carbohydrate structures, particularly on peptides produced in mammalian cells. For example, the terminal oligosaccharides of glycopeptides have been completely sialylated and/or fucosylated to provide more consistent sugar structures, which improves glycopeptide pharmacodynamics and a variety of other biological properties. For example, β-1,4-galactosyltransferase is used to synthesize lactosamine, an illustration of the utility of glycosyltransferases in the synthesis of carbohydrates (see, e.g., Wong et al., *J. Org. Chem.* 47: 5416-5418 (1982)). Moreover, numerous synthetic procedures have made use of α-sialyltransferases to transfer sialic acid from cytidine-5'-monophospho-N-acetylneuraminic acid to the 3-OH or 6-OH of galactose (see, e.g., Kevin et al., *Chem. Eur. J.* 2: 1359-1362 (1996)). Fucosyltransferases are used in synthetic pathways to transfer a fucose unit from guanosine-5'-diphosphofucose to a specific hydroxyl of a saccharide acceptor. For example, Ichikawa prepared sialyl Lewis-X by a method that involves the fucosylation of sialylated lactosamine with a cloned fucosyltransferase (Ichikawa et al., *J. Am. Chem. Soc.* 114: 9283-9298 (1992)). For a discussion of recent advances in glycoconjugate synthesis for therapeutic use see, Koeller et al., *Nature Biotechnology* 18: 835-841 (2000). See also, U.S. Pat. Nos. 5,876,980; 6,030,815; 5,728,554; 5,922,577; and WO/9831826.

Glycosidases can also be used to prepare saccharides. Glycosidases normally catalyze the hydrolysis of a glycosidic bond. However, under appropriate conditions, they can be used to form this linkage. Most glycosidases used for carbohydrate synthesis are exoglycosidases; the glycosyl transfer occurs at the non-reducing terminus of the substrate. The glycosidase binds a glycosyl donor in a glycosyl-enzyme intermediate that is either intercepted by water to yield the hydrolysis product, or by an acceptor, to generate a new glycoside or oligosaccharide. An exemplary pathway using an exoglycosidase is the synthesis of the core trisaccharide of all N-linked glycopeptides, including the β-mannoside linkage, which is formed by the action of β-mannosidase (Singh et al., *Chem. Commun.* 993-994 (1996)).

In another exemplary application of the use of a glycosidase to form a glycosidic linkage, a mutant glycosidase has been prepared in which the normal nucleophilic amino acid within the active site is changed to a non-nucleophilic amino acid. The mutant enzyme does not hydrolyze glycosidic linkages, but can still form them. Such a mutant glycosidase is used to prepare oligosaccharides using an α-glycosyl fluoride donor and a glycoside acceptor molecule (Withers et al., U.S. Pat. No. 5,716,812).

Although their use is less common than that of the exoglycosidases, endoglycosidases are also utilized to prepare carbohydrates. Methods based on the use of endoglycosidases have the advantage that an oligosaccharide, rather than a monosaccharide, is transferred. Oligosaccharide fragments have been added to substrates using endo-β-N-acetylglucosamines such as endo-F, endo-M (Wang et al., *Tetrahedron Lett.* 37: 1975-1978); and Haneda et al., *Carbohydr. Res.* 292: 61-70 (1996)).

In addition to their use in preparing carbohydrates, the enzymes discussed above are applied to the synthesis of glycopeptides as well. The synthesis of a homogenous glycoform of ribonuclease B has been published (Witte K. et al., J. Am. Chem. Soc. 119: 2114-2118 (1997)). The high mannose core of ribonuclease B was cleaved by treating the glycopeptide with endoglycosidase H. The cleavage occurred specifically between the two core GlcNAc residues. The tetrasaccharide sialyl Lewis X was then enzymatically rebuilt on the remaining GlcNAc anchor site on the now homogenous protein by the sequential use of β-1,4-galactosyltransferase, α-2, 3-sialyltransferase and α-1,3-fucosyltransferase V. However, while each enzymatically catalyzed step proceeded in excellent yield, such procedures have not been adapted for the generation of glycopeptides on an industrial scale.

Methods combining both chemical and enzymatic synthetic elements are also known in the art. For example, Yamamoto and coworkers (*Carbohydr. Res.* 305: 415-422 (1998)) reported the chemoenzymatic synthesis of the glycopeptide, glycosylated Peptide T, using an endoglycosidase. The N-acetylglucosaminyl peptide was synthesized by purely chemical means. The peptide was subsequently enzymatically elaborated with the oligosaccharide of human transferrin peptide. The saccharide portion was added to the peptide by treating it with an endo-β-N-acetylglucosaminidase. The resulting glycosylated peptide was highly stable and resistant to proteolysis when compared to the peptide T and N-acetylglucosaminyl peptide T.

The use of glycosyltransferases to modify peptide structure with reporter groups has been explored. For example, Brossmer et al. (U.S. Pat. No. 5,405,753) discloses the formation of a fluorescent-labeled cytidine monophosphate ("CMP") derivative of sialic acid and the use of the fluorescent glycoside in an assay for sialyl transferase activity and for the fluorescent-labeling of cell surfaces, glycoproteins and peptides. Gross et al. (*Analyt. Biochem.* 186: 127 (1990)) describe a similar assay. Bean et al. (U.S. Pat. No. 5,432,059) discloses an assay for glycosylation deficiency disorders utilizing reglycosylation of a deficiently glycosylated protein. The deficient protein is reglycosylated with a fluorescent-labeled CMP glycoside. Each of the fluorescent sialic acid derivatives is substituted with the fluorescent moiety at either the 9-position or at the amine that is normally acetylated in sialic acid. The methods using the fluorescent sialic acid derivatives are assays for the presence of glycosyltransferases or for non-glycosylated or improperly glycosylated glycoproteins. The assays are conducted on small amounts of enzyme or glycoprotein in a sample of biological origin. The enzymatic derivatization of a glycosylated or non-glycosylated peptide on a preparative or industrial scale using a modified sialic acid has not been disclosed or suggested in the prior art.

Considerable effort has also been directed towards the modification of cell surfaces by altering glycosyl residues presented by those surfaces. For example, Fukuda and coworkers have developed a method for attaching glycosides of defined structure onto cell surfaces. The method exploits the relaxed substrate specificity of a fucosyltransferase that can transfer fucose and fucose analogs bearing diverse glycosyl substrates (Tsuboi et al., *J. Biol. Chem.* 271: 27213 (1996)).

Enzymatic methods have also been used to activate glycosyl residues on a glycopeptide towards subsequent chemical elaboration. The glycosyl residues are typically activated using galactose oxidase, which converts a terminal galactose residue to the corresponding aldehyde. The aldehyde is subsequently coupled to an amine-containing modifying group. For example, Casares et al. (*Nature Biotech.* 19: 142 (2001)) have attached doxorubicin to the oxidized galactose residues of a recombinant MHCII-peptide chimera.

Glycosyl residues have also been modified to contain ketone groups. For example, Mahal and co-workers (*Science* 276: 1125 (1997)) have prepared N-levulinoyl mannosamine ("ManLev"), which has a ketone functionality at the position normally occupied by the acetyl group in the natural substrate. Cells were treated with the ManLev, thereby incorporating a ketone group onto the cell surface. See, also Saxon et al., *Science* 287: 2007 (2000); Hang et al., *J. Am. Chem. Soc.* 123: 1242 (2001); Yarema et al., *J. Biol. Chem.* 273: 31168 (1998); and Charter et al., *Glycobiology* 10: 1049 (2000).

The methods of modifying cell surfaces have not been applied in the absence of a cell to modify a glycosylated or non-glycosylated peptide. Further, the methods of cell surface modification are not utilized for the enzymatic incorporation preformed modified glycosyl donor moiety into a peptide. Moreover, none of the cell surface modification methods are practical for producing glycosyl-modified peptides on an industrial scale.

Despite the efforts directed toward the enzymatic elaboration of saccharide structures, there remains still a need for an industrially practical method for the modification of glycosylated and non-glycosylated peptides with modifying groups such as water-soluble polymers, therapeutic moieties, biomolecules and the like. Of particular interest are methods in which the modified peptide has improved properties, which enhance its use as a therapeutic or diagnostic agent. The present invention fulfills these and other needs.

SUMMARY OF THE INVENTION

The invention includes a multitude of methods of remodeling a peptide to have a specific glycan structure attached thereto. Although specific glycan structures are described herein, the invention should not be construed to be limited to any one particular structure. In addition, although specific peptides are described herein, the invention should not be limited by the nature of the peptide described, but rather should encompass any and all suitable peptides and variations thereof.

The description which follows discloses the preferred embodiments of the invention and provides a written description of the claims appended hereto. The invention encompasses any and all variations of these embodiments that are or become apparent following a reading of the present specification.

The invention includes a cell-free, in vitro method of remodeling a peptide comprising poly(ethylene glycol), the peptide having the formula:

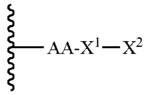

wherein

AA is a terminal or internal amino acid residue of the peptide;

$X^1$-$X^2$ is a saccharide covalently linked to the AA, wherein $X^1$ is a first glycosyl residue; and $X^2$ is a second glycosyl residue covalently linked to $X^1$, wherein $X^1$ and $X^2$ are selected from monosaccharyl and oligosaccharyl residues;

the method comprising:

(a) removing $X^2$ or a saccharyl subunit thereof from the peptide, thereby forming a truncated glycan.

In one aspect, the invention further comprises formation of a truncated glycan by removing a Sia residue.

In one embodiment of the invention, a peptide has the formula:

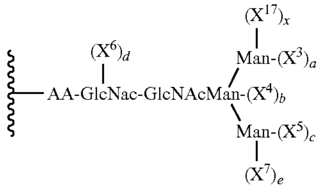

wherein $X^3$, $X^4$, $X^5$, $X^6$, $X^7$, and $X^{17}$, are independently selected monosaccharyl or oligosaccharyl residues; and a, b, c, d, e, and x are independently selected from the integers 0, 1 and 2.

In one aspect of the invention, an oligosaccharyl residue is a member selected from GlcNAc-Gal-Sia and GlcNAc-Gal. In another aspect, at least one oligosaccharide member is selected from a, b, c, d, e and x is 1 or 2. In yet another aspect, the removing of step (a) produces a truncated glycan in which at least one of a, b, c, e and x are 0.

The invention includes a method of remodeling a peptide wherein $X^3$, $X^5$ and $X^7$ are members independently selected from (mannose), and (mannose)$_z$-($X^8$)

wherein $X^8$ is a glycosyl moiety selected from mono- and oligosaccharides; and z is an integer between 1 and 20, wherein when z is 3 or greater, each (mannose)$_z$ is independently selected from linear and branched structures.

In one aspect, $X^4$ is selected from the group consisting of GlcNAc and xylose. In another aspect, $X^3$, $X^5$ and $X^7$ are (mannose)$_u$, wherein u is selected from the integers between 1 and 20, and when u is 3 or greater, each (mannose)$_u$ is independently selected from linear and branched structures.

The invention also includes a method of remodeling a peptide, wherein the peptide has the formula:

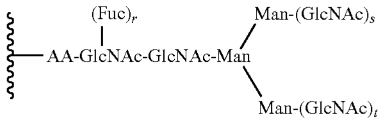

wherein r, s, and t are integers independently selected from 0 and 1.

In an embodiment of the invention, a peptide has the formula:

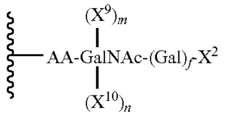

wherein $X^9$ and $X^{10}$ are independently selected monosaccharyl or oligosaccharyl residues and m, n and f are integers independently selected from 0 and 1.

In one aspect, a peptide has the formula:

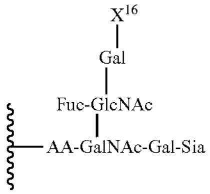

wherein $X^{16}$ is a member selected from:

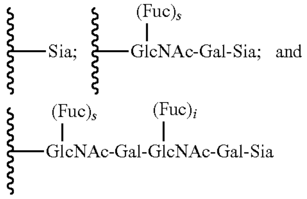

wherein s and i are integers independently selected from 0 and 1.

In another aspect, a peptide has the formula:

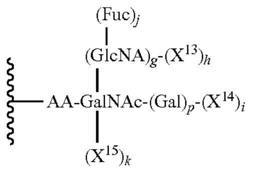

wherein $X^{13}$, $X^{14}$, and $X^{15}$ are independently selected glycosyl residues; and g, h, i, j, k, and p are independently selected from the integers 0 and 1.

In yet another aspect of the invention, at least one of g, h, i, j, k and p is 1. In another aspect, $X^{14}$ and $X^{15}$ are members independently selected from GlcNAc and Sia and i and k are independently selected from the integers 0 and 1. In still another aspect, at least one of i and k is 1, and if k is 1, g, h, and j are 0.

The invention also includes a method of remodeling a peptide, wherein the method comprises contacting the truncated glycan with at least one glycosyltransferase and at least one glycosyl donor under conditions suitable to transfer the at least one glycosyl donor to the truncated glycan, thereby remodeling the peptide comprising poly(ethylene glycol).

In one aspect, a glycosyl donor comprises a modifying group covalently linked thereto.

The invention also includes a method of remodeling a peptide, the method comprising removing $X^1$, thereby exposing AA. In one aspect, a method includes contacting AA with at least one glycosyltransferase and at least one glycosyl donor under conditions suitable to transfer said at least one glycosyl donor to AA, thereby remodeling said peptide comprising poly(ethylene glycol).

In one aspect, at least one glycosyl donor comprises a modifying group covalently linked thereto. In another aspect, a modifying group is poly(ethylene glycol). In one embodiment, a poly(ethylene glycol) has a molecular weight distribution that is essentially homodisperse.

The invention includes a method of remodeling a peptide, wherein, prior to contacting the truncated glycan with at least one glycosyltransferase and at least one glycosyl donor under conditions suitable to transfer the at least one glycosyl donor to the truncated glycan, thereby remodeling the peptide comprising poly(ethylene glycol), a group added to the saccharide during post-translational modification is removed.

In one aspect, a removed group is a member selected from phosphate, sulfate, carboxylate and esters thereof.

The invention includes a method of remodeling a peptide wherein a peptide has the formula:

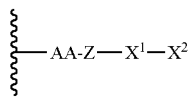

wherein

Z is a member selected from O, S, NH and a cross-linker.

The invention also includes a method of remodeling a peptide, wherein the peptide has the formula:

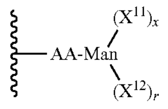

wherein $X^{11}$ and $X^{12}$ are independently selected glycosyl moieties; and r and x are integers independently selected from 0 and 1.

In one aspect of the invention, $X^{11}$ and $X^{12}$ are $(mannose)_q$, wherein q is selected from the integers between 1 and 20, and when q is three or greater, $(mannose)_q$ is selected from linear and branched structures.

The invention includes a pharmaceutical composition comprising a pharmaceutically acceptable diluent and a remodeled peptide according to a cell-free, in vitro method of remodeling a peptide comprising poly(ethylene glycol), the peptide having the formula:

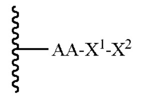

wherein

AA is a terminal or internal amino acid residue of the peptide;

$X^1$-$X^2$ is a saccharide covalently linked to the AA, wherein $X^1$ is a first glycosyl residue; and $X^2$ is a second glycosyl residue covalently linked to $X^1$, wherein $X^1$ and $X^2$ are selected from monosaccharyl and oligosaccharyl residues;

the method comprising:

(a) removing $X^2$ or a saccharyl subunit thereof from the peptide, thereby forming a truncated glycan.

The invention also includes a cell-free, in vitro method of remodeling a peptide comprising poly(ethylene glycol), the peptide having the formula:

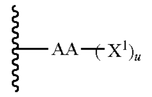

wherein

AA is a terminal or internal amino acid residue of the peptide;

$X^1$ is a glycosyl residue covalently linked to the AA, selected from monosaccharyl and oligosaccharyl residues; and u is an integer selected from 0 and 1, the method comprising:

contacting the peptide with at least one glycosyltransferase and at least one glycosyl donor under conditions suitable to transfer at least one glycosyl donor to the truncated glycan, thereby remodeling the peptide.

In one aspect, at least one glycosyl donor comprises a modifying group covalently linked thereto. In another aspect, the modifying group is poly(ethylene glycol). In yet another aspect, the poly(ethylene glycol) has a molecular weight distribution that is essentially homodisperse.

The invention also includes a pharmaceutical composition comprising a pharmaceutically acceptable diluent and a remodeled peptide according to a cell-free, in vitro method of remodeling a peptide comprising poly(ethylene glycol), the peptide having the formula:

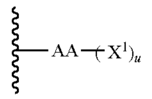

wherein

AA is a terminal or internal amino acid residue of the peptide;

$X^1$ is a glycosyl residue covalently linked to the AA, selected from monosaccharyl and oligosaccharyl residues; and u is an integer selected from 0 and 1, the method comprising:

contacting the peptide with at least one glycosyltransferase and at least one glycosyl donor under conditions suitable to transfer at least one glycosyl donor to the truncated glycan, thereby remodeling the peptide.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIG. 14, comprising

FIG. 18, comprising

FIG. 19, comprising

FIG. 23, comprising FIG. 23A is a scheme that illustrates addition of a PEGylated sugar, followed by the addition of a non-modified sugar. FIG. 23B is a scheme that illustrates the addition of more that one kind of modified sugar onto one glycan. FIG. 23C is a scheme that illustrates the addition of different modified sugars onto O-linked glycans and N-linked glycans.

FIG. 28, comprising FIG. 28A to FIG. 28Z and FIG. 28AA to FIG. 28CC, is a list of peptides useful in the methods of the invention.

FIG. 29, comprising FIGS. 29A to 29G, provides exemplary schemes for remodeling glycan structures on granulocyte colony stimulating factor (G-CSF). FIG. 29A is a diagram depicting the G-CSF peptide indicating the amino acid residue to which a glycan is bonded, and an exemplary glycan formula linked thereto. FIGS. 29B to 29G are diagrams of contemplated remodeling steps of the glycan of the peptide in FIG. 29A based on the type of cell the peptide is expressed in and the desired remodeled glycan structure.

FIG. 30, comprising FIGS. 30A to 30EE sets forth exemplary schemes for remodeling glycan structures on interferon-alpha. FIG. 30A is a diagram depicting the interferon-alpha isoform 14c peptide indicating the amino acid residue to which a glycan is bonded, and an exemplary glycan formula linked thereto. FIGS. 30B to 30D are diagrams of contemplated remodeling steps of the glycan of the peptide in FIG. 30A based on the type of cell the peptide is expressed in and the desired remodeled glycan structure. FIGS. 30F to 30N are diagrams of contemplated remodeling steps of the glycan of the peptide in FIG. 30E based on the type of cell the peptide is expressed in and the desired remodeled glycan structure. FIG. 30O is a diagram depicting the interferon-alpha isoform 2a or 2b peptides indicating the amino acid residue to which a glycan is linked, and an exemplary glycan formula linked thereto. FIGS. 30P to 30W are diagrams of contemplated remodeling steps of the glycan of the peptide in FIG. 30O based on the type of cell the peptide is expressed in and the desired remodeled glycan structure. FIGS. 30Y to 30AA are diagrams of contemplated remodeling steps of the glycan of the peptides in FIG. 30X based on the type of cell the peptide is expressed in and the desired remodeled glycan structure. FIG. 30BB is a diagram depicting the interferon-alpha-mucin fusion peptides and interferon-alpha peptides indicating the residue(s) which bind to glycans contemplated for remodeling, and formulas for the glycans. FIG. 30CC to 30EE are diagrams of contemplated remodeling steps of the glycan of the peptides in FIG. 30BB based on the type of cell the peptide is expressed in and the desired remodeled glycan structure.

FIG. 31, comprising FIGS. 31A to 31S, sets forth exemplary schemes for remodeling glycan structures on interferon-beta. FIG. 31A is a diagram depicting the interferon-beta peptide indicating the amino acid residue to which a glycan is linked, and an exemplary glycan formula linked thereto. FIGS. 31B to 31O are diagrams of contemplated remodeling steps of the glycan of the peptide in FIG. 31A based on the type of cell the peptide is expressed in and the desired remodeled glycan structure. FIG. 31P is a diagram depicting the interferon-beta peptide indicating the amino acid residue to which a glycan is linked, and an exemplary glycan formula linked thereto. FIGS. 31Q to 31S are diagrams of contemplated remodeling steps of the glycan of the peptide in FIG. 31P based on the type of cell the peptide is expressed in and the desired remodeled glycan structure.

FIG. 32, comprising FIGS. 32A to 32D, sets forth exemplary schemes for remodeling glycan structures on Factor VII and Factor VIIa. FIG. 32A is a diagram depicting the Factor-VII and Factor-VIIa peptides A (solid line) and B (dotted line) indicating the residues which bind to glycans contemplated for remodeling, and the formulas for the glycans. FIGS. 32B to 32D are diagrams of contemplated remodeling steps of the glycan of the peptide in FIG. 32A based on the type of cell the peptide is expressed in and the desired remodeled glycan structure.

FIG. 33, comprising FIGS. 33A to 33G, sets forth exemplary schemes for remodeling glycan structures on Factor IX. FIG. 33A is a diagram depicting the Factor-IX peptide indicating residues which bind to glycans contemplated for remodeling, and formulas of the glycans. FIGS. 33B to 33G are diagrams of contemplated remodeling steps of the glycan of the peptide in FIG. 33A based on the type of cell the peptide is expressed in and the desired remodeled glycan structure.

FIG. 34, comprising FIGS. 34A to 34J, sets forth exemplary schemes for remodeling glycan structures on follicle stimulating hormone (FSH), comprising α and β subunits. FIG. 34A is a diagram depicting the Follicle Stimulating Hormone peptides FSHα and FSHβ indicating the residues which bind to glycans contemplated for remodeling, and exemplary glycan formulas linked thereto. FIGS. 34B to 34J are diagrams of contemplated remodeling steps of the glycan of the peptides in FIG. 34A based on the type of cell the peptides are expressed in and the desired remodeled glycan structures.

FIG. 35, comprising FIGS. 35A to 35AA, sets forth exemplary schemes for remodeling glycan structures on Erythropoietin (EPO). FIG. 35A is a diagram depicting the EPO peptide indicating the residues which bind to glycans contemplated for remodeling, and formulas for the glycans. FIGS. 35B to 35S are diagrams of contemplated remodeling steps of the glycan of the peptide in FIG. 35A based on the type of cell the peptide is expressed in and the desired remodeled glycan structure. FIGS. 35U to 35W are diagrams of contemplated remodeling steps of the glycan of the peptide in FIG. 35T based on the type of cell the peptide is expressed in and the desired remodeled glycan structure. FIG. 35X is a diagram depicting the EPO peptide indicating the residues which bind to glycans contemplated for remodeling, and formulas for the glycans. FIGS. 35Y to 35AA are diagrams of contemplated remodeling steps of the glycan of the peptide in FIG. 35X based on the type of cell the peptide is expressed in and the desired remodeled glycan structure.

FIG. 36, comprising FIGS. 36A to 36K sets forth exemplary schemes for remodeling glycan structures on Granulocyte-Macrophage Colony Stimulating Factor (GM-CSF). FIG. 36A is a diagram depicting the GM-CSF peptide indicating the residues which bind to glycans contemplated for remodeling, and formulas for the glycans. FIGS. 36B to 36G are diagrams of contemplated remodeling steps of the glycan of the peptide in FIG. 36A based on the type of cell the peptide is expressed in and the desired remodeled glycan structure. FIG. 36H is a diagram depicting the GM-CSF peptide indicating the residues which bind to glycans contemplated for remodeling, and formulas for the glycans. FIGS. 36I to 36K are diagrams of contemplated remodeling steps of the glycan of the peptide in FIG. 36H based on the type of cell the peptide is expressed in and the desired remodeled glycan structure.

FIG. 37, comprising FIGS. 37A to 37N, sets forth exemplary schemes for remodeling glycan structures on interferon-gamma. FIG. 37A is a diagram depicting an interferon-gamma peptide indicating the residues which bind to glycans contemplated for remodeling, and exemplary glycan formulas linked thereto. FIGS. 37B to 37G are diagrams of contemplated remodeling steps of the peptide in FIG. 37A based on the type of cell the peptide is expressed in and the desired remodeled glycan structure. FIG. 37H is a diagram depicting an interferon-gamma peptide indicating the residues which bind to glycans contemplated for remodeling, and exemplary glycan formulas linked thereto. FIGS. 37I to 37N are diagrams of contemplated remodeling steps of the peptide in FIG. 37H based on the type of cell the peptide is expressed in and the desired remodeled glycan structure.

FIG. 38, comprising FIGS. 38A to 38N, sets forth exemplary schemes for remodeling glycan structures on $\alpha_1$-antitrypsin (ATT, or $\alpha$-1 protease inhibitor). FIG. 38A is a diagram depicting an AAT peptide indicating the residues which bind to glycans contemplated for remodeling, and exemplary glycan formulas linked thereto. FIGS. 38B to 38F are diagrams of contemplated remodeling steps of the glycan of the peptide in FIG. 38A based on the type of cell the peptide is expressed in and the desired remodeled glycan structure. FIG. 38G is a diagram depicting an AAT peptide indicating the residues which bind to glycans contemplated for remodeling, and exemplary glycan formulas linked thereto. FIGS. 38H to 38J are diagrams of contemplated remodeling steps of the peptide in FIG. 38G based on the type of cell the peptide is expressed in and the desired remodeled glycan structure. FIG. 38K is a diagram depicting an AAT peptide indicating the residues which bind to glycans contemplated for remodeling, and exemplary glycan formulas linked thereto. FIGS. 38L to 38N are diagrams of contemplated remodeling steps of the peptide in FIG. 38K based on the type of cell the peptide is expressed in and the desired remodeled glycan structure.

FIG. 39, comprising FIGS. 39A to 39J sets forth exemplary schemes for remodeling glycan structures on glucocerebrosidase. FIG. 39A is a diagram depicting the glucocerebrosidase peptide indicating the residues which bind to glycans contemplated for remodeling, and exemplary glycan formulas linked thereto. FIGS. 39B to 39F are diagrams of contemplated remodeling steps of the glycan of the peptide in FIG. 39A based on the type of cell the peptide is expressed in and the desired remodeled glycan structure. FIG. 39G is a diagram depicting the glucocerebrosidase peptide indicating the residues which bind to glycans contemplated for remodeling, and exemplary glycan formulas linked thereto. FIGS. 39H to 39J are diagrams of contemplated remodeling steps of the glycan of the peptide in FIG. 39G based on the type of cell the peptide is expressed in and the desired remodeled glycan structure.

FIG. 40, comprising FIGS. 40A to 40W, sets forth exemplary schemes for remodeling glycan structures on Tissue-Type Plasminogen Activator (TPA). FIG. 40A is a diagram depicting the TPA peptide indicating the residues which bind to glycans contemplated for remodeling, and formulas for the glycans. FIGS. 40B to 40G are diagrams of contemplated remodeling steps of the peptide in FIG. 40A based on the type of cell the peptide is expressed in and the desired remodeled glycan structure. FIG. 40H is a diagram depicting the TPA peptide indicating the residues which bind to glycans contemplated for remodeling, and formulas for the glycans. FIGS. 40I to 40K are diagrams of contemplated remodeling steps of the peptide in FIG. 40H based on the type of cell the peptide is expressed in and the desired remodeled glycan structure. FIG. 40L is a diagram depicting a mutant TPA peptide indicating the residues which bind to glycans contemplated for remodeling, and the formula for the glycans. FIGS. 40M to 40O are diagrams of contemplated remodeling steps of the peptide in FIG. 40L based on the type of cell the peptide is expressed in and the desired remodeled glycan structure. FIG. 40P is a diagram depicting a mutant TPA peptide indicating the residues which bind to glycans contemplated for remodeling, and formulas for the glycans. FIGS. 40Q to 40S are diagrams of contemplated remodeling steps of the peptide in FIG. 40P based on the type of cell the peptide is expressed in and the desired remodeled glycan structure. FIG. 40T is a diagram depicting a mutant TPA peptide indicating the residues which links to glycans contemplated for remodeling, and formulas for the glycans. FIGS. 40U to 40W are diagrams of contemplated remodeling steps of the peptide in FIG. 40T based on the type of cell the peptide is expressed in and the desired remodeled glycan structure.

FIG. 41, comprising FIGS. 41A to 41G, sets forth exemplary schemes for remodeling glycan structures on Interleukin-2 (IL-2).

FIG. 42, comprising FIGS. 42A to 42M, sets forth exemplary schemes for remodeling glycan structures on Factor VIII. FIG. 42A are the formulas for the glycans that bind to the N-linked glycosylation sites (A and A') and to the O-linked sites (B) of the Factor VIII peptides. FIGS. 42B to 42F are diagrams of contemplated remodeling steps of the peptides in FIG. 42A based on the type of cell the peptide is expressed in and the desired remodeled glycan structure. FIG. 42G are the formulas for the glycans that bind to the N-linked glycosylation sites (A and A') and to the O-linked sites (B) of the Factor VIII peptides. FIGS. 42H to 42M are diagrams of contemplated remodeling steps of the peptides in FIG. 42G based on the type of cell the peptide is expressed in and the desired remodeled glycan structures.

FIG. 43, comprising FIGS. 43A to 43L, sets forth exemplary schemes for remodeling glycan structures on urokinase. FIGS. 43B to 43F are diagrams of contemplated remodeling steps of the peptide in FIG. 43A based on the type of cell the peptide is expressed in and the desired remodeled glycan structure. FIG. 43G is a diagram depicting the urokinase peptide indicating a residue which is linked to a glycan contemplated for remodeling, and an exemplary glycan formula linked thereto. FIGS. 43H to 43L are diagrams of contemplated remodeling steps of the peptide in FIG. 43G based on the type of cell the peptide is expressed in and the desired remodeled glycan structure.

FIG. 44, comprising FIGS. 44A to 44J, sets forth exemplary schemes for remodeling glycan structures on human DNase (hDNase). FIGS. 44B to 44F are diagrams of contemplated remodeling steps of the peptide in FIG. 44A based on the type of cell the peptide is expressed in and the desired remodeled glycan structure. FIG. 44G is a diagram depicting the human DNase peptide indicating residues which bind to glycans contemplated for remodeling, and exemplary glycan formulas linked thereto. FIGS. 44H to 44J are diagrams of contemplated remodeling steps of the peptide in FIG. 44F based on the type of cell the peptide is expressed in and the desired remodeled glycan structure.

FIG. 45, comprising FIGS. 45A to 45L, sets forth exemplary schemes for remodeling glycan structures on insulin. FIGS. 45B to 45D are diagrams of contemplated remodeling steps of the peptide in FIG. 45A based on the type of cell the peptide is expressed in and the desired remodeled glycan structure. FIGS. 45F to 45H are diagrams of contemplated remodeling steps of the peptide in FIG. 45E based on the type of cell the peptide is expressed in and the desired remodeled glycan structure. FIGS. 45J to 45L are diagrams of contemplated remodeling steps of the peptide in FIG. 45I based on the type of cell the peptide is expressed in and the desired remodeled glycan structure.

FIG. 46, comprising FIGS. 46A to 46K, sets forth exemplary schemes for remodeling glycan structures on the M-antigen (preS and S) of the Hepatitis B surface protein (HbsAg). FIGS. 46B to 46G are diagrams of contemplated remodeling steps of the peptide in FIG. 46A based on the type of cell the peptide is expressed in and the desired remodeled glycan structure. FIGS. 46I to 46K are diagrams of contemplated remodeling steps of the peptide in FIG. 46H based on the type of cell the peptide is expressed in and the desired remodeled glycan structure.

FIG. 47, comprising FIGS. 47A to 47K, sets forth exemplary schemes for remodeling glycan structures on human growth hormone, including N, V and variants thereof. FIG. 47A is a diagram depicting the human growth hormone peptide indicating a residue which is linked to a glycan contemplated for remodeling, and an exemplary glycan formula linked thereto. FIGS. 47B to 47D are diagrams of contemplated remodeling steps of the glycan of the peptide in FIG. 47A based on the type of cell the peptide is expressed in and the desired remodeled glycan structure. FIG. 47E is a diagram depicting the three fusion peptides comprising the human growth hormone peptide and part or all of a mucin peptide, and indicating a residue(s) which is linked to a glycan contemplated for remodeling, and exemplary glycan formula (s) linked thereto. FIGS. 47F to 47K are diagrams of contemplated remodeling steps of the glycan of the peptides in FIG. 47E based on the type of cell the peptide is expressed in and the desired remodeled glycan structure.

FIG. 48, comprising FIGS. 48A to 48G, sets forth exemplary schemes for remodeling glycan structures on a TNF Receptor-IgG Fc region fusion protein (Enbrel™). FIG. 48A is a diagram depicting a TNF Receptor-IgG Fc region fusion peptide which may be mutated to contain additional N-glycosylation sites indicating the residues which bind to glycans contemplated for remodeling, and formulas for the glycans. The TNF receptor peptide is depicted in bold line, and the IgG Fc regions is depicted in regular line. FIGS. 48B to 48G are diagrams of contemplated remodeling steps of the peptide in FIG. 48A based on the type of cell the peptide is expressed in and the desired remodeled glycan structure.

FIG. 49, comprising FIGS. 49A to 49D, sets forth exemplary schemes for remodeling glycan structures on an anti-HER2 monoclonal antibody (Herceptin™). FIGS. 49B to 49D are diagrams of contemplated remodeling steps of the glycan of the peptides in FIG. 49A based on the type of cell the peptide is expressed in and the desired remodeled glycan structure.

FIG. 50, comprising FIGS. 50A to 50D, sets forth exemplary schemes for remodeling glycan structures on a monoclonal antibody to Protein F of Respiratory Syncytial Virus (Synagis™). FIGS. 50B to 50D are diagrams of contemplated remodeling steps of the peptide in FIG. 50A based on the type of cell the peptide is expressed in and the desired remodeled glycan structure.

FIG. 51, comprising FIGS. 51A to 51D, sets forth exemplary schemes for remodeling glycan structures on a monoclonal antibody to TNF-α (Remicade™). FIGS. 51B to 51D are diagrams of contemplated remodeling steps of the peptide in FIG. 51A based on the type of cell the peptide is expressed in and the desired remodeled glycan structure.

FIG. 52, comprising FIGS. 52A to 52L, sets forth exemplary schemes for remodeling glycan structures on a monoclonal antibody to glycoprotein IIb/IIIa (Reopro™) FIG. 52A is a diagram depicting a mutant monoclonal antibody to glycoprotein IIb/IIIa peptides which have been mutated to contain an N-glycosylation site(s) indicating the residue(s) which bind to glycans contemplated for remodeling, and exemplary glycan formulas linked thereto. FIGS. 52B to 52D are diagrams of contemplated remodeling steps based on the type of cell the peptide is expressed in and the desired remodeled glycan structure. FIGS. 52F to 52H are diagrams of contemplated remodeling steps based on the type of cell the peptide is expressed in and the desired remodeled glycan structure. FIGS. 52J to 52L are diagrams of contemplated remodeling steps based on the type of cell the peptide is expressed in and the desired remodeled glycan structure.

FIG. 53, comprising FIGS. 53A to 53G, sets forth exemplary schemes for remodeling glycan structures on a monoclonal antibody to CD20 (Rituxan™). FIGS. 53B to 53D are diagrams of contemplated remodeling steps of the glycan of the peptides in FIG. 53A based on the type of cell the peptide is expressed in and the desired remodeled glycan structure. FIG. 53E is a diagram depicting monoclonal antibody to CD20 which has been mutated to contain an N-glycosylation site(s) indicating the residue(s) which is linked to glycans contemplated for remodeling, and exemplary glycan formulas linked thereto. FIGS. 53F to 53G are diagrams of contemplated remodeling steps of the glycan of the peptides in FIG. 53E based on the type of cell the peptide is expressed in and the desired remodeled glycan structure.

FIG. 54, comprising FIGS. 54A to 54O, sets forth exemplary schemes for remodeling glycan structures on anti-thrombin III (AT III). FIG. 54A is a diagram depicting the anti-thrombin III peptide indicating the amino acid residues to which an N-linked glycan is linked, and an exemplary glycan formula linked thereto. FIGS. 54B to 54G are diagrams of contemplated remodeling steps of the glycan of the peptide in FIG. 54A based on the type of cell the peptide is expressed in and the desired remodeled glycan structure. FIGS. 54I to 54K are diagrams of contemplated remodeling steps of the glycan of the peptide in FIG. 54H based on the type of cell the peptide is expressed in and the desired remodeled glycan structure. FIG. 54L is a diagram depicting the anti-thrombin III peptide indicating the amino acid residues to which an N-linked glycan is linked, and an exemplary glycan formula linked thereto. FIGS. 54M to 54O are diagrams of contemplated remodeling steps of the glycan of the peptide in FIG. 54L based on the type of cell the peptide is expressed in and the desired remodeled glycan structure.

FIG. 55, comprising FIGS. 55A to 55J, sets forth exemplary schemes for remodeling glycan structures on subunits α and β of human Chorionic Gonadotropin (hCG). FIG. 55A is a diagram depicting the hCGα and hCGβ peptides indicating the residues which bind to N-linked glycans (A) and O-linked glycans (B) contemplated for remodeling, and formulas for the glycans. FIGS. 55B to 55J are diagrams of contemplated remodeling steps based on the type of cell the peptide is expressed in and the desired remodeled glycan structure.

FIG. 56, comprising FIGS. 56A to 56J, sets forth exemplary schemes for remodeling glycan structures on alpha-galactosidase (Fabrazyme™). FIG. 56A is a diagram depicting the alpha-galactosidase A peptide indicating the amino acid residues which bind to N-linked glycans (A) contemplated for remodeling, and formulas for the glycans. FIGS. 56B to 56J are diagrams of contemplated remodeling steps based on the type of cell the peptide is expressed in and the desired remodeled glycan structure.

FIG. 57, comprising FIGS. 57A to 57J, sets forth exemplary schemes for remodeling glycan structures on alpha-iduronidase (Aldurazyme™). FIG. 57A is a diagram depicting the alpha-iduronidase peptide indicating the amino acid residues which bind to N-linked glycans (A) contemplated for remodeling, and formulas for the glycans. FIGS. 57B to 57J are diagrams of contemplated remodeling steps based on the type of cell the peptide is expressed in and the desired remodeled glycan structure.

FIG. 58, comprising FIGS. 58A and 58B, is an exemplary nucleotide and corresponding amino acid sequence of granulocyte colony stimulating factor (G-CSF) (SEQ ID NOS: 1 and 2, respectively).

FIGS. 59A and 59B are an exemplary nucleotide and corresponding amino acid sequence of interferon alpha (IFN-alpha) (SEQ ID NOS. 3 and 4, respectively).

FIGS. 59C and 59D are an exemplary nucleotide and corresponding amino acid sequence of interferon omega (IFN-omega) (SEQ ID NOS. 74 and 76, respectively).

FIG. 60, comprising FIGS. 60A and 60B, is an exemplary nucleotide and corresponding amino acid sequence of interferon beta (IFN-beta) (SEQ ID NOS: 5 and 6, respectively).

FIG. 61, comprising FIGS. 61A and 61B, is an exemplary nucleotide and corresponding amino acid sequence of Factor VIIa (SEQ ID NOS: 7 and 8, respectively).

FIG. 62, comprising FIGS. 62A and 62B, is an exemplary nucleotide and corresponding amino acid sequence of Factor IX (SEQ ID NOS: 9 and 10, respectively).

FIG. 63, comprising FIGS. 63A through 63D, is an exemplary nucleotide and corresponding amino acid sequence of the alpha and beta chains of follicle stimulating hormone (FSH), respectively (SEQ ID NOS: 11 through 14, respectively).

FIG. 64, comprising FIGS. 64A and 64B, is an exemplary nucleotide and corresponding amino acid sequence of erythropoietin (EPO) (SEQ ID NOS: 15 and 16, respectively).

FIG. 65 is an amino acid sequence of mature EPO, i.e. 165 amino acids (SEQ ID NO:73).

FIG. 66, comprising FIGS. 66A and 66B, is an exemplary nucleotide and corresponding amino acid sequence of granulocyte-macrophage colony stimulating factor (GM-CSF) (SEQ ID NOS: 17 and 18, respectively).

FIG. 67, comprising FIGS. 67A and 67B, is an exemplary nucleotide and corresponding amino acid sequence of interferon gamma (IFN-gamma) (SEQ ID NOS: 19 and 20, respectively).

FIG. 68, comprising FIGS. 68A and 68B, is an exemplary nucleotide and corresponding amino acid sequence of α-1-protease inhibitor (A-1-PI, or α-antitrypsin) (SEQ ID NOS: 21 and 22, respectively).

FIG. 69, comprising FIGS. 69A-1 to 69A-2, and 69B, is an exemplary nucleotide and corresponding amino acid sequence of glucocerebrosidase (SEQ ID NOS: 23 and 24, respectively).

FIG. 70, comprising FIGS. 70A and 70B, is an exemplary nucleotide and corresponding amino acid sequence of tissue-type plasminogen activator (TPA) (SEQ ID NOS: 25 and 26, respectively).

FIG. 71, comprising FIGS. 71A and 71B, is an exemplary nucleotide and corresponding amino acid sequence of Interleukin-2 (IL-2) (SEQ ID NOS: 27 and 28, respectively).

FIG. 72, comprising FIGS. 72A-1 through 72A-4 and FIGS. 72B-1 through 72B-4, is an exemplary nucleotide and corresponding amino acid sequence of Factor VIII (SEQ ID NOS: 29 and 30, respectively).

FIG. 73, comprising FIGS. 73A and 73B, is an exemplary nucleotide and corresponding amino acid sequence of urokinase (SEQ ID NOS: 33 and 34, respectively).

FIG. 74, comprising FIGS. 74A and 74B, is an exemplary nucleotide and corresponding amino acid sequence of human recombinant DNase (hrDNase) (SEQ ID NOS: 39 and 40, respectively).

FIG. 75, comprising FIGS. 75A and 75B, is an exemplary nucleotide and corresponding amino acid sequence of an insulin molecule (SEQ ID NOS: 43 and 44, respectively).

FIG. 76, comprising FIGS. 76A and 76B, is an exemplary nucleotide and corresponding amino acid sequence of S-protein from a Hepatitis B virus (HbsAg) (SEQ ID NOS: 45 and 46, respectively).

FIG. 77, comprising FIGS. 77A and 77B, is an exemplary nucleotide and corresponding amino acid sequence of human growth hormone (hGH) (SEQ ID NOS: 47 and 48, respectively).

FIG. 78, comprising FIGS. 78A and 78B, are exemplary nucleotide and corresponding amino acid sequences of anti-thrombin III. FIGS. 78A and 78B, are an exemplary nucleotide and corresponding amino acid sequences of "WT" anti-thrombin III (SEQ ID NOS: 63 and 64, respectively).

FIG. 79, comprising FIGS. 79A to 79D, are exemplary nucleotide and corresponding amino acid sequences of human chorionic gonadotropin (hCG) α and β subunits. FIGS. 79A and 79B are an exemplary nucleotide and corresponding amino acid sequence of the α-subunit of human chorionic gonadotropin (SEQ ID NOS: 69 and 70, respectively). FIGS. 79C and 79D are an exemplary nucleotide and corresponding amino acid sequence of the beta subunit of human chorionic gonadotrophin (SEQ ID NOS: 71 and 72, respectively).

FIG. 80, comprising FIGS. 80A and 80B, is an exemplary nucleotide and corresponding amino acid sequence of α-iduronidase (SEQ ID NOS: 65 and 66, respectively).

FIG. 81, comprising FIGS. 81A and 81B, is an exemplary nucleotide and corresponding amino acid sequence of α-galactosidase A (SEQ ID NOS: 67 and 68, respectively).

FIG. 82, comprising FIGS. 82A and 82B, is an exemplary nucleotide and corresponding amino acid sequence of the 75 kDa tumor necrosis factor receptor (TNF-R), which comprises a portion of Enbrel™ (tumor necrosis factor receptor (TNF-R)/IgG fusion) (SEQ ID NOS: 31 and 32, respectively).

FIG. 83, comprising FIGS. 83A and 83B, is an exemplary amino acid sequence of the light and heavy chains, respectively, of Herceptin™ (monoclonal antibody (MAb) to Her-2, human epidermal growth factor receptor) (SEQ ID NOS: 35 and 36, respectively).

FIG. 84, comprising FIGS. 84A and 84B, is an exemplary amino acid sequence the heavy and light chains, respectively, of Synagis™ (MAb to F peptide of Respiratory Syncytial Virus) (SEQ ID NOS: 37 and 38, respectively).

FIG. 85, comprising FIGS. 85A and 85B, is an exemplary nucleotide and corresponding amino acid sequence of the non-human variable regions of Remicade™ (MAb to TNFα) (SEQ ID NOS: 41 and 42, respectively).

FIG. 86, comprising FIGS. 86A and 86B, is an exemplary nucleotide and corresponding amino acid sequence of the Fc portion of human IgG (SEQ ID NOS: 49 and 50, respectively).

FIG. 87 is an exemplary amino acid sequence of the mature variable region light chain of an anti-glycoprotein IIb/IIIa murine antibody (SEQ ID NO: 52).

FIG. 88 is an exemplary amino acid sequence of the mature variable region heavy chain of an anti-glycoprotein IIb/IIIa murine antibody (SEQ ID NO: 54).

FIG. 89 is an exemplary amino acid sequence of variable region light chain of a human IgG (SEQ ID NO: 51).

FIG. 90 is an exemplary amino acid sequence of variable region heavy chain of a human IgG (SEQ ID NO:53).

FIG. 91 is an exemplary amino acid sequence of a light chain of a human IgG (SEQ ID NO:55).

FIG. 92 is an exemplary amino acid sequence of a heavy chain of a human IgG (SEQ ID NO:56).

FIG. 93, comprising FIGS. 93A and 93B, is an exemplary nucleotide and corresponding amino acid sequence of the mature variable region of the light chain of an anti-CD20 murine antibody (SEQ ID NOS: 59 and 60, respectively).

FIG. 94, comprising FIGS. 94A and 94B, is an exemplary nucleotide and corresponding amino acid sequence of the mature variable region of the heavy chain of an anti-CD20 murine antibody (SEQ ID NOS: 61 and 62, respectively).

FIG. 95, comprising FIGS. 95A through 95E, is the nucleotide sequence of the tandem chimeric antibody expression vector TCAE 8 (SEQ ID NO:57).

FIG. 96, comprising FIGS. 96A through 96E, is the nucleotide sequence of the tandem chimeric antibody expression vector TCAE 8 containing the light and heavy variable domains of the anti-CD20 murine antibody (SEQ ID NO:58).

FIG. 97, comprising FIG. 97A depicts the analysis of the DEAE antibody sample. FIG. 97B depicts the analysis of the SPA antibody sample. FIG. 97C depicts the analysis of the Fc antibody sample. The percent area under the peaks for these graphs is summarized in Table 14.

FIG. 98, comprising FIG. 98A depicts the analysis of the DEAE antibody sample. FIG. 98B depicts the analysis of the SPA antibody sample. FIG. 98C depicts the analysis of the Fc antibody sample.

FIG. 99, comprising FIG. 99B depicts the analysis of the DEAE antibody sample. FIG. 99C depicts the analysis of the SPA antibody sample. FIG. 99D depicts the analysis of the Fc antibody sample. The percent area under the peaks for these graphs is summarized in Table 15.

FIG. 100, comprising FIG. 100B depicts the analysis of the DEAE antibody sample. FIG. 100C depicts the analysis of the SPA antibody sample. FIG. 100D depicts the analysis of the Fc antibody sample. The percent area under the peaks for these graphs is summarized in Table 16.

FIG. 101, comprising FIG. 101A depicts the analysis of the DEAE antibody sample. FIG. 101B depicts the analysis of the SPA antibody sample. FIG. 101C depicts the analysis of the Fc antibody sample. The percent area under the peaks for these graphs is summarized in Table 16

FIG. 102, comprising FIG. 102A depicts the analysis of the DEAE antibody sample. FIG. 102B depicts the analysis of the SPA antibody sample. FIG. 102C depicts the analysis of the Fc antibody sample.

FIG. 103, comprising FIG. 103B depicts the analysis of the DEAE antibody sample. FIG. 103C depicts the analysis of the SPA antibody sample. FIG. 103D depicts the analysis of the Fc antibody sample. The percent area under the peaks for these graphs is summarized in Table 17.

FIG. 104, comprising FIG. 104A depicts the analysis of the DEAE antibody sample. FIG. 104B depicts the analysis of the SPA antibody sample. FIG. 104C depicts the analysis of the Fc antibody sample. The percent area under the peaks for these graphs is summarized in Table 17.

FIG. 105, comprising FIG. 105A depicts the analysis of the DEAE antibody sample. FIG. 105B depicts the analysis of the SPA antibody sample. FIG. 105C depicts the analysis of the Fc antibody sample.

FIG. 106, comprising FIG. 106B depicts the analysis of the DEAE antibody sample. FIG. 106C depicts the analysis of the SPA antibody sample. FIG. 106D depicts the analysis of the Fc antibody sample.

FIG. 107, comprising FIG. 107A depicts the analysis of the DEAE antibody sample. FIG. 107B depicts the analysis of the SPA antibody sample. FIG. 107C depicts the analysis of the Fc antibody sample.

FIG. 108, comprising FIG. 108A depicts the analysis of the DEAE antibody sample. FIG. 108B depicts the analysis of the SPA antibody sample. FIG. 108C depicts the analysis of the Fc antibody sample.

FIG. 109, comprising FIG. 109B depicts the analysis of the DEAE antibody sample. FIG. 109C depicts the analysis of the SPA antibody sample. FIG. 109D depicts the analysis of the Fc antibody sample. The percent area under the peaks for these graphs is summarized in Table 18.

FIG. 110, comprising FIG. 110A depicts the analysis of the DEAE antibody sample. FIG. 110B depicts the analysis of the SPA antibody sample. FIG. 110C depicts the analysis of the Fc antibody sample. The percent area under the peaks for these graphs is summarized in Table 18.

FIG. 111, comprising FIG. 111A depicts the analysis of the DEAE antibody sample. FIG. 111B depicts the analysis of the SPA antibody sample. FIG. 111C depicts the analysis of the Fc antibody sample.

FIG. 112, comprising 112A to 112D, are graphs depicting 2-AA HPLC analysis of glycans released from Cri-IgG1 antibodies containing NGA2F isoforms before GalT1 treatment (FIGS. 112A and 112C) and after GalT1 treatment (FIGS. 112B and 112D).

FIG. 113, comprising 113A to 113C, are graphs depicting 2-AA HPLC analysis of glycans released from Cri-IgG1 antibodies that have been glycoremodeled by ST3Gal3 treatment of G2 glycoforms. The released glycans are labeled with 2-AA and then separated by HPLC on a NH2P-50 4D amino column.

FIG. 114, comprising FIG. 114A depicts the analysis of the DEAE antibody sample. FIG. 114B depicts the analysis of the SPA antibody sample. FIG. 114C depicts the analysis of the Fc antibody sample.

FIG. 115, comprising FIG. 115B depicts the analysis of the DEAE antibody sample. FIG. 115C depicts the analysis of the SPA antibody sample. FIG. 115D depicts the analysis of the Fc antibody sample.

FIG. 116, comprising FIG. 116A depicts the analysis of the DEAE antibody sample. FIG. 116B depicts the analysis of the SPA antibody sample. FIG. 116C depicts the analysis of the Fc antibody sample.

FIG. 117, comprising

Figure 117A:
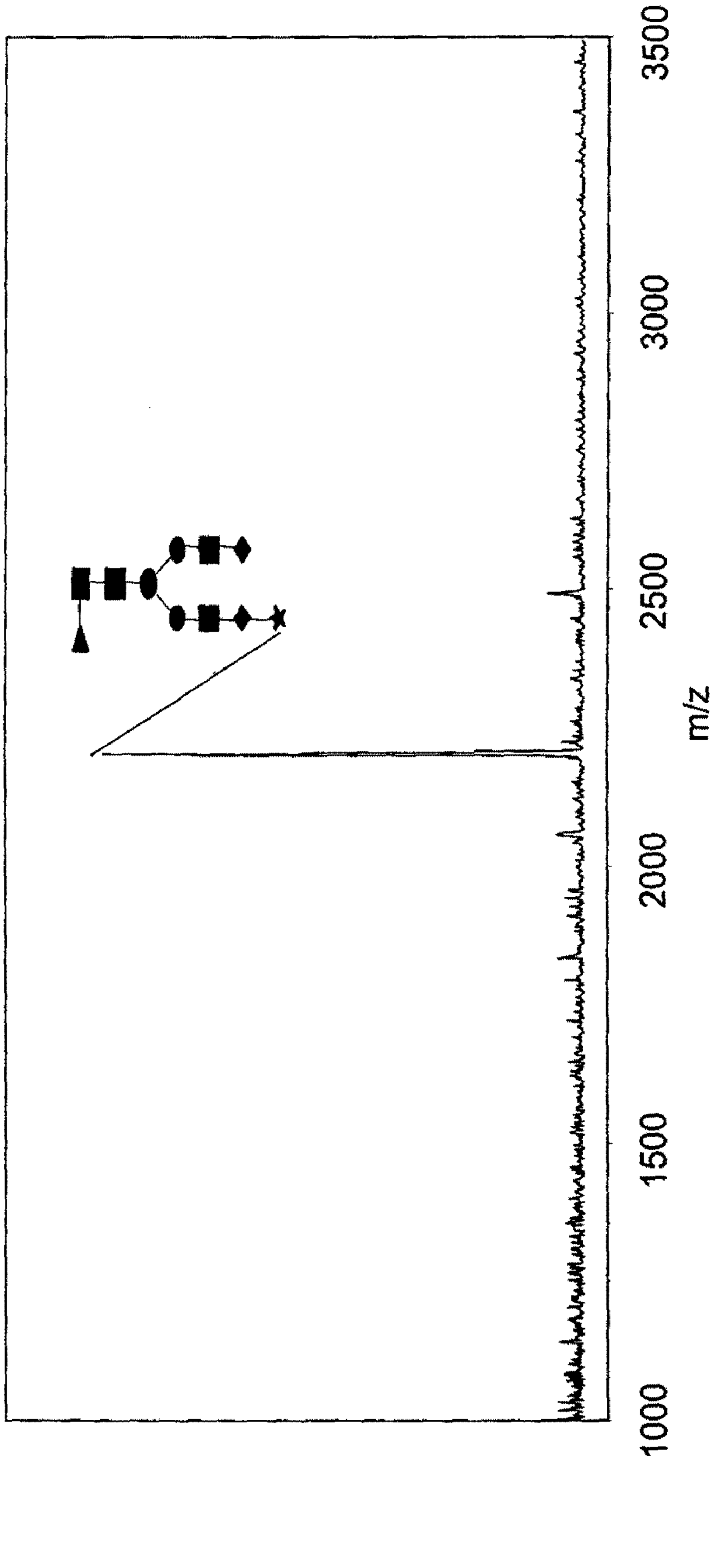
FIGS. 117A to 117C, are graphs depicting MALDI analysis of glycans released from Cri-IgG1 antibodies that had been glycoremodeled by ST6Gal1 treatment of G2 glycoforms. The released glycans were derivatized with 2-AA and then analyzed by MALDI. FIG.
Figure 117B:
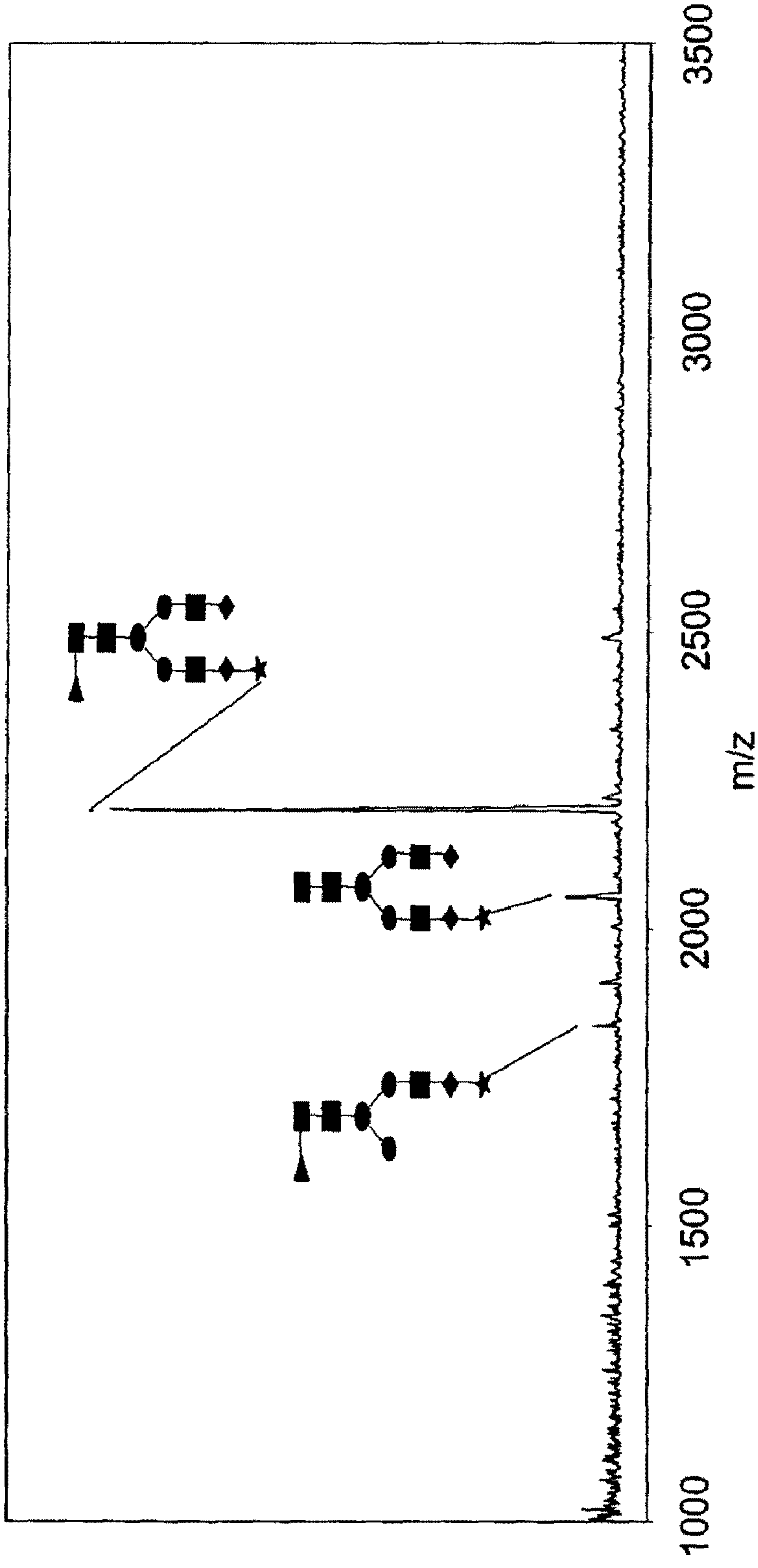
Figure 117C:
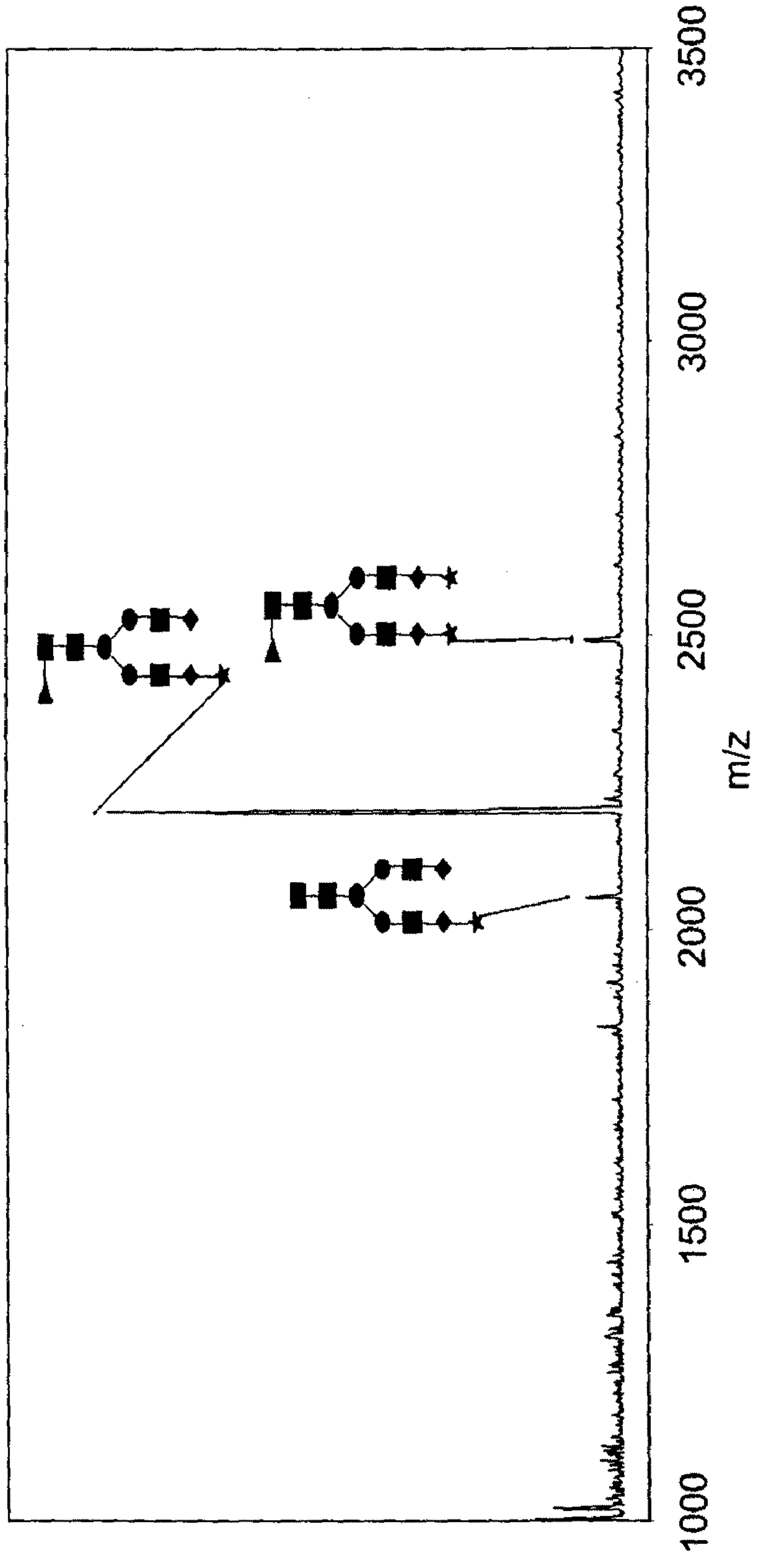

117A depicts the analysis of the DEAE antibody sample. FIG. 117B depicts the analysis of the SPA antibody sample. FIG. 117C depicts the analysis of the Fc antibody sample.

Figure 118B:
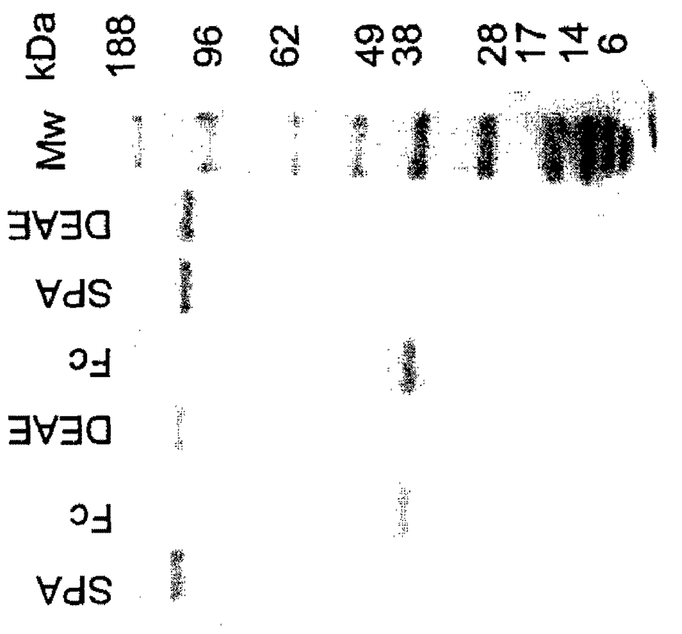
Figure 118A:
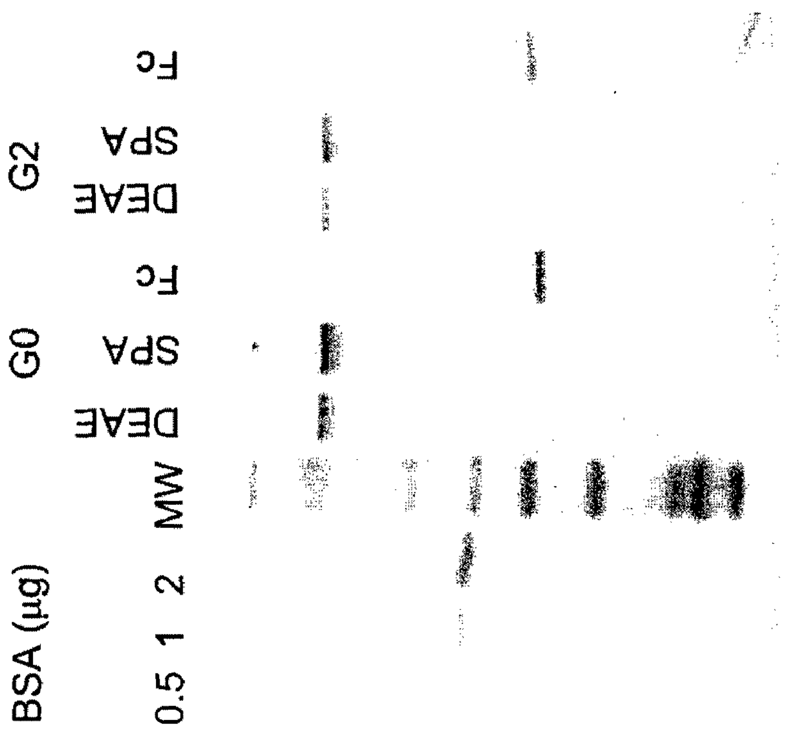
Figure 118D:
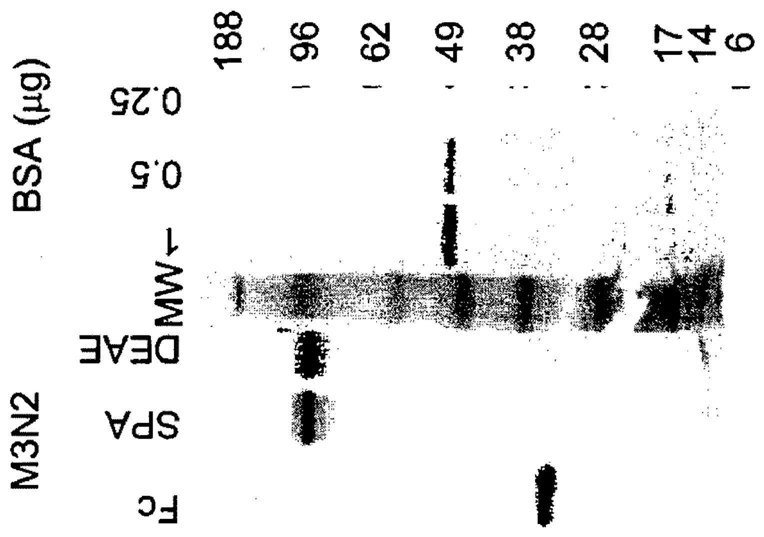
Figure 118C:
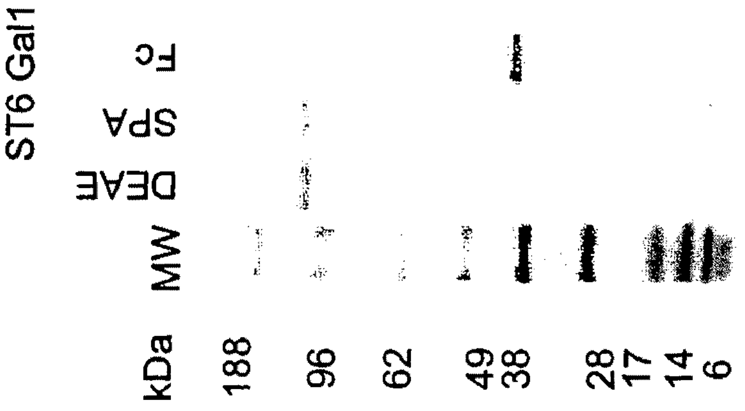
Figure 118E:
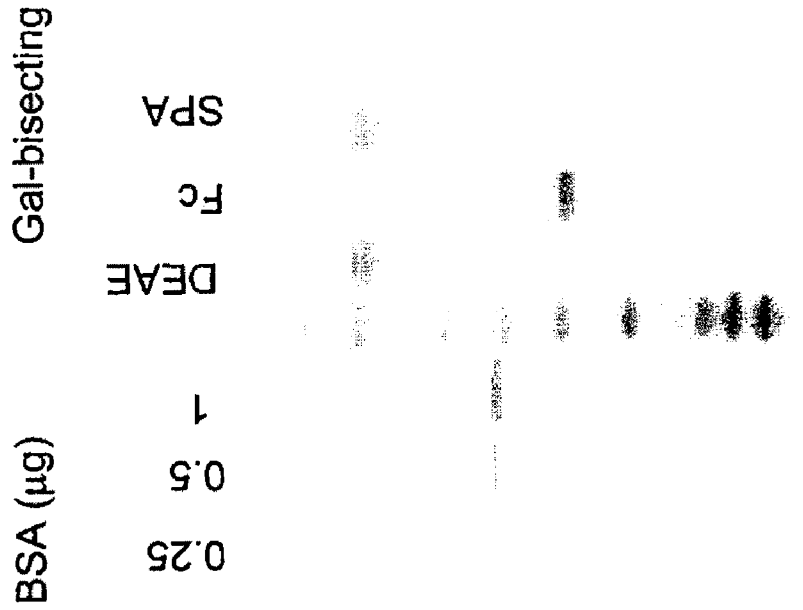

FIG. 118, comprising FIGS. 118A to 118E, depicts images of SDS-PAGE analysis of the glycoremodeled of Cri-IgG1 antibodies with different glycoforms under non-reducing conditions. Bovine serum albumin (BSA) was run under reducing conditions as a quantitative standard. Protein molecular weight standards are displayed and their size is indicated in kDa. FIG. 118A depicts SDS-PAGE analysis of the DEAE, SPA and Fc. Cri-IgG1 antibodies glycoremodeled to contain G0 and G2 glycoforms. FIG. 118B depicts SDS-PAGE analysis of the DEAE, SPA and Fc Cri-IgG1 antibodies glycoremodeled to contain NGA2F (bisecting) and GnT-1-M3N2 (GnT1) glycoforms. FIG. 118C depicts SDS-PAGE analysis of the DEAE, SPA and Fc Cri-IgG1 antibodies glycoremodeled to contain S2G2 (ST6Gal1) glycoforms. FIG. 118D depicts SDS-PAGE analysis of the DEAE, SPA and Fc Cri-IgG1 antibodies glycoremodeled to contain M3N2 glycoforms, and BSA. FIG. 118E depicts SDS-PAGE analysis of the DEAE, SPA and Fc Cri-IgG1 antibodies glycoremodeled to contain Gal-NGA2F (Gal-bisecting) glycoforms, and BSA.

Figure 119:
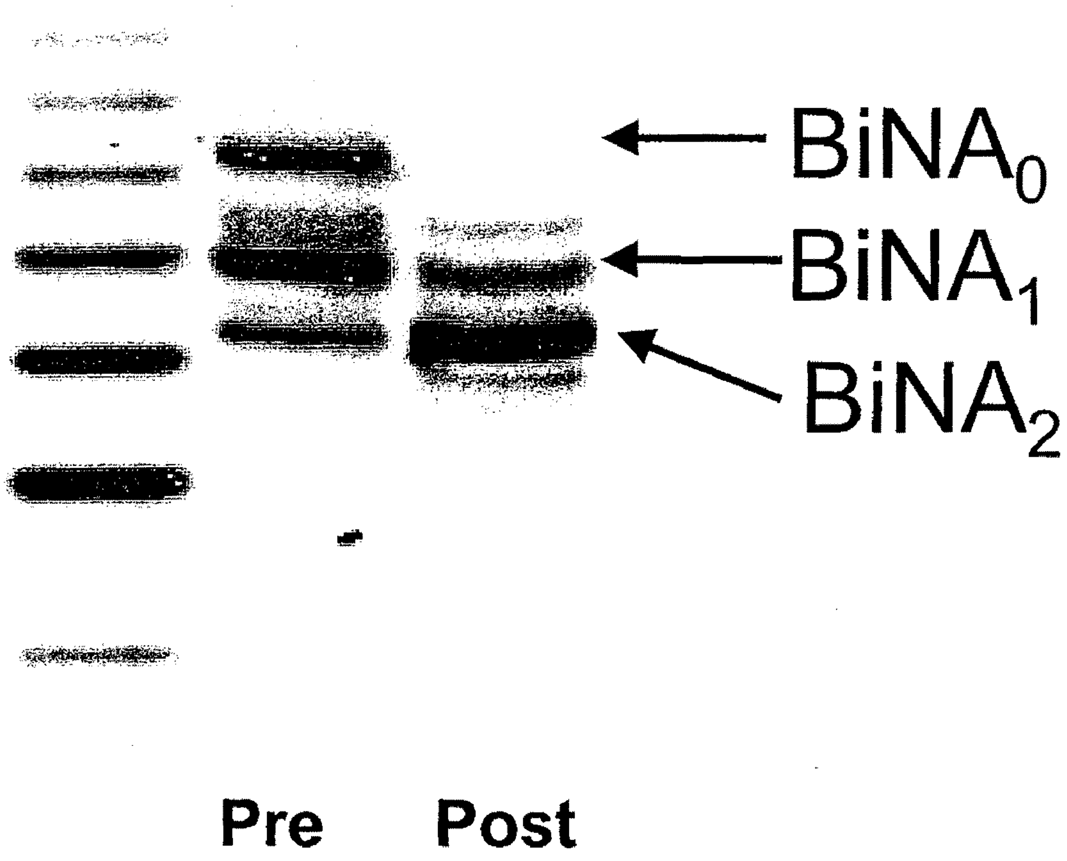

FIG. 119 is an image of an acrylamide gel depicting the results of FACE analysis of the pre- and post-sialylation of TP10. The $BiNA_0$ species has no sialic acid residues. The $BiNA_1$ species has one sialic acid residue. The $BiNA_2$ species has two sialic acid residues. Bi=biantennary; NA=neuraminic acid.

Figure 120:
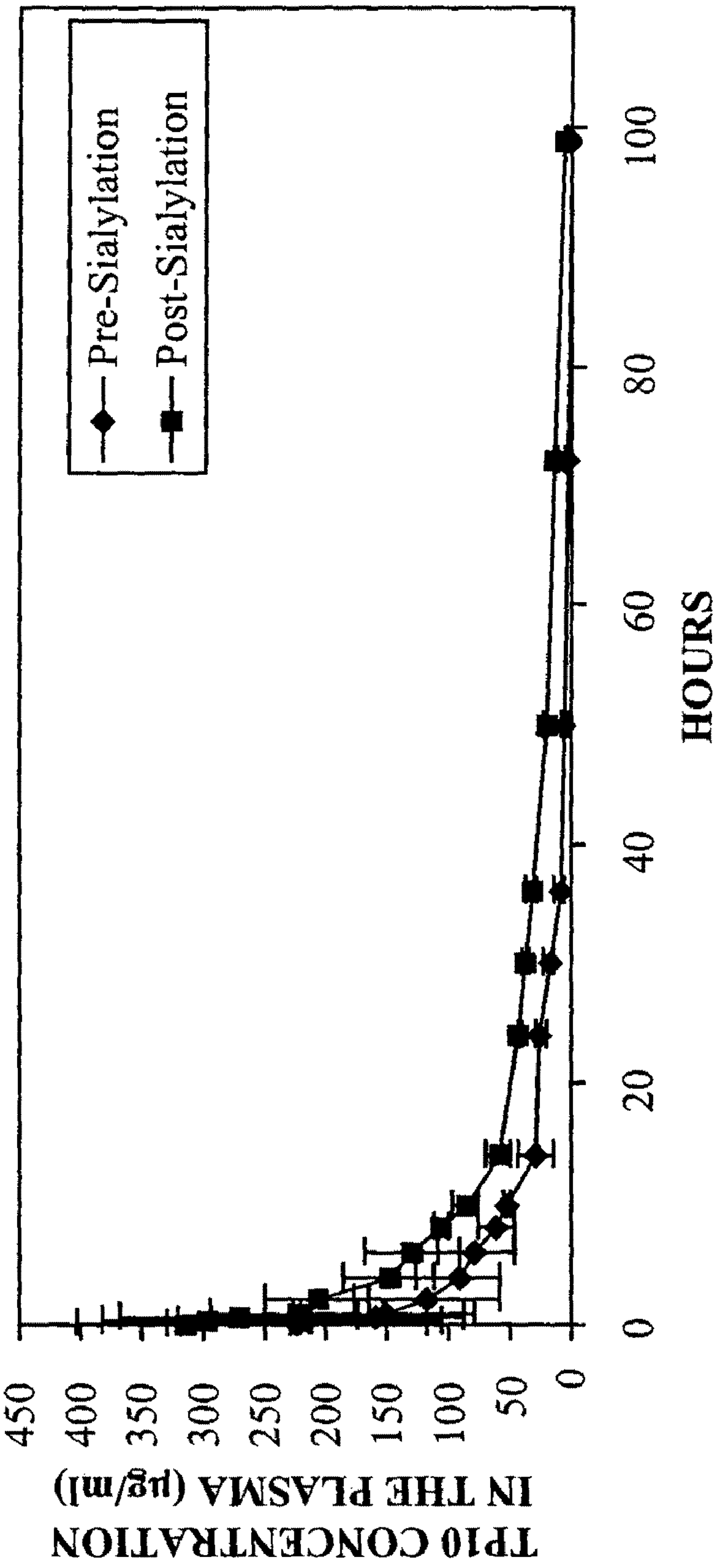

FIG. 120 is a graph depicting the plasma concentration in μg/ml over time of pre- and post-sialylation TP10 injected into rats.

Figure 121:
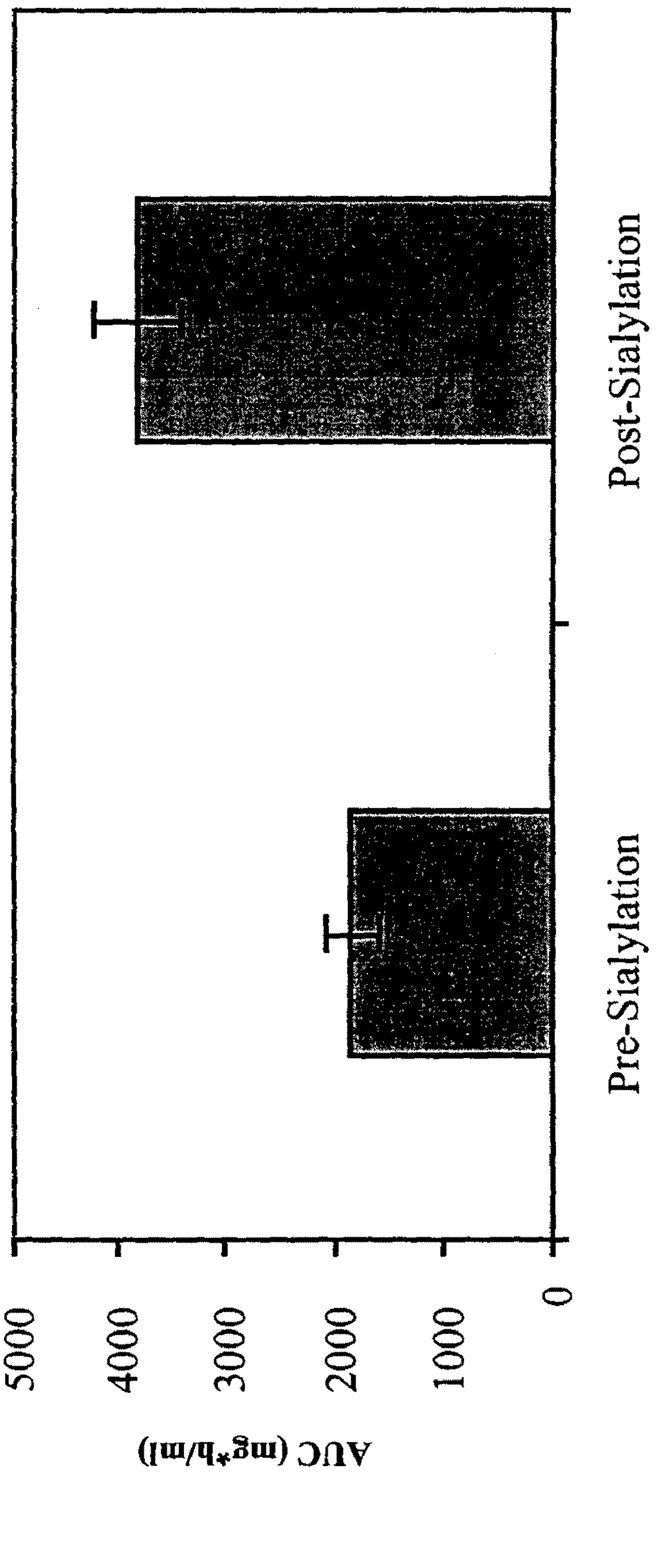

FIG. 121 is a graph depicting the area under the plasma concentration-time curve (AUC) in μg/hr/ml for pre- and post sialylated TP10.

Figure 122:
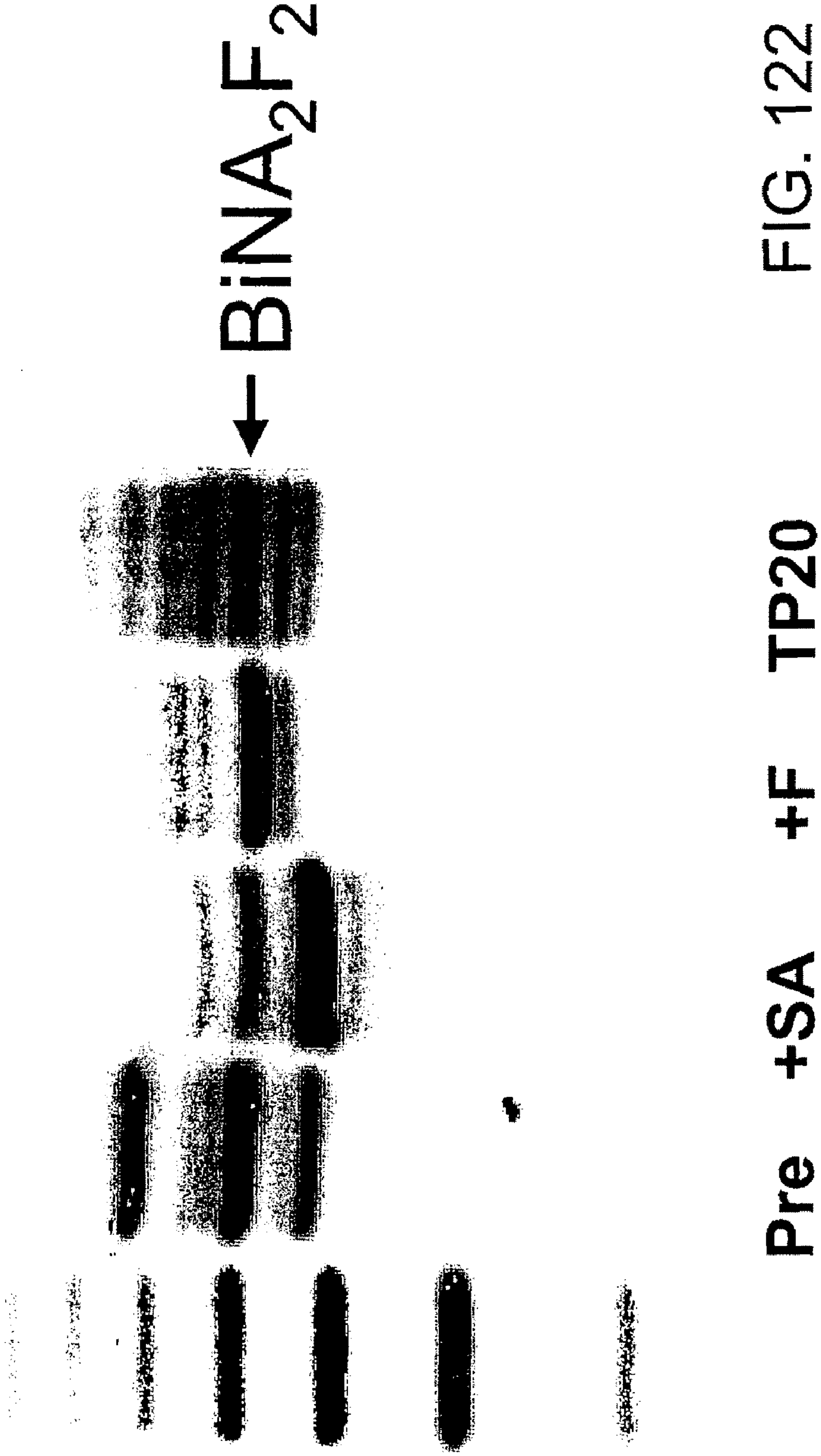

FIG. 122 is an image of an acrylamide gel depicting the results of FACE glycan analysis of the pre- and post-fucosylation of TP10 and FACE glycan analysis of CHO cell produced TP-20. The $BiNA_2F_2$ species has two neuraminic acid (NA) residues and two fucose residues (F).

Figure 123:
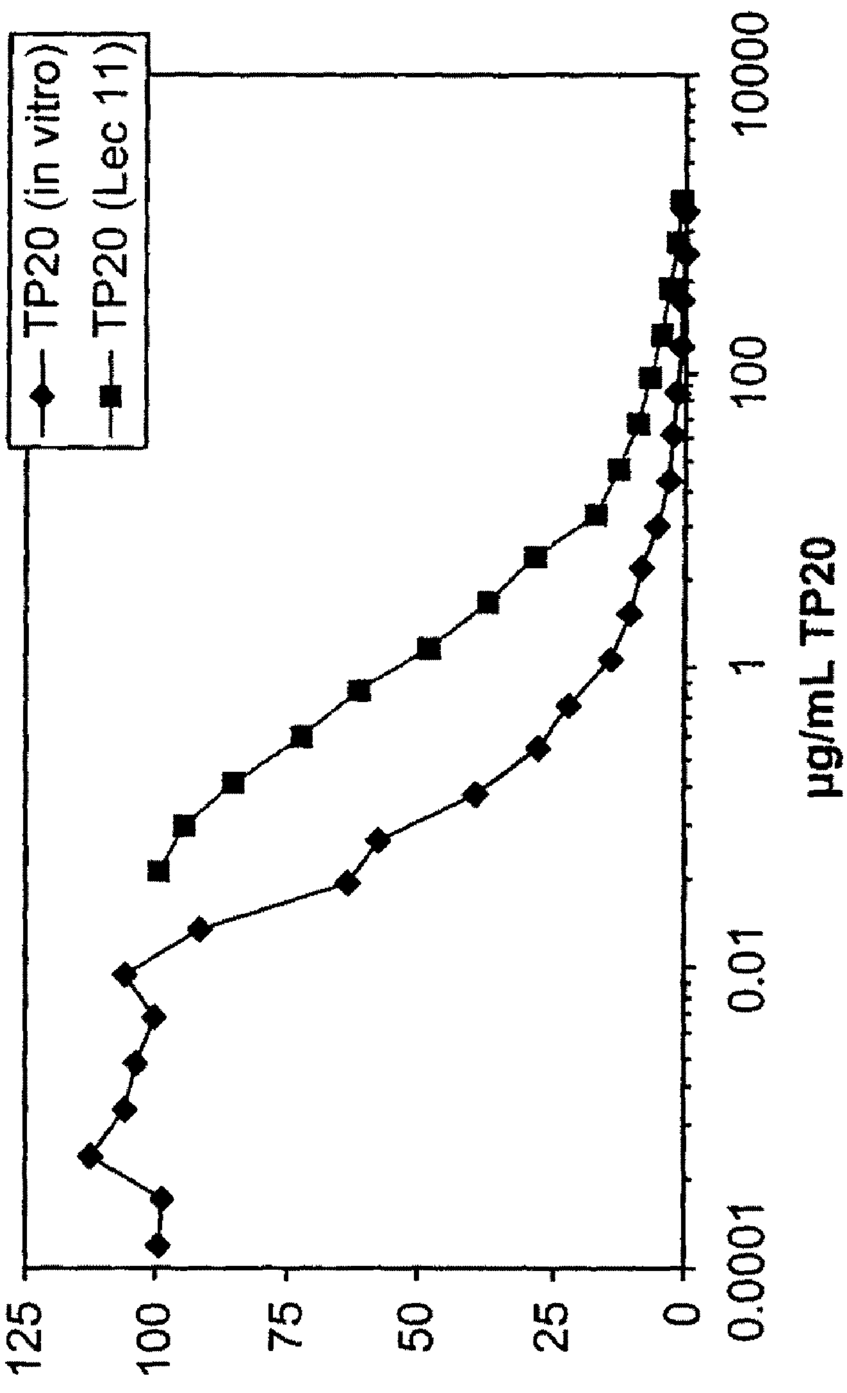

FIG. 123 is a graph depicting the in vitro binding of TP20 ($sCR1sLe^X$) glycosylated in vitro (diamonds) and in vivo in Lec11 CHO cells (squares).

Figure 124:
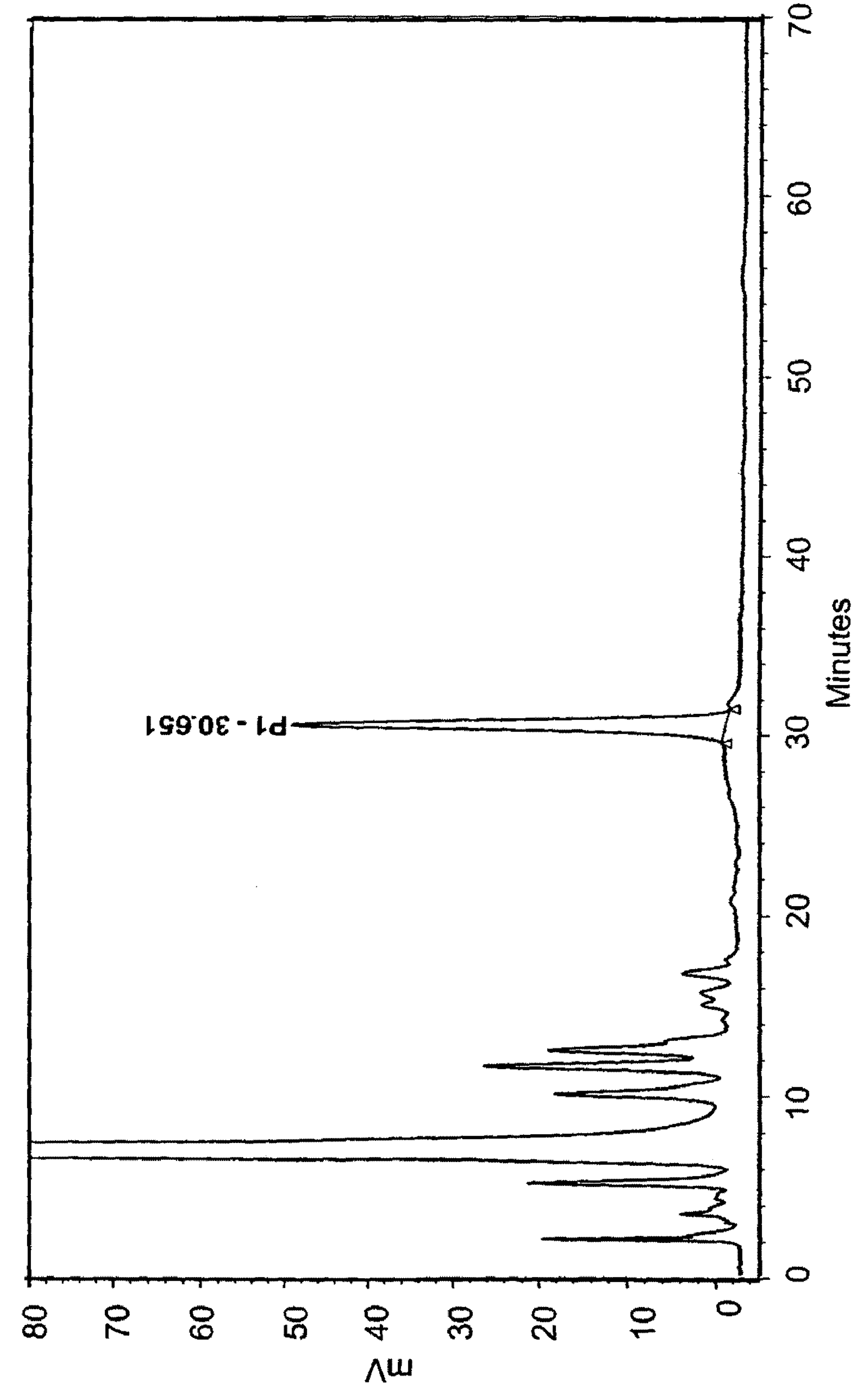

FIG. 124 is a graph depicting the analysis by 2-AA HPLC of glycoforms from the GlcNAc-ylation of EPO.

Figure 125A:
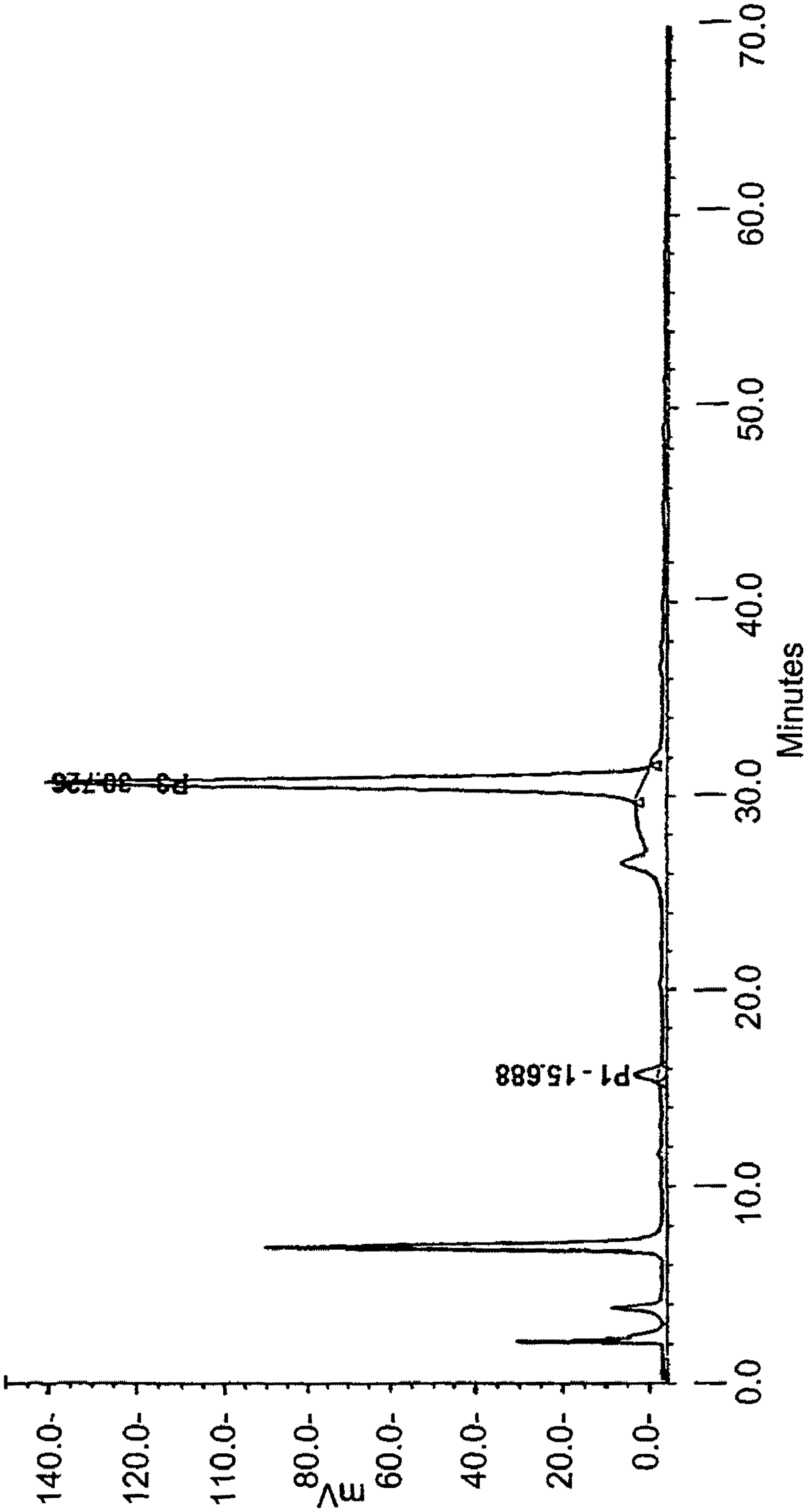
Figure 125B:
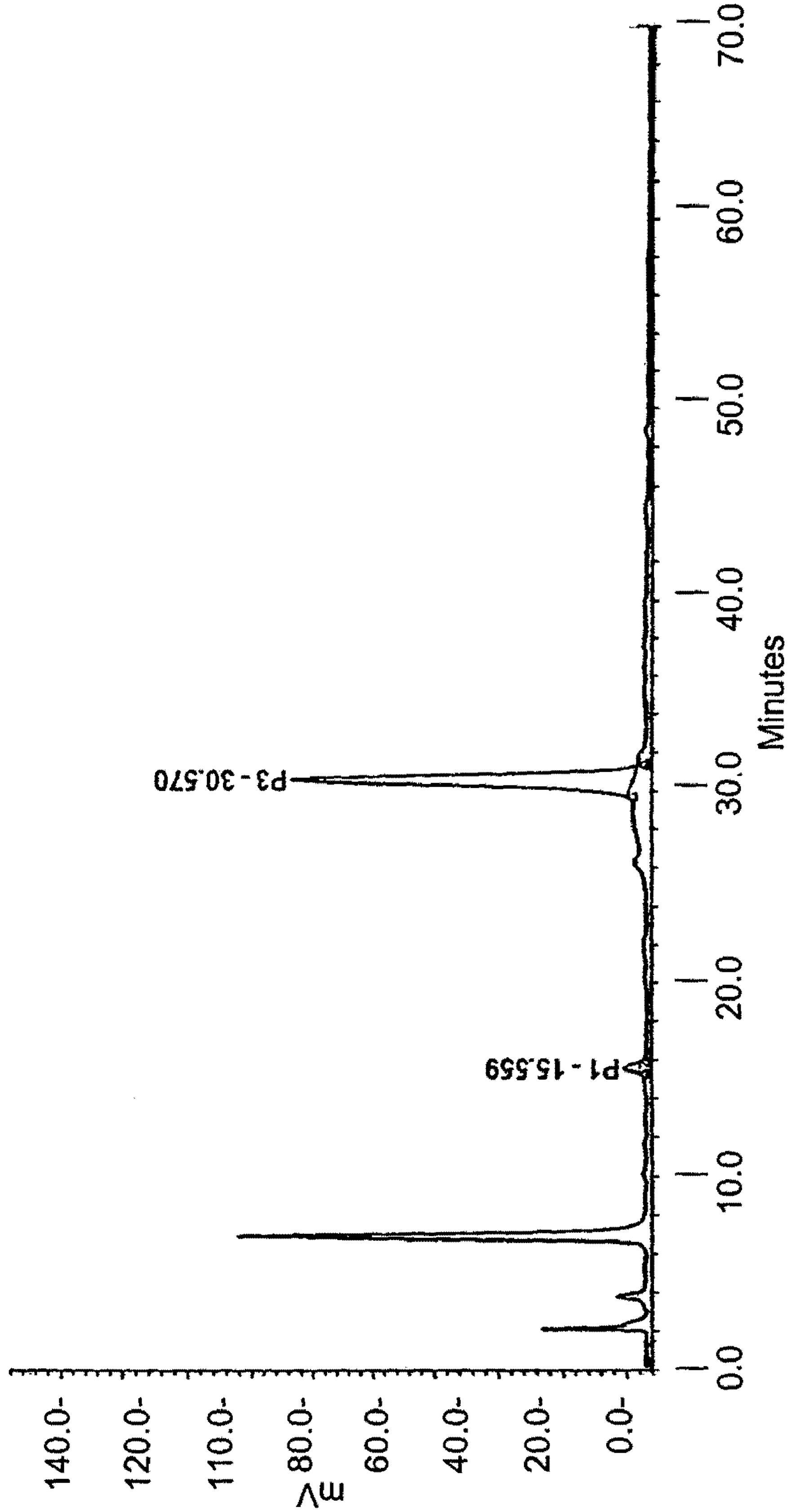

FIG. 125, comprising FIGS. 125A and 125B, are graphs depicting the 2-AA HPLC analysis of two lots of EPO to which N-acetylglucosamine was been added. FIG. 125A depicts the analysis of lot A, and FIG. 125B depicts the analysis of lot B.

Figure 126:
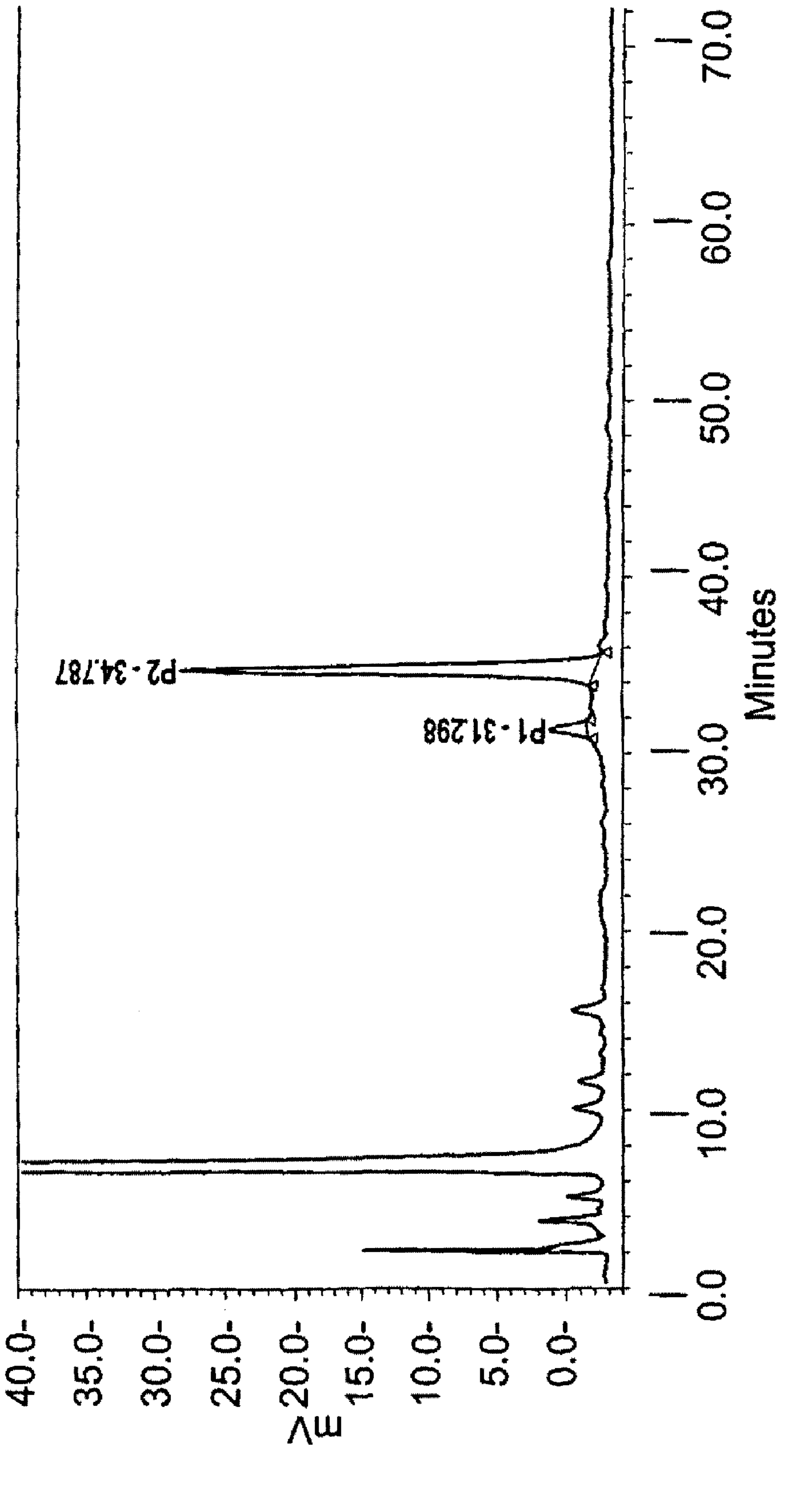

FIG. 126 is a graph depicting the 2-AA HPLC analysis of the products the reaction introducing a third glycan branch to EPO with GnT-V.

Figure 127:
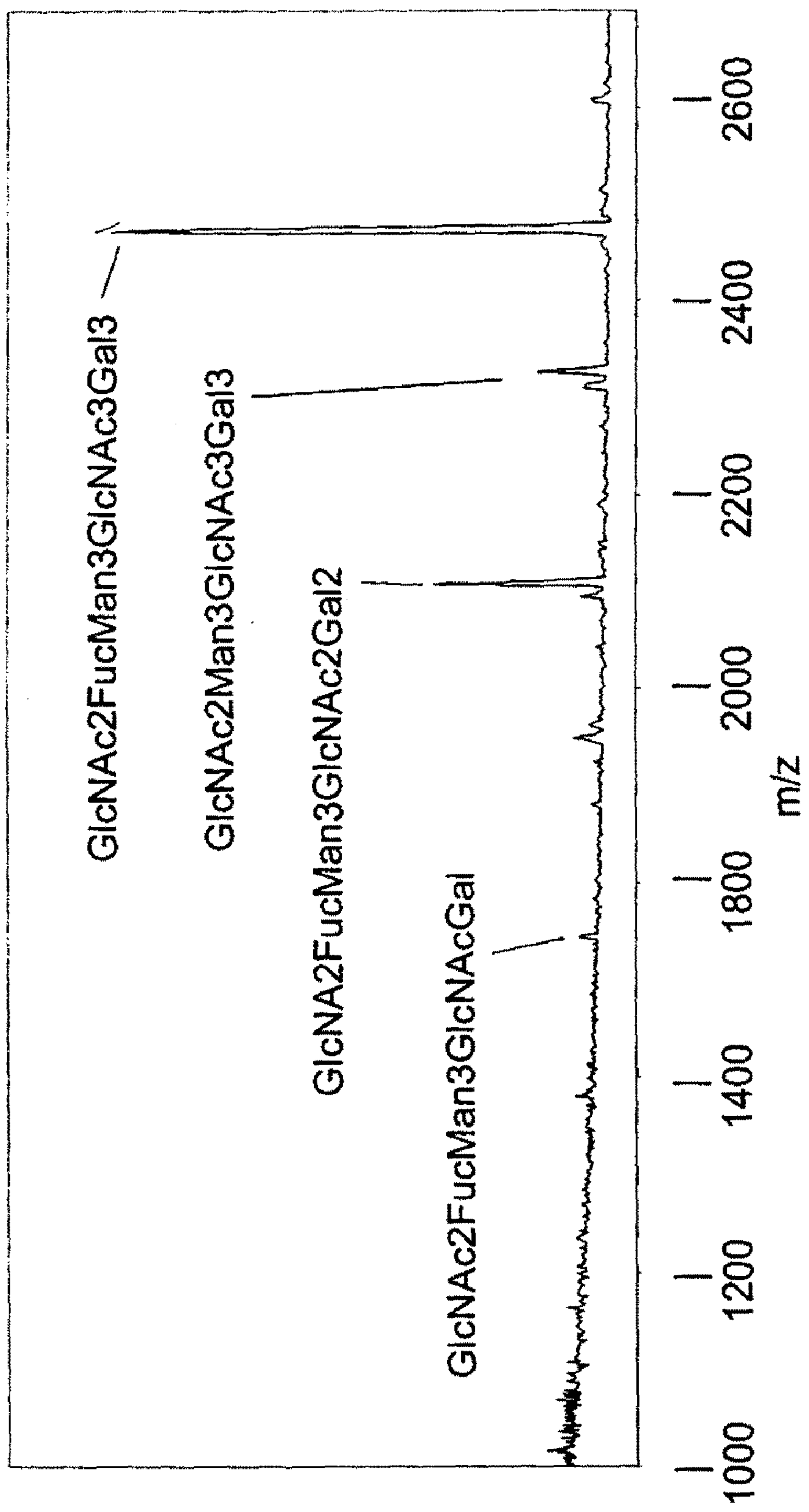

FIG. 127 is a graph depicting a MALDI-TOF spectrum of the glycans of the EPO preparation after treatment with GnT-I, GnT-II, GnT-III, GnT-V and GalT1, with appropriate donor groups.

Figure 128:
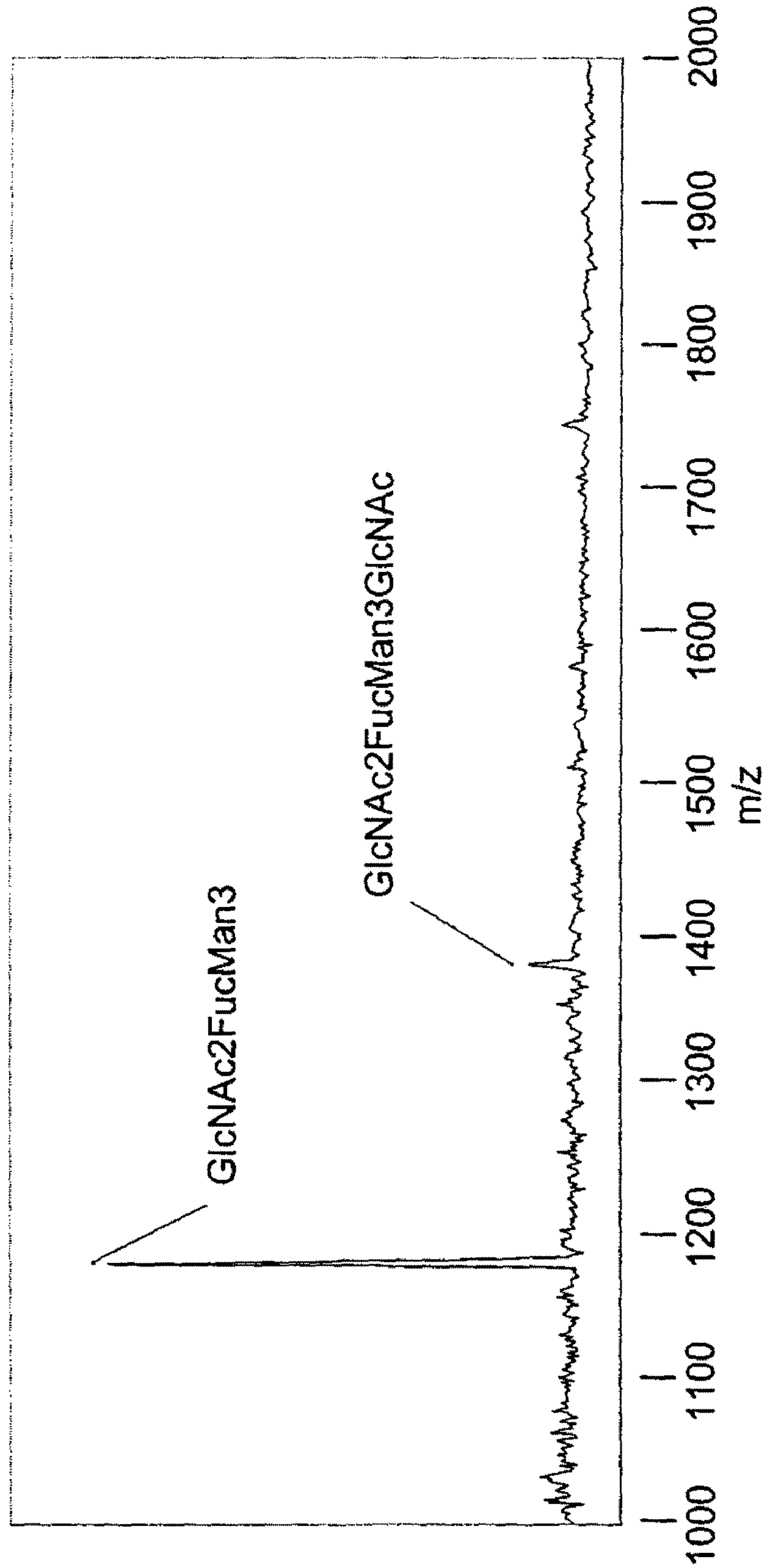

FIG. 128 is a graph depicting a MALDI spectrum the glycans of native EPO.

Figure 129:
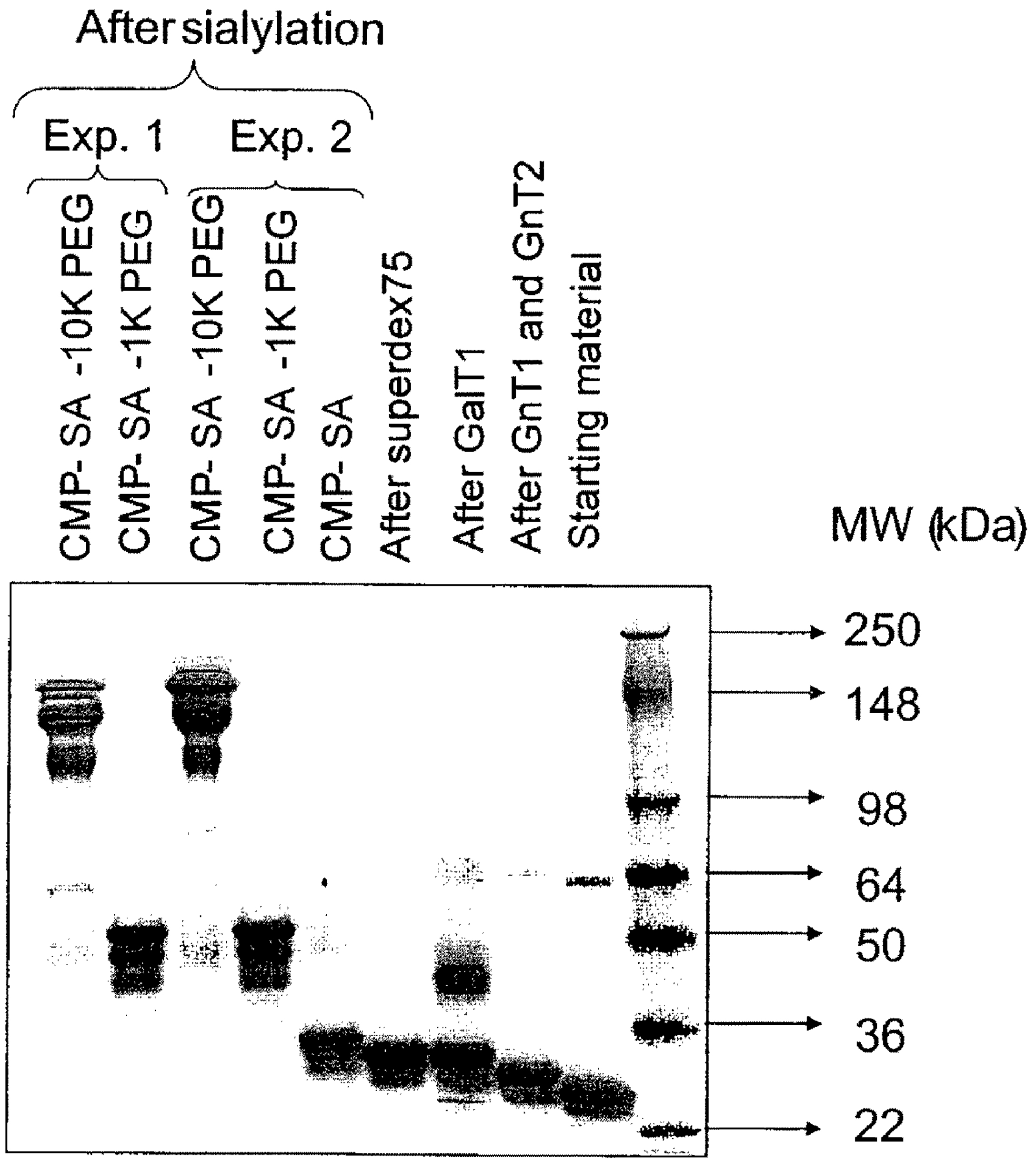

FIG. 129 is an image of an SDS-PAGE gel of the products of the PEGylation reactions using CMP-SA-PEG (1 kDa), and CMP-SA-PEG (10 kDa).

Figure 130:
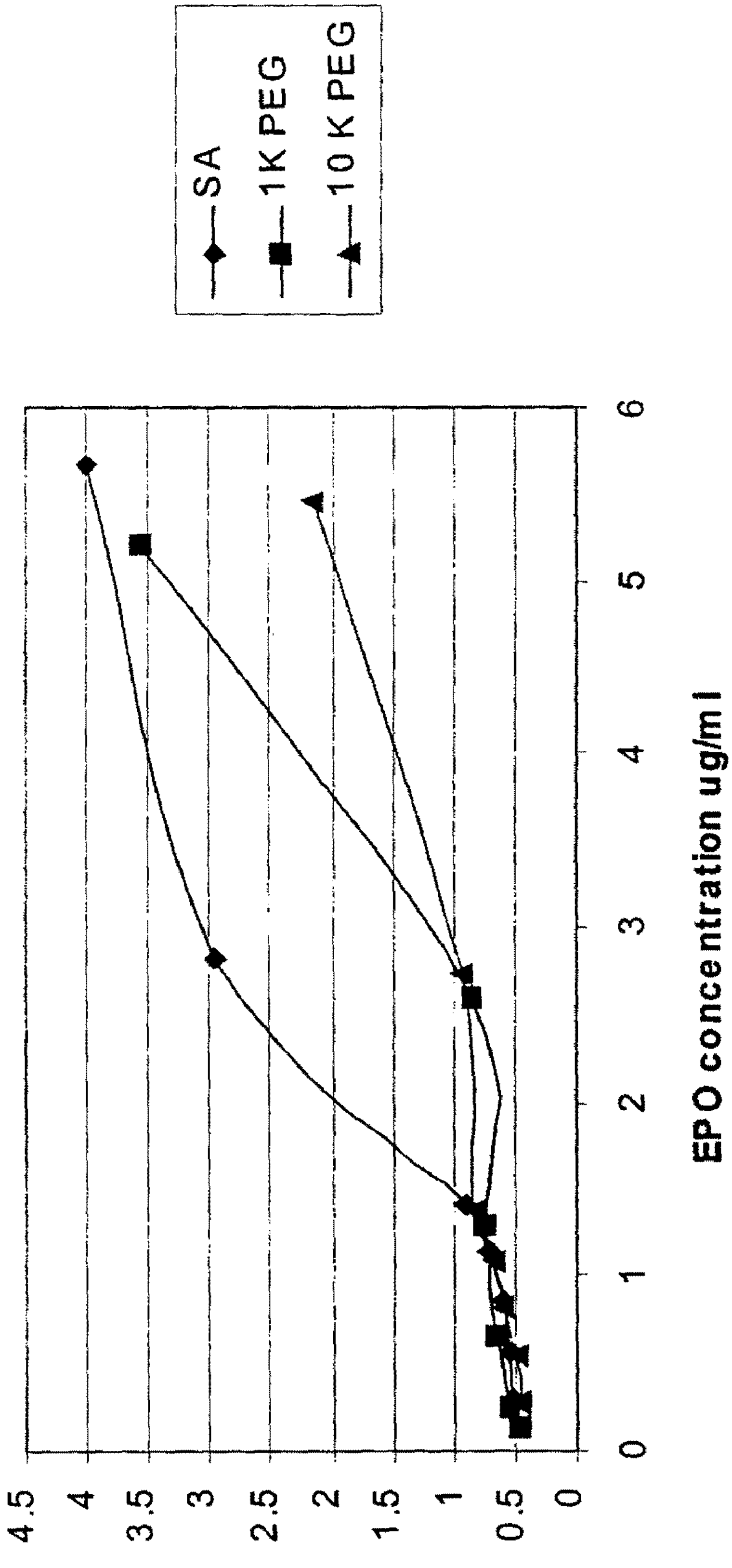

FIG. 130 is a graph depicting the results of the in vitro bioassay of PEGylated EPO. Diamonds represent the data from sialylated EPO having no PEG molecules. Squares represent the data obtained using EPO with PEG (1 kDa). Triangles represent the data obtained using EPO with PEG (10 kDa).

Figure 131:
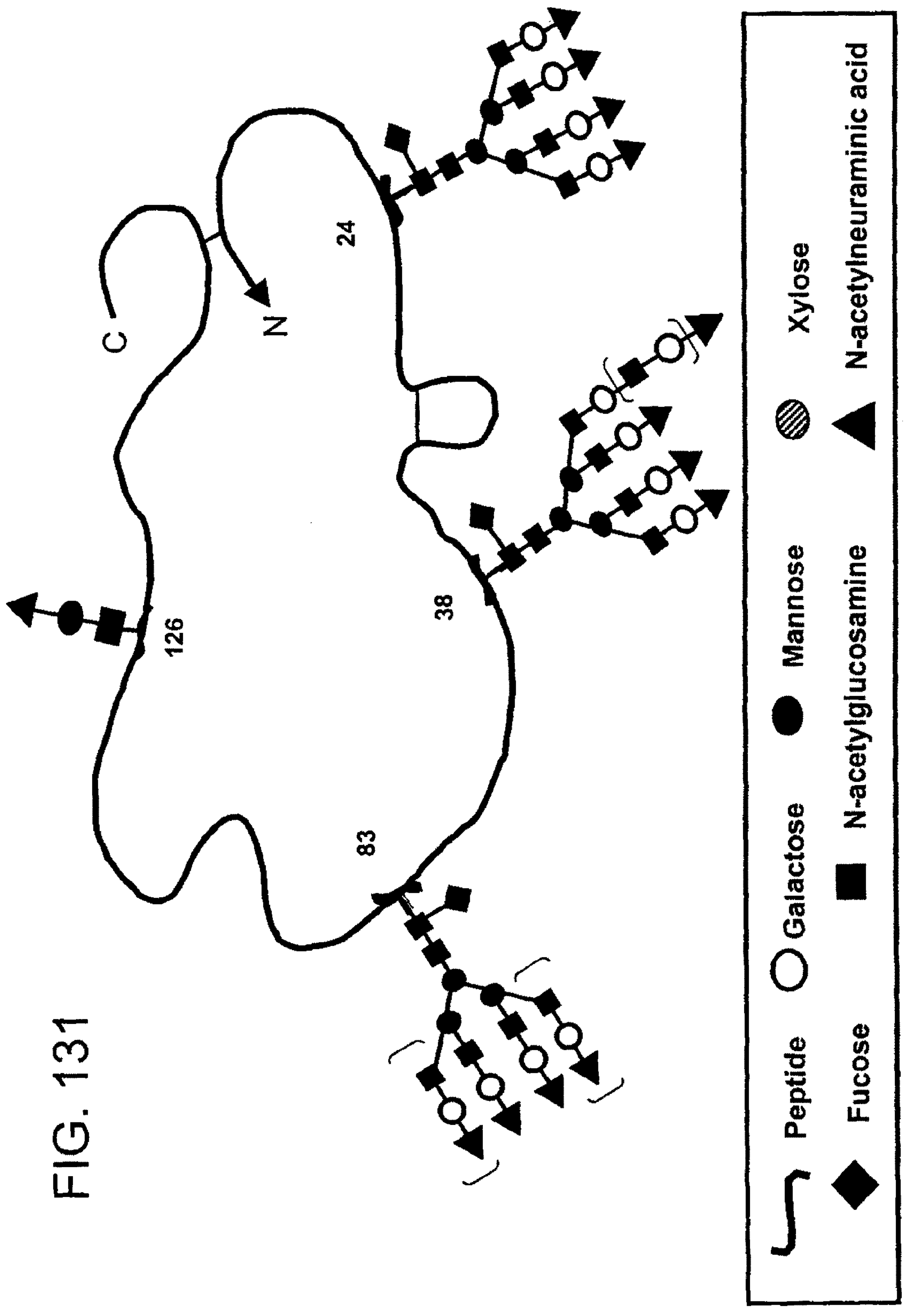

FIG. 131 is a diagram of CHO-expressed EPO. The EPO polypeptide is 165 amino acids in length, with a molecular weight of 18 kDa without glycosylation. The glycosylated forms of EPO produced in CHO cells have a molecular weight of about 33 kDa to 39 kDa. The shapes which represent the sugars in the glycan chains are identified in the box at the lower edge of the drawing.

Figure 132:
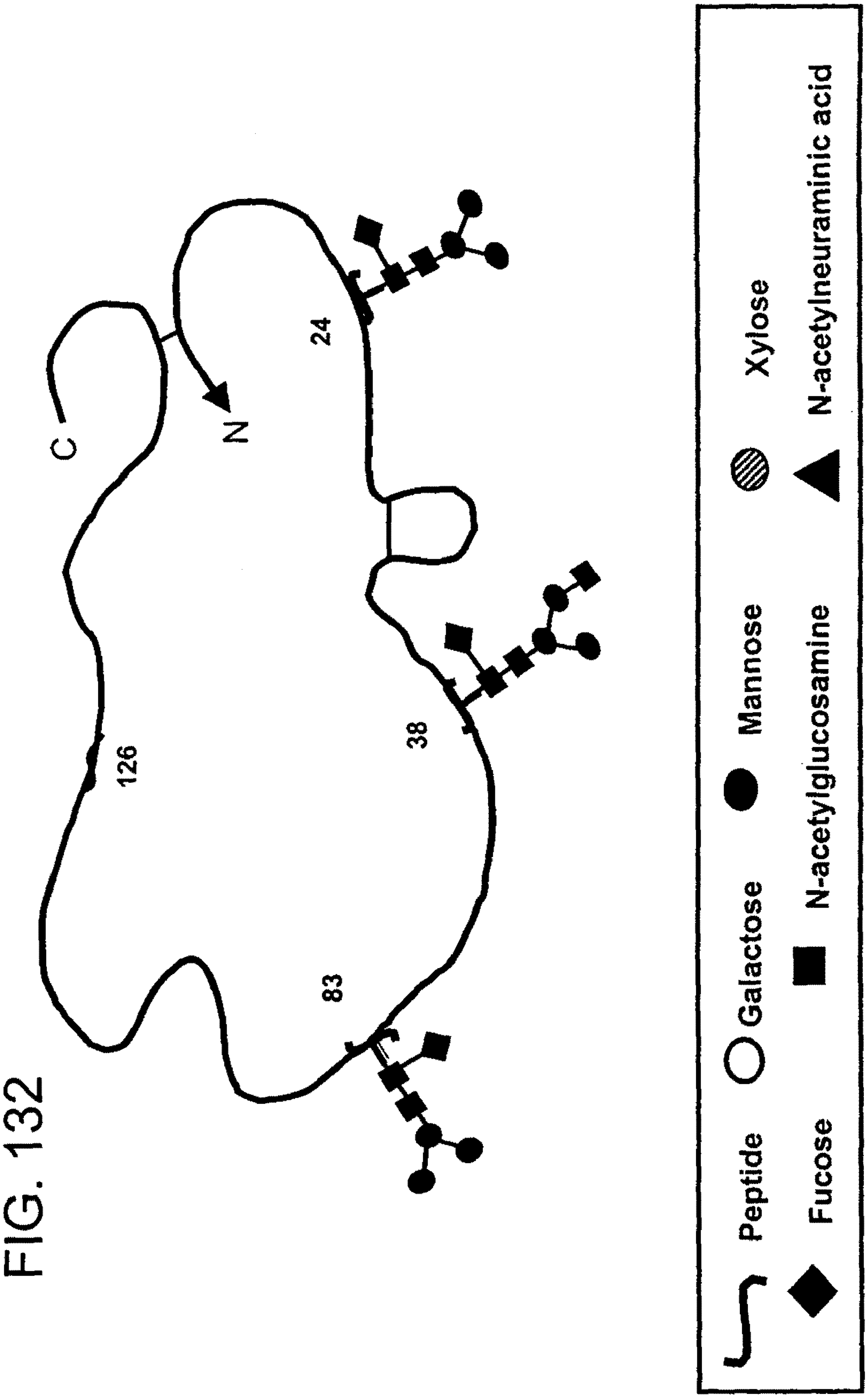

FIG. 132 is a diagram of insect cell expressed EPO. The shapes that represent the sugars in the glycan chains are identified in the box at the lower edge of FIG. 131.

Figure 133:
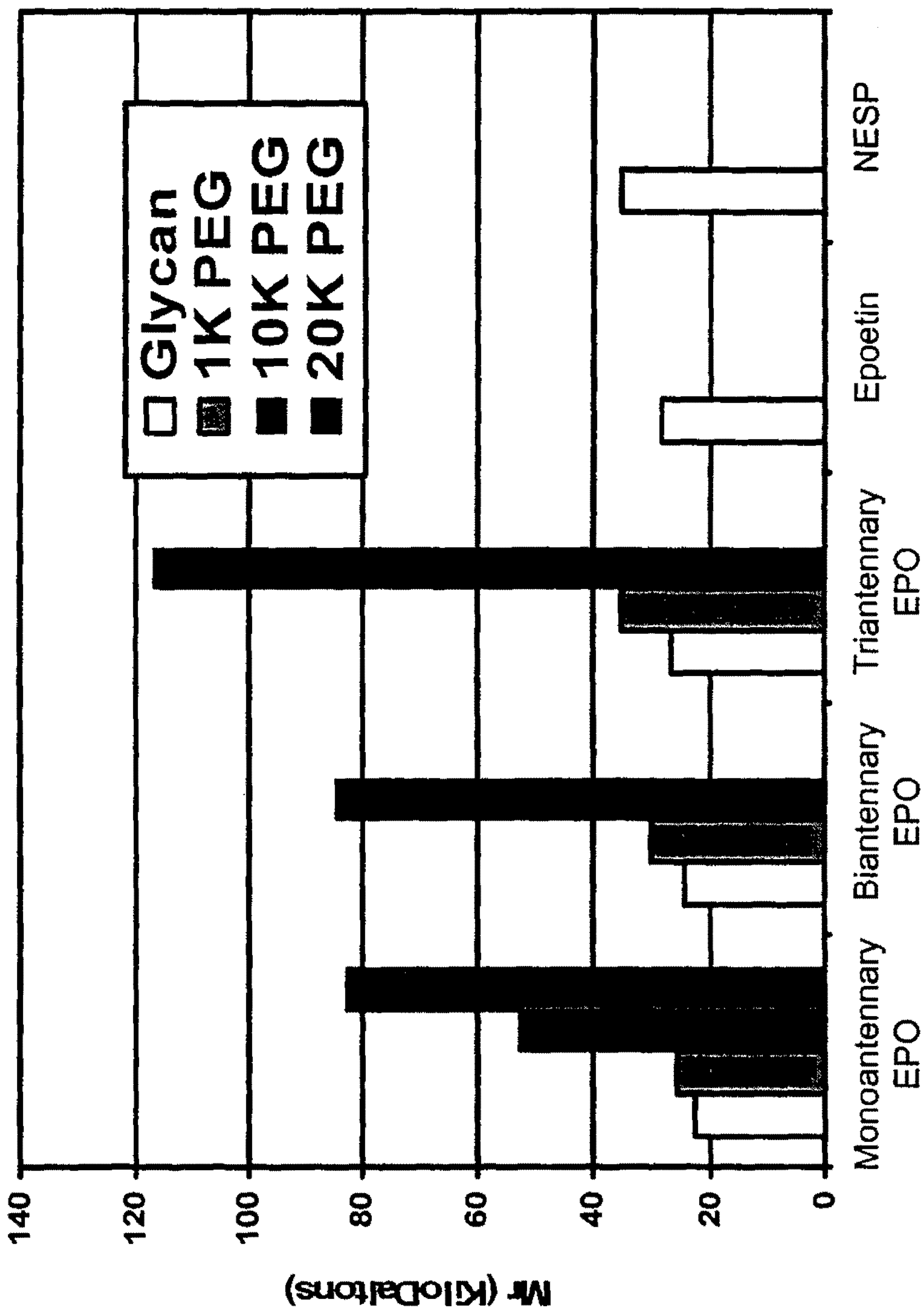

FIG. 133 is a bar graph depicting the molecular weights of the EPO peptides expressed in insect cells which were remodeled to form complete mono-, bi- and tri-antennary glycans, with optional glycoPEGylation with 1 kDa, 10 kDa or 20 kDa PEG. Epoetin™ is EPO expressed in mammalian cells without further glycan modification or PEGylation. NESP (Aranesp™, Amgen, Thousand Oaks, Calif.) is a form of EPO having 5 N-linked glycan sites that is also expressed in mammalian cells without further glycan modification or PEGylation.

Figure 134A:
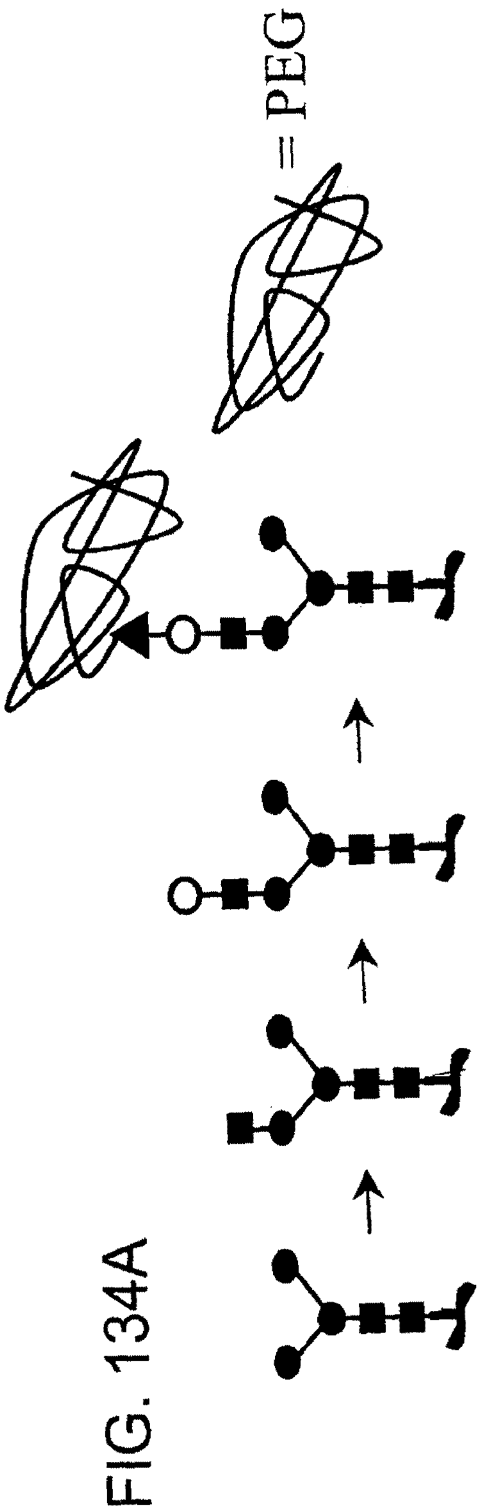
Figure 134B:
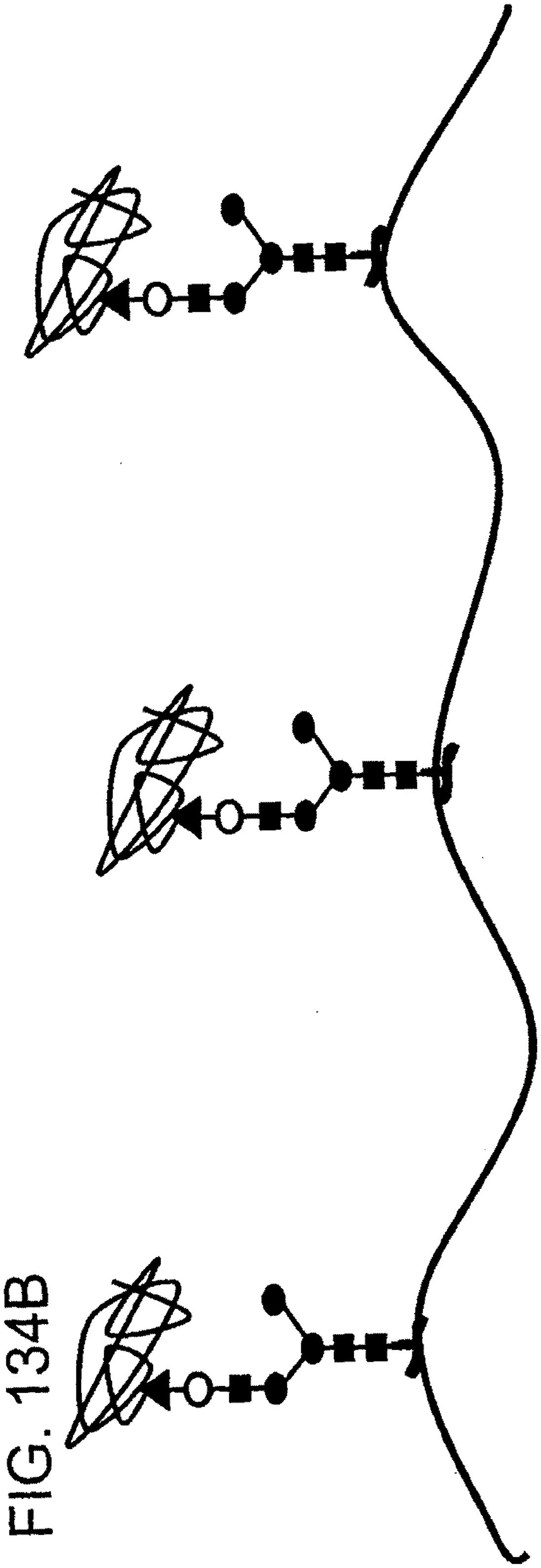

FIG. 134, comprising FIGS. 134A and 134B, depicts one scheme for the remodeling and glycoPEGylation of insect cell expressed EPO. FIG. 134A depicts the remodeling and glycoPEGylation steps that remodel the insect expressed glycan to a mono-antennary glycoPEGylated glycan. FIG. 134B depicts the remodeled EPO polypeptide having a completed glycoPEGylated mono-antennary glycan at each N-linked glycan site of the polypeptide. The shapes that represent the sugars in the glycan chains are identified in the box at the lower edge of FIG. 131, except that the triangle represents sialic acid.

Figure 135:
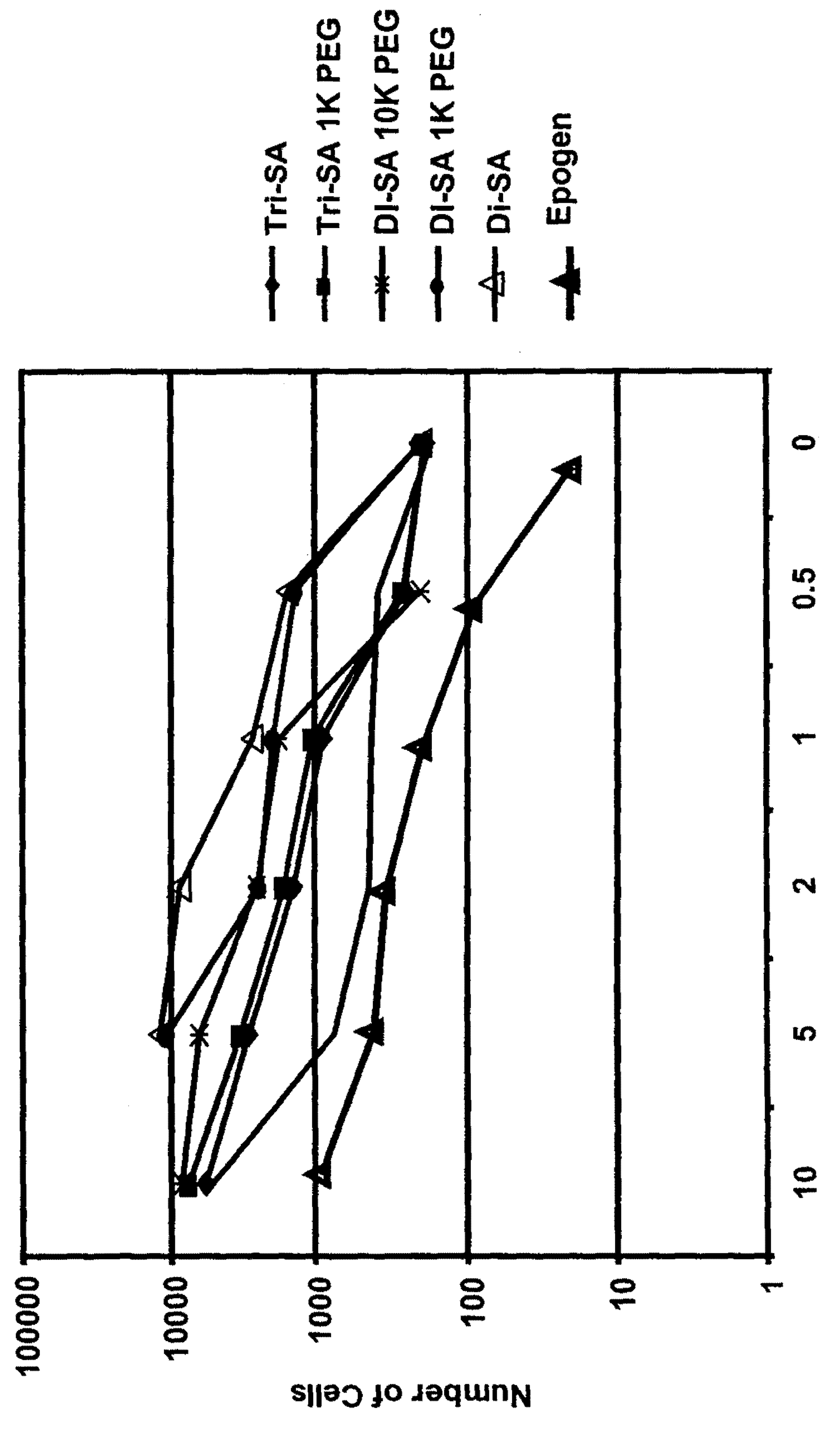

FIG. 135 is a graph depicting the in vitro bioactivities of EPO-SA and EPO-SA-PEG constructs. The in vitro assay measured the proliferation of TF-1 erythroleukemia cells which were maintained for 48 hr in RBMI+FBS 10%+GM-CSF (12 ng/ml) after the EPO construct was added at 10.0, 5.0, 2.0, 1.0, 0.5, and 0 μg/ml. Tri-SA refers to EPO constructs where the glycans are tri-antennary and have SA. Tri-SA 1K PEG refers to EPO constructs where the glycans are tri-antennary and have Gal and are then glycoPEGylated with SA-PEG 1 kDa. Di-SA 10K PEG refers to EPO constructs where the glycans are bi-antennary and have Gal and are then glycoPEGylated with SA-PEG 10 kDa. Di-SA 1K PEG refers to EPO constructs where the glycans are bi-antennary and have Gal and are then glycoPEGylated with SA-PEG 1 kDa. Di-SA refers to EPO constructs where the glycans are bi-antennary and are built out to SA. Epogen™ is EPO expressed in CHO cells with no further glycan modification.

Figure 136:
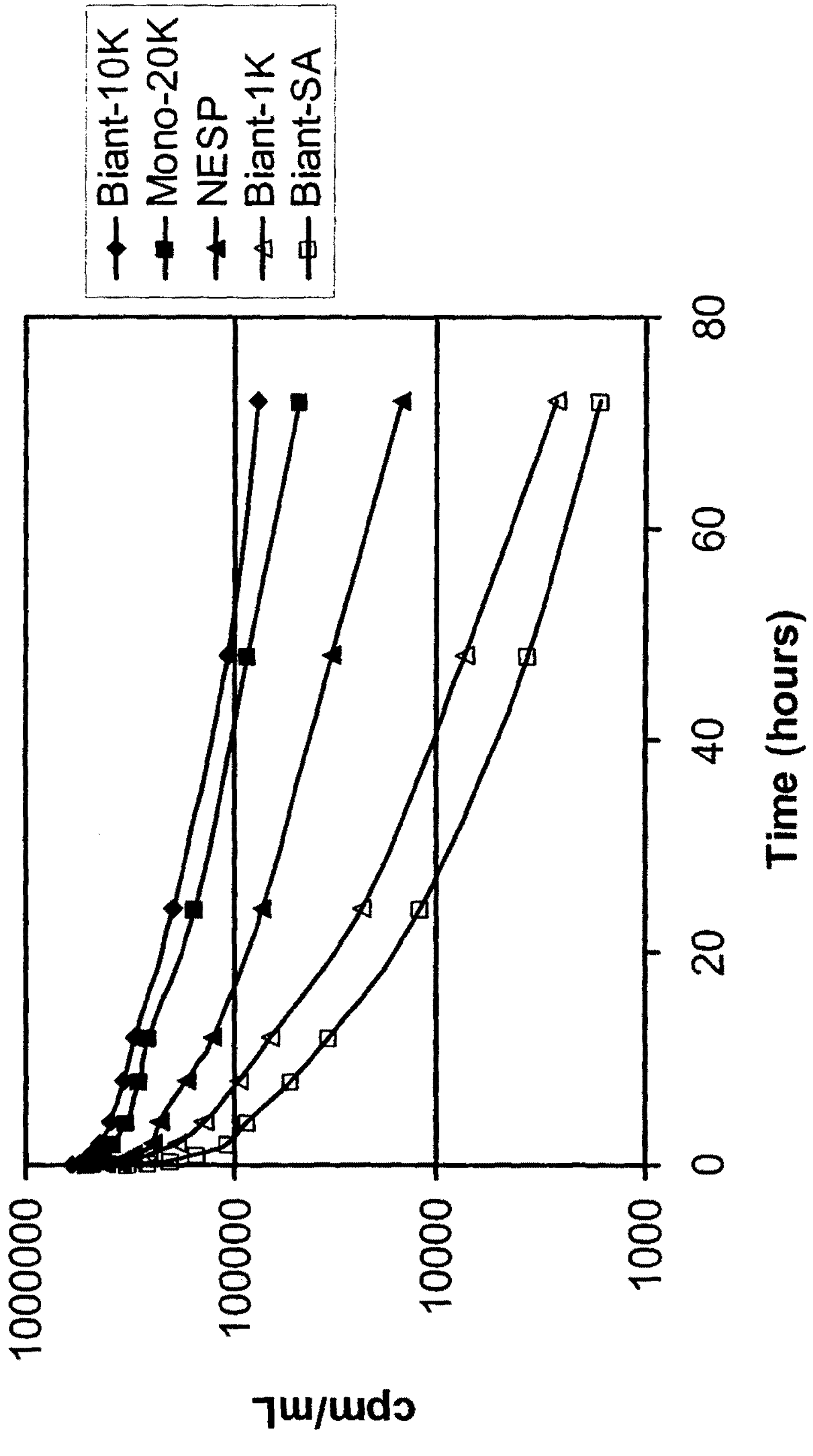

FIG. 136 is a graph depicting the pharmacokinetics of the EPO constructs in rat. Rats were bolus injected with $[I^{125}]$-labeled glycoPEGylated and non-glycoPEGylated EPO. The graph shows the concentration of the radio-labeled EPO in the bloodstream of the rat at 0 to about 72 minutes after injection. "Biant-10K" refers to EPO with biantennary glycan structures with terminal 10 kDa PEG moieties. "Mono-20K" refers to EPO with monoantennary glycan structures with terminal 20 kDa PEG moieties. NESP refers to the commercially available Aranesp. "Biant-1K" refers to EPO with biantennary glycan structures with terminal 1 kDa PEG moieties. "Biant-SA" refers to EPO with biantennary glycan structures with terminal 1 kDa moieties. The concentration of the EPO constructs in the bloodstream at 72 hr. is as follows: Biant-10K, 5.1 cpm/ml; Mono-20K, 3.2 cpm/ml; NESP, 1 cpm/ml; and Biant-1K, 0.2 cpm/ml; Biant-SA, 0.1 cpm/ml. The relative area under the curve of the EPO constructs is as follows: Biant-10K, 2.9; Mono-20K, 2.1; NESP, 1; Biant-1K, 0.5; and Biant-SA, 0.2.

Figure 137:
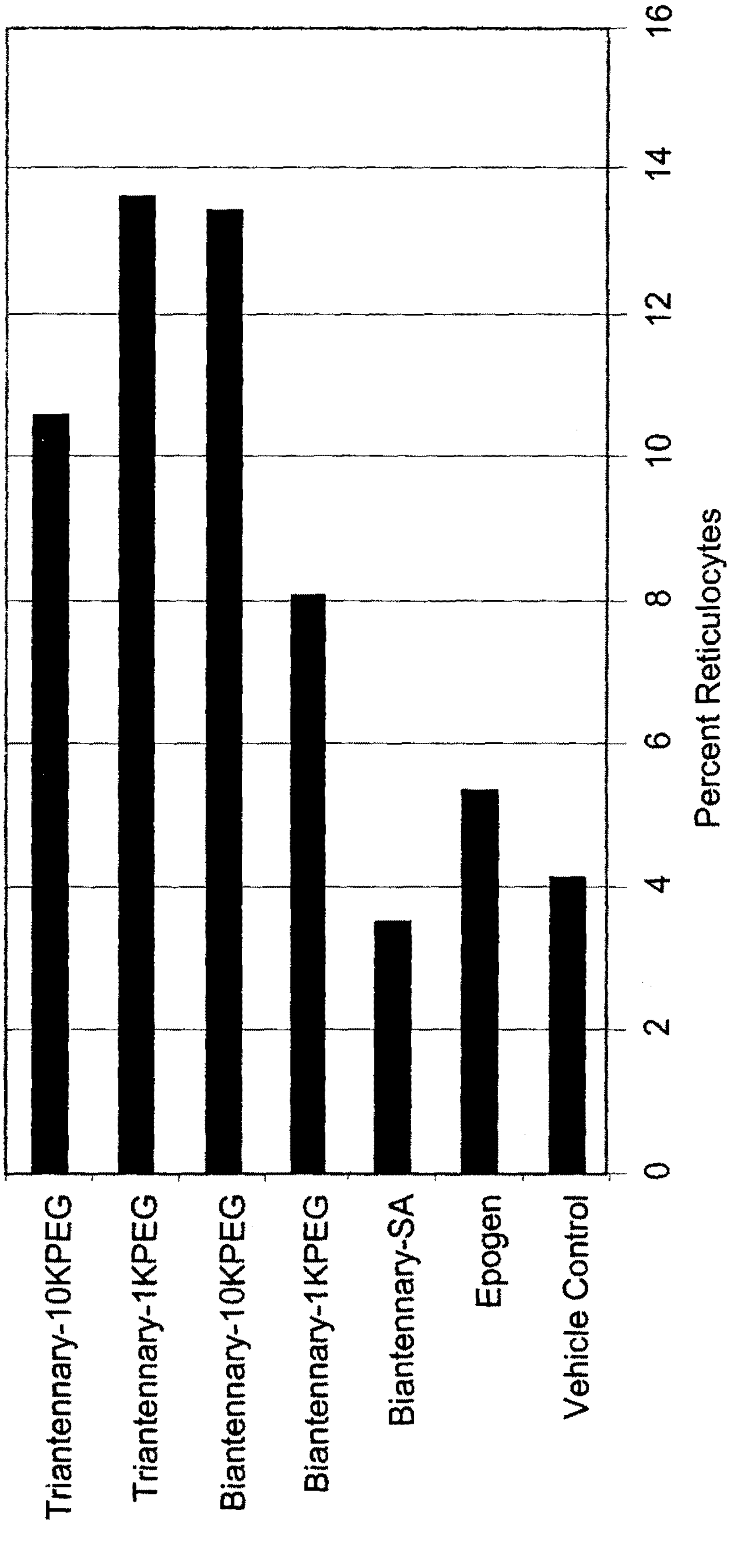

FIG. 137 is a bar graph depicting the ability of the EPO constructs to stimulate reticulocytosis in vivo. Each treatment group is composed of eight mice. Mice were given a single subcutaneous injection of 10 μg protein/kg body weight. The percent reticulocytosis was measured at 96 hr. Tri-antennary-SA2,3(6) construct has the SA molecule bonded in a 2, 3 or 2,6 linkage (see, Example 18 herein for preparation) wherein the glycan on EPO is tri-antennary N-glycans with SA-PEG 10 K is attached thereon. Similarly, bi-antennary-10K PEG is EPO having a bi-antennary N-glycan with SA-PEG at 10 K PEG attached thereon.

Figure 138:
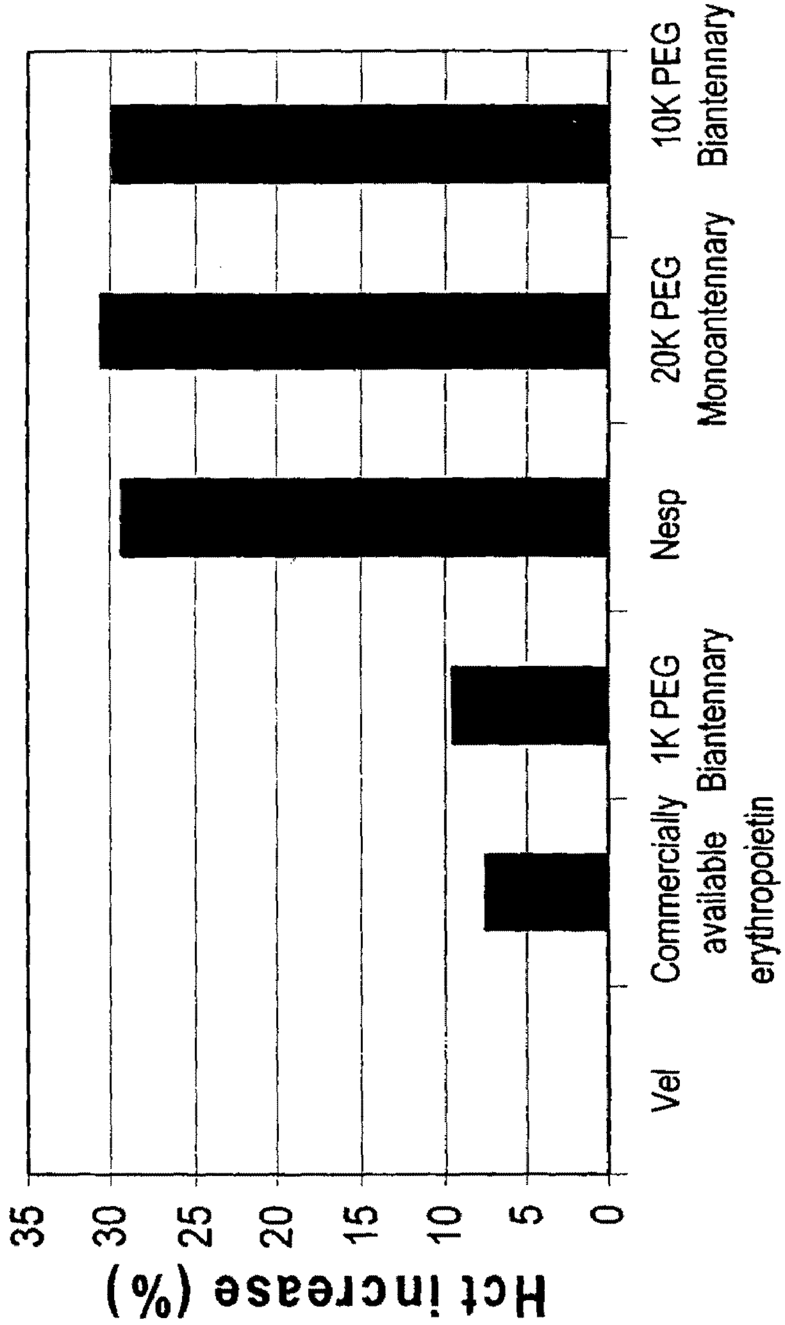

FIG. 138 is a bar graph depicting the ability of EPO constructs to increase the hematocrit of the blood of mice in vivo. CD-1 female mice were injected i.p. with 2.5 μg protein/kg body weight. The hematocrit of the mice was measured on day 15 after the EPO injection. Bi-1k refers to EPO constructs where the glycans are bi-antennary and are built out to the Gal and then glycoPEGylated with SA-PEG 1 kDa. Mono-20k refers to EPO constructs where the glycans are mono-antennary and are built out to the Gal and then glycoPEGylated with SA-PEG 20 kDa.

Figure 139A:
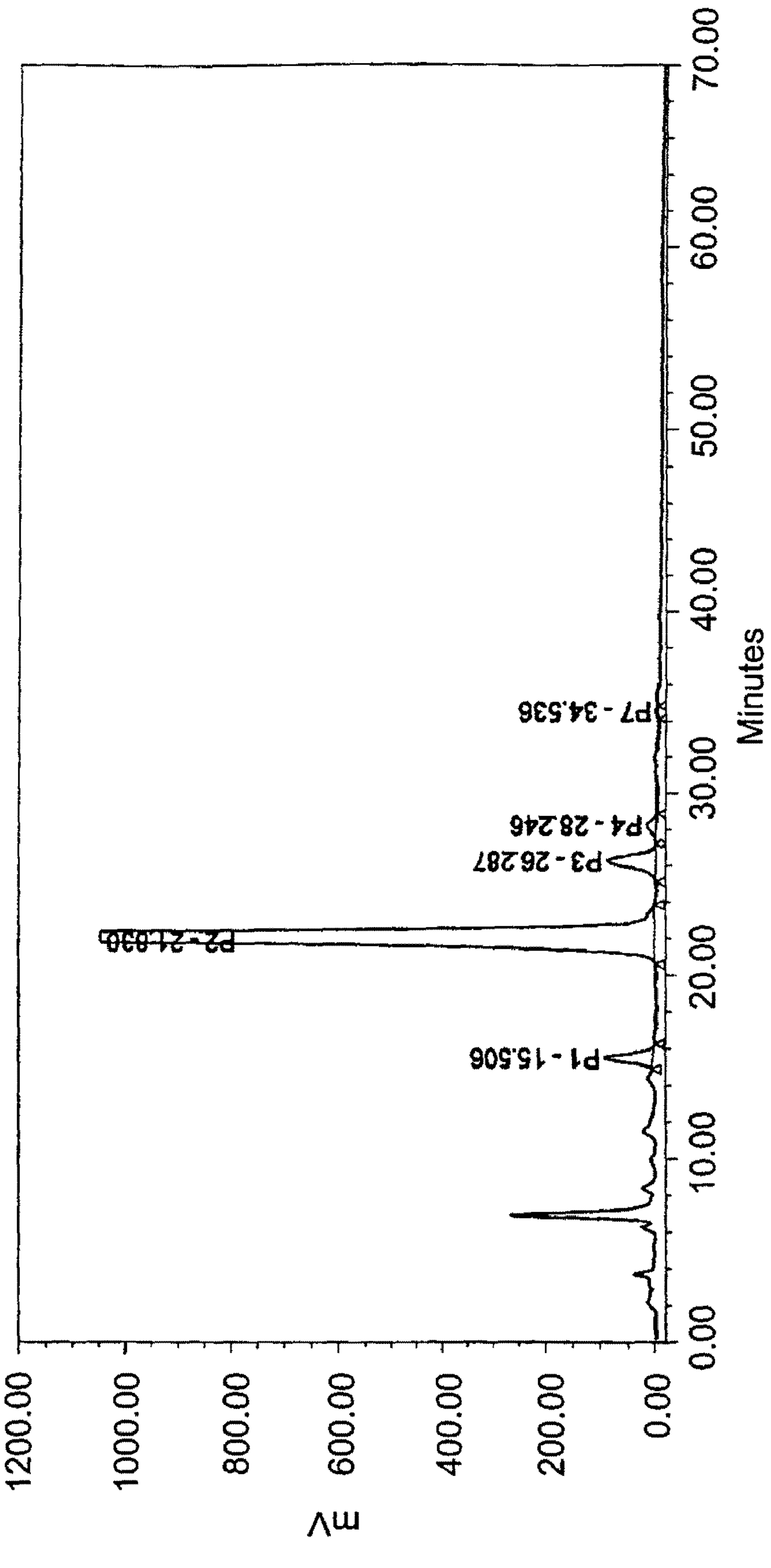
Figure 139B:
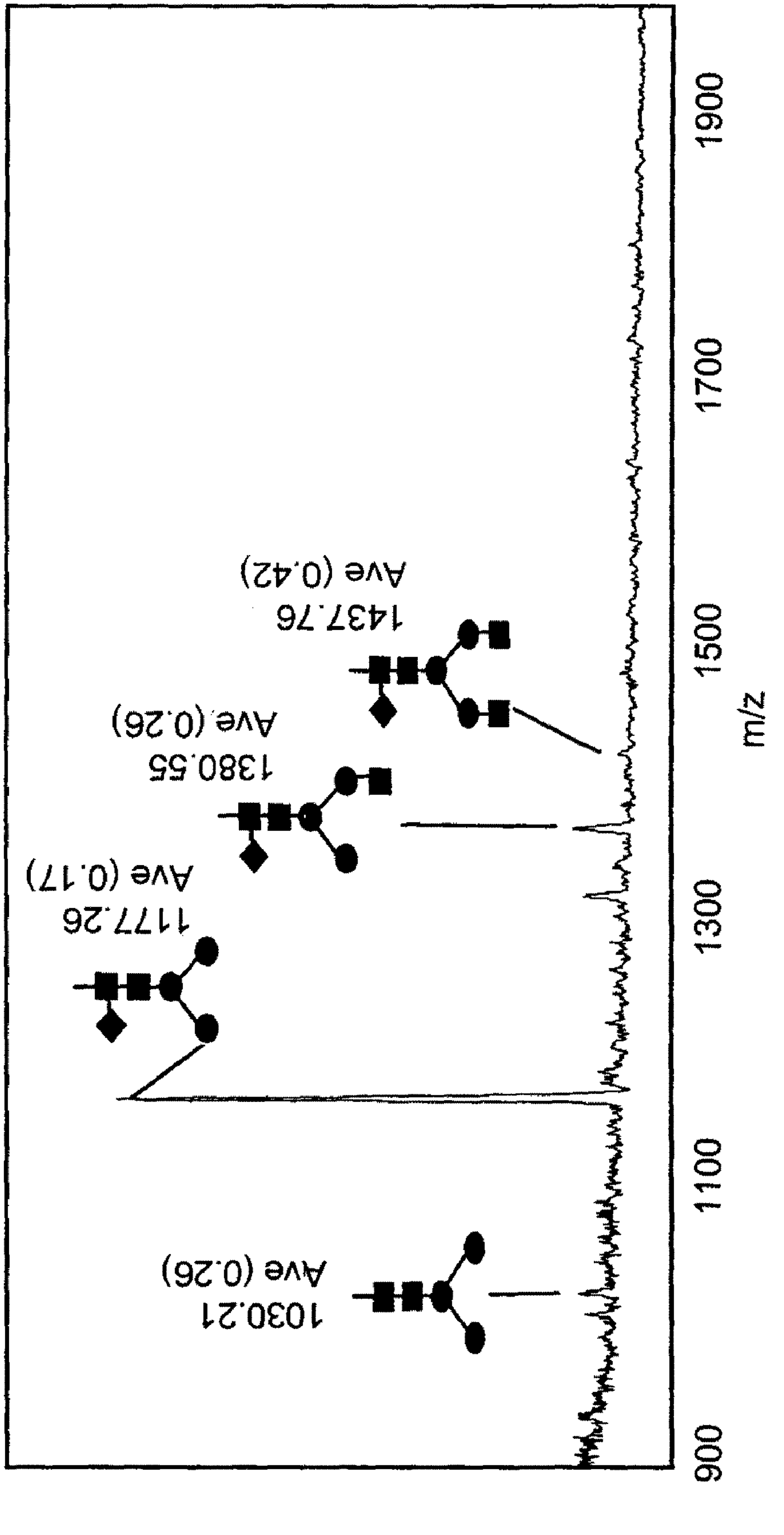

FIG. 139, comprising FIGS. 139A and 139B, depicts the analysis of glycans enzymatically released from EPO expressed in insect cells (Protein Sciences, Lot # 060302). FIG. 139A depicts the HPLC analysis of the released glycans. FIG. 139B depicts the MALDI analysis of the released glycans. Diamonds represent fucose, and squares represent GlcNAc, circles represent mannose.

Figure 140:
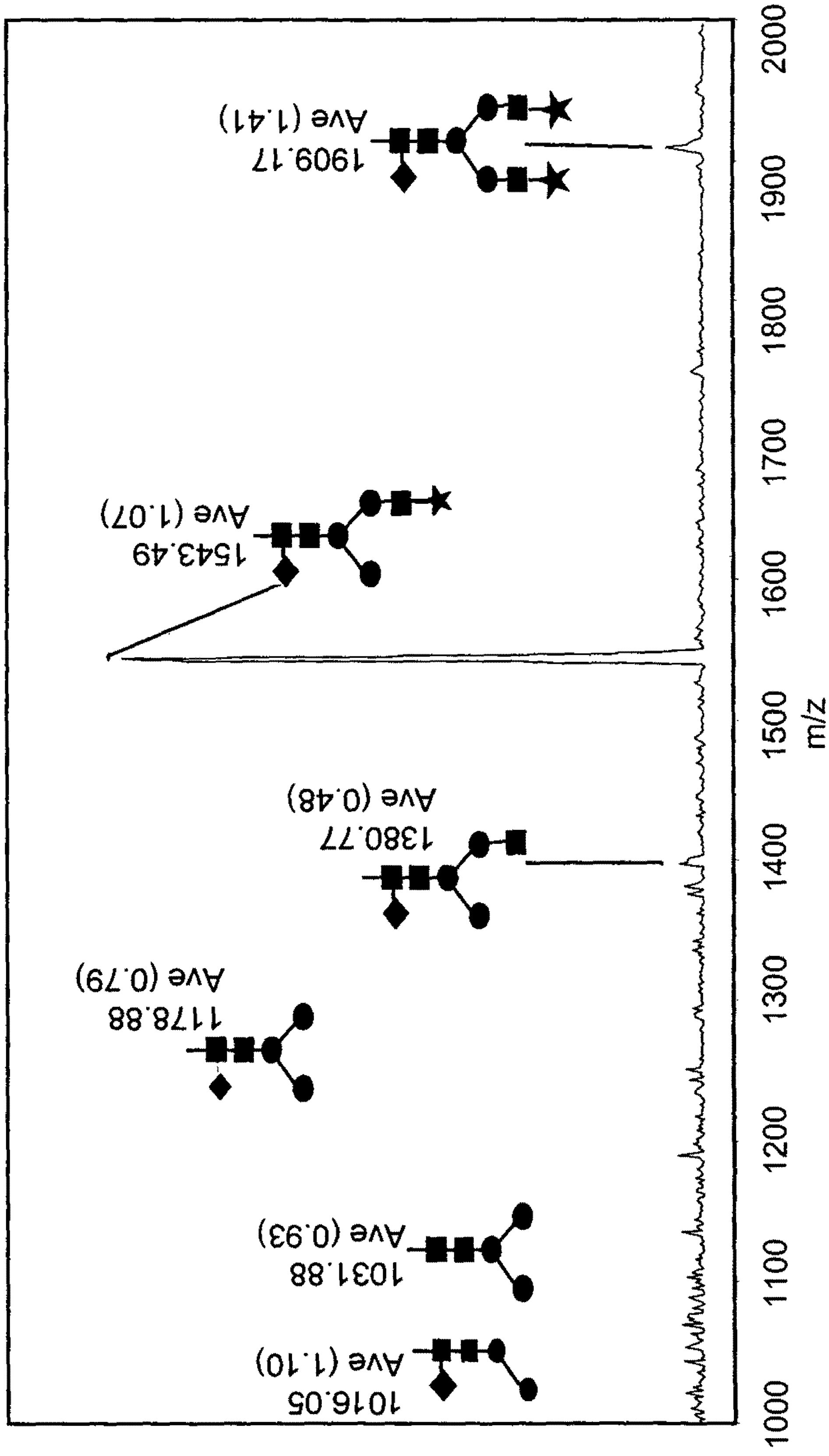

FIG. 140 depicts the MALDI analysis of glycans released from EPO after the GnT-I/GalT-1 reaction. The structures of the glycans have been determined by comparison of the peak spectrum with that of standard glycans. The glycan structures are depicted beside the peaks. Diamonds represent fucose, and squares represent GlcNAc, circles represent mannose, stars represent galactose.

Figure 141:
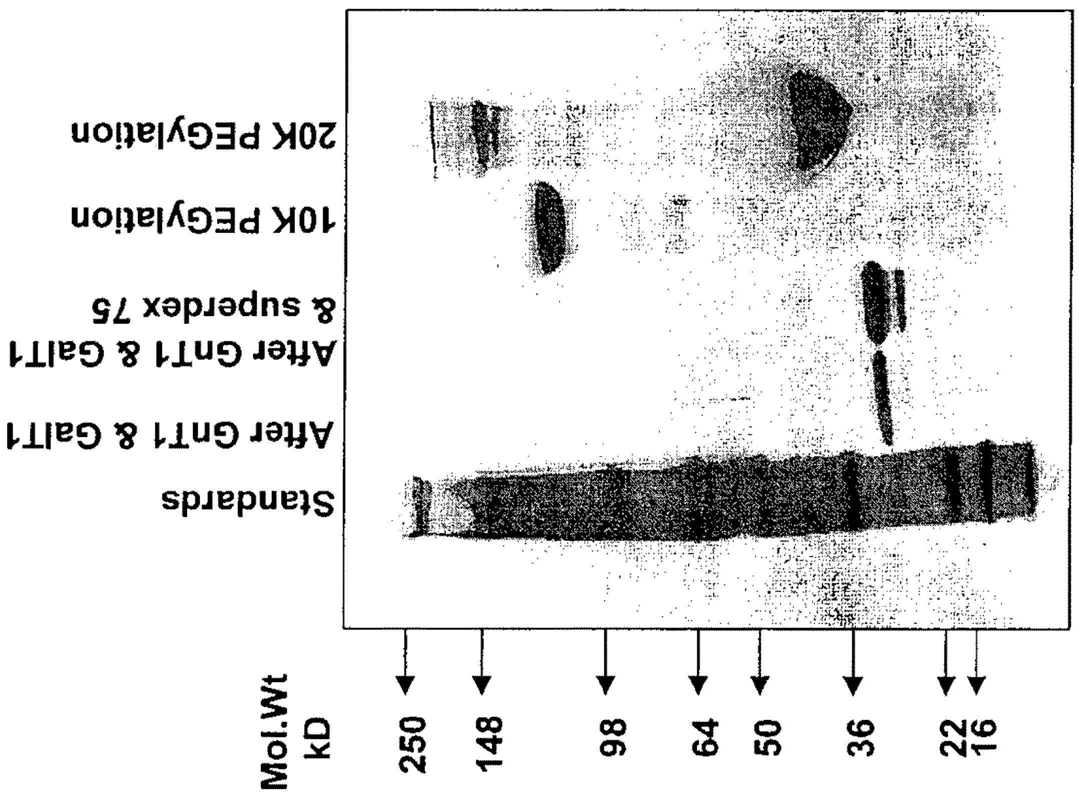

FIG. 141 depicts the SDS-PAGE analysis of EPO after the GnT-I/GalT-1 reaction, Superdex 75 purification, ST3Gal3 reaction with SA-PEG (10 kDa) and SA-PEG (20 kDa).

Figure 142:
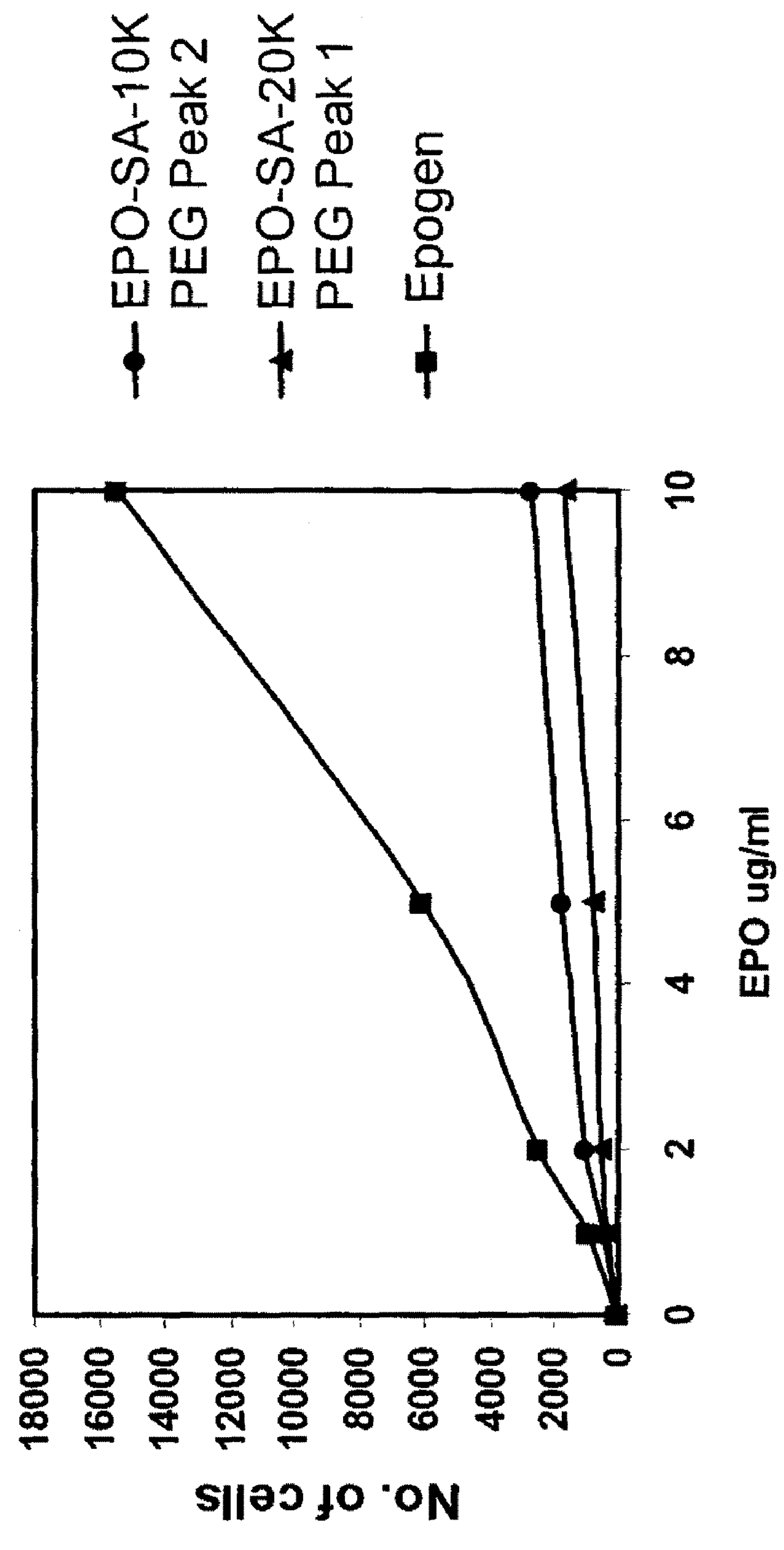

FIG. 142 depicts the results of the TF-1 cell in vitro bioassay of PEGylated mono-antennary EPO.

Figure 143A:
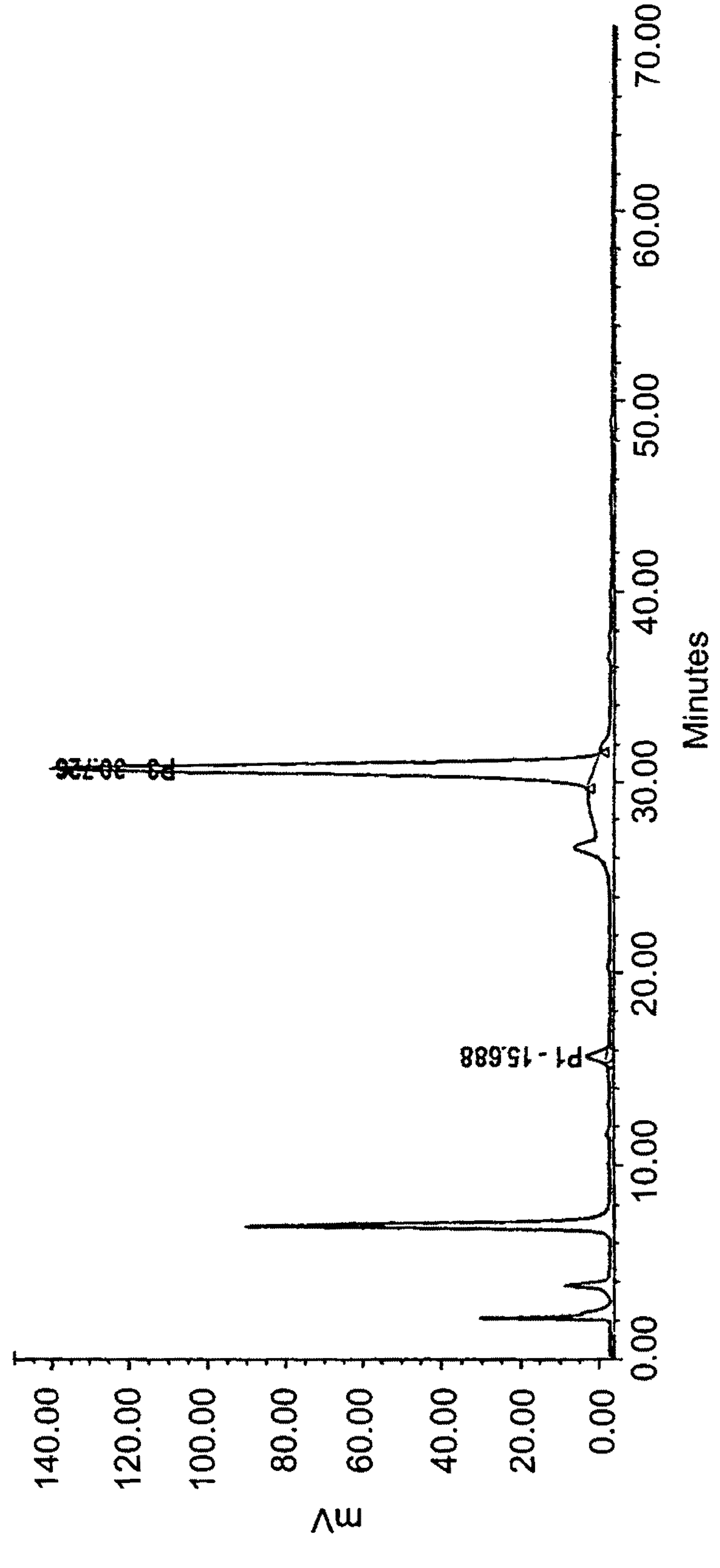
Figure 143B:
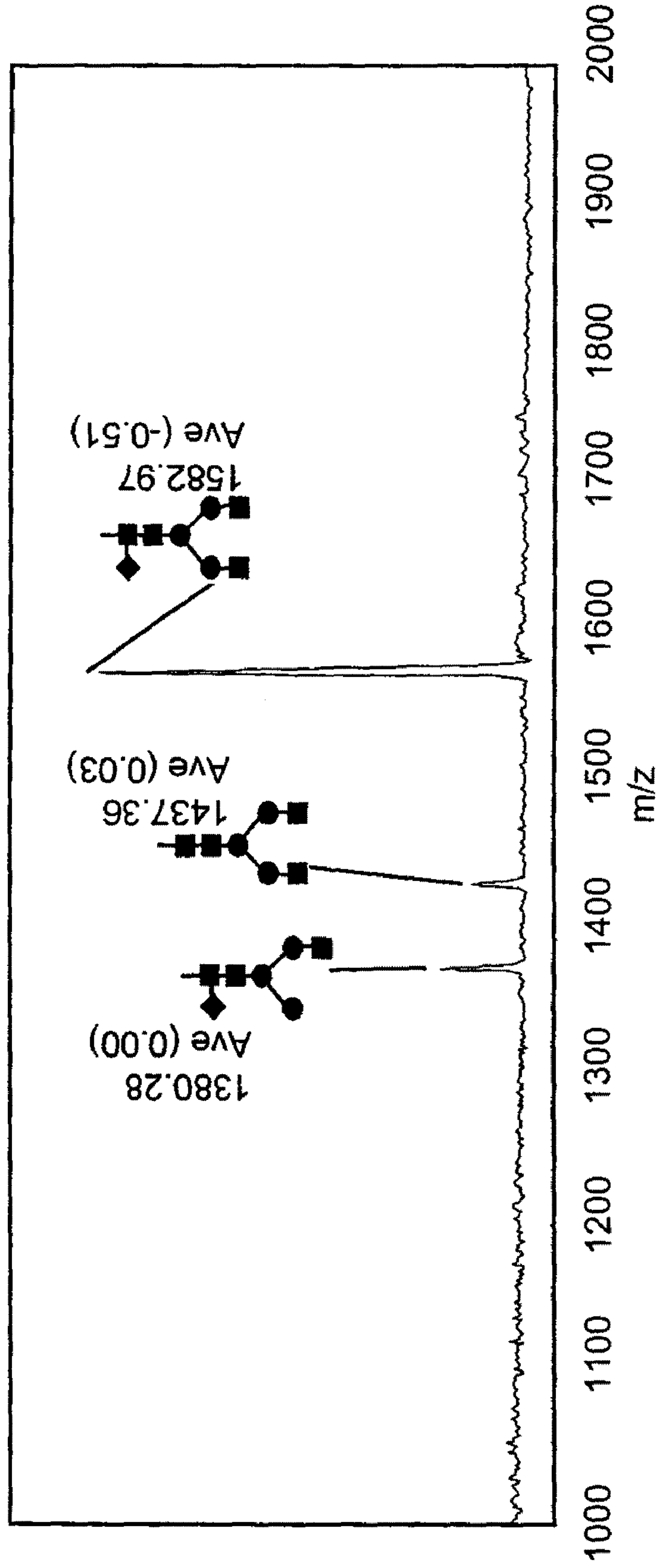

FIG. 143, comprising FIGS. 143A and 143B, depicts the analysis of glycan released from EPO after the GnT-I/GnT-II reaction. FIG. 143A depicts the HPLC analysis of the released glycans, where peak 3 represents the bi-antennary GlcNAc glycan. FIG. 143B depicts the MALDI analysis of the released glycans. The structures of the glycans have been determined by comparison of the peak spectrum with that of standard glycans. The glycan structures are depicted beside the peaks. Diamonds represent fucose, and squares represent GlcNAc, circles represent mannose.

Figure 144A:
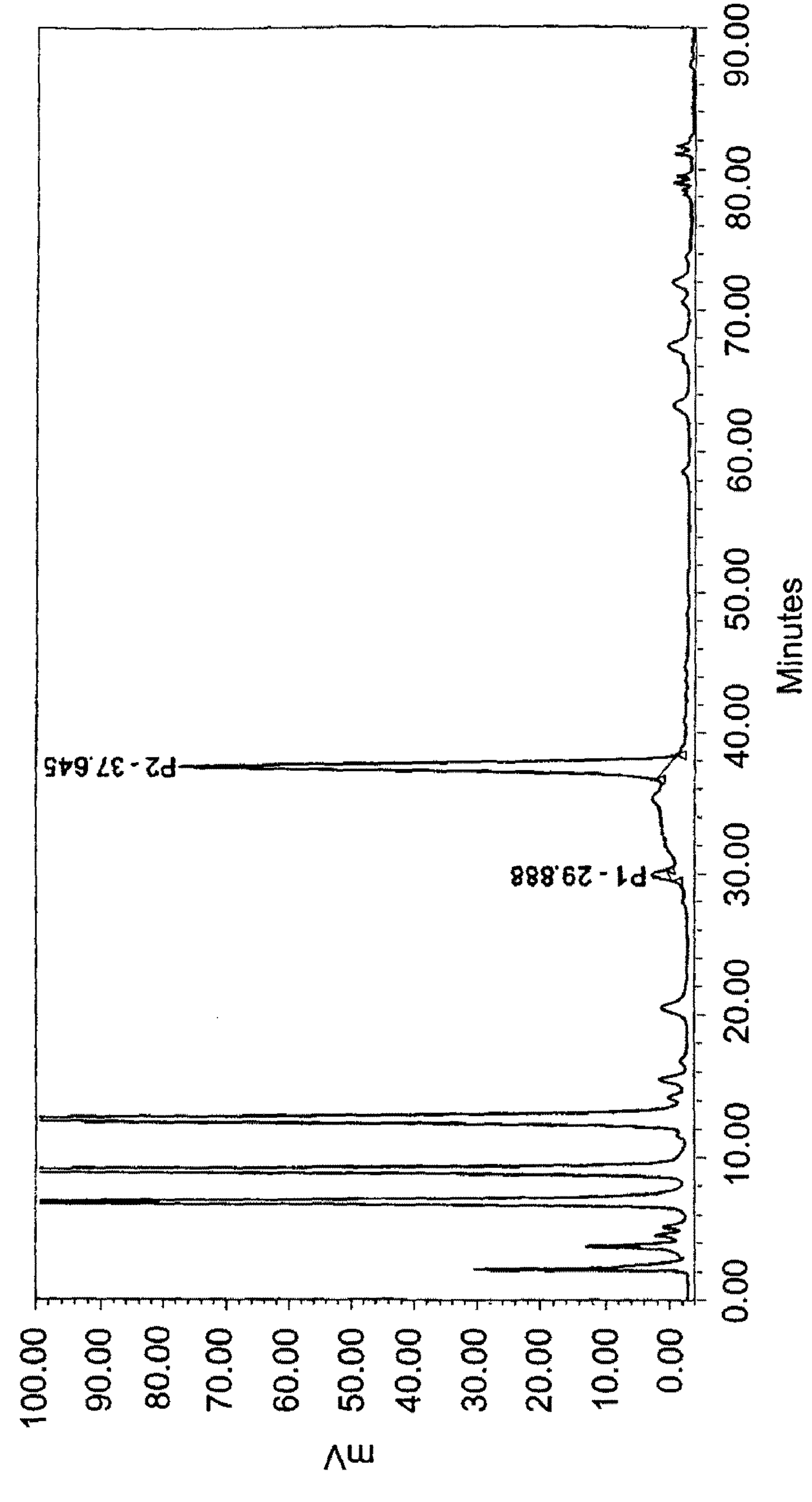
Figure 144B:
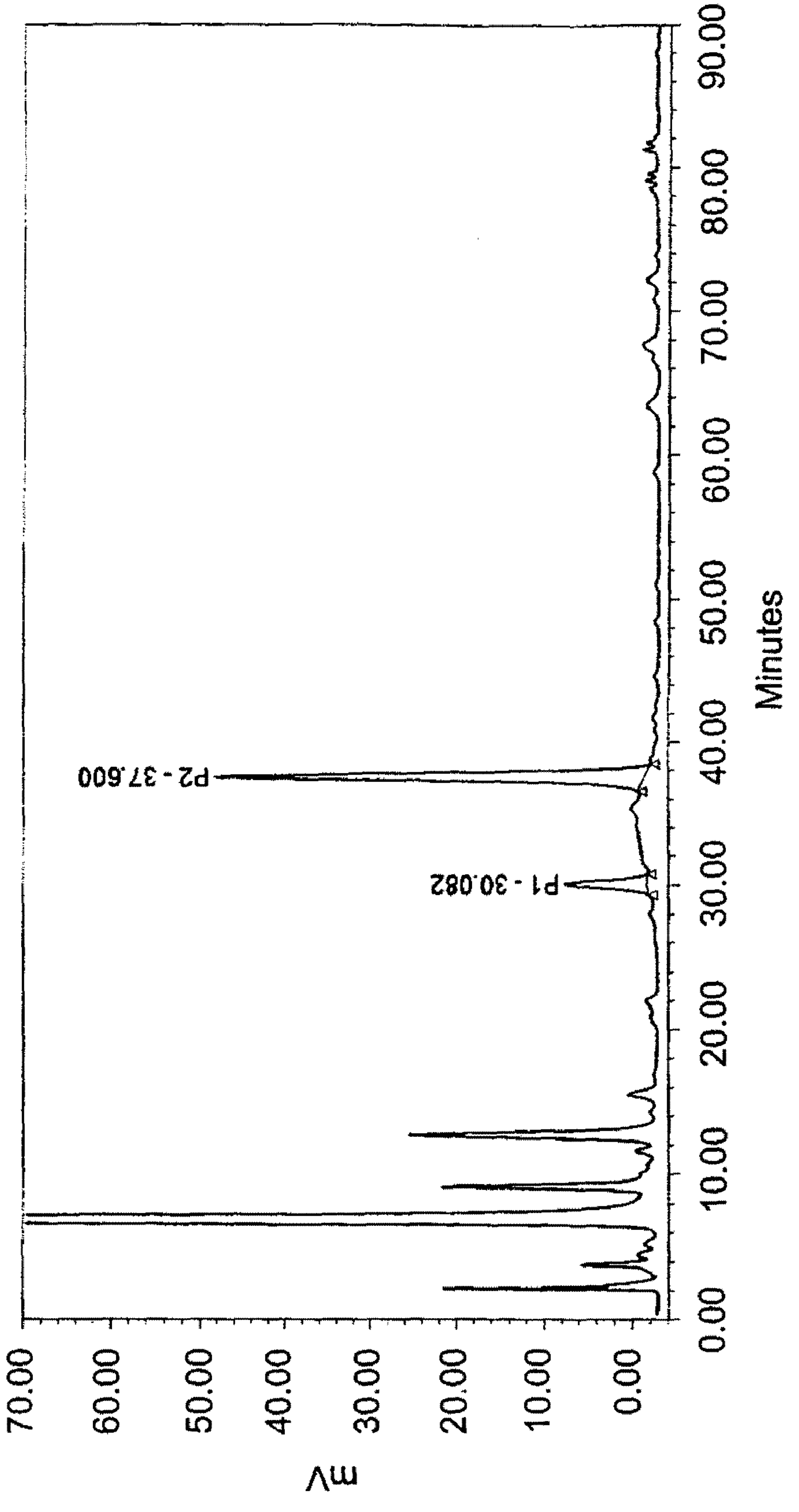

FIG. 144, comprising FIGS. 144A and 144B, depict the HPLC analysis of glycans released from EPO after the GalT-1 reaction. FIG. 144A depicts the glycans released after the small scale GalT-1 reaction. FIG. 144B depicts the glycans released after the large scale GalT-1 reaction. In both figures, Peak 1 is the bi-antennary glycan with terminal galactose moieties and Peak 2 is the bi-antennary glycan without terminal galactose moieties.

Figure 145:
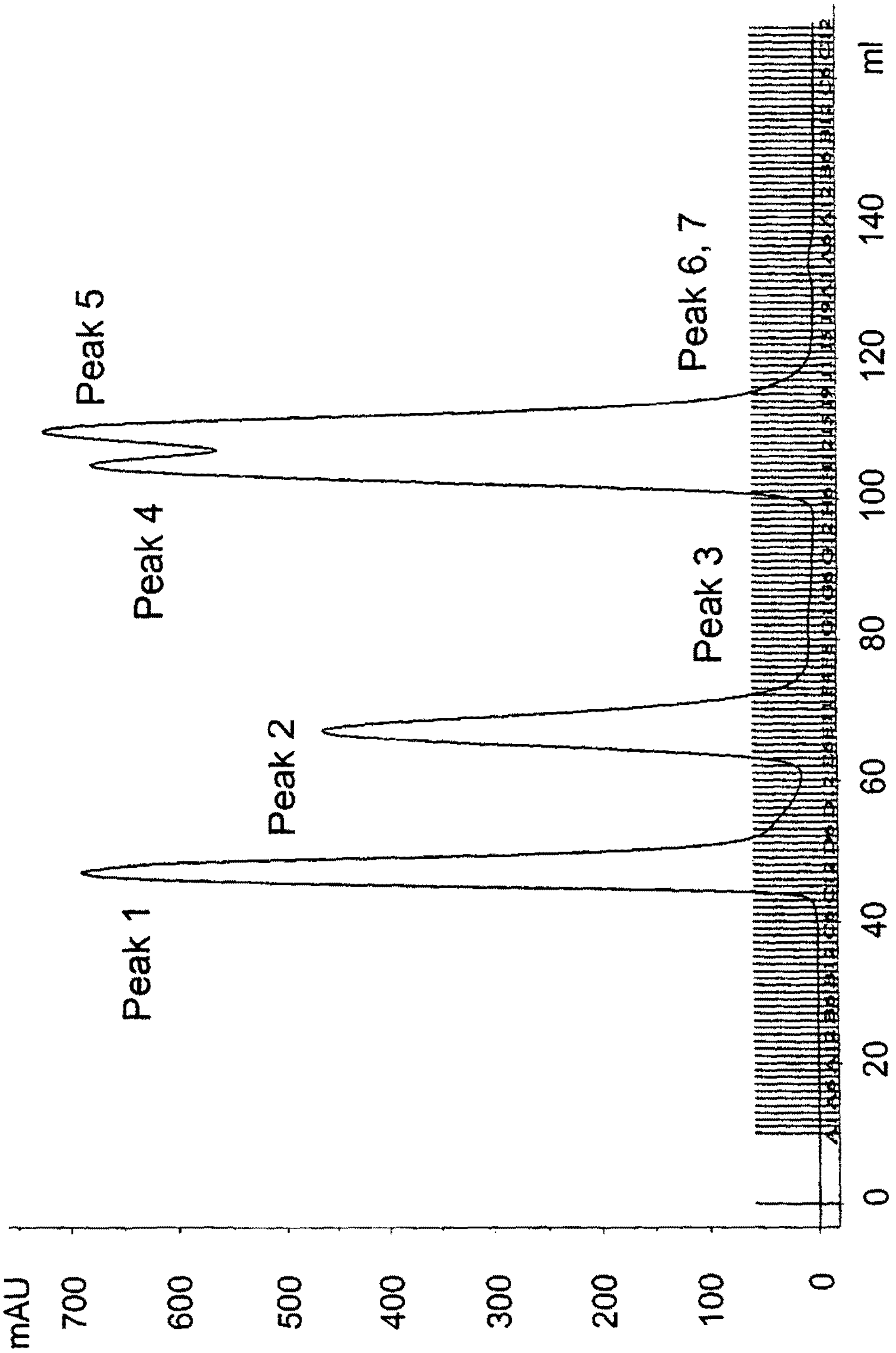

FIG. 145 depicts the Superdex 75 chromatography separation of EPO species after the GalT-1 reaction. Peak 2 contains EPO with bi-antennary glycans with terminal galactose moieties.

Figure 146:
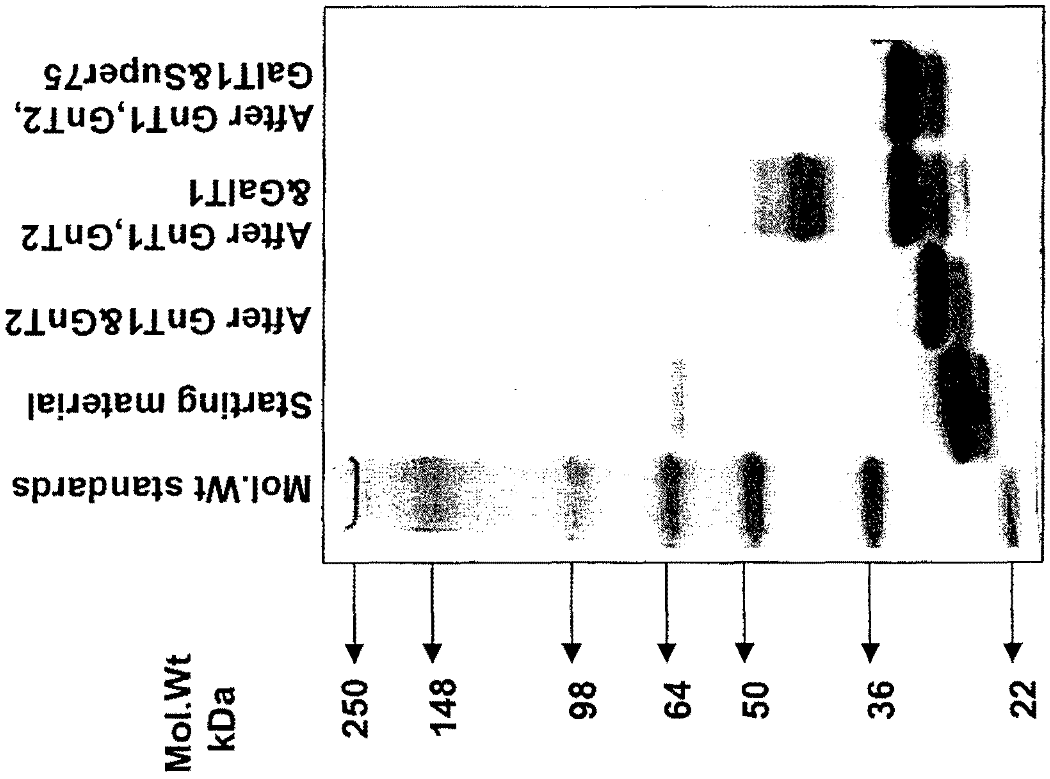

FIG. 146 depicts the SDS-PAGE analysis of each of the products of the glycoremodeling process to make bi-antennary glycans with terminal galactose moieties.

Figure 147:
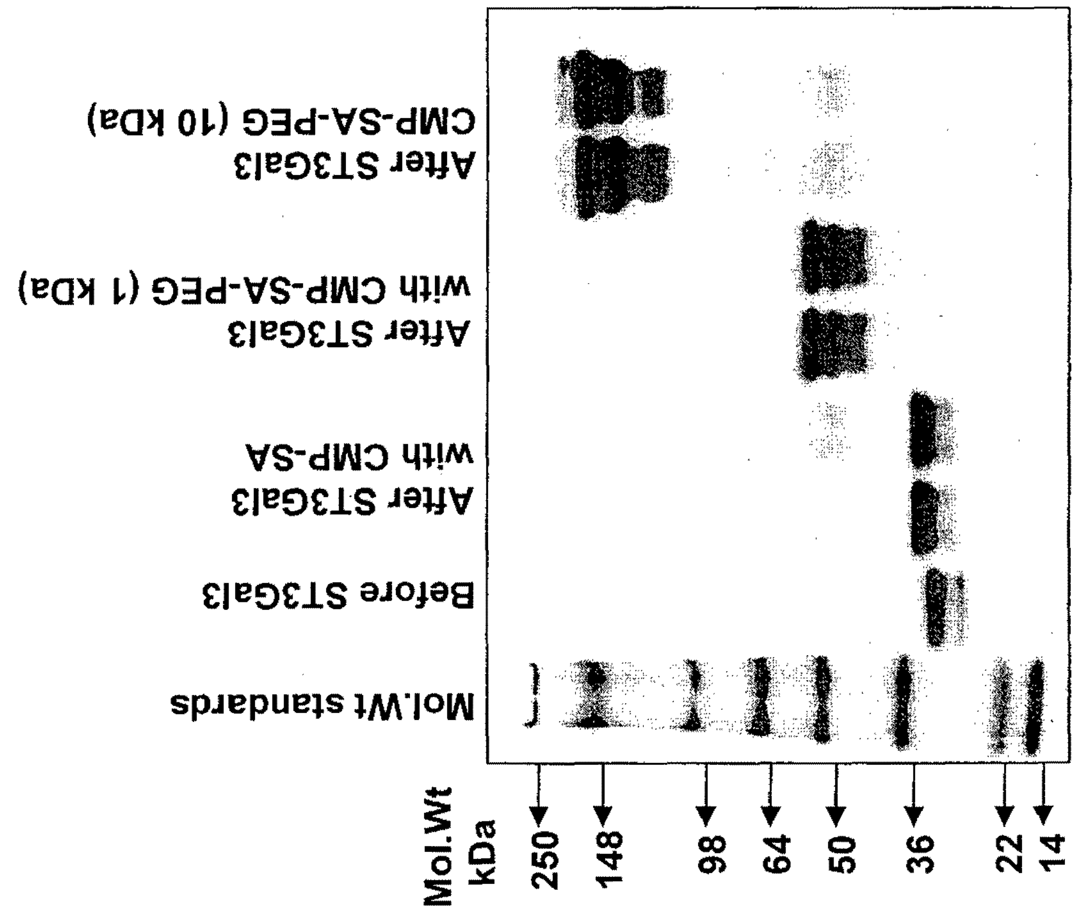

FIG. 147 depicts the SDS-PAGE analysis of EPO after ST3Gal3 sialylation or PEGylation with SA-PEG (1 kDa) or SA-PEG (10 kDa).

Figure 148:
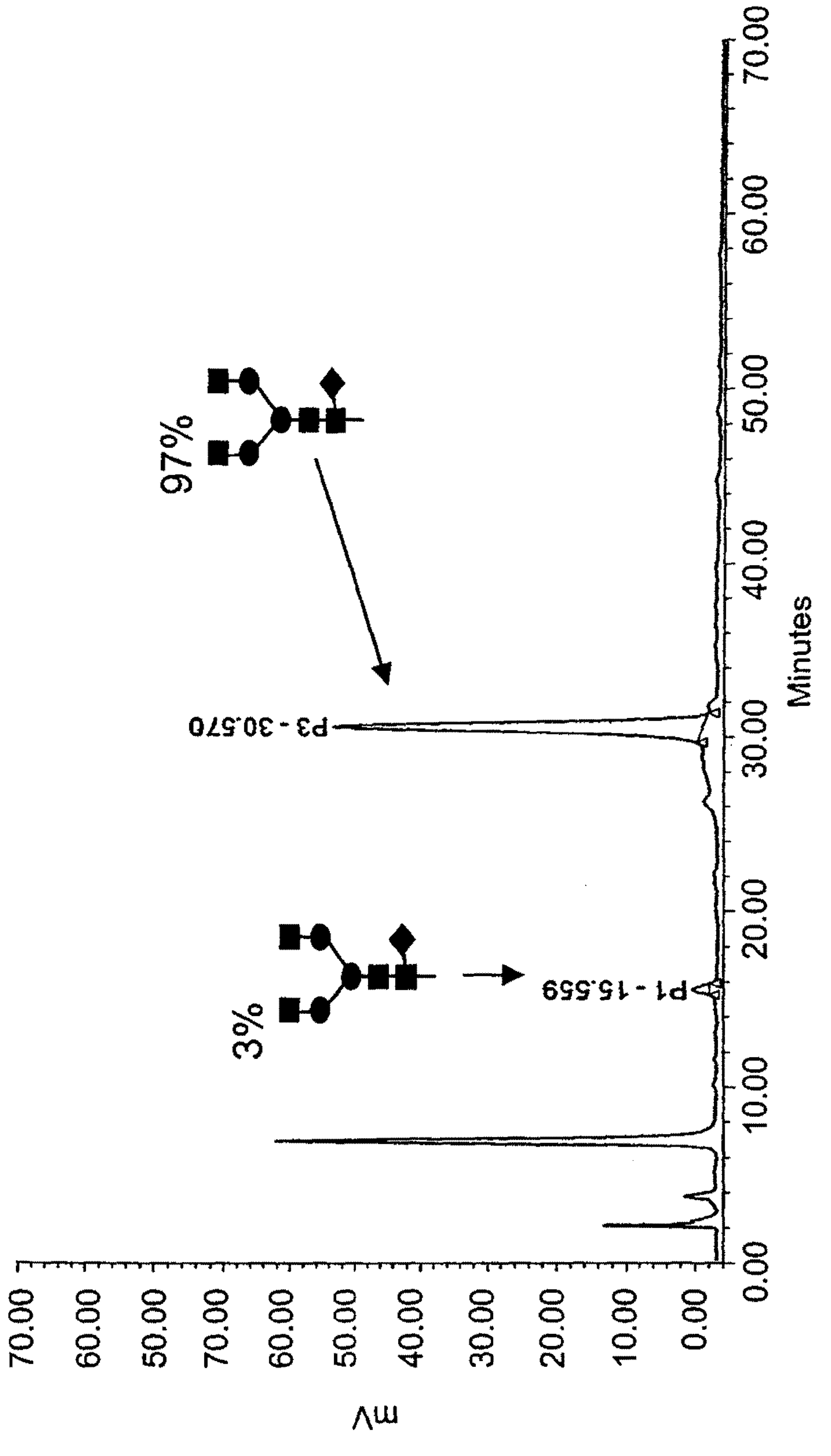

FIG. 148 depicts the HPLC analysis of glycans released from EPO after the GnT-I/GnT-II reaction. The structures of the glycans have been determined by comparison of the peak retention with that of standard glycans. The glycan structures are depicted beside the peaks. Diamonds represent fucose, and squares represent GlcNAc, circles represent mannose.

Figure 149:
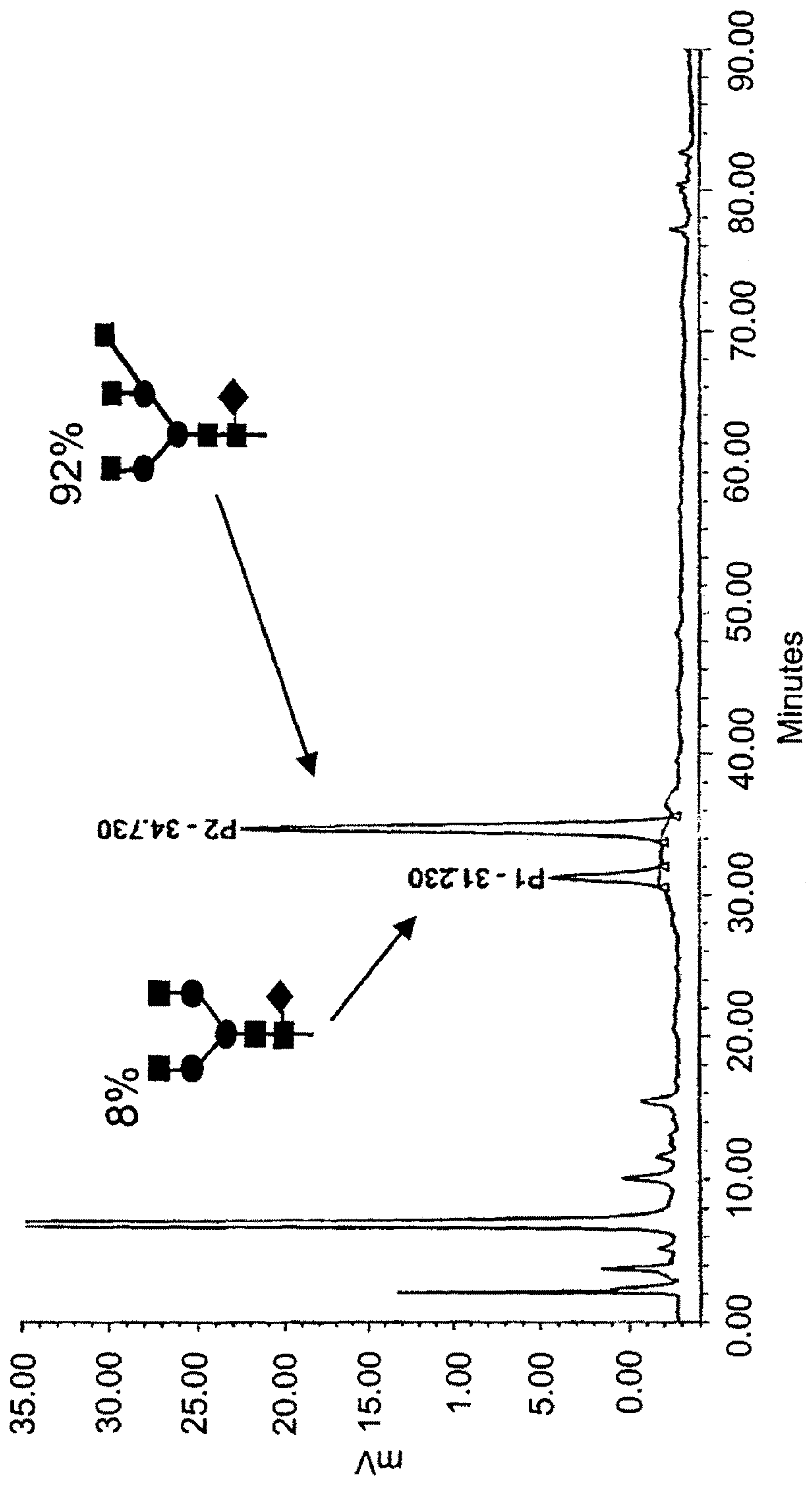

FIG. 149 depicts the HPLC analysis of glycans released from EPO after the GnT-V reaction. The structures of the glycans have been determined by comparison of the peak retention with that of standard glycans. The glycan structures are depicted beside the peaks. Diamonds represent fucose, and squares represent GlcNAc, circles represent mannose.

Figure 150:
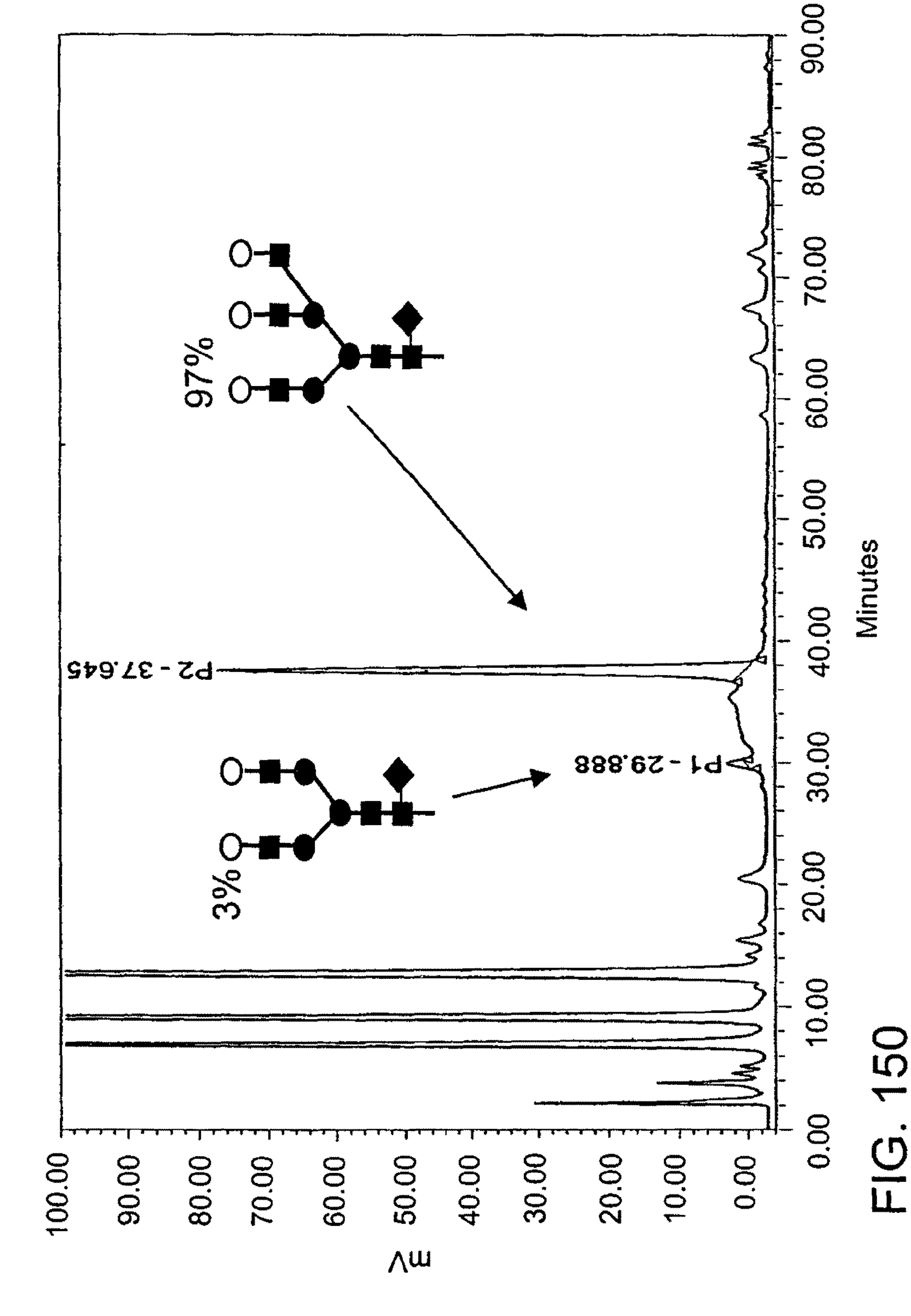

FIG. 150 depicts the HPLC analysis of glycans released from EPO after the GalT-1 reaction. The structures of the glycans have been determined by comparison of the peak retention with that of standard glycans. The glycan structures are depicted beside the peaks. Diamonds represent fucose, and squares represent GlcNAc, circles represent mannose, open circles represent galactose and triangles represent sialic acid.

Figure 151:
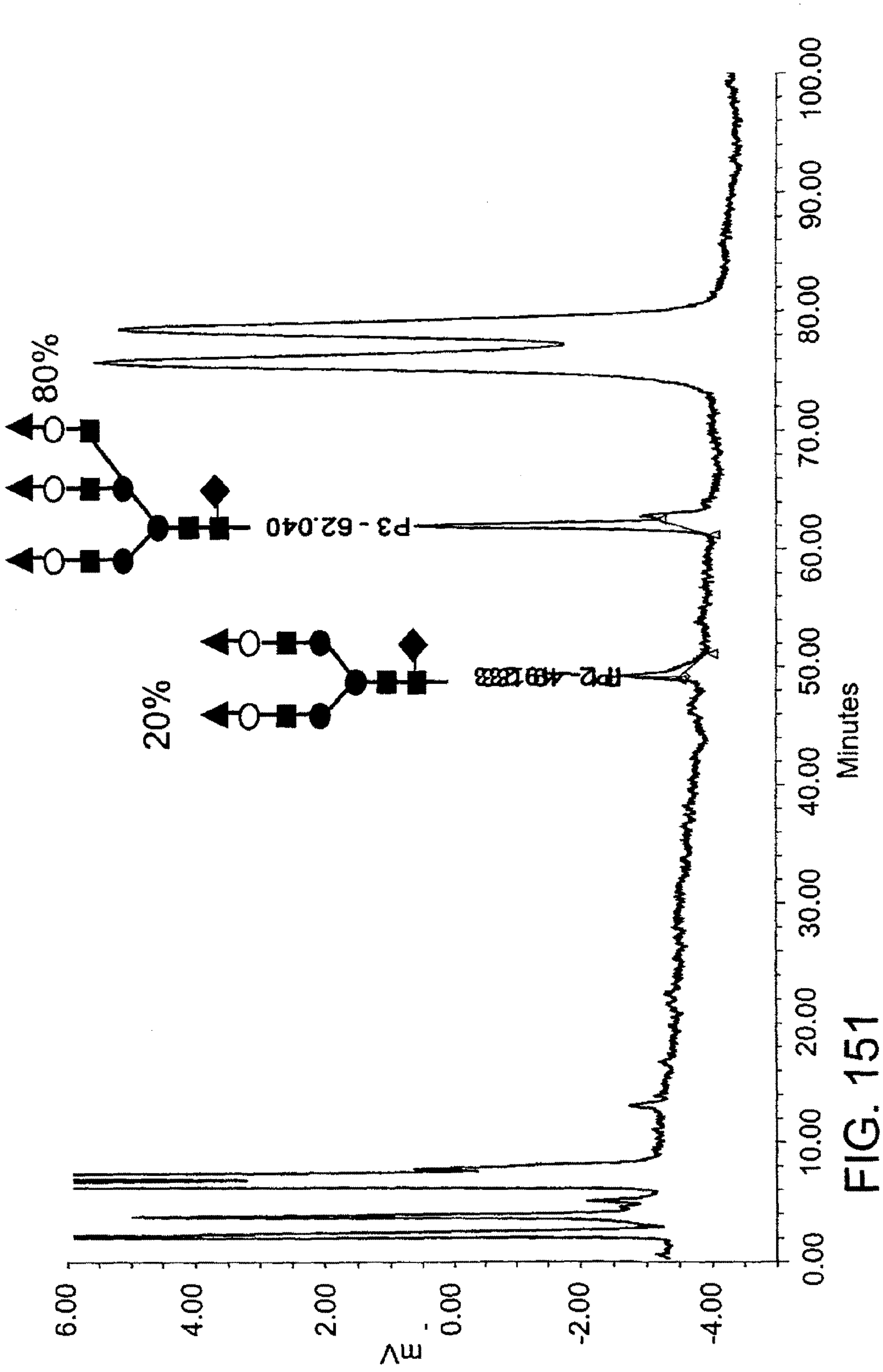

FIG. 151 depicts the HPLC analysis of glycans released from EPO after the ST3Gal3 reaction. The structures of the glycans have been determined by comparison of the peak retention with that of standard glycans. The glycan structures are depicted beside the peaks. Diamonds represent fucose, and squares represent GlcNAc, circles represent mannose, open circles represent galactose and triangles represent sialic acid.

Figure 152:
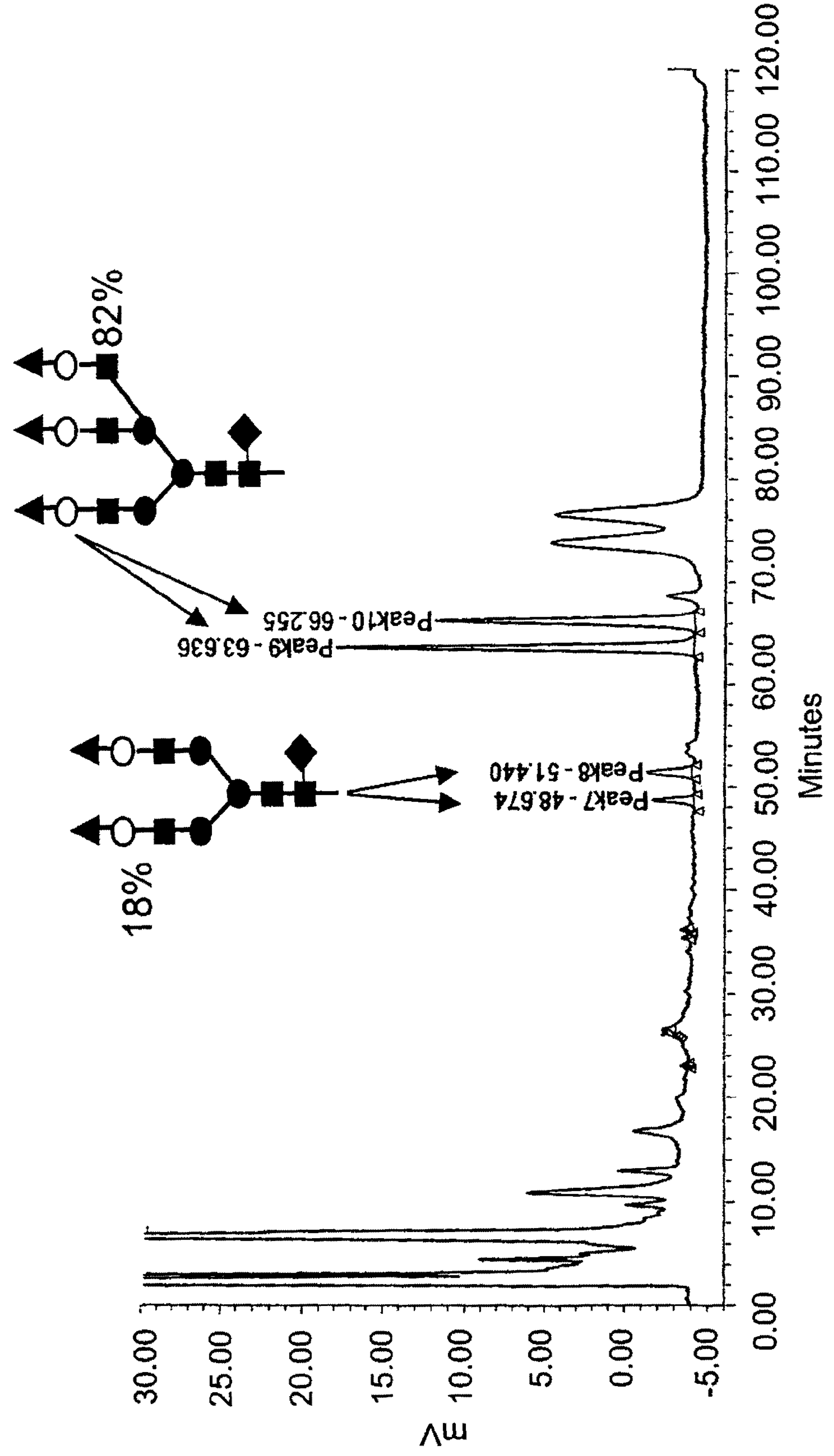

FIG. 152 depicts the HPLC analysis of glycans released from EPO after the ST6Gal1 reaction. The structures of the glycans have been determined by comparison of the peak retention with that of standard glycans. The glycan structures are depicted beside the peaks.

Figure 153:
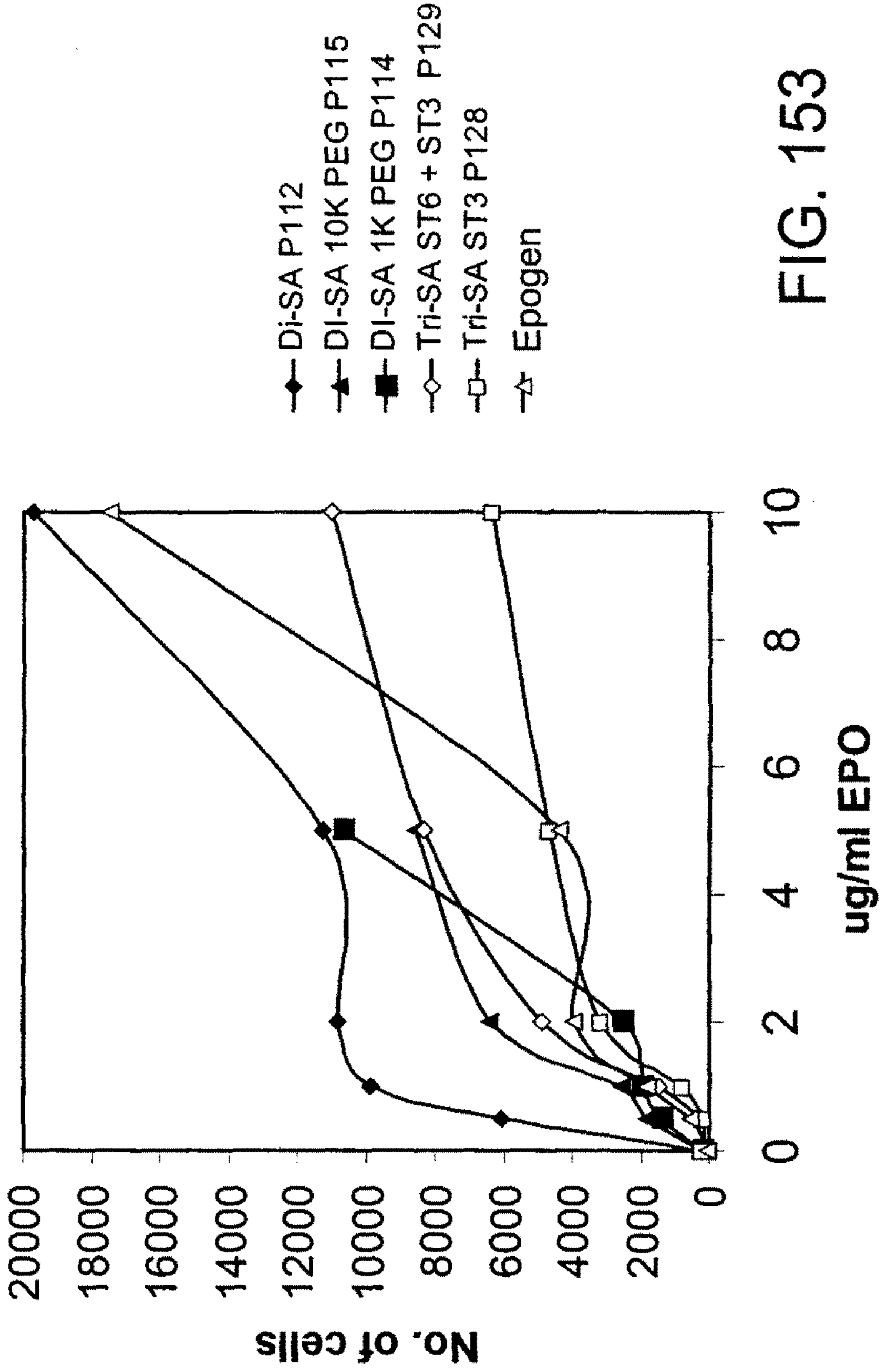

FIG. 153 depicts the results of the TF-1 cells in vitro bioassay of EPO with bi-antennary and triantennary glycans. "Di-SA" refers to EPO with bi-antennary glycans that terminate in sialic acid. "Di-SA 10K PEG" refers to EPO with bi-antennary glycans that terminate in sialic acid derivatized with PEG (10 kDa). "Di-SA 1K PEG" refers to EPO with bi-antennary glycans that terminate in sialic acid derivatized with PEG (1 kDa). "Tri-SA ST6+ST3" refers to EPO with tri-antennary glycans terminating in 2,6-SA capped with 2,3-SA. "Tri-SA ST3" refers to EPO with tri-antennary glycans terminating in 2,3-SA.

Figure 154:
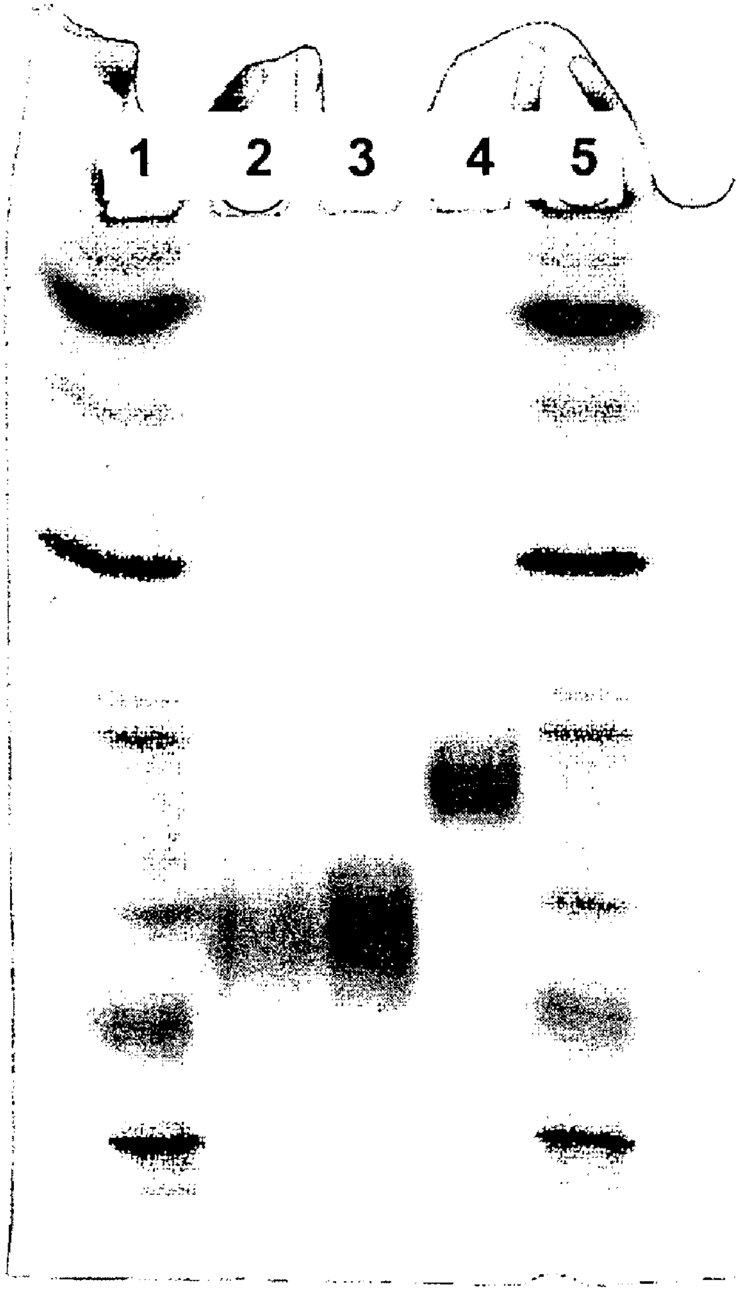

FIG. 154 is an image of an IEF gel depicting the pI of the products of the desialylation procedure. Lanes 1 and 5 are IEF standards. Lane 2 is Factor IX protein. Lane 3 is rFactor IX protein. Lane 4 is the desialylation reaction of rFactor IX protein at 20 hr.

Figure 155:
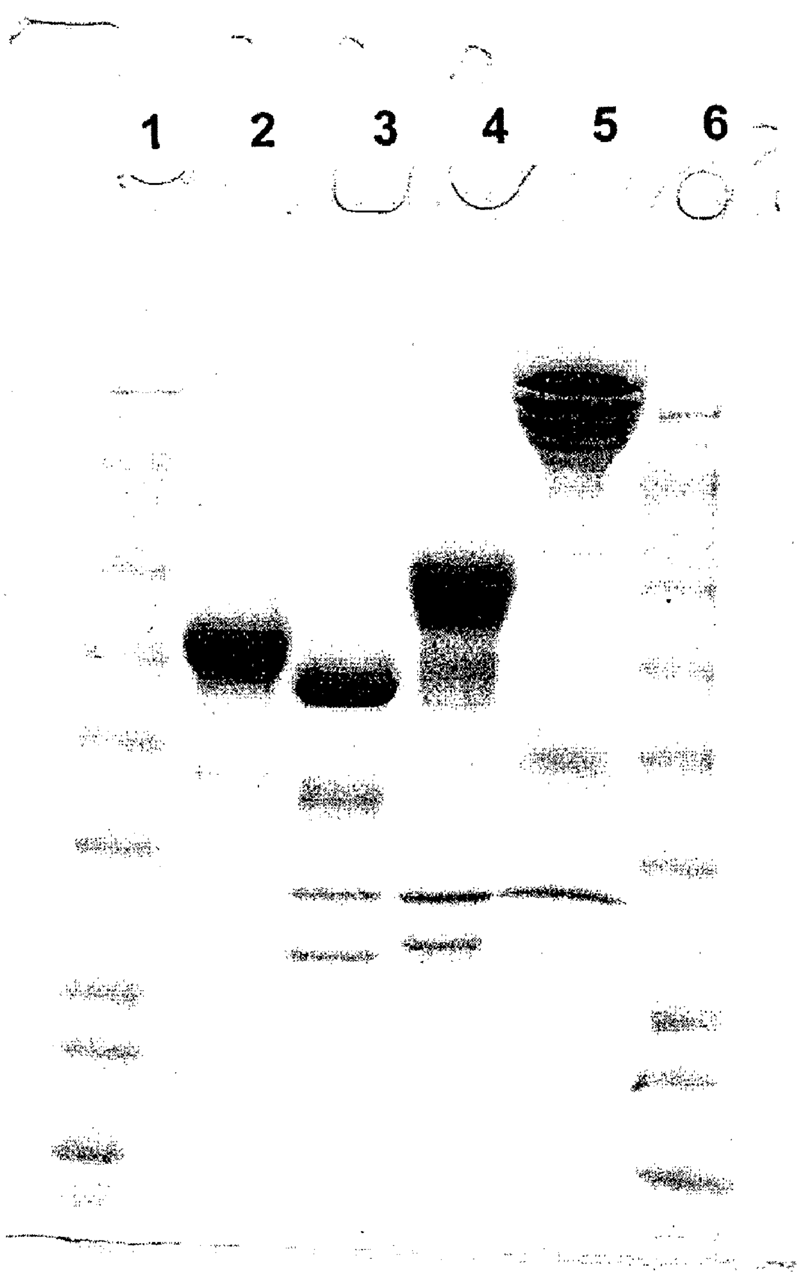

FIG. 155 is an image of an SDS-PAGE gel depicting the molecular weight of Factor IX conjugated with either SA-PEG (1 kDa) or SA-PEG (10 kDa) after reaction with CMP-SA-PEG. Lanes 1 and 6 are SeeBlue +2 molecular weight standards. Lane 2 is rF-IX. Lane 3 is desialylated rF-IX. Lane 4 is rFactor IX conjugated to SA-PEG (1 kDa). Lane 5 is rFactor IX conjugated to SA-PEG (10 kDa).

Figure 156:
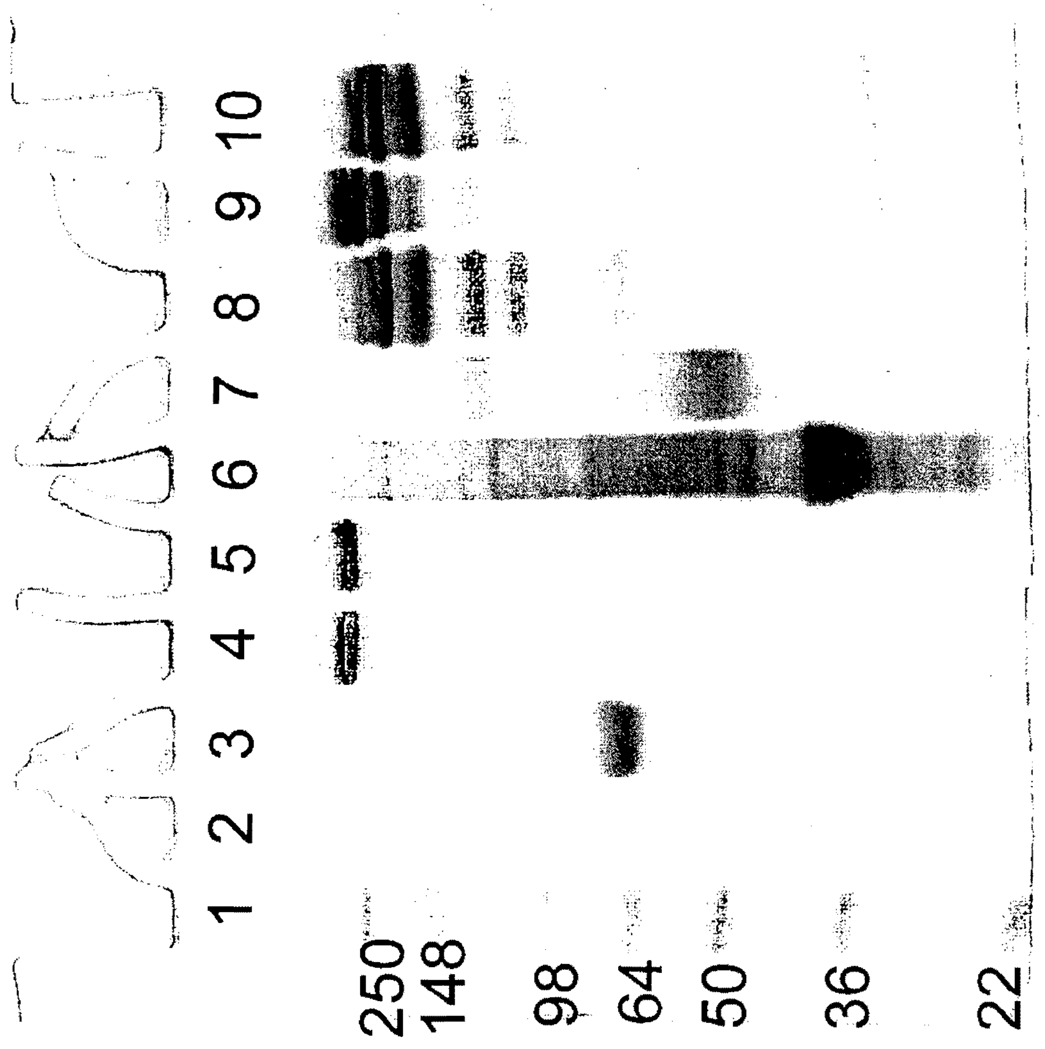

FIG. 156 is an image of an SDS-PAGE gel depicting the reaction products of direct-sialylation of Factor-IX and sialic acid capping of Factor-IX-SA-PEG. Lane 1 is protein standards, lane 2 is blank; lane 3 is rFactor-IX; lane 4 is SA capped rFactor-IX-SA-PEG (10 kDa); lane 5 is rFactor-IX-SA-PEG (10 kDa); lane 6 is ST3Gal1; lane 7 is ST3Gal3; lanes 8, 9, 10 are rFactor-IX-SA-PEG (10 kDa) with no prior sialidase treatment.

Figure 157:
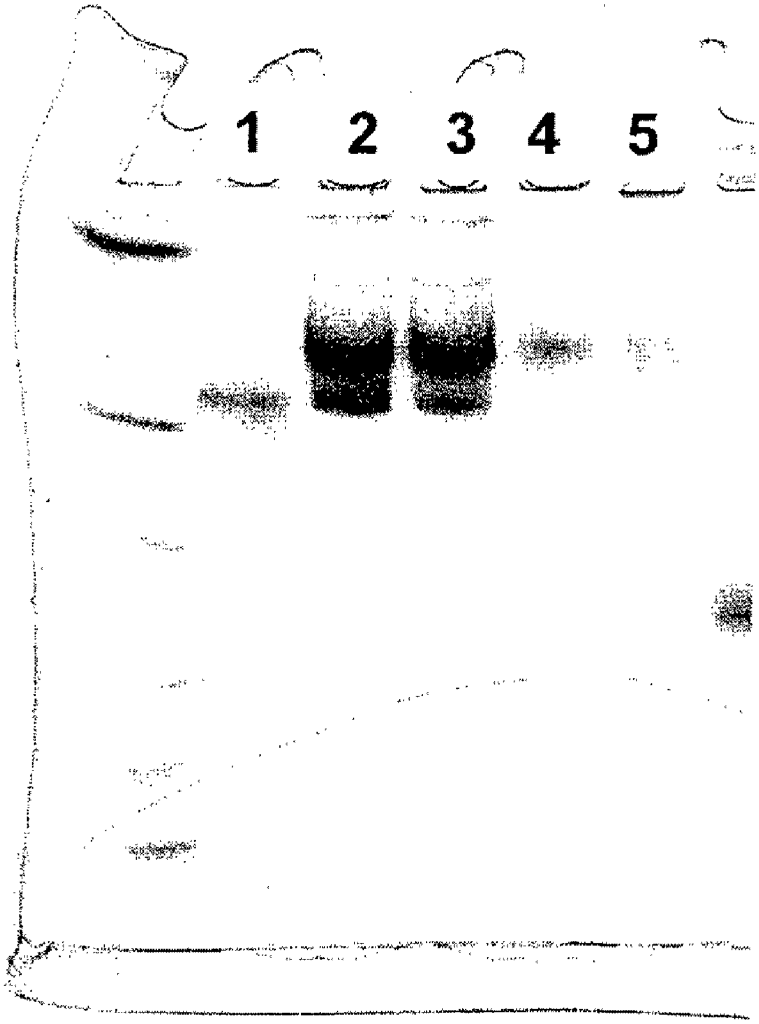

FIG. 157 is an image of an isoelectric focusing gel (pH 3-7) of asialo-Factor VIIa. Lane 1 is rFactor VIIa; lanes 2-5 are asialo-Factor VIIa.

Figure 158:
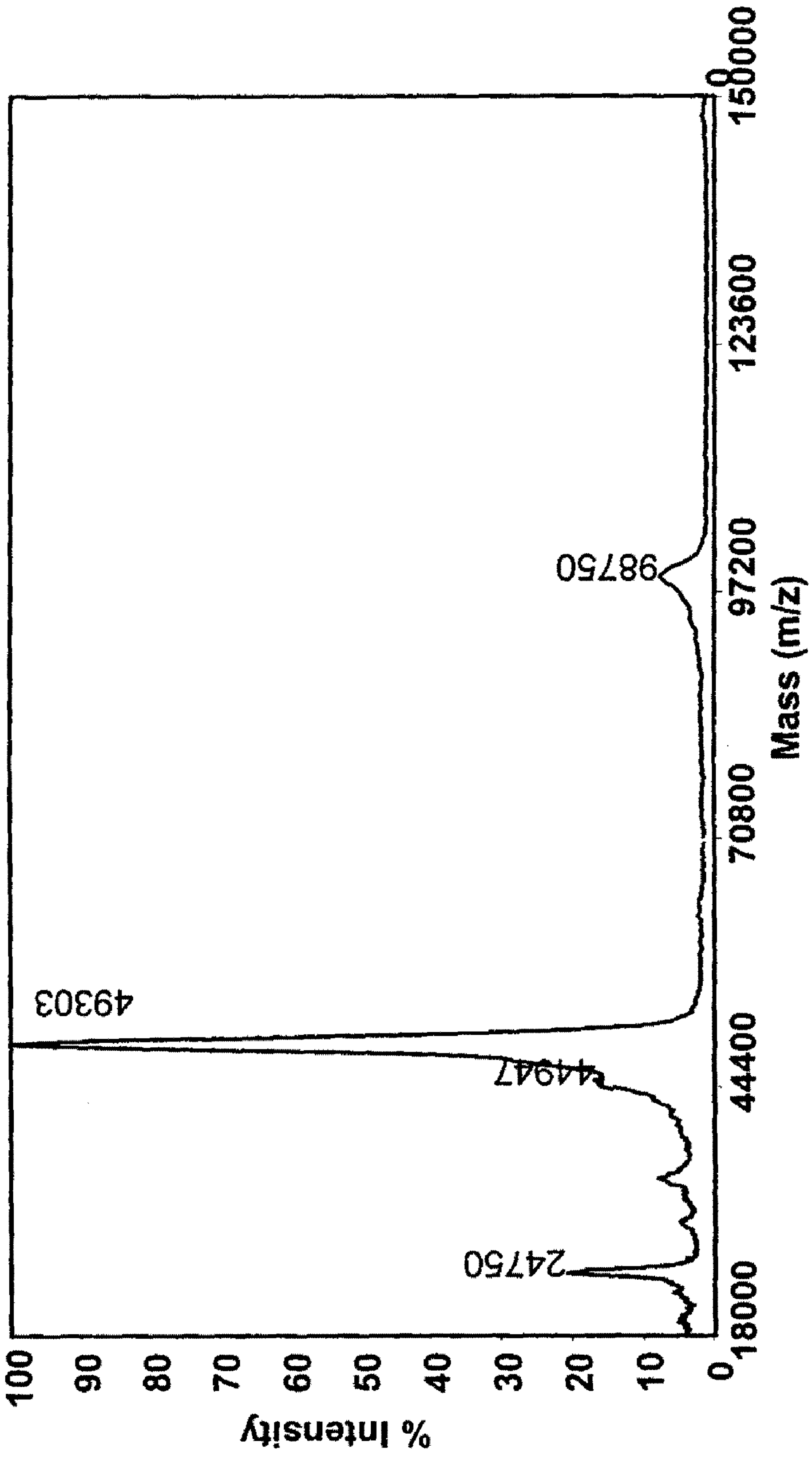

FIG. 158 is a graph of a MALDI spectra of Factor VIIa.

Figure 159:
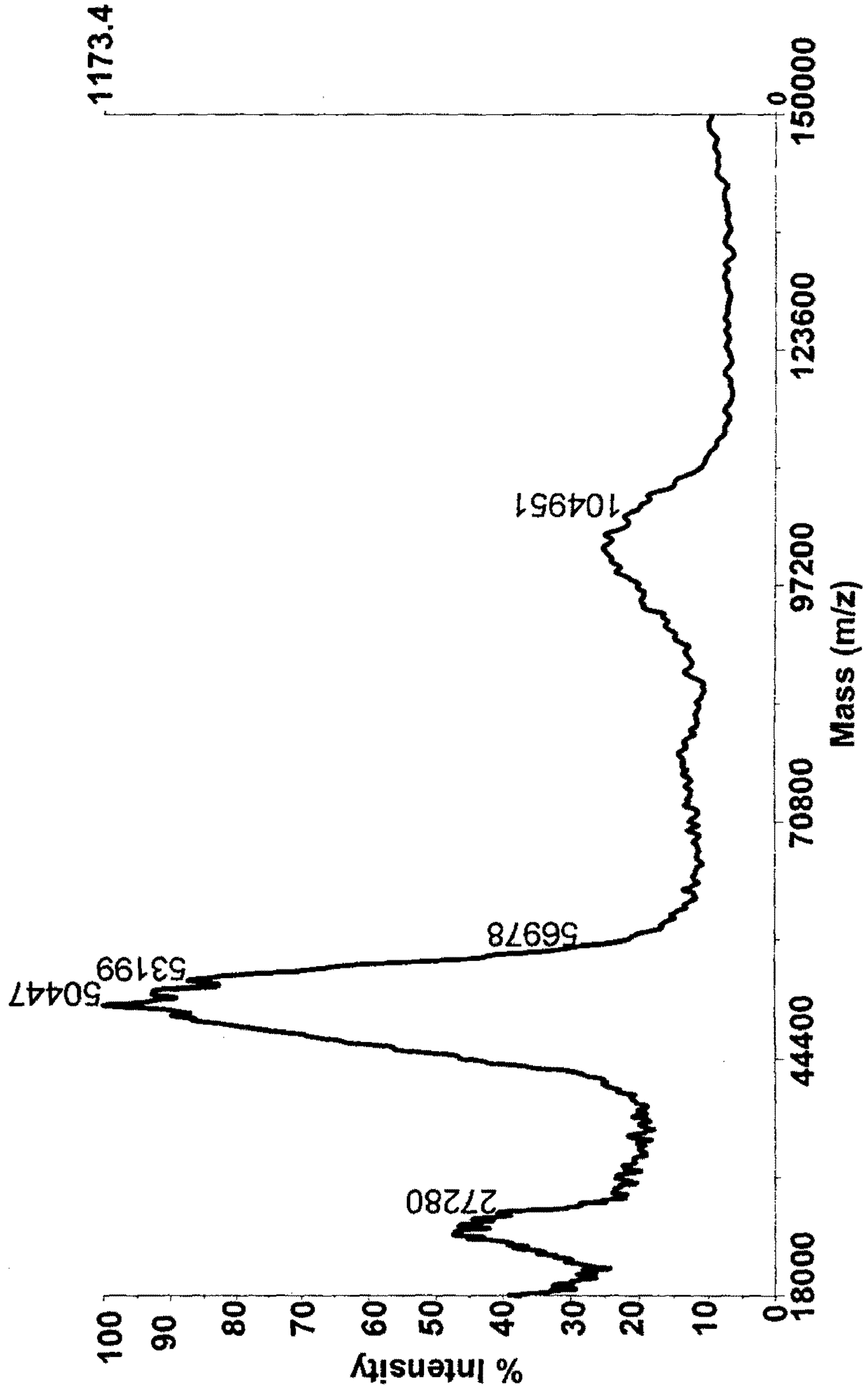

FIG. 159 is a graph of a MALDI spectra of Factor VIIa-PEG (1 kDa).

Figure 160:
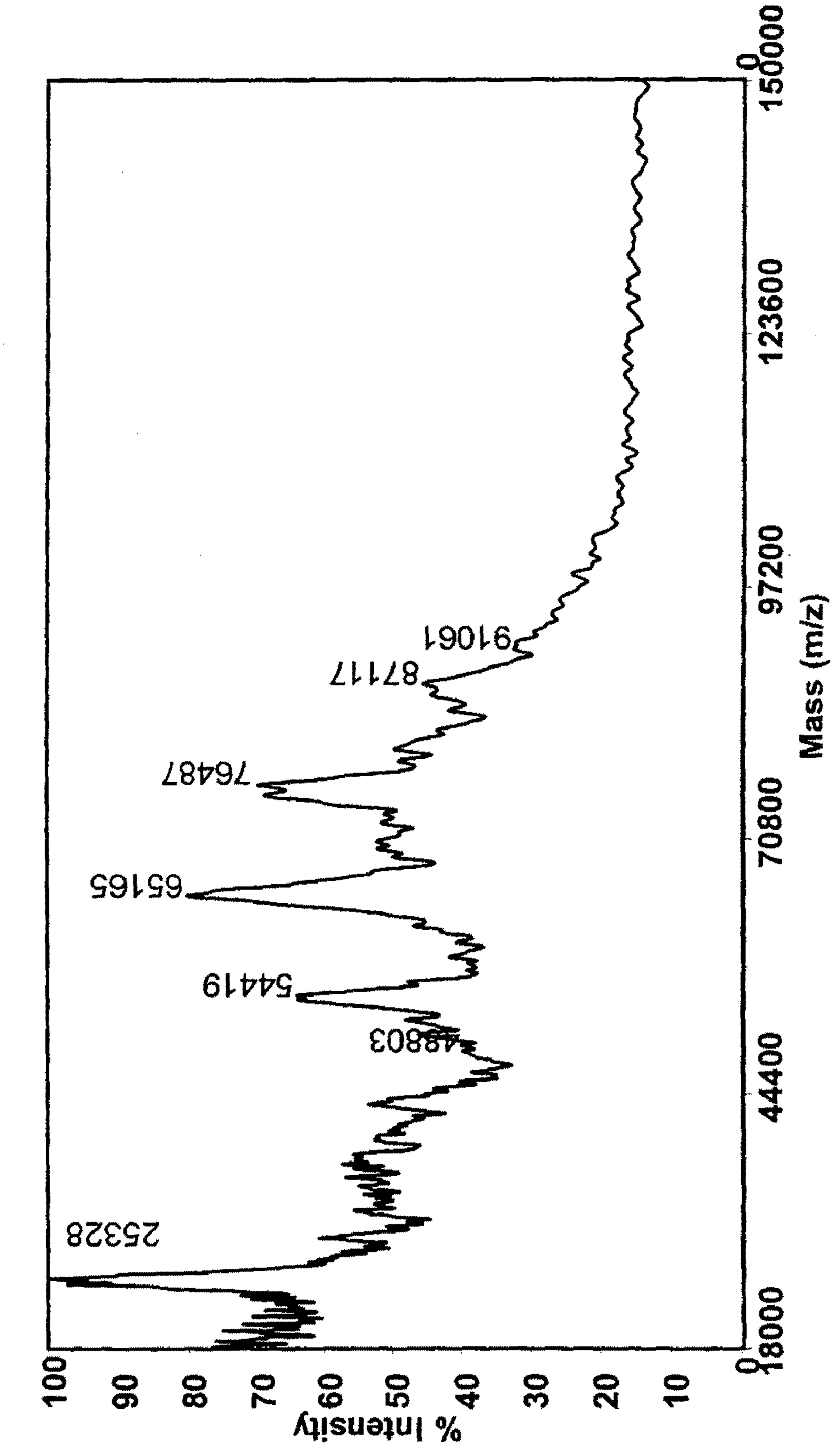

FIG. 160 is a graph depicting a MALDI spectra of Factor VIIa-PEG (10 kDa).

Figure 161:
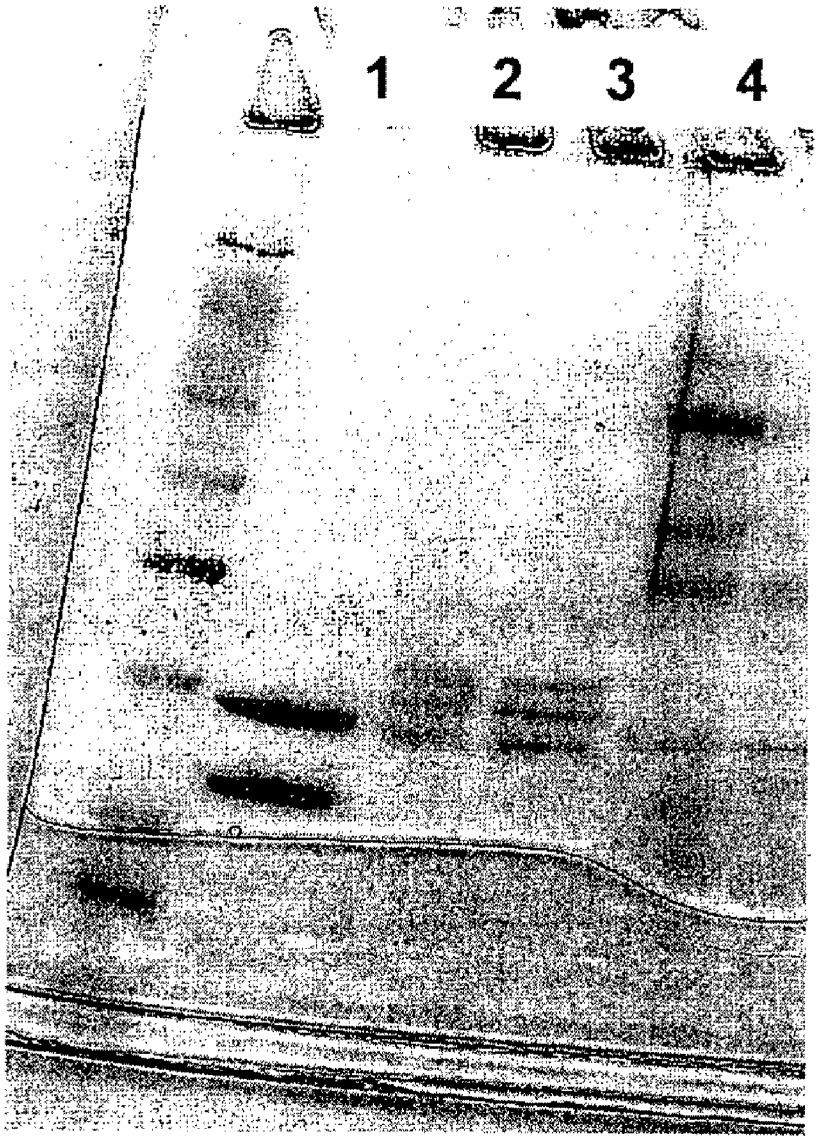

FIG. 161 is an image of an SDS-PAGE gel of PEGylated Factor VIIa. Lane 1 is asialo-Factor VIIa. Lane 2 is the product of the reaction of asialo-Factor VIIa and CMP-SA-PEG (1 kDa) with ST3Gal3 after 48 hr. Lane 3 is the product of the reaction of asialo-Factor VIIa and CMP-SA-PEG (1 kDa) with ST3Gal3 after 48 hr. Lane 4 is the product of the reaction of asialo-Factor VIIa and CMP-SA-PEG (10 kDa) with ST3Gal3 at 96 hr.

Figure 162:

FIG. 162 is an image of an isoelectric focusing (IEF) gel depicting the products of the desialylation reaction of human pituitary FSH. Lanes 1 and 4 are isoelectric focusing (IEF) standards. Lane 2 is native FSH. Lane 3 is desialylated FSH.

Figure 163:
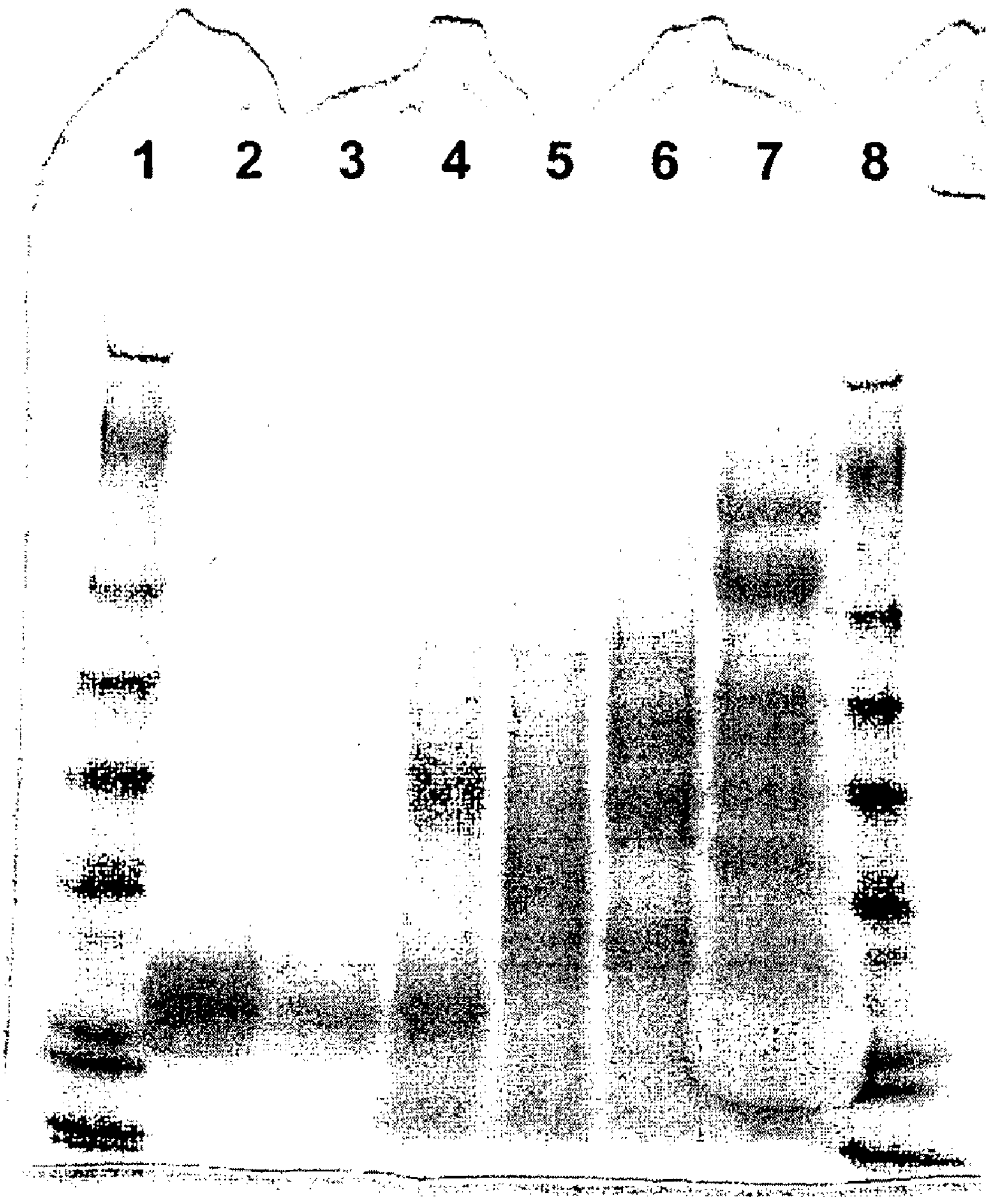

FIG. 163 is an image of an SDS-PAGE gel of the products of the reactions to make PEG-sialylation of rFSH. Lanes 1 and 8 are SeeBlue+2 molecular weight standards. Lane 2 is 15 μg of native FSH. Lane 3 is 15 μg of asialo-FSH (AS-FSH). Lane 4 is 15 μg of the products of the reaction of AS-FSH with CMP-SA. Lane 5 is 15 μg of the products of the reaction of AS-FSH with CMP-SA-PEG (1 kDa). Lane 6 is 15 μg of the products of the reaction of AS-FSH with CMP-SA-PEG (5 kDa). Lane 7 is 15 μg of the products of the reaction of AS-FSH with CMP-SA-PEG (10 kDa).

Figure 164:

FIG. 164 is an image of an isoelectric focusing gel of the products of the reactions to make PEG-sialylation of FSH. Lanes 1 and 8 are IEF standards. Lane 2 is 15 μg of native FSH. Lane 3 is 15 μg of asialo-FSH (AS-FSH). Lane 4 is 15 μg of the products of the reaction of AS-FSH with CMP-SA. Lane 5 is 15 μg of the products of the reaction of AS-FSH with CMP-SA-PEG (1 kDa). Lane 6 is 15 μg of the products of the reaction of AS-FSH with CMP-SA-PEG (5 kDa). Lane 7 is 15 μg of the products of the reaction of AS-FSH with CMP-SA-PEG (10 kDa).

Figure 165:
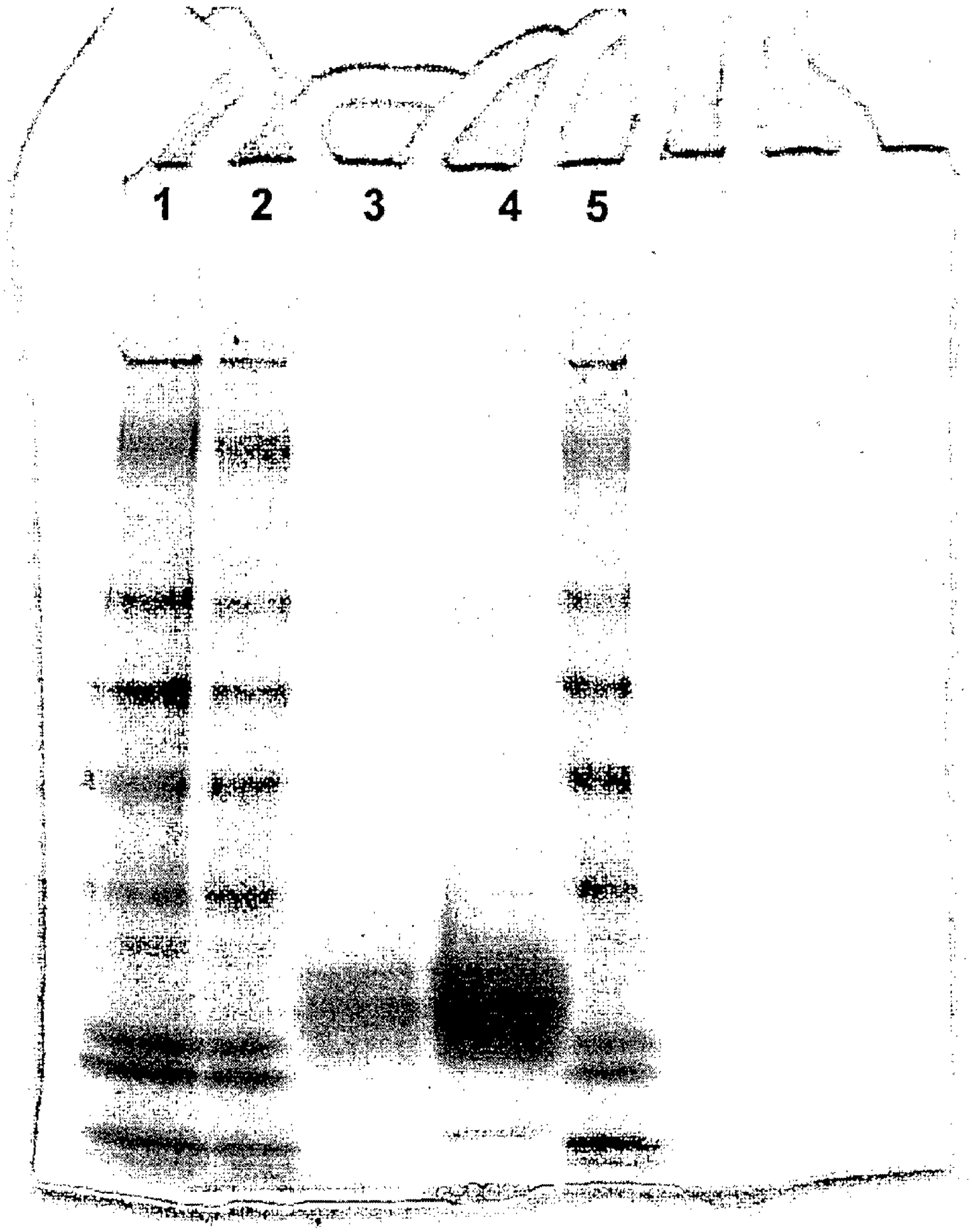

FIG. 165 is an image of an SDS-PAGE gel of native non-recombinant FSH produced in human pituitary cells. Lanes 1, 2 and 5 are SeeBlue™+2 molecular weight standards. Lanes 3 and 4 are native FSH at 5 μg and 25 μg, respectively.

Figure 166:
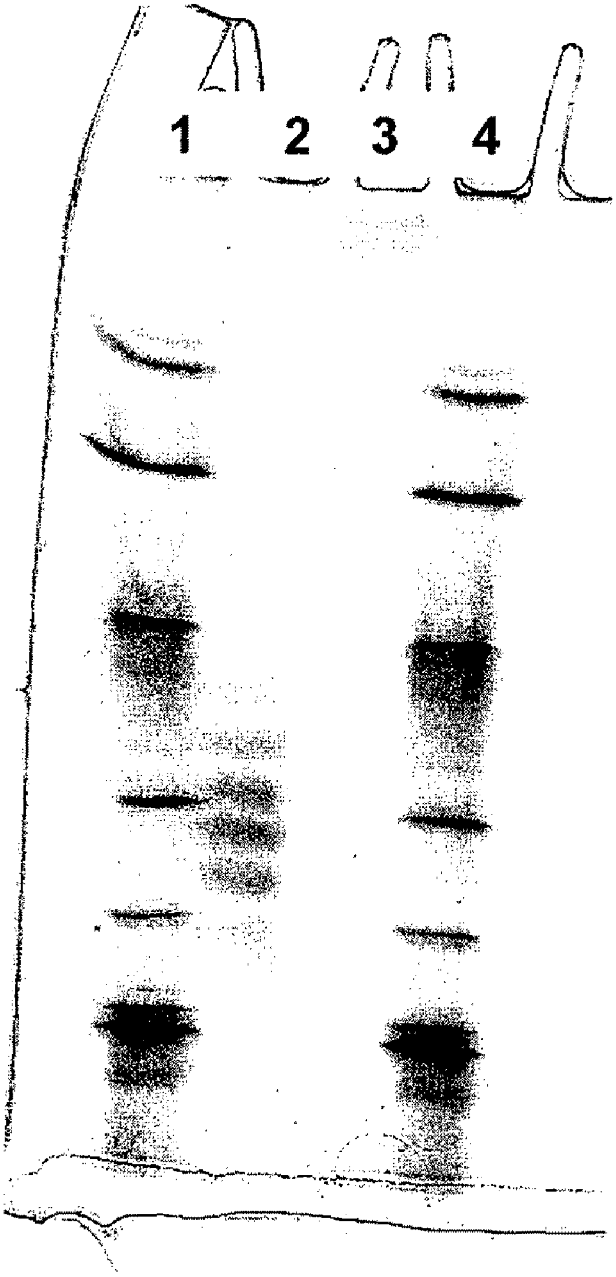

FIG. 166 is an image of an isoelectric focusing gel (pH 3-7) depicting the products of the asialylation reaction of rFSH. Lanes 1 and 4 are IEF standards. Lane 2 is native rFSH. Lane 3 is asialo-rFSH.

Figure 167:
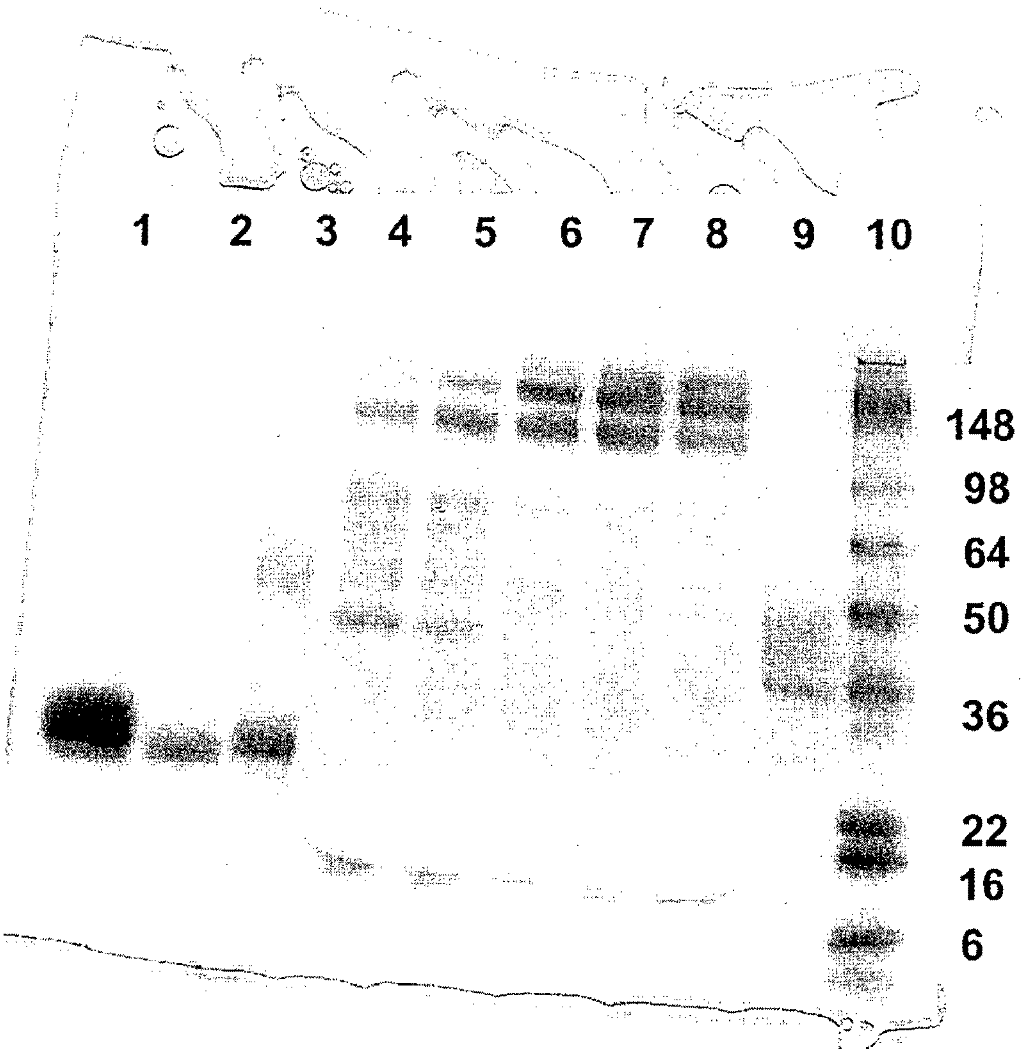

FIG. 167 is an image of an SDS-PAGE gel depicting the results of the PEG-sialylation of asialo-rFSH. Lane 1 is native rFSH. Lane 2 is asialo-FSH. Lane 3 is the products of the reaction of asialo-FSH and CMP-SA. Lanes 4-7 are the products of the reaction between asialoFSH and 0.5 mM CMP-SA-PEG (10 kDa) at 2 hr, 5 hr, 24 hr, and 48 hr, respectively. Lane 8 is the products of the reaction between asialo-FSH and 1.0 mM CMP-SA-PEG (10 kDa) at 48 hr. Lane 9 is the products of the reaction between asialo-FSH and 1.0 mM CMP-SA-PEG (1 kDa) at 48 hr.

Figure 168:
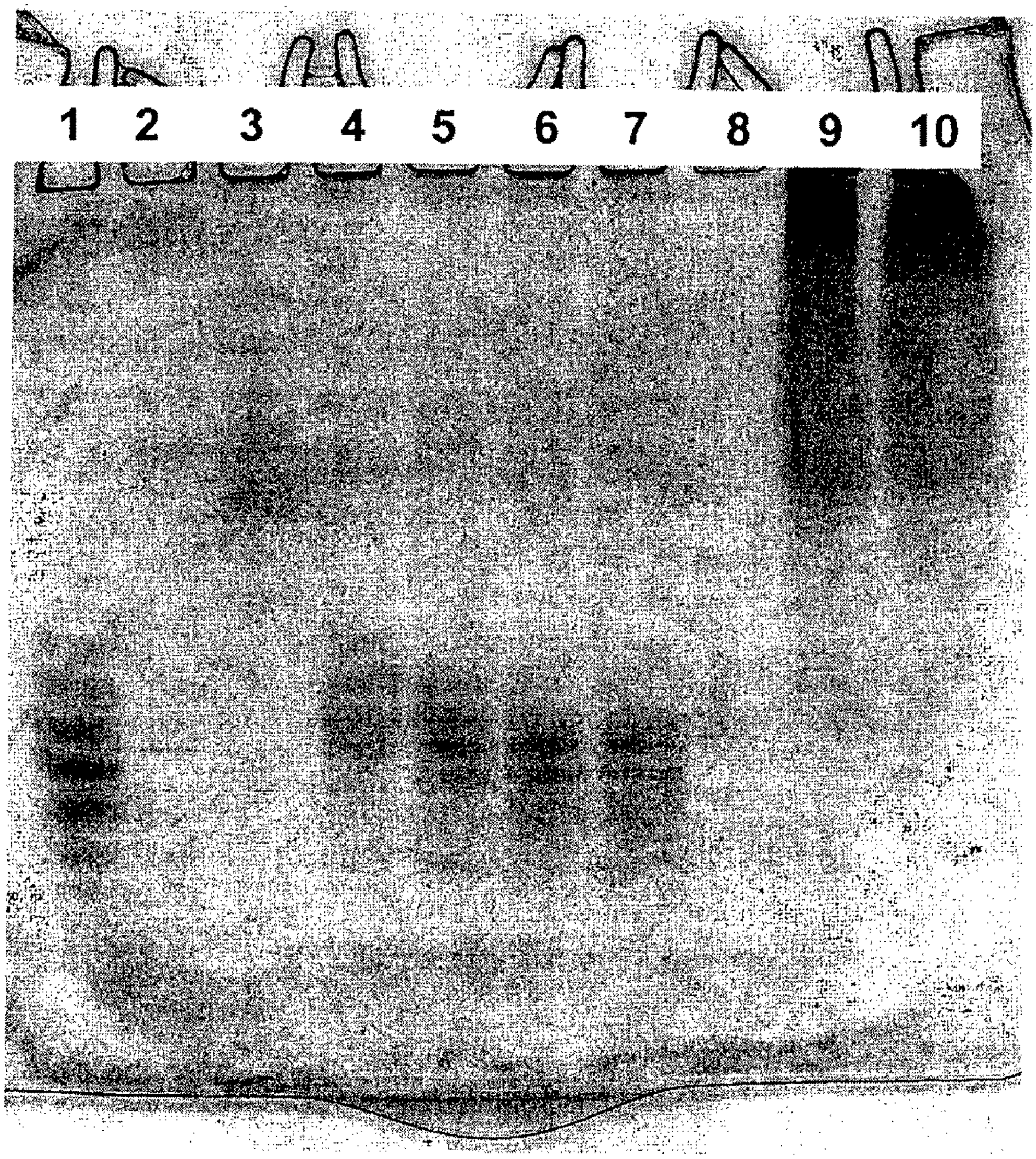

FIG. 168 is an image of an isoelectric focusing gel showing the products of PEG-sialylation of asialo-rFSH with a CMP-SA-PEG (1 kDa). Lane 1 is native rFSH. Lane 2 is asialo-rFSH. Lane 3 is the products of the reaction of asialo-rFSH and CMP-SA at 24 hr. Lanes 4-7 are the products of the reaction of asialo-rFSH and 0.5 mM CMP-SA-PEG (1 kDa) at 2 hr, 5 hr, 24 hr, and 48 hr, respectively. Lane 8 is blank. Lanes 9 and 10 are the products of the reaction at 48 hr of asialo-rFSH and CMP-SA-PEG (10 kDa) at 0.5 mM and 1.0 mM, respectively.

Figure 169:
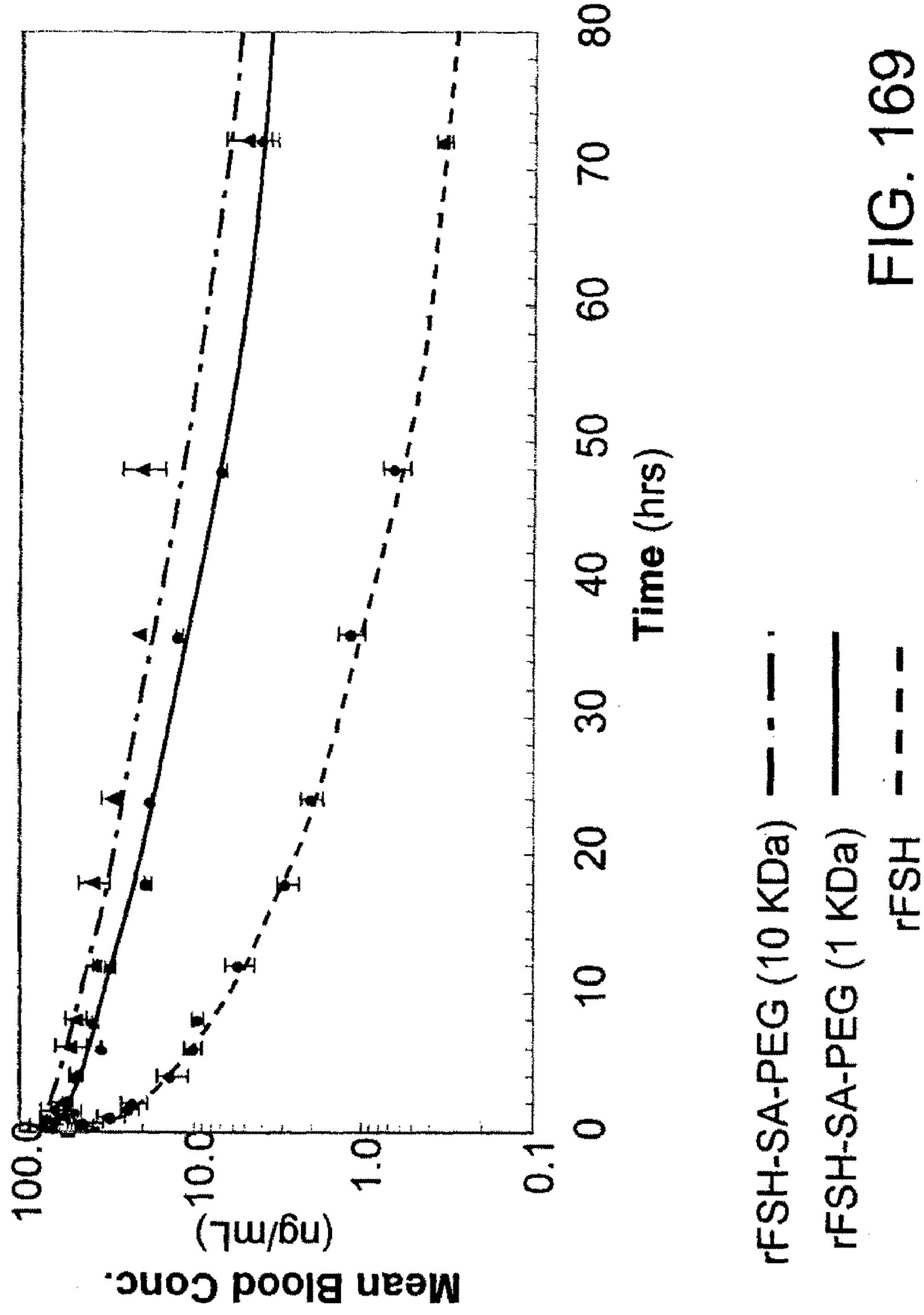

FIG. 169 is graph of the pharmacokinetics of rFSH and rFSH-SA-PEG (1 kDa and 10 kDa). This graph illustrates the relationship between the time a rFSH compound is in the blood stream of the rat, and the mean concentration of the rFSH compound in the blood for glycoPEGylated rFSH as compared to non-PEGylated rFSH.

Figure 170:
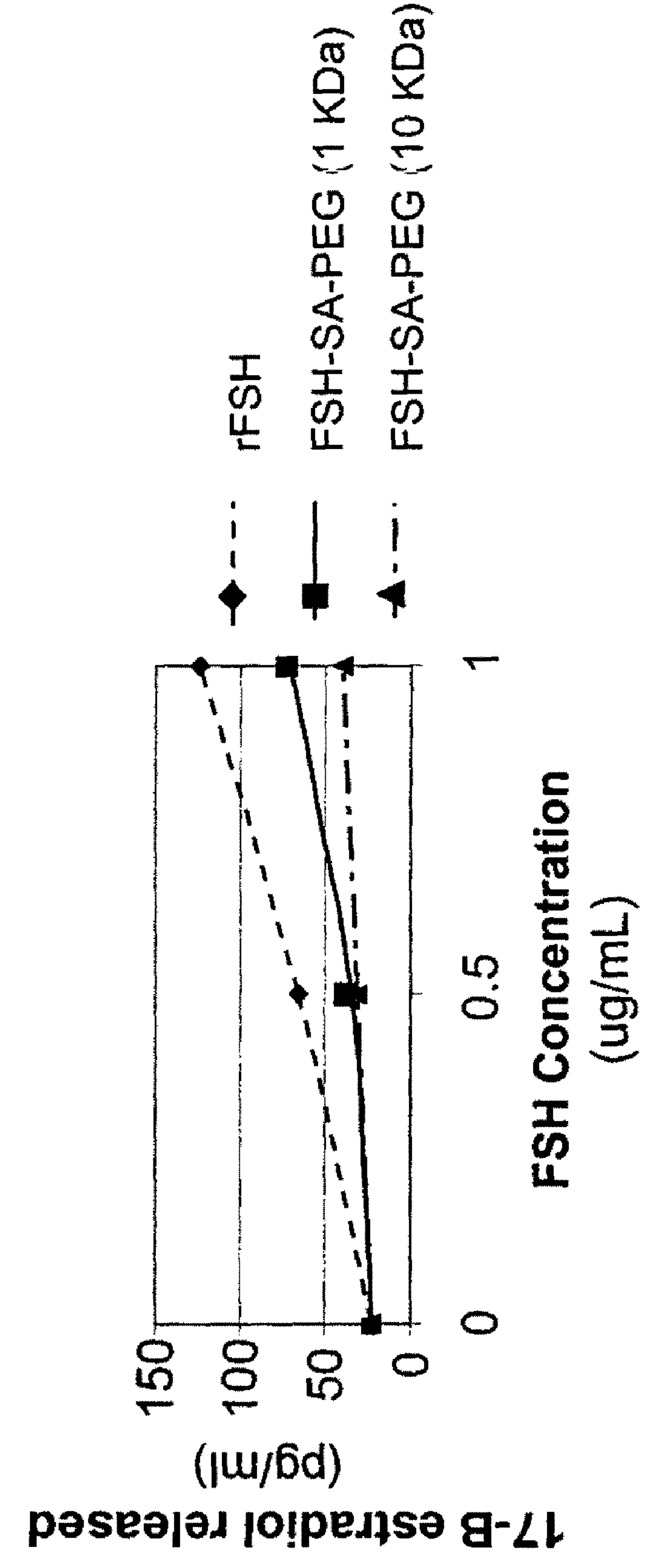

FIG. 170 is a graph of the results of the FSH bioassay using Sertoli cells. This graph illustrates the relationship between the FSH concentration in the Sertoli cell incubation medium and the amount of 17-β estradiol released from the Sertoli cells.

Figure 171:
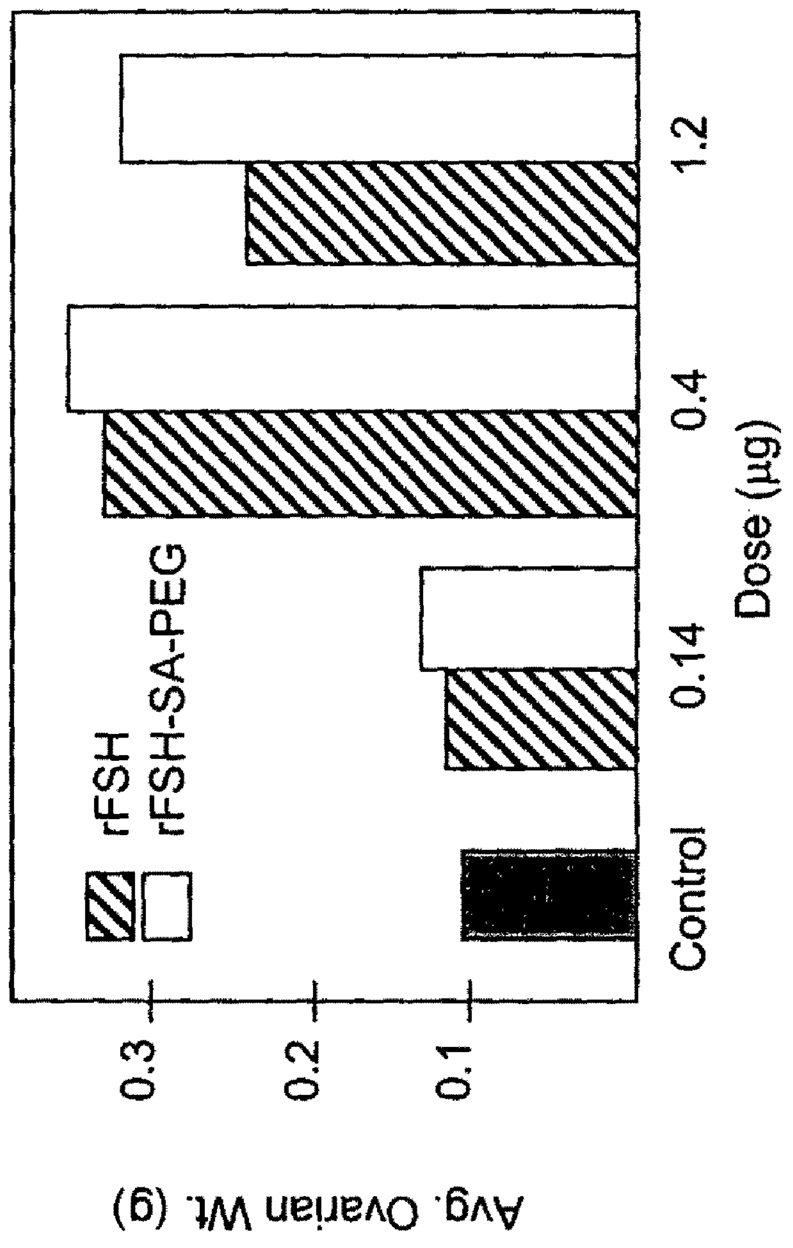

FIG. 171 is a graph depicting the results of the Steelman-Pohley bioassay of glycoPEGylated and non-glycoPEGylated FSH. Rats were subcutaneously injected with human chorionic gonadotropin and varying amounts of FSH for three days, and the average ovarian weight of the treatment group determined on day 4. rFSH-SA-PEG refers to recombinant FSH that has been glycoPEGylated with PEG (1 kDa). rFSH refers to non-glycoPEGylated FSH. Each treatment group contains 10 rats.

Figure 172A:
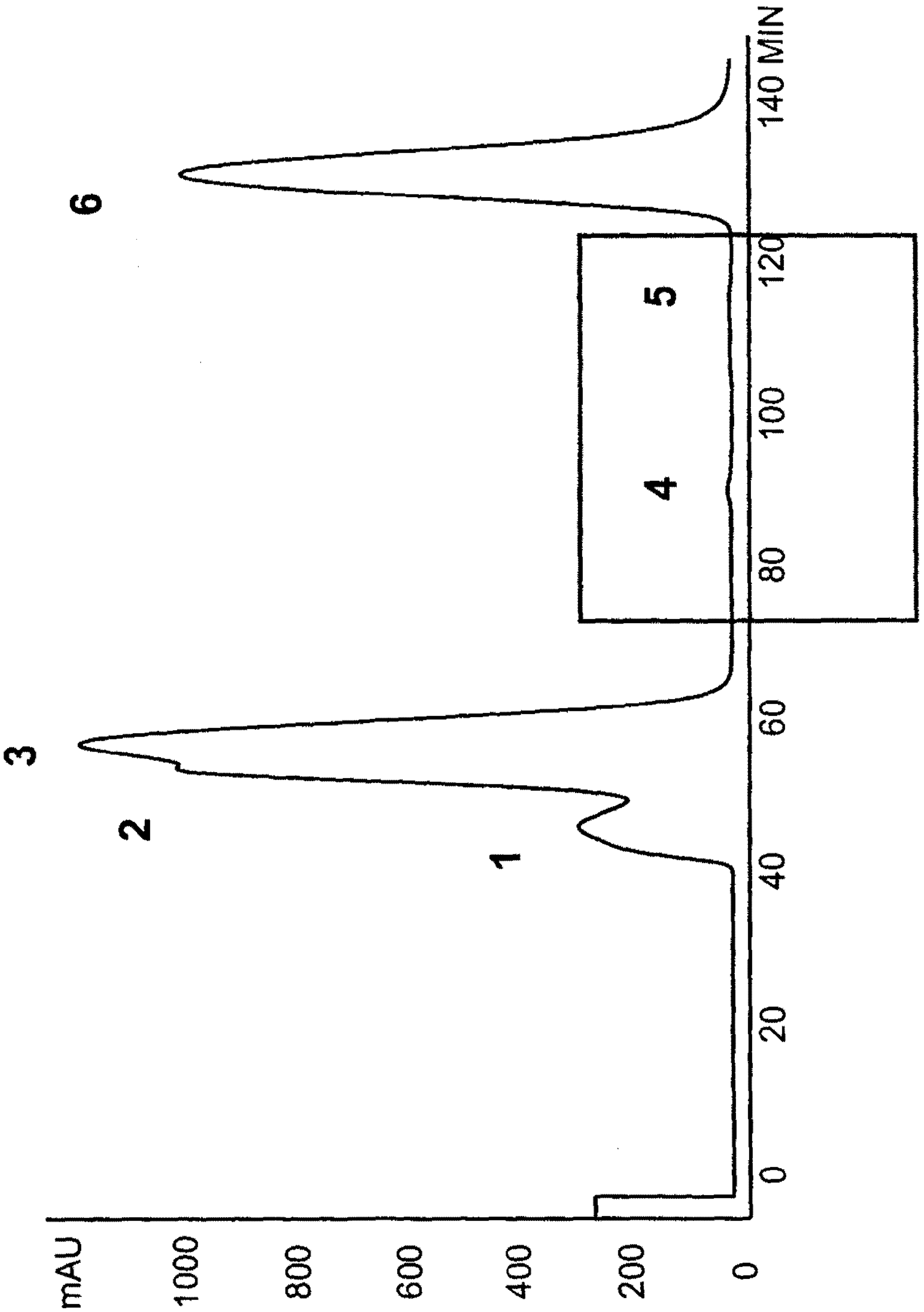
Figure 172B:
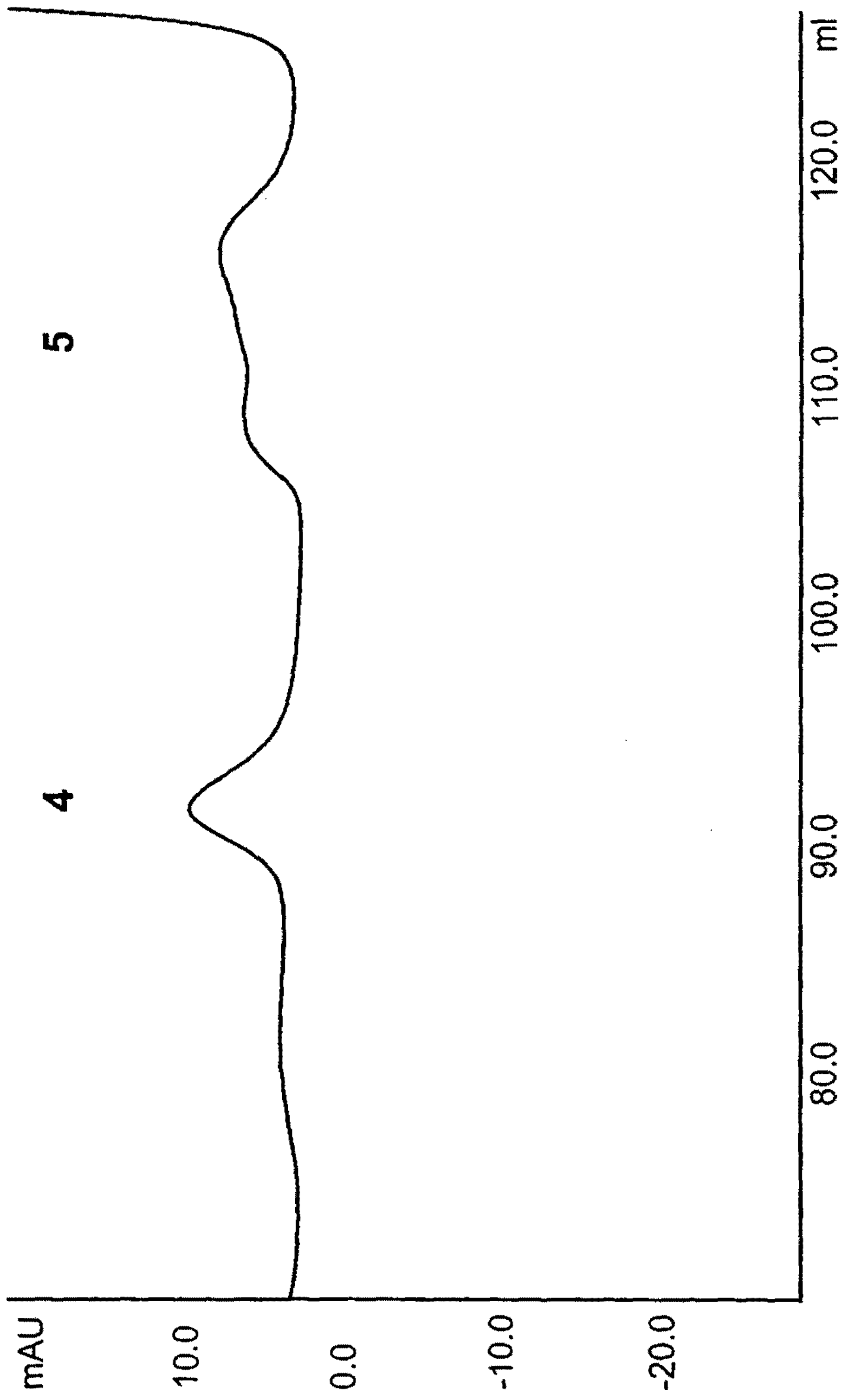

FIG. 172, comprising FIGS. 172A and 172B, depicts the chromatogram of INF-β elution from a Superdex-75 column. FIG. 172A depicts the entire chromatogram. FIG. 172B depicts the boxed area of FIG. 172A containing peaks 4 and 5 in greater detail.

Figure 173A:
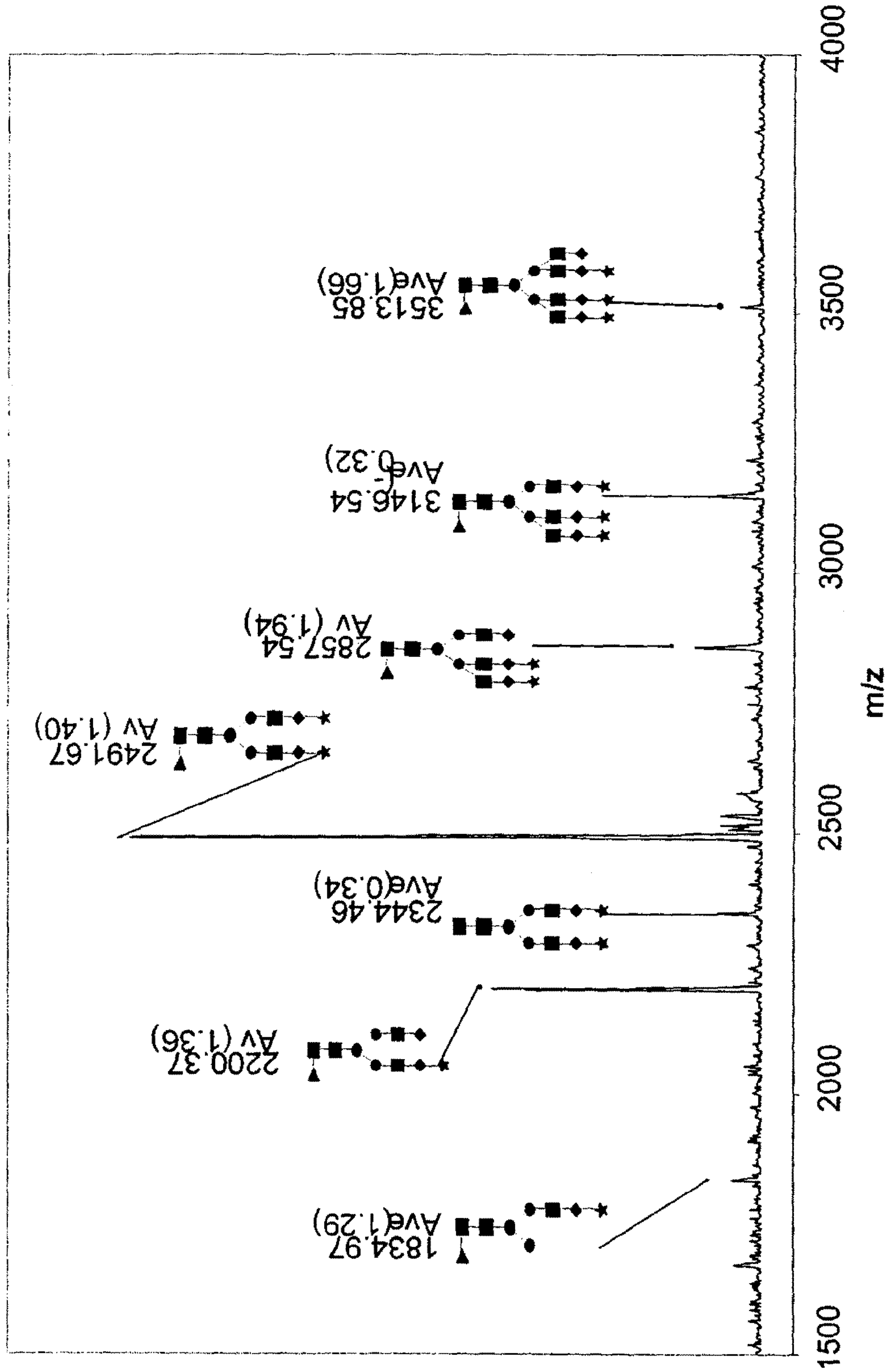
Figure 173B:
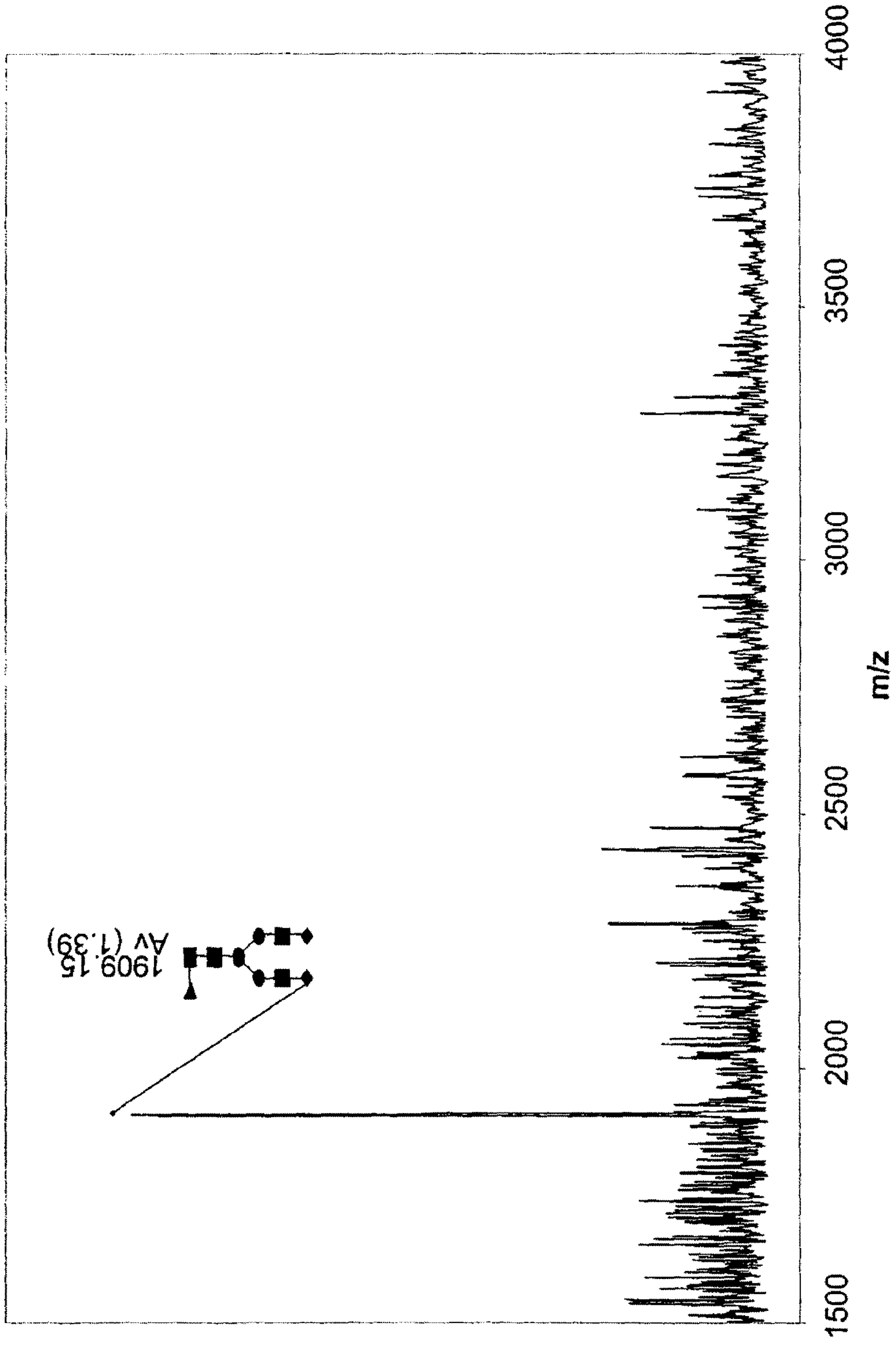

FIG. 173, comprising FIGS. 173A and 173B, depict MALDI analysis of glycans enzymatically released from INF-β. FIG. 173A depicts the MALDI analysis glycans released from native INF-β. FIG. 173B depicts the MALDI analysis of glycans released from desialylated INF-β. The structures of the glycans have been determined by comparison of the peak spectrum with that of standard glycans. The glycan structures are depicted beside the peaks. Squares represent GlcNAc, triangles represent fucose, circles represent mannose, diamonds represent galactose and stars represent sialic acid.

Figure 174:
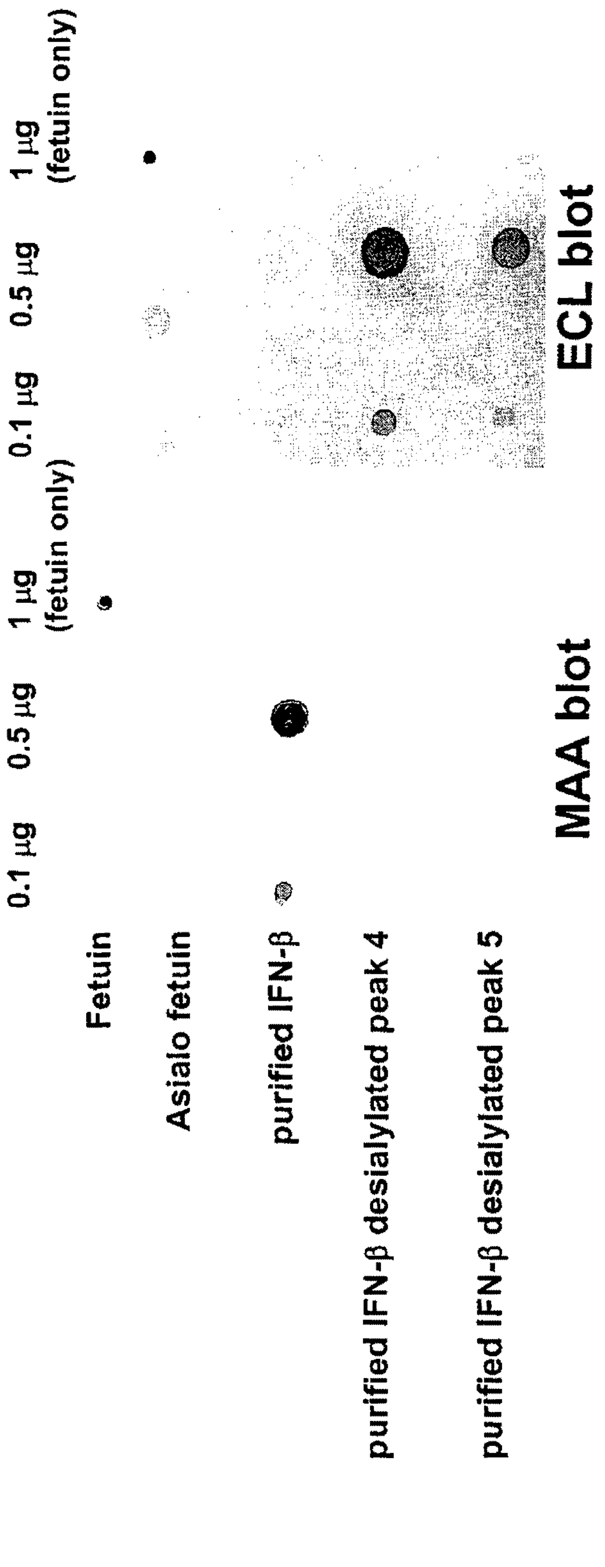

FIG. 174 depicts the lectin blot analysis of the sialylation of the desialylated INF-β. The blot on the right side is detected with *Maackia amurensis* agglutinin (MAA) labeled with digoxogenin (DIG) (Roche Applied Science, Indianapolis, Ill.) to detect α2,3-sialylation. The blot on the left is detected with *Erthrina cristagalli* lectin (ECL) labeled with biotin (Vector Laboratories, Burlingame, Calif.) to detect exposed galactose residues.

Figure 175:
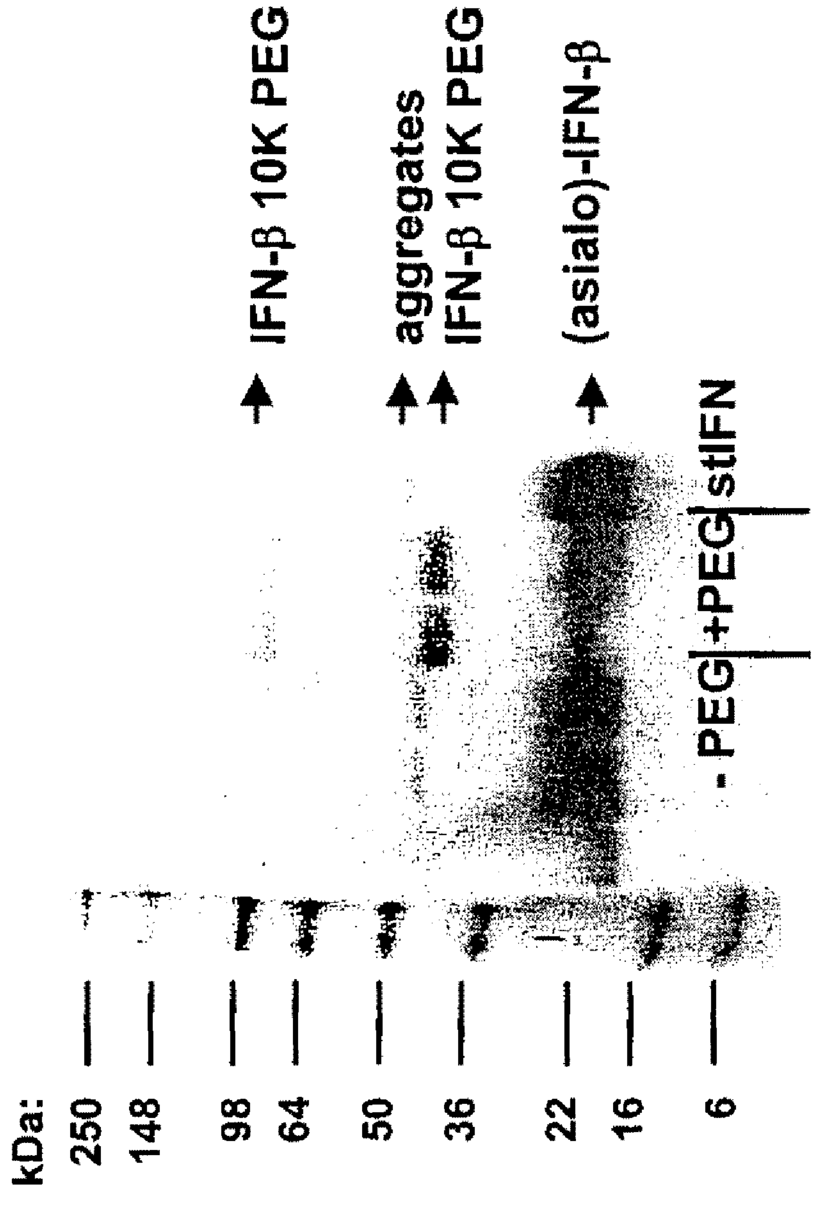

FIG. 175 depicts the SDS-PAGE analysis of the products of the PEG (10 kDa) PEGylation reaction of INF-β. "-PEG" refers to INF-β before the PEGylation reaction. "+PEG" refers to INF-β after the PEGylation reaction.

Figure 176:
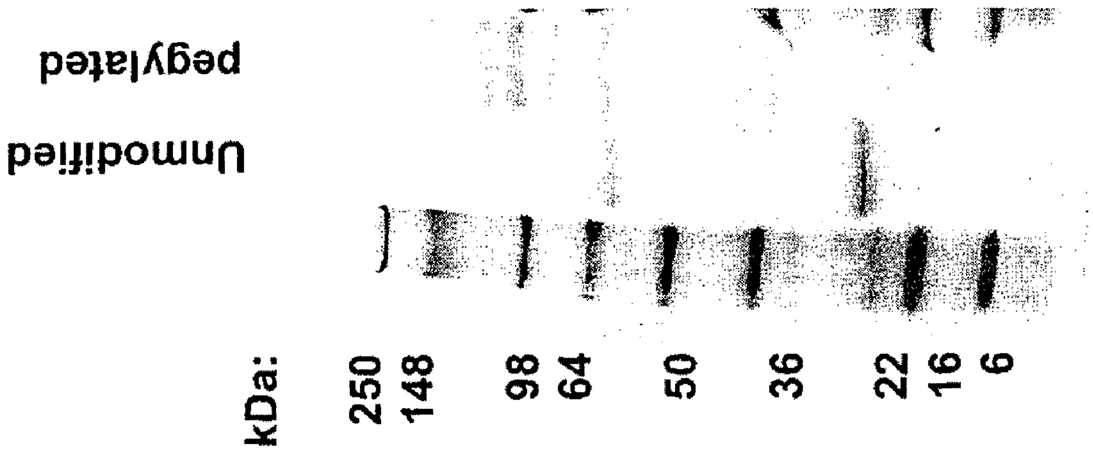

FIG. 176 depicts the SDS-PAGE analysis of the products of the PEG (20 kDa) PEGylation reaction of INF-β. "Unmodified" refers to INF-β before the PEGylation reaction. "Pegylated" refers to INF-β after the PEGylation reaction.

Figure 177:
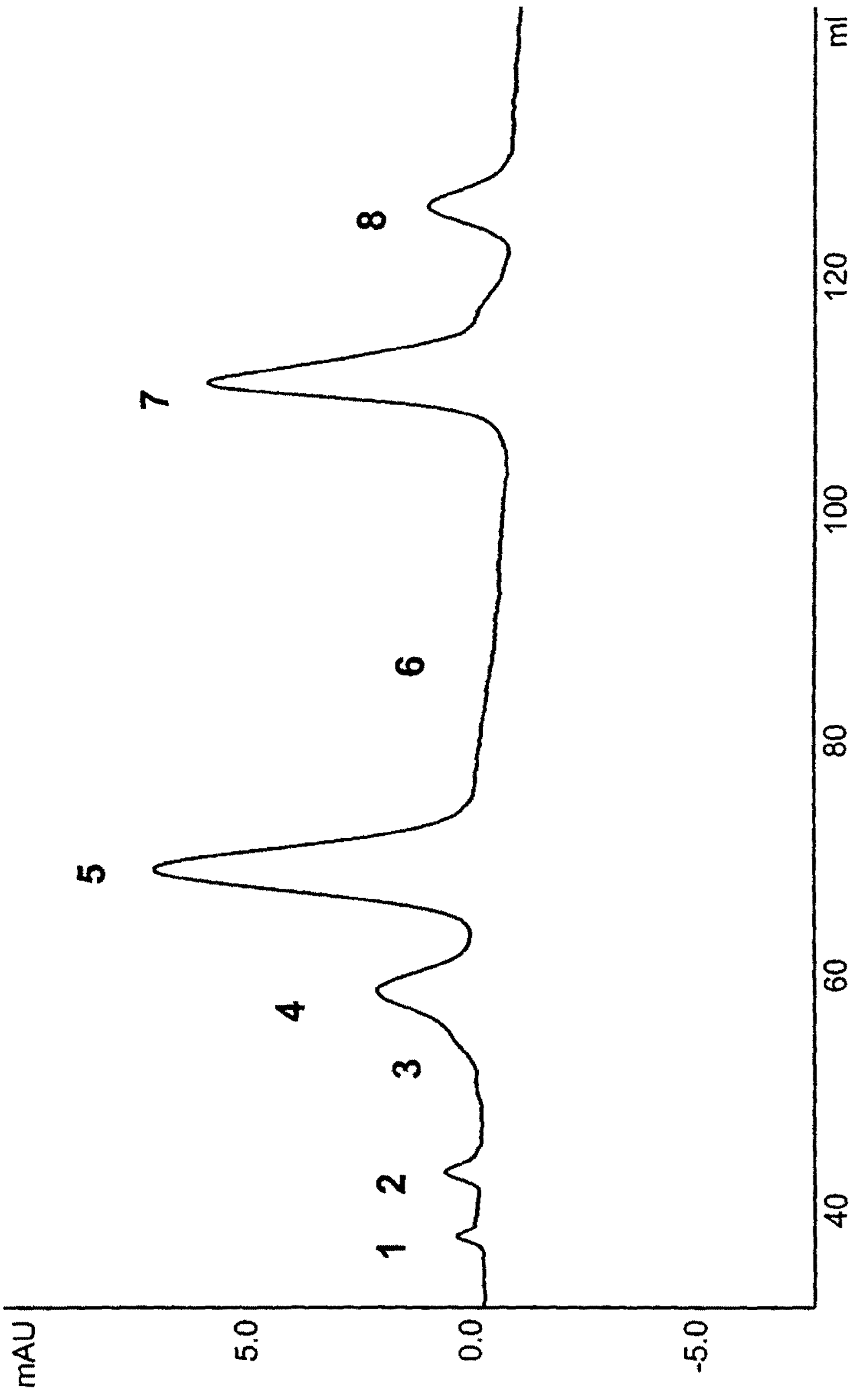

FIG. 177 depicts the chromatogram of PEG (10 kDa) PEGylated INF-β elution from a Superdex-200 column.

Figure 178:
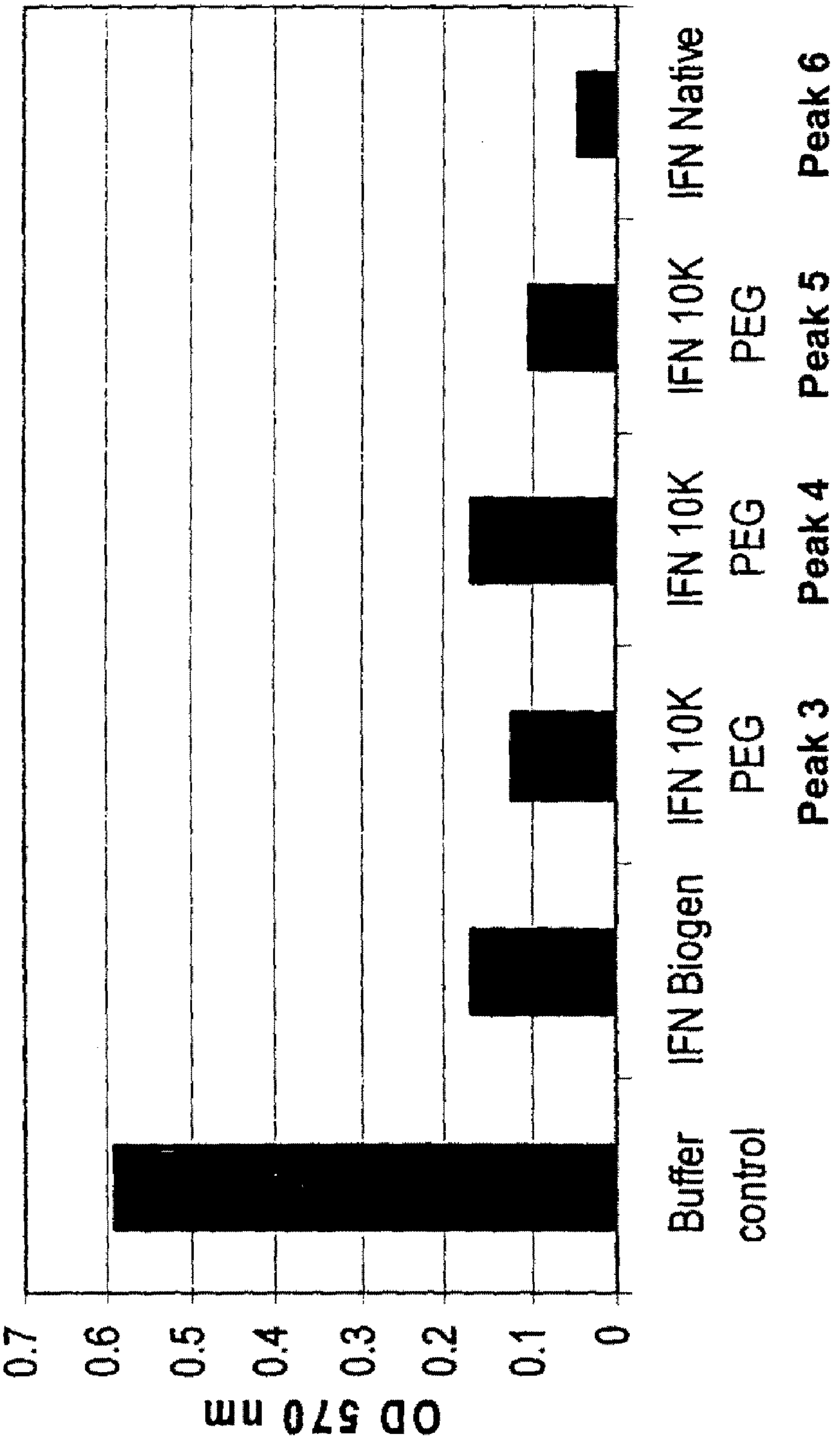

FIG. 178 depicts the results of a bioassay of peak fractions of PEG (10 kDa) PEGylated INF-β shown in the chromatogram depicted Figure INF-PEG 6.

Figure 179:
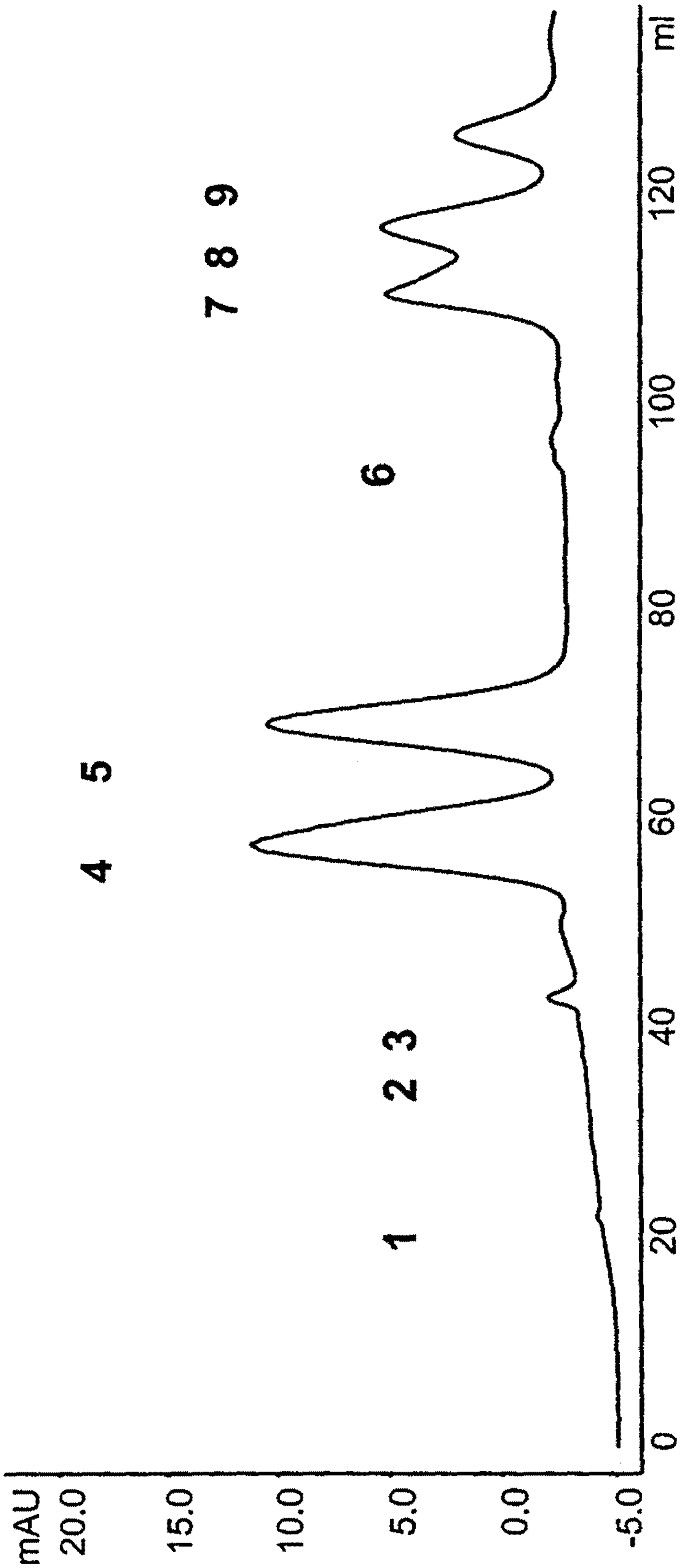

FIG. 179 depicts the chromatogram of PEG (20 kDa) PEGylated INF-β elution from a Superdex-200 column.

Figure 180A:
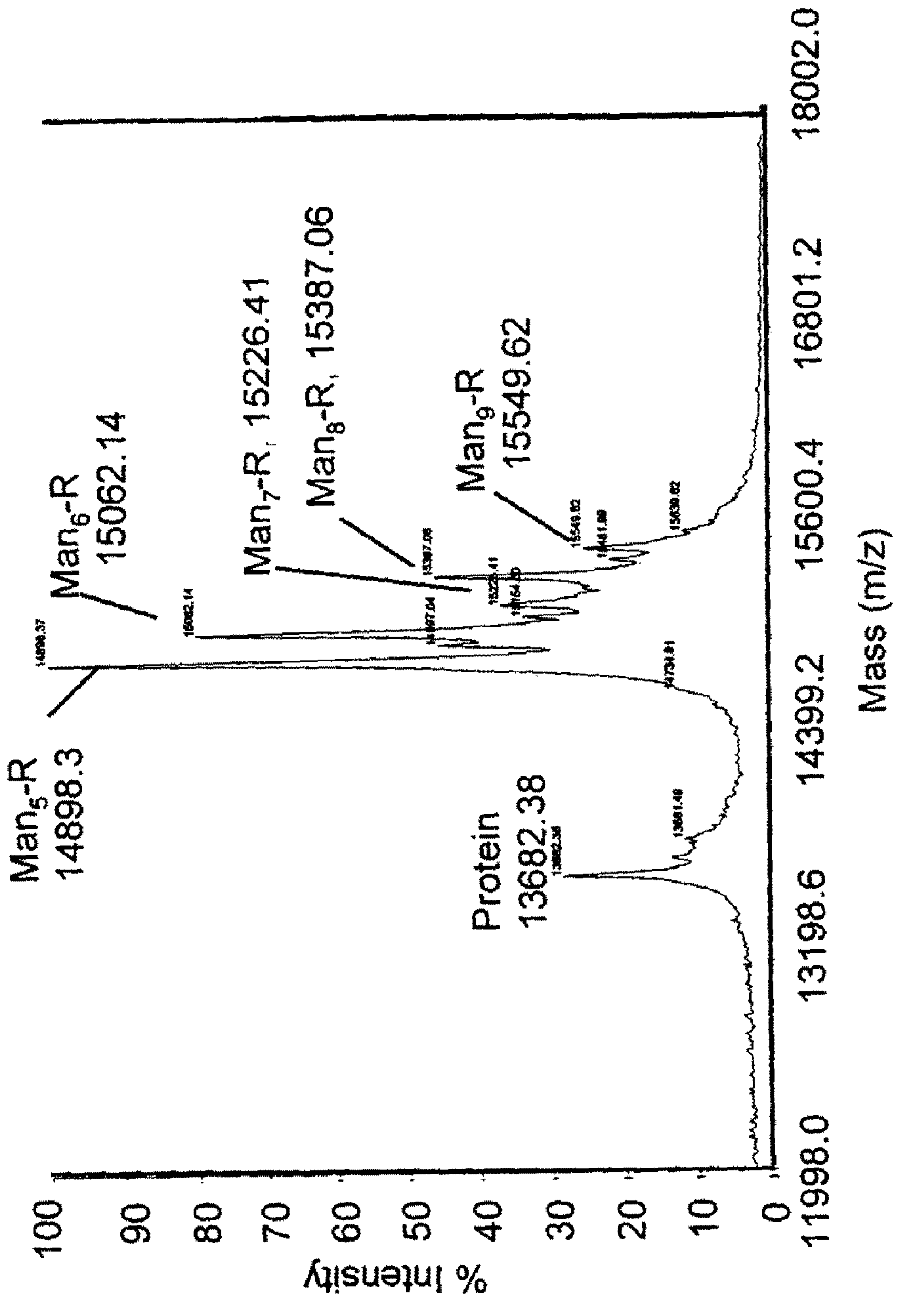
Figure 180B:
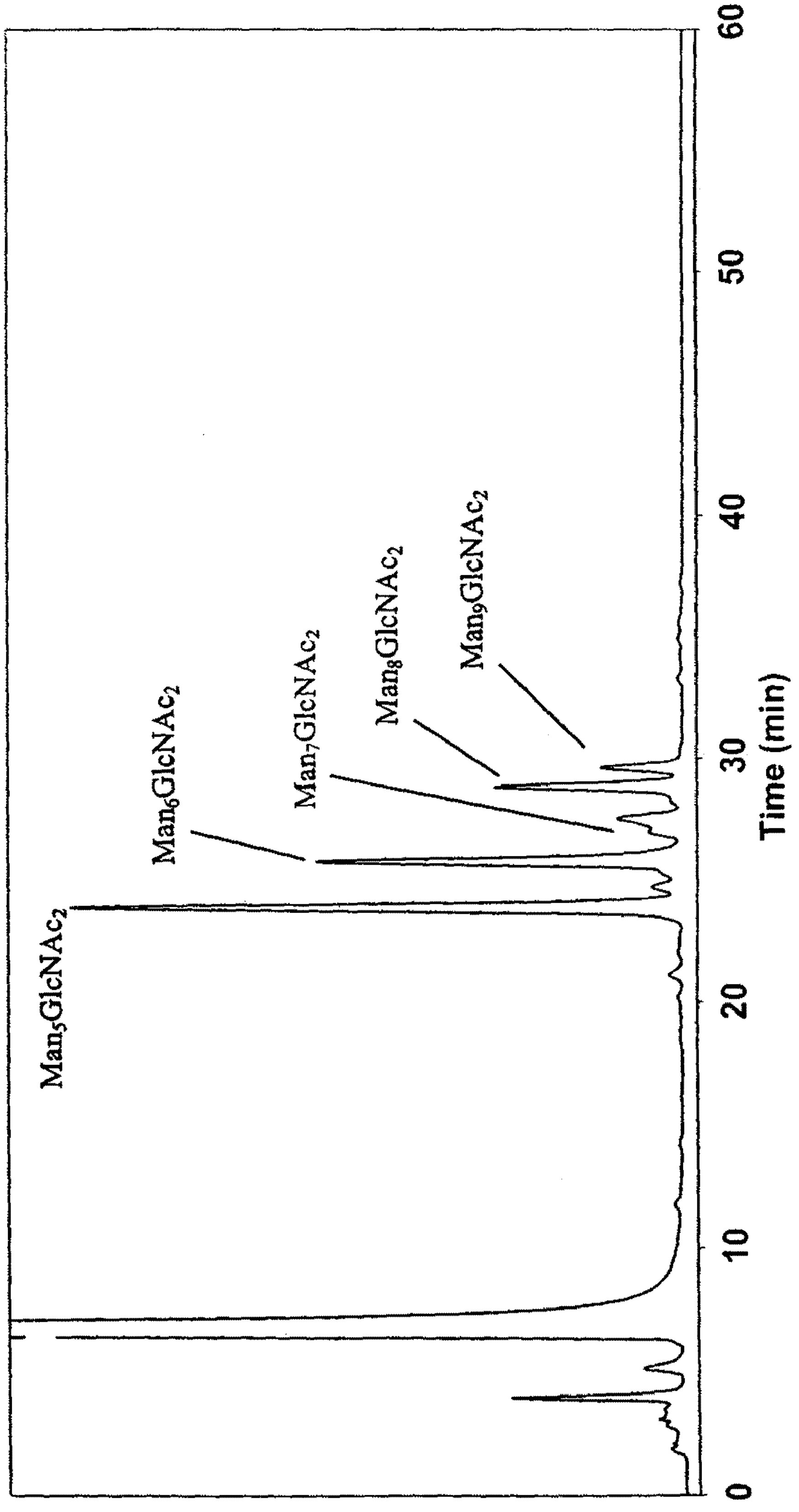

FIG. 180, comprising FIGS. 180A and 180B, is two graphs depicting the MALDI-TOF spectrum of RNaseB (FIG. 180A) and the HPLC profile of the oligosaccharides cleaved from RNaseB by N-Glycanase (FIG. 180B). The majority of N-glycosylation sites of the peptide are modified with high mannose oligosaccharides consisting of 5 to 9 mannose residues.

Figure 181:
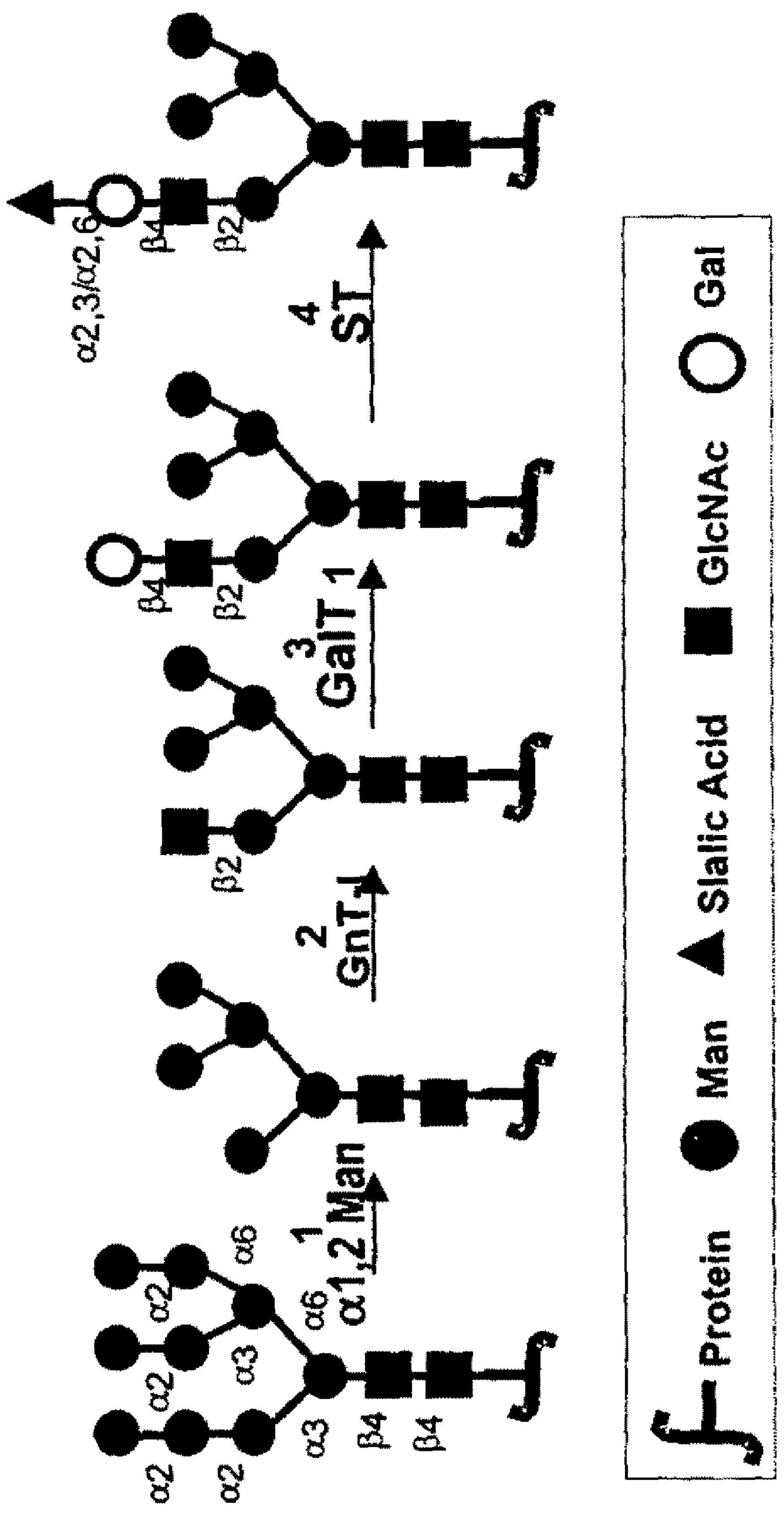

FIG. 181 is a scheme depicting the conversion of high mannose N-Glycans to hybrid N-Glycans. Enzyme 1 is α1,2-mannosidase, from *Trichodoma reesei* or *Aspergillus saitoi*. Enzyme 2 is GnT-I (β-1,2-N-acetyl glucosaminyl transferase I). Enzyme 3 is GalT-I (β1,4-galactosyltransfease 1). Enzyme 4 is α2,3-sialyltransferase or α2,6-sialyltransferase.

Figure 182A:
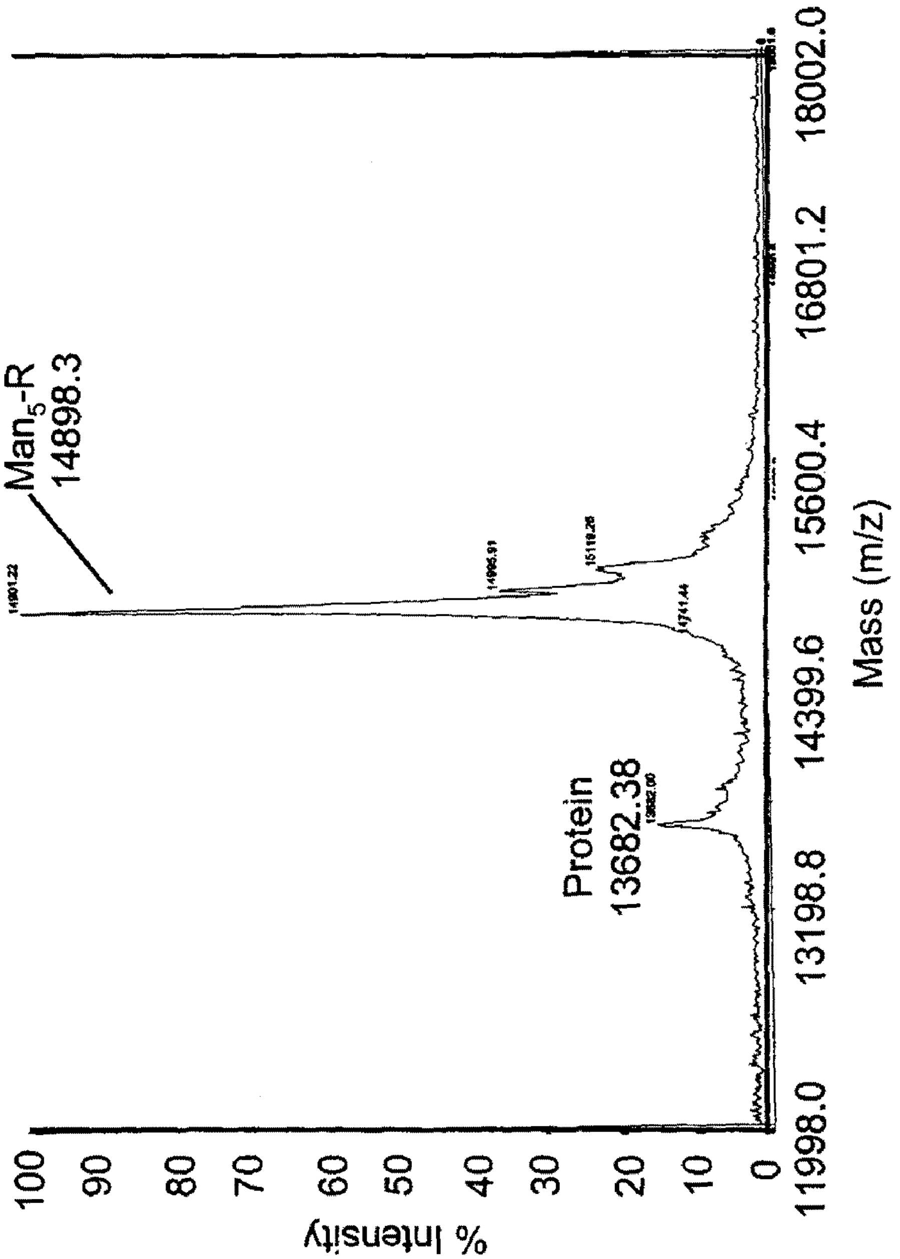
Figure 182B:
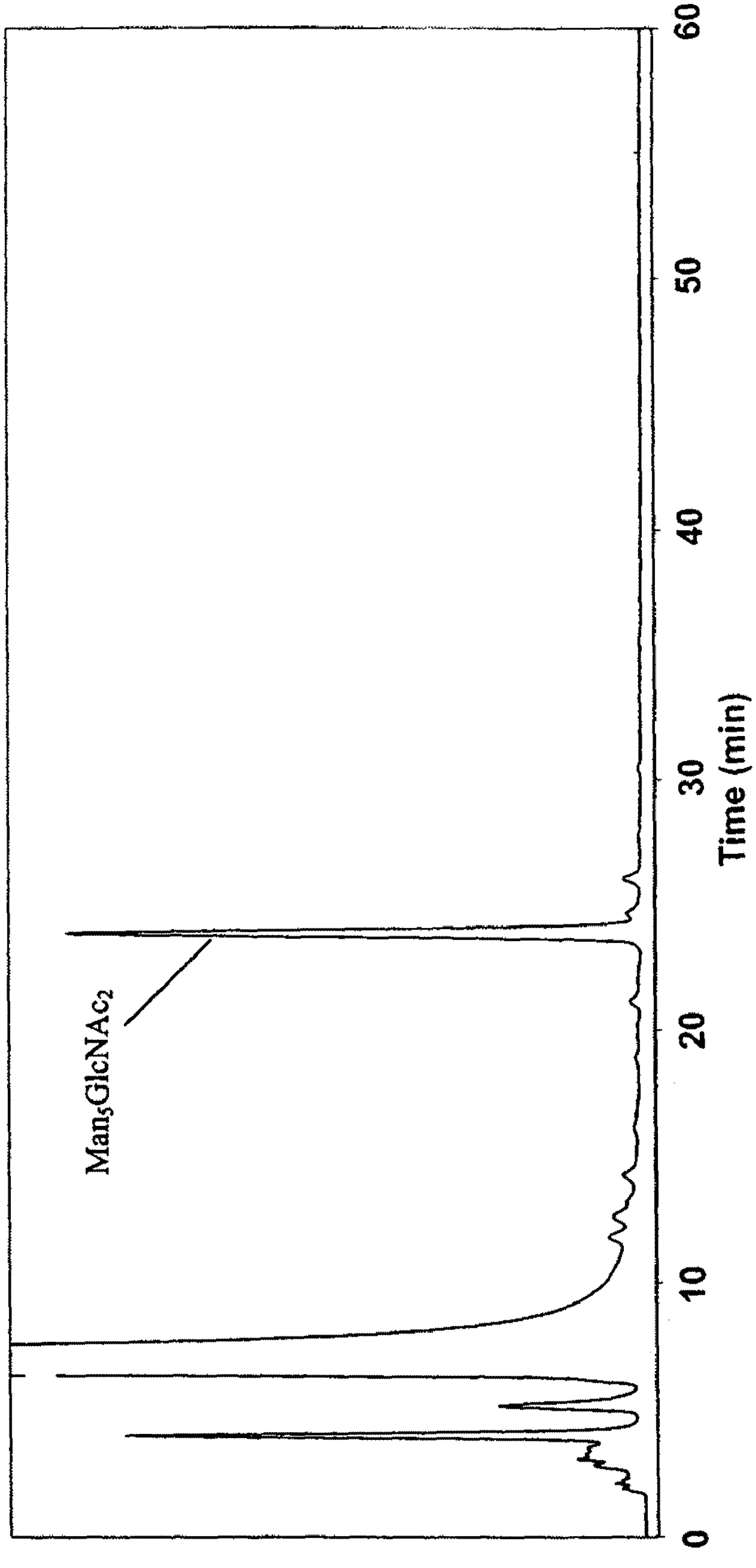

FIG. 182, comprising FIGS. 182A and 182B, is two graphs depicting the MALDI-TOF spectrum of RNaseB treated with a recombinant *T. reesei* α1,2-mannosidase (FIG. 182A) and the HPLC profile of the oligosaccharides cleaved by N-Glycanase from the modified RNaseB (FIG. 182B).

Figure 183:
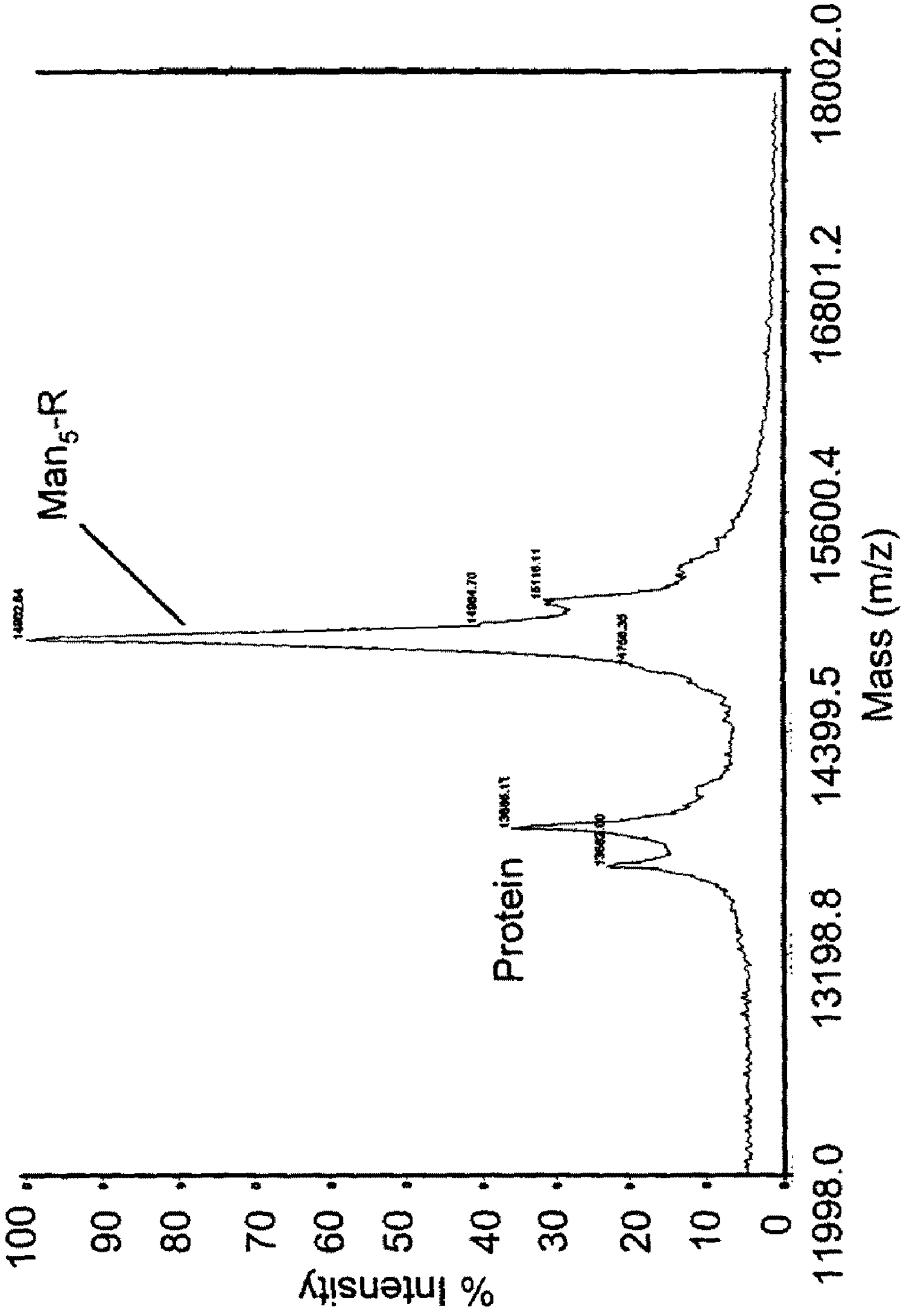

FIG. 183 is a graph depicting the MALDI-TOF spectrum of RNaseB treated with a commercially available α1,2-mannosidase purified from *A. saitoi* (Glyko & CalBioChem).

Figure 184:
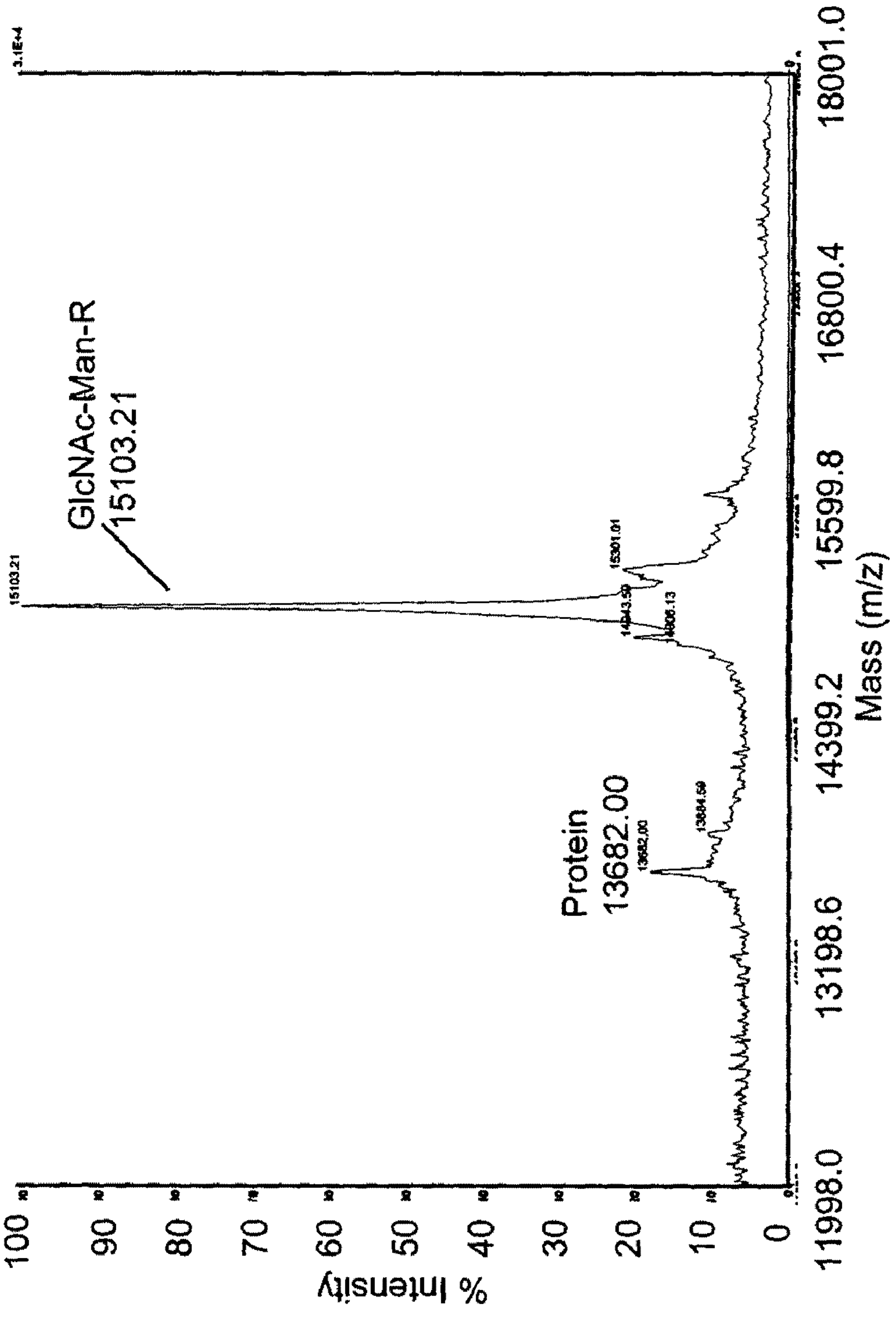

FIG. 184 is a graph depicting the MALDI-TOF spectrum of modified RNaseB by treating the product shown in FIG. 182 with a recombinant GnT-I (GlcNAc transferase-I).

Figure 185:
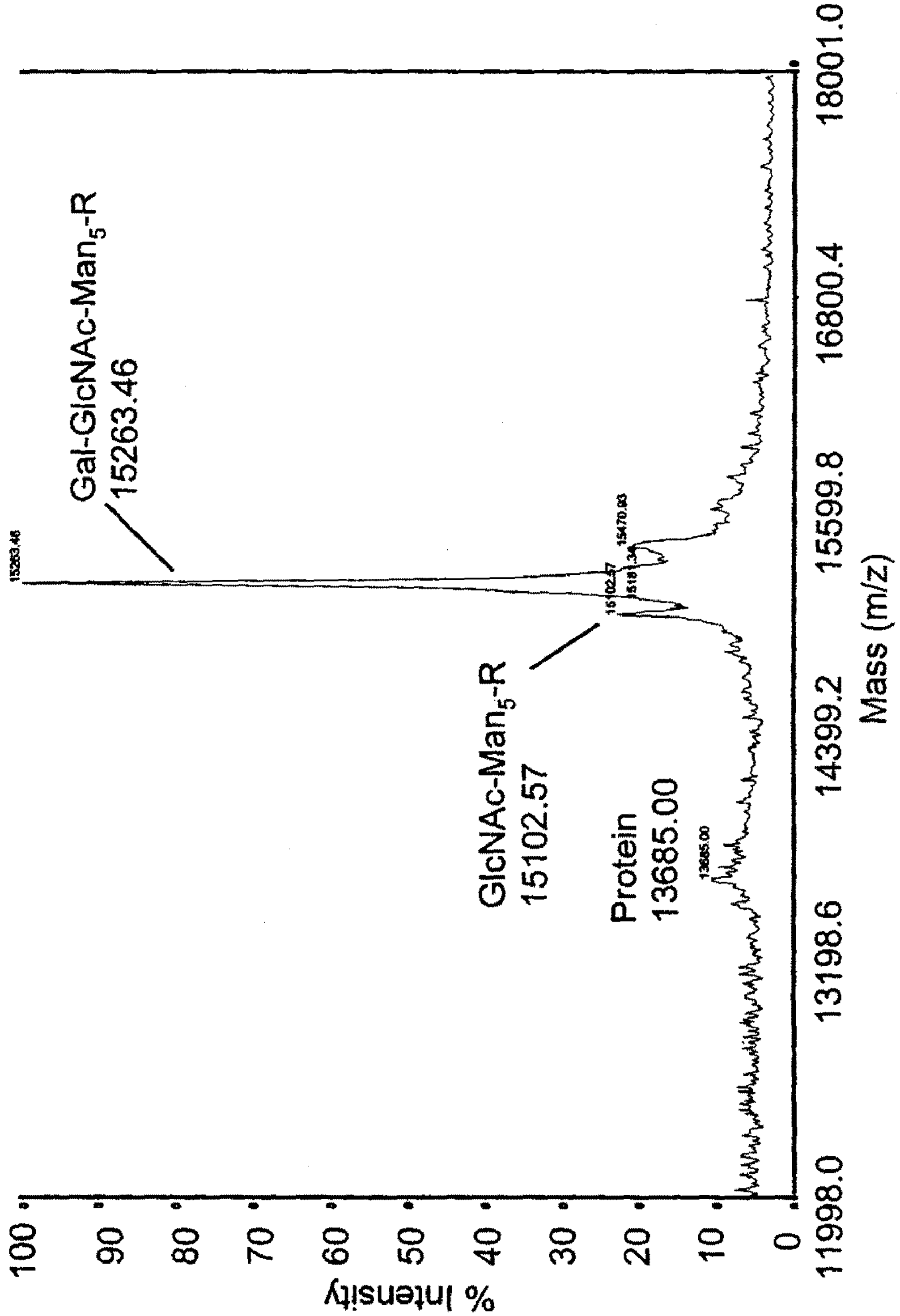

FIG. 185 is a graph depicting the MALDI-TOF spectrum of modified RNaseB by treating the product shown in FIG. 184 with a recombinant GalT1 (galactosyltransferase 1).

Figure 186:
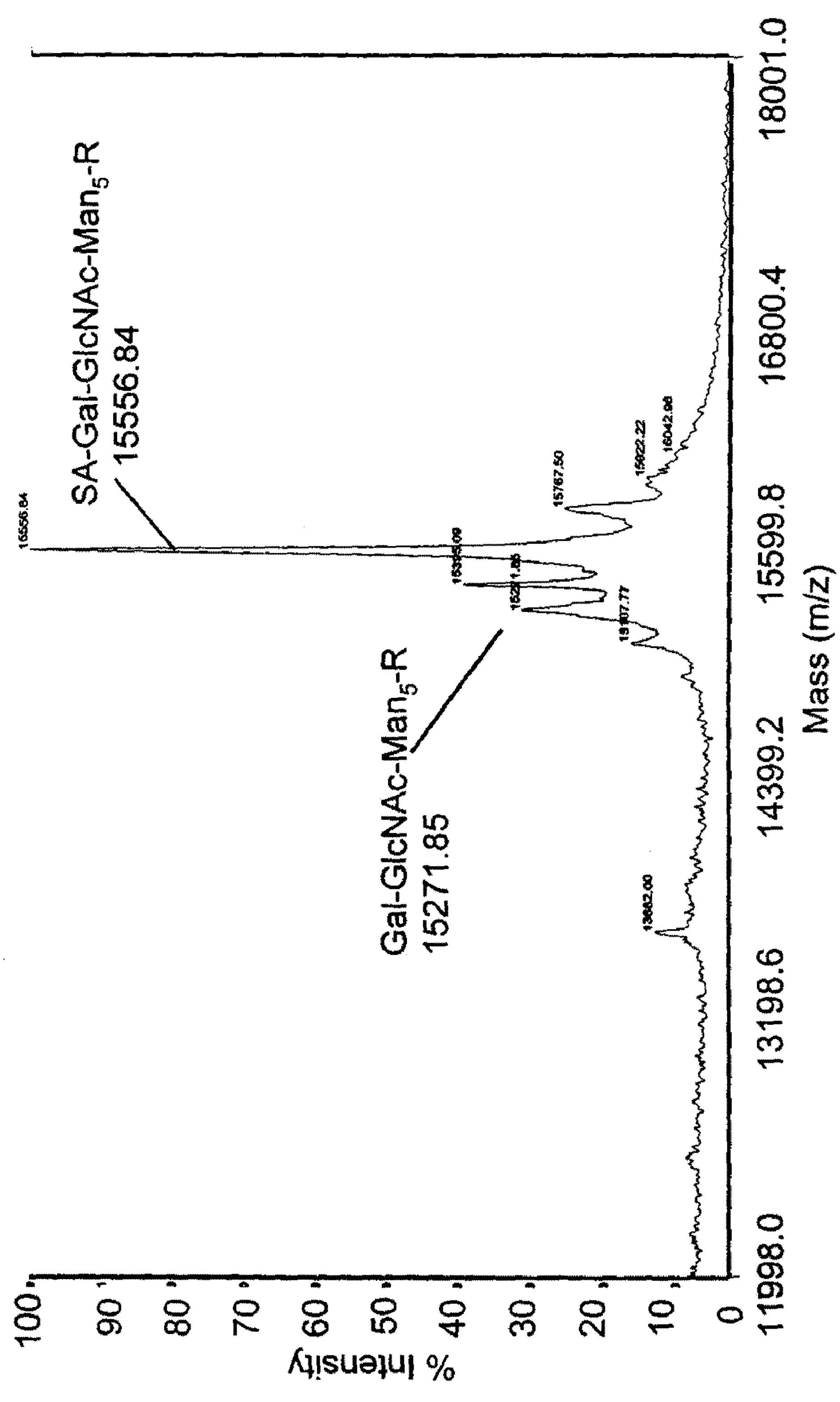

FIG. 186 is a graph depicting the MALDI-TOF spectrum of modified RNaseB by treating the product shown in FIG. 185 with a recombinant ST3Gal III (α2,3-sialyltransferase III) using CMP-SA as the donor for the transferase.

Figure 187A:
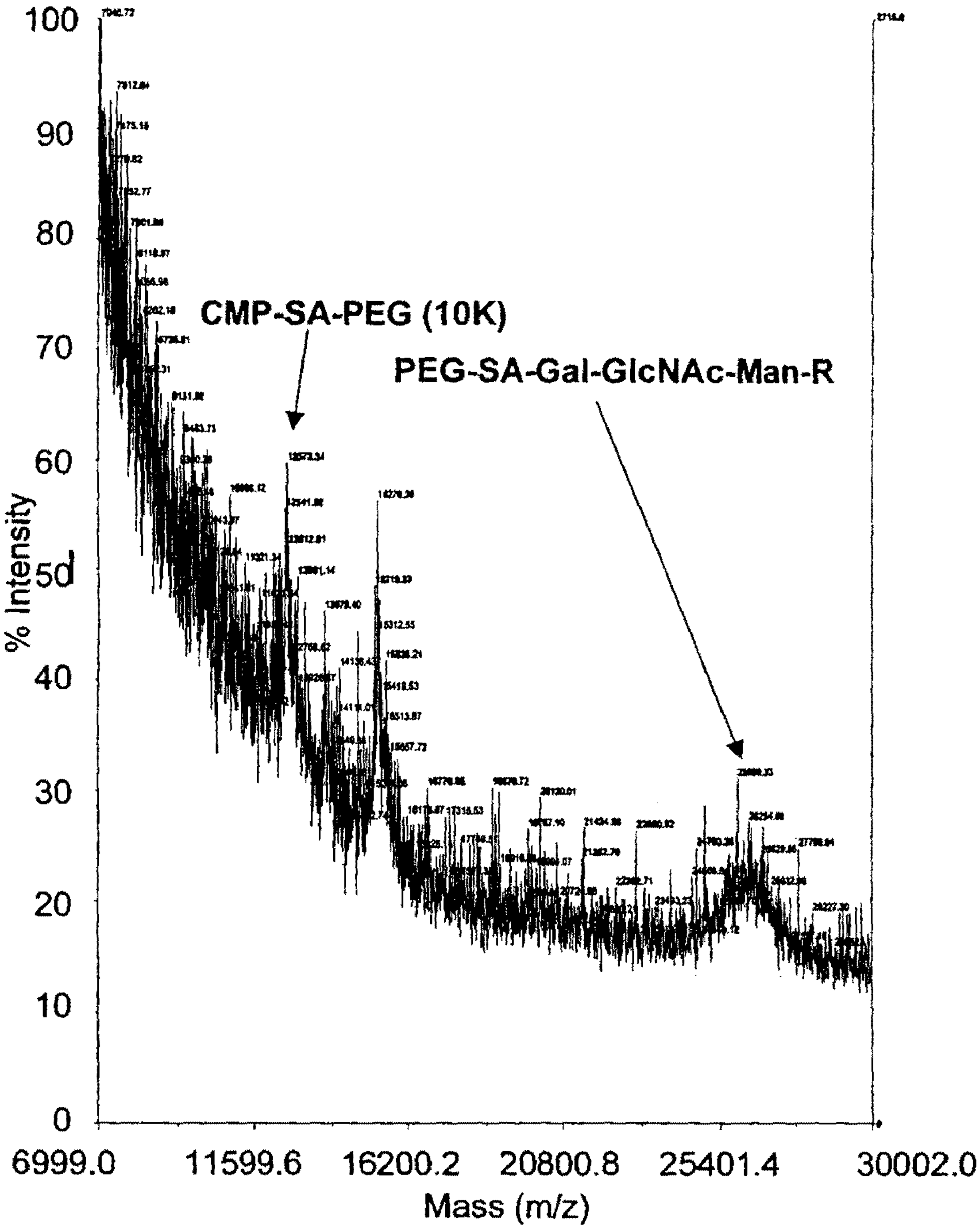
Figure 187B:
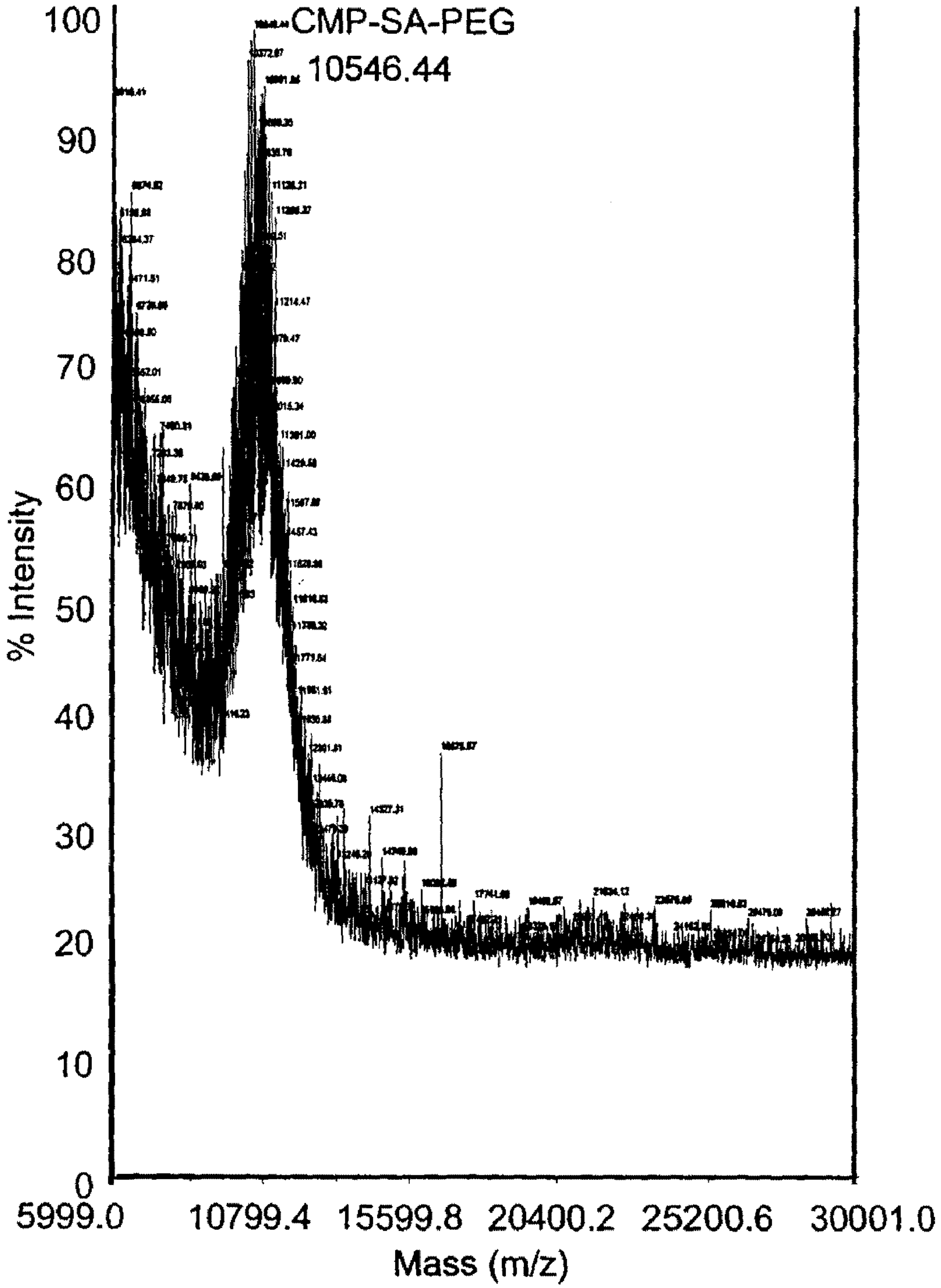

FIG. 187 is a graph depicting the MALDI-TOF spectrum of modified RNaseB by treating the product shown in FIG. 185 with a recombinant ST3Gal III (α2,3-sialyltransferase III) using CMP-SA-PEG (10 kDa) as the donor for the transferase.

Figure 188:
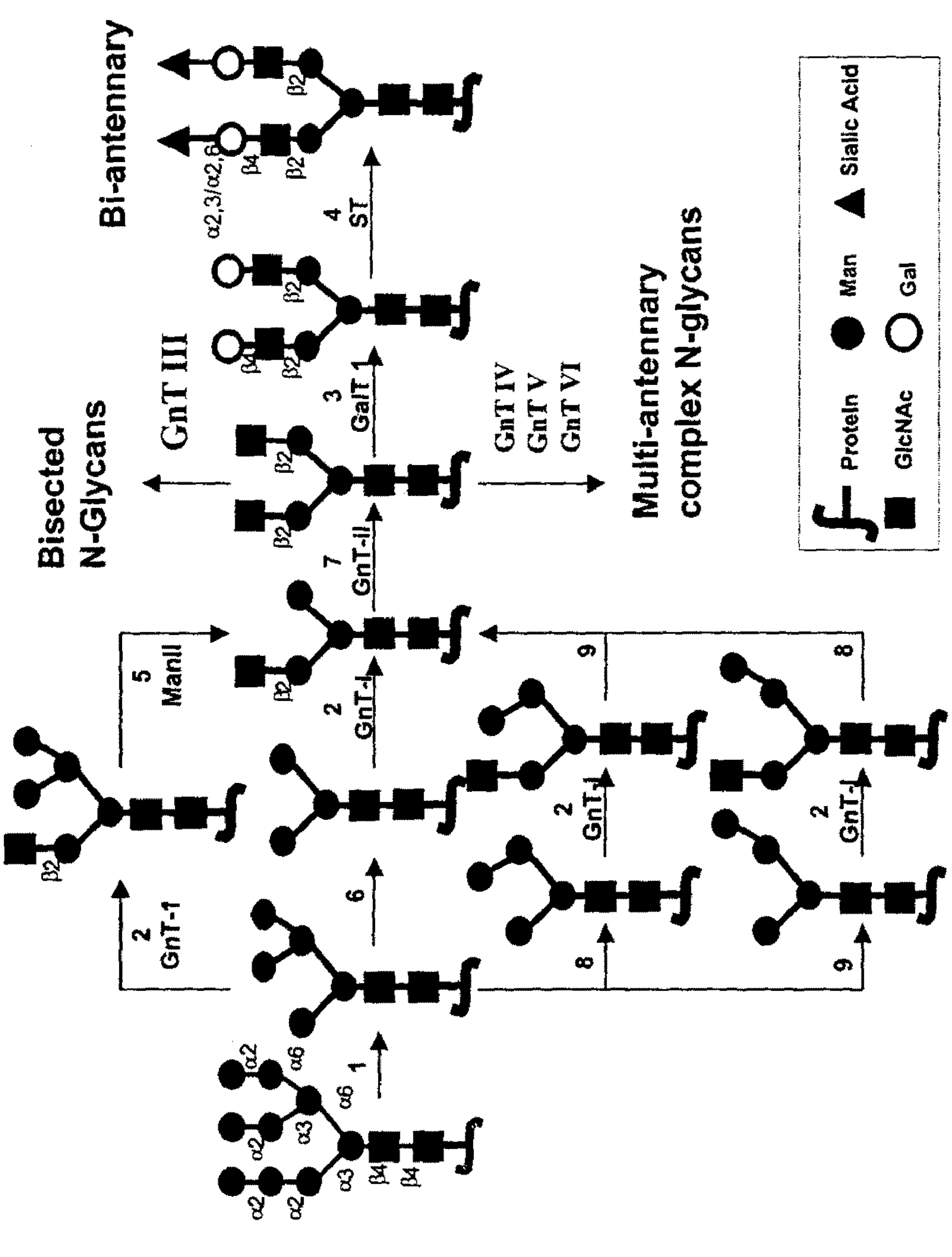

FIG. 188 is a series of schemes depicting the conversion of high mannose N-glycans to complex N-glycans. Enzyme 1 is α1,2-mannosidase from *Trichoderma reesei* or *Aspergillus saitoi*. Enzyme 2 is GnT-I. Enzyme 3 is GalT 1. Enzyme 4 is α2,3-sialyltransferase or α2,6-sialyltransferase. Enzyme 5 is α-mannosidase II. Enzyme 6 is α-mannosidase. Enzyme 7 is GnT-II. Enzyme 8 is α1,6-mannosidase. Enzyme 9 is α1,3-mannosidase.

Figure 189:
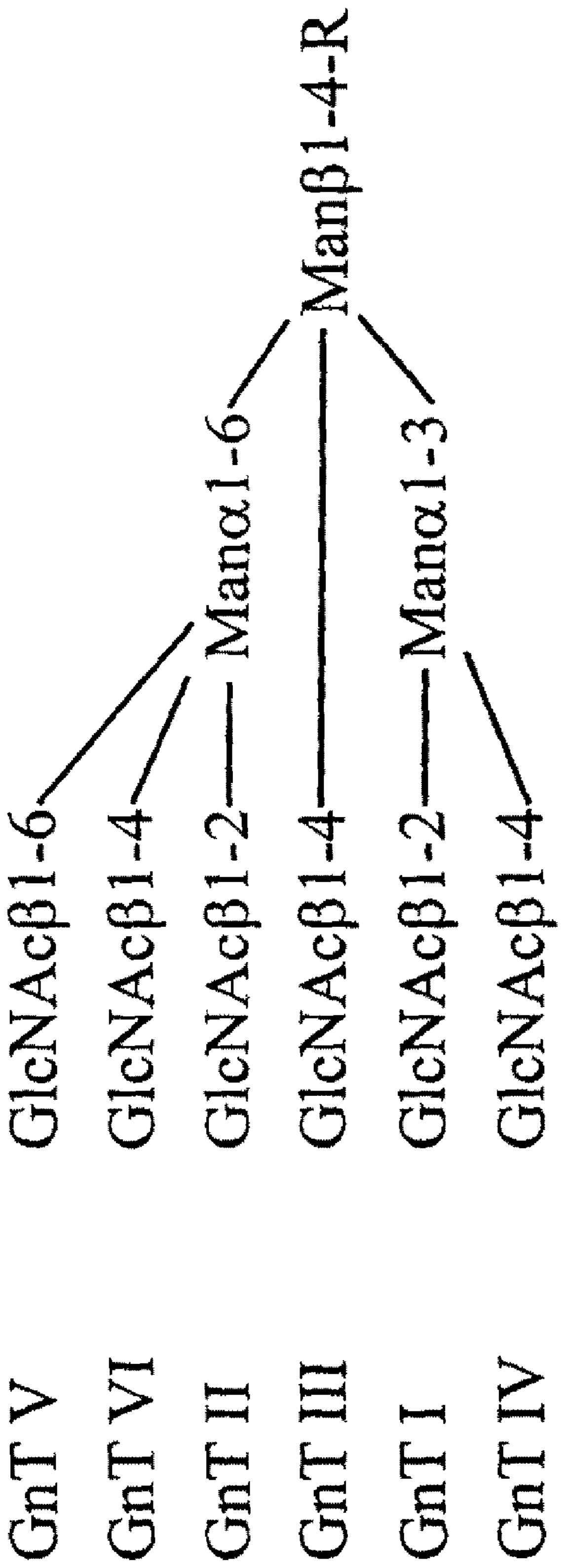

FIG. 189 is a diagram of the linkage catalyzed by N-acetylglucosaminyltransferase I to VI (GnT I-VI). R=GlcNAcβ1,4GlcNAc-Asn-X.

Figure 190:
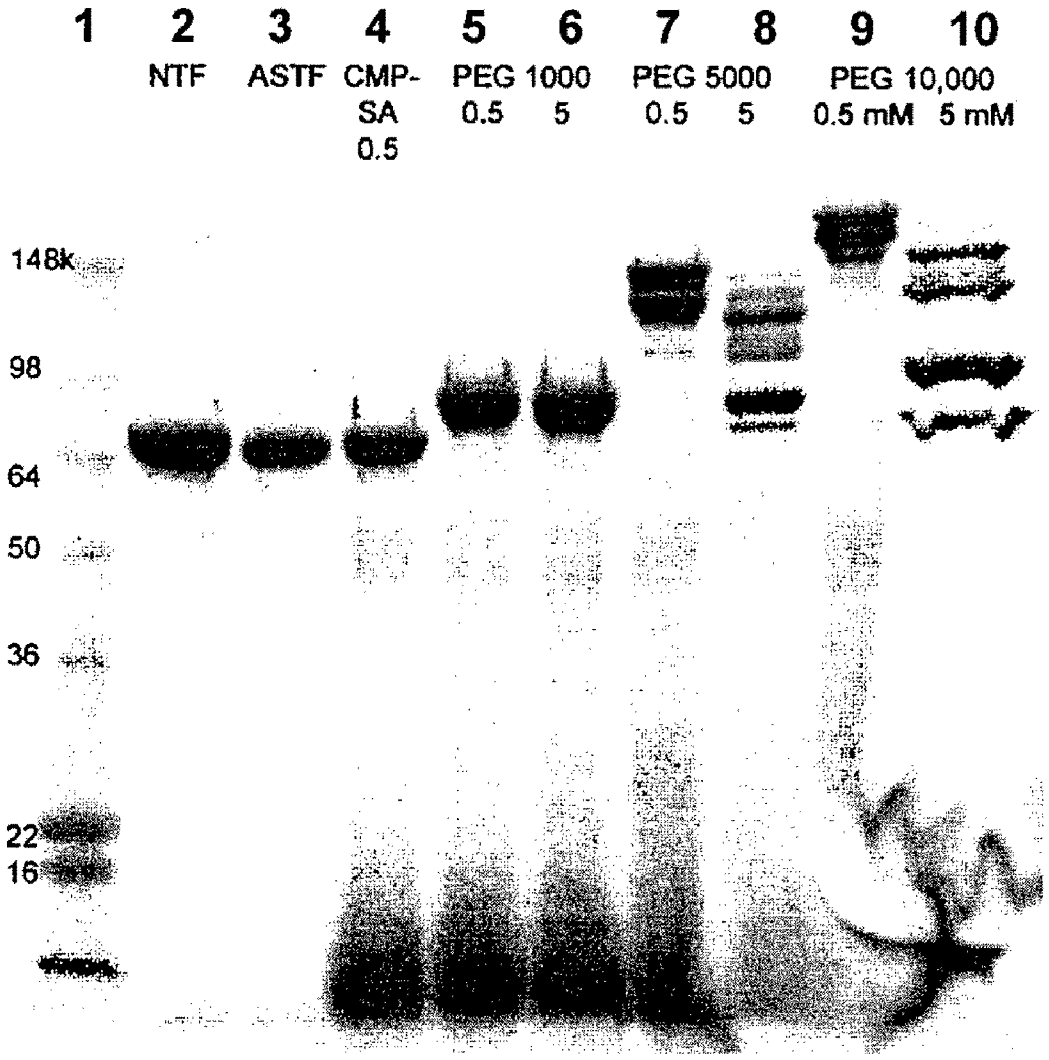

FIG. 190 is an image of an SDS-PAGE gel: standard (Lane 1); native transferrin (Lane 2); asialotransferrin (Lane 3); asialotransferrin and CMP-SA (Lane 4); Lanes 5 and 6, asialotransferrin and CMP-SA-PEG (1 kDa) at 0.5 mM and 5 mM, respectively; Lanes 7 and 8, asialotransferrin and CMP-SA-PEG (5 kDa) at 0.5 mM and 5 mM, respectively; Lanes 9 and 10, asialotransferrin and CMP-SA-PEG (10 kDa) at 0.5 mM and 5 mM, respectively.

Figure 191:
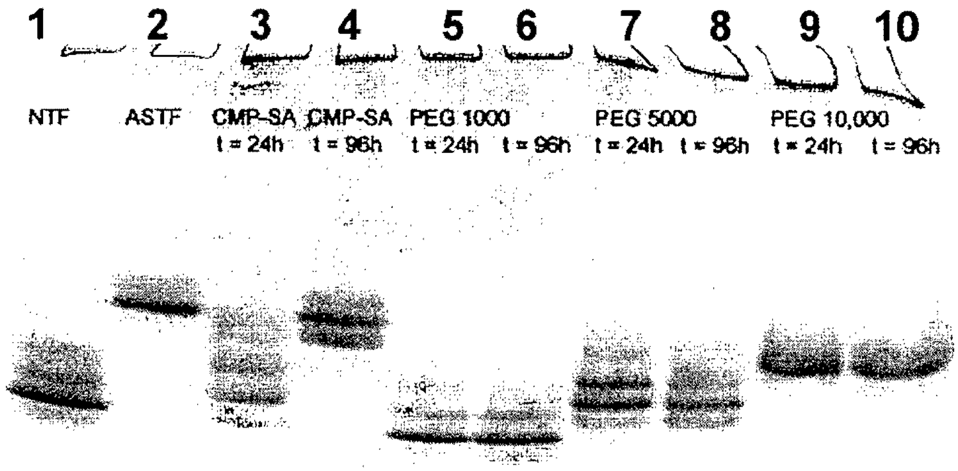

FIG. 191 is an image of an IEF gel: native transferrin (Lane 1); asialotransferrin (Lane 2); asialotransferrin and CMP-SA, 24 hr (Lane 3); asialotransferrin and CMP-SA, 96 hr (Lane 4) Lanes 5 and 6, asialotransferrin and CMP-SA-PEG (1 kDa) at 24 hr and 96 hr, respectively; Lanes 7 and 8, asialotransferrin and CMP-SA-PEG (5 kDa) at 24 hr and 96 hr, respectively; Lanes 9 and 10, asialotransferrin and CMP-SA-PEG (10 kDa) at 24 hr and 96 hr, respectively.

DETAILED DESCRIPTION OF THE INVENTION

The present invention includes methods and compositions for the cell free in vitro addition and/or deletion of sugars to or from a peptide molecule in such a manner as to provide a glycopeptide molecule having a specific customized or desired glycosylation pattern, wherein the glycopeptide is produced at an industrial scale. In a preferred embodiment of the invention, the glycopeptide so produced has attached thereto a modified sugar that has been added to the peptide via an enzymatic reaction. A key feature of the invention is to take a peptide produced by any cell type and generate a core glycan structure on the peptide, following which the glycan structure is then remodeled in vitro to generate a glycopeptide having a glycosylation pattern suitable for therapeutic use in a mammal. More specifically, it is possible according to the present invention, to prepare a glycopeptide molecule having a modified sugar molecule or other compound conjugated thereto, such that the conjugated molecule confers a beneficial property on the peptide. According to the present invention, the conjugate molecule is added to the peptide enzymatically because enzyme-based addition of conjugate molecules to peptides has the advantage of regioselectivity and stereoselectivity. The glycoconjugate may be added to the glycan on a peptide before or after glycosylation has been completed. In other words, the order of glycosylation with respect to glycoconjugation may be varied as described elsewhere herein. It is therefore possible, using the methods and compositions provided herein, to remodel a peptide to confer upon the peptide a desired glycan structure preferably having a modified sugar attached thereto. It is also possible, using the methods and compositions of the invention to generate peptide molecules having desired and or modified glycan structures at an industrial scale, thereby, for the first time, providing the art with a practical solution for the efficient production of improved therapeutic peptides.

DEFINITIONS

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry, and nucleic acid chemistry and hybridization are those well known and commonly employed in the art. Standard techniques are used for nucleic acid and peptide synthesis. The techniques and procedures are generally performed according to conventional methods in the art and various general references (e.g., Sambrook et al., 1989, Molecular Cloning: A Laboratory Manual, 2d ed. Cold Spring Harbor Laboratory Press, Cold Spring Harbor, N.Y.), which are provided throughout this document. The nomenclature used herein and the laboratory procedures used in analytical chemistry and organic syntheses described below are those well known and commonly employed in the art. Standard techniques or modifications thereof, are used for chemical syntheses and chemical analyses.

The articles "a" and "an" are used herein to refer to one or to more than one (i.e. to at least one) of the grammatical object of the article. By way of example, "an element" means one element or more than one element.

The term "antibody," as used herein, refers to an immunoglobulin molecule which is able to specifically bind to a specific epitope on an antigen. Antibodies can be intact immunoglobulins derived from natural sources or from recombinant sources and can be immunoreactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and $F(ab)_2$, as well as single chain antibodies and humanized antibodies (Harlow et al., 1999, Using Antibodies: A Laboratory Manual, Cold Spring Harbor Laboratory Press, NY; Harlow et al., 1989, Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

As used herein, a "functional" biological molecule is a biological molecule in a form in which it exhibits a property by which it is characterized. A functional enzyme, for example, is one which exhibits the characteristic catalytic activity by which the enzyme is characterized.

As used herein, the structure

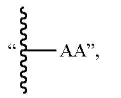

is the point of connection between an amino acid or an amino acid sidechain in the peptide chain and the glycan structure. "N-linked" oligosaccharides are those oligosaccharides that are linked to a peptide backbone through asparagine, by way of an asparagine-N-acetylglucosamine linkage. N-linked oligosaccharides are also called "N-glycans." All N-linked oligosaccharides have a common pentasaccharide core of $Man_3GlcNAc_2$. They differ in the presence of, and in the number of branches (also called antennae) of peripheral sugars such as N-acetylglucosamine, galactose, N-acetylgalactosamine, fucose and sialic acid. Optionally, this structure may also contain a core fucose molecule and/or a xylose molecule.

An "elemental trimannosyl core structure" refers to a glycan moiety comprising solely a trimannosyl core structure, with no additional sugars attached thereto. When the term "elemental" is not included in the description of the "trimannosyl core structure," then the glycan comprises the trimannosyl core structure with additional sugars attached thereto. Optionally, this structure may also contain a core fucose molecule and/or a xylose molecule.

The term "elemental trimannosyl core glycopeptide" is used herein to refer to a glycopeptide having glycan structures comprised primarily of an elemental trimannosyl core structure. Optionally, this structure may also contain a core fucose molecule and/or a xylose molecule.

"O-linked" oligosaccharides are those oligosaccharides that are linked to a peptide backbone through threonine, serine, hydroxyproline, tyrosine, or other hydroxy-containing amino acids.

All oligosaccharides described herein are described with the name or abbreviation for the non-reducing saccharide (i.e., Gal), followed by the configuration of the glycosidic bond (α or β), the ring bond (1 or 2), the ring position of the reducing saccharide involved in the bond (2, 3, 4, 6 or 8), and then the name or abbreviation of the reducing saccharide (i.e., GlcNAc). Each saccharide is preferably a pyranose. For a review of standard glycobiology nomenclature see, Essentials of Glycobiology Varki et al. eds., 1999, CSHL Press.

The term "sialic acid" refers to any member of a family of nine-carbon carboxylated sugars. The most common member of the sialic acid family is N-acetyl-neuraminic acid (2-keto-5-acetamido-3,5-dideoxy-D-glycero-D-galactononulopyranos-1-onic acid (often abbreviated as Neu5Ac, NeuAc, or NANA). A second member of the family is N-glycolyl-neuraminic acid (Neu5Gc or NeuGc), in which the N-acetyl group of NeuAc is hydroxylated. A third sialic acid family member is 2-keto-3-deoxy-nonulosonic acid (KDN) (Nadano et al. (1986) *J. Biol. Chem.* 261: 11550-11557; Kanamori et al., *J. Biol. Chem.* 265: 21811-21819 (1990)). Also included are 9-substituted sialic acids such as a 9-O—$C_1$-$C_6$ acyl-Neu5Ac like 9-O-lactyl-Neu5Ac or 9-O-acetyl-Neu5Ac, 9-deoxy-9-fluoro-Neu5Ac and 9-azido-9-deoxy-Neu5Ac. For review of the sialic acid family, see, e.g., Varki, *Glycobiology* 2: 25-40 (1992); *Sialic Acids Chemistry, Metabolism and Function*, R. Schauer, Ed. (Springer-Verlag, New York (1992)). The synthesis and use of sialic acid compounds in a sialylation procedure is disclosed in international application WO 92/16640, published Oct. 1, 1992.

A peptide having "desired glycosylation", as used herein, is a peptide that comprises one or more oligosaccharide molecules which are required for efficient biological activity of the peptide.

A "disease" is a state of health of an animal wherein the animal cannot maintain homeostasis, and wherein if the disease is not ameliorated then the animal's health continues to deteriorate.

The "area under the curve" or "AUC", as used herein in the context of administering a peptide drug to a patient, is defined as total area under the curve that describes the concentration of drug in systemic circulation in the patient as a function of time from zero to infinity.

The term "half-life" or "t ½", as used herein in the context of administering a peptide drug to a patient, is defined as the time required for plasma concentration of a drug in a patient to be reduced by one half. There may be more than one half-life associated with the peptide drug depending on multiple clearance mechanisms, redistribution, and other mechanisms well known in the art. Usually, alpha and beta half-lives are defined such that the alpha phase is associated with redistribution, and the beta phase is associated with clearance. However, with protein drugs that are, for the most part, confined to the bloodstream, there can be at least two clearance half-lives. For some glycosylated peptides, rapid beta phase clearance may be mediated via receptors on macrophages, or endothelial cells that recognize terminal galactose, N-acetylgalactosamine, N-acetylglucosamine, mannose, or fucose. Slower beta phase clearance may occur via renal glomerular filtration for molecules with an effective radius $<2$ nm (approximately 68 kD) and/or specific or non-specific uptake and metabolism in tissues. GlycoPEGylation may cap terminal sugars (e.g. galactose or N-acetylgalactosamine) and thereby block rapid alpha phase clearance via receptors that recognize these sugars. It may also confer a larger effective radius and thereby decrease the volume of distribution and tissue uptake, thereby prolonging the late beta phase. Thus, the precise impact of glycoPEGylation on alpha phase and beta phase half-lives will vary depending upon the size, state of glycosylation, and other parameters, as is well known in the art. Further explanation of "half-life" is found in Pharmaceutical Biotechnology (1997, DFA Crommelin and R D Sindelar, eds., Harwood Publishers, Amsterdam, pp 101-120).

The term "residence time", as used herein in the context of administering a peptide drug to a patient, is defined as the average time that drug stays in the body of the patient after dosing.

An "isolated nucleic acid" refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA which is part of a hybrid nucleic acid encoding additional peptide sequence.

A "polynucleotide" means a single strand or parallel and anti-parallel strands of a nucleic acid. Thus, a polynucleotide may be either a single-stranded or a double-stranded nucleic acid.

The term "nucleic acid" typically refers to large polynucleotides. The term "oligonucleotide" typically refers to short polynucleotides, generally no greater than about 50 nucleotides.

Conventional notation is used herein to describe polynucleotide sequences: the left-hand end of a single-stranded polynucleotide sequence is the 5'-end; the left-hand direction of a double-stranded polynucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand"; sequences on the DNA strand which are located 5' to a reference point on the DNA are referred to as "upstream sequences"; sequences on the DNA strand which are 3' to a reference point on the DNA are referred to as "downstream sequences."

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a nucleic acid sequence encodes a protein if transcription and translation of mRNA corresponding to that nucleic acid produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that nucleic acid or cDNA.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

"Homologous" as used herein, refers to the subunit sequence similarity between two polymeric molecules, e.g., between two nucleic acid molecules, e.g., two DNA molecules or two RNA molecules, or between two peptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, the DNA sequences 3'ATTGCC5' and 3'TATGGC share 50% homology.

As used herein, "homology" is used synonymously with "identity."

The determination of percent identity between two nucleotide or amino acid sequences can be accomplished using a mathematical algorithm. For example, a mathematical algorithm useful for comparing two sequences is the algorithm of Karlin and Altschul (1990, Proc. Natl. Acad. Sci. USA 87:2264-2268), modified as in Karlin and Altschul (1993, Proc. Natl. Acad. Sci. USA 90:5873-5877). This algorithm is incorporated into the NBLAST and XBLAST programs of Altschul, et al. (1990, J. Mol. Biol. 215:403-410), and can be accessed, for example at the National Center for Biotechnology Information (NCBI) world wide web site having the universal resource locator "http://www.ncbi.nlm.nih.gov/BLAST/". BLAST nucleotide searches can be performed with the NBLAST program (designated "blastn" at the NCBI web site), using the following parameters: gap penalty=5; gap extension penalty=2; mismatch penalty=3; match reward=1; expectation value 10.0; and word size=11 to obtain nucleotide sequences homologous to a nucleic acid described herein. BLAST protein searches can be performed with the XBLAST program (designated "blastn" at the NCBI web site) or the NCBI "blastp" program, using the following parameters: expectation value 10.0, BLOSUM62 scoring matrix to obtain amino acid sequences homologous to a protein molecule described herein. To obtain gapped alignments for comparison purposes, Gapped BLAST can be utilized as described in Altschul et al. (1997, Nucleic Acids Res. 25:3389-3402). Alternatively, PSI-Blast or PHI-Blast can be used to perform an iterated search which detects distant relationships between molecules (Id.) and relationships between molecules which share a common pattern. When utilizing BLAST, Gapped BLAST, PSI-Blast, and PHI-Blast programs, the default parameters of the respective programs (e.g., XBLAST and NBLAST) can be used. See http://www.ncbi.nlm.nih.gov.

The percent identity between two sequences can be determined using techniques similar to those described above, with or without allowing gaps. In calculating percent identity, typically exact matches are counted.

A "heterologous nucleic acid expression unit" encoding a peptide is defined as a nucleic acid having a coding sequence for a peptide of interest operably linked to one or more expression control sequences such as promoters and/or repressor sequences wherein at least one of the sequences is heterologous, i.e., not normally found in the host cell.

By describing two polynucleotides as "operably linked" is meant that a single-stranded or double-stranded nucleic acid moiety comprises the two polynucleotides arranged within the nucleic acid moiety in such a manner that at least one of the two polynucleotides is able to exert a physiological effect by which it is characterized upon the other. By way of example, a promoter operably linked to the coding region of a nucleic acid is able to promote transcription of the coding region.

As used herein, the term "promoter/regulatory sequence" means a nucleic acid sequence which is required for expression of a gene product operably linked to the promoter/regulator sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive promoter is a promoter which drives expression of a gene to which it is operably linked, in a constant manner in a cell. By way of example, promoters which drive expression of cellular housekeeping genes are considered to be constitutive promoters.

An "inducible" promoter is a nucleotide sequence which, when operably linked with a polynucleotide which encodes or specifies a gene product, causes the gene product to be produced in a living cell substantially only when an inducer which corresponds to the promoter is present in the cell.

A "tissue-specific" promoter is a nucleotide sequence which, when operably linked with a polynucleotide which encodes or specifies a gene product, causes the gene product to be produced in a living cell substantially only if the cell is a cell of the tissue type corresponding to the promoter.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses that incorporate the recombinant polynucleotide.

A "genetically engineered" or "recombinant" cell is a cell having one or more modifications to the genetic material of the cell. Such modifications are seen to include, but are not limited to, insertions of genetic material, deletions of genetic material and insertion of genetic material that is extrachromasomal whether such material is stably maintained or not.

A "peptide" is an oligopeptide, polypeptide, peptide, protein or glycoprotein. The use of the term "peptide" herein includes a peptide having a sugar molecule attached thereto when a sugar molecule is attached thereto.

As used herein, "native form" means the form of the peptide when produced by the cells and/or organisms in which it is found in nature. When the peptide is produced by a plurality of cells and/or organisms, the peptide may have a variety of native forms.

"Peptide" refers to a polymer in which the monomers are amino acids and are joined together through amide bonds, alternatively referred to as a peptide. Additionally, unnatural amino acids, for example, β-alanine, phenylglycine and homoarginine are also included. Amino acids that are not nucleic acid-encoded may also be used in the present invention. Furthermore, amino acids that have been modified to include reactive groups, glycosylation sites, polymers, therapeutic moieties, biomolecules and the like may also be used in the invention. All of the amino acids used in the present invention may be either the D- or L-isomer thereof. The L-isomer is generally preferred. In addition, other peptidomimetics are also useful in the present invention. As used herein, "peptide" refers to both glycosylated and unglycosylated peptides. Also included are peptides that are incompletely glycosylated by a system that expresses the peptide. For a general review, see, Spatola, A. F., in CHEMISTRY AND BIOCHEMISTRY OF AMINO ACIDS, PEPTIDES AND PROTEINS, B. Weinstein, eds., Marcel Dekker, New York, p. 267 (1983).

The term "peptide conjugate," refers to species of the invention in which a peptide is conjugated with a modified sugar as set forth herein.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, (-carboxyglutamate, and O-phosphoserine. Amino acid analogs refers to compounds that have the same basic chemical structure as a naturally occurring amino acid, i.e., an α carbon that is linked to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that function in a manner similar to a naturally occurring amino acid.

As used herein, amino acids are represented by the full name thereof, by the three letter code corresponding thereto, or by the one-letter code corresponding thereto, as indicated in the following Table 1:

TABLE 1

Amino acids, and the three letter and one letter codes.

| Full Name | Three-Letter Code | One-Letter Code |
|---|---|---|
| Aspartic Acid | Asp | D |
| Glutamic Acid | Glu | E |
| Lysine | Lys | K |
| Arginine | Arg | R |
| Histidine | His | H |
| Tyrosine | Tyr | Y |
| Cysteine | Cys | C |
| Asparagine | Asn | N |
| Glutamine | Gln | Q |
| Serine | Ser | S |
| Threonine | Thr | T |
| Glycine | Gly | G |
| Alanine | Ala | A |
| Valine | Val | V |
| Leucine | Leu | L |
| Isoleucine | Ile | I |
| Methionine | Met | M |
| Proline | Pro | P |
| Phenylalanine | Phe | F |
| Tryptophan | Trp | W |

The present invention also provides for analogs of proteins or peptides which comprise a protein as identified above. Analogs may differ from naturally occurring proteins or peptides by conservative amino acid sequence differences or by modifications which do not affect sequence, or by both. For example, conservative amino acid changes may be made, which although they alter the primary sequence of the protein or peptide, do not normally alter its function. Conservative amino acid substitutions typically include substitutions within the following groups:

glycine, alanine;
valine, isoleucine, leucine;
aspartic acid, glutamic acid;
asparagine, glutamine;
serine, threonine;
lysine, arginine;
phenylalanine, tyrosine.

Modifications (which do not normally alter primary sequence) include in vivo, or in vitro, chemical derivatization of peptides, e.g., acetylation, or carboxylation. Also included are modifications of glycosylation, e.g., those made by modifying the glycosylation patterns of a peptide during its synthesis and processing or in further processing steps; e.g., by exposing the peptide to enzymes which affect glycosylation, e.g., mammalian glycosylating or deglycosylating enzymes. Also embraced are sequences which have phosphorylated amino acid residues, e.g., phosphotyrosine, phosphoserine, or phosphothreonine. It will be appreciated, of course, that the peptides may incorporate amino acid residues which are modified without affecting activity. For example, the termini may be derivatized to include blocking groups, i.e. chemical substituents suitable to protect and/or stabilize the N- and C-termini from "undesirable degradation", a term meant to encompass any type of enzymatic, chemical or biochemical breakdown of the compound at its termini which is likely to affect the function of the compound, i.e. sequential degradation of the compound at a terminal end thereof.

Blocking groups include protecting groups conventionally used in the art of peptide chemistry which will not adversely affect the in vivo activities of the peptide. For example, suitable N-terminal blocking groups can be introduced by alkylation or acylation of the N-terminus. Examples of suitable N-terminal blocking groups include $C_1$-$C_5$ branched or unbranched alkyl groups, acyl groups such as formyl and acetyl groups, as well as substituted forms thereof, such as the acetamidomethyl (Acm), Fmoc or Boc groups. Desamino analogs of amino acids are also useful N-terminal blocking groups, and can either be coupled to the N-terminus of the peptide or used in place of the N-terminal reside. Suitable C-terminal blocking groups, in which the carboxyl group of the C-terminus is either incorporated or not, include esters, ketones or amides. Ester or ketone-forming alkyl groups, particularly lower alkyl groups such as methyl, ethyl and propyl, and amide-forming amino groups such as primary amines (—$NH_2$), and mono- and di-alkylamino groups such as methylamino, ethylamino, dimethylamino, diethylamino, methylethylamino and the like are examples of C-terminal blocking groups. Descarboxylated amino acid analogues such as agmatine are also useful C-terminal blocking groups and can be either coupled to the peptide's C-terminal residue or used in place of it. Further, it will be appreciated that the free amino and carboxyl groups at the termini can be removed altogether from the peptide to yield desamino and descarboxylated forms thereof without affect on peptide activity.

Other modifications can also be incorporated without adversely affecting the activity and these include, but are not limited to, substitution of one or more of the amino acids in the natural L-isomeric form with amino acids in the D-isomeric form. Thus, the peptide may include one or more D-amino acid resides, or may comprise amino acids which are all in the D-form. Retro-inverso forms of peptides in accordance with the present invention are also contemplated, for example, inverted peptides in which all amino acids are substituted with D-amino acid forms.

Acid addition salts of the present invention are also contemplated as functional equivalents. Thus, a peptide in accordance with the present invention treated with an inorganic acid such as hydrochloric, hydrobromic, sulfuric, nitric, phosphoric, and the like, or an organic acid such as an acetic, propionic, glycolic, pyruvic, oxalic, malic, malonic, succinic, maleic, fumaric, tataric, citric, benzoic, cinnamic, mandelic, methanesulfonic, ethanesulfonic, p-toluenesulfonic, salicyclic and the like, to provide a water soluble salt of the peptide is suitable for use in the invention.

Also included are peptides which have been modified using ordinary molecular biological techniques so as to improve their resistance to proteolytic degradation or to optimize solubility properties or to render them more suitable as a therapeutic agent. Analogs of such peptides include those containing residues other than naturally occurring L-amino acids, e.g., D-amino acids or non-naturally occurring synthetic amino acids. The peptides of the invention are not limited to products of any of the specific exemplary processes listed herein.

As used herein, the term "MALDI" is an abbreviation for Matrix Assisted Laser Desorption Ionization. During ionization, SA-PEG (sialic acid-poly(ethylene glycol)) can be partially eliminated from the N-glycan structure of the glycoprotein.

As used herein, the term "glycosyltransferase," refers to any enzyme/protein that has the ability to transfer a donor sugar to an acceptor moiety.

As used herein, the term "modified sugar," refers to a naturally- or non-naturally-occurring carbohydrate that is enzymatically added onto an amino acid or a glycosyl residue of a peptide in a process of the invention. The modified sugar is selected from a number of enzyme substrates including, but not limited to sugar nucleotides (mono-, di-, and tri-phosphates), activated sugars (e.g., glycosyl halides, glycosyl mesylates) and sugars that are neither activated nor nucleotides.

The "modified sugar" is covalently functionalized with a "modifying group." Useful modifying groups include, but are not limited to, water-soluble polymers, therapeutic moieties, diagnostic moieties, biomolecules and the like. The locus of functionalization with the modifying group is selected such that it does not prevent the "modified sugar" from being added enzymatically to a peptide.

The term "water-soluble" refers to moieties that have some detectable degree of solubility in water. Methods to detect and/or quantify water solubility are well known in the art. Exemplary water-soluble polymers include peptides, saccharides, poly(ethers), poly(amines), poly(carboxylic acids) and the like. Peptides can have mixed sequences or be composed of a single amino acid, e.g. poly(lysine). Similarly, saccharides can be of mixed sequence or composed of a single saccharide subunit, e.g., dextran, amylose, chitosan, and poly (sialic acid). An exemplary poly(ether) is poly(ethylene glycol). Poly(ethylene imine) is an exemplary polyamine, and poly(aspartic) acid is a representative poly(carboxylic acid).

"Poly(alkylene oxide)" refers to a genus of compounds having a polyether backbone. Poly(alkylene oxide) species of use in the present invention include, for example, straight- and branched-chain species. Moreover, exemplary poly(alkylene oxide) species can terminate in one or more reactive, activatable, or inert groups. For example, poly(ethylene glycol) is a poly(alkylene oxide) consisting of repeating ethylene oxide subunits, which may or may not include additional reactive, activatable or inert moieties at either terminus. Useful poly(alkylene oxide) species include those in which one terminus is "capped" by an inert group, e.g., monomethoxy-poly(alkylene oxide). When the molecule is a branched species, it may include multiple reactive, activatable or inert groups at the termini of the alkylene oxide chains and the reactive groups may be either the same or different. Derivatives of straight-chain poly(alkylene oxide) species that are heterobifunctional are also known in the art.

The term, "glycosyl linking group," as used herein refers to a glycosyl residue to which an agent (e.g., water-soluble polymer, therapeutic moiety, biomolecule) is covalently attached. In the methods of the invention, the "glycosyl linking group" becomes covalently attached to a glycosylated or unglycosylated peptide, thereby linking the agent to an amino acid and/or glycosyl residue on the peptide. A "glycosyl linking group" is generally derived from a "modified sugar" by the enzymatic attachment of the "modified sugar" to an amino acid and/or glycosyl residue of the peptide. More specifically, a "glycosyl linking group," as used herein, refers to a moiety that covalently joins a "modifying group," as discussed herein, and an amino acid residue of a peptide. The glycosyl linking group-modifying group adduct has a structure that is a substrate for an enzyme. The enzymes for which the glycosyl linking group-modifying group adduct are substrates are generally those capable of transferring a saccharyl moiety onto an amino acid residue of a peptide, e.g, a glycosyltransferase, amidase, glycosidase, trans-sialidase, etc. The "glycosyl linking group" is interposed between, and covalently joins a "modifying group" and an amino acid residue of a peptide.

An "intact glycosyl linking group" refers to a linking group that is derived from a glycosyl moiety in which the individual saccharide monomer that links the conjugate is not degraded, e.g., oxidized, e.g., by sodium metaperiodate. "Intact glycosyl linking groups" of the invention may be derived from a naturally occurring oligosaccharide by addition of glycosyl unit(s) or removal of one or more glycosyl unit from a parent saccharide structure. An exemplary "intact glycosyl linking group" includes at least one intact, e.g., non-degraded, saccharyl moiety that is covalently attached to an amino acid residue on a peptide. The remainder of the "linking group" can have substantially any structure. For example, the modifying group is optionally linked directly to the intact saccharyl moiety. Alternatively, the modifying group is linked to the intact saccharyl moiety via a linker arm. The linker arm can have substantially any structure determined to be useful in the selected embodiment. In an exemplary embodiment, the linker arm is one or more intact saccharyl moieties, i.e. "the intact glycosyl linking group" resembles an oligosaccharide. Another exemplary intact glycosyl linking group is one in which a saccharyl moiety attached, directly or indirectly, to the intact saccharyl moiety is degraded and derivatized (e.g., periodate oxidation followed by reductive amination). Still a further linker arm includes the modifying group attached to the intact saccharyl moiety, directly or indirectly, via a cross-linker, such as those described herein or analogues thereof.

"Degradation," as used herein refers to the removal of one or more carbon atoms from a saccharyl moiety.

The terms "targeting moiety" and "targeting agent", as used herein, refer to species that will selectively localize in a particular tissue or region of the body. The localization is mediated by specific recognition of molecular determinants, molecular size of the targeting agent or conjugate, ionic interactions, hydrophobic interactions and the like. Other mechanisms of targeting an agent to a particular tissue or region are known to those of skill in the art.

As used herein, "therapeutic moiety" means any agent useful for therapy including, but not limited to, antibiotics, anti-inflammatory agents, anti-tumor drugs, cytotoxins, and radioactive agents. "Therapeutic moiety" includes prodrugs of bioactive agents, constructs in which more than one therapeutic moiety is linked to a carrier, e.g., multivalent agents. Therapeutic moiety also includes peptides, and constructs that include peptides. Exemplary peptides include those disclosed in FIG. 28 and Tables 6 and 7, herein. "Therapeutic moiety" thus means any agent useful for therapy including, but not limited to, antibiotics, anti-inflammatory agents, anti-tumor drugs, cytotoxins, and radioactive agents. "Therapeutic moiety" includes prodrugs of bioactive agents, constructs in which more than one therapeutic moiety is linked to a carrier, e.g., multivalent agents.

As used herein, "anti-tumor drug" means any agent useful to combat cancer including, but not limited to, cytotoxins and agents such as antimetabolites, alkylating agents, anthracyclines, antibiotics, antimitotic agents, procarbazine, hydroxyurea, asparaginase, corticosteroids, interferons and radioactive agents. Also encompassed within the scope of the term "anti-tumor drug," are conjugates of peptides with anti-tumor activity, e.g. TNF-α. Conjugates include, but are not limited to those formed between a therapeutic protein and a glycoprotein of the invention. A representative conjugate is that formed between PSGL-1 and TNF-α.

As used herein, "a cytotoxin or cytotoxic agent" means any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracinedione, mitoxantrone, mithramycin, actinomycin D, 1-dehydrotestosterone, glucocorticoids, procaine, tetracaine, lidocaine, propranolol, and puromycin and analogs or homologs thereof. Other toxins include, for example, ricin, CC-1065 and analogues, the duocarmycins. Still other toxins include diphtheria toxin, and snake venom (e.g., cobra venom).

As used herein, "a radioactive agent" includes any radioisotope that is effective in diagnosing or destroying a tumor. Examples include, but are not limited to, indium-111, cobalt-60 and technetium. Additionally, naturally occurring radioactive elements such as uranium, radium, and thorium, which typically represent mixtures of radioisotopes, are suitable examples of a radioactive agent. The metal ions are typically chelated with an organic chelating moiety.

Many useful chelating groups, crown ethers, cryptands and the like are known in the art and can be incorporated into the compounds of the invention (e.g. EDTA, DTPA, DOTA, NTA, HDTA, etc. and their phosphonate analogs such as DTPP, EDTP, HDTP, NTP, etc). See, for example, Pitt et al., "The Design of Chelating Agents for the Treatment of Iron Overload," In, Inorganic Chemistry in Biology and Medicine; Martell, Ed.; American Chemical Society, Washington, D.C., 1980, pp. 279-312; Lindoy, The Chemistry of Macrocyclic Ligand Complexes; Cambridge University Press, Cambridge, 1989; Dugas, Bioorganic Chemistry; Springer-Verlag, New York, 1989, and references contained therein.

Additionally, a manifold of routes allowing the attachment of chelating agents, crown ethers and cyclodextrins to other molecules is available to those of skill in the art. See, for example, Meares et al., "Properties of In Vivo Chelate-Tagged Proteins and Polypeptides." In, Modification of Pro- TEINS: FOOD, NUTRITIONAL, AND PHARMACOLOGICAL ASPECTS;" Feeney, et al., Eds., American Chemical Society, Washington, D.C., 1982, pp. 370-387; Kasina et al., *Bioconjugate Chem.*, 9: 108-117 (1998); Song et al., *Bioconjugate Chem.*, 8: 249-255 (1997).

As used herein, "pharmaceutically acceptable carrier" includes any material, which when combined with the conjugate retains the activity of the conjugate activity and is non-reactive with the subject's immune system. Examples include, but are not limited to, any of the standard pharmaceutical carriers such as a phosphate buffered saline solution, water, emulsions such as oil/water emulsion, and various types of wetting agents. Other carriers may also include sterile solutions, tablets including coated tablets and capsules. Typically such carriers contain excipients such as starch, milk, sugar, certain types of clay, gelatin, stearic acid or salts thereof, magnesium or calcium stearate, talc, vegetable fats or oils, gums, glycols, or other known excipients. Such carriers may also include flavor and color additives or other ingredients. Compositions comprising such carriers are formulated by well known conventional methods.

As used herein, "administering" means oral administration, administration as a suppository, topical contact, intravenous, intraperitoneal, intramuscular, intralesional, intranasal or subcutaneous administration, intrathecal administration, or the implantation of a slow-release device e.g., a mini-osmotic pump, to the subject.

The term "isolated" refers to a material that is substantially or essentially free from components, which are used to produce the material. For peptide conjugates of the invention, the term "isolated" refers to material that is substantially or essentially free from components, which normally accompany the material in the mixture used to prepare the peptide conjugate. "Isolated" and "pure" are used interchangeably. Typically, isolated peptide conjugates of the invention have a level of purity preferably expressed as a range. The lower end of the range of purity for the peptide conjugates is about 60%, about 70% or about 80% and the upper end of the range of purity is about 70%, about 80%, about 90% or more than about 90%.

When the peptide conjugates are more than about 90% pure, their purities are also preferably expressed as a range. The lower end of the range of purity is about 90%, about 92%, about 94%, about 96% or about 98%. The upper end of the range of purity is about 92%, about 94%, about 96%, about 98% or about 100% purity.

Purity is determined by any art-recognized method of analysis (e.g., band intensity on a silver stained gel, polyacrylamide gel electrophoresis, HPLC, or a similar means).

"Commercial scale" as used herein means about one or more gram of final product produced in the method.

"Essentially each member of the population," as used herein, describes a characteristic of a population of peptide conjugates of the invention in which a selected percentage of the modified sugars added to a peptide are added to multiple, identical acceptor sites on the peptide. "Essentially each member of the population" speaks to the "homogeneity" of the sites on the peptide conjugated to a modified sugar and refers to conjugates of the invention, which are at least about 80%, preferably at least about 90% and more preferably at least about 95% homogenous.

"Homogeneity," refers to the structural consistency across a population of acceptor moieties to which the modified sugars are conjugated. Thus, in a peptide conjugate of the invention in which each modified sugar moiety is conjugated to an acceptor site having the same structure as the acceptor site to which every other modified sugar is conjugated, the peptide conjugate is said to be about 100% homogeneous. Homogeneity is typically expressed as a range. The lower end of the range of homogeneity for the peptide conjugates is about 60%, about 70% or about 80% and the upper end of the range of purity is about 70%, about 80%, about 90% or more than about 90%.

When the peptide conjugates are more than or equal to about 90% homogeneous, their homogeneity is also preferably expressed as a range. The lower end of the range of homogeneity is about 90%, about 92%, about 94%, about 96% or about 98%. The upper end of the range of purity is about 92%, about 94%, about 96%, about 98% or about 100% homogeneity. The purity of the peptide conjugates is typically determined by one or more methods known to those of skill in the art, e.g., liquid chromatography-mass spectrometry (LC-MS), matrix assisted laser desorption time of flight mass spectrometry (MALDI-TOF), capillary electrophoresis, and the like.

"Substantially uniform glycoform" or a "substantially uniform glycosylation pattern," when referring to a glycopeptide species, refers to the percentage of acceptor moieties that are glycosylated by the glycosyltransferase of interest (e.g., fucosyltransferase). For example, in the case of a α1,2 fucosyltransferase, a substantially uniform fucosylation pattern exists if substantially all (as defined below) of the Galβ1,4-GlcNAc-R and sialylated analogues thereof are fucosylated in a peptide conjugate of the invention. It will be understood by one of skill in the art, that the starting material may contain glycosylated acceptor moieties (e.g., fucosylated Galβ1,4-GlcNAc-R moieties). Thus, the calculated percent glycosylation will include acceptor moieties that are glycosylated by the methods of the invention, as well as those acceptor moieties already glycosylated in the starting material.

The term "substantially" in the above definitions of "substantially uniform" generally means at least about 40%, at least about 70%, at least about 80%, or more preferably at least about 90%, and still more preferably at least about 95% of the acceptor moieties for a particular glycosyltransferase are glycosylated.

DESCRIPTION OF THE INVENTION

I. Method to Remodel Glycan Chains

The present invention includes methods and compositions for the in vitro addition and/or deletion of sugars to or from a glycopeptide molecule in such a manner as to provide a peptide molecule having a specific customized or desired glycosylation pattern, preferably including the addition of a modified sugar thereto. A key feature of the invention therefore is to take a peptide produced by any cell type and generate a core glycan structure on the peptide, following which the glycan structure is then remodeled in vitro to generate a peptide having a glycosylation pattern suitable for therapeutic use in a mammal.

The importance of the glycosylation pattern of a peptide is well known in the art as are the limitations of present in vivo methods for the production of properly glycosylated peptides, particularly when these peptides are produced using recombinant DNA methodology. Moreover, until the present invention, it has not been possible to generate glycopeptides having a desired glycan structure thereon, wherein the peptide can be produced at industrial scale.

In the present invention, a peptide produced by a cell is enzymatically treated in vitro by the systematic addition of the appropriate enzymes and substrates therefor, such that sugar moieties that should not be present on the peptide are removed, and sugar moieties, optionally including modified sugars, that should be added to the peptide are added in a manner to provide a glycopeptide having "desired glycosylation", as defined elsewhere herein.

A. Method to Remodel N-Linked Glycans

Figure 1:
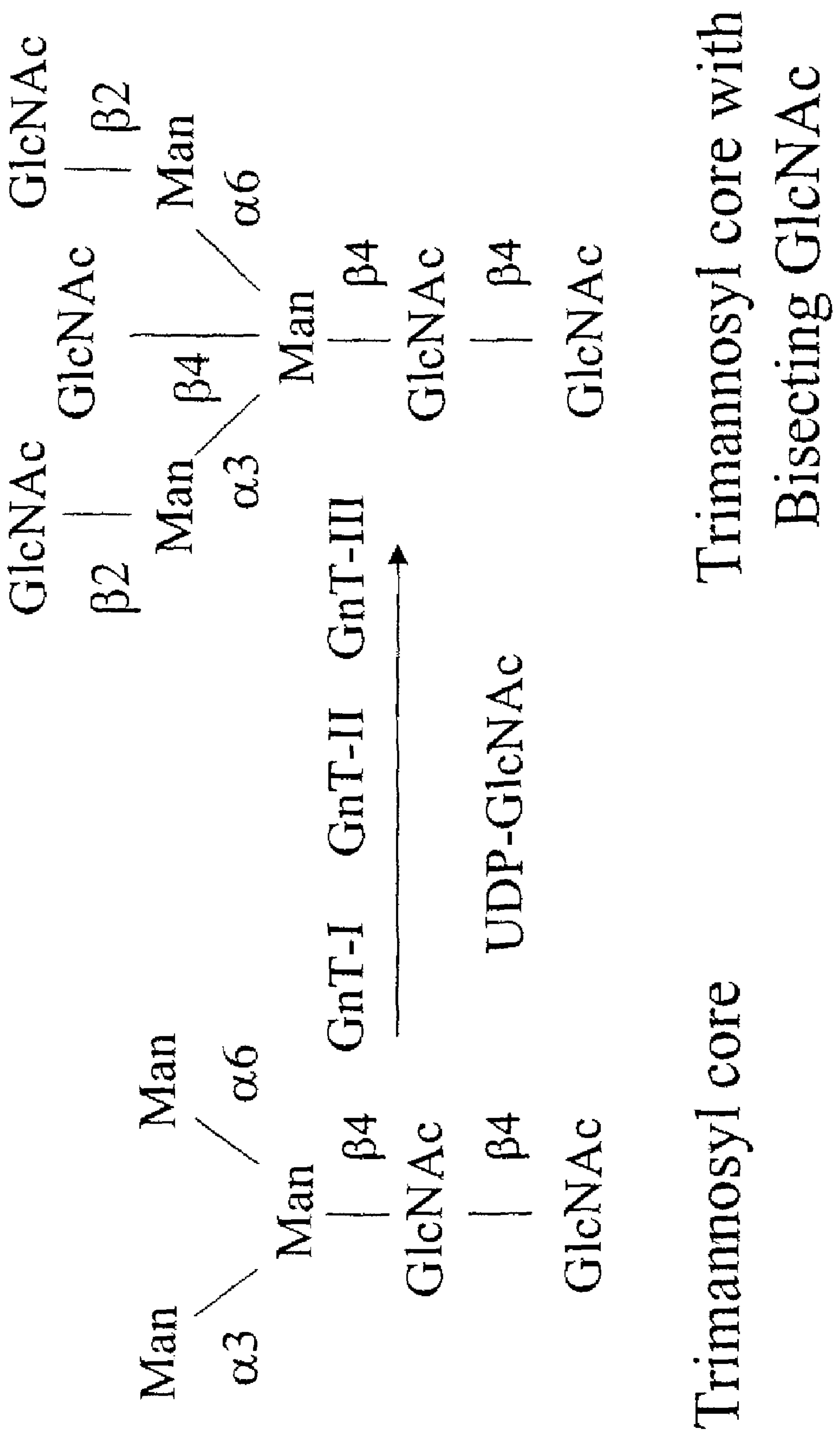
FIG. 1 is a scheme depicting a trimannosyl core glycan (left side) and the enzymatic process for the generation of a glycan having a bisecting GlcNAc (right side).

In one aspect, the present invention takes advantage of the fact that most peptides of commercial or pharmaceutical interest comprise a common five sugar structure referred to herein as the trimannosyl core, which is N-linked to asparagine at the sequence Asn-X-Ser/Thr on a peptide chain. The elemental trimannosyl core consists essentially of two N-acetylglucosamine (GlcNAc) residues and three mannose (Man) residues attached to a peptide, i.e., it comprises these five sugar residues and no additional sugars, except that it may optionally include a fucose residue. The first GlcNAc is attached to the amide group of the asparagine and the second GlcNAc is attached to the first via a β1,4 linkage. A mannose residue is attached to the second GlcNAc via a β1,4 linkage and two mannose residues are attached to this mannose via an α1,3 and an α1,6 linkage respectively. A schematic depiction of a trimannosyl core structure is shown in FIG. 1, left side. While it is the case that glycan structures on most peptides comprise other sugars in addition to the trimannosyl core, the trimannosyl core structure represents an essential feature of N-linked glycans on mammalian peptides.

The present invention includes the generation of a peptide having a trimannosyl core structure as a fundamental element of the structure of the glycan molecules contained thereon. Given the variety of cellular systems used to produce peptides, whether the systems are themselves naturally occurring or whether they involve recombinant DNA methodology, the present invention provides methods whereby a glycan molecule on a peptide produced in any cell type can be reduced to an elemental trimannosyl core structure. Once the elemental trimannosyl core structure has been generated then it is possible using the methods described herein, to generate in vitro, a desired glycan structure on the peptide which confers on the peptide one or more properties that enhances the therapeutic effectiveness of the peptide.

It should be clear from the discussion herein that the term "trimannosyl core" is used to describe the glycan structure shown in FIG. 1, left side. Glycopeptides having a trimannosyl core structure may also have additional sugars added thereto, and for the most part, do have additional structures added thereto irrespective of whether the sugars give rise to a peptide having a desired glycan structure. The term "elemental trimannosyl core structure" is defined elsewhere herein. When the term "elemental" is not included in the description of the "trimannosyl core structure," then the glycan comprises the trimannosyl core structure with additional sugars attached to the mannose sugars.

The term "elemental trimannosyl core glycopeptide" is used herein to refer to a glycopeptide having glycan structures comprised primarily of an elemental trimannosyl core structure. However, it may also optionally contain a fucose residue attached thereto. As discussed herein, elemental trimannosyl core glycopeptides are one optimal, and therefore preferred, starting material for the glycan remodeling processes of the invention.

Figure 2:
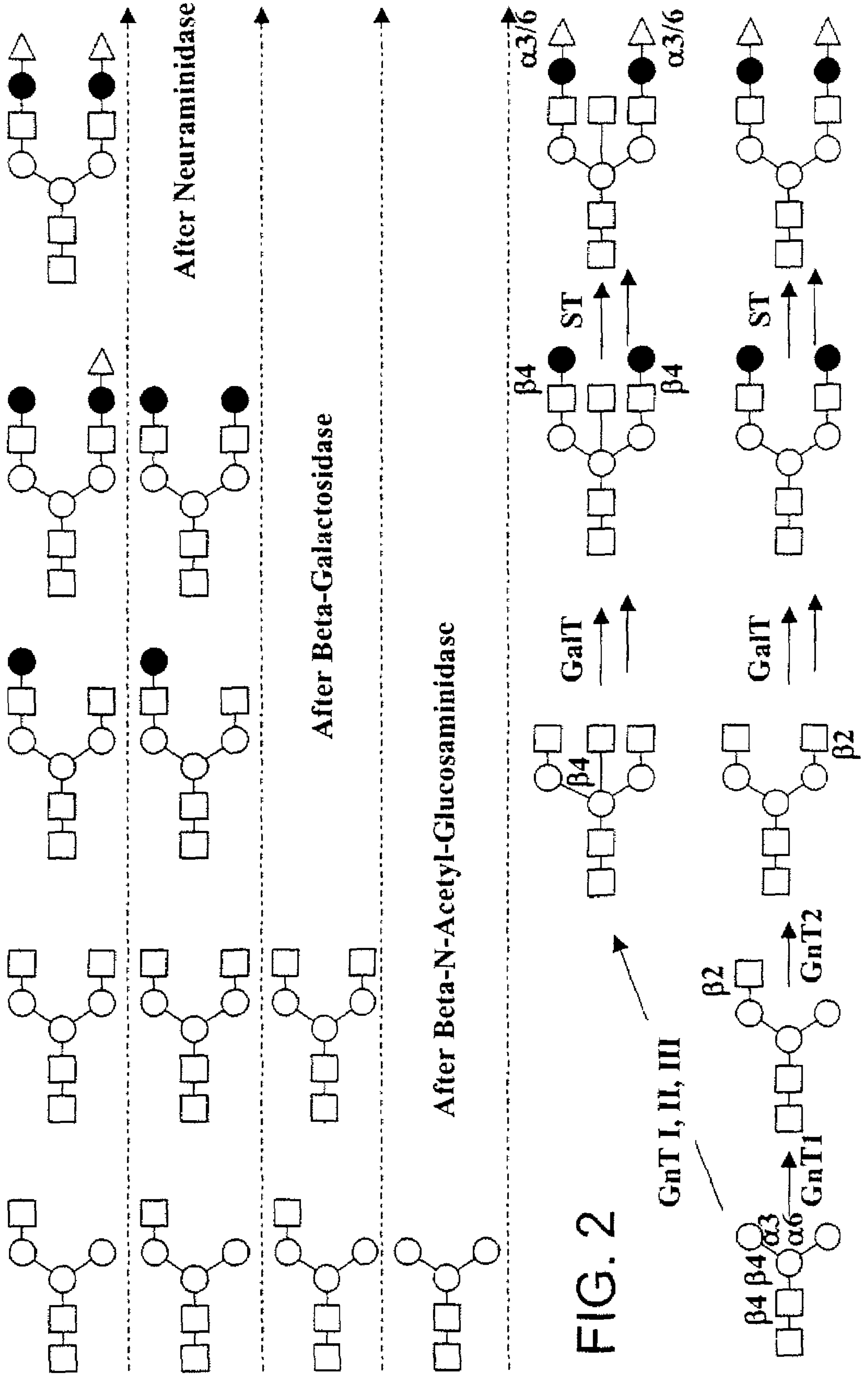
FIG. 2 is a scheme depicting an elemental trimannosyl core structure and complex chains in various degrees of completion. The in vitro enzymatic generation of an elemental trimannosyl core structure from a complex carbohydrate glycan structure which does not contain a bisecting GlcNAc residue is shown, as is the generation of a glycan structure therefrom which contains a bisecting GlcNAc. Symbols: squares: GlcNAc; light circles: Man; dark circles: Gal; triangles: NeuAc.

Another optimal starting material for the glycan remodeling process of the invention is a glycan structure having a trimannosyl core wherein one or two additional GlcNAc residues are added to each of the α1,3 and the α1,6 mannose residues (see for example, the structure on the second line of FIG. 2, second structure in from the left of the figure). This structure is referred to herein as "Man3GlcNAc4." When the structure is monoantenary, the structure is referred to herein as "Man3GlcNAc3." Optionally, this structure may also contain a core fucose molecule. Once the Man3GlcNAc3 or Man3GlcNAc4 structure has been generated then it is possible using the methods described herein, to generate in vitro, a desired glycan structure on the glycopeptide which confers on the glycopeptide one or more properties that enhances the therapeutic effectiveness of the peptide.

In their native form, the N-linked glycopeptides of the invention, and particularly the mammalian and human glycopeptides useful in the present invention, are N-linked glycosylated with a trimannosyl core structure and one or more sugars attached thereto.

The terms "glycopeptide" and "glycopolypeptide" are used synonymously herein to refer to peptide chains having sugar moieties attached thereto. No distinction is made herein to differentiate small glycopolypeptides or glycopeptides from large glycopolypeptides or glycopeptides. Thus, hormone molecules having very few amino acids in their peptide chain (e.g., often as few as three amino acids) and other much larger peptides are included in the general terms "glycopolypeptide" and "glycopeptide," provided they have sugar moieties attached thereto. However, the use of the term "peptide" does not preclude that peptide from being a glycopeptide.

An example of an N-linked glycopeptide having desired glycosylation is a peptide having an N-linked glycan having a trimannosyl core with at least one GlcNAc residue attached thereto. This residue is added to the trimannosyl core using N-acetyl glucosaminyltransferase I (GnT-I). If a second GlcNAc residue is added, N-acetyl glucosaminyltransferase II (GnT-II) is used. Optionally, additional GlcNAc residues may be added with GnT-IV and/or GnT-V, and a third bisecting GlcNAc residue may be attached to the β1,4 mannose of the trimannosyl core using N-acetyl glucosaminyltransferase III (GnT-III). Optionally, this structure may be extended by treatment with β1,4 galactosyltransferase to add a galactose residue to each non-bisecting GlcNAc, and even further optionally, using α2,3 or α2,6-sialyltransferase enzymes, sialic acid residues may be added to each galactose residue. The addition of a bisecting GlcNAc to the glycan is not required for the subsequent addition of galactose and sialic acid residues; however, with respect to the substrate affinity of the rat and human GnT-III enzymes, the presence of one or more of the galactose residues on the glycan precludes the addition of the bisecting GlcNAc in that the galactose-containing glycan is not a substrate for these forms of GnT-III. Thus, in instances where the presence of the bisecting GlcNAc is desired and these forms of GnT-III are used, it is important should the glycan contain added galactose and/or sialic residues, that they are removed prior to the addition of the bisecting GlcNAc. Other forms of GnT-III may not require this specific order of substrates for their activity. In the more preferred reaction, a mixture of GnT-I, GnT-II and GnT-III is added to the reaction mixture so that the GlcNAc residues can be added in any order.

Examples of glycan structures which represent the various aspects of peptides having "desired glycosylation" are shown in the drawings provided herein. The precise procedures for the in vitro generation of a peptide having "desired glycosylation" are described elsewhere herein. However, the invention should in no way be construed to be limited solely to any one glycan structure disclosed herein. Rather, the invention should be construed to include any and all glycan structures which can be made using the methodology provided herein.

In some cases, an elemental trimannosyl core alone may constitute the desired glycosylation of a peptide. For example, a peptide having only a trimannosyl core has been shown to be a useful component of an enzyme employed to treat Gaucher disease (Mistry et al., 1966, Lancet 348: 1555-1559; Bijsterbosch et al., 1996, Eur. J. Biochem. 237:344-349).

According to the present invention, the following procedures for the generation of peptides having desired glycosylation become apparent.

a) Beginning with a glycopeptide having one or more glycan molecules which have as a common feature a trimannosyl core structure and at least one or more of a heterogeneous or homogeneous mixture of one or more sugars added thereto, it is possible to increase the proportion of glycopeptides having an elemental trimannosyl core structure as the sole glycan structure or which have Man3GlcNAc3 or Man3GlcNAc4 as the sole glycan structure. This is accomplished in vitro by the systematic addition to the glycopeptide of an appropriate number of enzymes in an appropriate sequence which cleave the heterogeneous or homogeneous mixture of sugars on the glycan structure until it is reduced to an elemental trimannosyl core or Man3GlcNAc3 or Man3GlcNAc4 structure. Specific examples of how this is accomplished will depend on a variety of factors including in large part the type of cell in which the peptide is produced and therefore the degree of complexity of the glycan structure(s) present on the peptide initially produced by the cell. Examples of how a complex glycan structure can be reduced to an elemental trimannosyl core or a Man3GlcNAc3 or Man3GlcNAc4 structure are presented in FIG. 2 or are described in detail elsewhere herein.

b) It is possible to generate a peptide having an elemental trimannosyl core structure as the sole glycan structure on the peptide by isolating a naturally occurring cell whose glycosylation machinery produces such a peptide. DNA encoding a peptide of choice is then transfected into the cell wherein the DNA is transcribed, translated and glycosylated such that the peptide of choice has an elemental trimannosyl core structure as the sole glycan structure thereon. For example, a cell lacking a functional GnT-I enzyme will produce several types of glycopeptides. In some instances, these will be glycopeptides having no additional sugars attached to the trimannosyl core. However, in other instances, the peptides produced may have two additional mannose residues attached to the trimannosyl core, resulting in a Man5 glycan. This is also a desired starting material for the remodeling process of the present invention. Specific examples of the generation of such glycan structures are described herein.

c) Alternatively, it is possible to genetically engineer a cell to confer upon it a specific glycosylation machinery such that a peptide having an elemental trimannosyl core or Man3GlcNAc3 or Man3GlcNAc4 structure as the sole glycan structure on the peptide is produced. DNA encoding a peptide of choice is then transfected into the cell wherein the DNA is transcribed, translated and glycosylated such that the peptide of choice has an increased number of glycans comprising solely an elemental trimannosyl core structure. For example, certain types of cells that are genetically engineered to lack GnT-I, may produce a glycan having an elemental trimannosyl core structure, or, depending on the cell, may produce a glycan having a trimannosyl core plus two additional mannose residues attached thereto (Man5). When the cell produces a Man5 glycan structure, the cell may be further genetically engineered to express mannosidase 3 which cleaves off the two additional mannose residues to generate the trimannosyl core. Alternatively, the Man5 glycan may be incubated in vitro with mannosidase 3 to have the same effect.

d) When a peptide is expressed in an insect cell, the glycan on the peptide comprises a partially complex chain. Insect cells also express hexosaminidase in the cells which trims the partially complex chain back to a trimannosyl core structure which can then be remodeled as described herein.

e) It is readily apparent from the discussion in b), c) and d) that it is not necessary that the cells produce only peptides having elemental trimannosyl core or Man3GlcNAc3 or Man3GlcNAc4 structures attached thereto. Rather, unless the cells described in b) and c) produce peptides having 100% elemental trimannosyl core structures (i.e., having no additional sugars attached thereto) or 100% of Man3GlcNAc3 or Man3GlcNAc4 structures, the cells in fact produce a heterogeneous mixture of peptides having, in combination, elemental trimannosyl core structures, or Man3GlcNAc3 or Man3GlcNAc4 structures, as the sole glycan structure in addition to these structures having additional sugars attached thereto. The proportion of peptides having a trimannosyl core or Man3GlcNAc3 or Man3GlcNAc4 structures having additional sugars attached thereto, as opposed to those having one structure, will vary depending on the cell which produces them. The complexity of the glycans (i.e. which and how many sugars are attached to the trimannosyl core) will also vary depending on the cell which produces them.

f) Once a glycopeptide having an elemental trimannosyl core or a trimannosyl core with one or two GlcNAc residues attached thereto is produced by following a), b) or c) above, according to the present invention, additional sugar molecules are added in vitro to the trimannosyl core structure to generate a peptide having desired glycosylation (i.e., a peptide having an in vitro customized glycan structure).

g) However, when it is the case that a peptide having an elemental trimannosyl core or Man3GlcNAc4 structure with some but not all of the desired sugars attached thereto is produced, then it is only necessary to add any remaining desired sugars without reducing the glycan structure to the elemental trimannosyl core or Man3GlcNAc4 structure. Therefore, in some cases, a peptide having a glycan structure having a trimannosyl core structure with additional sugars attached thereto, will be a suitable substrate for remodeling.

Isolation of an Elemental Trimannosyl Core Glycopeptide

The elemental trimannosyl core or Man3GlcNAc3 or Man3GlcNAc4 glycopeptides of the invention may be isolated and purified, if necessary, using techniques well known in the art of peptide purification. Suitable techniques include chromatographic techniques, isoelectric focusing techniques, ultrafiltration techniques and the like. Using any such techniques, a composition of the invention can be prepared in which the glycopeptides of the invention are isolated from other peptides and from other components normally found within cell culture media. The degree of purification can be, for example, 90% with respect to other peptides or 95%, or even higher, e.g., 98%. See, e.g., Deutscher et al. (ed., 1990, Guide to Protein Purification, Harcourt Brace Jovanovich, San Diego).

The heterogeneity of N-linked glycans present in the glycopeptides produced by the prior art methodology generally only permits the isolation of a small portion of the target glycopeptides which can be modified to produce desired glycopeptides. In the present methods, large quantities of elemental trimannosyl core glycopeptides and other desired glycopeptides, including Man3GlcNAc3 or Man3GlcNAc4 glycans, can be produced which can then be further modified to generate large quantities of peptides having desired glycosylation.

Specific enrichment of any particular type of glycan linked to a peptide may be accomplished using lectins which have an affinity for the desired glycan. Such techniques are well known in the art of glycobiology.

A key feature of the invention which is described in more detail below, is that once a core glycan structure is generated on any peptide, the glycan structure is then remodeled in vitro to generate a peptide having desired glycosylation that has improved therapeutic use in a mammal. The mammal may be any type of suitable mammal, and is preferably a human.

The various scenarios and the precise methods and compositions for generating peptides with desired glycosylation will become evident from the disclosure which follows.

The ultimate objective of the production of peptides for therapeutic use in mammals is that the peptides should comprise glycan structures that facilitate rather than negate the therapeutic benefit of the peptide. As disclosed throughout the present specification, peptides produced in cells may be treated in vitro with a variety of enzymes which catalyze the cleavage of sugars that should not be present on the glycan and the addition of sugars which should be present on the glycan such that a peptide having desired glycosylation and thus suitable for therapeutic use in mammals is generated. The generation of different glycoforms of peptides in cells is described above. A variety of mechanisms for the generation of peptides having desired glycosylation is now described, where the starting material i.e., the peptide produced by a cell may differ from one cell type to another. As will become apparent from the present disclosure, it is not necessary that the starting material be uniform with respect to its glycan composition. However, it is preferable that the starting material be enriched for certain glycoforms in order that large quantities of end product, i.e., correctly glycosylated peptides are produced.

In a preferred embodiment according to the present invention, the degradation and synthesis events that result in a peptide having desired glycosylation involve at some point, the generation of an elemental trimannosyl core structure or a Man3GlcNAc3 or Man3GlcNAc4 structure on the peptide.

The present invention also provides means of adding one or more selected glycosyl residues to a peptide, after which a modified sugar is conjugated to at least one of the selected glycosyl residues of the peptide. The present embodiment is useful, for example, when it is desired to conjugate the modified sugar to a selected glycosyl residue that is either not present on a peptide or is not present in a desired amount. Thus, prior to coupling a modified sugar to a peptide, the selected glycosyl residue is conjugated to the peptide by enzymatic or chemical coupling. In another embodiment, the glycosylation pattern of a peptide is altered prior to the conjugation of the modified sugar by the removal of a carbohydrate residue from the peptide. See for example WO 98/31826.

Addition or removal of any carbohydrate moieties present on the peptide is accomplished either chemically or enzymatically. Chemical deglycosylation is preferably brought about by exposure of the peptide variant to the compound trifluoromethanesulfonic acid, or an equivalent compound. This treatment results in the cleavage of most or all sugars except the linking sugar (N-acetylglucosamine or N-acetylgalactosamine), while leaving the peptide intact. Chemical deglycosylation is described by Hakimuddin et al., 1987, Arch. Biochem. Biophys. 259: 52 and by Edge et al., 1981, Anal. Biochem. 118: 131. Enzymatic cleavage of carbohydrate moieties on peptide variants can be achieved by the use of a variety of endo- and exo-glycosidases as described by Thotakura et al., 1987, Meth. Enzymol. 138: 350.

Chemical addition of glycosyl moieties is carried out by any art-recognized method. Enzymatic addition of sugar moieties is preferably achieved using a modification of the methods set forth herein, substituting native glycosyl units for the modified sugars used in the invention. Other methods of adding sugar moieties are disclosed in U.S. Pat. Nos. 5,876,980, 6,030,815, 5,728,554, and 5,922,577.

Exemplary attachment points for selected glycosyl residue include, but are not limited to: (a) sites for N- and O-glycosylation; (b) terminal glycosyl moieties that are acceptors for a glycosyltransferase; (c) arginine, asparagine and histidine; (d) free carboxyl groups; (e) free sulfhydryl groups such as those of cysteine; (f) free hydroxyl groups such as those of serine, threonine, or hydroxyproline; (g) aromatic residues such as those of phenylalanine, tyrosine, or tryptophan; or (h) the amide group of glutamine. Exemplary methods of use in the present invention are described in WO 87/05330 published Sep. 11, 1987, and in Aplin and Wriston, CRC Crit. Rev. Biochem., pp. 259-306 (1981).

Dealing specifically with the examples shown in several of the figures provided herein, a description of the sequence of in vitro enzymatic reactions for the production of desired glycan structures on peptides is now presented. The precise reaction conditions for each of the enzymatic conversions disclosed below are well known to those skilled in the art of glycobiology and are therefore not repeated here. For a review of the reaction conditions for these types of reactions, see Sadler et al., 1982, Methods in Enzymology 83:458-514 and references cited therein.

In FIG. 1 there is shown the structure of an elemental trimannosyl core glycan on the left side. It is possible to convert this structure to a complete glycan structure having a bisecting GlcNAc by incubating the elemental trimannosyl core structure in the presence of GnT-I, followed by GnT-II, and further followed by GnT-III, and a sugar donor comprising UDP-GlcNAc, wherein GlcNAc is sequentially added to the elemental trimannosyl core structure to generate a trimannosyl core having a bisecting GlcNAc. In some instances, for example when remodeling Fc glycans as described herein, the order of addition of GnT-I, GnT-II and GnT-III may be contrary to that reported in the literature. The bisecting GlcNAc structure may be produced by adding a mixture of GnT-I, GnT-II and GnT-III and UDP-GlcNAc to the reaction mixture In FIG. 3 there is shown the conversion of a bisecting GlcNAc containing trimannosyl core glycan to a complex glycan structure comprising galactose and N-acetyl neuraminic acid. The bisecting GlcNAc containing trimannosyl core glycan is first incubated with galactosyltransferase and UDP-Gal as a donor molecule, wherein two galactose residues are added to the peripheral GlcNAc residues on the molecule. The enzyme NeuAc-transferase is then used to add two NeuAc residues one to each of the galactose residues.

Figure 3:
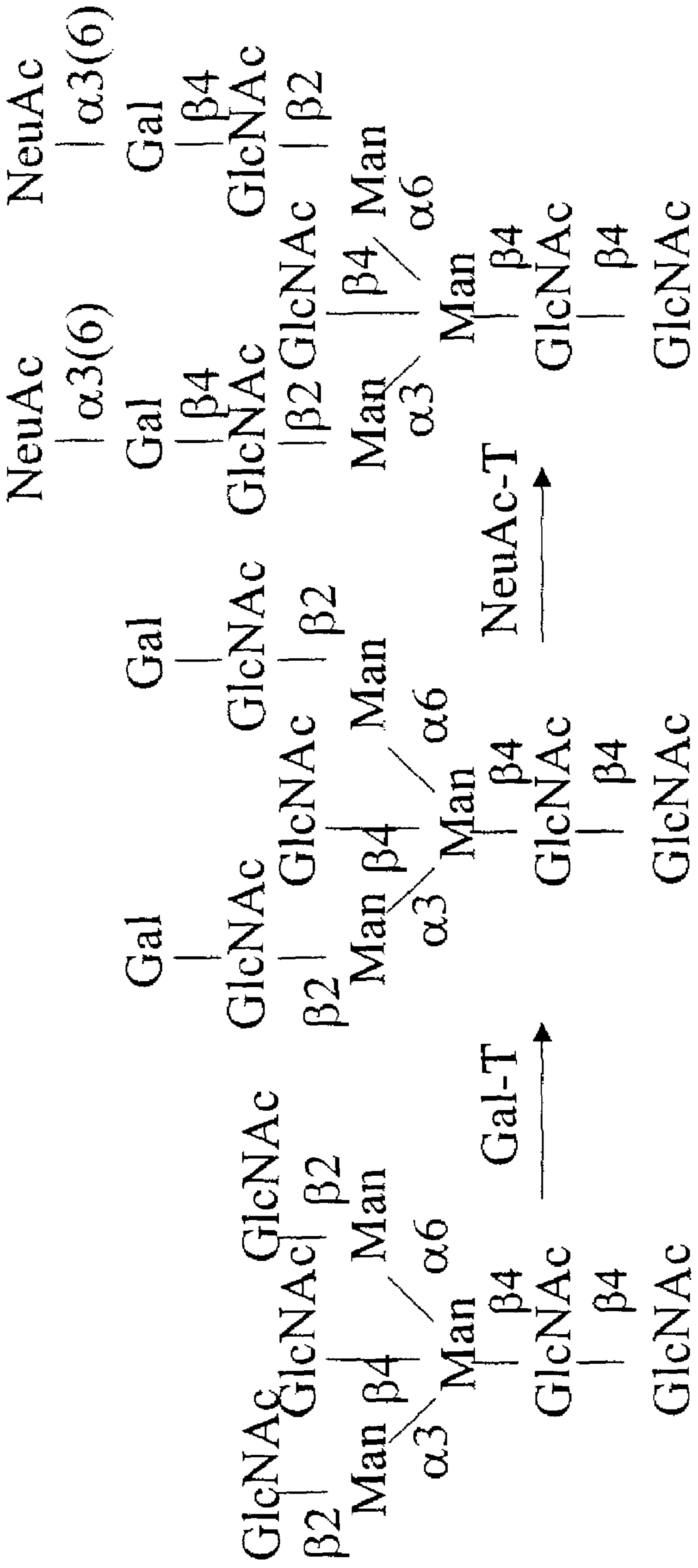
FIG. 3 is a scheme for the enzymatic generation of a sialylated glycan structure (right side) beginning with a glycan having a trimannosyl core and a bisecting GlcNAc (left side).
Figure 4:
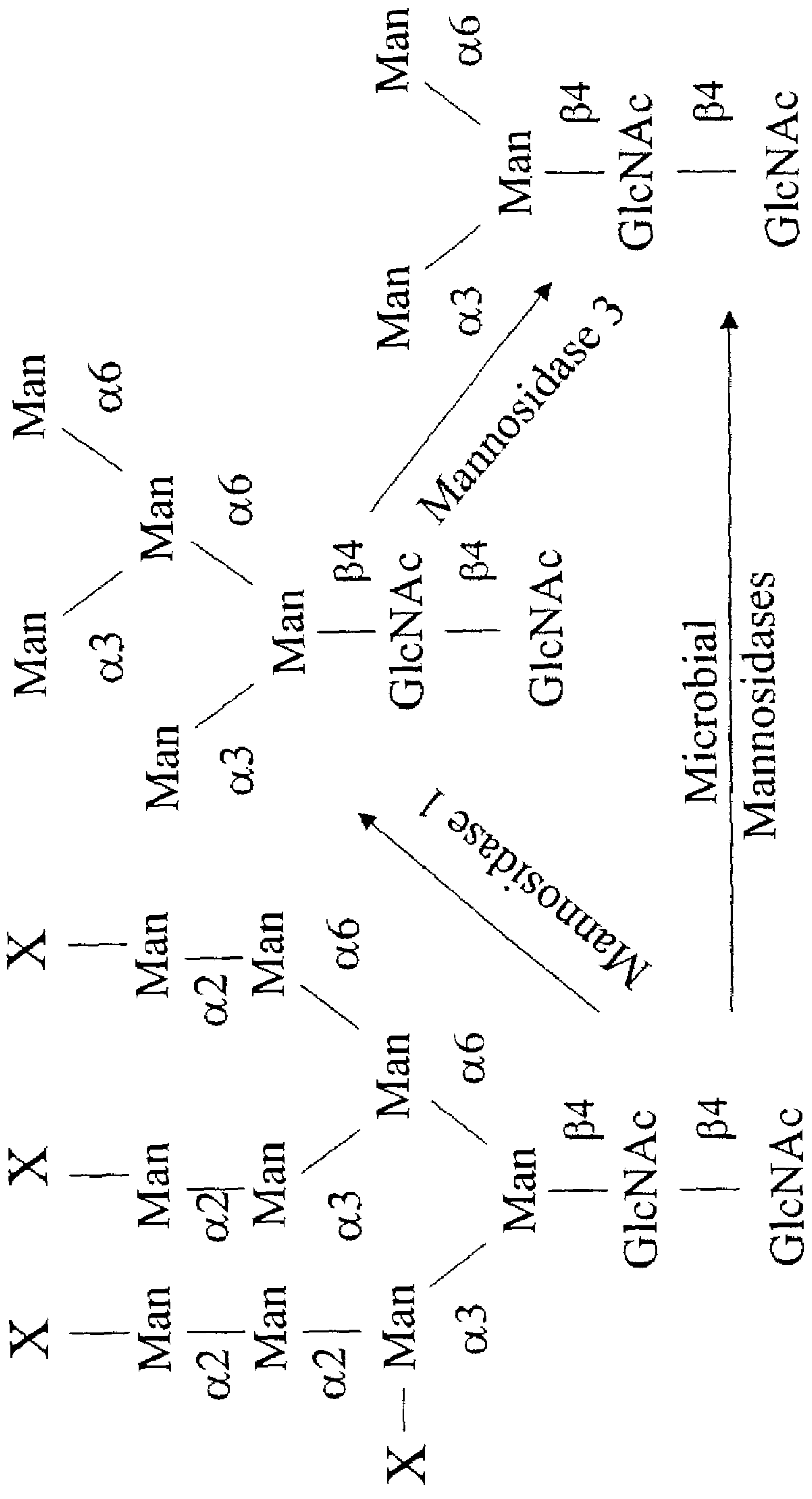
FIG. 4 is a scheme of a typical high mannose containing glycan structure (left side) and the enzymatic process for reduction of this structure to an elemental trimannosyl core structure. In this scheme, X is mannose as a monosaccharide, an oligosaccharide or a polysaccharide.

In FIG. 4 there is shown the conversion of a high mannose glycan structure to an elemental trimannosyl core glycan. The high mannose glycan (Man9) is incubated sequentially in the presence of the mannosidase 1 to generate a Man5 structure and then in the presence of mannosidase 3, wherein all but three mannose residues are removed from the glycan. Alternatively, incubation of the Man9 structure may be trimmed back to the trimannosyl core structure solely by incubation in the presence of mannosidase 3. According to the schemes presented in FIGS. 1 and 3 above, conversion of this elemental trimannosyl core glycan to a complex glycan molecule is then possible.

Figure 5:
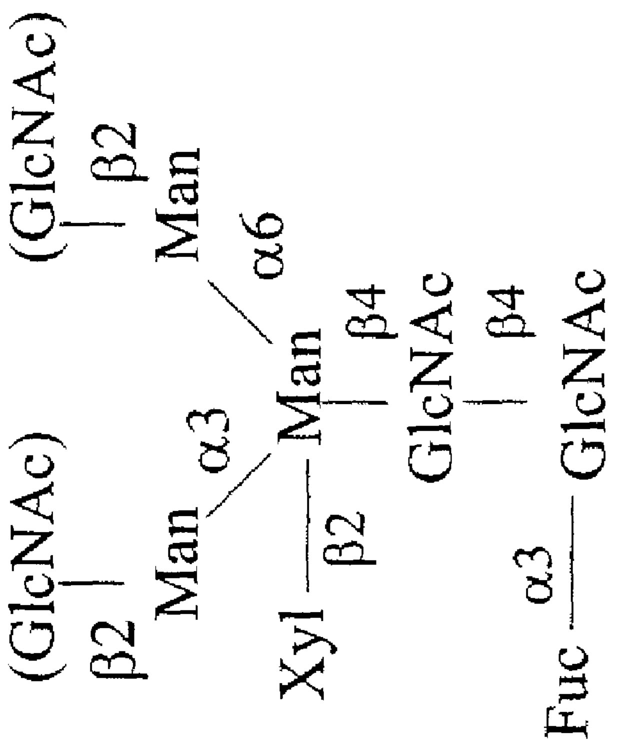
FIG. 5 is a diagram of a fucose and xylose containing N-linked glycan structure typically produced in plant cells.

In FIG. 5 there is shown a typical complex N-linked glycan structure produced in plant cells. It is important to note that when plant cells are deficient in GnT-I enzymatic activity, xylose and fucose cannot be added to the glycan. Thus, the use of GnT-I knock-out cells provides a particular advantage in the present invention in that these cells produce peptides having an elemental trimannosyl core onto which additional sugars can be added without performing any "trimming back" reactions. Similarly, in instances where the structure produced in a plant cell may be of the Man5 variety of glycan, if GnT-I is absent in these cells, xylose and fucose cannot be added to the structure. In this case, the Man5 structure may be trimmed back to an elemental trimannosyl core (Man3) using mannosidase 3. According to the methods provided herein, it is now possible to add desired sugar moieties to the trimannosyl core to generate a desired glycan structure.

Figure 6:
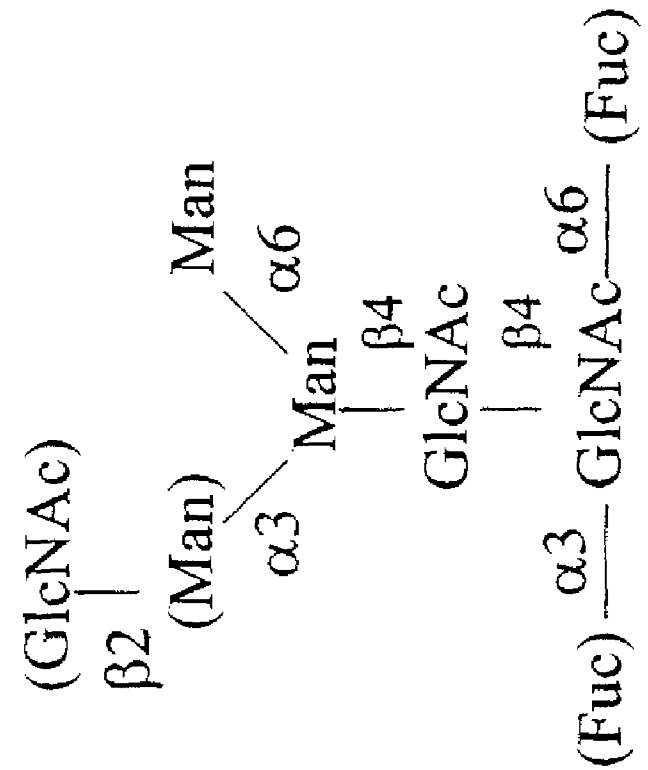
FIG. 6 is a diagram of a fucose containing N-linked glycan structure typically produced in insect cells. Note that the glycan may have no core fucose, it may have a single core fucose with either linkage, or it may have a single core fucose having a preponderance of one linkage.

In FIG. 6 there is shown a typical complex N-linked glycan structure produced in insect cells. As is evident, additional sugars, such as, for example, fucose may also be present. Further although not shown here, insect cells may produce high mannose glycans having as many as nine mannose residues and may have additional sugars attached thereto. It is also the case in insect cells that GnT-I knock out cells prevent the addition of fucose residues to the glycan. Thus, production of a peptide in insect cells may preferably be accomplished in a GnT-I knock out cell. The glycan thus produced may then be trimmed back in vitro if necessary using any of the methods and schemes described herein, and additional sugars may be added in vitro thereto also using the methods and schemes provided herein.

In FIG. 2 there is shown glycan structures in various stages of completion. Specifically, the in vitro enzymatic generation of an elemental trimannosyl core structure from a complex carbohydrate glycan structure which does not contain a bisecting GlcNAc residue is shown. Also shown is the generation of a glycan structure therefrom which contains a bisecting GlcNAc. Several intermediate glycan structures which can be produced are shown. These structures can be produced by cells, or can be produced in the in vitro trimming back reactions described herein. Sugar moieties may be added in vitro to the elemental trimannosyl core structure, or to any suitable intermediate structure in order that a desired glycan is produced.

Figure 7:
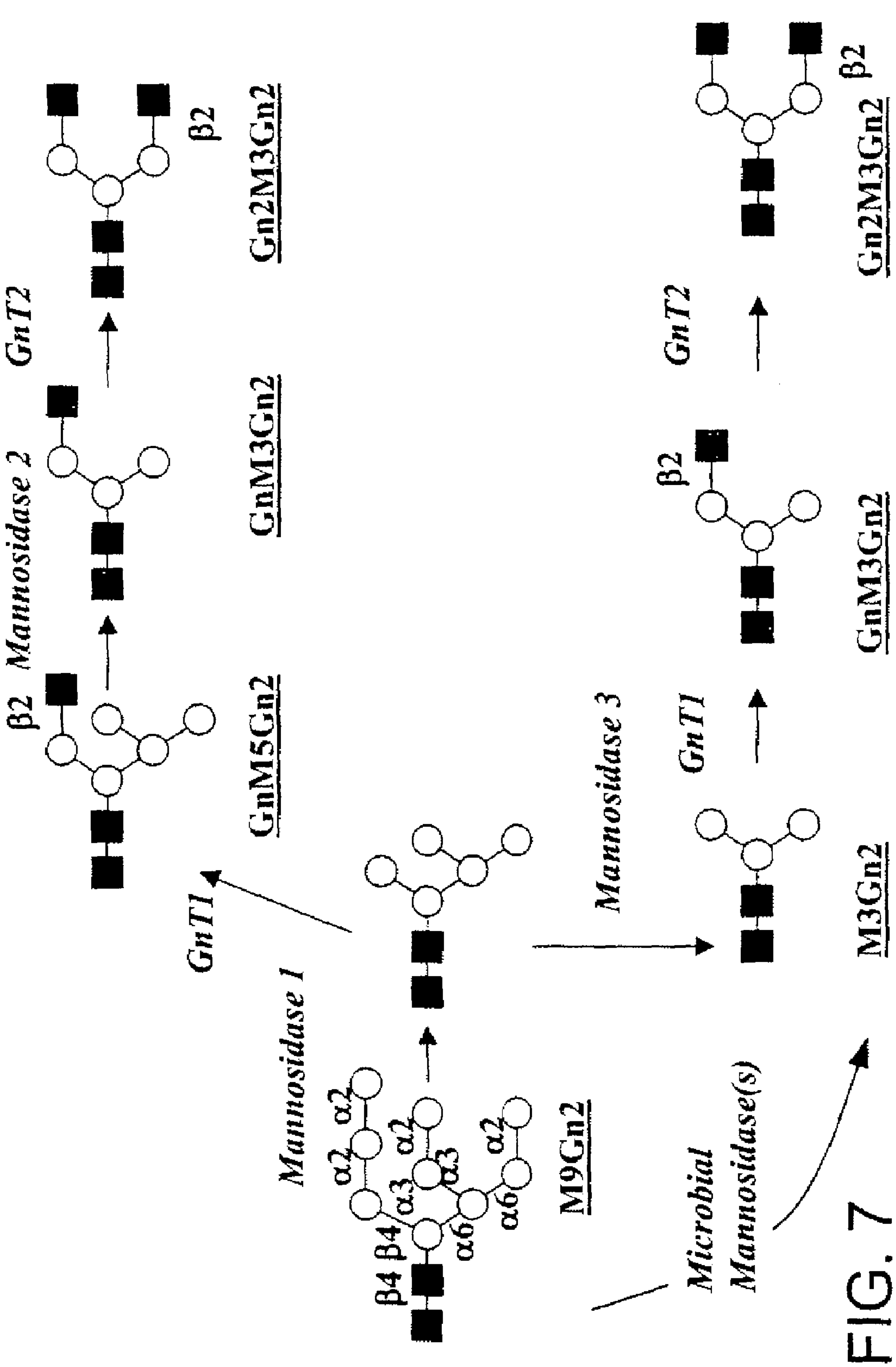
FIG. 7 is a scheme depicting a variety of pathways for the trimming of a high mannose structure and the synthesis of complex sugar chains therefrom. Symbols: squares: GlcNAc; circles: Man; diamonds: fucose; pentagon: xylose.

In FIG. 7 there is shown a series of possible in vitro reactions which can be performed to trim back and add onto glycans beginning with a high mannose structure. For example, a Man9 glycan may be trimmed using mannosidase 1 to generate a Man5 glycan, or it may be trimmed to a trimannosyl core using mannosidase 3 or one or more microbial mannosidases. GnT-I and or GnT-II may then be used to transfer additional GlcNAc residues onto the glycan. Further, there is shown the situation which would not occur when the glycan molecule is produced in a cell that does not have GnT-I (see shaded box). For example, fucose and xylose may be added to a glycan only when GnT-I is active and facilitates the transfer of a GlcNAc to the molecule.

Figure 8:
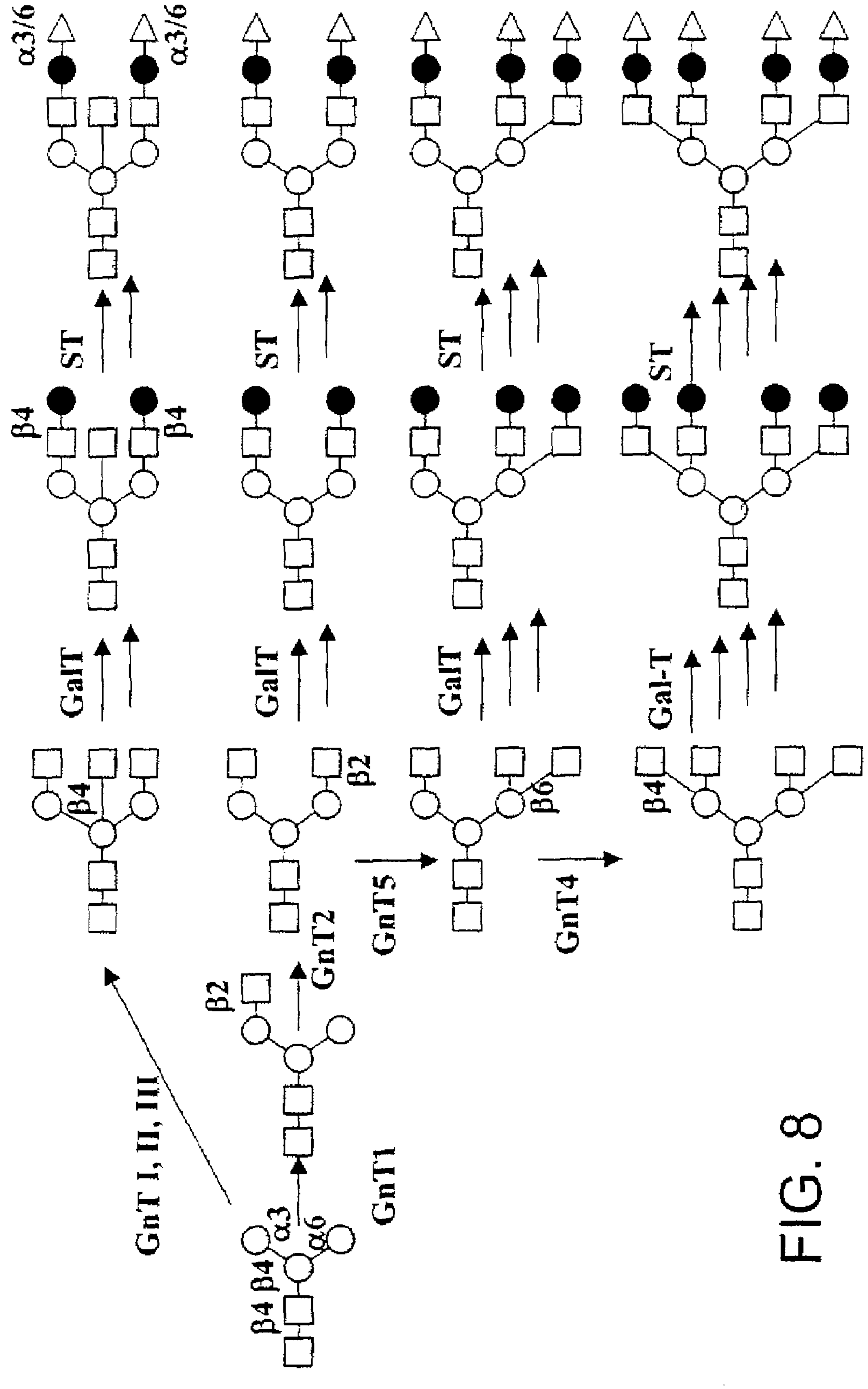
FIG. 8 is a scheme depicting in vitro strategies for the synthesis of complex structures from an elemental trimannosyl core structure. Symbols: Squares: GlcNAc; light circles: Man; dark circles: Gal; dark triangles: NeuAc; GnT: N-acetyl glucosaminyltransferase; GalT: galactosyltransferase; ST: sialyltransferase.

FIG. 8 depicts well known strategies for the synthesis of biantennary, triantennary and even tetraantennary glycan structures beginning with the trimannosyl core structure. According to the methods of the invention, it is possible to synthesize each of these structures in vitro using the appropriate enzymes and reaction conditions well known in the art of glycobiology.

Figure 9:
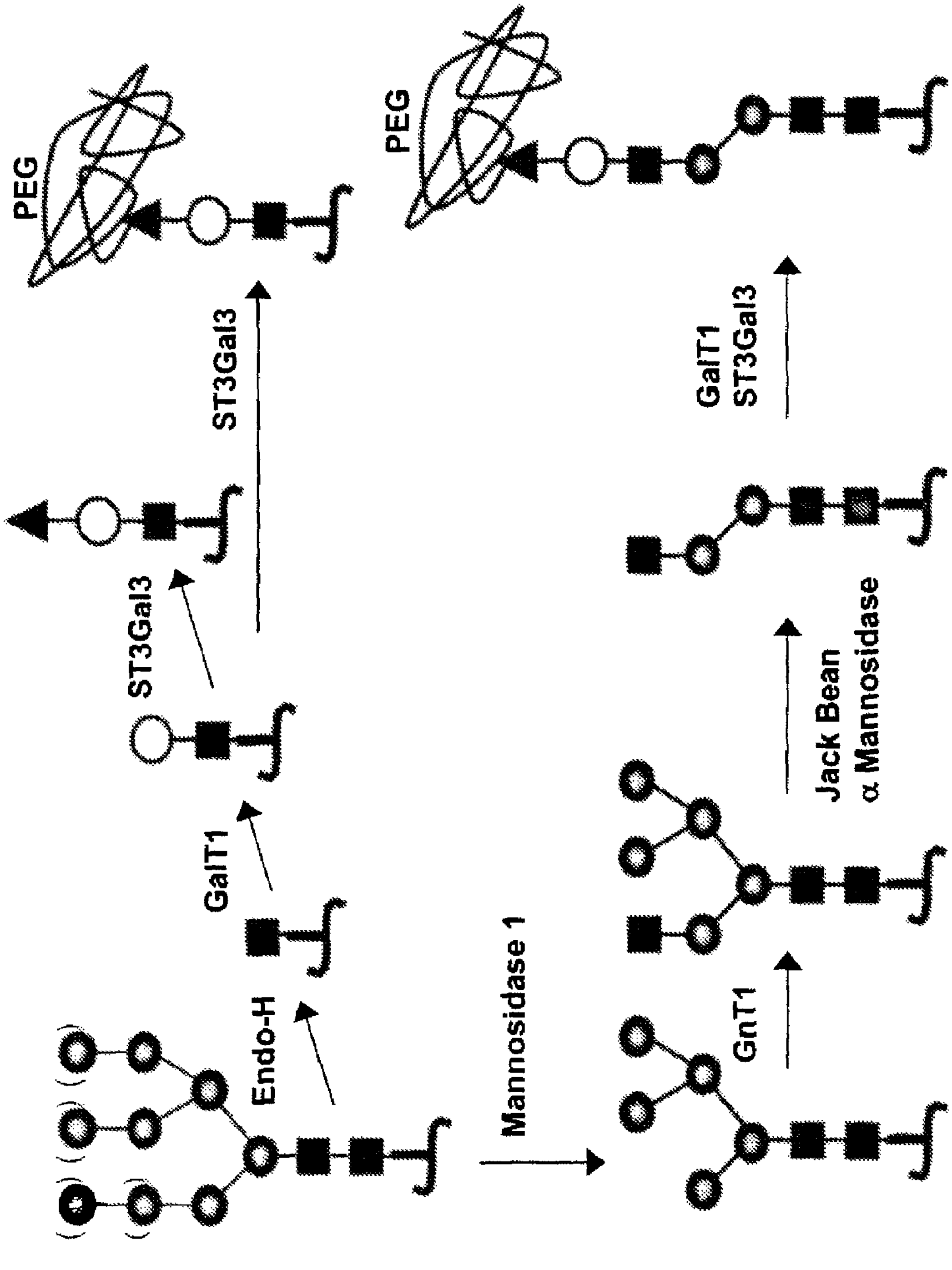
FIG. 9 is a scheme depicting two in vitro strategies for the synthesis of monoantennary glycans, and the optional glycoPEGylation of the same. Dark squares: GlcNAc; dark circles: Man; light circles: Gal; dark triangles: sialic acid.

FIG. 9 depicts two methods for synthesis of a monoantennary glycan structure beginning from a high mannose (6 to 9 mannose moieties) glycan structures. A terminal sialic acid-PEG moiety may be added in place of the sialic acid moiety in accordance with glycoPEGylation methodology described herein. In the first method, endo-His used to cleave the glycan structure on the peptide back to the first GlcNAc residue. Galactose is then added using galactosyltransferase and sialylated-PEG is added as described elsewhere herein. In the second method, mannosidase I is used to cleave mannose residues from the glycan structure in the peptide. A galactose residue is added to one arm of the remaining mannose residues which were cleaved off the glycan using Jack Bean α-mannosidase. Sialylated-PEG is then added to this structure as directed.

Figure 10:
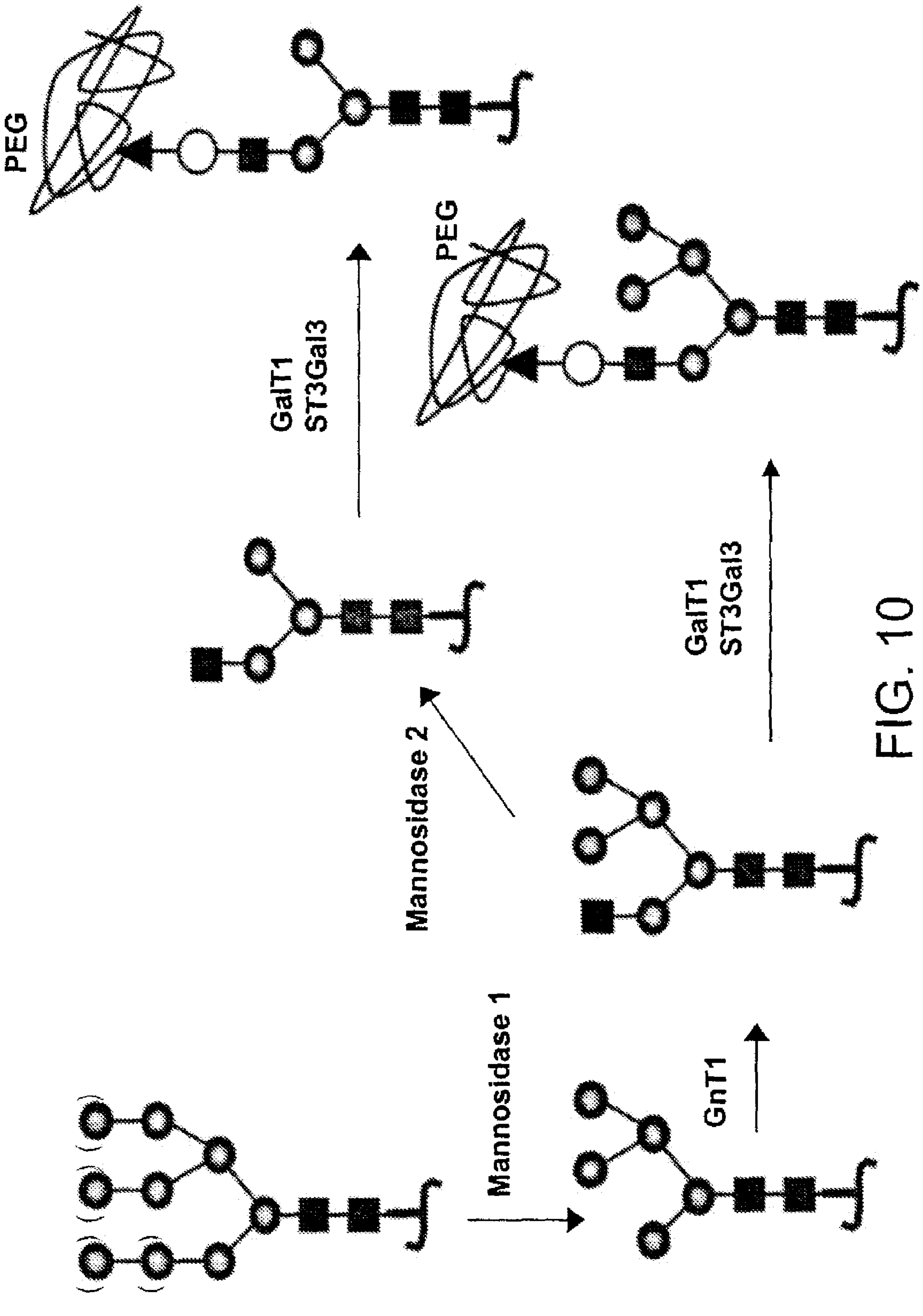
FIG. 10 is a scheme depicting two in vitro strategies for the synthesis of monoantennary glycans, and the optional glycoPEGylation of the same. Dark squares: GlcNAc; dark circles: Man; light circles: Gal; dark triangles: sialic acid.

FIG. 10 depicts two additional methods for synthesis of a monoantennary glycan structures beginning from high mannose (6 to 9 mannose moieties) glycan structure. As in FIG. 9, a terminal sialic acid-PEG moiety may be added in place of the sialic acid moiety in accordance with the glycoPEGylation methodology described herein. In the situation described here, some of the mannose residues from the arm to which sialylated-PEG is not added, are removed.

Figure 11:
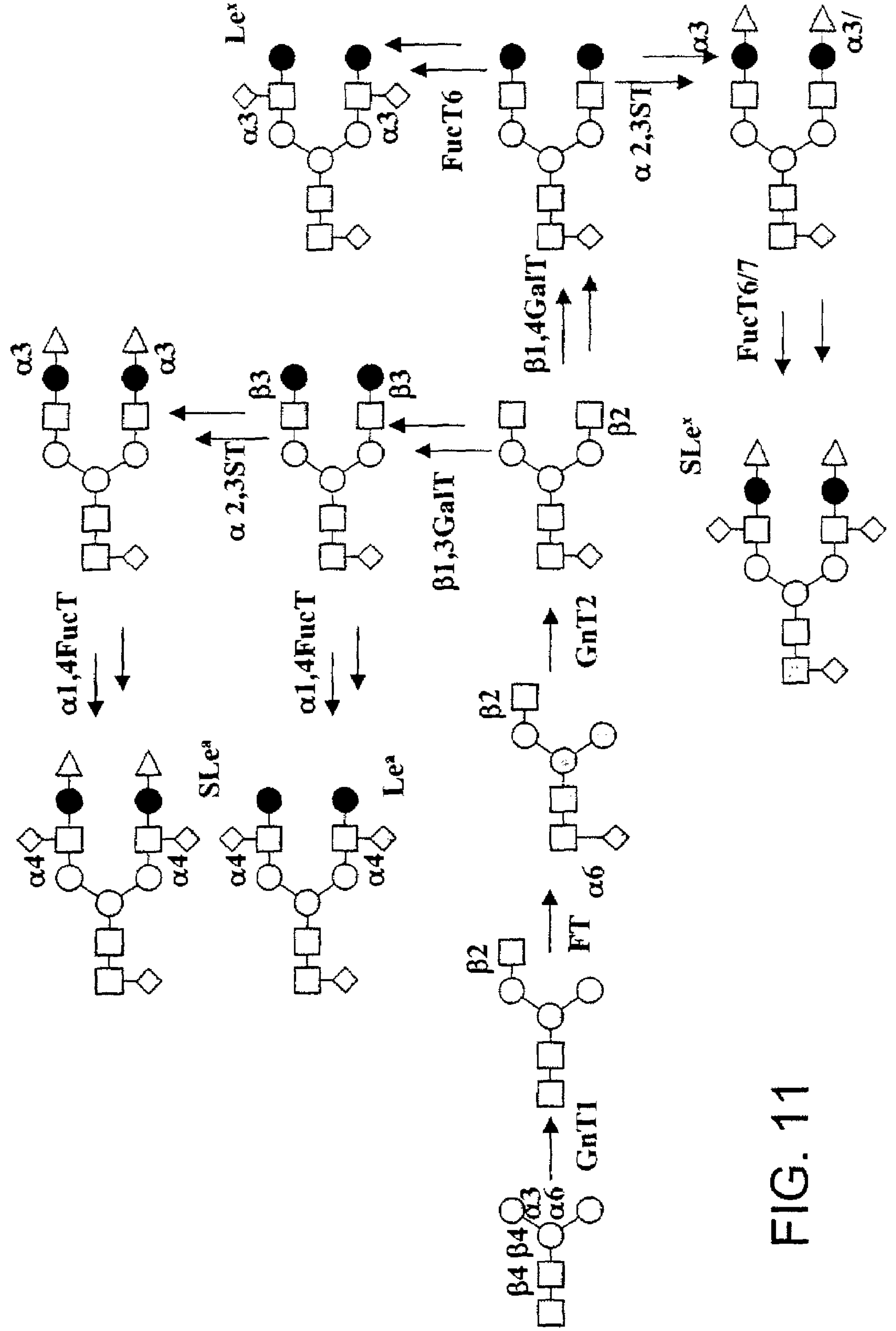
FIG. 11 is a scheme depicting various complex structures, which may be synthesized from an elemental trimannosyl core structure. Symbols: Squares: GlcNAc; light circles: Man; dark circles: Gal; triangles: NeuAc; diamonds: fucose; FT and FucT: fucosyltransferase; GalT: galactosyltransferase; ST: sialyltransferase; Le: Lewis antigen; SLe: sialylated Lewis antigen.

In FIG. 11 there is shown a scheme for the synthesis of yet more complex carbohydrate structures beginning with a trimannosyl core structure. For example, a scheme for the in vitro production of Lewis x and Lewis a antigen structures, which may or may not be sialylated is shown. Such structures when present on a peptide may confer on the peptide immunological advantages for upregulating or downregulating the immune response. In addition, such structures are useful for targeting the peptide to specific cells, in that these types of structures are involved in binding to cell adhesion peptides and the like.

Figure 12:
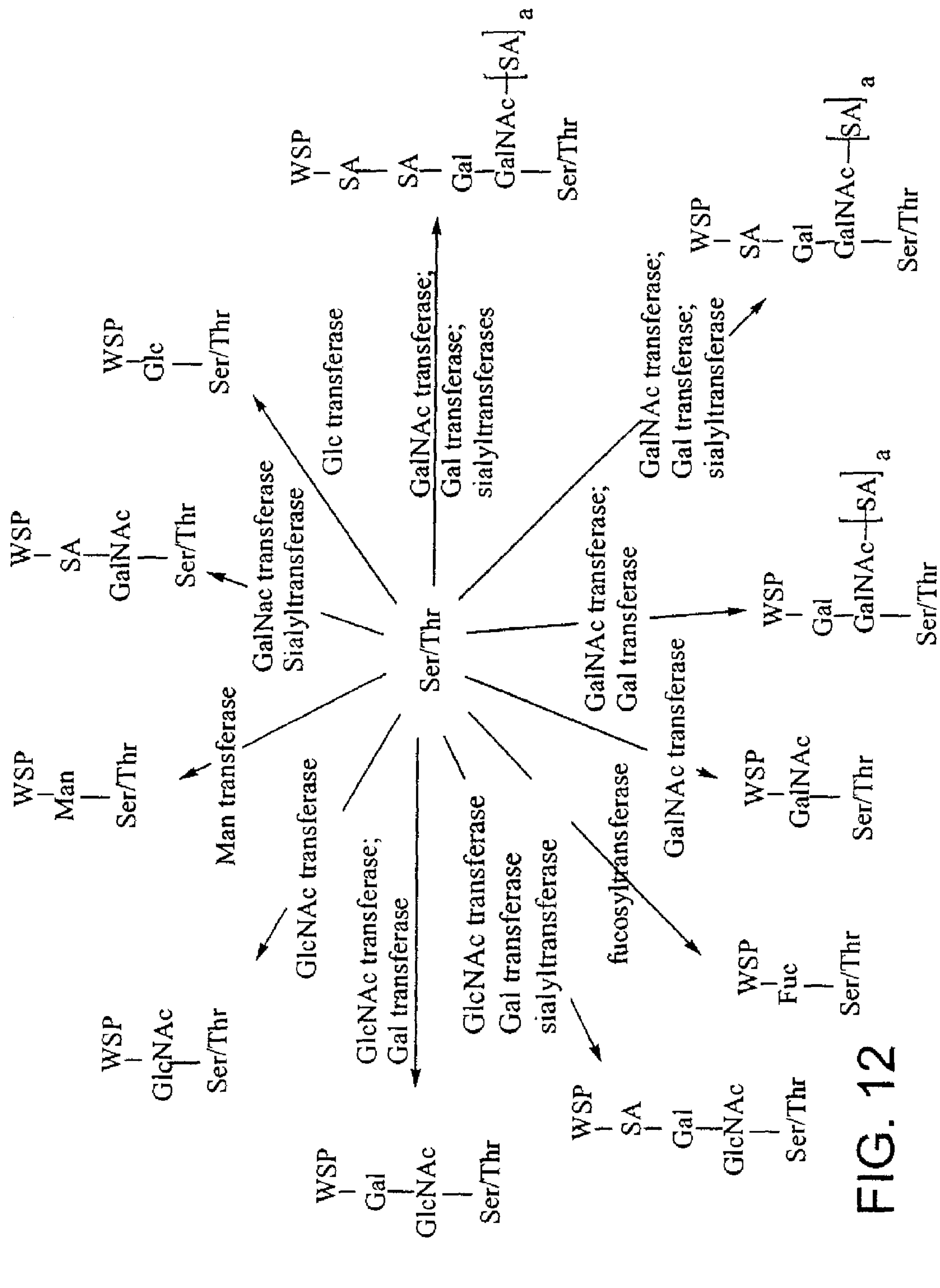
FIG. 12 is an exemplary scheme for preparing O-linked glycopeptides originating with serine or threonine. Optionally, a water soluble polymer (WSP) such as poly(ethylene glycol) is added to the final glycan structure.

FIG. 12 is an exemplary scheme for preparing an array of O-linked peptides originating with serine or threonine.

Figure 13:
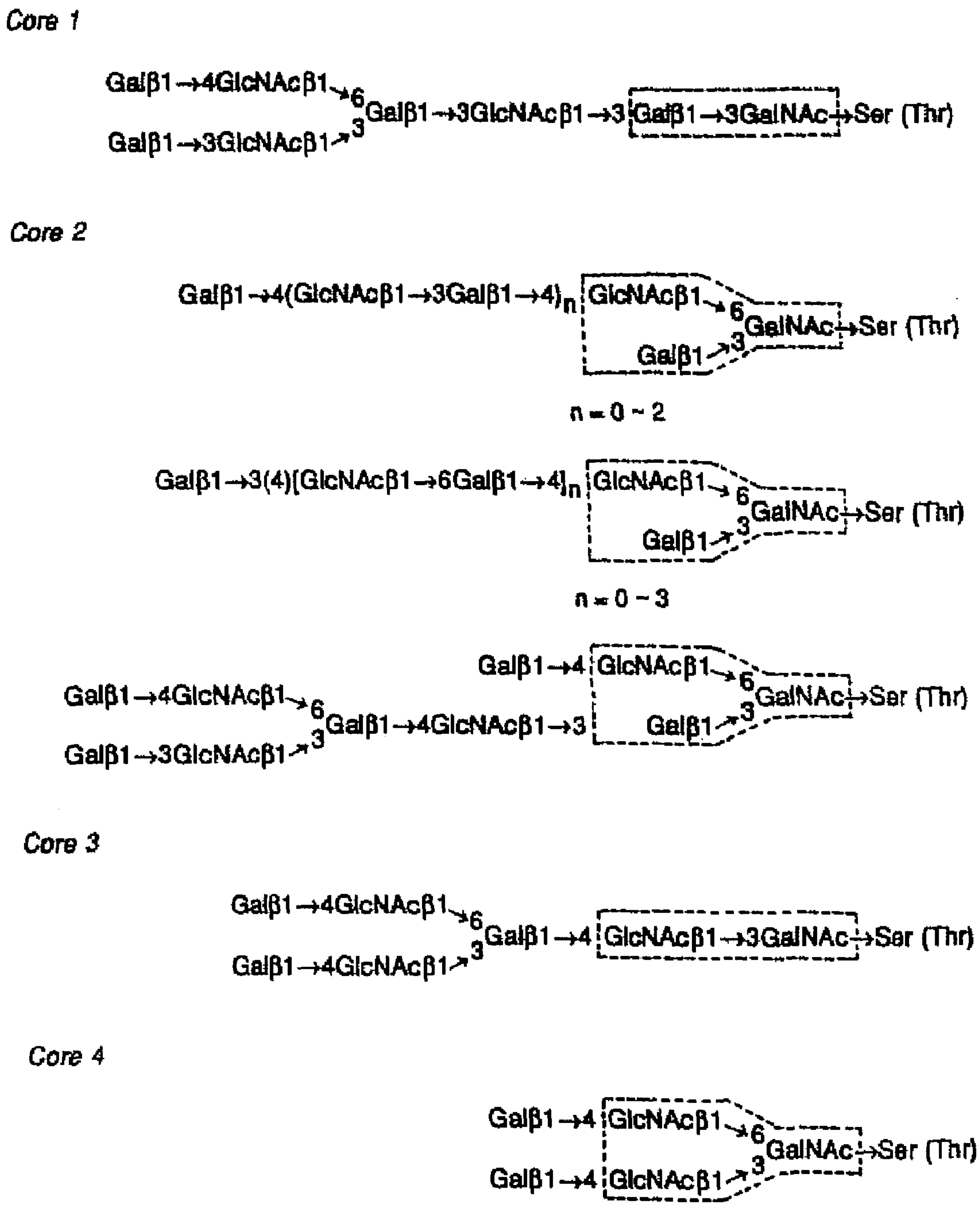
FIG. 13 is a series of diagrams depicting the four types of O-glycan structures, termed cores 1 through 4. The core structure is outlined in dotted lines.

FIG. 13 is a series of diagrams depicting the four types of O-linked glycan structure termed cores 1 through 4. The core structure is outlined in dotted lines. Sugars which may also be included in this structure include sialic acid residues added to the galactose residues, and fucose residues added to the GlcNAc residues.

Thus, in preferred embodiments, the present invention provides a method of making an N-linked glycosylated glycopeptide by providing an isolated and purified glycopeptide to which is attached an elemental trimannosyl core or a Man3GlcNAc4 structure, contacting the glycopeptide with a glycosyltransferase enzyme and a donor molecule having a glycosyl moiety under conditions suitable to transfer the glycosyl moiety to the glycopeptide. Customization of a trimannosyl core glycopeptide or Man3GlcNAc4 glycopeptide to produce a peptide having a desired glycosylation pattern is then accomplished by the sequential addition of the desired sugar moieties, using techniques well known in the art.

Determination of Glycan Primary Structure

When an N-linked glycopeptide is produced by a cell, as noted elsewhere herein, it may comprise a heterogeneous mixture of glycan structures which must be reduced to a common, generally elemental trimannosyl core or Man3GlcNAc4 structure, prior to adding other sugar moieties thereto. In order to determine exactly which sugars should be removed from any particular glycan structure, it is sometimes necessary that the primary glycan structure be identified. Techniques for the determination of glycan primary structure are well know in the art and are described in detail, for example, in Montreuil, "Structure and Biosynthesis of Glycopeptides" In Polysaccharides in Medicinal Applications, pp. 273-327, 1996, Eds. Severian Damitriu, Marcel Dekker, NY. It is therefore a simple matter for one skilled in the art of glycobiology to isolate a population of peptides produced by a cell and determine the structure(s) of the glycans attached thereto. For example, efficient methods are available for (i) the splitting of glycosidic bonds either by chemical cleavage such as hydrolysis, acetolysis, hydrazinolysis, or by nitrous deamination; (ii) complete methylation followed by hydrolysis or methanolysis and by gas-liquid chromatography and mass spectroscopy of the partially methylated monosaccharides; and (iii) the definition of anomeric linkages between monosaccharides using exoglycosidases, which also provide insight into the primary glycan structure by sequential degradation. In particular, the techniques of mass spectroscopy and nuclear magnetic resonance (NMR) spectrometry, especially high field NMR have been successfully used to determine glycan primary structure.

Kits and equipment for carbohydrate analysis are also commercially available. Fluorophore Assisted Carbohydrate Electrophoresis (FACE®) is available from Glyko, Inc. (Novato, Calif.). In FACE analysis, glycoconjugates are released from the peptide with either Endo H or N-glycanase (PNGase F) for N-linked glycans, or hydrazine for Ser/Thr linked glycans. The glycan is then labeled at the reducing end with a fluorophore in a non-structure discriminating manner. The fluorophore labeled glycans are then separated in polyacrylamide gels based on the charge/mass ratio of the saccharide as well as the hydrodynamic volume. Images are taken of the gel under UV light and the composition of the glycans are determined by the migration distance as compared with the standards. Oligosaccharides can be sequenced in this manner by analyzing migration shifts due to the sequential removal of saccharides by exoglycosidase digestion.

EXEMPLARY EMBODIMENT

The remodeling of N-linked glycosylation is best illustrated with reference to Formula 1:

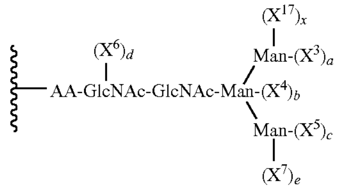

where $X^3$, $X^4$, $X^5$, $X^6$, $X^7$ and $X^{17}$ are (independently selected) monosaccharide or oligosaccharide residues; and a, b, c, d, e and x are (independently selected) 0, 1 or 2, with the proviso that at least one member selected from a, b, c, d, e and x are 1 or 2.

Formula 1 describes glycan structure comprising the trimannosyl core, which is preferably covalently linked to an asparagine residue on a peptide backbone. Preferred expression systems will express and secrete exogenous peptides with N-linked glycans comprising the tri-mannosyl core. Using the remodeling method of the invention, the glycan structures on these peptides can be conveniently remodeled to any glycan structure desired. Exemplary reaction conditions are found throughout the examples and in the literature.

In preferred embodiments, the glycan structures are remodeled so that the structure described in Formula 1 has specific determinates. The structure of the glycan can be chosen to enhance the biological activity of the peptide, give the peptide a new biological activity, remove the biological activity of peptide, or better approximate the glycosylation pattern of the native peptide, among others.

In the first preferred embodiment, the peptide N-linked glycans are remodeled to better approximate the glycosylation pattern of native human proteins. In this embodiment, the glycan structure described in Formula 1 is remodeled to have the following moieties:

$X^3$ and $X^5$=|-GlcNAc-Gal-SA;

a and c=1;

d=0or 1;

b, e and x=0.

This embodiment is particularly advantageous for human peptides expressed in heterologous cellular expression systems. By remodeling the N-linked glycan structures to this configuration, the peptide can be made less immunogenic in a human patient, and/or more stable, among others.

In the second preferred embodiment, the peptide N-linked glycans are remodeled to have a bisecting GlcNAc residue on the tri-mannosyl core. In this embodiment, the glycan structure described in Formula 1 is remodeled to have the following moieties:

$X^3$ and $X^5$ are |-GlcNAc-Gal-SA;

a and c=1;

$X^4$ is GlcNAc;

b=1;

d=0 or 1;

e and x=0.

This embodiment is particularly advantageous for recombinant antibody molecules expressed in heterologous cellular systems. When the antibody molecule includes a Fc-mediated cellular cytotoxicity, it is known that the presence of bisected oligosaccharides linked the Fc domain dramatically increased antibody-dependent cellular cytotoxicity.

In a third preferred embodiment, the peptide N-linked glycans are remodeled to have a sialylated Lewis X moiety. In this embodiment, the glycan structure described in Formula 1 is remodeled to have the following moieties:

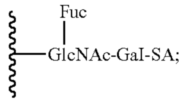

$X^3$ and $X^5$ are a, c, d=1;

b, e and x=0;

$X^6$=fucose.

This embodiment is particularly advantageous when the peptide which is being remodeling is intended to be targeted to selectin molecules and cells exhibiting the same. In a fourth preferred embodiment, the peptide N-linked glycans are remodeled to have a conjugated moiety. The conjugated moiety may be a PEG molecule, another peptide, a small molecule such as a drug, among others. In this embodiment, the glycan structure described in Formula 1 is remodeled to have the following moieties:

$X^3$ and $X^5$ are |-GlcNAc-Gal-SA-R;

a and c=1 or 2;

d=0or 1;

b, d, e and x=0;

where R=conjugate group.

The conjugated moiety may be a PEG molecule, another peptide, a small molecule such as a drug, among others. This embodiment therefore is useful for conjugating the peptide to PEG molecules that will slow the clearance of the peptide from the patient's bloodstream, to peptides that will target both peptides to a specific tissue or cell, or to another peptide of complementary therapeutic use.

It will be clear to one of skill in the art that the invention is not limited to the preferred glycan molecules described above. The preferred embodiments are only a few of the many useful glycan molecules that can be made by the remodeling method of the invention. Those skilled in the art will know how to design other useful glycans.

In the first exemplary embodiments, the peptide is expressed in a CHO (Chinese hamster ovarian cell line) according to methods well known in the art. When a peptide with N-linked glycan consensus sites is expressed and secreted from CHO cells, the N-linked glycans will have the structures depicted in top row of FIG. 2, but also comprising a core fucose. While all of these structures may be present, by far the most common structures are the two at the right side. In the terms of Formula 1, $X^3$ and $X^5$ are 1-GlcNAc-Gal-(SA);

a and c=1;

b, e and x=0, and d=0 or 1.

Therefore, in one exemplary embodiment, the N-linked glycans of peptides expressed in CHO cells are remodeled to the preferred humanized glycan by contacting the peptides with a glycosyltransferase that is specific for a galactose acceptor molecule and a sialic acid donor molecule. This process is illustrated in FIG. 2 and Example 17. In another exemplary embodiment, the N-linked glycans of a peptide expressed and secreted from CHO cells are remodeled to be the preferred PEGylated structures. The peptide is first contacted with a glycosidase specific for sialic acid to remove the terminal SA moiety, and then contacted with a glycosyltransferase specific for a galactose acceptor moiety and an sialic acid acceptor moiety, in the presence of PEG-sialic acid-nucleotide donor molecules. Optionally, the peptide may then be contacted with a glycosyltransferase specific for a galactose acceptor moiety and an sialic acid acceptor moiety, in the presence of sialic acid-nucleotide donor molecules to ensure complete the SA capping of all of the glycan molecules.

In other exemplary embodiments, the peptide is expressed in insect cells, such as the sf9 cell line, according to methods well known in the art. When a peptide with N-linked glycan consensus sites is expressed and secreted from sf9 cells, the N-linked glycans will often have the structures depicted in top row of FIG. 6. In the terms of Formula 1:

$X^3$ and $X^5$ are |-GlcNAc;

a and c=0 or 1;

b=0;

$X^6$ is fucose, d=0, 1 or 2; and e and x=0.

The trimannose core is present in the vast majority of the N-linked glycans made by insect cells, and sometimes an antennary GlcNAc and/or fucose residue(s) are also present. Note that the glycan may have no core fucose, it may have a single core fucose having either linkage, or it may have a single core fucose with a perponderance of a single linkage. In one exemplary embodiment, the N-linked glycans of a peptide expressed and secreted from insect cells is remodeled to the preferred humanized glycan by first contacting the glycans with a glycosidase specific to fucose molecules, then contacting the glycans with a glycosyltransferases specific to the mannose acceptor molecule on each antennary of the trimannose core, a GlcNAc donor molecule in the presence of nucleotide-GlcNAc molecules; then contacting the glycans with a glycosyltransferase specific to a GlcNAc acceptor molecule, a Gal donor molecule in the presence of nucleotide-Gal molecules; and then contacting the glycans with a glycosyltransferase specific to a galactose acceptor molecule, a sialic acid donor molecule in the presence of nucleotide-SA molecules. One of skill in the art will appreciate that the fucose molecules, if any, can be removed at any time during the procedure, and if the core fucose is of the same alpha 1,6 linkage as found in human glycans, it may be left intact. In another exemplary embodiment, the humanized glycan of the previous example is remodeled further to the sialylated Lewis X glycan by contacting the glycan further with a glycosyltransferase specific to a GlcNAc acceptor molecule, a fucose donor molecule in the presence of nucleotide-fucose molecules. This process is illustrated in FIG. 11 and Example 39.

In yet other exemplary embodiments, the peptide is expressed in yeast, such as *Saccharomyces cerevisiae*, according to methods well known in the art. When a peptide with N-linked glycan consensus sites is expressed and secreted from *S. cerevisiae* cells, the N-linked glycans will have the structures depicted at the left in FIG. 4. The N-linked glycans will always have the trimannosyl core, which will often be elaborated with mannose or related polysaccharides of up to 1000 residues. In the terms of Formula 1:

$X^3$ and $X^5$=|-Man-Man-$(Man)_{0-1000}$;

a and c=1 or 2;

b, d, e and x=0.

In one exemplary embodiment, the N-linked glycans of a peptide expressed and secreted from yeast cells are remodeled to the elemental trimannose core by first contacting the glycans with a glycosidase specific to $\alpha 2$ mannose molecules, then contacting the glycans with a glycosidase specific to $\alpha 6$ mannose molecules. This process is illustrated in FIG. 4 and Example 38.

In another exemplary embodiment, the N-linked glycans are further remodeled to make a glycan suitable for an recombinant antibody with Fc-mediated cellular toxicity function by contacting the elemental trimannose core glycans with a glycosyltransferase specific to the mannose acceptor molecule on each antennary of the trimannose core and a GlcNAc donor molecule in the presence of nucleotide-GlcNAc molecules. Then, the glycans are contacted with a glycosyltransferase specific to the acceptor mannose molecule in the middle of the trimannose core, a GlcNAc donor molecule in the presence of nucleotide-GlcNAc molecules and further contacting the glycans with a glycosyltransferase specific to a GlcNAc acceptor molecule, a Gal donor molecule in the presence of nucleotide-Gal molecules; and then optionally contacting the glycans with a glycosyltransferase specific to a galactose acceptor molecule and further optionally a sialic acid donor molecule in the presence of nucleotide-SA molecules. This process is illustrated in FIGS. 1, 2 and 3.

In another exemplary embodiment, the peptide is expressed in bacterial cells, in particular *E. coli* cells, according to methods well known in the art. When a peptide with N-linked glycans consensus sites is expressed in *E. coli* cells, the N-linked consensus sites will not be glycosylated. In an exemplary embodiment, a humanized glycan molecule is built out from the peptide backbone by contacting the peptides with a glycosyltransferase specific for a N-linked consensus site and a GlcNAc donor molecule in the presence of nucleotide-GlcNAc; and further sequentially contacting the growing glycans with glycosyltransferases specific for the acceptor and donor moieties in the present of the required donor moiety until the desired glycan structure is completed. When a peptide with N-linked glycans is expressed in a eukaryotic cells but without the proper leader sequences that direct the nascent peptide to the golgi apparatus, the mature peptide is likely not to be glycosylated. In this case as well the peptide may be given N-linked glycosylation by building out from the peptide N-linked consensus site as aforementioned. When a protein is chemically modified with a sugar moiety, it can be built out as aforementioned.

These examples are meant to illustrate the invention, and not to limit it. One of skill in the art will appreciate that the steps taken in each example may in some circumstances be able to be performed in a different order to get the same result.

One of skill in the art will also understand that a different set of steps may also produce the same resulting glycan. The preferred remodeled glycan is by no means specific to the expression system that the peptide is expressed in. The remodeled glycans are only illustrative and one of skill in the art will know how to take the principles from these examples and apply them to peptides produced in different expression systems to make glycans not specifically described herein.

B. Method to Remodel O-Linked Glycans

O-glycosylation is characterized by the attachment of a variety of monosaccharides in an O-glycosidic linkage to hydroxy amino acids. O-glycosylation is a widespread post-translational modification in the animal and plant kingdoms. The structural complexity of glycans O-linked to proteins vastly exceeds that of N-linked glycans. Serine or threonine residues of a newly translated peptide become modified by virtue of a peptidyl GalNAc transferase in the cis to trans compartments of the Golgi. The site of O-glycosylation is determined not only by the sequence specificity of the glycosyltransferase, but also epigenetic regulation mediated by competition between different substrate sites and competition with other glycosyltransferases responsible for forming the glycan.

The O-linked glycan has been arbitrarily defined as having three regions: the core, the backbone region and the peripheral region. The "core" region of an O-linked glycan is the inner most two or three sugars of the glycan chain proximal to the peptide. The backbone region mainly contributes to the length of the glycan chain formed by uniform elongation. The peripheral region exhibits a high degree of structural complexity. The structural complexity of the O-linked glycans begins with the core structure. In most cases, the first sugar residue added at the O-linked glycan consensus site is GalNAc; however the sugar may also be GlcNAc, glucose, mannose, galactose or fucose, among others. FIG. 12 is a diagram of some of the known O-linked glycan core structures and the enzymes responsible for their in vivo synthesis.

In mammalian cells, at least eight different O-linked core structures are found, all based on a core-α-GalNAc residue. The four core structures depicted in FIG. 13 are the most common. Core 1 and core 2 are the most abundant structures in mammalian cells, and core 3 and core 4 are found in more restricted, organ-characteristic expression systems. O-linked glycans are reviewed in Montreuil, Structure and Synthesis of Glycopeptides, In Polysaccharides in Medicinal Applications, pp. 273-327, 1996, Eds. Severian Damitriu, Marcel Dekker, NY, and in Schachter and Brockhausen, The Biosynthesis of Branched O-Linked Glycans, 1989, Society for Experimental Biology, pp. 1-26 (Great Britain).

It will be apparent from the present disclosure that the glycan structure of O-glycosylated peptides can be remodeled using similar techniques to those described for N-linked glycans. O-glycans differ from N-glycans in that they are linked to a serine or threonine residue rather than an asparagine residue. As described herein with respect to N-glycan remodeling, hydrolytic enzymes can be used to cleave unwanted sugar moieties in an O-linked glycan and additional desired sugars can then be added thereto, to build a customized O-glycan structure on the peptide (See FIGS. 12 and 13).

The initial step in O-glycosylation in mammalian cells is the attachment of N-acetylgalactosamine (GalNAc) using any of a family of at least eleven known α-N-acetylgalactosaminyltransferases, each of which has a restricted acceptor peptide specificity. Generally, the acceptor peptide recognized by each enzyme constitutes a sequence of at least ten amino acids. Peptides that contain the amino acid sequence recognized by one particular GalNAc-transferase become O-glycosylated at the acceptor site if they are expressed in a cell expressing the enzyme and if they are appropriately localized to the Golgi apparatus where UDP-GalNAc is also present.

However, in the case of recombinant proteins, the initial attachment of the GalNAc may not take place. The α-N-acetylgalactosaminyltransferase enzyme native to the expressing cell may have a consensus sequence specificity which differs from that of the recombinant peptide being expressed.

The desired recombinant peptide may be expressed in a bacterial cell, such as *E. coli*, that does not synthesize glycan chains. In these cases, it is advantageous to add the initial GalNAc moiety in vitro. The GalNAc moiety can be introduced in vitro onto the peptide once the recombinant peptide has been recovered in a soluble form, by contacting the peptide with the appropriate GalNAc transferase in the presence of UDP-GalNAc.

In one embodiment, an additional sequence of amino acids that constitute an effective acceptor for transfer of an O-linked sugar may be present. Such an amino acid sequence is encoded by a DNA sequence fused in frame to the coding sequence of the peptide, or alternatively, may be introduced by chemical means. The peptide may be otherwise lacking glycan chains. Alternately, the peptide may have N- and/or O-linked glycan chains but require an additional glycosylation site, for example, when an additional glycan substituent is desired.

In an exemplary embodiment, the amino acid sequence PTTTK-COOH, which is the natural GalNAc acceptor sequence in the human mucin MUC-1, is added as a fusion tag. The fusion protein is then expressed in *E. coli* and purified. The peptide is then contacted with recombinant human GalNAc-transferases T3 or T6 in the presence of UDP-GalNAc to transfer a GalNAc residue onto the peptide in vitro.

This glycan chain on the peptide may then be further elongated using the methods described in reference to the N-linked or O-linked glycans herein. Alternatively, the GalNAc transferase reaction can be carried out in the presence of UDP-GalNAc to which PEG is covalently substituted in the 0-3, 4, or 6 positions or the N-2 position. Glycoconjugation is described in detail elsewhere herein. Any antigenicity introduced into the peptide by the new peptide sequence can be conveniently masked by PEGylation of the associated glycan. The acceptor site fusion technique can be used to introduce not only a PEG moiety, but to introduce other glycan and non-glycan moieties, including, but not limited to, toxins, anti-infectives, cytotoxic agents, chelators for radionucleotides, and glycans with other functionalities, such as tissue targeting.

Exemplary Embodiments

The remodeling of O-linked glycosylation is best illustrated with reference to Formula 2:

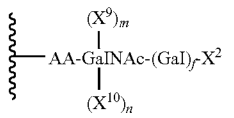

Formula 2 describes a glycan structure comprising a GalNAc which is covalently linked preferably to a serine or threonine residue on a peptide backbone. While this structure is used to illustrate the most common forms of O-linked glycans, it should not be construed to limit the invention solely to these O-linked glycans. Other forms of O-linked glycans are illustrated in FIG. 12. Preferred expression systems useful in the present invention express and secrete exogenous peptides having O-linked glycans comprising the GalNAc residue. Using the remodeling methods of the invention, the glycan structures on these peptides can be conveniently remodeled to generate any desired glycan structure. One of skill in the art will appreciate that O-linked glycans can be remodeled using the same principles, enzymes and reaction conditions as those available in the art once armed with the present disclosure. Exemplary reaction conditions are found throughout the Examples.

In preferred embodiments, the glycan structures are remodeled so that the structure described in Formula 2 has specific moieties. The structure of the glycan may be chosen to enhance the biological activity of the peptide, confer upon the peptide a new biological activity, remove or alter a biological activity of peptide, or better approximate the glycosylation pattern of the native peptide, among others.

In the first preferred embodiment, the peptide O-linked glycans are remodeled to better approximate the glycosylation pattern of native human proteins. In this embodiment, the glycan structure described in Formula 2 is remodeled to have the following moieties:

$X^2$ is |-SA; or |-SA-SA;

f and n=0 or 1;

$X^{10}$ is SA;

m=0.

This embodiment is particularly advantageous for human peptides expressed in heterologous cellular expression systems. By remodeling the O-linked glycan structures to have this configuration, the peptide can be rendered less immunogenic in a human patient and/or more stable.

In the another preferred embodiment, the peptide O-linked glycans are remodeled to display a sialylated Lewis X antigen. In this embodiment, the glycan structure described in Formula 2 is remodeled to have the following moieties:

$X^2$ is |-SA;

$X^{10}$ is Fuc or |-GlcNAc(Fuc)-Gal-SA;

f and n=1;

m=0.

This embodiment is particularly advantageous when the peptide which is being remodeled is most effective when targeted to a selectin molecule and cells exhibiting the same.

In a yet another preferred embodiment, the peptide O-linked glycans are remodeled to contain a conjugated moiety. The conjugated moiety may be a PEG molecule, another peptide, a small molecule such as a drug, among others. In this embodiment, the glycan structure described in Formula 2 is remodeled to have the following moieties:

$X^2$ is |-SA-R;

f=1;

n and m=0;

where R is the conjugate group.

This embodiment is useful for conjugating the peptide to PEG molecules that will slow the clearance of the peptide from the patient's bloodstream, to peptides that will target both peptides to a specific tissue or cell or to another peptide of complementary therapeutic use.

It will be clear to one of skill in the art that the invention is not limited to the preferred glycan molecules described above. The preferred embodiments are only a few of the many useful glycan molecules that can be made using the remodeling methods of the invention. Those skilled in the art will know how to design other useful glycans once armed with the present invention.

In the first exemplary embodiment, the peptide is expressed in a CHO (Chinese hamster cell line) according to methods well known in the art. When a peptide with O-linked glycan consensus sites is expressed and secreted from CHO cells, the majority of the O-linked glycans will often have the structure, in the terms of Formula 2, $X^2$=|-SA;

f=1;

m and n=0.

Therefore, most of the glycans in CHO cells do not require remodeling in order to be acceptable for use in a human patient. In an exemplary embodiment, the O-linked glycans of a peptide expressed and secreted from a CHO cell are remodeled to contain a sialylated Lewis X structure by contacting the glycans with a glycosyltransferase specific for the GalNAc acceptor moiety and the fucose donor moiety in the presence of nucleotide-fucose. This process is illustrated on N-linked glycans in FIG. 11 and Example 39.

In other exemplary embodiments, the peptide is expressed in insect cells such as sf9 according to methods well known in the art. When a peptide having O-linked glycan consensus sites is expressed and secreted from most sf9 cells, the majority of the O-linked glycans have the structure, in the terms of Formula 2:

$X^2$=H;

f=0 or 1;

n and m=0.

See, for example, Marchal et al., (2001, Biol. Chem. 382: 151-159). In one exemplary embodiment, the O-linked glycan on a peptide expressed in an insect cell is remodeled to a humanized glycan by contacting the glycans with a glycosyltransferase specific for a GalNAc acceptor molecule and a galactose donor molecule in the presence of nucleotide-Gal; and then contacting the glycans with a glycosyltransferase specific for a Gal acceptor molecule and a SA donor molecule in the presence of nucleotide-SA. In another exemplary embodiment, the O-linked glycans are remodeled further from the humanized form to the sialylated Lewis X form by further contacting the glycans with a glycosyltransferase specific for a GalNAc acceptor molecule and a fucose donor molecule in the presence of nucleotide-fucose.

In yet another exemplary embodiment, the peptide is expressed in fungal cells, in particular *S. cerevisiae* cells, according to methods well known in the art. When a peptide with O-linked glycans consensus sites is expressed and secreted from *S. cerevisiae* cells, the majority of the O-linked glycans have the structure:

|-AA-Man-$Man_{1-2}$.

See Gemmill and Trimble (1999, Biochim. Biophys. Acta 1426:227-237). In order to remodel these O-linked glycans for use in human, it is preferable that the glycan be cleaved at the amino acid level and rebuilt from there.

In an exemplary embodiment, the glycan is the O-linked glycan on a peptide expressed in a fungal cell and is remodeled to a humanized glycan by contacting the glycan with an endoglycosylase specific for an amino acid-GalNAc bond; and then contacting the glycan with a glycosyltransferase specific for a O-linked consensus site and a GalNAc donor molecule in the presence of nucleotide-GalNAc; contacting the glycan with a glycosyltransferase specific for a GalNAc acceptor molecule and a galactose donor molecule in the presence of nucleotide-Gal; and then contacting the glycans with a glycosyltransferase specific for a Gal acceptor molecule and a SA donor molecule in the presence of nucleotide-SA.

Alternately, in another exemplary embodiment, the glycan is the O-linked glycan on a peptide expressed in a fungal cell and is remodeled to a humanized glycan by contacting the glycan with an protein O-mannose β-1,2-N-acetylglucosaminyltransferase (POMGnTI) in the presence of GlcNAc-nucleotide; then contacting the glycan with an galactosyltransferase in the presence of nucleotide-Gal; and then contracting the glycan with an sialyltransferase in the presence of nucleotide-SA.

In another exemplary embodiment, the peptide is expressed in bacterial cells, in particular *E. coli* cells, according to methods well known in the art. When a peptide with an O-linked glycan consensus site is expressed in *E. coli* cells, the O-linked consensus site will not be glycosylated. In this case, the desired glycan molecule must be built out from the peptide backbone in a manner similar to that describe for *S. cerevisiae* expression above. Further, when a peptide having an O-linked glycan is expressed in a eukaryotic cell without the proper leader sequences to direct the nascent peptide to the golgi apparatus, the mature peptide is likely not to be glycosylated. In this case as well, an O-linked glycosyl structure may be added to the peptide by building out the glycan directly from the peptide O-linked consensus site. Further, when a protein is chemically modified with a sugar moiety, it can also be remodeled as described herein.

These examples are meant to illustrate the invention, and not to limit it in any way. One of skill in the art will appreciate that the steps taken in each example may in some circumstances be performed in a different order to achieve the same result. One of skill in the art will also understand that a different set of steps may also produce the same resulting glycan. Further, the preferred remodeled glycan is by no means specific to the expression system that the peptide is expressed in. The remodeled glycans are only illustrative and one of skill in the art will know how to take the principles from these examples and apply them to peptides produced in different expression systems to generate glycans not specifically described herein.

C. Glycoconjugation, in General

The invention provides methods of preparing a conjugate of a glycosylated or an unglycosylated peptide. The conjugates of the invention are formed between peptides and diverse species such as water-soluble polymers, therapeutic moieties, diagnostic moieties, targeting moieties and the like. Also provided are conjugates that include two or more peptides linked together through a linker arm, i.e., multifunctional conjugates. The multi-functional conjugates of the invention can include two or more copies of the same peptide or a collection of diverse peptides with different structures, and/or properties.

The conjugates of the invention are formed by the enzymatic attachment of a modified sugar to the glycosylated or unglycosylated peptide. The modified sugar, when interposed between the peptide and the modifying group on the sugar becomes what is referred to herein as "an intact glycosyl linking group." Using the exquisite selectivity of enzymes, such as glycosyltransferases, the present method provides peptides that bear a desired group at one or more specific locations. Thus, according to the present invention, a modified sugar is attached directly to a selected locus on the peptide chain or, alternatively, the modified sugar is appended onto a carbohydrate moiety of a peptide. Peptides in which modified sugars are linked to both a peptide carbohydrate and directly to an amino acid residue of the peptide backbone are also within the scope of the present invention.

In contrast to known chemical and enzymatic peptide elaboration strategies, the methods of the invention make it possible to assemble peptides and glycopeptides that have a substantially homogeneous derivatization pattern; the enzymes used in the invention are generally selective for a particular amino acid residue or combination of amino acid residues of the peptide or particular glycan structure. The methods are also practical for large-scale production of modified peptides and glycopeptides. Thus, the methods of the invention provide a practical means for large-scale preparation of peptides having preselected substantially uniform derivatization patterns. The methods are particularly well suited for modification of therapeutic peptides, including but not limited to, peptides that are incompletely glycosylated during production in cell culture cells (e.g., mammalian cells, insect cells, plant cells, fungal cells, yeast cells, or prokaryotic cells) or transgenic plants or animals.

The methods of the invention also provide conjugates of glycosylated and unglycosylated peptides with increased therapeutic half-life due to, for example, reduced clearance rate, or reduced rate of uptake by the immune or reticuloendothelial system (RES). Moreover, the methods of the invention provide a means for masking antigenic determinants on peptides, thus reducing or eliminating a host immune response against the peptide. Selective attachment of targeting agents can also be used to target a peptide to a particular tissue or cell surface receptor that is specific for the particular targeting agent. Moreover, there is provided a class of peptides that are specifically modified with a therapeutic moiety.

1. The Conjugates

In a first aspect, the present invention provides a conjugate between a peptide and a selected moiety. The link between the peptide and the selected moiety includes an intact glycosyl linking group interposed between the peptide and the selected moiety. As discussed herein, the selected moiety is essentially any species that can be attached to a saccharide unit, resulting in a "modified sugar" that is recognized by an appropriate transferase enzyme, which appends the modified sugar onto the peptide. The saccharide component of the modified sugar, when interposed between the peptide and a selected moiety, becomes an "intact glycosyl linking group." The glycosyl linking group is formed from any mono- or oligo-saccharide that, after modification with a selected moiety, is a substrate for an appropriate transferase.

The conjugates of the invention will typically correspond to the general structure:

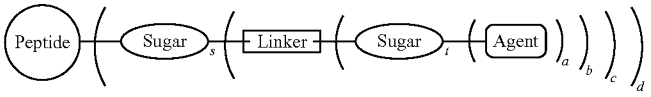

in which the symbols a, b, c, d and s represent a positive, non-zero integer; and t is either 0 or a positive integer. The "agent" is a therapeutic agent, a bioactive agent, a detectable label, water-soluble moiety or the like. The "agent" can be a peptide, e.g., enzyme, antibody, antigen, etc. The linker can be any of a wide array of linking groups, infra. Alternatively, the linker may be a single bond or a "zero order linker." The identity of the peptide is without limitation. Exemplary peptides are provided in FIG. 28.

In an exemplary embodiment, the selected moiety is a water-soluble polymer. The water-soluble polymer is covalently attached to the peptide via an intact glycosyl linking group. The glycosyl linking group is covalently attached to either an amino acid residue or a glycosyl residue of the peptide. Alternatively, the glycosyl linking group is attached to one or more glycosyl units of a glycopeptide. The invention also provides conjugates in which the glycosyl linking group is attached to both an amino acid residue and a glycosyl residue.

In addition to providing conjugates that are formed through an enzymatically added intact glycosyl linking group, the present invention provides conjugates that are highly homogenous in their substitution patterns. Using the methods of the invention, it is possible to form peptide conjugates in which essentially all of the modified sugar moieties across a population of conjugates of the invention are attached to multiple copies of a structurally identical amino acid or glycosyl residue. Thus, in a second aspect, the invention provides a peptide conjugate having a population of water-soluble polymer moieties, which are covalently linked to the peptide through an intact glycosyl linking group. In a preferred conjugate of the invention, essentially each member of the population is linked via the glycosyl linking group to a glycosyl residue of the peptide, and each glycosyl residue of the peptide to which the glycosyl linking group is attached has the same structure.

Also provided is a peptide conjugate having a population of water-soluble polymer moieties covalently linked thereto through an intact glycosyl linking group. In a preferred embodiment, essentially every member of the population of water soluble polymer moieties is linked to an amino acid residue of the peptide via an intact glycosyl linking group, and each amino acid residue having an intact glycosyl linking group attached thereto has the same structure.

The present invention also provides conjugates analogous to those described above in which the peptide is conjugated to a therapeutic moiety, diagnostic moiety, targeting moiety, toxin moiety or the like via an intact glycosyl linking group. Each of the above-recited moieties can be a small molecule, natural polymer (e.g., peptide) or synthetic polymer.

In an exemplary embodiment, interleukin-2 (IL-2) is conjugated to transferrin via a bifunctional linker that includes an intact glycosyl linking group at each terminus of the PEG moiety (Scheme 1). For example, one terminus of the PEG linker is functionalized with an intact sialic acid linker that is attached to transferrin and the other is functionalized with an intact GalNAc linker that is attached to IL-2.

In another exemplary embodiment, EPO is conjugated to transferrin. In another exemplary embodiment, EPO is conjugated to glial derived neurotropic growth factor (GDNF). In these embodiments, each conjugation is accomplished via a bifunctional linker that includes an intact glycosyl linking group at each terminus of the PEG moiety, as aforementioned. Transferrin transfers the protein across the blood brain barrier.

As set forth in the Figures appended hereto, the conjugates of the invention can include intact glycosyl linking groups that are mono- or multi-valent (e.g., antennary structures), see, FIGS. 14-22. The conjugates of the invention also include glycosyl linking groups that are O-linked glycans originating from serine or threonine (FIG. 11). Thus, conjugates of the invention include both species in which a selected moiety is attached to a peptide via a monovalent glycosyl linking group. Also included within the invention are conjugates in which more than one selected moiety is attached to a peptide via a multivalent linking group. One or more proteins can be conjugated together to take advantage of their biophysical and biological properties.

In a still further embodiment, the invention provides conjugates that localize selectively in a particular tissue due to the presence of a targeting agent as a component of the conjugate. In an exemplary embodiment, the targeting agent is a protein. Exemplary proteins include transferrin (brain, blood pool), human serum (HS)-glycoprotein (bone, brain, blood pool), antibodies (brain, tissue with antibody-specific antigen, blood pool), coagulation Factors V-XII (damaged tissue, clots, cancer, blood pool), serum proteins, e.g., α-acid glycoprotein, fetuin, α-fetal protein (brain, blood pool), β2-glycoprotein (liver, atherosclerosis plaques, brain, blood pool), G-CSF, GM-CSF, M-CSF, and EPO (immune stimulation, cancers, blood pool, red blood cell overproduction, neuroprotection), and albumin (increase in half-life).

In addition to the conjugates discussed above, the present invention provides methods for preparing these and other conjugates. Thus, in a further aspect, the invention provides a method of forming a covalent conjugate between a selected moiety and a peptide. Additionally, the invention provides methods for targeting conjugates of the invention to a particular tissue or region of the body.

In exemplary embodiments, the conjugate is formed between a water-soluble polymer, a therapeutic moiety, targeting moiety or a biomolecule, and a glycosylated or non-glycosylated peptide. The polymer, therapeutic moiety or biomolecule is conjugated to the peptide via an intact glycosyl linking group, which is interposed between, and covalently linked to both the peptide and the modifying group (e.g., water-soluble polymer). The method includes contacting the peptide with a mixture containing a modified sugar and a glycosyltransferase for which the modified sugar is a substrate. The reaction is conducted under conditions sufficient to form a covalent bond between the modified sugar and the peptide. The sugar moiety of the modified sugar is preferably selected from nucleotide sugars, activated sugars and sugars, which are neither nucleotides nor activated.

In one embodiment, the invention provides a method for linking two or more peptides through a linking group. The linking group is of any useful structure and may be selected from straight-chain and branched chain structures. Preferably, each terminus of the linker, which is attached to a peptide, includes a modified sugar (i.e., a nascent intact glycosyl linking group).

In an exemplary method of the invention, two peptides are linked together via a linker moiety that includes a PEG linker. The construct conforms to the general structure set forth in the cartoon above. As described herein, the construct of the invention includes two intact glycosyl linking groups (i.e., s+t=1). The focus on a PEG linker that includes two glycosyl groups is for purposes of clarity and should not be interpreted as limiting the identity of linker arms of use in this embodiment of the invention.

Thus, a PEG moiety is functionalized at a first terminus with a first glycosyl unit and at a second terminus with a second glycosyl unit. The first and second glycosyl units are preferably substrates for different transferases, allowing orthogonal attachment of the first and second peptides to the first and second glycosyl units, respectively. In practice, the $(glycosyl)^1$-PEG-$(glycosyl)^2$ linker is contacted with the first peptide and a first transferase for which the first glycosyl unit is a substrate, thereby forming $(peptide)^1$-$(glycosyl)^1$-PEG-$(glycosyl)^2$. The first transferase and/or unreacted peptide is then optionally removed from the reaction mixture. The second peptide and a second transferase for which the second glycosyl unit is a substrate are added to the $(peptide)^1$-(glycosyl)[1]-PEG-(glycosyl)[2] conjugate, forming (peptide)[1]-(glycosyl)[1]-PEG-(glycosyl)[2]-(peptide)[2]. Those of skill in the art will appreciate that the method outlined above is also applicable to forming conjugates between more than two peptides by, for example, the use of a branched PEG, dendrimer, poly (amino acid), polysaccharide or the like.

As noted previously, in an exemplary embodiment, interleukin-2 (IL-2) is conjugated to transferrin via a bifunctional linker that includes an intact glycosyl linking group at each terminus of the PEG moiety (Scheme 1). The IL-2 conjugate has an in vivo half-life that is increased over that of IL-2 alone by virtue of the greater molecular size of the conjugate. Moreover, the conjugation of IL-2 to transferrin serves to selectively target the conjugate to the brain. For example, one terminus of the PEG linker is functionalized with a CMP-sialic acid and the other is functionalized with an UDP-GalNAc. The linker is combined with IL-2 in the presence of a GalNAc transferase, resulting in the attachment of the GalNAc of the linker arm to a serine and/or threonine residue on the IL-2.

In another exemplary embodiment, transferrin is conjugated to a nucleic acid for use in gene therapy.

Scheme 1

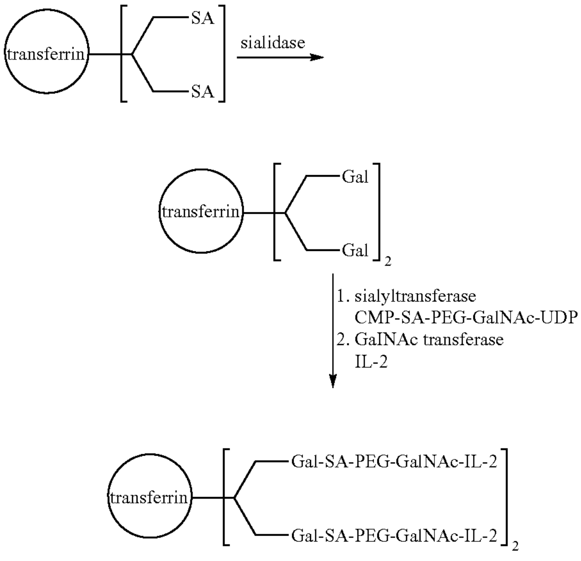

The processes described above can be carried through as many cycles as desired, and is not limited to forming a conjugate between two peptides with a single linker. Moreover, those of skill in the art will appreciate that the reactions functionalizing the intact glycosyl linking groups at the termini of the PEG (or other) linker with the peptide can occur simultaneously in the same reaction vessel, or they can be carried out in a step-wise fashion. When the reactions are carried out in a step-wise manner, the conjugate produced at each step is optionally purified from one or more reaction components (e.g., enzymes, peptides).

A still further exemplary embodiment is set forth in Scheme 2. Scheme 2 shows a method of preparing a conjugate that targets a selected protein, e.g., EPO, to bone and increases the circulatory half-life of the selected protein.

Scheme 2

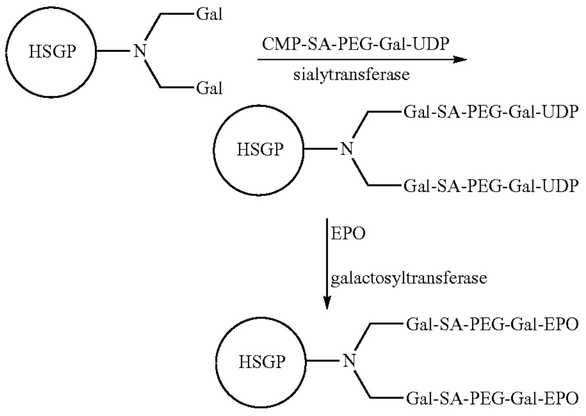

The use of reactive derivatives of PEG (or other linkers) to attach one or more peptide moieties to the linker is within the scope of the present invention. The invention is not limited by the identity of the reactive PEG analogue. Many activated derivatives of poly(ethylene glycol) are available commercially and in the literature. It is well within the abilities of one of skill to choose, and synthesize if necessary, an appropriate activated PEG derivative with which to prepare a substrate useful in the present invention. See, Abuchowski et al. *Cancer Biochem. Biophys.,* 7: 175-186 (1984); Abuchowski et al., *J. Biol. Chem.,* 252: 3582-3586 (1977); Jackson et al., *Anal. Biochem.,* 165: 114-127 (1987); Koide et al., *Biochem Biophys. Res. Commun.,* 111: 659-667 (1983)), tresylate (Nilsson et al., *Methods Enzymol.,* 104: 56-69 (1984); Delgado et al., *Biotechnol. Appl. Biochem.,* 12: 119-128 (1990)); N-hydroxysuccinimide derived active esters (Buckmann et al., *Makromol. Chem.,* 182: 1379-1384 (1981); Joppich et al., *Makromol. Chem.,* 180: 1381-1384 (1979); Abuchowski et al., *Cancer Biochem. Biophys.,* 7: 175-186 (1984); Katre et al. *Proc. Natl. Acad. Sci. U.S.A.,* 84: 1487-1491 (1987); Kitamura et al., *Cancer Res.,* 51: 4310-4315 (1991); Boccu et al., *Z. Naturforsch.,* 38C: 94-99 (1983), carbonates (Zalipsky et al., POLY(ETHYLENE GLYCOL) CHEMISTRY: BIOTECHNICAL AND BIOMEDICAL APPLICATIONS, Harris, Ed., Plenum Press, New York, 1992, pp. 347-370; Zalipsky et al., *Biotechnol. Appl. Biochem.,* 15: 100-114 (1992); Veronese et al., *Appl. Biochem. Biotech.,* 11: 141-152 (1985)), imidazolyl formates (Beauchamp et al., *Anal. Biochem.,* 131: 25-33 (1983); Berger et al., *Blood,* 71: 1641-1647 (1988)), 4-dithiopyridines (Woghiren et al., *Bioconjugate Chem.,* 4: 314-318 (1993)), isocyanates (Byun et al., *ASAIO Journal*, M649-M-653 (1992)) and epoxides (U.S. Pat. No. 4,806,595, issued to Noishiki et al., (1989). Other linking groups include the urethane linkage between amino groups and activated PEG. See, Veronese, et al., *Appl. Biochem. Biotechnol.,* 11: 141-152 (1985).

In another exemplary embodiment in which a reactive PEG derivative is utilized, the invention provides a method for extending the blood-circulation half-life of a selected peptide, in essence targeting the peptide to the blood pool, by conjugating the peptide to a synthetic or natural polymer of a size sufficient to retard the filtration of the protein by the glomerulus (e.g., albumin). This embodiment of the invention is illustrated in Scheme 3 in which erythropoietin (EPO) is conjugated to albumin via a PEG linker using a combination of chemical and enzymatic modification.

Scheme 3

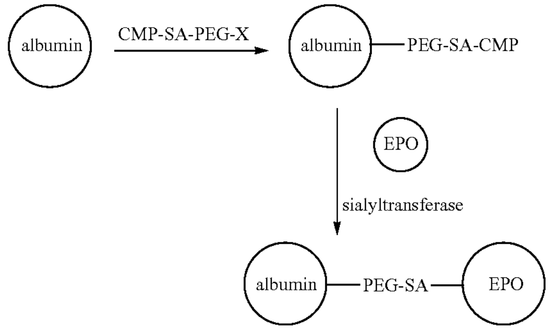

X = Activating group

Thus, as shown in Scheme 3, an amino acid residue of albumin is modified with a reactive PEG derivative, such as X-PEG-(CMP-sialic acid), in which X is an activating group (e.g., active ester, isothiocyanate, etc). The PEG derivative and EPO are combined and contacted with a transferase for which CMP-sialic acid is a substrate. In a further illustrative embodiment, an c-amine of lysine is reacted with the N-hydroxysuccinimide ester of the PEG-linker to form the albumin conjugate. The CMP-sialic acid of the linker is enzymatically conjugated to an appropriate residue on EPO, e.g., Gal, thereby forming the conjugate. Those of skill will appreciate that the above-described method is not limited to the reaction partners set forth. Moreover, the method can be practiced to form conjugates that include more than two protein moieties by, for example, utilizing a branched linker having more than two termini.

2. Modified Sugars

Modified glycosyl donor species ("modified sugars") are preferably selected from modified sugar nucleotides, activated modified sugars and modified sugars that are simple saccharides that are neither nucleotides nor activated. Any desired carbohydrate structure can be added to a peptide using the methods of the invention. Typically, the structure will be a monosaccharide, but the present invention is not limited to the use of modified monosaccharide sugars; oligosaccharides and polysaccharides are useful as well.

The modifying group is attached to a sugar moiety by enzymatic means, chemical means or a combination thereof, thereby producing a modified sugar. The sugars are substituted at any position that allows for the attachment of the modifying moiety, yet which still allows the sugar to function as a substrate for the enzyme used to ligate the modified sugar to the peptide. In a preferred embodiment, when sialic acid is the sugar, the sialic acid is substituted with the modifying group at either the 9-position on the pyruvyl side chain or at the 5-position on the amine moiety that is normally acetylated in sialic acid.

In certain embodiments of the present invention, a modified sugar nucleotide is utilized to add the modified sugar to the peptide. Exemplary sugar nucleotides that are used in the present invention in their modified form include nucleotide mono-, di- or triphosphates or analogs thereof. In a preferred embodiment, the modified sugar nucleotide is selected from a UDP-glycoside, CMP-glycoside, or a GDP-glycoside. Even more preferably, the modified sugar nucleotide is selected from an UDP-galactose, UDP-galactosamine, UDP-glucose, UDP-glucosamine, GDP-mannose, GDP-fucose, CMP-sialic acid; or CMP-NeuAc. N-acetylamine derivatives of the sugar nucleotides are also of use in the method of the invention.

The invention also provides methods for synthesizing a modified peptide using a modified sugar, e.g., modified-galactose, -fucose, and -sialic acid. When a modified sialic acid is used, either a sialyltransferase or a trans-sialidase (for α2,3-linked sialic acid only) can be used in these methods.

In other embodiments, the modified sugar is an activated sugar. Activated modified sugars, which are useful in the present invention are typically glycosides which have been synthetically altered to include an activated leaving group. As used herein, the term "activated leaving group" refers to those moieties, which are easily displaced in enzyme-regulated nucleophilic substitution reactions. Many activated sugars are known in the art. See, for example, Vocadlo et al., In Carbohydrate Chemistry and Biology, Vol. 2, Ernst et al. Ed., Wiley-VCH Verlag: Weinheim, Germany, 2000; Kodama et al., *Tetrahedron Lett.* 34: 6419 (1993); Lougheed, et al., *J. Biol. Chem.* 274: 37717 (1999)).

Examples of activating groups (leaving groups) include fluoro, chloro, bromo, tosylate ester, mesylate ester, triflate ester and the like. Preferred activated leaving groups, for use in the present invention, are those that do not significantly sterically encumber the enzymatic transfer of the glycoside to the acceptor. Accordingly, preferred embodiments of activated glycoside derivatives include glycosyl fluorides and glycosyl mesylates, with glycosyl fluorides being particularly preferred. Among the glycosyl fluorides, α-galactosyl fluoride, α-mannosyl fluoride, α-glucosyl fluoride, α-fucosyl fluoride, α-xylosyl fluoride, α-sialyl fluoride, α-N-acetylglucosaminyl fluoride, α-N-acetylgalactosaminyl fluoride, β-galactosyl fluoride, β-mannosyl fluoride, β-glucosyl fluoride, β-fucosyl fluoride, β-xylosyl fluoride, β-sialyl fluoride, β-N-acetylglucosaminyl fluoride and β-N-acetylgalactosaminyl fluoride are most preferred.

By way of illustration, glycosyl fluorides can be prepared from the free sugar by first acetylating the sugar and then treating it with HF/pyridine. This generates the thermodynamically most stable anomer of the protected (acetylated) glycosyl fluoride (i.e., the α-glycosyl fluoride). If the less stable anomer (i.e., the β-glycosyl fluoride) is desired, it can be prepared by converting the peracetylated sugar with HBr/HOAc or with HCl to generate the anomeric bromide or chloride. This intermediate is reacted with a fluoride salt such as silver fluoride to generate the glycosyl fluoride. Acetylated glycosyl fluorides may be deprotected by reaction with mild (catalytic) base in methanol (e.g. NaOMe/MeOH). In addition, many glycosyl fluorides are commercially available.

Other activated glycosyl derivatives can be prepared using conventional methods known to those of skill in the art. For example, glycosyl mesylates can be prepared by treatment of the fully benzylated hemiacetal form of the sugar with mesyl chloride, followed by catalytic hydrogenation to remove the benzyl groups.

In a further exemplary embodiment, the modified sugar is an oligosaccharide having an antennary structure. In a preferred embodiment, one or more of the termini of the antennae bear the modifying moiety. When more than one modifying moiety is attached to an oligosaccharide having an antennary structure, the oligosaccharide is useful to "amplify" the modifying moiety; each oligosaccharide unit conjugated to the peptide attaches multiple copies of the modifying group to the peptide. The general structure of a typical chelate of the invention as set forth in the drawing above, encompasses multivalent species resulting from preparing a conjugate of the invention utilizing an antennary structure. Many antennary saccharide structures are known in the art, and the present method can be practiced with them without limitation.

Exemplary modifying groups are discussed below. The modifying groups can be selected for one or more desirable property. Exemplary properties include, but are not limited to, enhanced pharmacokinetics, enhanced pharmacodynamics, improved biodistribution, providing a polyvalent species, improved water solubility, enhanced or diminished lipophilicity, and tissue targeting.

D. Peptide Conjugates a) Water-Soluble Polymers

The hydrophilicity of a selected peptide is enhanced by conjugation with polar molecules such as amine-, ester-, hydroxyl- and polyhydroxyl-containing molecules. Representative examples include, but are not limited to, polylysine, polyethyleneimine, poly(ethylene glycol) and poly(propyleneglycol). Preferred water-soluble polymers are essentially non-fluorescent, or emit such a minimal amount of fluorescence that they are inappropriate for use as a fluorescent marker in an assay. Polymers that are not naturally occurring sugars may be used. In addition, the use of an otherwise naturally occurring sugar that is modified by covalent attachment of another entity (e.g., poly(ethylene glycol), poly(propylene glycol), poly(aspartate), biomolecule, therapeutic moiety, diagnostic moiety, etc.) is also contemplated. In another exemplary embodiment, a therapeutic sugar moiety is conjugated to a linker arm and the sugar-linker arm is subsequently conjugated to a peptide via a method of the invention.

Methods and chemistry for activation of water-soluble polymers and saccharides as well as methods for conjugating saccharides and polymers to various species are described in the literature. Commonly used methods for activation of polymers include activation of functional groups with cyanogen bromide, periodate, glutaraldehyde, biepoxides, epichlorohydrin, divinylsulfone, carbodiimide, sulfonyl halides, trichlorotriazine, etc. (see, R. F. Taylor, (1991), Protein Immobilisation. Fundamentals and Applications, Marcel Dekker, N.Y.; S. S. Wong, (1992), Chemistry of Protein Conjugation and Crosslinking, CRC Press, Boca Raton; G. T. Hermanson et al., (1993), Immobilized Affinity Ligand Techniques, Academic Press, N.Y.; Dunn, R. L., et al., Eds. Polymeric Drugs And Drug Delivery Systems, ACS Symposium Series Vol. 469, American Chemical Society, Washington, D.C. 1991).

Routes for preparing reactive PEG molecules and forming conjugates using the reactive molecules are known in the art. For example, U.S. Pat. No. 5,672,662 discloses a water soluble and isolatable conjugate of an active ester of a polymer acid selected from linear or branched poly(alkylene oxides), poly(oxyethylated polyols), poly(olefinic alcohols), and poly(acrylomorpholine), wherein the polymer has about 44 or more recurring units. U.S. Pat. No. 6,376,604 sets forth a method for preparing a water-soluble 1-benzotriazolylcarbonate ester of a water-soluble and non-peptidic polymer by reacting a terminal hydroxyl of the polymer with di(1-benzotriazoyl)carbonate in an organic solvent. The active ester is used to form conjugates with a biologically active agent such as a protein or peptide.

WO 99/45964 describes a conjugate comprising a biologically active agent and an activated water soluble polymer comprising a polymer backbone having at least one terminus linked to the polymer backbone through a stable linkage, wherein at least one terminus comprises a branching moiety having proximal reactive groups linked to the branching moiety, in which the biologically active agent is linked to at least one of the proximal reactive groups. Other branched poly (ethylene glycols) are described in WO 96/21469, U.S. Pat. No. 5,932,462 describes a conjugate formed with a branched PEG molecule that includes a branched terminus that includes reactive functional groups. The free reactive groups are available to react with a biologically active species, such as a protein or peptide, forming conjugates between the poly (ethylene glycol) and the biologically active species. U.S. Pat. No. 5,446,090 describes a bifunctional PEG linker and its use in forming conjugates having a peptide at each of the PEG linker termini.

Conjugates that include degradable PEG linkages are described in WO 99/34833; and WO 99/14259, as well as in U.S. Pat. No. 6,348,558. Such degradable linkages are applicable in the present invention.

Although both reactive PEG derivatives and conjugates formed using the derivatives are known in the art, until the present invention, it was not recognized that a conjugate could be formed between PEG (or other polymer) and another species, such as a peptide or glycopeptide, through an intact glycosyl linking group.

Many water-soluble polymers are known to those of skill in the art and are useful in practicing the present invention. The term water-soluble polymer encompasses species such as saccharides (e.g., dextran, amylose, hyalouronic acid, poly (sialic acid), heparans, heparins, etc.); poly (amino acids), e.g., poly(glutamic acid); nucleic acids; synthetic polymers (e.g., poly(acrylic acid), poly(ethers), e.g., poly(ethylene glycol); peptides, proteins, and the like. The present invention may be practiced with any water-soluble polymer with the sole limitation that the polymer must include a point at which the remainder of the conjugate can be attached.

Methods for activation of polymers can also be found in WO 94/17039, U.S. Pat. No. 5,324,844, WO 94/18247, WO 94/04193, U.S. Pat. No. 5,219,564, U.S. Pat. No. 5,122,614, WO 90/13540, U.S. Pat. No. 5,281,698, and more WO 93/15189, and for conjugation between activated polymers and peptides, e.g. Coagulation Factor VIII (WO 94/15625), hemoglobin (WO 94/09027), oxygen carrying molecule (U.S. Pat. No. 4,412,989), ribonuclease and superoxide dismutase (Veronese at al., *App. Biochem. Biotech.* 11: 141-45 (1985)).

Preferred water-soluble polymers are those in which a substantial proportion of the polymer molecules in a sample of the polymer are of approximately the same molecular weight; such polymers are "homodisperse."

The present invention is further illustrated by reference to a poly(ethylene glycol) conjugate. Several reviews and monographs on the functionalization and conjugation of PEG are available. See, for example, Harris, *Macronol. Chem. Phys.* C25: 325-373 (1985); Scouten, *Methods in Enzymology* 135: 30-65 (1987); Wong et al., *Enzyme Microb. Technol.* 14: 866-874 (1992); Delgado et al., *Critical Reviews in Therapeutic Drug Carrier Systems* 9: 249-304 (1992); Zalipsky, *Bioconjugate Chem.* 6: 150-165 (1995); and Bhadra, et al., *Pharmazie,* 57:5-29 (2002).

Poly(ethylene glycol) molecules suitable for use in the invention include, but are not limited to, those described by the following Formula 3:

Formula 3

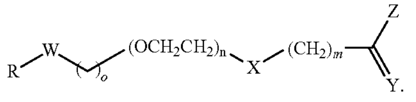

R=H, alkyl, benzyl, aryl, acetal, OHC—, $H_2N—CH_2CH_2—$, $HS—CH_2CH_2—$,

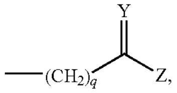

-sugar-nucleotide, protein, methyl, ethyl;

X, Y, W, U (independently selected)=O, S, NH, N—R';

R', R''' (independently selected)=alkyl, benzyl, aryl, alkyl aryl, pyridyl, substituted aryl, arylalkyl, acylaryl;

n=1 to 2000;

m, q, p (independently selected)=0 to 20 o=0 to 20;

Z=HO, $NH_2$, halogen, S—R''', activated esters,

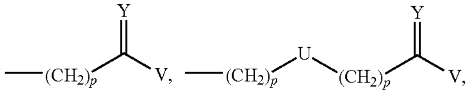

-sugar-nucleotide, protein, imidazole, HOBT, tetrazole, halide; and V=HO, $NH_2$, halogen, S—R''', activated esters, activated amides, -sugar-nucleotide, protein.

In preferred embodiments, the poly(ethylene glycol) molecule is selected from the following:

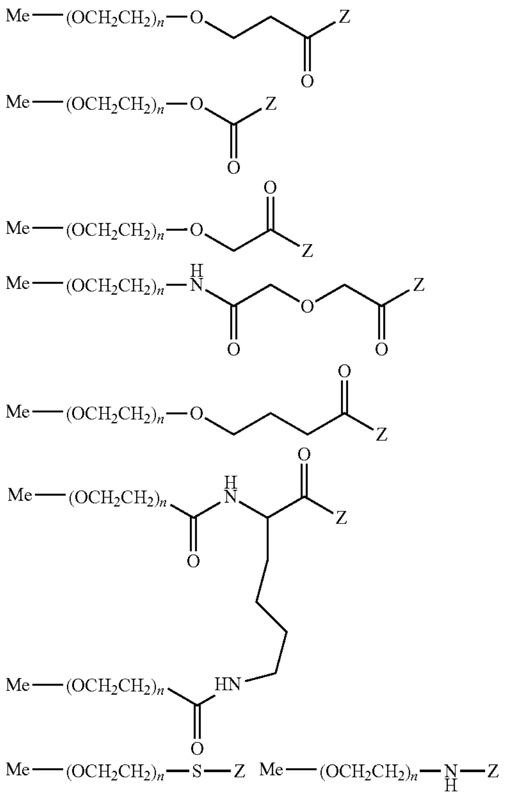

The poly(ethylene glycol) useful in forming the conjugate of the invention is either linear or branched. Branched poly (ethylene glycol) molecules suitable for use in the invention include, but are not limited to, those described by the following Formula:

Formula 4:

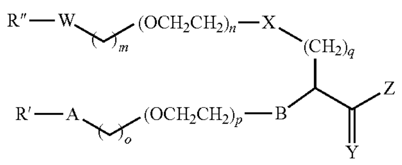

R', R'', R''' (independently selected)=H, alkyl, benzyl, aryl, acetal, OHC—, $H_2N—CH_2CH_2—$, $HS—CH^2CH_2—$, $—(CH_2)_qCY—Z$, -sugar-nucleotide, protein, methyl, ethyl, heteroaryl, acylalkyl, acylaryl, acylalkylaryl;

X, Y, W, A, B (independently selected)=O, S, NH, N—R', $(CH_2)_l$;

n, p (independently selected)=1 to 2000;

m, q, o (independently selected)=0 to 20;

Z=HO, $NH_2$, halogen, S—R''', activated esters,

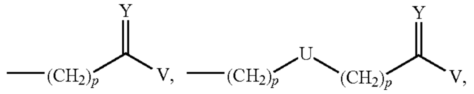

-sugar-nucleotide, protein;

V=HO, $NH_2$, halogen, S—R''', activated esters, activated amides,

-sugar-nucleotide, protein.

The in vivo half-life, area under the curve, and/or residence time of therapeutic peptides can also be enhanced with water-soluble polymers such as polyethylene glycol (PEG) and polypropylene glycol (PPG). For example, chemical modification of proteins with PEG (PEGylation) increases their molecular size and decreases their surface- and functional group-accessibility, each of which are dependent on the size of the PEG attached to the protein. This results in an improvement of plasma half-lives and in proteolytic-stability, and a decrease in immunogenicity and hepatic uptake (Chaffee et al. *J. Clin. Invest.* 89: 1643-1651 (1992); Pyatak et al. *Res. Commun. Chem. Pathol Pharmacol.* 29: 113-127 (1980)). PEGylation of interleukin-2 has been reported to increase its antitumor potency in vivo (Katre et al. *Proc. Natl. Acad. Sci. USA.* 84: 1487-1491 (1987)) and PEGylation of a F(ab')2 derived from the monoclonal antibody A7 has improved its tumor localization (Kitamura et al. *Biochem. Biophys. Res. Commun.* 28: 1387-1394 (1990)).

In one preferred embodiment, the in vivo half-life of a peptide derivatized with a water-soluble polymer by a method of the invention is increased relevant to the in vivo half-life of the non-derivatized peptide. In another preferred embodiment, the area under the curve of a peptide derivatized with a water-soluble polymer using a method of the invention is increased relevant to the area under the curve of the non-derivatized peptide. In another preferred embodiment, the residence time of a peptide derivatized with a water-soluble polymer using a method of the invention is increased relevant to the residence time of the non-derivatized peptide. Techniques to determine the in vivo half-life, the area under the curve and the residence time are well known in the art. Descriptions of such techniques can be found in J. G. Wagner, 1993, Pharmacokinetics for the Pharmaceutical Scientist, Technomic Publishing Company, Inc. Lancaster Pa.

The increase in peptide in vivo half-life is best expressed as a range of percent increase in this quantity. The lower end of the range of percent increase is about 40%, about 60%, about 80%, about 100%, about 150% or about 200%. The upper end of the range is about 60%, about 80%, about 100%, about 150%, or more than about 250%.

In an exemplary embodiment, the present invention provides a PEGylated follicle stimulating hormone (Examples 23 and 24). In a further exemplary embodiment, the invention provides a PEGylated transferrin (Example 42).

Other exemplary water-soluble polymers of use in the invention include, but are not limited to linear or branched poly(alkylene oxides), poly(oxyethylated polyols), poly(olefinic alcohols), and poly(acrylomorpholine), dextran, starch, poly(amino acids), etc.

b) Water-Insoluble Polymers

The conjugates of the invention may also include one or more water-insoluble polymers. This embodiment of the invention is illustrated by the use of the conjugate as a vehicle with which to deliver a therapeutic peptide in a controlled manner. Polymeric drug delivery systems are known in the art. See, for example, Dunn et al., Eds. Polymeric Drugs And Drug Delivery Systems, ACS Symposium Series Vol. 469, American Chemical Society, Washington, D.C. 1991. Those of skill in the art will appreciate that substantially any known drug delivery system is applicable to the conjugates of the present invention.

Representative water-insoluble polymers include, but are not limited to, polyphosphazines, poly(vinyl alcohols), polyamides, polycarbonates, polyalkylenes, polyacrylamides, polyalkylene glycols, polyalkylene oxides, polyalkylene terephthalates, polyvinyl ethers, polyvinyl esters, polyvinyl halides, polyvinylpyrrolidone, polyglycolides, polysiloxanes, polyurethanes, poly(methyl methacrylate), poly(ethyl methacrylate), poly(butyl methacrylate), poly (isobutyl methacrylate), poly(hexyl methacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate) polyethylene, polypropylene, poly(ethylene glycol), poly(ethylene oxide), poly (ethylene terephthalate), poly(vinyl acetate), polyvinyl chloride, polystyrene, polyvinyl pyrrolidone, pluronics and polyvinylphenol and copolymers thereof.

Synthetically modified natural polymers of use in conjugates of the invention include, but are not limited to, alkyl celluloses, hydroxyalkyl celluloses, cellulose ethers, cellulose esters, and nitrocelluloses. Particularly preferred members of the broad classes of synthetically modified natural polymers include, but are not limited to, methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, carboxymethyl cellulose, cellulose triacetate, cellulose sulfate sodium salt, and polymers of acrylic and methacrylic esters and alginic acid.

These and the other polymers discussed herein can be readily obtained from commercial sources such as Sigma Chemical Co. (St. Louis, Mo.), Polysciences (Warrenton, Pa.), Aldrich (Milwaukee, Wis.), Fluka (Ronkonkoma, N.Y.), and BioRad (Richmond, Calif.), or else synthesized from monomers obtained from these suppliers using standard techniques. Representative biodegradable polymers of use in the conjugates of the invention include, but are not limited to, polylactides, polyglycolides and copolymers thereof, poly (ethylene terephthalate), poly(butyric acid), poly(valeric acid), poly(lactide-co-caprolactone), poly(lactide-co-glycolide), polyanhydrides, polyorthoesters, blends and copolymers thereof. Of particular use are compositions that form gels, such as those including collagen, pluronics and the like.

The polymers of use in the invention include "hybrid' polymers that include water-insoluble materials having within at least a portion of their structure, a bioresorbable molecule. An example of such a polymer is one that includes a water-insoluble copolymer, which has a bioresorbable region, a hydrophilic region and a plurality of crosslinkable functional groups per polymer chain.

For purposes of the present invention, "water-insoluble materials" includes materials that are substantially insoluble in water or water-containing environments. Thus, although certain regions or segments of the copolymer may be hydrophilic or even water-soluble, the polymer molecule, as a whole, does not to any substantial measure dissolve in water. For purposes of the present invention, the term "bioresorbable molecule" includes a region that is capable of being metabolized or broken down and resorbed and/or eliminated through normal excretory routes by the body. Such metabolites or break down products are preferably substantially non-toxic to the body.

The bioresorbable region may be either hydrophobic or hydrophilic, so long as the copolymer composition as a whole is not rendered water-soluble. Thus, the bioresorbable region is selected based on the preference that the polymer, as a whole, remains water-insoluble. Accordingly, the relative properties, i.e., the kinds of functional groups contained by, and the relative proportions of the bioresorbable region, and the hydrophilic region are selected to ensure that useful bioresorbable compositions remain water-insoluble.

Exemplary resorbable polymers include, for example, synthetically produced resorbable block copolymers of poly(α-hydroxy-carboxylic acid)/poly(oxyalkylene, (see, Cohn et al., U.S. Pat. No. 4,826,945). These copolymers are not crosslinked and are water-soluble so that the body can excrete the degraded block copolymer compositions. See, Younes et al., *J. Biomed. Mater. Res.* 21: 1301-1316 (1987); and Cohn et al., *J. Biomed. Mater. Res.* 22: 993-1009 (1988).

Presently preferred bioresorbable polymers include one or more components selected from poly(esters), poly(hydroxy acids), poly(lactones), poly(amides), poly(ester-amides), poly (amino acids), poly(anhydrides), poly(orthoesters), poly (carbonates), poly(phosphazines), poly(phosphoesters), poly (thioesters), polysaccharides and mixtures thereof. More preferably still, the biosresorbable polymer includes a poly (hydroxy) acid component. Of the poly(hydroxy) acids, polylactic acid, polyglycolic acid, polycaproic acid, polybutyric acid, polyvaleric acid and copolymers and mixtures thereof are preferred.

In addition to forming fragments that are absorbed in vivo ("bioresorbed"), preferred polymeric coatings for use in the methods of the invention can also form an excretable and/or metabolizable fragment.

Higher order copolymers can also be used in the present invention. For example, Casey et al., U.S. Pat. No. 4,438,253, which issued on Mar. 20, 1984, discloses tri-block copolymers produced from the transesterification of poly(glycolic acid) and an hydroxyl-ended poly(alkylene glycol). Such compositions are disclosed for use as resorbable monofilament sutures. The flexibility of such compositions is controlled by the incorporation of an aromatic orthocarbonate, such as tetra-p-tolyl orthocarbonate into the copolymer structure.

Other coatings based on lactic and/or glycolic acids can also be utilized. For example, Spinu, U.S. Pat. No. 5,202,413, which issued on Apr. 13, 1993, discloses biodegradable multi-block copolymers having sequentially ordered blocks of polylactide and/or polyglycolide produced by ring-opening polymerization of lactide and/or glycolide onto either an oligomeric diol or a diamine residue followed by chain extension with a di-functional compound, such as, a diisocyanate, diacylchloride or dichlorosilane.

Bioresorbable regions of coatings useful in the present invention can be designed to be hydrolytically and/or enzymatically cleavable. For purposes of the present invention, "hydrolytically cleavable" refers to the susceptibility of the copolymer, especially the bioresorbable region, to hydrolysis in water or a water-containing environment. Similarly, "enzymatically cleavable" as used herein refers to the susceptibility of the copolymer, especially the bioresorbable region, to cleavage by endogenous or exogenous enzymes.

When placed within the body, the hydrophilic region can be processed into excretable and/or metabolizable fragments. Thus, the hydrophilic region can include, for example, polyethers, polyalkylene oxides, polyols, poly(vinyl pyrrolidine), poly(vinyl alcohol), poly(alkyl oxazolines), polysaccharides, carbohydrates, peptides, proteins and copolymers and mixtures thereof. Furthermore, the hydrophilic region can also be, for example, a poly(alkylene) oxide. Such poly(alkylene) oxides can include, for example, poly(ethylene) oxide, poly (propylene) oxide and mixtures and copolymers thereof.

Polymers that are components of hydrogels are also useful in the present invention. Hydrogels are polymeric materials that are capable of absorbing relatively large quantities of water. Examples of hydrogel forming compounds include, but are not limited to, polyacrylic acids, sodium carboxymethylcellulose, polyvinyl alcohol, polyvinyl pyrrolidine, gelatin, carrageenan and other polysaccharides, hydroxyethylenemethacrylic acid (HEMA), as well as derivatives thereof, and the like. Hydrogels can be produced that are stable, biodegradable and bioresorbable. Moreover, hydrogel compositions can include subunits that exhibit one or more of these properties.

Bio-compatible hydrogel compositions whose integrity can be controlled through crosslinking are known and are presently preferred for use in the methods of the invention. For example, Hubbell et al., U.S. Pat. Nos. 5,410,016, which issued on Apr. 25, 1995 and 5,529,914, which issued on Jun. 25, 1996, disclose water-soluble systems, which are crosslinked block copolymers having a water-soluble central block segment sandwiched between two hydrolytically labile extensions. Such copolymers are further end-capped with photopolymerizable acrylate functionalities. When crosslinked, these systems become hydrogels. The water soluble central block of such copolymers can include poly (ethylene glycol); whereas, the hydrolytically labile extensions can be a poly($\alpha$-hydroxy acid), such as polyglycolic acid or polylactic acid. See, Sawhney et al., *Macromolecules* 26: 581-587 (1993).

In another preferred embodiment, the gel is a thermoreversible gel. Thermoreversible gels including components, such as pluronics, collagen, gelatin, hyalouronic acid, polysaccharides, polyurethane hydrogel, polyurethane-urea hydrogel and combinations thereof are presently preferred.

In yet another exemplary embodiment, the conjugate of the invention includes a component of a liposome. Liposomes can be prepared according to methods known to those skilled in the art, for example, as described in Eppstein et al., U.S. Pat. No. 4,522,811, which issued on Jun. 11, 1985. For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound or its pharmaceutically acceptable salt is then introduced into the container. The container is then swirled by hand to free lipid material from the sides of the container and to disperse lipid aggregates, thereby forming the liposomal suspension.

The above-recited microparticles and methods of preparing the microparticles are offered by way of example and they are not intended to define the scope of microparticles of use in the present invention. It will be apparent to those of skill in the art that an array of microparticles, fabricated by different methods, are of use in the present invention.

c) Biomolecules

In another preferred embodiment, the modified sugar bears a biomolecule. In still further preferred embodiments, the biomolecule is a functional protein, enzyme, antigen, antibody, peptide, nucleic acid (e.g., single nucleotides or nucleosides, oligonucleotides, polynucleotides and single- and higher-stranded nucleic acids), lectin, receptor or a combination thereof.

Some preferred biomolecules are essentially non-fluorescent, or emit such a minimal amount of fluorescence that they are inappropriate for use as a fluorescent marker in an assay. Other biomolecules may be fluorescent. The use of an otherwise naturally occurring sugar that is modified by covalent attachment of another entity (e.g., PEG, biomolecule, therapeutic moiety, diagnostic moiety, etc.) is appropriate. In an exemplary embodiment, a sugar moiety, which is a biomolecule, is conjugated to a linker arm and the sugar-linker arm cassette is subsequently conjugated to a peptide via a method of the invention.

Biomolecules useful in practicing the present invention can be derived from any source. The biomolecules can be isolated from natural sources or they can be produced by synthetic methods. Peptides can be natural peptides or mutated peptides. Mutations can be effected by chemical mutagenesis, site-directed mutagenesis or other means of inducing mutations known to those of skill in the art. Peptides useful in practicing the instant invention include, for example, enzymes, antigens, antibodies and receptors. Antibodies can be either polyclonal or monoclonal; either intact or fragments. The peptides are optionally the products of a program of directed evolution.

Both naturally derived and synthetic peptides and nucleic acids are of use in conjunction with the present invention; these molecules can be attached to a sugar residue component or a crosslinking agent by any available reactive group. For example, peptides can be attached through a reactive amine, carboxyl, sulfhydryl, or hydroxyl group. The reactive group can reside at a peptide terminus or at a site internal to the peptide chain. Nucleic acids can be attached through a reactive group on a base (e.g., exocyclic amine) or an available hydroxyl group on a sugar moiety (e.g., 3'- or 5'-hydroxyl). The peptide and nucleic acid chains can be further derivatized at one or more sites to allow for the attachment of appropriate reactive groups onto the chain. See, Chrisey et al. *Nucleic Acids Res.* 24: 3031-3039 (1996).

In a further preferred embodiment, the biomolecule is selected to direct the peptide modified by the methods of the invention to a specific tissue, thereby enhancing the delivery of the peptide to that tissue relative to the amount of underivatized peptide that is delivered to the tissue. In a still further preferred embodiment, the amount of derivatized peptide delivered to a specific tissue within a selected time period is enhanced by derivatization by at least about 20%, more preferably, at least about 40%, and more preferably still, at least about 100%. Presently, preferred biomolecules for targeting applications include antibodies, hormones and ligands for cell-surface receptors. Exemplary targeting biomolecules include, but are not limited to, an antibody specific for the transferrin receptor for delivery of the molecule to the brain (Penichet et al., 1999, J. Immunol. 163:4421-4426; Pardridge, 2002, Adv. Exp. Med. Biol. 513:397-430), a peptide that recognizes the vasculature of the prostate (Arap et al., 2002, PNAS 99:1527-1531), and an antibody specific for lung caveolae (McIntosh et al., 2002, PNAS 99:1996-2001).

In a presently preferred embodiment, the modifying group is a protein. In an exemplary embodiment, the protein is an interferon. The interferons are antiviral glycoproteins that, in humans, are secreted by human primary fibroblasts after induction with virus or double-stranded RNA. Interferons are of interest as therapeutics, e.g., antivirals and treatment of multiple sclerosis. For references discussing interferon-β, see, e.g., Yu, et al., *J. Neuroimmunol.,* 64(1):91-100 (1996); Schmidt, J., *J. Neurosci. Res.,* 65(1):59-67 (2001); Wender, et al., *Folia Neuropathol.,* 39(2):91-93 (2001); Martin, et al., *Springer Semin. Immunopathol.,* 18(1):1-24 (1996); Takane, et al., *J. Pharmacol. Exp. Ther.,* 294(2):746-752 (2000); Sburlati, et al., *Biotechnol. Prog.,* 14:189-192 (1998); Dodd, et al., *Biochimica et Biophysica Acta,* 787:183-187 (1984); Edelbaum, et al., *J. Interferon Res.,* 12:449-453 (1992); Conradt, et al., *J. Biol. Chem.,* 262(30):14600-14605 (1987); Civas, et al., *Eur. J. Biochem.,* 173:311-316 (1988); Demolder, et al., *J. Biotechnol.,* 32:179-189 (1994); Sedmak, et al., *J. Interferon Res.,* 9(Suppl 1):S61-S65 (1989); Kagawa, et al., *J. Biol. Chem.,* 263(33):17508-17515 (1988); Hershenson, et al., U.S. Pat. No. 4,894,330; Jayaram, et al., *J. Interferon Res.,* 3(2):177-180 (1983); Menge, et al., *Develop. Biol. Standard.,* 66:391-401 (1987); Vonk, et al., *J. Interferon Res.,* 3(2):169-175 (1983); and Adolf, et al., *J. Interferon Res.,* 10:255-267 (1990). For references relevant to interferon-α, see, Asano, et al., *Eur. J. Cancer,* 27(Suppl 4):S21-S25 (1991); Nagy, et al., *Anticancer Research,* 8(3):467-470 (1988); Dron, et al., *J. Biol. Regul. Homeost. Agents,* 3(1):13-19 (1989); Habib, et al., *Am. Surg.,* 67(3):257-260 (March 2001); and Sugyiama, et al., *Eur. J. Biochem.,* 217:921-927 (1993).

In an exemplary interferon conjugate, interferon β is conjugated to a second peptide via a linker arm. The linker arm includes an intact glycosyl linking group through which it is attached to the second peptide via a method of the invention. The linker arm also optionally includes a second intact glycosyl linking group, through which it is attached to the interferon. In another exemplary embodiment, the invention provides a conjugate of follicle stimulating hormone (FSH). FSH is a glycoprotein hormone. See, for example, Saneyoshi, et al., *Biol. Reprod.,* 65:1686-1690 (2001); Hakola, et al., *J. Endocrinol.,* 158:441-448 (1998); Stanton, et al., *Mol. Cell. Endocrinol.,* 125:133-141 (1996); Walton, et al., *J. Clin. Endocrinol. Metab.,* 86(8):3675-3685 (August 2001); Ulloa-Aguirre, et al., *Endocrine,* 11(3):205-215 (December 1999); Castro-Fernández, et al. *J. Clin. Endocrinol. Matab.,* 85(12):4603-4610 (2000); Prevost, Rebecca R., *Pharmacotherapy,* 18(5):1001-1010 (1998); Linskens, et al., *The FASEB Journal,* 13:639-645 (April 1999); Butnev, et al., *Biol. Reprod.,* 58:458-469 (1998); Muyan, et al., *Mol. Endo.,* 12(5):766-772 (1998); Min, et al., *Endo. J.,* 43(5):585-593 (1996); Boime, et al., *Recent Progress in Hormone Research,* 34:271-289 (1999); and Rafferty, et al., *J. Endo.,* 145:527-533 (1995). The FSH conjugate can be formed in a manner similar to that described for interferon.

In yet another exemplary embodiment, the conjugate includes erythropoietin (EPO). EPO is known to mediate response to hypoxia and to stimulate the production of red blood cells. For pertinent references, see, Cerami, et al., *Seminars in Oncology,* 28(2)(Suppl 8):66-70 (April 2001). An exemplary EPO conjugate is formed analogously to the conjugate of interferon.

In a further exemplary embodiment, the invention provides a conjugate of human granulocyte colony stimulating factor (G-CSF). G-CSF is a glycoprotein that stimulates proliferation, differentiation and activation of neutropoietic progenitor cells into functionally mature neutrophils. Injected G-CSF is known to be rapidly cleared from the body. See, for example, Nohynek, et al., *Cancer Chemother. Pharmacol.,* 39:259-266 (1997); Lord, et al., *Clinical Cancer Research,* 7(7):2085-2090 (July 2001); Rotondaro, et al., *Molecular Biotechnology,* 11(2):117-128 (1999); and Bönig, et al., *Bone Marrow Transplantation,* 28:259-264 (2001). An exemplary conjugate of G-CSF is prepared as discussed above for the conjugate of the interferons. One of skill in the art will appreciate that many other proteins may be conjugated to interferon using the methods and compositions of the invention, including but not limited to, the peptides listed in Tables 7 and 8 (presented elsewhere herein) and FIG. 28, and in FIGS. 29-57, where individual modification schemes are presented.

In still a further exemplary embodiment, there is provided a conjugate with biotin. Thus, for example, a selectively biotinylated peptide is elaborated by the attachment of an avidin or streptavidin moiety bearing one or more modifying groups.

In a further preferred embodiment, the biomolecule is selected to direct the peptide modified by the methods of the invention to a specific intracellular compartment, thereby enhancing the delivery of the peptide to that intracellular compartment relative to the amount of underivatized peptide that is delivered to the tissue. In a still further preferred embodiment, the amount of derivatized peptide delivered to a specific intracellular compartment within a selected time period is enhanced by derivatization by at least about 20%, more preferably, at least about 40%; and more preferably still, at least about 100%. In another particularly preferred embodiment, the biomolecule is linked to the peptide by a cleavable linker that can hydrolyze once internalized. Presently, preferred biomolecules for intracellular targeting applications include transferrin, lactotransferrin (lactoferrin), melanotransferrin (p97), ceruloplasmin, and divalent cation transporter, as well as antibodies directed against specific vascular targets. Contemplated linkages include, but are not limited to, protein-sugar-linker-sugar-protein, protein-sugar-linker-protein and multivalent forms thereof, and protein-sugar-linker-drug where the drug includes small molecules, peptides, lipids, among others.

Site-specific and target-oriented delivery of therapeutic agents is desirable for the purpose of treating a wide variety of human diseases, such as different types of malignancies and certain neurological disorders. Such procedures are accompanied by fewer side effects and a higher efficiacy of drug. Various principles have been relied on in designing these delivery systems. For a review, see Garnett, *Advanced Drug Delivery Reviews* 53:171-216 (2001).

One important consideration in designing a drug delivery system to target tissues specifically. The discovery of tumor surface antigens has made it possible to develop therapeutic approaches where tumor cells displaying definable surface antigens are specifically targeted and killed. There are three main classes of therapeutic monoclonal antibodies (antibody) that have demonstrated effectiveness in human clinical trials in treating malignancies: (1) unconjugated MAb, which either directly induces growth inhibition and/or apoptosis, or indirectly activates host defense mechanisms to mediate antitumor cytotoxicity; (2) drug-conjugated MAb, which preferentially delivers a potent cytotoxic toxin to the tumor cells and therefore minimizes the systemic cytotoxicity commonly associated with conventional chemotherapy; and (3) radioisotope-conjugated MAb, which delivers a sterilizing dose of radiation to the tumor. See review by Reff et al., *Cancer Control* 9:152-166 (2002).

In order to arm MAbs with the power to kill malignant cells, the MAbs can be connected to a toxin, which may be obtained from a plant, bacterial, or fungal source, to form chimeric proteins called immunotoxins. Frequently used plant toxins are divided into two classes: (1) holotoxins (or class II ribosome inactivating proteins), such as ricin, abrin, mistletoe lectin, and modeccin, and (2) hemitoxins (class I ribosome inactivating proteins), such as pokeweed antiviral protein (PAP), saporin, Bryodin 1, bouganin, and gelonin. Commonly used bacterial toxins include diphtheria toxin (DT) and *Pseudomonas* exotoxin (PE). Kreitman, *Current Pharmaceutical Biotechnology* 2:313-325 (2001). Other toxins contemplated for use with the present invention include, but are not limited to, those in Table 2.

TABLE 2

Toxins

Chemical Structure

| Toxin Name/ Source/ Alternate ID | CAS RN/ Analogs | Indication/ Toxicity | Mechanism | Activity (IC50 nM); Tumor Type |
|---|---|---|---|---|
| 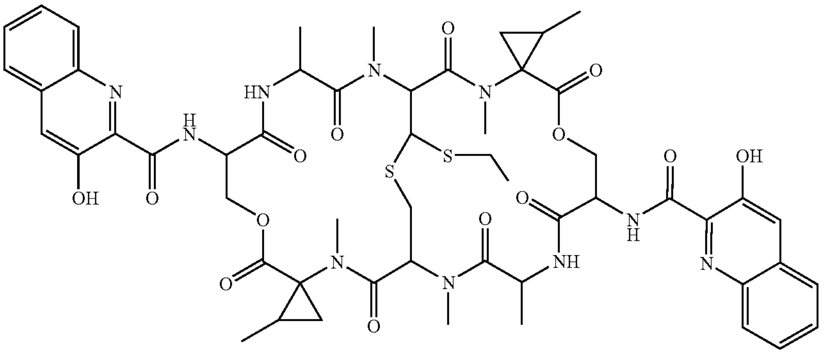 | | | | |
| SW-163E/ *Streptomyces* sp SNA 15896/ SW-163E | 260794-24-9; 260794-25-0/ SW-163C; SW-163A; SW-163B | Cancer and Antibacterial/ low toxicity (mice ip) | not reported | 0.3 P388 0.2 A2780 0.4 KB 1.6 colon 1.3 HL-60 |
| 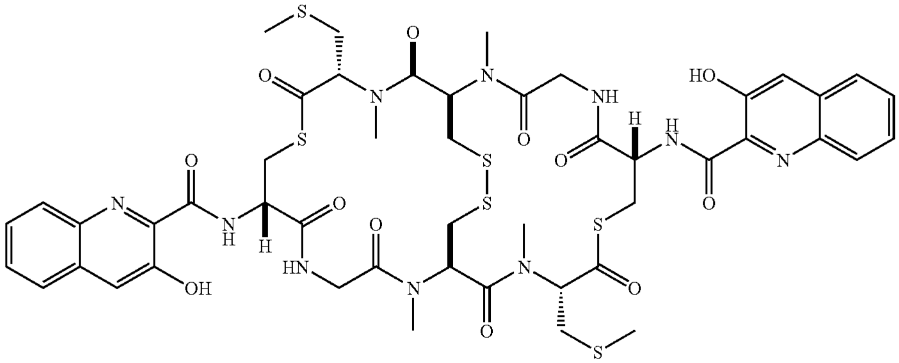 | | | | |
| Thiocoraline/ *Micromonospora marina* (actinomycete) | 173046-02-1 | Breast Cancer; Melanoma; Non-small lung cancer/ not reported | DNA Polymerase alpha inhibitor (blocks cell progression from G1 to S) | lung, colon, CNS melanoma |

TABLE 2-continued

| Toxins | | | | |
|---|---|---|---|---|
| Chemical Structure | | | | |
| Toxin Name/ Source/ Alternate ID | CAS RN/ Analogs | Indication/ Toxicity | Mechanism | Activity (IC50 nM); Tumor Type |
| 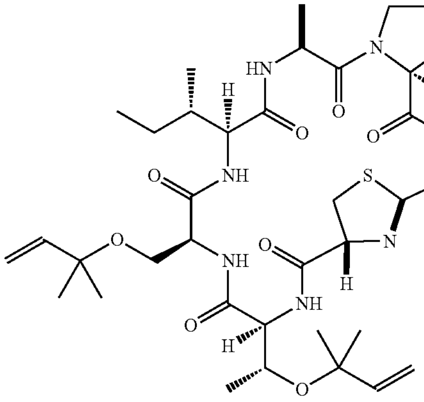 | | | | |
| Trunkamide A[1]/ *Lissoclinum* sp (aascidian) | 181758-83-8 | Cancer/ not reported | not reported | cell culture (IC50 in micrograms/mL); 0.5 P388; 0.5 A549; 0.5 HT-29; 1.0 MEL-28 |
| 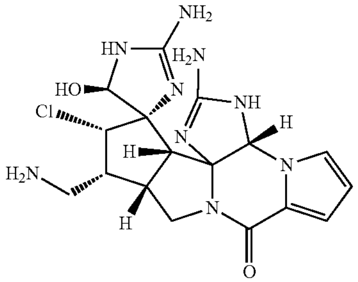 | | | | |
| Palauamine[2]/ *Stylotella agminata* (sponge) | 148717-58-2 | Lung cancer/ LD50 (i.p. in mice) is 13 mg/Kg | not reported | cell culture (IC50 in micrograms/mL); 0.1 P388 0.2 A549 (lung) 2 HT-29 (colon) 10 KB |
| 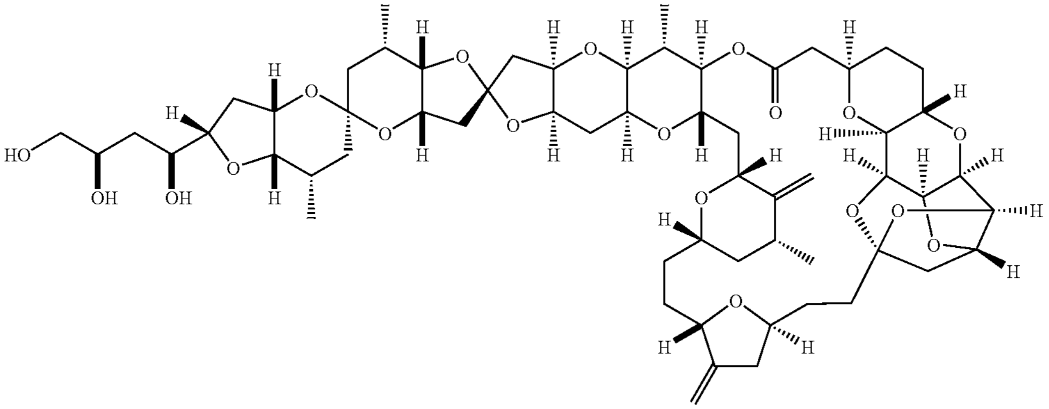 | | | | |
| Halichondrin B/ *Halichondria Okadai, Axinell Carteri* and *Phankell carteri* (sponges)/ NSC-609385 | 103614-76-2/ isohomohalic hondrin B | cancer/ myelotoxicity dose limiting (dogs, rats) | antitubulin; cell cycle inhibitor (inhibits GTP binding to tubulin) | NCI tumor panel; GI(50) from 50 nM to 0.1 nM; LC50's from 40 μM to 0.1 nM (many 0.1 to 25 nM) |

TABLE 2-continued

| Toxin Name/ Source/ Alternate ID | CAS RN/ Analogs | Indication/ Toxicity | Mechanism | Activity (IC50 nM); Tumor Type |
|---|---|---|---|---|
| Toxins | | | | |
| Chemical Structure | | | | |
| 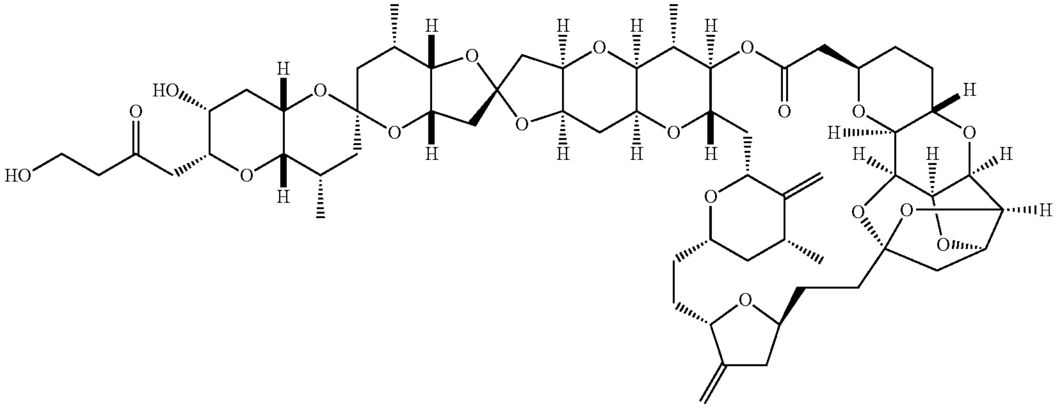 | | | | |
| Isohomo-halichondrin B/ *Halichondria Okadai*, *Axinell Carteri* and *Phankell carteri* (sponges)/ NSC-650467 | 157078-48-3/ halichondrin B | melanoma, lung, CNS colon, ovary/ not reported | antitubulin; cell cycle inhibitor (inhibits GTP binding to tubulin) | IC50's in 0.1 nM range (NCI tumor panel) |
| 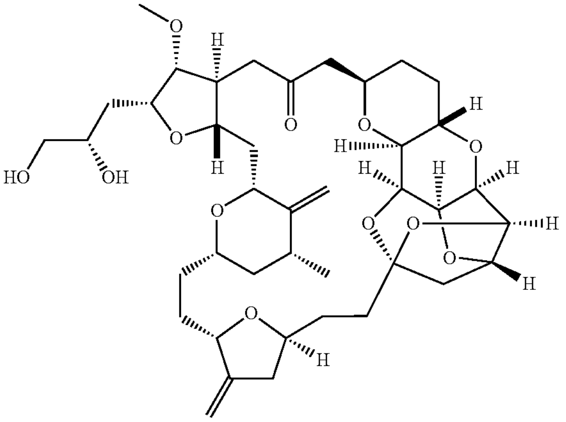 | | | | |
| Halichondrin B analogs/ semi-synthetic starting from *Halichondria Okadai*, *Axinell Carteri* and *Phankell carteri* (sponges)/ ER-076349; ER-086526; B-1793; E-7389 | 253128-15-3/ ER-076349; ER-086526; B-1793; E-7389 | solid tumors/ not reported | tubulin binding agent; disruption of mitotic spindles | cell culture (not reported); animal models active (tumor regression observed) in lymphoma, colon (multi-drug resistant). |

TABLE 2-continued

| Toxins | | | | |
|---|---|---|---|---|
| Chemical Structure | | | | |
| Toxin Name/ Source/ Alternate ID | CAS RN/ Analogs | Indication/ Toxicity | Mechanism | Activity (IC50 nM); Tumor Type |
| 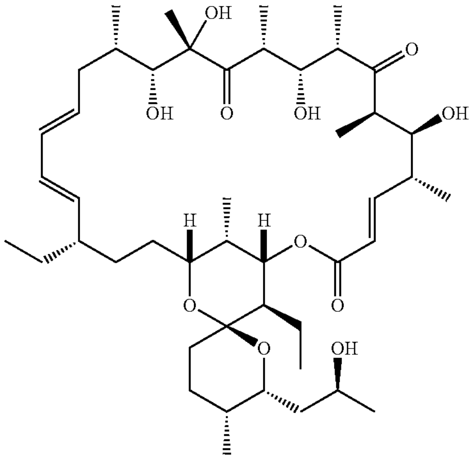 | | | | |
| NK-130119/ *Streptomyces bottropensis/* NK-130119 | 132707-68-7 | antifungal and anticancer/ not reported | not reported | 25 ng/mL colon 8.5 ng/mL lung |
| 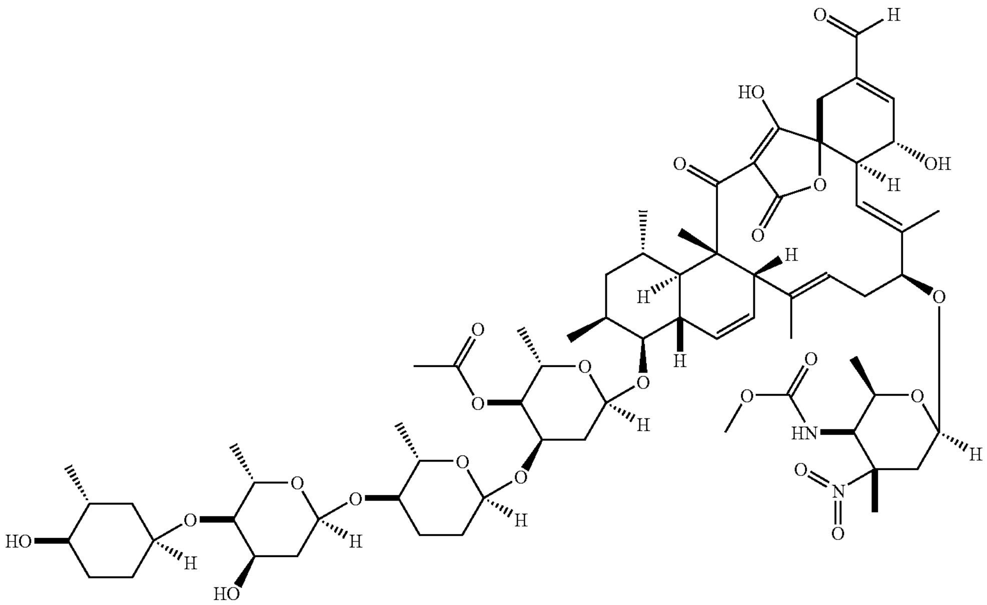 | | | | |
| Tetrocarcin A/ not reported/ KF-67544 | 73666-84-9/ analogs are reported | cancer/ not reported | inhibits the anti- apoptotic functino of Bc12 | not reported |

TABLE 2-continued

| Toxins | | | | |
|---|---|---|---|---|
| Chemical Structure | | | | |
| Toxin Name/ Source/ Alternate ID | CAS RN/ Analogs | Indication/ Toxicity | Mechanism | Activity (IC50 nM); Tumor Type |
| 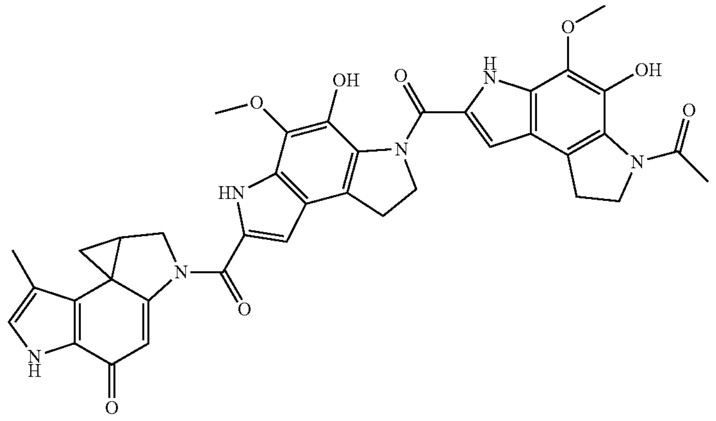 | | | | |
| Gilvusmycin/ *Streptomyces* QM16 | 195052-09-6 | cancer/ not reported | not reported | IC50's in ng/mL: 0.08 P388 0.86 K562 (CML) 0.72 A431 (EC) 0.75 MKN28 (GI); (for all < 1 nM) |
| 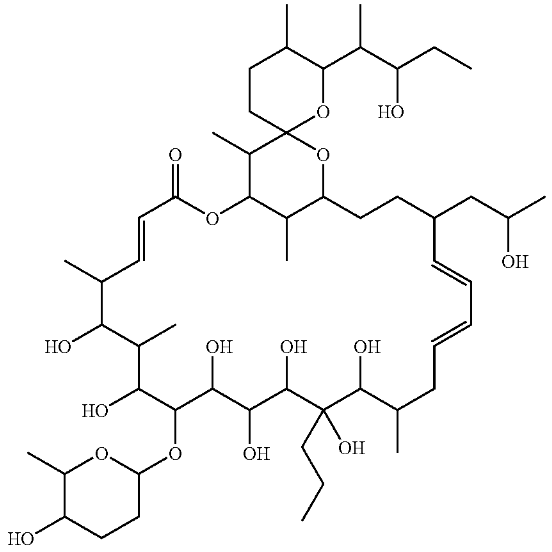 | | | | |
| IB-96212/ *marine actinomycete*/ IB-96212 | 220858-11-7/ IB-96212; IB-98214; IB-97227 | Cancer and Antibacterial/ not reported | not reported | IC50's in ng/mL: 0.1 P388 |

TABLE 2-continued

| Toxins | | | | |
|---|---|---|---|---|
| Chemical Structure | | | | |
| Toxin Name/ Source/ Alternate ID | CAS RN/ Analogs | Indication/ Toxicity | Mechanism | Activity (IC50 nM); Tumor Type |
| 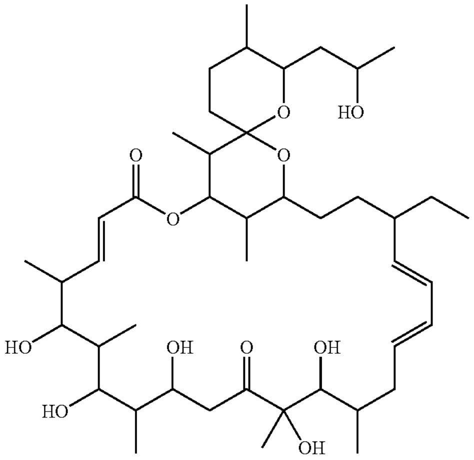 | | | | |
| BE-56384[3]/ *Streptomyces* Sp./ BE-56384 | 207570-04-5 | cancer/ not reported | not reported | IC50's in ng/mL: 0.1 P388 0.29 colon 26 34 DLD-1 0.12 PC-13 0.12 MKM-45 |
| 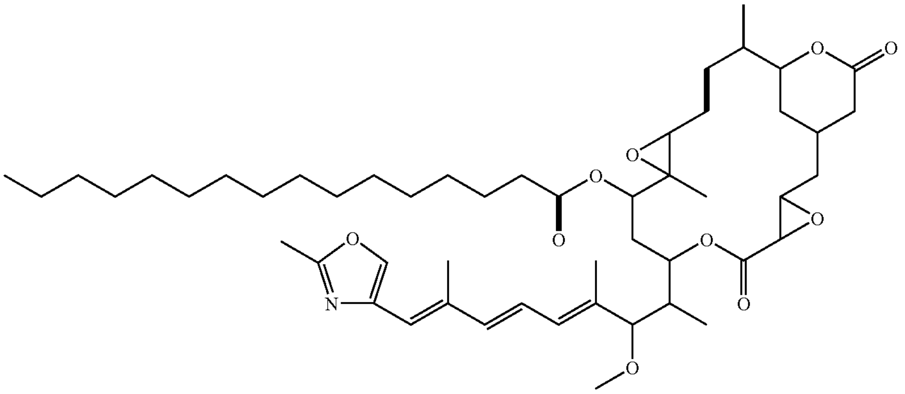 | | | | |
| Palmitoylrhizoxin/ semi-synthetic; *Rhizopus chinensis* | 135819-69-1/ Analog of rhizoxin | cancer/ binds LDL; less cytotoxic than rhizoxin | tubulin binding agent (cell cycle inhibitor) | not reported |

TABLE 2-continued

| Toxins | | | | |
|---|---|---|---|---|
| Chemical Structure | | | | |
| Toxin Name/ Source/ Alternate ID | CAS RN/ Analogs | Indication/ Toxicity | Mechanism | Activity (IC50 nM); Tumor Type |
| 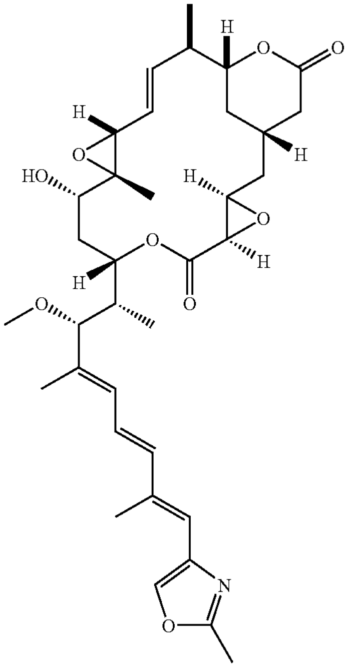 | | | | |
| Rhizoxin/ *Rhizopus chinensis*/ WF-1360; NSC-332598; FR-900216 | 95917-95-6; 90996-54-6 | melanoma, lung, CNS, colon, ovary, renal, breast, head and neck/ Rapid Drug clearance; High AUC correlates with high toxicity | tubulin binding agent (cell cycle inhibitor) | NCI tumor panel (NSC 332598); log GI50's: 50 nM to 50 fM; log LC50's: 50 μM to 0.5 nM (several cell lines at 50 fM). |
| 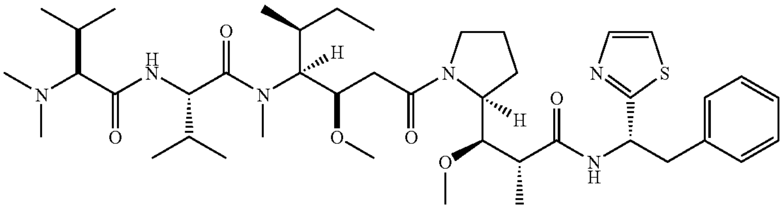 | | | | |
| Dolastatin-10/ *Dolabella auricularia* (sea hare)/ NSC-376128 | 110417-88-4/ other Dolistatins (ie. 15) and analogs | prostate, melanoma, leukemia/ myelotoxicity (at greater than 0.3 pM) | tubulin binding (tubulin aggregation) | NCI tumor panel (60 cell line; GI50); 25 nM to 1 pM (most < 1 nM) (three cell lines μM) |

TABLE 2-continued

| Toxin Name/ Source/ Alternate ID | CAS RN/ Analogs | Indication/ Toxicity | Mechanism | Activity (IC50 nM); Tumor Type |
|---|---|---|---|---|
| Toxins | | | | |
| Chemical Structure | | | | |
| 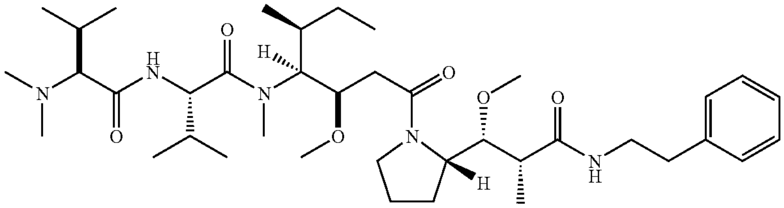 | | | | |
| soblidotin/ synthetic/ TZT-1027; auristatin PE | 149606-27-9/ analogs prepared | cancer (pancreas, esophageal colon, breast, lung, etc)/ MTD was 1.8 mg/Kg (IV); toxicity not reported | tubulin binding agent | cell culture: colon, melanoma, M5076 tumors, P388 with 75-85% inhibition (dose not reported) |
| 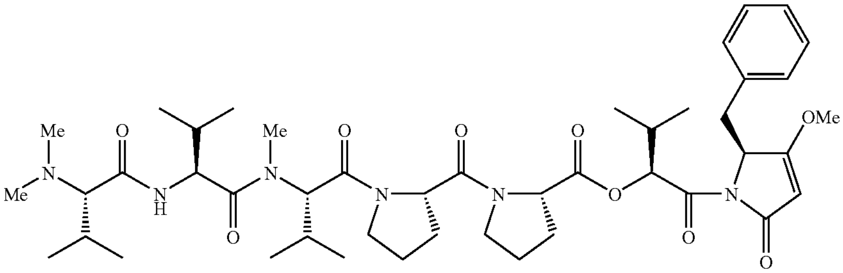 | | | | |
| Dolastatin-15/ *Dolabella auricularia* (sea hare) | not reported/ other Dolistatins (ie. 15) and analogs | cancer/ not reported | Tubulin binding (tubuline aggregation) | NCI tumor panel (60 cell line; GI50); 25 nM to 39 pM (most < 1 nM) (one cell line 2.5 μM); most active in breast |
| 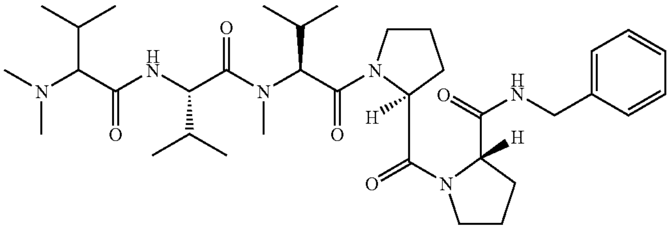 | | | | |
| Cemadotin[4]/ Synthetic; Parent Dolastatin-15 was isolated from *Dolabella auricularia* (sea hare)/ LU-103793; NSC D-669356 | 1159776-69-9/ many analogs | melanoma/ hypertension, myocardial ischemia and myelosuppression were dose-limiting toxicities. | tubulin binding (tubulin aggregation) | NCI tumore panel (NCS D-669356); active in breast, ovary, endometrial, sarcomas and drug resistant cell lines. Data not public. |

TABLE 2-continued

Toxins

Chemical Structure

| Toxin Name/ Source/ Alternate ID | CAS RN/ Analogs | Indication/ Toxicity | Mechanism | Activity (IC50 nM); Tumor Type |
|---|---|---|---|---|
| 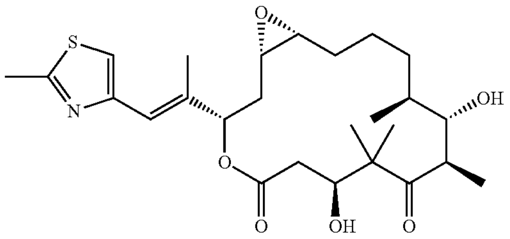 | | | | |
| Epothilone A/ Synthetic or isolated from *Sorangium cellulosum* (myxococcales) strain So ce90) | not reported/ many analogs | cancer/ not reported | tubulin binding (tubulin polymeriza-tion) | IC50's of; 1.5 nM MCF-7 (breast) 27.1 nM MCF-7/ADR 2.1 nM KB-31 (melanoma) 3.2 nM HCT-116 |
| 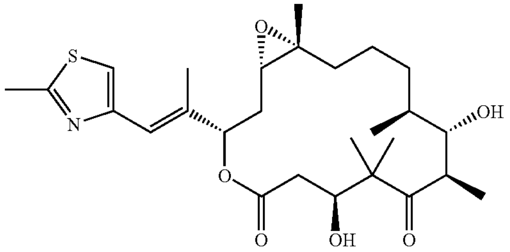 | | | | |
| Epothilone B/ Synthetic or isolated from *Sorangium cellulosum* (myxococcales) strain So ce90)/ EPO-906 | 152044054-7/ many analogs | Solid tumors (breast, ovarian, etc)/ well tolerated; t1/2 of 2.5 hrs; partial responses (phase I); diarrhea major side effect. | tubulin binding (tubulin polymeriza-tion) | IC50's of; 0.18 nM MCF-7 (breast) 2.92 nM MCF-7/ADR 0.19 nM KB-31 (melanoma) 0.42 nM HCT-116; broad activity reported |
| 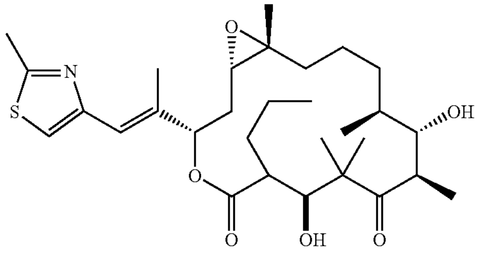 | | | | |
| Epothilone Analog/ Synthetic or semi-synthetic; Original lead, Epothilone A, isolated from *Sorangium cellulosum* (myxococcales) strain So ce90)/ ZK-EPO | not reported/ hundreds of analogs | cancer/ not reported | tubulin binding (tubulin polymeriza-tion) | IC50's of 0.30 to 1.80 nM in various tumor cell lines; active in drug resistant cell lines |

TABLE 2-continued

| Toxin Name/ Source/ Alternate ID | CAS RN/ Analogs | Indication/ Toxicity | Mechanism | Activity (IC50 nM); Tumor Type |
|---|---|---|---|---|
| Toxins | | | | |
| Chemical Structure | | | | |
| 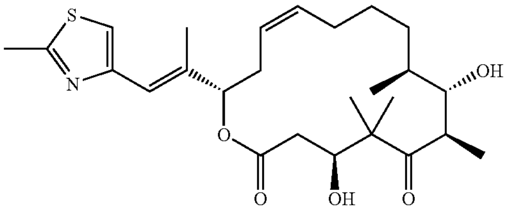 | | | | |
| Epothilone D/ Epothilone D, isolated from *Sorangium cellulosum* (myxococcales) strain So ce90)/ KOS-862 | 189452-10-9/ many analogs | Solid tumors (breast, ovarian, etc)/ emesis and anemia; t1/2 of 5-10 hrs. | tubulin binding (tubulin polymeriza-tion) | NCI tumor panel (NSC-703147; IC50); 0.19 nM KB-31 (melanoma) 0.42 nM HCT-116; broad activity reported |
| Structure Not Identified | | | | |
| Epothilone D analog[5]/ Synthetic or semi-synthetic; Original lead, Epothilone D, isolated from *Sorangium cellulosum* (myxococcales) strain So ce90)/ KOS-166-24 | 189453-10-9/ hundreds of analogs | Solid tumors; not reported | tubulin binding (tubulin polymeriza-tion) | not reported |
| 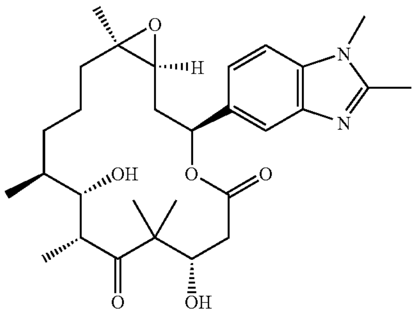 | | | | |
| Epothilone Analog/ Synthetic; Original lead, Epothilone A, isolated from *Sorangium cellulosum* (myxococcales) strain So ce90)/ CGP-85715 | not reported/ hundreds of analogs | cancer; not reported | tubulin binding (tubulin polymeriza-tion) | not reported |

TABLE 2-continued

Toxins

Chemical Structure

| Toxin Name/ Source/ Alternate ID | CAS RN/ Analogs | Indication/ Toxicity | Mechanism | Activity (IC50 nM); Tumor Type |
|---|---|---|---|---|
| 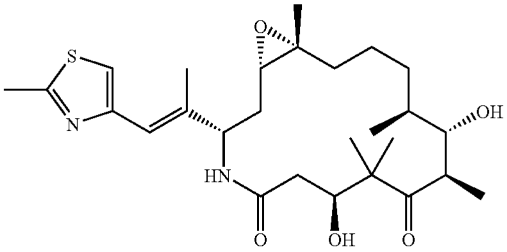 | | | | |
| Epothilone Analog/ Synthetic or semi-synthetic; Original lead, Epothilone B, isolated from *Sorangium cellulosum* (myxococcales) strain So ce90)/ BMS-247550 | 219989-84-1/ hundreds of analogs | non-small cell Lung, breast, stomach tumor (objective responses in breast ovarian and lung)/ sever toxicity (fatigue, anorexia, nauseas, vomiting, neuropathy myalgia) | tubulin binding (tubulin polymeriza-tion) | NCI tumor Panel (NSC-710428 & NSC-710468); 8-32 nM (NCI data not available) |
| 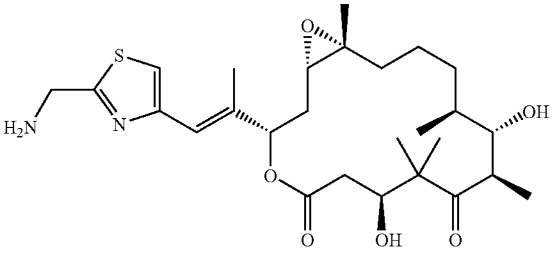 | | | | |
| Epothilone Analog/ Synthetic or semi-syntheitic; Original lead, Epothilone B, isolated from *Sorangium cellulosum* (myxococcales) strain So ce90)/ BMS-310705 | not reported/ hundreds of analogs | advanced cancers/ adverse events (diarrhea, nausea, vomiting, fatigue, neutropenia); t1/2 of 3.5 hrs; improved water solubility to BMS 247550. | tubulin binding (tubulin polymeriza-tion) | broad activity with IC50's of 0.7 to 10 nM |
| 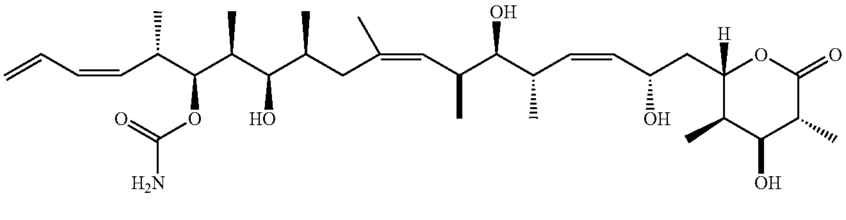 | | | | |
| Discodermolide/ synthetic; orginally isolated from *Discodermia dissoluta* (deep water sponge); rare compound (7 mg per 0.5 Kg sponge/ XAA-296 | 127943-53-7/ analogs less potent | solid tumors/ not reported; 100-fold increase in water solubility over taxol | tubulin stabilizing agent (similar to taxol) | Broad activity (A549-nsclung, prostate, P388, ovarian with IC50's about 10 nM) including multi-drug resistant cell lines; |

TABLE 2-continued

| Toxins | | | | |
|---|---|---|---|---|
| Chemical Structure | | | | |
| Toxin Name/ Source/ Alternate ID | CAS RN/ Analogs | Indication/ Toxicity | Mechanism | Activity (IC50 nM); Tumor Type |
| 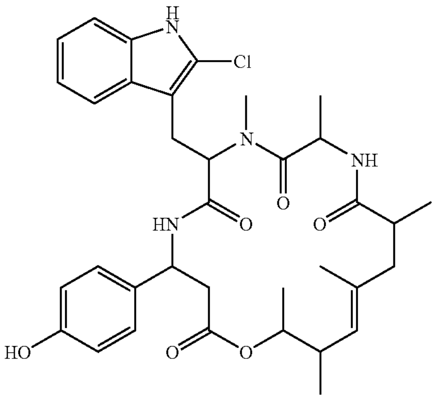 | | | | |
| Chondramide D/ not reported | 172430-63-6 | cancer/ not reported | tubulin binding agent; actin polymeriza-tion inhibitor | 5 nM A-549 (epidermoid carcinoma) 15 nM A-498 (kidney) 14 nM A549 (lung) 5 nM SK-OV-3 (ovary) 3 nM U-937 (lymphoma) |
| 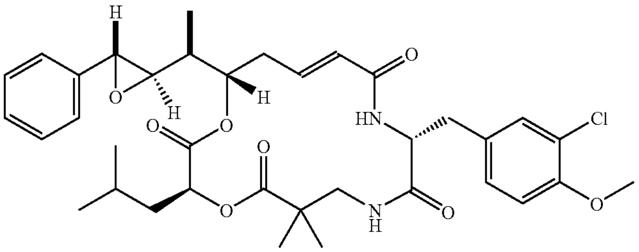 | | | | |
| Cryptophycin analogs (including 52, 55 and others)[6]/ *Nostoc* sp GSV 224 (blue-green algae) isolated Cryptophycin 1./ LY-355703; Ly-355702; NSC-667642 | 204990-60-3 and 186256-67-7/ many potent analogs prepared at Lilly | solid tumors, colon cancer/ Phase II studies halted because of severe toxicity with one death resulting from drug; | tubulin polymeriza-tion inhibitor | broad activity (lung, breast, colon, leukemia) with IC50's of 2 to 40 pM; active against multi-drug resistance cell lines (resistant to MDR pump). NCI tumor panel, GI50's from 100 nM to 10 pM; LC50's from 100 nM to 25 pM. |

TABLE 2-continued

| Toxins | | | | |
|---|---|---|---|---|
| Chemical Structure | | | | |
| Toxin Name/ Source/ Alternate ID | CAS RN/ Analogs | Indication/ Toxicity | Mechanism | Activity (IC50 nM); Tumor Type |
| 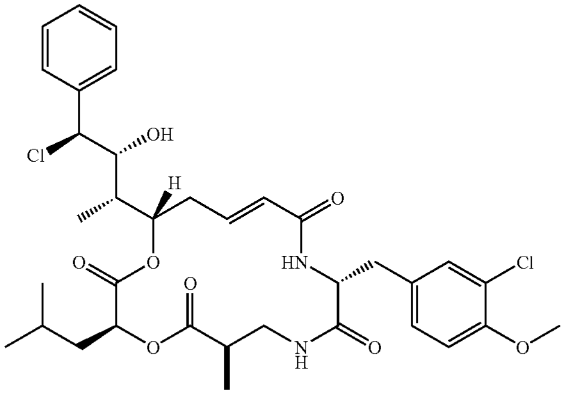 | | | | |
| Cryptophycin 8/ semi-synthetic; starting material from *Nostoc* sp. | 168482-36-8; 168482-40-4; 18665-94-1; 124689-65-2; 125546-14-7/ cryptophycin 5, 15 and 35 | solid tumors/ not reported | tubulin polymeriza-tion inhibitor | broad spectrum anticancer activity (cell culture) including multi-drug resistant tumors |
| 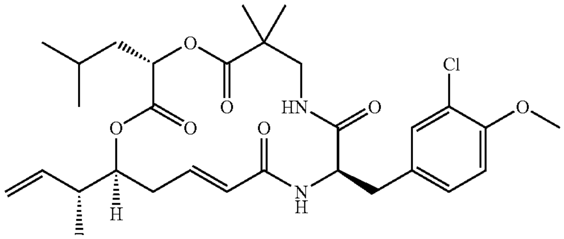 | | | | |
| Cryptophycin anaolgs[7]/ synthetic; semi-synthetic, starting material from *Nostoc* sp./ LY-404291 | 219660-54-5/ LY-404292 | solid tumors/ not reported | topoisomer-ase inhibitors | not reported |
| 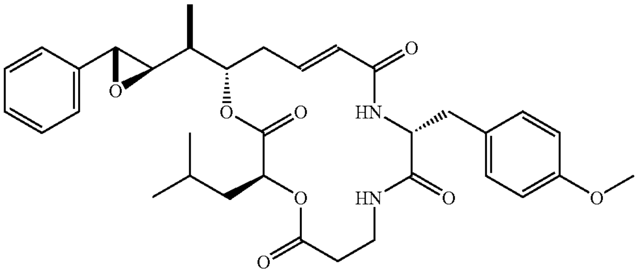 | | | | |
| Arenastatin A analogs[8]/ *Dysidea arenaria* (marine sponge)/ Cryptophycin B; NSC-670038 | not reported/ analogs prepared | cancer/ not repcorted | inhibits tubulin polymeriza-tion | 8.7 nM (5 pg/mL) KB (nasopharyngeal); NCI tumor panel (GI50's); 100 pM to 3 pM |

TABLE 2-continued

| Toxins | | | | |
|---|---|---|---|---|
| Chemical Structure | | | | |
| Toxin Name/ Source/ Alternate ID | CAS RN/ Analogs | Indication/ Toxicity | Mechanism | Activity (IC50 nM); Tumor Type |
| 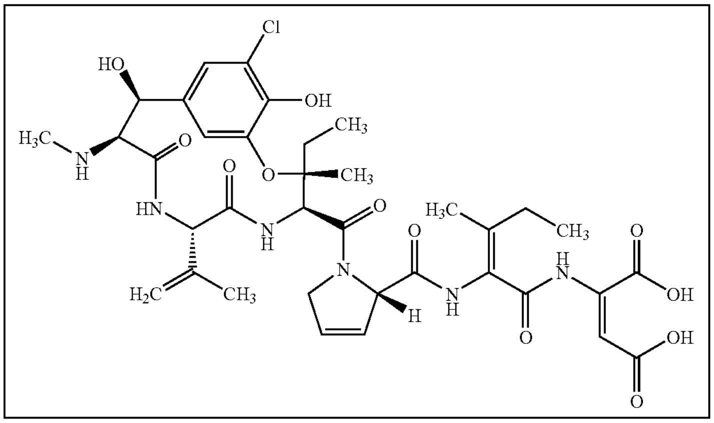 | | | | |
| Phomopsin A/ *Diaporte toxicus* or *Phomopsin leptostromiformis* (fungi) | not reported | Liver cancer (not as potent in other cancers)/ not reported | tubulin binding agent | potent anticancer activity especially against liver cancer |
| 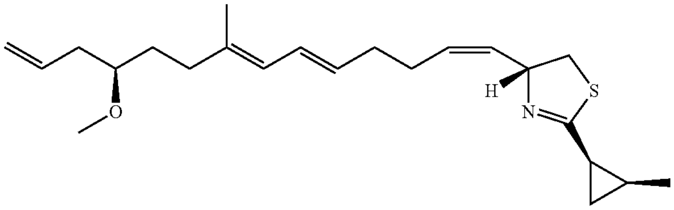 | | | | |
| Curacin A and analogs/ *Lyngbya majuscula* (blue green cyanobacterium) | 155233-30-0/ analogs have been prepared | Cancer/ not reported | Tubulin binding agent | broad activity (cancer cell lines); 1-29 nM |
| 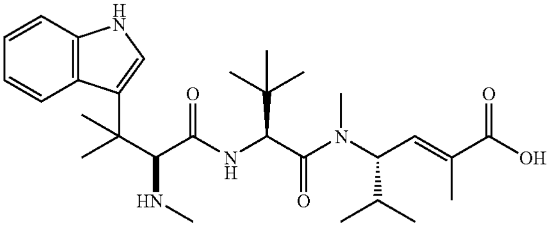 | | | | |
| Hemiasterlins A & B and analogs[9]/ *Cymbastela* sp. | not reported/ criamide A & B; geodiamiolid-G | Cancer/ not reported | Antimitotic agent (tubulin binding agent) | broad activity: 0.3-3 nM MCF7 (breast); 0.4 ng/mL P388 |

TABLE 2-continued

| Toxins | | | | |
|---|---|---|---|---|
| Chemical Structure | | | | |
| Toxin Name/ Source/ Alternate ID | CAS RN/ Analogs | Indication/ Toxicity | Mechanism | Activity (IC50 nM); Tumor Type |
| 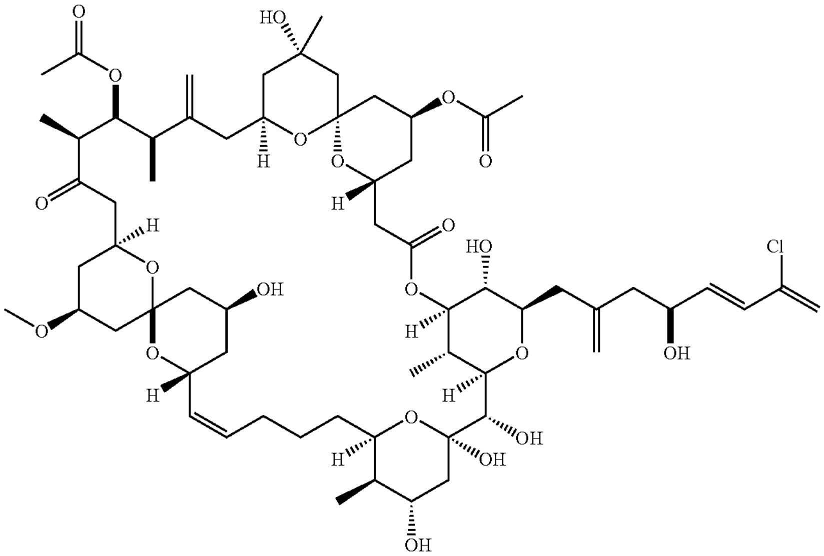 | | | | |
| Spongistatins (1-9)[10]/ *Spirastrell spinispirulifera* (sea sponge) | 149715-96-8; 158734-18-0; 158681-42-6; 158080-65-0; 150642-07-2; 153698-80-7; 153745-94-9; 150624-44-5; 158734-19-1/ other spongistatins | cancer/ not reported | tubulin binding agent | Most potent compounds ever tested in NCI panel cell line (mean GI50's of 0.1 nM; Spongistatin-1 GI50's of 0.025-0.035 nM with extremely potent activity against a subset of highly chemoresistant tumor types |
| 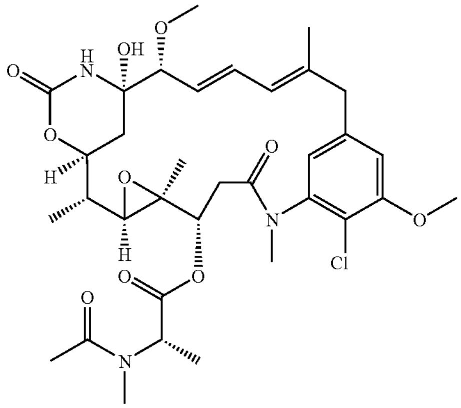 | | | | |
| Maytansine/ *Maytenus* sp./ NSC-153858 | 35846-53-8/ other related macrolides | cancer/ severe toxicity | tubulin binding agent (causes extensive disassembly of the microtubule and totally prevents tubulin spiralizaiton) | Broad Activity in NCI tumor panel (NSC-153858; NSC-153858); NCI tumor panel, GI50's from 3 μM to 0.1 pM; LC50's from 250 μM to 10 pM. Two different experiments gave very different potencies. |

TABLE 2-continued

| Toxin Name/ Source/ Alternate ID | CAS RN/ Analogs | Indication/ Toxicity | Mechanism | Activity (IC50 nM); Tumor Type |
|---|---|---|---|---|
| Toxins | | | | |
| Chemical Structure | | | | |
| 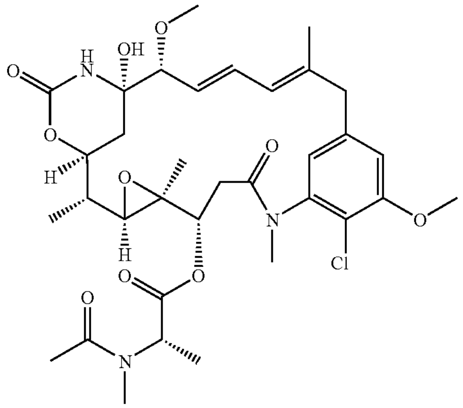 | | | | |
| Maytansine-IgG(EGFR directed)-conjugate[11]/ semi-synthetic; starting material from *Maytenus* sp. | not reported/ other related macrolides | breast, head and neck, Squamous cell carcinoma/ not reported | EGFR binding and tubulin binding | not reported |
| 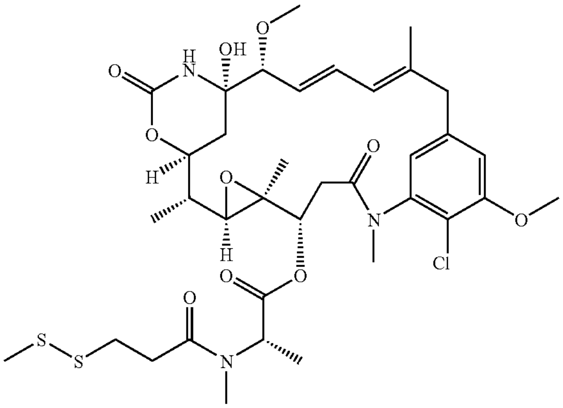 | | | | |
| Maytansine-IgG(CD56 antigen)-conjugate[12], 3.5 drug molecules per IgG/ semi-synthetic; starting material from *Maytenus* sp./ huN901-DM1 | not reported/ other related macrolides | Neuroendocrine, small-cell lung, carcinoma/ mild toxicity (fatigue, nausea, headaches and mild peripheral neuropathy); no hematological toxicity; MTD 60 mg/Kg, I.V., weekly for 4 weeks; only stable disease reported (humans) | CD56 binding and tubulin binding | antigen-specific cytotoxicity (cell culture; epidermal, breast, renal ovarian colon) with IC50's of 10-40 pM; animal studies (miceSCLC tumor--alone and in combination with taxol or cisplatin comletely eliminated tumors). |

TABLE 2-continued

| Toxins | | | | |
|---|---|---|---|---|
| Chemical Structure | | | | |
| Toxin Name/ Source/ Alternate ID | CAS RN/ Analogs | Indication/ Toxicity | Mechanism | Activity (IC50 nM); Tumor Type |
| 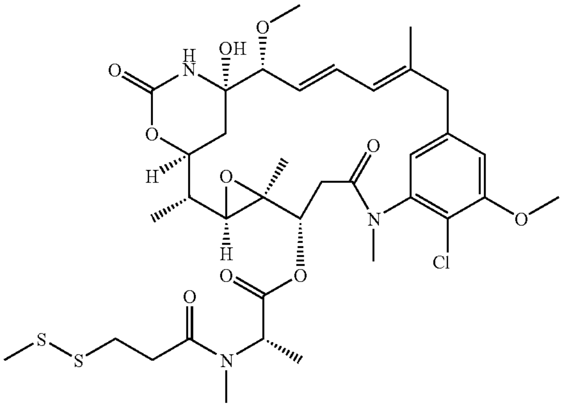 | | | | |
| Maytansine-IgG(CEA antigen)-conjugate[13], 4 drug molecules per IgG/ semi-synthetic; starting material from *Maytenus* sp./ C424-DM1 | not reported/ other related macrolides | non-small-cell lung, carcinoma pancreas, lung, colon/ mild toxicity (fatigue, nausea, heachaches and mild peripheral neuropathy); pancreatic lipase elevated; MTD 88 mg/Kg, I.V., every 21 days; only stable disease reported (humans); t1/2 was 44 hr. | CEA binding and tubulin binding | antigen-specific cytotoxicity (cell culture; epidermal, breast, renal ovarian colon) with IC50's of 10-40 pM; animal studies (mice: melanoma [COLO-205]--alone and in combination with taxol or cisplatin completely eliminated tumors); |
| 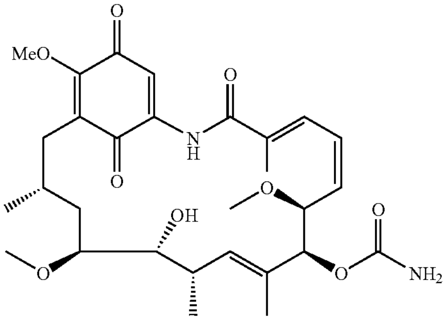 | | | | |
| Geldanamycin/*Streptomyces hygroscopicus* var. Geldanus NSC-212518; Antibiotic U 29135; NSC-122750 | 30562-34-6/ natural derivatives | cancer/ not reported | binds Hsp 90 chaperone and inhibits function | NCI tumor panel (cell culture); 5.3 to 100 nM; most active in colon, lung and leukemia. NCI tumor panel, GI50's from 10 μM to 0.1 nM; LC50's from 100 μM to 100 nM. Two assays with very different potencies. |

TABLE 2-continued

| Toxin Name/ Source/ Alternate ID | CAS RN/ Analogs | Indication/ Toxicity | Mechanism | Activity (IC50 nM); Tumor Type |
|---|---|---|---|---|
| | | Toxins | | |
| | | Chemical Structure | | |
| | | 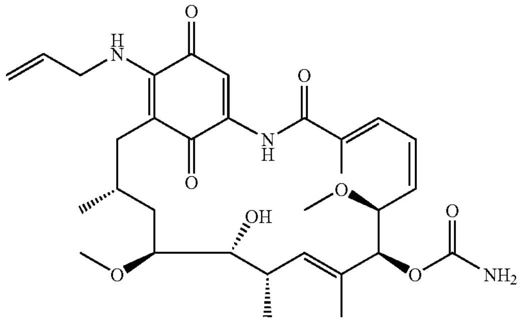 | | |
| Geldanamycin Analog/ semi-synthetic;/ CP-127374; 17-AAG; NSC-330507 | 745747-14-7/ Kosan, NCI and UK looking for analogs with longer t1/2 and oral activity; anaolgs include: NSC-255110; 682300; 683661; 683663. | solid tumors/ Dose limiting toxicites (anemia, anorexia, diarrhea, nausea and vomiting); t1/2 (i.v.) is about 90 min; no objective responses measured at 88 mg/Kg (i.v. daily for 5 days, every 21 days); | binds Hsp 90 chaperone and inhibits function | cell culture (not reported); animal models active (tumor regression observed) in breast, ovary, melanoma, colon. |
| | | 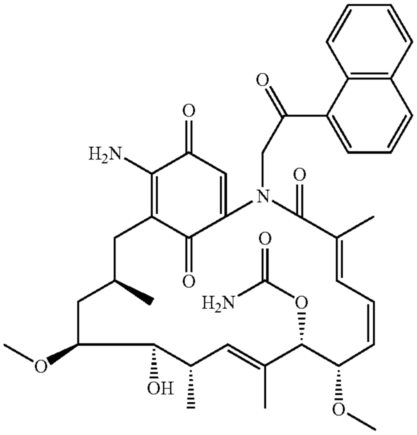 | | |
| Geldanamycin analog/ semi-synthetic;/ CP-202567 | not reported/ analogs prepared | solid tumors/ not reported | binds Hsp 90 chaperone and inhibits function | not reported |

TABLE 2-continued

| Toxin Name/ Source/ Alternate ID | CAS RN/ Analogs | Indication/ Toxicity | Mechanism | Activity (IC50 nM); Tumor Type |
|---|---|---|---|---|
| Toxins | | | | |
| Chemical Structure | | | | |
| 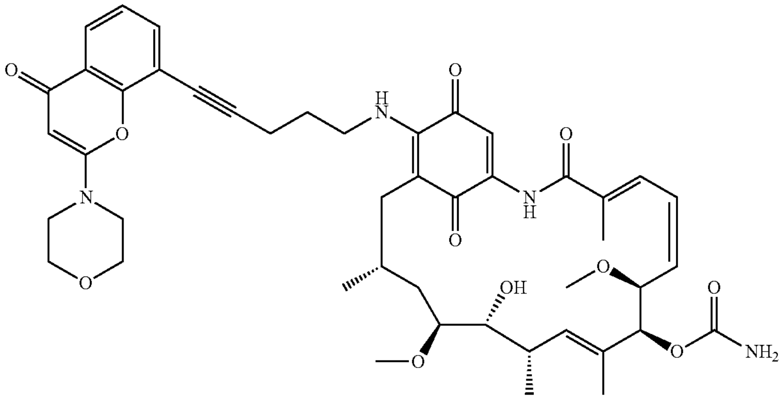 | | | | |
| Geldanamycin conjugates/ semi-synthetic;/ LY-294002-GM; PI3K-1-GM | 345232-44-2/ analogs prepared | breast/ not reported | binds Hsp 90 chaperone and inhibits function; binds and inhibits PI-3 kinase | cell culture (no reported); animal models performed |
| Structure Not Reported | | | | |
| Geldanamycin Analog/ not reported/ CNF-101 | not reported/ analogs prepared | breast, prostate/ not reported | binds Hsp 90 chaperone and inhibits function | not reported |
| Structure Not Reported | | | | |
| Geldanamycin-testosterone conjugate/ semi-synthetic/ GMT-1 | not reported/ analogs prepared | prostate/ not reported | binds Hsp 90 chaperone and inhibits function and testosterone receptors where it is internalized | not reported; conjugate has a 15-fold selective cytotoxicity for androgen positive prostate cells |
| 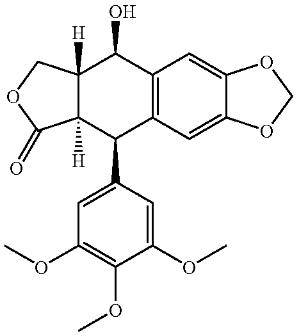 | | | | |
| Podophyllotoxin/ *Podophyllum* sp. | 518-28-5/ many analogs | *Verruca vulgaris*, Condyloma/ severe toxicity when given i.v. or s.c. | tubulin inhibitor and topoisomer-ase inhibitor | broad activity (cell culture) with IC50's in μM range |

TABLE 2-continued

| Toxins | | | | |
|---|---|---|---|---|
| Chemical Structure | | | | |
| Toxin Name/ Source/ Alternate ID | CAS RN/ Analogs | Indication/ Toxicity | Mechanism | Activity (IC50 nM); Tumor Type |
| 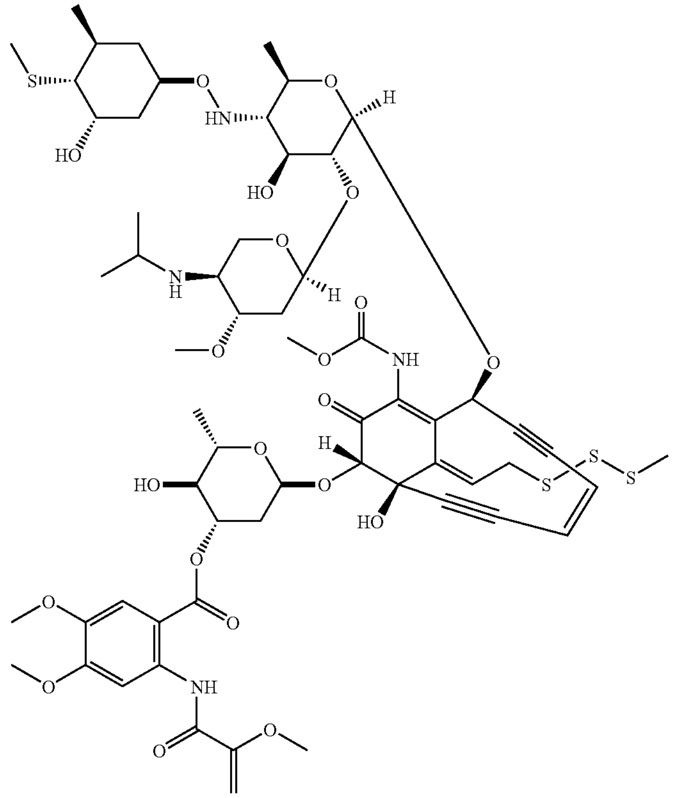 | | | | |
| esperamicin-A1/ not known/ BBM-1675A1; BMY-28175; GGM-1675 | 99674-26-7 | cancer/ not reported (suspected severe toxicity) | DNA cleaving agent | highly potent activity (cell culture); animal models highly potent with optimal dose of 0.16 micrograms/Kg |
| 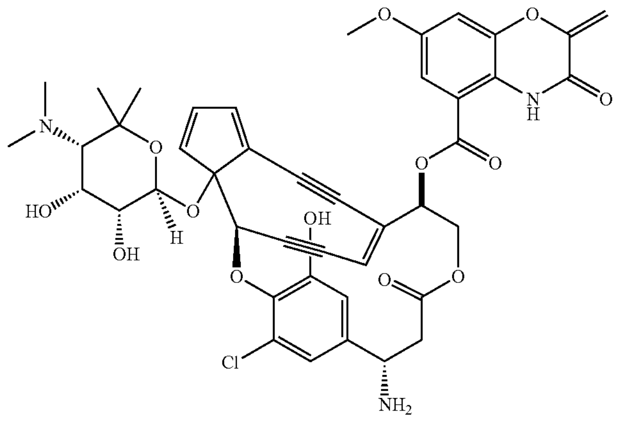 | | | | |
| C-1027[14]/ *Streptomyces setonii* C-1027/ C-1027 | 120177-69-7 | cancer (examined hepatoma, breast, lung and leukemia/ not reported | DNA cleaving agent | extremely potent (cell culture) IC50's in pM and fM; conjugated to antibodies the potency remains the same (ie. 5.5 to 42 pM); |

TABLE 2-continued

| Toxins | | | | |
|---|---|---|---|---|
| Chemical Structure | | | | |
| Toxin Name/<br>Source/<br>Alternate ID | CAS RN/<br>Analogs | Indication/<br>Toxicity | Mechanism | Activity<br>(IC50 nM);<br>Tumor Type |
| Pr(-X-S-S-W)$_m$<br><br>m = 0.5-15<br>Pr = proteinaceous carrier<br>W = calicheamicin minus Me-S-S-S<br>X = linker<br>Y = antibody P76.6 | 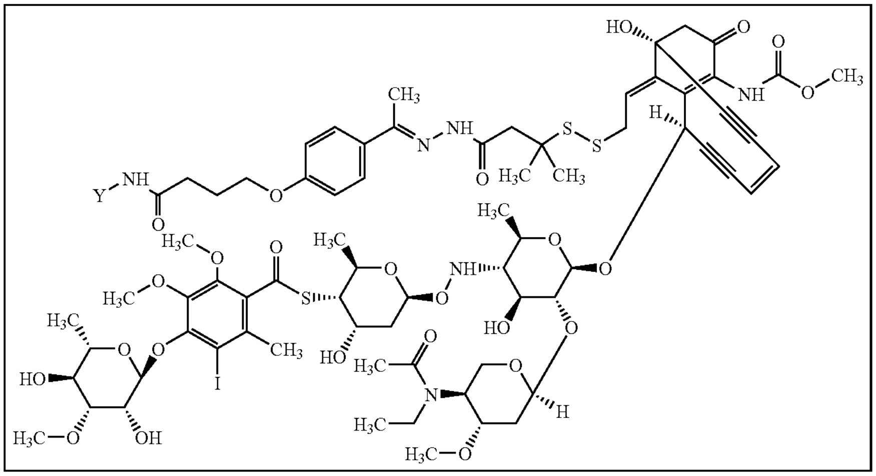 | | | |
| Calicheamicin-IgG(CD33 antigen)-conjugate[15]/<br>semi-synthetic: *Micromonospora echinospora*/<br>gemtuzumab ozogamicin; mylotarg; WAY-CMA-676; CMA-676; CDP-771 | 113440-58-7; 220578-59-6/<br>several reported in patents | AML/<br>mild toxicity | DNA cleaving agent | Kills CD33 + cells (HL-60, NOMO-1, and NKM-1) at 100 ng/mL; MDR cell lines are not effected by the drug. |
| 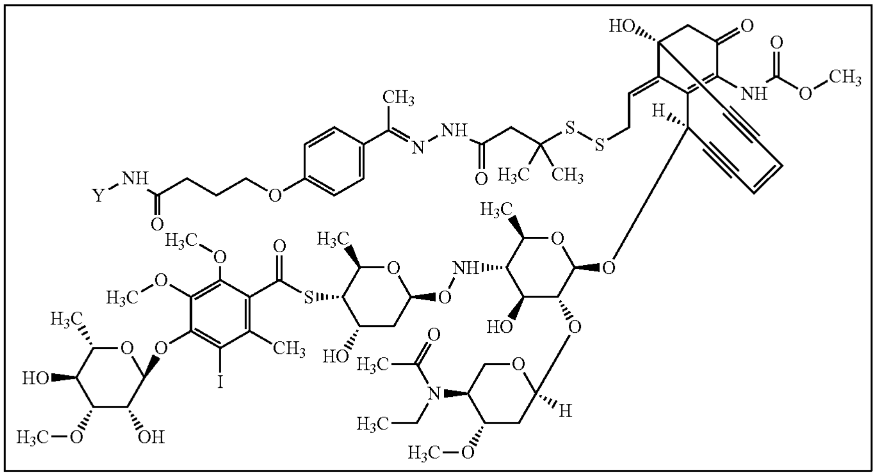 | | | | |
| Calicheamicin-IgG-conjugates[16]/<br>semi-synthetic: *Micromonospora echinospora* | 113440-58-7; 220578-59-6 | cancer/<br>not reported | DNA cleaving agent | TBD |

TABLE 2-continued

| Toxins | | | | |
|---|---|---|---|---|
| Chemical Structure | | | | |
| Toxin Name/ Source/ Alternate ID | CAS RN/ Analogs | Indication/ Toxicity | Mechanism | Activity (IC50 nM); Tumor Type |
| Pr(-X-S-S-W)$_m$<br>m = 0.5-15<br>Pr = proteinaceous carrier<br>W = calicheamicin minus Me-S-S-S<br>X = linker<br>Y = antibody P76.6 | 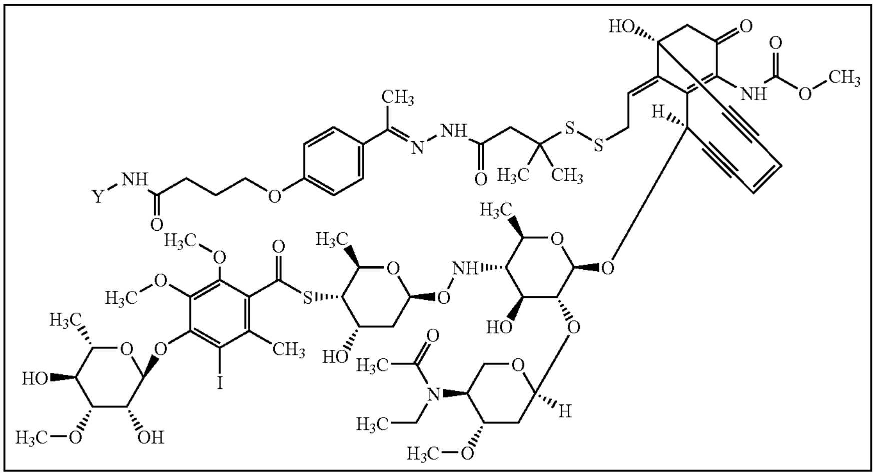 | | | |
| Calicheamicin-IgG(OBA1 antigen) conjugate/ semi-synthetic: *Micromonospora echinospora*/ OBA1-H8 | not reported | cancer/ not reported | DNA cleaving agent | all human cancer; data not reported |
| 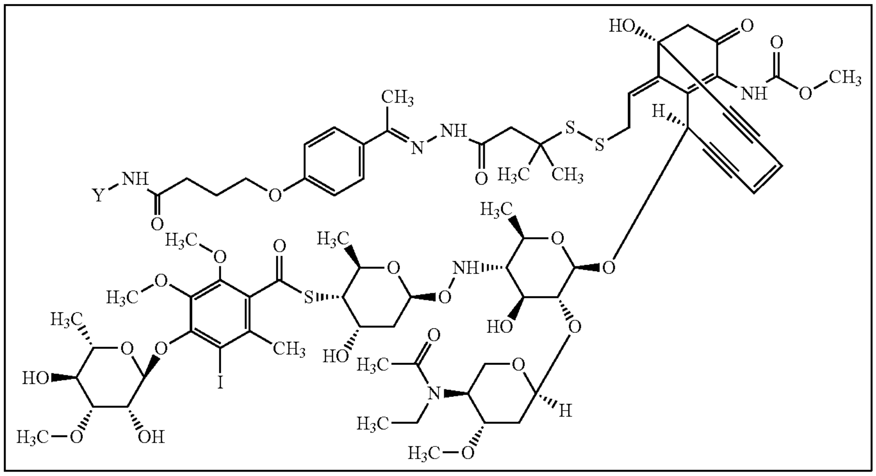 | | | | |
| Calicheamicin-IgG(CD22 antigen) conjugate/ semi-synthetic: *Micromonospora echinospora*/ CMC-544 | not reported | non-Hodgkin lymphoma, cancer/ not reported | DNA cleaving agent | all human cancer; data not reported |

TABLE 2-continued

| Toxin Name/ Source/ Alternate ID | CAS RN/ Analogs | Indication/ Toxicity | Mechanism | Activity (IC50 nM); Tumor Type |
|---|---|---|---|---|
| | | parially esterified polystyrene maleic acid copolymer (SMA) conjugated to neocarzinostatin (NCS) | | |
| Neocarzinostatin[17]/ semi-synthetic; *Streptomyces carconistaticus*/ Zinostatin stimalamer; YM-881; YM-16881 | 123760-07-6; 9014-02-2 | liver cancer and brain cancer/ not reported | DNA cleaving agent | cell culture data not reported. |
| | | IgG (TES-23)-conjugated to neocarzinostatin | | |
| Neocarzinostatin/ not reported/ TES-23-NCS | not reported | solid tumors/ toxicity not reported; TES-23 antibody (without anticancer agent) was as effective at eliminating tumors as the drug conjugated protein | DNA cleaving agent and immuno-stimulator | cell culture data not reported. |
| | | 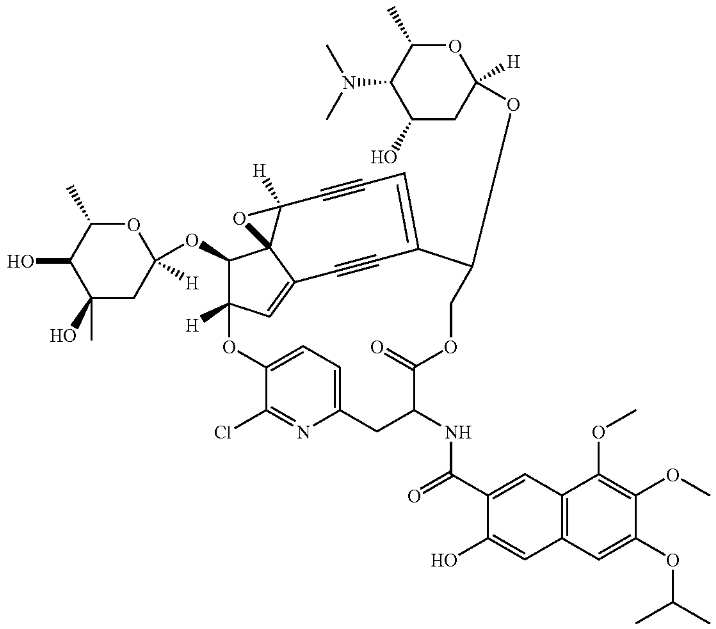 | | |
| Kedarcidin[18]/ *Streptoalloteichus* sp NOV strain L5856, ATCC 53650/ NSC-646276 | 128512-40-3; 128512-39-0/ chromophore and protein conjugate | cancer/ not reported | DNA cleaving agent | cell culture (IC50's in ng/mL), 0.4 HCT116; 0.3 HCT116/VP35; 0.3 HCT116/VM46; 0.2 A2780; 1.3 A2780/DDP. animal models in P388 and B-16 melanoma. NCI tumor panel, GI50's from 50 μM to 5 μM. |

TABLE 2-continued

Toxins

Chemical Structure

| Toxin Name/ Source/ Alternate ID | CAS RN/ Analogs | Indication/ Toxicity | Mechanism | Activity (IC50 nM); Tumor Type |
|---|---|---|---|---|
| 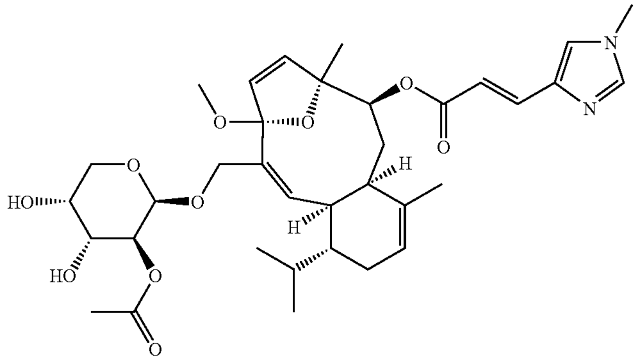 | | | | |
| Eleutherobins/ marine coral | 174545-76-7/ sarcodictyins (marine coral) | cancer/ not reported | tubulin binding agent | similar potency to taxol; not effective against MDR cell lines |
| 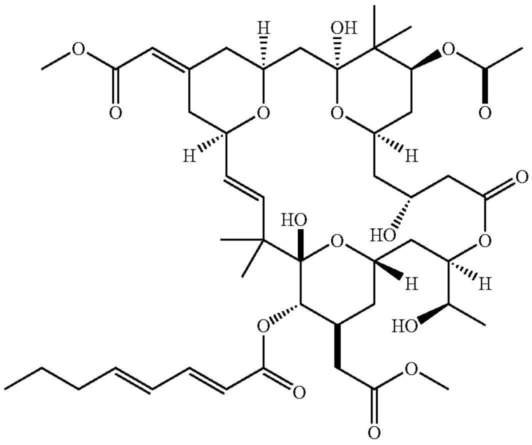 | | | | |
| Bryostatin-1/ *Bugula neritina* (marine bryosoan)/ GMY-45618; NSC-339555 | 83314-01-6 | leukemia, melanoma, lung, cancer/ myalgia; accumulated toxicity; poor water solubility; dose limiting toxicity | immunostimulant (TNF, GMCSF, etc); enhances cell kill by current anticancer agents | not reported |

TABLE 2-continued

| Toxins | | | | |
|---|---|---|---|---|
| Chemical Structure | | | | |
| Toxin Name/ Source/ Alternate ID | CAS RN/ Analogs | Indication/ Toxicity | Mechanism | Activity (IC50 nM); Tumor Type |
| 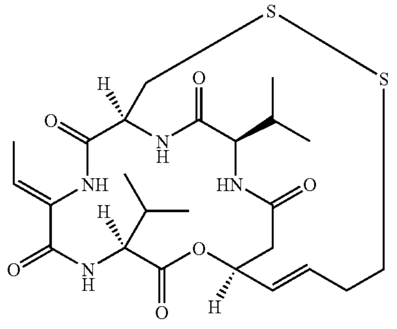 | | | | |
| FR-901228/ *Chromobacterium violaceum* strain 968/ NSC-63-176; FK-228 | 128517-07-7 | leukemia, T-cell lymphoma, cancer/ toxic doses (LD50) 6.4 and 10 mg/Kg, ip and iv respectively; GI toxicity, lymphoid atrophy; dose limiting toxicity (human) 18 mg/Kg; t1/2 of 8 hrs (human) | histone deacetylase inhiibitor | In vitro cell lines (NCI tumor panel); IC50's of between 0.56 and 4.1 nM (breast, lung, gastric colon, leukemia) |
| 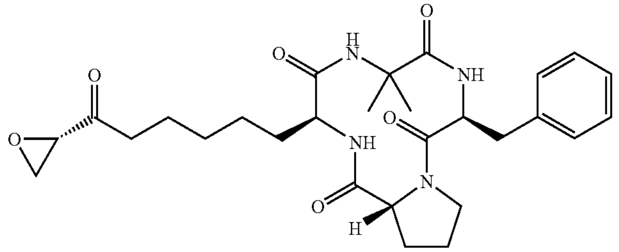 | | | | |
| Chlamydocin/ not reported | 53342-16-8 | cancer/ not reported | histone deacetylase inhiibitor | not reported (cell culture); inhibits histone deacetylase at an IC50 of 1.3 nM |
| 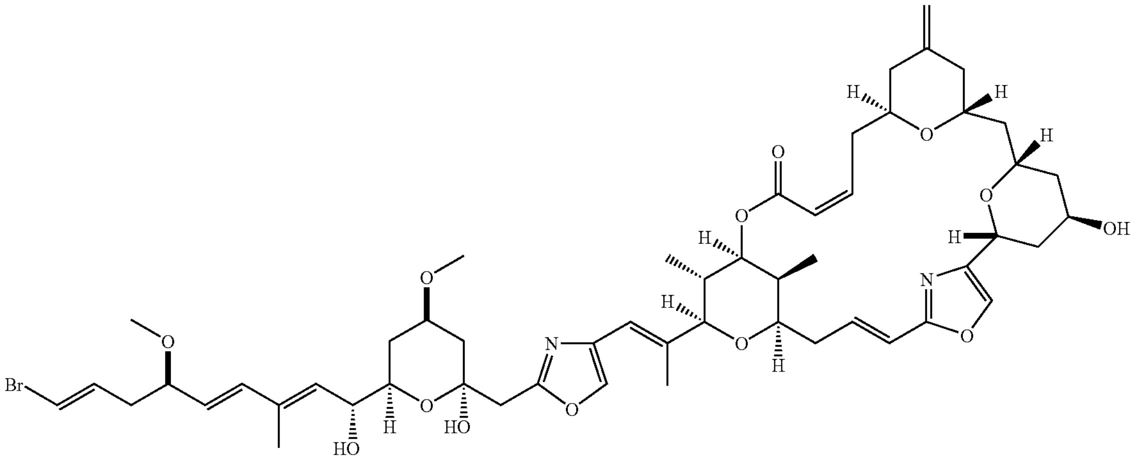 | | | | |
| Phorboxazole A[19]/ marine sponge | 181377-57-1; 165689-31-6; 180911-82-4; | leukemia, myeloma/ not reported | not reported (induces apoptosis) | NCI tumor panel (details not reported); IC50's of 1-10 nM. The |

TABLE 2-continued

| Toxin Name/ Source/ Alternate ID | CAS RN/ Analogs | Indication/ Toxicity | Mechanism | Activity (IC50 nM); Tumor Type |
|---|---|---|---|---|
| Toxins | | | | |
| Chemical Structure | | | | |
| | 165883-76-1/ analogs prepared | | | inhibition values (clonogenic growth of human cancer cells) at 10 nM ranged from 6.2 to >99.9% against NALM-6 human B-lineage acute lymophoblastic leukemia cells, BT-20 breast cancer cells and U373 glioblastoma cells, with the specified compound showing inhibition values in the range of 42.4 to >99.9% against these cell lines.; IC50's are nM for MDR cell lines. |
| 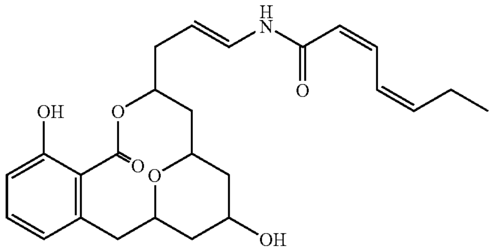 | | | | |
| Apicularen A/ *Chondromyces robustus* | 220757-06-2/ natural derivatives | cancer/ not reported | not reported | IC50's of 0.1 to 3 ng/mL (KB-3-A, KB-Va, K562, HL60, U937, A498, A549, PV3 and SK-OV3) |
| 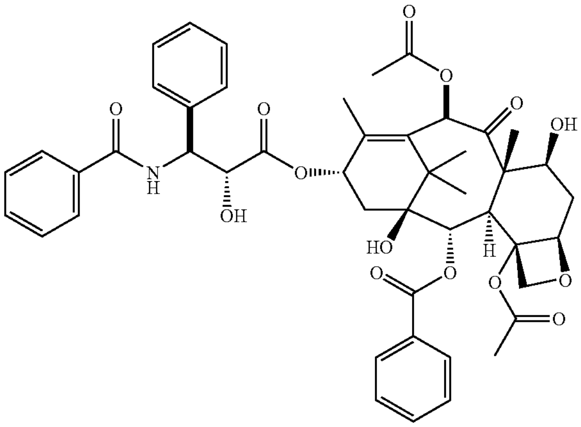 | | | | |
| Taxol/ Pacific yew and fungi/ Paclitaxel; NSC-125973 | 33069624/ many analogs | cancer; breast, prostate, ovary, colon, lung, head & neck, etc./ severe toxicity (grade III and IV) | tubulin binding agent | NCI tumor panel; GI50's of 3 nM to 1 μM; TGI 50 nM to 25 μM |

TABLE 2-continued

Toxins

Chemical Structure

| Toxin Name/ Source/ Alternate ID | CAS RN/ Analogs | Indication/ Toxicity | Mechanism | Activity (IC50 nM); Tumor Type |
|---|---|---|---|---|
| 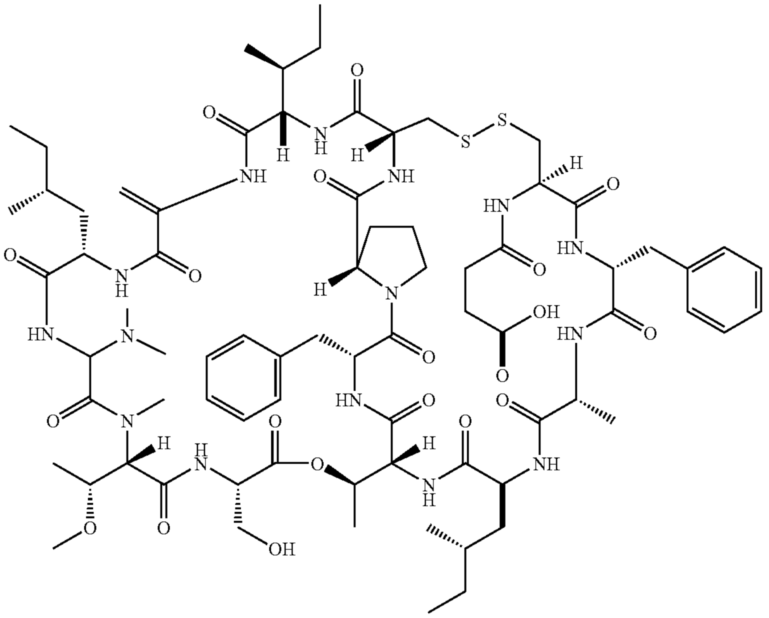 | | | | |
| Vitilevuamide/ *Didemnum cuculliferum* or *Polysyncraton lithostrotum* | 191681-63-7 | cancer/ not reported | tubulin binding agent | cell culture; IC50's of 6-311 nM (panel of tumor cell lines HCT116 cells, A549 cells, SK-MEL-5 cells A498 cells). The increase in lifespan (ILS) for CDF1 mice after ip injection of P388 tumor cells was in the range of −45 to +70% over the dose range of 0.13 to 0.006 mg/kg. |
| 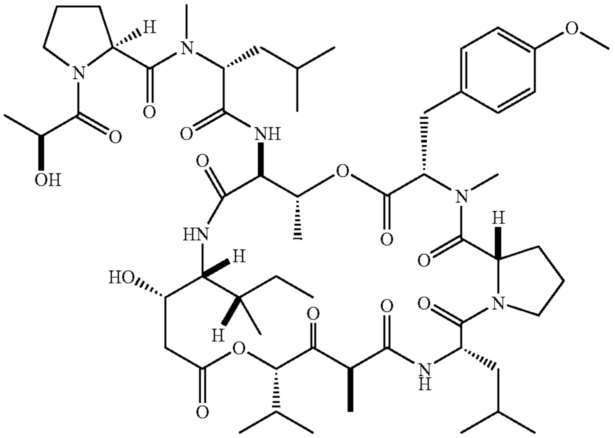 | | | | |
| Didemnin B/ *Trididemnum solidum*/ NSC-2325319; IND 24505 | 77327-05-0; 77327-04-9; 77327-06-1/ other related natural products | non-Hodgkin's lymphoma, breast, carcinoma, CNS, colon/ Discontinued due to cardiotoxicity; nausea, neuro-muscular toxicity and vomiting MTD 6.3 mg/Kg; toxicity | inhibits protein synthesis via EF-1 | NCI 60-tumor panel (GI50's): 100 nM to 50 fM. Not potent against MDR cell lines. |

TABLE 2-continued

| Toxins | | | | |
|---|---|---|---|---|
| Chemical Structure | | | | |
| Toxin Name/ Source/ Alternate ID | CAS RN/ Analogs | Indication/ Toxicity | Mechanism | Activity (IC50 nM); Tumor Type |
| | | prevented achieving a clinically signif. effect; rapidly cleared (t1/2 4.8 hrs | | |
| 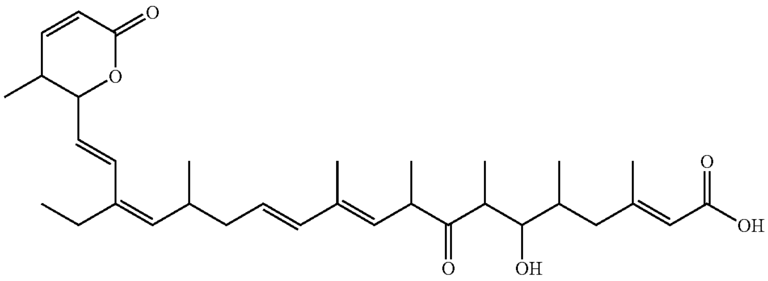 | | | | |
| Leptomycin B/ *Streptomyces* sp. strain ATS 1287/ NSC-364372; elactocin | 87081-35-4 | | | NCI 60-tumor panel (GI50's): 8 μM to 1 pM; (LC50): 250 μM to 10 nM (several cell lines at 0.1 nM). Two testing results with very different potencies. |
| 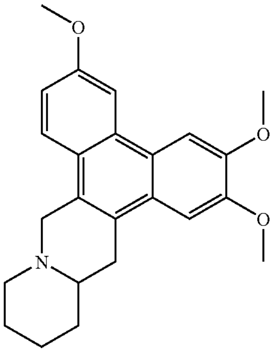 | | | | |
| Cryptopleurin/ not known/ NSC-19912 | | | | NCI 60-tumor panel (GI50's); 19 nM to 1 pM; (LC50): 40 μM to 10 nM (several cell lines at 1 pM). |
| 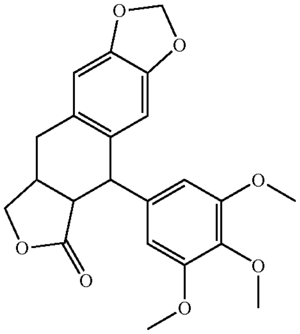 | | | | |
| Silicicolin/ not known/ | 19186-35-7 | | | NCI 60-tumor panel (GI50's): ~100 nM to |

TABLE 2-continued
| Toxins | | | | |
|---|---|---|---|---|
| Chemical Structure | | | | |
| Toxin Name/ Source/ Alternate ID | CAS RN/ Analogs | Indication/ Toxicity | Mechanism | Activity (IC50 nM); Tumor Type |
| NSC-403148, deoxypodophyllotoxin, desoxypodophyllotoxin podophyllotoxin, deoxysilicicolin | | | | 3 nM; (LC50): 50 µM to 10 nM |
| 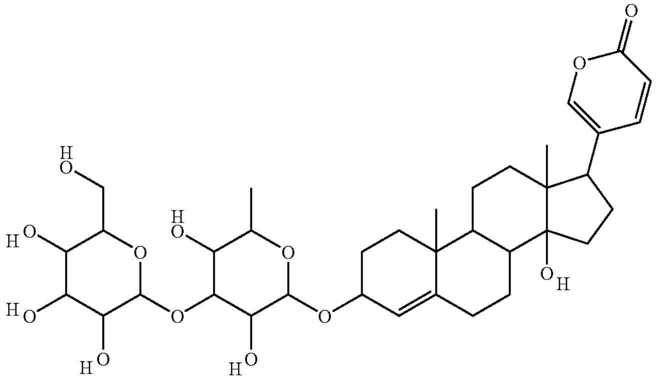 | | | | |
| Scillaren A/ not known/ NSC-7525; Gluco-proscillaridin A; Scillaren A | 124-99-2 | | | NCI 60-tumor panel (GI50's): 50 nM to 0.1 nM; (LC50): 250 µM to 0.1 nM |
| 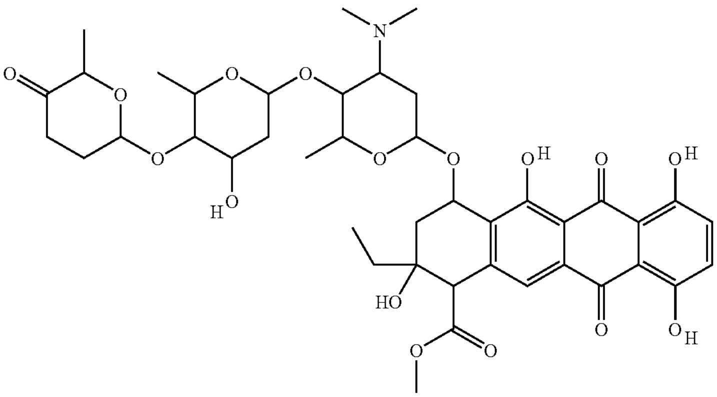 | | | | |

TABLE 2-continued

| Toxins | | | | |
|---|---|---|---|---|
| Chemical Structure | | | | |
| Toxin Name/ Source/ Alternate ID | CAS RN/ Analogs | Indication/ Toxicity | Mechanism | Activity (IC50 nM); Tumor Type |
| Cinerubin A-HCl/ not known/ NSC-243022; Cinerubin A hydrochloride; CL 86-F2 HCl; CL-86-F2-hydrochloride | not reported | | | NCI 60-tumor panel (GI50's): 15 nM to 10 pM; (LC50): 100 μM to 6 nM |

[1]WO-09739025; US-6025466
[2]EP-00626383 30 Nov. 1994
[3]JP-10101676
[4]WO-09705162; WO-09717364 (dolastatin synthesis and analogs)
[5]Kosan licensed patent for Epothilone analogs from Sloan-Kettering; US 001895968
[6]WO-09723211
[7]WO-09723211
[8]JP-08092232
[9]WO-09633211
[10]EP-00608111; EP-00632042; EP-00634414; WO-09748278
[11]EP-00425235; JP-53124692
[12]US-05416064; US-05208020; EP-00425235B
[13]EP-004252351 JP-53124692; US-06333410B1
[14]JP-1104183
[15]EP-00689845
[16]EP-00689845
[17]EP-00136791; EP-00087957
[18]US 50001112; US 5143906.
[19]WO-00136048

Conventional immunotoxins contain an MAb chemically conjugated to a toxin that is mutated or chemically modified to minimized binding to normal cells. Examples include anti-B4-blocked ricin, targeting CD5; and RFB4-deglycosylated ricin A chain, targeting CD22. Recombinant immunotoxins developed more recently are chimeric proteins consisting of the variable region of an antibody directed against a tumor antigen fused to a protein toxin using recombinant DNA technology. The toxin is also frequently genetically modified to remove normal tissue binding sites but retain its cytotoxicity. A large number of differentiation antigens, overexpressed receptors, or cancer-specific antigens have been identified as targets for immunotoxins, e.g., CD19, CD22, CD20, IL-2 receptor (CD25), CD33, IL-4 receptor, EGF receptor and its mutants, ErB2, Lewis carbohydrate, mesothelin, transferrin receptor, GM-CSF receptor, Ras, Bcr-Abl, and c-Kit, for the treatment of a variety of malignancies including hematopoietic cancers, glioma, and breast, colon, ovarian, bladder, and gastrointestinal cancers. See e.g., Brinkmann et al., *Expert Opin. Biol. Ther.* 1:693-702 (2001); Perentesis and Sievers, *Hematology/Oncology Clinics of North America* 15:677-701 (2001).

MAbs conjugated with radioisotope are used as another means of treating human malignancies, particularly hematopoietic malignancies, with a high level of specificity and effectiveness. The most commonly used isotopes for therapy are the high-energy-emitters, such as $^{131}I$ and $^{90}Y$. Recently, $^{213}Bi$-labeled anti-CD33 humanized MAb has also been tested in phase I human clinical trials. Reff et al., supra.

A number of MAbs have been used for therapeutic purposes. For example, the use of rituximab (Rituxan™), a recombinant chimeric anti-CD20 MAb, for treating certain hematopoietic malignancies was approved by the FDA in 1997. Other MAbs that have since been approved for therapeutic uses in treating human cancers include: alemtuzumab (Campath-1H™), a humanized rat antibody against CD52; and gemtuzumab ozogamicin (Mylotarg™), a calicheamicin-conjugated humanized mouse antCD33 MAb. The FDA is also currently examining the safety and efficacy of several other MAbs for the purpose of site-specific delivery of cytotoxic agents or radiation, e.g., radiolabeled Zevalin™ and Bexxar™. Reff et al., supra.

A second important consideration in designing a drug delivery system is the accessibility of a target tissue to a therapeutic agent. This is an issue of particular concern in the case of treating a disease of the central nervous system (CNS), where the blood-brain barrier prevents the diffusion of macromolecules. Several approaches have been developed to bypass the blood-brain barrier for effective delivery of therapeutic agents to the CNS. The understanding of iron transport mechanism from plasma to brain provides a useful tool in bypassing the blood-brain barrier (BBB). Iron, transported in plasma by transferrin, is an essential component of virtually all types of cells. The brain needs iron for metabolic processes and receives iron through transferrin receptors located on brain capillary endothelial cells via receptor-mediated transcytosis and endocytosis. Moos and Morgan, *Cellular and Molecular Neurobiology* 20:77-95 (2000). Delivery systems based on transferrin-transferrin receptor interaction have been established for the efficient delivery of peptides, proteins, and liposomes into the brain. For example, peptides can be coupled with a Mab directed against the transferrin receptor to achieve greater uptake by the brain, Moos and Morgan, Supra. Similarly, when coupled with an MAb directed against the transferrin receptor, the transportation of basic fibroblast growth factor (bFGF) across the blood-brain barrier is enhanced. Song et al., *The Journal of Pharmacology and Experimental Therapeutics* 301:605-610 (2002); Wu et al., *Journal of Drug Targeting* 10:239-245 (2002). In addition, a liposomal delivery system for effective transport of the chemotherapy drug, doxorubicin, into C6 glioma has been reported, where transferrin was attached to the distal ends of liposomal PEG chains. Eavarone et al., *J. Biomed. Mater. Res.* 51:10-14 (2000). A number of US patents also relate to delivery methods bypassing the blood-brain barrier based on transferrin-transferrin receptor interaction. See e.g., U.S. Pat. Nos. 5,154,924; 5,182,107; 5,527,527; 5,833,988; 6,015,555.

There are other suitable conjugation partners for a pharmaceutical agent to bypass the blood-brain barrier. For example, U.S. Pat. Nos. 5,672,683, 5,977,307 and WO 95/02421 relate to a method of delivering a neuropharmaceutical agent across the blood-brain barrier, where the agent is administered in the form of a fusion protein with a ligand that is reactive with a brain capillary endothelial cell receptor; WO 99/00150 describes a drug delivery system in which the transportation of a drug across the blood-brain barrier is facilitated by conjugation with an MAb directed against human insulin receptor; WO 89/10134 describes a chimeric peptide, which includes a peptide capable of crossing the blood brain barrier at a relatively high rate and a hydrophilic neuropeptide incapable of transcytosis, as a means of introducing hydrophilic neuropeptides into the brain; WO 01/60411 A1 provides a pharmaceutical composition that can easily transport a pharmaceutically active ingredient into the brain. The active ingredient is bound to a hibernation-specific protein that is used as a conjugate, and administered with a thyroid hormone or a substance promoting thyroid hormone production. In addition, an alternative route of drug delivery for bypassing the blood-brain barrier has been explored. For instance, intranasal delivery of therapeutic agents without the need for conjugation has been shown to be a promising alternative delivery method (Frey, 2002, Drug Delivery Technology, 2(5):46-49).

In addition to facilitating the transportation of drugs across the blood-brain barrier, transferrin-transferrin receptor interaction is also useful for specific targeting of certain tumor cells, as many tumor cells overexpress transferrin receptor on their surface. This strategy has been used for delivering bioactive macromolecules into K562 cells via a transferrin conjugate (Wellhoner et al., *The Journal of Biological Chemistry* 266:4309-4314 (1991)), and for delivering insulin into enterocyte-like Caco-2 cells via a transferrin conjugate (Shah and Shen, *Journal of Pharmaceutical Sciences* 85:1306-1311 (1996)).

Furthermore, as more becomes known about the functions of various iron transport proteins, such as lactotransferrin receptor, melanotransferrin, ceruloplasmin, and Divalent Cation Transporter and their expression pattern, some of the proteins involved in iron transport mechanism (e.g., melanotransferrin), or their fragments, have been found to be similarly effective in assisting therapeutic agents transport across the blood-brain barrier or targeting specific tissues (WO 02/13843 A2, WO 02/13873 A2). For a review on the use of transferrin and related proteins involved in iron uptake as conjugates in drug delivery, see Li and Qian, *Medical Research Reviews* 22:225-250 (2002).

The concept of tissue-specific delivery of therapeutic agents goes beyond the interaction between transferrin and transferrin receptor or their related proteins. For example, a bone-specific delivery system has been described in which proteins are conjugated with a bone-seeking aminobisphosphate for improved delivery of proteins to mineralized tissue. Uludag and Yang, *Biotechnol. Prog.* 18:604-611 (2002). For a review on this topic, see Vyas et al., *Critical Reviews in Therapeutic Drug Carrier System* 18:1-76 (2001).

A variety of linkers may be used in the process of generating bioconjugates for the purpose of specific delivery of therapeutic agents. Suitable linkers include homo- and heterobifunctional cross-linking reagents, which may be cleavable by, e.g., acid-catalyzed dissociation, or non-cleavable (see, e.g., Srinivasachar and Neville, *Biochemistry* 28:2501-2509 (1989); Wellhoner et al., *The Journal of Biological Chemistry* 266:4309-4314 (1991)). Interaction between many known binding partners, such as biotin and avidin/streptavidin, can also be used as a means to join a therapeutic agent and a conjugate partner that ensures the specific and effective delivery of the therapeutic agent. Using the methods of the invention, proteins may be used to deliver molecules to intracellular compartments as conjugates. Proteins, peptides, hormones, cytokines, small molecules or the like that bind to specific cell surface receptors that are internalized after ligand binding may be used for intracellular targeting of conjugated therapeutic compounds. Typically, the receptor-ligand complex is internalized into intracellular vesicles that are delivered to specific cell compartments, including, but not limited to, the nucleus, mitochondria, golgi, ER, lysosome, and endosome, depending on the intracellular location targeted by the receptor. By conjugating the receptor ligand with the desired molecule, the drug will be carried with the receptor-ligand complex and be delivered to the intracellular compartments normally targeted by the receptor. The drug can therefore be delivered to a specific intracellular location in the cell where it is needed to treat a disease.

Many proteins may be used to target therapeutic agents to specific tissues and organs. Targeting proteins include, but are not limited to, growth factors (EPO, HGH, EGF, nerve growth factor, FGF, among others), cytokines (GM-CSF, G-CSF, the interferon family, interleukins, among others), hormones (FSH, LH, the steroid families, estrogen, corticosteroids, insulin, among others), serum proteins (albumin, lipoproteins, fetoprotein, human serum proteins, antibodies and fragments of antibodies, among others), and vitamins (folate, vitamin C, vitamin A, among others). Targeting agents are available that are specific for receptors on most cells types.

Contemplated linkage configurations include, but are not limited to, protein-sugar-linker-sugar-protein and multivalent forms thereof, protein-sugar-linker-protein and multivalent forms thereof, protein-sugar-linker-therapeutic agent, where the therapeutic agent includes, but are not limited to, small molecules, peptides and lipids. In some embodiments, a hydrolysable linker is used that can be hydrolyzed once internalized. An acid labile linker can be used to advantage where the protein conjugate is internalized into the endosomes or lysosomes which have an acidic pH. Once internalized into the endosome or lysosome, the linker is hydrolyzed and the therapeutic agent is released from the targeting agent.

In an exemplary embodiment, transferrin is conjugated via a linker to an enzyme or a nucleic acid vector that encoded the enzyme desired to be targeted to a cell that presents transferrin receptors in a patient. The patient could, for example, require enzyme replacement therapy for that particular enzyme. In particularly preferred embodiments, the enzyme is one that is lacking in a patient with a lysosomal storage disease (see Table 5). Once in circulation, the transferrin-enzyme conjugate is linked to transferrin receptors and is internalized in early endosomes (Xing et al., 1998, Biochem. J. 336:667; Li et al., 2002, Trends in Pharmcol. Sci. 23:206; Suhaila et al., 1998, J. Biol. Chem. 273:14355). Other contemplated targeting agents that are related to transferrin include, but are not limited to, lactotransferrin (lactoferrin), melanotransferrin (p97), ceruloplasmin, and divalent cation transporter.

In another exemplary embodiment, transferrin-dystrophin conjugates would enter endosomes by the transferrin pathway. Once there, the dystrophin is released due to a hydrolysable linker which can then be taken to the intracellular compartment where it is required. This embodiment may be used to treat a patient with muscular dystrophy by supplementing a genetically defective dystrophin gene and/or protein with the functional dystrophin peptide connected to the transferrin.

E. Therapeutic Moieties

In another preferred embodiment, the modified sugar includes a therapeutic moiety. Those of skill in the art will appreciate that there is overlap between the category of therapeutic moieties and biomolecules; many biomolecules have therapeutic properties or potential.

The therapeutic moieties can be agents already accepted for clinical use or they can be drugs whose use is experimental, or whose activity or mechanism of action is under investigation. The therpeutic moieties can have a proven action in a given disease state or can be only hypothesized to show desirable action in a given disease state. In a preferred embodiment, the therapeutic moieties are compounds, which are being screened for their ability to interact with a tissue of choice. Therapeutic moieties, which are useful in practicing the instant invention include drugs from a broad range of drug classes having a variety of pharmacological activities. In some embodiments, it is preferred to use therapeutic moieties that are not sugars. An exception to this preference is the use of a sugar that is modified by covalent attachment of another entity, such as a PEG, biomolecule, therapeutic moiety, diagnostic moiety and the like. In an exemplary embodiment, an antisense nucleic acid moeity is conjugated to a linker arm which is attached to the targeting moiety. In another exemplary embodiment, a therapeutic sugar moiety is conjugated to a linker arm and the sugar-linker arm cassette is subsequently conjugated to a peptide via a method of the invention.

Methods of conjugating therapeutic and diagnostic agents to various other species are well known to those of skill in the art. See, for example Hermanson, Bioconjugate Techniques, Academic Press, San Diego, 1996; and Dunn et al., Eds. Polymeric Drugs And Drug Delivery Systems, ACS Symposium Series Vol. 469, American Chemical Society, Washington, D.C. 1991.

In an exemplary embodiment, the therapeutic moiety is attached to the modified sugar via a linkage that is cleaved under selected conditions. Exemplary conditions include, but are not limited to, a selected pH (e.g., stomach, intestine, endocytotic vacuole), the presence of an active enzyme (e.g., esterase, protease, reductase, oxidase), light, heat and the like. Many cleavable groups are known in the art. See, for example, Jung et al., *Biochem. Biophys. Acta,* 761: 152-162 (1983); Joshi et al, *J. Biol. Chem.,* 265: 14518-14525 (1990); Zarling et al., *J. Immunol.,* 124: 913-920 (1980); Bouizar et al., *Eur. J. Biochem.,* 155: 141-147 (1986); Park et al., *J. Biol. Chem.,* 261: 205-210 (1986); Browning et al., *J. Immunol.,* 143: 1859-1867 (1989).

Classes of useful therapeutic moieties include, for example, non-steroidal anti-inflammatory drugs (NSAIDS). The NSAIDS can, for example, be selected from the following categories: (e.g., propionic acid derivatives, acetic acid derivatives, fenamic acid derivatives, biphenylcarboxylic acid derivatives and oxicams); steroidal anti-inflammatory drugs including hydrocortisone and the like; adjuvants; antihistaminic drugs (e.g., chlorpheniramine, triprolidine); antitussive drugs (e.g., dextromethorphan, codeine, caramiphen and carbetapentane); antipruritic drugs (e.g., methdilazine and trimeprazine); anticholinergic drugs (e.g., scopolamine, atropine, homatropine, levodopa); anti-emetic and antinauseant drugs (e.g., cyclizine, meclizine, chlorpromazine, buclizine); anorexic drugs (e.g., benzphetamine, phentermine, chlorphentermine, fenfluramine); central stimulant drugs (e.g., amphetamine, methamphetamine, dextroamphetamine and methylphenidate); antiarrhythmic drugs (e.g., propanolol, procainamide, disopyramide, quinidine, encainide); β-adrenergic blocker drugs (e.g., metoprolol, acebutolol, betaxolol, labetalol and timolol); cardiotonic drugs (e.g., milrinone, amrinone and dobutamine); antihypertensive drugs (e.g., enalapril, clonidine, hydralazine, minoxidil, guanadrel, guanethidine); diuretic drugs (e.g., amiloride and hydrochlorothiazide); vasodilator drugs (e.g., diltiazem, amiodarone, isoxsuprine, nylidrin, tolazoline and verapamil); vasoconstrictor drugs (e.g., dihydroergotamine, ergotamine and methylsergide); antiulcer drugs (e.g., ranitidine and cimetidine); anesthetic drugs (e.g., lidocaine, bupivacaine, chloroprocaine, dibucaine); antidepressant drugs (e.g., imipramine, desipramine, amitryptiline, nortryptiline); tranquilizer and sedative drugs (e.g., chlordiazepoxide, benacytyzine, benzquinamide, flurazepam, hydroxyzine, loxapine and promazine); antipsychotic drugs (e.g., chlorprothixene, fluphenazine, haloperidol, molindone, thioridazine and trifluoperazine); antimicrobial drugs (antibacterial, antifungal, antiprotozoal and antiviral drugs).

Classes of useful therapeutic moieties include adjuvants. The adjuvants can, for example, be selected from keyhole lymphet hemocyanin conjugates, monophosphoryl lipid A, mycoplasma-derived lipopeptide MALP-2, cholera toxin B subunit, *Escherichia coli* heat-labile toxin, universal T helper epitope from tetanus toxoid, interleukin-12, CpG oligodeoxynucleotides, dimethyldioctadecylammonium bromide, cyclodextrin, squalene, aluminum salts, meningococcal outer membrane vesicle (OMV), montanide ISA, TiterMax™ (available from Sigma, St. Louis Mo.), nitrocellulose absorption, immune-stimulating complexes such as Quil A, Gerbu™ adjuvant (Gerbu Biotechnik, Kirchwald, Germany), threonyl muramyl dipeptide, thymosin alpha, bupivacaine, GM-CSF, Incomplete Freund's Adjuvant, MTP-PE/MF59 (Ciba/Geigy, Basel, Switzerland), polyphosphazene, saponin derived from the soapbark tree *Quillaja saponaria*, and Syntex adjuvant formulation (Biocine, Emeryville, Calif.), among others well known to those in the art.

Antimicrobial drugs which are preferred for incorporation into the present composition include, for example, pharmaceutically acceptable salts of β-lactam drugs, quinolone drugs, ciprofloxacin, norfloxacin, tetracycline, erythromycin, amikacin, triclosan, doxycycline, capreomycin, chlorhexidine, chlortetracycline, oxytetracycline, clindamycin, ethambutol, hexamidine isothionate, metronidazole, pentamidine, gentamycin, kanamycin, lineomycin, methacycline, methenamine, minocycline, neomycin, netilmycin, paromomycin, streptomycin, tobramycin, miconazole and amantadine.

Other drug moieties of use in practicing the present invention include antineoplastic drugs (e.g., antiandrogens (e.g., leuprolide or flutamide), cytocidal agents (e.g., adriamycin, doxorubicin, taxol, cyclophosphamide, busulfan, cisplatin, β-interferon) anti-estrogens (e.g., tamoxifen), antimetabolites (e.g., fluorouracil, methotrexate, mercaptopurine, thioguanine). Also included within this class are radioisotope-based agents for both diagnosis and therapy, and conjugated toxins, such as ricin, geldanamycin, mytansin, CC-1065, C-1027, the duocarmycins, calicheamycin and related structures and analogues thereof, and the toxins listed in Table 2.

The therapeutic moiety can also be a hormone (e.g., medroxyprogesterone, estradiol, leuprolide, megestrol, octreotide or somatostatin); muscle relaxant drugs (e.g., cinnamedrine, cyclobenzaprine, flavoxate, orphenadrine, papaverine, mebeverine, idaverine, ritodrine, diphenoxylate, dantrolene and azumolen); antispasmodic drugs; bone-active drugs (e.g., diphosphonate and phosphonoalkylphosphinate drug compounds); endocrine modulating drugs (e.g., contraceptives (e.g., ethinodiol, ethinyl estradiol, norethindrone, mestranol, desogestrel, medroxyprogesterone), modulators of diabetes (e.g., glyburide or chlorpropamide), anabolics, such as testolactone or stanozolol, androgens (e.g., methyltestosterone, testosterone or fluoxymesterone), antidiuretics (e.g., desmopressin) and calcitonins).

Also of use in the present invention are estrogens (e.g., diethylstilbesterol), glucocorticoids (e.g., triamcinolone, betamethasone, etc.) and progesterones, such as norethindrone, ethynodiol, norethindrone, levonorgestrel; thyroid agents (e.g., liothyronine or levothyroxine) or anti-thyroid agents (e.g., methimazole); antihyperprolactinemic drugs (e.g., cabergoline); hormone suppressors (e.g., danazol or goserelin), oxytocics (e.g., methylergonovine or oxytocin) and prostaglandins, such as mioprostol, alprostadil or dinoprostone, can also be employed.

Other useful modifying groups include immunomodulating drugs (e.g., antihistamines, mast cell stabilizers, such as lodoxamide and/or cromolyn, steroids (e.g., triamcinolone, beclomethazone, cortisone, dexamethasone, prednisolone, methylprednisolone, beclomethasone, or clobetasol), histamine H2 antagonists (e.g., famotidine, cimetidine, ranitidine), immunosuppressants (e.g., azathioprine, cyclosporin), etc. Groups with anti-inflammatory activity, such as sulindac, etodolac, ketoprofen and ketorolac, are also of use. Other drugs of use in conjunction with the present invention will be apparent to those of skill in the art.

Classes of useful therapeutic moieties include, for example, antisense drugs and also naked DNA. The antisense drugs can be selected from for example Affinitak (ISIS, Carlsbad, Calif.) and Genasense™ (from Genta, Berkeley Heights, N.J.). Naked DNA can be delivered as a gene therapy therapeutic for example with the DNA encoding for example factors VIII and IX for treatment of hemophilia disorders.

F. Preparation of Modified Sugars

Modified sugars useful in forming the conjugates of the invention are discussed herein. The discussion focuses on preparing a sugar modified with a water-soluble polymer for clarity of illustration. In particular, the discussion focuses on the preparation of modified sugars that include a poly(ethylene glycol) moiety. Those of skill will appreciate that the methods set forth herein are broadly applicable to the preparation of modified sugars, therefore, the discussion should not be interpreted as limiting the scope of the invention.

In general, the sugar moiety and the modifying group are linked together through the use of reactive groups, which are typically transformed by the linking process into a new organic functional group or unreactive species. The sugar reactive functional group(s), is located at any position on the sugar moiety. Reactive groups and classes of reactions useful in practicing the present invention are generally those that are well known in the art of bioconjugate chemistry. Currently favored classes of reactions available with reactive sugar moieties are those, which proceed under relatively mild conditions. These include, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, Smith and March, Advanced Organic Chemistry, 5th Ed., John Wiley & Sons, New York, 2001; Hermanson, Bioconjugate Techniques, Academic Press, San Diego, 1996; and Feeney et al., Modification of Proteins; Advances in Chemistry Series, Vol. 198, American Chemical Society, Washington, D.C., 1982.

Useful reactive functional groups pendent from a sugar nucleus or modifying group include, but are not limited to:

(a) carboxyl groups and various derivatives thereof including, but not limited to, N-hydroxysuccinimide esters, N-hydroxybenzotriazole esters, acid halides, acyl imidazoles, thioesters, p-nitrophenyl esters, alkyl, alkenyl, alkynyl and aromatic esters;

(b) hydroxyl groups, which can be converted to, e.g., esters, ethers, aldehydes, etc.

(c) haloalkyl groups, wherein the halide can be later displaced with a nucleophilic group such as, for example, an amine, a carboxylate anion, thiol anion, carbanion, or an alkoxide ion, thereby resulting in the covalent attachment of a new group at the functional group of the halogen atom;

(d) dienophile groups, which are capable of participating in Diels-Alder reactions such as, for example, maleimido groups;

(e) aldehyde or ketone groups, such that subsequent derivatization is possible via formation of carbonyl derivatives such as, for example, imines, hydrazones, semicarbazones or oximes, or via such mechanisms as Grignard addition or alkyllithium addition;

(f) sulfonyl halide groups for subsequent reaction with amines, for example, to form sulfonamides;

(g) thiol groups, which can be, for example, converted to disulfides or reacted with alkyl and acyl halides;

(h) amine or sulfhydryl groups, which can be, for example, acylated, alkylated or oxidized;

(i) alkenes, which can undergo, for example, cycloadditions, acylation, Michael addition, etc; and (j) epoxides, which can react with, for example, amines and hydroxyl compounds.

The reactive functional groups can be chosen such that they do not participate in, or interfere with, the reactions necessary to assemble the reactive sugar nucleus or modifying group. Alternatively, a reactive functional group can be protected from participating in the reaction by the presence of a protecting group. Those of skill in the art understand how to protect a particular functional group such that it does not interfere with a chosen set of reaction conditions. For examples of useful protecting groups, see, for example, Greene et al., Protective Groups in Organic Synthesis, John Wiley & Sons, New York, 1991.

In the discussion that follows, a number of specific examples of modified sugars that are useful in practicing the present invention are set forth. In the exemplary embodiments, a sialic acid derivative is utilized as the sugar nucleus to which the modifying group is attached. The focus of the discussion on sialic acid derivatives is for clarity of illustration only and should not be construed to limit the scope of the invention. Those of skill in the art will appreciate that a variety of other sugar moieties can be activated and derivatized in a manner analogous to that set forth using sialic acid as an example. For example, numerous methods are available for modifying galactose, glucose, N-acetylgalactosamine and fucose to name a few sugar substrates, which are readily modified by art recognized methods. See, for example, Elhalabi et al., *Curr. Med. Chem.* 6: 93 (1999); and Schafer et al., *J. Org. Chem.* 65: 24 (2000).

In an exemplary embodiment, the peptide that is modified by a method of the invention is a peptide that is produced in mammalian cells (e.g., CHO cells) or in a transgenic animal and thus, contains N- and/or O-linked oligosaccharide chains, which are incompletely sialylated. The oligosaccharide chains of the glycopeptide lacking a sialic acid and containing a terminal galactose residue can be PEGylated, PPGylated or otherwise modified with a modified sialic acid.

In Scheme 4, the mannosamine glycoside 1, is treated with the active ester of a protected amino acid (e.g., glycine) derivative, converting the sugar amine residue into the corresponding protected amino acid amide adduct. The adduct is treated with an aldolase to form the sialic acid 2. Compound 2 is converted to the corresponding CMP derivative by the action of CMP-SA synthetase, followed by catalytic hydrogenation of the CMP derivative to produce compound 3. The amine introduced via formation of the glycine adduct is utilized as a locus of PEG or PPG attachment by reacting compound 3 with an activated PEG or PPG derivative (e.g., PEG-C(O)NHS, PPG-C(O)NHS), producing 4 or 5, respectively.

Scheme 4

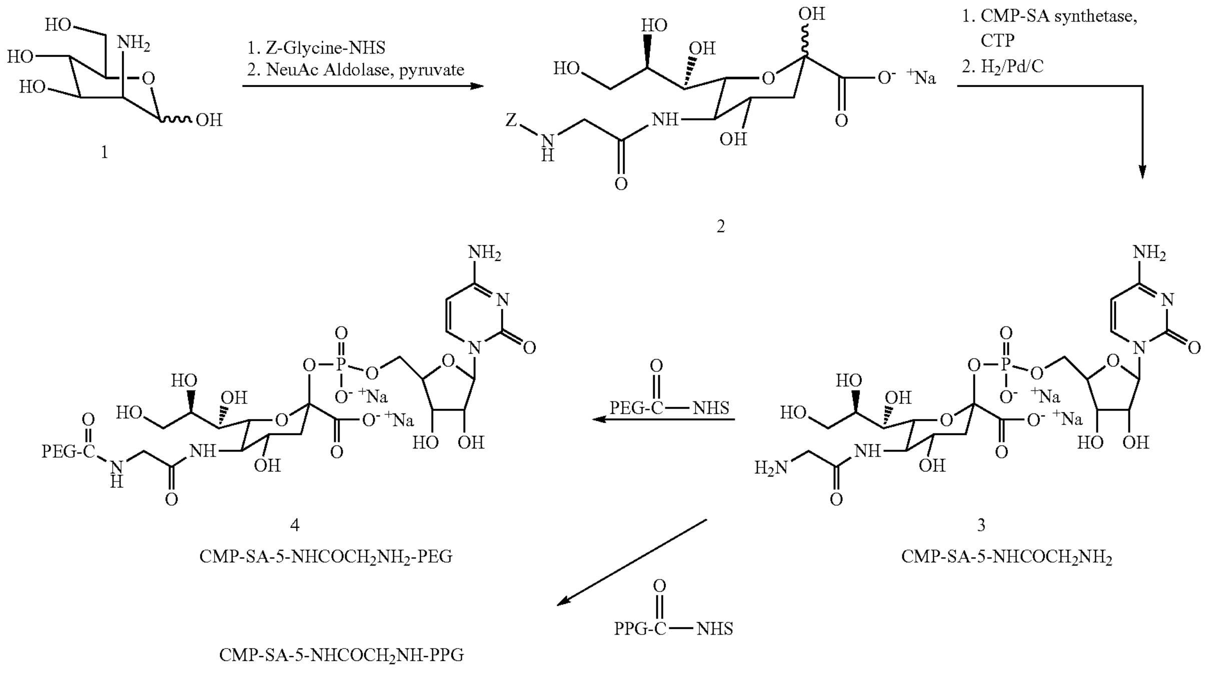

1

2

3

CMP-SA-5-$NHCOCH_2NH_2$

4

CMP-SA-5-$NHCOCH_2NH_2$-PEG

CMP-SA-5-$NHCOCH_2NH$-PPG

5

Table 3 sets forth representative examples of sugar monophosphates that are derivatized with a PEG or PPG moiety. Certain of the compounds of Table 3 are prepared by the method of Scheme 1. Other derivatives are prepared by art-recognized methods. See, for example, Keppler et al., *Glycobiology* 11: 11R (2001); and Charter et al., *Glycobiology* 10: 1049 (2000)). Other amine reactive PEG and PPG analogues are commercially available, or they can be prepared by methods readily accessible to those of skill in the art.

TABLE 3

| Examples of sugar monophosphates that are derivatized with a PEG or PPG moiety |
|---|
| 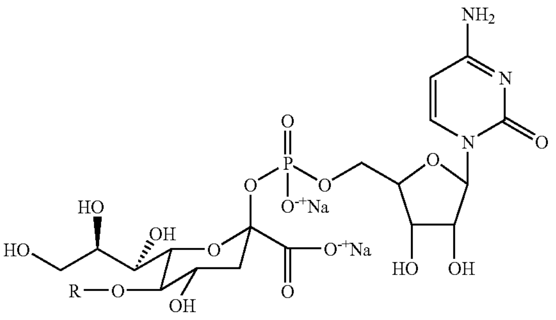 |
| CMP-KDN-5-O—R |

TABLE 3-continued

| Examples of sugar monophosphates that are derivatized with a PEG or PPG moiety |
|---|
| 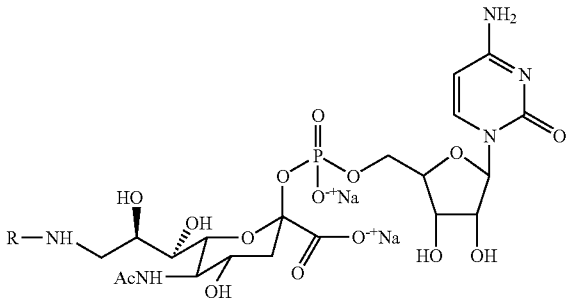 |
| CMP-NeuAc-9-NH—R |
| 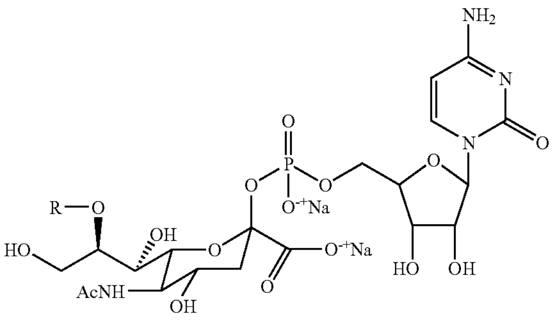 |
| CMP-NeuAc-8-O—R |

TABLE 3-continued

Examples of sugar monophosphates that are derivatized with a PEG or PPG moiety

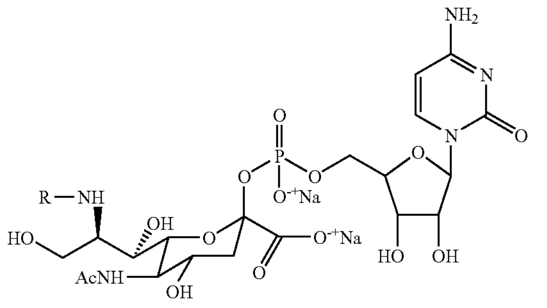

CMP-NeuAc-8-NH—R

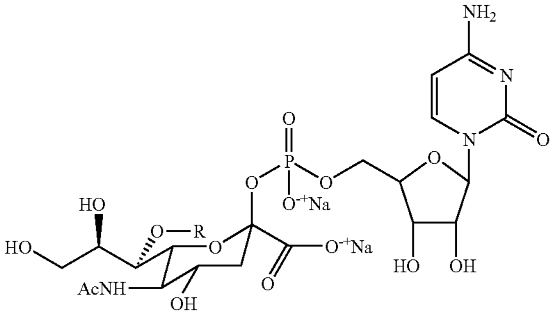

CMP-NeuAc-7-O—R

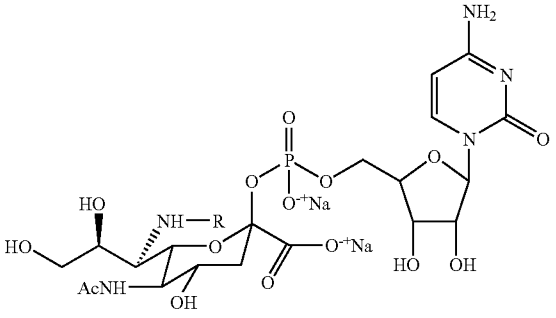

CMP-NeuAc-7-NH—R

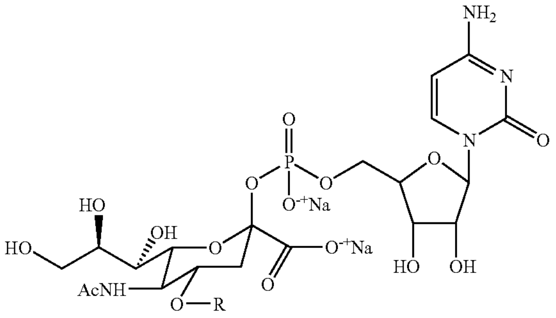

CMP-NeuAc-4-O—R

TABLE 3-continued

Examples of sugar monophosphates that are derivatized with a PEG or PPG moiety

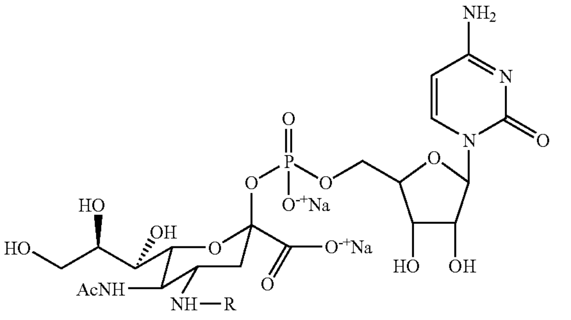

CMP-NeuAc-4-NH—R

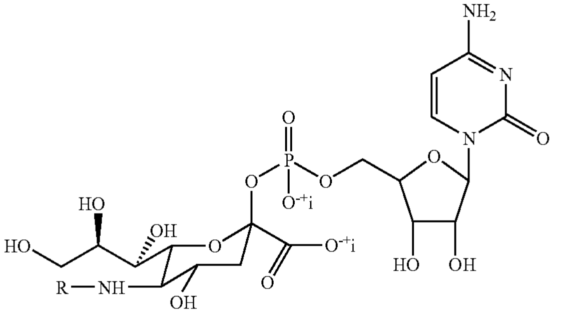

CMP-SA-5-NH—R

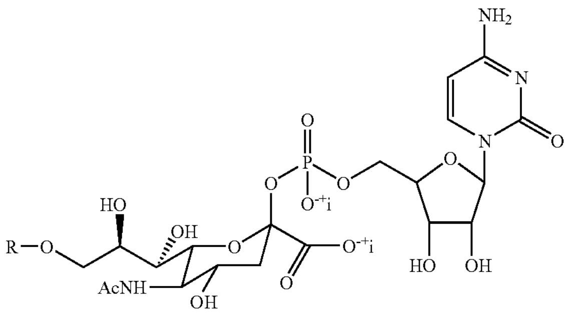

CMP-NeuAc-9-O—R

The modified sugar phosphates of use in practicing the present invention can be substituted in other positions as well as those set forth above. “i” may be Na or another salt and “i” may be interchangeable with Na. Presently preferred substitutions of sialic acid are set forth in Formula 5.

Formula 5:

(I)

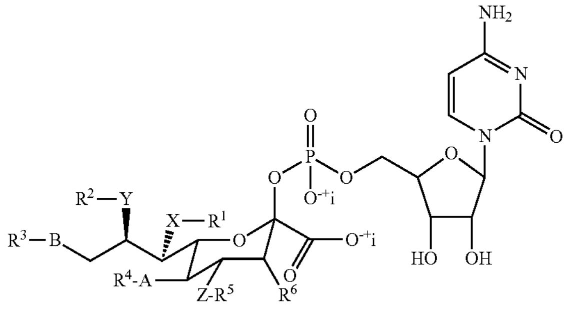

in which X is a linking group, which is preferably selected from —O—, —N(H)—, —S, $CH_2$—, and $N(R)_2$, in which each R is a member independently selected from $R^1$-$R^5$. "i" may be Na or another salt, and Na may be interchangeable with "i: The symbols Y, Z, A and B each represent a group that is selected from the group set forth above for the identity of X. X, Y, Z, A and B are each independently selected and, therefore, they can be the same or different. The symbols $R^1$, $R^2$, $R^3$, $R^4$ and $R^5$ represent H, polymers, a water-soluble polymer, therapeutic moiety, biomolecule or other moiety. The symbol R6 represents H, OH, or a polymer. Alternatively, these symbols represent a linker that is linked to a polymer, water-soluble polymer, therapeutic moiety, biomolecule or other moiety.

In another exemplary embodiment, a mannosamine is simultaneously acylated and activated for a nucleophilic substitution by the use of chloroacetic anhydride as set forth in Scheme 5. In each of the schemes presented in this section, $i^+$ or $Na^+$ can be interchangeable, wherein the salt can be sodium, or can be any other suitable salt.

Scheme 5
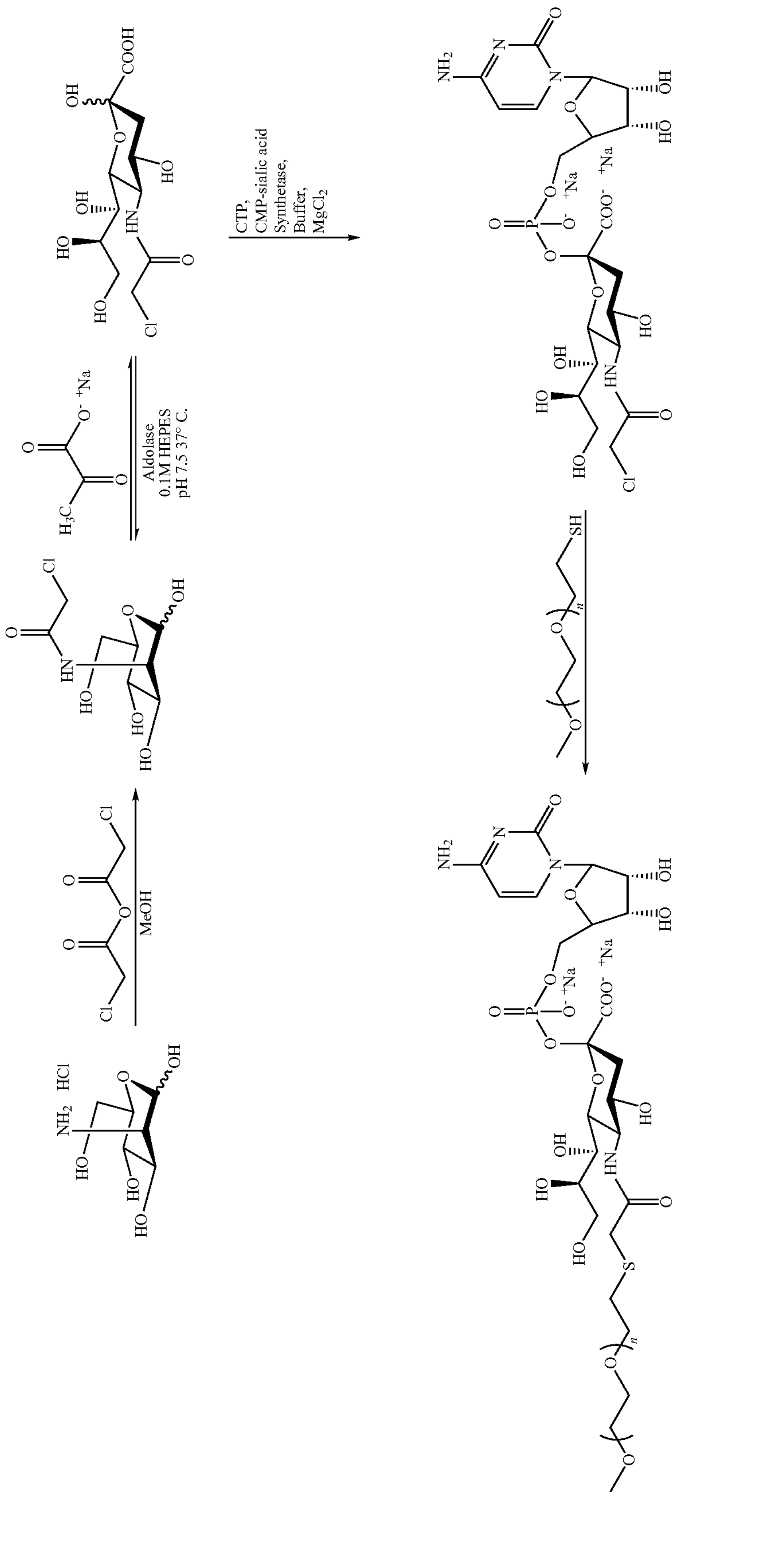

The resulting chloro-derivatized glycan is contacted with pyruvate in the presence of an aldolase, forming a chloro-derivatized sialic acid. The corresponding nucleotide sugar is prepared by contacted the sialic acid derivative with an appropriate nucleotide triphosphates and a synthetase. The chloro group on the sialic acid moiety is then displaced with a nucleophilic PEG derivative, such as thio-PEG.

In a further exemplary embodiment, as shown is Scheme 6, a mannosamine is acylated with a bis-HOBT dicarboxylate, producing the corresponding amido-alkyl-carboxylic acid, which is subsequently converted to a sialic acid derivative. The sialic acid derivative is converted to a nucleotide sugar, and the carboxylic acid is activated and reacted with a nucleophilic PEG derivative, such as amino-PEG.

Scheme 6
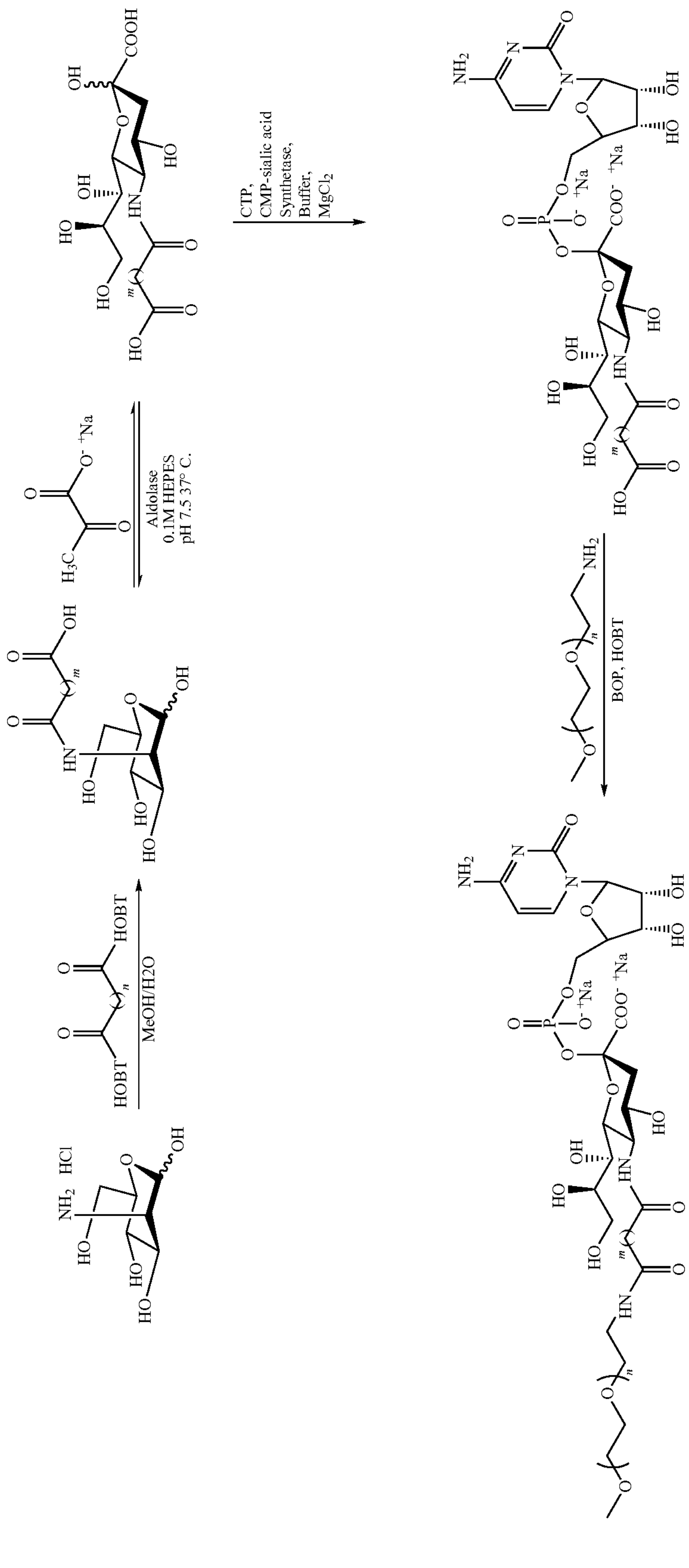
m = 0-20

In another exemplary embodiment, set forth in Scheme 7, amine- and carboxyl-protected neuraminic acid is activated by converting the primary hydroxyl group to the corresponding p-toluenesulfonate ester, and the methyl ester is cleaved. The activated neuraminic acid is converted to the corresponding nucleotide sugar, and the activating group is displaced by a nucleophilic PEG species, such as thio-PEG.

Scheme 7
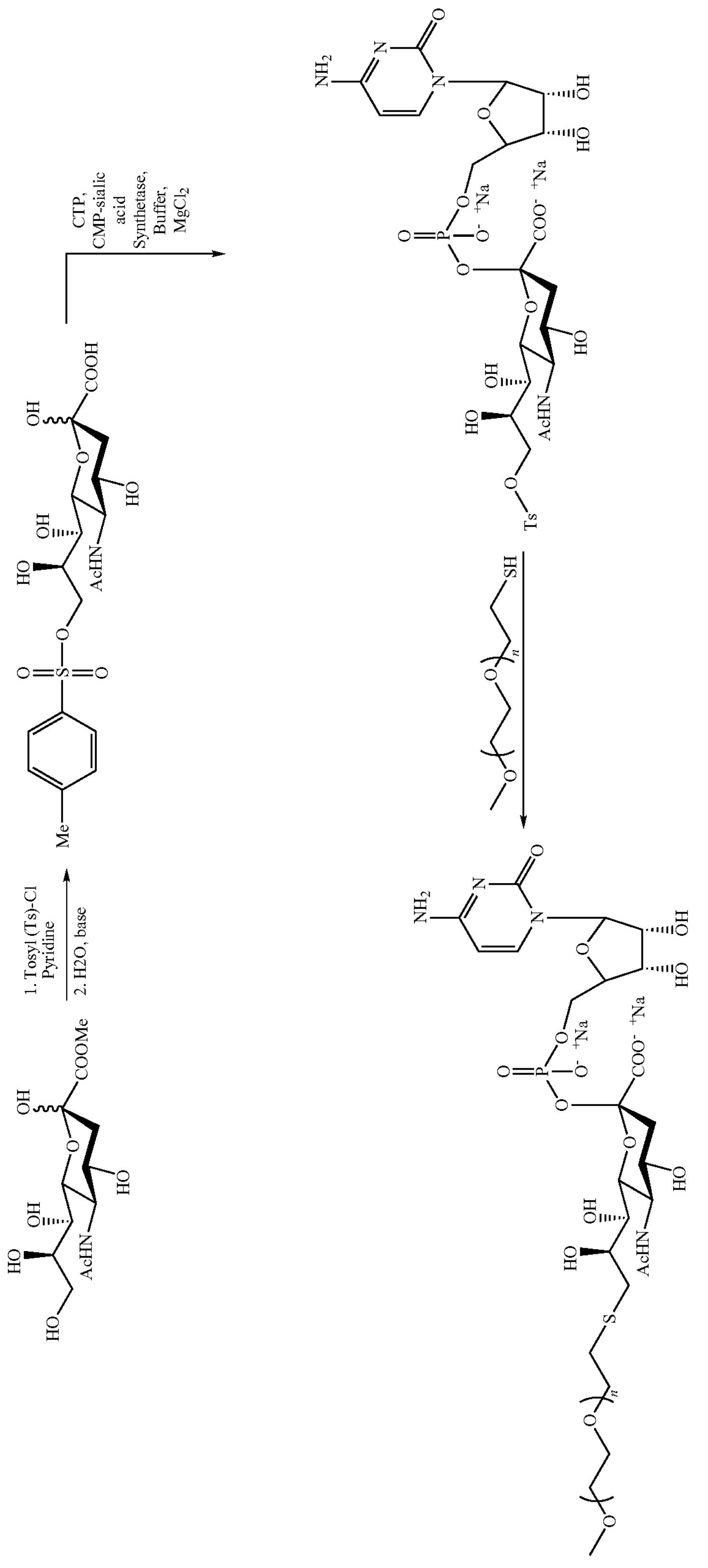

In yet a further exemplary embodiment, as set forth in Scheme 8, the primary hydroxyl moiety of an amine- and carboxyl-protected neuraminic acid derivative is alkylated using an electrophilic PEG, such as chloro-PEG. The methyl ester is subsequently cleaved and the PEG-sugar is converted to a nucleotide sugar.

Scheme 8

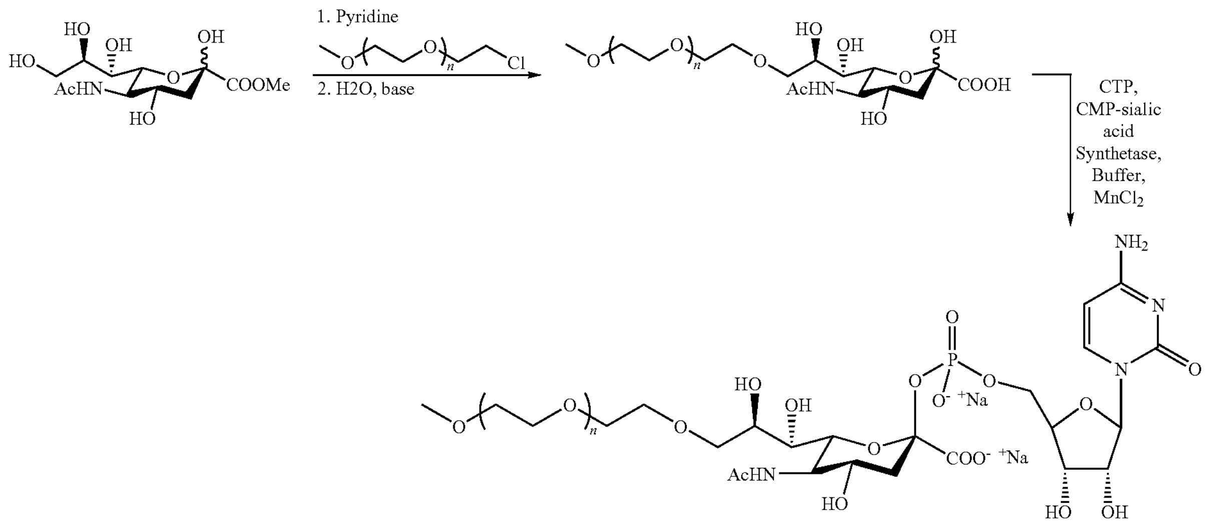

Glycans other than sialic acid can be derivatized with PEG using the methods set forth herein. The derivatized glycans, themselves, are also within the scope of the invention. Thus, Scheme 9 provides an exemplary synthetic route to a PEGylated galactose nucleotide sugar. The primary hydroxyl group of galactose is activated as the corresponding toluenesulfonate ester, which is subsequently converted to a nucleotide sugar.

Scheme 9

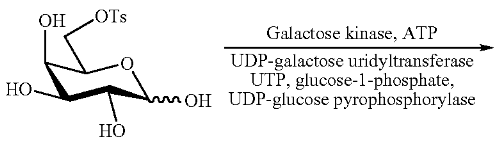

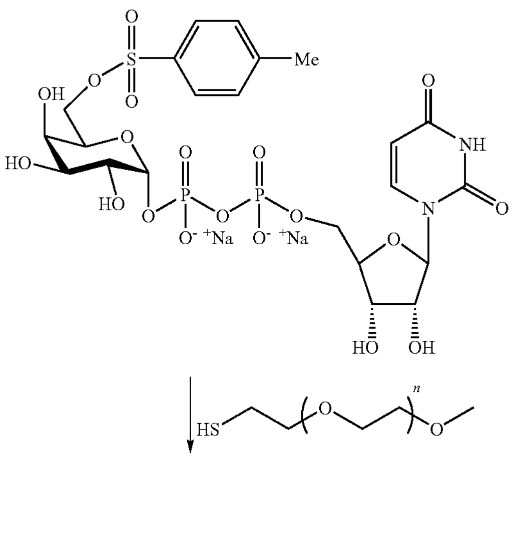

-continued

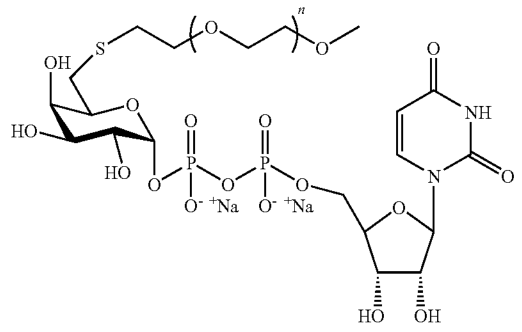

Scheme 10 sets forth an exemplary route for preparing a galactose-PEG derivative that is based upon a galactose-6-amine moiety. Thus, galactosamine is converted to a nucleotide sugar, and the amine moiety of galactosamine is functionalized with an active PEG derivative.

Scheme 10

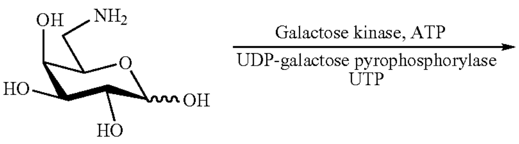

-continued

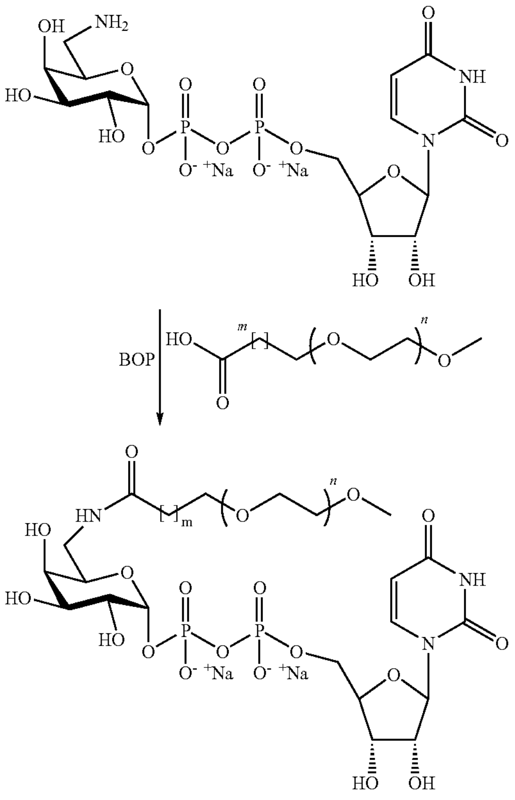

m = 0-10

Scheme 11 provides another exemplary route to galactose derivatives. The starting point for Scheme 11 is galactose-2-amine, which is converted to a nucleotide sugar. The amine moiety of the nucleotide sugar is the locus for attaching a PEG derivative, such as Methoxy-PEG (mPEG) carboxylic acid.

Scheme 11

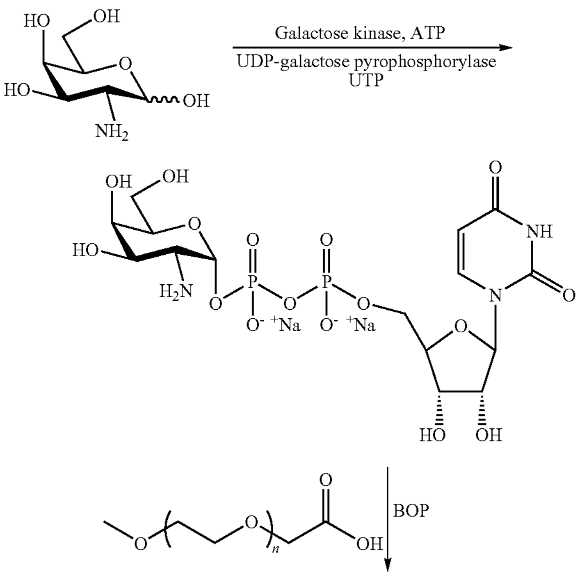

-continued

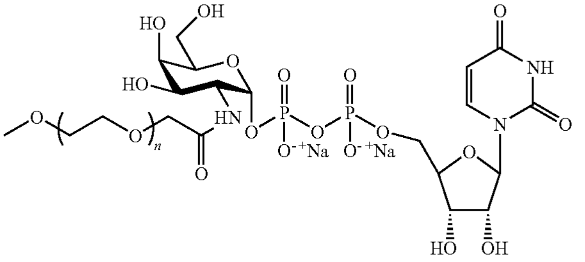

Exemplary moieties attached to the conjugates disclosed herein include, but are not limited to, PEG derivatives (e.g., acyl-PEG, acyl-alkyl-PEG, alkyl-acyl-PEG carbamoyl-PEG, aryl-PEG, alkyl-PEG), PPG derivatives (e.g., acyl-PPG, acyl-alkyl-PPG, alkyl-acyl-PPG carbamoyl-PPG, aryl-PPG), polyapartic acid, polyglutamate, polylysine, therapeutic moieties, diagnostic moieties, mannose-6-phosphate, heparin, heparan, $SLe^x$, mannose, mannose-6-phosphate, Sialyl Lewis X, FGF, VFGF, proteins (e.g., transferrin), chondroitin, keratan, dermatan, dextran, modified dextran, amylose, bisphosphate, poly-SA, hyaluronic acid, keritan, albumin, integrins, antennary oligosaccharides, peptides and the like. Methods of conjugating the various modifying groups to a saccharide moiety are readily accessible to those of skill in the art (Poly (Ethylene Glycol Chemistry: Biotechnical and Biomedical Applications, J. Milton Harris, Ed., Plenum Pub. Corp., 1992; Poly (Ethylene Glycol) Chemical and Biological Applications, J. Milton Harris, Ed., ACS Symposium Series No. 680, American Chemical Society, 1997; Hermanson, Bioconjugate Techniques, Academic Press, San Diego, 1996; and Dunn et al., Eds. Polymeric Drugs And Drug Delivery Systems, ACS Symposium Series Vol. 469, American Chemical Society, Washington, D.C. 1991).

Purification of Sugars, Nucleotide Sugars and Derivatives

The nucleotide sugars and derivatives produced by the above processes can be used without purification. However, it is usually preferred to recover the product. Standard, well-known techniques for recovery of glycosylated saccharides such as thin or thick layer chromatography, column chromatography, ion exchange chromatography, or membrane filtration can be used. It is preferred to use membrane filtration, more preferably utilizing a reverse osmotic membrane, or one or more column chromatographic techniques for the recovery as is discussed hereinafter and in the literature cited herein. For instance, membrane filtration wherein the membranes have molecular weight cutoff of about 3000 to about 10,000 can be used to remove proteins for reagents having a molecular weight of less than 10,000 Da. Membrane filtration or reverse osmosis can then be used to remove salts and/or purify the product saccharides (see, e.g., WO 98/15581). Nanofilter membranes are a class of reverse osmosis membranes that pass monovalent salts but retain polyvalent salts and uncharged solutes larger than about 100 to about 2,000 Daltons, depending upon the membrane used. Thus, in a typical application, saccharides prepared by the methods of the present invention will be retained in the membrane and contaminating salts will pass through.

G. Cross-Linking Groups

Preparation of the Modified Sugar for Use in the Methods of the Present Invention includes attachment of a modifying group to a sugar residue and forming a stable adduct, which is a substrate for a glycosyltransferase. Thus, it is often preferred to use a cross-linking agent to conjugate the modifying group and the sugar. Exemplary bifunctional compounds which can be used for attaching modifying groups to carbohydrate moieties include, but are not limited to, bifunctional poly(ethylene glycols), polyamides, polyethers, polyesters and the like. General approaches for linking carbohydrates to other molecules are known in the literature. See, for example, Lee et al., *Biochemistry* 28: 1856 (1989); Bhatia et al., *Anal. Biochem.* 178: 408 (1989); Janda et al., *J. Am. Chem. Soc.* 112: 8886 (1990) and Bednarski et al., WO 92/18135. In the discussion that follows, the reactive groups are treated as benign on the sugar moiety of the nascent modified sugar. The focus of the discussion is for clarity of illustration. Those of skill in the art will appreciate that the discussion is relevant to reactive groups on the modifying group as well.

An exemplary strategy involves incorporation of a protected sulfhydryl onto the sugar using the heterobifunctional crosslinker SPDP (n-succinimidyl-3-(2-pyridyldithio)propionate and then deprotecting the sulfhydryl for formation of a disulfide bond with another sulfhydryl on the modifying group.

If SPDP detrimentally affects the ability of the modified sugar to act as a glycosyltransferase substrate, one of an array of other crosslinkers such as 2-iminothiolane or N-succinimidyl S-acetylthioacetate (SATA) is used to form a disulfide bond. 2-iminothiolane reacts with primary amines, instantly incorporating an unprotected sulfhydryl onto the amine-containing molecule. SATA also reacts with primary amines, but incorporates a protected sulfhydryl, which is later deacetylated using hydroxylamine to produce a free sulfhydryl. In each case, the incorporated sulfhydryl is free to react with other sulfhydryls or protected sulfhydryl, like SPDP, forming the required disulfide bond.

The above-described strategy is exemplary, and not limiting, of linkers of use in the invention. Other crosslinkers are available that can be used in different strategies for crosslinking the modifying group to the peptide. For example, TPCH (S-(2-thiopyridyl)-L-cysteine hydrazide and TPMPH ((S-(2-thiopyridyl) mercapto-propionohydrazide) react with carbohydrate moieties that have been previously oxidized by mild periodate treatment, thus forming a hydrazone bond between the hydrazide portion of the crosslinker and the periodate generated aldehydes. TPCH and TPMPH introduce a 2-pyridylthione protected sulfhydryl group onto the sugar, which can be deprotected with DTT and then subsequently used for conjugation, such as forming disulfide bonds between components.

If disulfide bonding is found unsuitable for producing stable modified sugars, other crosslinkers may be used that incorporate more stable bonds between components. The heterobifunctional crosslinkers GMBS (N-gama-malimidobutyryloxy)succinimide) and SMCC (succinimidyl 4-(N-maleimido-methyl)cyclohexane) react with primary amines, thus introducing a maleimide group onto the component. The maleimide group can subsequently react with sulfhydryls on the other component, which can be introduced by previously mentioned crosslinkers, thus forming a stable thioether bond between the components. If steric hindrance between components interferes with either component's activity or the ability of the modified sugar to act as a glycosyltransferase substrate, crosslinkers can be used which introduce long spacer arms between components and include derivatives of some of the previously mentioned crosslinkers (i.e., SPDP). Thus, there is an abundance of suitable crosslinkers, which are useful; each of which is selected depending on the effects it has on optimal peptide conjugate and modified sugar production.

A variety of reagents are used to modify the components of the modified sugar with intramolecular chemical crosslinks (for reviews of crosslinking reagents and crosslinking procedures see: Wold, F., *Meth. Enzymol.* 25: 623-651, 1972; Weetall, H. H., and Cooney, D. A., In: Enzymes as Drugs. (Holcenberg, and Roberts, eds.) pp. 395-442, Wiley, New York, 1981; Ji, T. H., *Meth. Enzymol.* 91: 580-609, 1983; Mattson et al., *Mol. Biol. Rep.* 17: 167-183, 1993, all of which are incorporated herein by reference). Preferred crosslinking reagents are derived from various zero-length, homo-bifunctional, and hetero-bifunctional crosslinking reagents. Zero-length crosslinking reagents include direct conjugation of two intrinsic chemical groups with no introduction of extrinsic material. Agents that catalyze formation of a disulfide bond belong to this category. Another example is reagents that induce condensation of a carboxyl and a primary amino group to form an amide bond such as carbodiimides, ethylchloroformate, Woodward's reagent K (2-ethyl-5-phenylisoxazolium-3'-sulfonate), and carbonyldiimidazole. In addition to these chemical reagents, the enzyme transglutaminase (glutamyl-peptide γ-glutamyltransferase; EC 2.3.2.13) may be used as zero-length crosslinking reagent. This enzyme catalyzes acyl transfer reactions at carboxamide groups of protein-linked glutaminyl residues, usually with a primary amino group as substrate. Preferred homo- and hetero-bifunctional reagents contain two identical or two dissimilar sites, respectively, which may be reactive for amino, sulfhydryl, guanidino, indole, or nonspecific groups.

2. Preferred Specific Sites in Crosslinking Reagents a. Amino-Reactive Groups

In one preferred embodiment, the sites on the cross-linker are amino-reactive groups. Useful non-limiting examples of amino-reactive groups include N-hydroxysuccinimide (NHS) esters, imidoesters, isocyanates, acylhalides, arylazides, p-nitrophenyl esters, aldehydes, and sulfonyl chlorides.

NHS esters react preferentially with the primary (including aromatic) amino groups of a modified sugar component. The imidazole groups of histidines are known to compete with primary amines for reaction, but the reaction products are unstable and readily hydrolyzed. The reaction involves the nucleophilic attack of an amine on the acid carboxyl of an NHS ester to form an amide, releasing the N-hydroxysuccinimide. Thus, the positive charge of the original amino group is lost.

Imidoesters are the most specific acylating reagents for reaction with the amine groups of the modified sugar components. At a pH between 7 and 10, imidoesters react only with primary amines. Primary amines attack imidates nucleophilically to produce an intermediate that breaks down to amidine at high pH or to a new imidate at low pH. The new imidate can react with another primary amine, thus crosslinking two amino groups, a case of a putatively monofunctional imidate reacting bifunctionally. The principal product of reaction with primary amines is an amidine that is a stronger base than the original amine. The positive charge of the original amino group is therefore retained.

Isocyanates (and isothiocyanates) react with the primary amines of the modified sugar components to form stable bonds. Their reactions with sulfhydryl, imidazole, and tyrosyl groups give relatively unstable products.

Acylazides are also used as amino-specific reagents in which nucleophilic amines of the affinity component attack acidic carboxyl groups under slightly alkaline conditions, e.g. pH 8.5.

Arylhalides such as 1,5-difluoro-2,4-dinitrobenzene react preferentially with the amino groups and tyrosine phenolic groups of modified sugar components, but also with sulfhydryl and imidazole groups.

p-Nitrophenyl esters of mono- and dicarboxylic acids are also useful amino-reactive groups. Although the reagent specificity is not very high, α- and c-amino groups appear to react most rapidly.

Aldehydes such as glutaraldehyde react with primary amines of modified sugar. Although unstable Schiff bases are formed upon reaction of the amino groups with the aldehydes of the aldehydes, glutaraldehyde is capable of modifying the modified sugar with stable crosslinks. At pH 6-8, the pH of typical crosslinking conditions, the cyclic polymers undergo a dehydration to form α-β unsaturated aldehyde polymers. Schiff bases, however, are stable, when conjugated to another double bond. The resonant interaction of both double bonds prevents hydrolysis of the Schiff linkage. Furthermore, amines at high local concentrations can attack the ethylenic double bond to form a stable Michael addition product.

Aromatic sulfonyl chlorides react with a variety of sites of the modified sugar components, but reaction with the amino groups is the most important, resulting in a stable sulfonamide linkage.

b. Sulfhydryl-Reactive Groups

In another preferred embodiment, the sites are sulfhydryl-reactive groups. Useful, non-limiting examples of sulfhydryl-reactive groups include maleimides, alkyl halides, pyridyl disulfides, and thiophthalimides.

Maleimides react preferentially with the sulfhydryl group of the modified sugar components to form stable thioether bonds. They also react at a much slower rate with primary amino groups and the imidazole groups of histidines. However, at pH 7 the maleimide group can be considered a sulfhydryl-specific group, since at this pH the reaction rate of simple thiols is 1000-fold greater than that of the corresponding amine.

Alkyl halides react with sulfhydryl groups, sulfides, imidazoles, and amino groups. At neutral to slightly alkaline pH, however, alkyl halides react primarily with sulfhydryl groups to form stable thioether bonds. At higher pH, reaction with amino groups is favored. Pyridyl disulfides react with free sulfhydryls via disulfide exchange to give mixed disulfides. As a result, pyridyl disulfides are the most specific sulfhydryl-reactive groups. Thiophthalimides react with free sulfhydryl groups to form disulfides.

c. Carboxyl-Reactive Residue

In another embodiment, carbodiimides soluble in both water and organic solvent, are used as carboxyl-reactive reagents. These compounds react with free carboxyl groups forming a pseudourea that can then coupled to available amines yielding an amide linkage. Procedures to modify a carboxyl group with carbodiimide is well know in the art see, Yamada et al., *Biochemistry* 20: 4836-4842, 1981).

3. Preferred Nonspecific Sites in Crosslinking Reagents

In addition to the use of site-specific reactive moieties, the present invention contemplates the use of non-specific reactive groups to link the sugar to the modifying group. Exemplary non-specific cross-linkers include photoactivatable groups, completely inert in the dark, which are converted to reactive species upon absorption of a photon of appropriate energy. In one preferred embodiment, photoactivatable groups are selected from precursors of nitrenes generated upon heating or photolysis of azides. Electron-deficient nitrenes are extremely reactive and can react with a variety of chemical bonds including N—H, O—H, C—H, and C═C. Although three types of azides (aryl, alkyl, and acyl derivatives) may be employed, arylazides are presently preferred. The reactivity of arylazides upon photolysis is better with N—H and O—H than C—H bonds. Electron-deficient arylnitrenes rapidly ring-expand to form dehydroazepines, which tend to react with nucleophiles, rather than form C—H insertion products. The reactivity of arylazides can be increased by the presence of electron-withdrawing substituents such as nitro or hydroxyl groups in the ring. Such substituents push the absorption maximum of arylazides to longer wavelength. Unsubstituted arylazides have an absorption maximum in the range of 260-280 nm, while hydroxy and nitroarylazides absorb significant light beyond 305 nm. Therefore, hydroxy and nitroarylazides are most preferable since they allow to employ less harmful photolysis conditions for the affinity component than unsubstituted arylazides.

In another preferred embodiment, photoactivatable groups are selected from fluorinated arylazides. The photolysis products of fluorinated arylazides are arylnitrenes, all of which undergo the characteristic reactions of this group, including C—H bond insertion, with high efficiency (Keana et al., *J. Org. Chem.* 55: 3640-3647, 1990).

In another embodiment, photoactivatable groups are selected from benzophenone residues. Benzophenone reagents generally give higher crosslinking yields than arylazide reagents.

In another embodiment, photoactivatable groups are selected from diazo compounds, which form an electron-deficient carbene upon photolysis. These carbenes undergo a variety of reactions including insertion into C—H bonds, addition to double bonds (including aromatic systems), hydrogen attraction and coordination to nucleophilic centers to give carbon ions.

In still another embodiment, photoactivatable groups are selected from diazopyruvates. For example, the p-nitrophenyl ester of p-nitrophenyl diazopyruvate reacts with aliphatic amines to give diazopyruvic acid amides that undergo ultraviolet photolysis to form aldehydes. The photolyzed diazopyruvate-modified affinity component will react like formaldehyde or glutaraldehyde forming crosslinks.

4. Homobifunctional Reagents a. Homobifunctional Crosslinkers Reactive with Primary Amines Synthesis, properties, and applications of amine-reactive cross-linkers are commercially described in the literature (for reviews of crosslinking procedures and reagents, see above). Many reagents are available (e.g., Pierce Chemical Company, Rockford, Ill.; Sigma Chemical Company, St. Louis, Mo.; Molecular Probes, Inc., Eugene, Oreg.).

Preferred, non-limiting examples of homobifunctional NHS esters include disuccinimidyl glutarate (DSG), disuccinimidyl suberate (DSS), bis(sulfosuccinimidyl) suberate (BS), disuccinimidyl tartarate (DST), disulfosuccinimidyl tartarate (sulfo-DST), bis-2-(succinimidooxycarbonyloxy)ethylsulfone (BSOCOES), bis-2-(sulfosuccinimidooxy-carbonyloxy)ethylsulfone (sulfo-BSOCOES), ethylene glycolbis(succinimidylsuccinate) (EGS), ethylene glycolbis(sulfosuccinimidylsuccinate) (sulfo-EGS), dithiobis(succinimidyl-propionate (DSP), and dithiobis(sulfosuccinimidylpropionate (sulfo-DSP). Preferred, non-limiting examples of homobifunctional imidoesters include dimethyl malonimidate (DMM), dimethyl succinimidate (DMSC), dimethyl adipimidate (DMA), dimethyl pimelimidate (DMP), dimethyl suberimidate (DMS), dimethyl-3,3'-oxydipropionimidate (DODP), dimethyl-3,3'-(methylenedioxy)dipropionimidate (DMDP), dimethyl-,3'-(dimethylenedioxy)dipropionimidate (DDDP), dimethyl-3,3'-(tetramethylenedioxy)-dipropionimidate (DTDP), and dimethyl-3,3'-dithiobispropionimidate (DTBP).

Preferred, non-limiting examples of homobifunctional isothiocyanates include: p-phenylenediisothiocyanate (DITC), and 4,4'-diisothiocyano-2,2'-disulfonic acid stilbene (DIDS).

Preferred, non-limiting examples of homobifunctional isocyanates include xylene-diisocyanate, toluene-2,4-diisocyanate, toluene-2-isocyanate-4-isothiocyanate, 3-methoxydiphenylmethane-4,4'-diisocyanate, 2,2'-dicarboxy-4,4'-azophenyldiisocyanate, and hexamethylenediisocyanate.

Preferred, non-limiting examples of homobifunctional arylhalides include 1,5-difluoro-2,4-dinitrobenzene (DFDNB), and 4,4'-difluoro-3,3'-dinitrophenyl-sulfone. Preferred, non-limiting examples of homobifunctional aliphatic aldehyde reagents include glyoxal, malondialdehyde, and glutaraldehyde.

Preferred, non-limiting examples of homobifunctional acylating reagents include nitrophenyl esters of dicarboxylic acids.

Preferred, non-limiting examples of homobifunctional aromatic sulfonyl chlorides include phenol-2,4-disulfonyl chloride, and α-naphthol-2,4-disulfonyl chloride.

Preferred, non-limiting examples of additional amino-reactive homobifunctional reagents include erythritolbiscarbonate which reacts with amines to give biscarbamates.

b. Homobifunctional Crosslinkers Reactive with Free Sulfhydryl Groups

Synthesis, properties, and applications of such reagents are described in the literature (for reviews of crosslinking procedures and reagents, see above). Many of the reagents are commercially available (e.g., Pierce Chemical Company, Rockford, Ill.; Sigma Chemical Company, St. Louis, Mo.; Molecular Probes, Inc., Eugene, Oreg.).

Preferred, non-limiting examples of homobifunctional maleimides include bismaleimidohexane (BMH), N,N'-(1,3-phenylene) bismaleimide, N,N'-(1,2-phenylene)bismaleimide, azophenyldimaleimide, and bis(N-maleimidomethyl) ether. Preferred, non-limiting examples of homobifunctional pyridyl disulfides include 1,4-di-3'-(2'-pyridyldithio)propionamidobutane (DPDPB).

Preferred, non-limiting examples of homobifunctional alkyl halides include 2,2'-dicarboxy-4,4'-diiodoacetamidoazobenzene, α,α'-diiodo-p-xylenesulfonic acid, α, α'-dibromo-p-xylenesulfonic acid, N,N'-bis(b-bromoethyl)benzylamine, N,N'-di(bromoacetyl)phenylthydrazine, and 1,2-di(bromoacetyl)amino-3-phenylpropane.

c. Homobifunctional Photoactivatable Crosslinkers

Synthesis, properties, and applications of such reagents are described in the literature (for reviews of crosslinking procedures and reagents, see above). Some of the reagents are commercially available (e.g., Pierce Chemical Company, Rockford, Ill.; Sigma Chemical Company, St. Louis, Mo.; Molecular Probes, Inc., Eugene, Oreg.).

Preferred, non-limiting examples of homobifunctional photoactivatable crosslinker include bis-β-(4-azidosalicylamido)ethyldisulfide (BASED), di-N-(2-nitro-4-azidophenyl)-cystamine-S,S-dioxide (DNCO), and 4,4'-dithiobisphenylazide.

5. HeteroBifunctional Reagents a. Amino-Reactive HeteroBifunctional Reagents with a Pyridyl Disulfide Moiety Synthesis, properties, and applications of such reagents are described in the literature (for reviews of crosslinking procedures and reagents, see above). Many of the reagents are commercially available (e.g., Pierce Chemical Company, Rockford, Ill.; Sigma Chemical Company, St. Louis, Mo.; Molecular Probes, Inc., Eugene, Oreg.).

Preferred, non-limiting examples of hetero-bifunctional reagents with a pyridyl disulfide moiety and an amino-reactive NHS ester include N-succinimidyl-3-(2-pyridyldithio) propionate (SPDP), succinimidyl 6-3-(2-pyridyldithio)propionamidohexanoate (LC-SPDP), sulfosuccinimidyl 6-3-(2-pyridyldithio)propionamidohexanoate (sulfo-LCSPDP), 4-succinimidyloxycarbonyl-α-methyl-α-(2-pyridyldithio) toluene (SMPT), and sulfosuccinimidyl 6-α-methyl-α-(2-pyridyldithio)toluamidohexanoate (sulfo-LC-SMPT).

b. Amino-Reactive Heterobifunctional Reagents with a Maleimide Moiety

Synthesis, properties, and applications of such reagents are described in the literature. Preferred, non-limiting examples of hetero-bifunctional reagents with a maleimide moiety and an amino-reactive NHS ester include succinimidyl maleimidylacetate (AMAS), succinimidyl 3-maleimidylpropionate (BMPS), N-γ-maleimidobutyryloxysuccinimide ester (GMBS)N-γ-maleimidobutyryloxysulfo succinimide ester (sulfo-GMBS) succinimidyl 6-maleimidylhexanoate (EMCS), succinimidyl 3-maleimidylbenzoate (SMB), m-maleimidobenzoyl-N-hydroxysuccinimide ester (MBS), m-maleimidobenzoyl-N-hydroxysulfosuccinimide ester (sulfo-MBS), succinimidyl 4-(N-maleimidomethyl)-cyclohexane-1-carboxylate (SMCC), sulfosuccinimidyl 4-(N-maleimidomethyl)cyclohexane-1-carboxylate (sulfo-SMCC), succinimidyl 4-(p-maleimidophenyl)butyrate (SMPB), and sulfosuccinimidyl 4-(p-maleimidophenyl)butyrate (sulfo-SMPB).

c. Amino-Reactive HeteroBifunctional Reagents with an Alkyl Halide Moiety

Synthesis, properties, and applications of such reagents are described in the literature. Preferred, non-limiting examples of hetero-bifunctional reagents with an alkyl halide moiety and an amino-reactive NHS ester include N-succinimidyl-(4-iodoacetyl)aminobenzoate (SIAB), sulfosuccinimidyl-(4-iodoacetyl)aminobenzoate (sulfo-SIAB), succinimidyl-6-(iodoacetyl)aminohexanoate (SIAX), succinimidyl-6-(6-((iodoacetyl)-amino)hexanoylamino)hexanoate (SIAXX), succinimidyl-6-(((4-(iodoacetyl)-amino)-methyl)-cyclohexane-1-carbonyl)aminohexanoate (SIACX), and succinimidyl-4((iodoacetyl)-amino)methylcyclohexane-1-carboxylate (SIAC).

A preferred example of a hetero-bifunctional reagent with an amino-reactive NHS ester and an alkyl dihalide moiety is N-hydroxysuccinimidyl 2,3-dibromopropionate (SDBP). SDBP introduces intramolecular crosslinks to the affinity component by conjugating its amino groups. The reactivity of the dibromopropionyl moiety towards primary amine groups is controlled by the reaction temperature (McKenzie et al., *Protein Chem.* 7: 581-592 (1988)).

Preferred, non-limiting examples of hetero-bifunctional reagents with an alkyl halide moiety and an amino-reactive p-nitrophenyl ester moiety include p-nitrophenyl iodoacetate (NPIA).

Other cross-linking agents are known to those of skill in the art. See, for example, Pomato et al., U.S. Pat. No. 5,965,106. It is within the abilities of one of skill in the art to choose an appropriate cross-linking agent for a particular application.

d. Cleavable Linker Groups

In yet a further embodiment, the linker group is provided with a group that can be cleaved to release the modifying group from the sugar residue. Many cleavable groups are known in the art. See, for example, Jung et al., *Biochem. Biophys. Acta* 761: 152-162 (1983); Joshi et al., *J. Biol. Chem.* 265: 14518-14525 (1990); Zarling et al., *J. Immunol.* 124: 913-920 (1980); Bouizar et al., *Eur. J. Biochem.* 155: 141-147 (1986); Park et al., *J. Biol. Chem.* 261: 205-210 (1986); Browning et al., *J. Immunol.* 143: 1859-1867 (1989). Moreover a broad range of cleavable, bifunctional (both homo- and hetero-bifunctional) linker groups is commercially available from suppliers such as Pierce.

Exemplary cleavable moieties can be cleaved using light, heat or reagents such as thiols, hydroxylamine, bases, periodate and the like. Moreover, certain preferred groups are cleaved in vivo in response to being endocytosed (e.g., cis-aconityl; see, Shen et al., *Biochem. Biophys. Res. Commun.* 102: 1048 (1991)). Preferred cleavable groups comprise a cleavable moiety which is a member selected from the group consisting of disulfide, ester, imide, carbonate, nitrobenzyl, phenacyl and benzoin groups.

e. Conjugation of Modified Sugars to Peptides

The modified sugars are conjugated to a glycosylated or non-glycosylated peptide using an appropriate enzyme to mediate the conjugation. Preferably, the concentrations of the modified donor sugar(s), enzyme(s) and acceptor peptide(s) are selected such that glycosylation proceeds until the acceptor is consumed. The considerations discussed below, while set forth in the context of a sialyltransferase, are generally applicable to other glycosyltransferase reactions.

A number of methods of using glycosyltransferases to synthesize desired oligosaccharide structures are known and are generally applicable to the instant invention. Exemplary methods are described, for instance, WO 96/32491, Ito et al., *Pure Appl. Chem.* 65: 753 (1993), and U.S. Pat. Nos. 5,352, 670, 5,374,541, and 5,545,553.

The present invention is practiced using a single glycosyltransferase or a combination of glycosyltransferases. For example, one can use a combination of a sialyltransferase and a galactosyltransferase. In those embodiments using more than one enzyme, the enzymes and substrates are preferably combined in an initial reaction mixture, or the enzymes and reagents for a second enzymatic reaction are added to the reaction medium once the first enzymatic reaction is complete or nearly complete. By conducting two enzymatic reactions in sequence in a single vessel, overall yields are improved over procedures in which an intermediate species is isolated. Moreover, cleanup and disposal of extra solvents and by-products is reduced.

In a preferred embodiment, each of the first and second enzyme is a glycosyltransferase. In another preferred embodiment, one enzyme is an endoglycosidase. In another preferred embodiment, one enzyme is an exoglycosidase. In an additional preferred embodiment, more than two enzymes are used to assemble the modified glycoprotein of the invention. The enzymes are used to alter a saccharide structure on the peptide at any point either before or after the addition of the modified sugar to the peptide.

Figure 23A:
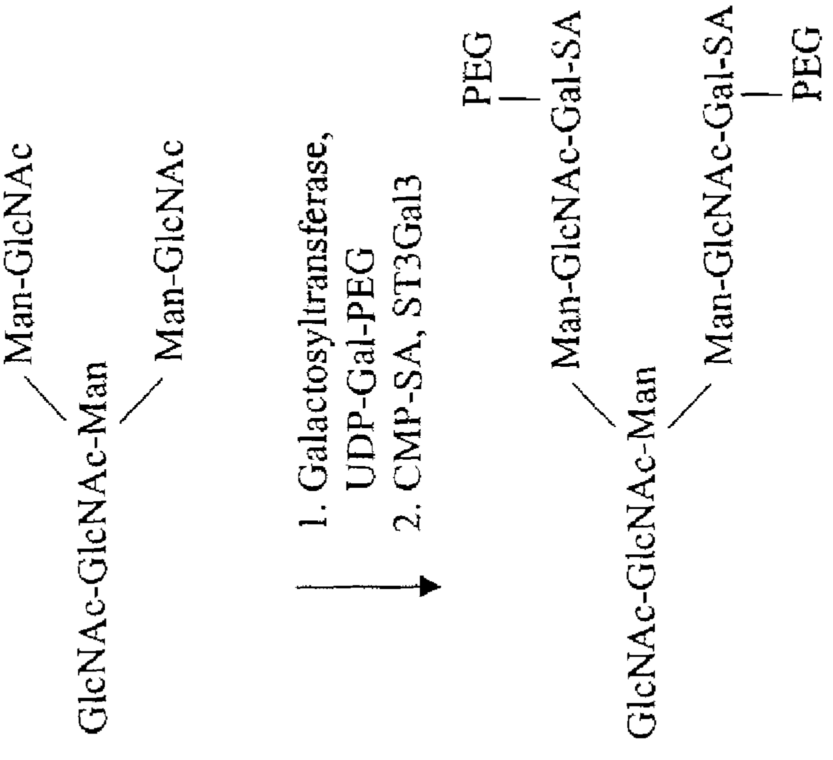
FIG. 23A to FIG. 23C, is a series of exemplary schemes.

In another embodiment, at least two of the enzymes are glycosyltransferases and the last sugar added to the saccharide structure of the peptide is a non-modified sugar. Instead, the modified sugar is internal to the glycan structure and therefore need not be the ultimate sugar on the glycan. In an exemplary embodiment, galactosyltransferase may catalyze the transfer of Gal-PEG from UDP-Gal-PEG onto the glycan, followed by incubation in the presence of ST3Gal3 and CMP-SA, which serves to add a "capping" unmodified sialic acid onto the glycan (FIG. 23A).

Figure 23B:
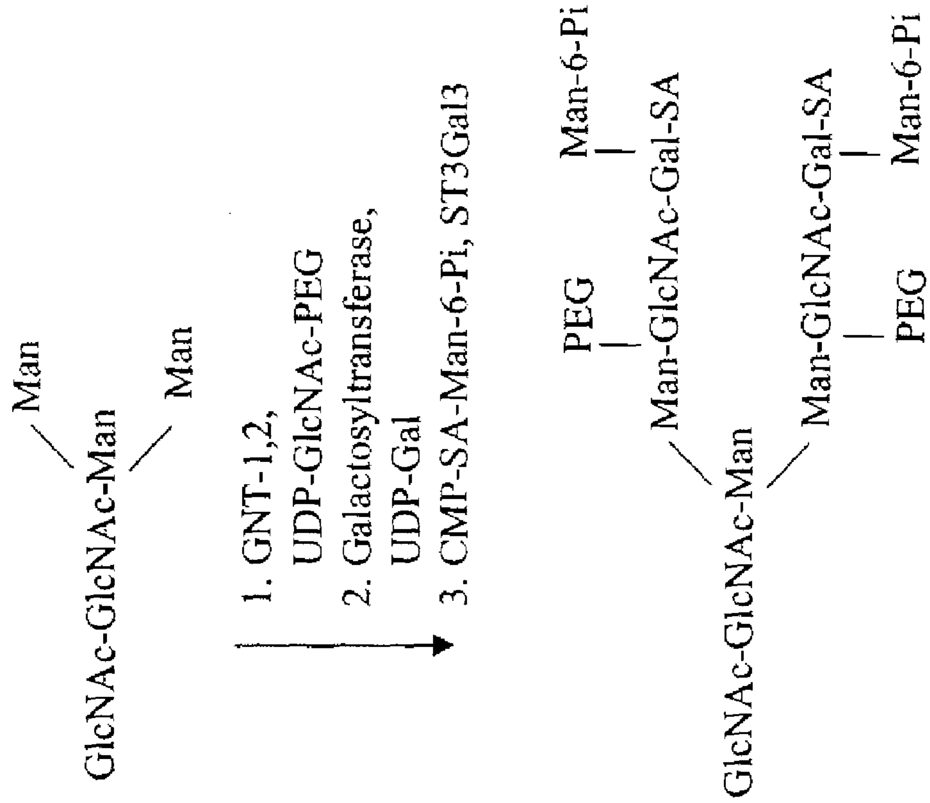

In another embodiment, at least two of the enzymes used are glycosyltransferases, and at least two modified sugars are added to the glycan structures on the peptide. In this manner, two or more different glycoconjugates may be added to one or more glycans on a peptide. This process generates glycan structures having two or more functionally different modified sugars. In an exemplary embodiment, incubation of the peptide with GnT-I, II and UDP-GlcNAc-PEG serves to add a GlcNAc-PEG molecule to the glycan; incubation with galactosyltransferase and UDP-Gal then serves to add a Gal residue thereto; and, incubation with ST3Gal3 and CMP-SA-Man-6-Phosphate serves to add a SA-mannose-6-phosphate molecule to the glycan. This series of reactions results in a glycan chain having the functional characteristics of a PEGylated glycan as well as mannose-6-phosphate targeting activity (FIG. 23B).

Figure 23C:
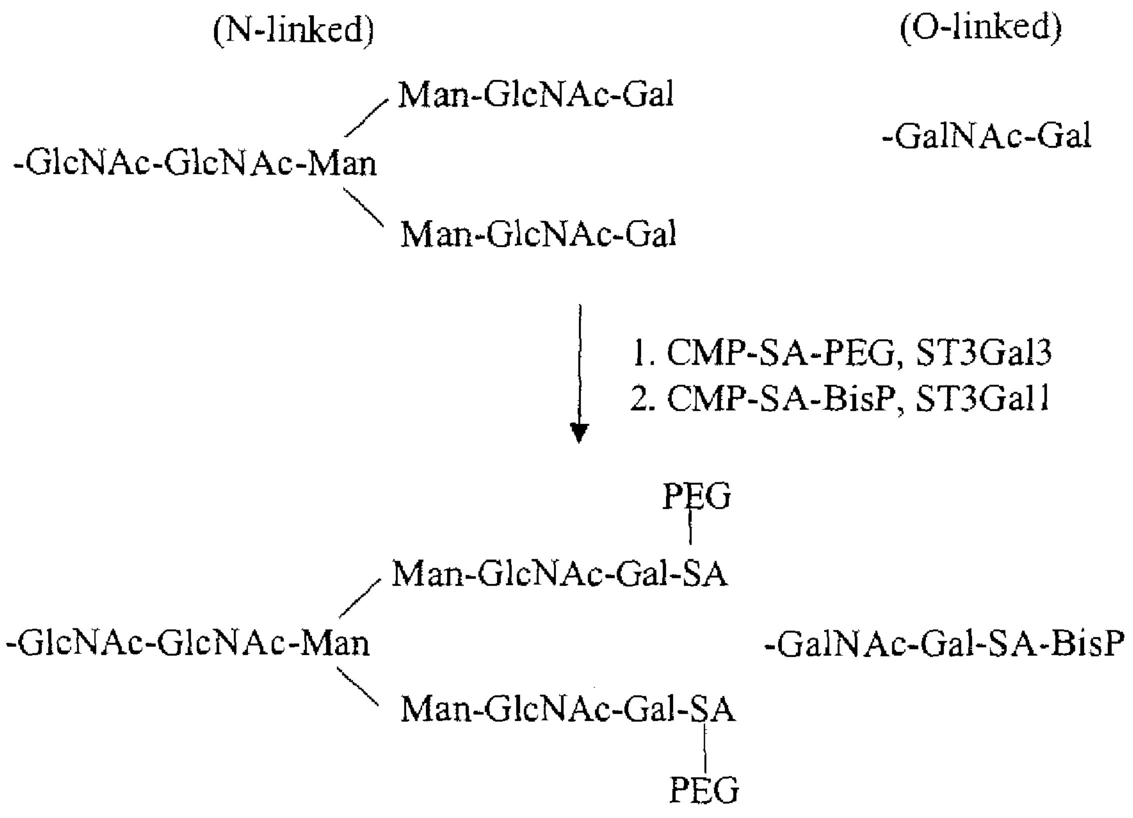

In another embodiment, at least two of the enzymes used in the reaction are glycosyltransferases, and again, different modified sugars are added to N-linked and O-linked glycans on the peptide. This embodiment is useful when two different modified sugars are to be added to the glycans of a peptide, but when it is important to spatially separate the modified sugars on the peptide from each other. For example, if the modified sugars comprise bulky molecules, including but not limited to, PEG and other molecules such as a linker molecule, this method may be preferable. The modified sugars may be added simultaneously to the glycan structures on a peptide, or they may be added sequentially. In an exemplary embodiment, incubation with ST3Gal3 and CMP-SA-PEG serves to add sialic acid-PEG to the N-linked glycans, while incubation with ST3Gal1 and CMP-SA-bisPhosphonate serves to add sialic acid-BisPhosphonate to the O-linked glycans (FIG. 23C).

In another embodiment, the method makes use of one or more exo- or endoglycosidase. The glycosidase is typically a mutant, which is engineered to form glycosyl bonds rather than rupture them. The mutant glycanase, sometimes called a glycosynthase, typically includes a substitution of an amino acid residue for an active site acidic amino acid residue. For example, when the endoglycanase is endo-H, the substituted active site residues will typically be Asp at position 130, Glu at position 132 or a combination thereof. The amino acids are generally replaced with serine, alanine, asparagine, or glutamine. Exoglycosidases such as transialylidase are also useful.

The mutant enzyme catalyzes the reaction, usually by a synthesis step that is analogous to the reverse reaction of the endoglycanase hydrolysis step. In these embodiments, the glycosyl donor molecule (e.g., a desired oligo- or monosaccharide structure) contains a leaving group and the reaction proceeds with the addition of the donor molecule to a GlcNAc residue on the protein. For example, the leaving group can be a halogen, such as fluoride. In other embodiments, the leaving group is a Asn, or a Asn-peptide moiety. In yet further embodiments, the GlcNAc residue on the glycosyl donor molecule is modified. For example, the GlcNAc residue may comprise a 1,2 oxazoline moiety.

In a preferred embodiment, each of the enzymes utilized to produce a conjugate of the invention are present in a catalytic amount. The catalytic amount of a particular enzyme varies according to the concentration of that enzyme's substrate as well as to reaction conditions such as temperature, time and pH value. Means for determining the catalytic amount for a given enzyme under preselected substrate concentrations and reaction conditions are well known to those of skill in the art.

The temperature at which an above-described process is carried out can range from just above freezing to the temperature at which the most sensitive enzyme denatures. Preferred temperature ranges are about 0° C. to about 55° C., and more preferably about 20° C. to about 37° C. In another exemplary embodiment, one or more components of the present method are conducted at an elevated temperature using a thermophilic enzyme.

The reaction mixture is maintained for a period of time sufficient for the acceptor to be glycosylated, thereby forming the desired conjugate. Some of the conjugate can often be detected after a few hours, with recoverable amounts usually being obtained within 24 hours or less. Those of skill in the art understand that the rate of reaction is dependent on a number of variable factors (e.g, enzyme concentration, donor concentration, acceptor concentration, temperature, solvent volume), which are optimized for a selected system.

The present invention also provides for the industrial-scale production of modified peptides. As used herein, an industrial scale generally produces at least one gram of finished, purified conjugate.

In the discussion that follows, the invention is exemplified by the conjugation of modified sialic acid moieties to a glycosylated peptide. The exemplary modified sialic acid is labeled with PEG. The focus of the following discussion on the use of PEG-modified sialic acid and glycosylated peptides is for clarity of illustration and is not intended to imply that the invention is limited to the conjugation of these two partners. One of skill understands that the discussion is generally applicable to the additions of modified glycosyl moieties other than sialic acid. Moreover, the discussion is equally applicable to the modification of a glycosyl unit with agents other than PEG including other water-soluble polymers, therapeutic moieties, and biomolecules.

An enzymatic approach can be used for the selective introduction of PEGylated or PPGylated carbohydrates onto a peptide or glycopeptide. The method utilizes modified sugars containing PEG, PPG, or a masked reactive functional group, and is combined with the appropriate glycosyltransferase or glycosynthase. By selecting the glycosyltransferase that will make the desired carbohydrate linkage and utilizing the modified sugar as the donor substrate, the PEG or PPG can be introduced directly onto the peptide backbone, onto existing sugar residues of a glycopeptide or onto sugar residues that have been added to a peptide.

An acceptor for the sialyltransferase is present on the peptide to be modified by the methods of the present invention either as a naturally occurring structure or one placed there recombinantly, enzymatically or chemically. Suitable acceptors, include, for example, galactosyl acceptors such as Galβ1,4GlcNAc, Galβ1,4GalNAc, Galβ1,3GalNAc, lacto-N-tetraose, Galβ1,3GlcNAc, Galβ1,3Ara, Galβ1,6GlcNAc, Galβ1,4Glc (lactose), and other acceptors known to those of skill in the art (see, e.g., Paulson et al., *J. Biol. Chem.* 253: 5617-5624 (1978)).

In one embodiment, an acceptor for the sialyltransferase is present on the peptide to be modified upon in vivo synthesis of the peptide. Such peptides can be sialylated using the claimed methods without prior modification of the glycosylation pattern of the peptide. Alternatively, the methods of the invention can be used to sialylate a peptide that does not include a suitable acceptor; one first modifies the peptide to include an acceptor by methods known to those of skill in the art. In an exemplary embodiment, a GalNAc residue is added by the action of a GalNAc transferase.

In an exemplary embodiment, the galactosyl acceptor is assembled by attaching a galactose residue to an appropriate acceptor linked to the peptide, e.g., a GlcNAc. The method includes incubating the peptide to be modified with a reaction mixture that contains a suitable amount of a galactosyltransferase (e.g., galβ1,3 or galβ1,4), and a suitable galactosyl donor (e.g., UDP-galactose). The reaction is allowed to proceed substantially to completion or, alternatively, the reaction is terminated when a preselected amount of the galactose residue is added. Other methods of assembling a selected saccharide acceptor will be apparent to those of skill in the art.

In yet another embodiment, peptide-linked oligosaccharides are first "trimmed," either in whole or in part, to expose either an acceptor for the sialyltransferase or a moiety to which one or more appropriate residues can be added to obtain a suitable acceptor. Enzymes such as glycosyltransferases and endoglycosidases (see, for example U.S. Pat. No. 5,716,812) are useful for the attaching and trimming reactions. A detailed discussion of "trimming" and remodeling N-linked and O-linked glycans is provided elsewhere herein.

In the discussion that follows, the method of the invention is exemplified by the use of modified sugars having a water-soluble polymer attached thereto. The focus of the discussion is for clarity of illustration. Those of skill will appreciate that the discussion is equally relevant to those embodiments in which the modified sugar bears a therapeutic moiety, biomolecule or the like.

Figure 14A:
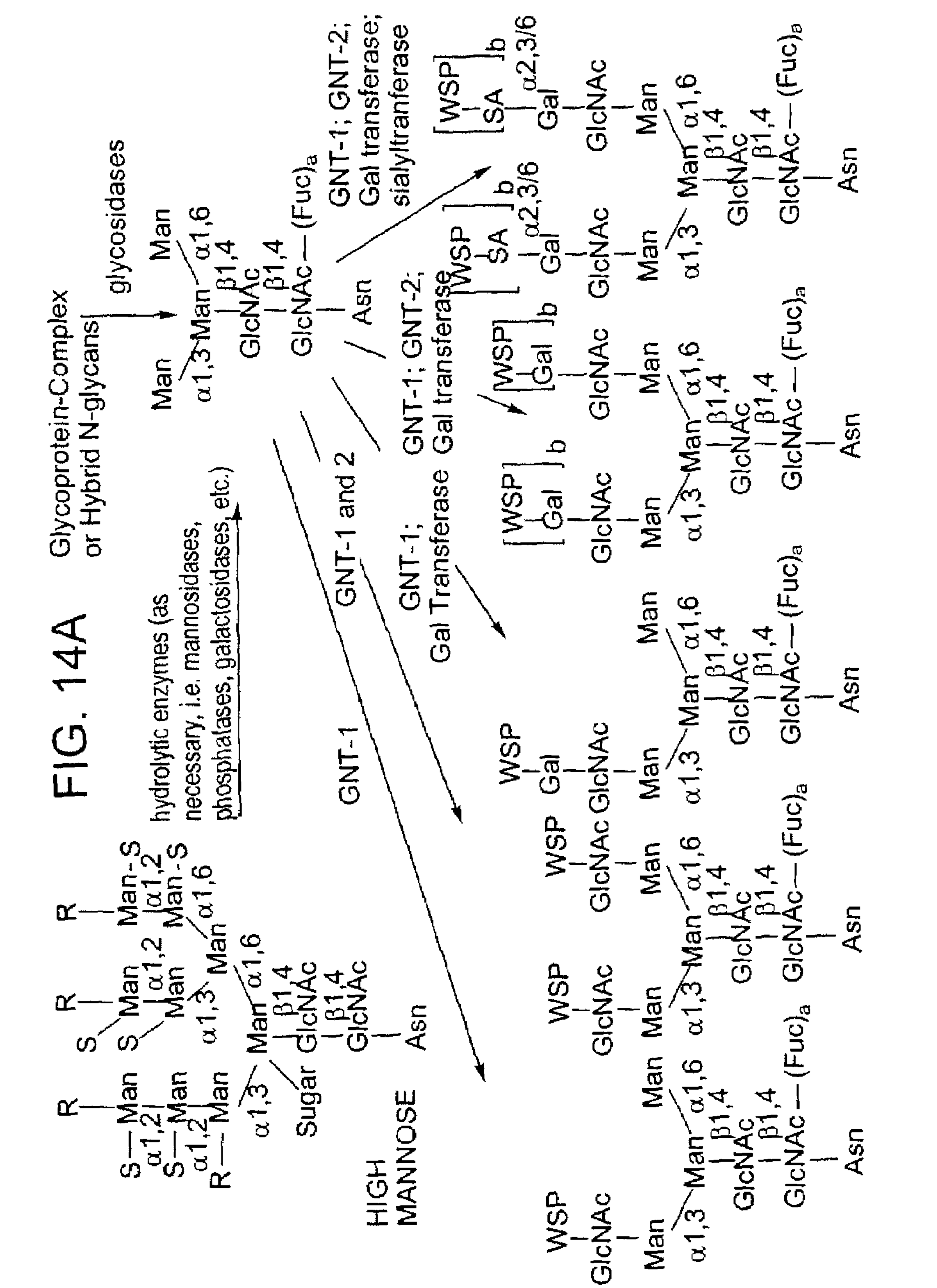
FIG. 14A and FIG. 14B, is a series of schemes showing an exemplary embodiment of the invention in which carbohydrate residues comprising complex carbohydrate structures and/or high mannose high mannose structures are trimmed back to the first generation biantennary structure. Optionally, fucose is added only after reaction with GnT I. A modified sugar bearing a water-soluble polymer (WSP) is then conjugated to one or more of the sugar residues exposed by the trimming back process.
Figure 14B:
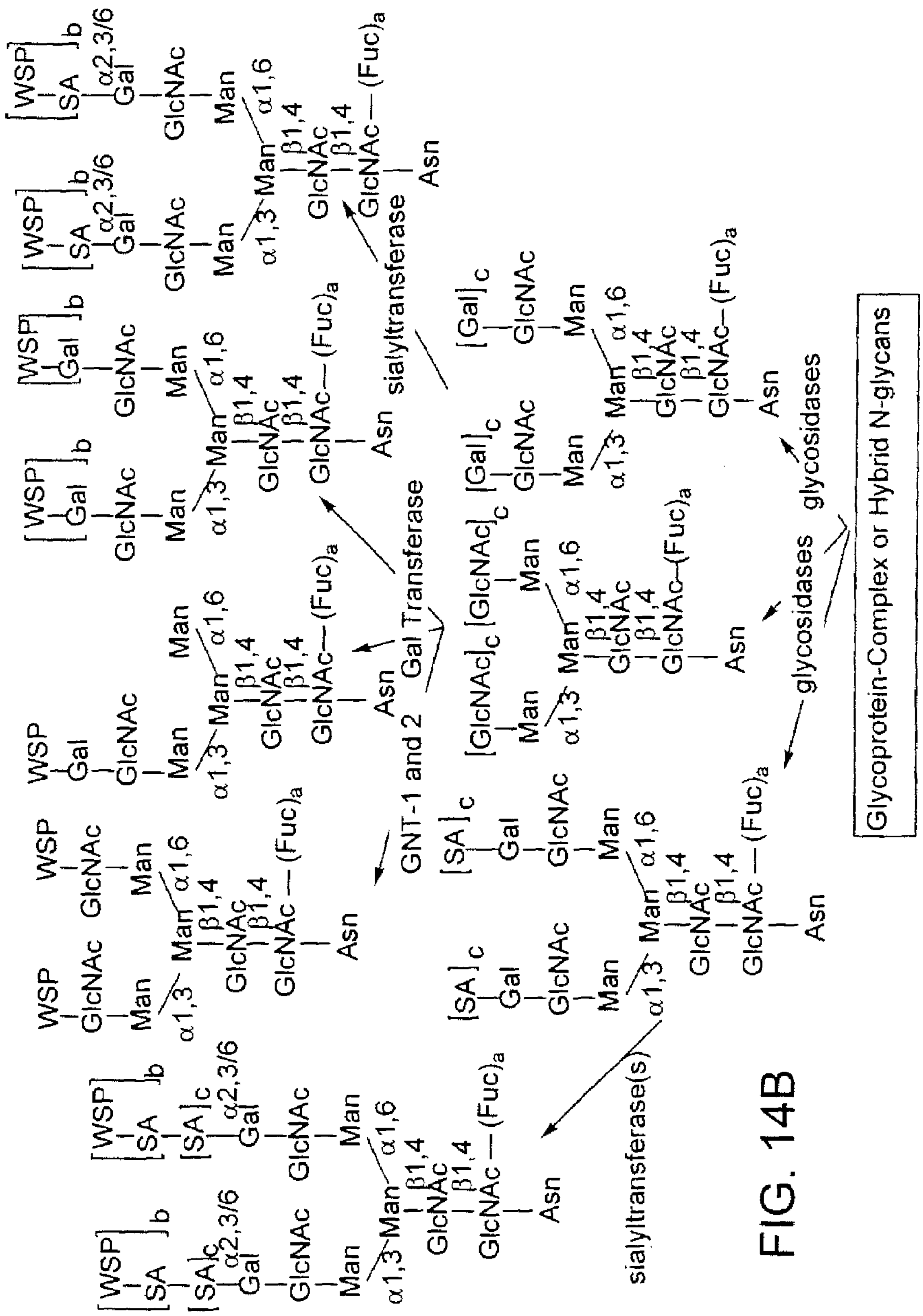

An exemplary embodiment of the invention in which a carbohydrate residue is "trimmed" prior to the addition of the modified sugar is set forth in FIG. 14, which sets forth a scheme in which high mannose is trimmed back to the first generation biantennary structure. A modified sugar bearing a water-soluble polymer is conjugated to one or more of the sugar residues exposed by the "trimming back." In one example, a water-soluble polymer is added via a GlcNAc moiety conjugated to the water-soluble polymer. The modified GlcNAc is attached to one or both of the terminal mannose residues of the biantennary structure. Alternatively, an unmodified GlcNAc can be added to one or both of the termini of the branched species.

In another exemplary embodiment, a water-soluble polymer is added to one or both of the terminal mannose residues of the biantennary structure via a modified sugar having a galactose residue, which is conjugated to a GlcNAc residue added onto the terminal mannose residues. Alternatively, an unmodified Gal can be added to one or both terminal GlcNAc residues.

In yet a further example, a water-soluble polymer is added onto a Gal residue using a modified sialic acid.

Figure 15:
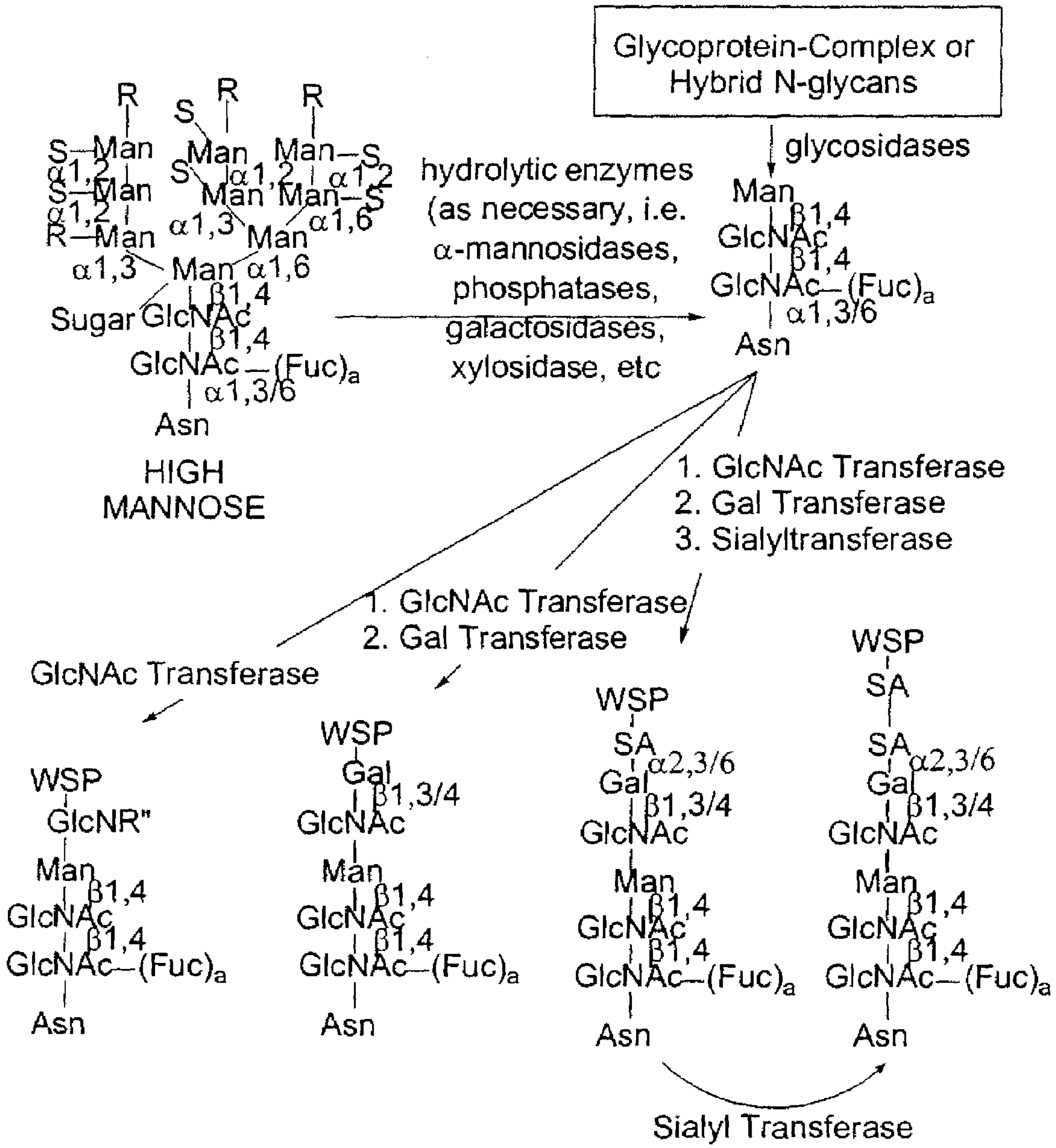
FIG. 15 is a scheme similar to that shown in FIG. 4, in which a high mannose or complex structure is “trimmed back” to the mannose beta-linked core and a modified sugar bearing a water soluble polymer is then conjugated to one or more of the sugar residues exposed by the trimming back process. Sugars are added sequentially using glycosyltransferases.

Another exemplary embodiment is set forth in FIG. 15, which displays a scheme similar to that shown in FIG. 14, in which the high mannose structure is "trimmed back" to the mannose from which the biantennary structure branches. In one example, a water-soluble polymer is added via a GlcNAc modified with the polymer. Alternatively, an unmodified GlcNAc is added to the mannose, followed by a Gal with an attached water-soluble polymer. In yet another embodiment, unmodified GlcNAc and Gal residues are sequentially added to the mannose, followed by a sialic acid moiety modified with a water-soluble polymer.

Figure 16:
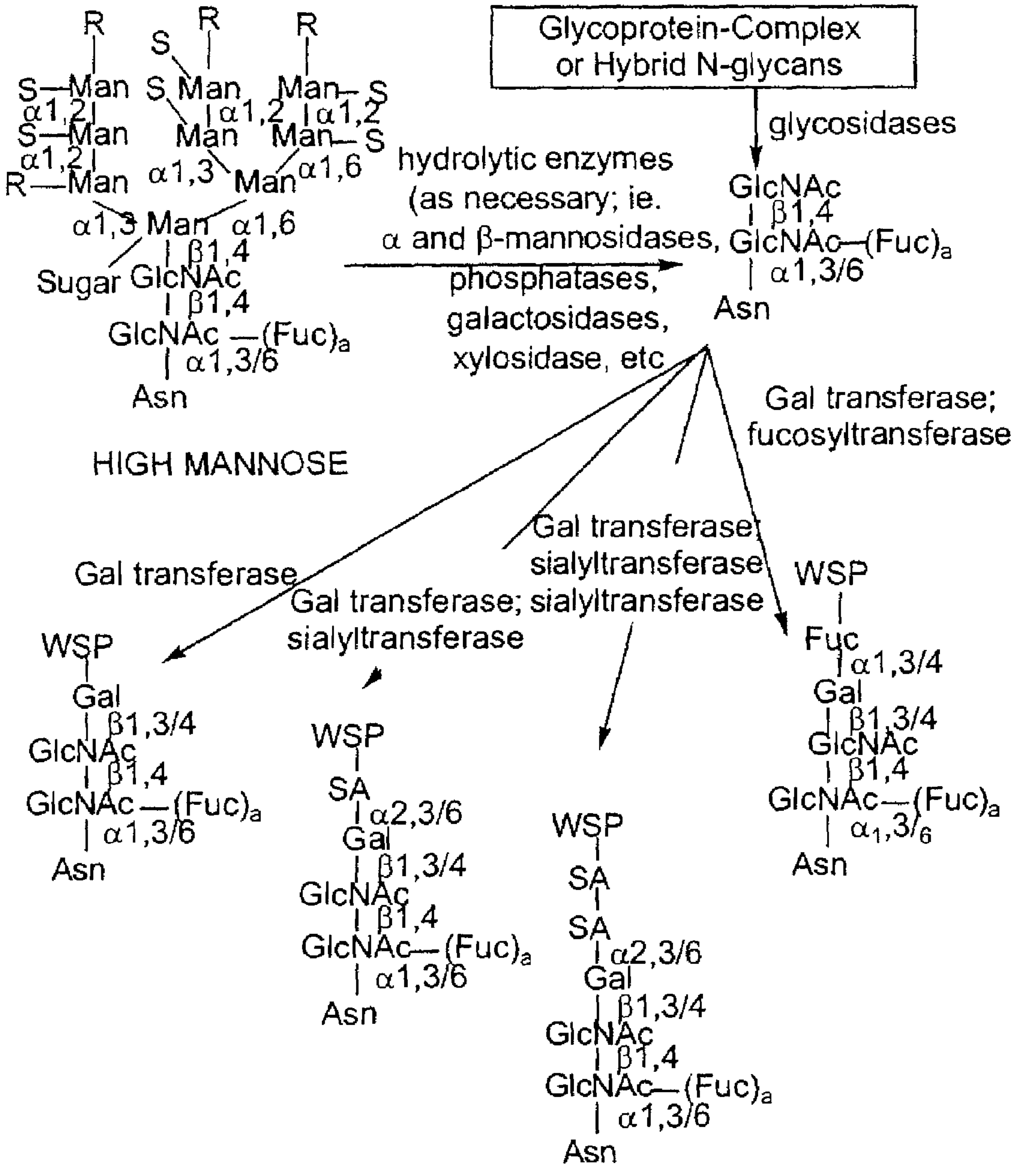
FIG. 16 is a scheme similar to that shown in FIG. 4, in which a high mannose or complex structure is trimmed back to the GlcNAc to which the first mannose is attached, and a modified sugar bearing a water soluble polymer is then conjugated to one or more of the sugar residues exposed by the trimming back process. Sugars are added sequentially using glycosyltransferases.

FIG. 16 sets forth a further exemplary embodiment using a scheme similar to that shown in FIG. 14, in which high mannose is "trimmed back" to the GlcNAc to which the first mannose is attached. The GlcNAc is conjugated to a Gal residue bearing a water-soluble polymer. Alternatively, an unmodified Gal is added to the GlcNAc, followed by the addition of a sialic acid modified with a water-soluble sugar. In yet a further example, the terminal GlcNAc is conjugated with Gal and the GlcNAc is subsequently fucosylated with a modified fucose bearing a water-soluble polymer.

Figure 17:
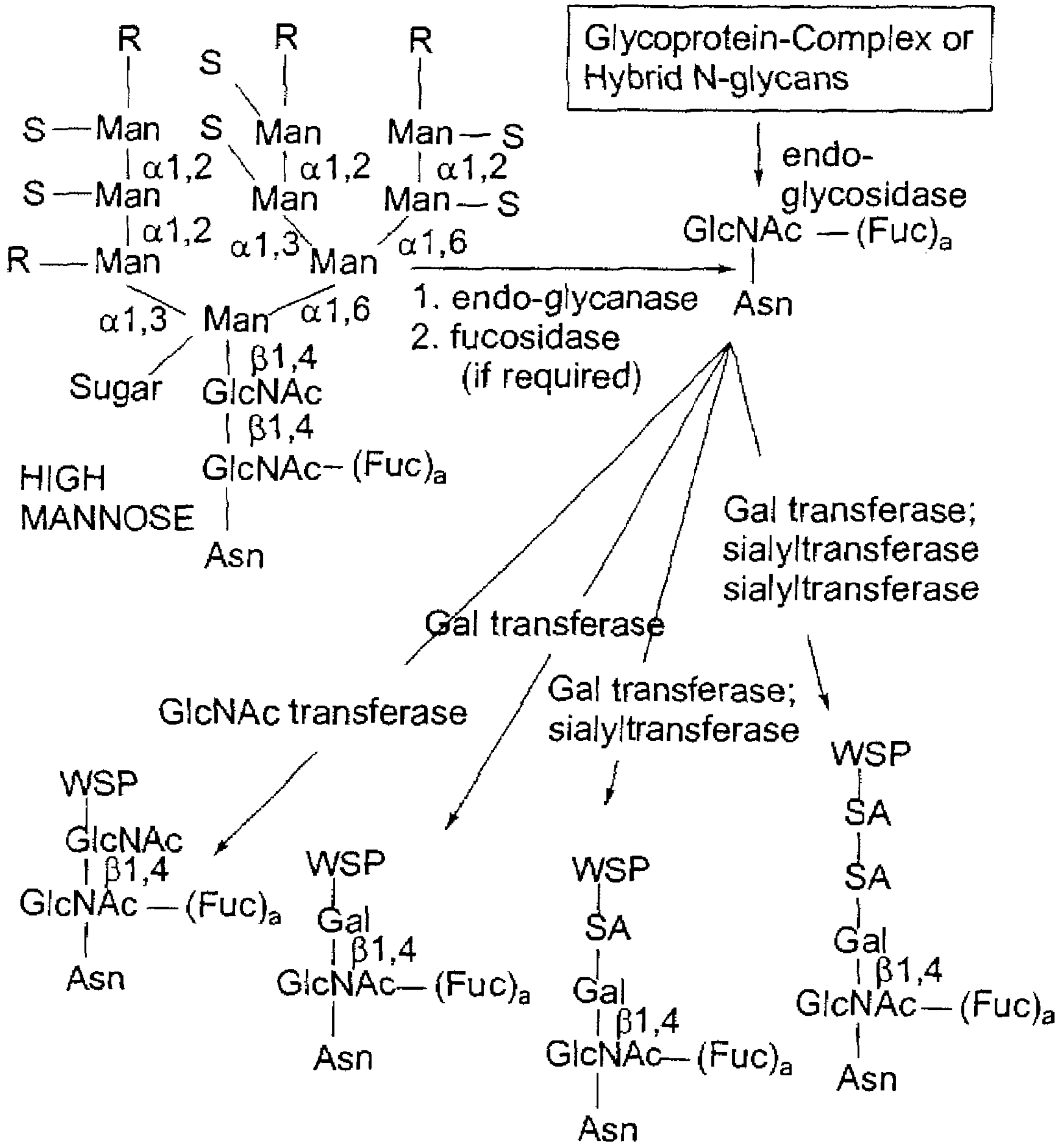
FIG. 17 is a scheme similar to that shown in FIG. 4, in which a high mannose or complex structure is trimmed back to the first GlcNAc attached to the Asn of the peptide, following which a water soluble polymer is conjugated to one or more sugar residues which have subsequently been added on. Sugars are added sequentially using glycosyltransferases.
Figure 18A:
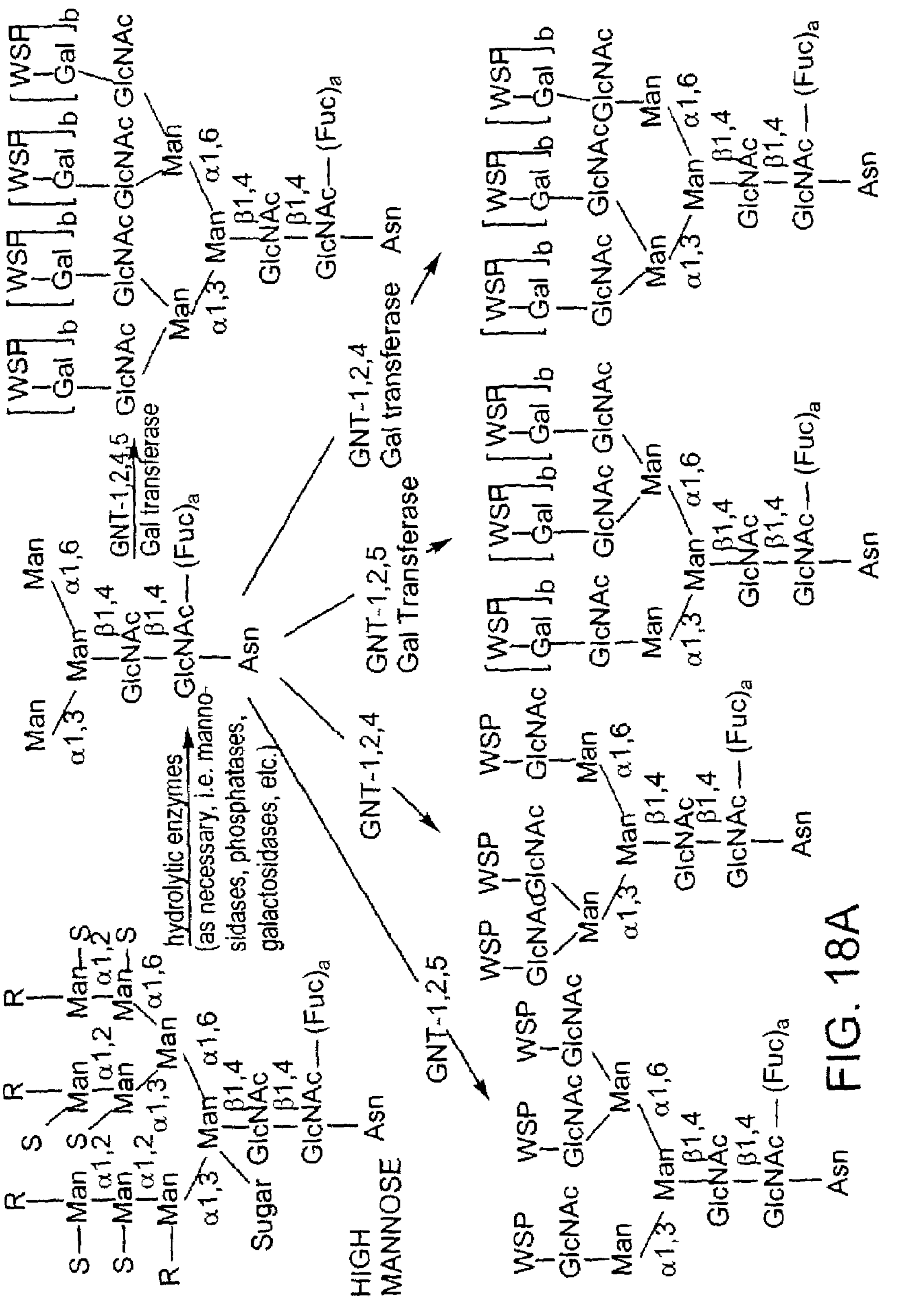
FIGS. 18A and 18B, is a scheme in which an N-linked carbohydrate is optionally trimmed back from a high mannose or complex structure, and subsequently derivatized with a modified sugar moiety (Gal or GlcNAc) bearing a water-soluble polymer.
Figure 18B:
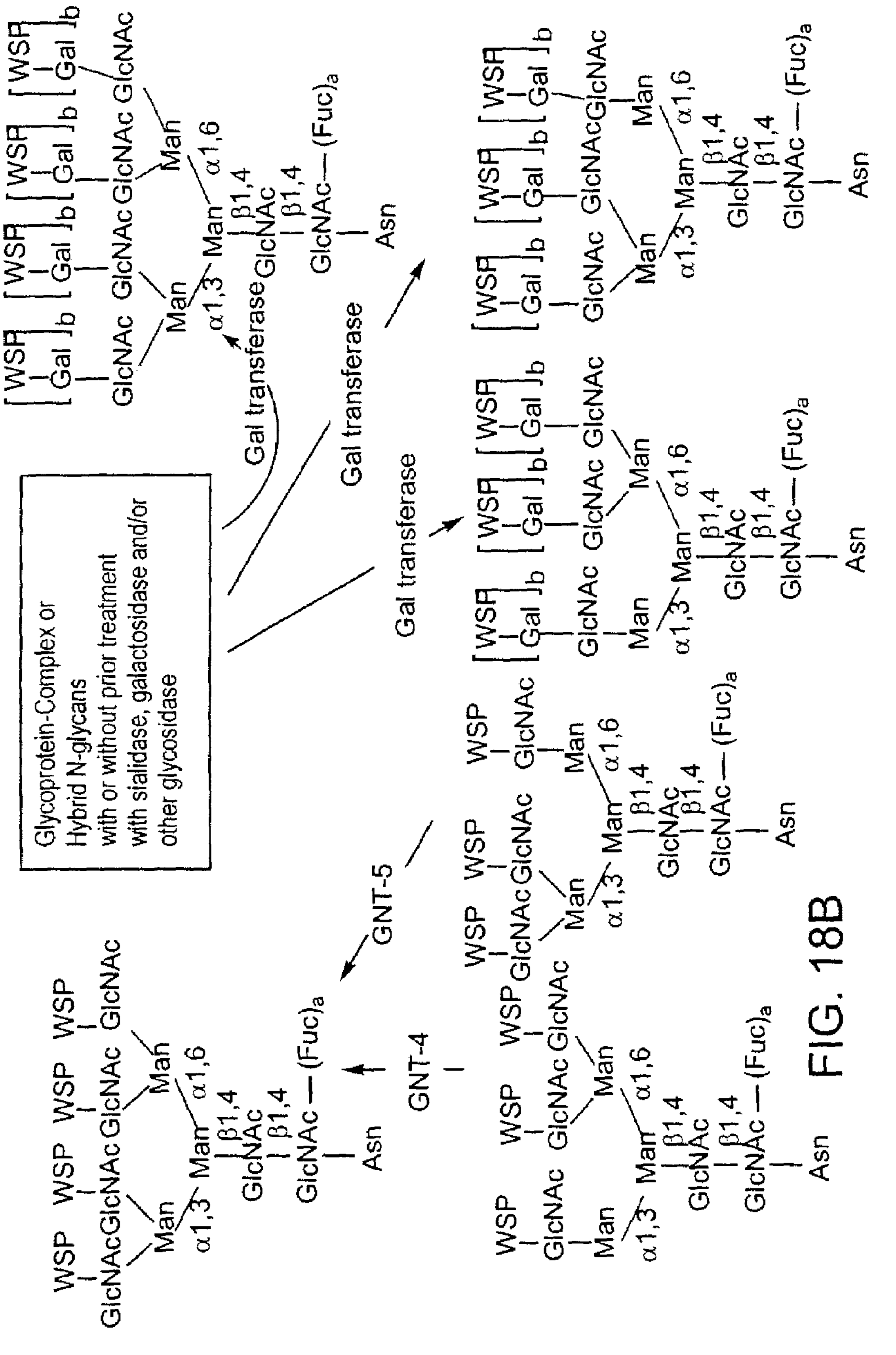
Figure 19A:
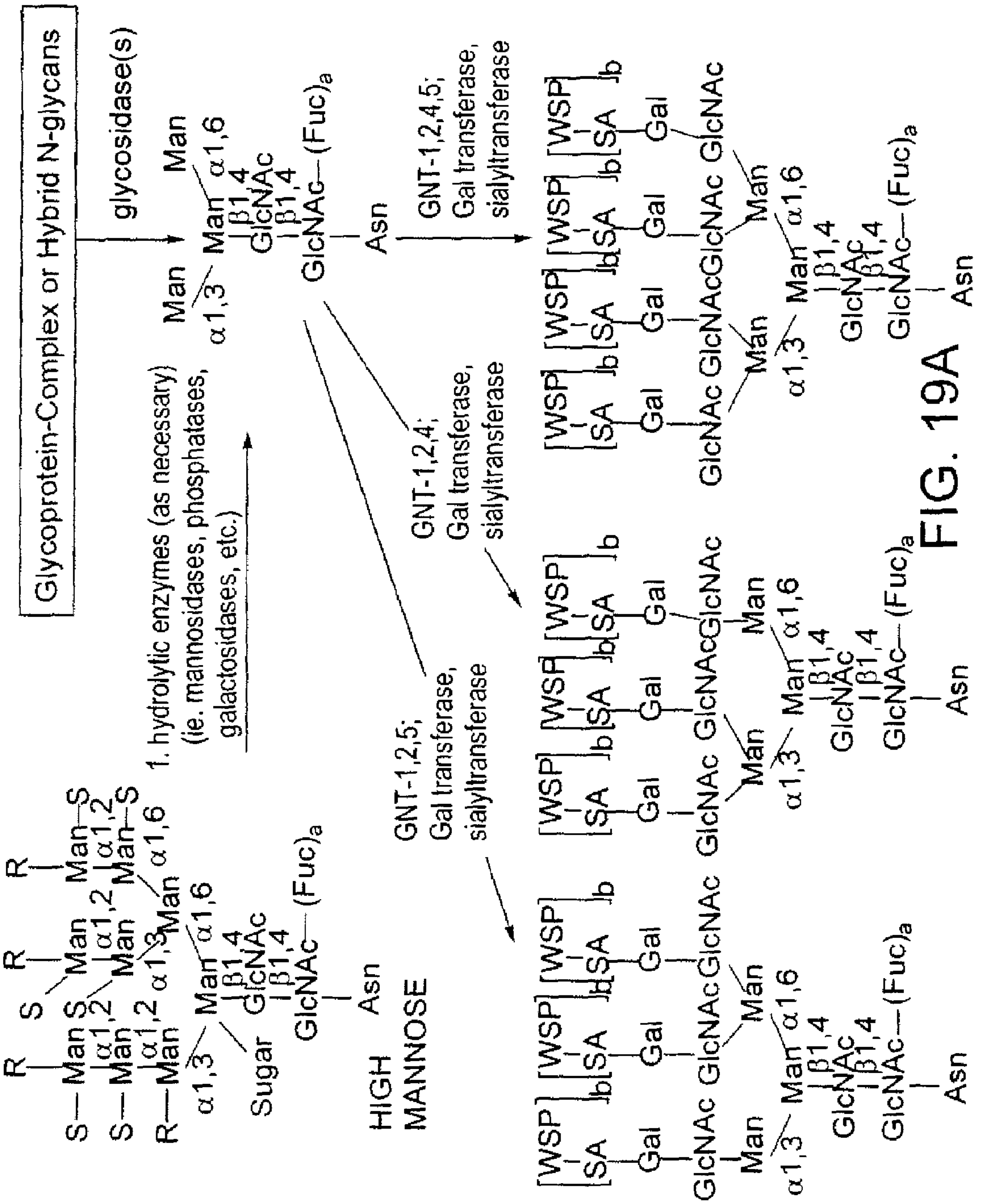
FIGS. 19A and 19B, is a scheme in which an N-linked carbohydrate is trimmed back from a high mannose or complex structure and subsequently derivatized with a sialic acid moiety bearing a water-soluble polymer. Sugars are added sequentially using glycosyltransferases.
Figure 19B:
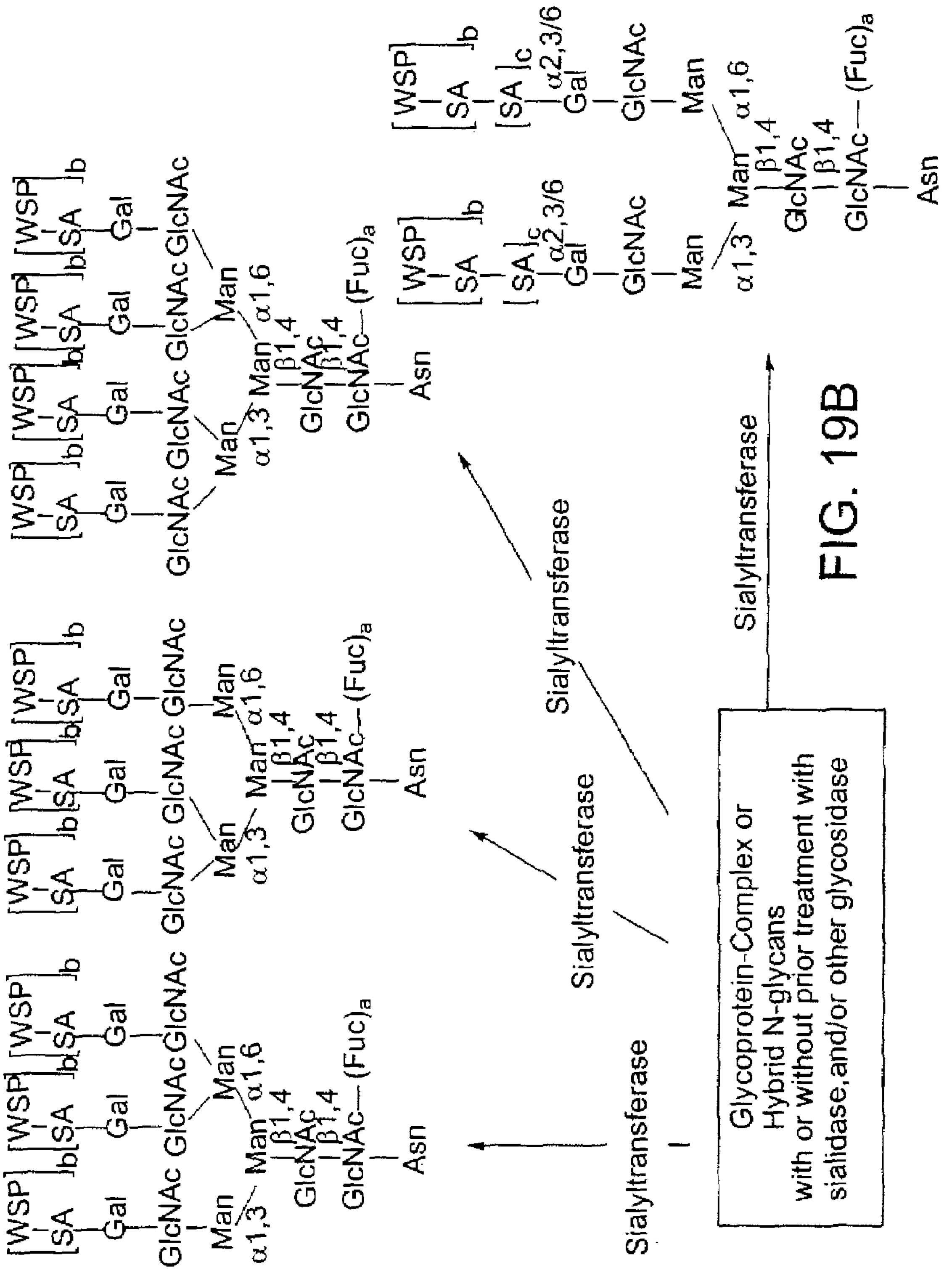
Figure 20:
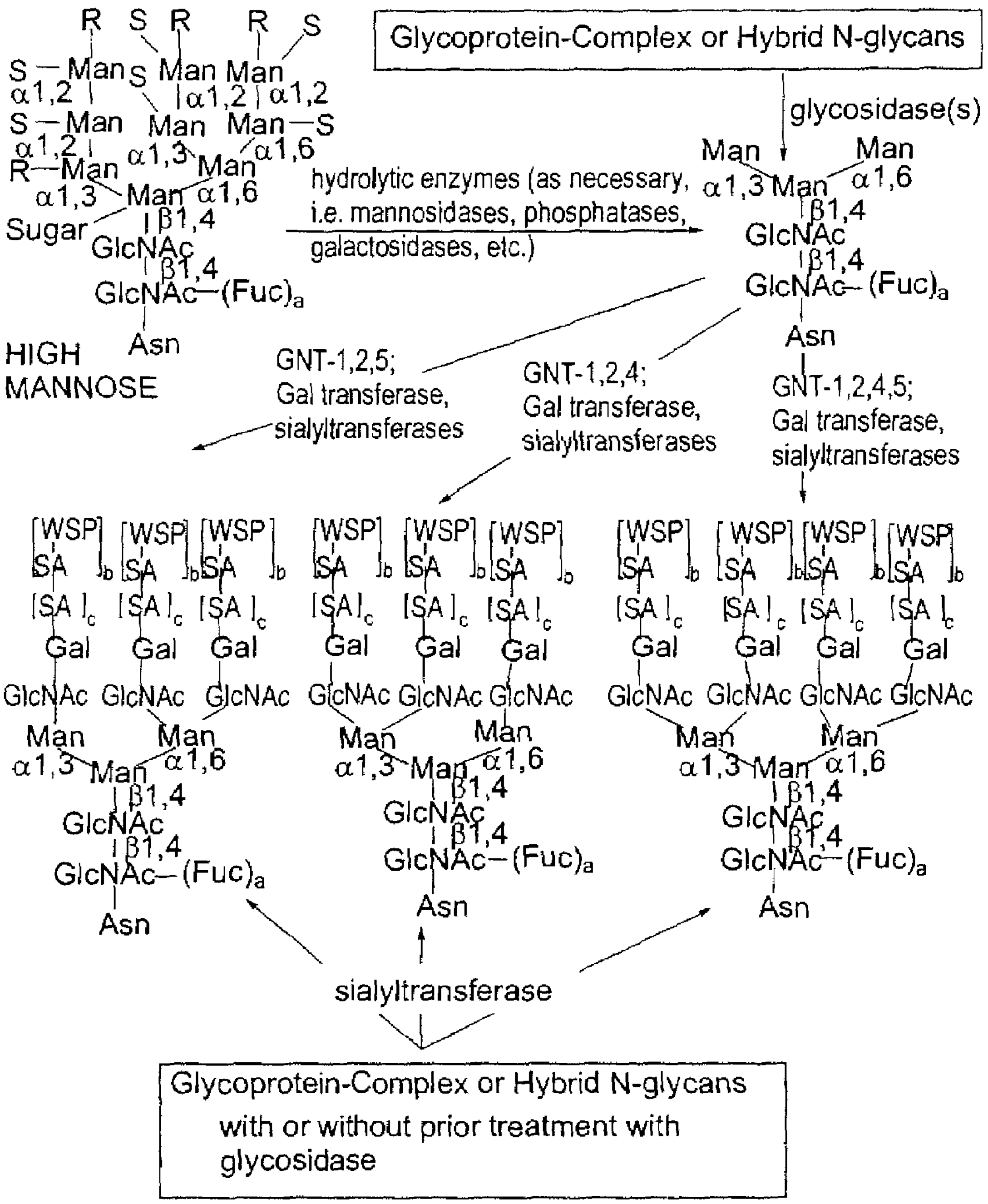
FIG. 20 is a scheme in which an N-linked carbohydrate is optionally trimmed back from a high mannose or complex structure and subsequently derivatized with one or more sialic acid moieties, and terminated with a sialic acid derivatized with a water-soluble polymer. Sugars are added sequentially using glycosyltransferases.
Figure 21:
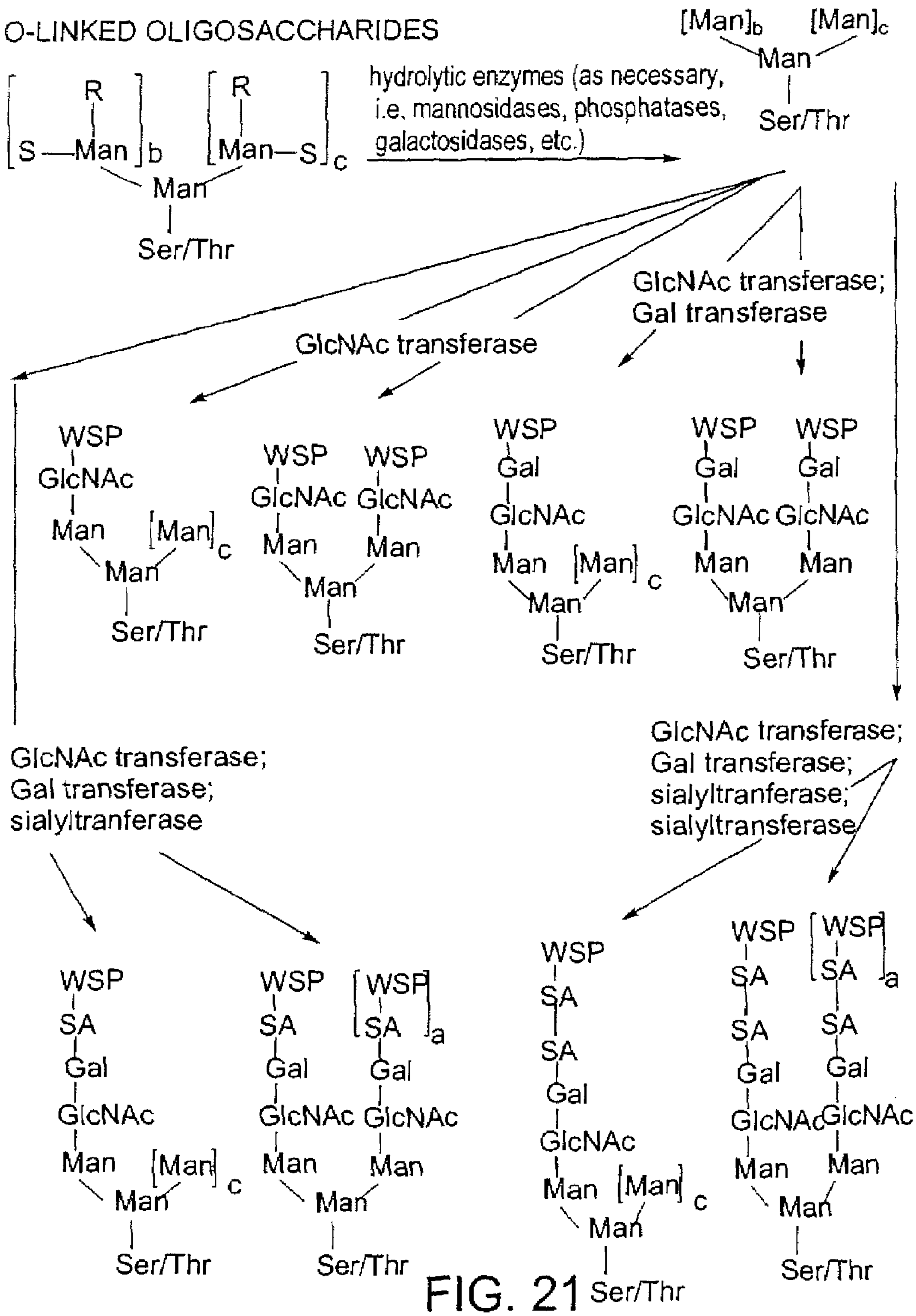
FIG. 21 is a scheme in which an O-linked saccharide is “trimmed back” and subsequently conjugated to a modified sugar bearing a water-soluble polymer. In the exemplary scheme, the carbohydrate moiety is “trimmed back” to the first generation of the biantennary structure.
Figure 22:
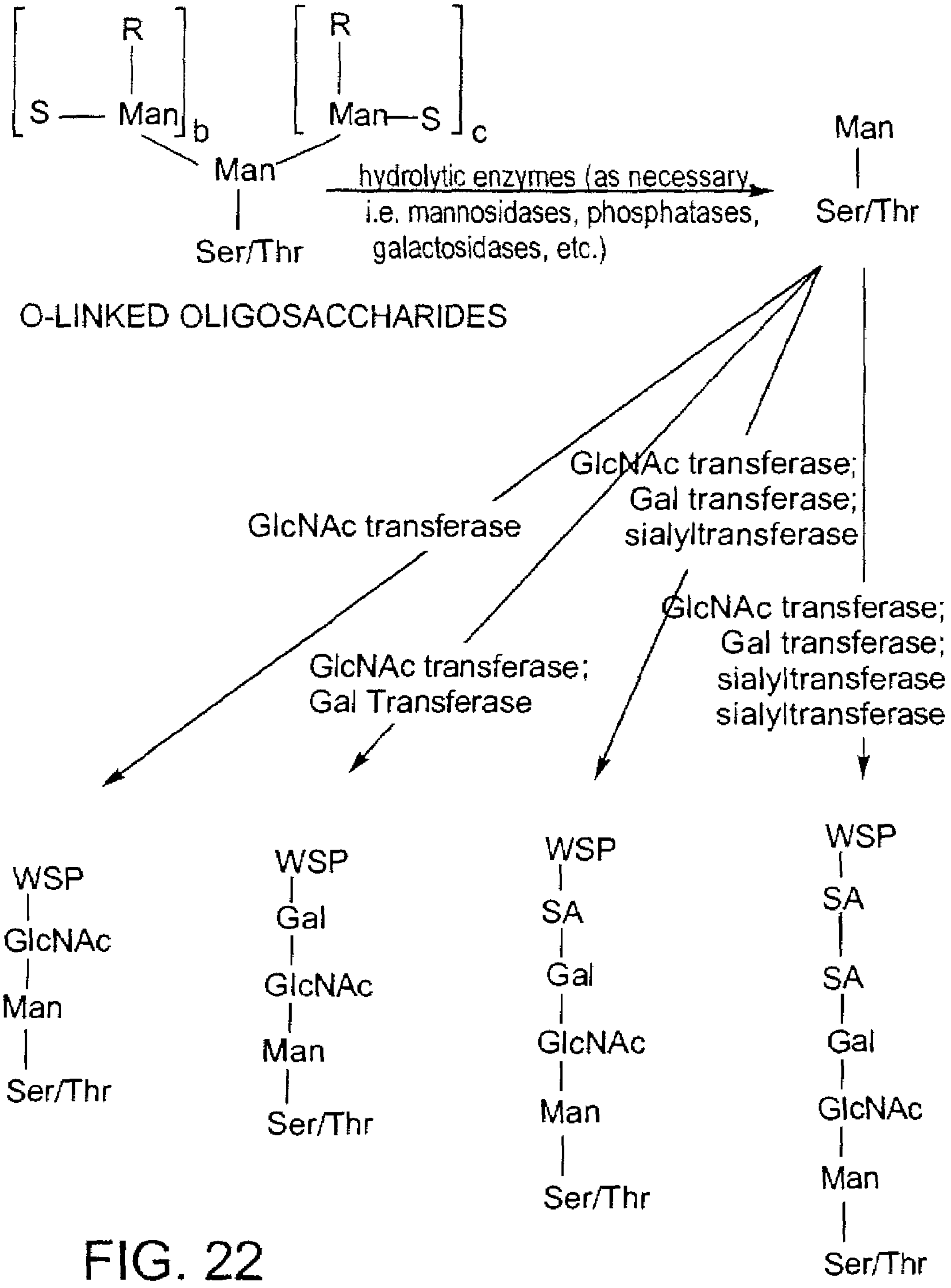
FIG. 22 is an exemplary scheme for trimming back the carbohydrate moiety of an O-linked glycopeptide to produce a mannose available for conjugation with a modified sugar having a water-soluble polymer attached thereto.

FIG. 17 is a scheme similar to that shown in FIG. 14, in which high mannose is trimmed back to the first GlcNAc attached to the Asn of the peptide. In one example, the GlcNAc of the GlcNAc-$(Fuc)_a$ residue is conjugated with a GlcNAc bearing a water soluble polymer. In another example, the GlcNAc of the GlcNAc-$(Fuc)_a$ residue is modified with Gal, which bears a water soluble polymer. In a still further embodiment, the GlcNAc is modified with Gal, followed by conjugation to the Gal of a sialic acid modified with a water-soluble polymer.

Other exemplary embodiments are set forth in FIGS. 18-22. An illustration of the array of reaction types with which the present invention may be practiced is provided in each of the aforementioned figures.

The Examples set forth above provide an illustration of the power of the methods set forth herein. Using the methods of the invention, it is possible to "trim back" and build up a carbohydrate residue of substantially any desired structure. The modified sugar can be added to the termini of the carbohydrate moiety as set forth above, or it can be intermediate between the peptide core and the terminus of the carbohydrate.

In an exemplary embodiment, an existing sialic acid is removed from a glycopeptide using a sialidase, thereby unmasking all or most of the underlying galactosyl residues. Alternatively, a peptide or glycopeptide is labeled with galactose residues, or an oligosaccharide residue that terminates in a galactose unit. Following the exposure of or addition of the galactose residues, an appropriate sialyltransferase is used to add a modified sialic acid. The approach is summarized in Scheme 12.

Scheme 12

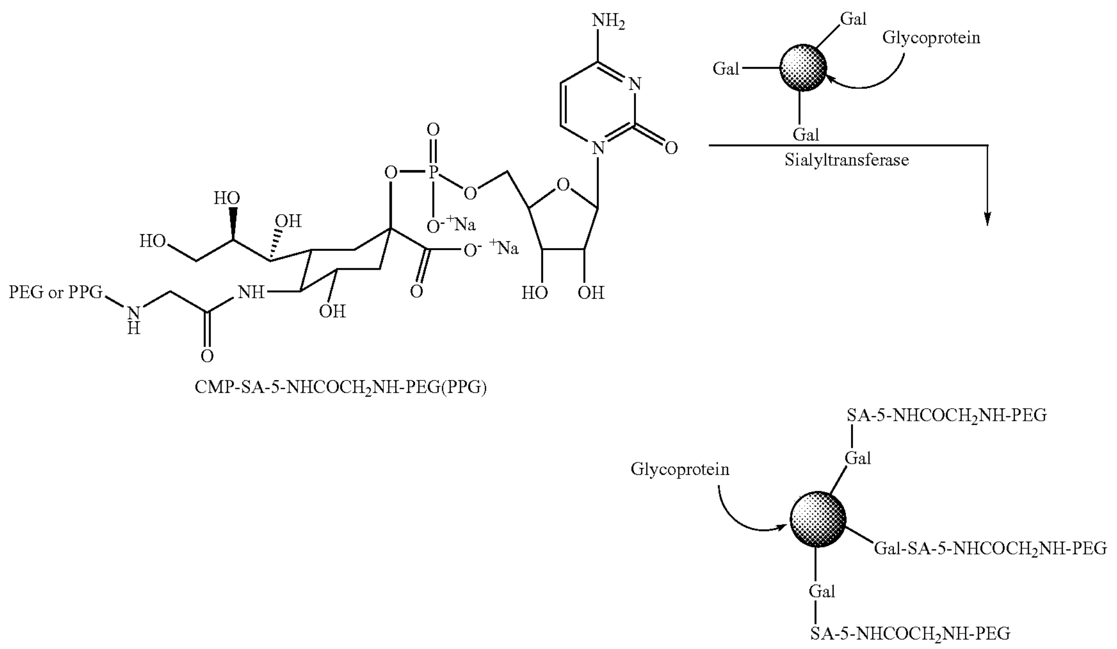

CMP-SA-5-$NHCOCH_2NH$-PEG(PPG)

In yet a further approach, summarized in Scheme 13, a masked reactive functionality is present on the sialic acid. The masked reactive group is preferably unaffected by the conditions used to attach the modified sialic acid to the peptide. After the covalent attachment of the modified sialic acid to the peptide, the mask is removed and the peptide is conjugated with an agent such as PEG, PPG, a therapeutic moiety, biomolecule or other agent. The agent is conjugated to the peptide in a specific manner by its reaction with the unmasked reactive group on the modified sugar residue.

Scheme 13

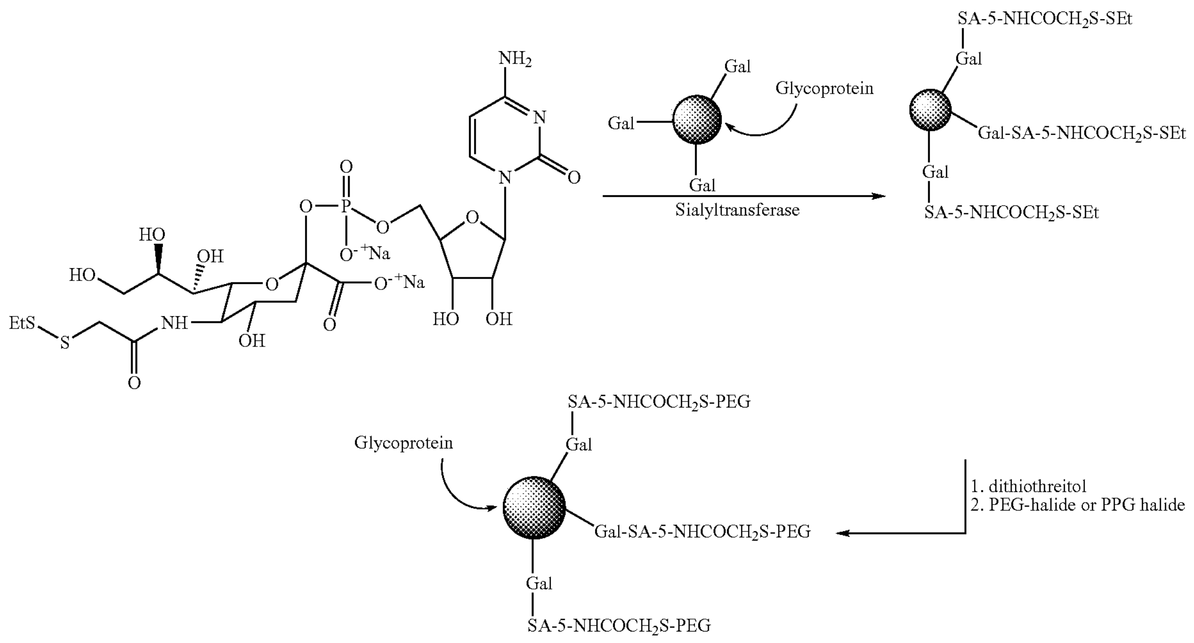

Any modified sugar can be used with its appropriate glycosyltransferase, depending on the terminal sugars of the oligosaccharide side chains of the glycopeptide (Table 4). As discussed above, the terminal sugar of the glycopeptide required for introduction of the PEGylated or PPGylated structure can be introduced naturally during expression or it can be produced post expression using the appropriate glycosidase(s), glycosyltransferase(s) or mix of glycosidase(s) and glycosyltransferase(s).

TABLE 4

Modified sugars.

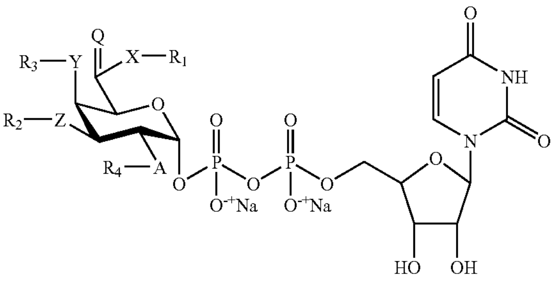

UDP-galactose-derivatives

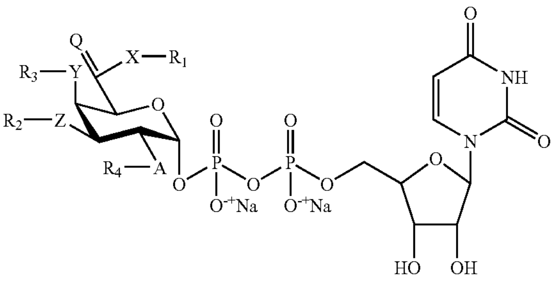

UDP-galactosamine-derivatives
(when A = NH, $R_4$ may be acetyl)

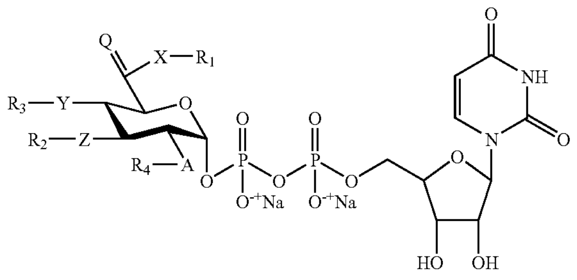

UDP-Glucose-derivatives

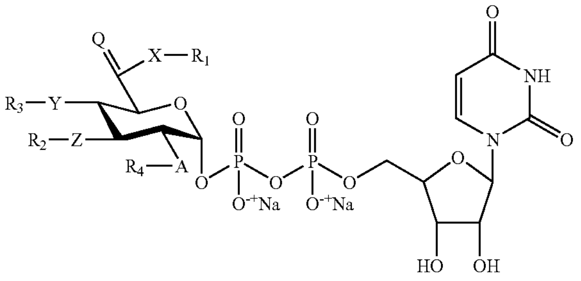

UDP-Glucosamine-derivatives
(when A = NH, $R_4$ may be acetyl)

TABLE 4-continued

Modified sugars.

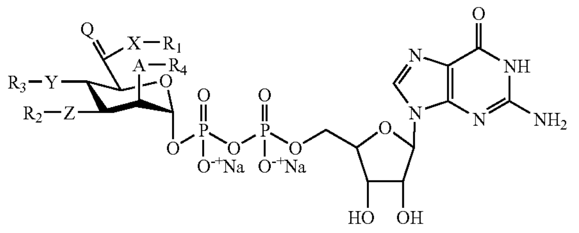

GDP-Mannose-derivatives

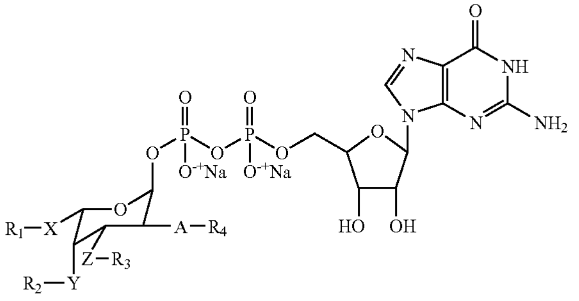

GDP-fucose-derivatives

X = O, NH, S, $CH_2$, N—$(R_{1-5})_2$.
Y = X; Z = X; A = X; B = X.
Q = $H_2$, O, S, NH, N—R.
R, $R_{1-4}$ = H, Linker-M, M.
M = Ligand of interest
Ligand of interest = acyl-PEG, acyl-PPG, alkyl-PEG, acyl-alkyl-PEG, acyl-alkyl-PEG, carbamoyl-PEG, carbamoyl-PPG, PEG, PPG, acyl-aryl-PEG, acyl-aryl-PPG, aryl-PEG, aryl-PPG, Mannose-6-phosphate, heparin, heparan, SLex, Mannose, FGF, VFGF, protein, chondroitin, keratan, dermantan, albumin, integrins, peptides, etc.

In a further exemplary embodiment, UDP-galactose-PEG is reacted with bovine milk β1,4-galactosyltransferase, thereby transferring the modified galactose to the appropriate terminal N-acetylglucosamine structure. The terminal GlcNAc residues on the glycopeptide may be produced during expression, as may occur in such expression systems as mammalian, insect, plant or fungus, but also can be produced by treating the glycopeptide with a sialidase and/or glycosidase and/or glycosyltransferase, as required.

In another exemplary embodiment, a GlcNAc transferase, such as GnT-I-IV, is utilized to transfer PEGylated-GlcNc to a mannose residue on a glycopeptide. In a still further exemplary embodiment, the N- and/or O-linked glycan structures are enzymatically removed from a glycopeptide to expose an amino acid or a terminal glycosyl residue that is subsequently conjugated with the modified sugar. For example, an endoglycanase is used to remove the N-linked structures of a glycopeptide to expose a terminal GlcNAc as a GlcNAc-linked-Asn on the glycopeptide. UDP-Gal-PEG and the appropriate galactosyltransferase is used to introduce the PEG- or PPG-galactose functionality onto the exposed GlcNAc.

In an alternative embodiment, the modified sugar is added directly to the peptide backbone using a glycosyltransferase known to transfer sugar residues to the peptide backbone. This exemplary embodiment is set forth in Scheme 14. Exemplary glycosyltransferases useful in practicing the present invention include, but are not limited to, GalNAc transferases (GalNAc T1-14), GlcNAc transferases, fucosyltransferases, glucosyltransferases, xylosyltransferases, mannosyltransferases and the like. Use of this approach allows the direct addition of modified sugars onto peptides that lack any carbohydrates or, alternatively, onto existing glycopeptides. In both cases, the addition of the modified sugar occurs at specific positions on the peptide backbone as defined by the substrate specificity of the glycosyltransferase and not in a random manner as occurs during modification of a protein's peptide backbone using chemical methods. An array of agents can be introduced into proteins or glycopeptides that lack the glycosyltransferase substrate peptide sequence by engineering the appropriate amino acid sequence into the peptide chain.

tissues of affected individuals. Table 5 provides a list of representative storage diseases and the enzymatic defect associated with the diseases. In such diseases the deficiency in enzyme function creates a progressive systemic deposition of lipid or carbohydrate substrate in lysosomes in cells in the body, eventually causing loss of organ function and death. The genetic etiology, clinical manifestations, molecular biology and possibility of the lysosomal storage diseases are detailed in Scriver et al., eds., The Metabolic and Molecular Basis of Inherited Disease, 7.sup.th Ed., Vol. II, McGraw Hill, (1995).

Scheme 14

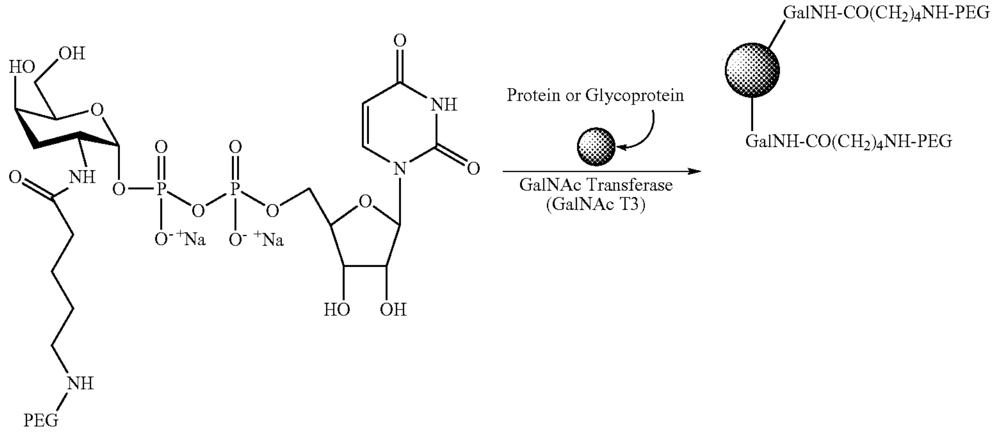

In each of the exemplary embodiments set forth above, one or more additional chemical or enzymatic modification steps can be utilized following the conjugation of the modified sugar to the peptide. In an exemplary embodiment, an enzyme (e.g., fucosyltransferase) is used to append a glycosyl unit (e.g., fucose) onto the terminal modified sugar attached to the peptide. In another example, an enzymatic reaction is utilized to "cap" sites to which the modified sugar failed to conjugate. Alternatively, a chemical reaction is utilized to alter the structure of the conjugated modified sugar. For example, the conjugated modified sugar is reacted with agents that stabilize or destabilize its linkage with the peptide component to which the modified sugar is attached. In another example, a component of the modified sugar is deprotected following its conjugation to the peptide. One of skill will appreciate that there is an array of enzymatic and chemical procedures that are useful in the methods of the invention at a stage after the modified sugar is conjugated to the peptide. Further elaboration of the modified sugar-peptide conjugate is within the scope of the invention.

Peptide Targeting With Mannose-6-Phosphate

In an exemplary embodiment the peptide is derivatized with at least one mannose-6-phosphate moiety. The mannose-6-phosphate moiety targets the peptide to a lysosome of a cell, and is useful, for example, to target therapeutic proteins to lysosomes for therapy of lysosomal storage diseases.

Lysosomal storage diseases are a group of over 40 disorders which are the result of defects in genes encoding enzymes that break down glycolipid or polysaccharide waste products within the lysosomes of cells. The enzymatic products, e.g., sugars and lipids, are then recycled into new products. Each of these disorders results from an inherited autosomal or X-linked recessive trait which affects the levels of enzymes in the lysosome. Generally, there is no biological or functional activity of the affected enzymes in the cells and

TABLE 5

Lysosomal storage diseases and associated enzymatic defects

| Disease | Enzymatic Defect |
|---|---|
| Pompe disease | acid α-glucosidase (acid maltase) |
| MPSI* (Hurler disease) | α-L-iduronidase |
| MPSII (Hunter disease) | iduronate sulfatase |
| MPSIII (Sanfilippo) | heparan N-sulfatase |
| MPS IV (Morquio A) | galactose-6-sulfatase |
| MPS IV (Morquio B) | acid β-galactosidase |
| MPS VII (Sly disease) | β-glucoronidase |
| I-cell disease | N-acetylglucosamine-1-phosphotransferase |
| Schindler disease | α-N-acetylgalactosaminidase (α-galactosidase B) |
| Wolman disease | acid lipase |
| Cholesterol ester storage disease | acid lipase |
| Farber disease | lysosomal acid ceramidase |
| Niemann-Pick disease | acid sphingomyelinase |
| Gaucher disease | glucocerebrosidase |
| Krabbe disease | galactosylceramidase |
| Fabry disease | α-galactosidase A |
| GM1 gangliosidosis | acid β-galactosidase |
| Galactosialidosis | β-galactosidase and neuraminidase |
| Tay-Sach's disease | hexosaminidase A |
| Magakaryotic leukodystrophy | arylsulphatase a |
| Sandhoff disease | hexosaminidase A and B |

*MPS = mucopolysaccaridosis

De Duve first suggested that replacement of the missing lysosomal enzyme with exogenous biologically active enzyme might be a viable approach to treatment of lysosomal storage diseases (De Duve, *Fed. Proc.* 23: 1045 (1964). Since that time, various studies have suggested that enzyme replacement therapy may be beneficial for treating various lysosomal storage diseases. The best success has been shown with individuals with type I Gaucher disease, who have been treated with exogenous enzyme (β-glucocerebrosidase), prepared from placenta (Ceredase™) or, more recently, recombinantly (Cerezyme™). It has been suggested that enzyme replacement may also be beneficial for treating Fabry's disease, as well as other lysosomal storage diseases. See, for example, Dawson et al., *Ped Res.* 7(8): 684-690 (1973) (in vitro) and Mapes et al., *Science* 169: 987 (1970) (in vivo). Clinical trials of enzyme replacement therapy have been reported for Fabry patients using infusions of normal plasma (Mapes et al., *Science* 169: 987-989 (1970)), α-galactosidase A purified from placenta (Brady et al., *N. Eng. J. Med.* 279: 1163 (1973)); or α-galactosidase A purified from spleen or plasma (Desnick et al., *Proc. Natl. Acad. Sci., USA* 76: 5326-5330 (1979)) and have demonstrated the biochemical effectiveness of direct enzyme replacement for Fabry disease. These studies indicate the potential for eliminating, or significantly reducing, the pathological glycolipid storage by repeated enzyme replacement. For example, in one study (Desnick et al., supra), intravenous injection of purified enzyme resulted in a transient reduction in the plasma levels of the stored lipid substrate, globotriasylceramide.

Accordingly, there exists a need in the art for methods for providing sufficient quantities of biologically active lysosomal enzymes, such as human α-galactosidase A, to deficient cells. Recently, recombinant approaches have attempted to address these needs, see, e.g., U.S. Pat. Nos. 5,658,567; 5,580,757; Bishop et al., *Proc. Natl. Acad. Sci., USA.* 83: 4859-4863 (1986); Medin et al., *Proc. Natl. Acad. Sci., USA.* 93: 7917-7922 (1996); Novo, F. J., *Gene Therapy.* 4: 488-492 (1997); Ohshima et al., *Proc. Natl. Acad. Sci., USA.* 94: 2540-2544 (1997); and Sugimoto et al., *Human Gene Therapy* 6: 905-915, (1995). Through the mannose-6-phosphate mediated targeting of therapeutic peptides to lysosomes, the present invention provides compositions and methods for delivering sufficient quantities of biologically active lysosomal peptides to deficient cells.

Figure 24:
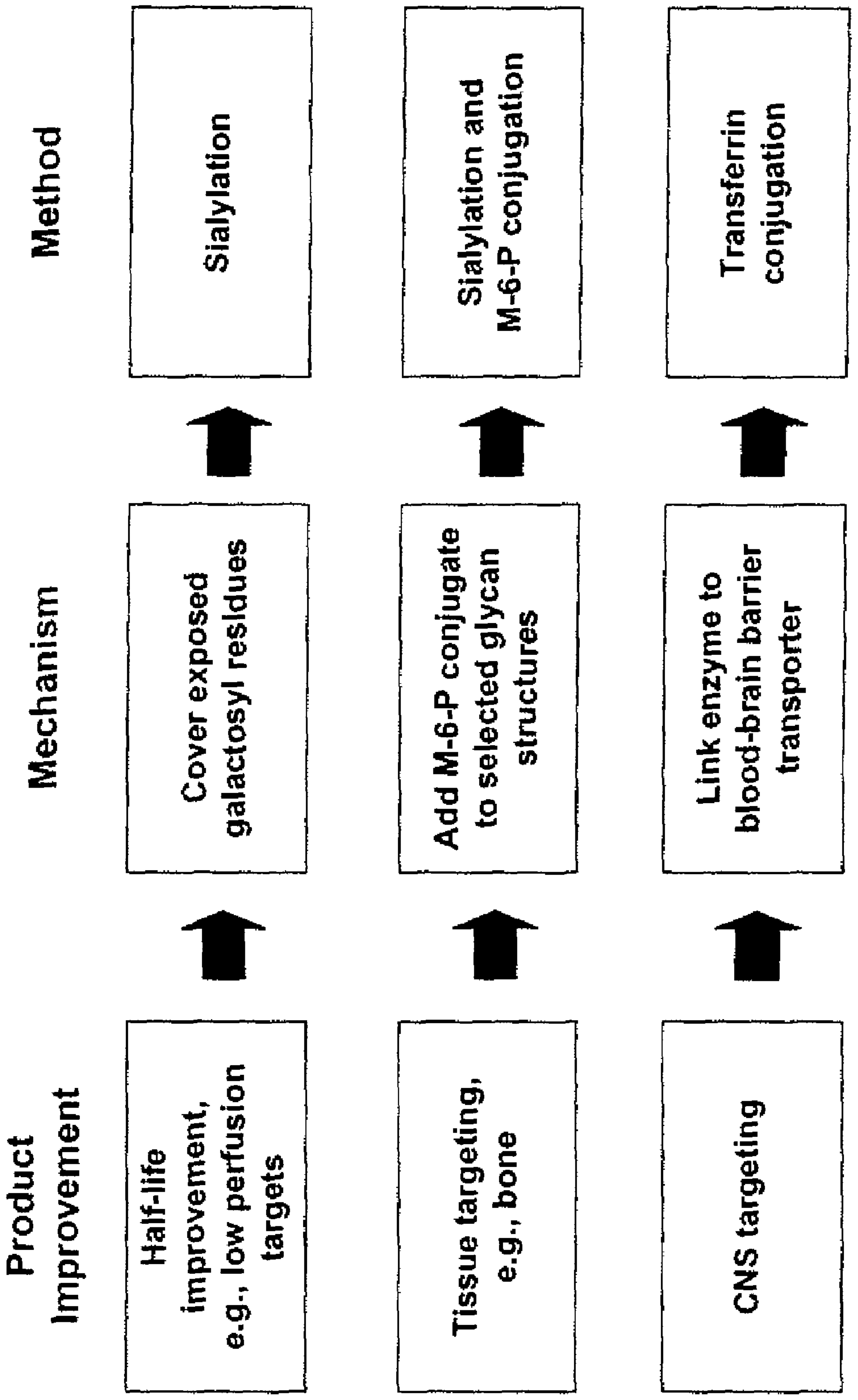
FIG. 24 is a diagram of various methods of improving the therapeutic function of a peptide by glycan remodeling, including conjugation.
Figure 25:
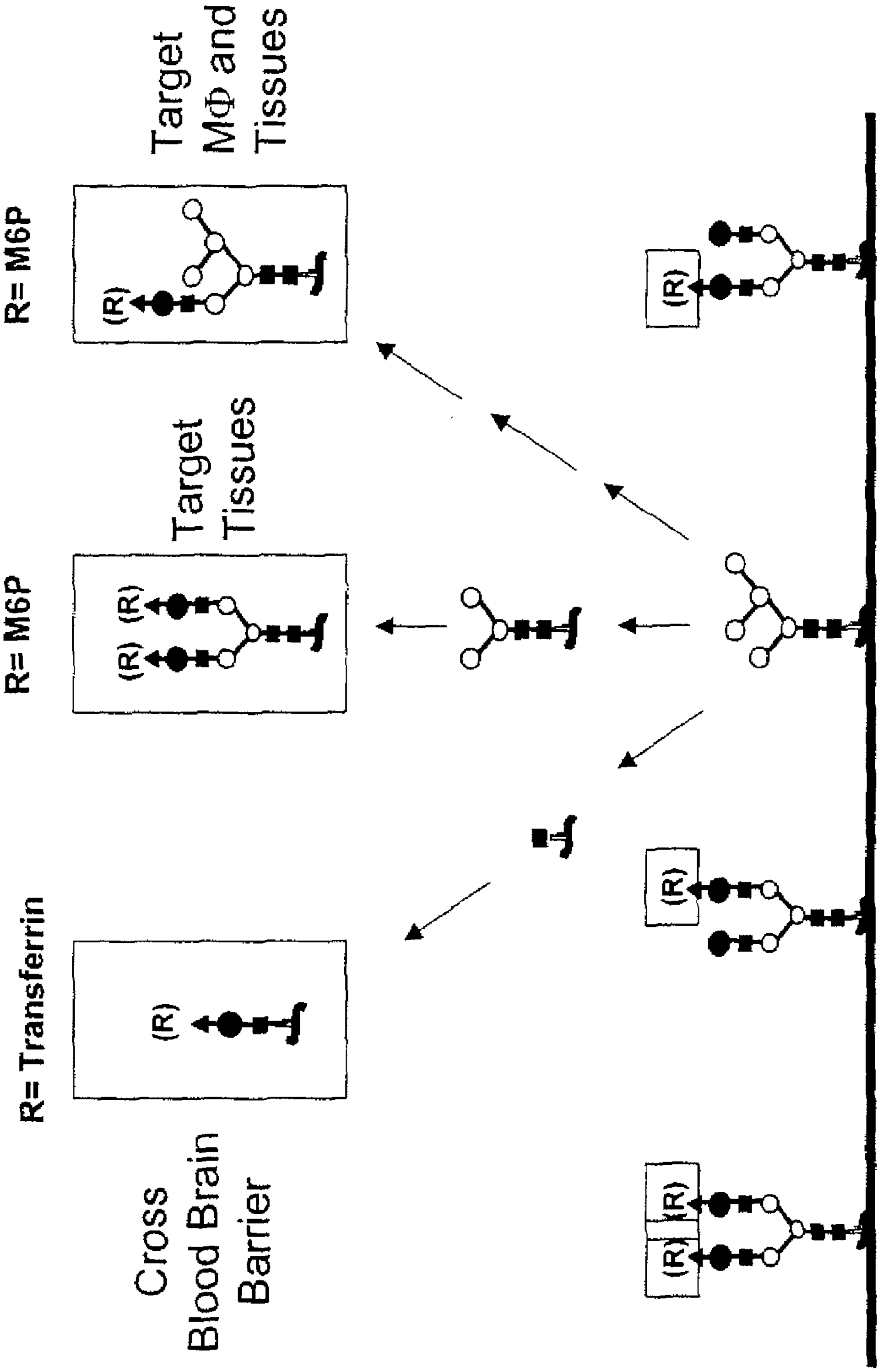
FIG. 25 is a set of schemes for glycan remodeling of a therapeutic peptide to treat Gaucher Disease.
Figure 26:
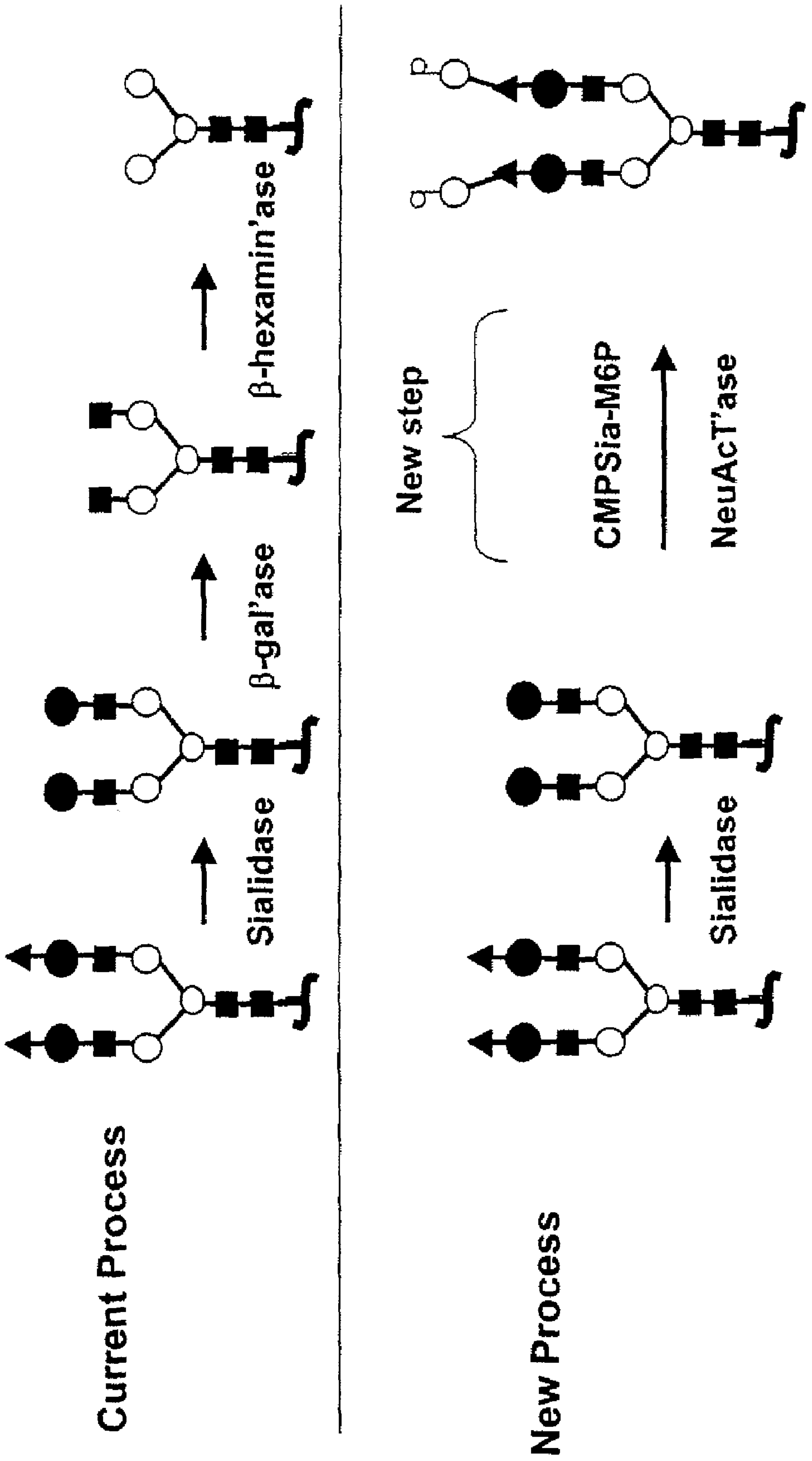
FIG. 26 is a scheme for glycan remodeling to generate glycans having a terminal mannose-6-phosphate moiety.

Thus, in an exemplary embodiment, the present invention provides a peptide according to Table 7 that is derivatized with mannose-6-phosphate (FIG. 24 and FIG. 25). The peptide may be recombinantly or chemically prepared. Moreover, the peptide can be the full, natural sequence, or it may be modified by, for example, truncation, extension, or it may include substitutions or deletions. Exemplary proteins that are remodeled using a method of the present invention include glucocerebrosidase, β-glucosidase, α-galactosidase A, acid-α-glucosidase (acid maltase). Representative modified peptides that are in clinical use include, but are not limited to, Ceredase™, Cerezyme™, and Fabryzyme™. A glycosyl group on modified and clinically relevant peptides may also be altered utilizing a method of the invention. The mannose-6-phosphate is attached to the peptide via a glycosyl linking group. In an exemplary embodiment, the glycosyl linking group is derived from sialic acid. Exemplary sialic acid-derived glycosyl linking groups are set forth in Table 3, in which one or more of the "R" moieties is mannose-6-phosphate or a spacer group having one or more mannose-6-phosphate moieties attached thereto. The modified sialic acid moiety is preferably the terminal residue of an oligosaccharide linked to the surface of the peptide (FIG. 26)

In addition to the mannose-6-phosphate, the peptides of the invention may be further derivatized with a moiety such as a water-soluble polymer, a therapeutic moiety, or an additional targeting moiety. Methods for attaching these and other groups are set forth herein. In an exemplary embodiment, the group other than mannose-6-phosphate is attached to the peptide via a derivatized sialic acid derivative according to Table 3, in which one or more of the "R" moieties is a group other than mannose-6-phosphate.

In an exemplary embodiment, a sialic acid moiety modified with a Cbz-protected glycine-based linker arm is prepared. The corresponding nucleotide sugar is prepared and the Cbz group is removed by catalytic hydrogenation. The resulting nucleotide sugar has an available, reactive amine that is contacted with an activated mannose-6-phosphate derivative, providing a mannose-6-phosphate derivatized nucleotide sugar that is useful in practicing the methods of the invention.

As shown in the scheme below (scheme 15), an exemplary activated mannose-6-phosphate derivative is formed by converting a 2-bromo-benzyl-protected phosphotriester into the corresponding triflate, in situ, and reacting the triflate with a linker having a reactive oxygen-containing moiety, forming an ether linkage between the sugar and the linker. The benzyl protecting groups are removed by catalytic hydrogenation, and the methyl ester of the linker is hydrolyzed, providing the corresponding carboxylic acid. The carboxylic acid is activated by any method known in the art. An exemplary activation procedure relies upon the conversion of the carboxylic acid to the N-hydroxysuccinimide ester.

Scheme 15

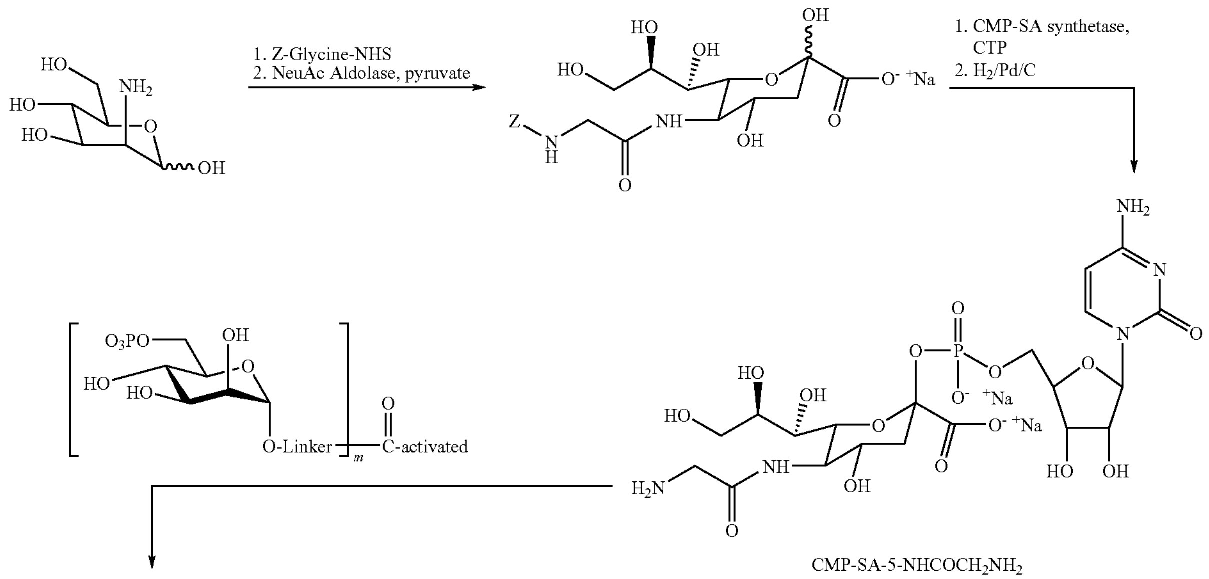

CMP-SA-5-NHCOCH2NH2

-continued

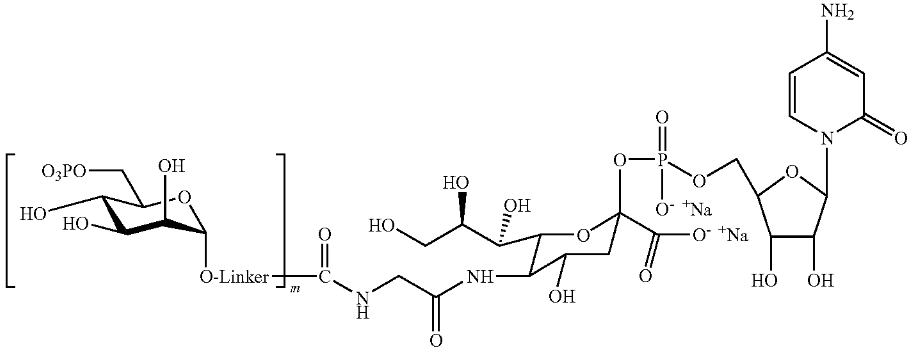

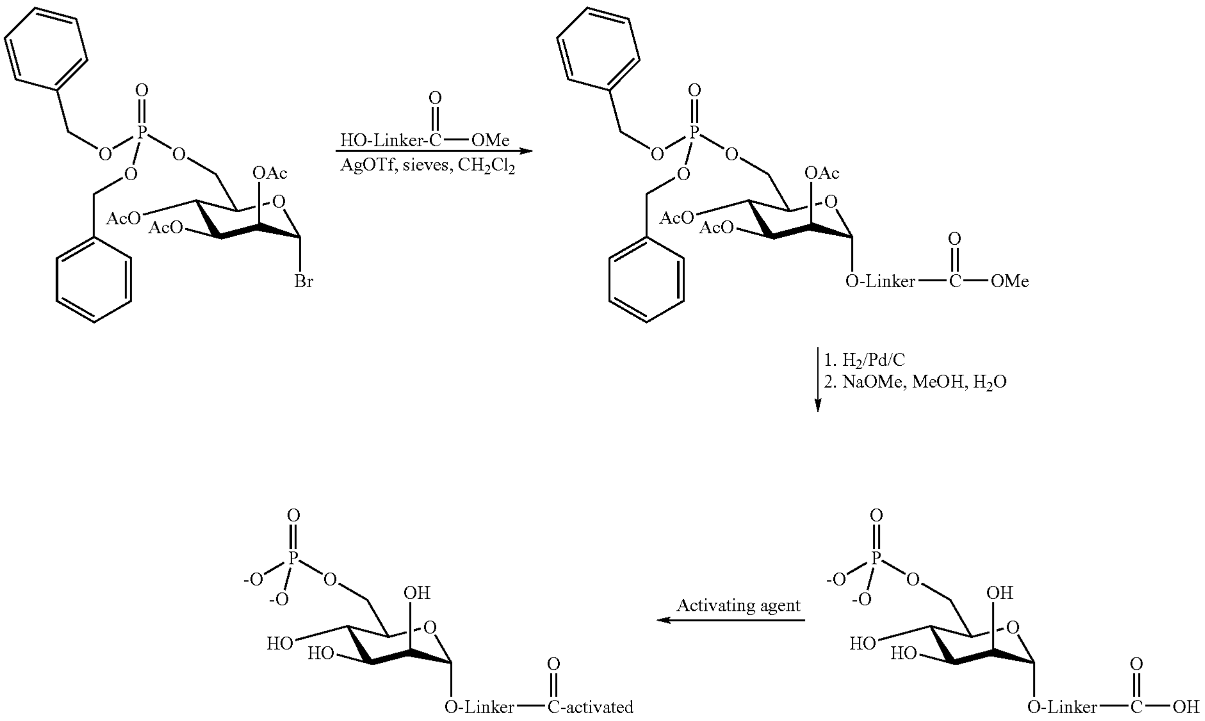

In another exemplary embodiment, as shown in the scheme below (scheme 16), a N-acetylated sialic acid is converted to an amine by manipulation of the pyruvyl moiety. Thus, the primary hydroxyl is converted to a sulfonate ester and reacted with sodium azide. The azide is catalytically reduced to the corresponding amine. The sugar is subsequently converted to its nucleotide analogue and coupled, through the amine group, to the linker arm-derivatized mannose-6-phosphate prepared as discussed above.

Scheme 16

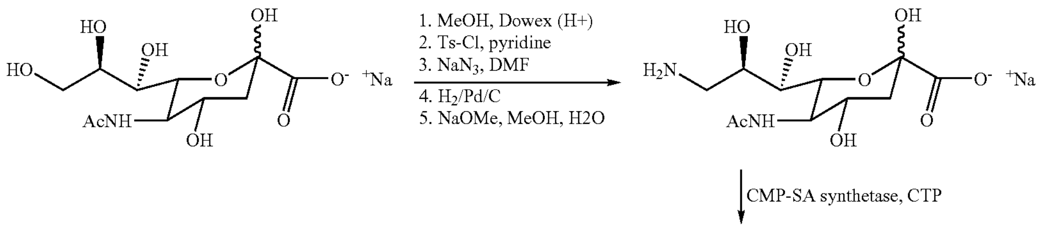

-continued

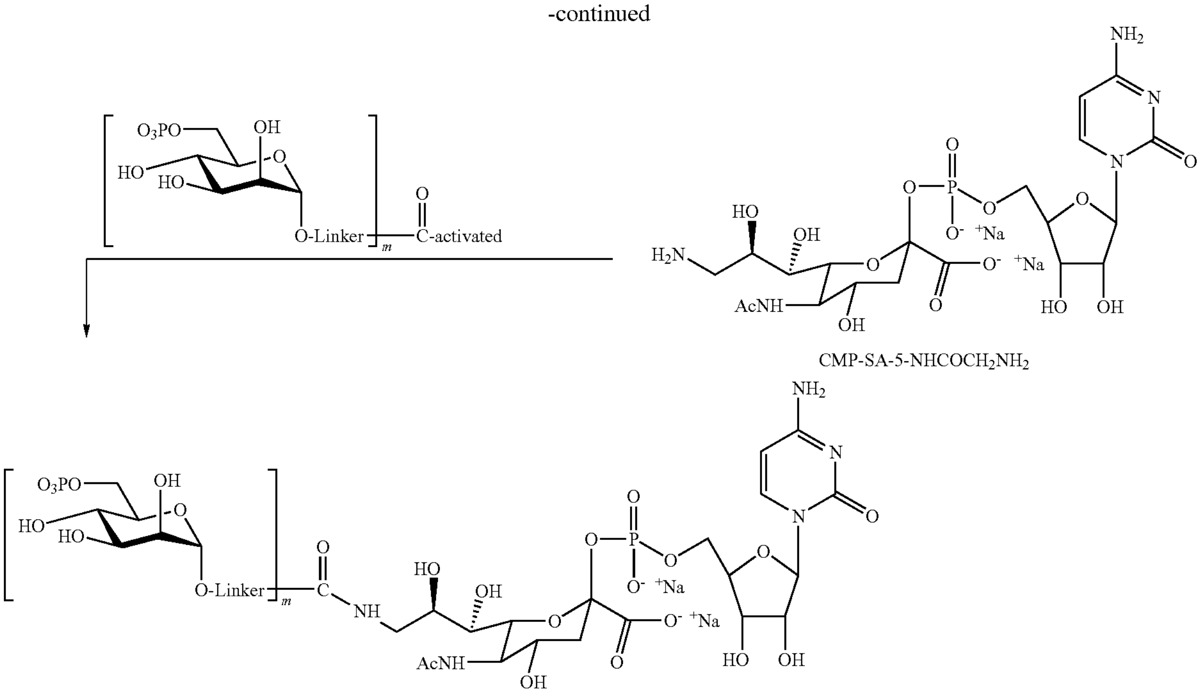

CMP-SA-5-NHCOCH$_2$NH$_2$

Peptides useful to treat lysosomal storage disease can be derivatized with other targeting moieties including, but not limited to, transferrin (to deliver the peptide across the blood-brain barrier, and to endosomes), carnitine (to deliver the peptide to muscle cells), and phosphonates, e.g, bisphosphonate (to target the peptide to bone and other calciferous tissues). The targeting moiety and therapeutic peptide are conjugated by any method discussed herein or otherwise known in the art.

In an exemplary embodiment, the targeting agent and the therapeutic peptide are coupled via a linker moiety. In this embodiment, at least one of the therapeutic peptide or the targeting agent is coupled to the linker moiety via an intact glycosyl linking group according to a method of the invention. In an exemplary embodiment, the linker moiety includes a poly(ether) such as poly(ethylene glycol). In another exemplary embodiment, the linker moiety includes at least one bond that is degraded in vivo, releasing the therapeutic peptide from the targeting agent, following delivery of the conjugate to the targeted tissue or region of the body.

Figure 27:
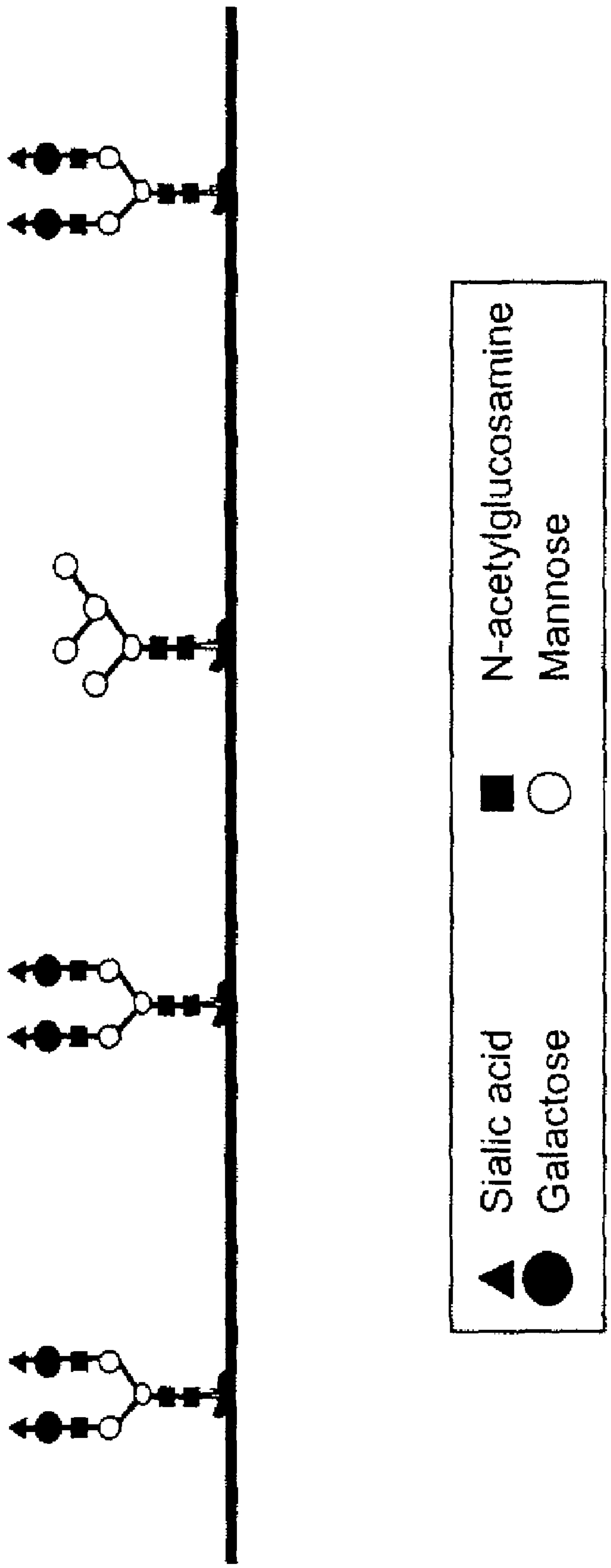
FIG. 27 is a diagram illustrating the array of glycan structures found on CHO-produced glucocerebrosidase (Cerezyme™) after sialylation.

In yet another exemplary embodiment, the in vivo distribution of the therapeutic moiety is altered via altering a glycoform on the therapeutic moiety without conjugating the therapeutic peptide to a targeting moiety. For example, the therapeutic peptide can be shunted away from uptake by the reticuloendothelial system by capping a terminal galactose moiety of a glycosyl group with sialic acid (or a derivative thereof) (FIGS. 24 and 27). Sialylation to cover terminal Gal avoids uptake of the peptide by hepatic asialoglycoprotein (ASGP) receptors, and may extend the half life of the peptide as compared with peptides having only complex glycan chains, in the absence of sialylation.

II. Peptide/Glycopeptides of the Invention

In one embodiment, the present invention provides a composition comprising multiple copies of a single peptide having an elemental trimannosyl core as the primary glycan structure attached thereto. In preferred embodiments, the peptide may be a therapeutic molecule. The natural form of the peptide may comprise complex N-linked glycans or may be a high mannose glycan. The peptide may be a mammalian peptide, and is preferably a human peptide. In some embodiments the peptide is selected from the group consisting of an immunoglobulin, erythropoietin, tissue-type activator peptide, and others (See FIG. 28). Exemplary peptides whose glycans can be remodeled using the methods of the invention are set forth in FIG. 28.

TABLE 6

| Preferred peptides for glycan remodeling |
|---|
| Hormones and Growth Factors |
| G-CSF |
| GM-CSF |
| TPO |
| EPO |
| EPO variants |
| FSH |
| HGH |
| insulin |
| alpha-TNF |
| Leptin |
| human chorionic gonadotropin |
| Enzymes and Inhibitors |
| TPA |
| TPA variants |
| Urokinase |
| Factors VII, VIII, IX, X |
| DNase |
| Glucocerebrosidase |
| Hirudin |
| α1 antitrypsin (α1 protease inhibitor) |
| Antithrombin III |
| Acid α-glucosidase (acid maltase) |
| α galactosidase A |
| α-L-iduronidase |
| Urokinase |

TABLE 6-continued

| Preferred peptides for glycan remodeling |
|---|
| Cytokines and Chimeric Cytokines |
| Interleukin-1 (IL-1), 1B, 2, 3, 4 |
| Interferon-alpha (IFN-alpha) |
| IFN-alpha-2b |
| IFN-beta |
| IFN-gamma |
| IFN-omega |
| Chimeric diphtheria toxin-IL-2 |
| Receptors and Chimeric Receptors |
| CD4 |
| Tumor Necrosis Factor receptor (TNF-R) |
| TNF-R: IgG Fc fusion |
| Alpha-CD20 |
| PSGL-1 |
| Complement |
| GlyCAM or its chimera |
| N-CAM or its chimera |
| Monoclonal Antibodies (Immunoglobulins) |
| MAb-anti-RSV |
| MAb-anti-IL-2 receptor |
| MAb-anti-CEA |
| MAb-anti-glycoprotein IIb/IIIa |
| MAb-anti-EGF |
| MAb-anti-Her2 |
| MAb-CD20 |
| MAb-alpha-CD3 |
| MAb-TNFα |
| MAb-CD4 |
| MAb-PSGL-1 |
| Mab-anti F protein of Respiratory Syncytial Virus |
| Anti-thrombin-III |
| Cells |
| Red blood cells |
| White blood cells (e.g., T cells, B cells, dendritic cells, macrophages, NK cells, neutrophils, monocytes and the like) |
| Stem cells |
| Others |
| Hepatits B surface antigen (HbsAg) |

TABLE 7

| Most preferred peptides for glycan remodeling | |
|---|---|
| Alpha-galactosidase A | Interleukin-2 (IL-2) |
| Alpha-L-iduronidase | Factor VIII |
| Anti-thrombin-III | hrDNase |
| Granulocyte colony stimulating factor (G-CSF) | Insulin |
| | Hepatitis B surface protein (HbsAg) |
| Interferon α | Human Growth Hormone (HGH) |
| Interferon β | Human chorionic gonadotropin |
| Interferon omega | Urokinase |
| Factor VII clotting factor | TNF receptor-IgG Fc fusion (Enbrel ™) |
| Factor IX clotting factor | MAb-Her-2 (Herceptin ™) |
| Follicle Stimulating Hormone (FSH) | MAb-F protein of Respiratory Syncytial Virus (Synagis ™) |
| Erythropoietin (EPO) | |

TABLE 7-continued

| Most preferred peptides for glycan remodeling | |
|---|---|
| Granulocyte-macrophage colony stimulating factor (GM-CSF) | MAb-CD20 (Rituxan ™) |
| | MAb-TNFα (Remicade ™) |
| Interferon γ | MAb-Glycoprotein IIb/IIIa (Reopro ™) |
| $\alpha_1$ protease inhibitor ($\alpha_1$ antitrypsin) | |
| Tissue-type plasminogen activator (TPA) | |
| Glucocerebrosidase (Cerezyme ™) | |

A more detailed list of peptides useful in the invention and their source is provided in FIG. 28.

Other exemplary peptides that are modified by the methods of the invention include members of the immunoglobulin family (e.g., antibodies, MHC molecules, T cell receptors, and the like), intercellular receptors (e.g., integrins, receptors for hormones or growth factors and the like) lectins, and cytokines (e.g., interleukins). Additional examples include tissue-type plasminogen activator (TPA), renin, clotting factors such as Factor VIII and Factor IX, bombesin, thrombin, hematopoietic growth factor, colony stimulating factors, viral antigens, complement peptides, α1-antitrypsin, erythropoietin, P-selectin glycopeptide ligand-1 (PSGL-1), granulocyte-macrophage colony stimulating factor, anti-thrombin III, interleukins, interferons, peptides A and C, fibrinogen, Herceptin™, leptin, glycosidases, among many others. This list of peptides is exemplary and should not be considered to be exclusive. Rather, as is apparent from the disclosure provided herein, the methods of the invention are applicable to any peptide in which a desired glycan structure can be fashioned.

The methods of the invention are also useful for modifying chimeric peptides, including, but not limited to, chimeric peptides that include a moiety derived from an immunoglobulin, such as IgG.

Peptides modified by the methods of the invention can be synthetic or wild-type peptides or they can be mutated peptides, produced by methods known in the art, such as site-directed mutagenesis. Glycosylation of peptides is typically either N-linked or O-linked. An exemplary N-linkage is the attachment of the modified sugar to the side chain of an asparagine residue. The tripeptide sequences asparagine-X-serine and asparagine-X-threonine, where X is any amino acid except proline, are the recognition sequences for enzymatic attachment of a carbohydrate moiety to the asparagine side chain. Thus, the presence of either of these tripeptide sequences in a peptide creates a potential glycosylation site. As described elsewhere herein, O-linked glycosylation refers to the attachment of one sugar (e.g., N-acetylgalactosamine, galactose, mannose, GlcNAc, glucose, fucose or xylose) to a hydroxy side chain of a hydroxyamino acid, preferably serine or threonine, although 5-hydroxyproline or 5-hydroxylysine may also be used.

Several exemplary embodiments of the invention are discussed below. While several of these embodiments use peptides having names having trademarks, and other specific peptides as the exemplary peptide, these examples are not confined to any specific peptide. The following exemplary embodiments are contemplated to include all peptide equivalents and variants of any peptide. Such variants include, but are not limited to, adding and deleting N-linked and O-linked glycosylation sites, and fusion proteins with added glycosylation sites. One of skill in the art will appreciate that the following embodiments and the basic methods disclosed therein can be applied to many peptides with equal success.

Figure 29B:
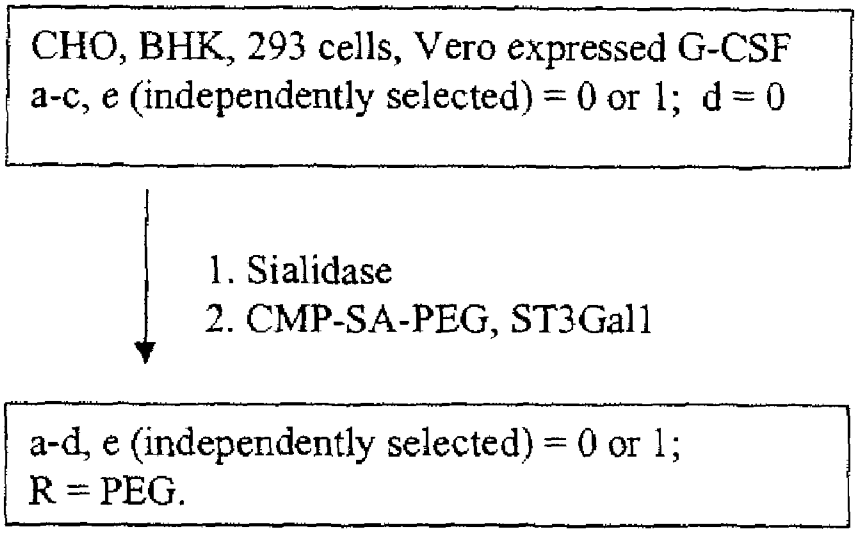
Figure 29C:
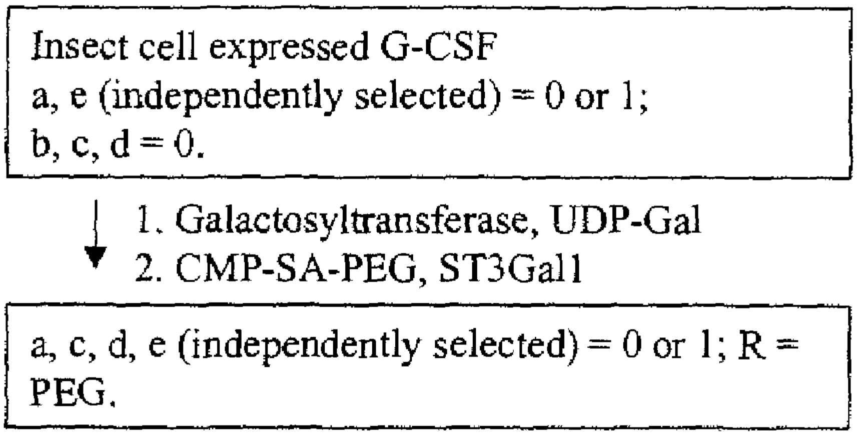
Figure 29F:
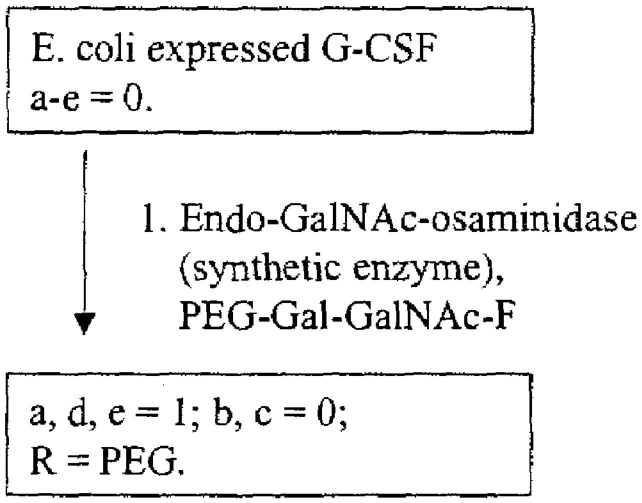
Figure 29G:
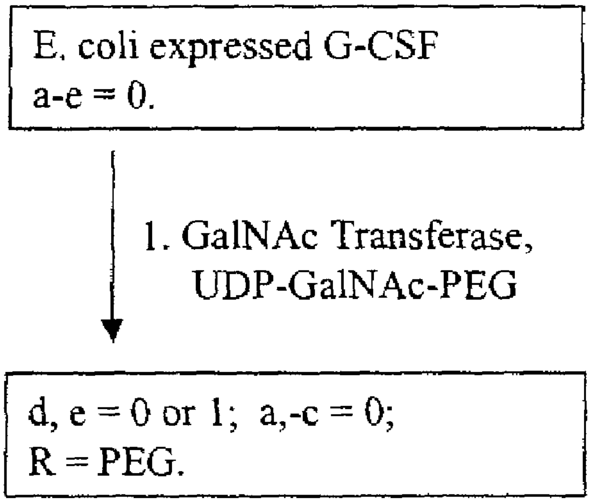

In one exemplary embodiment, the present invention provides methods for modifying Granulocyte Colony Stimulating Factor (G-CSF). FIGS. 29A to 29G set forth some examples of how this is accomplished using the methodology disclosed herein. In FIG. 29B, a G-CSF peptide that is expressed in a mammalian cell system is trimmed back using a sialidase. The residues thus exposed are modified by the addition of a sialic acid-poly(ethylene glycol) moiety (PEG moiety), using an appropriate donor therefor and ST3Gal1. FIG. 29C sets forth an exemplary scheme for modifying a G-CSF peptide that is expressed in an insect cell. The peptide is modified by adding a galactose moiety using an appropriate donor thereof and a galactosyltransferase. The galactose residues are functionalized with PEG via a sialic acid-PEG derivative, through the action of ST3Gal1. In FIG. 29D, bacterially expressed G-CSF is contacted with an N-acetylgalactosamine donor and N-acetylgalactosamine transferase. The peptide is functionalized with PEG, using a PEGylated sialic acid donor and a sialyltransferase. In FIG. 29E, mammalian cell expressed G-CSF is contacted with a sialic acid donor that is modified with levulinic acid, adding a reactive ketone to the sialic acid donor. After addition to a glycosyl residue on the glycan on the peptide, the ketone is derivatized with a moiety such as a hydrazine- or amine-PEG. In FIG. 29F, bacterially expressed G-CSF is remodeled by contacting the peptide with an endo-GalNAc enzyme under conditions where it functions in a synthetic, rather than a hydrolytic manner, thereby adding a PEG-Gal-GalNAc molecule from an activated derivative thereof. FIG. 29G provides another route for remodeling bacterially expressed G-CSF. The polypeptide is derivatized with a PEGylated N-acetylgalactosamine residue by contacting the polypeptide with an N-acetylgalactosamine transferase and an appropriate donor of PEGylated N-acetylgalactosamine.

In another exemplary embodiment, the invention provides methods for modifying Interferon α-14C (IFNα14C), as shown in FIGS. 30A to 30N. The various forms of IFNα are disclosed elsewhere herein. In FIG. 30B, IFNα14C expressed in mammalian cells is first treated with sialidase to trim back the sialic acid units thereon, and then the molecule is PEGylated using ST3Gal3 and a PEGylated sialic acid donor. In FIG. 30C, N-acetylglucosamine is first added to IFNα14C which has been expressed in insect or fungal cells, where the reaction is conducted via the action of GnT-I and/or II using an N-acetylglucosamine donor. The polypeptide is then PEGylated using a galactosyltransferase and a donor of PEG-galactose. In FIG. 30D, IFNα14C expressed in yeast is first treated with Endo-H to trim back the glycosyl units thereon. The molecules is galactosylated using a galactosyltransferase and a galactose donor, and it is then PEGylated using ST3Gal3 and a donor of PEG-sialic acid. In FIG. 30F, IFNα14C produced by mammalian cells is modified to inched a PEG moiety using ST3Gal3 and a donor of PEG-sialic acid. In FIG. 30G, IFNα14C expressed in insect of fungal cells first has N-acetylglucosamine added using one or more of GnT-I, II, IV, and V, and an N-acetylglucosamine donor. The protein is subsequently galactosylated using an appropriate donor and a galactosyltransferase. Then, IFNα14C is PEGylated using ST3Gal3 and a donor of PEG-sialic acid. In FIG. 30H, yeast produced IFNα14C is first treated with mannosidases to trim back the mannosyl groups. N-acetylglucosamine is then added using a donor of N-acetylglucosamine and one or more of GnT-I, II, IV, and V. IFNα14C is further galactosylated using an appropriate donor and a galactosyltransferase. Then, the polypeptide is PEGylated using ST3Gal3 and a donor of PEG-sialic acid. In FIG. 30I, NSO cell expressed IFNα14C is modified by capping appropriate terminal residues with a sialic acid donor that is modified with levulinic acid, thereby adding a reactive ketone to the sialic acid donor. After addition to a glycosyl residue of the peptide, the ketone is derivatized with a moiety such as a hydrazine- or amine-PEG. In FIG. 30J, IFNα14C expressed by mammalian cells is PEGylated using a donor of PEG-sialic acid and α 2,8-sialyltransferase. In FIG. 30K, IFNα14C produced by mammalian cells is first treated with sialidase to trim back the terminal sialic acid residues, and then the molecule is PEGylated using trans-sialidase and PEGylated sialic acid-lactose complex. In FIG. 30L, IFNα14C expressed in a mammalian system is sialylated using a donor of sialic acid and a 2,8-sialyltransferase. In FIG. 30M, IFNα14C expressed in insect or fungal cells first has N-acetylglucosamine added using an appropriate donor and GnT-I and/or II. The molecule is then contacted with a galactosyltransferase and a galactose donor that is derivatized with a reactive sialic acid via a linker, so that the polypeptide is attached to the reactive sialic acid via the linker and the galactose residue. The polypeptide is then contacted with ST3Gal3 and transferrin, and thus becomes connected with transferrin via the sialic acid residue. In FIG. 30N, IFNα14C expressed in either insect or fungal cells is first treated with endoglycanase to trim back the glycosyl groups, and is then contacted with a galactosyltransferase and a galactose donor that is derivatized with a reactive sialic acid via a linker, so that the polypeptide is attached to the reactive sialic acid via the linker and the galactose residue. The molecule is then contacted with ST3Gal3 and transferrin, and thus becomes connected with transferrin via the sialic acid residue.

Figure 30E:
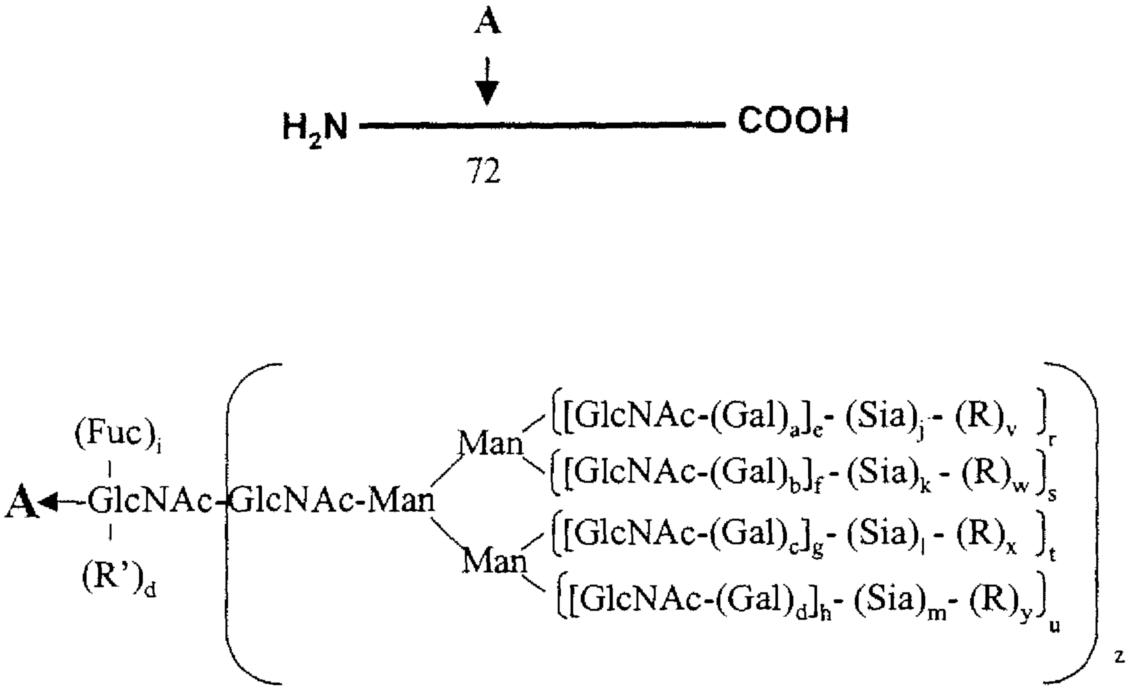
FIG. 30E is a diagram depicting the interferon-alpha isoform 14c peptide indicating the amino acid residue to which a glycan is linked, and an exemplary glycan formula linked thereto.
Figures 30P, 30Q:
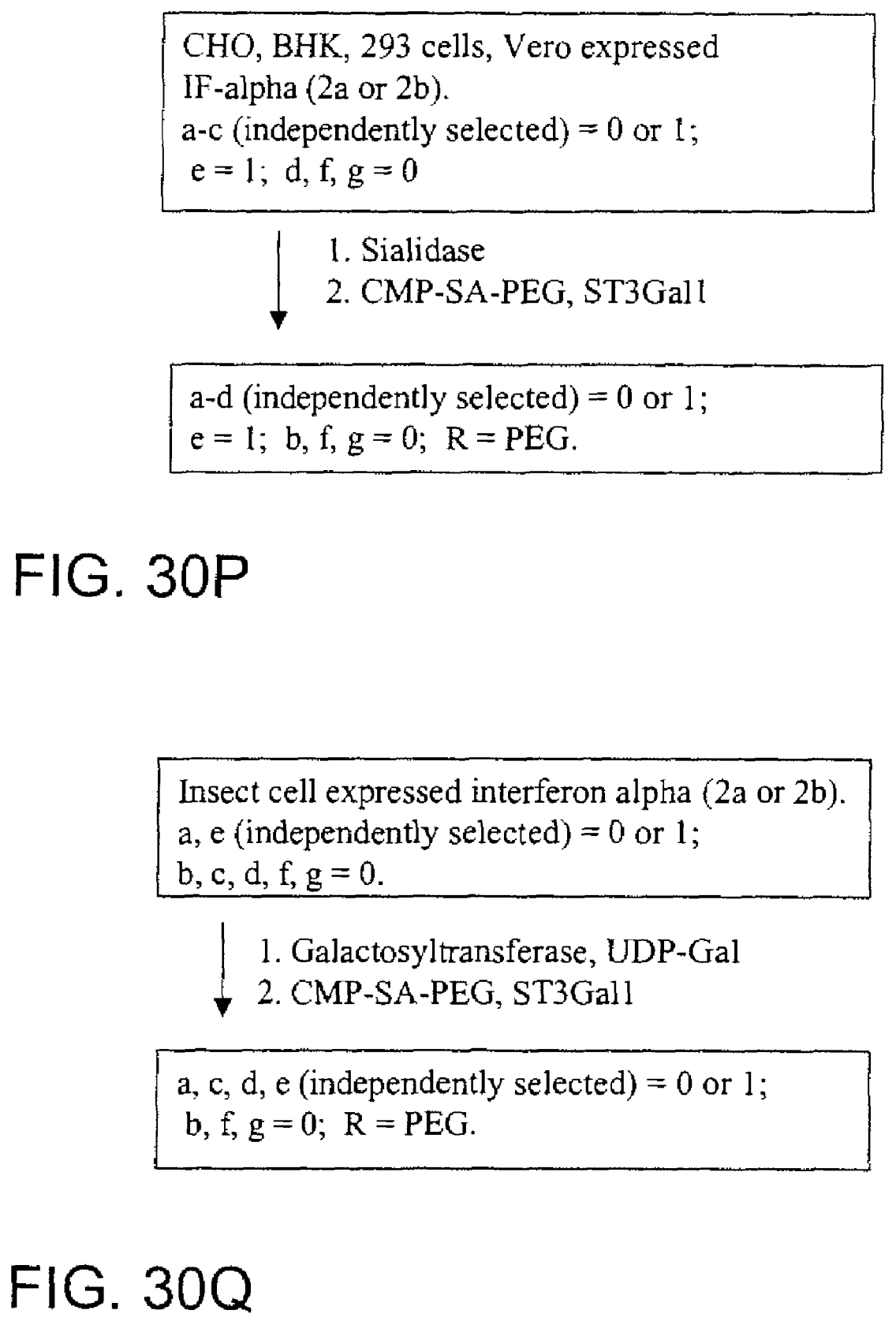
Figure 30R:
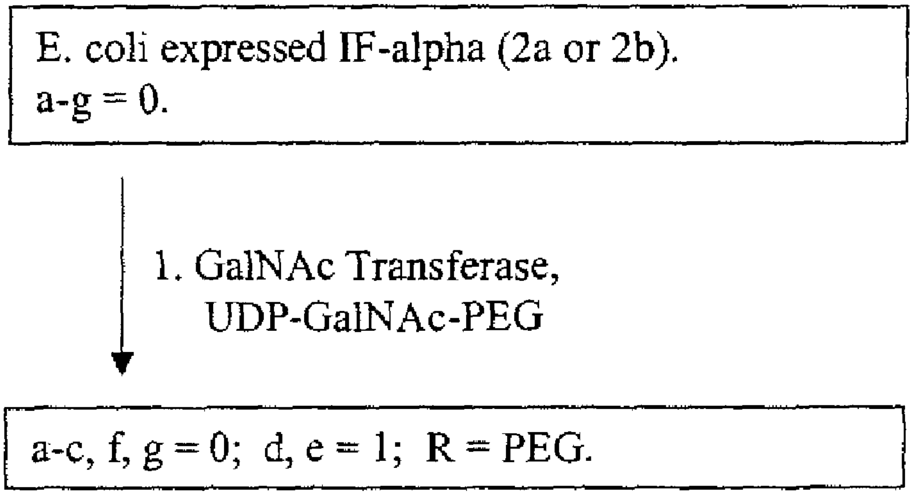
Figure 30S:
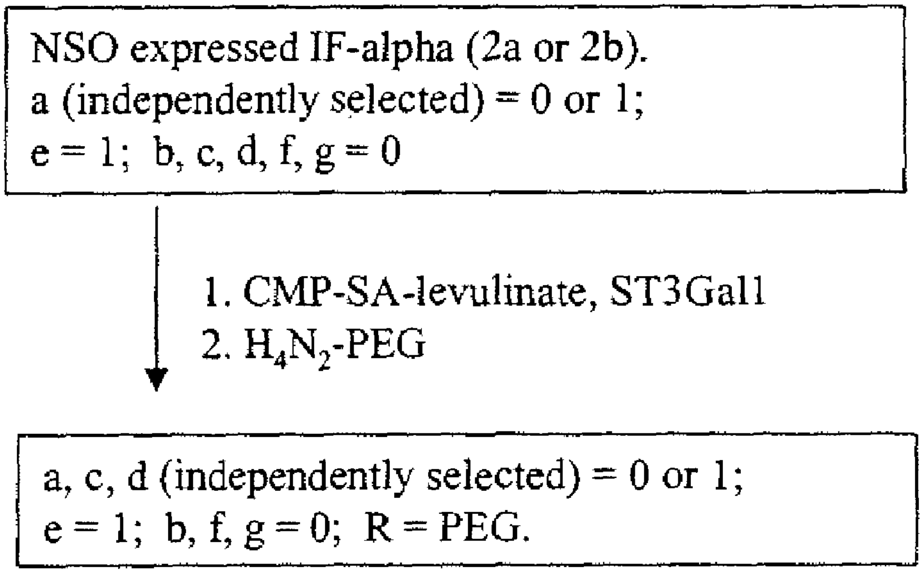
Figure 30T:
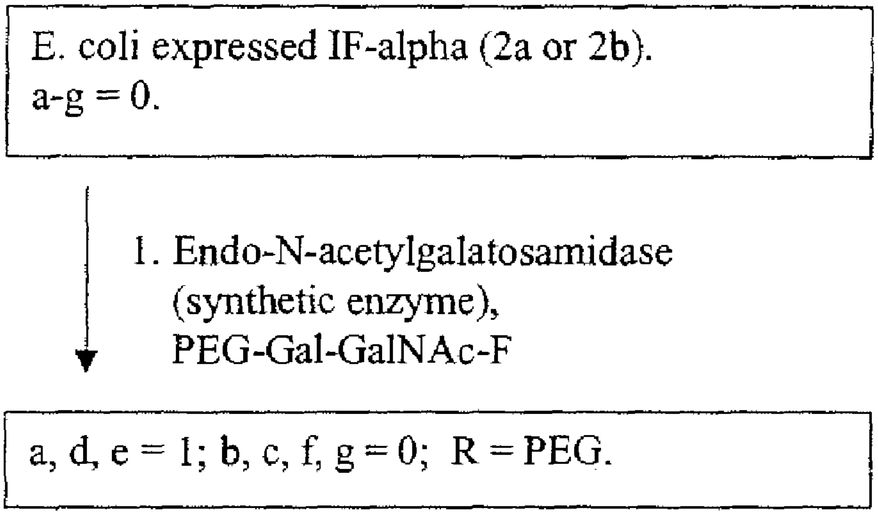
Figure 30U:
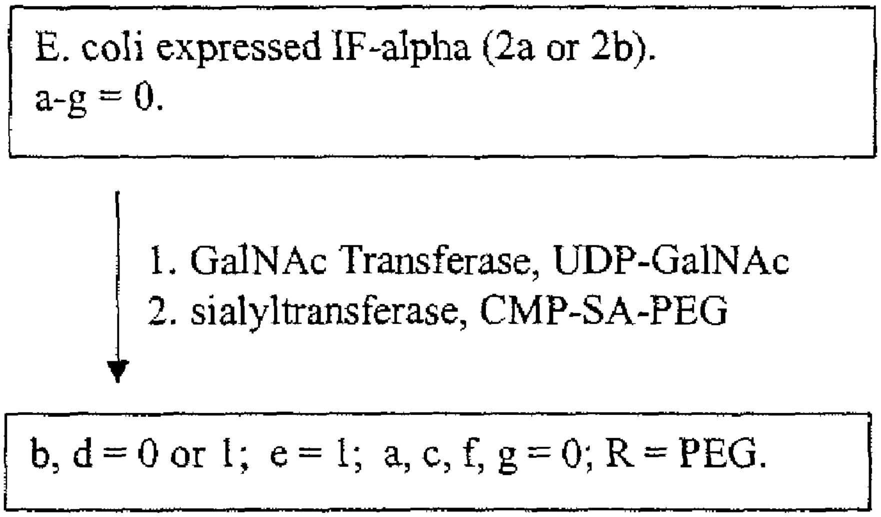
Figure 30V:
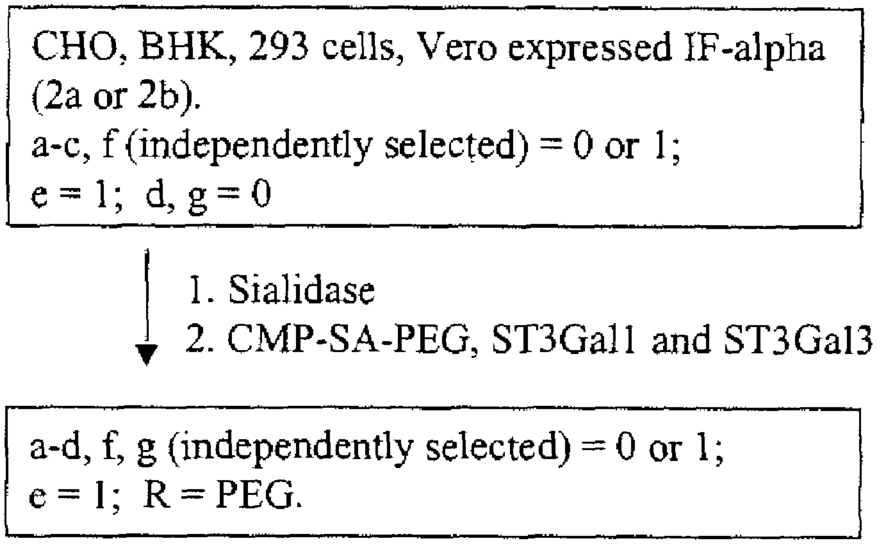
Figure 30W:
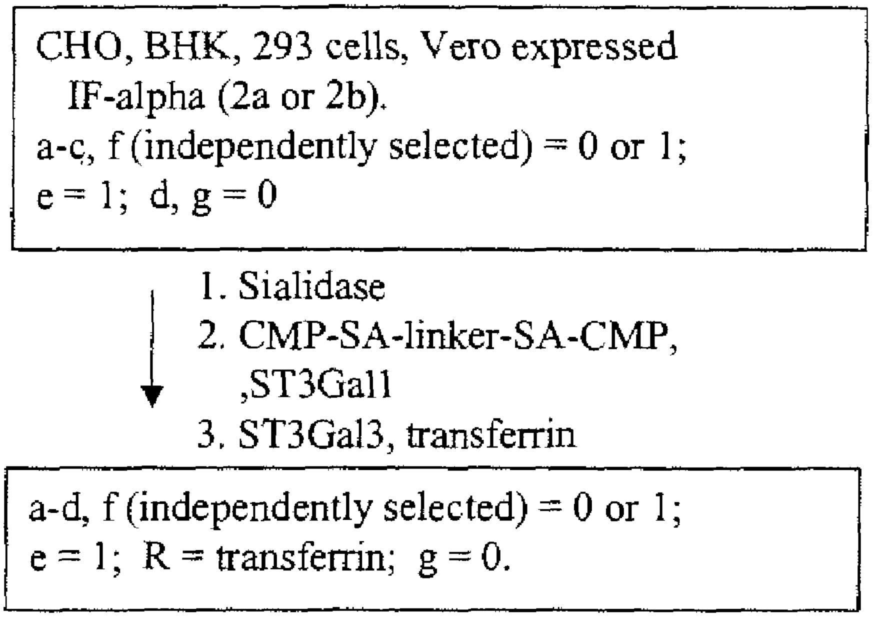
Figure 30X:
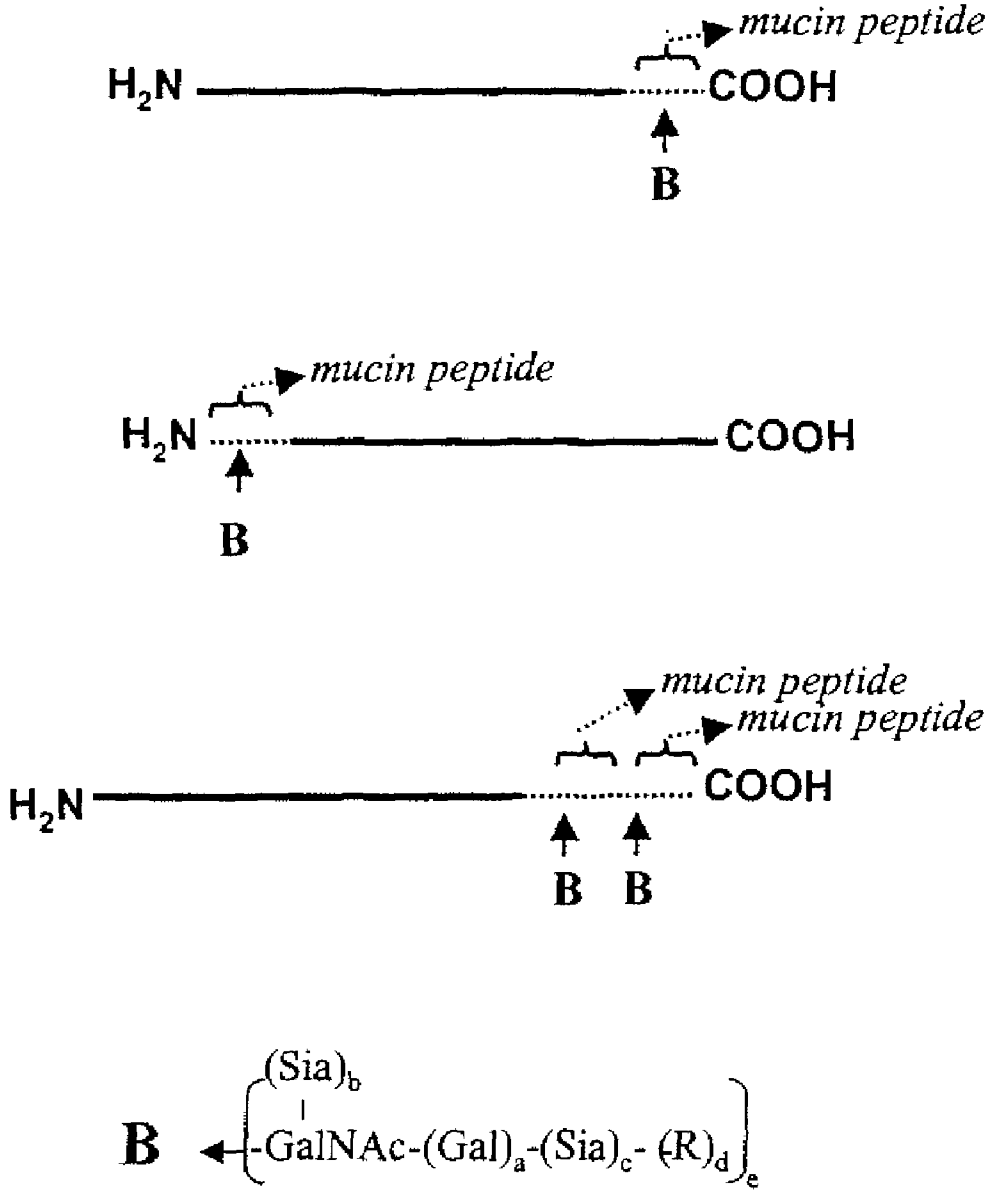
FIG. 30X is a diagram depicting the interferon-alpha-mucin fusion peptides indicating the residue(s) which is linked to glycans contemplated for remodeling, and exemplary glycan formulas linked thereto.

In another exemplary embodiment, the invention provides methods for modifying Interferon α-2a or 2b (IFNα), as shown in FIGS. 30O to 30EE. In FIG. 30P, IFNα produced in mammalian cells is first treated with sialidase to trim back the glycosyl units, and is then PEGylated using ST3Gal3 and a PEGylated sialic acid donor. In FIG. 30Q, IFNα expressed in insect cells is first galactosylated using an appropriate donor and a galactosyltransferase, and is then PEGylated using ST3Gal1 and a PEGylated sialic acid donor. FIG. 30R offers another method for remodeling IFNα expressed in bacteria: PEGylated N-acetylgalactosamine is added to the protein using an appropriate donor and N-acetylgalactosamine transferase. In FIG. 30S, IFNα expressed in mammalian cells is modified by capping appropriate terminal residues with a sialic acid donor that is modified with levulinic acid, adding a reactive ketone to the sialic acid donor. After addition to a glycosyl residue of the peptide, the ketone is derivatized with a moiety such as a hydrazine- or amine-PEG. In FIG. 30T, IFNα expressed in bacteria is PEGylated using a modified enzyme Endo-N-acetylgalactosamidase, which functions in a synthetic instead of a hydrolytic manner, and using a N-acetylgalactosamine donor derivatized with a PEG moiety. In FIG. 30U, N-acetylgalactosamine is first added IFNαusing an appropriate donor and N-acetylgalactosamine transferase, and then is PEGylated using a sialyltransferase and a PEGylated sialic acid donor. In FIG. 30V, IFNαexpressed in a mammalian system is first treated with sialidase to trim back the sialic acid residues, and is then PEGylated using a suitable donor and ST3Gal1 and/or ST3Gal3. In FIG. 30W, IFNα expressed in mammalian cells is first treated with sialidase to trim back the sialic acid residues. The polypeptide is then contacted with ST3Gal1 and two reactive sialic acid residues that are connect via a linker, so that the polypeptide is attached to one reactive sialic acid via the linker and the second sialic acid residue. The polypeptide is subsequently contacted with ST3Gal3 and transferrin, and thus becomes connected with transferrin via the sialic acid residue. In FIG. 30Y, IFNα expressed in mammalian cells is first treated with sialidase to trim back the sialic acid residues, and is then PEGylated using ST3Gal1 and a donor of PEG-sialic acid. In FIG. 30Z, IFNα produced by insect cells is PEGylated using a galactosyltransferase and a donor of PEGylated galactose. In FIG. 30AA, bacterially expressed IFNαfirst has N-acetylgalactosamine added using a suitable donor and N-acetylgalactosamine transferase. The protein is then PEGylated using a sialyltransferase and a donor of PEG-sialic acid. In FIG. 30CC, IFNα expressed in bacteria is modified in another procedure: PEGylated N-acetylgalactosamine is added to the protein by N-acetylgalactosamine transferase using a donor of PEGylated N-acetylgalactosamine. In FIG. 30DD, IFNα expressed in bacteria is remodeled in yet another scheme. The polypeptide is first contacted with N-acetylgalactosamine transferase and a donor of N-acetylgalactosamine that is derivatized with a reactive sialic acid via a linker, so that IFNα is attached to the reactive sialic acid via the linker and the N-acetylgalactosamine. IFNα is then contacted with ST3Gal3 and asialo-transferrin so that it becomes connected with transferrin via the sialic acid residue. Then, IFNα is capped with sialic acid residues using ST3Gal3 and a sialic acid donor. An additional method for modifying bacterially expressed IFNα is disclosed in FIG. 30EE, where IFNα is first exposed to NHS-CO-linker-SA-CMP and is then connected to a reactive sialic acid via the linker. It is subsequently conjugated with transferrin using ST3Gal3 and transferrin.

The methods for remodeling INN omega are essentially identical to those presented here for IFN alpha except that the attachment of the glycan to the IFN omega peptide occurs at amino acid residue 101 in SEQ ID NO:75. The nucleotide and amino acid sequences for IFN omega are presented herein as SEQ ID NOS:74 and 75. Methods of making and using IFN omega are found in U.S. Pat. Nos. 4,917,887 and 5,317,089, and in EP Patent No. 0170204-A.

Figures 31B, 31C:
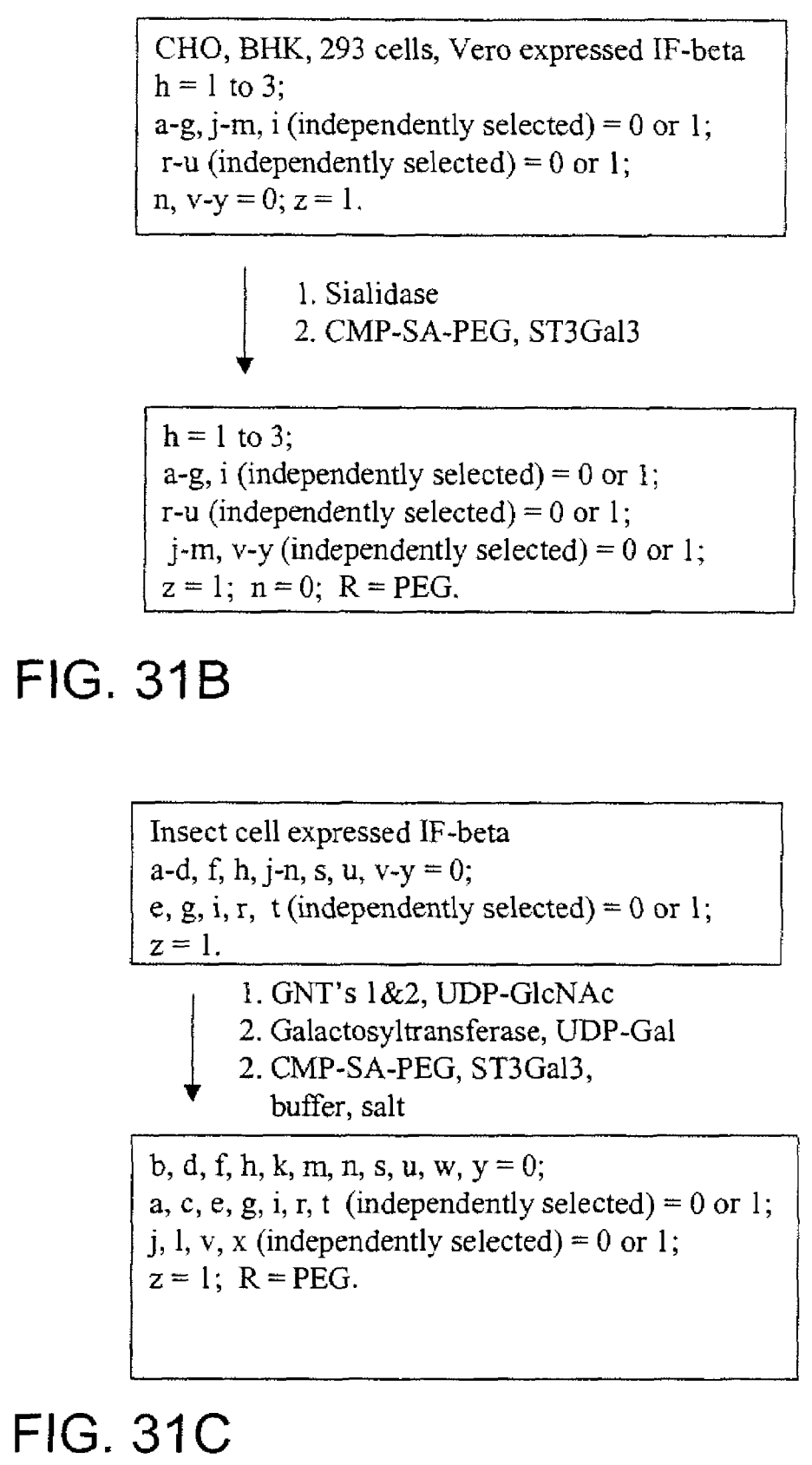
Figures 31Q, 31R:
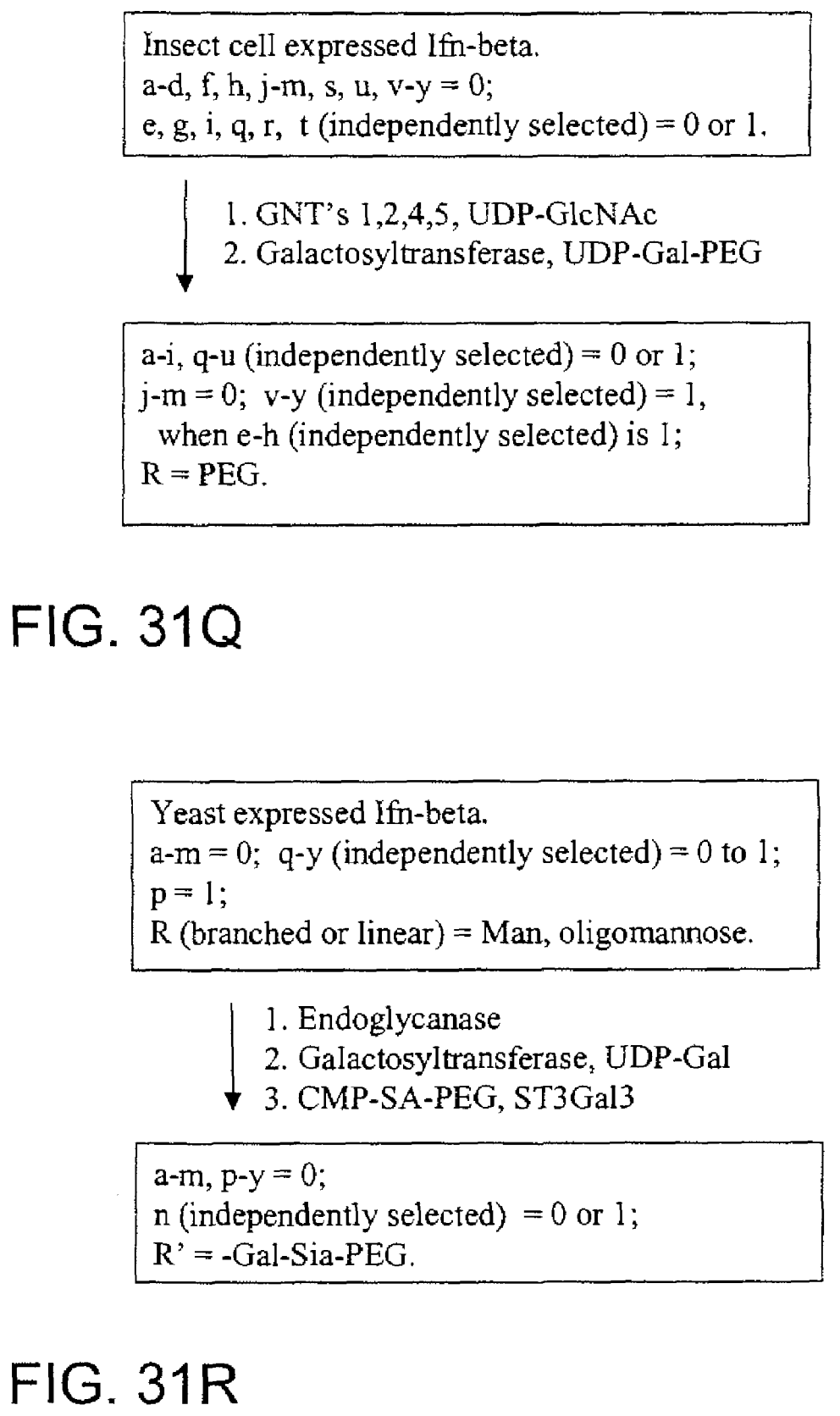

In another exemplary embodiment, the invention provides methods for modifying Interferon β (IFN-β), as shown in FIGS. 31A to 31S. In FIG. 31B, IFN-β expressed in a mammalian system is first treated with sialidase to trim back the terminal sialic acid residues. The protein is then PEGylated using ST3Gal3 and a donor of PEGylated sialic acid. FIG. 31C is a scheme for modifying IFN-β produced by insect cells. First, N-acetylglucosamine is added to IFN-β using an appropriate donor and GnT-I and/or -II. The protein is then galactosylated using a galactose donor and a galactosyltransferase. Finally, IFN-β is PEGylated using ST3Gal3 and a donor of PEG-sialic acid. In FIG. 31D, IFN-β expressed in yeast is first treated with Endo-H to trim back its glycosyl chains, and is then galactosylated using a galactose donor and a galactosyltransferase, and is then PEGylated using ST3Gal3 and a donor of PEGylated sialic acid. In FIG. 31E, IFN-β produced by mammalian cells is modified by PEGylation using ST3Gal3 and a donor of sialic acid already derivatized with a PEG moiety. In FIG. 31F, IFN-β expressed in insect cells first has N-acetylglucosamine added by one or more of GnT-I, II, IV, and V using a N-acetylglucosamine donor, and then is galactosylated using a galactose donor and a galactosyltransferase, and is then PEGylated using ST3Gal3 and a donor of PEG-sialic acid. In FIG. 31G, IFN-β expressed in yeast is first treated with mannosidases to trim back the mannosyl units, then has N-acetylglucosamine added using a N-acetylglucosamine donor and one or more of GnT-I, II, IV, and V. The protein is further galactosylated using a galactose donor and a galactosyltransferase, and then PEGylated using ST3Gal3 and a PEG-sialic acid donor. In FIG. 31H, mammalian cell expressed IFN-β is modified by capping appropriate terminal residues with a sialic acid donor that is modified with levulinic acid, adding a reactive ketone to the sialic acid donor. After addition to a glycosyl residue of the peptide, the ketone is derivatized with a moiety such as a hydrazine- or amine-PEG. In FIG. 31I, IFN-β expressed in a mammalian system is PEGylated using a donor of PEG-sialic acid and a 2,8-sialyltransferase. In FIG. 31J, IFN-β expressed by mammalian cells is first treated with sialidase to trim back its terminal sialic acid residues, and then PEGylated using trans-sialidase and a donor of PEGylated sialic acid. In FIG. 31K, IFN-β expressed in mammalian cells is first treated with sialidase to trim back terminal sialic acid residues, then PEGylated using ST3Gal3 and a donor of PEG-sialic acid, and then sialylated using ST3Gal3 and a sialic acid donor. In FIG. 31L, IFN-β expressed in mammalian cells is first treated with sialidase and galactosidase to trim back the glycosyl chains, then galactosylated using a galactose donor and an α-galactosyltransferase, and then PEGylated using ST3Gal3 or a sialyltransferase and a donor of PEG-sialic acid. In FIG. 31M, IFN-β expressed in mammalian cells is first treated with sialidase to trim back the glycosyl units. It is then PEGylated using ST3Gal3 and a donor of PEG-sialic acid, and is then sialylated using ST3Gal3 and a sialic acid donor. In FIG. 31N, IFN-β expressed in mammalian cells is modified by capping appropriate terminal residues with a sialic acid donor that is modified with levulinic acid, adding a reactive ketone to the sialic acid donor. After addition to a glycosyl residue of the peptide, the ketone is derivatized with a moiety such as a hydrazine- or amine-PEG. In FIG. 31O, IFN-β expressed in mammalian cells is sialylated using a sialic acid donor and α 2,8-sialyltransferase. In FIG. 31Q, IFN-β produced by insect cells first has N-acetylglucosamine added using a donor of N-acetylglucosamine and one or more of GnT-I, II, IV, and V, and is further PEGylated using a donor of PEG-galactose and a galactosyltransferase. In FIG. 31R, IFN-β expressed in yeast is first treated with endoglycanase to trim back the glycosyl groups, then galactosylated using a galactose donor and a galactosyltransferase, and then PEGylated using ST3Gal3 and a donor of PEG-sialic acid. In FIG. 31S, IFN-β expressed in a mammalian system is first contacted with ST3Gal3 and two reactive sialic acid residues connected via a linker, so that the polypeptide is attached to one reactive sialic acid via the linker and the second sialic acid residue. The polypeptide is then contacted with ST3Gal3 and desialylated transferrin, and thus becomes connected with transferrin via the sialic acid residue. Then, IFN-β is further sialylated using a sialic acid donor and ST3Gal3.

Figures 32B, 32C:
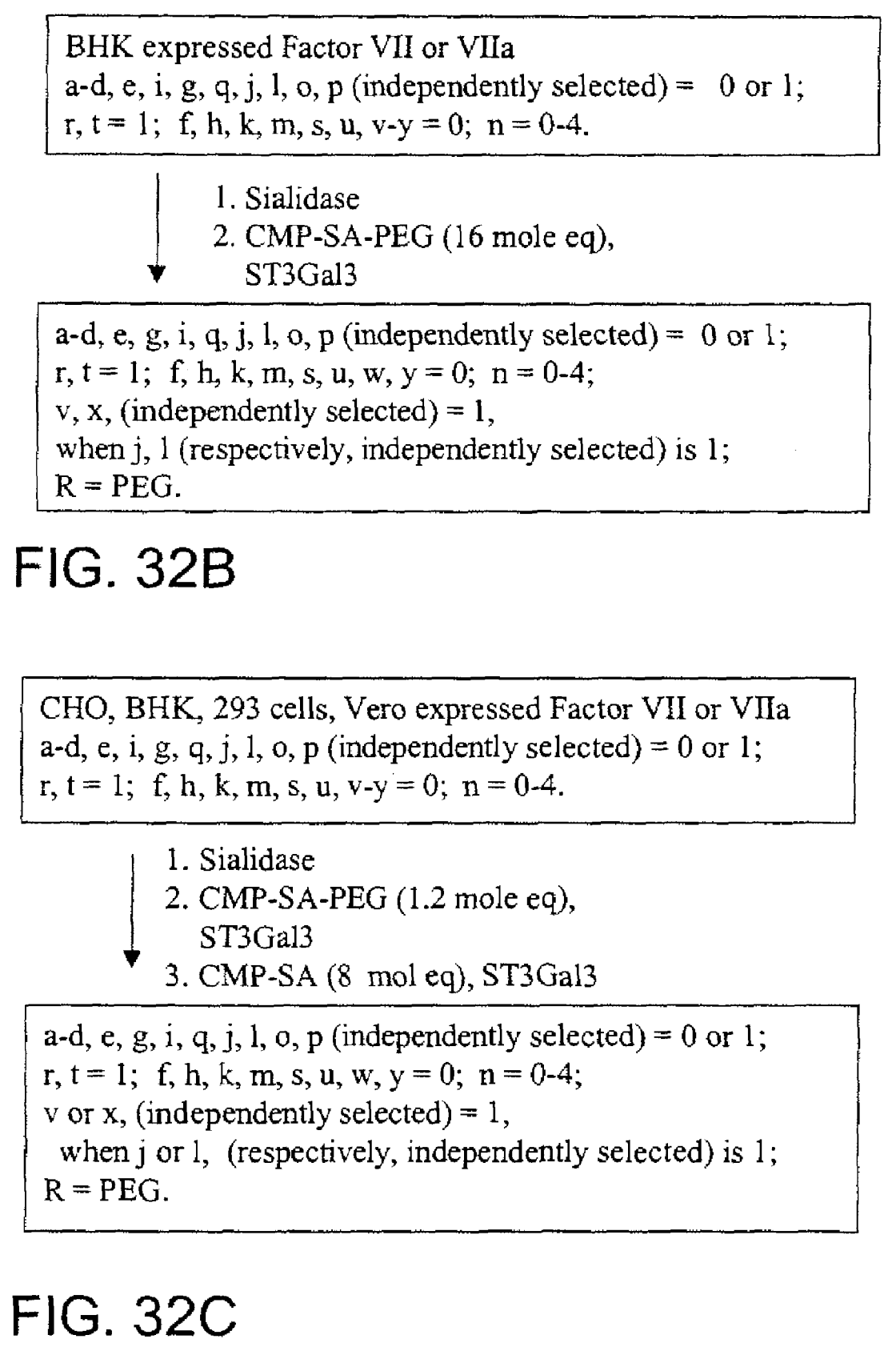

In another exemplary embodiment, the invention provides methods for modifying Factor VII or VIIa, as shown in FIGS. 32A to 32D. In FIG. 32B, Factor VII or VIIa produced by a mammalian system is first treated with sialidase to trim back the terminal sialic acid residues, and then PEGylated using ST3Gal3 and a donor of PEGylated sialic acid. FIG. 32C, Factor VII or VIIa expressed by mammalian cells is first treated with sialidase to trim back the terminal sialic acid residues, and then PEGylated using ST3Gal3 and a donor of PEGylated sialic acid. Further, the polypeptide is sialylated with ST3Gal3 and a sialic acid donor. FIG. 32D offers another modification scheme for Factor VII or VIIa produced by mammalian cells: the polypeptide is first treated with sialidase and galactosidase to trim back its sialic acid and galactose residues, then galactosylated using a galactosyltransferase and a galactose donor, and then PEGylated using ST3Gal3 and a donor of PEGylated sialic acid.

Figures 33B, 33C:
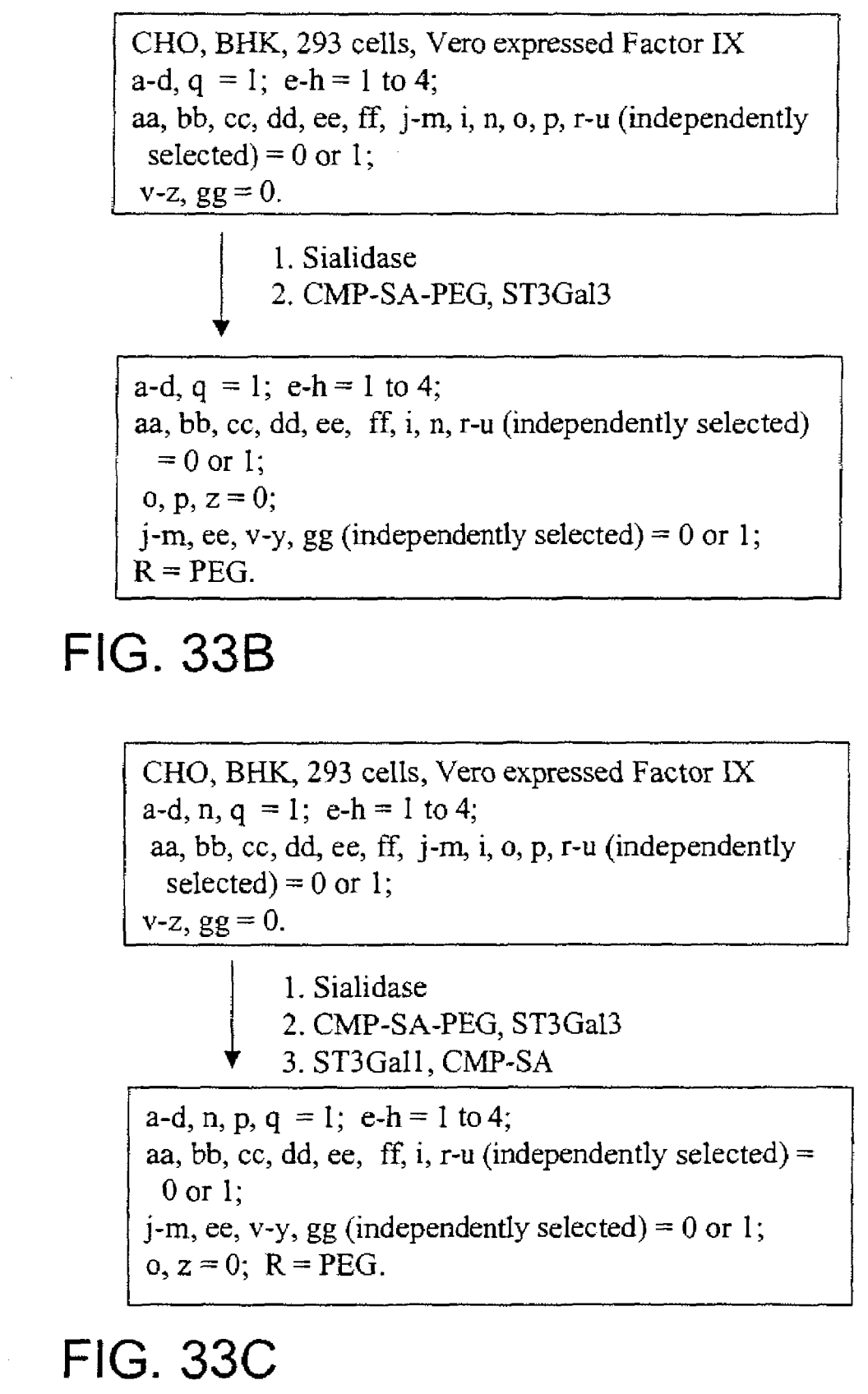

In another exemplary embodiment, the invention provides methods for modifying Factor IX, some examples of which are included in FIGS. 33A to 33G. In FIG. 33B, Factor IX produced by mammalian cells is first treated with sialidase to trim back the terminal sialic acid residues, and is then PEGylated with ST3Gal3 using a PEG-sialic acid donor. In FIG. 33C, Factor IX expressed by mammalian cells is first treated with sialidase to trim back the terminal sialic acid residues, it is then PEGylated using ST3Gal3 and a PEG-sialic acid donor, and further sialylated using ST3Gal1 and a sialic acid donor. Another scheme for remodeling mammalian cell produced Factor IX can be found in FIG. 33D. The polypeptide is first treated with sialidase to trim back the terminal sialic acid residues, then galactosylated using a galactose donor and a galactosyltransferase, further sialylated using a sialic acid donor and ST3Gal3, and then PEGylated using a donor of PEGylated sialic acid and ST3Gal1. In FIG. 33E, Factor IX that is expressed in a mammalian system is PEGylated through the process of sialylation catalyzed by ST3Gal3 using a donor of PEG-sialic acid. In FIG. 33F, Factor IX expressed in mammalian cells is modified by capping appropriate terminal residues with a sialic acid donor that is modified with levulinic acid, adding a reactive ketone to the sialic acid donor. After addition to a glycosyl residue of the peptide, the ketone is derivatized with a moiety such as a hydrazine- or amine-PEG. FIG. 33G provides an additional method of modifying Factor IX. The polypeptide, produced by mammalian cells, is PEGylated using a donor of PEG-sialic acid and a 2,8-sialyltransferase.

Figures 34B, 34C:
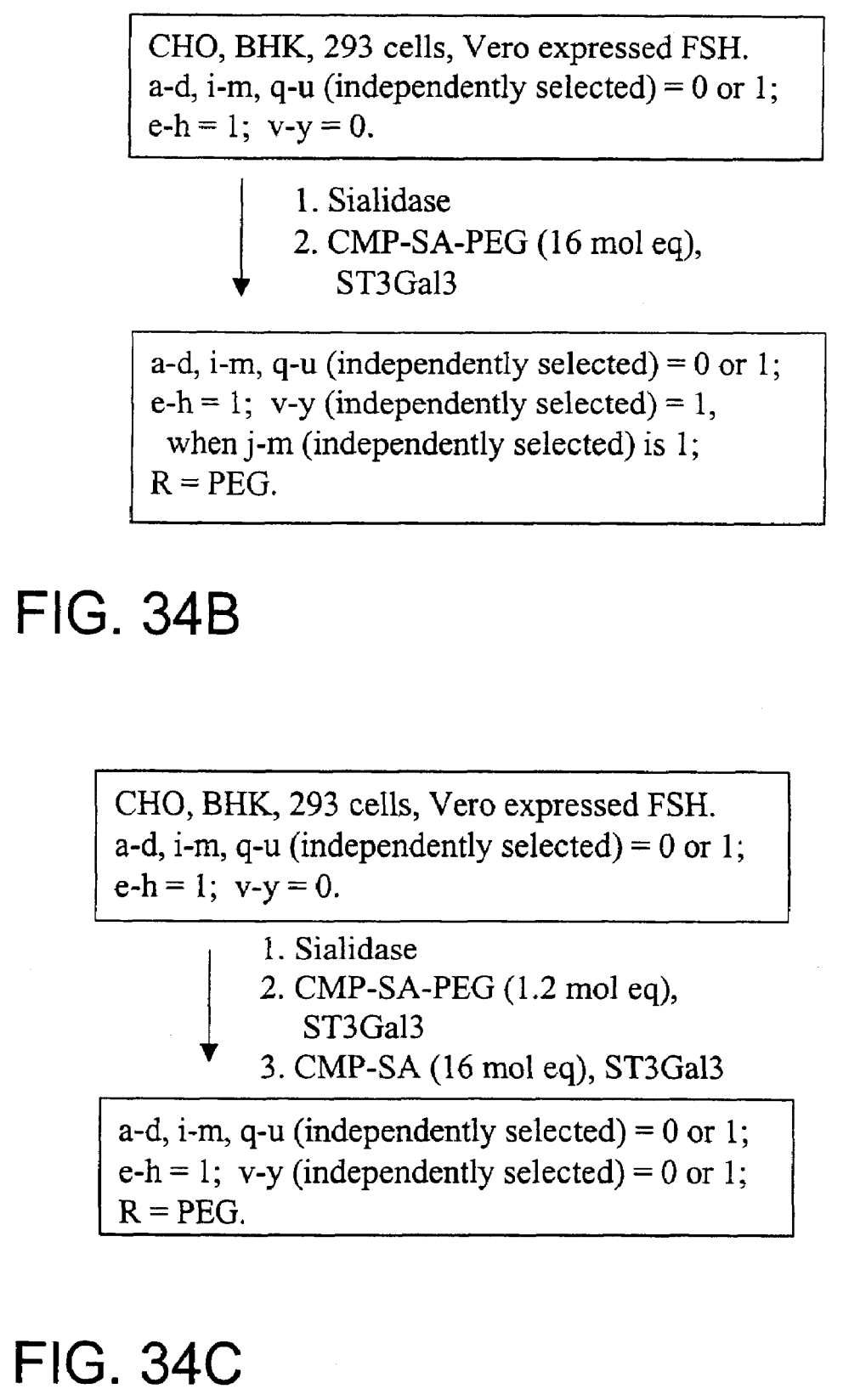

In another exemplary embodiment, the invention provides methods for modification of Follicle Stimulating Hormone (FSH). FIGS. 34A to 34J present some examples. In FIG. 34B, FSH is expressed in a mammalian system and modified by treatment of sialidase to trim back terminal sialic acid residues, followed by PEGylation using ST3Gal3 and a donor of PEG-sialic acid. In FIG. 34C, FSH expressed in mammalian cells is first treated with sialidase to trim back terminal sialic acid residues, then PEGylated using ST3Gal3 and a donor of PEG-sialic acid, and then sialylated using ST3Gal3 and a sialic acid donor. FIG. 34D provides a scheme for modifying FSH expressed in a mammalian system. The polypeptide is treated with sialidase and galactosidase to trim back its sialic acid and galactose residues, then galactosylated using a galactose donor and a galactosyltransferase, and then PEGylated using ST3Gal3 and a donor of PEG-sialic acid. In FIG. 34E, FSH expressed in mammalian cells is modified in the following procedure: FSH is first treated with sialidase to trim back the sialic acid residues, then PEGylated using ST3Gal3 and a donor of PEG-sialic acid, and is then sialylated using ST3Gal3 and a sialic acid donor. FIG. 34F offers another example of modifying FSH produced by mammalian cells: The polypeptide is modified by capping appropriate terminal residues with a sialic acid donor that is modified with levulinic acid, adding a reactive ketone to the sialic acid donor. After addition to a glycosyl residue of the peptide, the ketone is derivatized with a moiety such as a hydrazine- or amine-PEG. In FIG. 34G, FSH expressed in a mammalian system is modified in another procedure: the polypeptide is remodeled with addition of sialic acid using a sialic acid donor and an α 2,8-sialyltransferase. In FIG. 34H, FSH is expressed in insect cells and modified in the following procedure: N-acetylglucosamine is first added to FSH using an appropriate N-acetylglucosamine donor and one or more of GnT-I, II, IV, and V; FSH is then PEGylated using a donor of PEG-galactose and a galactosyltransferase. FIG. 34I depicts a scheme of modifying FSH produced by yeast. According to this scheme, FSH is first treated with endoglycanase to trim back the glycosyl groups, galactosylated using a galactose donor and a galactosyltransferase, and is then PEGylated with ST3Gal3 and a donor of PEG-sialic acid. In FIG. 34J, FSH expressed by mammalian cells is first contacted with ST3Gal3 and two reactive sialic acid residues via a linker, so that the polypeptide is attached to a reactive sialic acid via the linker and a second sialic acid residue. The polypeptide is then contacted with ST3Gal1 and desialylated chorionic gonadotrophin (CG) produced in CHO, and thus becomes connected with CG via the second sialic acid residue. Then, FSH is sialylated using a sialic acid donor and ST3Gal3 and/or ST3Gal1.

Figures 35B, 35C:
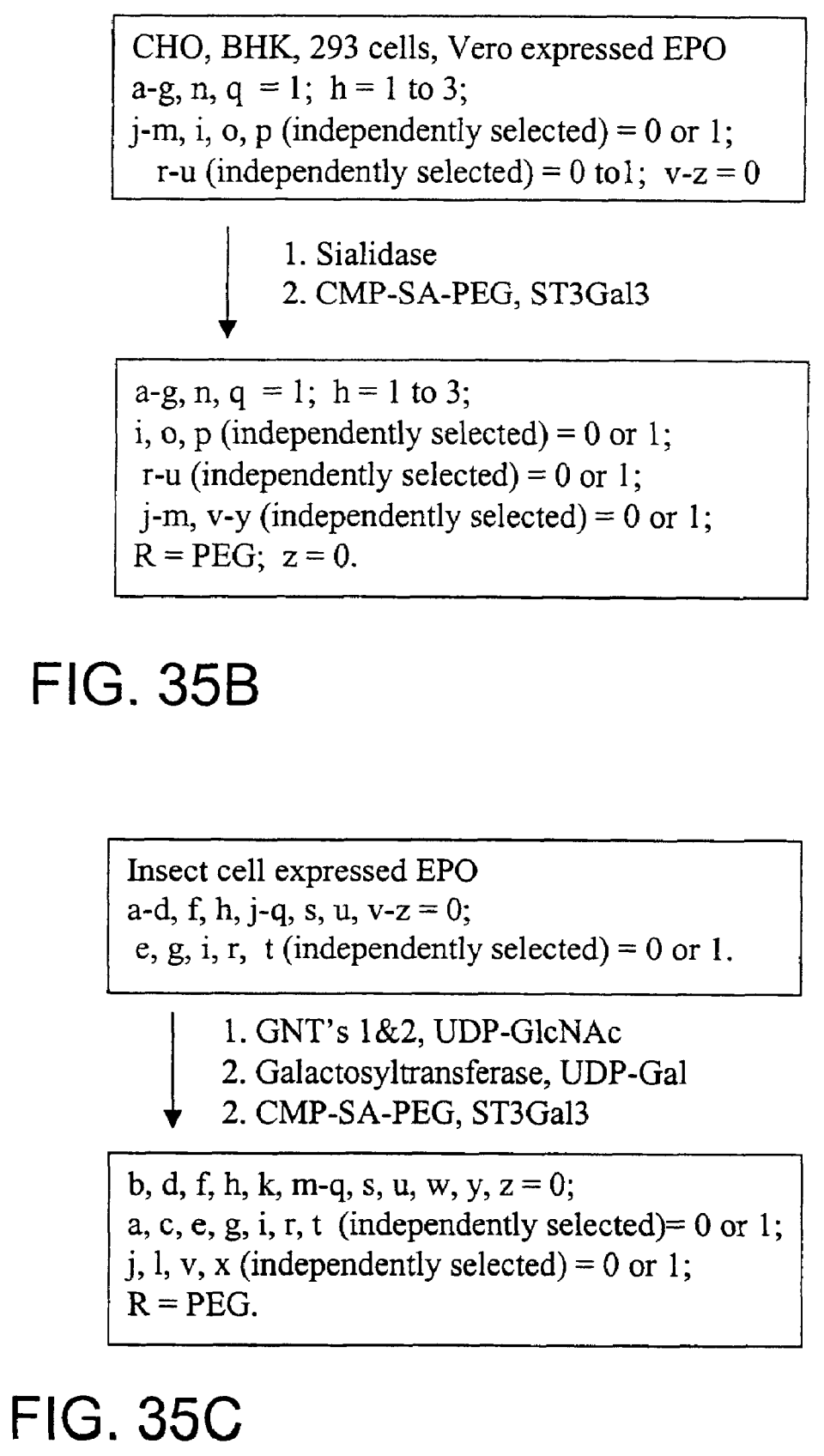
Figure 35T:
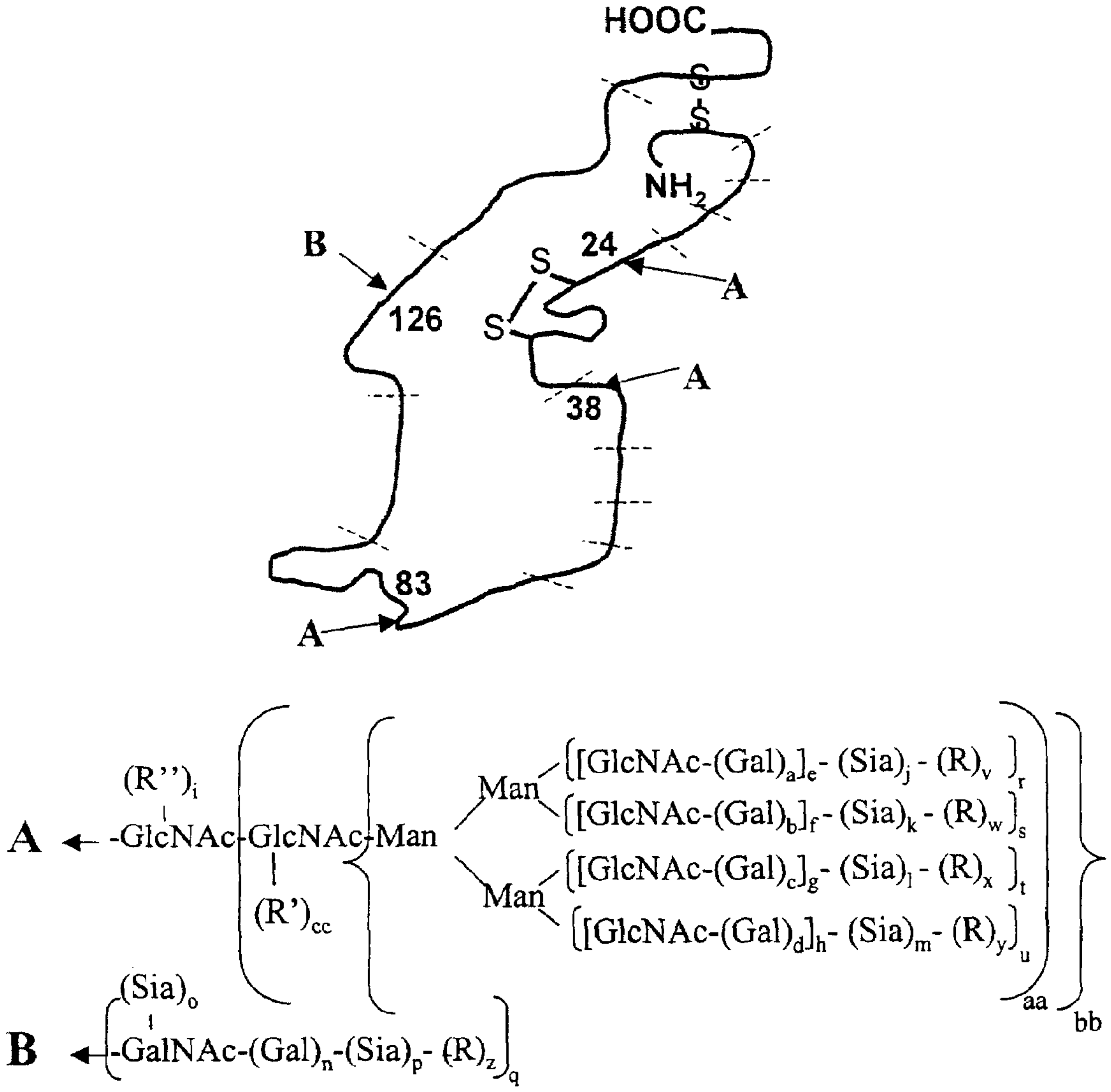
FIG. 35T is a diagram depicting the EPO peptide indicating the residues which bind to glycans contemplated for remodeling, and formulas for the glycans.
Figures 35Y, 35Z:
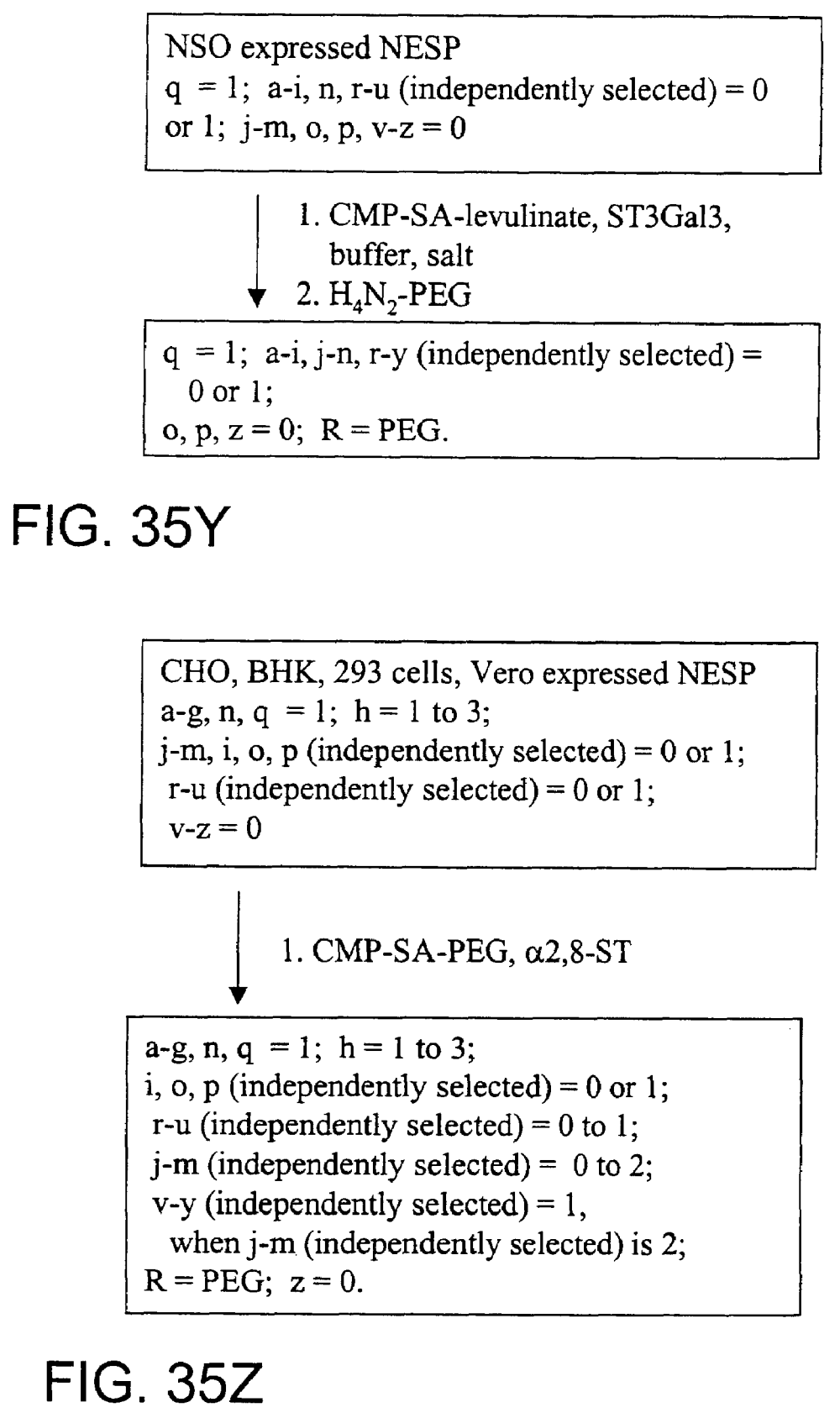

In another exemplary embodiment, the invention provides methods for modifying erythropoietin (EPO), FIGS. 35A to 35AA set forth some examples which are relevant to the remodeling of both wild-type and mutant EPO peptides. In FIG. 35B, EPO expressed in various mammalian systems is remodeled by contacting the expressed protein with a sialidase to remove terminal sialic acid residues. The resulting peptide is contacted with a sialyltransferase and a CMP-sialic acid that is derivatized with a PEG moiety. In FIG. 35C, EPO that is expressed in insect cells is remodeled with N-acetylglucosamine, using GnT-I and/or GnT-II. Galactose is then added to the peptide, using galactosyltransferase. PEG group is added to the remodeled peptide by contacting it with a sialyltransferase and a CMP-sialic acid that is derivatized with a PEG moiety. In FIG. 35D, EPO that is expressed in a mammalian cell system is remodeled by removing terminal sialic acid moieties via the action of a sialidase. The terminal galactose residues of the N-linked glycosyl units are "capped" with sialic acid, using ST3Gal3 and a sialic acid donor. The terminal galactose residues on the O-linked glycan are functionalized with a sialic acid bearing a PEG moiety, using an appropriate sialic acid donor and ST3Gal1. In FIG. 35E, EPO that is expressed in a mammalian cell system is remodeled by functionalizing the N-linked glycosyl residues with a PEG-derivatized sialic acid moiety. The peptide is contacted with ST3Gal3 and an appropriately modified sialic acid donor. In FIG. 35F, EPO that is expressed in an insect cell system, yeast or fungi, is remodeled by adding at least one N-acetylglucosamine residues by contacting the peptide with a N-acetylglucosamine donor and one or more of GnT-I, GnT-II, and GnT-V. The peptide is then PEGylated by contacting it with a PEGylated galactose donor and a galactosyltransferase. In FIG. 35G, EPO that is expressed in an insect cell system, yeast or fungi, is remodeled by the addition of at least one N-acetylglucosamine residues, using an appropriate N-acetylglucosamine donor and one or more of GnT-I, GnT-II, and GnT-V. A galactosidase that is altered to operate in a synthetic, rather than a hydrolytic manner is used to add an activated PEGylated galactose donor to the N-acetylglucosamine residues. In FIG. 35H, EPO that is expressed in an insect cell system, yeast or fungi, is remodeled by the addition of at least one terminal N-acetylglucosamine-PEG residue. The peptide is contacted with GnT-I and an appropriate N-acetylyglucosamine donor that is derivatized with a PEG moiety. In FIG. 35I, EPO that is expressed in an insect cell system, yeast or fungi, is remodeled by adding one or more terminal galactose-PEG residues. The peptide is contacted with GnT-I and an appropriate N-acetylglucosamine donor that is derivatized with a PEG moiety. The peptide is then contacted with galactosyltransferase and an appropriate galactose donor that is modified with a PEG moiety. In FIG. 35J, EPO expressed in an insect cell system, yeast or fungi, is remodeled by the addition of one more terminal sialic acid-PEG residues. The peptide is contacted with an appropriate N-acetylglucosamine donor and GnT-I. The peptide is further contacted with galactosyltransferase and an appropriate galactose donor. The peptide is then contacted with ST3Gal3 and an appropriate sialic acid donor that is derivatized with a PEG moiety. In FIG. 35K, EPO expressed in an insect cell system, yeast or fungi, is remodeled by the addition of terminal sialic acid-PEG residues. The peptide is contacted with an appropriate N-acetylglucosamine donor and one or more of GnT-I, GnT-II, and GnT-V. The peptide is then contacted with galactosyltransferase and an appropriate galactose donor. The peptide is further contacted with ST3Gal3 and an appropriate sialic acid donor that is derivatized with a PEG moiety. In FIG. 35L, EPO expressed in an insect cell system, yeast or fungi, is remodeled by the addition of one or more terminal α2,6-sialic acid-PEG residues. The peptide is contacted with an appropriate N-acetylglucosamine donor and one or more of GnT-I, GnT-II, and GnT-V. The peptide is further contacted with galactosyltransferase and an appropriate galactose donor. The peptide is then contacted with α2,6-sialyltransferase and an appropriately modified sialic acid donor. In FIG. 35M, EPO expressed in a mammalian cell system is remodeled by addition of one or more terminal sialic acid-PEG residues. The peptide is contacted with a sialidase to remove terminal sialic acid residues. The peptide is further contacted with a sialyltransferase and an appropriate sialic acid donor. The peptide is further contacted with a sialyltransferase and an appropriate sialic acid donor that is derivatized with a PEG moiety. In FIG. 35N, EPO expressed in a mammalian cell system is remodeled by the addition of one or more terminal sialic acid-PEG residues. The peptide is contacted with a sialyltransferase and an appropriate sialic acid donor that is derivatized with a PEG moiety. In FIG. 35O, EPO expressed in a mammalian cell system is remodeled by the addition of one or more terminal α2,8-sialic acid-PEG residues to primarily O-linked glycans. The peptide is contacted with α2,8-sialyltransferase and an appropriate sialic acid donor that is derivatized with a PEG moiety. In FIG. 35P, EPO expressed in a mammalian cell is remodeled by the addition of one or more terminal α2,8-sialic acid-PEG residues to O-linked and N-linked glycans. The peptide is contacted with α2,8-sialyltransferase and an appropriate sialic acid donor that is derivatized with a PEG moiety. In FIG. 35Q, EPO expressed in yeast or fungi is remodeled by the addition of one or more terminal sialic acid-PEG residues. The peptide is contacted with mannosidases to remove terminal mannose residues. Next, the peptide is contacted with GnT-I and an appropriate N-acetylglucosamine donor. The peptide is further contacted with galactosyltransferase and an appropriate galactose donor. The peptide is then contacted with a sialyltransferase and an appropriate sialic acid donor that is derivatized with a PEG moiety. In FIG. 35R, EPO expressed in yeast or fungi is remodeled by the addition of at least one terminal N-acetylglucosamine-PEG residues. The peptide is contacted with mannosidases to remove terminal mannose residue. The peptide is then contacted with GnT-I and an appropriate N-acetylglucosamine donor that is derivatized with a PEG moiety. In FIG. 35S, EPO expressed in yeast or fungi is remodeled by the addition of one more terminal sialic acid-PEG residues. The peptide is contacted with mannosidase-I to remove α2 mannose residues. The peptide is further contacted with GnT-I and an appropriate N-acetylglucosamine donor. The peptide is then contacted with galactosyltransferase and an appropriate galacose donor. The peptide is then contacted with a sialyltransferase and an appropriate sialic acid donor that is derivatized with a PEG moiety. In FIG. 35U, EPO expressed in yeast or fungi is remodeled by addition of one or more galactose-PEG residues. The peptide is contacted with endo-H to trim back glycosyl groups. The peptide is then contacted with galactosyltransferase and an appropriate galactose donor that is derivatized with a PEG moiety. In FIG. 35V, EPO expressed in yeast or fungi is remodeled by the addition of one or more terminal sialic acid-PEG residues. The peptide is contacted with endo-H to trim back glycosyl groups. The peptide is further contacted with galactosyltransferase and an appropriate galactose donor. The peptide is then contacted with a sialyltransferase and an appropriate sialic acid donor that is derivatized with a PEG moiety. In FIG. 35W, EPO expressed in an insect cell system is remodeled by the addition of terminal galactose-PEG residues. The peptide is contacted with mannosidases to remove terminal mannose residues. The peptide is then contacted with galactosyltransferase and an appropriate galactose donor that is derivatized with a PEG moeity. In FIG. 35Y, a mutant EPO called "novel erythropoiesis-stimulating protein" or NESP, expressed in NSO murine myeloma cells is remodeled by capping appropriate terminal residues with a sialic acid donor that is modified with levulinic acid, adding a reactive ketone to the sialic acid donor. After addition to a glycosyl residue of the peptide, the ketone is derivatized with a moiety such as a hydrazine- or amine-PEG. In FIG. 35Z, mutant EPO, i.e. NESP, expressed in a mammalian cell system is remodeled by addition of one or more terminal sialic acid-PEG residues. PEG is added to the glycosyl residue on the glycan using a PEG-modified sialic acid and an α 2,8-sialyltransferase. In FIG. 35AA, NESP expressed in a mammalian cell system is remodeled by the addition of terminal sialic acid residues. The sialic acid is added to the glycosyl residue using a sialic acid donor and an α2,8-sialyltransferase.

Figures 36B, 36C:
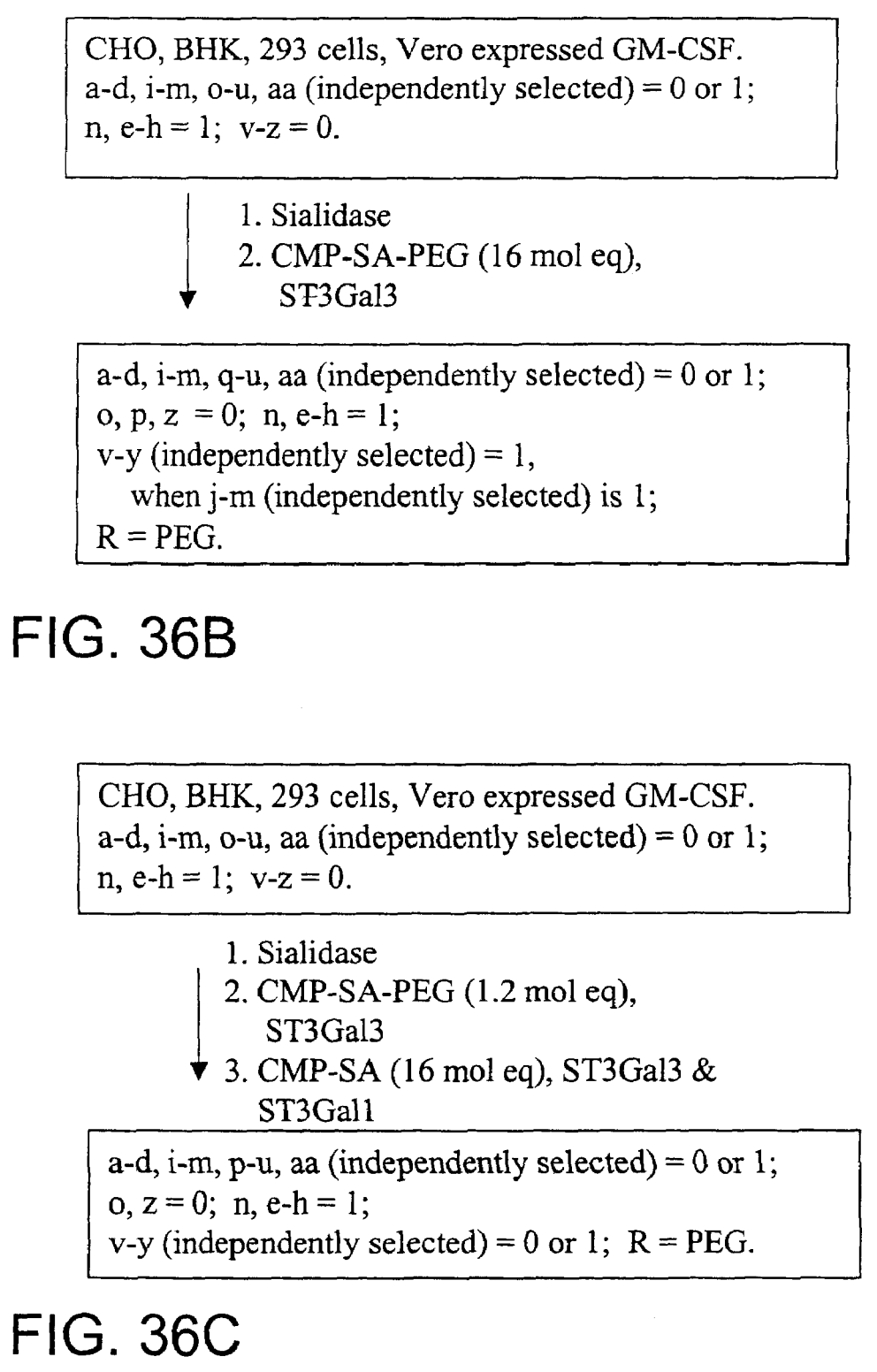
Figures 36I, 36J:
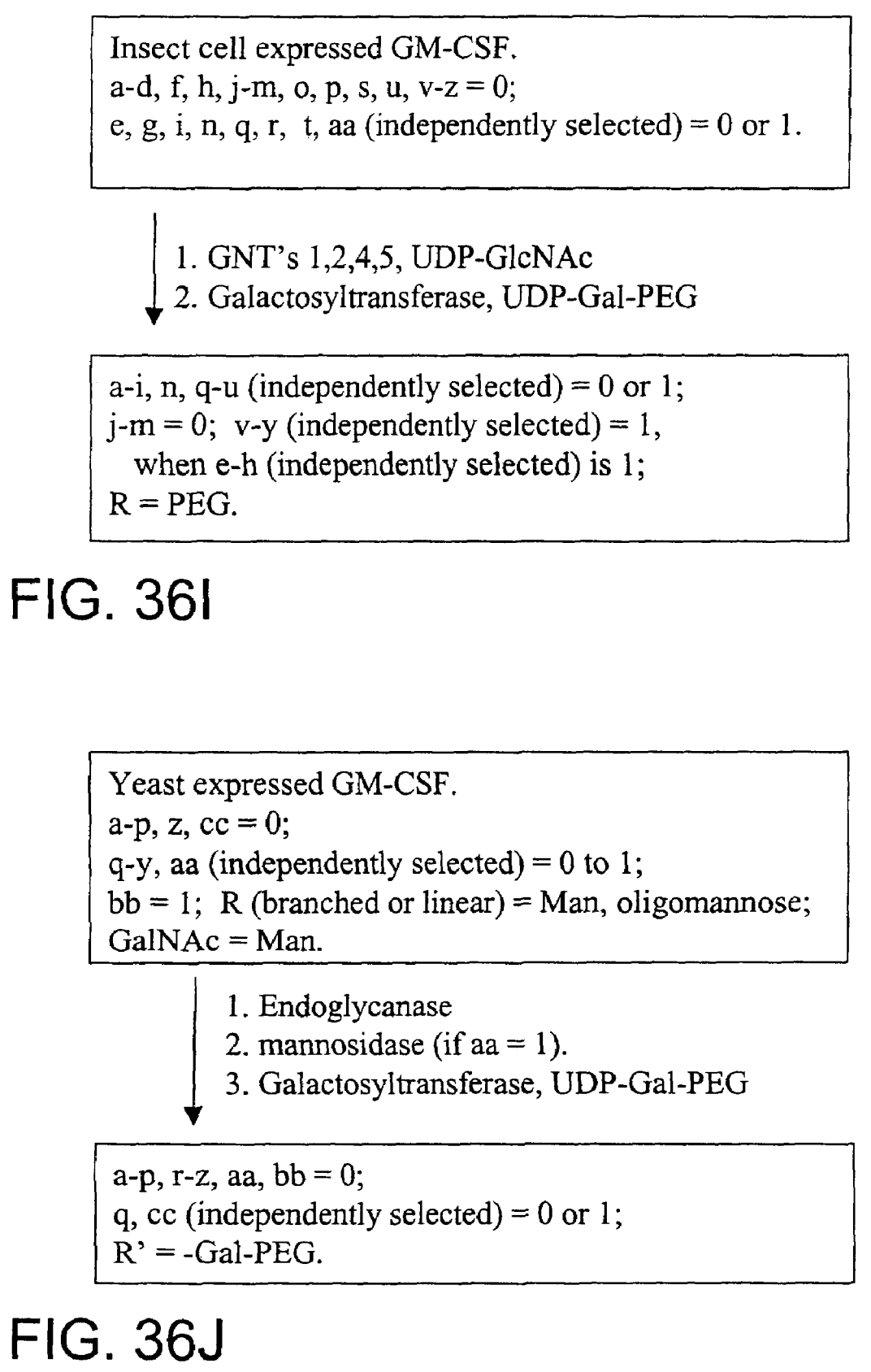

In another exemplary embodiment, the invention provides methods for modifying granulocyte-macrophage colony-stimulating factor (GM-CSF), as shown in FIGS. 36A to 36K. In FIG. 36B, GM-CSF expressed in mammalian cells is first treated with sialidase to trim back the sialic acid residues, and then PEGylated using ST3Gal3 and a donor of PEG-sialic acid. In FIG. 36C, GM-CSF expressed in mammalian cells is first treated with sialidase to trim back the sialic acid residues, then PEGylated using ST3Gal3 and a donor of PEG-sialic acid, and then is further sialylated using a sialic acid donor and ST3Gal1 and/or ST3Gal3. In FIG. 36D, GM-CSF expressed in NSO cells is first treated with sialidase and α-galactosidase to trim back the glycosyl groups, then sialylated using a sialic acid donor and ST3Gal3, and is then PEGylated using ST3Gal1 and a donor of PEG-sialic acid. In FIG. 36E, GM-CSF expressed in mammalian cells is first treated with sialidase to trim back sialic acid residues, then PEGylated using ST3Gal3 and a donor of PEG-sialic acid, and then is further sialylated using ST3Gal3 and a sialic acid donor. In FIG. 36F, GM-CSF expressed in mammalian cells is modified by capping appropriate terminal residues with a sialic acid donor that is modified with levulinic acid, adding a reactive ketone to the sialic acid donor. After addition to a glycosyl residue of the peptide, the ketone is derivatized with a moiety such as a hydrazine- or amine-PEG. In FIG. 36G, GM-CSF expressed in mammalian cells is sialylated using a sialic acid donor and α 2,8-sialyltransferase. In FIG. 36I, GM-CSF expressed in insect cells is modified by addition of N-acetylglucosamine using a suitable donor and one or more of GnT-I, II, IV, and V, followed by addition of PEGylated galactose using a suitable donor and a galactosyltransferase. In FIG. 36J, yeast expressed GM-CSF is first treated with endoglycanase and/or mannosidase to trim back the glycosyl units, and subsequently PEGylated using a galactosyltransferase and a donor of PEG-galactose. In FIG. 36K, GM-CSF expressed in mammalian cells is first treated with sialidase to trim back sialic acid residues, and is subsequently sialylated using ST3Gal3 and a sialic acid donor. The polypeptide is then contacted with ST3Gal1 and two reactive sialic acid residues connected via a linker, so that the polypeptide is attached to one reactive sialic acid via the linker and second sialic acid residue. The polypeptide is further contacted with ST3Gal3 and transferrin, and thus becomes connected with transferrin.

Figures 37B, 37C:
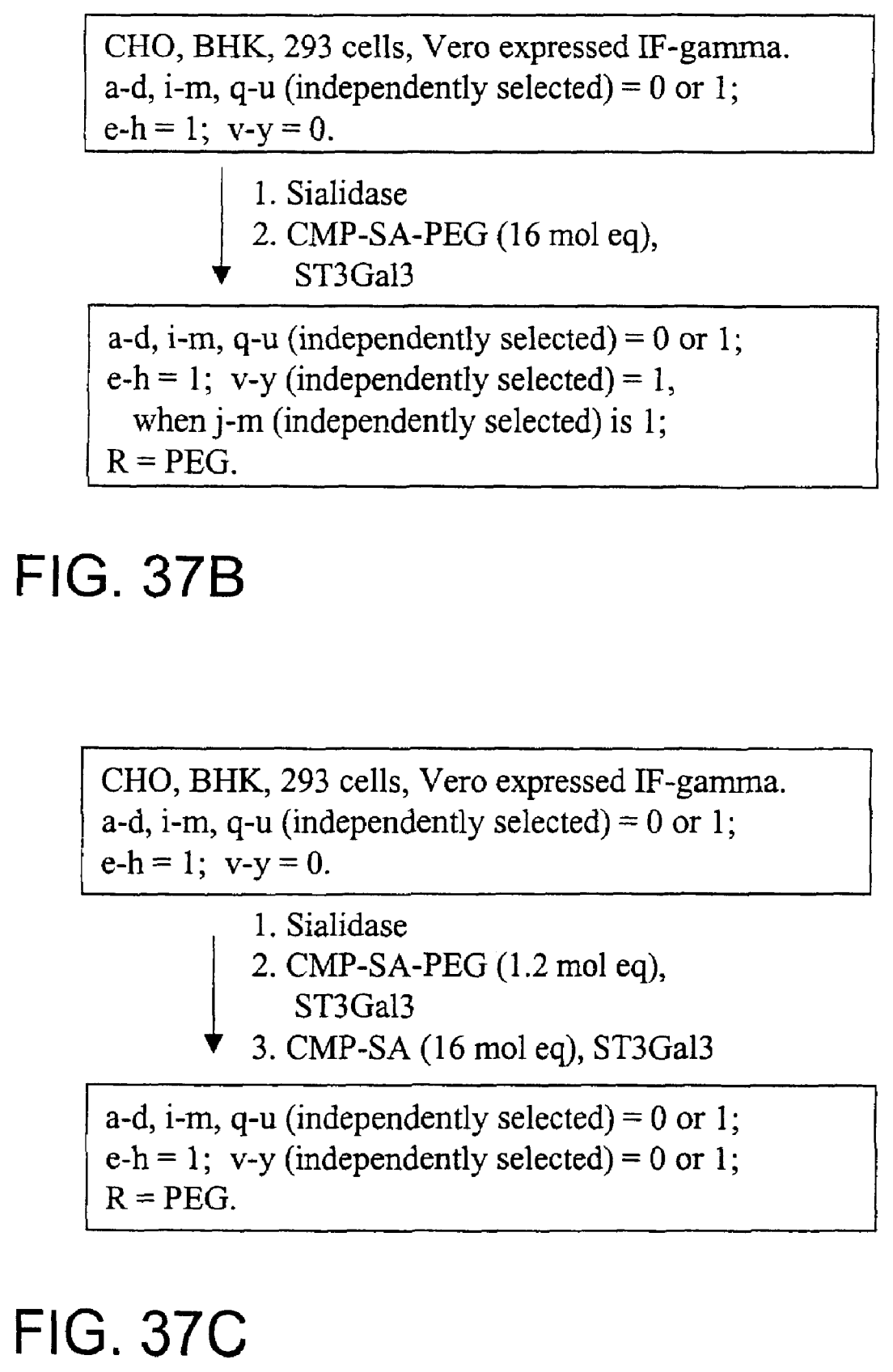
Figures 37I, 37J:
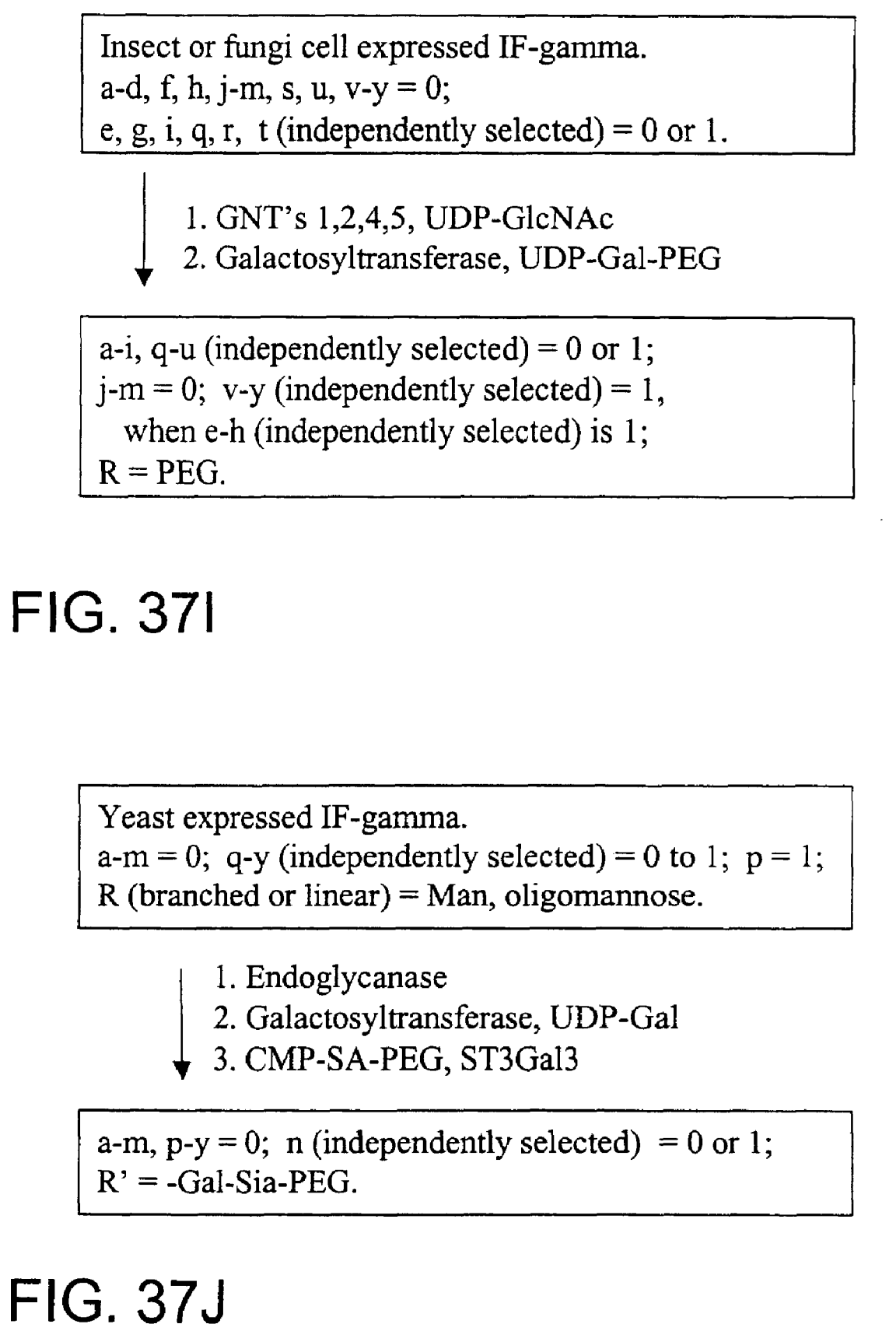
Figures 38B, 38C:
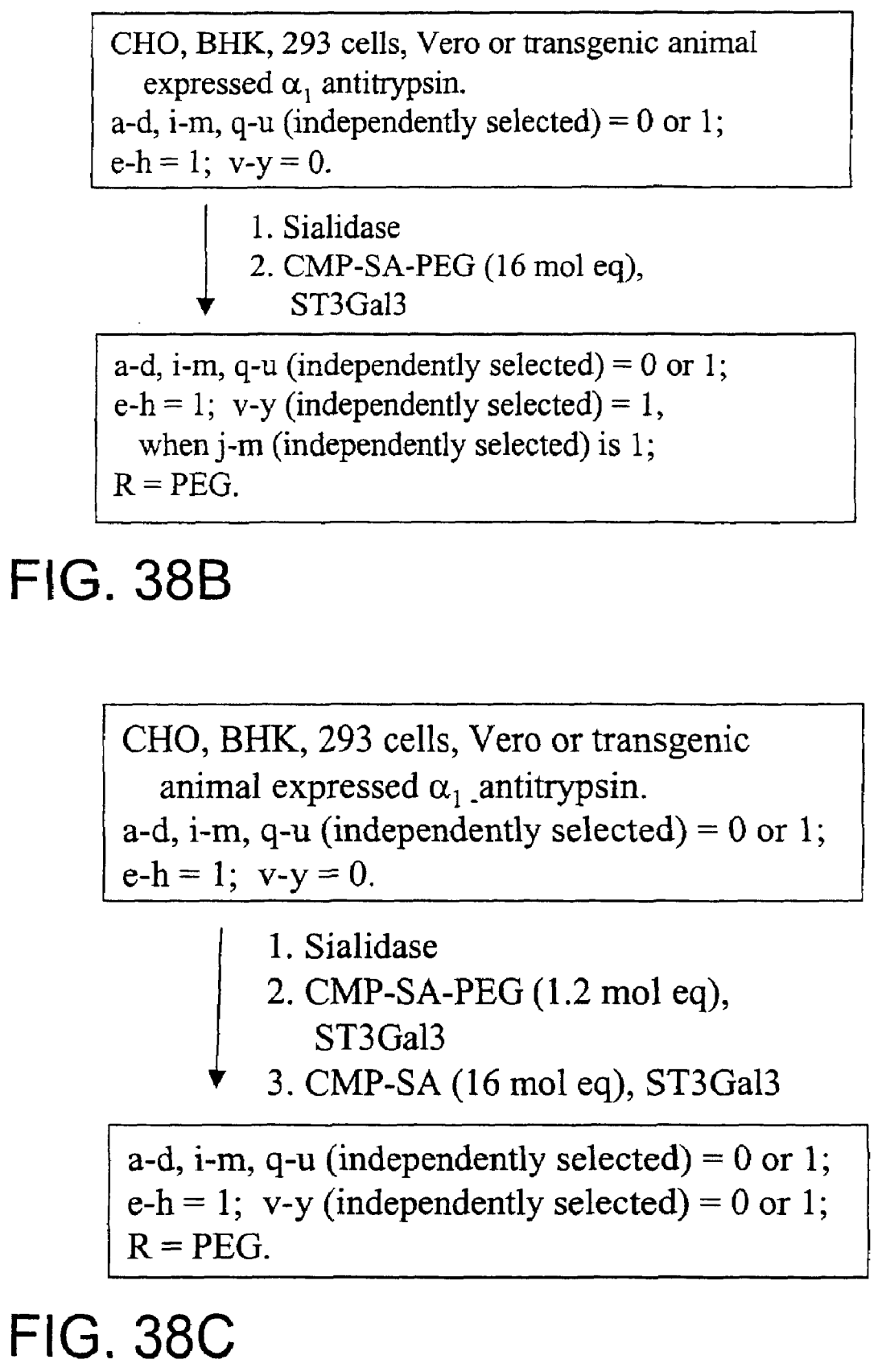
Figures 38H, 38I:
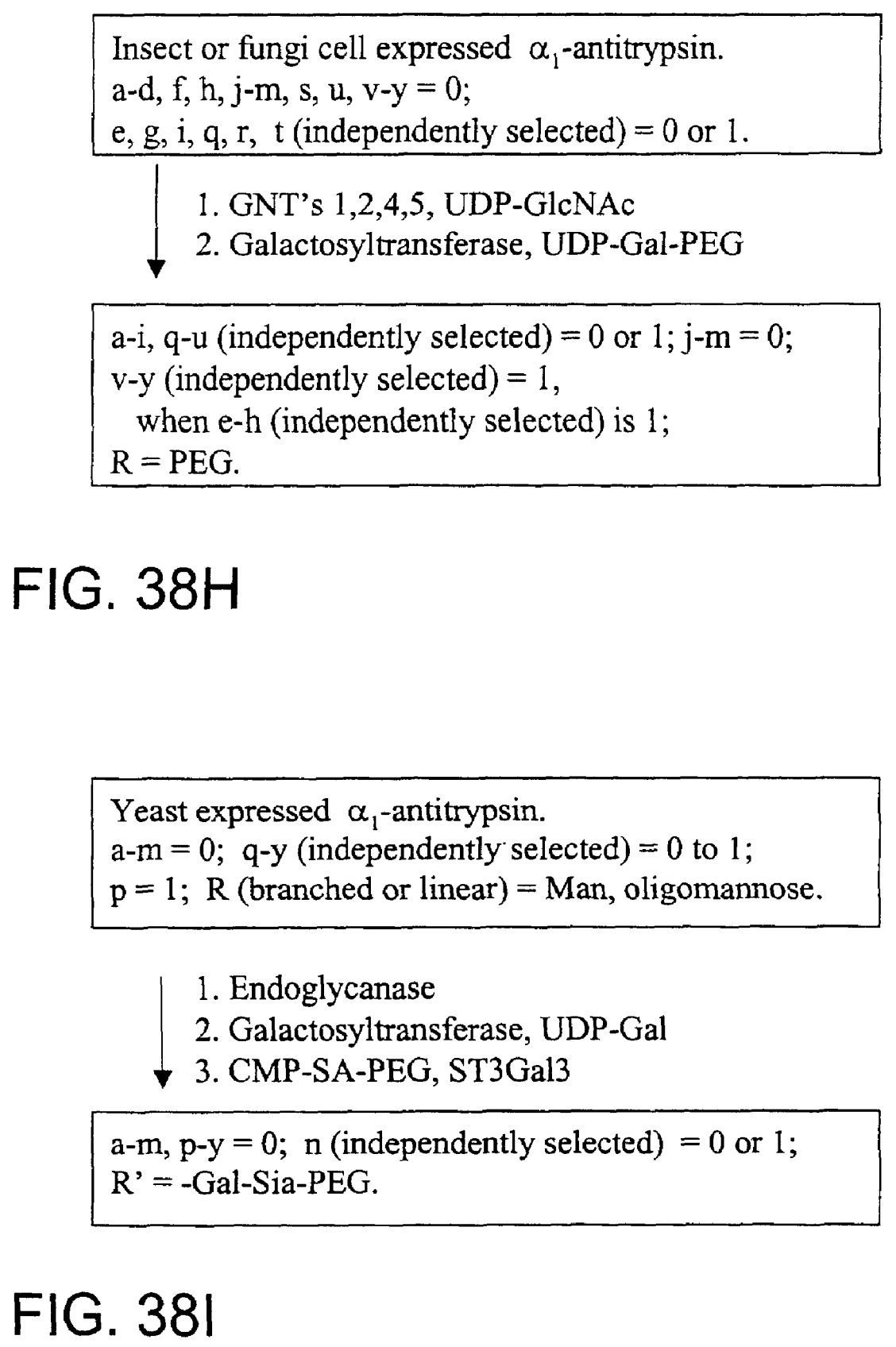
Figures 38L, 38M:
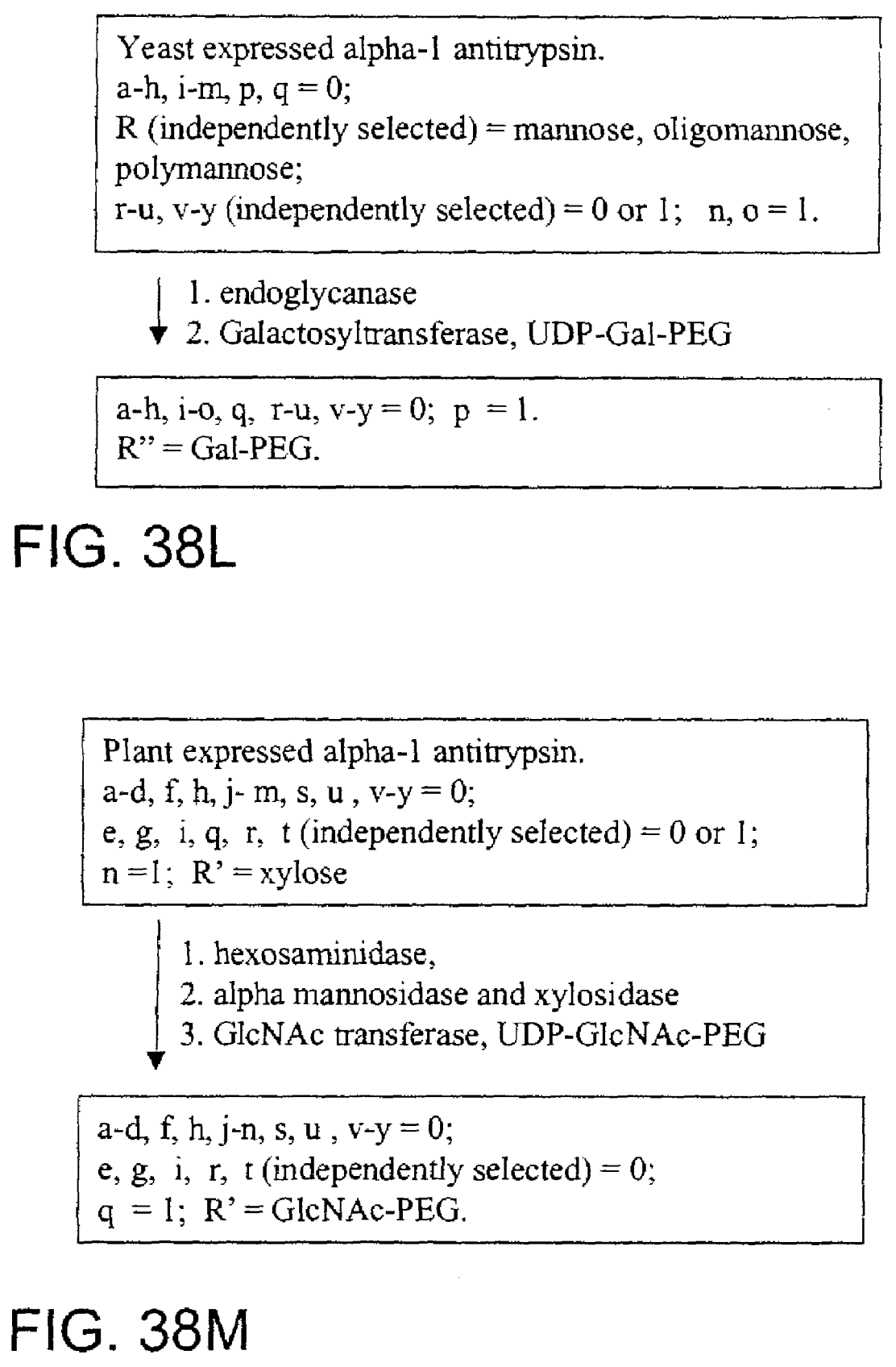

In another exemplary embodiment, the invention provides methods for modification of Interferon gamma (IFNγ). FIGS. 37A to 37N contain some examples. In FIG. 37B, IFNγ expressed in a variety of mammalian cells is first treated with sialidase to trim back terminal sialic acid residues, and is subsequently PEGylated using ST3Gal3 and a donor of PEG-sialic acid. In FIG. 37C, IFNγ expressed in a mammalian system is first treated with sialidase to trim back terminal sialic acid residues. The polypeptide is then PEGylated using ST3Gal3 and a donor of PEG-sialic acid, and is further sialylated with ST3Gal3 and a donor of sialic acid. In FIG. 37D, mammalian cell expressed IFNγ is first treated with sialidase and α-galactosidase to trim back sialic acid and galactose residues. The polypeptide is then galactosylated using a galactose donor and a galactosyltransferase. Then, IFNγ is PEGylated using a donor of PEG-sialic acid and ST3Gal3. In FIG. 37E, IFNγ that is expressed in a mammalian system is first treated with sialidase to trim back terminal sialic acid residues. The polypeptide is then PEGylated using ST3Gal3 and a donor of PEG-sialic acid, and is further sialylated with ST3Gal3 and a sialic acid donor. FIG. 37F describes another method for modifying IFNγ expressed in a mammalian system. The protein is modified by capping appropriate terminal residues with a sialic acid donor that is modified with levulinic acid, adding a reactive ketone to the sialic acid donor. After addition to a glycosyl residue of the peptide, the ketone is derivatized with a moiety such as a hydrazine- or amine-PEG. In FIG. 37G, IFNγ expressed in mammalian cells is remodeled by addition of sialic acid using a sialic acid donor and an α 2,8-sialyltransferase. In FIG. 37I, IFNγ expressed in insect or fungal cells is modified by addition of N-acetylglucosamine using an appropriate donor and one or more of GnT-I, II, IV, and V. The protein is further modified by addition of PEG moieties using a donor of PEGylated galactose and a galactosyltransferase. FIG. 37J offers a method for modifying IFNγ expressed in yeast. The polypeptide is first treated with endoglycanase to trim back the saccharide chains, and then galactosylated using a galactose donor and a galactosyltransferase. Then, IFNγ is PEGylated using a donor of PEGylated sialic acid and ST3Gal3. In FIG. 37K, IFNγ produced by mammalian cells is modified as follows: the polypeptide is first contacted with ST3Gal3 and a donor of sialic acid that is derivatized with a reactive galactose via a linker, so that the polypeptide is attached to the reactive galactose via the linker and sialic acid residue. The polypeptide is then contacted with a galactosyltransferase and transferrin pre-treated with endoglycanase, and thus becomes connected with transferrin via the galactose residue. In the scheme illustrated by FIG. 37L, IFNγ, which is expressed in a mammalian system, is modified via the action of ST3Gal3: PEGylated sialic acid is transferred from a suitable donor to IFNγ. FIG. 37M is an example of modifying IFNγ expressed in insect or fungal cells, where PEGylation of the polypeptide is achieved by transferring PEGylated N-acetylglucosamine from a donor to IFNγ using GnT-I and/or II. In FIG. 37N, IFNγ expressed in a mammalian system is remodeled with addition of PEGylated sialic acid using a suitable donor and an α 2,8-sialyltransferase. In another exemplary embodiment, the invention provides methods for modifying $\alpha_1$ anti-trypsin (α1-protease inhibitor). Some such examples can be found in FIGS. 38A to 38N. In FIG. 38B, $\alpha_1$ anti-trypsin expressed in a variety of mammalian cells is first treated with sialidase to trim back sialic acid residues. PEGylated sialic acid residues are then added using an appropriate donor, such as CMP-SA-PEG, and a sialyltransferase, such as ST3Gal3. FIG. 38C demonstrates another scheme of $\alpha_1$ anti-trypsin modification. $\alpha_1$ anti-trypsin expressed in a mammalian system is first treated with sialidase to trim back sialic acid residues. Sialic acid residues derivatized with PEG are then added using an appropriate donor and a sialyltransferase, such as ST3Gal3. Subsequently, the molecule is further modified by the addition of sialic acid residues using a sialic acid donor and ST3Gal3. Optionally, mammalian cell expressed $\alpha_1$ anti-trypsin is first treated with sialidase and α-galactosidase to trim back terminal sialic acid and α-linkage galactose residues. The polypeptide is then galactosylated using galactosyltransferase and a suitable galactose donor. Further, sialic acid derivatized with PEG is added by the action of ST3Gal3 using a PEGylated sialic acid donor. In FIG. 38D, $\alpha_1$ anti-trypsin expressed in a mammalian system first has the terminal sialic acid residues trimmed back using sialidase. PEG is then added to N-linked glycosyl residues via the action of ST3Gal3, which mediates the transfer of PEGylated sialic acid from a donor, such as CMP-SA-PEG, to $\alpha_1$ anti-trypsin. More sialic acid residues are subsequently attached using a sialic acid donor and ST3Gal3. FIG. 38E illustrates another process through which $\alpha_1$ anti-trypsin is remodeled. $\alpha_1$ anti-trypsin expressed in mammalian cells is modified by capping appropriate terminal residues with a sialic acid donor that is modified with levulinic acid, adding a reactive ketone to the sialic acid donor. After addition to a glycosyl residue of the peptide, the ketone is derivatized with a moiety such as a hydrazine- or amine-PEG. In FIG. 38F, yet another method of $\alpha_1$ anti-trypsin modification is disclosed. $\alpha_1$ anti-trypsin obtained from a mammalian expression system is remodeled with addition of sialic acid using a sialic acid donor and an α 2,8-sialyltransferase. In FIG. 38H, $\alpha_1$ anti-trypsin is expressed in insect or yeast cells, and remodeled by the addition of terminal N-acetylglucosamine residues by way of contacting the polypeptide with UDP-N-acetylglucosamine and one or more of GnT-I, II, IV, or V. Then, the polypeptide is modified with PEG moieties using a donor of PEGylated galactose and a galactosyltransferase. In FIG. 38I, $\alpha_1$ anti-trypsin expressed in yeast cells is treated first with endoglycanase to trim back glycosyl chains. It is then galactosylated with a galactosyltransferase and a galactose donor. Then, the polypeptide is PEGylated using ST3Gal3 and a donor of PEG-sialic acid. In FIG. 38J, $\alpha_1$ anti-trypsin is expressed in a mammalian system. The polypeptide is first contacted with ST3Gal3 and a donor of sialic acid that is derivatized with a reactive galactose via a linker, so that the polypeptide is attached to the reactive galactose via the linker and sialic acid residue. The polypeptide is then contacted with a galactosyltransferase and transferrin pre-treated with endoglycanase, and thus becomes connected with transferrin via the galactose residue. In FIG. 38L, $\alpha_1$ anti-trypsin expressed in yeast is first treated with endoglycanase to trim back its glycosyl groups. The protein is then PEGylated using a galactosyltransferase and a donor of galactose with a PEG moiety. In FIG. 38M, $\alpha_1$ anti-trypsin expressed in plant cells is treated with hexosaminidase, mannosidase, and xylosidase to trim back its glycosyl chains, and subsequently modified with N-acetylglucosamine derivatized with a PEG moiety, using N-acetylglucosamine transferase and a suitable donor. In FIG. 38N, $\alpha_1$ anti-trypsin expressed in mammalian cells is modified by adding PEGylated sialic acid residues using ST3Gal3 and a donor of sialic acid derivatized with PEG.

Figures 39B, 39C:
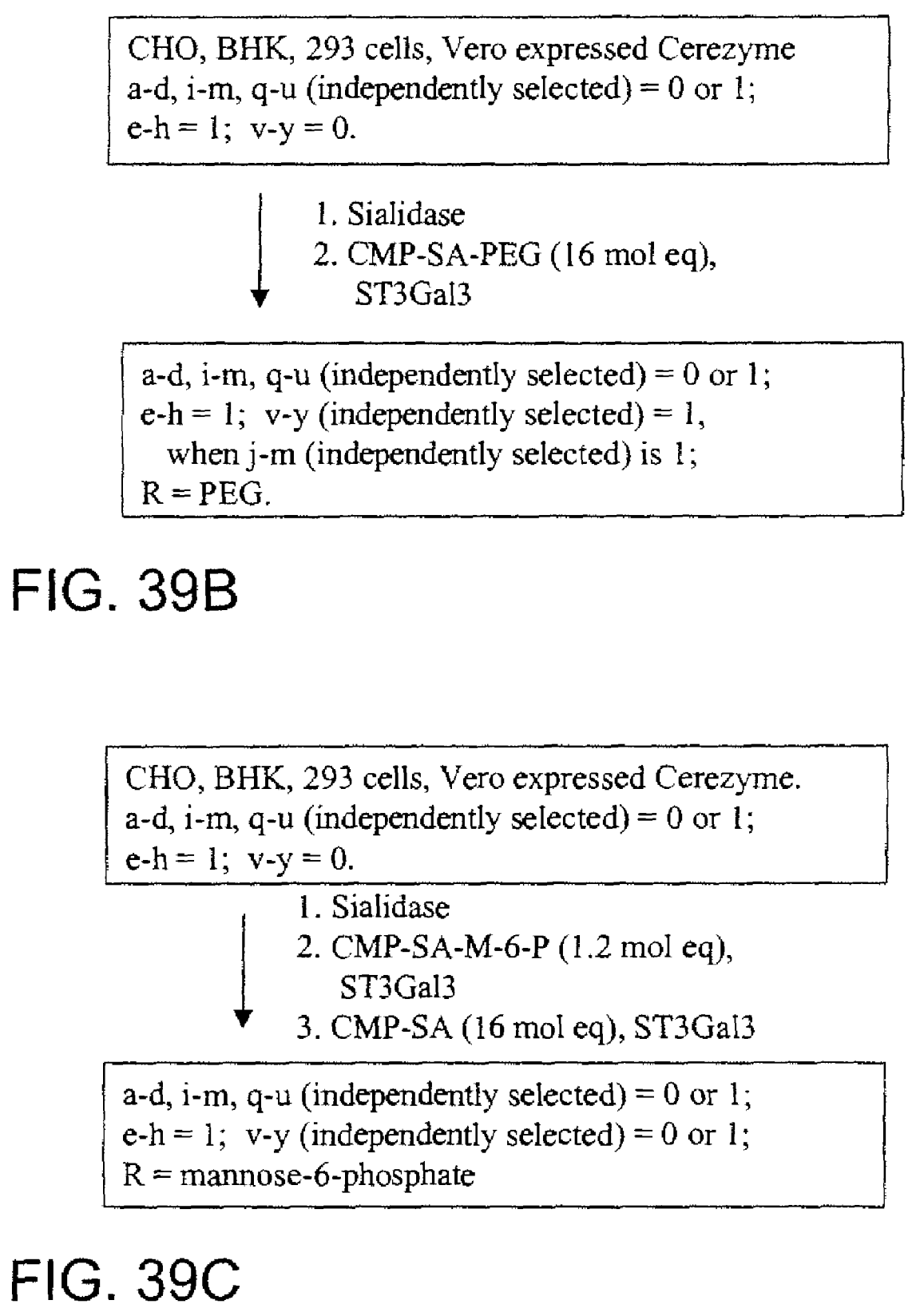
Figures 39H, 39I:
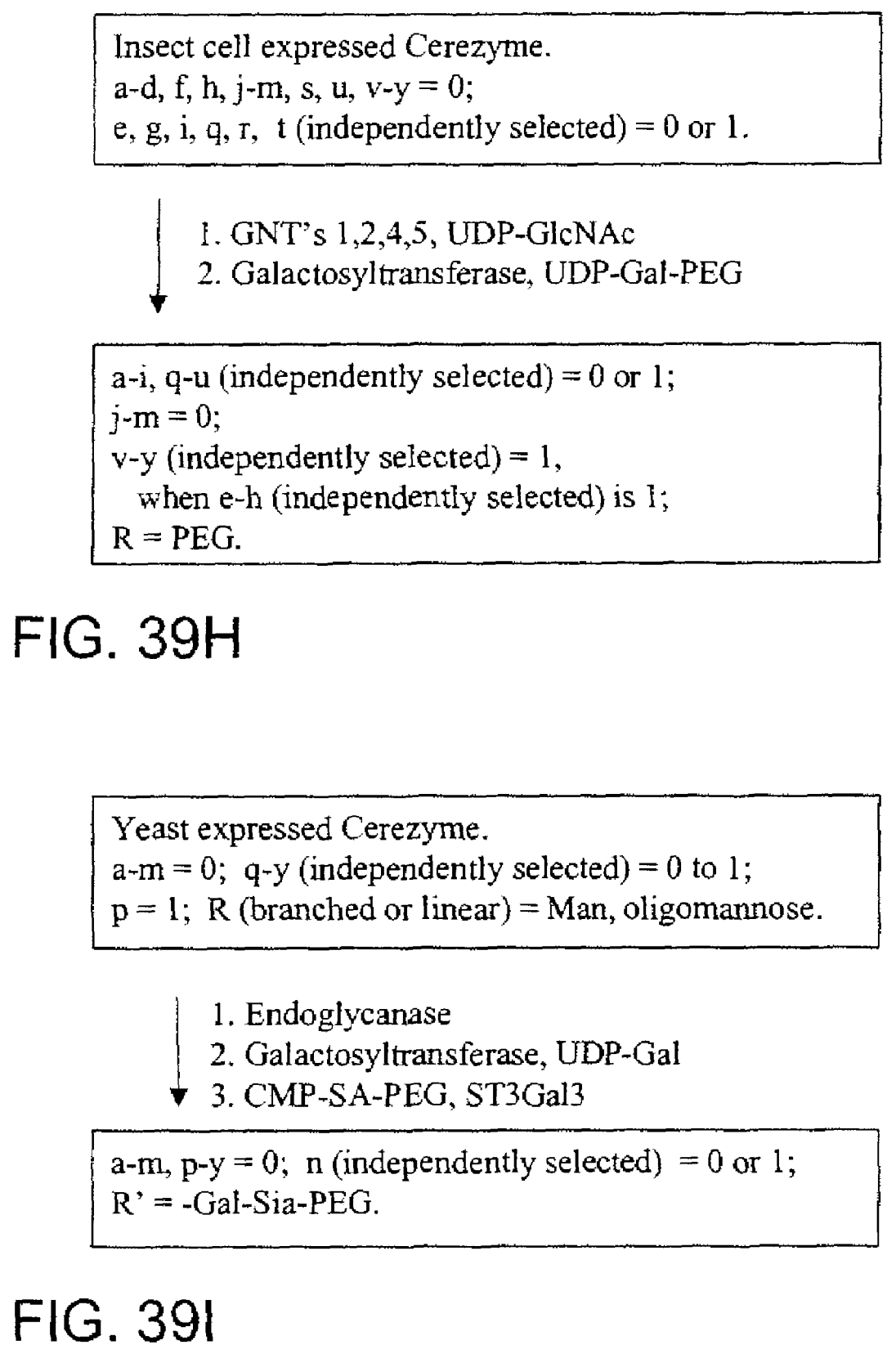

In another exemplary embodiment, the invention provides methods for modifying glucocerebrosidase (β-glucosidase, Cerezyme™ or Ceredase™), as shown in FIGS. 39A to 39K. In FIG. 39B, Cerezyme™ expressed in a mammalian system is first treated with sialidase to trim back terminal sialic acid residues, and is then PEGylated using ST3Gal3 and a donor of PEG-sialic acid. In FIG. 39C, Cerezyme™ expressed in mammalian cells is first treated with sialidase to trim back the sialic acid residues, then has mannose-6-phosphate group attached using ST3Gal3 and a reactive sialic acid derivatized with mannose-6-phosphate, and then is sialylated using ST3Gal3 and a sialic acid donor. Optionally, NSO cell expressed Cerezyme™ is first treated with sialidase and galactosidase to trim back the glycosyl groups, and is then galactosylated using a galactose donor and an α-galactosyltransferase. Then, mannose-6-phosphate moiety is added to the molecule using ST3Gal3 and a reactive sialic acid derivatized with mannose-6-phosphate. In FIG. 39D, Cerezyme™ expressed in mammalian cells is first treated with sialidase to trim back the sialic acid residues, it is then PEGylated using ST3Gal3 and a donor of PEG-sialic acid, and is then sialylated using ST3Gal3 and a sialic acid donor. In FIG. 39E, Cerezyme™ expressed in mammalian cells is modified by capping appropriate terminal residues with a sialic acid donor that is modified with levulinic acid, adding a reactive ketone to the sialic acid donor. After addition to a glycosyl residue of the peptide, the ketone is derivatized with a moiety such as one or more mannose-6-phosphate groups. In FIG. 39F, Cerezyme™ expressed in mammalian cells is sialylated using a sialic acid donor and a 2,8-sialyltransferase. In FIG. 39H, Cerezyme™ expressed in insect cells first has N-acetylglucosamine added using a suitable donor and one or more of GnT-I, II, IV, and V, and then is PEGylated using a galactosyltransferase and a donor of PEG-galactose. In FIG. 39I, Cerezyme™ expressed in yeast is first treated with endoglycanase to trim back the glycosyl groups, then galactosylated using a galactose donor and a galactosyltransferase, and then PEGylated using ST3Gal3 and a donor of PEG-sialic acid. In FIG. 39JK, Cerezyme™ expressed in mammalian cells is first contacted with ST3Gal3 and two reactive sialic acid residues connected via a linker, so that the polypeptide is attached to one reactive sialic acid via the linker and the second sialic acid residue. The polypeptide is then contacted with ST3Gal3 and desialylated transferrin, and thus becomes connected with transferrin. Then, the polypeptide is sialylated using a sialic acid donor and ST3Gal3.

Figures 40I, 40J:
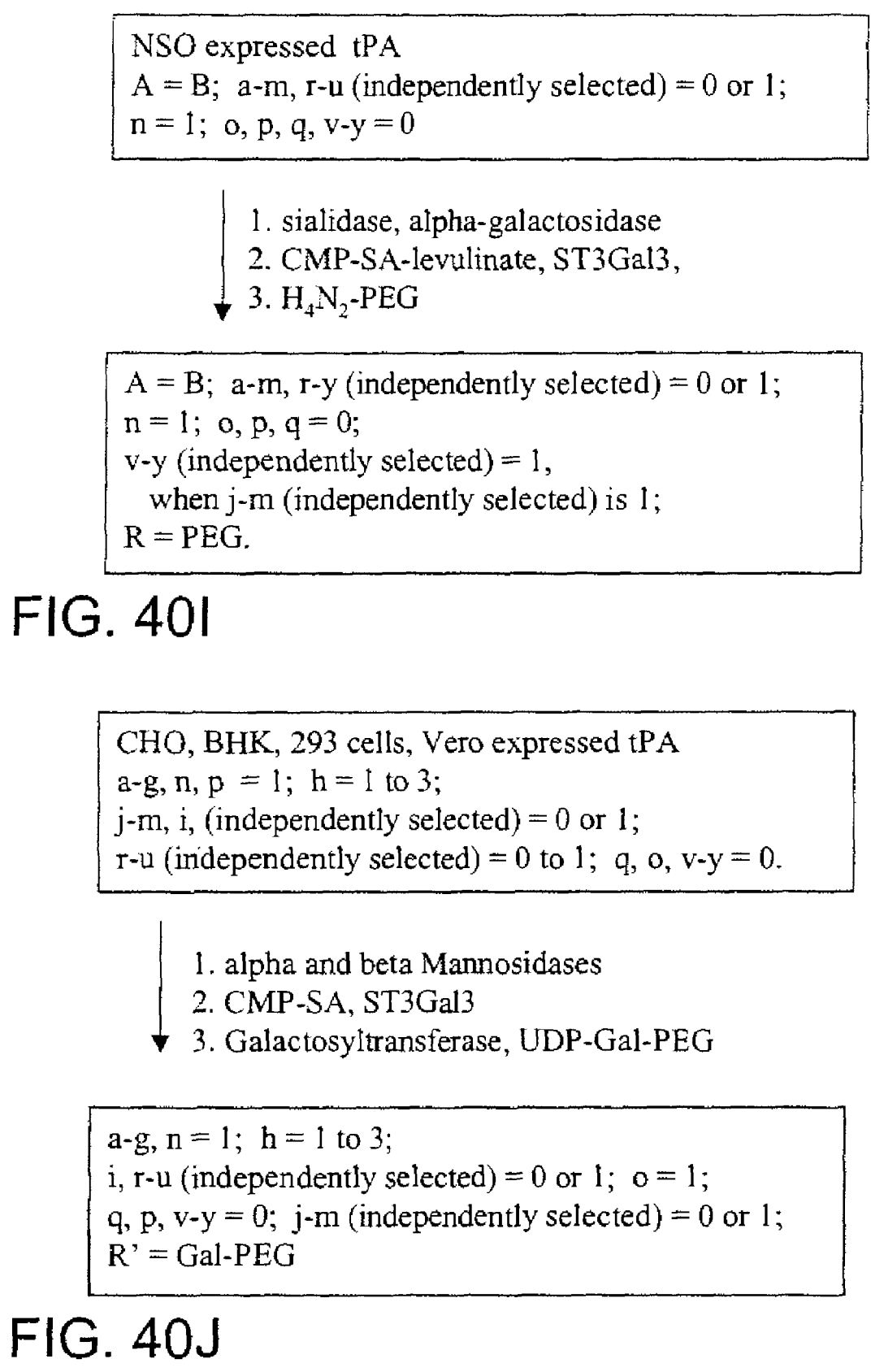
Figures 40M, 40N:
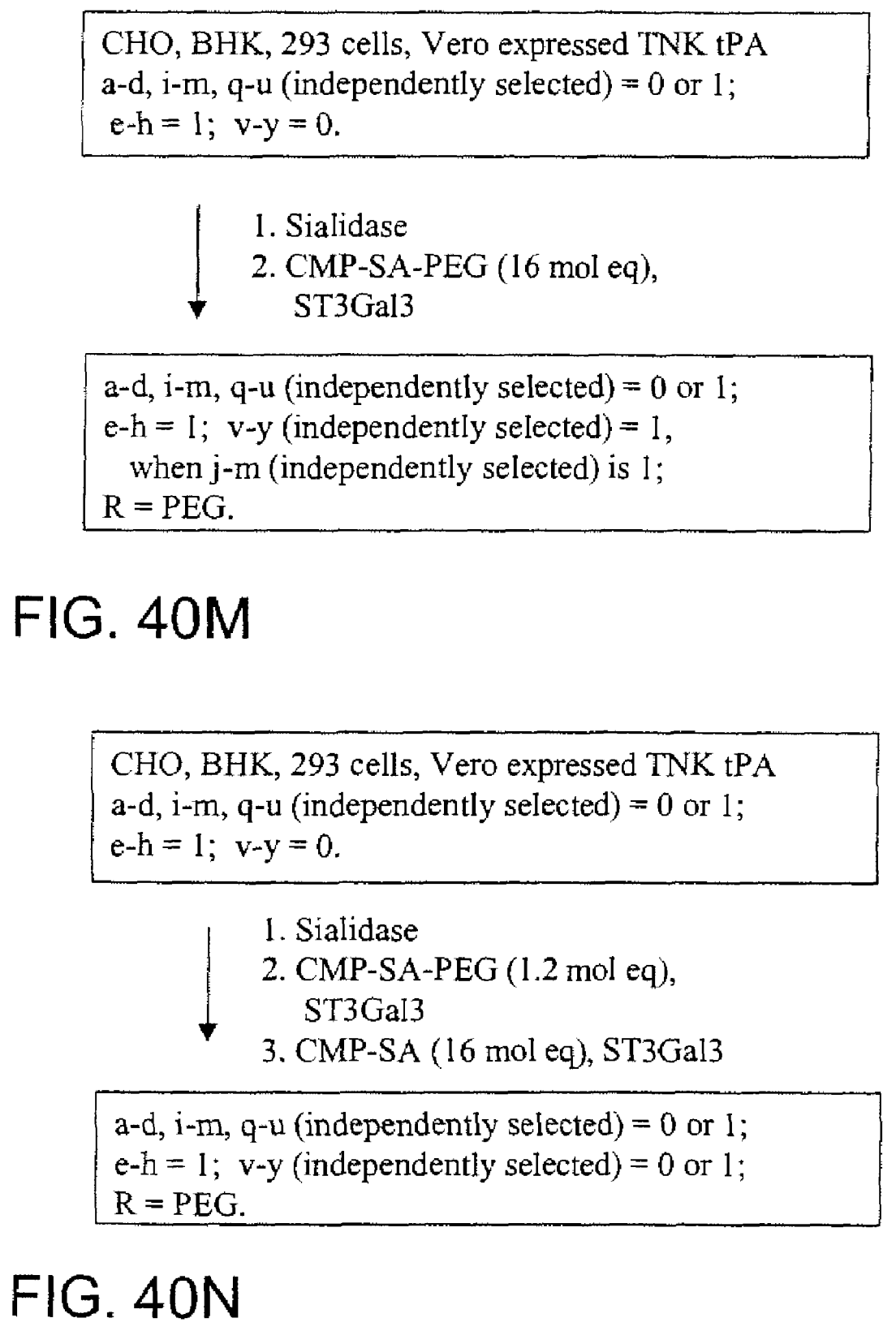
Figures 40Q, 40R:
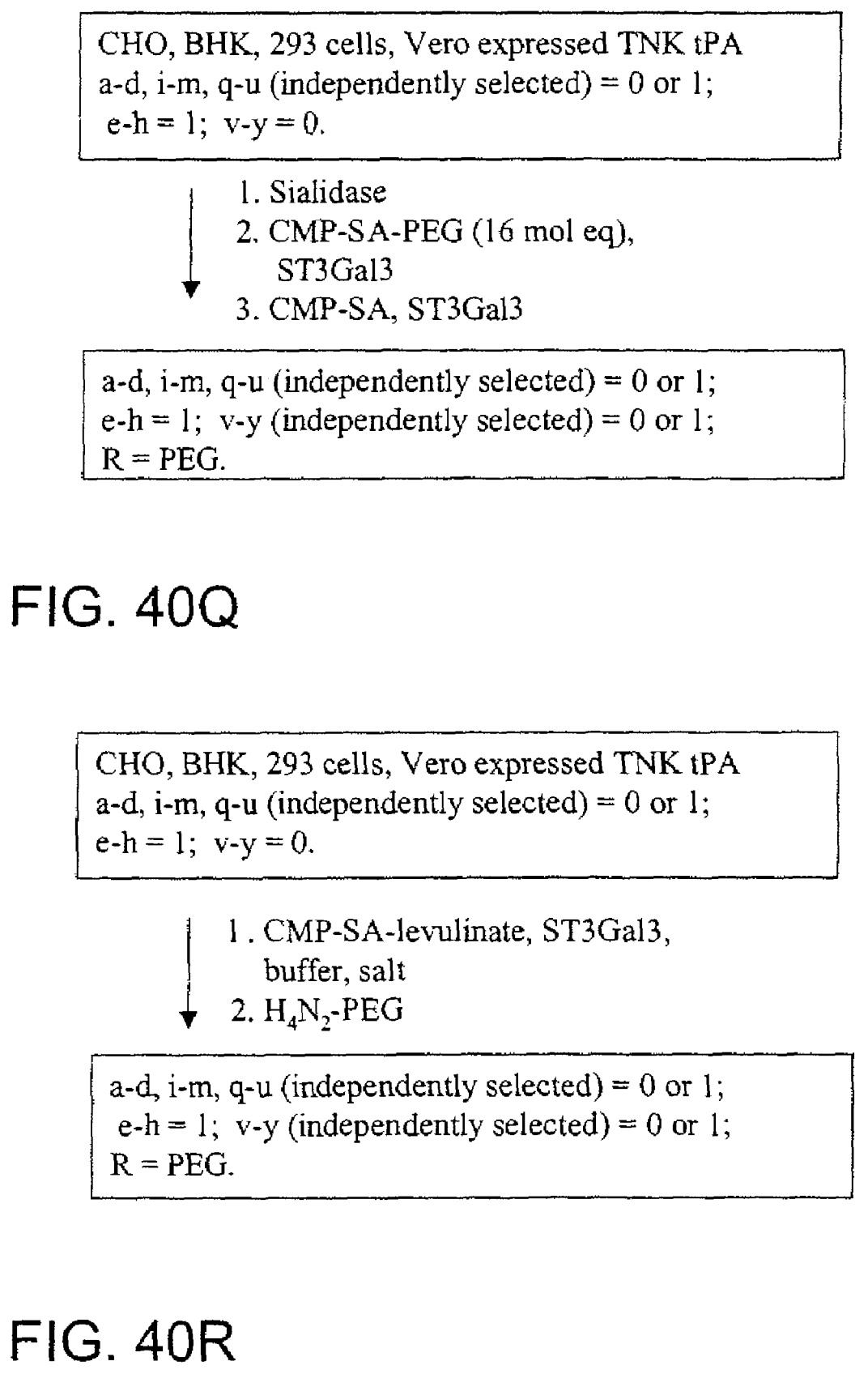
Figures 40U, 40V:
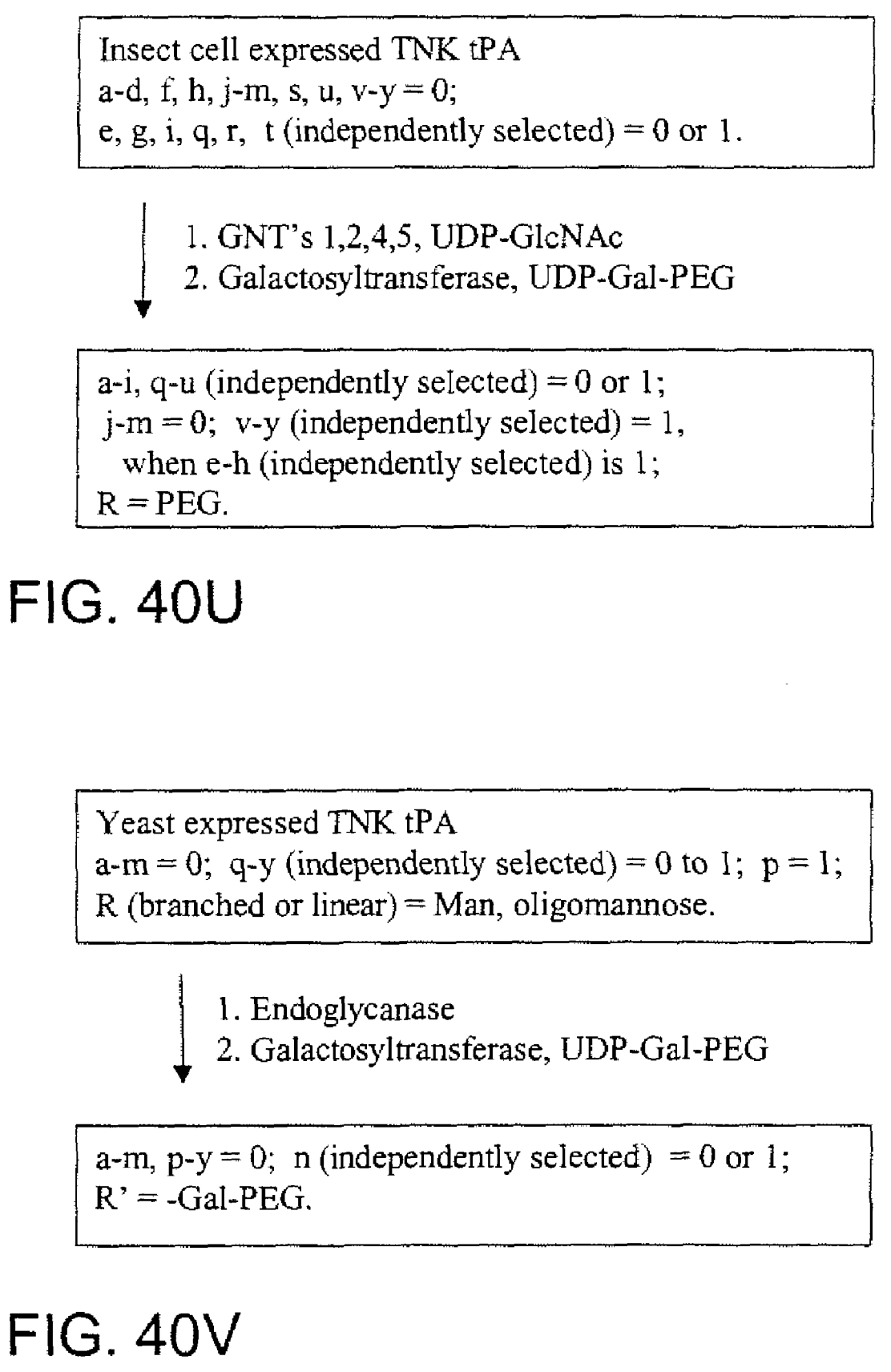

In another exemplary embodiment, the invention provides methods for modifying Tissue-Type Plasminogen Activator (TPA) and its mutant. Several specific modification schemes are presented in FIGS. 40A to 40W. FIG. 40B illustrates one modification procedure: after TPA is expressed by mammalian cells, it is treated with one or more of mannosidase(s) and sialidase to trim back mannosyl and/or sialic acid residues. Terminal N-acetylglucosamine is then added by contacting the polypeptide with a suitable donor of N-acetylglucosamine and one or more of GnT-I, II, IV, and V. TPA is further galactosylated using a galactose donor and a galactosyltransferase. Then, PEG is attached to the molecule by way of sialylation catalyzed by ST3Gal3 and using a donor of sialic acid derivatized with a PEG moiety. In FIG. 40C, TPA is expressed in insect or fungal cells. The modification includes the steps of addition of N-acetylglucosamine using an appropriate donor of N-acetylglucosamine and GnT-I and/or II; galactosylation using a galactose donor and a galactosyltransferase; and attachment of PEG by way of sialylation using ST3Gal3 and a donor of sialic acid derivatized with PEG. In FIG. 40D, TPA is expressed in yeast and subsequently treated with endoglycanase to trim back the saccharide chains. The polypeptide is further PEGylated via the action of a galactosyltransferase, which catalyzes the transfer of a PEG-galactose from a donor to TPA. In FIG. 40E, TPA is expressed in insect or yeast cells. The polypeptide is then treated with α- and β-mannosidases to trim back terminal mannosyl residues. Further, PEG moieties are attached to the molecule via transfer of PEG-galactose from a suitable donor to TPA, which is mediated by a galactosyltransferase. FIG. 40F provides a different method for modification of TPA obtained from an insect or yeast system: the polypeptide is remodeled by addition of N-acetylglucosamine using a donor of N-acetylglucosamine and GnT-I and/or II, followed by PEGylation using a galactosyltransferase and a donor of PEGylated galactose. FIG. 40G offers another scheme for remodeling TPA expressed in insect or yeast cells. Terminal N-acetylglucosamine is added using a donor of N-acetylglucosamine and GnT-I and/or II. A galactosidase that is modified to operate in a synthetic, rather than a hydrolytic manner, is utilized to add PEGylated galactose from a proper donor to the N-acetylglucosamine residues. In FIG. 40I, TPA expressed in a mammalian system is first treated with sialidase and galactosidase to trim back sialic acid and galactose residues. The polypeptide is further modified by capping appropriate terminal residues with a sialic acid donor that is modified with levulinic acid, adding a reactive ketone to the sialic acid donor. After addition to a glycosyl residue of the peptide, the ketone is derivatized with a moiety such as a hydrazine- or amine-PEG. In FIG. 40J, TPA, which is expressed in a mammalian system, is remodeled following this scheme: first, the polypeptide is treated with α- and β-mannosidases to trim back the terminal mannosyl residues; sialic acid residues are then attached to terminal galactosyl residues using a sialic acid donor and ST3Gal3; further, TPA is PEGylated via the transfer of PEGylated galactose from a donor to a N-acetylglucosaminyl residue catalyzed by a galactosyltransferase. In FIG. 40K, TPA is expressed in a plant system. The modification procedure in this example is as follows: TPA is first treated with hexosaminidase, mannosidase, and xylosidase to trim back its glycosyl groups; PEGylated N-acetylglucosamine is then added to TPA using a proper donor and N-acetylglucosamine transferase. In FIG. 40M, a TPA mutant (TNK TPA), expressed in mammalian cells, is remodeled. Terminal sialic acid residues are first trimmed back using sialidase; ST3Gal3 is then used to transfer PEGylated sialic acid from a donor to TNK TPA, such that the polypeptide is PEGylated. In FIG. 40N, TNK TPA expressed in a mammalian system is first treated with sialidase to trim back terminal sialic acid residues. The protein is then PEGylated using CMP-SA-PEG as a donor and ST3Gal3, and further sialylated using a sialic acid donor and ST3Gal3. In FIG. 40O, NSO cell expressed TNK TPA is first treated with sialidase and α-galactosidase to trim back terminal sialic acid and galactose residues. TNK TPA is then galactosylated using a galactose donor and a galactosyltransferase. The last step in this remodeling scheme is transfer of sialic acid derivatized with PEG moiety from a donor to TNK TPA using a sialyltransferase such as ST3Gal3. In FIG. 40Q, TNK TPA is expressed in a mammalian system and is first treated with sialidase to trim back terminal sialic acid residues. The protein is then PEGylated using ST3Gal3 and a donor of PEGylated sialic acid. Then, the protein is sialylated using a sialic acid donor and ST3Gal3. In FIG. 40R, TNK TPA expressed in a mammalian system is modified by capping appropriate terminal residues with a sialic acid donor that is modified with levulinic acid, adding a reactive ketone to the sialic acid donor. After addition to a glycosyl residue of the peptide, the ketone is derivatized with a moiety such as a hydrazine- or amine-PEG. In FIG. 40S, TNK TPA expressed in mammalian cells is modified via a different method: the polypeptide is remodeled with addition of sialic acid using a sialic acid donor and a 2,8-sialyltransferase. In FIG. 40U, TNK TPA expressed in insect cells is remodeled by addition of N-acetylglucosamine using an appropriate donor and one or more of GnT-I, II, IV, and V. The protein is further modified by addition of PEG moieties using a donor of PEGylated galactose and a galactosyltransferase. In FIG. 40V, TNK TPA is expressed in yeast. The polypeptide is first treated with endoglycanase to trim back its glycosyl chains and then PEGylated using a galactose donor derivatized with PEG and a galactosyltransferase. In FIG. 40W, TNK TPA is produced in a mammalian system. The polypeptide is first contacted with ST3Gal3 and a donor of sialic acid that is derivatized with a reactive galactose via a linker, so that the polypeptide is attached to the reactive galactose via the linker and sialic acid residue. The polypeptide is then contacted with a galactosyltransferase and anti-TNF IG chimera produced in CHO, and thus becomes connected with the chimera via the galactose residue.

Figure 41A:
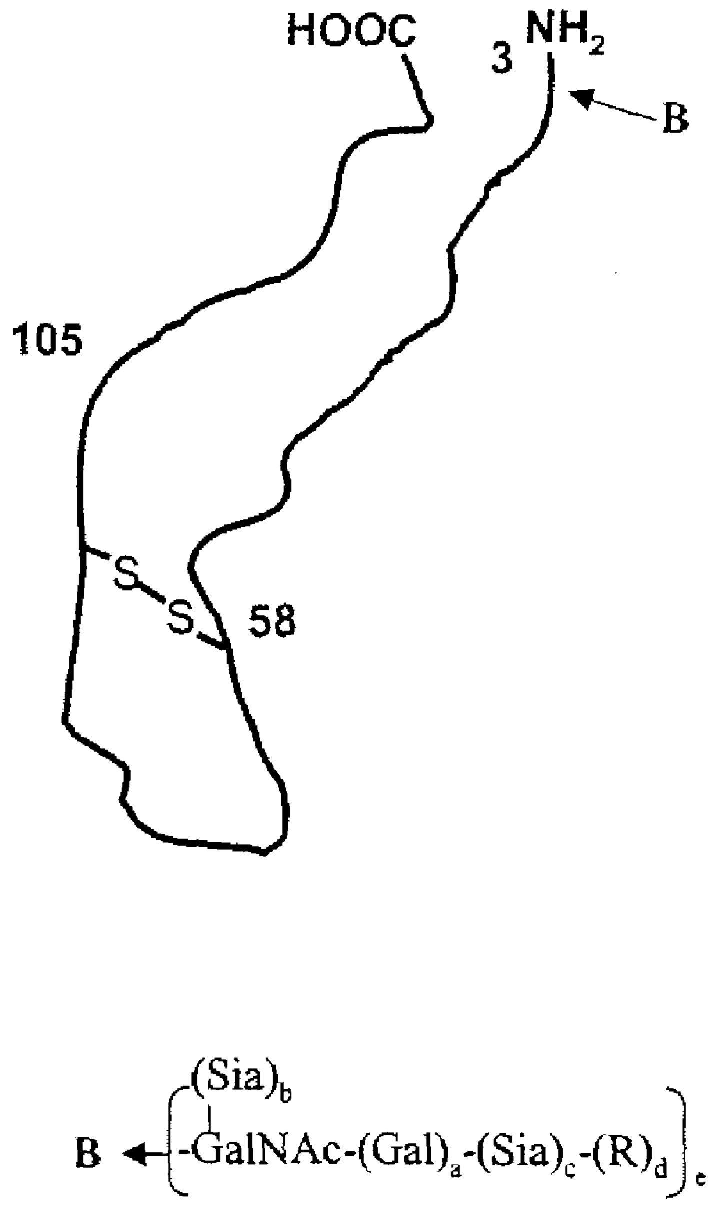
FIG. 41A is a diagram depicting the Interleukin-2 peptide indicating the amino acid residue to which a glycan is linked, and an exemplary glycan formula linked thereto.
Figure 41B:
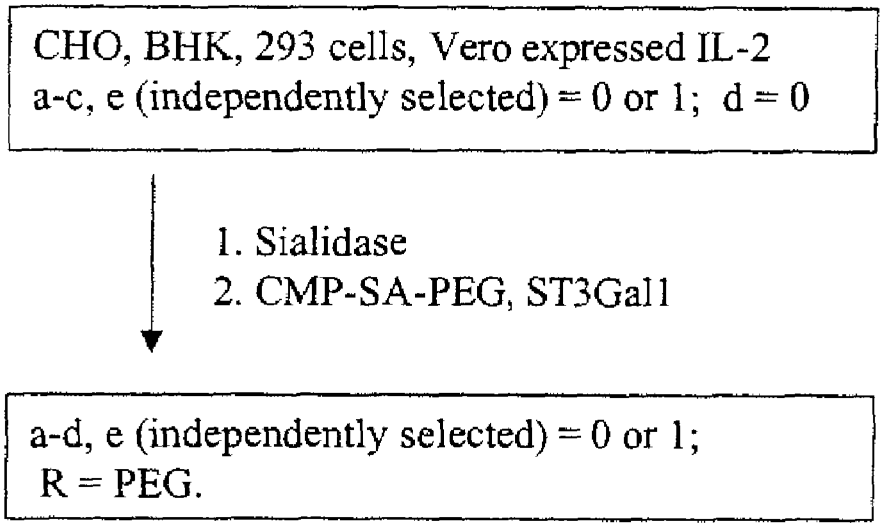
FIGS. 41B to 41G are diagrams of contemplated remodeling steps of the glycan of the peptide in FIG. 41A based on the type of cell the peptide is expressed in and the desired remodeled glycan structure.
Figure 41C:
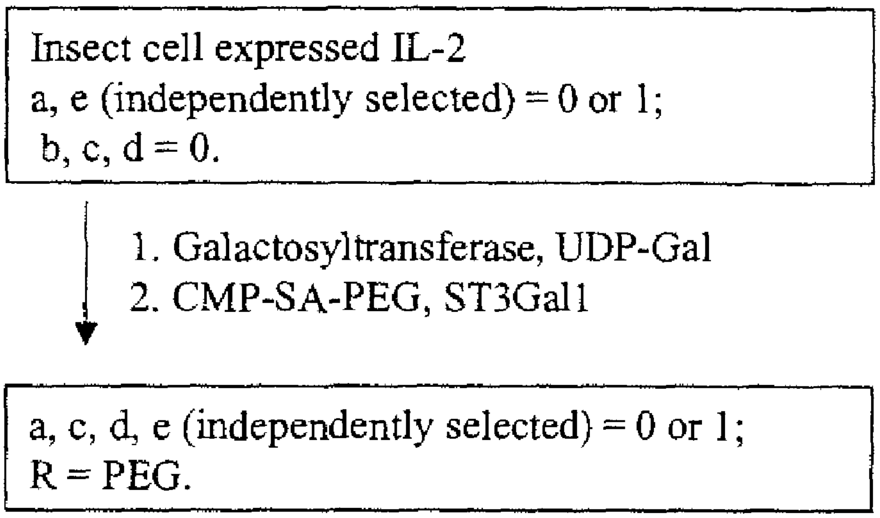
Figure 41D:
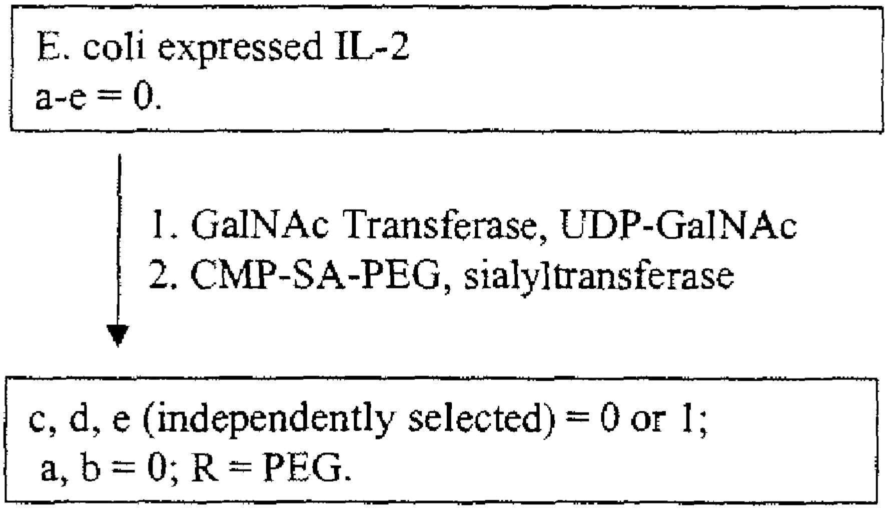
Figure 41E:
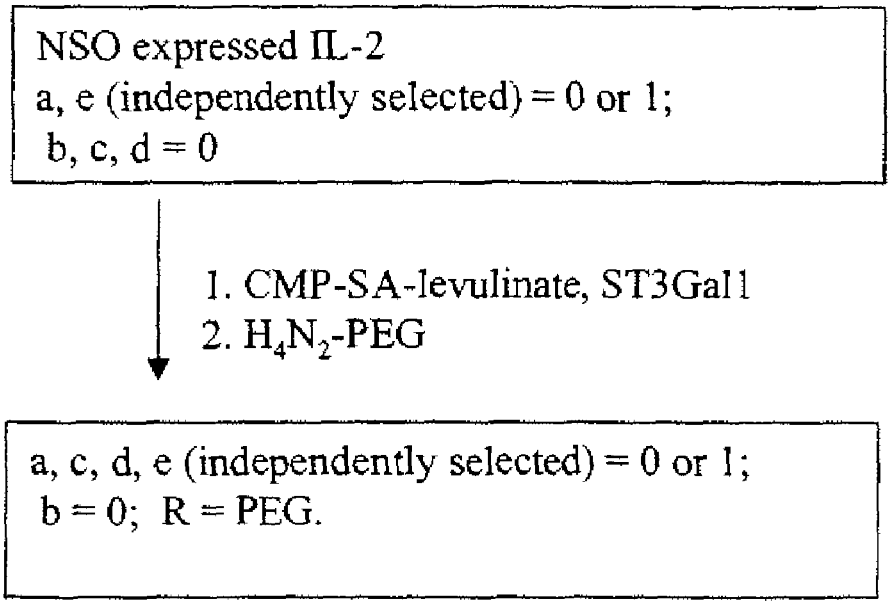
Figure 41F:
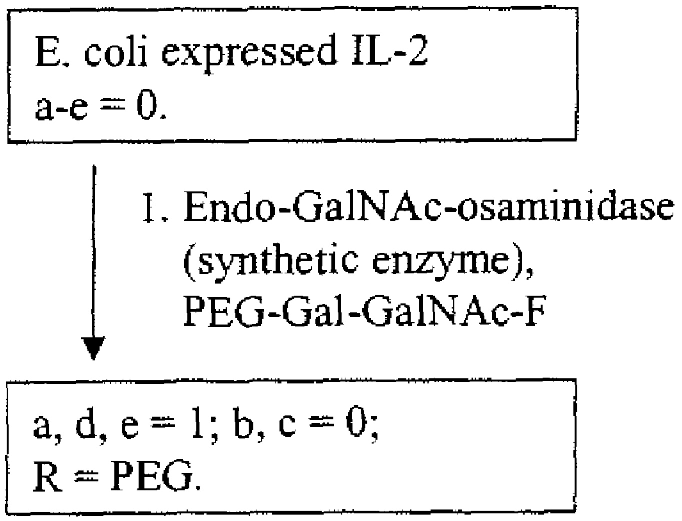
Figure 41G:
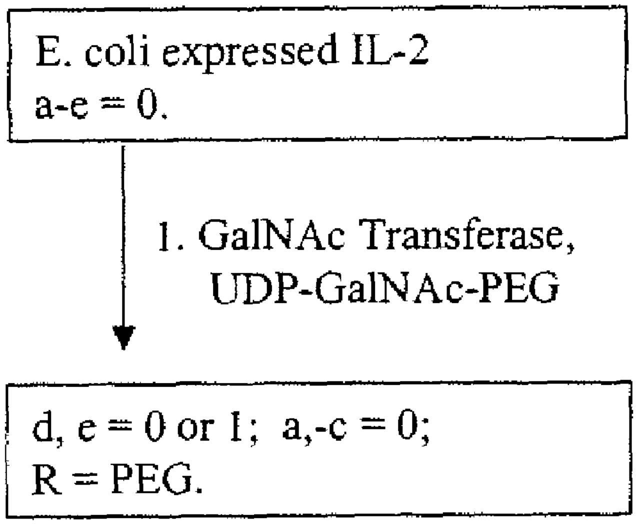

In another exemplary embodiment, the invention provides methods for modifying Interleukin-2 (IL-2). FIGS. 41A to 41G provide some examples. FIG. 41B provides a two-step modification scheme: IL-2 produced by mammalian cells is first treated with sialidase to trim back its terminal sialic acid residues, and is then PEGylated using ST3Gal3 and a donor of PEGylated sialic acid. In FIG. 41C, insect cell expressed IL-2 is modified first by galactosylation using a galactose donor and a galactosyltransferase. Subsequently, IL-2 is PEGylated using ST3Gal3 and a donor of PEGylated sialic acid. In FIG. 41D, IL-2 expressed in bacteria is modified with N-acetylgalactosamine using a proper donor and N-acetylgalactosamine transferase, followed by a step of PEGylation with a PEG-sialic acid donor and a sialyltransferase. FIG. 41E offers another scheme of modifying IL-2 produced by a mammalian system. The polypeptide is modified by capping appropriate terminal residues with a sialic acid donor that is modified with levulinic acid, adding a reactive ketone to the sialic acid donor. After addition to a glycosyl residue of the peptide, the ketone is derivatized with a moiety such as a hydrazine- or amine-PEG. FIG. 41F illustrates an example of remodeling IL-2 expressed by *E. coli*. The polypeptide is PEGylated using a reactive N-acetylgalactosamine complex derivatized with a PEG group and an enzyme that is modified so that it functions as a synthetic enzyme rather than a hydrolytic one. In FIG. 41G, IL-2 expressed by bacteria is modified by addition of PEGylated N-acetylgalactosamine using a proper donor and N-acetylgalactosamine transferase.

Figures 42B, 42C:
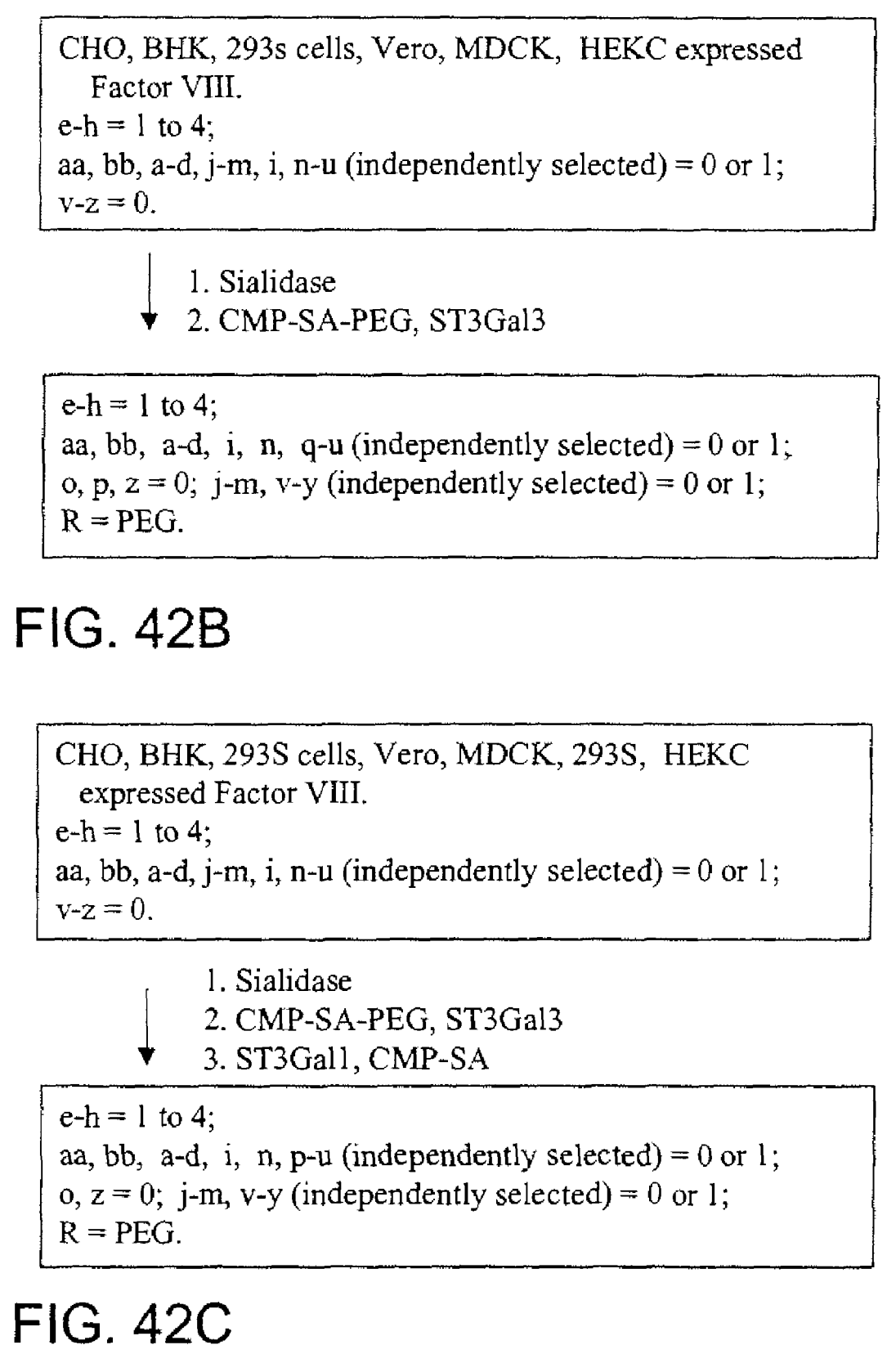

In another exemplary embodiment, the invention provides methods for modifying Factor VIII, as shown in FIGS. 42A to 42N. In FIG. 42B, Factor VIII expressed in mammalian cells is first treated with sialidase to trim back the sialic acid residues, and is then PEGylated using ST3Gal3 and a donor of PEG-sialic acid. In FIG. 42C, Factor VIII expressed in mammalian cells is first treated with sialidase to trim back the sialic acid residues, then PEGylated using ST3Gal3 and a proper donor, and is then further sialylated using ST3Gal1 and a sialic acid donor.

Figures 42H, 42I:
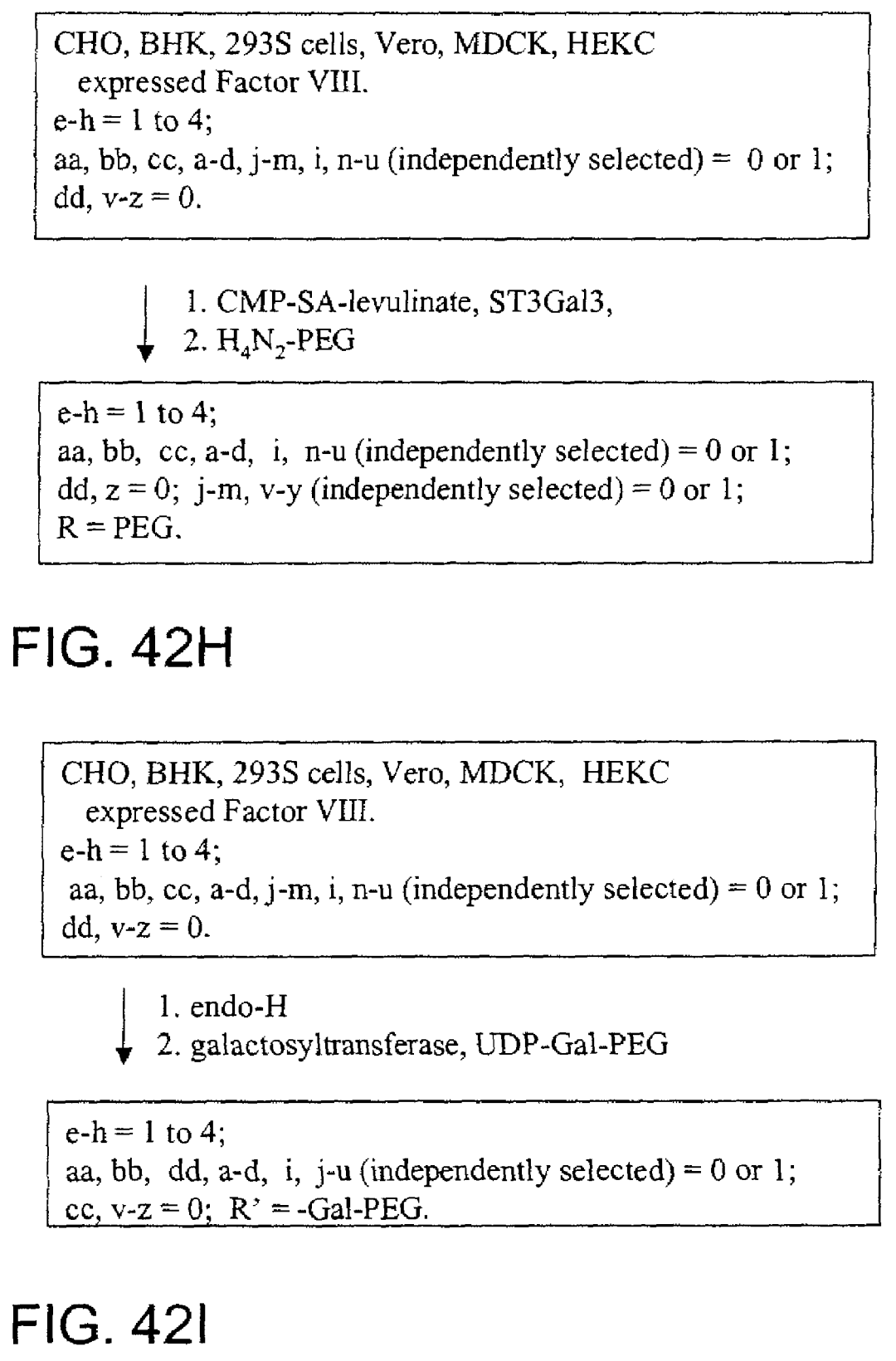

In FIG. 42E, mammalian cell produced Factor VIII is modified by the single step of PEGylation, using ST3Gal3 and a donor of PEGylated sialic acid. FIG. 42F offers another example of modification of Factor VIII that is expressed by mammalian cells. The protein is PEGylated using ST3Gal1 and a donor of PEGylated sialic acid. In FIG. 42G, mammalian cell expressed Factor VIII is remodeled following another scheme: it is PEGylated using a 2,8-sialyltransferase and a donor of PEG-sialic acid. In FIG. 42I, Factor VIII produce by mammalian cells is modified by capping appropriate terminal residues with a sialic acid donor that is modified with levulinic acid, adding a reactive ketone to the sialic acid donor. After addition to a glycosyl residue of the peptide, the ketone is derivatized with a moiety such as a hydrazine- or amine-PEG. In FIG. 42J, Factor VIII expressed by mammalian cells is first treated with Endo-H to trim back glycosyl groups. It is then PEGylated using a galactosyltransferase and a donor of PEG-galactose. In FIG. 42K, Factor VIII expressed in a mammalian system is first sialylated using ST3Gal3 and a sialic acid donor, then treated with Endo-H to trim back the glycosyl groups, and then PEGylated with a galactosyltransferase and a donor of PEG-galactose. In FIG. 42L, Factor VIII expressed in a mammalian system is first treated with mannosidases to trim back terminal mannosyl residues, then has an N-acetylglucosamine group added using a suitable donor and GnT-I and/or II, and then is PEGylated using a galactosyltransferase and a donor of PEG-galactose. In FIG. 42M, Factor VIII expressed in mammalian cells is first treated with mannosidases to trim back mannosyl units, then has N-acetylglucosamine group added using N-acetylglucosamine transferase and a suitable donor. It is further galactosylated using a galactosyltransferase and a galactose donor, and then sialylated using ST3Gal3 and a sialic acid donor. In FIG. 42N, Factor VIII is produced by mammalian cells and modified as follows: it is first treated with mannosidases to trim back the terminal mannosyl groups. A PEGylated N-acetylglucosamine group is then added using GnT-I and a suitable donor of PEGylated N-acetylglucosamine.

Figure 43A:
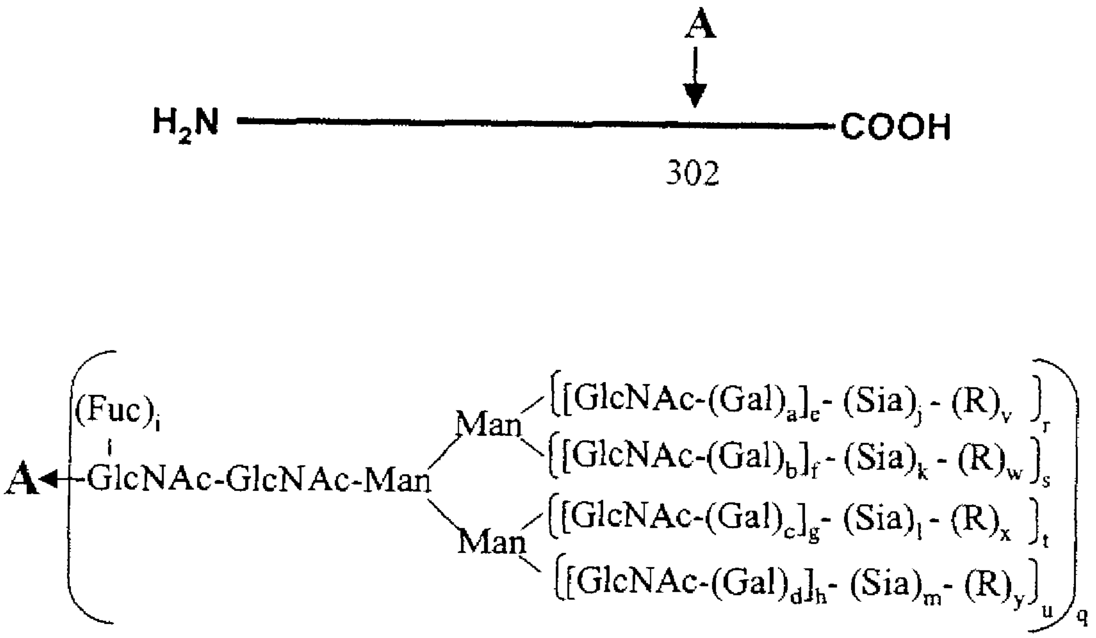
FIG. 43A is a diagram depicting the urokinase peptide indicating a residue which is linked to a glycan contemplated for remodeling, and an exemplary glycan formula linked thereto.
Figure 43F:
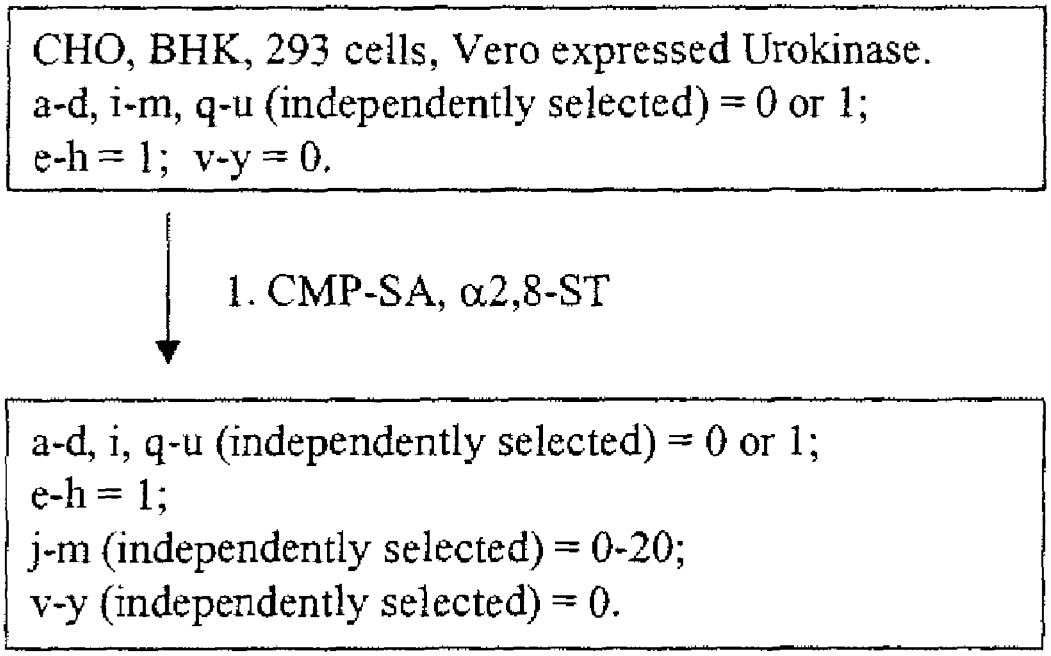
Figures 43H, 43I:
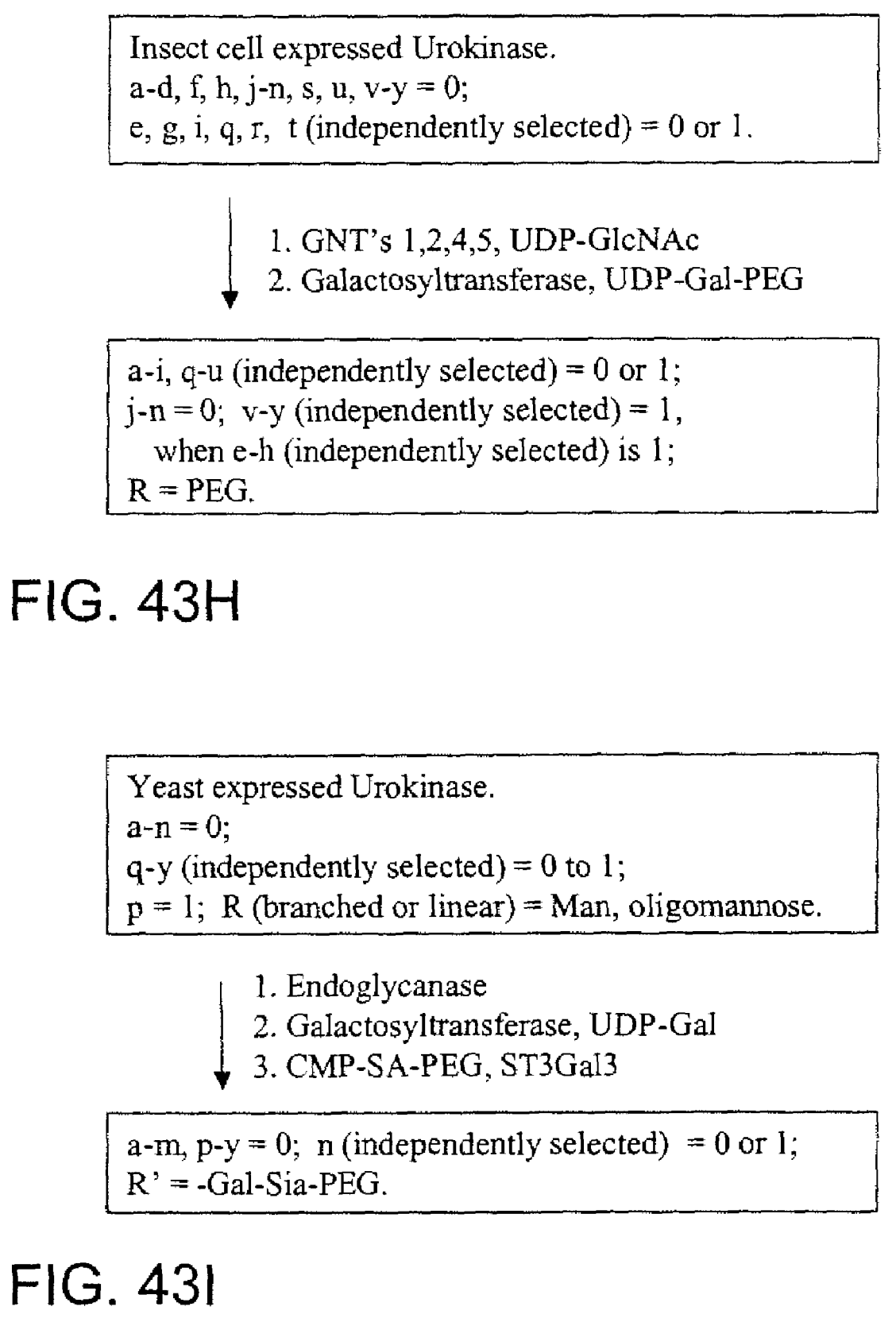

In another exemplary embodiment, the invention provides methods for modifying urokinase, as shown in FIGS. 43A to 43L. In FIG. 43B, urokinase expressed in mammalian cells is first treated with sialidase to trim back sialic acid residues, and is then PEGylated using ST3Gal3 and a donor of PEGylated sialic acid. In FIG. 43C, urokinase expressed in mammalian cells is first treated with sialidase to trim back sialic acid residues, then PEGylated using ST3Gal3 and a donor of PEGylated sialic acid, and then sialylated using ST3Gal3 and a sialic acid donor. Optionally, urokinase expressed in a mammalian system is first treated with sialidase and galactosidase to trim back glycosyl chains, then galactosylated using a galactose donor and an α-galactosyltransferase, and then PEGylated using ST3Gal3 or sialyltransferase and a donor of PEG-sialic acid. In FIG. 43D, urokinase expressed in mammalian cells is first treated with sialidase to trim back sialic acid residues, then PEGylated using ST3Gal3 and a donor of PEG-sialic acid, and then further sialylated using ST3Gal3 and a sialic acid donor. In FIG. 43E, urokinase expressed in mammalian cells is modified by capping appropriate terminal residues with a sialic acid donor that is modified with levulinic acid, adding a reactive ketone to the sialic acid donor. After addition to a glycosyl residue of the peptide, the ketone is derivatized with a moiety such as a hydrazine- or amine-PEG. In FIG. 43F, urokinase expressed in mammalian cells is sialylated using a sialic acid donor and a 2,8-sialyltransferase. In FIG. 43H, urokinase expressed in insect cells is modified in the following steps: first, N-acetylglucosamine is added to the polypeptide using a suitable donor of N-acetylglucosamine and one or more of GnT-I, II, IV, and V; then PEGylated galactose is added, using a galactosyltransferase and a donor of PEG-galactose. In FIG. 43I, urokinase expressed in yeast is first treated with endoglycanase to trim back glycosyl groups, then galactosylated using a galactose donor and a galactosyltransferase, and then PEGylated using ST3Gal3 and a donor of PEG-sialic acid. In FIG. 43J, urokinase expressed in mammalian cells is first contacted with ST3Gal3 and two reactive sialic acid residues that are connected via a linker, so that the polypeptide is attached to one reactive sialic acid via the linker and second sialic acid residue. The polypeptide is then contacted with ST3Gal1 and desialylated urokinase produced in mammalian cells, and thus becomes connected with a second molecule of urokinase. Then, the whole molecule is further sialylated using a sialic donor and ST3Gal1 and/or ST3Gal3. In FIG. 43K, isolated urokinase is first treated with sulfohydrolase to remove sulfate groups, and is then PEGylated using a sialyltransferase and a donor of PEG-sialic acid. In FIG. 43L, isolated urokinase is first treated with sulfohydrolase and hexosaminidase to remove sulfate groups and hexosamine groups, and then PEGylated using a galactosyltransferase and a donor of PEG-galactose.

Figure 44A:
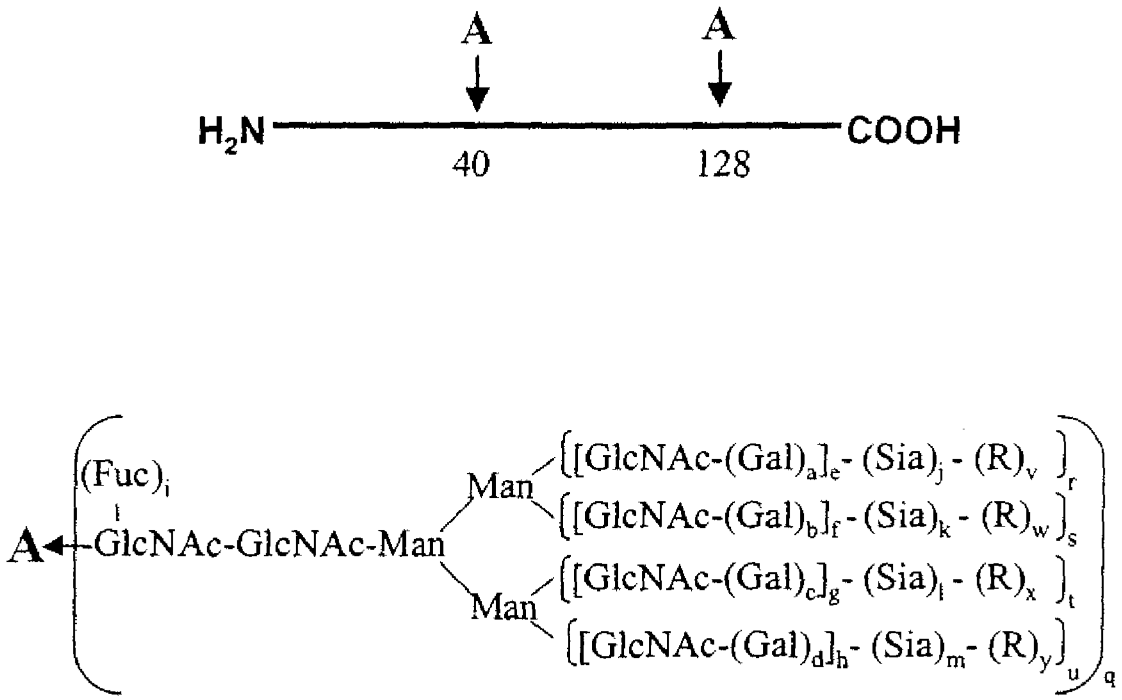
FIG. 44A is a diagram depicting the human DNase peptide indicating the residues which bind to glycans contemplated for remodeling, and exemplary glycan formulas linked thereto.
Figures 44H, 44I:
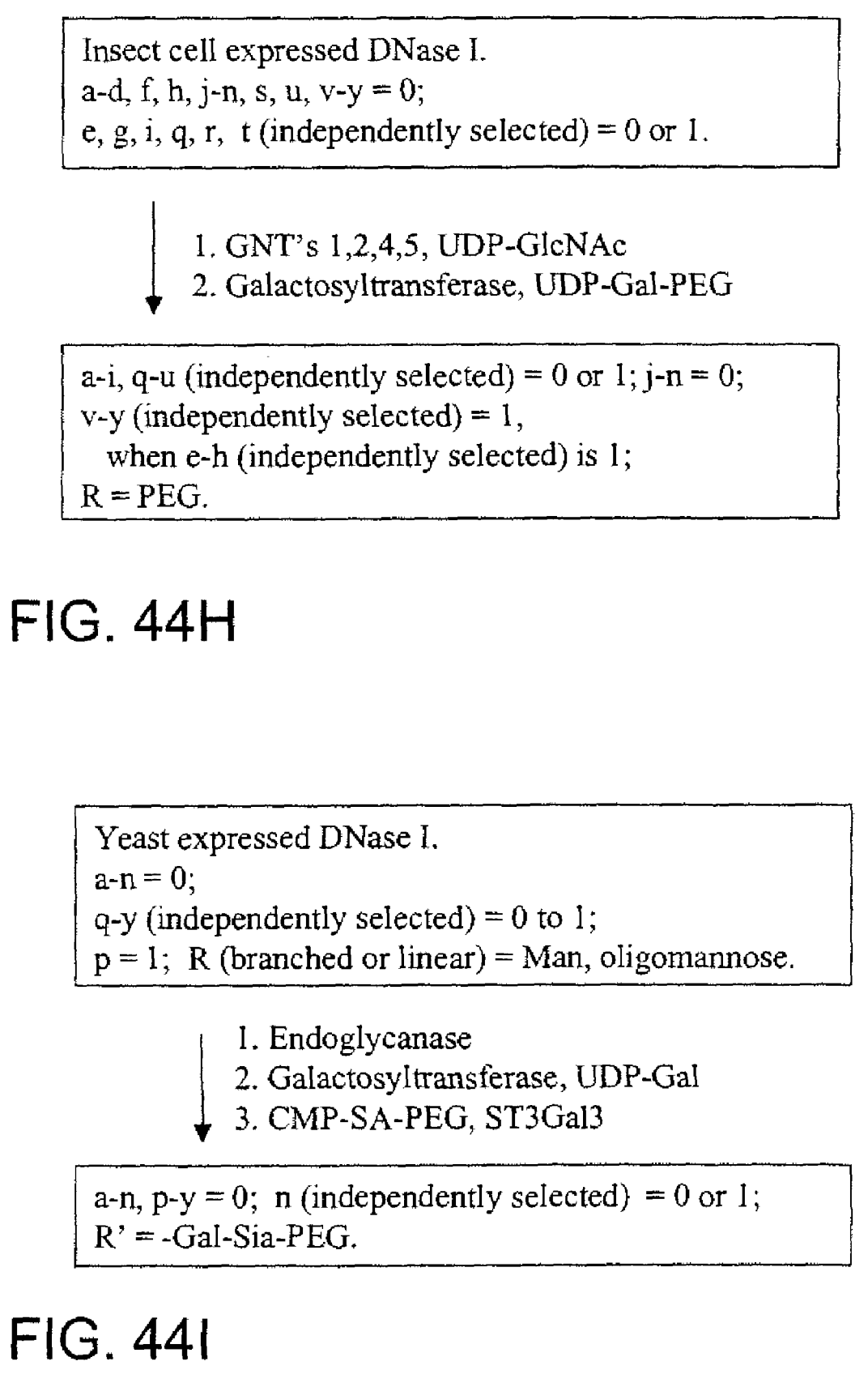

In another exemplary embodiment, the invention provides methods for modifying DNase I, as shown in FIGS. 44A to 44J. In FIG. 44B, DNase I is expressed in a mammalian system and modified in the following steps: first, the protein is treated with sialidase to trim back the sialic acid residues; then the protein is PEGylated with ST3Gal3 using a donor of PEG-sialic acid. In FIG. 44C, DNase I expressed in mammalian cells is first treated with sialidase to trim back the sialic acid residues, then PEGylated with ST3Gal3 using a PEG-sialic acid donor, and is then sialylated using ST3Gal3 and a sialic acid donor. Optionally, DNase I expressed in a mammalian system is first exposed to sialidase and galactosidase to trim back the glycosyl groups, then galactosylated using a galactose donor and an α-galactosyltransferase, and then PEGylated using ST3Gal3 or sialyltransferase and a donor of PEG-sialic acid. In FIG. 44D, DNase I expressed in mammalian cells is first treated with sialidase to trim back the sialic acid residues, then PEGylated using ST3Gal3 and a PEG-sialic acid donor, and then sialylated with ST3Gal3 using a sialic acid donor. In FIG. 44E, DNase I expressed in mammalian cells is modified by capping appropriate terminal residues with a sialic acid donor that is modified with levulinic acid, adding a reactive ketone to the sialic acid donor. After addition to a glycosyl residue of the peptide, the ketone is derivatized with a moiety such as a hydrazine- or amine-PEG. In FIG. 44F, DNase I expressed in mammalian cells is sialylated using a sialic acid donor and α 2,8-sialyltransferase. In FIG. 44H, DNase I expressed in insect cells first has N-acetylglucosamine added using a suitable donor and one or more of GnT-I, II, IV, and V. The protein is then PEGylated using a galactosyltransferase and a donor of PEG-galactose. In FIG. 44I, DNase I expressed in yeast is first treated with endoglycanase to trim back the glycosyl units, then galactosylated using a galactose donor and a galactosyltransferase, and then PEGylated using ST3Gal3 and a donor of PEG-sialic acid. In FIG. 44JK, DNase I expressed in mammalian cells is first contacted with ST3Gal3 and two reactive sialic acid residues connected via a linker, so that the polypeptide is attached to one reactive sialic acid via the linker and the second sialic acid residue. The polypeptide is then contacted with ST3Gal1 and desialylated α-1-protease inhibitor, and thus becomes connected with the inhibitor via the sialic acid residue. Then, the polypeptide is further sialylated using a suitable donor and ST3Gal1 and/or ST3Gal3.

Figure 45A:
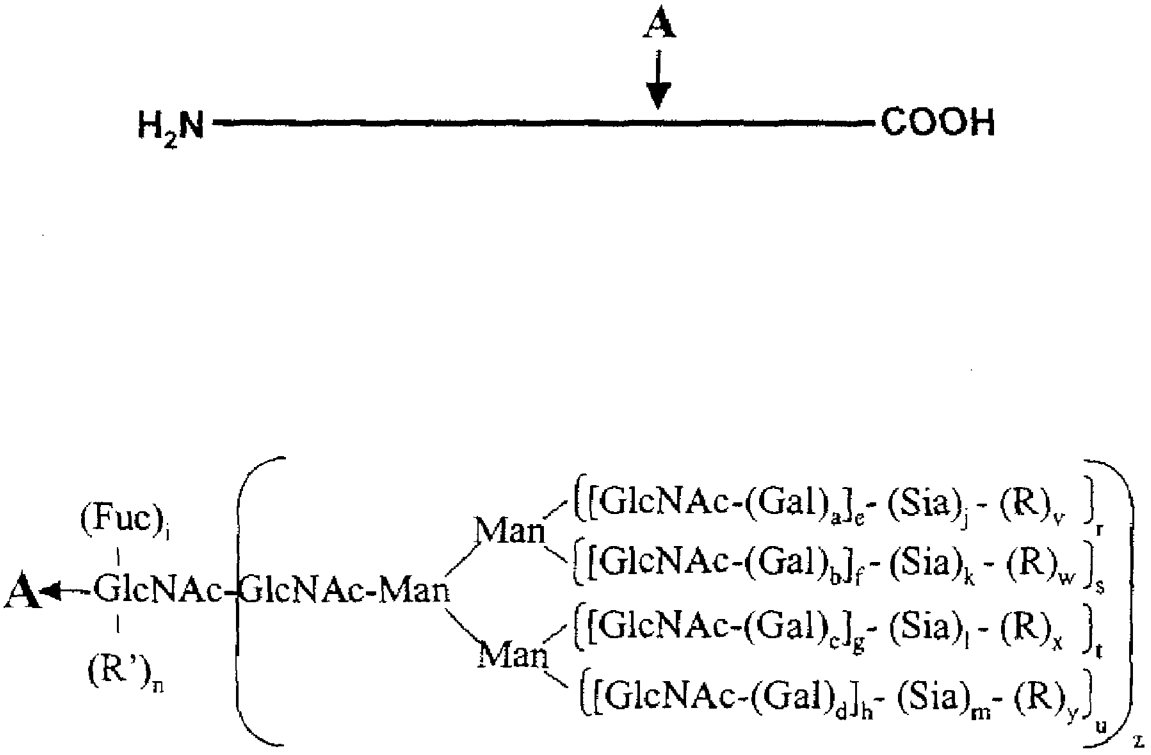
FIG. 45A is a diagram depicting the insulin peptide mutated to contain an N glycosylation site and an exemplary glycan formula linked thereto.
Figure 45E:
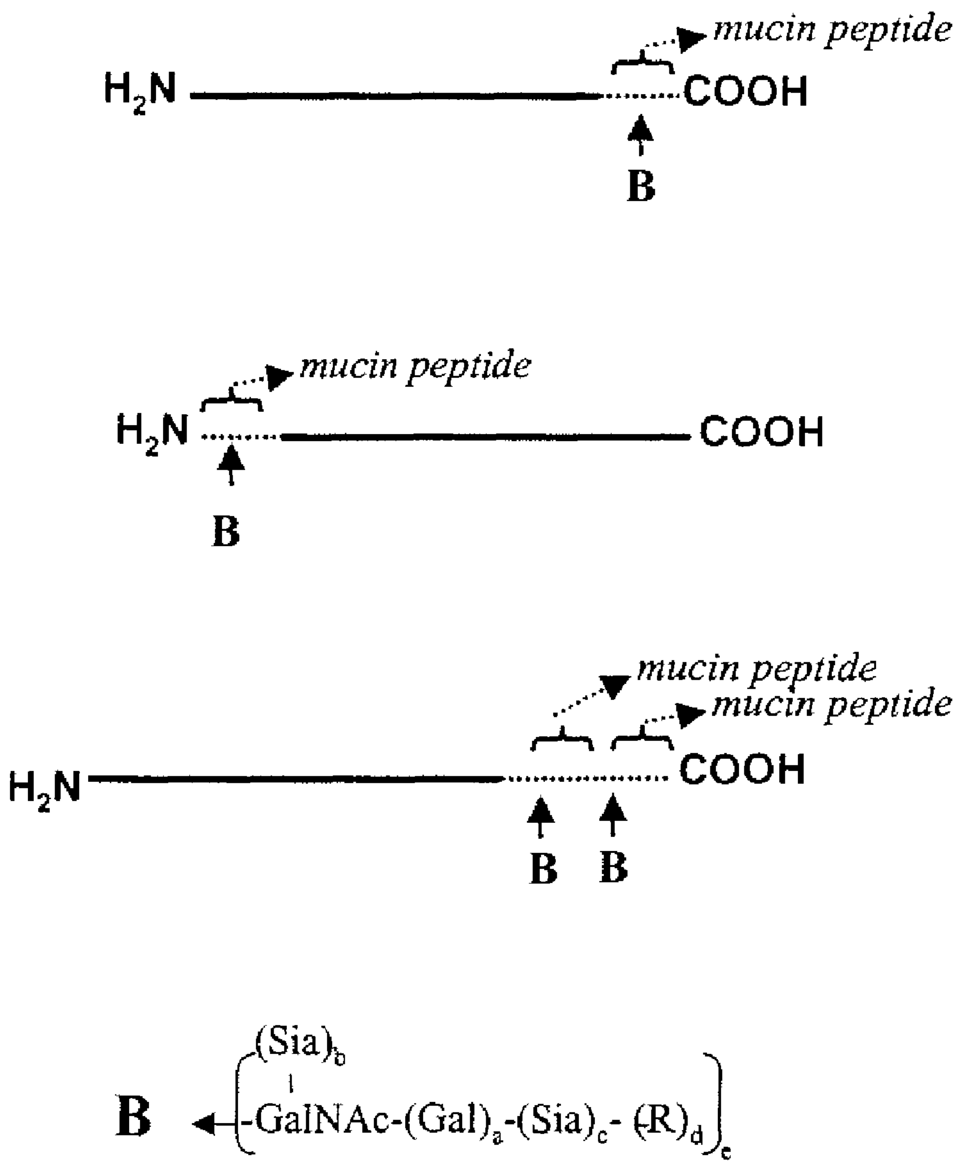
FIG. 45E is a diagram depicting insulin-mucin fusion peptides indicating a residue(s) which is linked to a glycan contemplated for remodeling, and an exemplary glycan formula linked thereto.
Figure 45H:
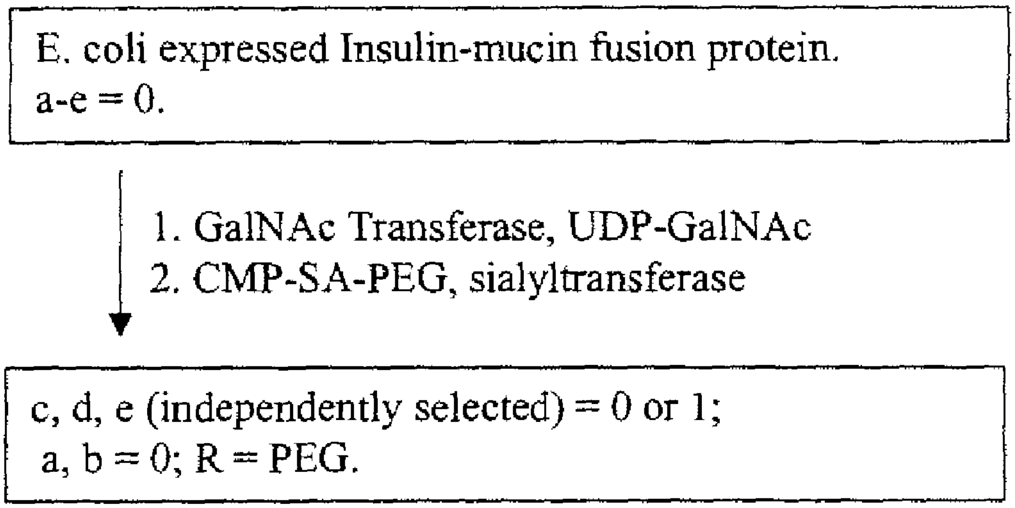
Figure 45I:
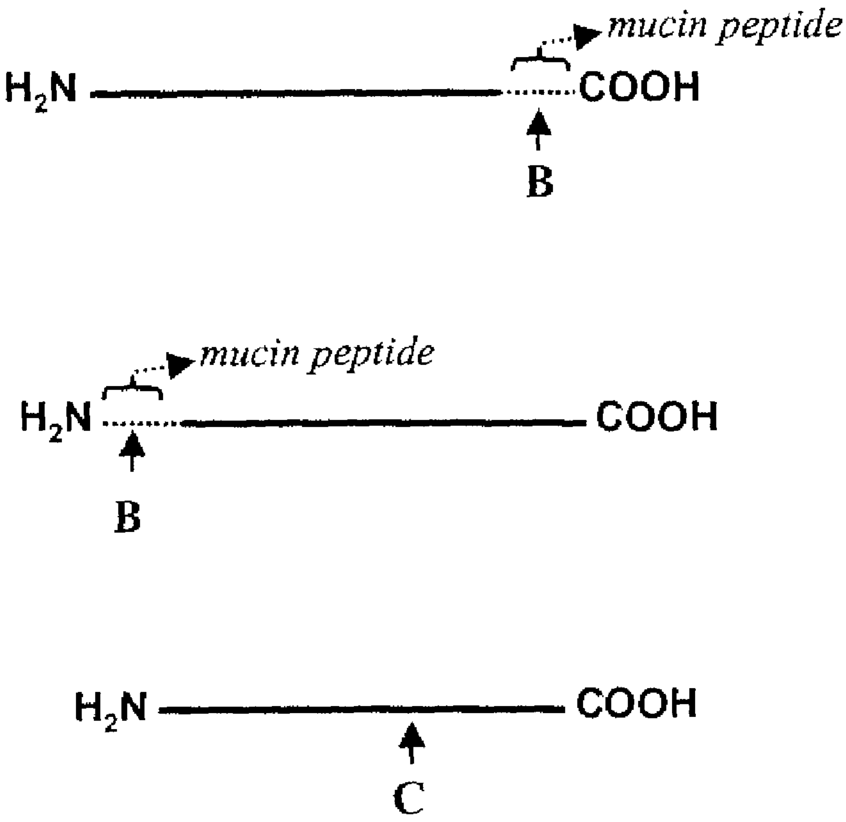
FIG. 45I is a diagram depicting the insulin-mucin fusion peptides and insulin peptides indicating a residue(s) which is linked to a glycan contemplated for remodeling, and formulas for the glycan.
Figure 45J:
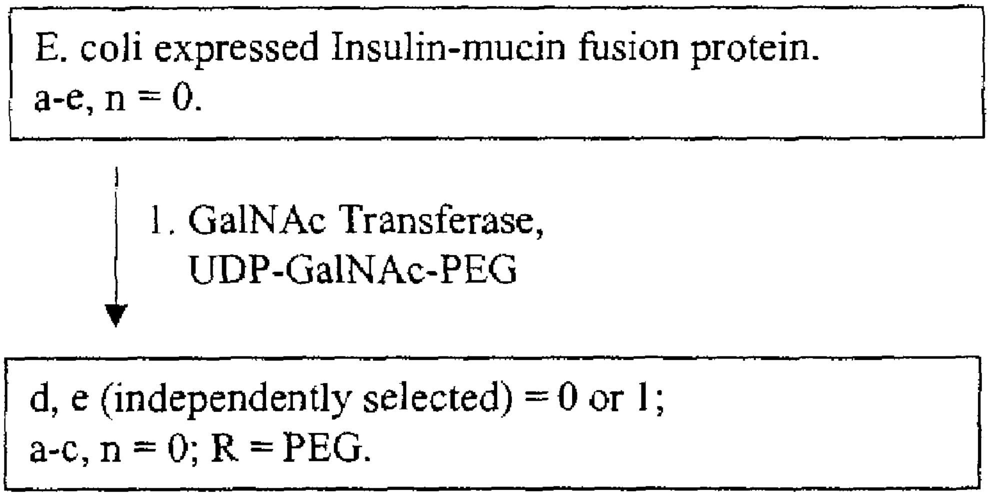
Figure 45K:
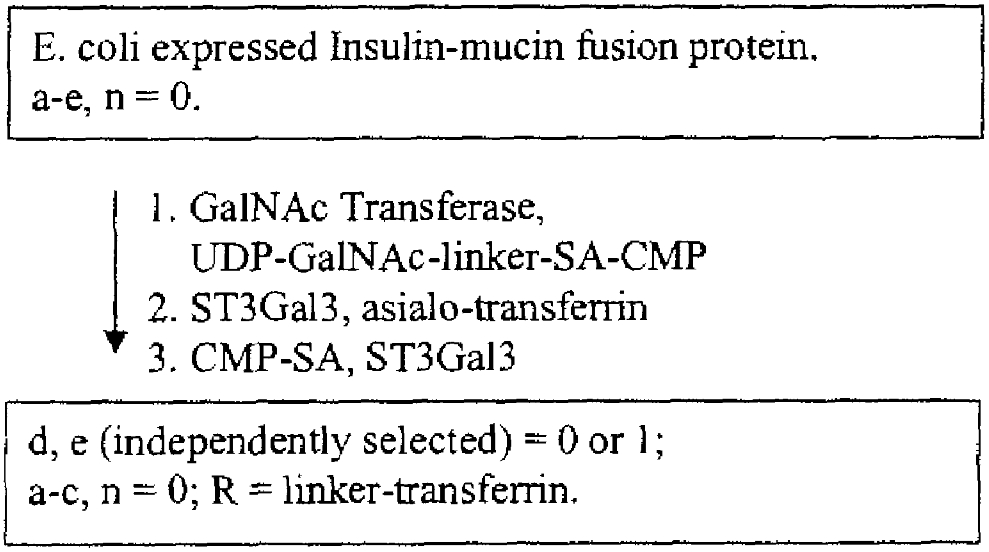

In another exemplary embodiment, the invention provides methods for modifying insulin that is mutated to contain an N-glycosylation site, as shown in FIGS. 45A to 45L. In FIG. 45B, insulin expressed in a mammalian system is first treated with sialidase to trim back the sialic acid residues, and then PEGylated using ST3Gal3 and a PEG-sialic acid donor. In FIG. 45C, insulin expressed in insect cells is modified by addition of PEGylated N-acetylglucosamine using an appropriate donor and GnT-I and/or II. In FIG. 45D, insulin expressed in yeast is first treated with Endo-H to trim back the glycosyl groups, and then PEGylated using a galactosyltransferase and a donor of PEG-galactose. In FIG. 45F, insulin expressed in mammalian cells is first treated with sialidase to trim back the sialic acid residues and then PEGylated using ST3Gal1 and a donor of PEG-sialic acid. In FIG. 45G, insulin expressed in insect cells is modified by means of addition of PEGylated galactose using a suitable donor and a galactosyltransferase. In FIG. 45H, insulin expressed in bacteria first has N-acetylgalactosamine added using a proper donor and N-acetylgalactosamine transferase. The polypeptide is then PEGylated using a sialyltransferase and a donor of PEG-sialic acid. In FIG. 45J, insulin expressed in bacteria is modified through a different method: PEGylated N-acetylgalactosamine is added to the protein using a suitable donor and N-acetylgalactosamine transferase. In FIG. 45K, insulin expressed in bacteria is modified following another scheme: the polypeptide is first contacted with N-acetylgalactosamine transferase and a reactive N-acetylgalactosamine that is derivatized with a reactive sialic acid via a linker, so that the polypeptide is attached to the reactive sialic acid via the linker and N-acetylgalactosamine. The polypeptide is then contacted with ST3Gal3 and asialo-transferrin, and therefore becomes connected with transferrin. Then, the polypeptide is sialylated using ST3Gal3 and a sialic acid donor. In FIG. 45L, insulin expressed in bacteria is modified using yet another method: the polypeptide is first exposed to NHS-CO-linker-SA-CMP and becomes connected to the reactive sialic acid residue via the linker. The polypeptide is then conjugated to transferrin using ST3Gal3 and asialo-transferrin. Then, the polypeptide is further sialylated using ST3Gal3 and a sialic acid donor.

Figure 46A:
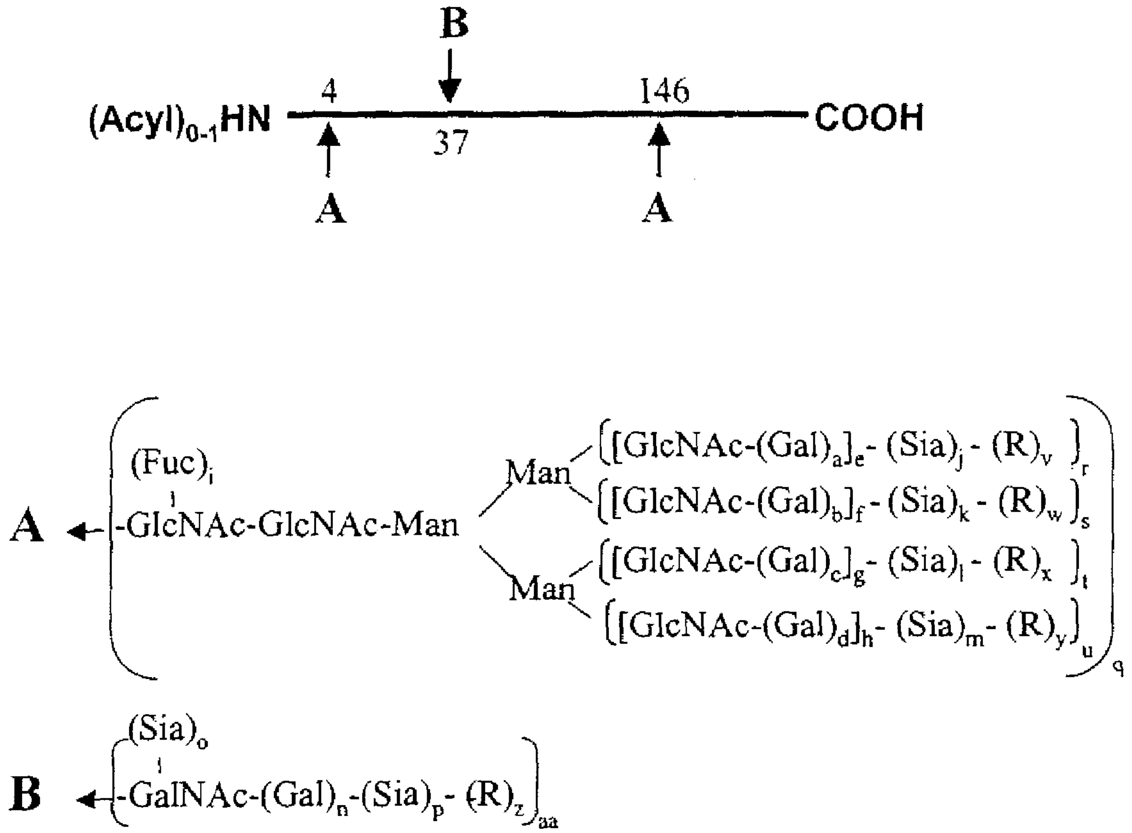
FIG. 46A is a diagram depicting the M-antigen peptide indicating the residues which bind to glycans contemplated for remodeling, and formulas for the glycans.
Figure 46H:
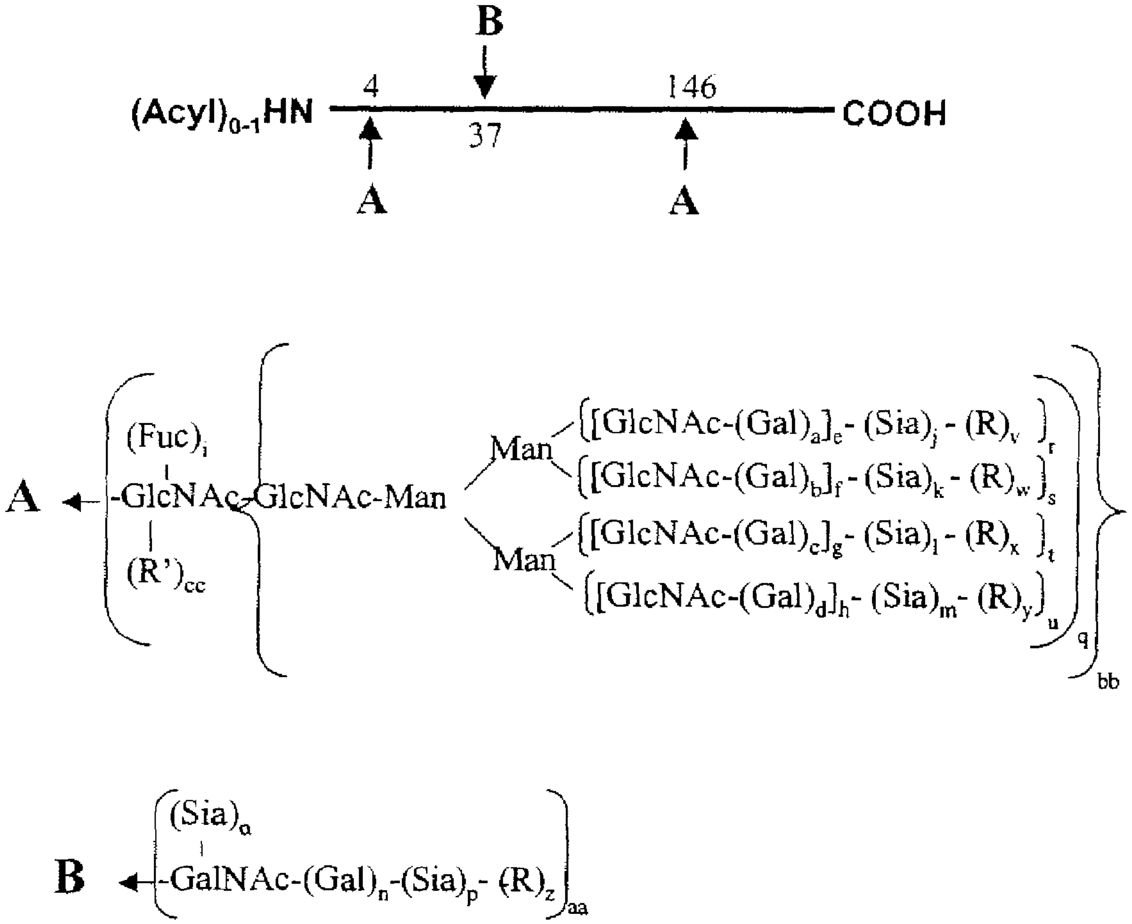
FIG. 46H is a diagram depicting the M-antigen peptide indicating the residues which bind to glycans contemplated for remodeling, and formulas for the glycans.

In another exemplary embodiment, the invention provides methods for modifying Hepatitis B antigen (M antigen-preS2 and S), as shown in FIGS. 46A to 46K. In FIG. 46B, M-antigen is expressed in a mammalian system and modified by initial treatment of sialidase to trim back the sialic acid residues and subsequent conjugation with lipid A, using ST3Gal3 and a reactive sialic acid linked to lipid A via a linker. In FIG. 46C, M-antigen expressed in mammalian cells is first treated with sialidase to trim back the terminal sialic acid residues, then conjugated with tetanus toxin via a linker using ST3Gal1 and a reactive sialic acid residue linked to the toxin via the linker, and then sialylated using ST3Gal3 and a sialic acid donor. In FIG. 46D, M-antigen expressed in a mammalian system is first treated with a galactosidase to trim back galactosyl residues, and then sialylated using ST3Gal3 and a sialic acid donor. The polypeptide then has sialic acid derivatized with KLH added using ST3Gal1 and a suitable donor. In FIG. 46E, yeast expressed M-antigen is first treated with a mannosidase to trim back the mannosyl residues, and then conjugated to a diphtheria toxin using GnT-I and a donor of N-acetylglucosamine linked to the diphtheria toxin. In FIG. 46F, mammalian cell expressed M-antigen is modified by capping appropriate terminal residues with a sialic acid donor that is modified with levulinic acid, adding a reactive ketone to the sialic acid donor. After addition to a glycosyl residue of the peptide, the ketone is derivatized with a moiety such as a hydrazine- or amine-PEG. In FIG. 46G, M-antigen obtained from a mammalian system is remodeled by sialylation using a sialic acid donor and poly a 2,8-sialyltransferase. In FIG. 46I, M-antigen expressed in insect cells is conjugated to a *Neisseria* protein by using GnT-II and a suitable donor of N-acetylglucosamine linked to the *Neisseria* protein. In FIG. 46J, yeast expressed M-antigen is first treated with endoglycanase to trim back its glycosyl chains, and then conjugated to a *Neisseria* protein using a galactosyltransferase and a proper donor of galactose linked to the *Neisseria* protein. FIG. 46K is another example of modification of M-antigen expressed in yeast. The polypeptide is first treated with mannosidases to trim back terminal mannosyl residues, and then has N-acetylglucosamine added using GnT-I and/or II. Subsequently, the polypeptide is galactosylated using a galactose donor and a galactosyltransferase, and then capped with sialic acid residues using a sialyltransferase and a sialic acid donor.

Figures 47B, 47C:
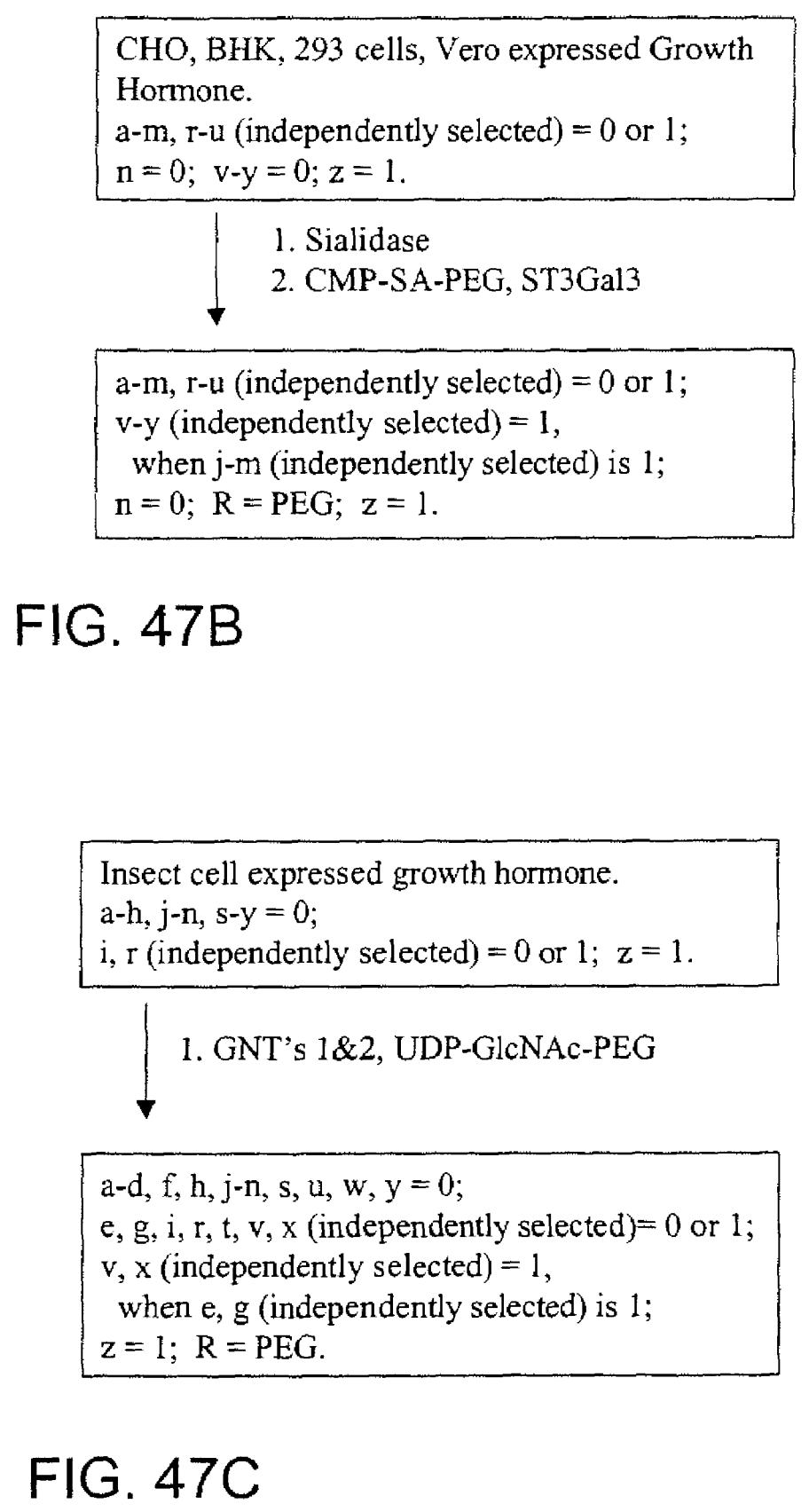
Figures 47F, 47G:
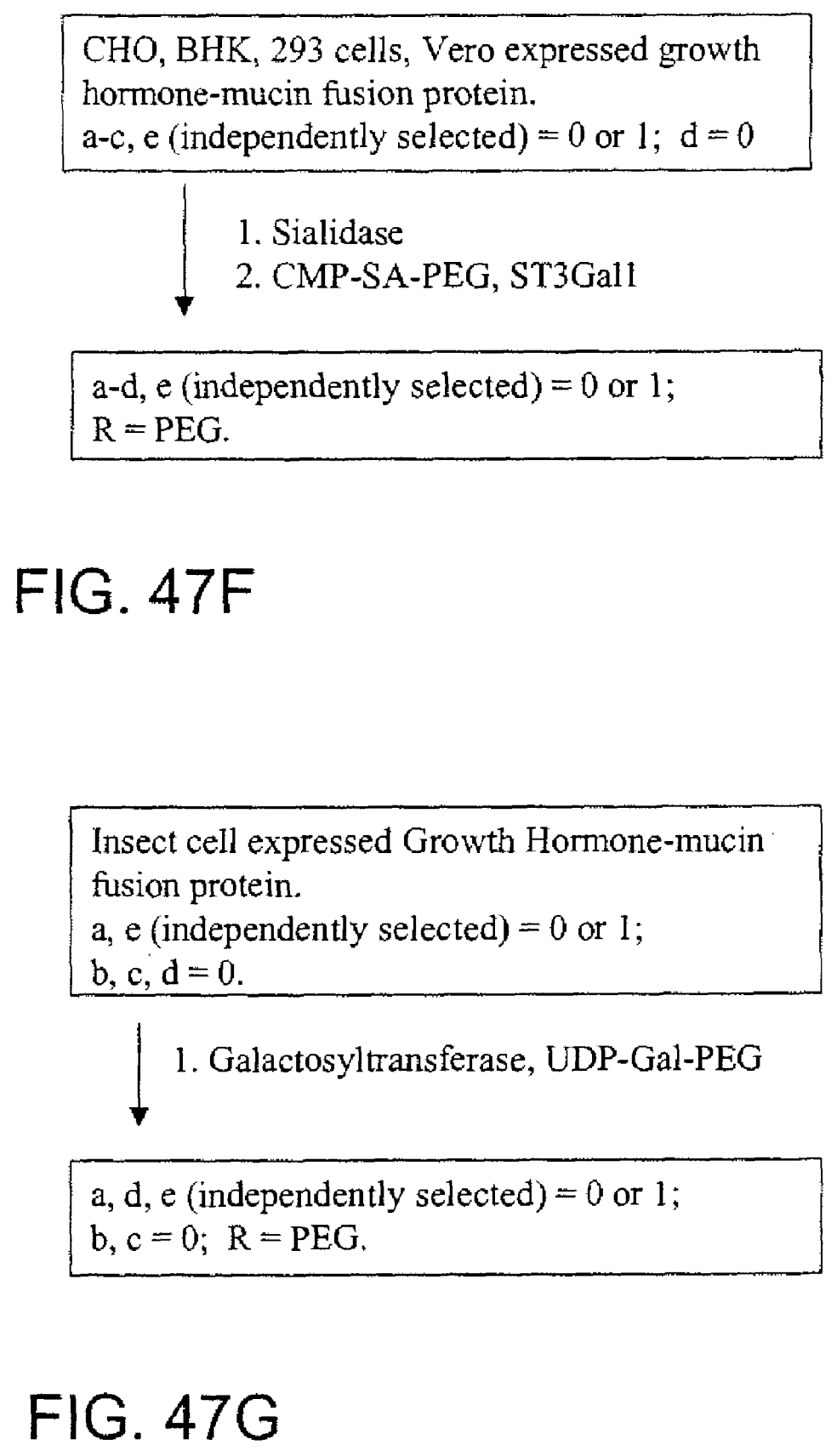
Figure 47H:
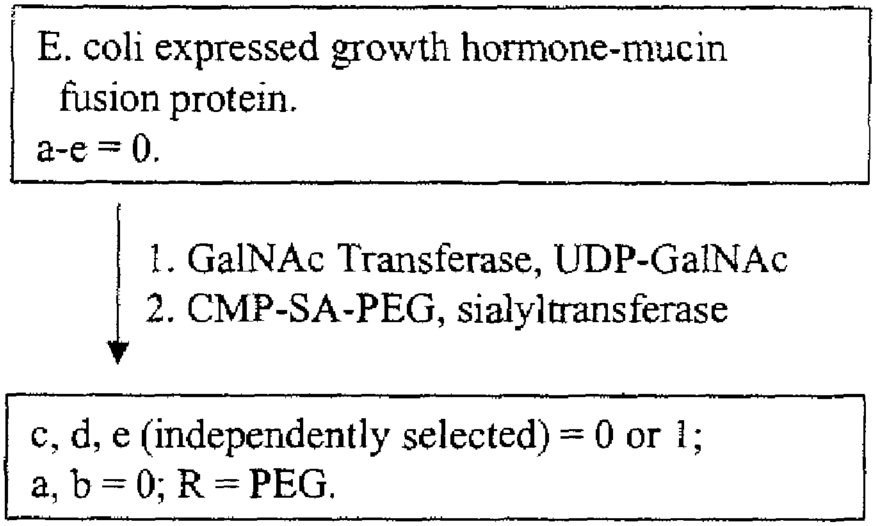
Figure 47I:
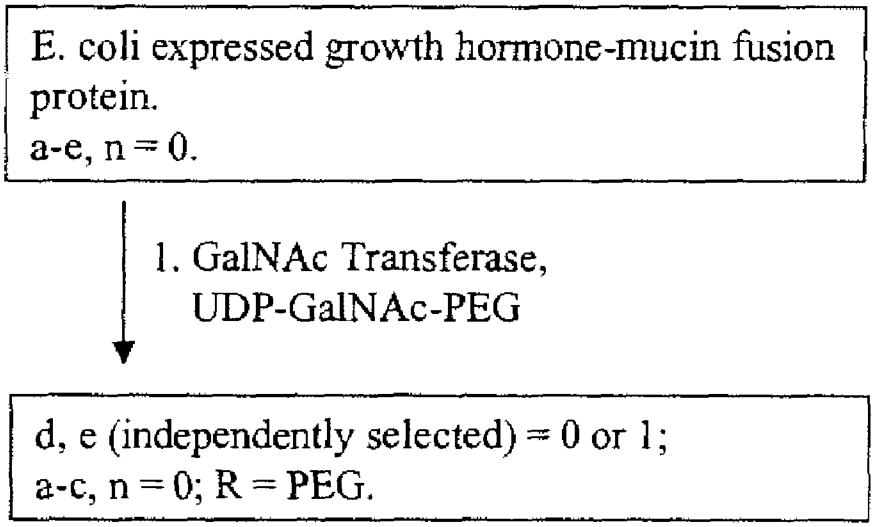

In another exemplary embodiment, the invention provides methods for modifying human growth hormone (N, V, and variants thereof), as shown in FIGS. 47A to 47K. In FIG. 47B, human growth hormone either mutated to contain a N-linked site, or a naturally occurring isoform that has an N-linked side (i.e., the placental enzyme) produced by mammalian cells is first treated with sialidase to trim back terminal sialic acid residues and subsequently PEGylated with ST3Gal3 and using a donor of PEGylated sialic acid. In FIG. 47C, human growth hormone expressed in insect cells is modified by addition of PEGylated N-acetylglucosamine using GnT-I and/or II and a proper donor of PEGylated N-acetylglucosamine. In FIG. 47D, human growth hormone is expressed in yeast, treated with Endo-H to trim back glycosyl groups, and further PEGylated with a galactosyltransferase using a donor of PEGylated galactose. In FIG. 47F, human growth hormone-mucin fusion protein expressed in a mammalian system is modified by initial treatment of sialidase to trim back sialic acid residues and subsequent PEGylation using a donor of PEG-sialic acid and ST3Gal1. In FIG. 47G, human growth hormone-mucin fusion protein expressed in insect cells is remodeled by PEGylation with a galactosyltransferase and using a donor of PEGylated galactose. In FIG. 47H, human growth hormone-mucin fusion protein is produced in bacteria. N-acetylgalactosamine is first added to the fusion protein by the action of N-acetylgalactosamine transferase using a donor of N-acetylgalactosamine, followed by PEGylation of the fusion protein using a donor of PEG-sialic acid and a sialyltransferase. FIG. 47I describes another scheme of modifying bacterially expressed human growth hormone-mucin fusion protein: the fusion protein is PEGylated through the action of N-acetylgalactosamine transferase using a donor of PEGylated N-acetylgalactosamine. FIG. 47J provides a further remodeling scheme for human growth hormone-mucin fusion protein. The fusion protein is first contacted with N-acetylgalactosamine transferase and a donor of N-acetylgalactosamine that is derivatized with a reactive sialic acid via a linker, so that the fusion protein is attached to the reactive sialic acid via the linker and N-acetylgalactosamine. The fusion protein is then contacted with a sialyltransferase and asialo-transferrin, and thus becomes connected with transferrin via the sialic acid residue. Then, the fusion protein is capped with sialic acid residues using ST3Gal3 and a sialic acid donor. In FIG. 47K, yet another scheme is given for modification of human growth hormone (N) produced in bacteria. The polypeptide is first contacted with NHS-CO-linker-SA-CMP and becomes coupled with the reactive sialic acid through the linker. The polypeptide is then contacted with ST3Gal3 and asialo-transferrin and becomes linked to transferrin via the sialic acid residue. Then, the polypeptide is sialylated using ST3Gal3 and a sialic acid donor.

Figures 48B, 48C:
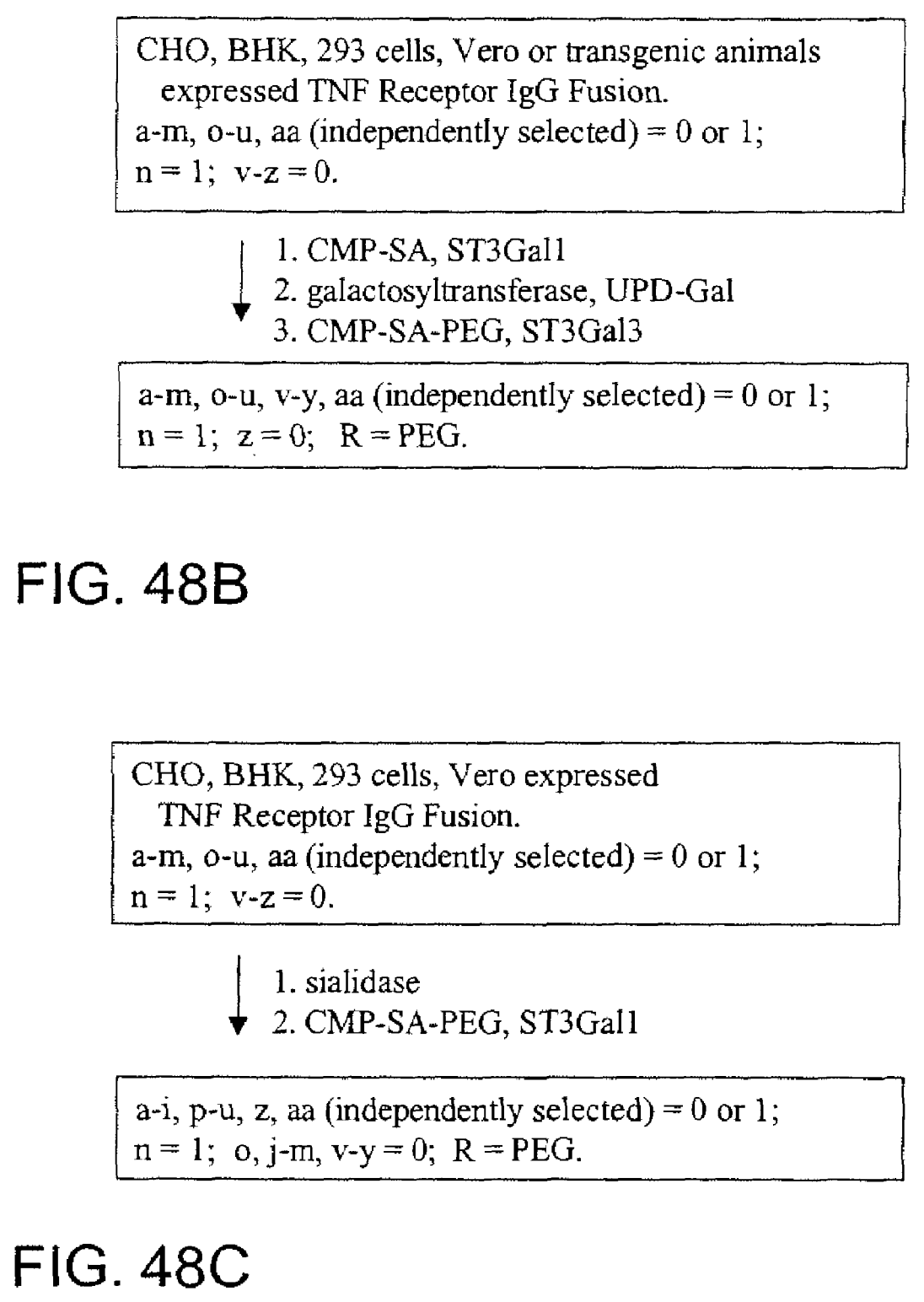

In another exemplary embodiment, the invention provides methods for remodeling TNF receptor IgG fusion protein (TNFR-IgG, or Enbrel™), as shown in FIGS. 48A to 48G. FIG. 48B illustrates a modification procedure in which TNFR-IgG, expressed in a mammalian system is first sialylated with a sialic acid donor and a sialyltransferase, ST3Gal1; the fusion protein is then galactosylated with a galactose donor and a galactosyltransferase; then, the fusion protein is PEGylated via the action of ST3Gal3 and a donor of sialic acid derivatized with PEG. In FIG. 48C, TNFR-IgG expressed in mammalian cells is initially treated with sialidase to trim back sialic acid residues. PEG moieties are subsequently attached to TNFR-IgG by way of transferring PEGylated sialic acid from a donor to the fusion protein in a reaction catalyzed by ST3Gal1. In FIG. 48D, TNFR-IgG is expressed in a mammalian system and modified by addition of PEG through the galactosylation process, which is mediated by a galactosyltransferase using a PEG-galactose donor. In FIG. 48E, TNFR-IgG is expressed in a mammalian system. The first step in remodeling of the fusion protein is adding O-linked sialic acid residues using a sialic acid donor and a sialyltransferase, ST3Gal1. Subsequently, PEGylated galactose is added to the fusion protein using a galactosyltransferase and a suitable donor of galactose with a PEG moiety. In FIG. 48F, TNFR-IgG expressed in mammalian cells is modified first by capping appropriate terminal residues with a sialic acid donor that is modified with levulinic acid, adding a reactive ketone to the sialic acid donor. After addition to a glycosyl residue of the fusion protein, the ketone is derivatized with a moiety such as a hydrazine- or amine-PEG. In FIG. 48G, TNFR-IgG expressed in mammalian cells is remodeled by 2,8-sialyltransferase, which catalyzes the reaction in which PEGylated sialic acid is transferred to the fusion protein from a donor of sialic acid with a PEG moiety.

Figure 49A:
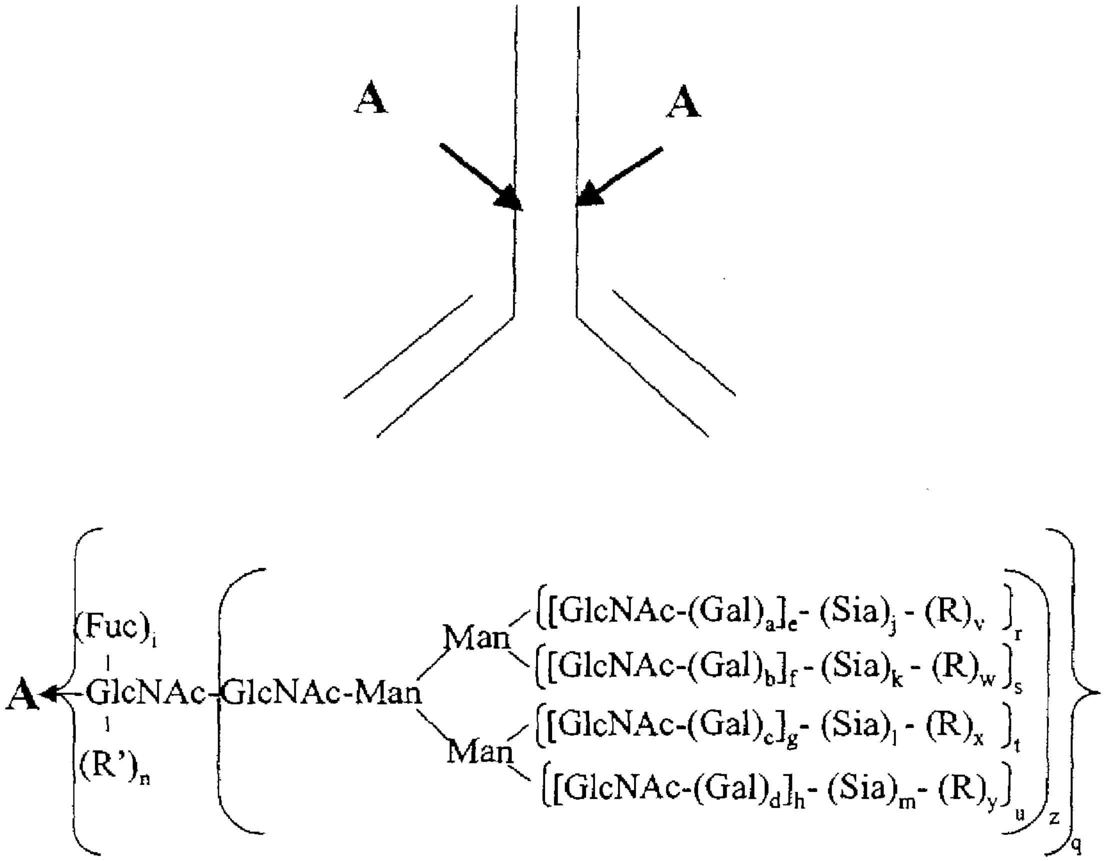
FIG. 49A is a diagram depicting an anti-HER2 monoclonal antibody which has been mutated to contain an N-glycosylation site(s) indicating a residue(s) on the antibody heavy chain which is linked to a glycan contemplated for remodeling, and an exemplary glycan formula linked thereto.

In another exemplary embodiment, the invention provides methods for generating Herceptin™ conjugates, as shown in FIGS. 49A to 49D. In FIG. 49B, Herceptin™ is expressed in a mammalian system and is first galactosylated using a galactose donor and a galactosyltransferase. Herceptin™ is then conjugated with a toxin via a sialic acid through the action of ST3Gal3 using a reactive sialic acid-toxin complex. In FIG. 49C, Herceptin™ produced in either mammalian cells or fungi is conjugated to a toxin through the process of galactosylation, using a galactosyltransferase and a reactive galactose-toxin complex. FIG. 49D contains another scheme of making Herceptin™ conjugates: Herceptin™ produced in fungi is first treated with Endo-H to trim back glycosyl groups, then galactosylated using a galactose donor and a galactosyltransferase, and then conjugated with a radioisotope by way of sialylation, by using ST3Gal3 and a reactive sialic acid-radioisotope complex. Alternatively, the reactive sialic acid moiety may have attached only the chelating moiety can then be loaded with radioisotope at a subsequent stage.

Figure 50A:
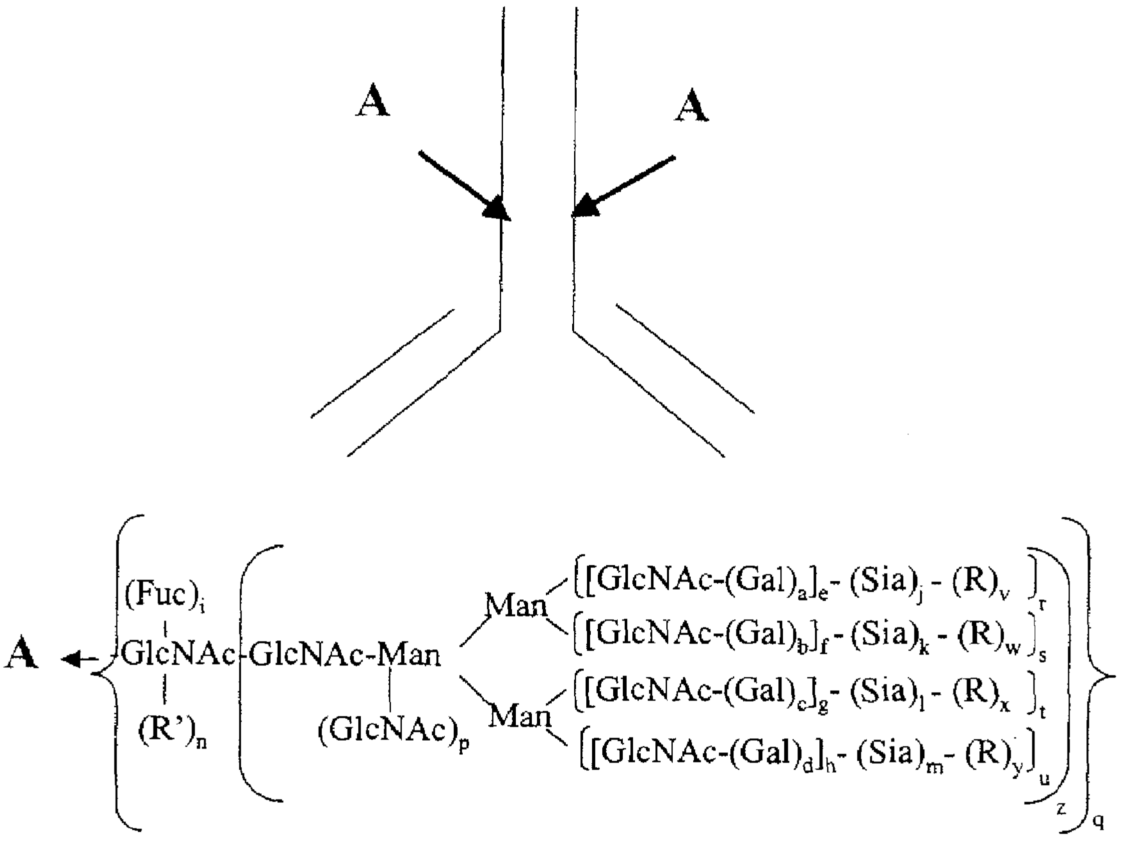
FIG. 50A is a diagram depicting a monoclonal antibody to Protein F peptide which is mutated to contain an N-glycosylation site(s) indicating a residue(s) which is linked to a glycan contemplated for remodeling, and an exemplary glycan formula linked thereto.

In another exemplary embodiment, the invention provides methods for making Synagis™ conjugates, as shown in FIGS. 50A to 50D. In FIG. 50B, Synagis™ expressed in mammalian cells is first galactosylated using a galactose donor and a galactosyltransferase, and then PEGylated using ST3Gal3 and a donor of PEG-sialic acid. In FIG. 50C, Synagis™ expressed in mammalian or fungal cells is PEGylated using a galactosyltransferase and a donor of PEG-galactose. In FIG. 50D, Synagis™ expressed in first treated with Endo-H to trim back the glycosyl groups, then galactosylated using a galactose donor and a galactosyltransferase, and is then PEGylated using ST3Gal3 and a donor of PEG-sialic acid.

Figure 51A:
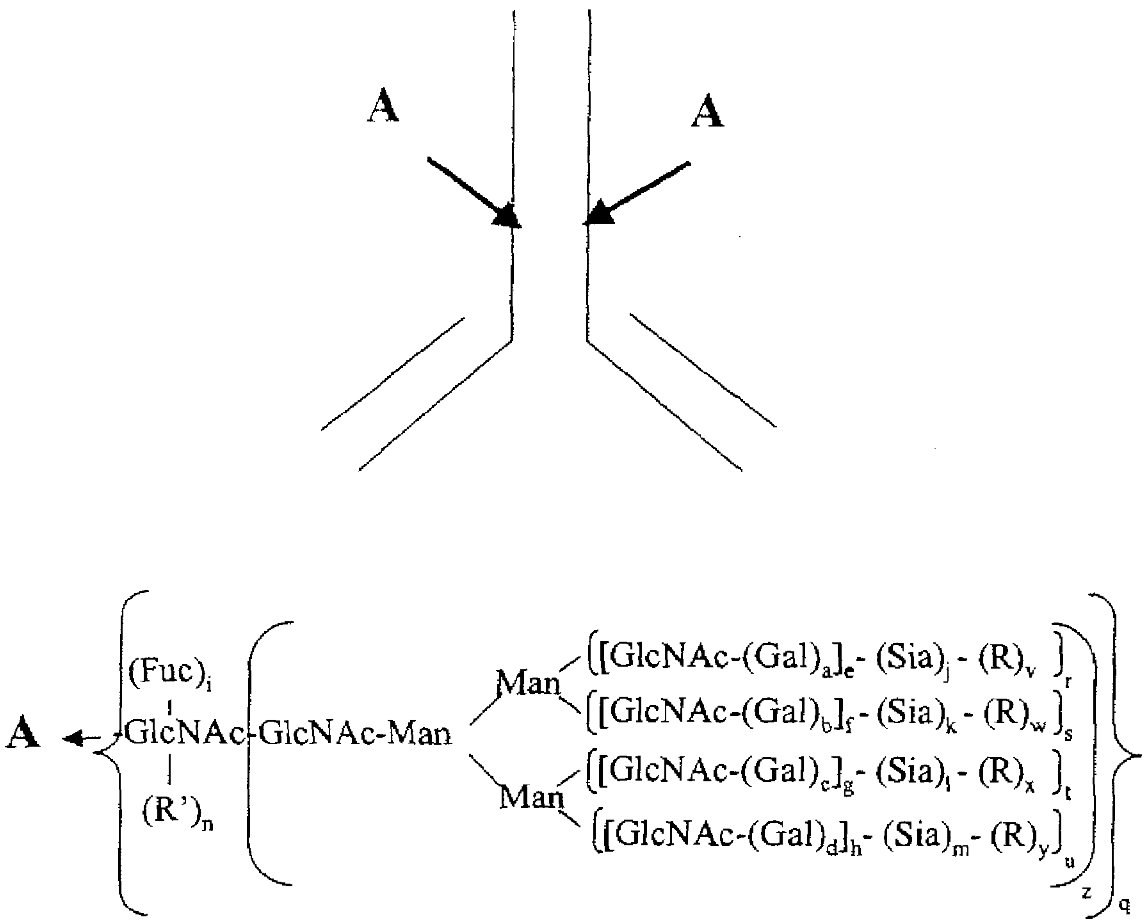
FIG. 51A is a diagram depicting a monoclonal antibody to TNF-α which has an N-glycosylation site(s) indicating a residue which is linked to a glycan contemplated for remodeling, and an exemplary glycan formula linked thereto.
Figure 51D:
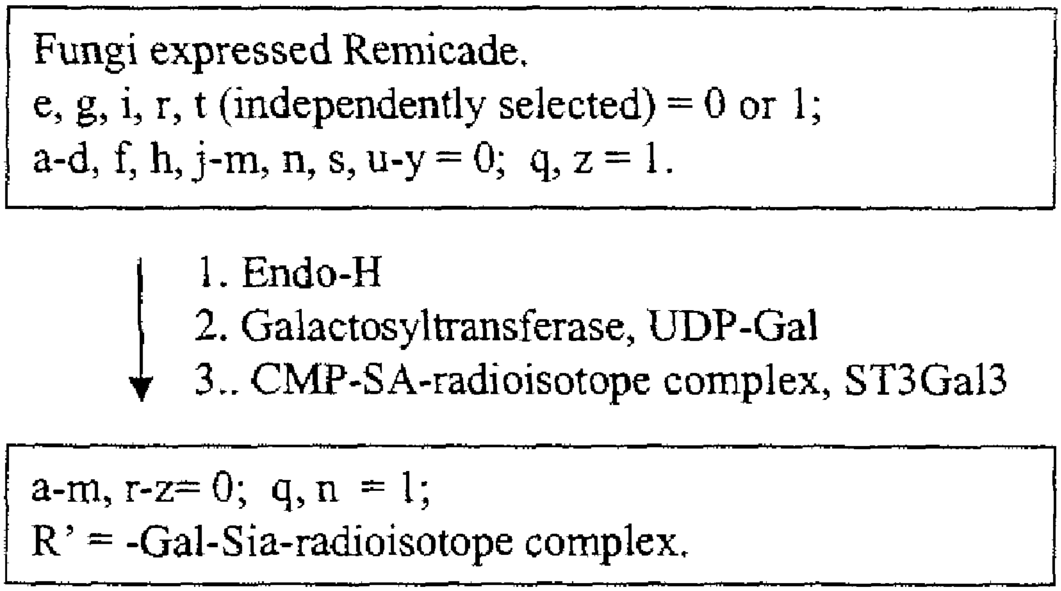

In another exemplary embodiment, the invention provides methods for generating Remicade™ conjugates, as shown in FIGS. 51A to 51D. In FIG. 51B, Remicade™ expressed in a mammalian system is first galactosylated using a galactose donor and a galactosyltransferase, and then PEGylated using ST3Gal3 and a donor of PEG-sialic acid. In FIG. 51C, Remicade™ expressed in a mammalian system is modified by addition of PEGylated galactose using a suitable donor and a galactosyltransferase. In FIG. 51D, Remicade™ expressed in fungi is first treated with Endo-H to trim back the glycosyl chains, then galactosylated using a galactose donor and a galactosyltransferase, and then conjugated to a radioisotope using ST3Gal3 and a reactive sialic acid derivatized with the radioisotope.

Figures 52B, 52C:
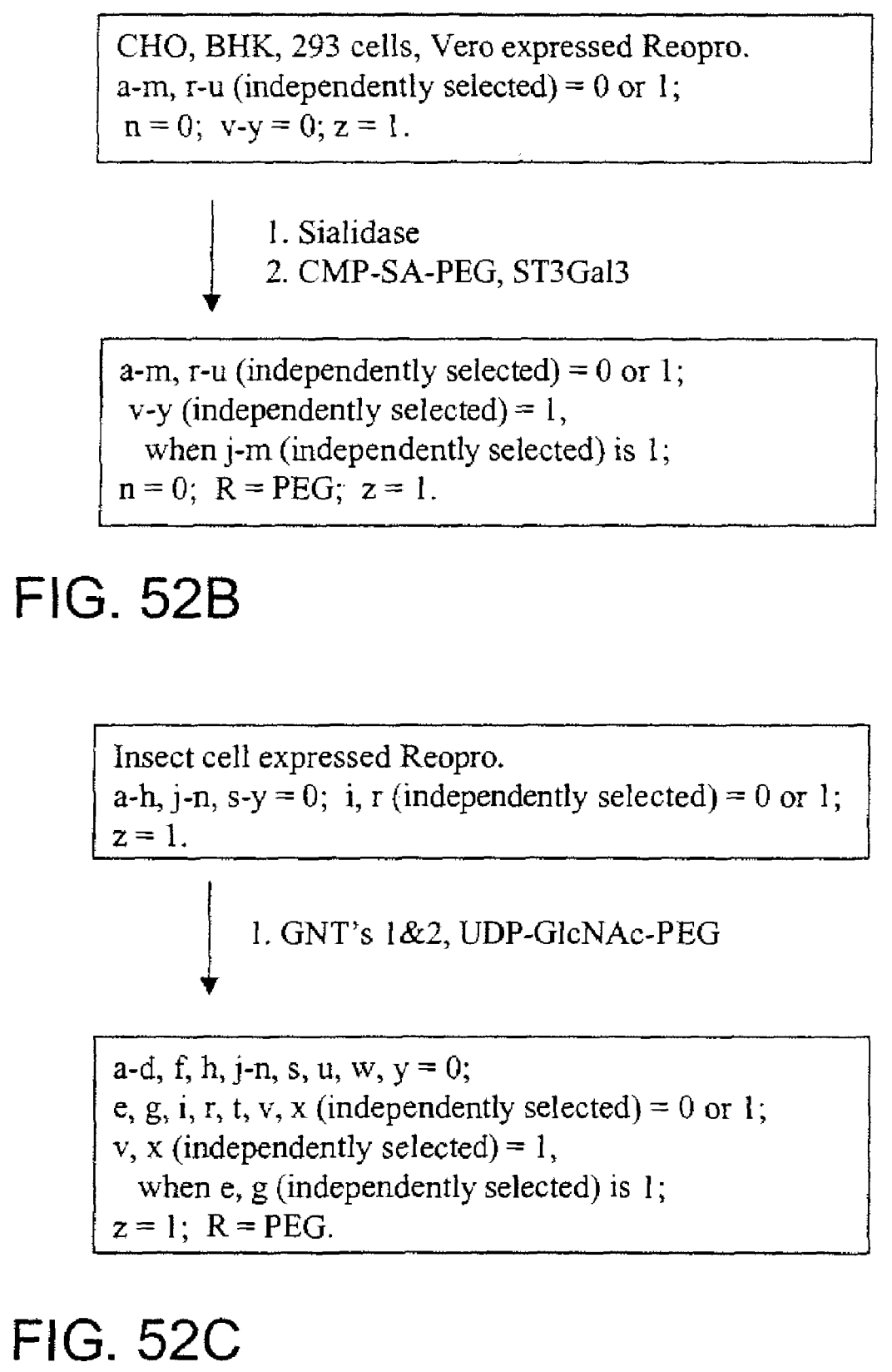
Figure 52E:
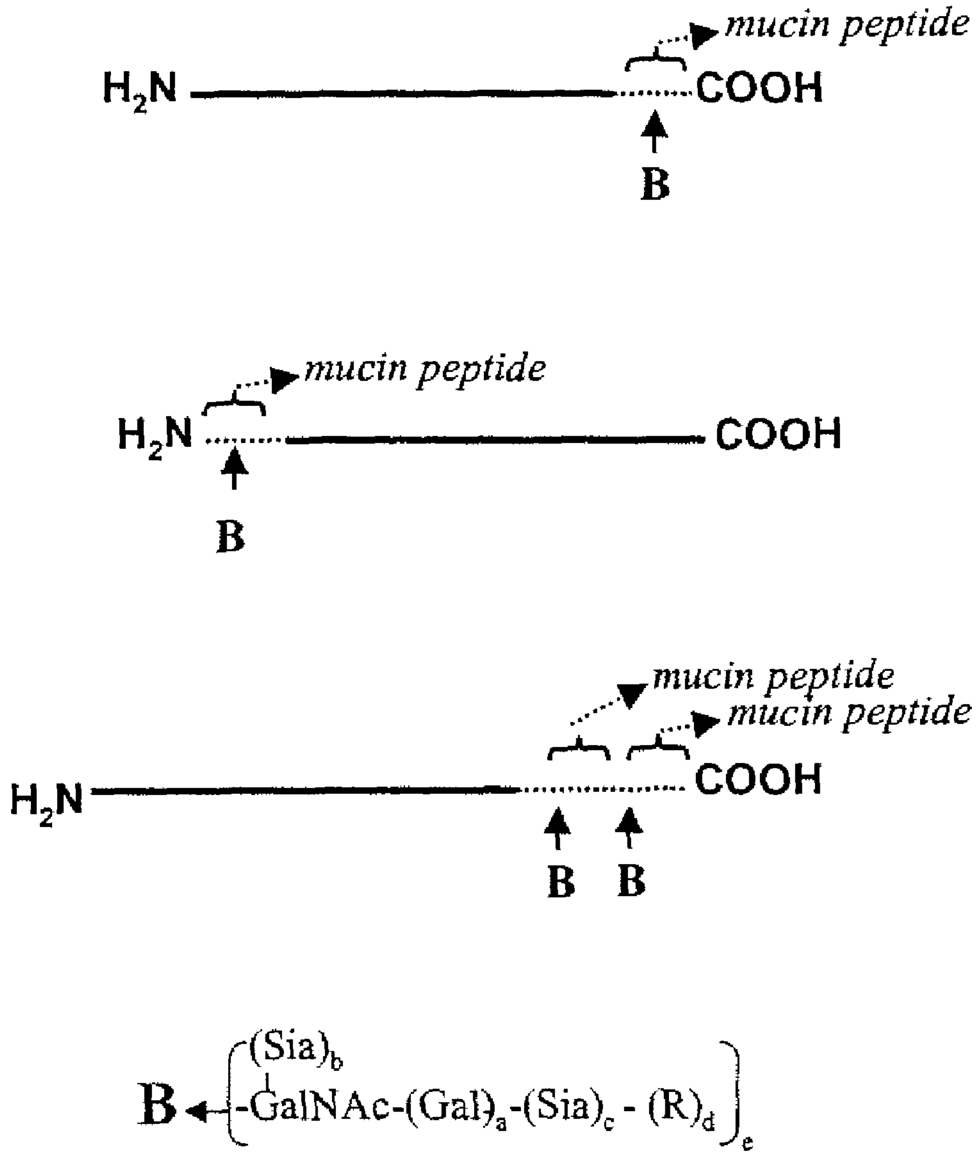
FIG. 52E is a diagram depicting monoclonal antibody to glycoprotein IIb/IIIa-mucin fusion peptides indicating the residues which bind to glycans contemplated for remodeling, and exemplary glycan formulas linked thereto.
Figure 52I:
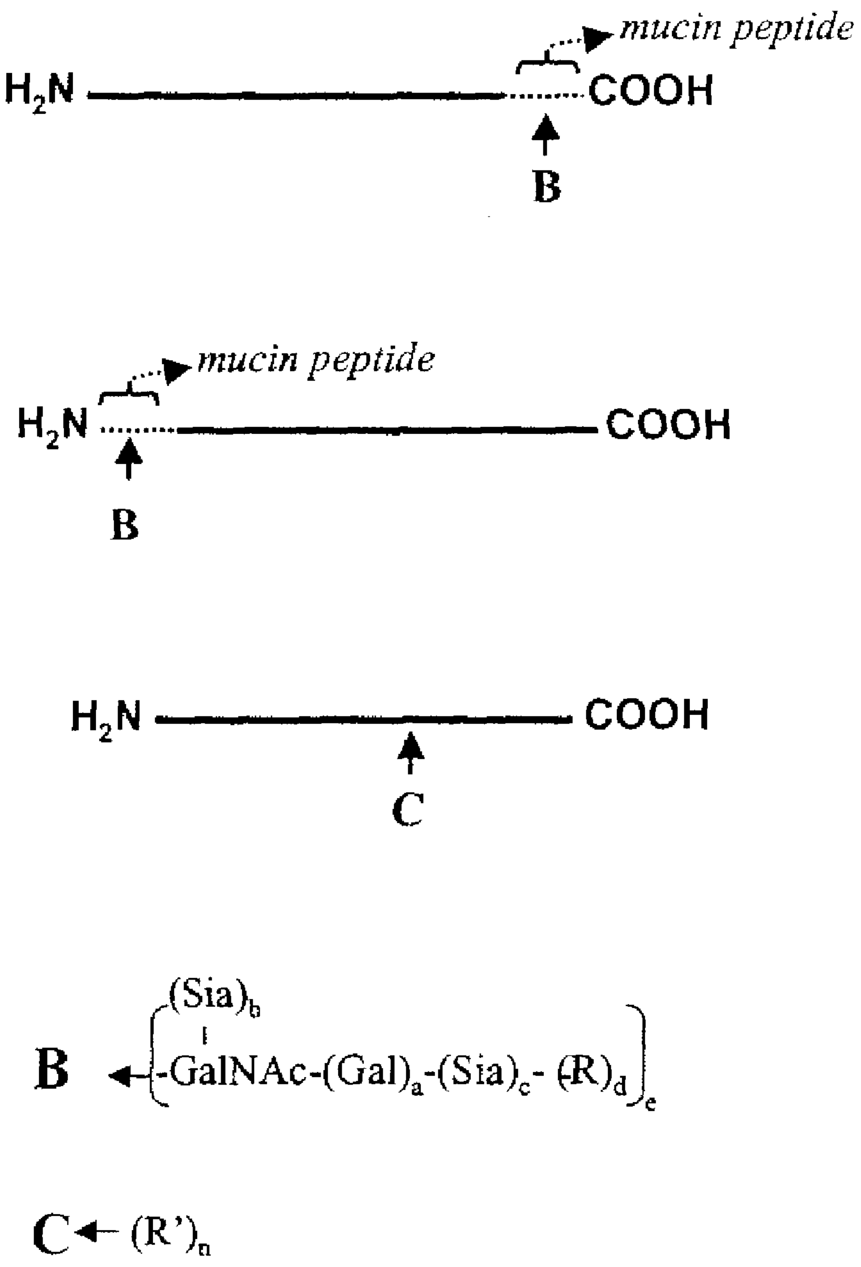
FIG. 52I is a diagram depicting monoclonal antibody to glycoprotein mucin fusion peptides and monoclonal antibody to glycoprotein IIb/IIIa peptides indicating the residues which bind to glycans contemplated for remodeling, and exemplary glycan formulas linked thereto.

In another exemplary embodiment, the invention provides methods for modifying Reopro, which is mutated to contain an N glycosylation site. FIGS. 52A to 52L contain such examples. In FIG. 52B, Reopro expressed in a mammalian system is first treated with sialidase to trim back the sialic acid residues, and then PEGylated using ST3Gal3 and a donor of PEG-sialic acid. In FIG. 52C, Reopro expressed in insect cells is modified by addition of PEGylated N-acetylglucosamine using an appropriate donor and GnT-I and/or II. In FIG. 52D, Reopro expressed in yeast is first treated with Endo-H to trim back the glycosyl groups. Subsequently, the protein is PEGylated using a galactosyltransferase and a donor of PEG-galactose. In FIG. 52F, Reopro expressed in mammalian cells is first treated with sialidase to trim back the sialic acid residues and then PEGylated with ST3Gal1 using a donor of PEGylated sialic acid. In FIG. 52G, Reopro expressed in insect cells is modified by PEGylation using a galactosyltransferase and a donor of PEG-galactose. In FIG. 52H, Reopro expressed in bacterial first has N-acetylgalactosamine added using N-acetylgalactosamine transferase and a suitable donor. The protein is then PEGylated using a sialyltransferase and a donor of PEG-sialic acid. In FIG. 52J, Reopro expressed in bacteria is modified in a different scheme: it is PEGylated via the action of N-acetylgalactosamine transferase, using a donor of PEGylated N-acetylgalactosamine. In FIG. 52K, bacterially expressed Reopro is modified in yet another method: first, the polypeptide is contacted with N-acetylgalactosamine transferase and a donor of N-acetylgalactosamine that is derivatized with a reactive sialic acid via a linker, so that the polypeptide is attached to the reactive sialic acid via the linker and N-acetylgalactosamine. The polypeptide is then contacted with ST3Gal3 and asialo-transferrin and thus becomes connected with transferrin via the sialic acid residue. Then, the polypeptide is capped with sialic acid residues using a proper donor and ST3Gal3. FIG. 52L offers an additional scheme of modifying bacterially expressed Reopro. The polypeptide is first exposed to NHS-CO-linker-SA-CMP and becomes connected with the reactive sialic acid through the linker. The polypeptide is then contacted with ST3Gal3 and asialo-transferrin and thus becomes connected with transferrin via the sialic acid residue. Then, the polypeptide is capped with sialic acid residues using a proper donor and ST3Gal3.

Figure 53A:
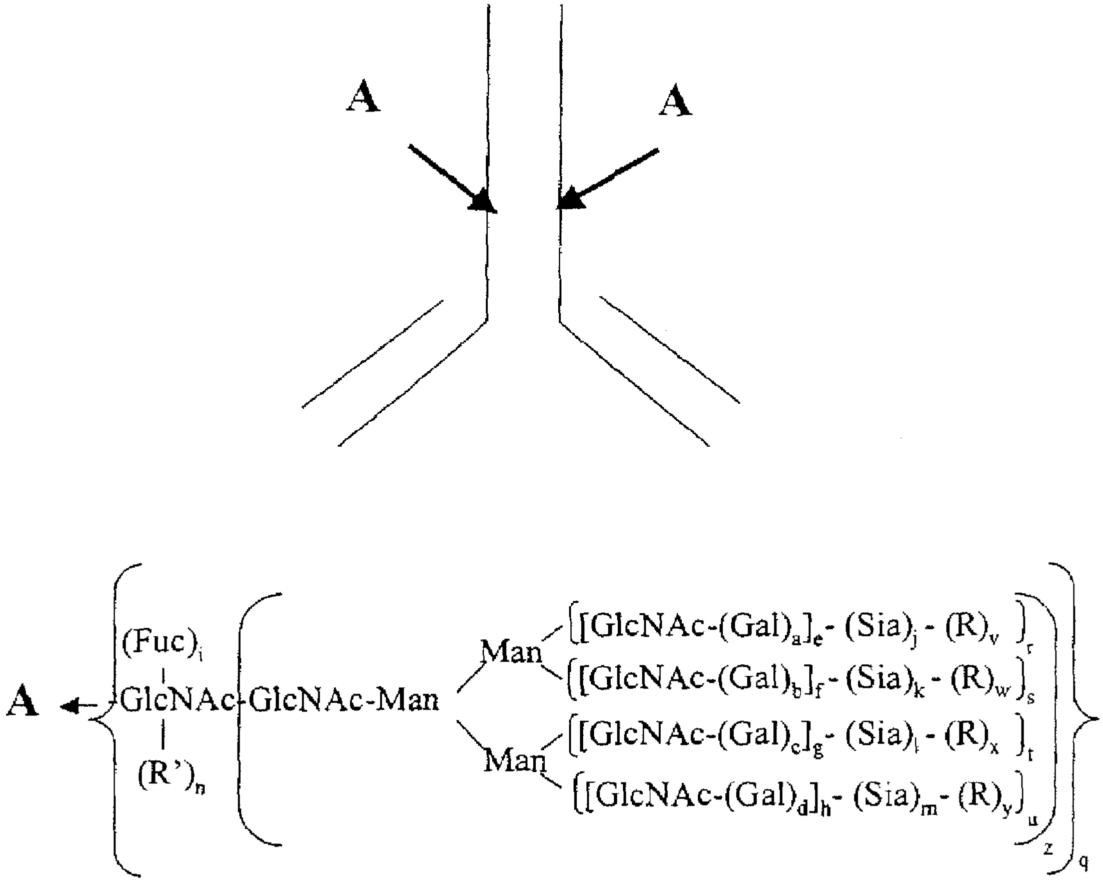
FIG. 53A is a diagram depicting monoclonal antibody to CD20 which have been mutated to contain an N-glycosylation site(s) indicating the residue which is linked to glycans contemplated for remodeling, and exemplary glycan formulas linked thereto.
Figures 53F, 53G:
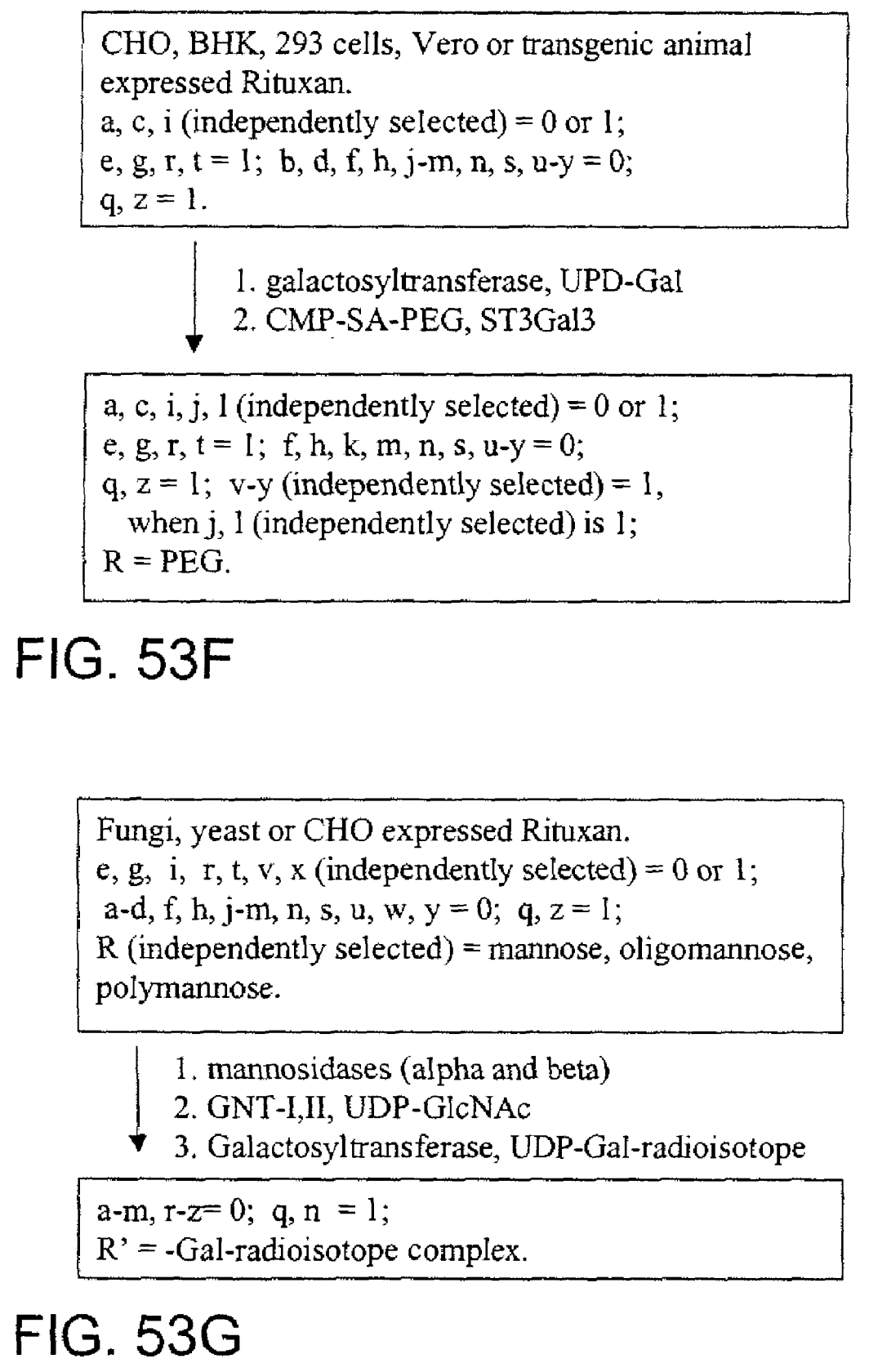

In another exemplary embodiment, the invention provides methods for producing Rituxan™ conjugates. FIGS. 53A to 53G presents some examples. In FIG. 53B, Rituxan™ expressed in various mammalian systems is first galactosylated using a proper galactose donor and a galactosyltransferase. The peptide is then functionalized with a sialic acid derivatized with a toxin moiety, using a sialic acid donor and ST3Gal3. In FIG. 53C, Rituxan™ expressed in mammalian cells or fungal cells is galactosylated using a galactosyltransferase and a galactose donor, which provides the peptide galactose containing a drug moiety. FIG. 53D provides another example of remodeling Rituxan™ expressed in a fungal system. The polypeptide's glycosyl groups are first trimmed back using Endo-H. Galactose is then added using a galactosyltransferase and a galactose donor. Subsequently, a radioisotope is conjugated to the molecule through a radioisotope-complexed sialic acid donor and a sialyltransferase, ST3Gal3. In FIG. 53F, Rituxan™ is expressed in a mammalian system and first galactosylated using a galactosyltransferase and a proper galactose donor; sialic acid with a PEG moiety is then attached to the molecule using ST3Gal3 and a PEGylated sialic acid donor. As shown in FIG. 53G, Rituxan™ expressed in fungi, yeast, or mammalian cells can also be modified in the following process: first, the polypeptide is treated with α- and β-mannosidases to remove terminal mannosyl residues; GlcNAc is then attached to the molecule using GnT-I, II and a GlcNAc donor, radioisotope is then attached by way of galactosylation using a galactosyltransferase and a donor of galactose that is coupled to a chelating moiety capable of binding a radioisotope.

Figures 54B, 54C:
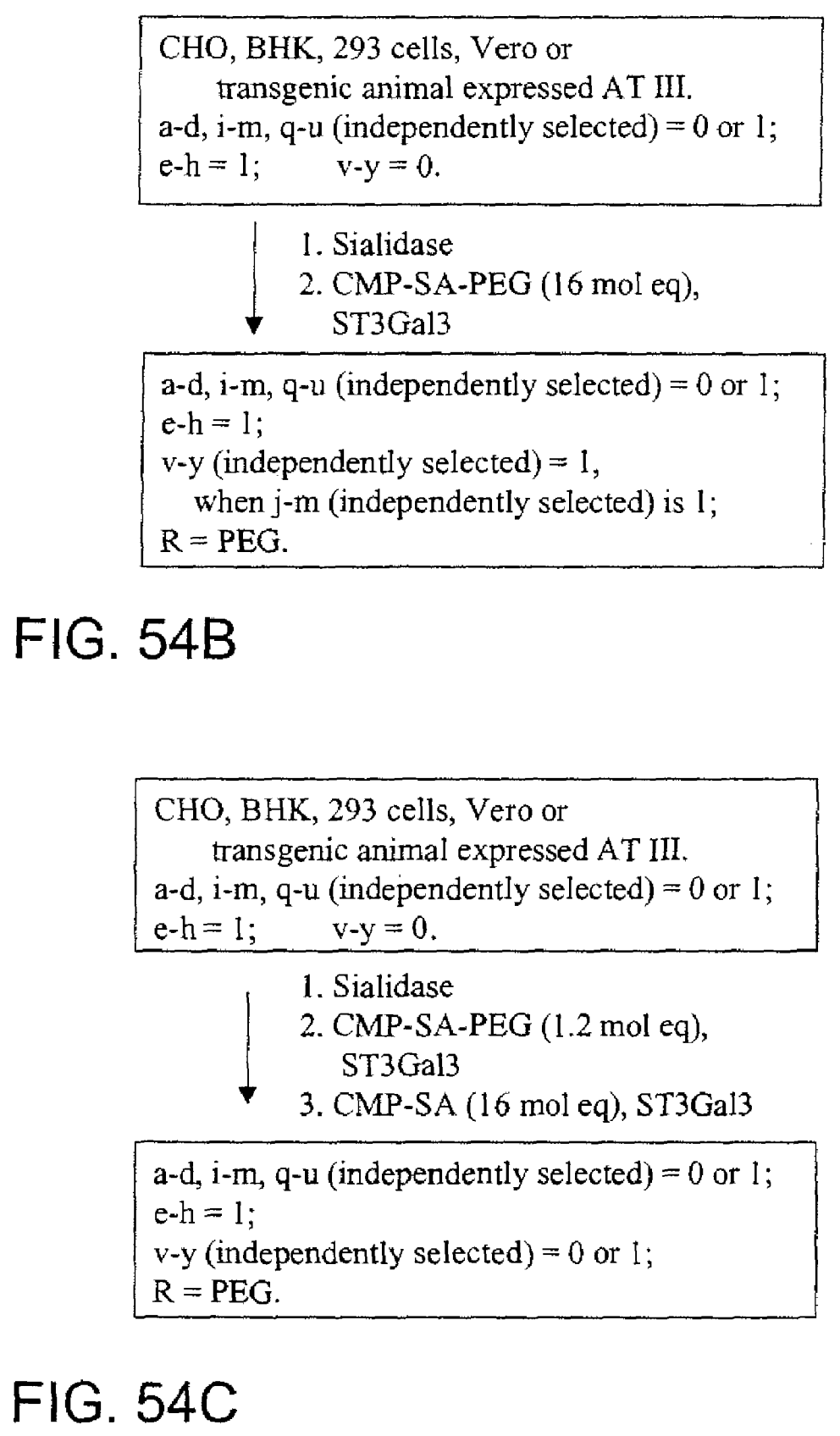
Figure 54H:
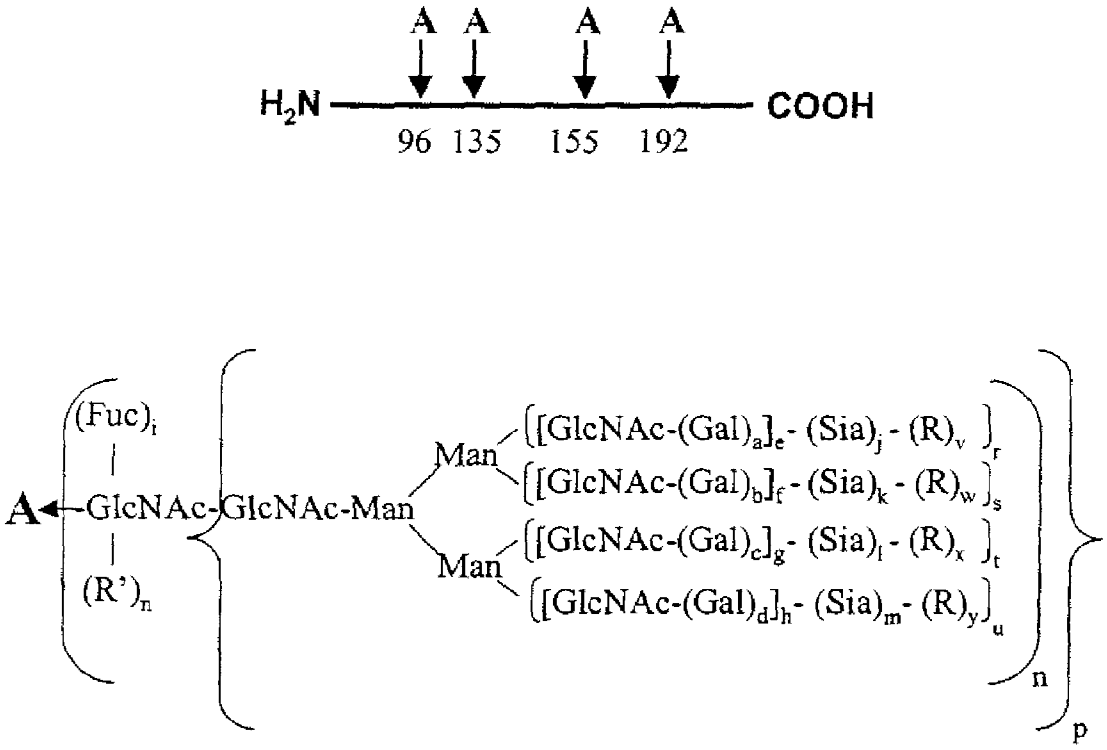
FIG. 54H is a diagram depicting the anti-thrombin III peptide indicating the amino acid residues to which an N-linked glycan is linked, and an exemplary glycan formula linked thereto.
Figures 54M, 54N:
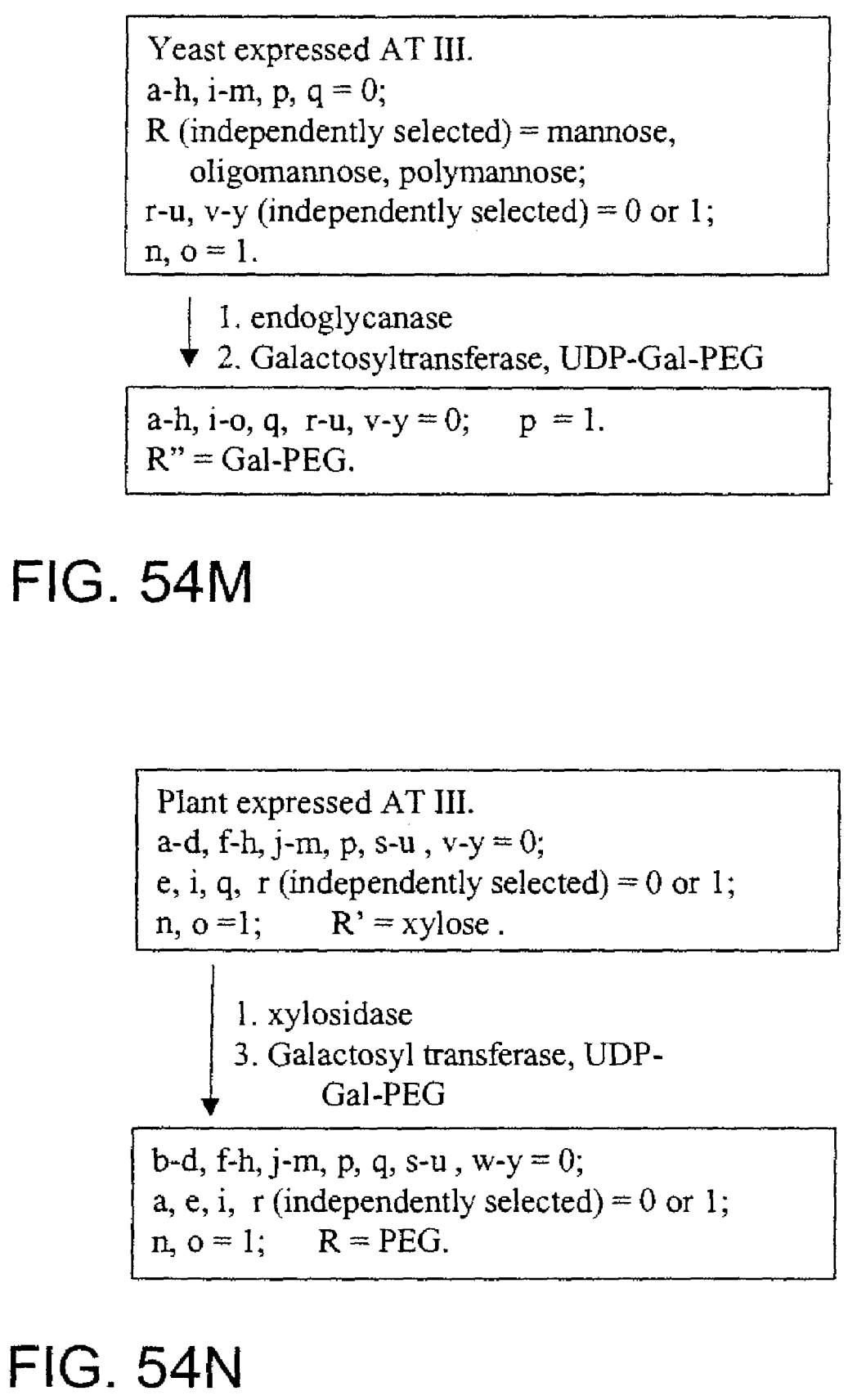

In another exemplary embodiment, the invention provides methods for modifying anti-thrombin III (AT III). FIGS. 54A to 54O present some examples. In FIG. 54B, anti-thrombin III expressed in various mammalian systems is remodeled by the addition of one or more terminal sialic acid-PEG moieties. The AT III molecule is first contacted with sialidase to remove terminal sialic acid moieties. Then, the molecule is contacted with a sialyltransferase and an appropriate sialic acid donor that has been derivatized with a PEG moiety. In FIG. 54C, AT III expressed in various mammalian systems is remodeled by the addition of sialic acid-PEG moieties. The AT III molecule is contacted with sialidase to remove terminal sialic acid moieties. The molecule is then contacted with a ST3Gal3 and an appropriate sialic acid donor that has been derivatized with a PEG moiety at 1.2 mol eq. The molecule is then contacted with a ST3Gal3 and an appropriate sialic acid donor to cap remaining terminal galactose moieties. In FIG. 54D, AT III is expressed in NSO murine myeloma cells is remodeled to have complex glycan molecules with terminal sialic acid-PEG moieties. The AT III molecule is contacted with sialidase and α-galactosidase to remove terminal sialic acid and galactose moieties. The molecule is then contacted with galactosyltransferase and an appropriated galactose donor. The molecule is then contacted with a ST3Gal3 and an appropriate sialic acid donor that has been derivatized with a PEG moiety. In FIG. 54E, AT III expressed in various mammalian systems is remodeled to have nearly complete terminal sialic acid-PEG moieties. The AT III molecule is contacted with sialidase to remove terminal sialic acid moieties. The molecule is then contacted with a ST3Gal3 and an appropriate sialic acid donor that has been derivatized with a PEG moiety at 16 mol eq. The molecule is then contacted with ST3Gal3 and an appropriate sialic acid donor to cap remaining terminal galactose moieties. In FIG. 54F, AT III expressed in various mammalian systems is remodeled by the addition of one or more terminal sialic acid PEG moieties. The AT III molecule is contacted with ST3Gal3 and an appropriate sialic acid donor that has been derivatized with a levulinate moiety. The molecule is then contacted with hydrazine-PEG. In FIG. 54G, AT III expressed in various mammalian systems is remodeled by the addition of one or more terminal poly-α2,8-linked sialic acid moieties. The AT III molecule is contacted with poly-α2,8-sialyltransferase and an appropriate sialic acid donor. In FIG. 54I, AT III expressed in insect, yeast or fungi cells is remodeled by the addition of branching N-N-acetylglucosamine-PEG moieties. The AT III molecule is contacted with GnT-I and an appropriate N-acetylglucosamine donor that has been derivatized with PEG. In FIG. 54J, AT III expressed in yeast is remodeled by removing high mannose glycan structures and the addition of terminal sialic acid-PEG moieties. The AT III molecule is contacted with endoglycanase to trim back glycosyl groups. The molecule is then contacted with galactosyltransferase and an appropriate galactose donor. The molecule is then contacted with ST3Gal3 and an appropriate sialic acid donor that has been derivatized with a PEG moiety. In FIG. 54K, AT III expressed in various mammalian systems is remodeled by the addition of glycoconjugated transferrin. The AT III molecule is contacted with ST3Gal3 and an appropriate sialic acid donor that has been derivatized with a linker-galactose donor moiety. The molecule is then contacted with galactosyltransferase and endoglycanase-treated transferrin. In FIG. 54M, AT III expressed in yeast is remodeled by the removal of mannose glycan structures and the addition of terminal galactose-PEG moieties. The molecule is contacted with endoglycanase to trim back glycosyl groups. The molecule is further contacted with galactosyltransferase and an appropriate galactose donor that has been derivatized with a PEG moiety. In FIG. 54N, AT III expressed in plant cells is remodeled by converting the glycan structures into mammalian-type complex glycans and then adding one or more terminal galactose-PEG moieties. The AT III molecule is contacted with xylosidase to remove xylose residues. The molecule is then contacted with galactosyltransferase and an appropriate galactose donor that has been derivatized with a PEG moiety. In FIG. 54O, AT III expressed in various mammalian systems is remodeled by the addition of one or more terminal sialic acid-PEG moieties to terminal galactose moieties. The AT III molecule is contacted with ST3Gal3 and an appropriate sialic acid PEG donor that has been derivatized with PEG.

Figures 55B, 55C:
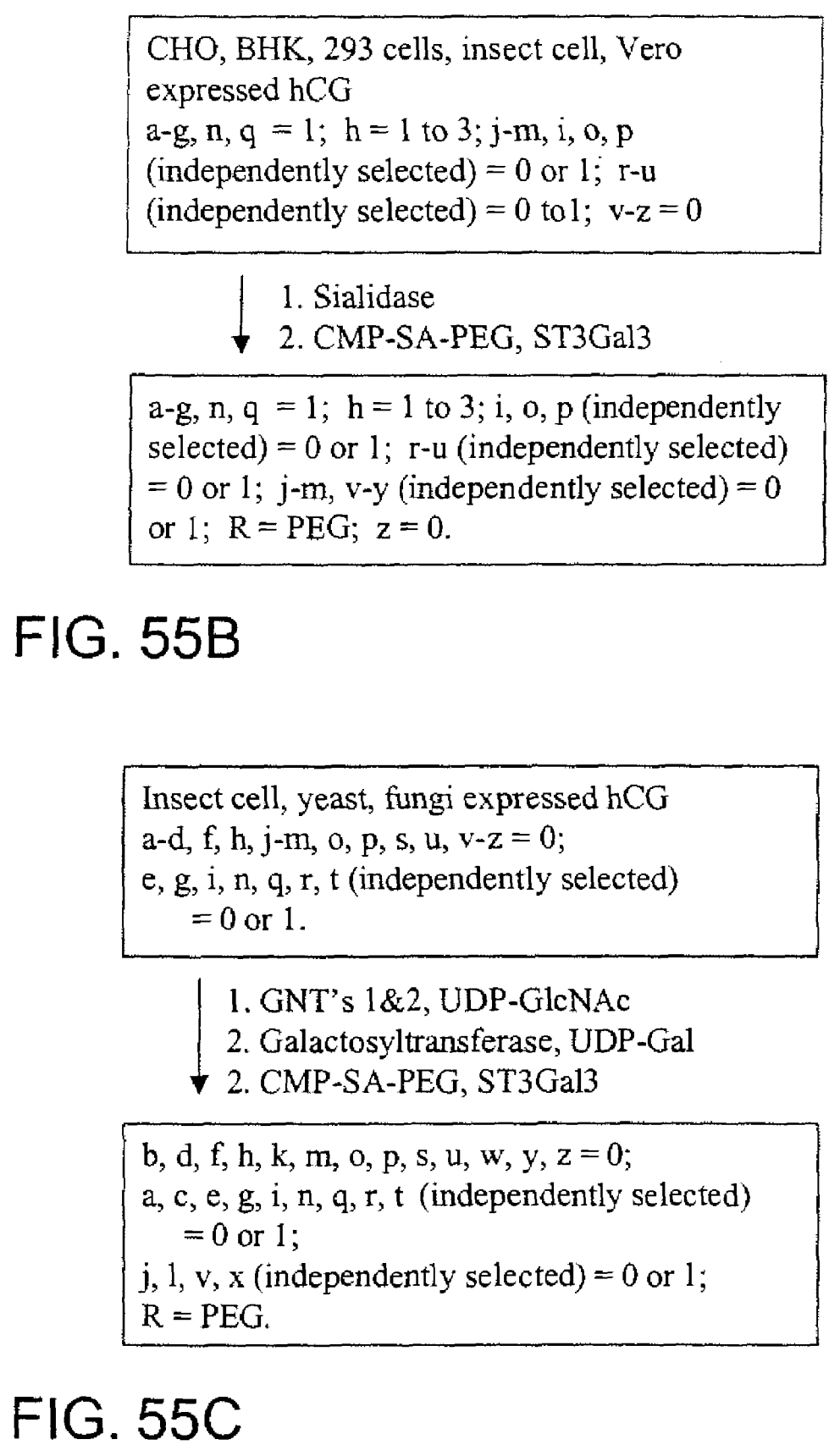
Figure 55F:
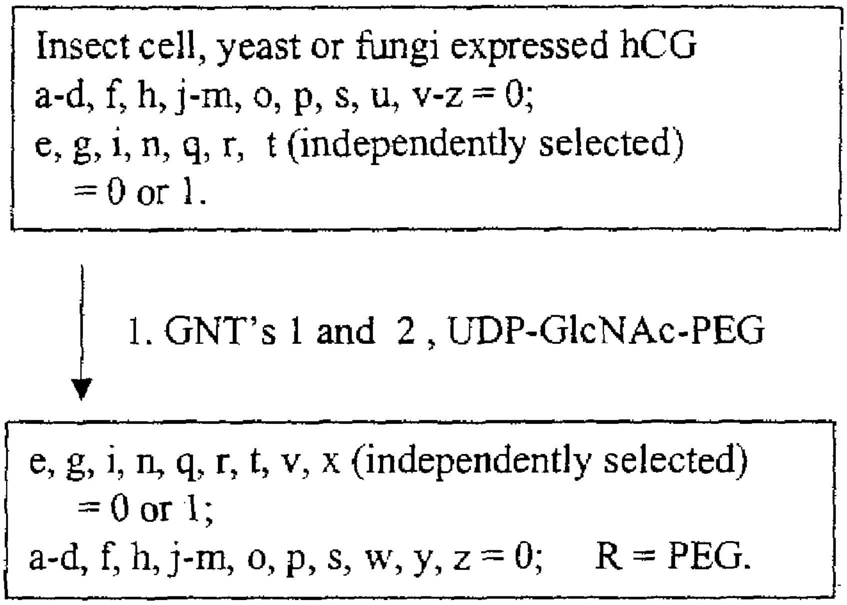
Figure 55G:
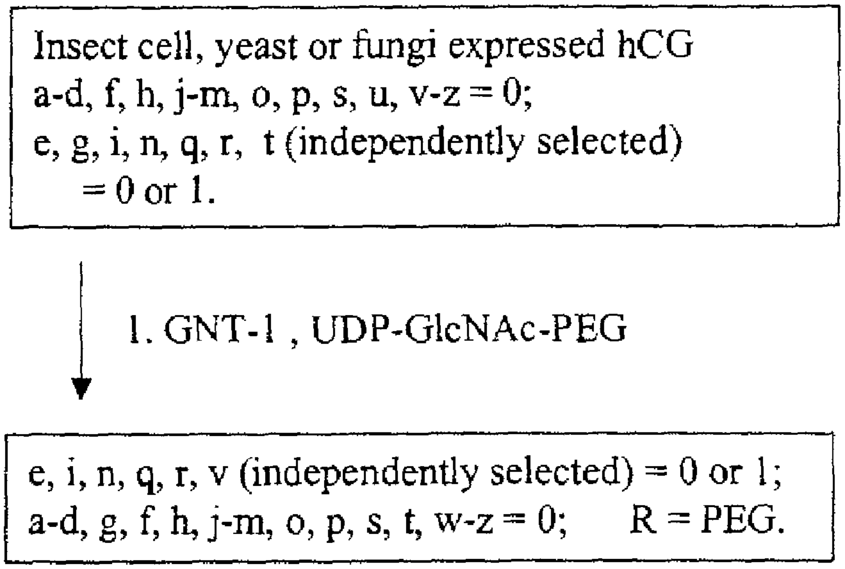
Figure 55J:
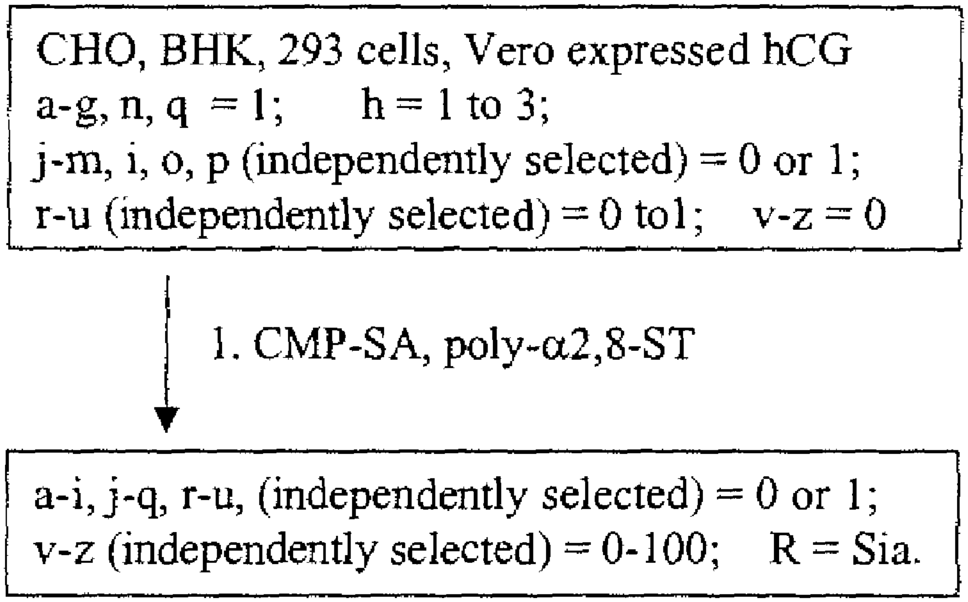

In another exemplary embodiment, the invention provides methods for modifying the α and β subunits of human Chorionic Gonadotropin (hCG). FIGS. 55A to 55J present some examples. In FIG. 55B, hCG expressed in various mammalian and insect systems is remodeled by the addition of terminal sialic acid-PEG moieties. The hCG molecule is contacted with sialidase to remove terminal sialic acid moieties. The molecule is then contacted with ST3Gal3 and an appropriate sialic acid donor molecule that has been derivatized with a PEG moiety. In FIG. 55C, hCG expressed in insect cell, yeast or fungi systems is remodeled by building out the N-linked glycans and the addition of terminal sialic acid-PEG moieties. The hCG molecule is contacted with GnT-I and GnT-II, and an appropriated N-acetylglucosamine donor. The molecule is then contacted with galactosyltransferase and an appropriate galactose donor. The molecule is further contacted with ST3Gal3 and an appropriate sialic acid donor that has been derivatized with a PEG moiety. In FIG. 55D, hCG expressed in various mammalian and insect systems is remodeled by the addition of one or more terminal sialic acid-PEG moieties on O-linked glycan structures. The hCG molecule is contacted with sialidase to remove terminal sialic acid moieties. The molecule is then contacted with ST3Gal3 and an appropriate sialic acid donor to cap the glycan structures with sialic acid moieties. The molecule is then contacted with ST3Gal 1 and an appropriate sialic acid donor that has been derivatized with PEG. In FIG. 55E, hCG expressed in various mammalian and insect systems is remodeled by the addition of sialic acid-PEG moieties to N-linked glycan structures. The hCG molecule is contacted with ST3Gal3 and an appropriate sialic acid donor that has been derivatized with PEG. In FIG. 55F, hCG expressed in insect cells, yeast or fungi, is remodeled by the addition of terminal N-acetylglucosamine-PEG molecules. The hCG molecule is contacted with GnT-I and GnT-II, and an appropriate N-acetylglucosamine donor that has been derivatized with PEG. In FIG. 55G, hCG expressed in insect cells, yeast or fungi, is remodeled by the addition of not more than one N-acetylglucosamine-PEG moiety per N-linked glycan structure. The hCG molecule is contacted with GnT-I and an appropriate N-acetylglucosamine donor that has been derivatized with a PEG moiety. In FIG. 55H, hCG expressed in various mammalian systems is remodeled by the addition of one or more terminal sialic acid-PEG moiety to O-linked glycan structures. The hCG molecule is contacted with ST3Gal3 and an appropriate sialic acid donor that has been derivatized with PEG. In FIG. 55I, hCG expressed in various mammalian systems is remodeled by the addition of terminal sialic acid-PEG moieties. The hCG molecule is contacted with α2,8-SA and an appropriate sialic acid donor that has been derivatized with a PEG moiety. In FIG. 55J, hCG expressed in various mammalian systems is remodeled by the addition of terminal sialic acid moieties. The hCG molecule is contacted with poly-alpha-2,8-ST and an appropriate sialic acid donor that has been derivatized with a PEG moiety.

In another exemplary embodiment, the invention provides methods for modifying alpha-galactosidase A (Fabrazyme™). FIGS. 56A to 56J present some examples. In FIG. 56B, alpha-galactosidase A expressed in and secreted from various mammalian and insect systems is remodeled by the addition of one or more terminal galactose-PEG-transferrin moieties. The alpha-galactosidase A molecule is contacted with Endo-H to trim back glycosyl groups. The molecule is then contacted with galactosyltransferase and an appropriate galactose donor that has been derivatized with PEG and transferrin. In FIG. 56C, alpha-galactosidase A expressed in and secreted from various mammal and insect cell systems is remodeled by the addition of one or more terminal sialic acid-linker-mannose-6-phosphate moieties. The alpha-galactosidase A molecule is contacted with sialidase to remove terminal sialic acid moieties. The molecule is further contacted with ST3Gal3 and an appropriate sialic acid donor that has been conjugated via a linker to mannose-6-phosphate. In FIG. 56D, alpha-galactosidase A expressed in NSO murine myeloma cells is remodeled by the addition of terminal sialic acid-linker-mannose-6-phosphate moieties. The alpha-galactosidase A molecule is contacted with sialidase and α-galactosidase to remove terminal sialic acid and galactose moieties. The molecule is then contacted with galactosyltransferase and an appropriate galactose donor. The molecule is then contacted with sialyltransferase and an appropriate sialic acid donor that has been conjugated via a linker to mannose-6-phosphate. In FIG. 56E, alpha-galactosidase A expressed in and secreted from various mammalian and insect cell systems is remodeled by the addition of one or more terminal sialic acid-PEG moieties. The alpha-galactosidase A molecule is contacted with sialidase to remove terminal sialic acid moieties. The molecule is then contacted with sialyltransferase and an appropriate sialic acid donor that has been derivatized with a PEG moiety. In FIG. 56F, alpha-galactosidase A expressed in mammalian, insect, yeast or fungi systems, is remodeled by the addition of one or more terminal mannose-linker-ApoE moieties. The alpha-galactosidase A molecule is contacted with mannosyltransferase and an appropriate mannose donor that has been conjugated via a linker to ApoE. In FIG. 56G, alpha-galactosidase A expressed in mammalian, insect, yeast or fungal systems is remodeled by the addition of galactose-linker-alpha2-macroglobulin moieties. The alpha-galactosidase A molecule is contacted with Endo-H to trim back glycosyl groups. The molecule is then contacted with galactosyltransferase and an appropriate galactose donor that has been conjugated via a linker to alpha2-macroglobulin. In FIG. 56H, alpha-galactosidase A expressed in insect, yeast and fungal systems, is remodeled by the addition of one or more N-acetylglucosamine-PEG-mannose-6-phosphate moieties. The alpha-galactosidase molecule is contacted with GnT-I and an appropriate N-acetyl-glucosamine donor that has been derivatized with PEG and mannose-6-phosphate. In FIG. 56I, alpha-galactosidase A expressed in insect, yeast or fungal systems, is remodeled by the addition of one or more terminal galactose-PEG-transferrin moieties. The alpha-galactosidase A molecule is contacted with GnT-I and an appropriate N-acetyl-glucosamine donor. The molecule is then contacted with galactosyltransferase and an appropriate galactose donor that has been derivatized with PEG and transferrin. In FIG. 56J, alpha-galactosidase A expressed in insect, yeast or fungi systems is remodeled by the addition of one or more terminal sialic acid-PEG-melanotransferrin moieties. The alpha-galactosidase A molecule is contacted with GnT-I and GnT-II and an appropriate N-acetyl-glucosamine donor. The molecule is then contacted with galactosyltransferase and an appropriate galactose donor. The molecule is then contacted with sialyltransferase and an appropriate sialic acid donor that has been derivatized with PEG and melanotransferrin.

Figures 57B, 57C:
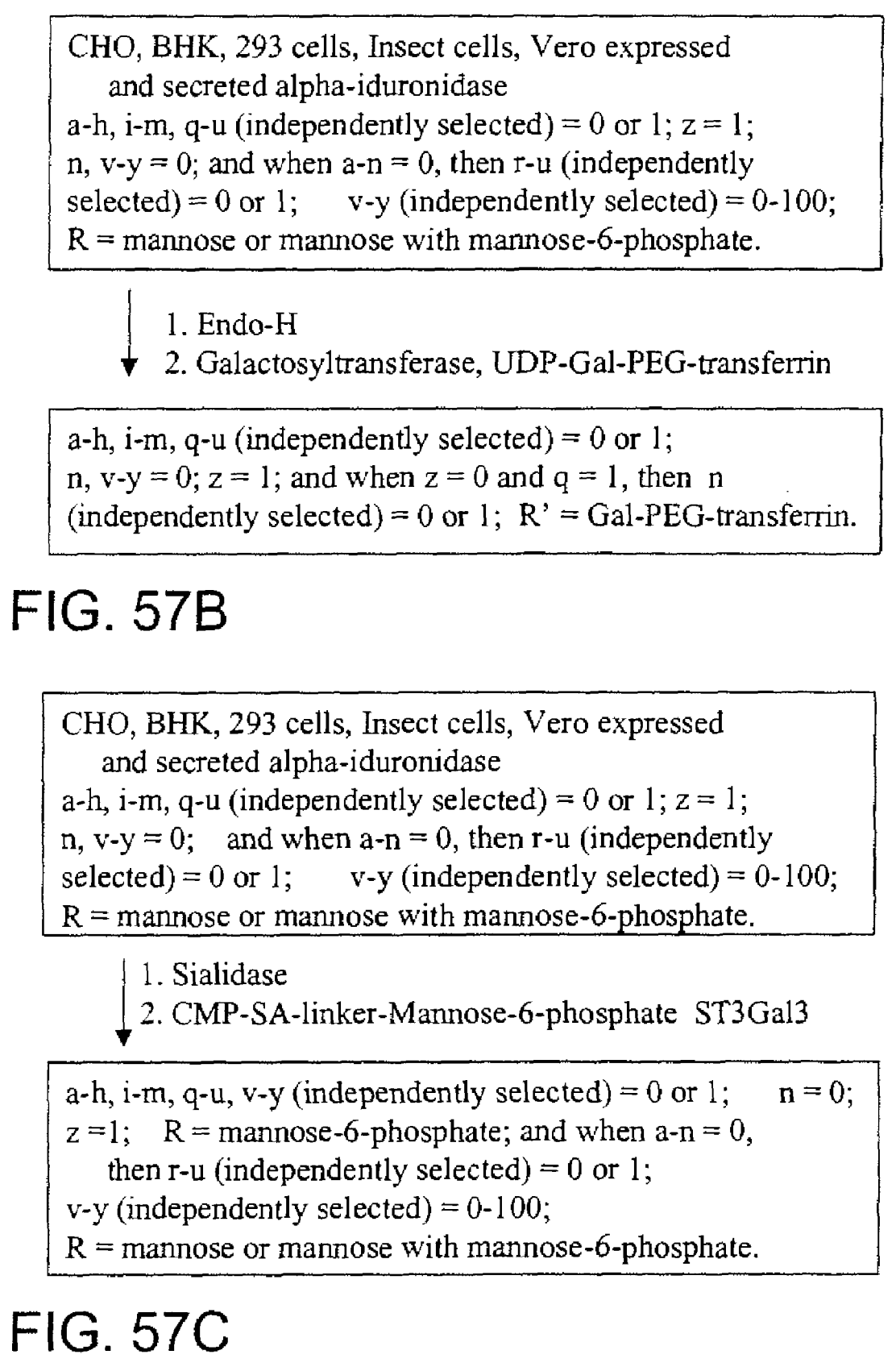

In another exemplary embodiment, the invention provides methods for modifying alpha-iduronidase (Aldurazyme™). FIGS. 57A to 57J present some examples. In FIG. 57B, alpha-iduronidase expressed in and secreted from various mammalian and insect systems is remodeled by the addition of one or more terminal galactose-PEG-transferrin moieties. The alpha-iduronidase molecule is contacted with Endo-H to trim back glycosyl groups. The molecule is then contacted with galactosyltransferase and an appropriate galactose donor that has been derivatized with PEG and transferrin. In FIG. 57C, alpha-iduronidase expressed in and secreted from various mammal and insect cell systems is remodeled by the addition of terminal sialic acid-linker-mannose-6-phosphate moieties. The alpha-iduronidase molecule is contacted with sialidase to remove terminal sialic acid moieties. The molecule is then contacted with ST3Gal3 and an appropriate sialic acid donor that has been conjugated via a linker to mannose-6-phosphate. In FIG. 57D, alpha-iduronidase expressed in NSO murine myeloma cells is remodeled by the addition of one or more terminal sialic acid-linker-mannose-6-phosphate moieties. The alpha-iduronidase molecule is contacted with sialidase and α-galactosidase to remove terminal sialic acid and galactose moieties. The molecule is then contacted with galactosyltransferase and an appropriate galactose donor. The molecule is further contacted with sialyltransferase and an appropriate sialic acid donor that has been conjugated via a linker to mannose-6-phosphate. In FIG. 57E, alpha-iduronidase expressed in and secreted from various mammalian and insect cell systems is remodeled by the addition of one or more terminal sialic acid-PEG moieties. The alpha-iduronidase molecule is contacted with sialidase to remove terminal sialic acid moieties. The molecule is further contacted with sialyltransferase and an appropriate sialic acid donor that has been derivatized with a PEG moiety. In FIG. 57F, alpha-iduronidase expressed in mammalian, insect, yeast or fungi systems is remodeled by the addition of one or more terminal mannose-linker-ApoE moieties. The alpha-iduronidase molecule is contacted with mannosyltransferase and an appropriate mannose donor that has been conjugated via a linker to ApoE. In FIG. 57G, alpha-iduronidase expressed in mammalian, insect, yeast or fungal systems is remodeled by the addition of one or more galactose-linker-alpha2-macroglobulin moieties. The alpha-iduronidase molecule is contacted with Endo-H to trim back glycosyl groups. The molecule is then contacted with galactosyltransferase and an appropriate galactose donor that has been conjugated via a linker to alpha2-macroglobulin. In FIG. 57H, alpha-iduronidase expressed in insect, yeast and fungal systems, is remodeled by the addition of one or more N-acetylglucosamine-PEG-mannose-6-phosphate moieties. The alpha-galactosidase molecule is contacted with GnT-I and an appropriate N-acetyl-glucosamine donor that has been derivatized with PEG and mannose-6-phosphate. In FIG. 57I, alpha-iduronidase expressed in insect, yeast or fungal systems, is remodeled by the addition of one or more terminal galactose-PEG-transferrin moieties. The alpha-iduronidase molecule is contacted with GnT-I and an appropriate N-acetyl-glucosamine donor. The molecule is then contacted with galactosyltransferase and an appropriate galactose donor that has been derivatized with PEG and transferrin. In FIG. 57J, alpha-iduronidase expressed in insect, yeast or fungi systems, is remodeled by the addition of one or more terminal sialic acid-PEG-melanotransferrin moieties. The alpha-iduronidase molecule is contacted with GnT-I and GnT-II and an appropriate N-acetyl-glucosamine donor. The molecule is then contacted with galactosyltransferase and an appropriate galactose donor. The molecule is further contacted with sialyltransferase and an appropriate sialic acid donor that has been derivatized with PEG and melanotransferrin.

A. Creation or Elimination of N-Linked Glycosylation Sites

The present invention contemplates the use of peptides in which the site of the glycan chain(s) on the peptide have been altered from that of the native peptide. Typically, N-linked glycan chains are linked to the primary peptide structure at asparagine residues where the asparagine residue is within an amino acid sequence that is recognized by a membrane-bound glycosyltransferase in the endoplasmic reticulum (ER). Typically, the recognition site on the primary peptide structure is the sequence asparagine-X-serine/threonine where X can be any amino acid except proline and aspartic acid. While this recognition site is typical, the invention further encompasses peptides that have N-linked glycan chains at other recognition sites where the N-linked chains are added using natural or recombinant glycosyltransferases.

Since the recognition site for N-linked glycosylation of a peptide is known, it is within the skill of persons in the art to create mutated primary peptide sequences wherein a native N-linked glycosylation recognition site is removed, or alternatively or in addition, one or more additional N-glycosylation recognition sites are created. Most simply, an asparagine residue can be removed from the primary sequence of the peptide thereby removing the attachment site for a glycan, thus removing one glycan from the mature peptide. For example, a native recognition site with the sequence of asparagine-serine-serine can be genetically engineered to have the sequence leucine-serine-serine, thus eliminating a N-linked glycosylation site at this position.

Further, an N-linked glycosylation site can be removed by altering the residues in the recognition site so that even though the asparagine residue is present, one or more of the additional recognition residues are absent. For example, a native sequence of asparagine-serine-serine can be mutated to asparagine-serine-lysine, thus eliminating an N-glycosylation site at that position. In the case of N-linked glycosylation sites comprising residues other than the typical recognition sites described above, the skilled artisan can determine the sequence and residues required for recognition by the appropriate glycosyltransferase, and then mutate at least one residue so the appropriate glycosyltransferase no longer recognizes that site. In other words, it is well within the skill of the artisan to manipulate the primary sequence of a peptide such that glycosylation sites are either created or are removed, or both, thereby generating a peptide having an altered glycosylation pattern. The invention should therefore not be construed to be limited to any primary peptide sequence provided herein as the sole sequence for glycan remodeling, but rather should be construed to include any and all peptide sequences suitable for glycan remodeling.

To create a mutant peptide, the nucleic acid sequence encoding the primary sequence of the peptide is altered so that native codons encoding native amino acid residues are mutated to generate a codon encoding another amino acid residue. Techniques for altering nucleic acid sequence are common in the art and are described for example in any well-known molecular biology manual.

In addition, the nucleic acid encoding a primary peptide structure can be synthesized in vitro, using standard techniques. For example, a nucleic acid molecule can be synthesized in a "gene machine" using protocols such as the phosphoramidite method. If chemically-synthesized double stranded DNA is required for an application such as the synthesis of a nucleic acid or a fragment thereof, then each complementary strand is synthesized separately. The production of short nucleic acids (60 to 80 base pairs) is technically straightforward and can be accomplished by synthesizing the complementary strands and then annealing them. For the production of longer nucleic acids (>300 base pairs), special strategies may be required, because the coupling efficiency of each cycle during chemical DNA synthesis is seldom 100%. To overcome this problem, synthetic genes (double-stranded) are assembled in modular form from single-stranded fragments that are from 20 to 100 nucleotides in length. For reviews on polynucleotide synthesis, see, for example, Glick and Pasternak (Molecular Biotechnology, Principles and Applications of Recombinant DNA, 1994, ASM Press), Itakura et al. (1984, Annu. Rev. Biochem. 53:323), and Climie et al. (1990, Proc. Nat'l Acad. Sci. USA 87:633).

Additionally, changes in the nucleic acid sequence encoding the peptide can be made by site-directed mutagenesis. As will be appreciated, this technique typically employs a phage vector which exists in both a single stranded and double stranded form. Typical vectors useful in site-directed mutagenesis include vectors such as the M13 phage. These phage are readily available and their use is generally well known to those skilled in the art. Double stranded plasmids are also routinely employed in site-directed mutagenesis which eliminates the step of transferring the nucleic acid of interest from a plasmid to a phage. In general, site-directed mutagenesis is performed by first obtaining a single-stranded vector or melting the two strands of a double stranded vector which includes within its sequence a DNA sequence which encodes the desired peptide. An oligonucleotide primer bearing the desired mutated sequence is prepared generally synthetically. This primer is then annealed with the single-stranded vector, and subjected to DNA polymerizing enzymes such as *E. coli* polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform or transfect appropriate cells, such as *E. coli* cells, and clones are selected which include recombinant vectors bearing the mutated sequence arrangement. A genetic selection scheme was devised by Kunkel et al. (1987, Kunkel et al., Methods Enzymol. 154:367-382) to enrich for clones incorporating the mutagenic oligonucleotide. Alternatively, the use of PCR™ with commercially available thermostable enzymes such as Taq polymerase may be used to incorporate a mutagenic oligonucleotide primer into an amplified DNA fragment that can then be cloned into an appropriate cloning or expression vector. The PCR™-mediated mutagenesis procedures of Tomic et al. (1990, Nucl. Acids Res., 12:1656) and Upender et al. (1995, Biotechniques, 18:29-31) provide two examples of such protocols. A PCR™ employing a thermostable ligase in addition to a thermostable polymerase may also be used to incorporate a phosphorylated mutagenic oligonucleotide into an amplified DNA fragment that may then be cloned into an appropriate cloning or expression vector. The mutagenesis procedure described by Michael (1994, Biotechniques 16:410-412) provides an example of one such protocol.

Not all Asn-X-Ser/Thr sequences are N-glycosylated suggesting the context in which the motif is presented is important. In another approach, libraries of mutant peptides having novel N-linked consensus sites are created in order to identify novel N-linked sites that are glycosylated in vivo and are beneficial to the activity, stability or other characteristics of the peptide.

As noted previously, the consensus sequence for the addition of N-linked glycan chains in glycoproteins is Asn-X-Ser/Thr where X can be any amino acid. The nucleotide sequence encoding the amino acid two positions to the carboxyl terminal side of the Asn may be mutated to encode a Ser and/or Thr residue using standard procedures known to those of ordinary skill in the art. As stated above not all Asn-X-Ser/Thr sites are modified by the addition of glycans. Therefore, each recombinant mutated glycoprotein must be expressed in a fungal, yeast or animal or mammalian expression system and analyzed for the addition of an N-linked glycan chain. The techniques for the characterization of glycosylation sites are well known to one skilled in the art. Further, the biological function of the mutated recombinant glycoprotein can be determined using assays standard for the particular protein being examined. Thus, it becomes a simple matter to manipulate the primary sequence of a peptide and identify novel glycosylation sites contained therein, and further determine the effect of the novel site on the biological activity of the peptide.

In an alternative embodiment, the nucleotide sequence encoding the amino acid two positions to the amino terminal side of Ser/Thr residues may be mutated to encode an Asn using standard procedures known to those of ordinary skill in the art. The procedures to determine whether a novel glycosylation site has been created and the effect of this site on the biological activity of the peptide are described above.

B. Creation or Elimination of O-Linked Glycosylation Sites

The addition of an O-linked glycosylation site to a peptide is conveniently accomplished by altering the primary amino acid sequence of the peptide such that it contains one or more additional O-linked glycosylation sites compared with the beginning primary amino acid sequence of the peptide. The addition of an O-linked glycosylation site to the peptide may also be accomplished by incorporation of one or more amino acid species into the peptide which comprises an —OH group, preferably serine or threonine residues, within the sequence of the peptide, such that the OH group is accessible and available for O-linked glycosylation. Similar to the discussion of alteration of N-linked glycosylation sites in a peptide, the primary amino acid sequence of the peptide is preferably altered at the nucleotide level. Specific nucleotides in the DNA sequence encoding the peptide may be altered such that a desired amino acid is encoded by the sequence. Mutation(s) in DNA are preferably made using methods known in the art, such as the techniques of phosphoramidite method DNA synthesis and site-directed mutagenesis described above.

Alternatively, the nucleotide sequence encoding a putative site for O-linked glycan addition can be added to the DNA molecule in one or several copies to either 5' or the 3' end of the molecule. The altered DNA sequence is then expressed in any one of a fungal, yeast, or animal or mammalian expression system and analyzed for the addition of the sequence to the peptide and whether or not this sequence is a functional O-linked glycosylation site. Briefly, a synthetic peptide acceptor sequence is introduced at either the 5' or 3' end of the nucleotide molecule. In principle, the addition of this type of sequence is less disruptive to the resulting glycoprotein when expressed in a suitable expression system. The altered DNA is then expressed in CHO cells or other suitable expression system and the proteins expressed thereby are examined for the presence of an O-linked glycosylation site. In addition, the presence or absence of glycan chains can be determined.

In yet another approach, advantageous sites for new O-linked sites may be found in a peptide by creating libraries of the peptide containing various new O-linked sites. For example, the consensus amino acid sequence for N-acetylgalactosamine addition by an N-acetylgalactosaminyltransferase depends on the specific transferase used. The amino acid sequence of a peptide may be scanned to identify contiguous groups of amino acids that can be mutated to generate potential sites for addition of O-linked glycan chains. These mutations can be generated using standard procedures known to those of ordinary skill in the art as described previously. In order to determine if any discovered glycosylation site is actually glycosylated, each recombinant mutated peptide is then expressed in a suitable expression system and is subsequently analyzed for the addition of the site and/or the presence of an O-linked glycan chain.

C. Chemical Synthesis of Peptides

While the primary structure of peptides useful in the invention can be generated most efficiently in a cell-based expression system, it is within the scope of the present invention that the peptides may be generated synthetically. Chemical synthesis of peptides is well known in the art and include, without limitation, stepwise solid phase synthesis, and fragment condensation either in solution or on solid phase. A classic stepwise solid phase synthesis of involves covalently linking an amino acid corresponding to the carboxy-terminal amino acid of the desired peptide chain to a solid support and extending the peptide chain toward the amino end by stepwise coupling of activated amino acid derivatives having activated carboxyl groups. After completion of the assembly of the fully protected solid phase bound peptide chain, the peptide-solid phase covalent attachment is cleaved by suitable chemistry and the protecting groups are removed to yield the product peptide. See, R. Merrifield, Solid Phase Peptide Synthesis: The Synthesis of a Tetrapeptide, J. Am. Chem. Soc., 85:2149-2154 (1963). The longer the peptide chain, the more challenging it is to obtain high-purity well-defined products. Due to the production of complex mixtures, the stepwise solid phase synthesis approach has size limitations. In general, well-defined peptides of 100 contiguous amino acid residues or more are not routinely prepared via stepwise solid phase synthesis.

The segment condensation method involves preparation of several peptide segments by the solid phase stepwise method, followed by cleavage from the solid phase and purification of these maximally protected segments. The protected segments are condensed one-by-one to the first segment, which is bound to the solid phase.

The peptides useful in the present invention may be synthesized by exclusive solid phase synthesis, partial solid phase methods, fragment condensation or classical solution synthesis. These synthesis methods are well-known to those of skill in the art (see, for example, Merrifield, J. Am. Chem. Soc. 85:2149 (1963), Stewart et al., "Solid Phase Peptide Synthesis" (2nd Edition), (Pierce Chemical Co. 1984), Bayer and Rapp, Chem. Pept. Prot. 3:3 (1986), Atherton et al., Solid Phase Peptide Synthesis: A Practical Approach (IRL Press 1989), Fields and Colowick, "Solid-Phase Peptide Synthesis," Methods in Enzymology Volume 289 (Academic Press 1997), and Lloyd-Williams et al., Chemical Approaches to the Synthesis of Peptides and Peptides (CRC Press, Inc. 1997)). Variations in total chemical synthesis strategies, such as "native chemical ligation" and "expressed peptide ligation" are also standard (see, for example, Dawson et al., Science 266:776 (1994), Hackeng et al., Proc. Nat'l Acad. Sci. USA 94:7845 (1997), Dawson, Methods Enzymol. 287: 34 (1997), Muir et al, Proc. Nat'l Acad. Sci. USA 95:6705 (1998), and Severinov and Muir, J. Biol. Chem. 273:16205 (1998)). Also useful are the solid phase peptide synthesis methods developed by Gryphon Sciences, South San Francisco, Calif. See, U.S. Pat. Nos. 6,326,468, 6,217,873, 6,174,530, and 6,001,364, all of which are incorporated in their entirety by reference herein.

D. Post-Translational Modifications

It will be appreciated to one of ordinary skill in the art that peptides may undergo post-translational modification besides the addition of N-linked and/or O-linked glycans thereto. It is contemplated that peptides having post-translational modifications other than glycosylation can be used as peptides in the invention, as long as the desired biological activity or function of the peptide is maintained or improved. Such post-translational modifications may be natural modifications usually carried out in vivo, or engineered modifications of the peptide carried out in vitro. Contemplated known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent crosslinks, formation of cysteine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to peptides such as arginylation, and ubiquitination. Enzymes that may be used to carry out many of these modifications are well known in the art, and available commercially from companies such as Boehringer Mannheim (Indianapolis, Ind.) and Sigma Chemical Company (St. Louis, Mo.), among others.

Such modifications are well known to those of skill in the art and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as Peptides—Structure and Molecular Properties, 2nd Ed., T. E. Creighton, W. H. Freeman and Company, New York (1993). Many detailed reviews are available on this subject, such as by Wold, F., Post-translational Covalent Modification of Peptides, B. C. Johnson, Ed., Academic Press, New York 1-12 (1983); Seifter et al. (Meth. Enzymol. 182: 626-646 (1990)) and Rattan et al. (Ann. N.Y. Acad. Sci. 663:48-62 (1992)).

Covalent modifications of a peptide may also be introduced into the molecule in vitro by reacting targeted amino-acid residues of the peptide with an organic derivatizing agent that is capable of reacting with selected side chains or terminal amino-acid residues. Most commonly derivatized residues are cysteinyl, histidyl, lysinyl, arginyl, tyrosyl, glutaminyl, asparaginyl and amino terminal residues. Hydroxylation of proline and lysine, phosphorylation of hydroxyl groups of seryl and threonyl residues, methylation of the alpha-amino groups of lysine, histidine, and histidine side chains, acetylation of the N-terminal amine and amidation of the C-terminal carboxylic groups. Such derivatized moieties may improve the solubility, absorption, biological half life and the like. The moieties may also eliminate or attenuate any undesirable side effect of the peptide and the like.

In addition, derivatization with bifunctional agents is useful for cross-linking the peptide to water insoluble support matrices or to other macromolecular carriers. Commonly used cross-linking agents include glutaraldehyde, N-hydroxysuccinimide esters, homobifunctional imidoesters, 1,1-bis(-diazoloacetyl)-2-phenylethane, and bifunctional maleimides. Derivatizing agents such as methyl-3-[9p-azidophenyl)] dithiopropioimidate yield photoactivatable intermediates that are capable of forming crosslinks in the presence of light. Alternatively, reactive water-insoluble matrices such as cyanogen bromide activated carbohydrates and the reactive substrates described in U.S. Pat. Nos. 3,969,287 and 3,691,016 may be employed for peptide immobilization.

E. Fusion Peptides/Peptides

Peptides useful in the present invention may comprise fusion peptides. Fusion peptides are particularly advantageous where biological and/or functional characteristics of two peptides are desired to be combined in one peptide molecule. Such fusion peptides can present combinations of biological activity and function that are not found in nature to create novel and useful molecules of therapeutic and industrial applications. Biological activities of interest include, but are not limited to, enzymatic activity, receptor and/or ligand activity, immunogenic motifs, and structural domains.

Such fusion peptides are well known in the art, and the methods of creation will be well-known to those in the art. For example, a human α-interferon—human albumin fusion peptide has been made wherein the resulting peptide has the therapeutic benefits of α-interferon combined with the long circulating life of albumin, thereby creating a therapeutic composition that allows reduced dosing frequency and potentially reduced side effects in patients. See, Albuferon™ from Human Genome Sciences, Inc. and U.S. Pat. No. 5,766,883. Other fusion peptides include antibody molecules that are described elsewhere herein.

F. Generation of Smaller "Biologically Active" Molecules

The peptides used in the invention may be variants of native peptides, wherein a fragment of the native peptide is used in place of the full length native peptide. In addition, pre-pro-, and pre-peptides are contemplated. Variant peptides may be smaller in size that the native peptide, and may comprise one or more domains of a larger peptide. Selection of specific peptide domains can be advantageous when the biological activity of certain domains in the peptide is desired, but the biological activity of other domains in the peptide is not desired. Also included are truncations of the peptide and internal deletions which may enhance the desired therapeutic effect of the peptide. Any such forms of a peptide is contemplated to be useful in the present invention provided that the desired biological activity of the peptide is preserved.

Shorter versions of peptides may have unique advantages not found in the native peptide. In the case of human albumin, it has been found that a truncated form comprising as little as 63% of the native albumin peptide is advantageous as a plasma volume expander. The truncated albumin peptide is considered to be better than the native peptide for this therapeutic purpose because an individual peptide dose of only one-half to two-thirds that of natural-human serum albumin, or recombinant human serum albumin is required for the equivalent colloid osmotic effect. See U.S. Pat. No. 5,380,712, the entirety of which is incorporated by reference herein.

Smaller "biologically active" peptides have also been found to have enhanced therapeutic activity as compared to the native peptide. The therapeutic potential of IL-2 is limited by various side effects dominated by the vascular leak syndrome. A shorter chemically synthesized version of the peptide consisting of residues 1-30 corresponding to the entire α-helix was found to fold properly and contain the natural IL-2 biological activity with out the attending side effects.

G. Generation of Novel Peptides

The peptide of the invention may be derived from a primary sequence of a native peptide, or may be engineered using any of the many means known to those of skill in the art. Such engineered peptides can be designed and/or selected because of enhanced or novel properties as compared with the native peptide. For example, peptides may be engineered to have increased enzyme reaction rates, increased or decreased binding affinity to a substrate or ligand, increased or decreased binding affinity to a receptor, altered specificity for a substrate, ligand, receptor or other binding partner, increased or decreased stability in vitro and/or in vivo, or increased or decreased immunogenicity in an animal.

H. Mutations

1. Rational Design Mutation

The peptides useful in the methods of the invention may be mutated to enhance a desired biological activity or function, to diminish an undesirable property of the peptide, and/or to add novel activities or functions to the peptide. "Rational peptide design" may be used to generate such altered peptides. Once the amino acid sequence and structure of the peptide is known and a desired mutation planned, the mutations can be made most conveniently to the corresponding nucleic acid codon which encodes the amino acid residue that is desired to be mutated. One of skill in the art can easily determine how the nucleic acid sequence should be altered based on the universal genetic code, and knowledge of codon preferences in the expression system of choice. A mutation in a codon may be made to change the amino acid residue that will be polymerized into the peptide during translation. Alternatively, a codon may be mutated so that the corresponding encoded amino acid residue is the same, but the codon choice is better suited to the desired peptide expression system. For example, cys-residues may be replaced with other amino acids to remove disulfide bonds from the mature peptide, catalytic domains may be mutated to alter biological activity, and in general, isoforms of the peptide can be engineered. Such mutations can be point mutations, deletions, insertions and truncations, among others.

Techniques to mutate specific amino acids in a peptide are well known in the art. The technique of site-directed mutagenesis, discussed above, is well suited for the directed mutation of codons. The oligonucleotide-mediated mutagenesis method is also discussed in detail in Sambrook et al. (2001, Molecular Cloning: A Laboratory Manual, Cold Spring Harbor Laboratory, New York, starting at page 15.51). Systematic deletions, insertions and truncations can be made using linker insertion mutagenesis, digestion with nuclease Bal31, and linker-scanning mutagenesis, among other method well known to those in the art (Sambrook et al., 2001, Molecular Cloning: A Laboratory Manual, Cold Spring Harbor Laboratory, New York).

Rational peptide design has been successfully used to increase the stability of enzymes with respect to thermoinactivation and oxidation. For example, the stability of an enzyme was improved by removal of asparagine residues in α-amylase (Declerck et al., 2000, J. Mol. Biol. 301:1041-

1057), the introduction of more rigid structural elements such as proline into α-amylase (Igarashi et al., 1999, Biosci. Biotechnol. Biochem. 63:1535-1540) and D-xylose isomerase (Zhu et al., 1999, Peptide Eng. 12:635-638). Further, the introduction of additional hydrophobic contacts stabilized 3-isopropylmalate dehydrogenase (Akanuma et al., 1999, Eur. J. Biochem. 260:499-504) and formate dehydrogenase obtained from *Pseudomonas* sp. (Rojkova et al., 1999, FEBS Lett. 445:183-188). The mechanisms behind the stabilizing effect of these mutations is generally applicable to many peptides. These and similar mutations are contemplated to be useful with respect to the peptides remodeled in the methods of the present invention.

2. Random Mutagenesis Techniques

Novel peptides useful in the methods of the invention may be generated using techniques that introduce random mutations in the coding sequence of the nucleic acid. The nucleic acid is then expressed in a desired expression system, and the resulting peptide is assessed for properties of interest. Techniques to introduce random mutations into DNA sequences are well known in the art, and include PCR mutagenesis, saturation mutagenesis, and degenerate oligonucleotide approaches. See Sambrook and Russell (2001, Molecular Cloning, A Laboratory Approach, Cold Spring Harbor Press, Cold Spring Harbor, N.Y.) and Ausubel et al. (2002, Current Protocols in Molecular Biology, John Wiley & Sons, NY). In PCR mutagenesis, reduced Taq polymerase fidelity is used to introduce random mutations into a cloned fragment of DNA (Leung et al., 1989, Technique 1:11-15). This is a very powerful and relatively rapid method of introducing random mutations into a DNA sequence. The DNA region to be mutagenized is amplified using the polymerase chain reaction (PCR) under conditions that reduce the fidelity of DNA synthesis by Taq DNA polymerase, e.g., by using an altered dGTP/dATP ratio and by adding $Mn^{2+}$ to the PCR reaction. The pool of amplified DNA fragments are inserted into appropriate cloning vectors to provide random mutant libraries.

Saturation mutagenesis allows for the rapid introduction of a large number of single base substitutions into cloned DNA fragments (Mayers et al., 1985, Science 229:242). This technique includes generation of mutations, e.g., by chemical treatment or irradiation of single-stranded DNA in vitro, and synthesis of a complementary DNA strand. The mutation frequency can be modulated by modulating the severity of the treatment, and essentially all possible base substitutions can be obtained. Because this procedure does not involve a genetic selection for mutant fragments, both neutral substitutions as well as those that alter function, are obtained. The distribution of point mutations is not biased toward conserved sequence elements.

A library of nucleic acid homologs can also be generated from a set of degenerate oligonucleotide sequences. Chemical synthesis of a degenerate oligonucleotide sequences can be carried out in an automatic DNA synthesizer, and the synthetic genes may then be ligated into an appropriate expression vector. The synthesis of degenerate oligonucleotides is known in the art (see for example, Narang, S A (1983) Tetrahedron 39:3; Itakura et al. (1981) Recombinant DNA, Proc 3rd Cleveland Sympos. Macromolecules, ed. A G Walton, Amsterdam: Elsevier pp. 273-289; Itakura et al. (1984) Annu. Rev. Biochem. 53:323; Itakura et al. (1984) Science 198:1056; Ike et al. (1983) Nucleic Acid Res. 11:477. Such techniques have been employed in the directed evolution of other peptides (see, for example, Scott et al. (1990) Science 249:386-390; Roberts et al. (1992) PNAS 89:2429-2433; Devlin et al. (1990) Science 249: 404-406; Cwirla et al. (1990) PNAS 87: 6378-6382; as well as U.S. Pat. Nos. 5,223,409, 5,198,346, and 5,096,815).

a. Directed Evolution

Peptides useful in the methods of the invention may also be generated using "directed evolution" techniques. In contrast to site directed mutagenesis techniques where knowledge of the structure of the peptide is required, there now exist strategies to generate libraries of mutations from which to obtain peptides with improved properties without knowledge of the structural features of the peptide. These strategies are generally known as "directed evolution" technologies and are different from traditional random mutagenesis procedures in that they involve subjecting the nucleic acid sequence encoding the peptide of interest to recursive rounds of mutation, screening and amplification.

In some "directed evolution" techniques, the diversity in the nucleic acids obtained is generated by mutation methods that randomly create point mutations in the nucleic acid sequence. The point mutation techniques include, but are not limited to, "error-prone PCR™" (Caldwell and Joyce, 1994; PCR Methods Appl. 2: 28-33; and Ke and Madison, 1997, Nucleic Acids Res. 25: 3371-3372), repeated oligonucleotide-directed mutagenesis (Reidhaar-Olson et al., 1991, Methods Enzymol. 208:564-586), and any of the aforementioned methods of random mutagenesis.

Another method of creating diversity upon which directed evolution can act is the use of mutator genes. The nucleic acid of interest is cultured in a mutator cell strain the genome of which typically encodes defective DNA repair genes (U.S. Pat. No. 6,365,410; Selifonova et al., 2001, Appl. Environ. Microbiol. 67:3645-3649; Long-McGie et al., 2000, Biotech. Bioeng. 68:121-125; see, Genencor International Inc, Palo Alto Calif.).

Achieving diversity using directed evolution techniques may also be accomplished using saturation mutagenesis along with degenerate primers (Gene Site Saturation Mutagenesis™, Diversa Corp., San Diego, Calif.). In this type of saturation mutagenesis, degenerate primers designed to cover the length of the nucleic acid sequence to be diversified are used to prime the polymerase in PCR reactions. In this manner, each codon of a coding sequence for an amino acid may be mutated to encode each of the remaining common nineteen amino acids. This technique may also be used to introduce mutations, deletions and insertions to specific regions of a nucleic acid coding sequence while leaving the rest of the nucleic acid molecule untouched. Procedures for the gene saturation technique are well known in the art, and can be found in U.S. Pat. No. 6,171,820.

b. DNA Shuffling

Novel peptides useful in the methods of the invention may also be generated using the techniques of gene-shuffling, motif-shuffling, exon-shuffling, and/or codon-shuffling (collectively referred to as "DNA shuffling"). DNA shuffling techniques are may be employed to modulate the activities of peptides useful in the invention and may be used to generate peptides having altered activity. See, generally, U.S. Pat. Nos. 5,605,793; 5,811,238; 5,830,721; 5,834,252; and 5,837,458, and Stemmer et al. (1994, Nature 370(6488):389-391); Crameri et al. (1998, Nature 391 (6664):288-291); Zhang et al. (1997, Proc. Natl. Acad. Sci. USA 94(9):4504-4509); Stemmer et al. (1994, Proc. Natl. Acad. Sci. USA 91(22): 10747-10751), Patten et al. (1997, Curr. Opinion Biotechnol. 8:724-33); Harayama, (1998, Trends Biotechnol. 16(2):76-82); Hansson, et al., (1999, J. Mol. Biol. 287:265-76); and Lorenzo and Blasco (1998, Biotechniques 24(2):308-13) (each of these patents are hereby incorporated by reference in its entirety).

DNA shuffling involves the assembly of two or more DNA segments by homologous or site-specific recombination to generate variation in the polynucleotide sequence. DNA shuffling has been used to generate novel variations of human immunodeficiency virus type 1 proteins (Pekrun et al., 2002, J. Virol. 76(6):2924-35), triazine hydrolases (Raillard et al. 2001, Chem Biol 8(9):891-898), murine leukemia virus (MLV) proteins (Powell et al. 2000, Nat Biotechnol 18(12): 1279-1282), and indoleglycerol phosphate synthase (Merz et al. 2000, Biochemistry 39(5):880-889).

The technique of DNA shuffling was developed to generate biomolecular diversity by mimicking natural recombination by allowing in vitro homologous recombination of DNA (Stemmler, 1994, Nature 370: 389-391; and Stemmler, 1994, PNAS 91: 10747-10751). Generally, in this method a population of related genes is fragmented and subjected to recursive cycles of denaturation, rehybridization, followed by the extension of the 5' overhangs by Taq polymerase. With each cycle, the length of the fragments increases, and DNA recombination occurs when fragments originating from different genes hybridize to each other. The initial fragmentation of the DNA is usually accomplished by nuclease digestion, typically using DNase (see Stemmler references, above), but may also be accomplished by interrupted PCR synthesis (U.S. Pat. No. 5,965,408, incorporated herein by reference in its entirety; see, Diversa Corp., San Diego, Calif.). DNA shuffling methods have advantages over random point mutation methods in that direct recombination of beneficial mutations generated by each round of shuffling is achieved and there is therefore a self selection for improved phenotypes of peptides.

The techniques of DNA shuffling are well known to those in art. Detailed explanations of such technology is found in Stemmler, 1994, Nature 370: 389-391 and Stemmler, 1994, PNAS 91: 10747-10751. The DNA shuffling technique is also described in U.S. Pat. Nos. 6,180,406, 6,165,793, 6,132,970, 6,117,679, 6,096,548, 5,837,458, 5,834,252, 5,830,721, 5,811,238, and 5,605,793 (all of which are incorporated by reference herein in their entirety).

The art also provides even more recent modifications of the basic technique of DNA shuffling. In one example, exon shuffling, exons or combinations of exons that encode specific domains of peptides are amplified using chimeric oligonucleotides. The amplified molecules are then recombined by self-priming PCR assembly (Kolkman and Stemmler, 2001, Nat. Biotech. 19:423-428). In another example, using the technique of random chimeragenesis on transient templates (RACHITT) library construction, single stranded parental DNA fragments are annealed onto a full-length single-stranded template (Coco et al., 2001, Nat. Biotechnol. 19:354-359). In yet another example, staggered extension process (StEP), thermocycling with very abbreviated annealing/extension cycles is employed to repeatedly interrupt DNA polymerization from flanking primers (Zhao et al., 1998, Nat. Biotechnol. 16: 258-261). In the technique known as CLERY, in vitro family shuffling is combined with in vivo homologous recombination in yeast (Abecassis et al., 2000, Nucleic Acids Res. 28:E88;). To maximize intergenic recombination, single stranded DNA from complementary strands of each of the nucleic acids are digested with DNase and annealed (Kikuchi et al., 2000, Gene 243:133-137). The blunt ends of two truncated nucleic acids of variable lengths that are linked by a cleavable sequence are then ligated to generate gene fusion without homologous recombination (Sieber et al., 2001, Nat. Biotechnol. 19:456-460; Lutz et al., 2001, Nucleic Acids Res. 29:E16; Ostermeier et al., 1999, Nat. Biotechnol. 17:1205-1209; Lutz and Benkovic, 2000, Curr. Opin. Biotechnol. 11:319-324). Recombination between nucleic acids with little sequence homology in common has also been enhanced using exonuclease-mediated blunt-ending of DNA fragments and ligating the fragments together to recombine them (U.S. Pat. No. 6,361,974, incorporated herein by reference in its entirety). The invention contemplates the use of each and every variation described above as a means of enhancing the biological properties of any of the peptides and/or enzymes useful in the methods of the invention.

In addition to published protocols detailing directed evolution and gene shuffling techniques, commercial services are now available that will undertake the gene shuffling and selection procedures on peptides of choice. Maxygen (Redwood City, Calif.) offers commercial services to generate custom DNA shuffled libraries. In addition, this company will perform customized directed evolution procedures including gene shuffling and selection on a peptide family of choice.

Optigenix, Inc. (Newark, Del.) offers the related service of plasmid shuffling. Optigenix uses families of genes to obtain mutants therein having new properties. The nucleic acid of interest is cloned into a plasmid in an *Aspergillus* expression system. The DNA of the related family is then introduced into the expression system and recombination in conserved regions of the family occurs in the host. Resulting mutant DNAs are then expressed and the peptide produced therefrom are screened for the presence of desired properties and the absence of undesired properties.

c. Screening Procedures

Following each recursive round of "evolution," the desired peptides expressed by mutated genes are screened for characteristics of interest. The "candidate" genes are then amplified and pooled for the next round of DNA shuffling. The screening procedure used is highly dependant on the peptide that is being "evolved" and the characteristic of interest. Characteristics such as peptide stability, biological activity, antigenicity, among others can be selected using procedures that are well known in the art. Individual assays for the biological activity of preferred peptides useful in the methods of the invention are described elsewhere herein.

d. Combinations of Techniques

It will be appreciated by the skilled artisan that the above techniques of mutation and selection can be combined with each other and with additional procedures to generate the best possible peptide molecule useful in the methods of the invention. Thus, the invention is not limited to any one method for the generation of peptides, and should be construed to encompass any and all of the methodology described herein. For example, a procedure for introducing point mutations into a nucleic acid sequence may be performed initially, followed by recursive rounds of DNA shuffling, selection and amplification. The initial introduction of point mutations may be used to introduce diversity into a gene population where it is lacking, and the following round of DNA shuffling and screening will select and recombine advantageous point mutations.

III. Glycosidases and Glycotransferases

A. Glycosidases

Glycosidases are glycosyltransferases that use water as an acceptor molecule, and as such, are typically glycoside-hydrolytic enzymes. Glycosidases can be used for the formation of glycosidic bonds in vitro by controlling the thermodynamics or kinetics of the reaction mixture. Even with modified reaction conditions, though, glycosidase reactions can be difficult to work with, and glycosidases tend to give low synthetic yields as a result of the reversible transglycosylase reaction and the competing hydrolytic reaction.

A glycosidase can function by retaining the stereochemistry at the bond being broken during hydrolysis or by inverting the stereochemistry at the bond being broken during hydrolysis, classifying the glycosidase as either a "retaining" glycosidase or an "inverting" glycosidase, respectively. Retaining glycosidases have two critical carboxylic acid moieties present in the active site, with one carboxylate acting as an acid/base catalyst and the other as a nucleophile, whereas with the inverting glycosidases, one carboxylic acid functions as an acid and the other functions as a base.

Methods to determine the activity and linkage specificity of any glycosidase are well known in the art, including a simplified HPLC protocol (Jacob and Scudder, 1994, Methods in Enzymol. 230: 280-300). A general discussion of glycosidases and glycosidase treatment is found in Glycobiology, A Practical Approach, (1993, Fukuda and Kobata eds., Oxford University Press Inc., New York).

Glycosidases useful in the invention include, but are not limited to, sialidase, galactosidase, endoglycanase, mannosidase (i.e., α and β, ManI, ManII and ManIII,) xylosidase, fucosidase, *Agrobacterium* sp. β-glucosidase, *Cellulomonas fimi* mannosidase 2A, *Humicola insolens* glycosidase, *Sulfolobus solfataricus* glycosidase and *Bacillus licheniformis* glycosidase.

The choice of fucosidases for use in the invention depends on the linkage of the fucose to other molecules. The specificities of many α-fucosidases useful in the methods of the invention are well known to those in the art, and many varieties of fucosidase are also commercially available (Glyko, Novato, Calif.; PROzyme, San Leandro, Calif.; Calbiochem-Novabiochem Corp., San Diego, Calif.; among others). α-Fucosidases of interest include, but are not limited to, α-fucosidases from *Turbo cornutus, Charonia lampas, Bacillus fulminans, Aspergillus niger, Clostridium perfringens*, Bovine kidney (Glyko), chicken liver (Tyagarajan et al., 1996, Glycobiology 6:83-93) and α-fucosidase II from *Xanthomonas manihotis* (Glyko, PROzyme). Chicken liver fucosidase is particularly useful for removal of core fucose from N-linked glycans.

B. Glycosyltransferases

Glycosyltransferases catalyze the addition of activated sugars (donor NDP-sugars), in a step-wise fashion, to a protein, glycopeptide, lipid or glycolipid or to the non-reducing end of a growing oligosaccharide. N-linked glycopeptides are synthesized via a transferase and a lipid-linked oligosaccharide donor Dol-PP-$NAG_2Glc_3Man_9$ in an en block transfer followed by trimming of the core. In this case the nature of the "core" saccharide is somewhat different from subsequent attachments. A very large number of glycosyltransferases are known in the art.

The glycosyltransferase to be used in the present invention may be any as long as it can utilize the modified sugar as a sugar donor. Examples of such enzymes include Leloir pathway glycosyltransferases, such as galactosyltransferase, N-acetylglucosaminyltransferase, N-acetylgalactosaminyltransferase, fucosyltransferase, sialyltransferase, mannosyltransferase, xylosyltransferase, glucurononyltransferase and the like.

For enzymatic saccharide syntheses that involve glycosyltransferase reactions, glycosyltransferases can be cloned, or isolated from any source. Many cloned glycosyltransferases are known, as are their polynucleotide sequences. See, e.g., Taniguchi et al., 2002, Handbook of glycosyltransferases and related genes, Springer, Tokyo.

Glycosyltransferase amino acid sequences and nucleotide sequences encoding glycosyltransferases from which the amino acid sequences can be deduced are also found in various publicly available databases, including GenBank, Swiss-Prot, EMBL, and others.

Glycosyltransferases that can be employed in the methods of the invention include, but are not limited to, galactosyltransferases, fucosyltransferases, glucosyltransferases, N-acetylgalactosaminyltransferases, N-acetylglucosaminyltransferases, glucuronyltransferases, sialyltransferases, mannosyltransferases, glucuronic acid transferases, galacturonic acid transferases, and oligosaccharyltransferases. Suitable glycosyltransferases include those obtained from eukaryotes, as well as from prokaryotes.

DNA encoding glycosyltransferases may be obtained by chemical synthesis, by screening reverse transcripts of mRNA from appropriate cells or cell line cultures, by screening genomic libraries from appropriate cells, or by combinations of these procedures. Screening of mRNA or genomic DNA may be carried out using oligonucleotide probes generated from the glycosyltransferases nucleic acid sequence. Probes may be labeled with a detectable label, such as, but not limited to, a fluorescent group, a radioactive atom or a chemiluminescent group in accordance with known procedures and used in conventional hybridization assays. In the alternative, glycosyltransferases nucleic acid sequences may be obtained by use of the polymerase chain reaction (PCR) procedure, with the PCR oligonucleotide primers being produced from the glycosyltransferases nucleic acid sequence. See, U.S. Pat. No. 4,683,195 to Mullis et al. and U.S. Pat. No. 4,683,202 to Mullis.

A glycosyltransferases enzyme may be synthesized in a host cell transformed with a vector containing DNA encoding the glycosyltransferases enzyme. A vector is a replicable DNA construct. Vectors are used either to amplify DNA encoding the glycosyltransferases enzyme and/or to express DNA which encodes the glycosyltransferases enzyme. An expression vector is a replicable DNA construct in which a DNA sequence encoding the glycosyltransferases enzyme is operably linked to suitable control sequences capable of effecting the expression of the glycosyltransferases enzyme in a suitable host. The need for such control sequences will vary depending upon the host selected and the transformation method chosen. Generally, control sequences include a transcriptional promoter, an optional operator sequence to control transcription, a sequence encoding suitable mRNA ribosomal binding sites, and sequences which control the termination of transcription and translation. Amplification vectors do not require expression control domains. All that is needed is the ability to replicate in a host, usually conferred by an origin of replication, and a selection gene to facilitate recognition of transformants.

1. Fucosyltransferases

In some embodiments, a glycosyltransferase used in the method of the invention is a fucosyltransferase. Fucosyltransferases are known to those of skill in the art. Exemplary fucosyltransferases include enzymes, which transfer L-fucose from GDP-fucose to a hydroxy position of an acceptor sugar. Fucosyltransferases that transfer from non-nucleotide sugars to an acceptor are also of use in the present invention.

In some embodiments, the acceptor sugar is, for example, the GlcNAc in a Galβ(1→3,4)GlcNAcβ-group in an oligosaccharide glycoside. Suitable fucosyltransferases for this reaction include the Galβ(1→3,4)GlcNAcβ1-α(1→3,4)fucosyltransferase (FTIII E.C. No. 2.4.1.65), which was first characterized from human milk (see, Palcic, et al., Carbohydrate Res. 190:1-11 (1989); Prieels, et al., J. Biol. Chem. 256: 10456-10463 (1981); and Nunez, et al., Can. J. Chem. 59: 2086-2095 (1981)) and the Galβ(1→4)GlcNAcβ-αfucosyltransferases (FTIV, FTV, FTVI) which are found in human serum. FTVII (E.C. No. 2.4.1.65), a sialyl α(2→3)Galβ ((1→3)GlcNAcβ fucosyltransferase, has also been characterized. A recombinant form of the Galβ(1→3,4) GlcNAcβ-α (1→3,4)fucosyltransferase has also been characterized (see, Dumas, et al., Bioorg. Med. Letters 1: 425-428 (1991) and Kukowska-Latallo, et al., Genes and Development 4: 1288-1303 (1990)). Other exemplary fucosyltransferases include, for example, α1,2 fucosyltransferase (E.C. No. 2.4.1.69). Enzymatic fucosylation can be carried out by the methods described in Mollicone, et al., Eur. J. Biochem. 191: 169-176 (1990) or U.S. Pat. No. 5,374,655.

2. Galactosyltransferases

In another group of embodiments, the glycosyltransferase is a galactosyltransferase. Exemplary galactosyltransferases include α(1,3) galactosyltransferases (E.C. No. 2.4.1.151, see, e.g., Dabkowski et al., Transplant Proc. 25:2921 (1993) and Yamamoto et al. Nature 345: 229-233 (1990), bovine (GenBank j04989, Joziasse et al., J. Biol. Chem. 264: 14290-14297 (1989)), murine (GenBank m26925; Larsen et al., Proc. Nat'l. Acad. Sci. USA 86: 8227-8231 (1989)), porcine (GenBank L36152; Strahan et al., Immunogenetics 41: 101-105 (1995)). Another suitable α1,3 galactosyltransferase is that which is involved in synthesis of the blood group B antigen (EC 2.4.1.37, Yamamoto et al., *J. Biol. Chem.* 265: 1146-1151 (1990) (human)).

Also suitable for use in the methods of the invention are β(1,4) galactosyltransferases, which include, for example, EC 2.4.1.90 (LacNAc synthetase) and EC 2.4.1.22 (lactose synthetase) (bovine (D'Agostaro et al., Eur. J. Biochem. 183: 211-217 (1989)), human (Masri et al., Biochem. Biophys. Res. Commun. 157: 657-663 (1988)), murine (Nakazawa et al., J. Biochem. 104: 165-168 (1988)), as well as E.C. 2.4.1.38 and the ceramide galactosyltransferase (EC 2.4.1.45, Stahl et al., J. Neurosci. Res. 38: 234-242 (1994)). Other suitable galactosyltransferases include, for example, α1,2 galactosyltransferases (from e.g., *Schizosaccharomyces pombe*, Chapell et al., Mol. Biol. Cell 5: 519-528 (1994)). For further suitable galactosyltransferases, see Taniguchi et al. (2002, Handbook of Glycosyltransferases and Related Genes, Springer, Tokyo), Guo et al. (2001, Glycobiology, 11(10): 813-820), and Breton et al. (1998, J. Biochem. 123:1000-1009).

The production of proteins such as the enzyme GalNAc $T_{I-XIV}$ from cloned genes by genetic engineering is well known. See, e.g., U.S. Pat. No. 4,761,371. One method involves collection of sufficient samples, then the amino acid sequence of the enzyme is determined by N-terminal sequencing. This information is then used to isolate a cDNA clone encoding a full-length (membrane bound) transferase which upon expression in the insect cell line Sf9 resulted in the synthesis of a fully active enzyme. The acceptor specificity of the enzyme is then determined using a semiquantitative analysis of the amino acids surrounding known glycosylation sites in 16 different proteins followed by in vitro glycosylation studies of synthetic peptides. This work has demonstrated that certain amino acid residues are overrepresented in glycosylated peptide segments and that residues in specific positions surrounding glycosylated serine and threonine residues may have a more marked influence on acceptor efficiency than other amino acid moieties.

3. Sialyltransferases

Sialyltransferases are another type of glycosyltransferase that is useful in the recombinant cells and reaction mixtures of the invention. Examples of sialyltransferases that are suitable for use in the present invention include ST3Gal III (e.g., a rat or human ST3Gal III), ST3Gal IV, ST3Gal I, ST6Gal I, ST3Gal V, ST6Gal II, ST6GalNAc I, ST6GalNAc II, and ST6GalNAc III (the sialyltransferase nomenclature used herein is as described in Tsuji et al., Glycobiology 6: v-xiv (1996)). An exemplary α(2,3)sialyltransferase referred to as α(2,3)sialyltransferase (EC 2.4.99.6) transfers sialic acid to the non-reducing terminal Gal of a Galβ1→3Glc disaccharide or glycoside. See, Van den Eijnden et al., J. Biol. Chem. 256: 3159 (1981), Weinstein et al., J. Biol. Chem. 257: 13845 (1982) and Wen et al., J. Biol. Chem. 267: 21011 (1992). Another exemplary α2,3-sialyltransferase (EC 2.4.99.4) transfers sialic acid to the non-reducing terminal Gal of the disaccharide or glycoside. see, Rearick et al., J. Biol. Chem. 254: 4444 (1979) and Gillespie et al., J. Biol. Chem. 267: 21004 (1992). Further exemplary enzymes include Gal-β-1, 4-GlcNAc α-2,6 sialyltransferase (See, Kurosawa et al. Eur. J. Biochem. 219: 375-381 (1994)).

Preferably, for glycosylation of carbohydrates of glycopeptides the sialyltransferase will be able to transfer sialic acid to the sequence Galβ1,4GlcNAc-, Galβ1,3GlcNAc-, or Galβ1,3GalNAc-, the most common penultimate sequences underlying the terminal sialic acid on fully sialylated carbohydrate structures (see, Table 8). α2,8-Sialyltransferases capable of transferring sialic acid to α2,3Galβ1,4GlcNAc are also useful in the methods of the invention.

TABLE 8

Sialyltransferases which use the Galβ1,4GlcNAc sequence as an acceptor substrate

| Sialyl-transferase | Source | Sequence(s) formed | Ref. |
|---|---|---|---|
| ST6Gal I | Mammalian | NeuAcα2,6Galβ1,4GlcNAc- | 1 |
| ST3Gal III | Mammalian | NeuAcα2,3Galβ1,4GlcNAc-<br>NeuAcα2,3Galβ1,3GlcNAc- | 1 |
| ST3Gal IV | Mammalian | NeuAcα2,3Galβ1,4GlcNAc-<br>NeuAcα2,3Galβ1,3GlcNAc- | 1 |
| ST6Gal II | Mammalian | NeuAcα2,6Galβ1,4GlcNAc- | |
| ST6Gal II | *Photobacterium* | NeuAcα2,6Galβ1,4GlcNAc- | 2 |
| ST3Gal V | *N. meningitides*<br>*N. gonorrhoeae* | NeuAcα2,3Galβ1,4GlcNAc- | 3 |

1) Goochee et al., Bio/Technology 9: 1347-1355 (1991)
2) Yamamoto et al., J. Biochem. 120: 104-110 (1996)
3) Gilbert et al., J. Biol. Chem. 271: 28271-28276 (1996)

An example of a sialyltransferase that is useful in the claimed methods is ST3Gal III, which is also referred to as α(2,3)sialyltransferase (EC 2.4.99.6). This enzyme catalyzes the transfer of sialic acid to the Gal of a Galβ1,3GlcNAc or Galβ1,4GlcNAc glycoside (see, e.g., Wen et al., J. Biol. Chem. 267: 21011 (1992); Van den Eijnden et al., J. Biol. Chem. 256: 3159 (1991)) and is responsible for sialylation of asparagine-linked oligosaccharides in glycopeptides. The sialic acid is linked to a Gal with the formation of an α-linkage between the two saccharides. Bonding (linkage) between the saccharides is between the 2-position of NeuAc and the 3-position of Gal. This particular enzyme can be isolated from rat liver (Weinstein et al., J. Biol. Chem. 257: 13845 (1982)); the human cDNA (Sasaki et al. (1993) J. Biol. Chem. 268: 22782-22787; Kitagawa & Paulson (1994) J. Biol. Chem. 269: 1394-1401) and genomic (Kitagawa et al. (1996) J. Biol. Chem. 271: 931-938) DNA sequences are known, facilitating production of this enzyme by recombinant expression. In a preferred embodiment, the claimed sialylation methods use a rat ST3Gal III.

An example of a sialyltransferase that is useful in the claimed methods is CST-I from *Campylobacter* (see, for example, U.S. Pat. Nos. 6,503,744, 6,096,529, and 6,210,933 and WO99/49051, and published U.S. Pat. Application 2002/

2,042,369). This enzyme catalyzes the transfer of sialic acid to the Gal of a Galβ1,4Glc or Galβ1,3GalNAc. Other exemplary sialyltransferases of use in the present invention include those isolated from *Campylobacter jejuni*, including the α(2,3) sialyltransferase. See, e.g, WO99/49051.

Other sialyltransferases, including those listed in Table 8, are also useful in an economic and efficient large-scale process for sialylation of commercially important glycopeptides. As a simple test to find out the utility of these other enzymes, various amounts of each enzyme (1-100 mU/mg protein) are reacted with asialo-$\alpha_1$ AGP (at 1-10 mg/ml) to compare the ability of the sialyltransferase of interest to sialylate glycopeptides relative to either bovine ST6Gal I, ST3Gal III or both sialyltransferases. Alternatively, other glycopeptides or glycopeptides, or N-linked oligosaccharides enzymatically released from the peptide backbone can be used in place of asialo-$\alpha_1$ AGP for this evaluation. Sialyltransferases with the ability to sialylate N-linked oligosaccharides of glycopeptides more efficiently than ST6Gal I are useful in a practical large-scale process for peptide sialylation (as illustrated for ST3Gal III in this disclosure).

4. Other Glycosyltransferases

One of skill in the art will understand that other glycosyltransferases can be substituted into similar transferase cycles as have been described in detail for the sialyltransferase. In particular, the glycosyltransferase can also be, for instance, glucosyltransferases, e.g., Alg8 (Stagljov et al., Proc. Natl. Acad. Sci. USA 91: 5977 (1994)) or Alg5 (Heesen et al., Eur. J. Biochem. 224: 71 (1994)).

N-acetylgalactosaminyltransferases are also of use in practicing the present invention. Suitable N-acetylgalactosaminyltransferases include, but are not limited to, α(1,3)N-acetylgalactosaminyltransferase, β(1,4) N-acetylgalactosaminyltransferases (Nagata et al., J. Biol. Chem. 267: 12082-12089 (1992) and Smith et al., J. Biol. Chem. 269: 15162 (1994)) and peptide N-acetylgalactosaminyltransferase (Homa et al., J. Biol. Chem. 268: 12609 (1993)). Suitable N-acetylglucosaminyltransferases include GnT-I (2.4.1.101, Hull et al., BBRC 176: 608 (1991)), GnT-II, GnT-III (Ihara et al., J. Biochem. 113: 692 (1993)), GnT-IV, GnT-V (Shoreibah et al., J. Biol. Chem. 268: 15381 (1993)) and GnT-VI, O-linked N-acetylglucosaminyltransferase (Bierhuizen et al., Proc. Natl. Acad. Sci. USA 89: 9326 (1992)), N-acetylglucosamine-1-phosphate transferase (Rajput et al., Biochem J. 285: 985 (1992), and hyaluronan synthase.

Mannosyltransferases are of use to transfer modified mannose moieties. Suitable mannosyltransferases include α(1,2) mannosyltransferase, α(1,3) mannosyltransferase, α(1,6) mannosyltransferase, β(1,4) mannosyltransferase, Dol-P-Man synthase, OCh1, and Pmt1 (see, Kornfeld et al., Annu. Rev. Biochem. 54: 631-664 (1985)).

Xylosyltransferases are also useful in the present invention. See, for example, Rodgers, et al., Biochem. J., 288:817-822 (1992); and Elbain, et al., U.S. Pat. No., 6,168,937.

Other suitable glycosyltransferase cycles are described in Ichikawa et al., JACS 114: 9283 (1992), Wong et al., J. Org. Chem. 57: 4343 (1992), and Ichikawa et al. in Carbohydrates and Carbohydrate Polymers. Yaltami, ed. (ATL Press, 1993).

Prokaryotic glycosyltransferases are also useful in practicing the invention. Such glycosyltransferases include enzymes involved in synthesis of lipooligosaccharides (LOS), which are produced by many gram negative bacteria. The LOS typically have terminal glycan sequences that mimic glycoconjugates found on the surface of human epithelial cells or in host secretions (Preston et al., Critical Reviews in Microbiology 23(3): 139-180 (1996)). Such enzymes include, but are not limited to, the proteins of the rfa operons of species such as *E. coli* and *Salmonella typhimurium*, which include a β1,6 galactosyltransferase and a β1,3 galactosyltransferase (see, e.g., EMBL Accession Nos. M80599 and M86935 (*E. coli*); EMBL Accession No. S56361 (*S. typhimurium*)), a glucosyltransferase (Swiss-Prot Accession No. P25740 (*E. coli*), an β1,2-glucosyltransferase (rfaJ)(Swiss-Prot Accession No. P27129 (*E. coli*) and Swiss-Prot Accession No. P19817 (*S. typhimurium*)), and an β1,2-N-acetylglucosaminyltransferase (rfaK)(EMBL Accession No. U00039 (*E. coli*). Other glycosyltransferases for which amino acid sequences are known include those that are encoded by operons such as rfaB, which have been characterized in organisms such as *Klebsiella pneumoniae, E. coli, Salmonella typhimurium, Salmonella enterica, Yersinia enterocolitica, Mycobacterium* leprosum, and the rh1 operon of *Pseudomonas aeruginosa.*

Also suitable for use in the present invention are glycosyltransferases that are involved in producing structures containing lacto-N-neotetraose, D-galactosyl-β-1,4-N-acetyl-D-glucosaminyl-β-1,3-D-galactosyl-β-1,4-D-glucose, and the $P^k$ blood group trisaccharide sequence, D-galactosyl-α-1,4-D-galactosyl-β-1,4-D-glucose, which have been identified in the LOS of the mucosal pathogens *Neisseria gonorrhoeae* and *N. meningitidis* (Scholten et al., J. Med. Microbiol. 41: 236-243 (1994)). The genes from *N. meningitidis* and *N. gonorrhoeae* that encode the glycosyltransferases involved in the biosynthesis of these structures have been identified from *N. meningitidis* immunotypes L3 and L1 (Jennings et al., Mol. Microbiol. 18: 729-740 (1995)) and the *N. gonorrhoeae* mutant F62 (Gotshlich, J. Exp. Med. 180: 2181-2190 (1994)). In *N. meningitidis*, a locus consisting of three genes, lgtA, lgtB and lg E, encodes the glycosyltransferase enzymes required for addition of the last three of the sugars in the facto-N-neotetraose chain (Wakarchuk et al., J. Biol. Chem. 271: 19166-73 (1996)). Recently the enzymatic activity of the lgtB and lgtA gene product was demonstrated, providing the first direct evidence for their proposed glycosyltransferase function (Wakarchuk et al., J. Biol. Chem. 271(45): 28271-276 (1996)). In *N. gonorrhoeae*, there are two additional genes, lgtD which adds β-D-GalNAc to the 3 position of the terminal galactose of the lacto-N-neotetraose structure and lgtC which adds a terminal α-D-Gal to the lactose element of a truncated LOS, thus creating the $P^k$ blood group antigen structure (Gotshlich (1994), supra.). In *N. meningitidis*, a separate immunotype L1 also expresses the $P^k$ blood group antigen and has been shown to carry an lgtC gene (Jennings et al., (1995), supra.). *Neisseria* glycosyltransferases and associated genes are also described in U.S. Pat. No. 5,545,553 (Gotschlich). Genes for α1,2-fucosyltransferase and α1,3-fucosyltransferase from *Helicobacter pylori* has also been characterized (Martin et al., J. Biol. Chem. 272: 21349-21356 (1997)). Also of use in the present invention are the glycosyltransferases of *Campylobacter jejuni* (see, Taniguchi et al., 2002, Handbook of glycosyltransferases and related genes, Springer, Tokyo).

B. Sulfotransferases

The invention also provides methods for producing peptides that include sulfated molecules, including, for example sulfated polysaccharides such as heparin, heparan sulfate, carragenen, and related compounds. Suitable sulfotransferases include, for example, chondroitin-6-sulphotransferase (chicken cDNA described by Fukuta et al., J. Biol. Chem. 270: 18575-18580 (1995); GenBank Accession No. D49915), glycosaminoglycan N-acetylglucosamine N-deacetylase/N-sulphotransferase 1 (Dixon et al., Genomics 26: 239-241 (1995); UL18918), and glycosaminoglycan N-acetylglucosamine N-deacetylase/N-sulphotransferase 2

(murine cDNA described in Orellana et al., J. Biol. Chem. 269: 2270-2276 (1994) and Eriksson et al., J. Biol. Chem. 269: 10438-10443 (1994); human cDNA described in GenBank Accession No. U2304).

C. Cell-Bound Glycosyltransferases

In another embodiment, the enzymes utilized in the method of the invention are cell-bound glycosyltransferases. Although many soluble glycosyltransferases are known (see, for example, U.S. Pat. No. 5,032,519), glycosyltransferases are generally in membrane-bound form when associated with cells. Many of the membrane-bound enzymes studied thus far are considered to be intrinsic proteins; that is, they are not released from the membranes by sonication and require detergents for solubilization. Surface glycosyltransferases have been identified on the surfaces of vertebrate and invertebrate cells, and it has also been recognized that these surface transferases maintain catalytic activity under physiological conditions. However, the more recognized function of cell surface glycosyltransferases is for intercellular recognition (Roth, 1990, Molecular Approaches to Supracellular Phenomena,). Methods have been developed to alter the glycosyltransferases expressed by cells. For example, Larsen et al., Proc. Natl. Acad. Sci. USA 86: 8227-8231 (1989), report a genetic approach to isolate cloned cDNA sequences that determine expression of cell surface oligosaccharide structures and their cognate glycosyltransferases. A cDNA library generated from mRNA isolated from a murine cell line known to express UDP-galactose: β.-D-galactosyl-1,4-N-acetyl-D-glucosaminide α-1,3-galactosyltransferase was transfected into COS-1 cells. The transfected cells were then cultured and assayed for α 1-3 galactosyltransferase activity.

Francisco et al., Proc. Natl. Acad. Sci. USA 89: 2713-2717 (1992), disclose a method of anchoring β-lactamase to the external surface of *Escherichia coli*. A tripartite fusion consisting of (i) a signal sequence of an outer membrane protein, (ii) a membrane-spanning section of an outer membrane protein, and (iii) a complete mature β-lactamase sequence is produced resulting in an active surface bound β-lactamase molecule. However, the Francisco method is limited only to prokaryotic cell systems and as recognized by the authors, requires the complete tripartite fusion for proper functioning.

D. Fusion Enzymes

In other exemplary embodiments, the methods of the invention utilize fusion peptides that have more than one enzymatic activity that is involved in synthesis of a desired glycopeptide conjugate. The fusion peptides can be composed of, for example, a catalytically active domain of a glycosyltransferase that is joined to a catalytically active domain of an accessory enzyme. The accessory enzyme catalytic domain can, for example, catalyze a step in the formation of a nucleotide sugar that is a donor for the glycosyltransferase, or catalyze a reaction involved in a glycosyltransferase cycle. For example, a polynucleotide that encodes a glycosyltransferase can be joined, in-frame, to a polynucleotide that encodes an enzyme involved in nucleotide sugar synthesis. The resulting fusion peptide can then catalyze not only the synthesis of the nucleotide sugar, but also the transfer of the sugar moiety to the acceptor molecule. The fusion peptide can be two or more cycle enzymes linked into one expressible nucleotide sequence. In other embodiments the fusion peptide includes the catalytically active domains of two or more glycosyltransferases. See, for example, U.S. Pat. No. 5,641,668. The modified glycopeptides of the present invention can be readily designed and manufactured utilizing various suitable fusion peptides (see, for example, PCT Patent Application PCT/CA98/01180, which was published as WO 99/31224 on Jun. 24, 1999.)

E. Immobilized Enzymes

In addition to cell-bound enzymes, the present invention also provides for the use of enzymes that are immobilized on a solid and/or soluble support. In an exemplary embodiment, there is provided a glycosyltransferase that is conjugated to a PEG via an intact glycosyl linker according to the methods of the invention. The PEG-linker-enzyme conjugate is optionally attached to solid support. The use of solid supported enzymes in the methods of the invention simplifies the work up of the reaction mixture and purification of the reaction product, and also enables the facile recovery of the enzyme. The glycosyltransferase conjugate is utilized in the methods of the invention. Other combinations of enzymes and supports will be apparent to those of skill in the art.

F. Mutagenesis of Glycosyltransferases

The novel forms of the glycosyltransferases, sialyltransferases, sulfotransferases, and any other enzymes used in the method of the invention can be created using any of the methods described previously, as well as others well known to those in the art. Of particular interest are transferases with altered acceptor specificity and/or donor specificity. Also of interest are enzymes with higher conversion rates and higher stability among others.

The techniques of rational design mutagenesis can be used when the sequence of the peptide is known. Since the sequences as well as many of the tertiary structures of the transferases and glucosidases used in the invention are known, these enzymes are ideal for rational design of mutants. For example, the catalytic site of the enzyme can be mutated to alter the donor and/or acceptor specificity of the enzyme.

The extensive tertiary structural data on the glycosyltransferases and glycosidase hydrolases also make these enzyme idea for mutations involving domain exchanges. Glycosyltransferases and glycosidase hydrolases are modular enzymes (see, Bourne and Henrissat, 2001, Current Opinion in Structural Biology 11:593-600). Glycosyltransferases are divided into two families bases on their structure: GT-A and GT-B. The glycosyltransferases of the GT-A family comprise two dissimilar domains, one involved in nucleotide binding and the other in acceptor binding. Thus, one could conveniently fuse the DNA sequence encoding the domain from one gene in frame with a domain from a second gene to create a new gene that encodes a protein with a new acceptor/donor specificity. Such exchanges of domains could additionally include the carbohydrate modules and other accessory domains.

The techniques of random mutation and/or directed evolution, as described above, may also be used to create novel forms of the glycosyltransferases and glycosidases used in the invention.

IV. In Vitro and In Vivo Expression Systems

A. Cells for the Production of Glycopeptides

The action of glycosyltransferases is key to the glycosylation of peptides, thus, the difference in the expression of a set of glycosyltransferases in any given cell type affects the pattern of glycosylation on any given peptide produced in that cell. For a review of host cell dependent glycosylation of peptides, see Kabata and Takasaki, "Structure and Biosynthesis of Cell Surface Carbohydrates," in Cell Surface Carbohydrates and Cell Development, 1991, pp. 1-24, Eds. Minoru Fukuda, CRC Press, Boca Raton, Fla.

According to the present disclosure, the type of cell in which the peptide is produced is relevant only with respect to the degree of remodeling required to generate a peptide having desired glycosylation. For example, the number and sequence of enzymatic digestion reactions and the number and sequence of enzymatic synthetic reactions that are required in vitro to generate a peptide having desired glycosylation will vary depending on the structure of the glycan on the peptide produced by a particular cell type. While the invention should in no way be construed to be limited to the production of peptides from any one particular cell type including any cell type disclosed herein, a discussion of several cell systems is now presented which establishes the power of the present invention and its independence of the cell type in which the peptides are generated.

In general, and to express a peptide from a nucleic acid encoding it, the nucleic acid must be incorporated into an expression cassette, comprising a promoter element, a terminator element, and the coding sequence of the peptide operably linked between the two. The expression cassette is then operably linked into a vector. Toward this end, adapters or linkers may be employed to join the nucleotide fragments or other manipulations may be involved to provide for convenient restriction sites, removal of superfluous nucleotides, removal of restriction sites, or the like. For this purpose, in vitro mutagenesis, primer repair, restriction, annealing, resubstitutions, e.g., transitions and transversions, may be involved. A shuttle vector has the genetic elements necessary for replication in a cell. Some vectors may be replicated only in prokaryotes, or may be replicated in both prokaryotes and eukaryotes. Such a plasmid expression vector will be maintained in one or more replication systems, preferably two replication systems, that allow for stable maintenance within a yeast host cell for expression purposes, and within a prokaryotic host for cloning purposes. Many vectors with diverse characteristics are now available commercially. Vectors are usually plasmids or phages, but may also be cosmids or mini-chromosomes. Conveniently, many commercially available vectors will have the promoter and terminator of the expression cassette already present, and a multi-linker site where the coding sequence for the peptide of interest can be inserted. The shuttle vector containing the expression cassette is then transformed in *E. coli* where it is replicated during cell division to generate a preparation of vector that is sufficient to transform the host cells of the chosen expression system. The above methodology is well know to those in the art, and protocols by which to accomplish can be found Sambrook et al. (2001, Molecular Cloning: A Laboratory Manual, Cold Spring Harbor Laboratory, New York).

The vector, once purified from the cells in which it is amplified, is then transformed into the cells of the expression system. The protocol for transformation depended on the kind of the cell and the nature of the vector. Transformants are grown in an appropriate nutrient medium, and, where appropriate, maintained under selective pressure to insure retention of endogenous DNA. Where expression is inducible, growth can be permitted of the yeast host to yield a high density of cells, and then expression is induced. The secreted, mature heterologous peptide can be harvested by any conventional means, and purified by chromatography, electrophoresis, dialysis, solvent-solvent extraction, and the like.

The techniques of molecular cloning are well-known in the art. Further, techniques for the procedures of molecular cloning can be found in Sambrook et al. (2001, Molecular Cloning: A Laboratory Manual, Cold Spring Harbor Laboratory Press, Cold Spring Harbor, N.Y.); Glover et al., (1985, DNA Cloning: A Practical Approach, Volumes I and II); Gait et al., (1985, Oligonucleotide Synthesis); Hames and Higgins (1985, Nucleic Acid Hybridization); Hames and Higgins (1984, Transcription And Translation); Freshney et al., (1986, Animal Cell Culture); Perbal, (1986, Immobilized Cells And Enzymes, IRL Press); Perbal, (1984, A Practical Guide To Molecular Cloning); Ausubel et al. (2002, Current Protocols in Molecular Biology, John Wiley & Sons, Inc.).

B. Fungi and Yeast

Peptides produced in yeast are glycosylated and the glycan structures present thereon are primarily high mannose structures. In the case of N-glycans, the glycan structures produced in yeast may contain as many as nine or more mannose residues which may or may not contain additional sugars added thereto. An example of the type of glycan on peptides produced by yeast cells is shown in FIG. 4, left side. Irrespective of the number of mannose residues and the type and complexity of additional sugars added thereto, N-glycans as components of peptides produced in yeast cells comprise a trimannosyl core structure as shown in FIG. 4. When the glycan structure on a peptide produced by a yeast cell is a high mannose structure, it is a simple matter for the ordinary skilled artisan to remove, in vitro using available mannosidase enzymes, all of the mannose residues from the molecule except for those that comprise the trimannosyl core of the glycan, thereby generating a peptide having an elemental trimannosyl core structure attached thereto. Now, using the techniques available in the art and armed with the present disclosure, it is a simple matter to enzymatically add, in vitro, additional sugar moieties to the elemental trimannosyl core structure to generate a peptide having a desired glycan structure attached thereto. Similarly, when the peptide produced by the yeast cell comprises a high mannose structure in addition to other complex sugars attached thereto, it is a simple matter to enzymatically cleave off all of the additional sugars, including extra mannose residues, to arrive at the elemental trimannosyl core structure. Once the elemental trimannosyl core structure is produced, generation of a peptide having desired glycosylation is possible following the directions provided herein.

By "yeast" is intended ascosporogenous yeasts (Endomycetales), basidiosporogenous yeasts, and yeast belonging to the Fungi Imperfecti (Blastomycetes). The ascosporogenous yeasts are divided into two families, Spermophthoraceae and Saccharomycetaceae. The later is comprised of four subfamilies, Schizosaccharomycoideae (e.g., genus *Schizosaccharomyces*), Nadsonioideae, Lipomycoideae, and Saccharomycoideae (e.g., genera *Pichia, Kluyveromyces*, and *Saccharomyces*). The basidiosporogenous yeasts include the genera *Leucosporidium, Rhodosporidium, Sporidiobolus, Filobasidium, and Filobasidiella*. Yeast belonging to the Fungi Imperfecti are divided into two families, Sporobolomycetaceae (e.g., genera *Sporobolomyces, Bullera*) and Cryptococcaceae (e.g., genus *Candida*). Of particular interest to the present invention are species within the genera *Saccharomyces, Pichia, Aspergillus, Trichoderma, Kluyveromyces*, especially *K. lactis* and *K. drosophilum, Candida, Hansenula, Schizpsaccaromyces, Yarrowia*, and *Chrysoporium*. Since the classification of yeast may change in the future, for the purposes of this invention, yeast shall be defined as described in Skinner et al., eds. 1980) Biology and Activities of Yeast (Soc. App. Bacteriol. Symp. Series No. 9).

In addition to the foregoing, those of ordinary skill in the art are presumably familiar with the biology of yeast and the manipulation of yeast genetics. See, for example, Bacila et al., eds. (1978, Biochemistry and Genetics of Yeast, Academic Press, New York); and Rose and Harrison. (1987, The Yeasts ($2^{nd}$ ed.) Academic Press, London). Methods of introducing exogenous DNA into yeast hosts are well known in the art. There are a wide variety of methods for transformation of yeast. Spheroplast transformation is taught by Hinnen et al (1978, Proc. Natl. Acad. Sci. USA 75:1919-1933); Beggs, (1978, Nature 275(5676):104-109); and Stinchcomb et al., (EPO Publication No. 45,573; herein incorporated by reference), Electroporation is taught by Becker and Gaurante, (1991, Methods Enzymol. 194:182-187), Lithium acetate is taught by Gietz et al. (2002, Methods Enzymol. 350:87-96) and Mount et al. (1996, Methods Mol. Biol. 53:139-145). For a review of transformation systems of non-*Saccharomyces* yeasts, see Wang et al. (Crit. Rev Biotechnol. 2001; 21(3): 177-218). For general procedures on yeast genetic engineering, see Barr et al., (1989, Yeast genetic engineering, Butterworths, Boston).

In addition to wild-type yeast and fungal cells, there are also strains of yeast and fungi that have been mutated and/or selected to enhance the level of expression of the exogenous gene, and the purity, the post-translational processing of the resulting peptide, and the recovery and purity of the mature peptide. Expression of an exogenous peptide may also be direct to the cell secretory pathway, as illustrated by the expression of insulin (see (Kjeldsen, 2000, Appl. Microbiol. Biotechnol. 54:277-286, and references cited therein). In general, to cause the exogenous peptide to be secreted from the yeast cell, secretion signals derived from yeast genes may be used, such as those of the genes of the killer toxin (Stark and Boyd, 1986, EMBO J. 5:1995-2002) or of the alpha pheromone (Kurjan and Herskowitz, 1982, Cell 30:933; Brake et al., 1988, Yeast 4:S436).

Regarding the filamentous fungi in general, methods for genetic manipulation can be found in Kinghorn and Turner (1992, Applied Molecular Genetics of Filamentous Fungi, Blackie Academic and Professional, New York). Guidance on appropriate vectors can be found in Martinelli and Kinghorn (1994, *Aspergillus:* 50 years, Elsevier, Amsterdam).

1. *Saccharomyces*

In *Saccharomyces*, suitable yeast vectors for use producing a peptide include YRp7 (Struhl et al., Proc. Natl. Acad. Sci. USA 76: 1035-1039, 1978), YEp13 (Broach et al., Gene 8: 121-133, 1979), POT vectors (Kawasaki et al, U.S. Pat. No. 4,931,373, which is incorporated by reference herein), pJDB249 and pJDB219 (Beggs, Nature 275:104-108, 1978) and derivatives thereof. Preferred promoters for use in yeast include promoters for yeast glycolytic gene expression (Hitzeman et al., J. Biol. Chem. 255: 12073-12080, 1980; Alber and Kawasaki, J. Mol. Appl. Genet. 1: 419-434, 1982; Kawasaki, U.S. Pat. No. 4,599,311) or alcohol dehydrogenase genes (Young et al., in Genetic Engineering of Microorganisms for Chemicals, Hollaender et al., (eds.), p. 355, Plenum, New York, 1982; Ammerer, Meth. Enzymol. 101: 192-201, 1983), and the ADH2-$4^c$ promoter (Russell et al., Nature 304: 652-654, 1983; Irani and Kilgore, U.S. patent application Ser. No. 07/784,653, CA 1,304,020 and EP 284 044, which are incorporated herein by reference). The expression units may also include a transcriptional terminator. A preferred transcriptional terminator is the TPI1 terminator (Alber and Kawasaki, ibid.).

Examples of such yeast-bacteria shuttle vectors include Yep24 (Botstein et al. (1979) Gene 8:17-24; pC1 (Brake et al. (1984) Proc. Natl. Acad. Sci. USA 81:4642-4646), and Yrp17 (Stnichomb et al. (1982) J. Mol. Biol. 158:157). Additionally, a plasmid expression vector may be a high or low copy number plasmid, the copy number generally ranging from about 1 to about 200. In the case of high copy number yeast vectors, there will generally be at least 10, preferably at least 20, and usually not exceeding about 150 copies of the vector in a single host. Depending upon the heterologous peptide selected, either a high or low copy number vector may be desirable, depending upon the effect of the vector and the recombinant peptide on the host. See, for example, Brake et al. (1984) Proc. Natl. Acad. Sci. USA 81:4642-4646. DNA constructs of the present invention can also be integrated into the yeast genome by an integrating vector. Examples of such vectors are known in the art. See, for example, Botstein et al. (1979) Gene 8:17-24.

The selection of suitable yeast and other microorganism hosts for the practice of the present invention is within the skill of the art. Of particular interest are the *Saccharomyces* species *S. cerevisiae, S. carlsbergensis, S. diastaticus, S. douglasii, S. kluyveri, S. norbensis*, and *S. oviformis*. When selecting yeast host cells for expression of a desired peptide, suitable host cells may include those shown to have, inter alia, good secretion capacity, low proteolytic activity, and overall vigor. Yeast and other microorganisms are generally available from a variety of sources, including the Yeast Genetic Stock Center, Department of Biophysics and Medical Physics, University of California, Berkeley, Calif.; and the American Type Culture Collection, Manassas Va. For a review, see Strathern et al., eds. (1981, The Molecular Biology of the Yeast *Saccharomyces*, Cold Spring Harbor Laboratory, Cold Spring Harbor, N.Y.)

Methods of introducing exogenous DNA into yeast hosts are well known in the art.

2. *Pichia*

The use of *Pichia methanolica* as a host cell for the production of recombinant peptides is disclosed in PCT Applications WO 97/17450, WO 97/17451, WO 98/02536, and WO 98/02565. DNA molecules for use in transforming *P. methanolica* are commonly prepared as double-stranded, circular plasmids, which are preferably linearized prior to transformation. For peptide production in *P. methanolica*, it is preferred that the promoter and terminator in the plasmid be that of a *P. methanolica* gene, such as a *P. methanolica* alcohol utilization gene (AUG1 or AUG2). Other useful promoters include those of the dihydroxyacetone synthase (DHAS), formate dehydrogenase (FMD), and catalase (CAT) genes, as well as those disclosed in U.S. Pat. No. 5,252,726. To facilitate integration of the DNA into the host chromosome, it is preferred to have the entire expression segment of the plasmid flanked at both ends by host DNA sequences. A preferred selectable marker for use in *Pichia methanolica* is a *P. methanolica* ADE2 gene, which encodes phosphoribosyl-5-aminoimidazole carboxylase (AIRC; EC 4.1.1.21), which allows ade2 host cells to grow in the absence of adenine. For large-scale, industrial processes where it is desirable to minimize the use of methanol, host cells in which both methanol utilization genes (AUG1 and AUG2) are deleted are preferred. For production of secreted peptides, host cells deficient in vacuolar protease genes (PEP4 and PRB1) are preferred. Electroporation is used to facilitate the introduction of a plasmid containing DNA encoding a peptide of interest into *P. methanolica* cells. It is preferred to transform *P. methanolica* cells by electroporation using an exponentially decaying, pulsed electric field having a field strength of from 2.5 to 4.5 kV/cm, preferably about 3.75 kV/cm, and a time constant (t) of from 1 to 40 milliseconds, most preferably about 20 milliseconds. For a review of the use of *Pichia pastoris* for large-scale production of antibody fragments, see Fischer et al., (1999, Biotechnol Appl Biochem. 30 (Pt 2):117-120).

3. *Aspergillus*

Methods to express peptides in *Aspergillus* spp. are well known in the art, including but not limited to those described in Carrez et al., 1990, Gene 94:147-154; Contreras, 1991, Bio/Technology 9:378-381; Yelton et al., 1984, Proc. Natl. Acad. Sci. USA 81:1470-1474; Tilburn et al., 1983, Gene 26:205-221; Kelly and. Hynes, 1985, EMBO J. 4:475-479; Ballance et al., 1983, Biochem. Biophys. Res. Comm. 112: 284-289; Buxton et al., 1985, Gene 37:207-214, and U.S. Pat.

No. 4,935,349, incorporated by reference herein in its entirety. Examples of promoters useful in *Aspergillus* are found in U.S. Pat. No. 5,252,726. Strains of *Aspergillus* useful for peptide expression are found in U.S. Pat. No. 4,935,349. Commercial production of exogenous peptides is available from Novoenzymes for *Aspergillus niger* and *Aspergillus oryzae*.

4. *Trichoderma*

*Trichoderma* has certain advantages over other species of recombinant host cells for expression of desired peptides. This organism is easy to grow in large quantities and it has the ability to glycosylate and efficiently secrete high yields of recombinant mammalian peptides into the medium, making isolation of the peptide relatively easy. In addition, the glycosylation pattern on expressed peptides is more similar to that on human peptides than peptides expressed in many other systems. However, there are still differences in the glycan structures on expressed peptides from these cells. For example, terminal sialic acid residues are important to the therapeutic function of a peptide in a mammalian system, since the presence of these moieties at the end of the glycan structure impedes peptide clearance from the mammalian bloodstream. The mechanism behind the increased biologic half-life of sialylated molecules is believed to lie in their decreased recognition by lectins (Drickamer, 1988, J. Biol. Chem. 263:9557-9560). However, in general fungal cells do not add terminal sialic acid residues to glycans on peptides, and peptides synthesized in fungal cells are therefore asialic. According to the present invention, this deficiency can be remedied using the in vitro glycan remodeling methods of the invention described in detail elsewhere herein.

*Trichoderma* species useful as hosts for the production of peptides to be remodeled include *T. reesei*, such as QM6a, ALKO2442 or CBS383.78 (Centraalbureau voor Schimmelcultures, Oosterstraat 1, PO Box 273, 3740 AG Baarn, The Netherlands, or, ATCC13631 (American Type Culture Collection, Manassas Va., 10852, USA, type); *T. viride* (such as CBS189.79 (det. W. Gams); *T. longibrachiatum*, such as CBS816.68 (type); *T. pseudokoningii* (such as MUCL19358; Mycotheque de l'Universite Catholique de Louvain); *T. saturnisporum* CBS330.70 (type); *T. harzianum* CBS316.31 (det. W. Gams); *T. virgatum* (*T. pseudokoningii*) ATCC24961. Most preferably, the host is *T. reesei* and more preferably, it is *T. reesei* strains QM9414 (ATCC 26921), RUT-C-30 (ATCC 56765), and highly productive mutants such as VTT-D-79125, which is derived from QM9414 (Nevalainen, Technical Research Centre of Finland Publications 26, (1985), Espoo, Finland).

The transformation of *Trichoderma* with DNA is performed using any technique known in the art, including that taught in European patent No. EP0244234, Harkki (1989, Bio/Technology 7:596-601) and Uusitalo (1991, J. Biotech. 17:35-50). Culture of *Trichoderma* is supported by previous extensive experience in industrial scale fermentation techniques; for example, see Finkelstein, 1992, Biotechnology of Filamentous Fungi: Technology and Products, Butterworth-Heinemann, publishers, Stoneham, Mass.

5. *Kluyveromyces*

Yeast belonging to the genus *Kluyveromyces* have been used as host organisms for the production of recombinant peptides. Peptides produced by this genus of yeast are, in particular, chymosin (European Patent 96 430), thaumatin (European Patent 96 910), albumin, interleukin-1β, TPA, TIMP (European Patent 361 991) and albumin derivatives having a therapeutic function (European Patent 413 622). Species of particular interest in the genus *Kluyveromyces* include *K. lactis*.

Methods of expressing recombinant peptides in *Kluyvermyces* spp. are well known in the art. Vectors for the expression and secretion of human recombinant peptides in *Kluyvermyces* are known in the art (Yeh, J. Cell. Biochem. Suppl. 14C:68, Abst. H402; Fleer, 1990, Yeast 6 (Special Issue):S449) as are procedures for transformation and expression of recombinant peptides (Ito et al., 1983, J. Bacteriol. 153:163-168; van den Berg, 1990, Bio/Technology 8:135-139; U.S. Pat. No. 5,633,146, WO8304050A1, EP0096910, EP0241435, EP0301670, EP0361991, all of which are incorporated by reference herein in their entirety). For a review of genetic manipulation of *Kluyveromyces lactis* linear DNA plasmids by gene targeting and plasmid shuffles, see Schaffrath et al. (1999, FEMS Microbiol Lett. 178(2):201-210).

6. *Chrysoporium*

The fungal genus *Chrysoporium* has recently been used to expression of foreign recombinant peptides. A description of the procedures by which one of skill in the art can use *Chrysoporium* can be used to express foreign peptides is found in WO 00/20555 (incorporated by reference herein in its entirety). Species particularly suitable for expression system include, but are not limited to, *C. botryoides, C. carmichaelii, C. crassitunicatum, C. europae, C. evolceannui, F. fastidium, C. filiforme, C. gerogiae, C. globiferum, C. globiferum* var. *articulatum, C. globiferum* var. *niveum, C. hirundo, C. hispanicum, C. holmii, C. indicum, C. mops, C. keratinophilum, C. kreiselii, C. kuzurovianum, C. lignorum, C. lobatum, C. lucknowense, C. lucknowense* Garg 27K, *C. medium, C. medium* var. *spissescens, C. mephiticum, C. merdarium, C. merdarium* var. *roseum, C. minor, C. pannicola, C. parvum, C. parvum* var. *crescens, C. pilosum, C. peodomerderium, C. pyriformis, C. queenslandicum, C. sigleri, C. sulfureum, C. synchronum, C. tropicum, C. undulatum, C. vallenarense, C. vespertilium*, and *C. zonatum*.

7. Others

Methods for transforming *Schwanniomyces* are disclosed in European Patent 394 538. Methods for transforming *Acremonium chrysogenum* are disclosed by U.S. Pat. No. 5,162,228. Methods for transforming *Neurospora* are disclosed by U.S. Pat. No. 4,486,533. Also know is an expression system specifically for *Schizosaccharomyces pombe* (European Patent 385 391). General methods for expressing peptides in fission yeast, *Schizosaccharomyces pombe* can be found in Giga-Hama and Kumagai (1997, Foreign gene expression in fission yeast: *Schizosaccharomyces pombe*, Springer, Berlin).

C. Mammalian Systems

As discussed above, mammalian cells typically produce a heterogeneous mixture of N-glycan structures which vary with respect to the number and arrangement of additional sugars attached to the trimannosyl core. Typically, mammalian cells produce peptides having a complex glycan structure, such as that shown in FIG. 3, right side. Using the methods of the present invention, a peptide produced in a mammalian cell may be remodeled in vitro to generate a peptide having desired glycosylation by first identifying the primary glycan structure and then determining which sugars must be removed in order to remodel the glycan structure. As discussed herein, the sugars to be removed will determine which cleavage enzymes will be used and thus, the precise steps of the remodeling process will vary depending on the primary glycan structure used as the initial substrate. A sample scheme for remodeling a glycan structure commonly produced in mammalian cells is shown in FIG. 2.

The N-glycan biosynthetic pathway in mammalian cells has been well characterized (reviewed in Moremen, 1994, Glycobiology 4:113-125). Many of the enzymes necessary for glycan synthesis have been identified, and mutant cell lines defective in this enzymatic pathway have been isolated including the Chinese hamster ovary (CHO) cell lines Lec23 (defective in alpha-glucosidase I) and Led 8 (novel GlcNAc-TVIII). The glycosylation pattern of peptides produced by these mutant cells is altered relative to normal CHO cells. As discussed herein, the glycosylation defects in these and other mutant cells can be exploited for the purposes of producing a peptide that lacks a complex glycan structure. For example, peptides produced by Lec23 cells lack sialic acid residues, and thus require less enzymatic manipulation in order to reduce the glycan structure to an elemental trimannosyl core or to Man3GlcNAc4. Thus, peptides produced in these cells can serve as preferred substrates for glycan remodeling. One of ordinary skill in the art could isolate or identify other glycosylation-defective cell lines based on known methods, for example the method described in Stanley et al., 1990, Somatic Cell Mol. Genet., 16: 211-223. Use of glycosylation-defective cell lines, those identified and as yet unidentified, is included in the invention for the purpose of generating preferred peptide substrates for the remodeling processes described herein.

Expression vectors useful for expressing exogenous peptides in mammalian cells are numerous, and are well known to those in the art. Many mammalian expression vectors are now commercially available from companies, including Novagen, Inc (Madison, Wis.), Gene Therapy Systems (San Diego, Calif.), Promega (Madison, Wis.), ClonTech Inc. (Palo Alto, Calif.), and Stratagene (La Jolla, Calif.), among others.

There are several mammalian cell lines that are particularly adept at expressing exogenous peptides. Typically mammalian cell lines originate from tumor cells extracted from mammals that have become immortalized, that is to say, they can replicate in culture essentially indefinitely. These cell lines include, but are not limited to, CHO (Chinese hamster ovary, e.g. CHO-K1; ATCC No. CCL 61) and variants thereof, NSO (mouse myeloma), BNK, BHK 570 (ATCC No. CRL 10314), BHK (ATCC No. CRL 1632), Per.C6™ (immortalized human cells, Crucell N.V., Leiden, The Netherlands), COS-1 (ATCC No. CRL 1650), COS-7 (ATCC No. CRL 1651), HEK 293, mouse L cells, T lymphoid cell lines, BW5147 cells and MDCK (Madin-Darby canine kidney), HeLa (human), A549 (human lung carcinoma), 293 (ATCC No. CRL 1573; Graham et al., 1977, Gen. Virol. 36:59-72), BGMK (Buffalo Green Monkey kidney), Hep-2 (human epidermoid larynx carcinoma), LLC-$MK_2$ (African Green Monkey Kidney), McCoy, NCI-H292 (human pulmonary mucoepidermoid carcinoma tube), RD (rhabdomyosarcoma), Vero (African Green Monkey kidney), HEL (human embryonic lung), Human Fetal Lung-Chang, MRCS (human embryonic lung), MRHF (human foreskin), and WI-38 (human embryonic lung). In some cases, the cells in which the therapeutic peptide is expressed may be cells derived from the patient to be treated, or they may be derived from another related or unrelated mammal. For example, fibroblast cells may be isolated from the mammal's skin tissue, and cultured and transformed in vitro. This technology is commercially available from Transkaryotic Therapies, Inc. (Cambridge, Mass.). Almost all currently used cell lines are available from the American Type Culture Collection (ATCC, Manassas, Va.) and BioWhittaker (Walkersville, Md.).

Mammalian cells may be transformed with DNA using any one of several techniques that are well known to those in the art. Such techniques include, but are not limited to, calcium phosphate transformation (Chen and Okayama, 1988; Graham and van der Eb, 1973; Corsaro and Pearson, 1981, Somatic Cell Genetics 7:603), Diethylaminoethyl (DEAE)-dextran transfection (Fujita et al., 1986; Lopata et al., 1984; Selden et al., 1986,), electroporation (Neumann et al., 1982; Potter, 1988; Potter et al., 1984; Wong and Neuman, 1982), cationic lipid reagent transfection (Elroy-Stein and Moss, 1990; Feigner et al., 1987; Rose et al., 1991; Whitt et al., 1990; Hawley-Nelson et al., 1993, Focus 15:73; Ciccarone et al., 1993, Focus 15:80), retroviral (Cepko et al., 1984; Miller and Baltimore, 1986; Pear et al., 1993; Austin and Cepko, 1990; Bodine et al., 1991; Fekete and Cepko, 1993; Lemischka et al., 1986; Turner et al., 1990; Williams et al., 1984; Miller and Rosman, 1989, BioTechniques 7:980-90; Wang and Finer, 1996, Nature Med. 2:714-6), polybrene (Chaney et al, 1986; Kawai and Nishizawa, 1984), microinjection (Capecchi, 1980), and protoplast fusion (Rassoulzadegan et al., 1982; Sandri-Goldin et al., 1981; Schaffer, 1980), among others. In general, see Sambrook et al. (2001, Molecular Cloning: A Laboratory Manual, Cold Spring Harbor Laboratory, New York) and Ausubel et al. (2002, Current Protocols in Molecular Biology, John Wiley & Sons, New York) for transformation techniques.

Recently the baculovirus system, popular for transformation of insect cells, has been adapted for stable transformation of mammalian cells (see, for review, Koat and Condreay, 2002, Trends Biotechnol. 20:173-180, and references cited therein). The production of recombinant peptides in cultured mammalian cells is disclosed, for example, in U.S. Pat. Nos. 4,713,339, 4,784,950; 4,579,821; and 4,656,134. Several companies offer the services of transformation and culture of mammalian cells, including Cell Trends, Inc. (Middletown, Md.). Techniques for culturing mammalian cells are well known in the art, and further found in Hauser et al. (1997, *Mammalian Cell Biotechnology*, Walter de Gruyer, Inc., Hawthorne, N.Y.), and Sambrook et al. (2001, *Molecular Cloning: A Laboratory Manual*, Cold Spring Harbor and references cited therein.

D. Insect

Insect cells and in particular, cultured insect cells, express peptides having N-linked glycan structures that are rarely sialylated and usually comprise mannose residues which may or may not have additional fucose residues attached thereto. Examples of the types of glycan structures present on peptides produced in cultured insect cells are shown in FIG. 6, and mannose glycans thereof. In this situation, there may or may not be a core fucose present, which if present, may be linked to the glycan via several different linkages.

Baculovirus-mediated expression in insect cells has become particularly well-established for the production of recombinant peptides (Altmann et al., 1999, Glycoconjugate J. 16:109-123). With regard to peptide folding and post-translational processing, insect cells are second only to mammalian cell lines. However, as noted above, N-glycosylation of peptides in insect cells differs in many respects from N-glycosylation in mammalian cells particularly in that insect cells frequently generate truncated glycan structures comprising oligosaccharides containing just three or sometimes only two mannose residues. These structures may be additionally substituted with fucose residues.

According to the present invention, a peptide produced in an insect cell may be remodeled in vitro to generate a peptide with desired glycosylation by first optionally removing any substituted fucose residues using an appropriate fucosidase enzyme. In instances where the peptide comprises an elemental trimannosyl core structure following the removal of fucose residues, then all that is required is the in vitro addition of the appropriate sugars to the trimannosyl core structure to generate a peptide having desired glycosylation. In instances when the peptide might contain only two mannose residues in the glycan structure following removal of any fucose residues, a third mannose residue may be added using a mannosyltransferase enzyme and a suitable donor molecule such as GDP-mannose, and thereafter the appropriate residues are added to generate a peptide having desired glycosylation. Optionally, monoantennary glycans can also be generated from these species.

Protocols for the use of baculovirus to transform insect cells are well known to those in the art. Several books have been published which provide the procedures to use the baculovirus system to express peptides in insect cells. These books include, but are not limited to, Richardson (Baculovirus Expression Protocols, 1998, Methods in Molecular Biology, Vol 39, Humana Pr), O'Reilly et al. (1994, Baculovirus Expression Vectors: A Laboratory Manual, Oxford Univ Press), and King and Possee (1992, The Baculovirus Expression System: A Laboratory Guide, Chapman & Hall). In addition, there are also publications such as Lucklow (1993, Curr. Opin. Biotechnol. 4:564-572) and Miller (1993, Curr. Opin. Genet. Dev. 3:97-101).

Many patents have also been issued that related to systems for baculoviral expression of foreign proteins. These patents include, but are not limited to, U.S. Pat. No. 6,210,966 (Culture medium for insect cells lacking glutamine and containing ammonium salt), U.S. Pat. No. 6,090,584 (Use of BVACs (BaculoVirus Artificial Chromosomes) to produce recombinant peptides), U.S. Pat. No. 5,871,986 (Use of a baculovirus to express a recombinant nucleic acid in a mammalian cell), U.S. Pat. No. 5,759,809 (Methods of expressing peptides in insect cells and methods of killing insects), U.S. Pat. No. 5,753,220 (Cysteine protease gene defective baculovirus, process for its production, and process for the production of economic peptide by using the same), U.S. Pat. No. 5,750,383 (Baculovirus cloning system), U.S. Pat. No. 5,731,182 (Non-mammalian DNA virus to express a recombinant nucleic acid in a mammalian cell), U.S. Pat. No. 5,728,580 (Methods and culture media for inducing single cell suspension in insect cell lines), U.S. Pat. No. 5,583,023 (Modified baculovirus, its preparation process and its application as a gene expression vector), U.S. Pat. No. 5,571,709 (Modified baculovirus and baculovirus expression vectors), U.S. Pat. No. 5,521,299 (Oligonucleotides for detection of baculovirus infection), U.S. Pat. No. 5,516,657 (Baculovirus vectors for expression of secretory and membrane-bound peptides), U.S. Pat. No. 5,475,090 (Gene encoding a peptide which enhances virus infection of host insects), U.S. Pat. No. 5,472,858 (Production of recombinant peptides in insect larvae), U.S. Pat. No. 5,348,886 (Method of producing recombinant eukaryotic viruses in bacteria), U.S. Pat. No. 5,322,774 (Prokaryotic leader sequence in recombinant baculovirus expression system), U.S. Pat. No. 5,278,050 (Method to improve the efficiency of processing and secretion of recombinant genes in insect systems), U.S. Pat. No. 5,244,805 (Baculovirus expression vectors), U.S. Pat. No. 5,229,293 (Recombinant baculovirus), U.S. Pat. No. 5,194,376 (Baculovirus expression system capable of producing recombinant peptides at high levels), U.S. Pat. No. 5,179,007 (Method and vector for the purification of recombinant peptides), U.S. Pat. No. 5,169,784 (Baculovirus dual promoter expression vector), U.S. Pat. No. 5,162,222 (Use of baculovirus early promoters for expression of recombinant nucleic acids in stably transformed insect cells or recombinant baculoviruses), U.S. Pat. No. 5,155,037 (Insect signal sequences useful to improve the efficiency of processing and secretion of recombinant nucleic acids in insect systems), U.S. Pat. No. 5,147,788 (Baculovirus vectors and methods of use), U.S. Pat. No. 5,110,729 (Method of producing peptides using baculovirus vectors in cultured cells), U.S. Pat. No. 5,077,214 (Use of baculovirus early promoters for expression of recombinant genes in stably transformed insect cells), U.S. Pat. No. 5,023,328 (Lepidopteran AKH signal sequence), and U.S. Pat. Nos. 4,879,236 and 4,745,051 (Method for producing a recombinant baculovirus expression vector). All of the aforementioned patents are incorporated in their entirety by reference herein. Insect cell lines of several different species origin are currently being used for peptide expression, and these lines are well known to those in the art. Insect cell lines of interest include, but are not limited to, dipteran and lepidopteran insect cells in general, Sf9 and variants thereof (fall armyworm *Spodoptera frugiperda*), *Estigmene acrea, Trichoplusia ni, Bombyx mori, Malacosoma disstri. drosophila* lines Kc1 and SL2 among others, and mosquito.

E. Plants

Plant cells as peptide producers present a different set of issues. While N-linked glycans produced in plants comprise a trimannosyl core structure, this pentasaccharide backbone may comprise several different additional sugars as shown in FIG. 5. For example, in one instance, the trimannosyl core structure is substituted by a β1,2 linked xylose residue and an α1,3 linked fucose residue. In addition, plant cells may also produce a Man5GlcNAc2 structure. Peptides produced in plant cells are often highly antigenic as a result of the presence of the core α1,3 fucose and xylose on the glycan structure, and are rapidly cleared from the blood stream when introduced into a mammal due to the absence of terminal sialic acid residues. Therefore, unless these peptides are remodeled using the methods provided herein, they are generally considered to be unsuitable as therapeutic agents in mammals. While some monoclonal antibodies expressed in plant cells were found to be non-immunogenic in mouse, it is likely that the glycan chains were not immunogenic because they were buried in the Fc region in these antibodies (Chargelegue et al., 2000, Transgenic Res. 9(3):187-194).

Following the directions provided herein, it is now possible to generate a peptide produced in a plant cell wherein an increased number of the glycan structures present thereon comprise an elemental trimannosyl core structure, or a Man3GlcNAc4 structure. This is accomplished by cleaving off any additional sugars in vitro using a combination of appropriate glycosidases, including fucosidases, until the elemental trimannosyl core structure or the Man3GlcNAc4 structure is arrived at. These cleavage reactions should also include removal of any fucose or xylose residues from the structures in order to diminish the antigenicity of the final peptide when introduced into a mammal. Plant cells having mutations that inhibit the addition of fucose and xylose residues to the trimannosyl core structure are known in the art (von Schaewen et al., 1993, Plant Physiology 102:1109-1118). The use of these cells to produce peptides having glycans which lack fucose and xylose is contemplated by the invention. Upon production of the elemental trimannosyl core or Man3GlcNAc4 structure, additional sugars may then be added thereto to arrive at a peptide having desired glycosylation that is therefore suitable for therapeutic use in a mammal.

Transgenic plants are considered by many to be the expression system of choice for pharmaceutical peptides. Potentially, plants can provide a cheaper source of recombinant peptides. It has been estimated that the production costs of recombinant peptides in plants could be between 10 to 50 times lower that that of producing the same peptide in *E. coli*. While there are slight differences in the codon usage in plants as compared to animals, these can be compensated for by adjusting the recombinant DNA sequences (see, Kusnadi et al., 1997, Biotechnol. Bioeng. 56:473-484; Khoudi et al., 1999, Biotechnol. Bioeng. 135-143; Hood et al., 1999, Adv. Exp. Med. Biol. 464:127-147). In addition, peptide synthesis, secretion and post-translational modification are very similar in plants and animals, with only minor differences in plant glycosylation (see, Fischer et al., 2000, J. Biol. Regul. Homest. Agents 14: 83-92). Then, products from transgenic plants are also less likely to be contaminated by animal pathogens, microbial toxins and oncogenic sequences.

The expression of recombinant peptides in plant cells is well known in the art. In addition to transgenic plants, peptides can also produced in transgenic plant cell cultures (Lee et al., 1997, Mol. Cell. 7:783-787), and non-transgenic plants inoculated with recombinant plant viruses. Several books have been published that describe protocols for the genetic transformation of plant cells: Potrykus (1995, Gene transfer to plants, Springer, New York), Nickoloff (1995, Plant cell electroporation and electrofusion protocols, Humana Press, Totowa, N.Y.) and Draper (1988, Plant genetic transformation, Oxford Press, Boston).

Several methods are currently used to stably transform plant cells with recombinant genetic material. These methods include, but are not limited to, *Agrobacterium* transformation (Bechtold and Pelletier, 1998; Escudero and Hohn, 1997; Hansen and Chilton, 1999; Touraev et al., 1997), biolistics (microprojectiles) (Finer et al., 1999; Hansen and Chilton, 1999; Shilito, 1999), electroporation of protoplasts (Fromm et al., 1985, Ou-Lee et al., 1986; Rhodes et al., 1988; Saunders et al., 1989; Trick et al., 1997), polyethylene glycol treatment (Shilito, 1999; Trick et al., 1997), in planta mircroinjection (Leduc et al., 1996; Zhou et al., 1983), seed imbibition (Trick et al., 1997), laser beam (1996), and silicon carbide whiskers (Thompson et al., 1995; U.S. Patent Appln. No. 20020100077, incorporated by reference herein in its entirety).

Many kinds of plants are amenable to transformation and expression of exogenous peptides. Plants of particular interest to express the peptides to be used in the remodeling method of the invention include, but are not limited to, *Arabidopsis thalliana*, rapeseed (*Brassica* spp.; Ruiz and Blumwald, 2002, Planta 214:965-969)), soybean (*Glycine max*), sunflower (*Helianthus unnuus*), oil palm (*Elaeis guineeis*), groundnut (peanut, *Arachis hypogaea*; Deng et al., 2001, Cell. Res. 11:156-160), coconut (*Cocus nucifera*), castor (*Ricinus communis*), safflower (*Carthamus tinctorius*), mustard (*Brassica* spp. and *Sinapis alba*), coriander, (*Coriandrum sativum*), squash (*Cucurbita maxima*; Spencer and Snow, 2001, Heredity 86(Pt 6):694-702), linseed/flax (*Linum usitatissimum*; Lamblin et al., 2001, Physiol Plant 112:223-232), Brazil nut (*Bertholletia excelsa*), jojoba (*Simmondsia chinensis*), maize (*Zea mays*; Hood et al., 1999, Adv. Exp. Med. Biol. 464:127-147; Hood et al., 1997, Mol. Breed. 3:291-306; Petolino et al., 2000, Transgenic Research 9:1-9), alfalfa (Khoudi et al., 1999, Biotechnol. Bioeng. 64:135-143), tobacco (*Nicotiana tabacum*; Wright et al., Transgenic Res. 10:177-181; Frigerio et al., 2000, Plant Physiol. 123: 1483-1493; Cramer et al., 1996, Ann. New York Acad. Sci. 792:62-8-71; Cabanes-Macheteau et al., 1999, Glycobiology 9:365-372; Ruggiero et al., 2000, FEBS Lett. 469:132-136), canola (Bai et al., 2001, Biotechnol. Prog. 17:168-174; Zhang et al., 2000, J. Anim. Sci. 78:2868-2878)), potato (Tacket et al., 1998, J. Infect. Dis. 182:302-305; Richter et al., 2000, Nat. Biotechnol. 18:1167-1171; Chong et al., 2000, Transgenic Res. 9:71-78), alfalfa (Wigdorovitz et al., 1999, Virology 255:347-353), Pea (*Pisum sativum*; Perrin et al., 2000, Mol. Breed. 6:345-352), rice (*Oryza sativa*; Stoger et al., 2000, Plant Mol. Biol. 42:583-590), cotton (*Gossypium hirsutum*; Kornyeyev et al., 2001, Physiol Plant 113:323-331), barley (*Hordeum vulgare*; Petersen et al., 2002, Plant Mol Biol 49:45-58); wheat (*Triticum* spp.; Pellegrineschi et al., 2002, Genome 45:421-430) and bean (*Vicia* spp.; Saalbach et al., 1994, Mol Gen Genet. 242:226-236).

If expression of the recombinant nucleic acid is desired in a whole plant rather than in cultured cells, plant cells are first transformed with DNA encoding the peptide, following which, the plant is regenerated. This involves tissue culture procedures that are typically optimized for each plant species. Protocols to regenerate plants are already well known in the art for many species. Furthermore, protocols for other species can be developed by one of skill in the art using routine experimentation. Numerous laboratory manuals are available that describe procedures for plant regeneration, including but not limited to, Smith (2000, Plant tissue culture: techniques and experiments, Academic Press, San Diego), Bhojwani and Razdan (1996, Plant tissue culture: theory and practice, Elsevier Science Pub., Amsterdam), Islam (1996, Plant tissue culture, Oxford & IBH Pub. Co., New Delhi, India), Dodds and. Roberts (1995, Experiments in plant tissue culture, New York: Cambridge University Press, Cambridge England), Bhojwani (Plant tissue culture: applications and limitations, Elsevier, Amsterdam, 1990), Trigiano and Gray (2000, Plant tissue culture concepts and laboratory exercises, CRC Press, Boca Raton, Fla.), and Lindsey (1991, Plant tissue culture manual: fundamentals and applications, Kluwer Academic, Boston).

While purifying recombinant peptides from plants may potentially be costly, several systems have been developed to minimize these costs. One method directs the synthesized peptide to the seed endosperm from where it can easily extracted (Wright et al., 2001, Transgenic Res. 10:177-181, Guda et al., 2000, Plant Cell Res. 19:257-262; and U.S. Pat. No. 5,767,379, which is incorporated by reference herein in its entirety). An alternative approach is the co-extraction of the recombinant peptide with conventional plant products such as starch, meal or oil. In oil-seed rape, a fusion peptide of oleosin-hurudin when expressed in the plant, attaches to the oil body of the seed, and can be extracted from the plant seed along with the oil (Parmenter, 1995, Plant Mol. Biol. 29:1167-1180; U.S. Pat. Nos. 5,650,554, 5,792,922, 5,948,682 and 6,288,304, and US application 2002/0037303, all of which are incorporated in their entirely by reference herein). In a variation on this approach, the oleosin is fused to a peptide having affinity for the exogenous co-expressed peptide of interest (U.S. Pat. No. 5,856,452, incorporated by reference herein in its entirety).

Expression of recombinant peptides in plant plastids, such as the chloroplast, generates peptides having no glycan structures attached thereto, similar to the situation in prokaryotes. However, the yield of such peptides is vastly greater when expressed in these plant cell organelles, and thus this type of expression system may have advantages over other systems. For a general review on the technology for plastid expression of exogenous peptides in higher plants, see Hager and Beck (2000, Appl. Microbiol. Biotechnol. 54:302-310, and references cited therein). Plastid expression has been particularly successful in tobacco (see, for example, Staub et al., 2000, Nat. Biotechnol. 18:333-338).

F. Transgenic Animals

Introduction of a recombinant DNA into the fertilized egg of an animal (e.g., a mammal) may be accomplished using any number of standard techniques in transgenic animal technology. See, e.g., Hogan et al., Manipulating the Mouse Embryo: A Laboratory Manual, Cold Spring Harbor Laboratory Press, Cold Spring Harbor, N.Y., 1986; and U.S. Pat. No. 5,811,634, which is incorporated by reference herein in its entirety. Most commonly, the recombinant DNA is introduced into the embryo by way of pronuclear microinjection (Gordon et al., 1980, PNAS 77:7380-7384; Gordon and Ruddle, 1981, Science 214:1244-1246; Brinster et al., 1981, Cell 27:223-231; Costantini and Lacy, 1981, Nature 294:92-94). Microinjection has the advantage of being applicable to a wide variety of species. Preimplantation embryos may also be transformed with retroviruses (Jaenisch and Mintz, 1974, Proc. Natl. Acad. Sci. U.S.A. 71:1250-1254; Jaenisch et al., 1976, Hamatol Bluttransfus. 19:341-356; et al., 1984, Proc. Natl. Acad. Sci. U.S.A. 81:7151-7155). Retroviral mediated transformation has the advantage of adding single copies of the recombinant nucleic acid to the cell, but it produces a high degree of mosaicism. Most recently, embryonic stem cell-mediated techniques have been used (Gossler et al., 1986, Proc. Natl. Acad. Sci. U.S.A. 83:9065-9069), transfer of entire chromosomal segments (Lavitrano et al., 1989, Cell 57:717-723), and gamete transfection in conjunction with in vitro fertilization (Lavitrano et al., 1989, Cell 57:717-723) have also been used. Several books of laboratory procedures have been published disclosing these techniques: Cid-Arregui and García-Carrancá (1998, Microinjection and Transgenesis: Strategies and Protocols, Springer, Berlin), Clarke (2002, Transgenesis Techniques: Principles and Protocols, Humana Press, Totowa, N.J.), and Pinkert (1994, Transgenic Animal Technology: A Laboratory Handbook, Academic Press, San Diego).

Once the recombinant DNA is introduced into the egg, the egg is incubated for a short period of time and is then transferred into a pseudopregnant animal of the same species from which the egg was obtained (Hogan et al., supra). In the case of mammals, typically 125 eggs are injected per experiment, approximately two-thirds of which will survive the procedure. Twenty viable eggs are transferred into a pseudopregnant mammal, four to ten of which will develop into live progeny. Typically, 10-30% of the progeny (in the case of mice) carry the recombinant DNA.

While the entire animal can be used as an expression system for the peptides of the invention, in a preferred embodiment, the exogenous peptide accumulates in products of the animal, from which it can be harvested without injury to the animal. In preferred embodiments, the exogenous peptide accumulates in milk, eggs, hair, blood, and urine.

If the recombinant peptide is to be accumulated in the milk of the animal, suitable mammals are ruminants, ungulates, domesticated mammals, and dairy animals. Particularly preferred animals are goats, sheep, camels, cows, pigs, horses, oxen, and llamas. Methods for generating transgenic cows that accumulate a recombinant peptide in their milk are well known: see, Newton (1999, J. Immunol. Methods 231:159-167), Ebert et al. (1991, Biotechnology 9: 835-838), and U.S. Pat. Nos. 6,210,736, 5,849,992, 5,843,705, 5,827,690, 6,222,094, all of which are incorporated herein by reference in their entirety. The generation of transgenic mammals that produce a desired recombinant peptide is commercially available from GTC Biotherapeutics, Framingham, Mass.

If the recombinant peptide is to be accumulated in eggs, suitable birds include, but are not limited to, chickens, geese, and turkeys. Other animals of interest include, but are not limited to, other species of avians, fish, reptiles and amphibians. The introduction of recombinant DNA to a chicken by retroviral transformation is well known in the art: Thoraval et al. (1995, Transgenic Research 4:369-376), Bosselman et al., (1989, Science 243: 533-535), Petropoulos et al. (1992, J. Virol. 66: 3391-3397), U.S. Pat. No. 5,162,215, incorporated by reference herein in its entirety. Successful transformation of chickens with recombinant DNA also been achieved wherein DNA is introduced into blastodermal cells and blastodermal cells so transfected are introduced into the embryo: Brazolot et al. (1991, Mol. Reprod. Dev. 30: 304-312), Fraser, et al. (1993, Int. J. Dev. Biol. 37: 381-385), and Petitte et al. (1990, Development 108: 185-189). High throughput technology has been developed to assess whether a transgenic chicken expresses the desired peptide (Harvey et al., 2002, Poult. Sci. 81:202-212, U.S. Pat. No. 6,423,488, incorporated by reference herein in its entirety). Using retroviral transformation of chicken with a recombinant DNA, exogenous beta-lactamase was accumulated in the egg white of the chicken (Harvey et al., 2002, Nat. Biotechnol. 20(4):396-399). The production of chickens producing exogenous peptides in egg is commercially available from AviGenics, Inc., Athens Ga.

G. Bacteria

Recombinantly expressed peptides produced in bacteria are not generally glycosylated. However, bacteria systems capable of glycosylating peptides are becoming evident and therefore it is likely that glycosylated recombinant peptides may be produced in bacteria in the future.

Numerous bacterial expression systems are known in the art. Preferred bacterial species include, but are not limited to, *E. coli*. and *Bacillus* species.

The expression of recombinant peptides in *E. coli* is well known in the art. Protocols for *E. coli*-based expression systems are found in U.S. Appln No. 20020064835, U.S. Pat. Nos. 6,245,539, 5,606,031, 5,420,027, 5,151,511, and U33, 653, among others. Methods to transform bacteria include, but are not limited to, calcium chloride (Cohen et al., 1972, Proc. Natl. Acad. Sci. U.S.A. 69:2110-2114; Hanahan, 1983, J. Mol. Biol. 166:557-580; Mandel and Higa, 1970, J. Mol. Biol. 53:159-162) and electroporation (Shigekawa and Dower, 1988, Biotechniques 6:742-751), and those described in Sambrook et al., 2001 (supra). For a review of laboratory protocols on microbial transformation and expression systems, see Saunders and Saunders (1987, Microbial Genetics Applied to Biotechnology: Principles and Techniques of Gene Transfer and Manipulation, Croom Helm, London), Pühler (1993, Genetic Engineering of Microorganisms, Weinheim, New York), Lee et al., (1999, Metabolic Engineering, Marcel Dekker, New York), Adolph (1996, Microbial Genome Methods, CRC Press, Boca Raton), and Birren and Lai (1996, Nonmammalian Genomic Analysis: A Practical Guide, Academic Press, San Diego), For a general review on the literature for peptide expression in *E. coli* see Balbas (2001, Mol. Biotechnol. 19:251-267). Several companies now offer bacterial strains selected for the expression of mammalian peptides, such as the Rosetta™ strains of *E. coli* (Novagen, inc., Madison, Wis.; with enhanced expression of eukaryotic codons not normally used in bacteria cells, and enhanced disulfide bond formation), H. Cell Engineering It will be apparent from the present disclosure that the more uniform the starting material produced by a cell, the more efficient will be the generation in vitro of large quantities of peptides having desired glycosylation. Thus, the genetic engineering of host cells to produce uniformly glycosylated peptides as starting material for the in vitro enzymatic reactions disclosed herein, provides a significant advantage over using a peptide starting material having a heterogeneous set of glycan structures attached thereto. One preferred peptide starting material for use in the present invention is a peptide having primarily glycan molecules which consist solely of an elemental trimannosyl core structure. Another preferred starting material is Man3GlcNAc4. Following the remodeling process, the preferred peptides will give rise to the greatest amount of peptides having desired glycosylation, and thus improved clinical efficacy. However, other glycan starting material is also suitable for use in the methods described herein, in that for example, high mannose glycans may be easily reduced, in vitro, to elemental trimannosyl core structures using a series of mannosidases. As described elsewhere herein, other glycan starting material may also be used, provided it is possible to cleave off all extraneous sugar moieties so that the elemental trimannosyl core structure or Man3GlcNAc4 is generated. Thus, the purpose of using genetically engineered cells for the production of the peptides of the present invention is to generate peptides having as uniform as possible a glycan structure attached thereto, wherein the glycan structure can be remodeled in vitro to generate a peptide having desired glycosylation. This will result in a dramatic reduction in production costs of these peptides. Since the glycopeptides produced using this methodology will predominantly have the same N-linked glycan structure, the post-production modification protocol can be standardized and optimized to produce a greater batch-to-batch consistency of final product. As a result, the final completed-chain products may be less heterogeneous than those presently available. The products will have an improved biological half-life and bioactivity as compared to the products of the prior art. Alternatively, if desired, the invention can be used to introduce limited and specific heterogeneity, e.g., by choosing reaction conditions that result in differential addition of sugar moieties.

Preferably, though not as a rigid requirement, the genetically engineered cell is one which produces peptides having glycan structures comprised primarily of an elemental trimannosyl core structure or Man3GlcNAc4. At a minimum, the proportion of these preferred structures produced by the genetically engineered cell must be enough to yield a peptide having desired glycosylation following the remodeling protocol.

In general, any eukaryotic cell type can be modified to become a host cell of the present invention. First, the glycosylation pattern of both endogenous and recombinant glycopeptides produced by the organism are determined in order to identify suitable additions/deletions of enzymatic activities that result in the production of elemental trimannosyl core glycopeptides or Man3GlcNAc4 glycopeptides. This will typically entail deleting activities that use trimannosyl glycopeptides as substrates for a glycosyltransferase reaction and inserting enzymatic activities that degrade more complex N-linked glycans to produce shorter chains. In addition, genetically engineered cells may produce high mannose glycans, which may be cleaved by mannosidase to produce desired starting glycan structures. The mannosidase may be active in vivo in the cell (i.e., the cell may be genetically engineered to produce them), or they may be used in in vitro post production reactions.

Techniques for genetically modifying host cells to alter the glycosylation profile of expressed peptides are well-known. See, e.g., Altmann et al. (1999, Glycoconjugate J. 16: 109-123), Ailor et al. (2000, Glycobiology 10(8): 837-847), Jarvis et al., (In vitrogen Conference, March, 1999, abstract), Hollister and Jarvis, (2001, Glycobiology 11(1): 1-9), and Palacpac et al., (1999, PNAS USA 96: 4697), Jarvis et al., (1998. Curr. Opin. Biotechnol. 9:528-533), Gerngross (U.S. Patent Publication No. 20020137134), all of which disclose techniques to “mammalianize” insect or plant cell expression systems by transfecting insect or plant cells with glycosyltransferase genes.

Techniques also exist to genetically alter the glycosylation profile of peptides expressed in *E. coli. E. coli* has been engineered with various glycosyltransferases from the bacteria *Neisseria meningitidis* and *Azorhizobium* to produce oligosaccharides in vivo (Bettler et al., 1999, Glycoconj. J. 16:205-212). K coli which has been genetically engineered to over-express *Neisseria meningitidis* β1,3 N acetyl glucosaminyltransferase lgtA gene will efficiently glycosylate exogenous lactose (Priem et al., 2002, Glycobiology 12:235-240). Fungal cells have also been genetically modified to produce exogenous glycosyltransferases (Yoshida et al., 1999, Glycobiology, 9(1):53-58; Kalsner et al., 1995, Glycoconj. J. 12:360-370; Schwientek and Ernst, 1994, Gene 145 (2):299-303; Chiba et al, 1995, Biochem J. 308:405-409).

Thus, in one aspect, the present invention provides a cell that glycosylates a glycopeptide population such that a proportion of glycopeptides produced thereby have an elemental trimannosyl core or a Man3GlcNAc4 structure. Preferably, the cell produces a peptide having a glycan structure comprised solely of an elemental trimannosyl core. At a minimum, the proportion of peptides having an elemental trimannosyl core or a Man3GlcNAc4 structure is enough to yield peptides having desired glycosylation following the remodeling process. The cell has introduced into it one or more heterologous nucleic acid expression units, each of which may comprise one or more nucleic acid sequences encoding one or more peptides of interest. The natural form of the glycopeptide of interest may comprise one or more complex N-linked glycans or may simply be a high mannose glycan.

The cell may be any type of cell and is preferably a eukaryotic cell. The cell may be a mammalian cell such as human, mouse, rat, rabbit, hamster or other type of mammalian cell. When the cell is a mammalian cell, the mammalian cell may be derived from or contained within a non-human transgenic mammal where the cell in the mammal encodes the desired glycopeptide and a variety of glycosylating and glycosidase enzymes as necessary for the production of desired glycopeptide molecules. In addition, the cell may be a fungal cell, preferably, a yeast cell, or the cell may be an insect or a plant cell. Similarly, when the cell is a plant cell, the plant cell may be derived from or contained within a transgenic plant, wherein the plant encodes the desired glycopeptide and a variety of glycosylating and glycosidase enzymes as are necessary for the production of desired glycopeptide molecules.

In some embodiments the host cell may be a eukaryotic cell expressing one or more heterologous glycosyltransferase enzymes and/or one or more heterologous glycosidase enzymes, wherein expression of a recombinant glycopeptide in the host cell results in the production of a recombinant glycopeptide having an elemental trimannosyl core as the primary glycan structure attached thereto.

In some embodiments the heterologous glycosyltransferase enzyme useful in the cell may be selected from a group consisting of any known glycosyltransferase enzyme included for example, in the list of Glycosyltransferase Families available in Taniguchi et al. (2002, Handbook of Glycosyltransferases and Related Genes, Springer, New York).

In other embodiments, the heterologous glycosylase enzyme may be selected from a group consisting of mannosidase 1, mannosidase 2, mannosidase 3, and other mannosidases, including, but not limited to, microbial mannosidases. Additional disclosure regarding enzymes useful in the present invention is provided elsewhere herein.

In yet other embodiments, the host cell may be a eukaryotic cell wherein one or more endogenous glycosyltransferase enzymes and/or one or more endogenous glycosidase enzymes have been inactivated such that expression of a recombinant glycopeptide in the host cell results in the production of a recombinant glycopeptide having an elemental trimannosyl core as the primary glycan structure attached thereto.

In additional embodiments, the host cell may express heterologous glycosyltransferase enzymes and/or glycosidase enzymes while at the same time one or more endogenous glycosyltransferase enzymes and/or glycosidase enzymes are inactivated. Endogenous glycosyltransferase enzymes and/or glycosidase enzymes may be inactivated using any technique known to those skilled in the art including, but not limited to, antisense techniques and techniques involving insertion of nucleic acids into the genome of the host cell. In some embodiments, the endogenous enzymes may be selected from a group consisting of GnT-I, a selection of mannosidases, xylosyltransferase, core α1,3 fucosyltransferase, serine/threonine O-mannosyltransferases, and the like.

Alternatively, an expression system that naturally glycosylates peptides such that the N-linked glycans are predominantly the trimannosyl core type, or the Man3GlcNAc4 type, can be exploited. An example of a cell type that produces the trimannosyl core is Sf9 cells. Other such expression systems can be identified by analyzing glycopeptides that are naturally or recombinantly expressed in cells and selecting those which exhibit the desired glycosylation characteristics. The invention should be construed to include any and all such cells for the production of the peptides of the present invention.

V. Purification of Glycan Remodeled and/or Glycoconjugated Peptides

If the modified glycoprotein is produced intracellularly or secreted, as a first step, the particulate debris, either host cells, lysed fragments, is removed, for example, by centrifugation or ultrafiltration; optionally, the protein may be concentrated with a commercially available protein concentration filter, followed by separating the peptide variant from other impurities by one or more steps selected from immunoaffinity chromatography, ion-exchange column fractionation (e.g., on diethylaminoethyl (DEAE) or matrices containing carboxymethyl or sulfopropyl groups), chromatography on Blue-Sepharose, CM Blue-Sepharose, MONO-Q, MONO-S, lentil lectin-Sepharose, WGA-Sepharose, Con A-Sepharose, Ether Toyopearl, Butyl Toyopearl, Phenyl Toyopearl, or protein A Sepharose, SDS-PAGE chromatography, silica chromatography, chromatofocusing, reverse phase HPLC (RP-HPLC), gel filtration using, e.g., Sephadex molecular sieve or size-exclusion chromatography, chromatography on columns that selectively bind the peptide, and ethanol, pH or ammonium sulfate precipitation, membrane filtration and various techniques.

Modified peptides produced in culture are usually isolated by initial extraction from cells, enzymes, etc., followed by one or more concentration, salting-out, aqueous ion-exchange, or size-exclusion chromatography steps. Additionally, the modified glycoprotein may be purified by affinity chromatography. Then, HPLC may be employed for final purification steps.

A protease inhibitor, e.g., phenylmethylsulfonylfluoride (PMSF) may be included in any of the foregoing steps to inhibit proteolysis and antibiotics may be included to prevent the growth of adventitious contaminants.

Within another embodiment, supernatants from systems which produce the modified peptide of the invention are first concentrated using a commercially available protein concentration filter, for example, an Amicon or Millipore Pellicon ultrafiltration unit. Following the concentration step, the concentrate may be applied to a suitable purification matrix. For example, a suitable affinity matrix may comprise a ligand for the peptide, a lectin or antibody molecule bound to a suitable support. Alternatively, an anion-exchange resin may be employed, for example, a matrix or substrate having pendant DEAE groups. Suitable matrices include acrylamide, agarose, dextran, cellulose, or other types commonly employed in protein purification. Alternatively, a cation-exchange step may be employed. Suitable cation exchangers include various insoluble matrices comprising sulfopropyl or carboxymethyl groups. Sulfopropyl groups are particularly preferred.

Then, one or more RP-HPLC steps employing hydrophobic RP-HPLC media, e.g., silica gel having pendant methyl or other aliphatic groups, may be employed to further purify a peptide variant composition. Some or all of the foregoing purification steps, in various combinations, can also be employed to provide a homogeneous modified glycoprotein.

The modified peptide of the invention resulting from a large-scale fermentation may be purified by methods analogous to those disclosed by Urdal et al., *J. Chromatog.* 296: 171 (1984). This reference describes two sequential, RP-HPLC steps for purification of recombinant human IL-2 on a preparative HPLC column. Alternatively, techniques such as affinity chromatography may be utilized to purify the modified glycoprotein.

VI. Preferred Peptides and Nucleic Acids Encoding Preferred Peptides

The present invention includes isolated nucleic acids encoding various peptides and proteins, and similar molecules or fragments thereof. The invention should not be construed to be limited in any way solely to the use of these peptides in the methods of the invention, but rather should be construed to include any and all peptides presently available or which become available to those in the art. In addition, the invention should not be construed to include only one particular nucleic acid or amino acid sequence for the peptides listed herein, but rather should be construed to include any and all variants, homologs, mutants, etc. of each of the peptides. It should be noted that when a particular peptide is identified as having a mutation or other alteration in the sequence for that peptide, the numbering of the amino acids which identify the alteration or mutation is set so that the first amino acid in the mature peptide sequence is amino acid no. 1, unless otherwise stated herein.

Preferred peptides include, but are not limited to human granulocyte colony stimulating factor (G-CSF), human interferon alpha (IFN-alpha), human interferon beta (IFN-beta), human Factor VII (Factor VII), human Factor IX (Factor IX), human follicle stimulating hormone (FSH), human erythropoietin (EPO), human granulocyte/macrophage colony stimulating factor (GM-CSF), human interferon gamma (IFN-gamma), human alpha-1-protease inhibitor (also known as alpha-1-antitrypsin or alpha-1-trypsin inhibitor; A-1-PI), glucocerebrosidase, human tissue-type activator (TPA), human interleukin-2 (IL-2), human Factor VIII (Factor VIII), a 75 kDa tumor necrosis factor receptor fused to a human IgG immunoglobulin Fc portion, commercially known as ENBREL™ or ETANERCEPT™ (chimeric TNFR), human urokinase (urokinase), a Fab fragment of the human/mouse chimeric monoclonal antibody that specifically binds glycoprotein IIb/IIIa and the vitronectin $alpha_V$ $beta_3$ receptor, known commercially as REOPRO™ or ABCIXIMAB (chimeric anti-glycoprotein IIb/IIIa), a mouse/human chimeric monoclonal antibody that specifically binds human HER2, known commercially as HERCEPTIN™ (chimeric anti-HER2), a human/mouse chimeric antibody that specifically binds the A antigenic site or the F protein of respiratory syncytial virus commercially known as SYNAGIS™ or PALIVIZUMAB (chimeric anti-RSV), a chimeric human/mouse monoclonal antibody that specifically binds CD20 on human B-cells, known commercially as RITUXAN™ or RITUXAMAB (chimeric anti-CD20), human recombinant DNase (DNase), a chimeric human/mouse monoclonal antibody that specifically binds human tumor necrosis factor, known commercially as REMICADE™ or INFLIXIMAB (chimeric anti-TNF), human insulin, the surface antigen of a hepatitis B virus (adw subtype; HBsAg), and human growth hormone (HGH), alpha-galactosidase A (Fabryzyme™), α-Iduronidase (Aldurazyme™), antithrombin (antithrombin III, AT-III), human chorionic gonadotropin (hCG), interferon omega, and the like.

The isolated nucleic acid of the invention should be construed to include an RNA or a DNA sequence encoding any of the above-identified peptides of the invention, and any modified forms thereof, including chemical modifications of the DNA or RNA which render the nucleotide sequence more stable when it is cell free or when it is associated with a cell. As a non-limiting example, oligonucleotides which contain at least one phosphorothioate modification are known to confer upon the oligonucleotide enhanced resistance to nucleases. Specific examples of modified oligonucleotides include those which contain phosphorothioate, phosphotriester, methyl phosphonate, short chain alkyl or cycloalkyl intersugar linkages, or short chain heteroatomic or heterocyclic intersugar ("backbone") linkages. In addition, oligonucleotides having morpholino backbone structures (U.S. Pat. No. 5,034,506) or polyamide backbone structures (Nielsen et al., 1991, Science 254: 1497) may also be used.

Chemical modifications of nucleotides may also be used to enhance the efficiency with which a nucleotide sequence is taken up by a cell or the efficiency with which it is expressed in a cell. Any and all combinations of modifications of the nucleotide sequences are contemplated in the present invention.

The present invention should not be construed as being limited solely to the nucleic and amino acid sequences disclosed herein. As described in more detail elsewhere herein, once armed with the present invention, it is readily apparent to one skilled in the art that other nucleic acids encoding the peptides of the present invention can be obtained by following the procedures described herein (e.g., site-directed mutagenesis, frame shift mutations, and the like), and procedures that are well-known in the art.

Also included are isolated nucleic acids encoding fragments of peptides, wherein the peptide fragments retain the desired biological activity of the peptide. In addition, although exemplary nucleic acids encoding preferred peptides are disclosed herein in relation to specific SEQ ID NOS, the invention should in no way be construed to be limited to any specific nucleic acid disclosed herein. Rather, the invention should be construed to include any and all nucleic acid molecules having a sufficient percent identity with the sequences disclosed herein such that these nucleic acids also encode a peptide having the desired biological activity disclosed herein. Also contemplated are isolated nucleic acids that are shorter than full length nucleic acids, wherein the biological activity of the peptide encoded thereby is retained. Methods to determine the percent identity between one nucleic acid and another are disclosed elsewhere herein as are assays for the determination of the biological activity of any specific preferred peptide.

Also as disclosed elsewhere herein, any other number of procedures may be used for the generation of derivative, mutant, or variant forms of the peptides of the present invention using recombinant DNA methodology well known in the art such as, for example, that described in Sambrook et al. (1989, Molecular Cloning: A Laboratory Manual, Cold Spring Harbor Laboratory Press, New York) and Ausubel et al. (1997, Current Protocols in Molecular Biology, Green & Wiley, New York). Procedures for the introduction of amino acid changes in a peptide or polypeptide by altering the DNA sequence encoding the peptide are well known in the art and are also described in Sambrook et al. (1989, supra); Ausubel et al. (1997, supra).

The invention includes a nucleic acid encoding a G-CSF, IFN-alpha, IFN-beta, Factor VII, Factor IX, FSH, EPO, GM-CSF, IFN-gamma, A-1-PI, glucocerebrosidase, TPA, IL-2, Factor VIII, chimeric TNFR, urokinase, chimeric anti-glycoprotein IIb/IIa, chimeric anti-HER2, chimeric anti-RSV, chimeric anti-CD20, DNase, chimeric anti-TNF, human insulin, HBsAg, and HGH, wherein a nucleic acid encoding a tag peptide is covalently linked thereto. That is, the invention encompasses a chimeric nucleic acid wherein the nucleic acid sequence encoding a tag peptide is covalently linked to the nucleic acid encoding a peptide of the present invention. Such tag peptides are well known in the art and include, for instance, green fluorescent protein (GFP), myc, myc-pyruvate kinase (myc-PK), $His_6$, maltose binding protein (MBP), an influenza virus hemagglutinin tag polypeptide, a flag tag polypeptide (FLAG), and a glutathione-S-transferase (GST) tag polypeptide. However, the invention should in no way be construed to be limited to the nucleic acids encoding the above-listed tag peptides. Rather, any nucleic acid sequence encoding a peptide which may function in a manner substantially similar to these tag peptides should be construed to be included in the present invention.

The nucleic acid comprising a nucleic acid encoding a tag peptide can be used to localize a peptide of the present invention within a cell, a tissue, and/or a whole organism (e.g., a mammalian embryo), detect a peptide of the present invention secreted from a cell, and to study the role(s) of the peptide in a cell. Further, addition of a tag peptide facilitates isolation and purification of the "tagged" peptide such that the peptides of the invention can be produced and purified readily.

The invention includes the following preferred isolated peptides: G-CSF, IFN-alpha, IFN-beta, Factor VII, Factor IX, FSH, EPO, GM-CSF, IFN-gamma, A-1-PI, glucocerebrosidase, TPA, IL-2, Factor VIII, chimeric TNFR, urokinase, chimeric anti-glycoprotein IIb/IIIa, chimeric anti-HER2, chimeric anti-RSV, chimeric anti-CD20, DNase, chimeric anti-TNF, human insulin, HBsAg, HGH, alpha-galactosidase A, α-Iduronidase, antithrombin III, hCG, and interferon omega, and the like.

The present invention should also be construed to encompass "derivatives," "mutants", and "variants" of the peptides of the invention (or of the DNA encoding the same) which derivatives, mutants, and variants are peptides which are altered in one or more amino acids (or, when referring to the nucleotide sequence encoding the same, are altered in one or more base pairs) such that the resulting peptide (or DNA) is not identical to the sequences recited herein, but has the same biological property as the peptides disclosed herein, in that the peptide has biological/biochemical properties of G-CSF, IFN-alpha, IFN-beta, Factor VII, Factor IX, FSH, EPO, GM-CSF, IFN-gamma, A-1-PI, glucocerebrosidase, TPA, IL-2, Factor VIII, chimeric TNFR, urokinase, chimeric anti-glycoprotein IIb/IIIa, chimeric anti-HER2, chimeric anti-RSV, chimeric anti-CD20, DNase, chimeric anti-TNF, human insulin, HBsAg, and HGH.

Further included are fragments of peptides that retain the desired biological activity of the peptide irrespective of the length of the peptide. It is well within the skill of the artisan to isolate smaller than full length forms of any of the peptides useful in the invention, and to determine, using the assays provided herein, which isolated fragments retain a desired biological activity and are therefore useful peptides in the invention.

A biological property of a protein of the present invention should be construed to include, but not be limited to include the ability of the peptide to function in the biological assay and environments described herein, such as reduction of inflammation, elicitation of an immune response, blood-clotting, increased hematopoietic output, protease inhibition, immune system modulation, binding an antigen, growth, alleviation of treatment of a disease, DNA cleavage, and the like.

A. G-CSF

The present invention encompasses a method for the modification of the glycan structure on G-CSF. G-CSF is well known in the art as a cytokine produced by activated T-cells, macrophages, endothelial cells, and stromal fibroblasts. G-CSF primarily acts on the bone marrow to increase the production of inflammatory leukocytes, and further functions as an endocrine hormone to initiate the replenishment of neutrophils consumed during inflammatory functions. G-CSF also has clinical applications in bone marrow replacement following chemotherapy.

A remodeled G-CSF peptide may be administered to a patient selected from the group consisting of a non-myeloid cancer patient receiving myelosuppressive chemotherapy, a patient having Acute Myeloid Leukemia (AML) receiving induction or consolidation chemotherapy, a non-myeloid cancer patient receiving a bone marrow transplant, a patient undergoing peripheral blood progenitor cell collection, a patient having severe chronic neutropenia, and a patient having persistent neutropenia and also having advanced HIV infection. Preferably, the patient is a human patient.

While G-CSF has been shown to be an important and useful compound for therapeutic applications in mammals, especially humans, present methods for the production of G-CSF from recombinant cells results in a product having a relatively short biological life, an inaccurate glycosylation pattern that could potentially lead to immunogenicity, loss of function, and an increased need for both larger and more frequent doses in order to achieve the same effect, and the like.

G-CSF has been isolated and cloned, the nucleic acid and amino acid sequences of which are presented as SEQ ID NO:1 and SEQ ID NO:2, respectively (FIGS. 58A and 58B, respectively). The present invention encompasses a method for modifying G-CSF, particularly as it relates to the ability of G-CSF to function as a potent and functional biological molecule. The skilled artisan, when equipped with the present disclosure and the teachings herein, will readily understand that the present invention provides compositions and methods for the modification of G-CSF.

The present invention further encompasses G-CSF variants, as well known in the art. As an example, but in no way meant to be limiting to the present invention, a G-CSF variant has been described in U.S. Pat. No. 6,166,183, in which a G-CSF comprising the natural complement of lysine residues and further linked to one or two polyethylene glycol molecules is described. Additionally, U.S. Pat. Nos. 6,004,548, 5,580,755, 5,582,823, and 5,676,941 describe a G-CSF variant in which one or more of the cysteine residues at position 17, 36, 42, 64, and 74 are replaced by alanine or alternatively serine. U.S. Pat. No. 5,416,195 describes a G-CSF molecule in which the cysteine at position 17, the aspartic acid at position 27, and the serines at positions 65 and 66 are substituted with serine, serine, proline, and proline, respectively. Other variants are well known in the art, and are described in, for example, U.S. Pat. No. 5,399,345.

The expression and activity of a modified G-CSF molecule of the present invention can be assayed using methods well known in the art, and as described in, for example, U.S. Pat. No. 4,810,643. As an example, activity can be measured using radio-labeled thymidine uptake assays. Briefly, human bone marrow from healthy donors is subjected to a density cut with Ficoll-Hypaque (1.077 g/ml, Pharmacia, Piscataway, N.J.) and low density cells are suspended in Iscove's medium (GIBCO, La Jolla, Calif.) containing 10% fetal bovine serum, glutamine and antibiotics. About $2\times10^4$ human bone marrow cells are incubated with either control medium or the G-CSF or the present invention in 96-well flat bottom plates at about 37° C. in 5% $CO_2$ in air for about 2 days. Cultures are then pulsed for about 4 hours with 0.5 μCi/well of $^3$H-thymidine (New England Nuclear, Boston, Mass.) and uptake is measured as described in, for example, Ventua, et al. (1983, Blood 61:781). An increase in $^3$H-thymidine incorporation into human bone marrow cells as compared to bone marrow cells treated with a control compound is an indication of a active and viable G-CSF compound.

B. IFN Alpha, IFN Beta and IFN Omega

The present invention further encompasses a method for the remodeling and modification of IFN alpha, IFN beta and IFN omega. IFN alpha is part of a family of approximately twenty peptides of approximately 18 kDa in weight. IFN omega is very similar in structure and function to IFN alpha. IFN omega is useful for treatment of hepatitis C virus infection when an immune response to IFN alpha is mounted in the host rendering that treatment ineffective. Antibodies raised against IFN alpha do not cross-react with IFN omega. Thus, treatment of hepatitis C may continue using IFN omega when IFN alpha therapy is no longer possible.

IFN alpha, omega, and IFN beta, collectively known as the Type I interferons, bind to the same cellular receptor and elicit similar responses. Type I IFNs inhibit viral replication, increase the lytic potential of NK cells, modulate MHC molecule expression, and inhibit cellular proliferation, among other things. Type I IFN has been used as a therapy for viral infections, particularly hepatitis viruses, and as a therapy for multiple sclerosis.

Current compositions of Type I IFN are, as described above, useful compounds for both the modulation of aberrant immunological responses and as a therapy for a variety of diseases. However, they are hampered by decreased potency and function, and a limited half-life in the body as compared to natural cytokines comprising the natural complement of glycosylation.

A remodeled interferon-alpha peptide may be administered to a patient selected from the group consisting of a patient having hairy cell leukemia, a patient having malignant melanoma, a patient having follicular lymphoma, a patient having condylomata acuminata, a patient having AIDS-related Kaposi's sarcoma, a patient having Hepatitis C, a patient having Hepatitis B, a patient having a human papilloma virus infection, a patient having Chronic Myeloid Leukemia (CML), a patient having chronic phase Philadelphia chromosome (Ph) positive Chronic Myelogenous Leukemia, a patient having non-Hodgkin's lymphoma (NHL), a patient having lymphoma, a patient having bladder cancer, and a patient having renal cancer. Preferably, the patient is a human patient.

A remodeled interferon-beta peptide may be administered to a patient selected from the group consisting of a patient having multiple sclerosis (MS), a patient having Hepatitis B, a patient having Hepatitis C, a patient having human papilloma virus infection, a patient having breast cancer, a patient having brain cancer, a patient having colorectal cancer, a patient having pulmonary fibrosis, and a patient having rheumatoid arthritis. Preferably, the patient is a human patient.

A remodeled interferon-omega peptide may be administered to a patient selected from the group consisting of a patient having hairy cell leukemia, a patient having malignant melanoma, a patient having follicular lymphoma, a patient having condylomata acuminata, a patient having AIDS-related Kaposi's sarcoma, a patient having Hepatitis C, a patient having Hepatitis B, a patient having a human papilloma virus infection, a patient having Chronic Myeloid Leukemia (CML), a patient having chronic phase Philadelphia chromosome (Ph) positive Chronic Myelogenous Leukemia, a patient having non-Hodgkin's lymphoma (NHL), a patient having lymphoma, a patient having bladder cancer, and a patient having renal cancer. Preferably, the patient is a human patient.

The prototype nucleotide and amino acid sequence for IFN alpha is set forth herein as SEQ ID NO:3 and SEQ ID NO:4, respectively (FIGS. 59A and 59B, respectively). The prototype nucleotide and amino acid sequence for IFN omega is set forth herein as SEQ ID NO:74 and SEQ ID NO:75, respectively (FIGS. 84A and 84B, respectively). IFN beta comprises a single gene product of approximately 20 kDa, the nucleic acid and amino acid sequence of which are presented herein as SEQ ID NO:5 and SEQ ID NO:6 (FIGS. 60A and 60B, respectively). The present invention is not limited to the nucleotide and amino acid sequences herein. One of skill in the art will readily appreciate that many variants of IFN alpha exist both naturally and as engineered derivatives. Similarly, IFN beta has been modified in attempts to achieve a more beneficial therapeutic profile. Examples of modified Type I IFNs are well known in the art (see Table 9), and are described in, for example U.S. Pat. No. 6,323,006, in which cysteine-60 is substituted for tyrosine, U.S. Pat. Nos. 4,737,462, 4,588,585, 5,545,723, and 6,127,332 where an IFN beta with a substitution of a variety of amino acids is described. Additionally, U.S. Pat. Nos. 4,966,843, 5,376,567, 5,795,779 describe IFN alpha-61 and IFN-alpha-76. U.S. Pat. Nos. 4,748,233 and 4,695,543 describe IFN alpha gx-1, whereas U.S. Pat. No. 4,975,276 describes IFN alpha-54. In addition, U.S. Pat. Nos. 4,695,623, 4,897,471, 5,661,009, and 5,541,293 all describe a consensus IFN alpha sequence to represent all variants known at the date of filing. While this list of Type I IFNs and variants thereof is in no way meant to be exhaustive, one of skill in the art will readily understand that the present invention encompasses IFN beta and IFN alpha molecules, derivatives, and variants known or to be discovered in the future.

TABLE 9

Interferon-α Isoforms.

| α type | AA characteristic |
|---|---|
| 1a | $A^{114}$ |
| 1b | $V^{114}$ |
| 2a | $K^{23}$-$H^{34}$ |
| 2b | $R^{23}$-$H^{34}$ |
| 2c | $R^{23}$-$R^{34}$ |
| 4a | $A^{51}$-$E^{114}$ |
| 4b | $T^{51}$-$V^{114}$ |
| 7a | $M^{132}$-$K^{159}$-$G^{161}$ |
| 7b | $M^{132}$-$Q^{159}$-$R^{161}$ |
| 7c | $T^{132}$-$K^{159}$-$G^{161}$ |
| 8a | $V^{98}$-$L^{99}$-$C^{100}$-$D^{101}$-$R^{161}$ |
| 8b | $S^{98}$-$C^{99}$-$V^{100}$-$M^{101}$-$R^{161}$ |
| 8c | $S^{98}$-$C^{99}$-$V^{100}$-$M^{101}$-$D^{161}\Delta$(162-166) |
| 10a | $S^{8}$-$L^{89}$ |
| 10b | $T^{8}$-$I^{89}$ |
| 14a | $F^{152}$-$Q^{159}$-$R^{161}$ |
| 14b | $F^{152}$-$K^{159}$-$G^{161}$ |
| 14c | $L^{152}$-$Q^{159}$-$R^{161}$ |
| 17a | $P^{34}$-$S^{55}$-$I^{161}$ |
| 17b | $H^{34}$-$S^{55}$-$I^{161}$ |
| 17c | $H^{34}$-$S^{55}$-$R^{161}$ |
| 17d | $H^{34}$-$P^{55}$-$R^{161}$ |
| 21a | $M^{96}$ |
| 21b | $L^{96}$ |

Methods of expressing IFN in recombinant cells are well known in the art, and is easily accomplished using techniques described in, for example U.S. Pat. No. 4,966,843, and in Sambrook et al. (2001, Molecular Cloning: A Laboratory Manual, Cold Spring Harbor Laboratory Press, New York) and Ausubel et al. (1997, Current Protocols in Molecular Biology, Green & Wiley, New York). Assays to determine the biological activity of a Type I IFN modified by the present invention will be well known to the skilled artisan. For example, the assay described in Rubinstein et al., (1981, Journal of Virology 37:755-758) is commonly used to determine the effect of an Type I IFN by measuring the cytopathic effects of viral infection on a population of cells. This method is only one of many known in the art for assaying the biological function of a Type IFN.

C. Factor VIIa

The present invention further encompasses a method for the remodeling and modification of Factor VII. The blood coagulation pathway is a complex reaction comprising many events. An intermediate event in this pathway is Factor VII, a proenzyme that participates in the extrinsic pathway of blood coagulation by converting (upon its activation to Factor VIIa) Factor X to Xa in the presence of tissue factor and calcium ions. Factor Xa in turn then converts prothrombin to thrombin in the presence of Factor Va, calcium ions and phospholipid. The activation of Factor X to Factor Xa is an event shared by both the intrinsic and extrinsic blood coagulation pathways, and therefore, Factor VIIa can be used for the treatment of patients with deficiencies or inhibitors of Factor VIII. There is also evidence to suggest that Factor VIIa may participate in the intrinsic pathway as well therefore increasing the prominence and importance of the role of Factor VII in blood coagulation.

Factor VII is a single-chain glycoprotein with a molecular weight of approximately 50 kDa. In this form, the factor circulates in the blood as an inactive zymogen. Activation of Factor VII to VIIa may be catalyzed by several different plasma proteases, such as Factor XIIa. Activation of Factor VII results in the formation of a heavy chain and a light chain held together by at least one disulfide bond. Further, modified Factor VII molecules that cannot be converted to Factor VIIa have been described, and are useful as anti-coagulation remedies, such as in the case of blood clots, thrombosis, and the like. Given the importance of Factor VII in the blood coagulation pathway, and its use as a treatment for both increased and decreased levels of coagulation, it follows that a molecule that has a longer biological half-life, increased potency, and in general, a therapeutic profile more similar to wild-type Factor VII as it is synthesized and secreted in the healthy human would be beneficial and useful as a treatment for blood coagulation disorders.

A remodeled Factor VII peptide may be administered to a patient selected from the group consisting of a hemophiliac patient having a bleeding episode, a patient having Hemophilia A, a patient with Hemophilia B, a patient having Hemophilia A, wherein the patient also has antibodies to Factor VIII, a patient having Hemophilia B, wherein the patient also has antibodies to Factor IX, a patient having liver cirrhosis, a cirrhotic patient having an orthotopic liver transplant, a cirrhotic patient having upper gastrointestinal bleeding, a patient having a bone marrow transplant, and a patient having a liver resection. Preferably, the patient is a human patient.

Factor VII has been cloned and sequenced, and the nucleic acid and amino acid sequences are presented herein as SEQ ID NO:7 and SEQ ID NO:8 (FIGS. 61A and 61B, respectively). The present invention should in no way be construed as limited to the Factor VII nucleic acid and amino acid sequences set forth herein. Variants of Factor VII are described in, for example, U.S. Pat. Nos. 4,784,950 and 5,580,560, in which lysine-38, lysine-32, arginine-290, arginine-341, isoleucine-42, tyrosine-278, and tyrosine-332 is replaced by a variety of amino acids. Further, U.S. Pat. Nos. 5,861,374, 6,039,944, 5,833,982, 5,788,965, 6,183,743, 5,997,864, and 5,817,788 describe Factor VII variants that are not cleaved to form Factor VIIa. The skilled artisan will recognize that the blood coagulation pathway and the role of Factor VII therein are well known, and therefore many variants, both naturally occurring and engineered, as described above, are included in the present invention.

Methods for the expression and to determine the activity of Factor VII are well known in the art, and are described in, for example, U.S. Pat. No. 4,784,950. Briefly, expression of Factor VII, or variants thereof, can be accomplished in a variety of both prokaryotic and eukaryotic systems, including *E. coli*, CHO cells, BHK cells, insect cells using a baculovirus expression system, all of which are well known in the art.

Assays for the activity of a modified Factor VII prepared according to the methods of the present invention can be accomplished using methods well known in the art. As a non-limiting example, Quick et al. (Hemorragic Disease and Thrombosis, 2nd ed., Leat Febiger, Philadelphia, 1966), describes a one-stage clotting assay useful for determining the biological activity of a Factor VII molecule prepared according to the methods of the present invention.

D. Factor IX

The present invention further encompasses a method for remodeling and/or modifying Factor IX. As described above, Factor IX is vital in the blood coagulation cascade. A deficiency of Factor IX in the body characterizes a type of hemophilia (type B). Treatment of this disease is usually limited to intravenous transfusion of human plasma protein concentrates of Factor IX. However, in addition to the practical disadvantages of time and expense, transfusion of blood concentrates involves the risk of transmission of viral hepatitis, acquired immune deficiency syndrome or thromboembolic diseases to the recipient.

While Factor IX has demonstrated itself as an important and useful compound for therapeutic applications, present methods for the production of Factor IX from recombinant cells (U.S. Pat. No. 4,770,999) results in a product with a rather short biological life, an inaccurate glycosylation pattern that could potentially lead to immunogenicity, loss of function, an increased need for both larger and more frequent doses in order to achieve the same effect, and the like.

A remodeled Factor IX peptide may be administered to a patient selected from the group consisting of a hemophiliac patient having a bleeding episode and also having Hemophilia B, a patient having Hemophilia B, a patient having Hemophilia B and having antibodies to Factor IX, a patient having liver cirrhosis, a cirrhotic patient having an orthotopic liver transplant, a cirrhotic patient having upper gastrointestinal bleeding, a patient having a bone marrow transplant, and a patient having a liver resection. A remodeled Factor IX peptide may also be administered to control and/or prevent hemorrhagic episodes in a patient having Hemophilia B, congenital Factor IX deficiency, or Christmas disease. A remodeled Factor IX peptide may also be administered to a patient to control and/or prevent hemorrhagic episodes in the patient during surgery. Preferably, the patient is a human patient.

The nucleic and amino acid sequences of Factor IX is set forth herein as SEQ ID NO:9 and SEQ ID NO:10 (FIGS. 62A and 62B, respectively). The present invention is in no way limited to the sequences set forth herein. Factor IX variants are well known in the art, as described in, for example, U.S. Pat. Nos. 4,770,999, 5,521,070 in which a tyrosine is replaced by an alanine in the first position, U.S. Pat. No. 6,037,452, in which Factor XI is linked to an alkylene oxide group, and U.S. Pat. No. 6,046,380, in which the DNA encoding Factor IX is modified in at least one splice site. As demonstrated herein, variants of Factor IX are well known in the art, and the present disclosure encompasses those variants known or to be developed or discovered in the future.

Methods for determining the activity of a modified Factor IX prepared according to the methods of the present invention can be carried out using the methods described above, or additionally, using methods well known in the art, such as a one stage activated partial thromboplastin time assay as described in, for example, Biggs (1972, Human Blood Coagulation Haemostasis and Thrombosis (Ed. 1), Oxford, Blackwell, Scientific, pg. 614). Briefly, to assay the biological activity of a Factor IX molecule developed according to the methods of the present invention, the assay can be performed with equal volumes of activated partial thromboplastin reagent, Factor IX deficient plasma isolated from a patient with hemophilia B using sterile phlebotomy techniques well known in the art, and normal pooled plasma as standard, or the sample. In this assay, one unit of activity is defined as that amount present in one milliliter of normal pooled plasma. Further, an assay for biological activity based on the ability of Factor IX to reduce the clotting time of plasma from Factor IX-deficient patients to normal can be performed as described in, for example, Proctor and Rapaport (1961, Amer. J. Clin. Path. 36: 212).

E. FSH

The present invention further includes a method for remodeling and/or modifying FSH. Human reproductive function is controlled in part by a family of heterodimeric human glycoprotein hormones which have a common 92 amino acid glycoprotein alpha subunit, but differ in their hormone-specific beta subunits. The family includes follicle-stimulating hormone (FSH), luteinizing hormone (LH), thyrotropin or thyroid-stimulating hormone (TSH), and human chorionic gonadotropin (hCG). Human FSH and LH are used therapeutically to regulate various aspects of metabolism pertinent to reproduction in the human female. For example, FSH partially purified from urine is used clinically to stimulate follicular maturation in anovulatory women with anovulatory syndrome or luteal phase deficiency. Luteinizing hormone (LH) and FSH are used in combination to stimulate the development of ovarian follicles for in vitro fertilization. The role of FSH in the reproductive cycle is sufficiently well-known to permit therapeutic use, but difficulties have been encountered due, in part, to the heterogeneity and impurity of the preparation from native sources. This heterogeneity is due to variations in glycosylation pattern.

FSH is a valuable tool in both in vitro fertilization and stimulation of fertilization in vivo, but as stated above, its clinical efficacy has been hampered by inconsistency in glycosylation of the protein. It therefore seems apparent that a method for remodeling FSH will be of great benefit to the reproductive sciences.

A remodeled FSH peptide may be administered to a patient selected from the group consisting of a patient undergoing intrauterine insemination (IUI), a patient undergoing in vitro fertilization (IVF), and an infertile patient. A remodeled FSH peptide may also be administered to induce or increase ovulation in a patient, to stimulate development of an ovarian follicle in a patient, to induce gametogenic follicle growth in a patient, to stimulate, induce or increase follicle development and subsequent ovulation in a patient, or to treat infertility in a patient. Preferably, the patient is a human female patient. A remodeled FSH peptide may also be administered to a patient having a pituitary deficiency or to a patient during puberty. Preferably this patient is a human male patient.

FSH has been cloned and sequenced, the nucleic and amino acid sequences of which are presented herein as SEQ ID NO:11, SEQ ID NO: 12, respectively (alpha subunit) and SEQ ID NO:13 and SEQ ID NO:14, respectively (beta subunit) (FIGS. 63A, 63B, 63C and 63D, respectively). The skilled artisan will readily appreciate that the present invention is not limited to the sequences depicted herein, as variants of FSH are well known in the art. As a non-limiting example, U.S. Pat. No. 5,639,640 describes the beta subunit comprising two different amino acid sequences and U.S. Pat. No. 5,338,835 describes a beta subunit comprising an additional amino acid sequence of approximately twenty-seven amino acids derived from the beta subunit of human chorionic gonadotropin. Therefore, the present invention comprises FSH variants, both natural and engineered by the human hand, all well known in the art.

Methods to express FSH in cells, both prokaryotic and eukaryotic, are well known in the art and abundantly described in the literature (U.S. Pat. Nos. 4,840,896, 4,923,805, 5,156,957). Further, methods for evaluating the biological activity of a remodeled FSH molecule of the present invention are well known in the art, and are described in, for example, U.S. Pat. No. 4,589,402, in which methods for determining the effect of FSH on fertility, egg production, and pregnancy rates is described in both non-human primates and human subjects.

F. EPO

The present invention further comprises a method of remodeling and/or modifying EPO. EPO is an acidic glycoprotein of approximately 34 kDa and may occur in three natural forms: alpha, beta, and asialo. The alpha and beta forms differ slightly in carbohydrate components but have the same potency, biological activity and molecular weight. The asialo form is an alpha or beta form with the terminal sialic acid removed. EPO is present in very low concentrations in plasma when the body is in a healthy state wherein tissues receive sufficient oxygenation from the existing number of erythrocytes. This normal concentration is enough to stimulate replacement of red blood cells which are lost normally through aging. The amount of erythropoietin in the circulation is increased under conditions of hypoxia when oxygen transport by blood cells in the circulation is reduced. Hypoxia may be caused by loss of large amounts of blood through hemorrhage, destruction of red blood cells by over-exposure to radiation, reduction in oxygen intake due to high altitudes or prolonged unconsciousness, or various forms of anemia. Therefore EPO is a useful compound for replenishing red blood cells after radiation therapy, anemia, and other life-threatening conditions.

A remodeled EPO peptide may be administered to a patient selected from the group consisting of a patient having anemia, an anemic patient having chronic renal insufficiency, an anemic patient having end stage renal disease, an anemic patient undergoing dialysis, an anemic patient having chronic renal failure, an anemic Zidovudine-treated HIV infected patient, an anemic patient having non-myeloid cancer and undergoing chemotherapy, and an anemic patient scheduled to undergo non-cardiac, non-vascular surgery. A remodeled EPO peptide may also be administered to a patient undergoing surgery to reduce the need for an allogenic blood transfusion. A remodeled EPO peptide may also be administered to a patient at increased risk for a perioperative blood transfusion with significant anticipated blood loss. Preferably, the patient is a human patient.

In light of the importance of EPO in aiding in the recovery from a variety of diseases and disorders, the present invention is useful for the production of EPO with a natural, and therefore more effective saccharide component. EPO, as it is currently synthesized, lacks the full glycosylation complement, and must therefore be administered more frequently and in higher doses due to its short life in the body. The invention also provides for the production of PEGylated EPO molecules with greatly improved half-life compared with what might be achieved by maximizing desirable glycoforms.

EPO has been cloned and sequenced, and the nucleotide and amino acid sequences are present herein as SEQ ID NO:15 and SEQ ID NO:16, respectively (FIGS. 64A and 64B, respectively). It will be readily understood by one of skill in the art that the sequences set forth herein are only an example of the sequences encoding and comprising EPO. As an example, U.S. Pat. No. 6,187,564 describes a fusion protein comprising the amino acid sequence of two or more EPO peptides, U.S. Pat. Nos. 6,048,971 and 5,614,184 describe mutant EPO molecules having amino acid substitutions at positions 101, 103, 104, and 108. U.S. Pat. No. 5,106,954 describes a truncated EPO molecule, and U.S. Pat. No. 5,888,772 describes an EPO analog with substitutions at position 33, 139, and 166. Therefore, the skilled artisan will realize that the present invention encompasses EPO and EPO derivatives and variants as are well documented in the literature and art as a whole.

Additionally, methods of expressing EPO in a cell are well known in the art. As exemplified in U.S. Pat. Nos. 4,703,008, 5,688,679, and 6,376,218, among others, EPO can be expressed in prokaryotic and eukaryotic expression systems. Methods for assaying the biological activity of EPO are equally well known in the art. As an example, the Krystal assay (Krystal, 1983, Exp. Hematol. 11:649-660) can be employed to determine the activity of EPO prepared according to the methods of the present invention. Briefly, the assay measures the effect of erythropoietin on intact mouse spleen cells. Mice are treated with phenylhydrazine to stimulate production of erythropoietin-responsive red blood cell progenitor cells. After treatment, the spleens are removed, intact spleen cells are isolated and incubated with various amounts of wild-type erythropoietin or the erythropoietin proteins described herein. After an overnight incubation, $^3$H-thymidine is added and its incorporation into cellular DNA is measured. The amount of $^3$H-thymidine incorporation is indicative of erythropoietin-stimulated production of red blood cells via interaction of erythropoietin with its cellular receptor. The concentration of the erythropoietin protein of the present invention, as well as the concentration of wild-type erythropoietin, is quantified by competitive radioimmunoassay methods well known in the art. Specific activities are calculated as international units measured in the Krystal assay divided by micrograms as measured as immunoprecipitable protein by radioimmunoassay.

Several different mutated EPO's with different glycosylation patterns have been reported. Many have improved stimulation of reticulocytosis activity without effecting the half-life of the peptide in the blood stream of the animal. It is contemplated that mutated EPO peptides can be used in place of the native EPO peptides in any of the glycan remodeling, glycoPEGylation and/or glycoconjugation embodiments described herein. Preferred mutations of EPO are listed in the following table, but not limited to those listed in the table (see, for example, Chem et al., 1991, Eur. J. Biochem. 202:225-229; Grodberg et al., 1993, Eur. J. Biochem. 218:597-601; Burns et al., 2002, Blood 99:4400-4405; U.S. Pat. No. 5,614,184; GenBank Accession No. AAN76993; O'Connell et al., 1992, J. Biol. Chem. 267:25010-25018; Elliott et al., 1984, Proc. Natl. Acad. Sci. U.S.A. 81:2708-2712; Biossel et al., 1993, J. Biol. Chem. 268:15983-15993). The most preferred mutations of EPO are $Arg^{139}$ to $Ala^{139}$, $Arg^{143}$ to $Ala^{143}$ and $Lys^{154}$ to $Ala^{154}$. The preferred native EPO from which to make these mutants is the 165 aa form, which is depicted in FIG. 65; however other native forms of EPO may also be used. Finally, the mutations described in Table 10 may be combined with each other and with other mutations to make EPO peptides that are useful in the present invention.

TABLE 10

Mutations of EPO.

| Mutation | Citation | Notes |
|---|---|---|
| $Arg^{139}$ to $Ala^{139}$ | J. Biol. Chem. 269: 22839 (1994) | Increased activity in bioassays of 120% to 150%. |
| $Arg^{143}$ to $Ala^{143}$ | | Increased activity in bioassays than native EPO. |
| $Lys^{154}$ to $Ala^{154}$ | J. Biol. Chem. 269: 22839 (1994) | Increased activity in bioassays of 120% to 150%. |
| $Ser^{126}$ to $Met^{126}$ | | |
| $Met^{54}$ to $Leu^{54}$ | U.S. Pat. No. 4,385,260 | |
| $Met^{54}$ to $Leu^{54}$ | U.S. Pat. No. 4,385,260 | |
| $Asn^{38}$ to $Gln^{38}$ | | |
| Δ1-30 | Funakoshi et al., 1993, | Mutant isolated from |
| $Ser^{131}Leu^{132}$ to | Biochem. Biophys. Res. | hepatocellular carcinoma. |
| $Asn^{131}Phe^{132}$ | Commun. 195: 717-722. | |
| $Pro^{149}$ to $Gln^{149}$ | Genbank Accession No. AAD13964. | |
| $Gly^{101}$ to $Ala^{101}$ | U.S. Pat. No. 5,615,184 J. Biol. Chem. 269: 22839 (1994) | Increased activity in bioassays of 120% to 150%. |
| $Ser^{147}$ to $Ala^{147}$ and/or $Ile^{146}$ to $Ala^{146}$ | Wen et al., 1994, J. Biol. Chem. 269: 22839-22846. | Mutation results in increased bioactivity. |
| $Ser^{126}$ to $Thr^{126}$ | J. Biol. Chem. 267: 25010 (1992) | |

G. GM-CSF

The present invention encompasses a method for the modification of GM-CSF. GM-CSF is well known in the art as a cytokine produced by activated T-cells, macrophages, endothelial cells, and stromal fibroblasts. GM-CSF primarily acts on the bone marrow to increase the production of inflammatory leukocytes, and further functions as an endocrine hormone to initiate the replenishment of neutrophils consumed during inflammatory functions. Further GM-CSF is a macrophage-activating factor and promotes the differentiation of Lagerhans cells into dendritic cells. Like G-CSF, GM-CSF also has clinical applications in bone marrow replacement following chemotherapy.

While G-CSF has demonstrated itself as an important and useful compound for therapeutic applications, present methods for the production of G-CSF from recombinant cells results in a product with a rather short biological life, an inaccurate glycosylation pattern that could potentially lead to immunogenicity, loss of function, an increased need for both larger and more frequent doses in order to achieve the same effect, and the like.

A remodeled GM-CSF peptide may be administered to a patient selected from the group consisting of a patient having Acute Myelogenous Leukemia (AML) or acute non-lymphocytic leukemia (ANLL), a patient undergoing leukapheresis to collect hematopoietic progenitor cells from the peripheral blood, a patient undergoing transplantation of autologous peripheral blood progenitor cells, a non-Hodgkin's lymphoma (NHL) patient undergoing an autologous bone marrow transplant, a Hodgkin's disease patient undergoing an autologous bone marrow transplant, and an acute lymphoblastic leukemia (ALL) patient undergoing an autologous bone marrow transplant. A remodeled GM-CSF peptide may also be administered to a patient to accelerate myeloid engraftment, to shorten time to neutrophil recovery following chemotherapy, to mobilize hematopoietic progenitor cells into the peripheral blood for collection by leukapheresis, or to promote myeloid reconstitution after autologous or allogeneic bone marrow transplantation (BMT). A remodeled GM-CSF peptide may also be administered to a patient in which bone marrow transplantation has failed or in which myeloid engraftment is delayed. Preferably, the patient is a human patient.

GM-CSF has been isolated and cloned, the nucleic acid and amino acid sequences of which are presented as SEQ ID NO:17 and SEQ ID NO:18, respectively (FIGS. 66A and 66B, respectively). The present invention encompasses a method for modifying GM-CSF, particularly as it relates to the ability of GM-CSF to function as a potent and functional biological molecule. The skilled artisan, when equipped with the present disclosure and the teachings herein, will readily understand that the present invention provides compositions and methods for the modification of GM-CSF.

The present invention further encompasses GM-CSF variants, as well known in the art. As an example, but in no way meant to be limiting to the present invention, a GM-CSF variant has been described in WO 86/06358, where the protein is modified for an alternative quaternary structure. Further, U.S. Pat. No. 6,287,557 describes a GM-CSF nucleic acid sequence ligated into the genome of a herpesvirus for gene therapy applications. Additionally, European Patent Publication No. 0288809 (corresponding to PCT Patent Publication No. WO 87/02060) reports a fusion protein comprising IL-2 and GM-CSF. The IL-2 sequence can be at either the N- or C-terminal end of the GM-CSF such that after acid cleavage of the fusion protein, GM-CSF having either N- or C-terminal sequence modifications can be generated. Therefore, GM-CSF derivatives, mutants, and variants are well known in the art, and are encompassed within the methods of the present invention.

The expression and activity of a modified GM-CSF molecule of the present invention can be assayed using methods well known in the art, and as described in, for example, U.S. Pat. No. 4,810,643. As an example, activity can be measured using radio-labeled thymidine uptake assays. Briefly, human bone marrow from healthy donors is subjected to a density cut with Ficoll-Hypaque (1.077 g/ml, Pharmacia, Piscataway, N.J.) and low density cells are suspended in Iscove's medium (GIBCO, La Jolla, Calif.) containing 10% fetal bovine serum, glutamine and antibiotics. About $2\times10^4$ human bone marrow cells are incubated with either control medium or the GM-CSF or the present invention in 96-well flat bottom plates at about 37° C. in 5% $CO_2$ in air for about 2 days. Cultures are then pulsed for about 4 hours with 0.5 μCi/well of $^3$H-thymidine (New England Nuclear, Boston, Mass.) and uptake is measured as described in, for example, Ventua, et al. (1983, Blood 61:781). An increase in $^3$H-thymidine incorporation into human bone marrow cells as compared to bone marrow cells treated with a control compound is an indication of a active and viable GM-CSF compound.

H. IFN-gamma

It is an object of the present invention to encompass a method of modifying and/or remodeling IFN-gamma. IFN-gamma, otherwise known as Type II interferon, in contrast to IFN alpha and IFN beta, is a homodimeric glycoprotein comprising two subunits of about 21-24 kDa. The size variation is due to variable glycosylation patterns, usually not replicated when reproduced recombinantly in various expression systems known in the art. IFN-gamma is a potent activator of macrophages, increases MHC class I molecule expression, and to a lesser extent, a MHC class II molecule stimulatory agent. Further, IFN-gamma promotes T-cell differentiation and isotype switching in B-cells. IFN-gamma is also well documented as a stimulator of neutrophils, NK cells, and antibody responses leading to phagocyte-mediated clearance. IFN-gamma has been proposed as a treatment to be used in conjunction with infection by intracellular pathogens, such as tuberculosis and leishmania, and also as an anti-proliferative therapeutic, useful in conditions with abnormal cell proliferation as a hallmark, such as various cancers and other neoplasias.

IFN-gamma has demonstrated potent immunological activity, but due to variations in glycosylation from systems currently used to express IFN-gamma, the potency, efficacy, biological half-life, and other important factors of a therapeutic have been variable at best. The present invention encompasses methods to correct this crucial defect.

A remodeled interferon-gamma peptide may be administered to a patient selected from the group consisting of a patient having chronic granulomatous disease, a patient having malignant osteopetrosis, a patient having pulmonary fibrosis, a patient having tuberculosis, a patient having Cryptococcal meningitis, and a patient having pulmonary *Mycobacterium avium* complex (MAC) infection. Preferably, the patient is a human patient.

The nucleotide and amino acid sequences of IFN-gamma are presented herein as SEQ ID NO:19 and SEQ ID NO:20, respectively (FIGS. 67A and 67B, respectively). It will be readily understood that the sequences set forth herein are in no way limiting to the present invention. In contrast, variants, derivatives, and mutants of IFN-gamma are well known to the skilled artisan. As an example, U.S. Pat. No. 6,083,724 describes a recombinant avian IFN-gamma and U.S. Pat. No. 5,770,191 describes C-terminus variants of human IFN-gamma. In addition, U.S. Pat. No. 4,758,656 describes novel IFN-gamma derivatives, and methods of synthesizing them in various expression systems. Therefore, the present invention is not limited to the sequences of IFN-gamma disclosed elsewhere herein, but encompasses all derivatives, variants, muteins, and the like well known in the art.

Expression systems for IFN-gamma are equally well known in the art, and include prokaryotic and eukaryotic systems, as well as plant and insect cell preparations, methods of which are known to the skilled artisan. As an example, U.S. Pat. No. 4,758,656 describes a system for expressing IFN-gamma derivatives in *E. coli*, whereas U.S. Pat. No. 4,889,803 describes an expression system employing Chinese hamster ovary cells and an SV40 promoter.

Assays for the biological activity of a remodeled IFN-gamma prepared according to the methods disclosed herein will be well known to one of skill in the art. Biological assays for IFN-gamma expression can be found in, for example, U.S. Pat. No. 5,807,744. Briefly, IFN-gamma is added to cultures of CD34$^{++}$CD38$^-$ cells (100 cells per well) stimulated by cytokine combinations to induce proliferation of CD34$^{++}$ CD38$^-$ cells, such as IL-3, c-kit ligand and either IL-1, IL-6 or G-CSF. Cell proliferation, and generation of secondary colony forming cells will be profoundly inhibited in a dose dependent way, with near complete inhibition occurring at 5000 U/milliliter of IFN-gamma. As a confirmatory test to the inhibitory effect of IFN-gamma, addition of IFN-gamma antibodies can be performed as a control.

I. Alpha-Protease Inhibitor (α-Antitrypsin)

The present invention further includes a method for the remodeling of alpha-protease inhibitor (A-1-PI, α-1-antitrypsin or α-1-trypsin inhibitor), also known as alpha-antitrypsin. A-1-PI is a glycoprotein having molecular weight of 53 kDa. A-1-PI plays a role in controlling tissue destruction by endogenous serine proteases, and is the most pronounced serine protease inhibitor in blood plasma. In particular, A-1-PI inhibits various elastases including neutrophil elastase. Elastase is a protease which breaks down tissues, and can be particularly problematic when its activity is unregulated in lung tissue. This protease functions by breaking down foreign proteins. However, when API is not present in sufficient quantities to regulate elastase activity, the elastase breaks down lung tissue. In time, this imbalance results in chronic lung tissue damage and emphysema. In fact, a genetic deficiency of A-1-PI has been shown to be associated with premature development of pulmonary emphysema. A-1-PI replenishment has been successfully used for treatment of this form of emphysema. Further, a deficiency of A-1-PI may also contribute to the aggravation of other diseases such as cystic fibrosis and arthritis, where leukocytes move in to the lungs or joints to fight infection.

Therefore, A-1-PI could conceivably be used to treat diseases where an imbalance between inhibitor and protease(s), especially neutrophil elastase, is causing progression of a disease state. Antiviral activity has also been attributed to A-1-PI. In light of this, it logically follows that the present invention is useful for the production of A-1-PI that is safe, effective, and potent in the ever changing atmosphere of the lungs.

A remodeled A-1-P1 peptide may be administered to a patient selected from the group consisting of a patient having congenital alpha-1-antitrypsin deficiency and emphysema, a patient having cystic fibrosis, and a patient having pulmonary fibrosis. Preferably, the patient is a human patient.

A-1-PI has been cloned and sequenced, and is set forth in SEQ ID NO:21 and SEQ ID NO:22 (FIGS. 68A and 68B, respectively). As is understood by one of skill in the art, natural and engineered variants of A-1-PI exist, and are encompassed in the present invention. As an example, U.S. Pat. No. 5,723,316 describes A-1-PI derivatives having amino acid substitutions at positions 356-361 and further comprises an N-terminal extension of approximately three amino acids. U.S. Pat. No. 5,674,708 describes A-1-PI analogs with amino acid substitutions at position 358 in the primary amino acid sequence. The skilled artisan will readily realize that the present invention encompasses A-1-PI variants, derivatives, and mutants known or to be discovered.

Methods for the expression and determination of activity of a remodeled A-1-PI produced according to the methods of the present invention are well known in the art, and are described in, for example, U.S. Pat. No. 5,674,708 and U.S. Pat. No. 5,723,316. Briefly, biological activity can be determined using assays for antichymotrypsin activity by measuring the inhibition of the chymotrypsin-catalyzed hydrolysis of substrate N-suc-Ala-Ala-Pro-Phe-p-nitroanilide (0.1 ml of a 10 mM solution in 90% DMSO), as described in, for example, DelMar et al. (1979, Anal. Biochem. 99: 316). A typical chymotrypsin assay contains, in 1.0 milliliters: 100 mM Tris-Cl buffer, pH 8.3, 0.005% (v/v) Triton X-100, bovine pancreatic chymotrypsin (18 kmmol) and A-1-PI of the present invention. The assay mixture is pre-incubated at room temperature for 5 minutes, substrate (0.01 ml of a 10 mM solution in 90% DMSO) is added and remaining chymotrypsin activity is determined by the rate of change in absorbance at 410 nm caused by the release of p-nitroaniline. Measurements of optical absorbance are conducted at 25° C. using a spectrophotometer fitted with a temperature controlled sample compartment.

J. Glucocerebrosidase

The invention described herein further includes a method for the modification of glucocerebrosidase. Glucocerebrosidase is a lysosomal glycoprotein enzyme which catalyzes the hydrolysis of the glycolipid glucocerebroside to glucose and ceramide. Variants of glucocerebrosidase are sold commercially as Cerezyme™ and Ceredase™, and is an approved therapeutic for the treatment of Gaucher disease. Ceredase™ is a placental derived form of glucocerebrosidase with complete N-linked structures. Cerezyme™ is a recombinant variant of glucocerebrosidase which is 497 amino acids in length and is expressed in CHO cells. The 4 N-linked glycans of Cerezyme have been modified to terminate in the trimannose core.

Glucocerebrosidase is presently produced in recombinant mammalian cell cultures, and therefore reflects the glycosylation patterns of those cells, usually rodent cells such as Chinese hamster ovary cells or baby hamster kidney cells, which differ drastically from those of human glycosylation patterns, leading to, among other things, immunogenicity and lack of potency.

A remodeled glucocerebrosidase peptide may be administered to a patient selected from the group consisting of a patient having a lysosomal storage disease, a patient having a glucocerebrosidase deficiency, and a patient having Gaucher disease. Preferably, the patient is a human patient.

The nucleic acid and amino acid sequences of glucocerebrosidase are set forth herein as SEQ ID NO:23 and 24 (FIGS. 69A and 69B, respectively). However, as will be appreciated by the skilled artisan, the sequences represented herein are prototypical sequences, and do not limit the invention. In fact, variants of glucocerebrosidase are well known, and are described in, for example, U.S. Pat. No. 6,015,703 describes enhanced production of glucocerebrosidase analogs and variants thereof. Further, U.S. Pat. No. 6,087,131 describes the cloning and sequencing of yet another glucocerebrosidase variant. It is the intention of the present invention to encompass these and other derivatives, variants, and mutants known or to be discovered in the future.

Methods for the expression of glucocerebrosidase are well known in the art using standard techniques, and are described in detail in, for example, U.S. Pat. No. 6,015,703. Assays for the biological efficacy of a glucocerebrosidase molecule prepared according to the methods of the present invention are similarly well known in the art, and a mouse Gaucher disease model for evaluation and use of a glucocerebrosidase therapeutic is described in, for example, Marshall et al. (2002, Mol. Ther. 6:179).

K. TPA

The present invention further encompasses a method for the remodeling of tissue-type activator (TPA). TPA activates plasminogen to form plasmin which dissolves fibrin, the main component of the protein substrate of the thrombus. TPA preparations were developed as a thrombolytic agents having a very high selectivity toward the thrombus in the thrombolytic treatment for thrombosis which causes myocardial infarction and cerebral infarction.

Further, various modified TPA's have been produced by genetic engineering for the purpose of obtaining higher affinity to fibrin and longer half-life in blood than that of natural TPA. TPA's are proteins that are generally extremely difficult to solubilize in water. In particular, the modified TPA's are more difficult to solubilize in water than natural TPA, making very difficult the preparation of modified TPA's. Modified TPA's are thus difficult to dissolve in water at the time of the administration to a patient. However, the modified TPA's have various advantages, such as increased affinity for fibrin and longer half-life in blood. It is the object of the present invention to increase the solubility of modified TPA's.

A remodeled TPA peptide may be administered to a patient selected from the group consisting of a patient suffering from an acute myocardial infarction and a patient suffering from an acute ischemic stroke. A remodeled TPA peptide may also be administered to a patient to improve ventricular function following an acute myocardial infarction, to reduce the incidence of congestive heart failure following an acute myocardial infarction, or to reduce mortality associated with acute myocardial infarction. A remodeled TPA peptide may also be administered to a patient to improve neurological recovery following an acute ischemic stroke or to reduce the incidence of disability or paralysis following an acute ischemic stroke. Preferably, the patient is a human patient.

The nucleic and amino acid sequences of TPA are set forth herein as SEQ ID NO:25 and SEQ ID NO:26, respectively (FIGS. 70A and 70B, respectively). As described above, variants of TPA have been constructed and used in therapeutic applications. For example, U.S. Pat. No. 5,770,425 described TPA variants in which some of all of the fibrin domain has been deleted. Further, U.S. Pat. No. 5,736,134 describes TPA in which modifications to the amino acid at position 276 are disclosed. The skilled artisan, when equipped with the present disclosure and the teachings herein, will readily realize that the present invention comprises the TPA sequences set forth herein, as well as those variants well known to one versed in the literature.

The expression of TPA from a nucleic acid sequence encoding the same is well known in the art, and is described, in detail, in, for example, U.S. Pat. No. 5,753,486. Assays for determining the biological properties of a TPA molecule prepared according to the methods of the present invention are similarly well known in the art. Briefly, a TPA molecule synthesized as disclosed elsewhere herein can be assayed for their ability to lyse fibrin in the presence of saturating concentrations of plasminogen, according to the method of Carlsen et al. (1988, Anal. Biochem. 168: 428). The in vitro clot lysis assay measures the activity of tissue-type activators by turbidimetry using a microcentrifugal analyzer. A mixture of thrombin and TPA is centrifuged into a mixture of fibrinogen and plasminogen to initiate clot formation and subsequent clot dissolution. The resultant profile of absorbance versus time is analyzed to determine the assay endpoint. Activities of the TPA variants are compared to a standard curve of TPA. The buffer used throughout the assay is 0.06M sodium phosphate, pH 7.4 containing 0.01% (v/v) TWEEN 80 and 0.01% (w/v) sodium azide. Human thrombin is at a concentration of about 33 units/ml. Fibrinogen (at 2.0 mg/ml clottable protein) is chilled on wet ice to precipitate fibronectin and then gravity filtered. Glu-plasminogen is at a concentration of 1 mg/ml. The analyzer chamber temperature is set at 37° C. The loader is set to dispense 20 microliters of TPA (about 500 nanograms/milliliter to about 1.5 micrograms per milliliter) as the sample for the standard curve, or 20 microliters of variant TPAs at a concentration to cause lysis within the range of the standard curve. Twenty microliters of thrombin as the secondary reagent, and 200 microliters of a 50:1 (v/v) fibrinogen: plasminogen mixture as the primary reagent. The absorbance/time program is used with a 5 min incubation time, 340-nanometer-filter and 90 second interval readings.

L. IL-2

The present invention further encompasses a method for the remodeling and modification of IL-2. IL-2 is the main growth factor of T lymphocytes and increases the humoral and cellular immune responses by stimulating cytotoxic CD8 T cells and NK cells. IL-2 is therefore crucial in the defense mechanisms against tumors and viral infections. IL-2 is also used in therapy against metastatic melanoma and renal adenocarcinoma, and has been used in clinical trials in many forms of cancer. Further, IL-2 has also been used in HIV infected patients where it leads to a significant increase in CD4 counts.

Given the success IL-2 has demonstrated in the management and treatment of life-threatening diseases such as various cancers and AIDS, it follows that the methods of the present invention would be useful for developing an IL-2 molecule that has a longer biological half-life, increased potency, and in general, a therapeutic profile more similar to wild-type IL-2 as it is synthesized secreted in the healthy human.

A remodeled IL-2 peptide may be administered to a patient selected from the group consisting of a patient having metastatic renal cell carcinoma, a patient having metastatic melanoma, a patient having ovarian cancer, a patient having Acute Myelogenous Leukemia (AML), a patient having non-Hodgkin's lymphoma (NHL), a patient infected with HIV, and a patient infected with Hepatitis C. A remodeled IL-2 peptide may also be useful for administration to a patient as a cancer vaccine adjuvant. Preferably, the patient is a human patient.

IL-2 has been cloned and sequenced, and the nucleic acid and amino acid sequences are presented herein as SEQ ID NO:27 and SEQ ID NO:28 (FIGS. 71A and 71B, respectively). The present invention should in no way be construed as limited to the IL-2 nucleic acid and amino acid sequences set forth herein. Variants of IL-2 are described in, for example, U.S. Pat. No. 6,348,193, in which the asparagine at position 88 is substituted for arginine, and in U.S. Pat. No. 5,206,344, in which a polymer comprising IL-2 variants with various amino acid substitutions is described. The present invention encompasses these IL-2 variants and others well known in the art.

Methods for the expression and to determine the activity of IL-2 are well known in the art, and are described in, for example, U.S. Pat. No. 5,417,970. Briefly, expression of IL-2, or variants thereof, can be accomplished in a variety of both prokaryotic and eukaryotic systems, including *E. coli*, CHO cells, BHK cells, insect cells using a baculovirus expression system, all of which are well known in the art.

Assays for the activity of a modified IL-2 prepared according to the methods of the present invention can proceed as follows. Peripheral blood lymphocytes can be separated from the erythrocytes and granulocytes by centrifuging on a Ficoll-Hypaque (Pharmacia, Piscataway, N.J.) gradient by the method described in, for example, A. Boyum et al. (Methods in Enzymology, 1984, Vol. 108, page 88, Academic Press, Inc.). Lymphocytes are subsequently washed about three times in culture medium consisted of RPMI 1640 (Gibco-BRL, La Jolla, Calif.) plus 10% AB human serum (CTS Purpan, Toulouse, France) inactivated by heat (1 hour at 56° C.), 2 mM sodium pyruvate, 5 mM HEPES, 4 mM L-glutamine, 100 U/ml penicillin, 100 μg/ml streptomycin and 0.25 μg/ml amphotericin B (complete medium). Adhesive cells (monocytes and macrophages) are eliminated by adhesion to plastic and the remainder of the cells are suspended in complete medium at a concentration of about 5 to $10\times10^5$ cells per milliliter and seeded in culture flasks at a density of about 1-$2\times10^5$ cells per square centimeter. Flasks are then incubated at 37° C. in a 5% $CO_2$ atmosphere for about 1 hour, after which the non-adhesive lymphocytes are recovered by aspiration after gentle agitation of the culture flasks.

Non-adhesive lymphocytes are washed once and cultivated at a concentration of about $10^5$ cells per milliliter in complete medium in the presence of the IL-2 of the present invention for about 48 hours in an incubator as described above. The cells are then washed once.

The cytotoxic activity of the cells is evaluated after about 4 hours of contact with target cells of the human T lymphoid line C8166-45/C63 (HT1 cells) resistant to NK cell cytotoxicity, as described by Salahuddin et al. (1983, Virology 129: 51-64; 1984, Science: 223, 703-707). $6\times10^5$ HT1 cells are radio-tagged with about 200 μCi of $^{51}Cr$ (sodium chromate, Amersham, Arlington Heights, Ill.) at 37° C. for about 1 hour in complete medium without serum, and then washed several times. The target cells and effective cells are distributed in round-bottomed microtitration plates with varying ratios of effective cells to target cells (50:1, 10:1, 1:1). The microtitration plates are centrifuged and, after incubation as described above, the supernatant from each well is recovered and the radioactivity is measured using a gamma counter. Cytotoxicity is determined from the quantity of $^{51}Cr$ released by dead target cells. Non-specific cytotoxicity is determined from the amount of radioactivity spontaneously released from the target cells in the absence of effective cells.

The present method is just one of many well known in the art for measuring the cytotoxicity of effector cells, and is should not be construed as limiting to the present invention.

M. Factor VIII

The invention further encompasses a method for the remodeling and modification of Factor VIII. As described earlier for Factor VII and Factor IX, Factor VIII is a critical component of the blood coagulation pathway. Human Factor VIII, (antihemophilic factor; FVIII:C) is a human plasma protein consisting of 2 peptides (light chain molecular weight of 80 kDa and heavy chain molecular weight variable from 90 to 220 kDa, depending on glycosylation state). It is an essential cofactor in the coagulation pathway and is required for the conversion of Factor X into its active form (Factor Xa). Factor VIII circulates in plasma as a non-covalent complex with von Willibrand Factor (aka FVIII:RP), a dimer of a 2050 aa peptide (See, U.S. Pat. No. 6,307,032). Blood concentrations of Factor VIII below 20% of normal cause a bleeding disorder designated hemophilia A. Factor VIII blood levels less than 1% result in a severe bleeding disorder, with spontaneous joint bleeding being the most common symptom.

Similar to other blood coagulation factors, Factor VIII is a therapeutic with a great deal of potential for the treatment of various bleeding disorders, such as hemophilia A and hemophilia B. Due to the glycosylation of the heavy chain, current methods for the preparation of Factor VIII from recombinant cells results in a product that is not as effective as natural Factor VIII. Purification methods from human plasma result in a crude composition that is less effective and more difficult to prepare than recombinant Factor VIII. The current invention seeks to improve this situation.

A remodeled Factor VIII peptide may be administered to a patient selected from the group consisting of a patient having von Willebrand's disease, a patient having Hemophilia A, a patient having Factor VIII:C deficiency, a patient having fibrinogen deficiency, a patient having Factor XIII deficiency, and a patient having acquired Factor VIII inhibitors (acquired hemophilia). A remodeled Factor VIII peptide may also be administered to a patient to prevent, treat or control bleeding or hemorrhagic episodes. Preferably, the patient is a human patient.

The nucleic acid and amino acid sequences of Factor VIII are presented herein as SEQ ID NO:29 and SEQ ID NO:30, respectively (FIGS. 72A and 72B, respectively). The art is rife with variants of Factor VIII, as described in, for example, U.S. Pat. No. 5,668,108, in which the aspartic acid at position 1241 is replaced by a glutamic acid with the accompanying nucleic acid changes as well. U.S. Pat. No. 5,149,637 describes a Factor VIII variants comprising the C-terminal fraction, either glycosylated or unglycosylated, and U.S. Pat. No. 5,661,008 describes a Factor VIII variant comprising amino acids 1-740 linked to amino acids 1649 to 2332 by at least 3 amino acid residues. Therefore, variants, derivatives, modifications and complexes of Factor VIII are well known in the art, and are encompassed in the present invention.

Expression systems for the production of Factor VIII are well known in the art, and include prokaryotic and eukaryotic cells, as exemplified in U.S. Pat. Nos. 5,633,150, 5,804,420, and 5,422,250.

To determine the biological activity of a Factor VIII molecule synthesized according the methods of the present invention, the skilled artisan will recognize that the assays described herein for the evaluation of Factor VII and Factor IX are applicable to Factor VIII.

N. Urokinase

The present invention also includes a method for the remodeling and/or modification of urokinase. Urokinase is a serine protease which activates plasminogen to plasmin. The protein is synthesized in a variety of tissues including endothelium and kidney, and is excreted in trace amounts into urine. Purified urokinase exists in two active forms, a high molecular weight form (HUK; approximately 50 kDa) and a low molecular weight form (LUK; approximately 30 kDa). LUK has been shown to be derived from HUK by a proteolysis after lysine 135, releasing the first 135 amino acids from HUK. Conventional wisdom has held that HUK or LUK must be converted to proteolytically active forms by the proteolytic hydrolysis of a single chain precursor, also termed prourokinase, between lysine 158 and isoleucine 159 to generate a two-chain activated form (which continues to correspond to either HUK or LUK). The proteolytically active urokinase species resulting from this hydrolytic clip contains two amino acid chains held together by a single disulfide bond. The two chains formed by the activation clip are termed the A or $A_1$ chains (HUK or LUK, respectively), and the B chain comprising the protease domain of the molecule.

Urokinase has been shown to be an effective thrombolytic agent. However, since it is produced naturally in trace quantities the cost of the enzyme is high for an effective dosage. Urokinase has been produced in recombinant cell culture, and DNA encoding urokinase is known together with suitable vectors and host microorganisms. Present compositions comprising urokinase and methods for producing urokinase recombinantly are hampered by a product that has deficient glycosylation patterns, and given the complex proteolytic cleavage events surrounding the activation of urokinase, this aberrant glycosylation leads to a less effective and less potent product.

A remodeled urokinase peptide may be administered to a patient selected from the group consisting of a patient having an embolism, a patient having an acute massive pulmonary embolism, and a patient having coronary artery thrombosis. Preferably, the patient is a human patient. A remodeled urokinase peptide may also be used to restore patency to an intravenous catheter, including a central venous catheter obstructed by clotted blood or fibrin.

The sequence of the nucleotides encoding the primary amino acid chain of urokinase are depicted in SEQ ID NO:33 and SEQ ID NO:34 (FIGS. 73A and 73B, respectively). Variants of urokinase are well known in the art, and therefore the present invention is not limited to the sequences set forth herein. In fact, the skilled artisan will readily realize that urokinase variants described in, for example U.S. Pat. Nos. 5,219,569, 5,648,253, and 4,892,826, exist as functional moieties, and are therefore encompassed in the present invention.

The expression and evaluation of a urokinase molecule prepared according to the methods of the present invention are similarly well known in the art. As a non-limiting example, the expression of urokinase in various systems is detailed in U.S. Pat. No. 5,219,569. An assay for determining the activity and functionality of a urokinase prepared in accordance to the methods set forth herein are described throughout the literature, and are similar to assays for other plasminogen and fibrin related assays described elsewhere throughout. One example of an assay to determine the activity of an urokinase molecule synthesized as described herein can be as described in, for example, Ploug, et al. (1957, Biochim. Biophys. Acta 24: 278-282), using fibrin plates comprising 1.25% agarose, 4.1 mg/ml human fibrinogen, 0.3 units/ml of thrombin and 0.5 μg/ml of soybean trypsin inhibitor.

O. Human DNase

The present invention further encompasses a method for the remodeling and/or modification of recombinant human DNase. Human DNase I has been tested as a therapeutic agent and was shown to diminish the viscosity of cystic fibrosis mucus in vitro. It has been determined that purulent mucus contains about 10-13 mg/ml of DNA, an ionic polymer predicted to affect the rheologic properties of airway fluids. Accordingly, bovine pancreatic DNase I, an enzyme that degrades DNA, was tested as a mucolytic agent many years ago but did not enter clinical practice, because of side effects induced by antigenicity and/or contaminating proteases. Recombinant human DNase is currently used as a therapeutic agent to alleviate the symptoms of diseases such as cystic fibrosis.

A remodeled rDNase peptide may be administered to a patient having cystic fibrosis. A remodeled rDNase peptide may also be administered to a cystic fibrosis patient to improve pulmonary function. Preferably, the patient is a human patient.

Similar to DNase derived from bovine sources, recombinant human DNase poses some problems, mostly due to lowered efficacy due to improper glycosylation imparted by mammalian expression systems currently in use. The present invention describes a method for remodeling DNase, leading to increased efficacy and better therapeutic results.

The nucleotide and amino acid sequences of human DNAse are presented herein as SEQ ID NO:39 and SEQ ID NO:40 (FIGS. 74A and 74B, respectively). Variants of the peptide comprising DNase are well known in the art. As an example, U.S. Pat. No. 6,348,343 describes a human DNase with multiple amino acid substitutions throughout the primary structure. Additionally, U.S. Pat. No. 6,391,607 describes a hyperactive variant of DNase with multiple amino acid substitutions at positions 9, 14, 74, 75; and 205. The present examples, and others well known in the art or to be discovered in the future are encompassed in the present invention.

Expression systems for producing a DNase peptide are well known to the skilled artisan, and have been described in prokaryotic and eukaryotic systems. For example, PCT Patent Publication No. WO 90/07572 describes these methods in considerable detail.

Assays to determine the biological activity of a DNase molecule developed according to the methods of the present invention are well known in the art. As an example, but in no way meant to be limiting to the present invention, an assay to determine the DNA-hydrolytic activity of human DNase I is presented herein. Briefly, two different plasmid digestion assays are used. The first assay ("supercoiled DNA digestion assay") measures the conversion of supercoiled double-stranded plasmid DNA to relaxed (nicked), linear, and degraded forms. The second assay ("linear DNA digestion assay") measured the conversion of linear double-stranded plasmid DNA to degraded forms. Specifically, DNase prepared according to the methods of the present invention is added to 160 microliters of a solution comprising 25 micrograms per milliliter of either supercoiled plasmid DNA or EcoRI-digested linearized plasmid DNA in 25 mM HEPES, pH 7.1, 100 μg/ml bovine serum albumin, 1 mM $MgCl_2$, 2.5 mM $CaCl_2$, 150 mM NaCl, and the samples are incubated at room temperature. At various times, aliquots of the reaction mixtures are removed and quenched by the addition of 25 mM EDTA, together with xylene cyanol, bromophenol blue, and glycerol. The integrity of the plasmid DNA in the quenched samples is analyzed by electrophoresis of the samples on agarose gels. After electrophoresis, the gels are stained with a solution of ethidium bromide and the DNA in the gels is visualized by ultraviolet light. The relative amounts of supercoiled, relaxed, and linear forms of plasmid DNA are determined by scanning the gels with a fluorescent imager (such as the Molecular Dynamics Model 575 FluorImager) and quantitating the amount of DNA in the bands of the gel that correspond to the different forms.

P. Insulin

The invention further includes a method for remodeling insulin. Insulin is well known as the most effective treatment for type I diabetes, in which the beta islet cells of the pancreas do not produce insulin for the regulation of blood glucose levels. The ramifications of diabetes and uncontrolled blood glucose include circulatory and foot problems, and blindness, not to mention a variety of other complications that either result from or are exacerbated by diabetes.

Prior to the cloning and sequencing of human insulin, porcine insulin was used as a treatment for diabetes. Insulin is now produced recombinantly, but the short, 51 amino acid sequence of the mature molecule is a complex structure comprising multiple sulfide bonds. Current methods to recombinantly produce insulin result in a product that lacks similarity to the native protein as produced in healthy non-diabetic subjects. The present invention seeks to repair this flaw.

A remodeled insulin peptide may be administered to a patient selected from the group consisting of a patient having Type I Diabetes (diabetes mellitus) and a patient having Type 2 diabetes mellitus who requires basal (long-acting) insulin for the control of hyperglycemia. A remodeled insulin peptide may also be administered to a diabetic patient to control hyperglycemia. Preferably, the patient is a human patient.

The nucleotide and amino acid sequence of human insulin is portrayed in SEQ ID NO:43 and SEQ ID NO:44, respectively (FIGS. 75A and 75B, respectively). Variants of insulin are abundant throughout the art. U.S. Pat. No. 6,337,194 describes insulin fusion protein analogs, U.S. Pat. No. 6,323,311 describes insulin derivatives comprising a cyclic anhydride of a dicarboxylic acid, and U.S. Pat. No. 6,251,856 describes an insulin derivative comprising multiple amino acid substitutions and a lipophilic group. The skilled artisan will recognize that the following examples of insulin derivatives are in no way exhaustive, but simply represent a small sample of those well known in the art. Therefore, the present invention comprises insulin derivatives known or to be discovered.

Expression systems for the production of insulin are well known in the art, and can be accomplished using molecular biology techniques as described in, for example, Sambrook et al. (1989, Molecular Cloning: A Laboratory Manual, Cold Spring Harbor Laboratory Press, New York).

Assays to determine the functionality of an insulin molecule prepared according to the methods of the present invention are similarly well known in the art. For example, an in vivo model of glucose depression can be used to evaluate the biological activity of insulin synthesized using the methods of the present invention. Useful for this purpose is a rat model. The animals are fasted overnight (16 hours) prior to the experiment, and then anesthetized with intraperitoneally administered sodium pentobarbital or another suitable anesthetic such as ketamine. Each animal receives an i.v. injection (tail vein) of the particular insulin derivative (20 μg/ml/kg). Blood samples are taken from the jugular vein 15 and 5 minutes before injection and 15, 30, 60, 90, 120, 180, and 240 minutes after injection. Blood glucose levels are measured with a blood glucose monitor, available from a variety of commercial suppliers.

Q. Hepatitis B Vaccines (HBsAg)

The present invention further comprises a method for the remodeling the antigen used in hepatitis B vaccines (HbsAg or Hepatitis B sAg). HBsAg is a recombinantly produced surface antigen of the hepatitis B S-protein, and is used to illicit an immune response to the hepatitis B virus, an increasing dangerous virus that results in, among other things, liver disease including cirrhosis and carcinoma, and results in over 1 million deaths worldwide annually. Currently the HBsAg vaccine is administered three times over a six month interval to illicit a protective and neutralizing immune response.

HBsAg is currently produced in yeast strains, and therefore reflects the glycosylation patterns native to a fungus. The present invention provides a method to remodel HBsAg, resulting in among other things, improved immunogenicity, antibodies with improved affinity for the virus, and the like.

A remodeled HBsAg peptide may be administered to a patient to immunize the patient against disease caused by a Hepatitis B virus. A remodeled HBsAg peptide may also be administered to a predialysis patient or a dialysis patient to immunize the patient against disease caused by a Hepatitis B virus. Preferably, the patient is a human patient.

The sequences of the S-protein from a Hepatitis B virus (HBsAg) nucleic acid and primary amino acid chain are set forth herein as SEQ ID NO:45 and SEQ ID NO:46 (FIGS. 76A and 76B, respectively). The nucleotide is 1203 bases in length. The amino acid is 400 residues long. The last 226 amino acid residues are the small S-antigen, which is used in the GlaxoSmithKline vaccine and the Merck vaccine. Fifty-five amino acids upstream from the small S-antigen is the Pre-S start codon. The Pre-S+S regions are the middle S antigen, which is used in the Aventis Pasteur vaccine. From the first start codon to the Pre-S start codon comprises the rest of the S-protein, and is called the large S-protein. This is but one example of the HBsAg used in vaccines, and other subtypes are well known, as exemplified in GenBank Acc Nos.: AF415222, AF415221, AF415220, and AF415219. The sequences presented herein are simply examples of HBsAg known in the art. Similar antigens have been isolated from other strains of hepatitis B virus, and may or may not have been evaluated for antigenicity and potential as vaccine candidates. The present invention therefore encompasses hepatitis B vaccine S-protein surface antigens known or to be discovered.

Expression of an HBsAg in an expression system is a routine procedure for one of skill in the art, and is described in, for example, U.S. Pat. No. 5,851,823. Assays for the immunogenicity of a vaccine are well known in the art, and comprise various tests for the production of neutralizing antibodies, and employ techniques such as ELISA, neutralization assays, Western blots, immunoprecipitation, and the like. Briefly, a sandwich ELISA for the detection of effective anti-HBsAg antibodies is described. The Enzygnost HBsAg assay (Aventis Behring, King of Prussia, Pa.) is used for such methods. Wells are coated with anti-HBs. Serum plasma or purified protein and appropriate controls are added to the wells and incubated. After washing, peroxidase-labeled antibodies to HBsAg are reacted with the remaining antigenic determinants. The unbound enzyme-linked antibodies are removed by washing and the enzyme activity on the solid phase is determined by methods well known in the art. The enzymatically catalyzed reaction of hydrogen peroxide and chromogen is stopped by adding diluted sulfuric acid. The color intensity is proportional to the HBsAg concentration of the sample and is obtained by photometric comparison of the color intensity of the unknown samples with the color intensities of the accompanying negative and positive control sera.

R. Human Growth Hormone

The present invention further encompasses a method for the remodeling of human growth hormone (HGH). The isoform of HGH which is secreted in the human pituitary, consists of 191 amino acids and has a molecular weight of about 21,500. The isoform of HGH which is made in the placenta is a glycosylated form. HGH participates in much of the regulation of normal human growth and development, including linear growth (somatogenesis), lactation, activation of macrophages, and insulin-like and diabetogenic effects, among others.

HGH is a complex hormone, and its effects are varied as a result of interactions with various cellular receptors. While compositions comprising HGH have been used in the clinical setting, especially to treat dwarfism, the efficacy is limited by the absence of glycosylation of the HGH produced recombinantly.

A remodeled HGH peptide may be administered to a patient selected from the group consisting of a patient having a growth hormone deficiency, a patient having Turner syndrome, a patient having growth failure due to a lack of adequate endogenouse growth hormone secretion, a patient having growth failure due to Prader-Willi syndrome (PWS), a patient having growth failure associated with chronic renal insufficiency, and a patient having AIDS associated wasting or cachexia. A remodeled HGH peptide may also be administered to a patient having short stature. Preferably, the patient is a human patient.

The nucleic and amino acid sequence of HGH are set forth elsewhere herein as SEQ ID NO:47 and SEQ ID NO:48 (FIGS. 77A and 77B, respectively). The skilled artisan will recognize that variants, derivatives, and mutants of HGH are well known. Examples can be found in U.S. Pat. No. 6,143,523 where amino acid residues at positions 10, 14, 18, 21, 167, 171, 174, 176 and 179 are substituted, and in U.S. Pat. No. 5,962,411 describes splice variants of HGH. The present invention encompasses these HGH variants known in the art of to be discovered.

Methods for the expression of HGH in recombinant cells is described in, for example, U.S. Pat. No. 5,795,745. Methods for expression of HGH in, inter alia, prokaryotes, eukaryotes, insect cell systems, plants, and in vitro translation systems are well known in the art.

An HGH molecule produced using the methods of the current invention can be assayed for activity using a variety of methods known to the skilled artisan. For example, U.S. Pat. No. 5,734,024 describes a method to determine the biological functionality of an expressed HGH.

S. Anti-Thrombin III

Antithrombin (antithrombin III, AT-III) is a potent inhibitor of the coagulation cascade in blood. It is a non-vitamin K-dependent protease that inhibits the action of thrombin as well as other procoagulant factors (e.g., Factor Xa). Congenital antithrombin III deficiency is an autosomal dominant disorder in which an individual inherits one copy of a defective gene. This condition leads to increased risk of venous and arterial thrombosis, with onset of clinical manifestations typically presenting in young adulthood. Severe congenital antithrombin III deficiency, in which the individual inherits two defective genes, is an autosomal recessive condition associated with increased thrombogenesis, typically noted in infancy. Acquired antithrombin III deficiency most commonly is seen in situations where there is inappropriate activation of the coagulation system. Common conditions that result in acquired antithrombin III deficiency include disseminated intravascular coagulation, microangiopathic hemolytic anemias due to endothelial damage (i.e., Hemolytic-uremic syndrome), and veno-occlusive disease (VOD) seen in patients undergoing bone marrow transplant. AT-III deficiency may be corrected acutely by infusions of AT-III concentrates.

A remodeled AT-III peptide may be administered to a patient selected from the group consisting of a patient having a hereditary AT-III deficiency in connection with a surgical or obstetrical procedure and a hereditary AT-III deficient patient having a thromboembolism. Preferably, the patient is a human patient.

Antithrombin III (AT-III) is an $\alpha$2-glycoprotein of molecular weight 58,000. It is sold commercially as Thrombate III™ (Bayer Corp., West Haven, Conn.). The nucleic acid and amino acid sequences of human antithrombin III are displayed in FIG. 78A (SEQ ID NO:63) and 78B (SEQ ID NO:64), respectively.

Methods to make anti-thrombin III are well know to those in the art. For example, published nucleic acid and amino acid sequences are available for human antithrombin III (see, U.S. Pat. No. 4,517,294) and mutants of human antithrombin III (see, U.S. Pat. Nos. 5,420,252, 5,618,713, 5,700,663). The methods of the invention may be used with any of these amino acid sequences and any nucleic acid sequences that encode them, but are not limited to these sequences. Exemplary methods to produce recombinant antithrombin III are well known in the art, and several are described in U.S. Pat. Nos. 5,420,252, 5,843,705, 6,441,145 and 5,994,628. Exemplary methods to purify recombinant antithrombin III are described in U.S. Pat. Nos. 5,989,593, 6,268,487, 6,395,888, 6,395,881, 6,451,978 and 6,518,406.

There are many known uses for recombinant antithrombin III. Antithrombin III can be used as a anticoagulant during surgery (U.S. Pat. Nos. 5,252,557, 5,182,259), as part of a pharmaceutical preparation or method to inhibit thrombosis (U.S. Pat. Nos. 5,565,471, 6,001,820), and to reduce the adverse side effects of cellular transplantation (U.S. Pat. No. 6,387,366). Additionally, antithrombin III preparations can be used to increase placental blood flow (U.S. Pat. No. 5,888, 964), inhibit fertilization (U.S. Pat. No. 5,545,615), treat asthma (U.S. Pat. No. 6,355,626) and treat arthritis (U.S. Pat. No. 5,252,557) and other inflammatory processes (U.S. Pat. No. 6,399,572). Antithrombin III can also be used to manufacture replacement blood plasma (U.S. Pat. Nos. 4,900,720) or prepare a stabilized cellular blood product (U.S. Pat. No. 6,139,878) for transfusions. Antithrombin III may be administered as a pharmaceutical preparation (U.S. Pat. Nos. 5,084, 273, 5,866,122, 6,399,572, 6,156,731 and 6,514,940) or using gene therapy methodology (U.S. Pat. No. 6,410,015). Compositions comprising antithrombin III can be used as tissue adhesives (U.S. Pat. No. 6,500,427) or lubricants for medical devices that are introduced to the patient (U.S. Pat. No. 6,391,832). Antithrombin III can also be used to coat endovascular stents (U.S. Pat. Nos. 6,355,055, 6,240,616, 5,985,307, 5,685,847 and 5,222,971), ocular implants (U.S. Pat. No. 5,944,753) and prostheses in general (U.S. Pat. Nos. 6,503,556, 6,491,965 and 6,451,373). Antithrombin III can also be used in methods to locate an internal bleeding site in a patient (U.S. Pat. No. 6,314,314) and to determine hemostatic dysfunction in a patient (U.S. Pat. No. 6,429,017).

T. Human Chorionic Gonadotropin

Human Chorionic Gonadotropin (hCG) is a glycoprotein composed of an alpha subunit and a beta subunit. HCG is closely related to two other gonadotropins, luteinizing hormone (LH) and follicle stimulating hormone (FSH), as well as thyroid stimulating hormone (TSH), all three of which are glycoprotein hormones. The alpha subunits of these various glycoprotein hormones are structurally very similar, but the beta subunits differ in amino acid sequence.

The nucleic acid and amino acid sequences of the human chorionic gonadotropin α-subunit are displayed in FIGS. 79A (SEQ ID NO:69) and 79B (SEQ ID NO:70), respectively. The nucleic acid and amino acid sequences of the human chorionic gonadotropin β-subunit are displayed in FIGS. 79C (SEQ ID NO:71) and 79D (SEQ ID NO:72), respectively.

Human chorionic gonadotropin is used in an infertility treatment to promote ovulation or release of an egg from the ovary in women who do not ovulate on their own. Human chorionic gonadotropin is also given to young males to treat undescended or underdeveloped testicles. It is used in men to stimulate the production of testosterone. Some physicians also prescribe human chorionic gonadotropin for men having erictile dysfunctionor lack of sexual desire, and for treatment of male "menopause."

A remodeled hCG peptide may be administered to a patient selected from the group consisting of a patient undergoing assisted reproductive technology (ART), a patient undergoing in vitro fertilization (IVF), a patient undergoing embryo transfer, an infertile patient, a male patient having prepubertal cryptoorchidism not due to anatomical obstruction, and a male patient having hypogonadotropic hypogonadism. A remodeled hCG peptide may also be administered to induce final follicular maturation and early luteinization in an infertile female patient, wherein the infertile female patient has undergone pituitary desensitization and pretreatment with follicle stimulating hormones. A remodeled hCG peptide may also be administered to induce ovulation and pregnancy in an anovulatory infertile patient. Preferably, the patient is a human patient.

Methods to make human chorionic gonadotropin are well known in the art. The heterodimeric hCG can be recombinantly made in any one of many expression systems currently used for industrial manufacture of recombinant proteins. One method of making recombinant hCG is described in U.S. Pat. No. 5,639,639. Methods for making recombinant heterodimeric proteins by expressing both subunits in the same cell are, in general, well known in the art, and several methods are described in the U.S. Pat. Nos. 5,643,745 (expression in a filamentous fungus), 5,985,611 and 6,087,129 (expression in secretory cells). Alternatively, each subunit can be expressed individually in cells, and the two subunits later brought together in vitro for assembly into the heterdimer.

Methods for using human chorionic gonadotropin are numerous and well known in the art. Commonly, hCG is used to induce or synchronize ovulation in mammals (see, U.S. Pat. Nos. 6,489,288, 5,589,457, 5,532,155, 4,196,123, 4,062, 942 and 4,845,077). Additionally, hCG can be used in pregnancy tests, and in particular agglutination-based tests (see, U.S. Pat. Nos. 3,991,175, 4,003,988, 4,071,314 and 4,088, 749). hCG can also be used in a contraceptive vaccine (see, U.S. Pat. Nos. 4,161,519 and 4,966,888). In addition, hCG can be used to treat conditions related to aging and altered hormonal balance such as benign prostatic hypertrophy (see, U.S. Pat. No. 5,610,136) and central nervous system diseases common in the elderly (see, U.S. Pat. No. 4,791,099).

Alternatively, hCG can be used to detect and treat cancers that express hCG or one of its subunits. hCG-expressing tumors include, but are not limited to, breast, prostate, ovary and stomach carcinomas, and neuroblastomas such as Karposi's sarcoma. Antibodies can be raised to hCG which has been glycoremodeled so as to have glycan structures similar to those found on the tumor-expressed hCG, and these antibodies may be used to detect hCG-expressing tumors in patients according to methods well known in the art (see, U.S. Pat. Nos. 4,311,688, 4,478,815 and 4,323,546). Additionally, remodeled hCG can be used to raise an immune response to a tumor that is expressing hCG (see, U.S. Pat. Nos. 5,677,275, 5,762,931, 5,877,148, 4,970,071 and 4,966,753).

hCG can also be used in methods to generally immunomodulate an animal, such as described in U.S. Pat. Nos. 5,554,595, 5,851,997 and 5,700,781. In addition, hCG can be used as an inhibitor of the matrix metalloprotease in conditions benefiting from such treatment, such as chronic inflammatory diseases, multiple sclerosis and angiogenesis-dependent diseases (see, U.S. Pat. No. 6,444,639).

U. α-Iduronidase

α-Iduronidase is sold commercially as Aldurazyme™ (BioMarin and Genzyme). It is useful for replacement therapy for the treatment of MPS I, a lysosomal storage disease. MPS I (also known as Hurler disease) is a genetic disease caused by the deficiency of alpha-L-iduronidase, an enzyme normally required for the breakdown of certain complex carbohydrates known as glycosaminoglycans (GAGs). The normal breakdown of GAGs is incomplete or blocked if the enzyme is not present in sufficient quantity. The cell is then unable to excrete the carbohydrate residues and they accumulate in the lysosomes of the cell and cause MPS I.

A remodeled alpha-iduronidase peptide may be administered to a patient selected from the group consisting of a patient having a lysosomal storage disease, a patient having an alpha-L-iduronidase deficiency, a patient having mucopolysaccaridosis I (MPS I), and a patient having Hurler disease. Preferably, the patient is a human patient.

Methods to produce and purify α-iduronidase, as well as methods to treat certain genetic disorders including α-L-iduronidase deficiency and mucopolysaccharidosis I (MPS I) are described in U.S. Pat. No. 6,426,208. The nucleic acid and amino acid sequences of human α-iduronidase are found in FIGS. 80A (SEQ ID NO:65) and 80B (SEQ ID NO:66), respectively.

V. α-Galactosidase A

α-Galactosidase A (also known as agalsidase beta) is sold commercially as Fabrazyme™ (Genzyme). α-Galactosidase A is useful for the treatment of Fabry disease. Fabry disease is a rare, inherited disorder caused by the deficiency of the essential enzyme α-galactosidase. Without this enzyme, Fabry patients are unable to breakdown a fatty acid substance in their body called globotriasylceramide (GL-3), which accumulates in cells in the blood vessels of the heart, kidney, brain and other vital organs. The progressive buildup of this substance puts patients a risk for stroke, heart attack, kidney damage and debilitating pain. Most patients develop kidney failure during adulthood, and severe organ complications lead to death around age forty.

A remodeled alpha-galactosidase A peptide may be administered to a patient selected from the group consisting of a patient having a lysosomal storage disease, a patient having an alpha-galactosidase A deficiency, and a patient having Fabry disease. Preferably, the patient is a human patient.

The α-galactosidase A enzyme is a lysosomal enzyme which hydrolyzes globotriaosylceramide and related glycolipids which have terminal α-galactosidase linkages. It is a 45 kDa N-glycosylated protein encoded on the long arm of the X chromosome. The initial glycosylated forms (Mr=55,000 to 58,000) synthesized in human fibroblasts or Chang liver cells are processed to a mature glycosylated form (Mr=50,000). The mature active enzyme as purified from human tissues and plasma is a homodimer (Bishop et al., 1986, Proc. Natl. Acad. Sci. USA 83: 4859-4863). The nucleic acid and amino acid sequences of α-galactosidase A are found in FIGS. 81A (SEQ ID NO:67) and 81B (SEQ ID NO:68). Other useful nucleic acid and amino acid sequences of alpha-galactosidase A are found in U.S. Pat. No. 6,329,191.

References teaching how to make alpha-galactosidase A are found in U.S. Pat. Nos. 5,179,023 and 5,658,567 (expression in insect cells), U.S. Pat. No. 5,356,804 (expression and secretion from mammalian cells, including CHO cells), U.S. Pat. No. 5,401,451 (expression in mammalian cells), U.S. Pat. No. 5,580,757 (expression in mammalian cells as a fusion protein) and U.S. Pat. No. 5,929,304 (expression in plant cells). Methods for purifying recombinant alpha-galactosidase A are found in U.S. Pat. No. 6,395,884.

References teaching how to use alpha-galactosidase A to treat patients include, but are not limited to, U.S. Pat. No. 6,066,626 (gene therapy) and U.S. Pat. No. 6,461,609 (treatment with the protein). Mutant forms of alpha-galactosidase A that are useful in the methods of the invention include, but are not limited to, those described in U.S. Pat. No. 6,210,666.

W. Antibodies

The present invention further comprises a method for the remodeling of various antibody preparations including chimeric antibody preparations, including, chimeric TNFR, chimeric anti-glycoprotein IIb/IIIa, chimeric anti-HER2, chimeric anti-RSV, chimeric anti-CD20, and chimeric anti-TNF. Chimeric antibody preparations comprise a human Fc portion from an IgG antibody and the variable regions from a monoclonal antibody specific for an antigen. Other preparations comprise a receptor, for example the 75 kDa TNF receptor, fused to a human IgG Fc portion. These molecules further include Fab fragments comprising light and heavy chains from human and mice. A chimeric TNFR is useful in the treatment of inflammatory diseases, such as rheumatoid arthritis. Chimeric anti-glycoprotein IIb/IIIa is useful in the treatment of cardiac abnormalities, blood clotting, and platelet function disturbances. A chimeric anti-HER2 is useful as a treatment for breast cancer, chimeric anti-RSV is useful for the treatment of respiratory syncytial virus, chimeric anti-CD20 is useful for the treatment of Non-Hodgkin's lymphoma, and chimeric anti-TNF is used for treatment of Crohn's disease.

While these chimeric antibodies have proved useful in the management of varied diseases, administration has to be fairly frequent and at fairly high doses due to the relatively short half-life of a recombinant protein produced in rodent cells. While a majority of the chimeric antibody is human, and therefore regarded as "self" by the immune system, they are degraded and destroyed due to non-native glycosylation patterns. The present invention proposes to repair this problem, greatly increasing the efficacy of these novel medicines.

Antibodies and Methods of their Generation

The term "antibody," as used herein, refers to an immunoglobulin molecule which is able to specifically bind to a specific epitope on an antigen. Antibodies can be intact immunoglobulins derived from natural sources or from recombinant sources and can be immunoreactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and $F(ab)_2$, as well as single chain antibodies and humanized antibodies (Harlow et al., 1999, Using Antibodies: A Laboratory Manual, Cold Spring Harbor Laboratory Press, NY; Harlow et al., 1989, Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody peptide, or an amino acid sequence specifying the antibody, wherein the DNA or amino acid sequence has been obtained using synthetic DNA or amino acid sequence technology which is available and well known in the art.

Monoclonal antibodies directed against full length or peptide fragments of a peptide or peptide may be prepared using any well known monoclonal antibody preparation procedures, such as those described, for example, in Harlow et al. (1988, In: Antibodies, A Laboratory Manual, Cold Spring Harbor, N.Y.) and in Tuszynski et al. (1988, Blood, 72:109-115). Quantities of the desired peptide may also be synthesized using chemical synthesis technology. Alternatively, DNA encoding the desired peptide may be cloned and expressed from an appropriate promoter sequence in cells suitable for the generation of large quantities of peptide. Monoclonal antibodies directed against the peptide are generated from mice immunized with the peptide using standard procedures as referenced herein.

Nucleic acid encoding the monoclonal antibody obtained using the procedures described herein may be cloned and sequenced using technology which is available in the art, and is described, for example, in Wright et al. (1992, Critical Rev. in Immunol. 12(3,4):125-168) and the references cited therein. Further, the antibody of the invention may be "humanized" using the technology described in Wright et al., (supra) and in the references cited therein, and in Gu et al. (1997, Thrombosis and Hematocyst 77(4):755-759).

To generate a phage antibody library, a cDNA library is first obtained from mRNA which is isolated from cells, e.g., the hybridoma, which express the desired peptide to be expressed on the phage surface, e.g., the desired antibody. cDNA copies of the mRNA are produced using reverse transcriptase. cDNA which specifies immunoglobulin fragments are obtained by PCR and the resulting DNA is cloned into a suitable bacteriophage vector to generate a bacteriophage DNA library comprising DNA specifying immunoglobulin genes. The procedures for making a bacteriophage library comprising heterologous DNA are well known in the art and are described, for example, in Sambrook and Russell (2001, Molecular Cloning: A Laboratory Manual, Cold Spring Harbor, N.Y.).

Bacteriophage which encode the desired antibody, may be engineered such that the peptide is displayed on the surface thereof in such a manner that it is available for binding to its corresponding binding peptide, e.g., the antigen against which the antibody is directed. Thus, when bacteriophage which express a specific antibody are incubated in the presence of a cell which expresses the corresponding antigen, the bacteriophage will bind to the cell. Bacteriophage which do not express the antibody will not bind to the cell. Such panning techniques are well known in the art and are described for example, in Wright et al., (supra).

Processes such as those described above, have been developed for the production of human antibodies using M13 bacteriophage display (Burton et al., 1994, Adv. Immunol. 57:191-280). Essentially, a cDNA library is generated from mRNA obtained from a population of antibody-producing cells. The mRNA encodes rearranged immunoglobulin genes and thus, the cDNA encodes the same. Amplified cDNA is cloned into M13 expression vectors creating a library of phage which express human antibody fragments on their surface. Phage which display the antibody of interest are selected by antigen binding and are propagated in bacteria to produce soluble human immunoglobulin. Thus, in contrast to conventional monoclonal antibody synthesis, this procedure immortalizes DNA encoding human immunoglobulin rather than cells which express human immunoglobulin.

Remodeling Glycans of Antibody Molecules

The specific glycosylation of one class of peptides, namely immunoglobulins, has a particularly important effect on the biological activity of these peptides. The invention should not be construed to be limited solely to immunoglobulins of the IgG class, but should also be construed to include immunoglobulins of the IgA, IgE and IgM classes of antibodies.

Further, the invention should not be construed to be limited solely to any type of traditional antibody structure. Rather, the invention should be construed to include all types of antibody molecules, including, for example, fragments of antibodies, chimeric antibodies, human antibodies, humanized antibodies, etc.

A typical immunoglobulin molecule comprises an effector portion and an antigen binding portion. For a review of immunoglobulins, see Harlow et al., 1988, Antibodies: A Laboratory Manual, Cold Spring Harbor, N.Y., and Harlow et al., 1999, Using Antibodies: A Laboratory Manual, Cold Spring Harbor Laboratory Press, NY. The effector portion of the immunoglobulin molecule resides in the Fc portion of the molecule and is responsible in part for efficient binding of the immunoglobulin to its cognate cellular receptor. Improper glycosylation of immunoglobulin molecules particularly in the CH2 domain of the Fc portion of the molecule, affects the biological activity of the immunoglobulin.

More specifically with respect to the immunoglobulin IgG, IgG effector function is governed in large part by whether or not the IgG contains an N-acetylglucosamine (GlcNAc) residue attached at the 4-O position of the branched mannose of the trimannosyl core of the N-glycan at Asparagine (Asn) 297 in the CH2 domain of the IgG molecule. This residue is known as a "bisecting GlcNAc." The purpose of adding bisecting GlcNAc to the N-glycan chains of a natural or recombinant IgG molecule or a IgG-Fc-containing chimeric construct is to optimize Fc immune effector function of the Fc portion of the molecule. Such effector functions may include antibody-dependent cellular cytotoxicity (ADCC) and any other biological effects that require efficient binding to FcγR receptors, and binding to the C1 component of complement. The importance of bisecting GlcNAc for achieving maximum immune effector function of IgG molecules has been described (Lifely et al., 1995, Glycobiology 5 (8): 813-822; Jeffris et al., 1990, Biochem. J. 268 (3): 529-537).

The glycans found at the N-glycosylation site at Asn 297 in the CH2 domain of IgG molecules have been structurally characterized for IgG molecules found circulating in human and animal blood plasma, IgG produced by myeloma cells, hybridoma cells, and a variety of transfected immortalized mammalian and insect cell lines. In all cases the N-glycan is either a high mannose chain or a complete (Man3, GlcNAc4, Gal2, NeuAc2, Fuc1) or variably incomplete biantennary chain with or without bisecting GlcNAc (Raju et al., 2000, Glycobiology 10 (5): 477-486; Jeffris et al., 1998, Immunological. Rev. 163L59-76; Lerouge et al., 1998, Plant Mol. Biol. 38: 31-48; James et al., 1995, Biotechnology 13: 592-596).

The present invention provides an in vitro customized glycosylated immunoglobulin molecule. The immunoglobulin molecule may be any immunoglobulin molecule, including, but not limited to, a monoclonal antibody, a synthetic antibody, a chimeric antibody, a humanized antibody, and the like. Specific methods of generating antibody molecules and their characterization are disclosed elsewhere herein. Preferably, the immunoglobulin is IgG, and more preferably, the IgG is a humanized or human IgG, most preferably, IgG1. The present invention specifically contemplates using β1,4-mannosyl-glycopeptide β1,4-N-acetylglucosaminyltransferase, GnT-III: EC2.4.1.144 as an in vitro reagent to glycosidically link N-acetylglucosamine (GlcNAc) onto the 4-O position of the branched mannose of the trimannosyl core of the N-glycan at Asn 297 in the CH2 domain of an IgG molecule. However, as will be appreciated from the disclosure provided herein, the invention should not be construed to solely include the use of this enzyme to provide a bisecting GlcNAc to an immunoglobulin molecule. Rather, it has been discovered that it is possible to modulate the glycosylation pattern of an antibody molecule such that the antibody molecule has enhanced biological activity, i.e., effector function, in addition to potential enhancement of other properties, e.g., stability, and the like.

There is provided in the present invention a general method for removing fucose molecules from the Asn(297) N-linked glycan for the purpose of enhancing binding to Fc-gammaRIIIA, and enhanced antibody-dependent cellular cytotoxicity (see, Shields et al., 2002, J. Biol. Chem. 277:26733-26740). The method entails contacting the antibody molecule with a fucosidase appropriate for the linkage of the fucose molecule(s) on the antibody glycan(s). Alternately, the recombinant antibody can be expressed in cells that do express fucosyltransferases, such as the Lec13 varient of CHO cells. The removal of fucose from the glycan(s) of the antibody can be done alone, or in conjunction with other methods to remodel the glycans, such as adding a bisecting GlcNAc. Expression of antibodies in cells lacking GnT-I may also result in Fc glycans lacking core fucose, which can be further modified by the present invention.

There is provided in the present invention a general method for introducing a bisecting GlcNAc for the purpose of enhancing Fc immune effector function in any preparation of IgG molecules containing N-linked oligosaccharides in the CH2 domain, typically at Asn 297. The method requires that the population of IgG molecules is brought to a state of glycosylation such that the glycan chain is an acceptor for GnT-III. This is accomplished in any one of three ways: 1) by selection or genetic manipulation of a host expression system that secretes IgG with N-glycan chains that are substrates for GnT-III; 2) by treatment of a population of IgG glycoforms with exoglycosidases such that the glycan structure(s) remaining after exoglycosidase treatment is an acceptor for GnT-III; 3) some combination of host selection and exoglycosidase treatment as in 1) and 2) above plus successive additions of GlcNAc by GnT-I and GnT-II to create an acceptor for GnT-III.

For example, IgG obtained from chicken plasma contains primarily high mannose chains and would require digestion with one or more α-mannosidases to create a substrate for addition of GlcNAc to the α1,3 mannose branch of the trimannosyl core by GnT-I. This substrate could be the elemental trimannosyl core, Man3GlcNAc2. Treatment of this core structure with a combination of GnT-I, GnT-II, and GnT-III using UDP-GlcNAc as a sugar donor creates Man3GlcNAc5 as shown in FIG. 1. The order of action of these glycosyltransferases may be varied to optimize the production of the desired product. Optionally, this structure can then be extended by treatment with β1,4 galactosyltransferase. If required, the galactosylated oligosaccharide can be further extended using α2,3- or α2,6-sialyltransferase to achieve a completed biantennary structure. Using this method biantennary glycan chains can be remodeled as required for the optimal Fc immune effector function of any therapeutic IgG under development (FIG. 3).

Alternatively, IgG molecules found in the plasma of most animals or IgG which is secreted as a recombinant product by most animal cells or by transgenic animals typically include a spectrum of biantennary glycoforms including complete (NeuAc2, Gal2, GlcNAc4, Man3, ±Fuc1) (FIG. 3) and variably incomplete forms, with or without bisecting GlcNAc (Raju et al., 2000, Glycobiology 10 (5): 477-486; Jeffris et al., 1998, Immunological Rev. 163: 59-76). To ensure that bisecting GlcNAc is present in the entire population of immunoglobulin molecules so produced, the mixture of molecules can be treated with the following exoglycosidases, successively or in a mixture: neuraminidase, β-galactosidase, β-hexosaminidase, α-fucosidase. The resulting trimannosyl core can then be remodeled using glycosyltransferases as noted above.

In some cases it may be desired to abolish effector function from existing antibody molecules. The present invention also includes modifying the Fc glycans with appropriate glycosidases and glycosyltransferases to eliminate effector function. Also anticipated is the addition of sugars modified with PEG or other polymers that serve to hinder or abolish binding of Fc receptors or complement to the antibody.

In addition, IgG secreted by transgenic animals or stored as "plantibodies" by transgenic plants have been characterized. An IgG molecule produced in a transgenic plant having N-glycans that contain β1,2 linked xylose and/or α1,3 linked fucose can be treated with exoglycosidases to remove those residues, in addition to the above described exoglycosidases in order to create the trimannosyl core or a Man3GlcNAc4 structure, and are then treated with glycosyltransferases to remodel the N-glycan as described above.

The primary novel aspect of the current invention is the application of appropriate glycosyltransferases, with or without prior exoglycosidase treatment, applied in the correct sequence to optimize the effector function of the antibody. In one exemplary embodiment, a bisecting GlcNAc is introduced into the glycans of IgG molecules or other IgG-Fc-chimeric constructs where bisecting GlcNAc is required. In another exemplary embodiment, the core fucose is removed from the glycans of IgG molecules or other IgG-Fc-chimeric constructs.

X. TNF Receptor-IgG Fc Fusion Protein

The nucleotide and amino acid sequences of the 75 kDa human TNF receptor are set forth herein as SEQ ID NO:31 and SEQ ID NO:32, respectively (FIGS. 82A and 82B, respectively). The amino acid sequences of the light and heavy variable regions of chimeric anti-HER2 are set forth as SEQ ID NO:35 and SEQ ID NO:36, respectively (FIGS. 83A and 83B, respectively). The amino acid sequences of the heavy and light variable regions of chimeric anti-RSV are set forth as SEQ ID NO:38 and SEQ ID NO:37, respectively (FIGS. 84A and 84B, respectively). The amino acid sequences of the non-human variable regions of anti-TNF are set forth herein as SEQ ID NO:41 and SEQ ID NO:42, respectively (FIGS. 85A and 85B, respectively). The nucleotide and amino acid sequence of the Fc portion of human IgG is set forth as SEQ ID NO:49 and SEQ ID NO:50 (FIGS. 86A and 86B, respectively).

A remodeled chimeric ENBREL™ may be administered to a patient selected from the group consisting of a patient having rheumatoid arthritis and a patient having polyarticular-course juvenile arthritis. A remodeled chimeric ENBREL™ may also be administered to an arthritis patient to reduce signs, symptoms, or structural damage in the patient. Preferably, the patient is a human patient.

A remodeled Synagis™ antibody may be administered to a patient to immunize the patient against infection by respiratory syncytial virus (RSV). A remodeled Synagis™ antibody may also be administered to a patient to prevent or reduce the severity of a lower respiratory tract disease caused by RSV. Preferably, the patient is a human patient.

Y. MAb Anti-Glycoprotein IIb/IIIa

The amino acid sequences of a murine anti-glycoprotein IIb/IIIa antibody variable regions are set forth in SEQ ID NO:52 (murine mature variable light chain, FIG. 87) and SEQ ID NO: 54 (murine mature variable heavy chain, FIG. 88). These murine sequences can be combined with human IgG amino acid sequences SEQ ID NO:51 (human mature variable light chain, FIG. 89), SEQ ID NO: 53 (human mature variable heavy chain, FIG. 90), SEQ ID NO: 55 (human light chain, FIG. 91) and SEQ ID NO: 56 (human heavy chain, FIG. 92) according to the procedures found in U.S. Pat. No. 5,777,085 to create a chimeric humanized murine anti-glycoprotein IIb/IIIa antibody. Other anti-glycoprotein IIb/IIIa humanized antibodies are found in U.S. Pat. No. 5,877,006. A cell line expressing the anti-glycoprotein IIb/IIIa MAb 7E3 can be commercially obtained from the ATCC (Manassas, Va.) as accession no. HB-8832.

Indications for Selected Antibodies

A remodeled Reopro™ may be administered to a patient selected from the group consisting of a patient undergoing percutaneous coronary intervention and a patient having unstable angina, wherein the patient is scheduled for percutaneous coronary intervention within 24 hours. A remodeled Reopro™ may also be administered to a patient undergoing percutaneous coronary intervention to reduce or prevent a cardiac ischemic complication in the patient. Preferably, the patient is a human patient.

A remodeled Herceptin™ may be administered to a patient having metastatic breast cancer that overexpresses the HER2 protein. Preferably, the patient is a human patient.

A remodeled Remicade™ antibody may be administered to a patient selected from the group consisting of a patient having rheumatoid arthritis, a patient having Crohn's disease, and a patient having fistulizing Crohn's disease. A remodeled Remicade™ antibody may also be administered to a rheumatoid arthritis patient to reduce signs and symptoms of rheumatoid arthritis in the patient. A remodeled Remicade™ antibody may also be administered to a Crohn's disease patient to reduce signs and symptoms of Crohn's disease in the patient. Preferably, the patient is a human patient.

Z. MAb Anti-CD20

The nucleic acid and amino acid sequences of a chimeric anti-CD20 antibody are set forth in SEQ ID NO: 59 (nucleic acid sequence of murine variable region light chain, FIG. 93A), SEQ ID NO:60 (amino acid sequence of murine variable region light chain, FIG. 93B), SEQ ID NO:61 (nucleic acid sequence of murine variable region heavy chain, FIG. 94A) and SEQ ID NO:62 (amino acid sequence of murine variable region heavy chain, FIG. 94B). In order to humanize a murine antibody, the TCAE 8 (SEQ ID NO:57, FIG. 95A-95E), which contains the human IgG heavy and light constant domains, may be conveniently used. By cloning the above murine variable region encoding DNA into the TCAE 8 vector according to instructions given in U.S. Pat. No. 5,736,137, a vector is created (SEQ ID NO: 58, FIG. 96A-96E) which when transformed into a mammaliam cell line, expresses a chimeric anti-CD20 antibody. Other humanized anti-CD20 antibodies are found in U.S. Pat. No. 6,120,767. A cell line expressing the anti-CD20 MAb C273 can be commercially obtained from the ATCC (Manassas, Va.) as accession no. HB-9303.

The skilled artisan will readily appreciate that the sequences set forth herein are not exhaustive, but are rather examples of the variable regions, receptors, and other binding moieties of chimeric antibodies. Further, methods to construct chimeric or "humanized" antibodies are well known in the art, and are described in, for example, U.S. Pat. No. 6,329,511 and U.S. Pat. No. 6,210,671. Coupled with the present disclosure and methods well known throughout the art, the skilled artisan will recognize that the present invention is not limited to the sequences disclosed herein.

The expression of a chimeric antibody is well known in the art, and is described in detail in, for example, U.S. Pat. No. 6,329,511. Expression systems can be prokaryotic, eukaryotic, and the like. Further, the expression of chimeric antibodies in insect cells using a baculovirus expression system is described in Putlitz et al. (1990, Bio/Technology 8:651-654). Additionally, methods of expressing a nucleic acid encoding a fusion or chimeric protein are well known in the art, and are described in, for example, Sambrook et al. (2001, Molecular Cloning: A Laboratory Manual, Cold Spring Harbor Laboratory Press, New York) and Ausubel et al. (1997, Current Protocols in Molecular Biology, Green & Wiley, New York).

Determining the function and biological activity of a chimeric antibody produced according to the methods of the present invention is a similarly basic operation for one of skill in the art. Methods for determining the affinity of an antibody by competition assays are detailed in Berzofsky (J. A. Berzofsky and I. J. Berkower, 1984, in Fundamental Immunology (ed. W. E. Paul), Raven Press (New York), 595). Briefly, the affinity of the chimeric antibody is compared to that of the monoclonal antibody from which it was derived using a radio-iodinated monoclonal antibody.

A remodeled anti-CD20 antibody may be administered to a patient having relapsed or refractory low grade or follicular, CD20-positive, B-cell non-Hodgkin's lymphoma. Preferably, the patient is a human patient.

VII. Pharmaceutical Compositions

In another aspect, the invention provides a pharmaceutical composition. The pharmaceutical composition includes a pharmaceutically acceptable diluent and a covalent conjugate between a non-naturally-occurring, water-soluble polymer, therapeutic moiety or biomolecule and a glycosylated or non-glycosylated peptide. The polymer, therapeutic moiety or biomolecule is conjugated to the peptide via an intact glycosyl linking group interposed between and covalently linked to both the peptide and the polymer, therapeutic moiety or biomolecule.

Pharmaceutical compositions of the invention are suitable for use in a variety of drug delivery systems. Suitable formulations for use in the present invention are found in *Remington's Pharmaceutical Sciences*, Mace Publishing Company, Philadelphia, Pa., 17th ed. (1985). For a brief review of methods for drug delivery, see, Langer, *Science* 249:1527-1533 (1990).

The pharmaceutical compositions may be formulated for any appropriate manner of administration, including for example, topical, oral, nasal, intravenous, intracranial, intraperitoneal, subcutaneous or intramuscular administration. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactate polyglycolate) may also be employed as carriers for the pharmaceutical compositions of this invention. Suitable biodegradable microspheres are disclosed, for example, in U.S. Pat. Nos. 4,897,268 and 5,075,109.

Commonly, the pharmaceutical compositions are administered parenterally, e.g., intravenously. Thus, the invention provides compositions for parenteral administration which comprise the compound dissolved or suspended in an acceptable carrier, preferably an aqueous carrier, e.g., water, buffered water, saline, PBS and the like. The compositions may contain pharmaceutically acceptable auxiliary substances as required to approximate physiological conditions, such as pH adjusting and buffering agents, tonicity adjusting agents, wetting agents, detergents and the like.

These compositions may be sterilized by conventional sterilization techniques, or may be sterile filtered. The resulting aqueous solutions may be packaged for use as is, or lyophilized, the lyophilized preparation being combined with a sterile aqueous carrier prior to administration. The pH of the preparations typically will be between 3 and 11, more preferably from 5 to 9 and most preferably from 7 and 8.

In some embodiments the peptides of the invention can be incorporated into liposomes formed from standard vesicle-forming lipids. A variety of methods are available for preparing liposomes, as described in, e.g., Szoka et al., *Ann. Rev. Biophys. Bioeng.* 9: 467 (1980), U.S. Pat. Nos. 4,235,871, 4,501,728 and 4,837,028. The targeting of liposomes using a variety of targeting agents (e.g., the sialyl galactosides of the invention) is well known in the art (see, e.g., U.S. Pat. Nos. 4,957,773 and 4,603,044).

Standard methods for coupling targeting agents to liposomes can be used. These methods generally involve incorporation into liposomes of lipid components, such as phosphatidylethanolamine, which can be activated for attachment of targeting agents, or derivatized lipophilic compounds, such as lipid-derivatized peptides of the invention.

Targeting mechanisms generally require that the targeting agents be positioned on the surface of the liposome in such a manner that the target moieties are available for interaction with the target, for example, a cell surface receptor. The carbohydrates of the invention may be attached to a lipid molecule before the liposome is formed using methods known to those of skill in the art (e.g., alkylation or acylation of a hydroxyl group present on the carbohydrate with a long chain alkyl halide or with a fatty acid, respectively). Alternatively, the liposome may be fashioned in such a way that a connector portion is first incorporated into the membrane at the time of forming the membrane. The connector portion must have a lipophilic portion, which is firmly embedded and anchored in the membrane. It must also have a reactive portion, which is chemically available on the aqueous surface of the liposome. The reactive portion is selected so that it will be chemically suitable to form a stable chemical bond with the targeting agent or carbohydrate, which is added later. In some cases it is possible to attach the target agent to the connector molecule directly, but in most instances it is more suitable to use a third molecule to act as a chemical bridge, thus linking the connector molecule which is in the membrane with the target agent or carbohydrate which is extended, three dimensionally, off of the vesicle surface. The dosage ranges for the administration of the peptides of the invention are those large enough to produce the desired effect in which the symptoms of the immune response show some degree of suppression. The dosage should not be so large as to cause adverse side effects. Generally, the dosage will vary with the age, condition, sex and extent of the disease in the animal and can be determined by one of skill in the art. The dosage can be adjusted by the individual physician in the event of any counterindications.

Additional pharmaceutical methods may be employed to control the duration of action. Controlled release preparations may be achieved by the use of polymers to conjugate, complex or adsorb the peptide. The controlled delivery may be exercised by selecting appropriate macromolecules (for example, polyesters, polyamino carboxymethylcellulose, and protamine sulfate) and the concentration of macromolecules as well as the methods of incorporation in order to control release. Another possible method to control the duration of action by controlled release preparations is to incorporate the peptide into particles of a polymeric material such as polyesters, polyamino acids, hydrogels, poly (lactic acid) or ethylene vinylacetate copolymers.

In order to protect peptides from binding with plasma proteins, it is preferred that the peptides be entrapped in microcapsules prepared, for example, by coacervation techniques or by interfacial polymerization, for example, hydroxymethylcellulose or gelatin-microcapsules and poly (methymethacrylate) microcapsules, respectively, or in colloidal drug delivery systems, for example, liposomes, albumin microspheres, microemulsions, nanoparticles, and nanocapsules or in macroemulsions. Such teachings are disclosed in Remington's Pharmaceutical Sciences (16th Ed., A. Oslo, ed., Mack, Easton, Pa., 1980).

The peptides of the invention are well suited for use in targetable drug delivery systems such as synthetic or natural polymers in the form of macromolecular complexes, nanocapsules, microspheres, or beads, and lipid-based systems including oil-in-water emulsions, micelles, mixed micelles, liposomes, and resealed erythrocytes. These systems are known collectively as colloidal drug delivery systems. Typically, such colloidal particles containing the dispersed peptides are about 50 nm-2 μm in diameter. The size of the colloidal particles allows them to be administered intravenously such as by injection, or as an aerosol. Materials used in the preparation of colloidal systems are typically sterilizable via filter sterilization, nontoxic, and biodegradable, for example albumin, ethylcellulose, casein, gelatin, lecithin, phospholipids, and soybean oil. Polymeric colloidal systems are prepared by a process similar to the coacervation of microencapsulation.

In an exemplary embodiment, the peptides are components of a liposome, used as a targeted delivery system. When phospholipids are gently dispersed in aqueous media, they swell, hydrate, and spontaneously form multilamellar concentric bilayer vesicles with layers of aqueous media separating the lipid bilayer. Such systems are usually referred to as multilamellar liposomes or multilamellar vesicles (MLVs) and have diameters ranging from about 100 nm to about 4 μm. When MLVs are sonicated, small unilamellar vesicles (SUVS) with diameters in the range of from about 20 to about 50 nm are formed, which contain an aqueous solution in the core of the SUV.

Examples of lipids useful in liposome production include phosphatidyl compounds, such as phosphatidylglycerol, phosphatidylcholine, phosphatidylserine, and phosphatidylethanolamine. Particularly useful are diacylphosphatidylglycerols, where the lipid moiety contains from 14-18 carbon atoms, particularly from 16-18 carbon atoms, and are saturated. Illustrative phospholipids include egg phosphatidylcholine, dipalmitoylphosphatidylcholine, and distearoylphosphatidylcholine.

In preparing liposomes containing the peptides of the invention, such variables as the efficiency of peptide encapsulation, lability of the peptide, homogeneity and size of the resulting population of liposomes, peptide-to-lipid ratio, permeability instability of the preparation, and pharmaceutical acceptability of the formulation should be considered. Szoka, et al, *Annual Review of Biophysics and Bioengineering,* 9: 467 (1980); Deamer, et al., in LIPOSOMES, Marcel Dekker, New York, 1983, 27: Hope, et al., *Chem. Phys. Lipids,* 40: 89 (1986)).

The targeted delivery system containing the peptides of the invention may be administered in a variety of ways to a host, particularly a mammalian host, such as intravenously, intramuscularly, subcutaneously, intra-peritoneally, intravascularly, topically, intracavitarily, transdermally, intranasally, and by inhalation. The concentration of the peptides will vary upon the particular application, the nature of the disease, the frequency of administration, or the like. The targeted delivery system-encapsulated peptide may be provided in a formulation comprising other compounds as appropriate and an aqueous physiologically acceptable medium, for example, saline, phosphate buffered saline, or the like.

The compounds prepared by the methods of the invention may also find use as diagnostic reagents. For example, labeled compounds can be used to locate areas of inflammation or tumor metastasis in a patient suspected of having an inflammation. For this use, the compounds can be labeled with $^{125}I$, $^{14}C$, or tritium.

EXPERIMENTAL EXAMPLES

The invention is now described with reference to the following Examples. These Examples are provided for the purpose of illustration only and the invention should in no way be construed as being limited to these Examples, but rather should be construed to encompass any and all variations which become evident as a result of the teaching provided herein.

The materials and methods used in the experiments presented in this Example are now described.

A. General Procedures

1. Preparation of CMP-SA-PEG

This example sets forth the preparation of CMP-SA-PEG.

Preparation of 2-(benzyloxycarboxamido)-glycylamido-2-deoxy-D-mannopyranose

N-benzyloxycarbonyl-glycyl-N-hydroxysuccinimide ester (3.125 g, 10.2 mmol) was added to a solution containing D-mannosamine-HCl (2 g, 9.3 mmol) and triethylamine (1.42 mL, 10.2 mmol) dissolved in MeOH (10 mL) and $H_2O$ (6 mL). The reaction was stirred at room temperature for 16 hours and concentrated using rotoevaporation. Chromatography (silica, 10% MeOH/$CH_2Cl_2$) yielded 1.71 g (50% yield) of product as a white solid: $R_f$=0.62 (silica; $CHCl_3$:MeOH:$H_2O$, 6/4/1); $^1H$ NMR ($CD_3OD$, 500 MHz) δ 3.24-3.27 (m, 2H), 3.44 (t, 1H), 3.55 (t, 1H), 3.63-3.66 (m, 1H), 3.76-3.90 (m, 6H), 3.91 (s, 2H), 4.0 (dd, 2H), 4.28 (d, 1H, J=4.4), 4.41 (d, 1H, J=3.2), 5.03 (s, 1H), 5.10 (m, 3H), 7.29-7.38 (m, 10H).

Preparation of 5-(N-benzyloxycarboxamido)glycylamido-3,5-dideoxy-D-glycero-D-galacto-2-nonulopyranosuronate 2-(N-Benzyloxycarboxamido) glycylamide-2-deoxy-D-mannopyranose (1.59 g, 4.3 mmol) was dissolved in a solution of 0.1 M HEPES (12 mL, pH 7.5) and sodium pyruvate (4.73 g, 43 mmol). Neuraminic acid aldolase (540 U of enzyme in 45 mL of a 10 mM phosphate buffered solution containing 0.1 M NaCl at pH 6.9) and the reaction mixture was heated to 37° C. for 24 hr. The reaction mixture was then centrifuged and the supernatant was chromatographed (C18 silica, gradient from $H_2O$ (100%) to 30% MeOH/water). Appropriate fractions were pooled, concentrated and the residue chromatographed (silica, gradient from 10% MeOH/$CH_2Cl_2$ to $CH_2Cl_2$/MeOH/$H_2O$ 6/4/1). Appropriate fractions were collected, concentrated and the residue resuspended in water. After freeze-drying, the product (1.67 g, 87% yield) was obtained as a white solid: $R_f$=0.26 (silica, $CHCl_3$/MeOH/$H_2O$ 6/4/1); $^1H$ NMR ($D_2O$, 500 MHz) δ 1.82 (t, 1H), 2.20 (m, 1H), 3.49 (d, 1H), 3.59 (dd, 1H), 3.67-3.86 (m, 2H), 3.87 (s, 2H), 8.89-4.05 (m, 3H), 5.16 (s, 2H), 7.45 (m, 5H).

Preparation of 5-glycylamido-3,5-dideoxy-D-glycero-D-galacto-2-nonulopyranosuronate 5-(N-Benzyloxycarboxamido)glycylamido-3,5-dideoxy-D-glycero-D-galacto-2-nonulopyranosuronate (1.66 g, 3.6 mmol) was dissolved in 20 mL of 50% water/methanol. The flask was repeatedly evacuated and placed under argon and then 10% Pd/C (0.225 g) was added. After repeated evacuation, hydrogen (about 1 atm) was then added to the flask and the reaction mixture stirred for 18 hr. The reaction mixture was filtered through celite, concentrated by rotary evaporation and freeze-dried to yield 1.24 g (100% yield) of product as a white solid: $R_f$=0.25 (silica, IPA/$H_2O$/$NH_4H$ 7/2/1); $^1H$ NMR ($D_2O$, 500 MHz) δ 1.83 (t, 1H, J=9.9), 2.23 (dd, 1H, J=12.9, 4.69), 3.51-3.70 (m, 2H), 3.61 (s, 2H), 3.75-3.84 (m, 2H), 3.95-4.06 (m, 3H).

Preparation of cytidine-5'-monophosphoryl-[5-(N-fluorenylmethoxy-carboxamido)glycylamido-3,5-dideoxy-β-D-glycero-D-galacto-2-nonulopyranosuronate]

A solution containing 5-glycylamido-3,5-dideoxy-D-glycero-D-galacto-2-nonulopyranosuronate (0.55 g, 1.70 mmol) dissolved in 20 mL $H_2O$ was added to a solution of Tris (1.38 g, 11.4 mmol), 1 M $MgCl_2$ (1.1 mL) and BSA (55 mg). The pH of the solution was adjusted to 8.8 with 1M NaOH (2 mL) and CTP-$2Na^+$ (2.23 g, 4.2 mmol) was added. The reaction mixture pH was controlled with a pH controller which delivered 1 M NaOH as needed to maintain pH 8.8. The fusion protein (sialyltransferase/CMP-neuraminic acid synthetase) was added to the solution and the reaction mixture was stirred at room temperature. After 2 days, an additional amount of fusion protein was added and the reaction stirred an additional 40 hours. The reaction mixture was precipitated in EtOH and the precipitate was washed 5 times with cold EtOH to yield 2.3 grams of a white solid. About 1.0 g of the crude product was dissolved in 1,4 dioxane (4 mL), $H_2O$ (4 mL) and saturated $NaHCO_3$(3 mL) and a solution of FMOC-Cl (308 mg, 1.2 mmol) dissolved in 2 ml dioxane was added dropwise. After stirring for 16 hr at room temperature, the reaction mixture was concentrated to about 6 mL by rotary evaporation and purified using chromatography (C18 silica, gradient 100% $H_2O$ to 30% MeOH/$H_2O$). Appropriate fractions were combined and concentrated. The residue was dissolved in water and freeze-dried to yield 253 mg of a white solid: $R_f$=0.50 (silica, IPA/$H_2O$/$NH_4OH$ 7/2/1); $^1H$ NMR ($D_2O$, 500 MHz) δ 1.64 (dt, 1H, J=12.0, 6.0), 2.50 (dd, 1H, J=13.2, 4.9), 3.38 (d, J=9.67, 1H), 3.60 (dd, J=11.65, 6.64, 1H), 3.79 (d, J=4.11, 1H), 3.87 (dd, J=12.24, 1.0, 1H), 3.97 (m, 2H), 4.07 (td, J=10.75, 4.84, 1H), 4.17 (dd, J=10.68, 1.0, 1H), 4.25 (s, 2H), 4.32 (t, J=4.4, 1H), 4.37 (t, J=5.8 1H), 4.6-4.7 (m, obscured by solvent peak), 5.95 (d, J=4, 1H), 6.03 (d, J=7.4, 1H), 7.43-7.53 (m, 3H), 7.74 (m, 2H), 7.94 (q, J=7, 3H). MS (ES); calc. for $C_{35}H_{42}N_5O_{18}P$ ($[M-H]^-$), 851.7; found 850.0.

Preparation of cytidine-5'-monophosphoryl-(5-glycylamido-3,5-dideoxy-β-D-glycero-D-galacto-2-nonulopyranosuronate)

Diisopropylamine (83 uL, 0.587 μmol) was added to a solution of cytidine-5'-monophosphoryl-[5-(N-fluorenylmethoxycarboxamido)glycylamido-3,5-dideoxy-β-D-glycero-D-galacto-2-nonulopyranosuronate] (100 mg, 0.117 mmol) dissolved in water (3 mL) and methanol (1 mL). The reaction mixture was stirred 16 hr at room temperature and the reaction methanol removed from the reaction mixture by rotary evaporation. The crude reaction mixture was filtered through a C18 silica gel column using water and the effluant was collected and freeze-dried to yield (87 mg, 100%) of product as a white solid: $R_f$=0.21 (silica, IPA/$H_2O$/$NH_4OH$ 7/2/1); $^1H$ NMR ($D_2O$, 500 MHz) δ 1.66 (td, 1H, J=5.3), 2.50 (dd, 1H, J=13.2, 4.6), 3.43 (d, J=9.58, 1H), 3.63 (dd, J=11.9, 6.44, 1H), 3.88 (dd, J=11.8, 1.0, 1H), 3.95 (td, J=9.0, 2.3, 1H), 4.10 (t, J=10.42, 1H), 4.12 (td, J=10.34, 4.66, 1H), 4.18 (d, J=10.36, 1H), 4.24 (m, 2H), 4.31 (t, J=4.64, 1H), 4.35 (t, 1H), 6.00 (d, J=4.37, 1H), 6.13 (d, J=7.71, 1H), 7.98 (d, J=7.64, 1H). MS (ES); calc. for $C_{21}H_{32}N_5O_{11}P$ ($[M-H]^-$), 629.47; found 627.9.

Preparation of cytidine-5'-monophosphoryl-[5-(N-methoxy-polyoxyethylene-(1 kDa)-3-oxypropionamido)-glycylamido-3,5-dideoxy-β-D-glycero-D-galacto-2-nonulopyranosuronate]

Benzyltriazol-1-yloxy-tris(dimethylamino)-phosphonium hexafluorophosphate (BOP, 21 mg, 48 μmol) was added to a solution of methoxypolyoxyethylene-(1 kDa average molecular weight)-3-oxypropionic acid (48 mg, 48 μmol) dissolved in anhydrous DMF (700 μL) and triethylamine (13 μL, 95 μmol). After 30 min, a solution containing cytidine-5'-monophosphoryl-(5-glycylamido-3,5-dideoxy-β-D-glycero-D-galacto-2-nonulopyranosuronate) (30 mg, 48 μmol), water (400 μL) and triethylamine (13 μL, 95 μmol) was added. This solution was stirred 20 min at room temperature and then chromatographed (C18 silica, gradient of methanol/water). Appropriate fractions were collected, concentrated, the residue dissolved in water and freeze-dried to afford 40 mg (50% yield) of a white solid: $R_f$=0.36 (silica, IPA/$H_2O$/$NH_4OH$ 7/2/1); $^1H$ NMR ($D_2O$, 500 MHz) δ 1.66 (td, 1H, J=5.3), 2.50 (dd, 1H, J=13.2, 4.6), 2.64 (t, J=5.99, 3H) 3.43 (d, J=9.58, 1H), 3.63 (m, 1H), 3.71 (s, 70H), 3.79 (m, obscured by 3.71 peak), 3.82 (t, J=6.19, 1H) 3.88 (dd, J=11.8, 1.0, 1H), 3.95 (td, J=9.0, 2.3, 1H), 3.98 (t, J=5.06, 1H), 4.12 (td, J=10.34, 4.66, 1H), 4.18 (d, J=10.36, 1H), 4.23 (d, J=4.85, 2H), 4.31 (t, J=4.64, 1H), 4.35 (t, 1H), 6.00 (d, J=4.55, 1H), 6.13 (d, J=7.56, 1H), 7.98 (d, J=7.54, 1H). MS (MALDI), observe [M-H]; 1594.5, 1638.5, 1682.4, 1726.4, 1770.3, 1814.4, 1858.2, 1881.5, 1903.5, 1947.3.

Preparation of cytidine-5'-monophosphoryl-[5-(N-methoxy-polyoxyethylene-(10 kDa)-oxycarboxamido)-glycylamido-3,5-dideoxy-β-D-glycero-D-galacto-2-nonulopyranosuronate]

Cytidine-5'-monophosphoryl-(5-glycylamido-3,5-dideoxy-β-D-glycero-D-galacto-2-nonulopyranosuronate) (2.5 mg, 4 μmol) and water (180 μL) was added to a solution of (Methoxypolyoxyethylene-(10 kDa, average molecular weight)-oxycarbonyl-(N-oxybenzotriazole) ester (40 mg, 4 μmol) in anhydrous DMF (800 μL) containing triethylamine (1.1 μL, 8 μmol) and the reaction mixture stirred for 1 hr at room temperature. The reaction mixture was then diluted with water (8 mL) and was purified by reversed phase flash chromatography (C18 silica, gradient of methanol/water). Appropriate fractions were combined, concentrated, the residue dissolved in water and freeze-dried yielding 20 mg (46% yield) of product as a white solid: $R_f$=0.35 (silica, IPA/$H_2O$/$NH_4OH$ 7/2/1); $^1H$ NMR ($D_2O$, 500 MHz) δ 1.66 (td, 1H), 2.50 (dd, 1H), 2.64 (t, 3H) 3.55-3.7 (m, obscured by 3.71 peak), 3.71 (s, 488H), 3.72-4.0 (m, obscured by 3.71 peak), 4.23 (m, 3H), 4.31 (t, 1H), 4.35 (t, 1H), 6.00 (d, J=4.77, 1H), 6.12 (d, J=7.52, 1H), 7.98 (d, J=7.89, 1H). MS (MALDI), observe [M−CMP+Na]; 10780.

2. Preparation of CMP-SA-PEG II

This example sets forth the general procedure for making CMP-SA-PEG, and specific procedures for making CMP-SA-PEG (1 kDa) and CMP-SA-PEG (20 kDa).

General Procedures Preparing Cytidine-5'-monophosphoryl-(5-glycylamido-3,5-dideoxy-β-D-glycero-D-galacto-2-nonulopyranosuronate)

Cytidine-5'-monophosphoryl-(5-glycylamido-3,5-dideoxy-β-D-glycero-D-galacto-2-nonulopyranosuronate (870 mg, 1.02 mmol) was dissolved in 25 mL of water and 5.5 mL of 40 wt % dimethylamine solution in $H_2O$ was added. The reaction was stirred for 1 hr and the excess dimethyl amine was then removed by rotary evaporation. The aqueous solution was filtered through a C-18 silica gel column and the column was washed with water. The eluants were combined and lyophilized to afford 638 mg (93%) of a white solid. $R_f$=0.10 (silica, IPA/$H_2O$/$NH_4OH$; 7/2/1). $^1H$ NMR ($D_2O$, 500 MHz) δ 1.66 (td, 1H, J=5.3), 2.50 (dd, 1H, J=13.2, 4.6), 3.43 (d, J=9.58, 1H), 3.63 (dd, J=11.9, 6.44, 1H), 3.88 (dd, J=11.8, 1.0, 1H), 3.95 (td, J=9.0, 2.3, 1H), 4.10 (t, J=10.42, 1H), 4.12 (td, J=10.34, 4.66, 1H), 4.18 (d, J=10.36, 1H), 4.24 (m, 2H), 4.31 (t, J=4.64, 1H), 4.35 (t, 1H), 6.00 (d, J=4.37, 1H), 6.13 (d, J=7.71, 1H), 7.98 (d, J=7.64, 1H). MS (ES); calc. for $C_{21}H_{32}N_5O_{11}P$ ($[M-H]^-$), 629.47; found 627.9.

General Procedures for Preparing CMP-SA-PEG using mPEG-(p-nitrophenol)carbonate. Cytidine-5'-monophosphoryl-(5-glycylamido-3,5-dideoxy-β-D-glycero-D-galacto-2-nonulopyranosuronate) (175 mg, 0.259 mMol) was dissolved in a mixture of water, pH 8.5, and DMF or THF (in a ratio of 1:2). The mPEG-nitrophenol carbonate (2 to 20 kDa mPEG's) (0.519 mMole) was added in several portions over 8 hr at room temperature and the reaction mixture was stirred at room temperature for 3 days. When complete, water (40 ml) and 1.5 ml of $NH_4OH$ (29% aqueous solution) were added. The yellow reaction mixture was stirred for another 2 hr and then concentrated by rotary evaporation. The reaction mixture was then diluted with water (pH 8.5) to about 500 ml volume and was purified by reversed phase flash chromatography (Biotage 40M, C18 silica column) with a gradient of methanol/water. Appropriate fractions were combined and concentrated to afford the products as white solids. $R_f$(silica; 1-propanol/water/29% $NH_4OH$; 7/2/1); (2 kDa PEG)=0.31; (5 kDa PEG)=0.33; (10 kDa PEG)=0.36; (20 kDa PEG)=0.38 (TLC silica, IPA/$H_2O$/$NH_4OH$ 7/2/1); MS (MALDI), observe [M−CMP+Na]; (2 kDa)=2460; (5 kDa)=5250; (10 kDa)=10700; (20 kDa)=22500.

Preparation of Cytidine-5'-monophosphoryl-[5-(N-fluorenylmethoxycarboxamido)-glycylamido-3,5-dideoxy-β-D-glycero-D-galacto-2-nonulopyranosuronate]

Solium pyruvate (2.4 g, 218 mmol), HEPES buffer (0.25 M, pH 7.34) and 1.0 g (22 mmol) of Fmoc-glycylmannosamide were mixed in a 150 mL polycarbonate bottle. A neuraminic acid aldolase solution (19 mL, ~600 U) was then added and the reaction mixture was incubated at 30° C. on an orbital shaker. After 23 hours, Thin layer chromatography (TLC) indicated that approximately 75% conversion to product had occurred. The CTP (1.72 g, 33 mmol) and 0.1 M of $MnCl_2$ (6 mL) were then added to the reaction mixture. The pH was adjusted to 7.5 with 1 M NaOH (5.5 mL) and a solution containing CMP-neuraminic acid synthetase (*Neisseria*) was added (25 mL, 386 U). The reaction was complete after 24 hrs and the reaction mixture was chromatographed (C-18 silica, gradient from $H_2O$ (100%) to 10% MeOH/$H_2O$). Appropriate fractions were recombined, concentrated and lyophilized to afford a white solid, $R_f$(IPA/$H_2O$/$NH_4OH$, 7/2/1)=0.52. $^1H$ NMR ($D_2O$, 500 MHz) δ 1.64 (dt, 1H, J=12.0, 6.0), 2.50 (dd, 1H, J=13.2, 4.9), 3.38 (d, J=9.67, 1H), 3.60 (dd, J=11.65, 6.64, 1H), 3.79 (d, J=4.11, 1H), 3.87 (dd, J=12.24, 1.0, 1H), 3.97 (m, 2H), 4.07 (td, J=10.75, 4.84, 1H), 4.17 (dd, J=10.68, 1.0, 1H), 4.25 (s, 2H), 4.32 (t, J=4.4, 1H), 4.37 (t, J=5.8 1H), 4.6-4.7 (m, obscured by solvent peak), 5.95 (d, J=4, 1H), 6.03 (d, J=7.4, 1H), 7.43-7.53 (m, 3H), 7.74 (m, 2H), 7.94 (q, J=7, 3H) MS(ES); calc. for $C_{35}H_{42}N_5O_{18}P$ ($[M-H]^-$), 850.7; found 850.8.

Preparation of Cytidine-5'-monophosphoryl-[5-(N-methoxypolyoxyethylene-(1 kDa)-3-oxypropionamido)-glycylamido-3,5-dideoxy-β-D-glycero-D-galacto-2-nonulopyranosuronate]

Methoxypolyoxyethylene-(1 kDa average molecular weight)-3-oxypropionate-N-succinimidyl ester (52 mg, 52

μmol) dissolved in anhydrous DMF (450 μL) and triethylamine (33 μL, 238 μmol). Cytidine-5'-monophosphoryl-(5-glycylamido-3,5-dideoxy-β-D-glycero-D-galacto-2-nonulopyranosuronate) (30 mg, 48 μmol) was added as a solid. Water, pH 8 (330 μmol) was added and after 30 min, an additional 28 mg of NHS-activated PEG was added. After an additional 5 min, the reaction mixture was chromatographed (C-18 silica, gradient of methanol/water), and appropriate fractions were concentrated to afford 32 mg (40% yield) of a white solid, $R_f$=0.31 (silica, IPA/$H_2O$/$NH_4OH$ 7/2/1); $^1H$ NMR ($D_2O$, 500 MHz) δ 1.66 (td, 1H, J=5.3), 2.50 (dd, 1H, J=13.2, 4.6), 2.64 (t, J=5.99, 3H) 3.43 (d, J=9.58, 1H), 3.63 (m, 1H), 3.71 (s, 70H), 3.79 (m, obscured by 3.71 peak), 3.82 (t, J=6.19, 1H) 3.88 (dd, J=11.8, 1.0, 1H), 3.95 (td, J=9.0, 2.3, 1H), 3.98 (t, J=5.06, 1H), 4.12 (td, J=10.34, 4.66, 1H), 4.18 (d, J=10.36, 1H), 4.23 (d, J=4.85, 2H), 4.31 (t, J=4.64, 1H), 4.35 (t, 1H), 6.00 (d, J=4.55, 1H), 6.13 (d, J=7.56, 1H), 7.98 (d, J=7.54, 1H). MS (MALDI), observe [(M–CMP)-H]; 1506.4, 1550.4, 1594.5, 1638.5, 1682.4, 1726.4, 1770.3, 1814.4, 1858.2.

Preparation of Cytidine-5'-monophosphoryl-{5-[N-(2,6-dimethoxypolyoxyethylene-(20 kDa)-3oxypropionamidyl-lysylamido]-glycylamido-3,5-dideoxy-β-D-glycero-D-galacto-2-nonulopyranosuronate}

The 2,6-Di-[methoxypolyoxyethylene-(20 kDa average molecular weight)-3-oxypropionamidyl]-lysylamido-N-succinimidyl ester (367 mg, 9 μmol) was dissolved in anhydrous THF (7 mL) and triethylamine (5 μL, 36 μmol). Cytidine-5'-monophosphoryl-(5-glycylamido-3,5-dideoxy-β-D-glycero-D-galacto-2-nonulopyranosuronate) (30 mg, 48 μmol) was dissolved in 1.0 mL of water, and added to the reaction mixture. The reaction was stirred for 4 hours at room temperature and was then chromotographed (HPLC, Waters Xterra RP8, gradient from water/$NH_4OH$, 100% to 20% methanol/water/$NH_4OH$ at 1 mL/min) to afford a white solid with a $R_t$=22.8 min. MS (MALDI), observe [(M–CMP)-H]; 43027.01 (40,000-45,500).

3. Preparation of UDP-Gal-PEG.

This example sets forth the general procedure for making UDP-Gal-PEG. Methoxypolyoxyethylenepropionate N-hydroxysuccinimide ester (mPEG-SPA, MW 1,000) 348 mg in THF (0.5 mL) was added to a solution of 25 mg of galactosamine-1-phosphate in 1 ml of water, followed by the addition of 67 μL triethylamine. The resulting mixture was stirred at room temperature for 17 hr. Concentration at reduce pressures provided a crude reaction mixture which was purified by chromatography (C-18 silica, using a step gradient of 10%, 20%, 30%, 40% aqueous MeOH) to afford 90 mg (74%) of product after the appropriate fractions were combined and concentrated to dryness. $R_f$=0.5 (silica, Propanol/$H_2O$/$NH_4OH$ 30/20/2); MS (MALDI), observed 1356, 1400, 1444, 1488, 1532, 1576, 1620.

[α-1-(Uridine-5'-diphosphoryl)]-2-deoxy-2-(methoxypolyoxyethylene-propionoylamido-1 kDa)-α-D-galactosamine The 2-deoxy-2-(methoxy-polyoxyethylenepropionoylamido-1 kDa)-α-1-monophosphate-D-galactosamine (58 mg) was dissolved in 6 mL of DMF and 1.2 mL of pyridine. UMP-morpholidate (60 mg) was then added and the resulting mixture was stirred at 70° C. for 48 hr. After concentration, the residue was chromatographed (C18-silica, using a step gradient of 10%, 20%, 30%, 40%, 50%, 80% MeOH) to yield 50 mg of product after concentration of the appropriate fractions. $R_f$=0.54 (silica, propanol/$H_2O$/$NH_4OH$ 30/20/2). MS (MALDI); Observed 1485, 1529, 1618, 1706.

[α-1-(Uridine-5'-diphosphoryl)]-6-deoxy-6-(methoxypolyoxyethylene-amino-2 kDa)-α-D-galactose

[α-(Uridine-5'-diphosphoryl)]-6-carboxaldehyde-α-D-galactose (10 mg) was dissolved in 2 mL of 25 mM sodium phosphate buffer (pH 6.0) and treated with methoxypolyethyleneglycol amine (MW 2,000, 70 mg) and then 25 μL of 1M $NaBH_3CN$ solution at 0° C. The resulting mixture was frozen at −20° C. for three days. The reaction mixture was chromatographed (HPLC, Water Xterra P8) using 0.015 M $NH_4OH$ as mobile phase A and MeOH as mobile phase B as eluent at the speed of 1.0 mL/min. The product was collected, an concentrated to yield a solid; $R_t$=9.4 minutes. $R_f$=0.27(silica, EtOH/$H_2O$ 7/3).

[α-1-(Uridine-5'-diphosphoryl)]-6-amino-6-deoxy-α-D-galactose

Ammonium acetate 15 mg was added to a solution of [α-1-(Uridine-5'-diphosphoryl)]-6-carboxaldehyde-α-D-galactopyranoside (10 mg) in sodium phosphate buffer (pH 6.0). A solution of (25 μL) 1M $NaBH_3CN$ was then added and the mixture was stirred for 24 hr. The solution was concentrated and the residue was chromotographed (sephadex $G_{10}$) to afford 10 mg of a white solid, $R_f$=0.62 (silica, EtOH/0.1 M $NH_4Ac$).

[α-1-(Uridine-5'-diphosphoryl)]-6-deoxy-6-(methoxypolyoxyethylenepropionoyl amido, ~2 kDa)-α-D-galactopyranoside

[α-1-(Uridine-5'-diphosphoryl)]-6-amino-6-deoxy-α-D-galactopyranoside (5 mg) was dissolved in 1 mL of $H_2O$. Then methoxypolyetheneglycolpropionoyl-NHS ester (MW ~2,000, 66 mg) was added, followed by 4.6 μL triethylamine. The resulting mixture was stirred at room temperature overnight, and then purified on HPLC (C-8 silica) to afford the product, $R_t$=9.0 min.

[α-1-(Uridine-5'-diphosphoryl)]-6-deoxy-6-(methoxypolyoxyethylenecarboxamido, ~2 kDa)-α-D-galactopyranoside

[α-1-(Uridine-5'-diphosphoryl)]-6-amino-6-deoxy-α-D-galactopyranoside (10 mg) was mixed with methoxypolyethyleneglycolcarboxy-HOBT (MW 2000, 67 mg) in 1 mL of $H_2O$, followed by the addition of EDC(1-ethyl-3-(3-dimethylaminopropyl)carbodiimide hydrochloride 6.4 mg and 4.6 μL triethylamine. The resulting mixture was stirred at room temperature 24 hr. The mixture was chromatographed (C-8 silica) to afford the product.

4. Preparation of UDP-GlcNAc-PEG

This example sets forth the general procedure for making UDP-GlcNAc-PEG. On the left side of scheme 17, the protected amino sugar diphospho-nucleotide is oxidized to form an aldehyde at the 6-position of the sugar. The aldehyde is converted to the corresponding primary amine by formation and reduction of the Schiff base. The resulting adduct is contacted with the p-nitrophenol carbonate of m-PEG, which reacts with the amine, binding the m-PEG to the saccharide nucleus via an amide bond. On the right side of scheme 17 at the top, the protected amino sugar diphospho-nucleotide is treated with a chemical oxidant to form a carboxyl group at the 6-carbon of the sugar nucleus. The carboxyl group is activated and reacted with m-PEG amine, binding the m-PEG to the saccharide nucleus via an amide bond. On the right side of scheme 17 at the bottom the reactions are substantially similar to that on the top right, with the exception that the starting sugar nucleotide is contacted with an oxidizing enzyme, such as a dehydrogenase, rather than a chemical oxidant.
Scheme 17.
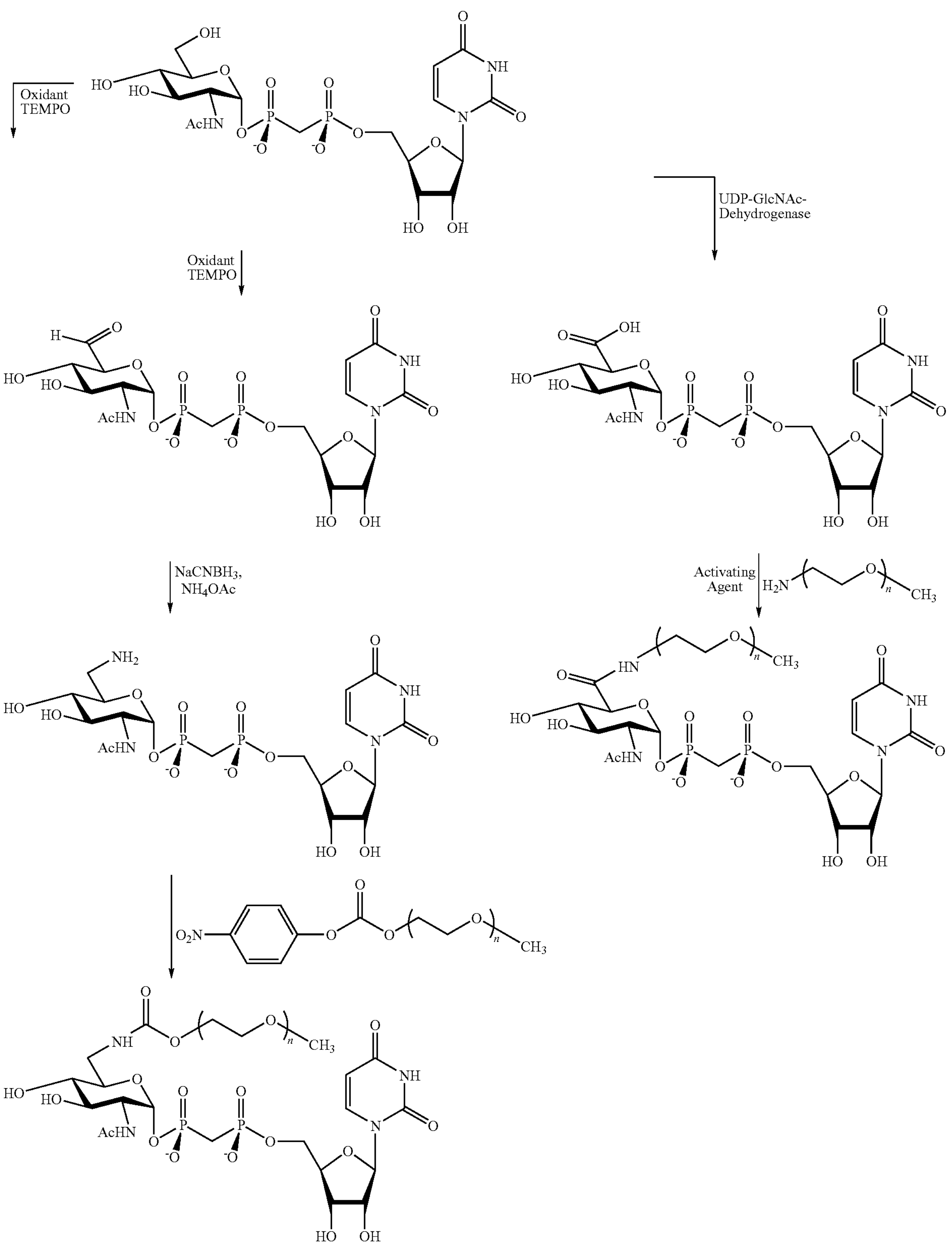

5. Preparation of UDP-GalNAc-PEG

This example (scheme 18) sets forth the general procedure for making UDP-GalNAc-PEG. The reaction set forth above originates with a sugar diphospho-nucleotide, in which R is either a hydroxyl 1 or a protected amine 2. In step a, the starting sugar is treated with a mixture of an oxidase and a catalase, converting the 6-position of the sugar into an aldehyde moiety (3 and 4). In step c, the aldehyde is converted to the corresponding amine (7 and 8) by formation and reduction of a Schiff base. In step e, the amine is optionally treated with an activated m-PEG derivative, thereby acylating the amine to produce the corresponding m-PEG amide (11 and 13). Alternatively, in step f, the amine is contacted with an activated m-PEG species, such as a m-PEG active ester, thereby forming the corresponding m-PEG amide (12 and 14). In step b, the starting material is also treated with a catalase and oxidase, completely oxidizing the hydroxymethyl moiety, forming a carboxyl group at the 6-position. In step d, the carboxyl moiety is activated and subsequently converted to a m-PEG adduct (9 and 10) by reaction with a m-PEG amine intermediate. This is shown in scheme 18.

Scheme 18.

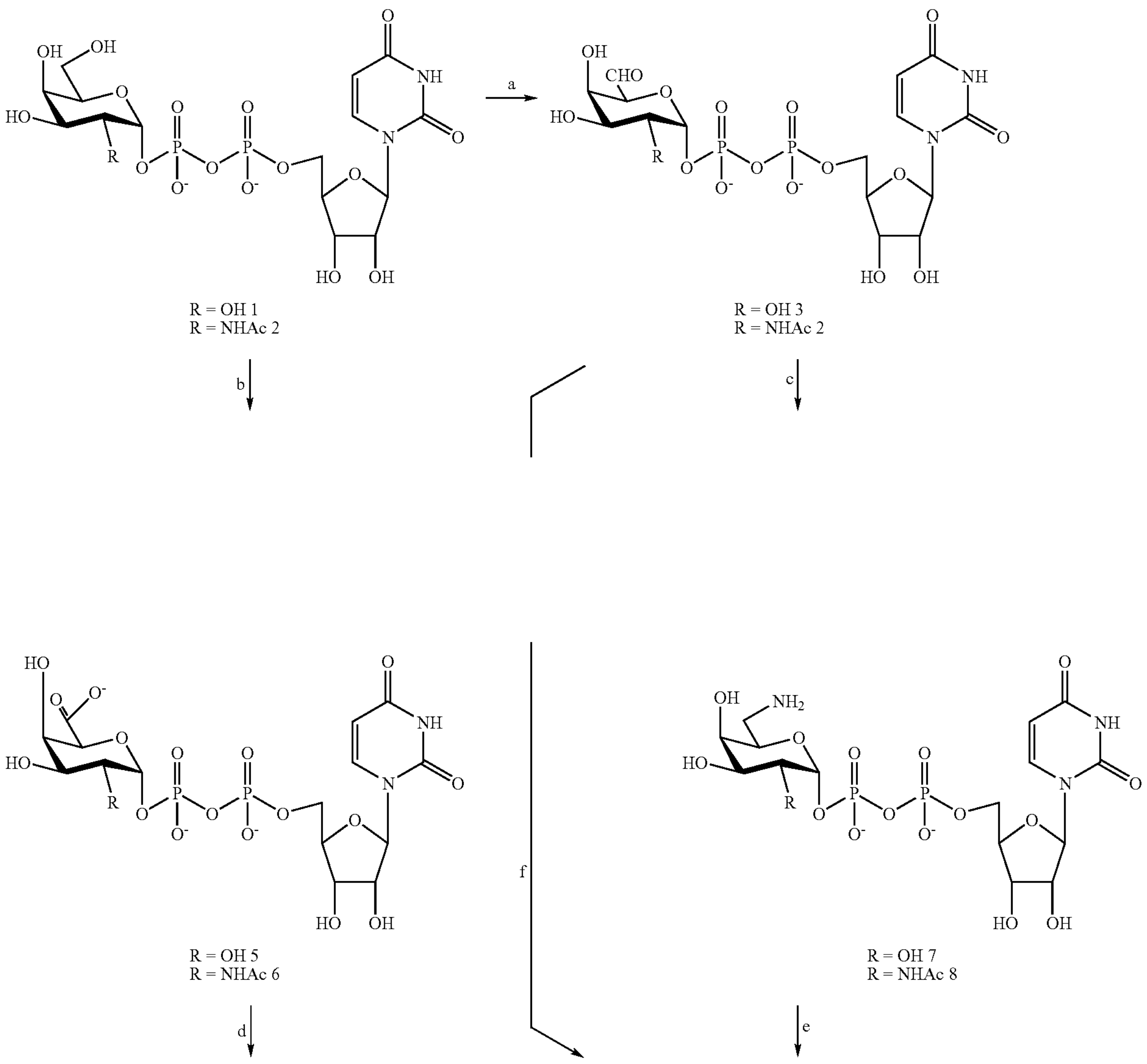

R = OH 1
R = NHAc 2

R = OH 3
R = NHAc 2

R = OH 5
R = NHAc 6

R = OH 7
R = NHAc 8

-continued

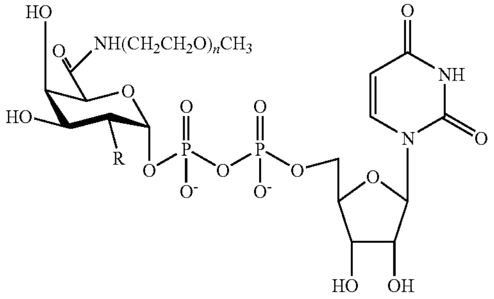

R = OH 9
R = NHAc 10

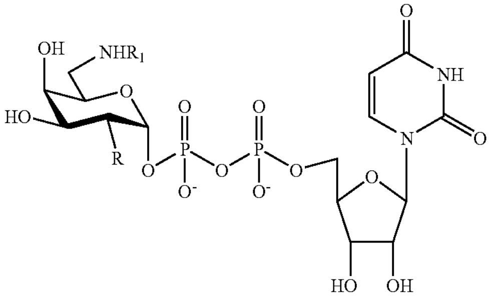

R = OH, 11; R = NHAc, 12
R = OH, 13; R = NHAc, 14
R = OH, 15; R = NHAc, 16

$R_1 = COCH_2CH_2(OCH_2CH_2)_nOCH_3$
$R_1 = NHCH_2CH_2(OCH_2CH_2)_nOCH_3$ a and b): Galactose oxidase and catalase in 25 mM sodium phosphate buffer (pH 6.0); c): $NH_4Ac$, $NaBH_3CN$ in 25 mM sodium phosphate buffer (pH 6.0); d) $CH_3(OCH_2CH_2)NH_2$, EDC, $H_2O$; e). $CH_3(OCH_2CH_2)_nNH_2$, $NaBH_3CN$, $H_2O$ for 15 and 16; f) $CH_3O(CH_2CH_2O)_nCH_2CH_2CONHS$, $H_2O$, $Et_3N$ The amino-sugar phosphate is contacted with a m-PEG N-hydroxy succinimide active ester, thereby forming the corresponding sugar-PEG-amide. The amide is contacted with UMP-morpholidate to form the corresponding active sugar diphospho-nucleotide.

Scheme 19.

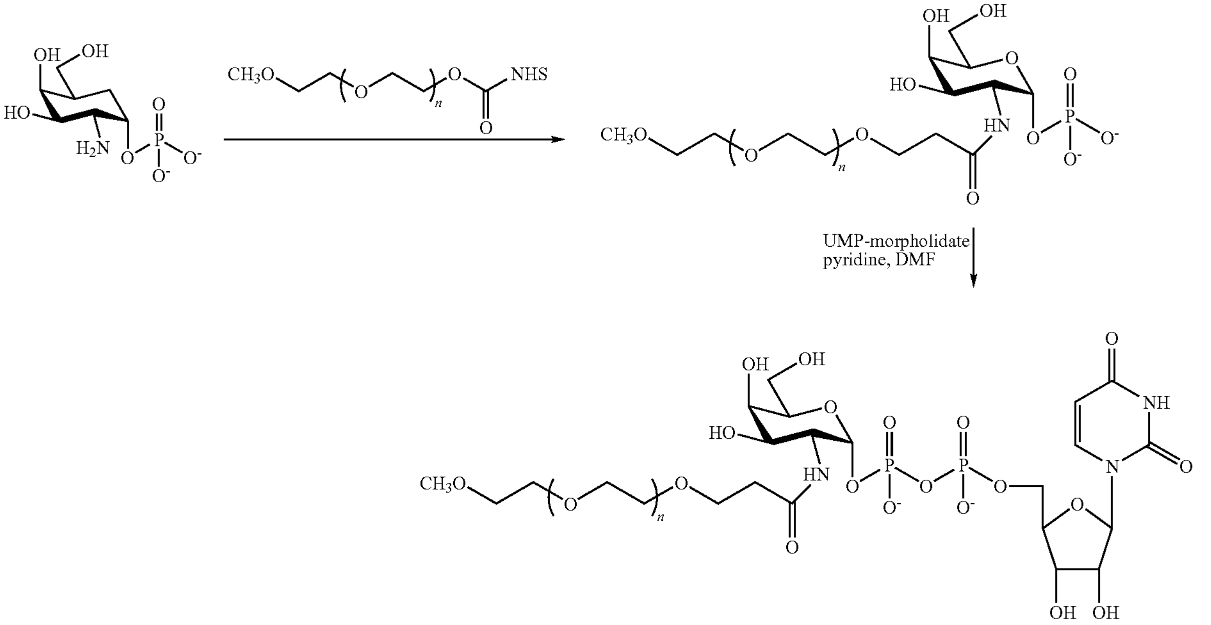

6. Synthesis of CMP-SA-Levulinate

This example sets forth the procedure for the synthesis of CMP-SA-levulinate.

Preparation of 2-levulinamido-2-deoxy-D-mannopyranose

Isobutylchloroformate (100 μL, 0.77 mmol) was added dropwise to a solution of levulinic acid (86 μL, 0.84 mmol), anhydrous THF (3 mL) and triethylamine (127 μL, 0.91 mmol). This solution was stirred for 3 hours at room temperature and was then added dropwise to a solution containing D-mannosamine hydrochloride (151 mg, 0.7 mmol), triethylamine (127 μL, 0.91 mmol), THF (2 mL) and water (2 mL). The reaction mixture was stirred 15 hours and then concentrated to dryness by rotary evaporation. Chromatography (silica, step gradient of 5-15% $MeOH/CH_2Cl_2$) was used to isolate the product yielding 0.156 g (73% yield) of a white solid: $R_f$=0.41 (silica, $CHCl_3$/MeOH/water 6/4/1); $^1H$ NMR ($D_2O$, 500 MHz) δ 2.23 (s, 3H), 2.24 (s, 3H), 2.57 (td, J=6.54, 3.68, 2H) 2.63 (t, J=6.71, 2H), 2.86-2.90 (m, 4H), 3.42 (m, 1H), 3.53 (t, J=9.76, 1H), 3.64 (t, J=9.43, 1H), 3.80-3.91 (m, 4H), 4.04 (dd, J=9.79, 4.71, 1H), 4.31 (dd, J=4.63, 1.14, 1H), 4.45 (dd, J=4.16, 1.13, 1H), 5.02 (d, J=1.29, 1H), 5.11 (s, J=1.30, 1H), MS (ES); calculated for $C_{11}H_{19}NO_7$, 277.27; found [M+1] 277.9.

Preparation of 5-levulinamido-3,5-dideoxy-D-glycero-D-galacto-2-nonulopyranosuronate Sodium pyruvate (0.616 g, 5.6 mmol) and N-acetyl-neuraminic acid aldolase (50 U) was added to a solution of 2-levulinamido-2-deoxy-D-mannopyranose (0.156 g, 0.56 mmol) in 0.1 M HEPES (pH 7.5). The reaction mixture was heated to 37° C. for 20 hours and after freezing. The reaction mixture was then filtered through C18 silica, frozen and freeze-dried. The crude solid was purified using flash chromatography (silica, first using 10-40% $MeOH/CH_2Cl_2$ and then $CH_2Cl_2/MeOH/H_2O$ 6/4/0.5). Appropriate fractions were combined and concentrated yielding 45 mg (80% yield) of a white solid: $R_f$=0.15 (silica, $CHCl_3$/MeOH/water 6/4/1); $^1H$ NMR ($D_2O$, 500 MHz) δ 1.82 (t, J=11.9, 1H), 2.21 (dd, J=13.76, 4.84, 1H), 2.23 (s, 3H), 2.57 (app q, J=6.6, 2H), 2.86-2.95 (m, 2H), 3.15-3.18 (m, 1H), 3.28-3.61 (complex, 1H), 3.60 (dd, J=11.91, 6.66, 1H), 3.75 (td, J=6.65, 2.62, 1H), 3.84 (dd, J=11.89, 2.65, 1H), 3.88-4.01 (complex, 2H), 4.04 (td, J=11.18, 4.67, 1H), MS (ES); calculated for $C_{14}H_{23}NO_{10}$, 365.33; found ($[M-1]^-$), 363.97.

Preparation of cytidine-5'-monophosphoryl-(5-levulinamido-3,5-dideoxy-β-D-glycero-D-galacto-2-nonulopyranosuronate)

5-Levulinamido-3,5-dideoxy-D-glycero-D-galacto-2-nonulopyranosuronate (50 mg, 137 μmol) was dissolved in 2 mL of 100 mM HEPES pH 7.5 buffer and 1 M $MnCl_2$ (300 μL, 300 μmol) was added. CTP-$2Na^+$ (79 mg, 1.5 μmol) was dissolved in 5 mL HEPES buffer and was added to the sugar. The sialyltransferase/CMP-neuraminic acid synthetase fusion enzyme (11 U) was added and the reaction mixture stirred at room temperature for 45 hours. The reaction mixture was filtered through a 10,000 MWCO filter and the filtrate, which contained the product of the reaction, was used directly without further purification: $R_f$=0.35 (silica, IPA/water/$NH_4OH$ 7/2/1).

B. Glycoconjugation and GlycoPEGylation of Peptides α-Protease Inhibitor (α-Antitrypsin)

7. Sialylation of Recombinant Glycoproteins Antithrombin III, Fetuin and α1-Antitrypsin This example sets forth the preparation of sialylated forms of several recombinant peptides.

Sialylation of Recombinant Glycoproteins Using ST3Gal III. Several glycoproteins were examined for their ability to be sialylated by recombinant rat ST3Gal III. For each of these glycoproteins, sialylation will be a valuable process step in the development of the respective glycoproteins as commercial products.

Reaction Conditions. Reaction conditions were as summarized in Table 11. The sialyltransferase reactions were carried out for 24 hour at a temperature between room temperature and 37°. The extent of sialylation was established by determining the amount of $^{14}C$-NeuAc incorporated into glycoprotein-linked oligosaccharides. See Table 11 for the reaction conditions for each protein.

TABLE 11

Reaction conditions.

| Protein | Source | Protein Total (mg) | Protein Conc. (mg/ml) | ST (mU/mL) | ST/Protein (mU/mg) | CMP-NeuAc of "cycle"[1] |
|---|---|---|---|---|---|---|
| ATIII | Genzyme Transgenics | 8.6 | 4.3 | 210 | 48 | cycle |
| ATIII | Genzyme Transgenics | 860 | 403 | 53 | 12 | cycle |
| Asialo-fetuin | Sigma | 0.4 | 105 | 20 | 13 | 10 mM |
| asilao-AAAT | PPL | 0.4 | 0.5 | 20 | 20 | 20 mM |

[1]"Cycle" refers to generation of CMP-NeuAc "in situ" enzymatically using standard conditions as described in specification (20 mM NeuAc and 2 mM CMP). The buffer was 0.1 M HEPES, pH 7.5.

The results presented in Table 12 demonstrate that a remarkable extent of sialylation was achieved in every case, despite low levels of enzyme used. Essentially, complete sialylation was obtained, based on the estimate of available terminal galactose. Table 12 shows the results of the sialylation reactions. The amount of enzyme used per mg of protein (mU/mg) as a basis of comparison for the various studies. In several of the examples shown, only 7-13 mU ST3Gal III per mg of protein was required to give essentially complete sialylation after 24 hours.

TABLE 12

Analytical results

| Protein | Source | Terminal Gal[1] mol/mol | NeuAc Incorp.[2] mol/mol | % Rxn[3] | Other characterization |
|---|---|---|---|---|---|
| ATIII[4] | Genzyme Transgenics | 102 | 104 | 117 | None |
| ATIII[4] | Genzyme Transgenics | 102 | 1.3 | 108 | SDS-gels: protein purity FACs: carbohydrate glycoforms |
| Asialo-fetuin | Sigma | 802 | 905 | 116 | None |
| asilao-AAAT[5] | PPL | 7 | 7.0 | 100 | SDS-gels: protein purity |

[1]Terminal (exposed) Gal content on N-linked oligosaccharides determined by supplier, or from literatures values (fetuin, asialo-AAAT).
[2]NeuAc incorporated determined by incorporation of 14C-NeuAc after separation from free radiolabeled precursors by gel filtration.
[3]The % Rxn refers to % completion of the reaction based on the terminal Gal content as a theoretical maximum.
[4]Antithrombin III.
[5]α1 Antitrypsin.

These results are in marked contrast to those reported in detailed studies with bovine ST6Gal I where less than 50 mU/mg protein gave less than 50% sialylation, and 1070 mU/mg protein gave approximately 85-90% sialylation in 24 hours. Paulson et al. (1977) J. Biol. Chem. 252: 2363-2371; Paulson et al. (1978) J. Biol. Chem. 253: 5617-5624. A study of rat α2,3 and α2,6 sialyltransferases by another group revealed that complete sialylation of asialo-AGP required enzyme concentrations of 150-250 mU/mg protein (Weinstein et al. (1982) J. Biol. Chem. 257: 13845-13853). These earlier studies taken together suggested that the ST6Gal I sialyltransferase requires greater than 50 mU/mg and up to 150 mU/mg to achieve complete sialylation.

This Example demonstrates that sialylation of recombinant glycoproteins using the ST3 Gal III sialyltransferase required much less enzyme than expected. For a one kilogram scale reaction, approximately 7,000 units of the ST3Gal III sialyltransferase would be needed, instead of 100,000-150,000 units that earlier studies indicated. Purification of these enzymes from natural sources is prohibitive, with yields of only 1-10 units for a large scale preparation after 1-2 months work. Assuming that both the ST6Gal I and ST3Gal III sialyltransferases are produced as recombinant sialyltransferases, with equal levels of expression of the two enzymes being achieved, a fermentation scale 14-21 times greater (or more) would be required for the ST6Gal I sialyltransferase relative to the ST3Gal III sialyltransferase. For the ST6Gal I sialyltransferase, expression levels of 0.3 U/l in yeast has been reported (Borsig et al. (1995) Biochem. Biophys. Res. Commun. 210: 14-20). Expression levels of 1000 U/liter of the ST3 Gal III sialyltransferase have been achieved in *Aspergillus niger*. At current levels of expression 300-450,000 liters of yeast fermentation would be required to produce sufficient enzyme for sialylation of 1 kg of glycoprotein using the ST6Gal I sialyltransferase. In contrast, less than 10 liter fermentation of *Aspergillus niger* would be required for sialylation of 1 kg of glycoprotein using the ST3Gal III sialyltransferase. Thus, the fermentation capacity required to produce the ST3Gal III sialyltransferase for a large scale sialylation reaction would be 10-100 fold less than that required for producing the ST6Gal I; the cost of producing the sialyltransferase would be reduced proportionately.

Cri-IgG Antibody

8. Glyco-Remodeling of Cri-IgG1 Antibodies

This example sets forth the procedures for in vitro remodeling of Cri-IgG1 antibodies. N-glycosylation at one conserved site at Asn 297 in the Fc domain of a monoclonal antibody can modulate its pharmacokinetic behavior and effector functions (Dwek et al., 1995, J. Anat. 187:279-292; Boyd et al., 1995, Mol. Immunol. 32:1311-1318; Lund et al., 1995, FASEB J. 1995, 9:115-119; Lund et al., 1996, J. Immunol. 157:4963-4969; Wright & Morrison, 1998, J. Immunol. 160:3393-3402; Flynn & Byrd, 2000, Curr. Opin. Oncol. 12:574-581). During cell culture fermentation or in certain pathological conditions, significant heterogeneity arises in the glycosylation pattern at this site. The resulting different patterns of glycosylation on the Fc domain are characterized by complex biantennary structures with zero, one, and two terminal galactose residues (G0, G1, and G2, respectively, see Table 13). The observed glycoform variations, such as the variation in terminal galactosylation, truncated N-glycoforms and bisecting modification, have been shown to influence the antibody's therapeutic properties, especially its ability to mediate targeted cell killing through complement binding and activation (Boyd et al., 1995, supra; Wright & Morrison, 1998, supra, Mimura et al., 2000, Molec. Immunol. 37:697-706; Davies et al., 2001, Biotechnol. Bioeng. 74:288-294).

In order to obtain different glycoforms of Cri-IgG1 antibodies and test their Fc effector functions, Cri-IgG1 antibodies were trimmed back stepwise using exoglycosidases to generate glycoforms lacking sialic acid (G2, G1), glycoforms lacking sialic acid and galactose (G0), and glycoforms lacking sialic acid, galactose and N-acetyl glucosamine (M3N2F), as illustrated in Table 13. These molecules were subsequently modified using different glycosyltransferases and appropriate sugars. Modification conditions were developed that resulted in the conversion of the original antibody glycan structures into different glycoforms: M3N2, GnT-I-M3N2 (the M3M2 glycoform with a GlcNAc moiety added using GnT-I), G0, Bisecting-G0 (the GO moiety with a bisecting GlcNAc added with GnT-III), galactosylated bisecting-G0 (the bisecting-G0 glycoform with terminal galactose moieties added), G2, mono-sialylated S1(α2,6)-G2 (the G2 glycoform with one terminal sialic acid moiety added using α2,6-sialyltransferase), S1(α2,3)-G2 (the G2 glycoform with one terminal sialic acid moiety added using α2,3-sialyltransferase) and disialylated S2(α2,3)-G2 (the G2 glycoform). After every glycoremodeling step, the glycan structures were enzymatically released from the antibody protein and were analyzed by various methods, including separation by capillary electrophoresis, 2-AA HPLC profiling and MALDI-TOF mass spectrometry.

TABLE 13

Abbreviations for glycoform structures.

| Abbreviation | Glycan Structure(s) |
| --- | --- |
| M3N2(F) | 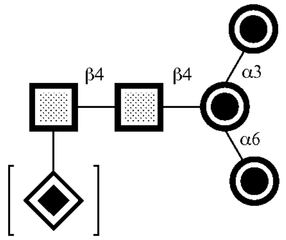  |
| G0 | 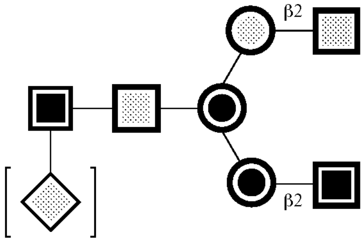  |
| G1 | 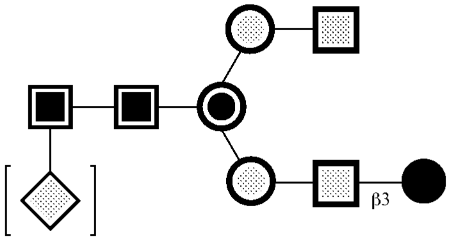  OR 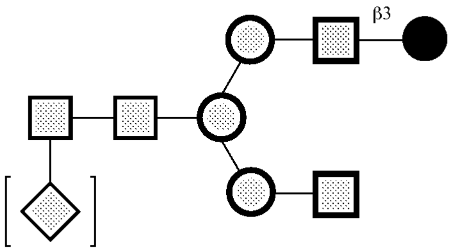  |

TABLE 13-continued

| Abbreviations for glycoform structures. | |
|---|---|
| Abbreviation | Glycan Structure(s) |
| G2 | 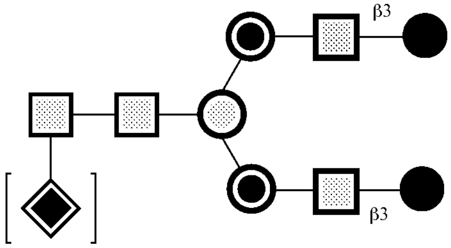 |

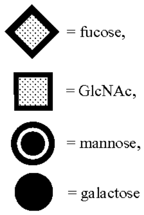

The materials are methods used in these experiments are now described. *The Cri-IgG1 Monoclonal Antibody*. The Cri-IgG1 antibody was obtained from R. Jefferies, MRC Center for Immune Regulation, The Medical School, University of Birmingham, UK. The antibody is a non-recombinant antibody, and is isolated from a human myeloma. The antibody was prepared using three methods. In the first method, referred to as "DEAE," the antibody was isolated under relatively mild conditions using a DEAE ion exchange column. In the second method, referred to as "SPA," the antibody was purified on a protein A column (*Staphylococcus aureus* protein A) with a low pH elution step. In the third method, referred to as "Fc," the antibody was treated with a protease so that only the Fc portion of the antibody remained and the antigen binding domains were removed. These methods for antibody purification are well known to those of skill in the art and are not repeated in detail here.

Affinity purification of remodeled antibodies. Antibody, modified either by exoglycosidase or glycosyltransferase, was affinity purified on a ProA-sepharose 4-fast flow column (Amersham Bioscience, Arlington Heights, Ill.), eluted with 0.1 M glycine-HCl buffer, pH 2.7, and immediately neutralized with 1 M Tris, pH 9.5. The eluates were buffer-exchanged using a NAP-10 column (Amersham Bioscience, Arlington Heights, Ill.) to an appropriate buffer for the next step of glycosylation, such as 100 mM MES, pH 6.5 or 50 mM Tris-HCl, pH 7.2. The remodeled final products were dialyzed extensively against PBS at 4° C. in Tube-O-Dialyzers™ (Chemicon International, Temecula, Calif.) with a MWCO of 8 kDa.

In vitro glucosidase treatment of Cri-antibodies. Antibody was buffer-exchanged into 50 mM Na phosphate/Citrate, pH 6.0 using NAP-10 column (Amersham Bioscience, Arlington Heights, Ill.). In vitro trimming back of sugar moieties was carried out stepwise, by contacting the antibody (5 mg/mL) with 20 mU/mg protein neuraminidase at 37° C. overnight (to remove terminal sialic acid moieties), 20 mU/mg protein β-galactosidase at 37° C., overnight (to remove terminal galactose moieties to result in the G0 glycoform), and/or 2 U/mg β-N-acetylhexosaminidase (from Jack Bean, Seikagaku, Tokyo, Japan) at 37° C., overnight (to remove terminal N-acetyl glucosamine to result in the M3N2 glycoform). The samples were affinity purified as described above.

In vitro glycosylation of Cri-antibodies. In vitro GnT1 modification was performed using 1 mg/ml of the M3N2 glycoform antibody as the substrate, and 25 mU/mg of recombinant human β1,2-mannosyl-UDP-N-acetylglucosaminosyltransferase in a buffer of 100 mM MES, pH 6.5, 5 mM $MnCl_2$, 5 mM UDP-GlcNAc, and 0.02% $NaN_3$ at 32° C. for 24 hr. An aliquot was removed for glycan analysis, and the resulting products were affinity purified as described above.

In vitro modification of the bisecting-glycoform was carried out using 1 mg/ml of the M3N2 glycoform antibody as the substrate and 25 mU/mg of β1,2-recombinant human mannosyl-UDP-N-acetylglucosaminosyltransferase I, 25 mU/mg of β1,2-recombinant human mannosyl-UDP-N-acetylglucosaminosyltransferase II and 3.5 mU/mg of β1,4-recombinant mouse mannosyl-UDP-N-acetylglucosaminosyltransferase III in a buffer of 100 mM MES pH 6.5, 10 mM $MnCl_2$, 5 mM UDP-GlcNAc, and 0.02% $NaN_3$ at 32° C. for 24 hrs. An aliquot was removed for glycan analysis, and the remaining product was affinity purified as described above.

In vitro galactosylation was performed using G0 glycoform antibody or bisecting glycoform antibody by contacting the antibody with 0.6 U/mg recombinant bovine milk β1,4 galactosyltransferase in a buffer of 50 mM Tris-HCl pH 7.4, 150 mM NaCl, 5 mM UDP-galactose, 5 mM $MnCl_2$, at 32° C. for 24 hrs. An aliquot was removed for glycan analysis, and the remaining products were affinity purified as described above.

In vitro sialylation was carried out using the G2 glycoform antibody (1 mg/mL) by contacting it with 0.1 U/mg ST3Gal3 or 0.1 U/mg ST6Gal1, 5 mM CMP-sialic acid, at 32° C. for 24 hr in a buffer of 50 mM Tris pH 7.4, 150 mM NaCl, and 3 mM CMP-SA. An aliquot was removed for glycan analysis, and the remaining products were affinity purified as described above.

Glycan Analysis:

Capillary Electrophoresis with Laser Induced Fluorescence Detection. Buffer components and nucleotide sugars were removed from an aliquot of the glycoremodeled antibody by dilution and concentration in a Microcon™ YM-30 microconcentrator (Millipore, Bedford, Mass.). N-linked oligosaccharides were released from the protein by contacting it with PNGase F (Prozyme, San Leandro, Calif.) using the methodology provided by the manufacturer. In brief, the sample was denatured in the buffer of 50 mM sodium phosphate pH 7.5, 0.1% SDS, and 50 mM β-mercaptoethanol for 10 min at 100° C. TX100 was then added to 0.75% (v/v) as well as IOU PNGaseF/200 μg protein. After 3 hours incubation at 37° C., the protein was ethanol precipitated and the supernatant was dried down. The released free oligosaccharides were then labeled with 8-aminopyrene-1,3,6-trisulfonic acid and analyzed by capillary electrophoresis with a carbohydrate labeling and analysis kit from Beckman-Coulter, Inc. (Fullerton, Calif.), as indicated by the manufacturer (see also, Ma and Nashabeh, 1999, Anal. Chem. 71:5185-5192).

Capillary electrophoresis (CE) was carried out in an eCAP™ N-CHO coated Capillary (50 μm I.D., length to detector 40 cm; Beckman-Coulter, Inc., Fullerton, Calif.), using a P/ACE™ MDQ Glycoprotein System (Beckman-Coulter, Inc. Fullerton, Calif.) with Laser Induced Fluorescence Detector (Beckman-Coulter, Inc. Fullerton, Calif.). Samples were introduced into the cartridge by 20 psi pressure for 10 sec. and separated under 25 kV with reverse polarity for 20 min. Cartridge temperature was kept at 20° C. The electropherogram was generated by laser-induced fluorescence detection at an excitation wavelength of 488 nm and an emission wavelength of 520 nm.

Carbohydrate standards (Calbiochem®, EMD Biosciences, Inc., San Diego, Calif.), including M3N2 (N-linked trimannosyl core without core fucose), G0 (N-linked oligosaccharide, asialo, agalacto, biantennary with core fucose), G2 (N-linked oligosaccharide, asialo, biantennary with core fucose), and G2 without fucose, S1-G2 (mono-sialylated, galactosylated biantennary oligosaccharide without core fucose) and S2-G2 (di-sialylated, galactosylated biantennary oligosaccharide without core fucose), (from Glyko, see, ProZyme, San Leandro, Calif.), M3N2F (N-linked trimannosyl core with core fucose) and NGA2F (N-linked oligosaccharide asialo, agalacto, biantennary with core fucose and with bisecting GlcNAc) were labeled with 1-aminopyrene-3,6,8-trisulfonate (APTS, Beckman-Coulter, Inc. Fullerton, Calif.) and used to identify the distribution of glycans released from the antibody.

2-AA HPLC. PNGaseF released glycans were labeled with 2-AA (2-anthranilic acid) according to the method described by Anumula and Dhume with slight modifications (1998, Glycobiology 8:685-694). Reductively-aminated N-glycans were analyzed using a Shodex Asahipak NH2P-50 4D amino column (4.6 mm×150 mm) (Showa Denko K.K., Tokyo, Japan). The two solvents used for the separation are A) 2% acetic acid and 1% tetrahydrofuran in acetonitrile and B) 5% acetic acid, 3% triethylamine and 1% tetrahydrofuran in water.

To separate neutral 2AA-labeled glycans, the column was eluted isocratically with 70% A for 5 minutes, followed by a linear gradient over a period of 60 minutes going from 70% to 50% B, followed by a steep gradient over a period of 5 minutes going from 50% to 5% B and a final isocratic elution with 5% B for 10 minutes. Eluted peaks were detected using fluorescence detection with an excitation at 230 nm and detection wavelength at 420 nm. In this gradient condition, the G0 glycoform will elute at about 30.5 minutes, the G1 glycoform at about 34.0 minutes and the G2 glycoform at about 37.0 minutes. Under these conditions, the presence of fucose does not change the elution time.

To separate anionic 2AA-labeled glycans, the column was eluted isocratically with 70% A for 2.5 minutes, followed by a linear gradient over a period of 97.5 min going from 70% to 5% A and a final isocratic elution with 5% A for 15 minutes. Eluted peaks were detected using fluorescence detection with excitation at 230 nm and detection at 420 nm. In this gradient, neutral glycans are expected to elute between 18.00-29.00 minutes, glycans with one charge elute between 30.00-40.00 minutes, glycans with two charges elute between 43.00-52.00 minutes, glycans with three charges elute between 54.00-63.00 minutes, and glycans with four charges elute between 65.00-74.00 minutes.

MALDI analysis of reductively-aminated N-glycans. A small aliquot of the PNGase-released N-glycans that were labeled with 2-anthranilic acid (2AA) were then dialyzed for 45 minutes on a MF-Millipore membrane filter (0.025 μm pore, 47 mm dia.), which was floating on water. The dialyzed aliquot was dried in a Speedvac™ (ThermoSavant, Holbrook, N.Y.), redissolved in a small amount of water, and mixed with a solution of 2,5-dihydroxybenzoic acid (10 g/L) dissolved in water/acetonitrile (50:50).

The mixture was dried onto a MALDI target and analyzed using an Applied Biosystems DE-Pro mass spectrometer (Applied Biosystems, Inc., Foster City, Calif.) operated in the linear/negative-ion mode. Oligosaccharide structures were assigned based on the observed mass-to-charge ratio and literature precedence. No attempt was made to fully characterize isobaric structures.

SDS-PAGE. To determine the stability of the glycoremodeled antibody, all the samples were analyzed by SDS-PAGE. The final products of the samples were run under non-reducing conditions using 8-16% Tris-glycine gel (Invitrogen, Carlsbad, Calif.). Bovine serum albumin was run under reducing condition as quantitative standards. The gel was stained with GelCode Blue Stain Reagent (Pierce Chemical Co., Rockford, Ill.) for visualization.

The results of the experiments are now described.

Figure 97A:
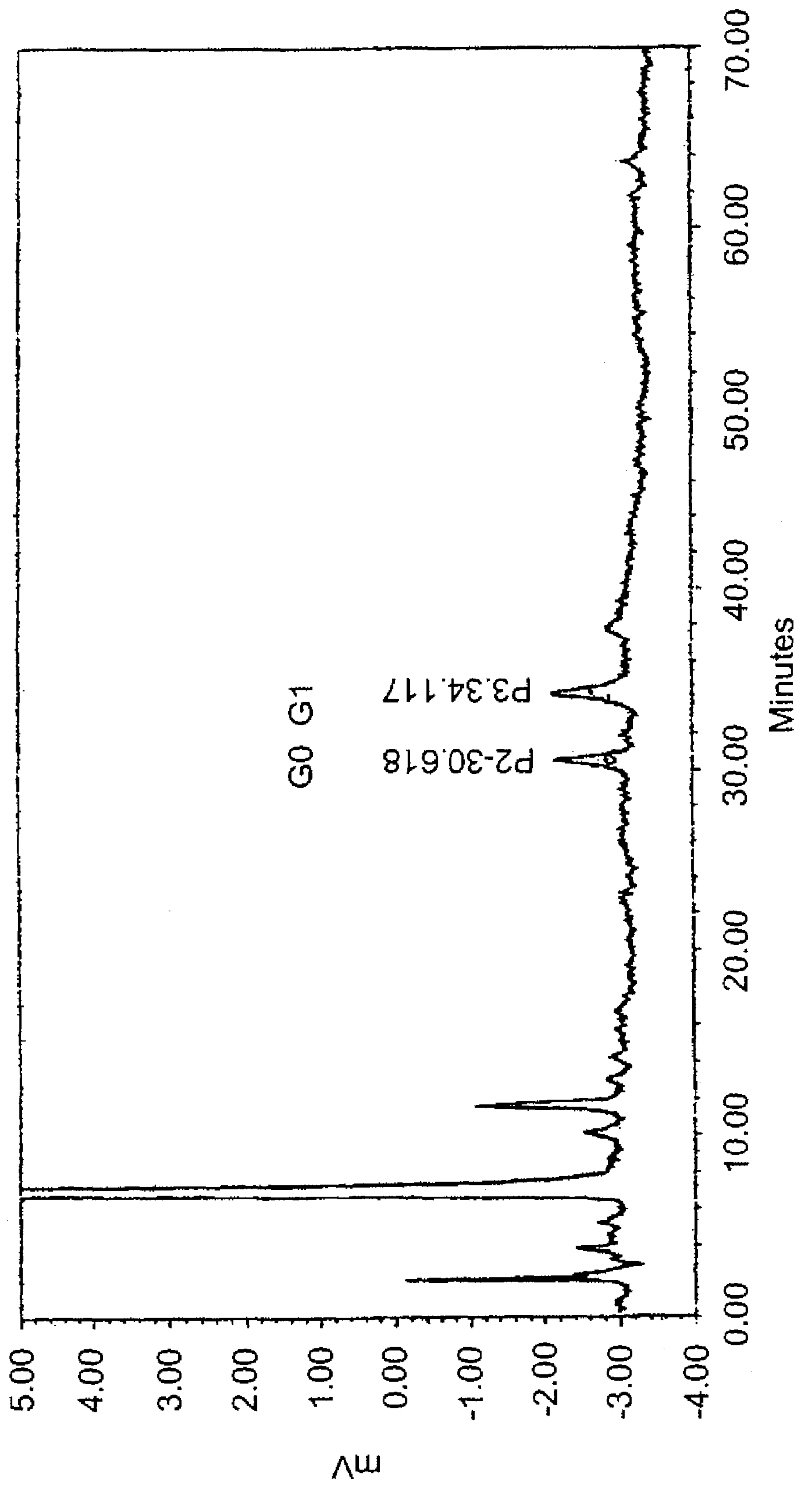
FIGS. 97A to 97C, are graphs depicting 2-AA HPLC analysis of glycans released by PNGaseF from myeloma-expressed Cri-IgG1 antibody. The structure of the glycans is determined by retention time: the G0 glycoform elutes at 30 min., the G1 glycoform elutes at ~33 min., the G2 glycoform elutes at about approximately 37 min. and the S1-G1 glycoform elutes at ~70 min.
Figure 97B:
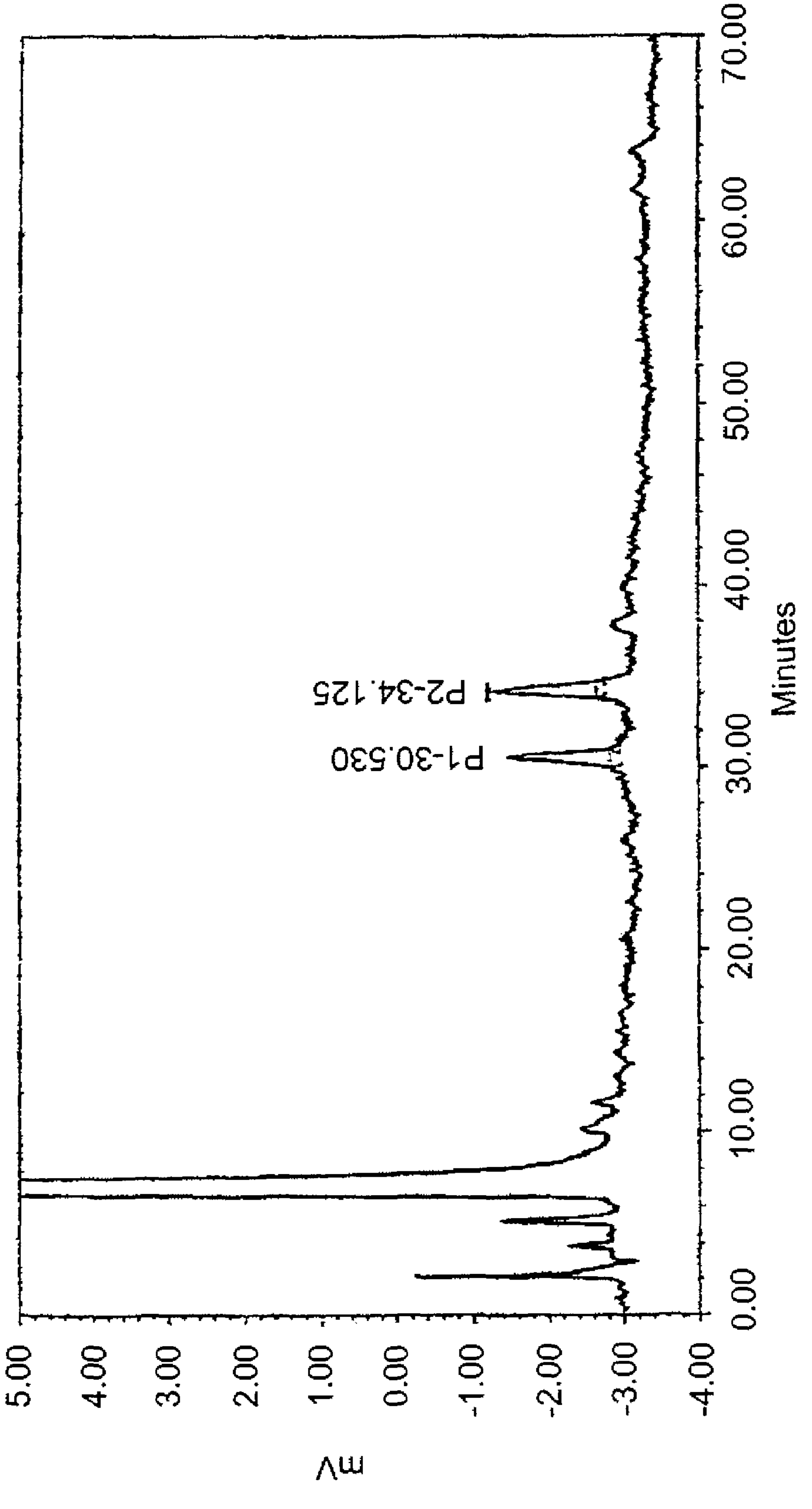
Figure 97C:
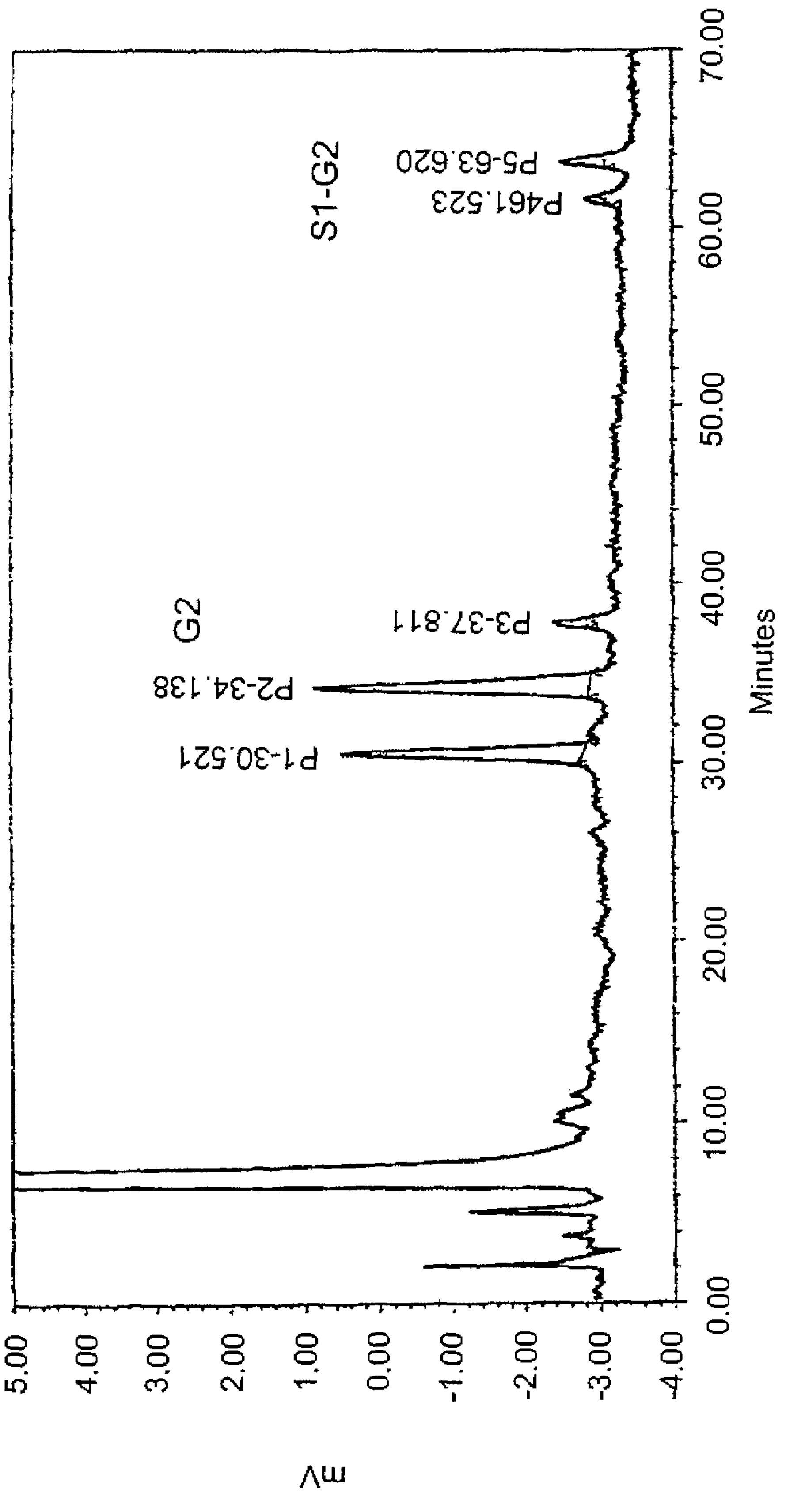
Figure 98A:
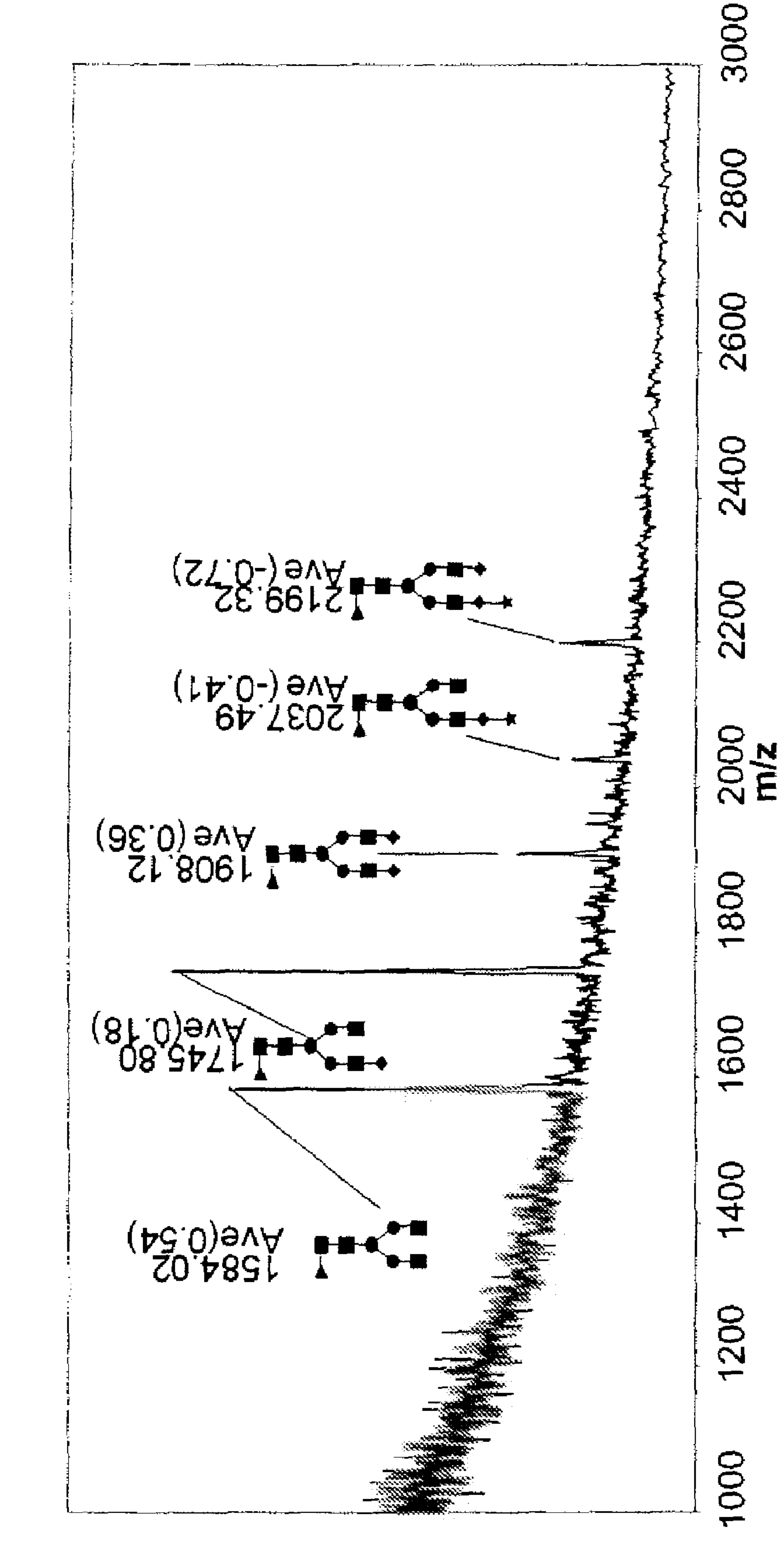
FIGS. 98A to 98C, are graphs depicting the MALDI analysis of glycans released by PNGaseF from myeloma-expressed Cri-IgG1 antibody. The glycans were derivatized with 2-AA and then analyzed by MALDI.
Figure 98B:
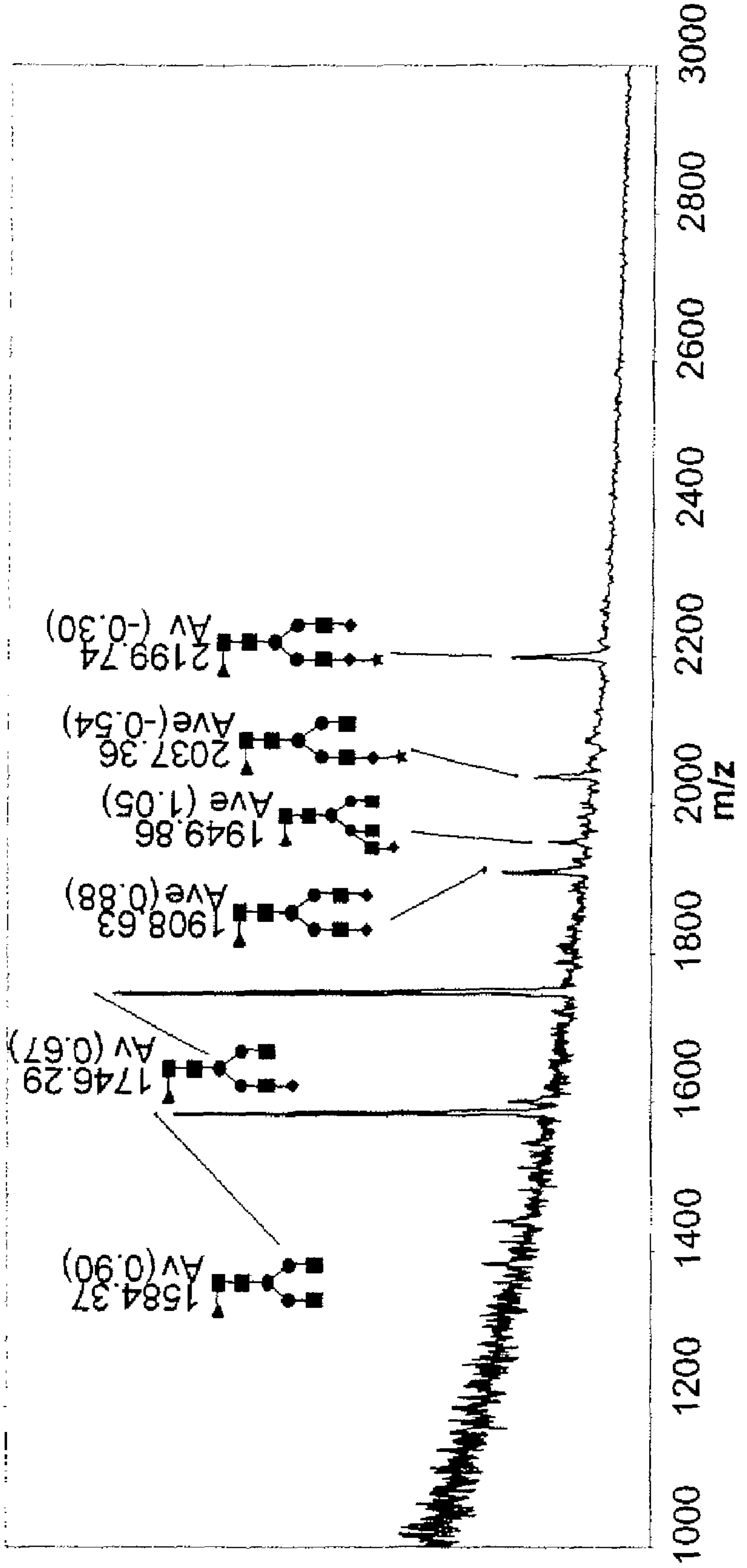
Figure 98C:
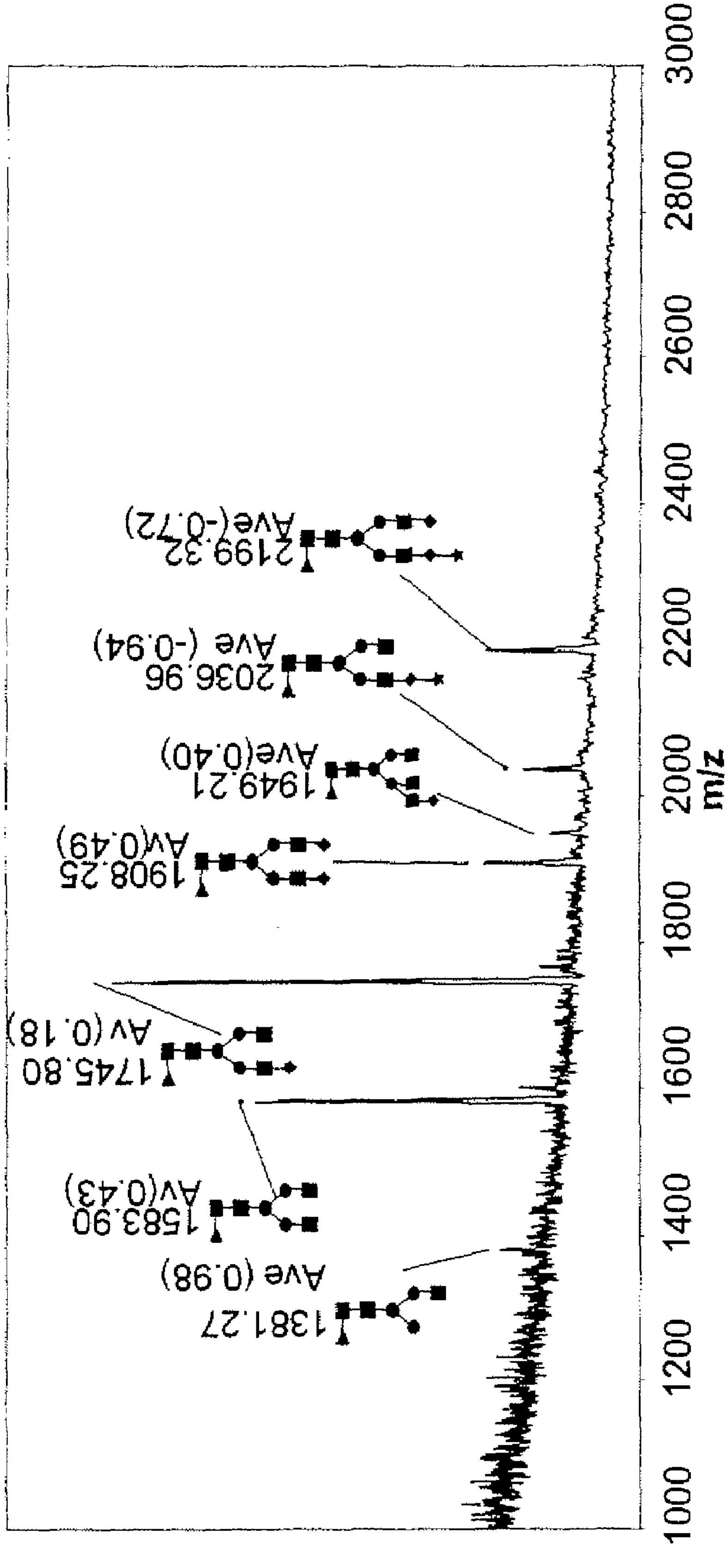

Native glycoforms of Cri expressed in human myeloma cells. Cri-IgG1 antibody purified from the serum of a patient having multiple myeloma contains variable glycoforms. FIGS. 97A-97C shows the HPLC profiles of glycans enzymatically released from Cri-IgG 1 antibody. FIGS. 98A-98C shows the MALDI profiles of glycans enzymatically released from Cri-IgG1 antibody expressed in human myeloma cells. The major forms are under-galactosylated G0, G1, while G2 and sialylated structures are relatively minor (Table 14 and FIG. 97C). To test the impact of modified glycans on the therapeutic properties of the monoclonal antibody, Cri-IgG1 antibody was modified by performing in vitro exoglycosidases trimming and in vitro glycosylation remodeling to generate different glycoforms of this antibody.

TABLE 14

Relative amount of different glycoforms of human myeloma cell-expressed Cri-IgG1 separated by HPLC was calculated from the areas of individual peaks.

| Criantibodies | S1G2 | G2 | G1 | G0 |
|---|---|---|---|---|
| DEAE | | | 45.04 | 54.96 |
| SPA | 6 | 3.17 | 48.25 | 51.75 |
| Fc | | | 51.41 | 38.83 |

Initially, optimization of each step in exoglycosidases trimming and glycosylation was performed at small scale (100 μg of each).

Trimannosyl core glycoform of Cri-IgG1 Antibody (M3N2). M3N2 was created by stepwise treatment of glycosidases, including neuraminidase, β1,4-galactosidase and β1-2, 3, 4, 6 N-acetylhexosaminidase. To assess the removal of terminal galactose and GlcNAc on the glycoremodeled Cri-IgG1 antibody samples, a quantitative capillary electrophoresis (CE) method was used. The glycans were enzymatically released from the glycoremodeled antibody with PNGase F and were derivatized with 8-aminopyrene-1,3,6-trisulfonic acid (APTS) at the reducing terminus. The resulting products were analyzed by CE with on-column laser-induced fluorescence detection (LIF) (Ma & Nashabeh, 1999, supra). Since the separation of the glycans is based on the differences in hydrodynamic size, the APTS labeled glycans migrate in order of increasing size (M3N2<M3N2F<G0<G1<G2).

Figure 99A:
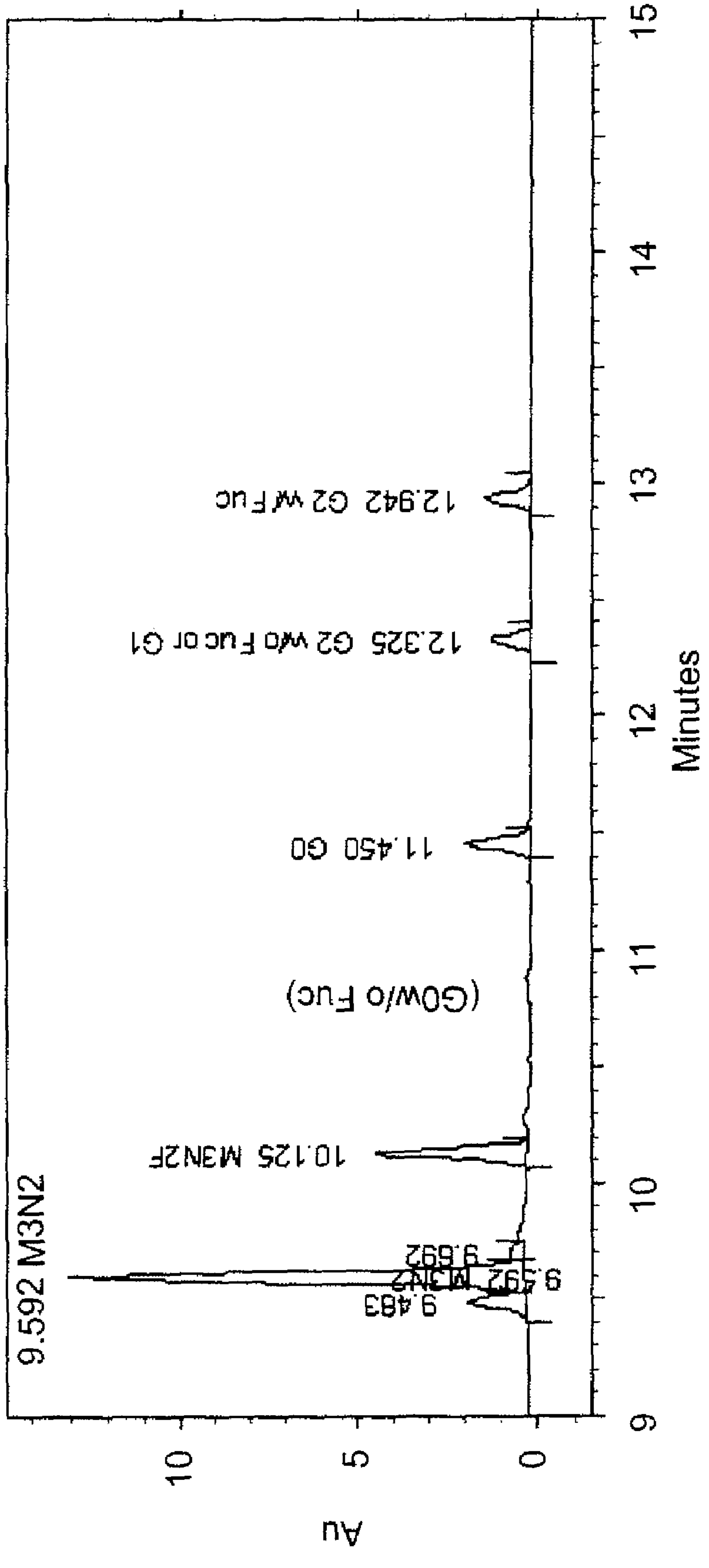
FIGS. 99A to 99D, are graphs depicting the capillary electrophoresis analysis of glycans released from Cri-IgG1 antibodies that have been glycoremodeled to contain M3N2 glycoforms. A graph depicting the capillary electrophoresis analysis of glycan standards derivatized with APTS is shown in FIG. 99A.
Figure 99B:
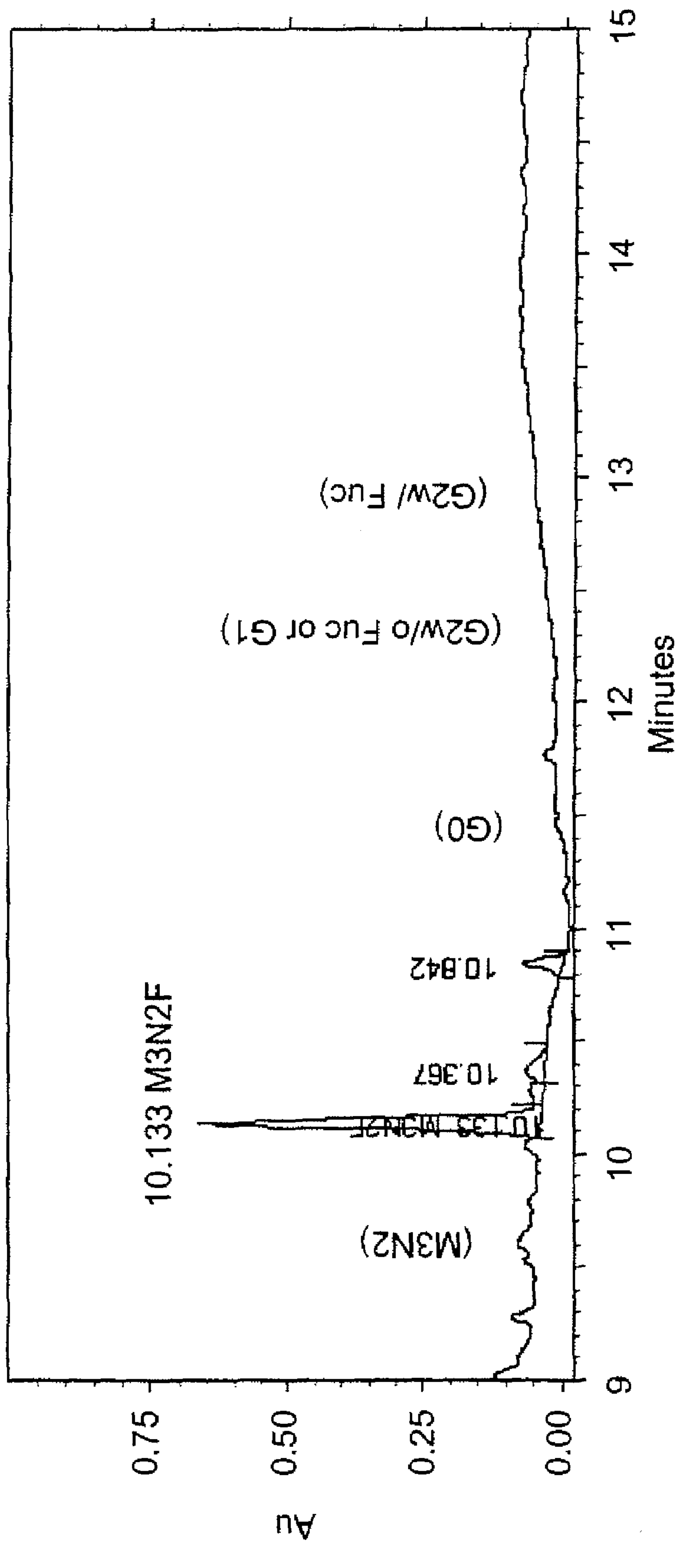
Figure 99C:
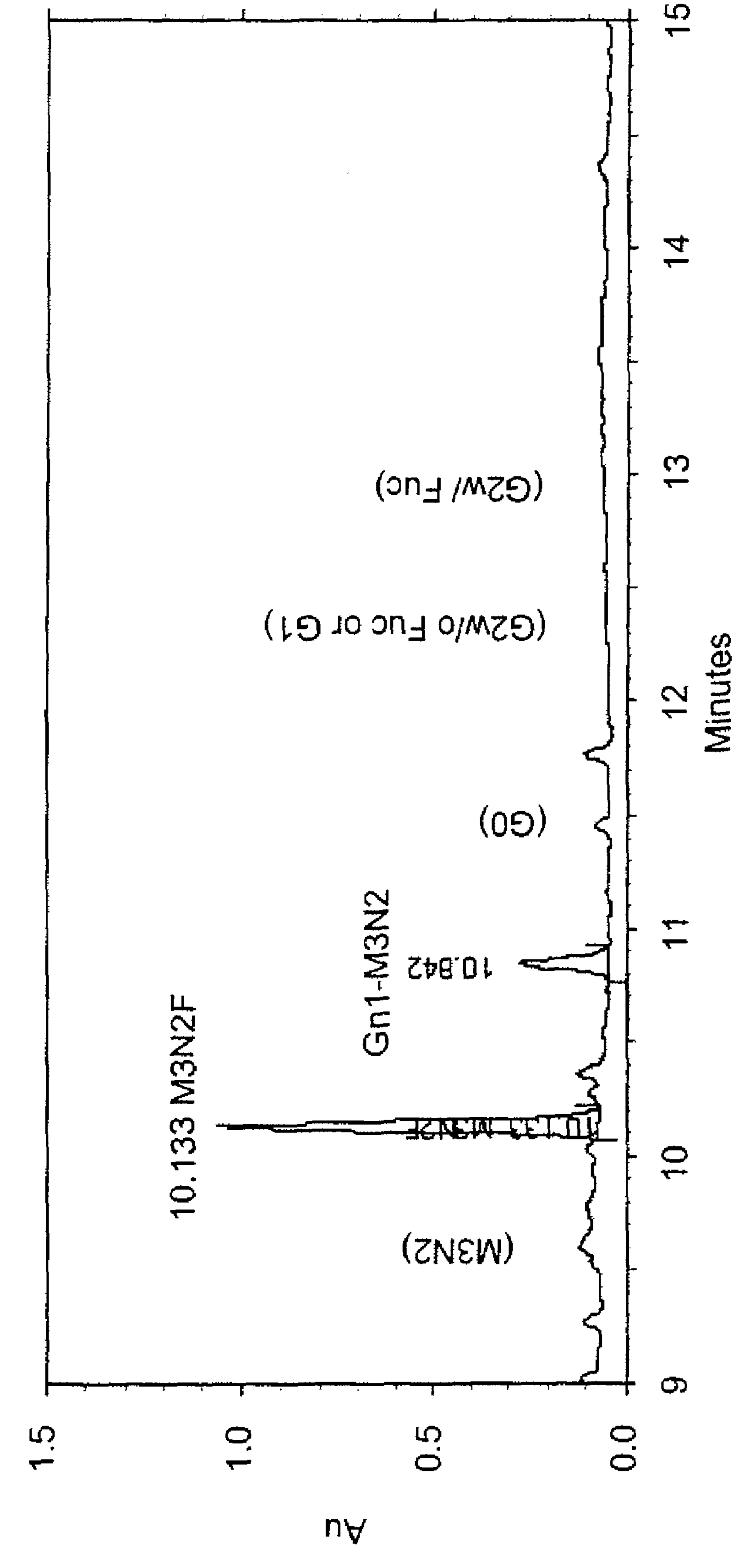
Figure 99D:
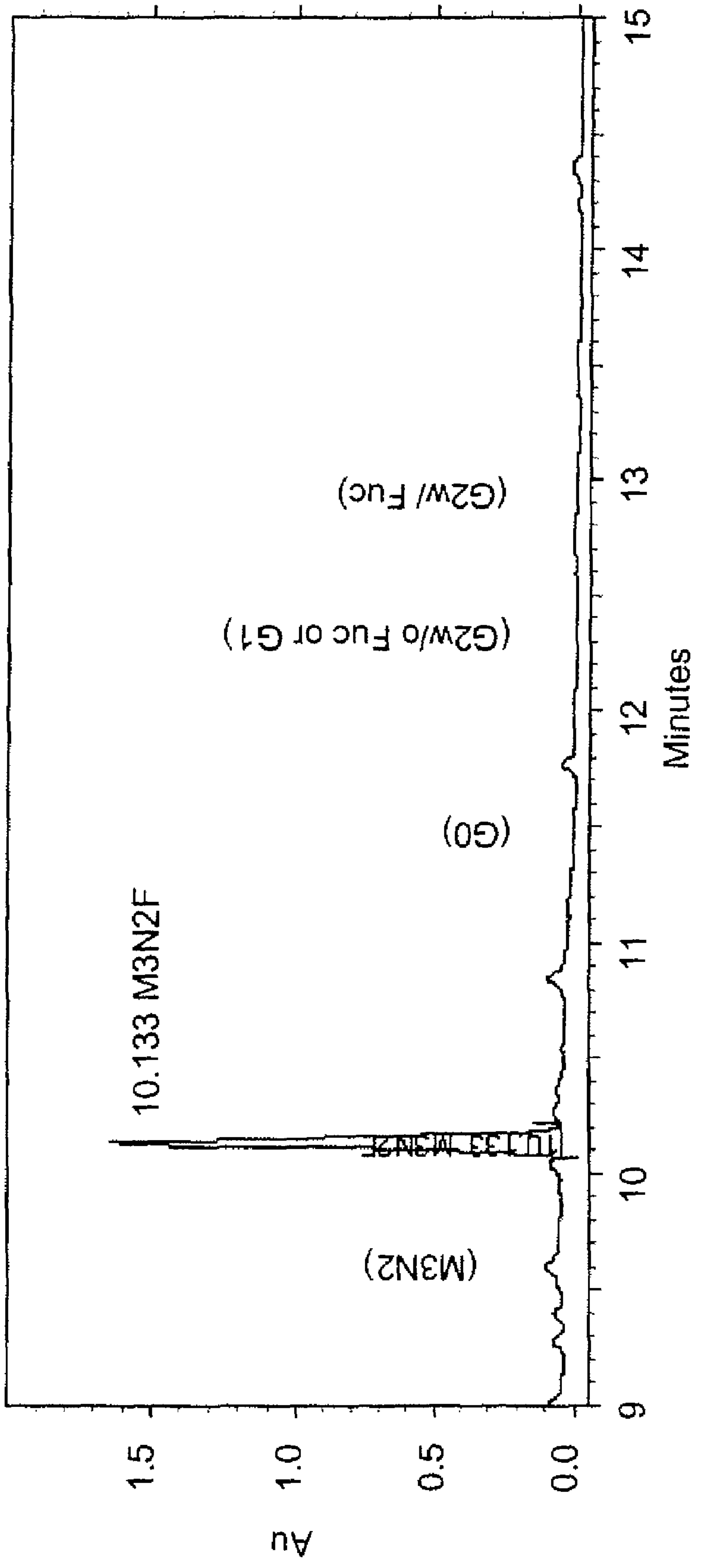

FIGS. 99A-99D show the electropherograms indicating the glycans released from glycoremodeled Cri-IgG1 antibody as well as glycan standards derivatized with APTS (FIG. 99A). The glycoforms were identified by comparing their electrophoretic mobilities to the standards. The relative amount of each glycan species was calculated from the relative area percentage of each indicated peak, and the results are presented in Table 15. The M3N2F glycoform represents 91% of the glycans of DEAE-Cri, 80% of the glycans of SPA-Cri, and 100% of the glycans of Fc-Cri. Incomplete removal of GlcNAc moiety resulting in the GnT-1-M3N2F glycoform (see, Table 15) was observed in the glycan structures from DEAE-Cri (8.6%) and SPA-Cri (~20%). Glycoform GnT-1-M3N2F is the M3N2F glycoform with one additional GlcNAc, such as would be added by GnT-I.

TABLE 15

The areas of individual peaks from CE profile in FIG. 99 were calculated, and relative amounts of the M3N2F and GnT-I-M3N2F glycoforms were determined.

| | M3N2F | | GnT-I-M3N2F | |
|---|---|---|---|---|
| | RT (min.) | % | RT (min.) | % |
| DEAE | 10.133 | 91.4 | 10.842 | 8.6 |
| SPA | 10.133 | 80.01 | 10.842 | 19.99 |
| Fc | 10.133 | 100 | 10.842 | 0 |

Figure 100A:
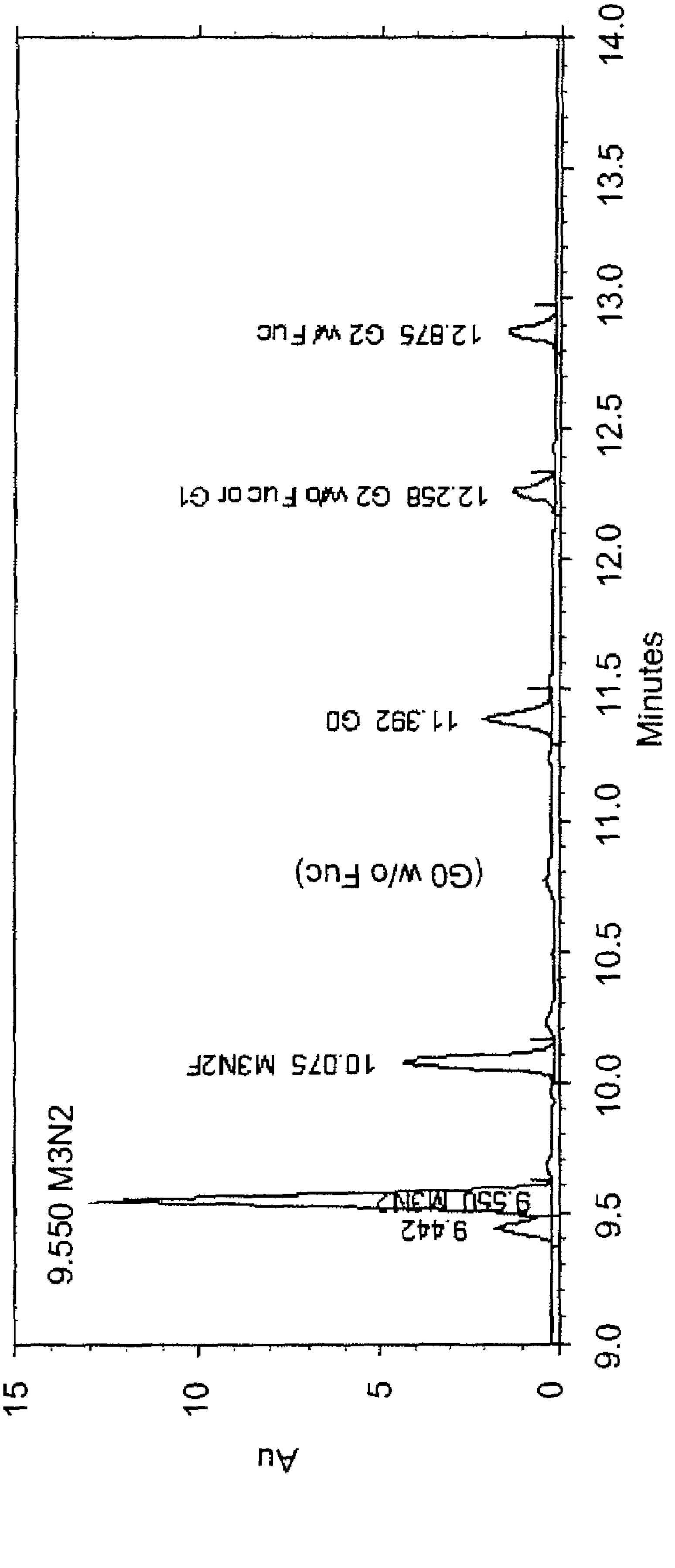
FIGS. 100A to 100D, are graphs depicting the capillary electrophoresis analysis of glycans released from Cri-IgG1 antibodies that have been glycoremodeled to contain G0 glycoforms. A graph depicting the capillary electrophoresis analysis of glycan standards derivatized with APTS is shown in FIG. 100A.
Figure 100B:
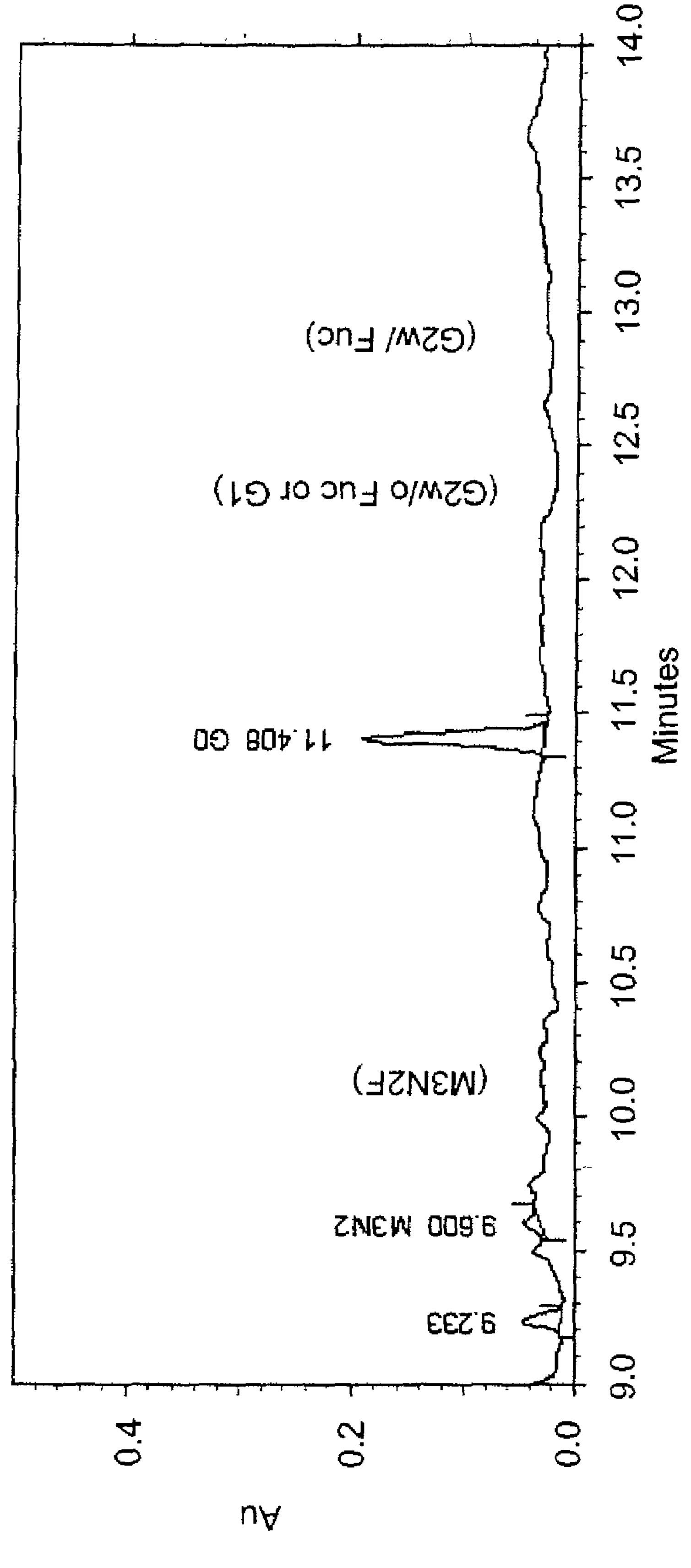
Figure 100C:
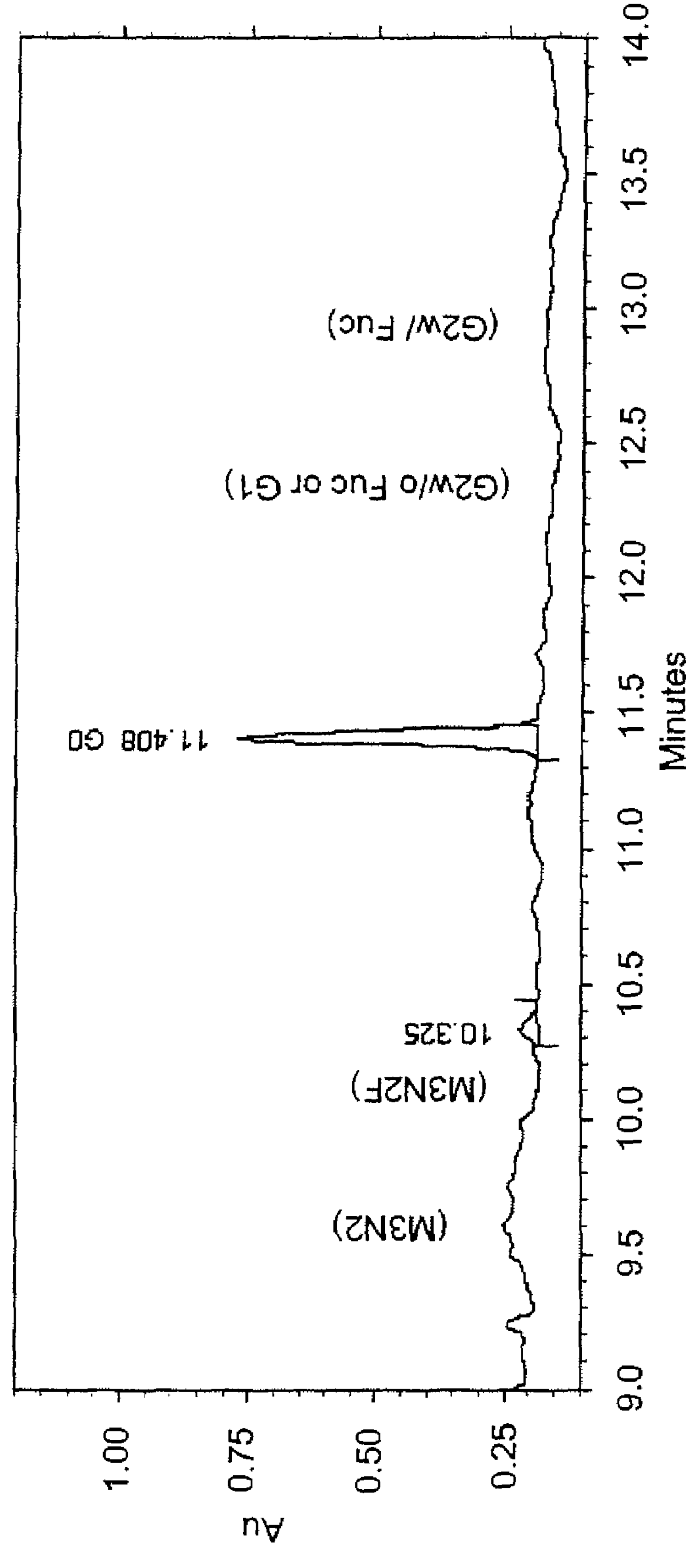
Figure 100D:
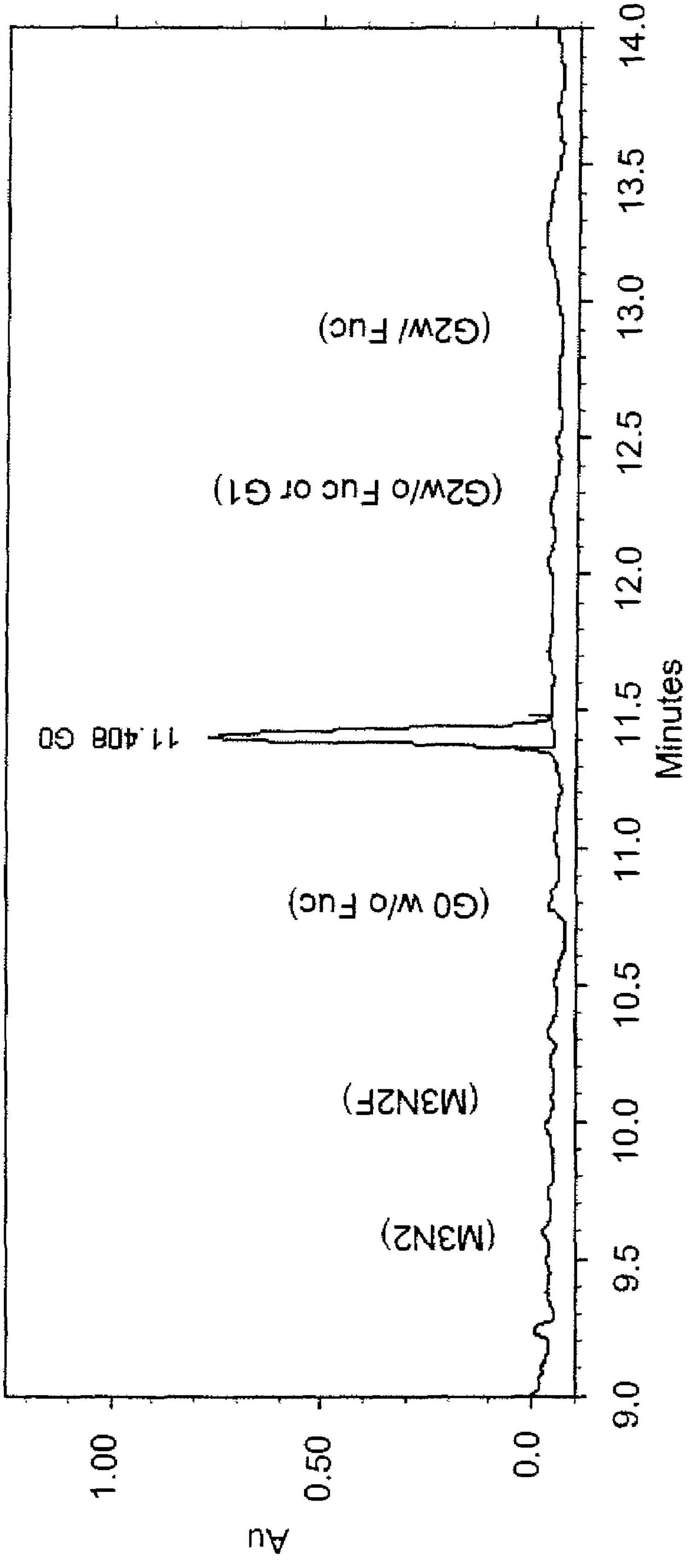

Degalactosylated glycoform (G0). Cri-IgG1 antibody with G0 glycoforms was obtained by stepwise treatment the native Cri-IgG1 antibody with neuraminidase and β1,4-galactosidase in for 24 hours for each reaction. The glycans released from the glycoremodeled antibody were analyzed by CE, HPLC and MALDI. FIG. 100A shows the CE profile of the released glycans. In all three samples, only one peak was observed which was designated as the G0 glycoform based on comparison with the standards (FIG. 100A and Table 16).

TABLE 16

The relative amount of the G0 glycoform of Cri-IgG1 determined by CE and HPLC.

| | CE | | HPLC | |
|---|---|---|---|---|
| | RT (min.) | % | RT (min.) | % |
| DEAE | 11.408 | 100.0 | 31.194 | 100.0 |
| SPA | 11.408 | 100.0 | 31.194 | 100.0 |
| Fc | 11.408 | 100.0 | 31.194 | 100.0 |

Figure 101A:
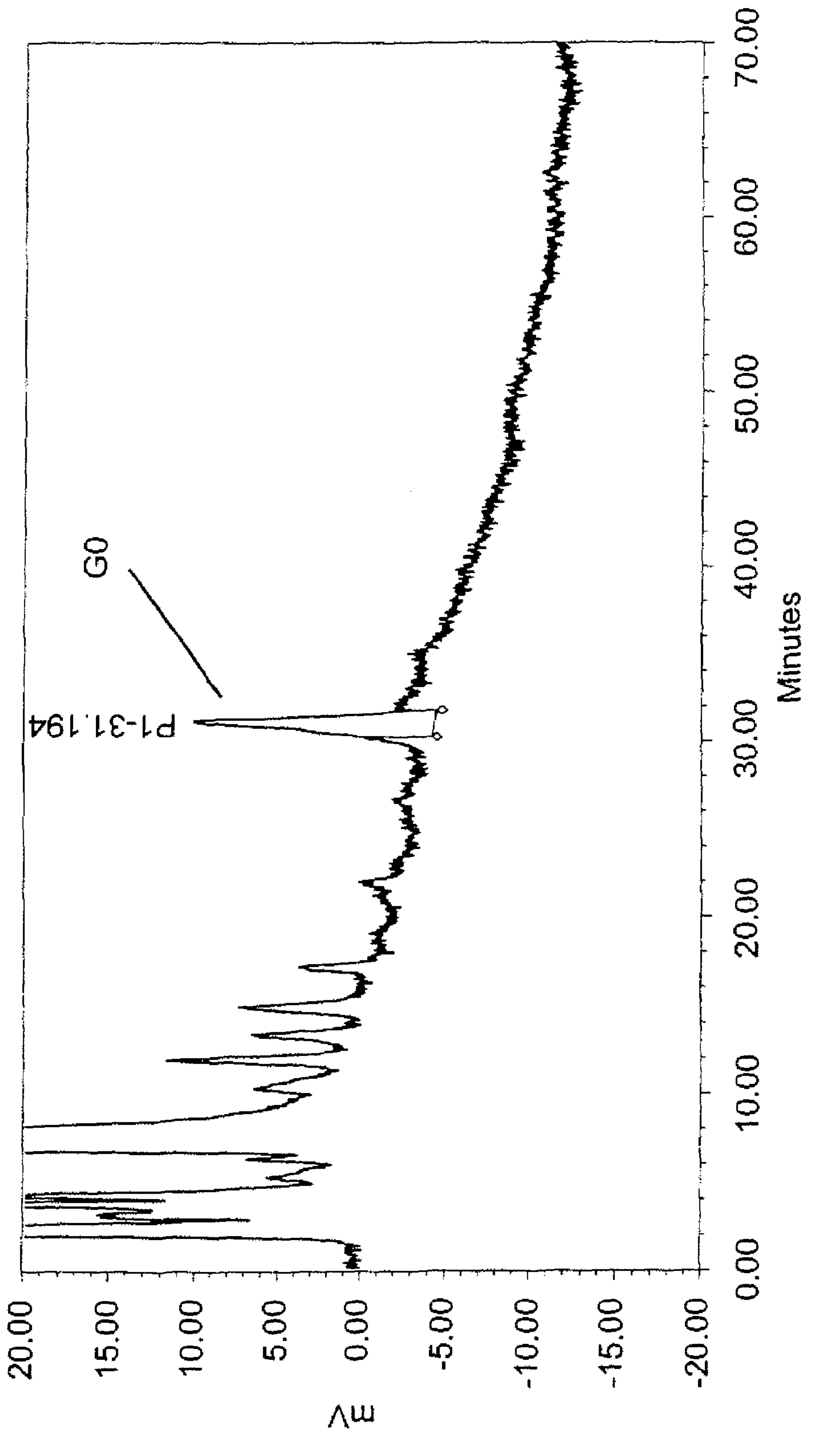
FIGS. 101A to 101C, are graphs depicting 2-AA HPLC analysis of glycans released from Cri-IgG1 antibodies that have been glycoremodeled to contain G0 glycoforms. The released glycans were labeled with 2AA and separated by HPLC on a NH2P-50 4D amino column.
Figure 101B:
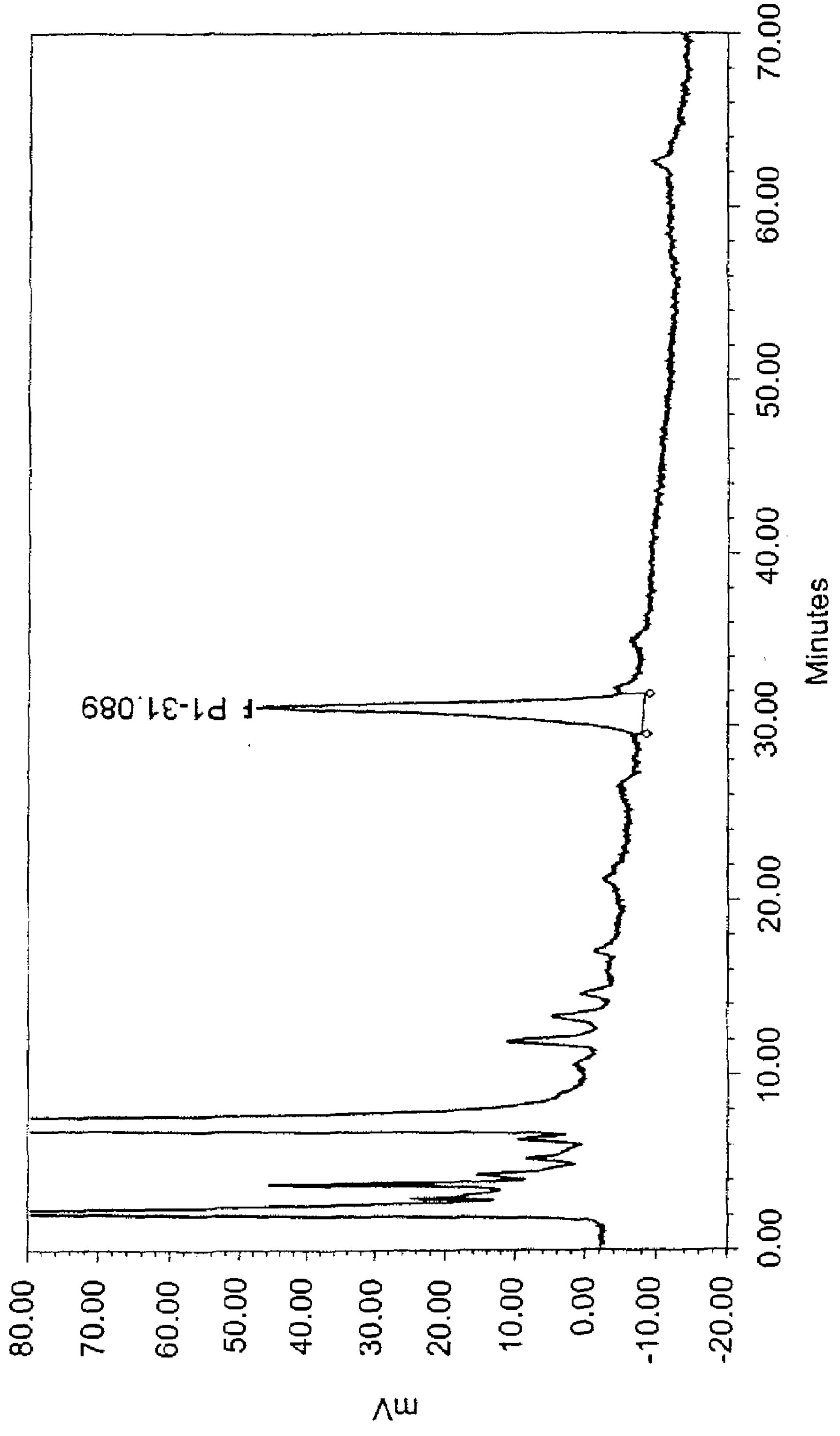
Figure 101C:
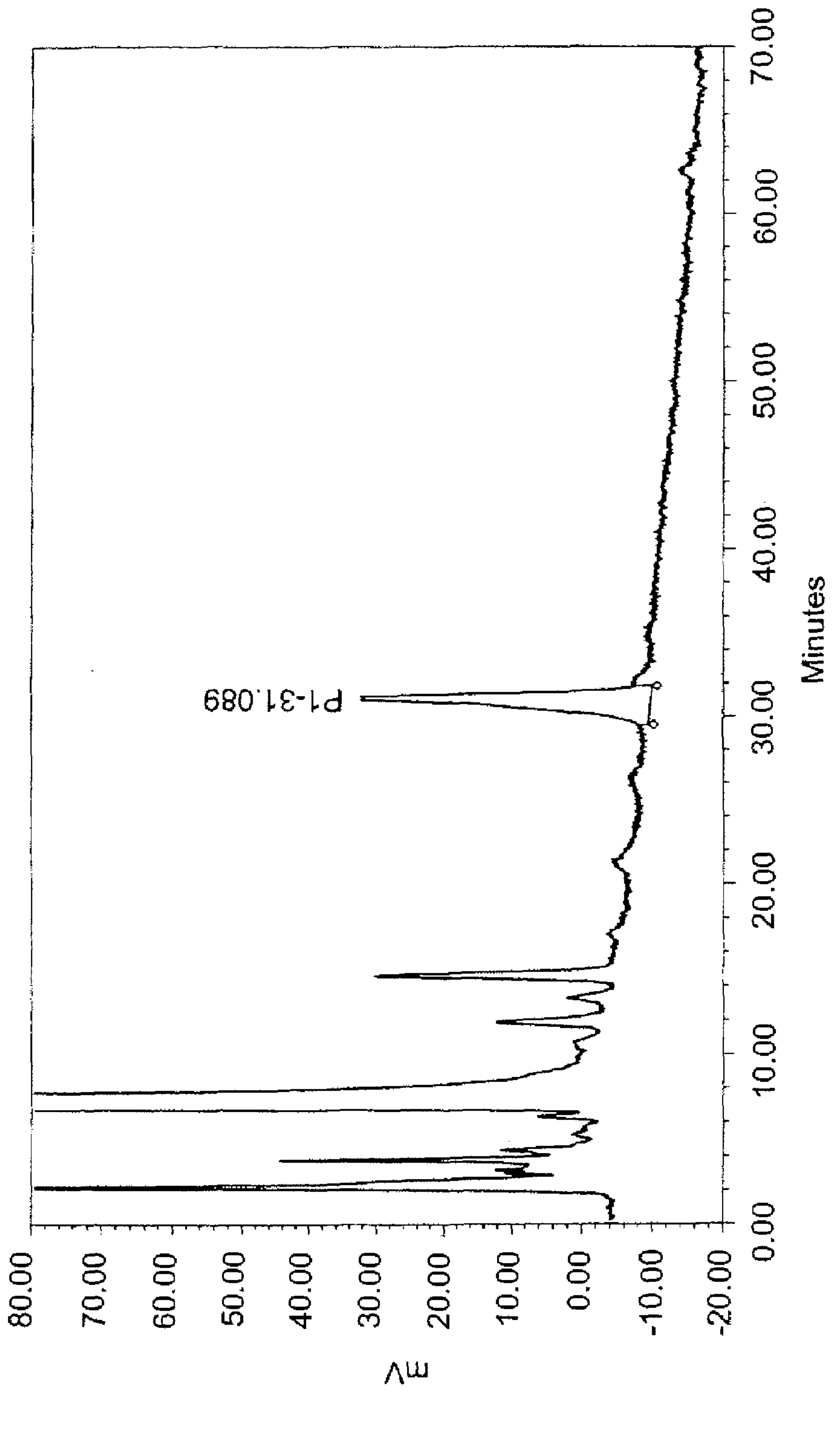
Figure 102A:
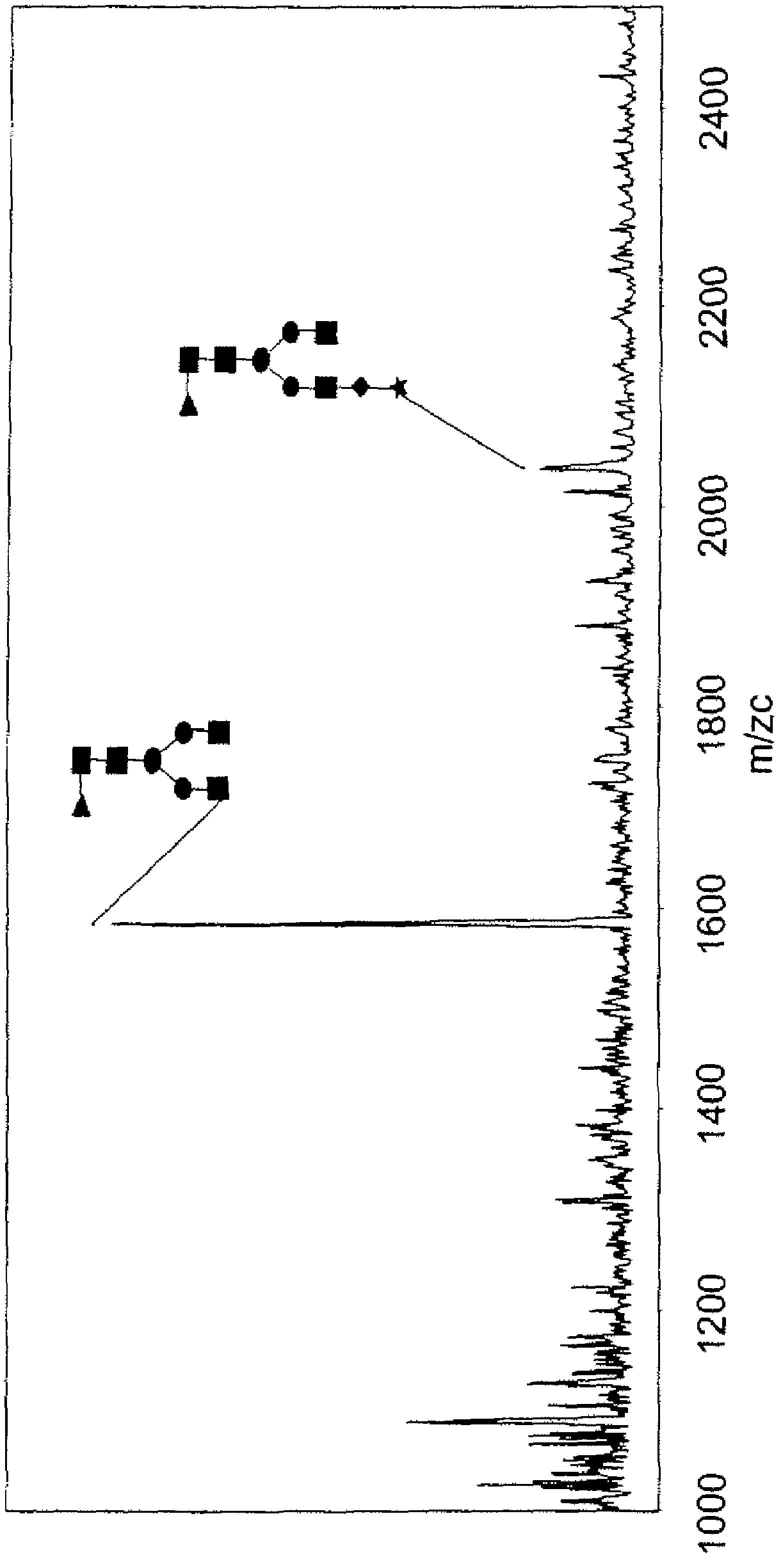
FIGS. 102A to 102C, are graphs depicting the MALDI analysis of glycans released from Cri-IgG1 antibodies that have been glycoremodeled to contain G0 glycoforms. The released glycans were derivatized with 2-AA and then analyzed by MALDI.
Figure 102B:
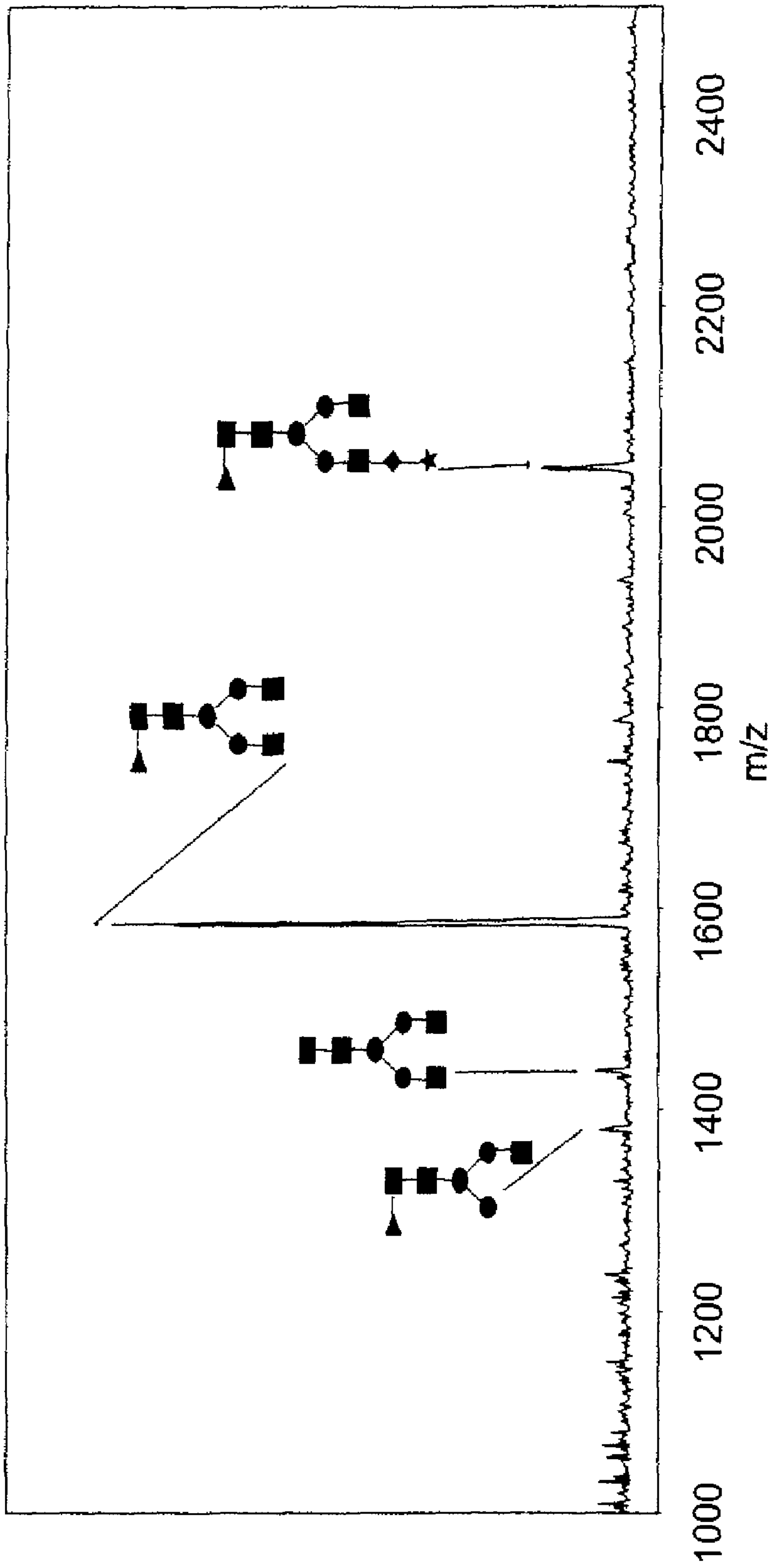
Figure 102C:
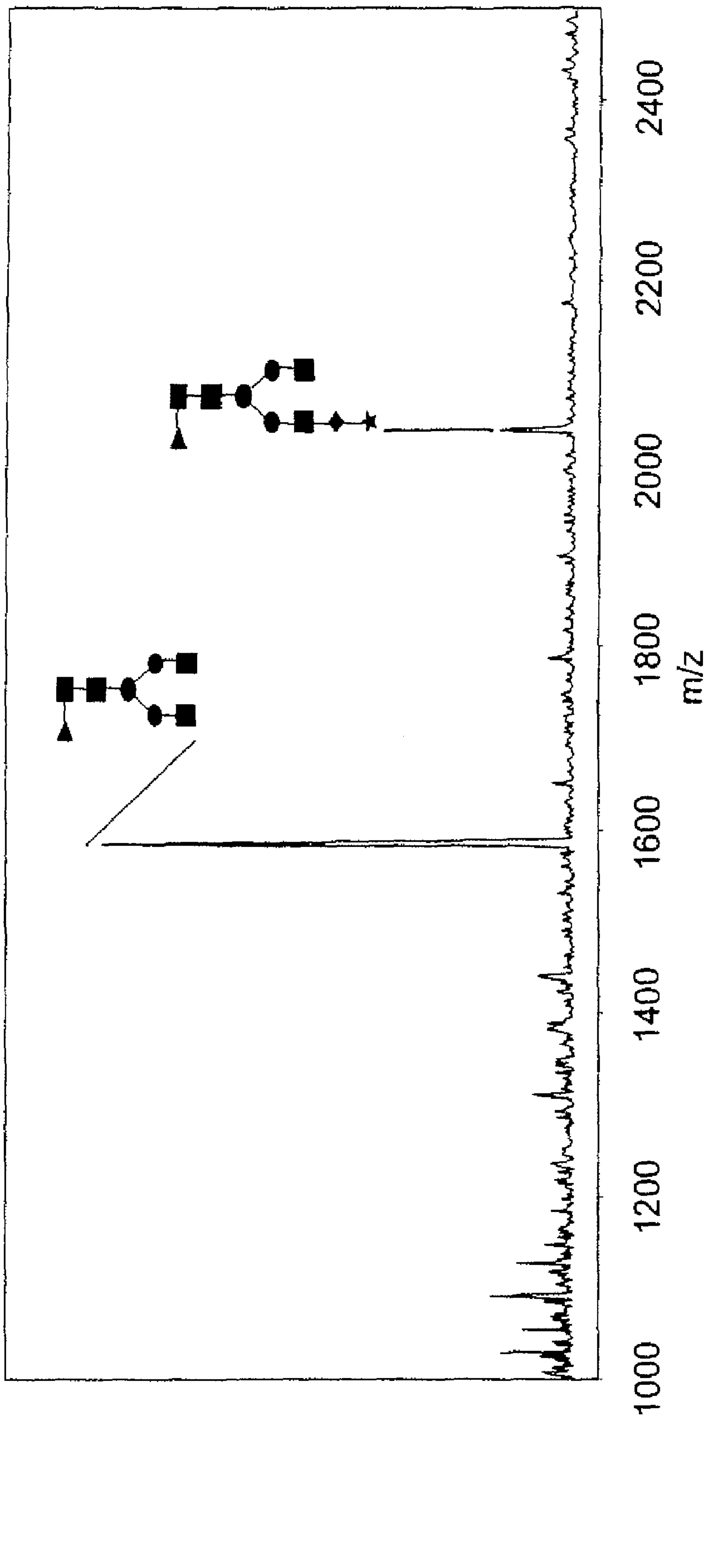
Figure 103A:
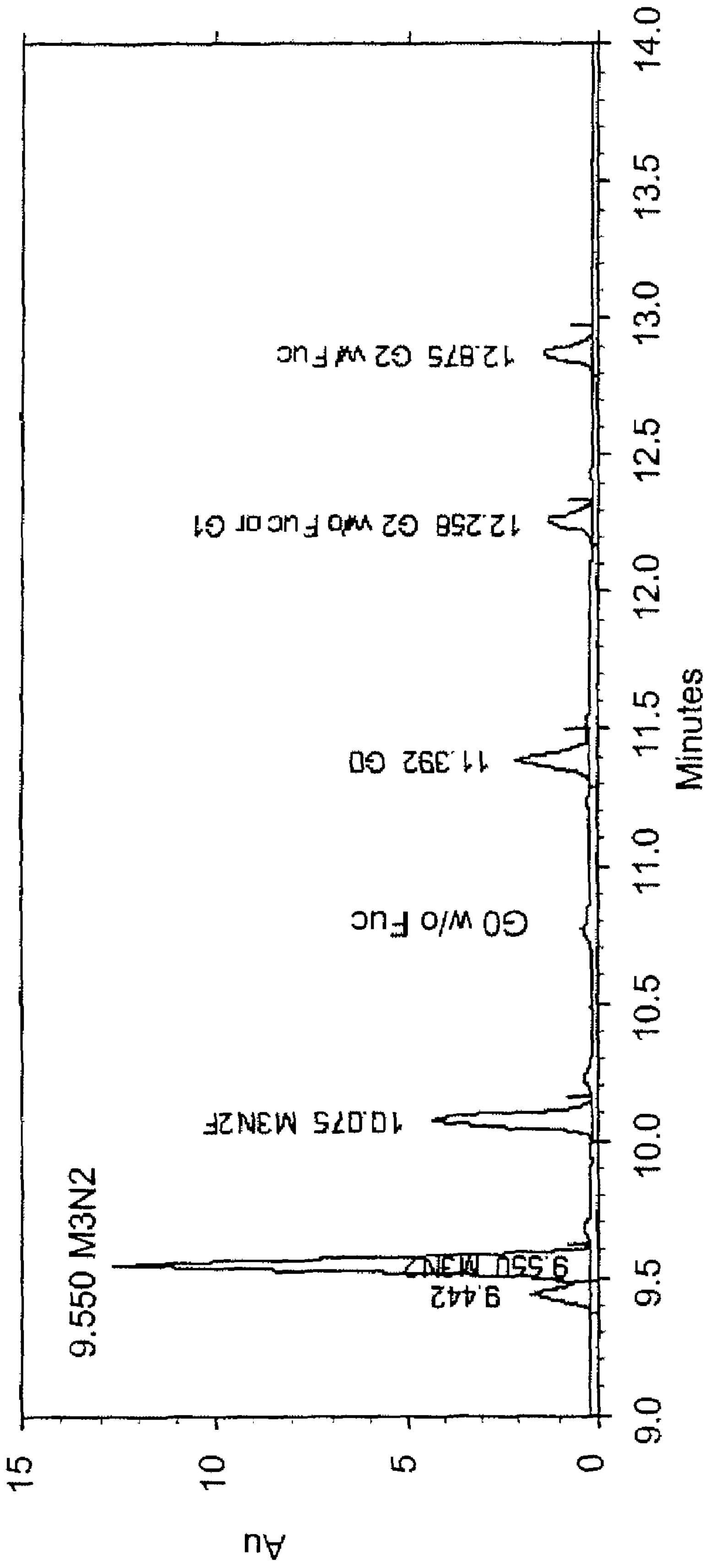
FIGS. 103A to 103D, are graphs depicting the capillary electrophoresis analysis of glycans released from Cri-IgG1 antibodies that have been glycoremodeled to contain G2 glycoforms. A graph depicting the capillary electrophoresis analysis of glycan standards derivatized with APTS is shown in FIG. 103A.
Figure 103B:
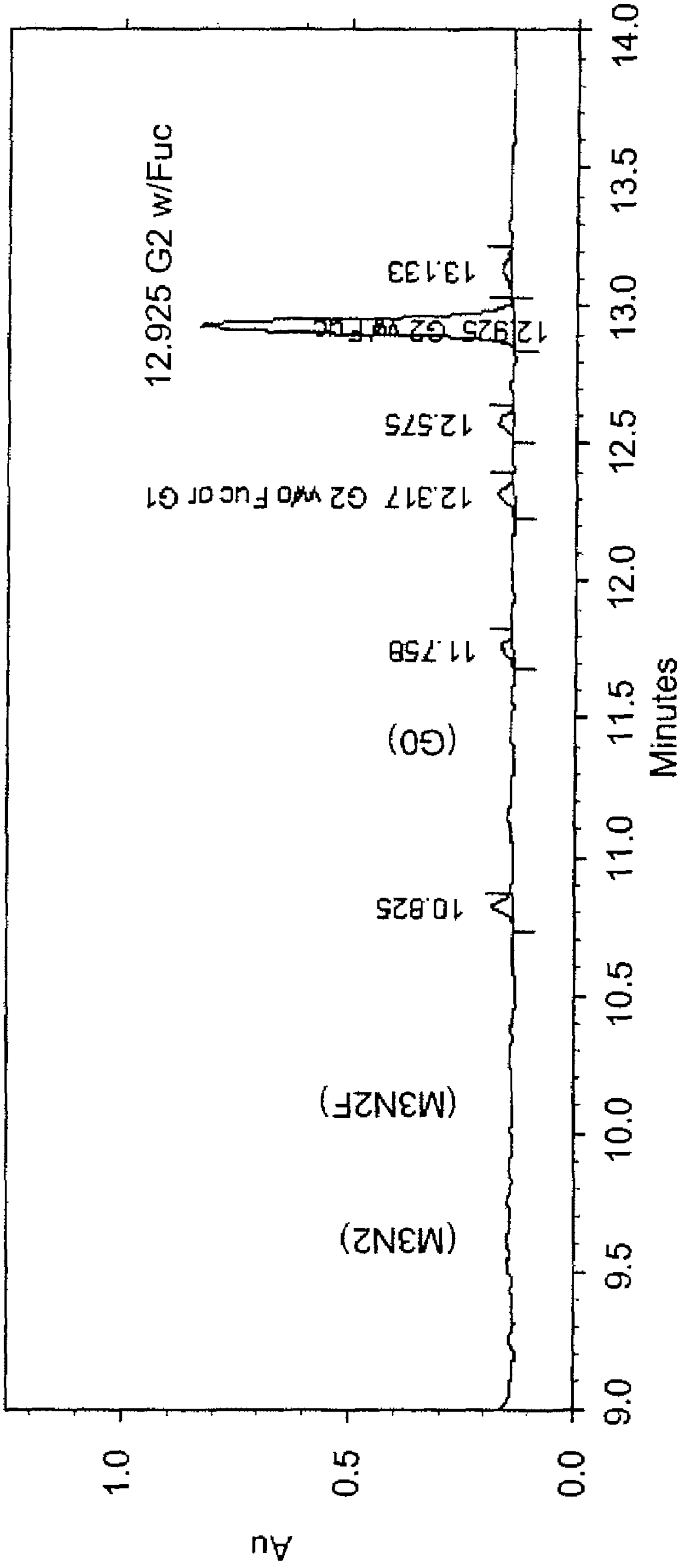
Figure 103C:
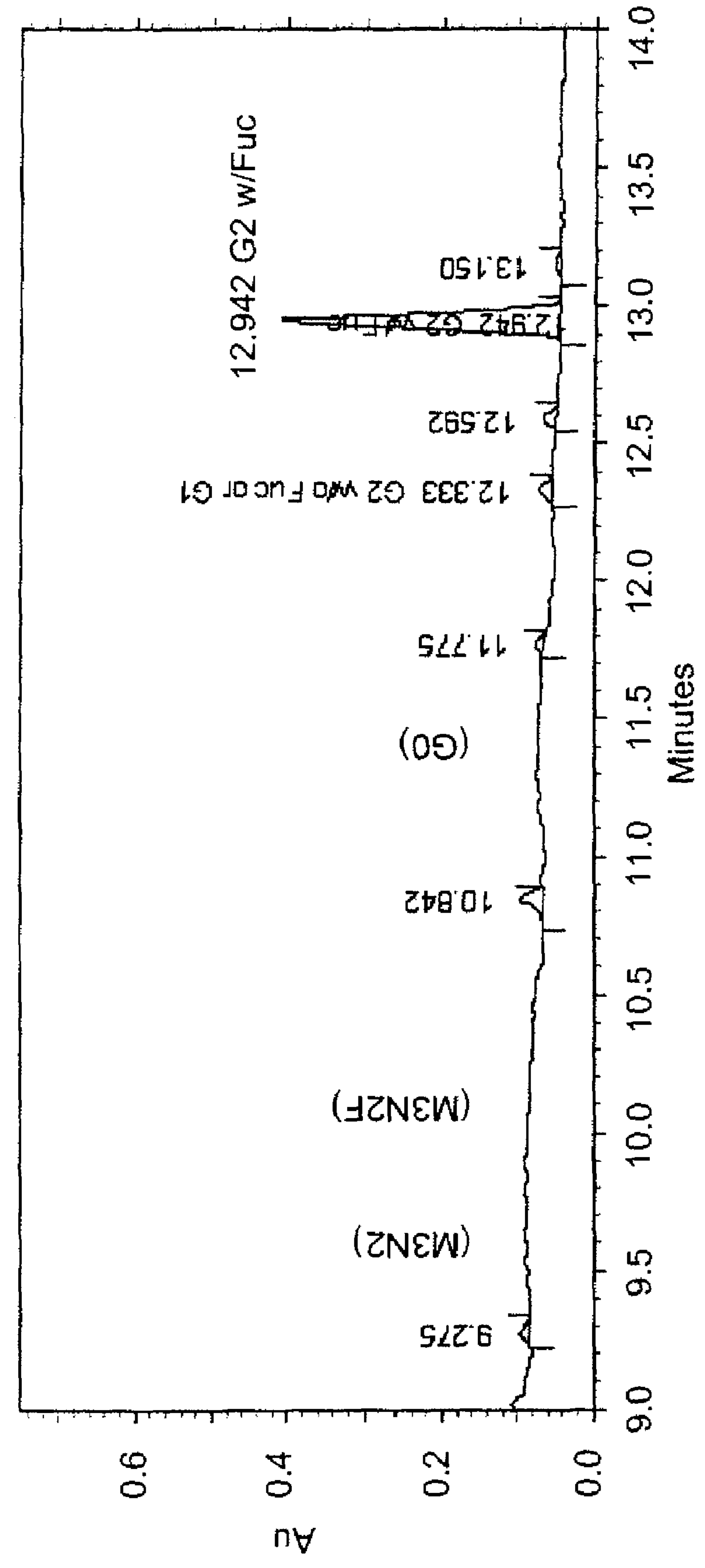
Figure 103D:
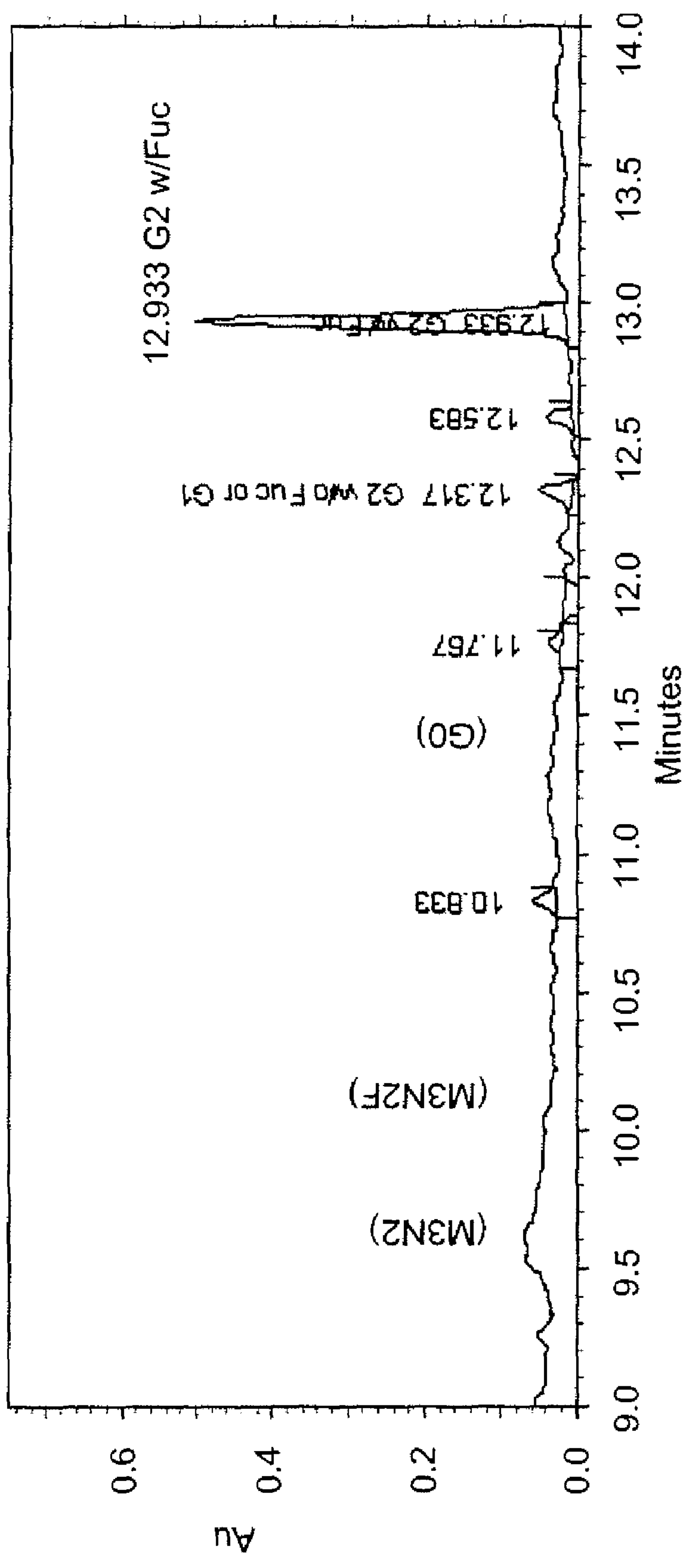
Figure 104A:
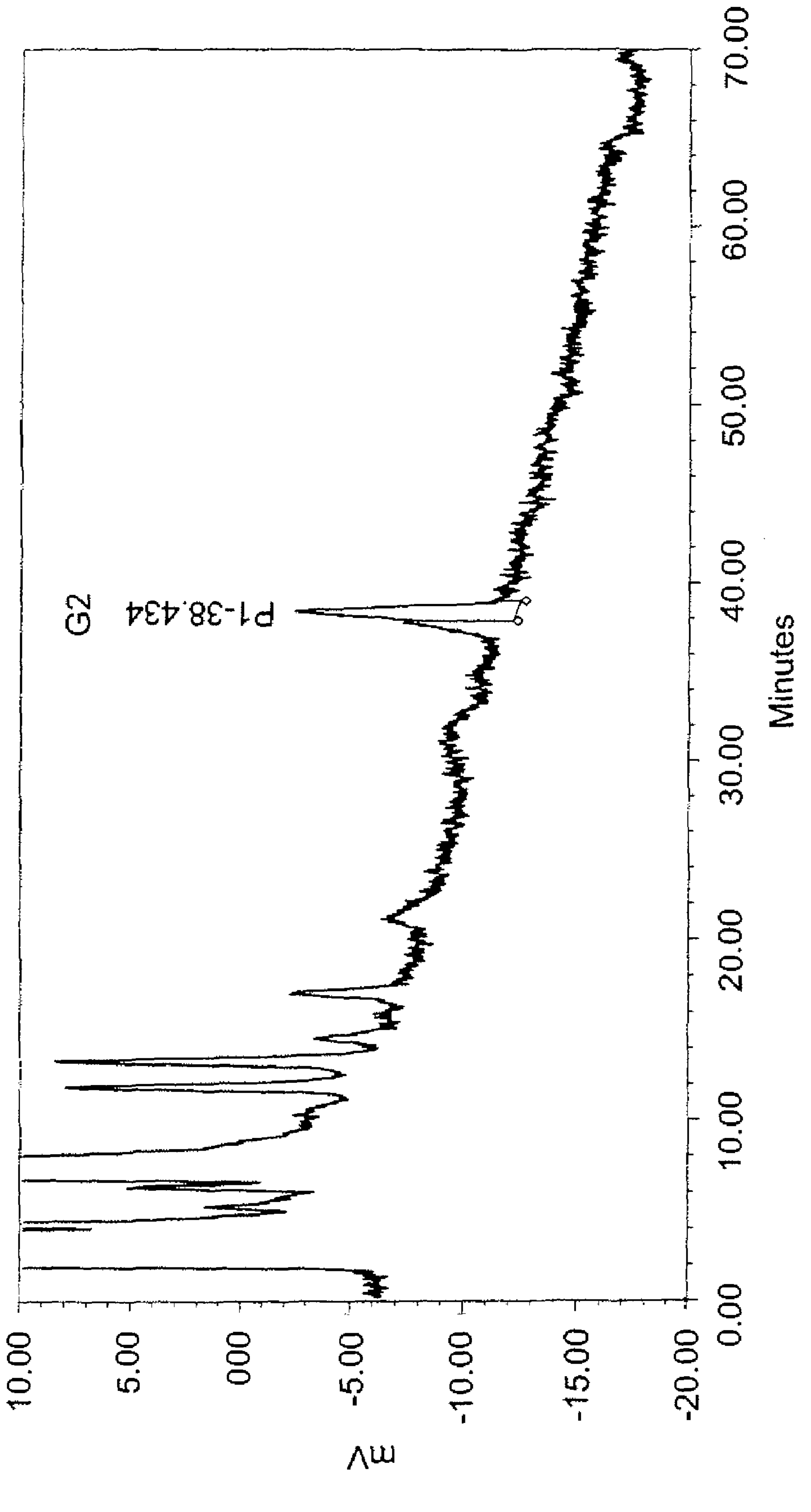
FIGS. 104A to 104C, are graphs depicting the 2-AA HPLC analysis of glycans released from remodeled Cri-IgG1 antibodies that have been glycoremodeled to contain G2 glycoforms. The released glycans were labeled with 2AA and then separated by HPLC on a NH2P-50 4D amino column.
Figure 104B:
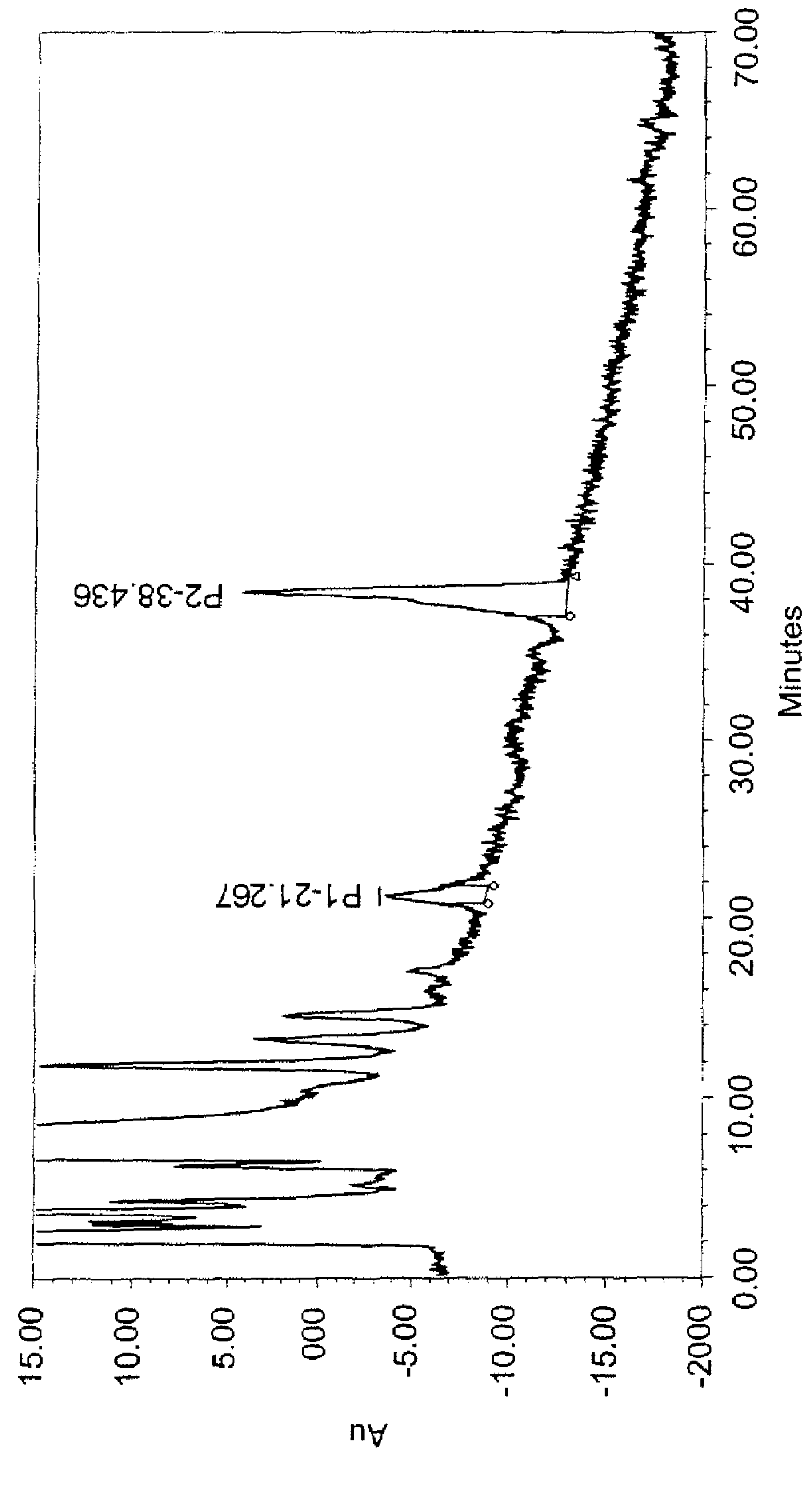
Figure 104C:
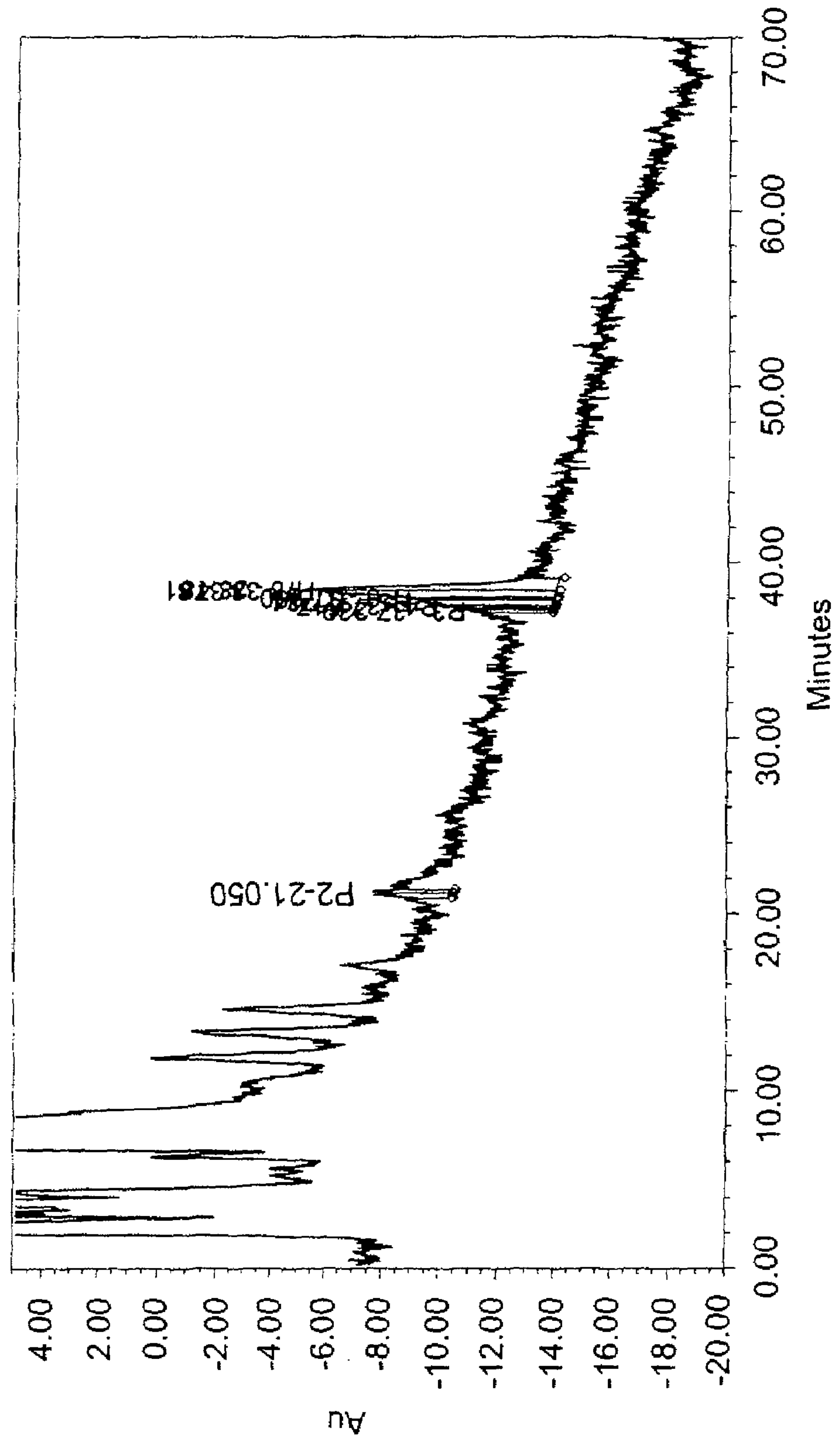

In addition to the glycan analysis provided by CE, a quantitative HPLC method was also used to determine the percent of the G0 glycoform represented by remodeled glycans of the Cri-IgG1 antibody. The glycan distribution on the glycoremodeled antibody was monitored by enzymatically releasing the glycans with PNGase F and derivatizing the released products with 2-anthranilic acid (2-AA) at the reducing terminus. The derivatized mixture was separated by HPLC on a Shodex Asahipak NH2P-50 4D column with fluorescence detection. FIGS. 101A-101C show the chromatograms obtained from the released glycans. HPLC results confirmed CE analysis, as only one major peak was found in all three samples. In agreement with CE and HPLC data, MALDI analysis also showed almost complete glycoremodeling to the G0 glycoform (FIGS. 102A-102C).

Figure 105A:
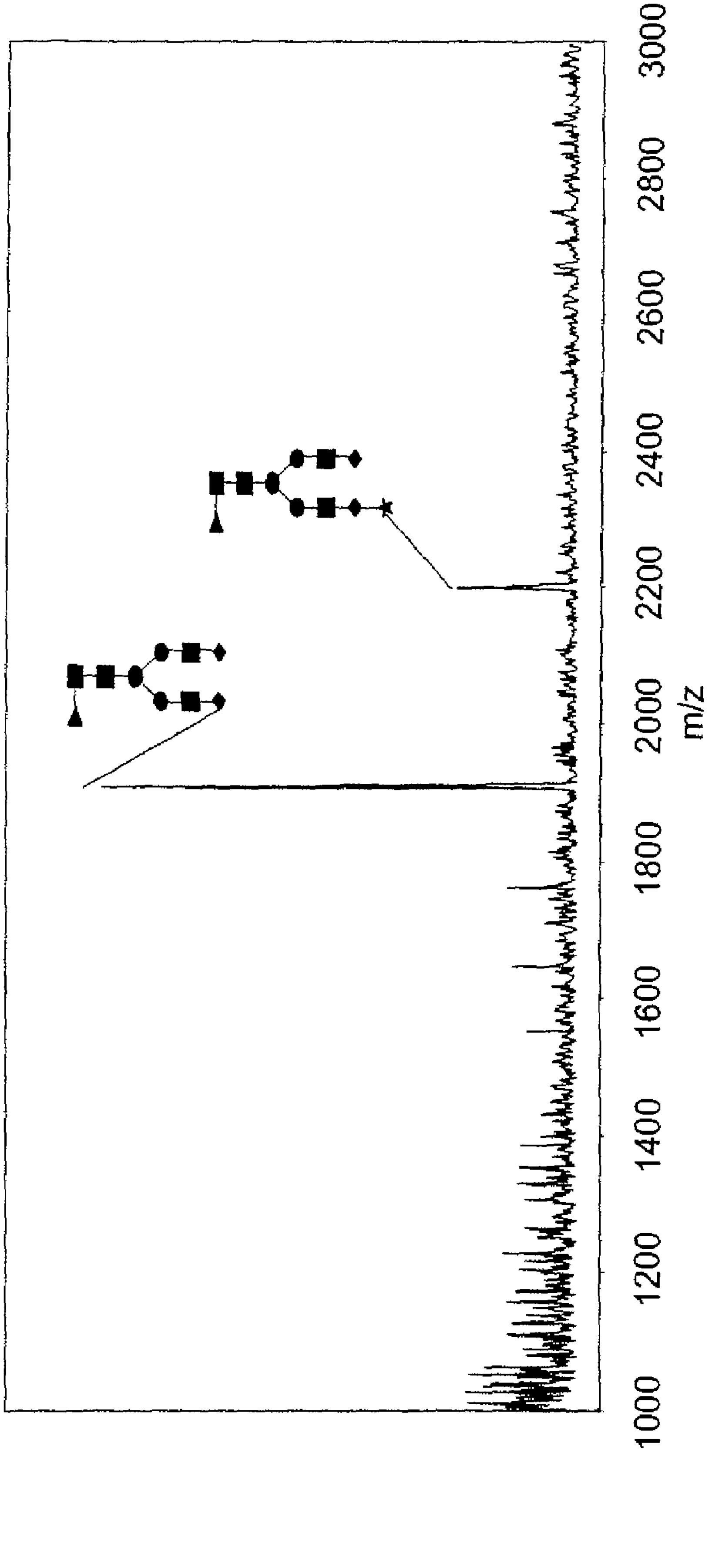
FIGS. 105A to 105C, are graphs depicting MALDI analysis of glycans released from Cri-IgG1 antibodies that have been glycoremodeled to contain G2 glycoforms. The released glycans were derivatized with 2-AA and then analyzed by MALDI.
Figure 105B:
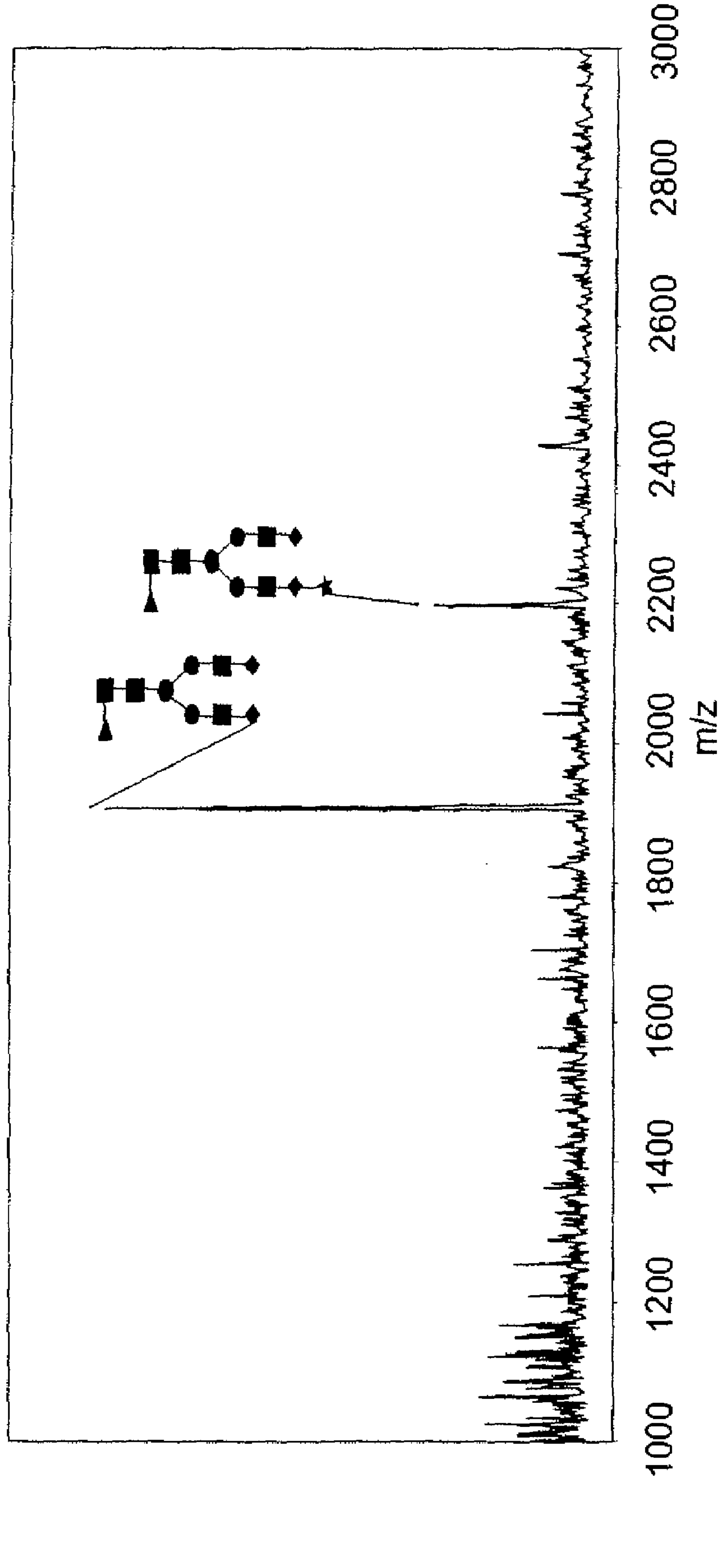
Figure 105C:
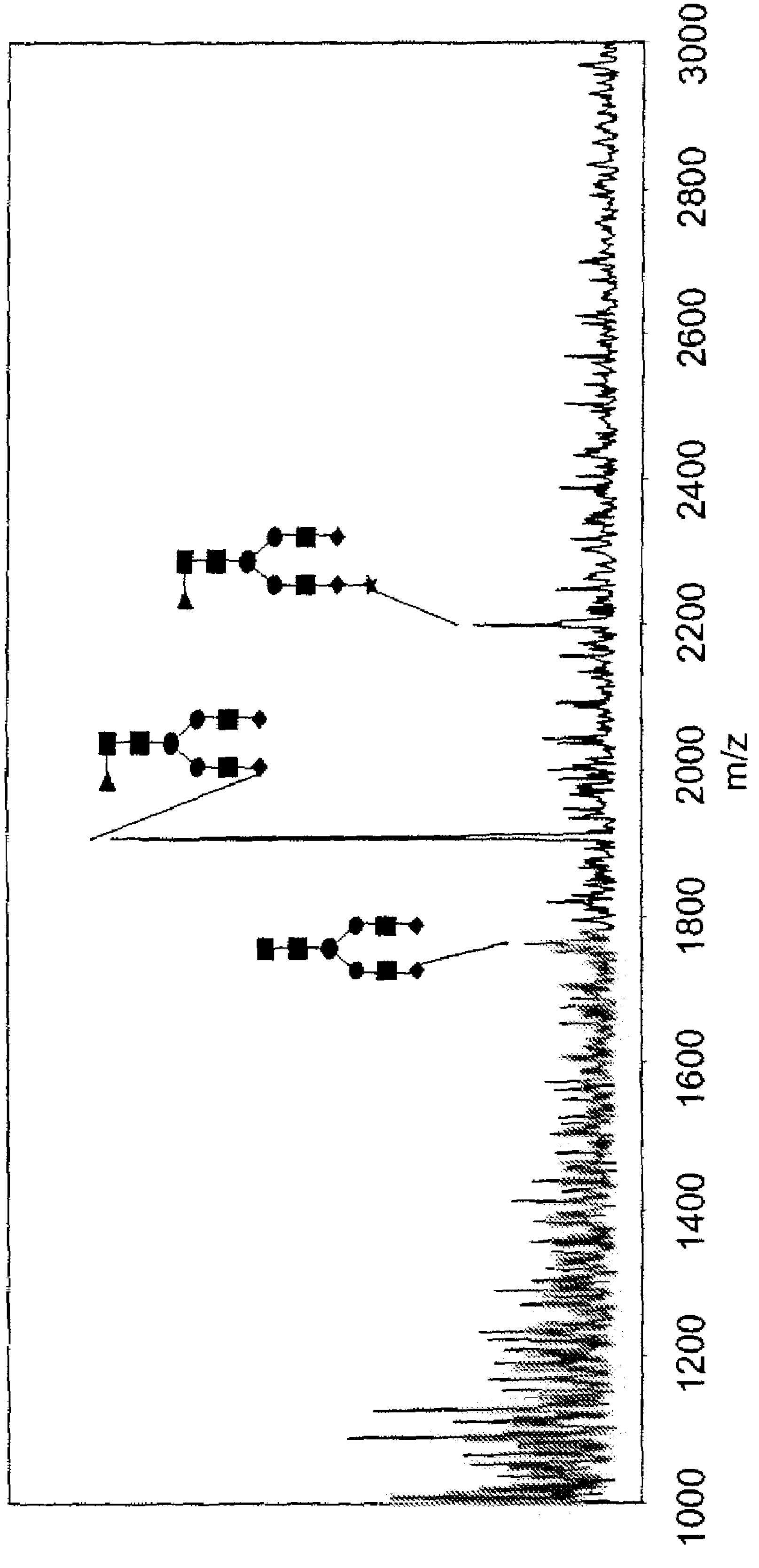
Figure 106A:
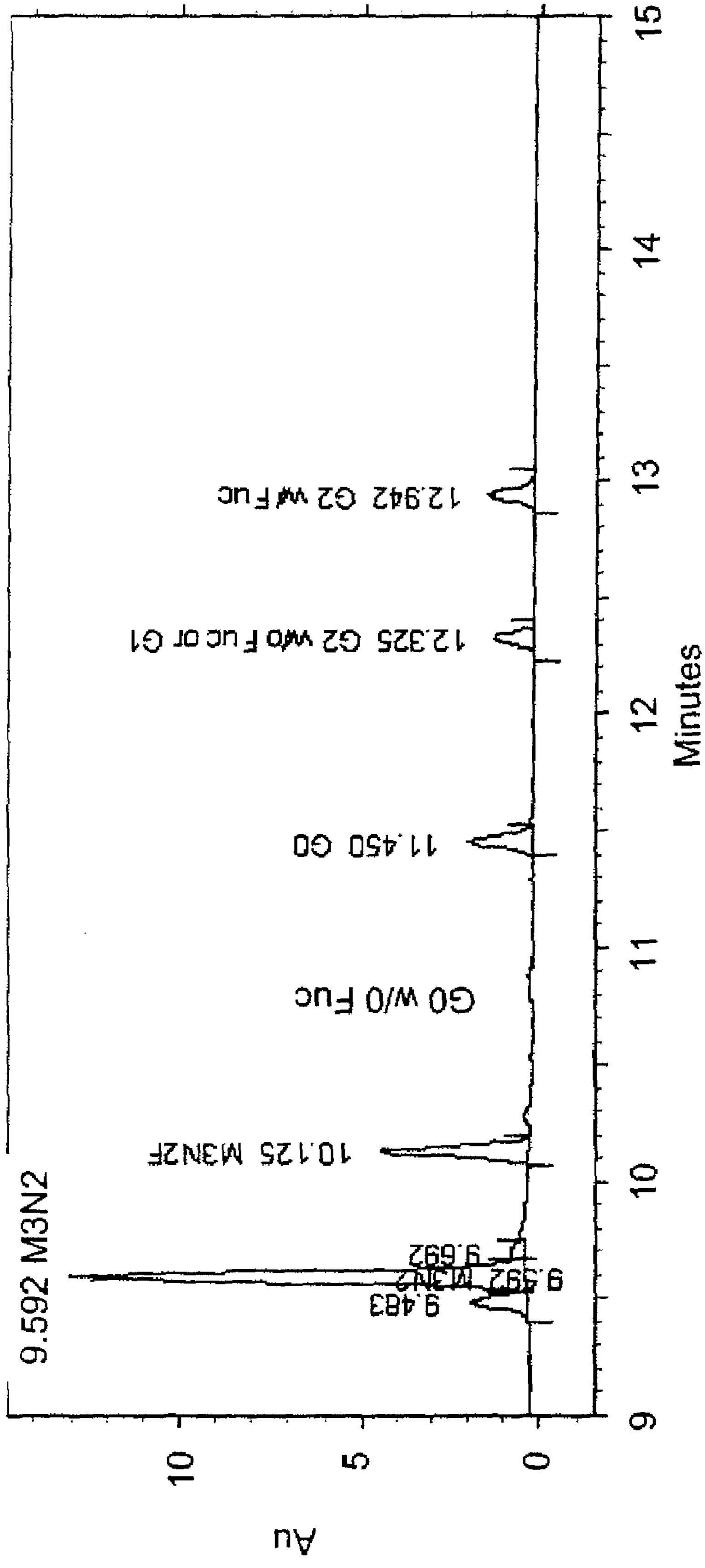
FIGS. 106A to 106D, are graphs depicting capillary electrophoresis analysis of glycans released from Cri-IgG1 antibodies that have been glycoremodeled by GnT-I treatment of M3N2 glycoforms. A graph depicting the capillary electrophoresis analysis of glycan standards derivatized with APTS is shown in FIG. 106A.
Figure 106B:
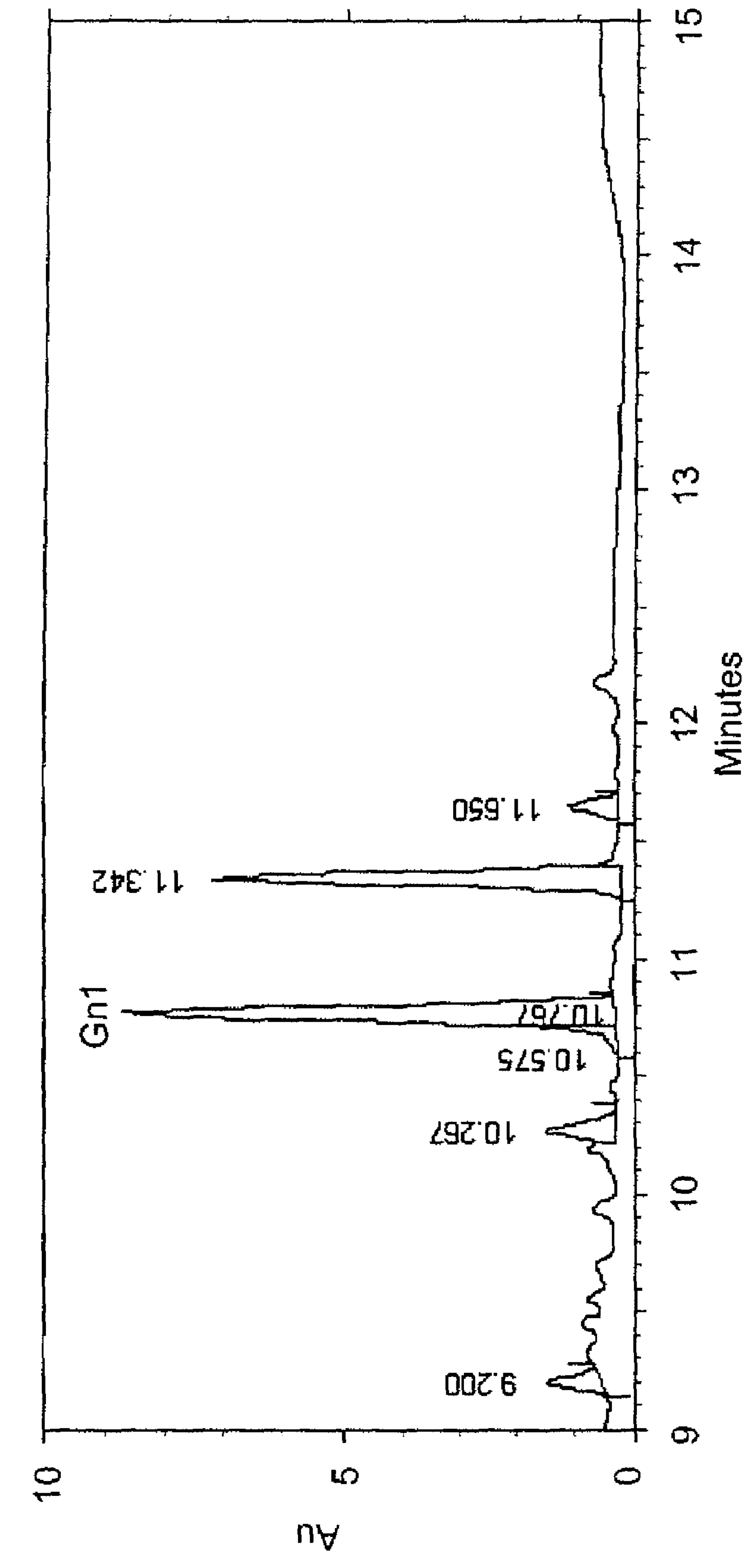
Figure 106C:
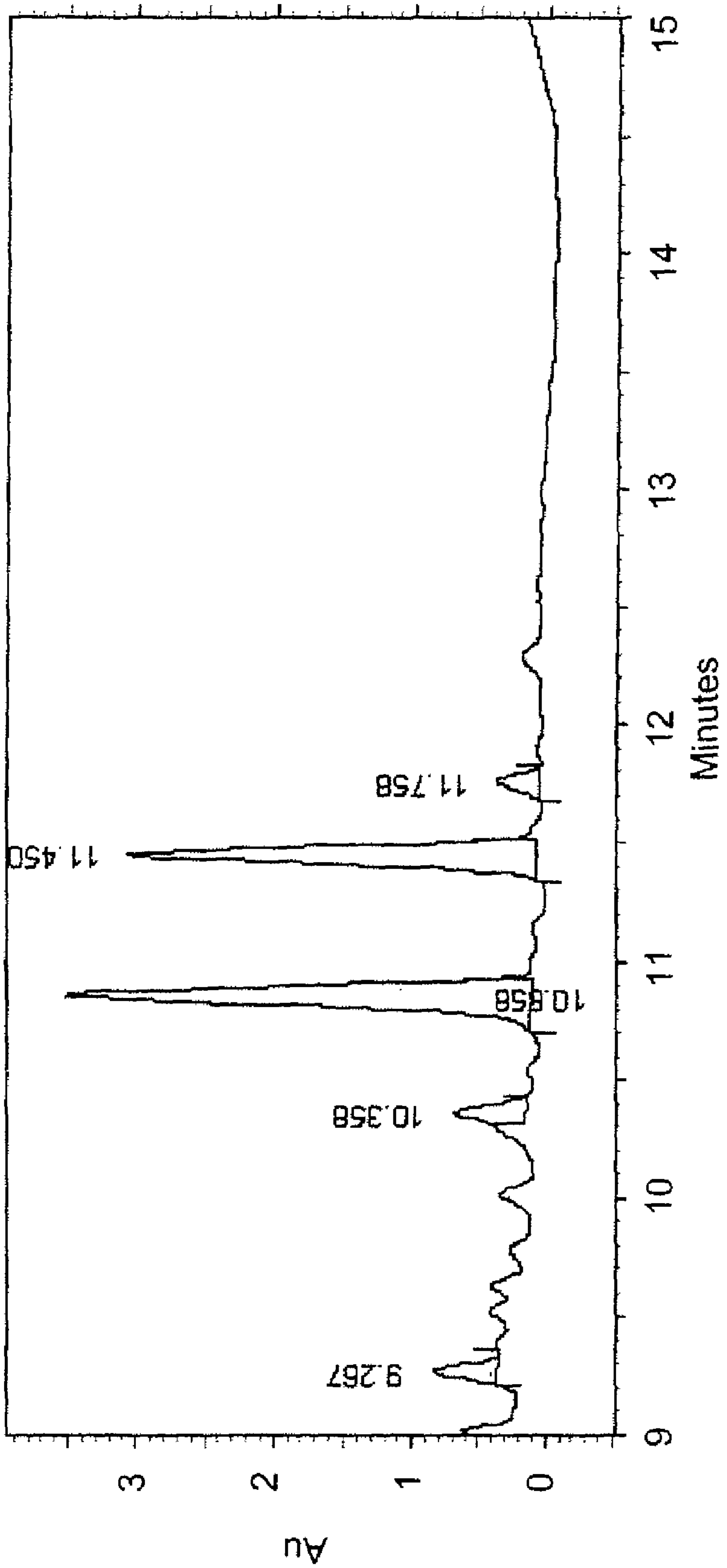
Figure 106D:
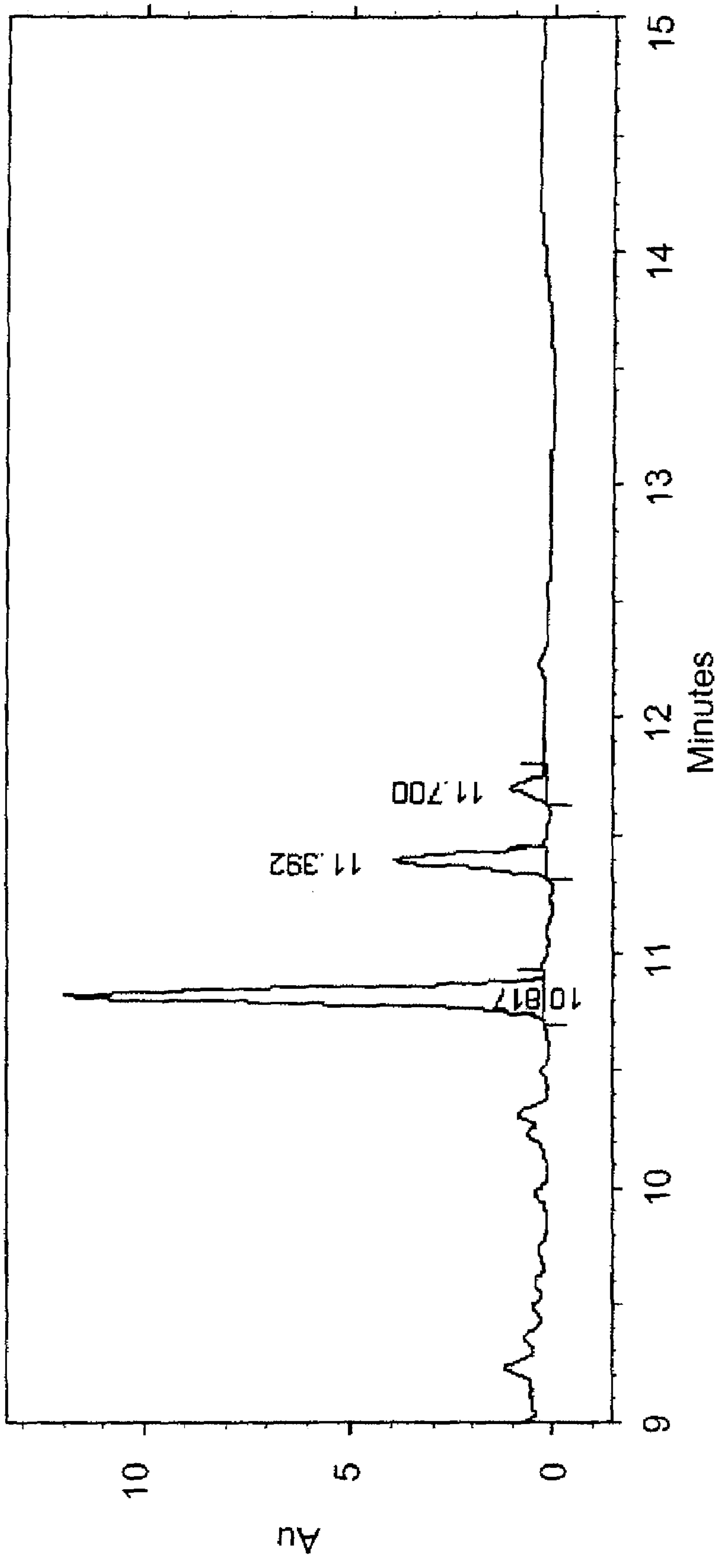
Figure 107A:
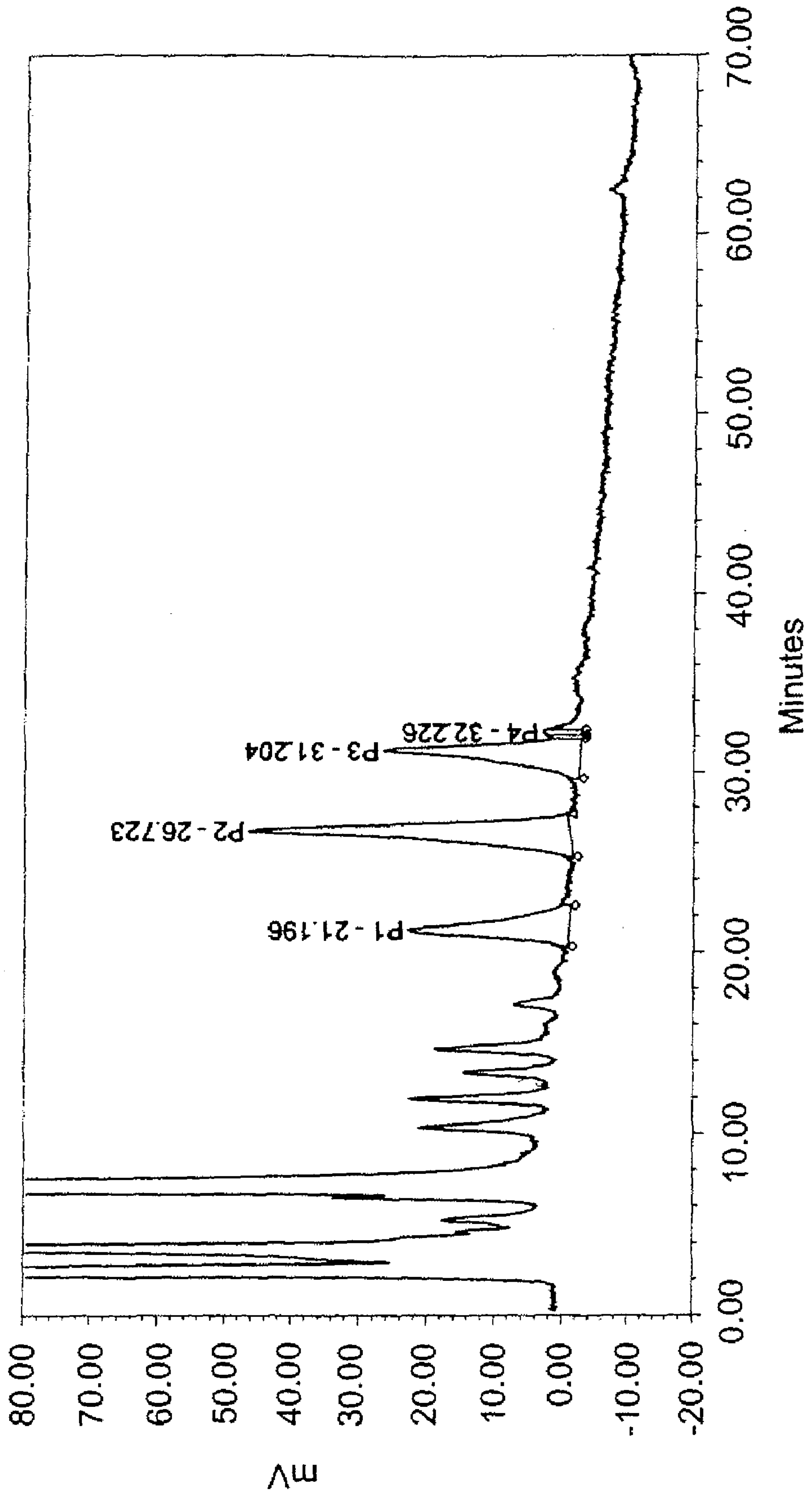
FIGS. 107A to 107C, are graphs depicting 2-AA HPLC analysis of glycans released from Cri-IgG1 antibodies that have been remodeled by GnT-I treatment of M3N2 glycoforms. The released glycans were labeled with 2-AA and separated by HPLC on a NH2P-50 4D amino column.
Figure 107B:
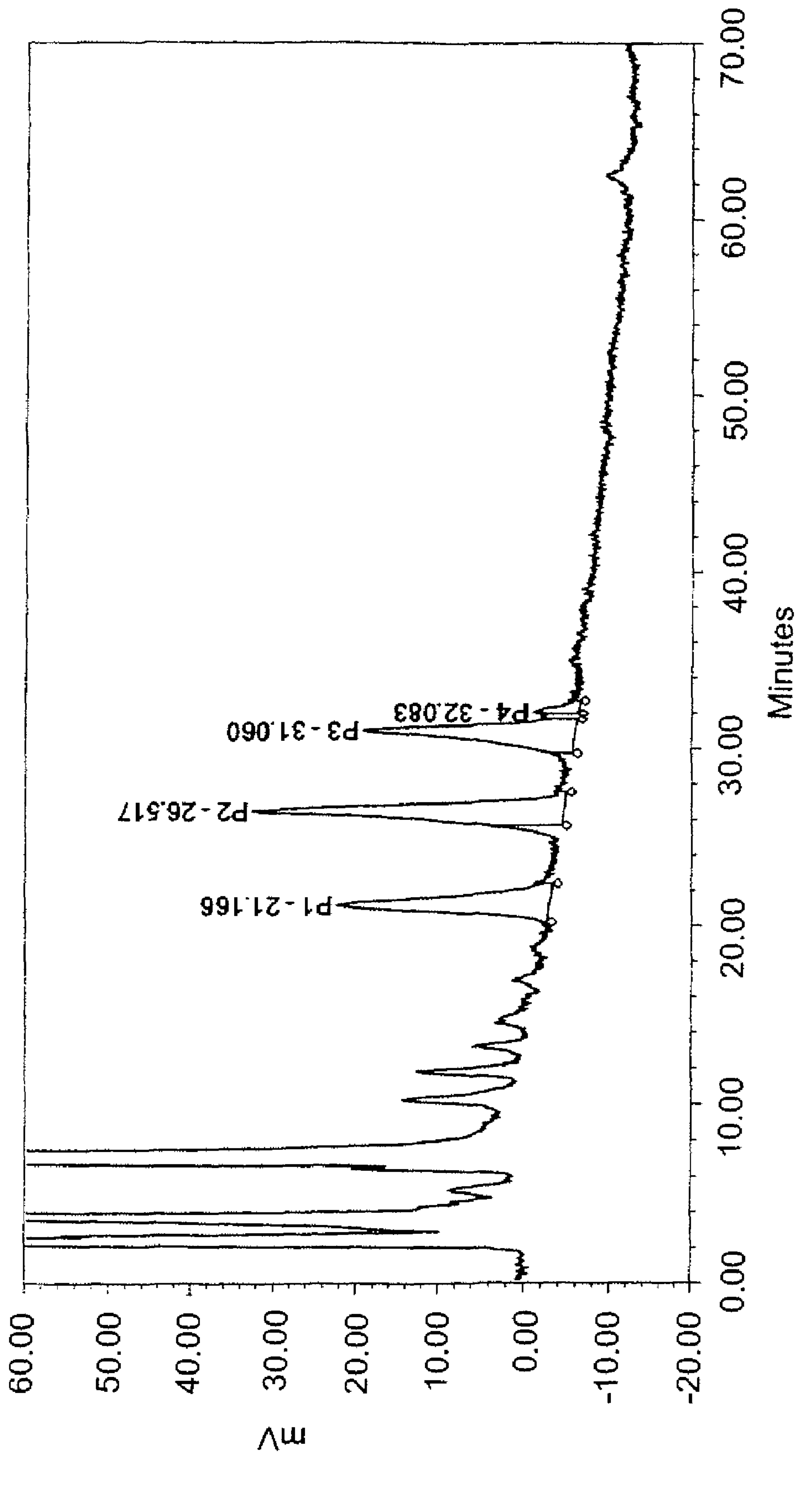
Figure 107C:
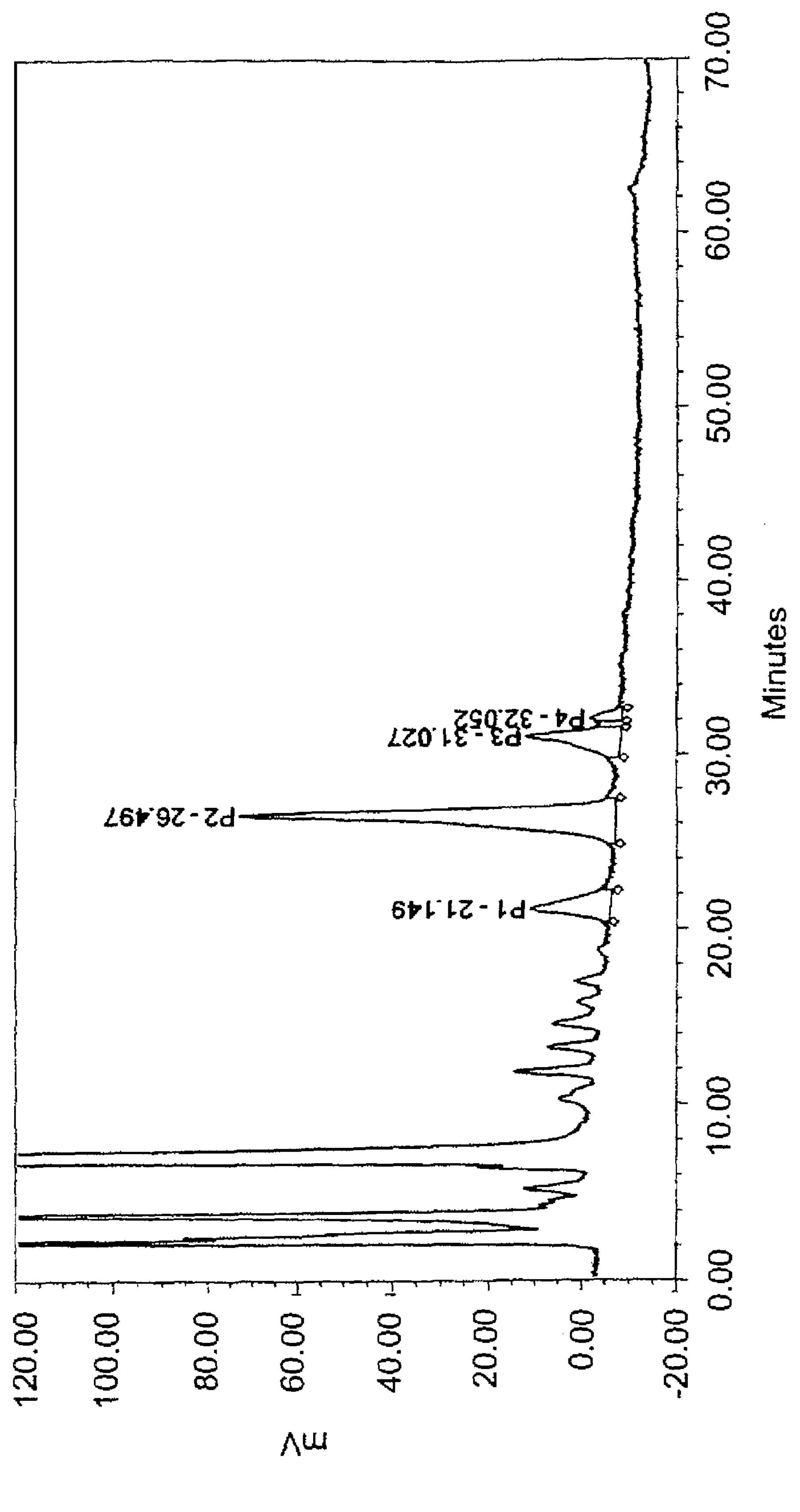
Figure 108A:
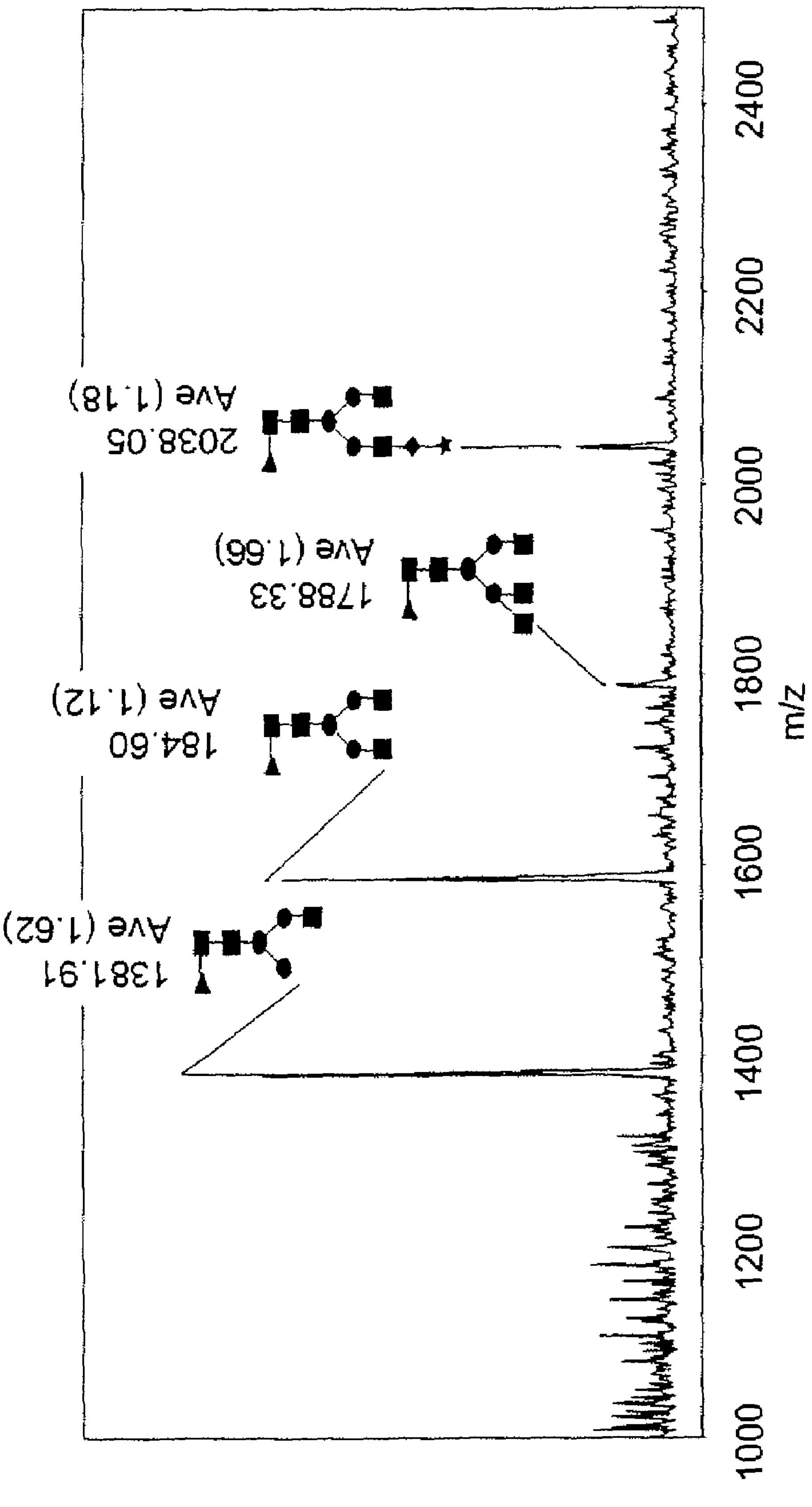
FIGS. 108A to 108C, are graphs depicting MALDI analysis of glycans released from Cri-IgG1 antibodies that have been glycoremodeled by GnT-I treatment of M3N2 glycoforms. The released glycans were derivatized with 2-AA and then analyzed by MALDI.
Figure 108B:
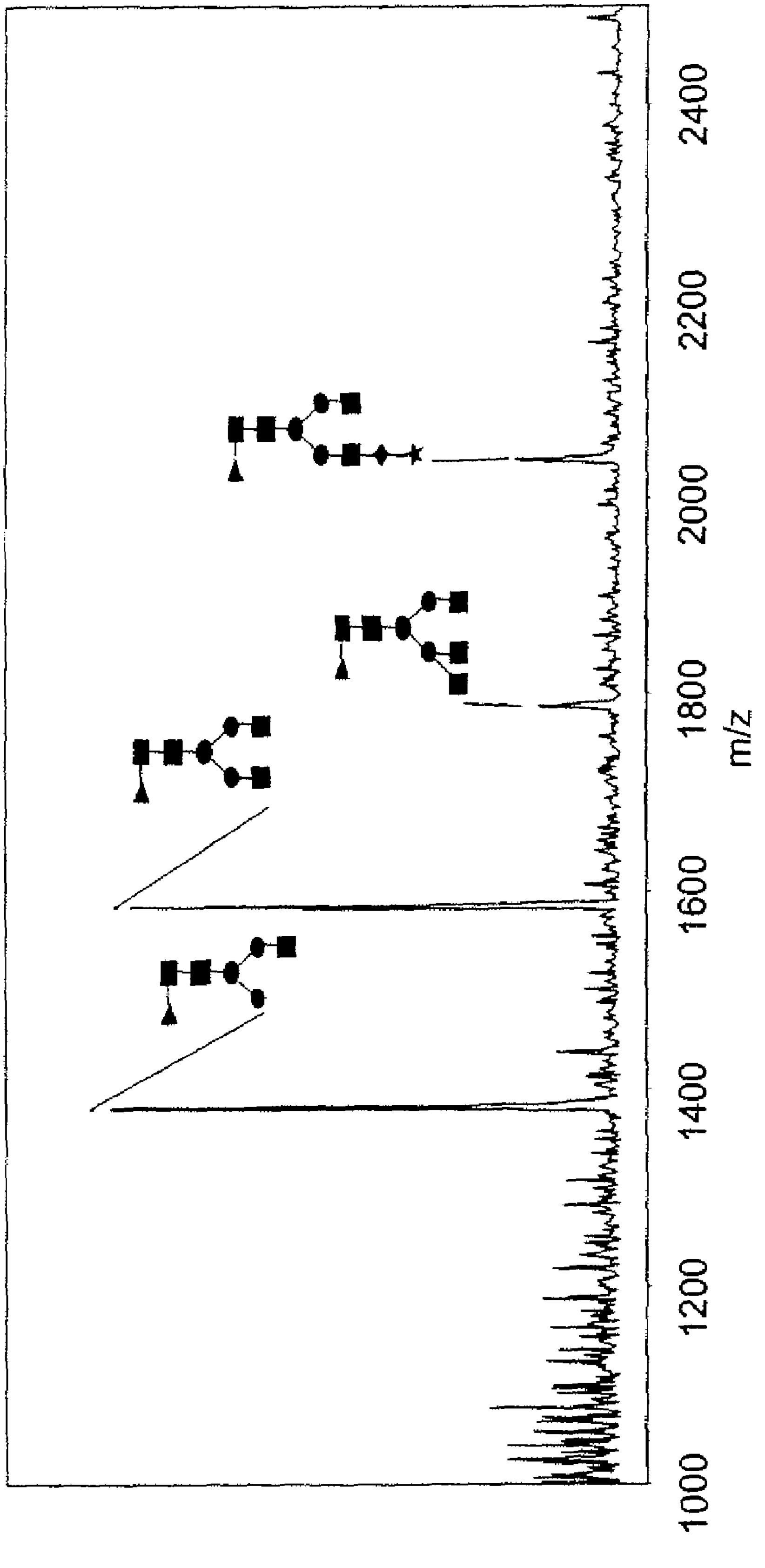
Figure 108C:
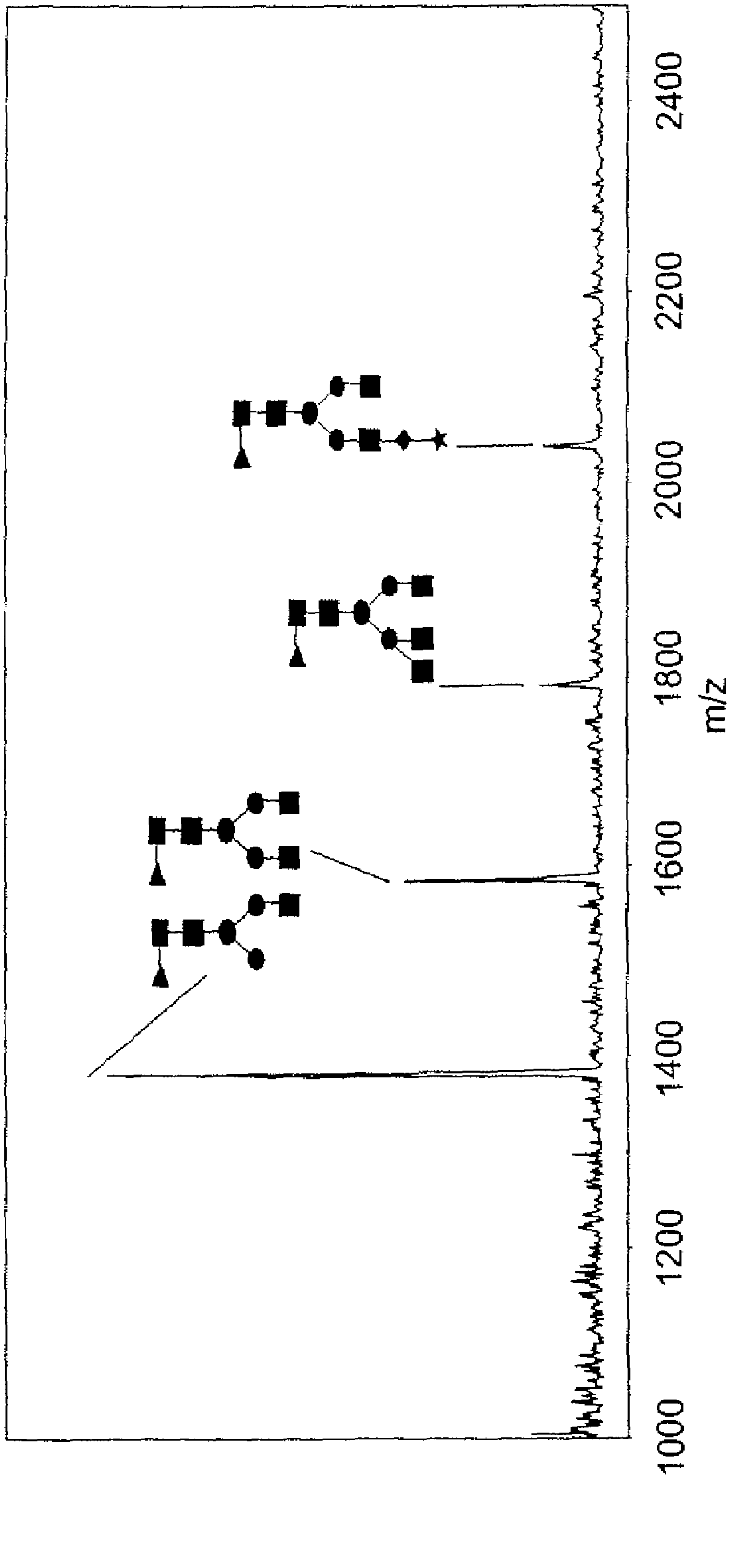
Figure 109A:
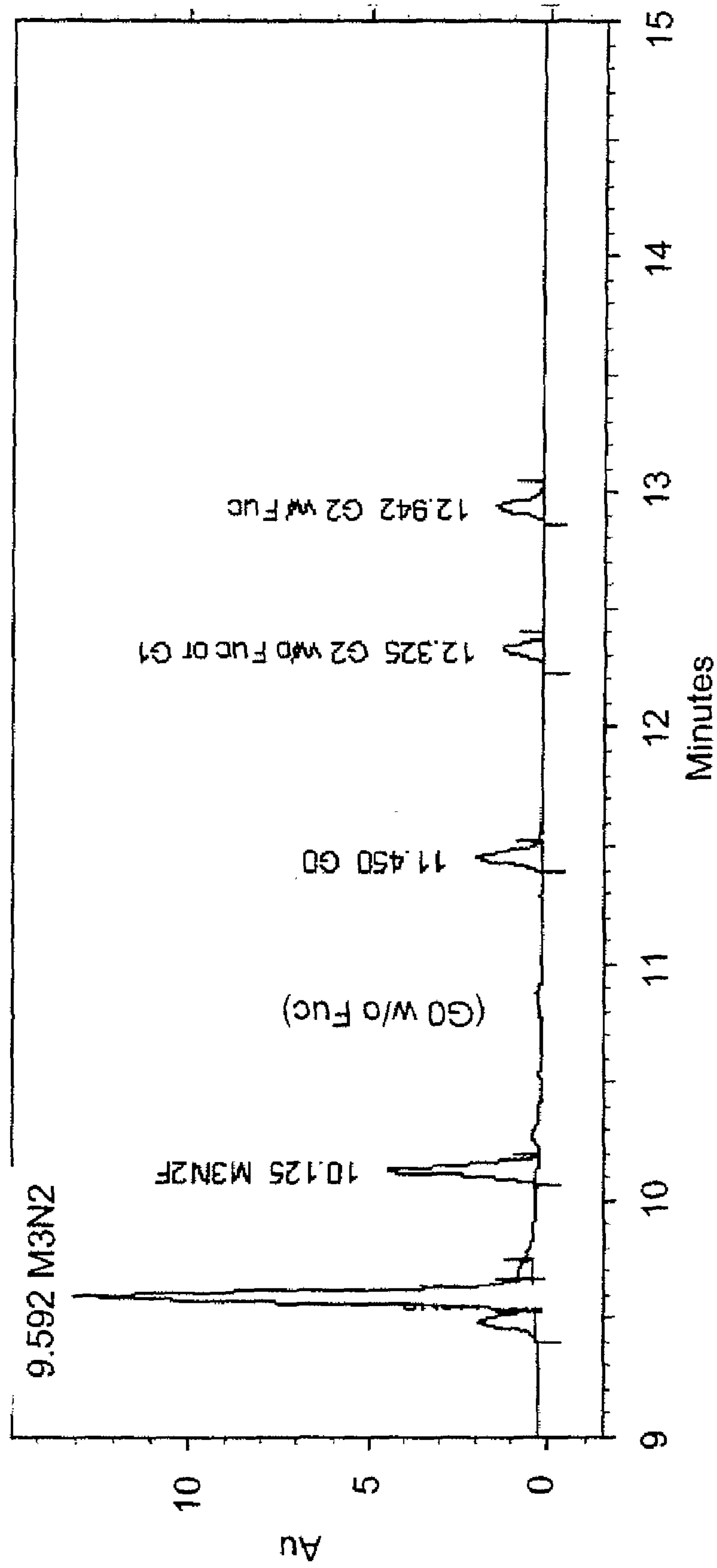
FIGS. 109A to 109D, are graphs depicting capillary electrophoresis of glycans released from Cri-IgG1 antibodies that have been glycoremodeled by GnT-I, II and III treatment of M3N2 glycoforms. A graph depicting the capillary electrophoresis analysis of glycan standards derivatized with APTS is shown in FIG. 109A.
Figure 109B:
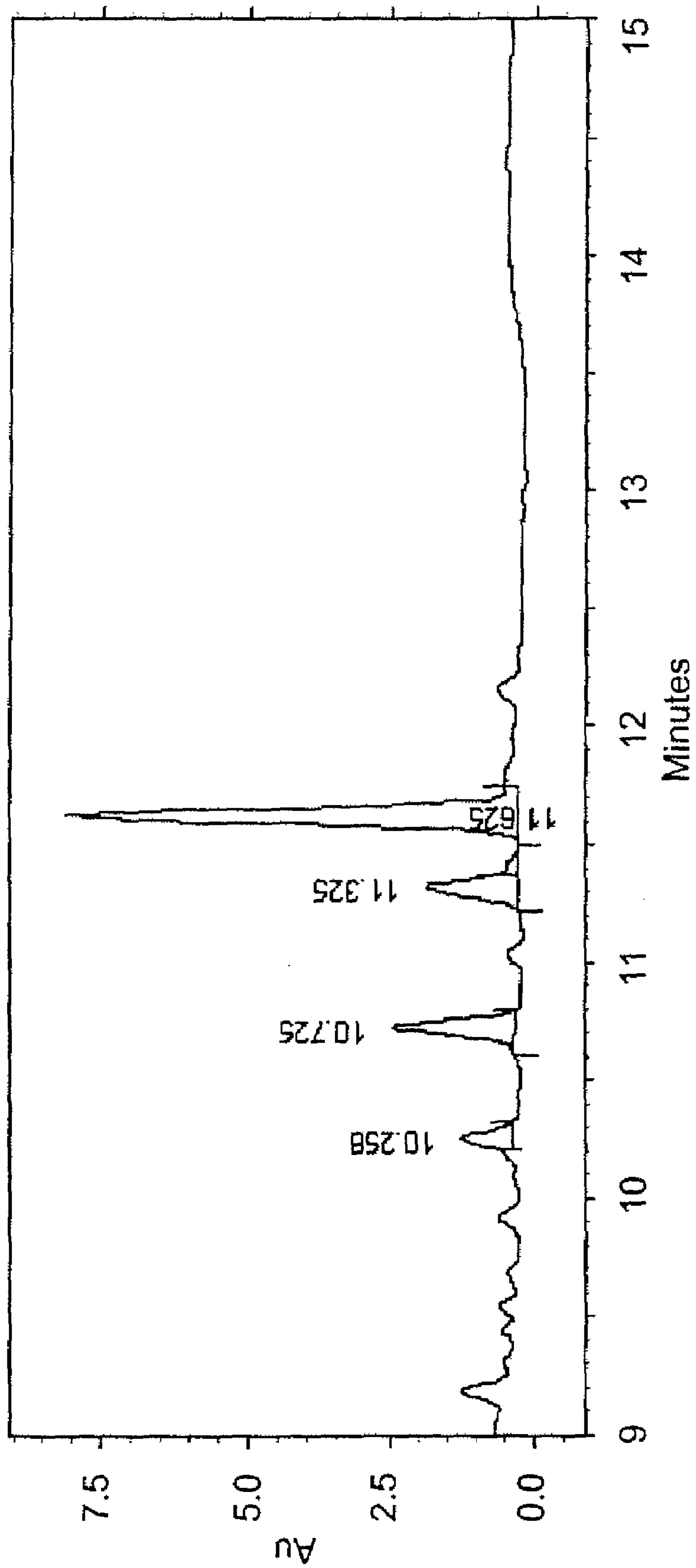
Figure 109C:
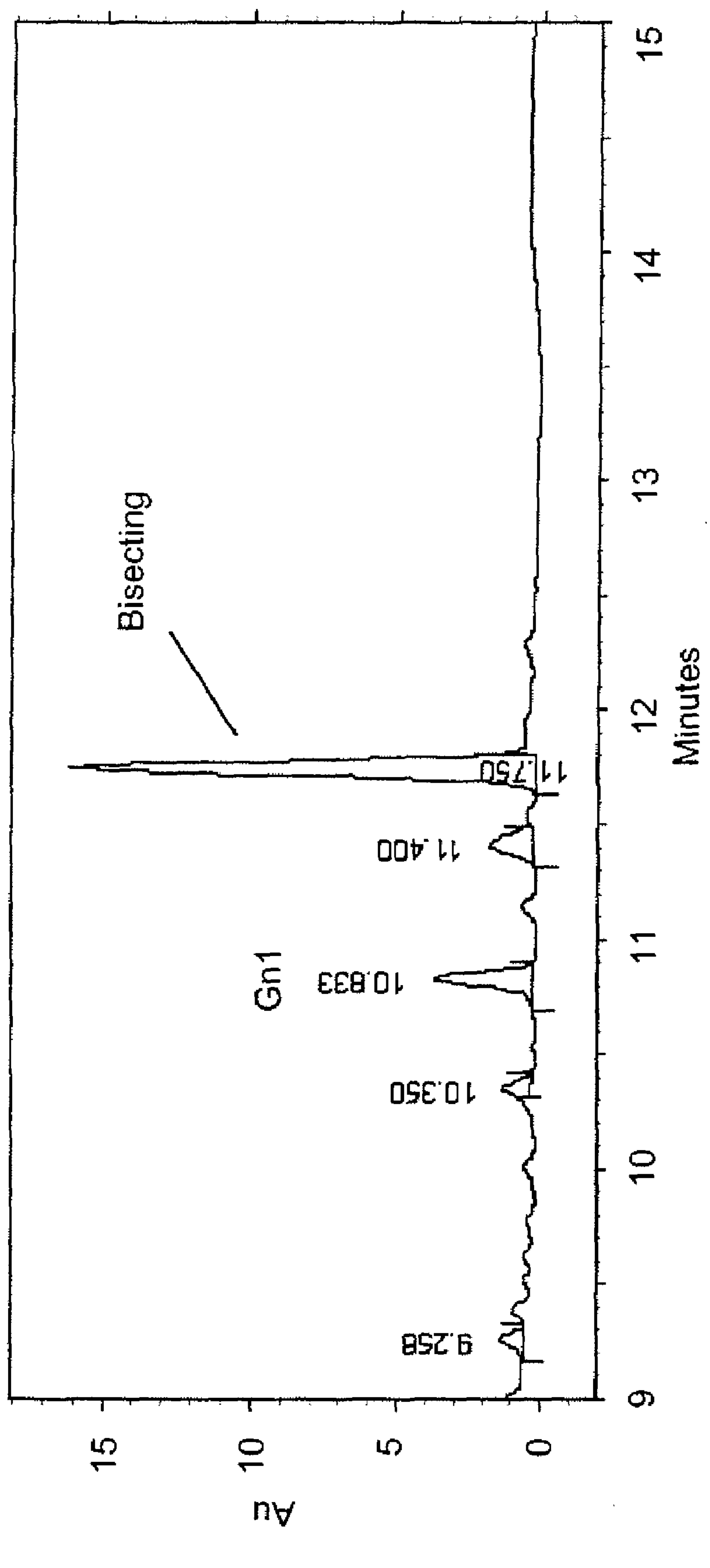
Figure 109D:
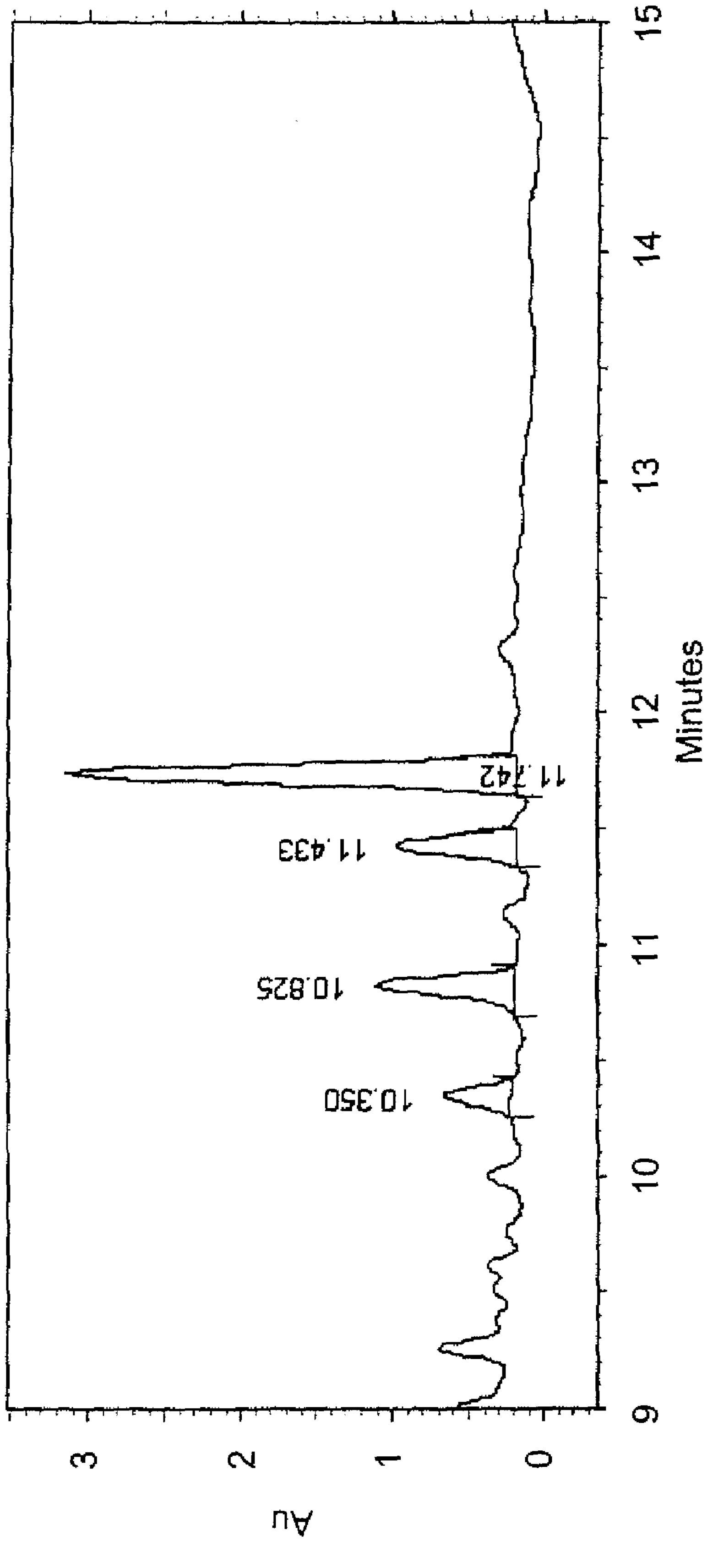

Fully galactosylated G2 glycoform (G2). Cri-IgG antibodies were treated with neuraminidase to yield asialo-glycoforms which were also under galactosylated. These asialoglycoforms were then treated with 0.6 U/ml of bovine β1,4 galactosyltransferase and a galactose donor molecule to glycoremodel the antibody to have the G2 glycoform. The extent of terminal galactosylation was determined by glycan analysis. Only one major peak was observed in both CE and HPLC profiles (FIGS. 103A-103C and FIGS. 104A-104C). This peak corresponds to the G2 glycoform in each case. Calculation of the percent total peak area showed almost complete (~90%) conversion to the G2 from the under galactosylated glycoforms of the original samples (see, Table 14). These results are summarized in Table 17. MALDI analysis of the glycans further supported the almost to complete glycoremodeling to the G2 glycoform in all of the samples (FIGS. 105A-105C).

TABLE 17

Relative amount of G2 glycoform of remodeled Cri-IgI1 antibody determined by percent total peak area in CE and HPLC analysis.

| | CE | | HPLC | |
|---|---|---|---|---|
| | RT (min.) | % | RT (min.) | % |
| DEAE | 12.94 | 90 | 31.194 | 100 |
| SPA | 12.94 | 92 | 31.194 | 90 |
| Fc | 12.94 | 84 | 31.194 | 89 |

GnT-I-glycoform (GnT-I-M3N2). The M3N2 glycoform Cri-IgG antibody was glycoremodeled to the GnT-1-M3N2 glycoform by adding one GlcNAc moiety to the molecule. The molecule was contacted with 25 mU GnT-I/mg antibody and an appropriate GlcNAc donor molecule. CE, HPLC and MALDI analysis of released glycans (FIGS. 106A-106D, FIGS. 107A-107C and FIGS. 108A-108C, respectively) indicated that the original M3N2F glycoform was completely remodeled. However, only 40-60% of the modified structures were the GnT-1-M3N2 glycoform, and about 30% were the G0 glycoform. The presence of the G0 glycoform may be the result of incomplete GlcNAc trimming when making the original M3N2 form.

Bisecting glycoform (NGA2F). The M3N2 glycoform Cri-IgG antibody was glycoremodeled to the NGA2F glycoform by contacting it with a combination the three transferases, GnT-I, GnT-II and GnT-III, and an appropriate N-acetylglucosamine donor molecule. The reaction was completed in 24 hours. To determine the extent to which the bisecting-GlcNAc moiety was added to the glycans, CE analysis was used to determine the glycoforms present on the glycoremodeled antibody.

Figure 110A:
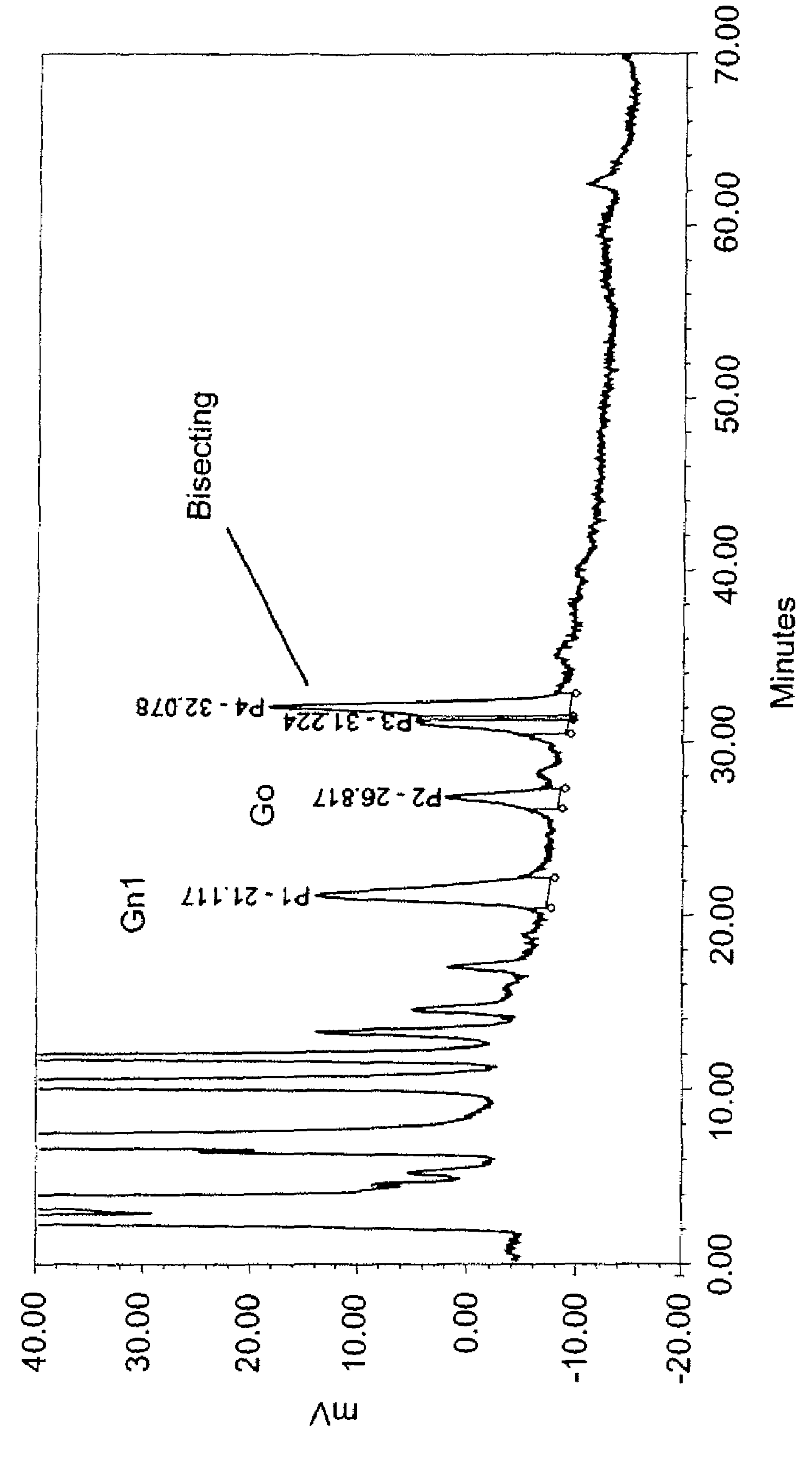
FIGS. 110A to 110C, are graphs depicting 2-AA HPLC analysis of glycans released from Cri-IgG1 antibodies that have been glycoremodeled by GnT-I, II and III treatment of M3N2 glycoforms. The released glycans were labeled with 2AA and then separated by HPLC on a NH2P-50 4D amino column.
Figure 110B:
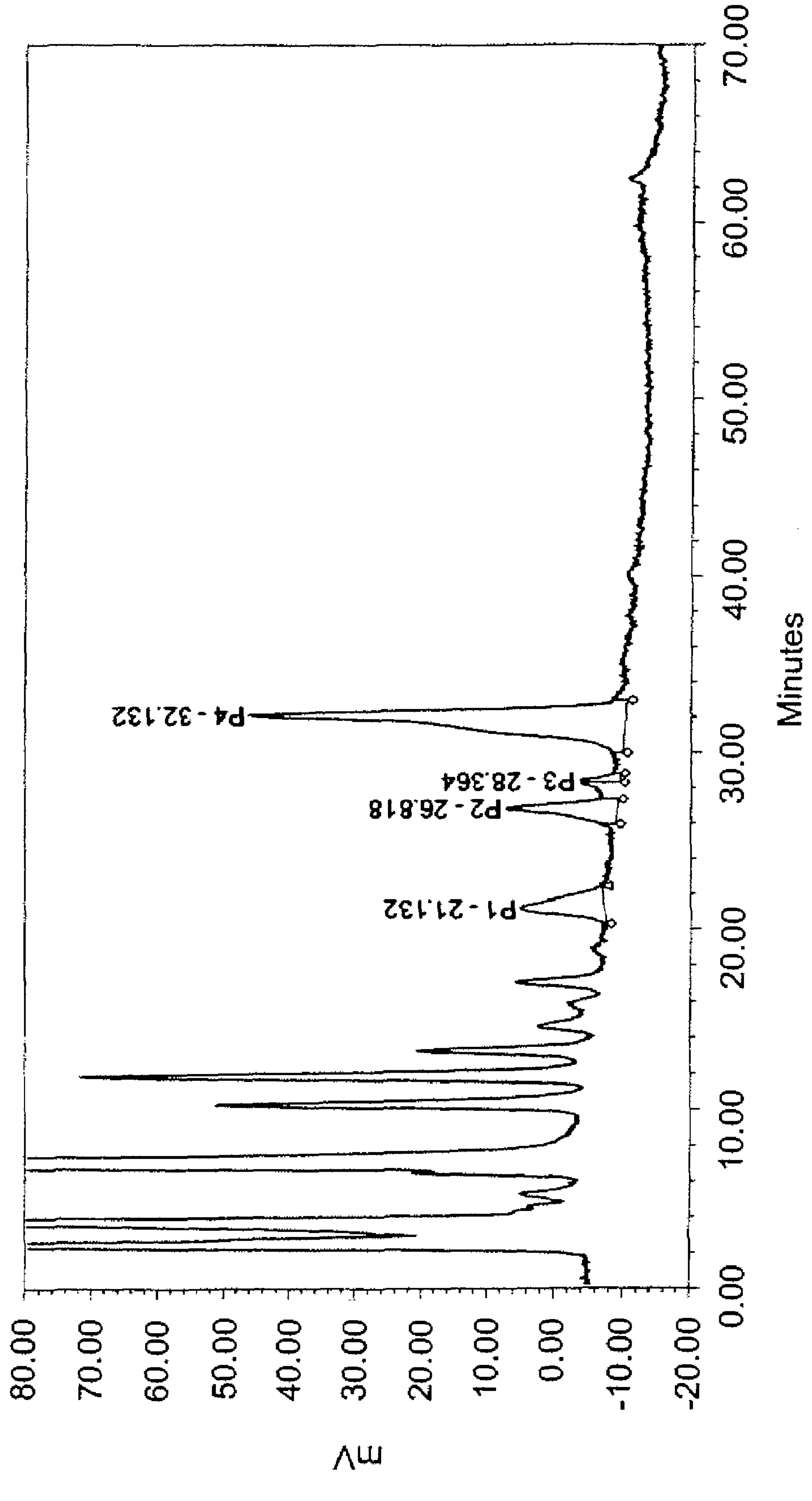
Figure 110C:
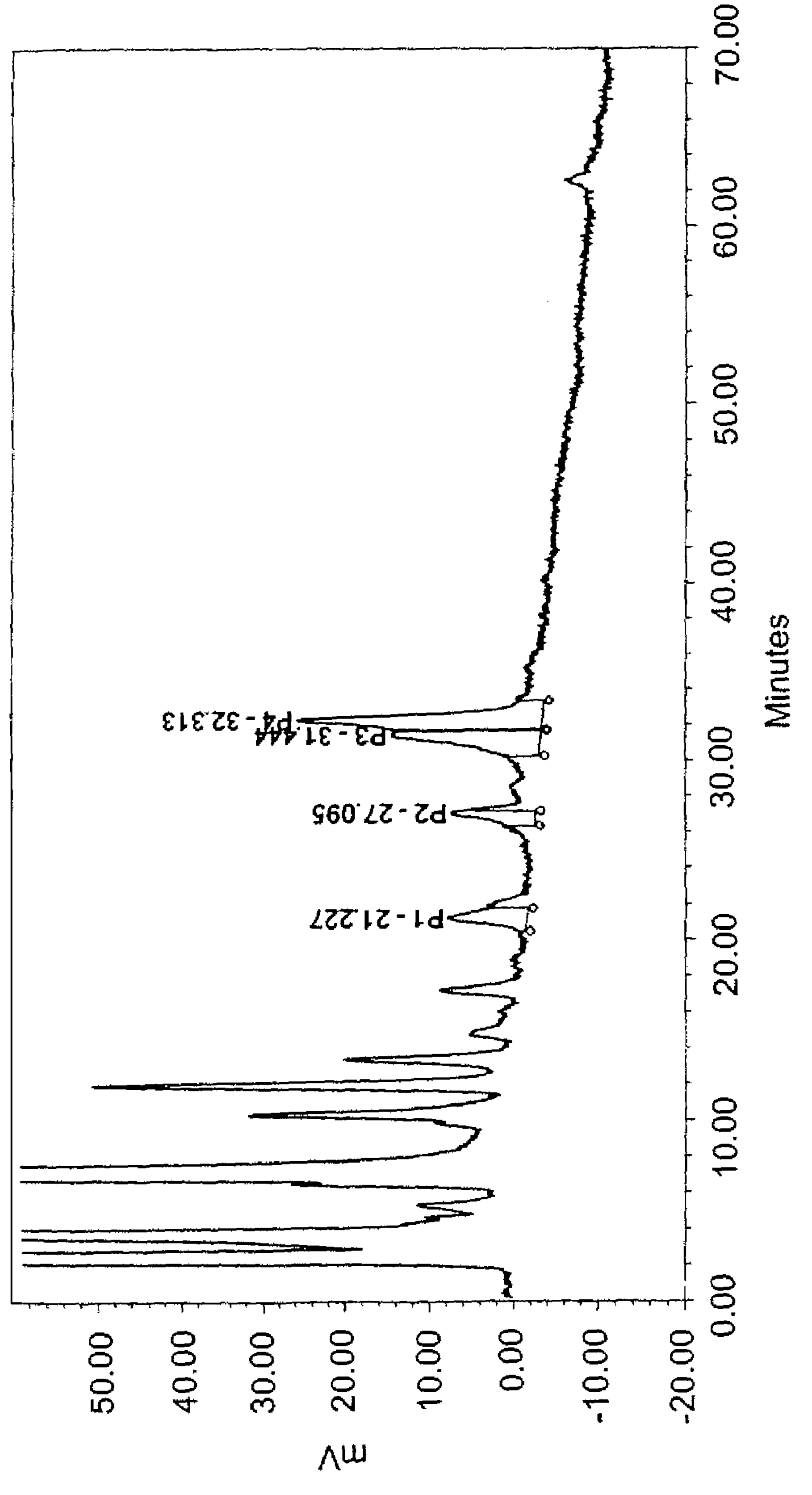
Figure 111A:
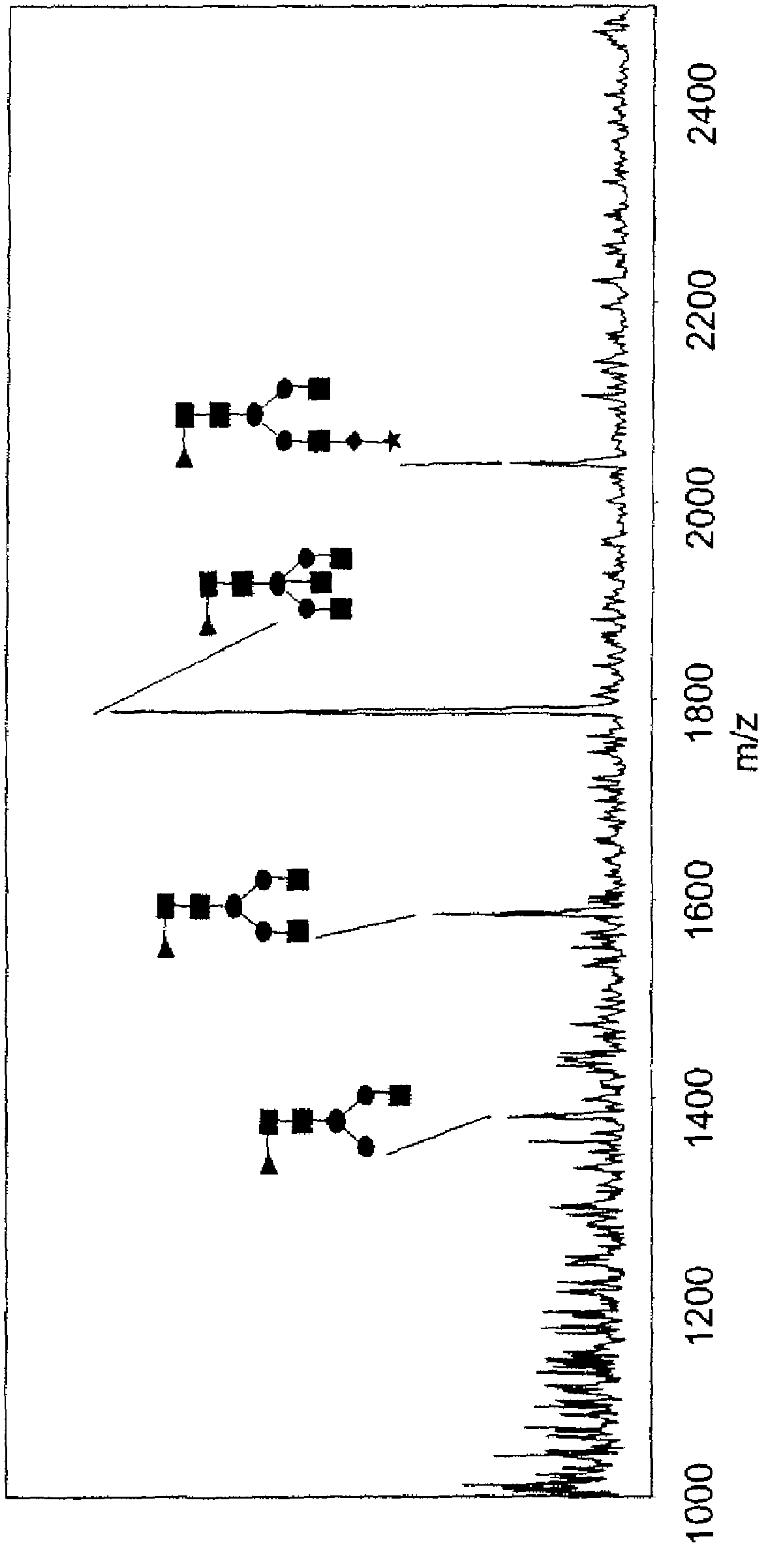
FIGS. 111A to 111C, are graphs depicting MALDI analysis of glycans released from Cri-IgG1 antibodies that have been glycoremodeled by galactosyltransferase treatment of NGA2F glycoforms. The released glycans were derivatized with 2-AA and then analyzed by MALDI.
Figure 111B:
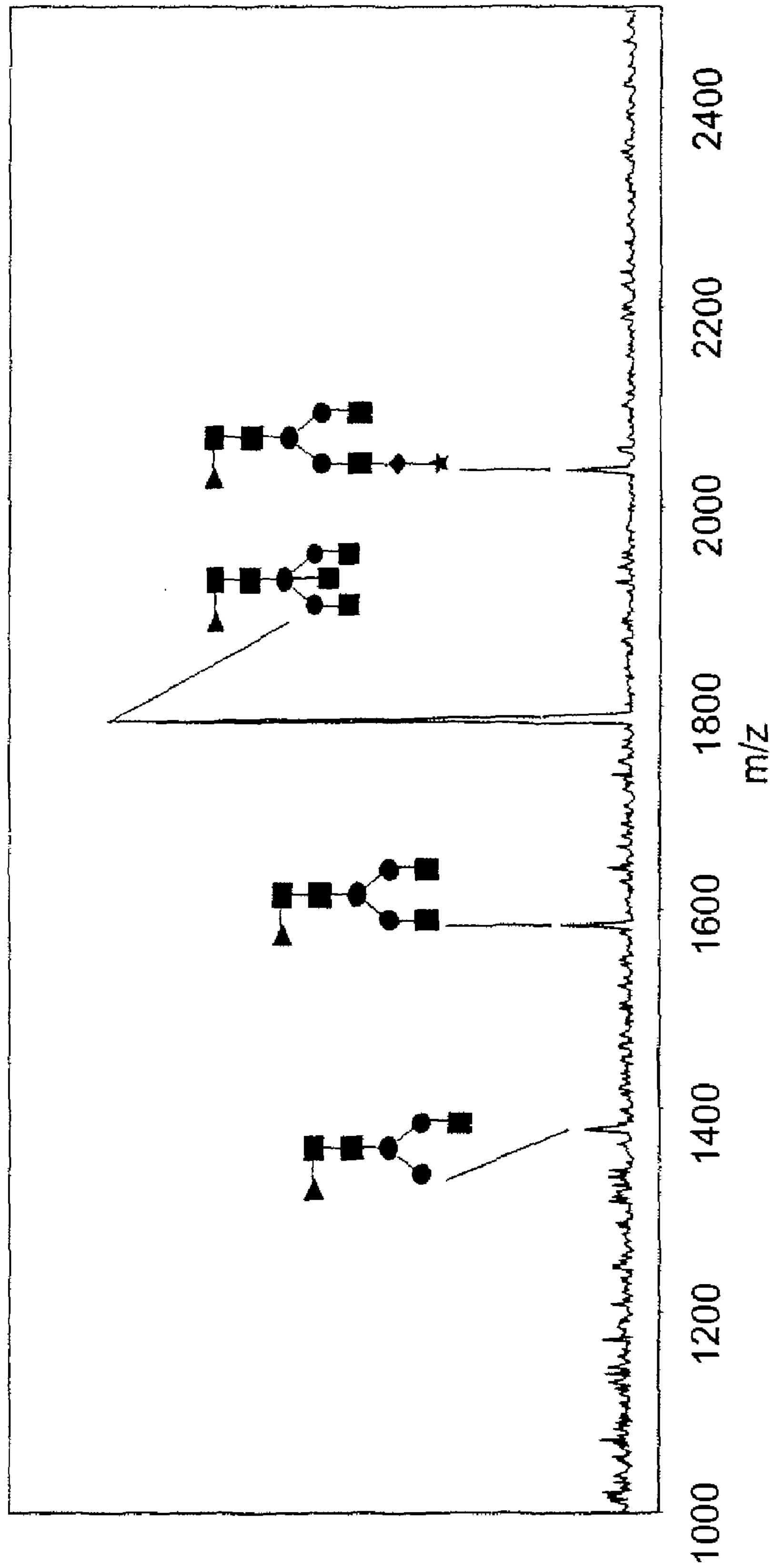
Figure 111C:
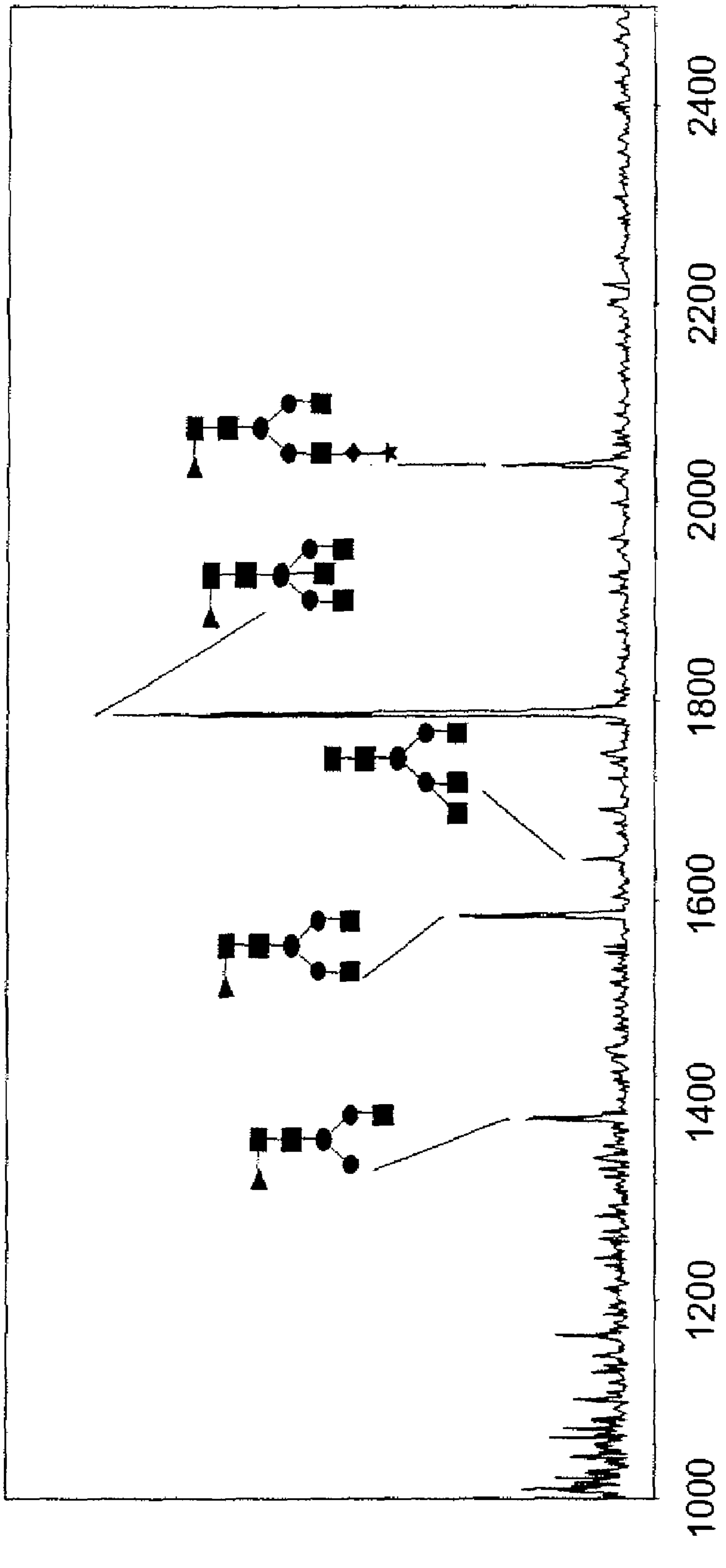

FIGS. 109A-109D shows the electropherograms obtained from CE analysis of the glycans released from glycoremodeled Cri-IgG1 antibody. Four peaks appeared after remodeling. A major peak migrated at the same retention time as the NGA2F standard glycoform. The three other minor peaks are likely to be the incompletely remodeled glycans. For comparison, a quantitative HPLC method was also used, where the 2-AA labeled glycans eluted in order of increasing size (Gn1<G0<NGA2F). As shown in FIG. 110A-110C, similar results were obtained from the CE analysis of the glycans. No M3N2F was found using either the CE or HPLC analysis. NGA2F glycans were the major peaks I both CE and HPLC analysis. The Gn1 and G0 glycans still remaining in the sample likely are the result of incomplete modification. Most of the original M3N2F glycoforms were remodeled by three GlcNAc moieties to the NGA2F glycoform (60~70%), about 15~18% were remodeled by the addition of two GlcNAc moieties to the G0 glycoform, and only small amount (~7%) were remodeled by the addition of only one GlcNAc moiety. MALDI-MS analysis of the released glycans (FIGS. 111A-111C) shows peaks of glycoforms with one, two or three terminal GlcNAc moieties, in agreement with CE and HPLC analysis (FIGS. 109 and 110). The relative amount of each glycan species was calculated from the relative area percentage of each indicated peak, and is summarized in Table 18.

TABLE 18

Relative amounts of different glycoforms from GnT-I, II, and III remodeled Cri-IgG1, as determined by CE and HPLC.

| | | Retention (min.) | % Peak Area DEAE | SPA | Fc |
|---|---|---|---|---|---|
| CE | Peak 1 | 10.238 | 6.39 | 6.89 | 7.98 |
| | Peak 2 | 10.775 | 15.82 | 14.29 | 17.9 |
| | Peak 3 | 11.325 | 14.14 | 8.87 | 15.69 |
| | Bisec. | 11.625 | 63.65 | 70.04 | 58.43 |
| HPLC | Peak 1 | 21.117 | 37.4 | 15.02 | 14 |
| | Peak 2 | 26.817 | 12.9 | 14.24 | 10.15 |
| | Peak 3 | 31.224 | 14.78 | 2.11 | 30.2 |
| | Bisec. | 32.078 | 34.93 | 68.63 | 45.64 |

Figure 112A:
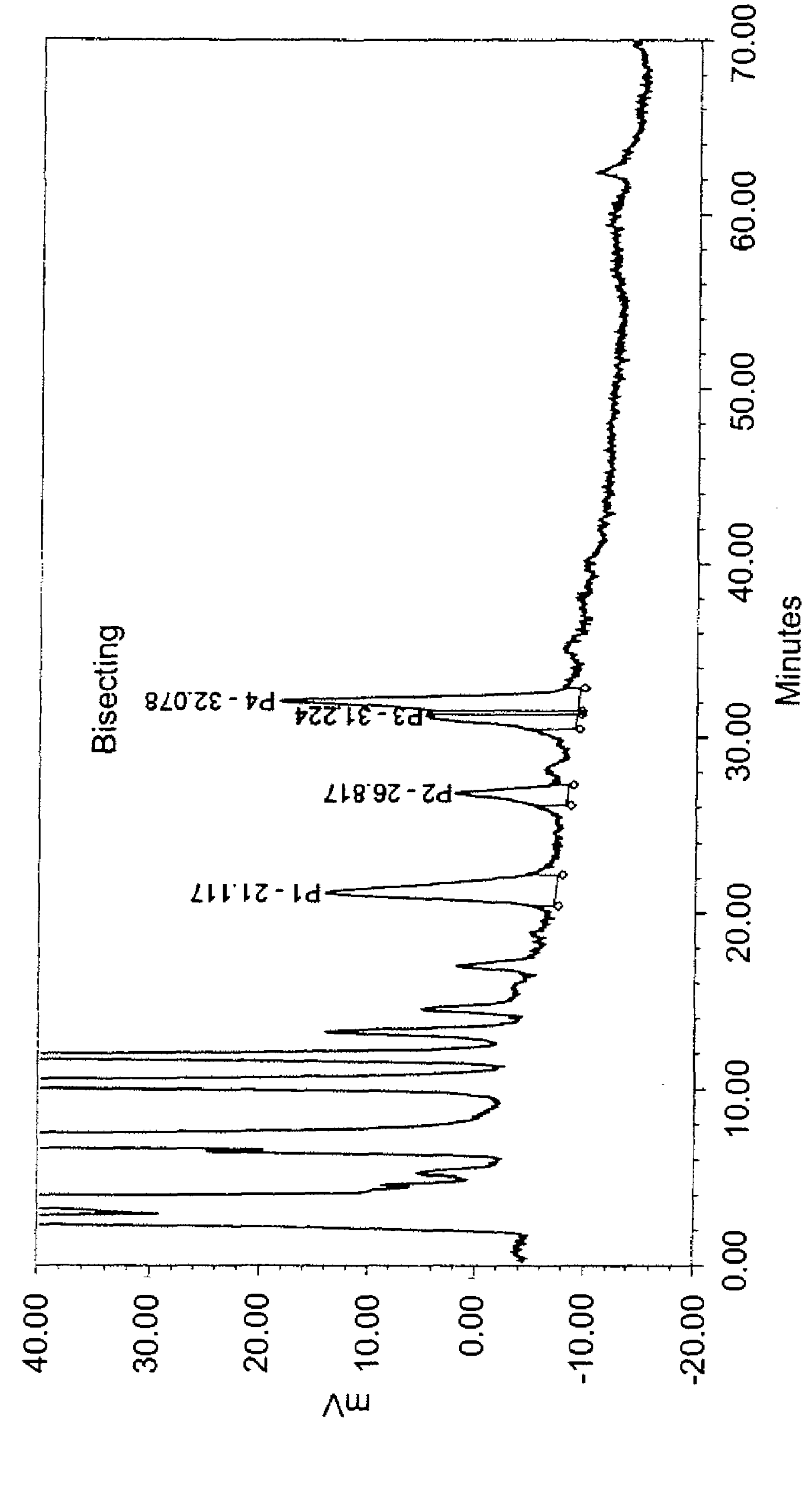
FIGS. 112A and 112B depict the analysis of the DEAE sample of antibodies.
Figure 112B:
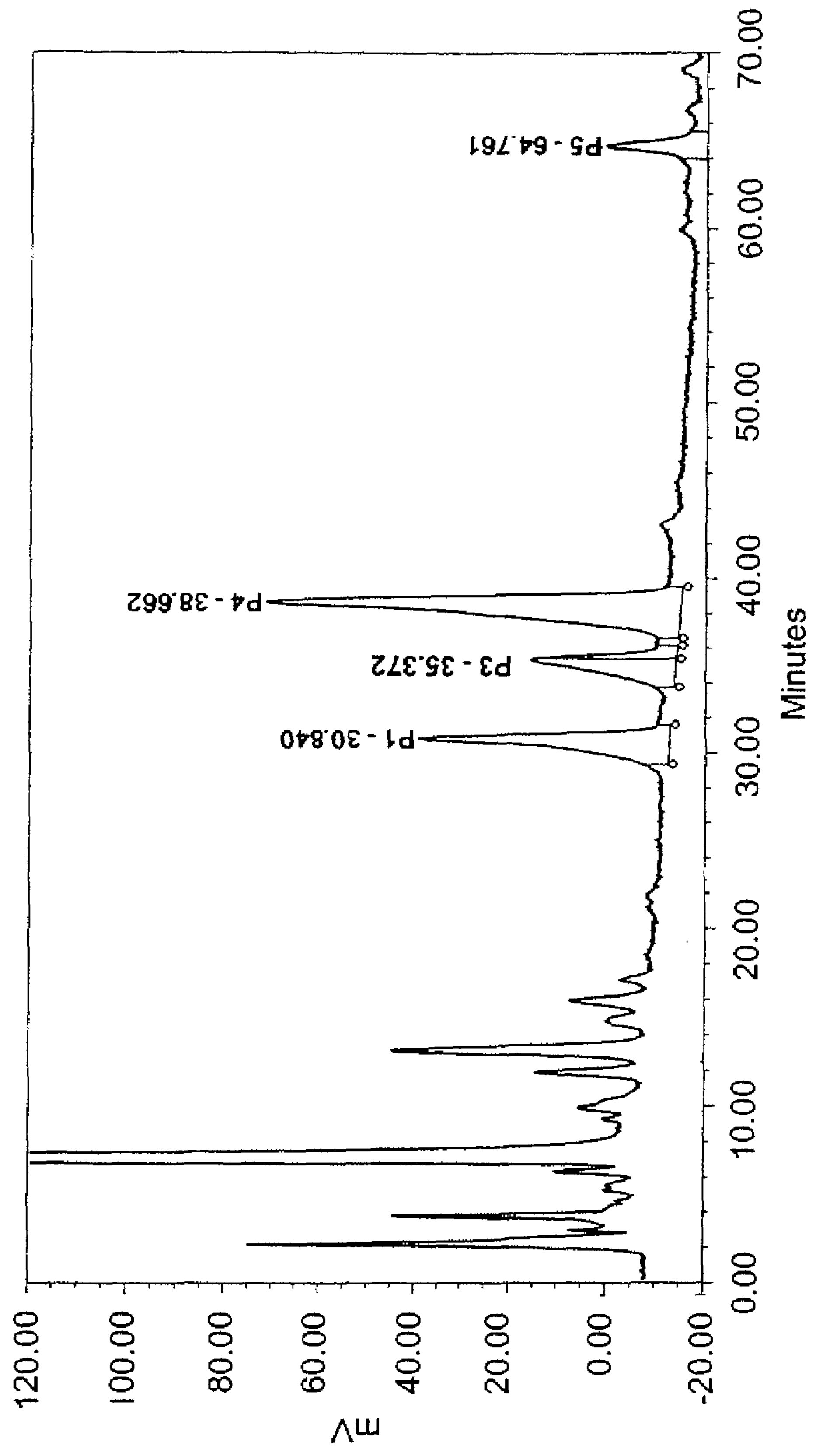
Figure 112C:
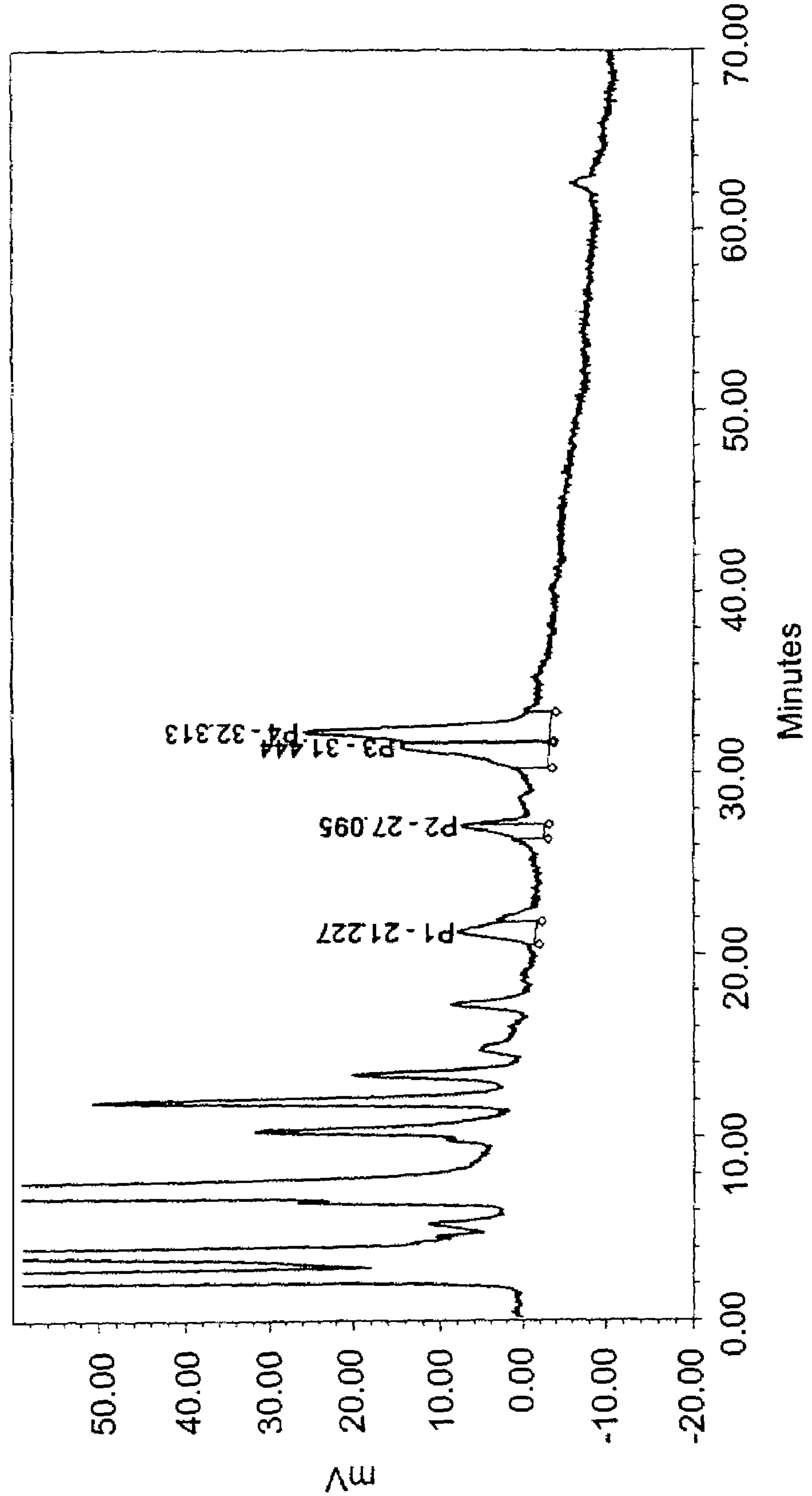
FIGS. 112C and 112D depict the analysis of the Fc sample of antibodies. The released glycans were labeled with 2AA and separated by HPLC on a NH2P-50 4D amino column.
Figure 112D:
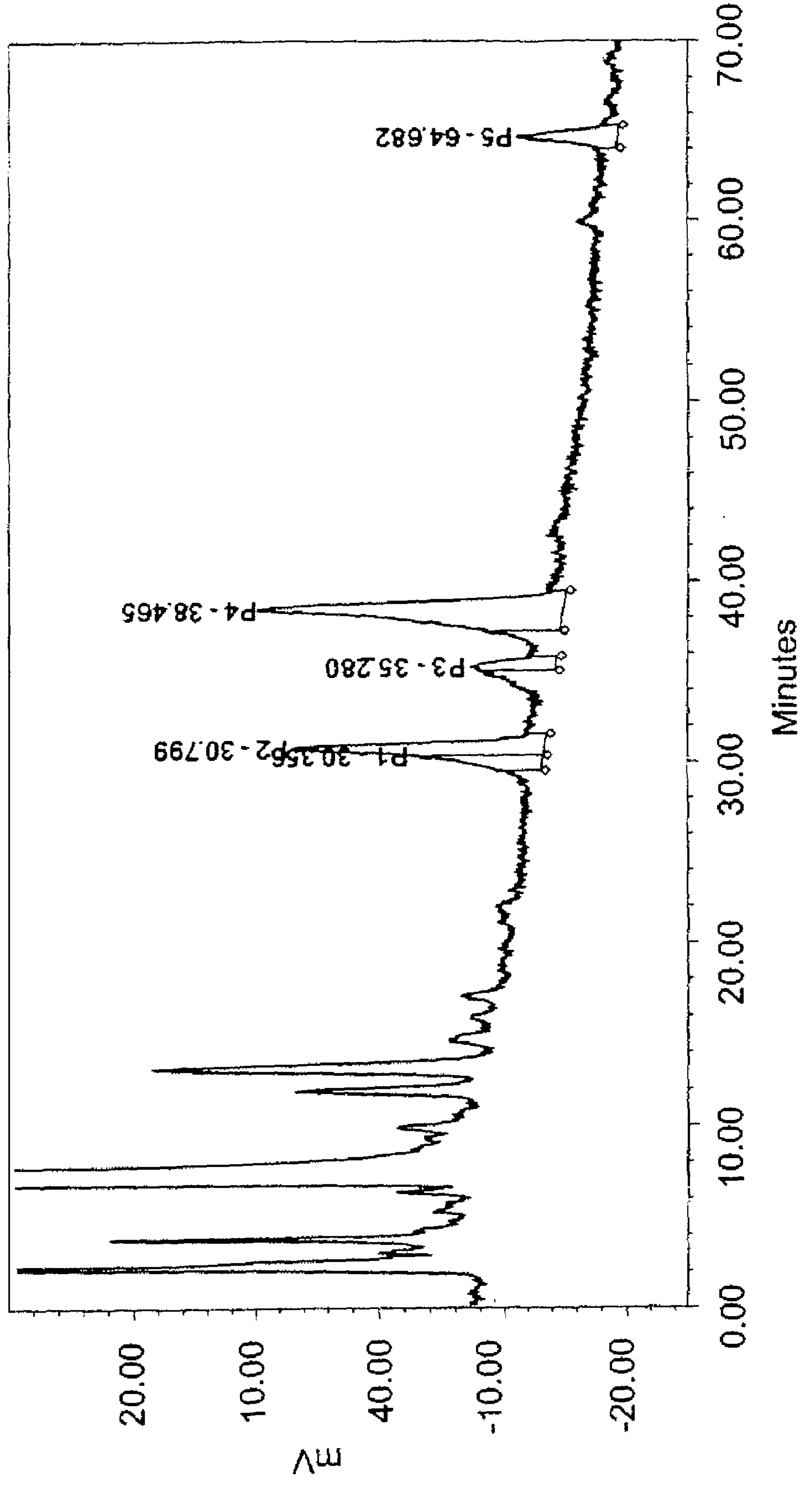

Galactosylated Bisecting (Gal-NGA2F) glycoforms. NGA2F glycoforms of Cri-IgG1 antibodies were glycoremodeled with bovine β1,4-galactosyltransferase and an appropriate galactose donor. The terminal galactose moieties were added using 0.6 U/ml of β1,4 galactosyltransferase. FIGS. 112A-112D shows the electropherograms obtained using the 2-AA HPLC method. In brief, the glycoforms terminating in GalNAc were almost 100% galactosylated. Comparing FIG. 112A to FIG. 112B for DEAE Cri-IgG1, and FIG. 112C to FIG. 112D for Fc Cri-IgG1, the 2-AA HPLC profile of GnT-I, II and III modified glycans (FIGS. 112A and 112C) is modified by GalT1 so that all of the glycan peakes were shifted to elute later due to the size increase from added galactose moieties (FIGS. 112B and 112D). These results were further confirmed by MALDI-MS analysis.

Figure 113A:
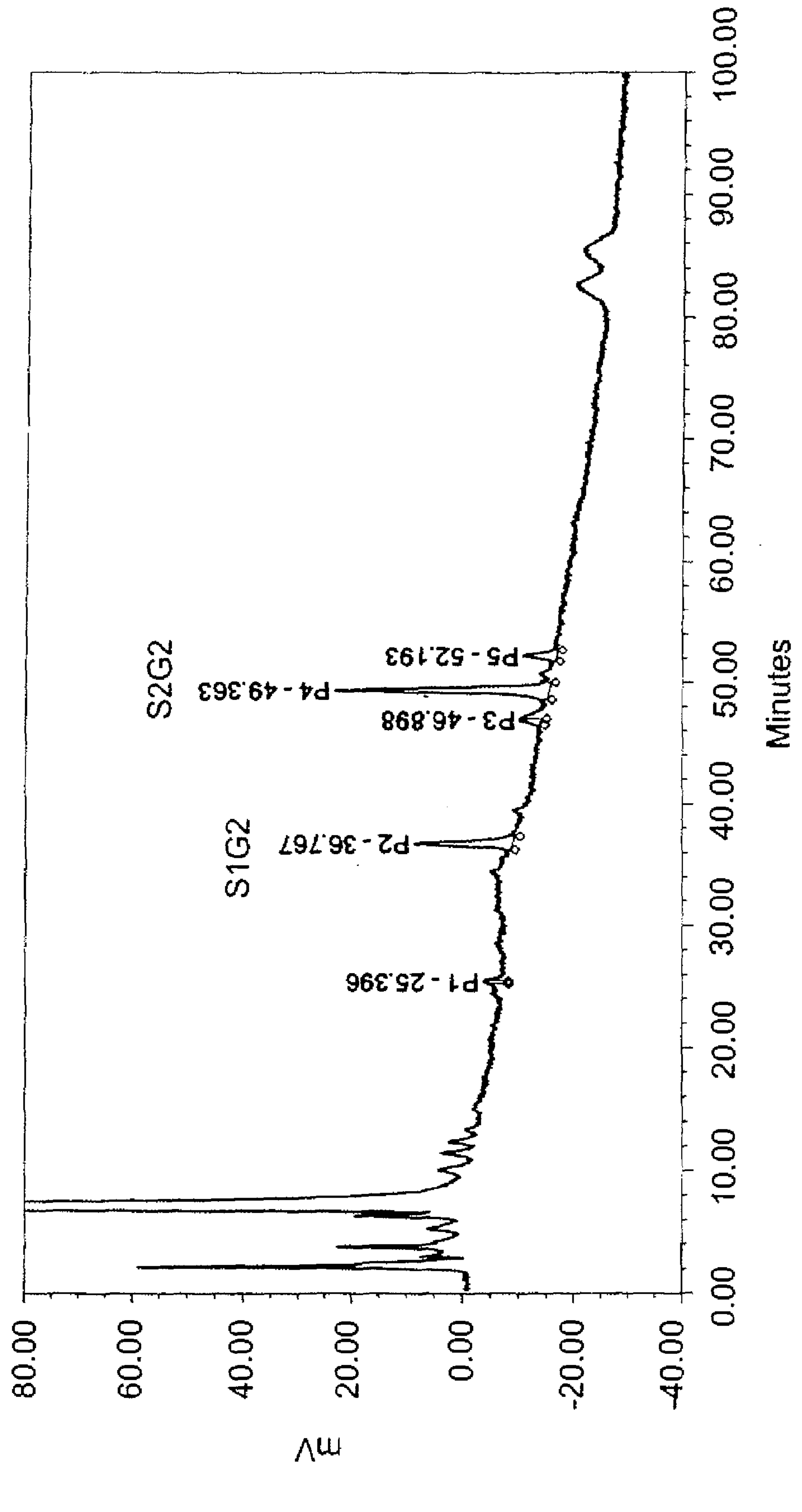
FIG. 113A depicts the analysis of the DEAE antibody sample.
Figure 113B:
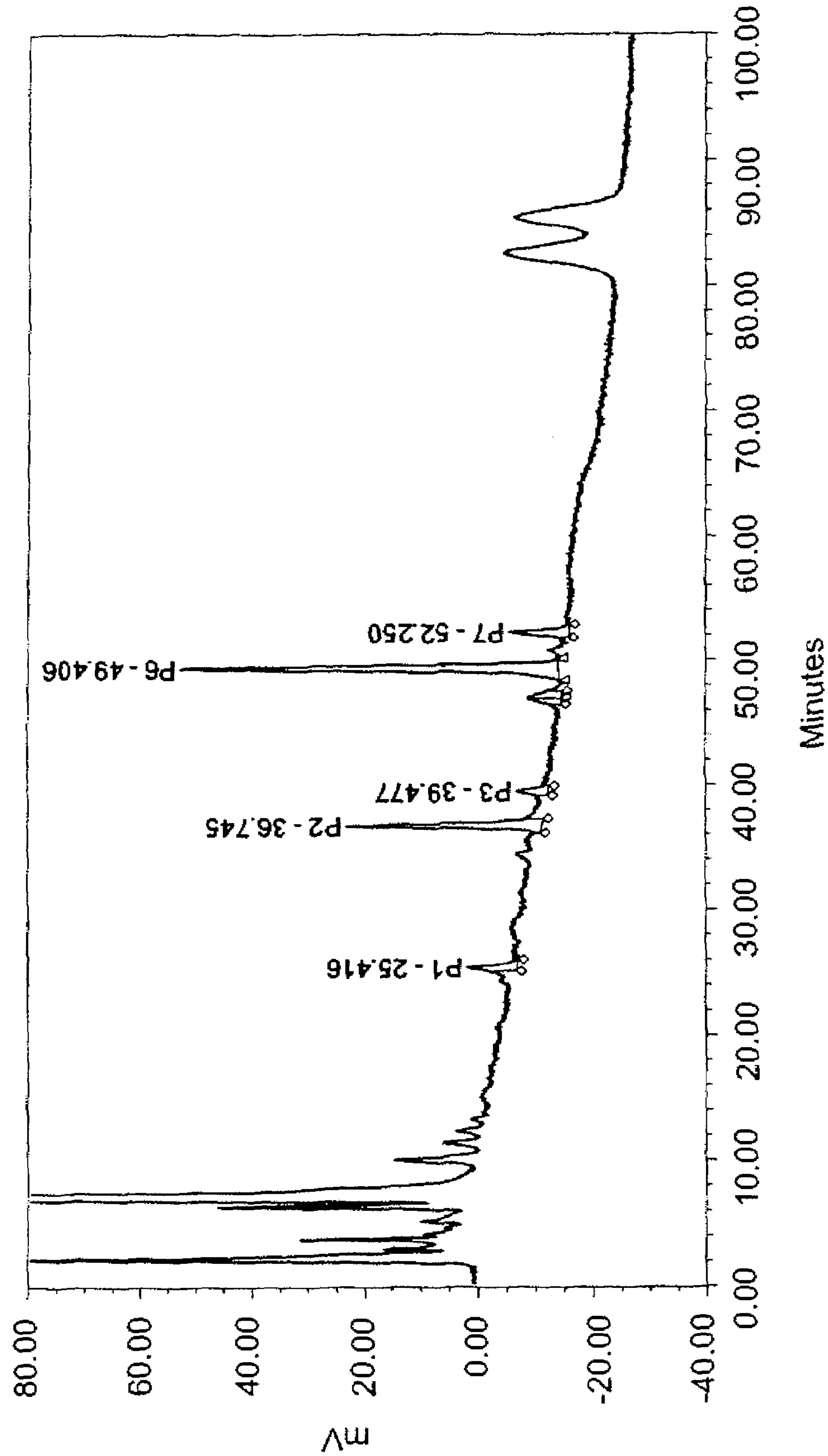
FIG. 113B depicts the analysis of the SPA antibody sample.
Figure 113C:
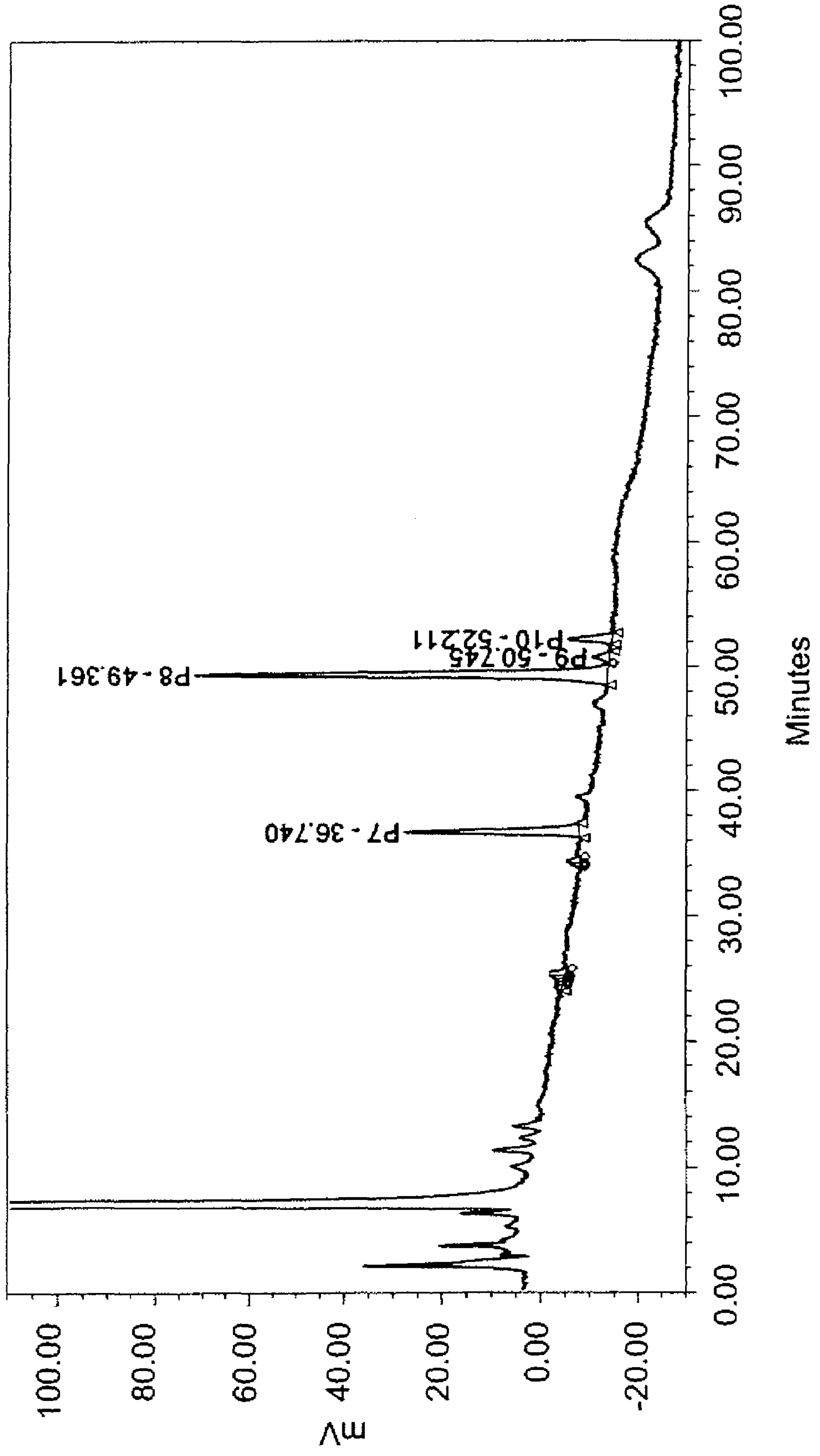
FIG. 113C depicts the analysis of the Fc antibody sample. The percent area under the peaks for these graphs is summarized in Table 19.
Figure 114A:
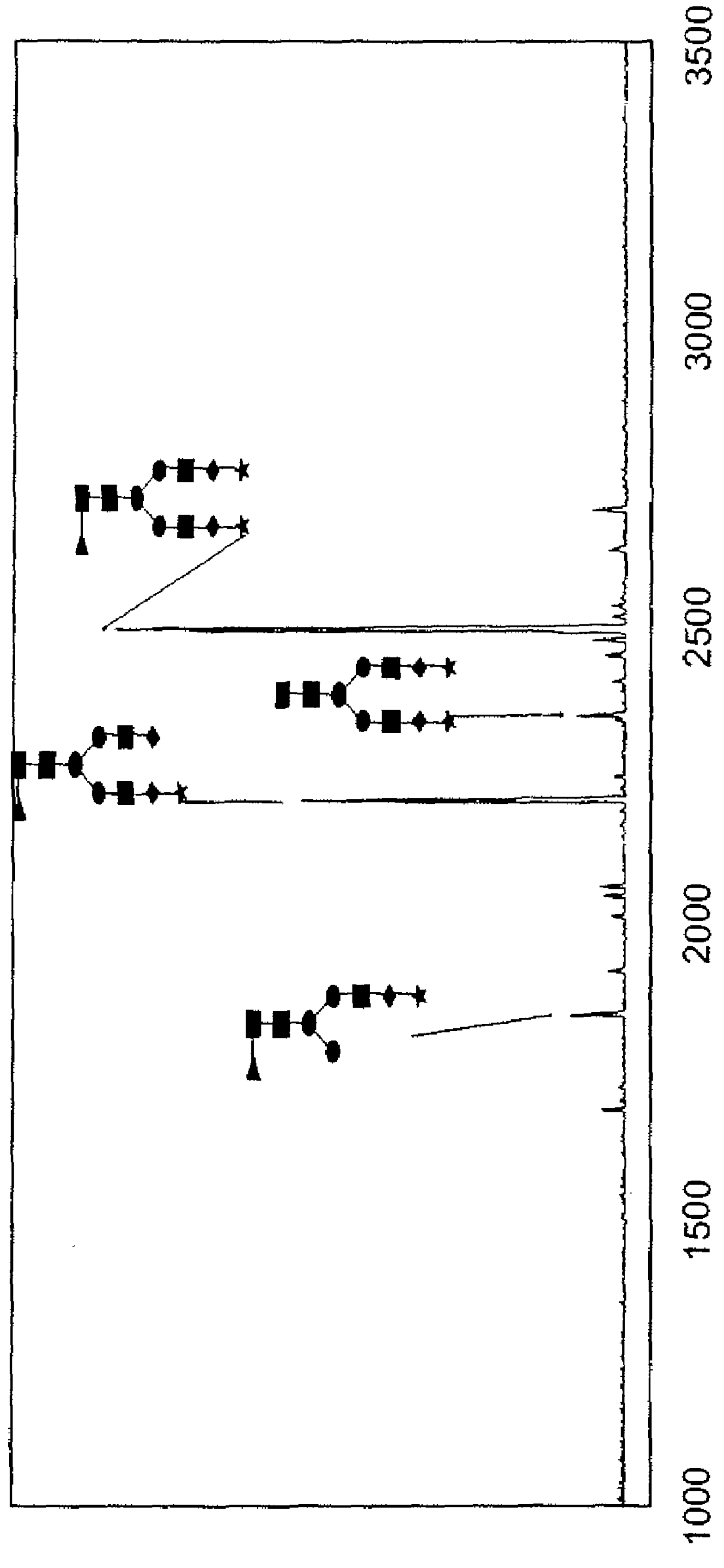
FIGS. 114A to 114C, are graphs depicting MALDI analysis of glycans released from Cri-IgG1 antibodies that had been glycoremodeled by ST3Gal3 treatment of G2 glycoforms. The released glycans were derivatized with 2-AA and then analyzed by MALDI.
Figure 114B:
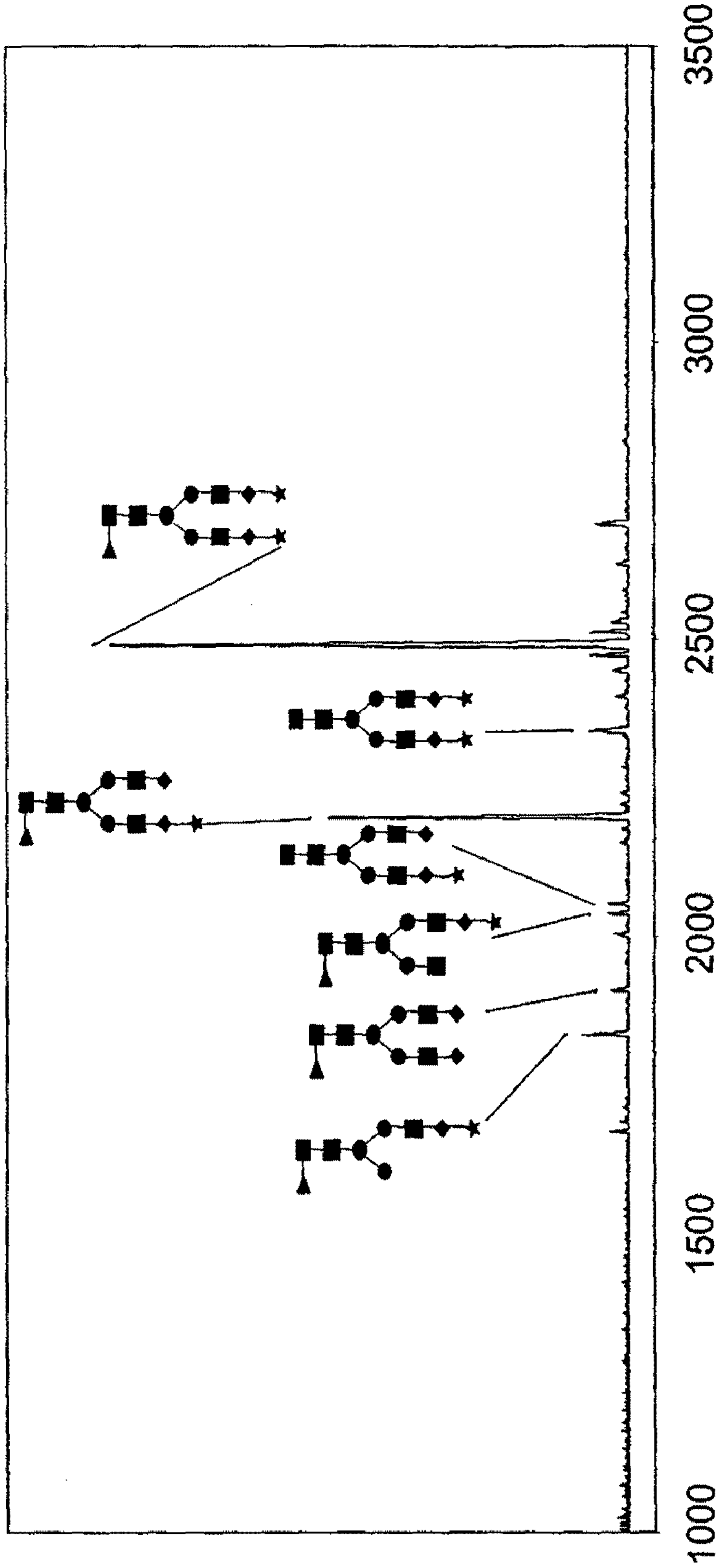
Figure 114C:
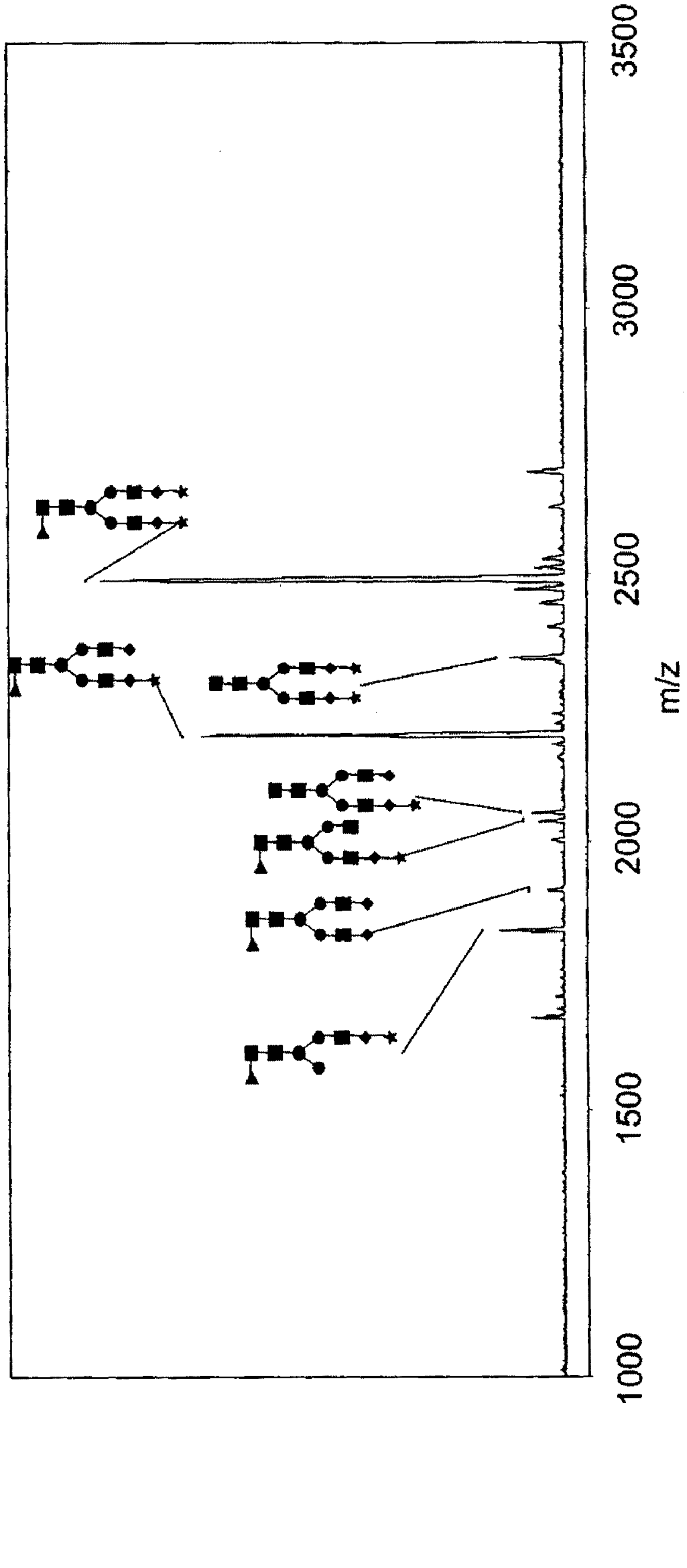
Figure 115A:
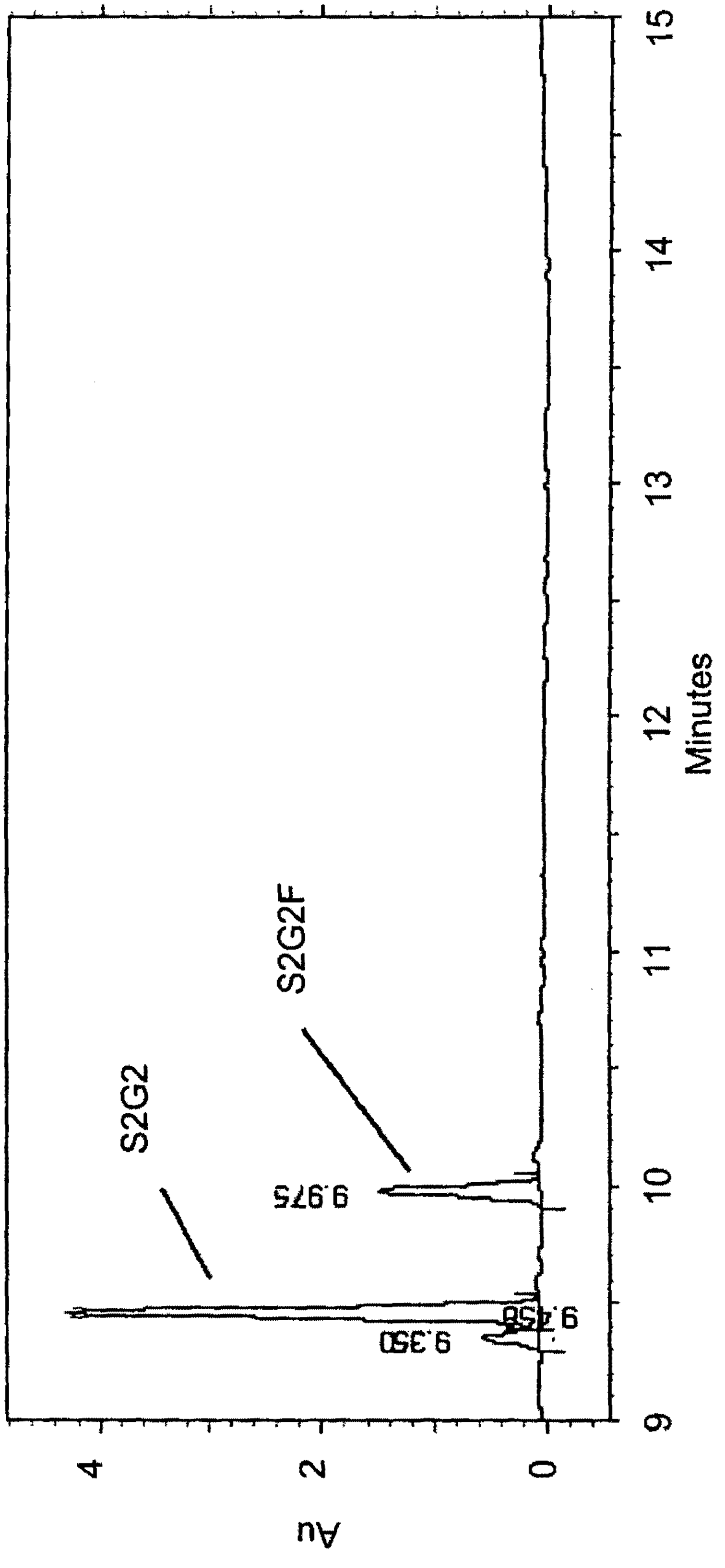
FIGS. 115A to 115D, are graphs depicting capillary electrophoresis analysis of glycans released from Cri-IgG1 antibodies that had been glycoremodeled by ST6Gal1 treatment of G2 glycoforms. A graph depicting the capillary electrophoresis analysis of glycan standards derivatized with APTS is shown in FIG. 115A.
Figure 115B:
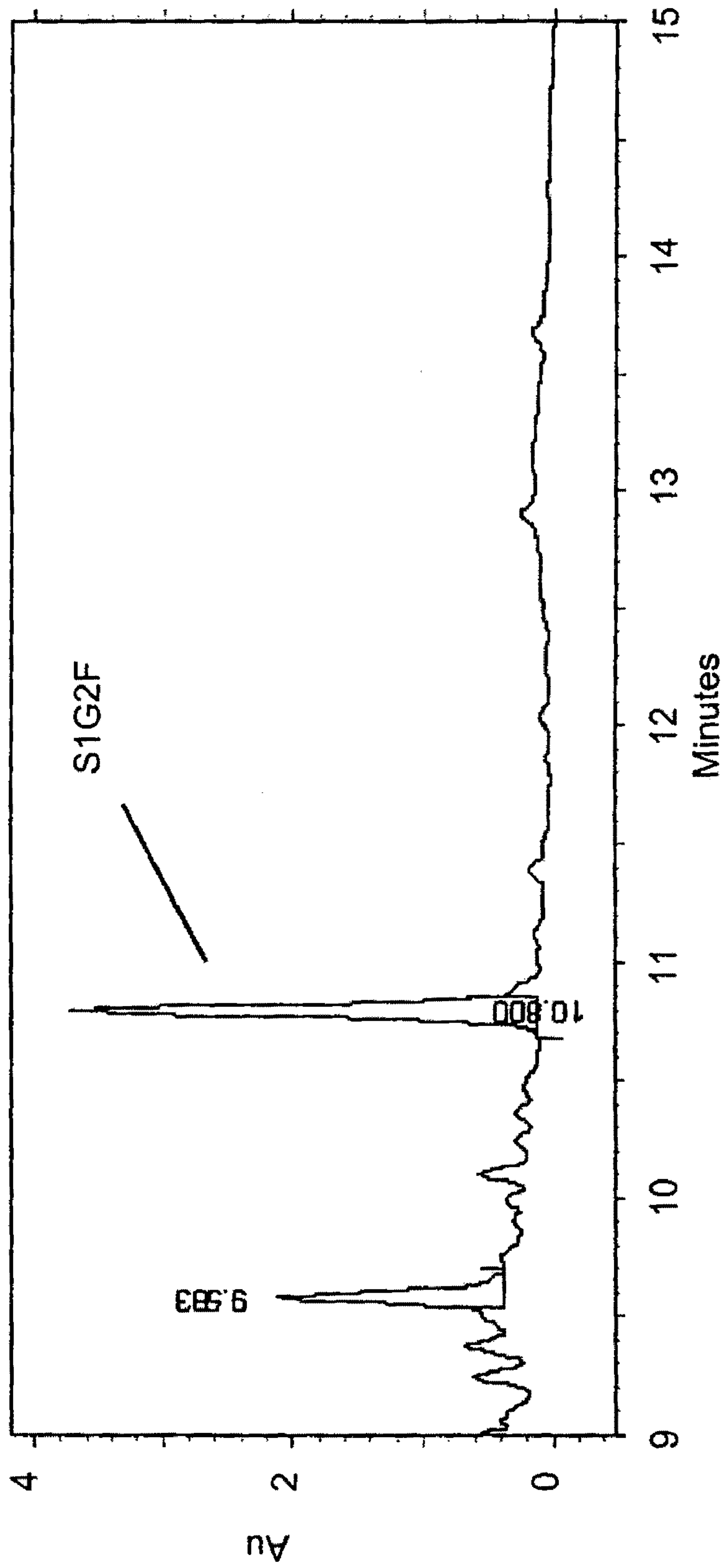
Figure 115C:
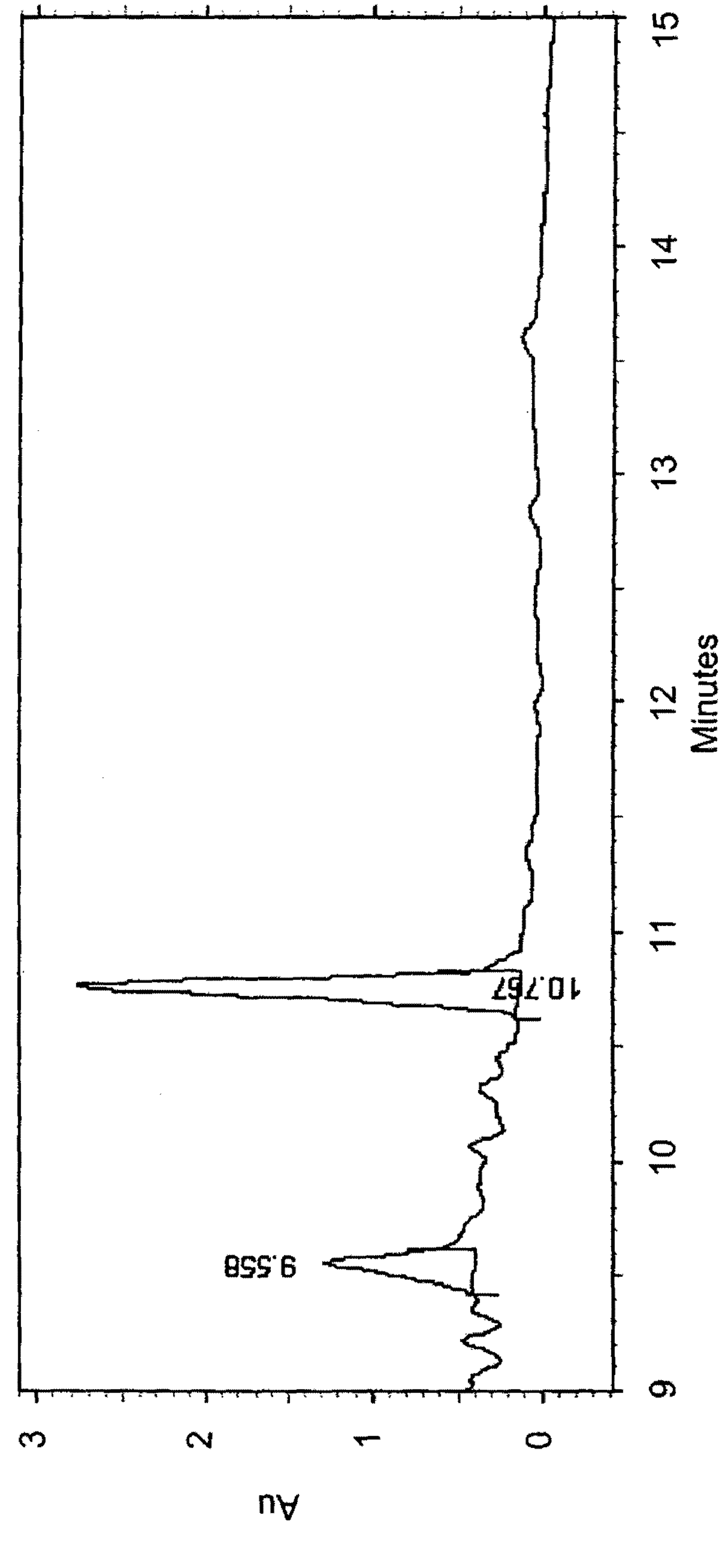
Figure 115D:
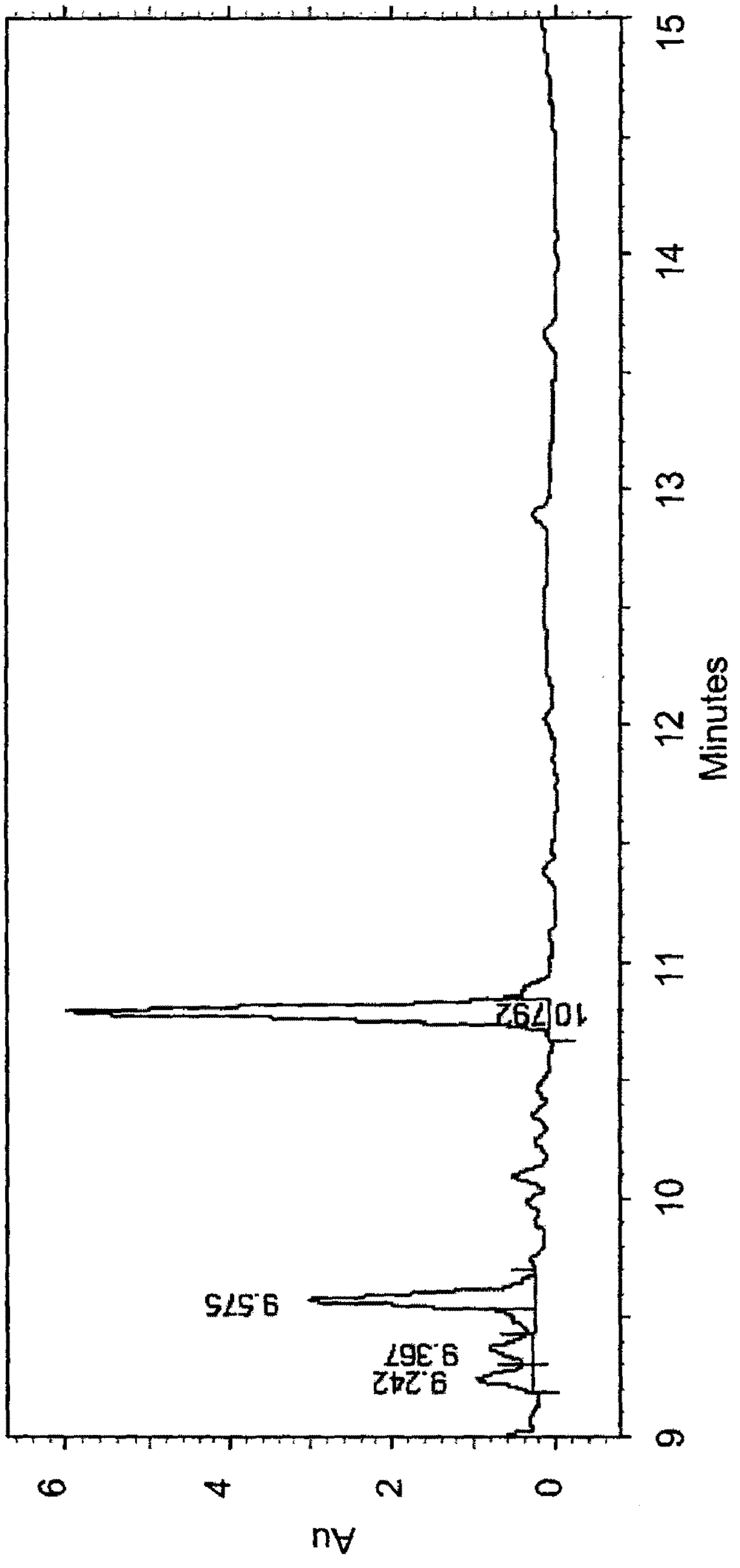
Figure 116A:
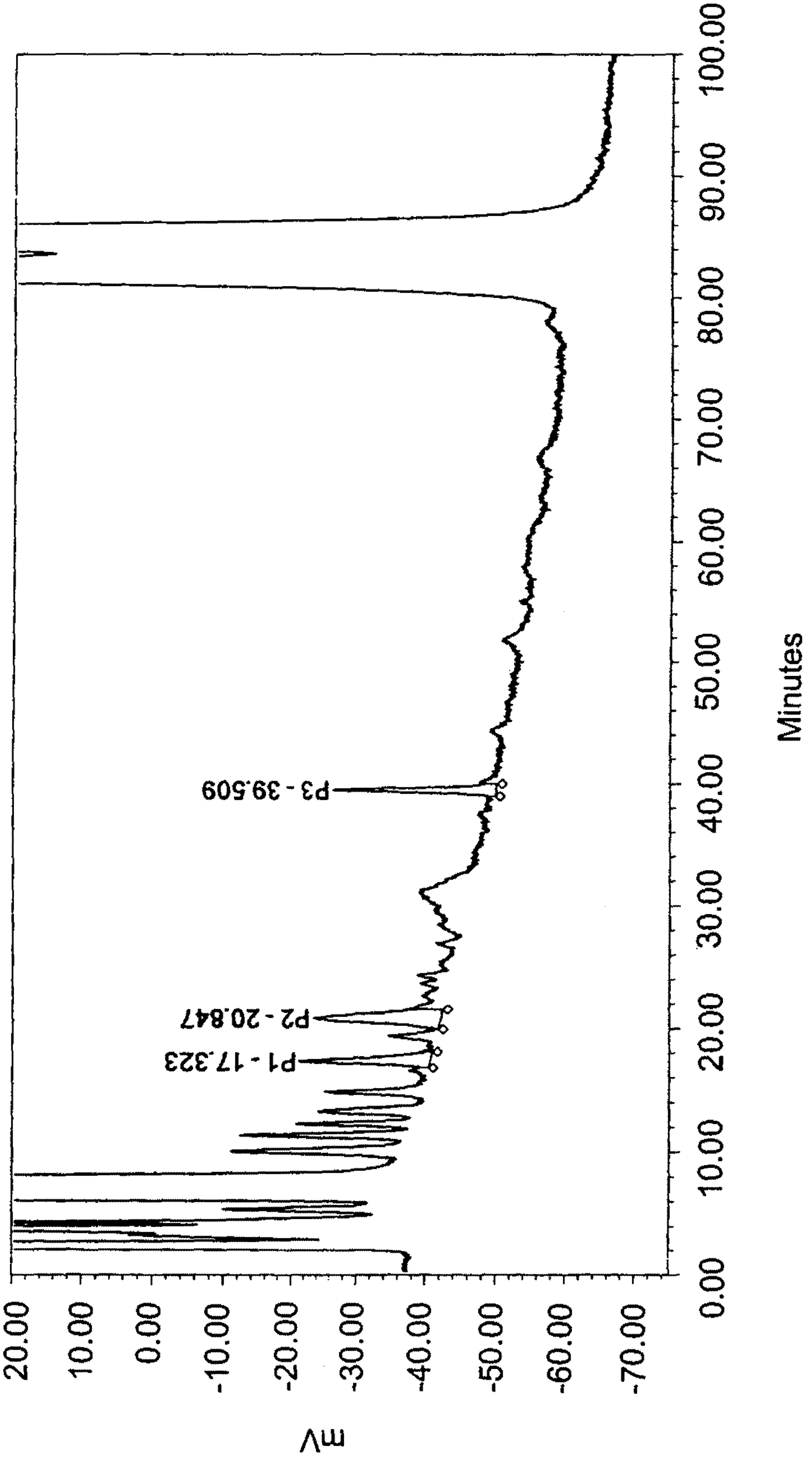
FIGS. 116A to 116C, are graphs depicting 2-AA HPLC analysis of glycans released from Cri-IgG1 antibodies that had been glycoremodeled by ST6Gal1 treatment of G2 glycoforms. The released glycans were labeled with 2-AA and separated by HPLC on a NH2P-50 4D amino column.
Figure 116B:
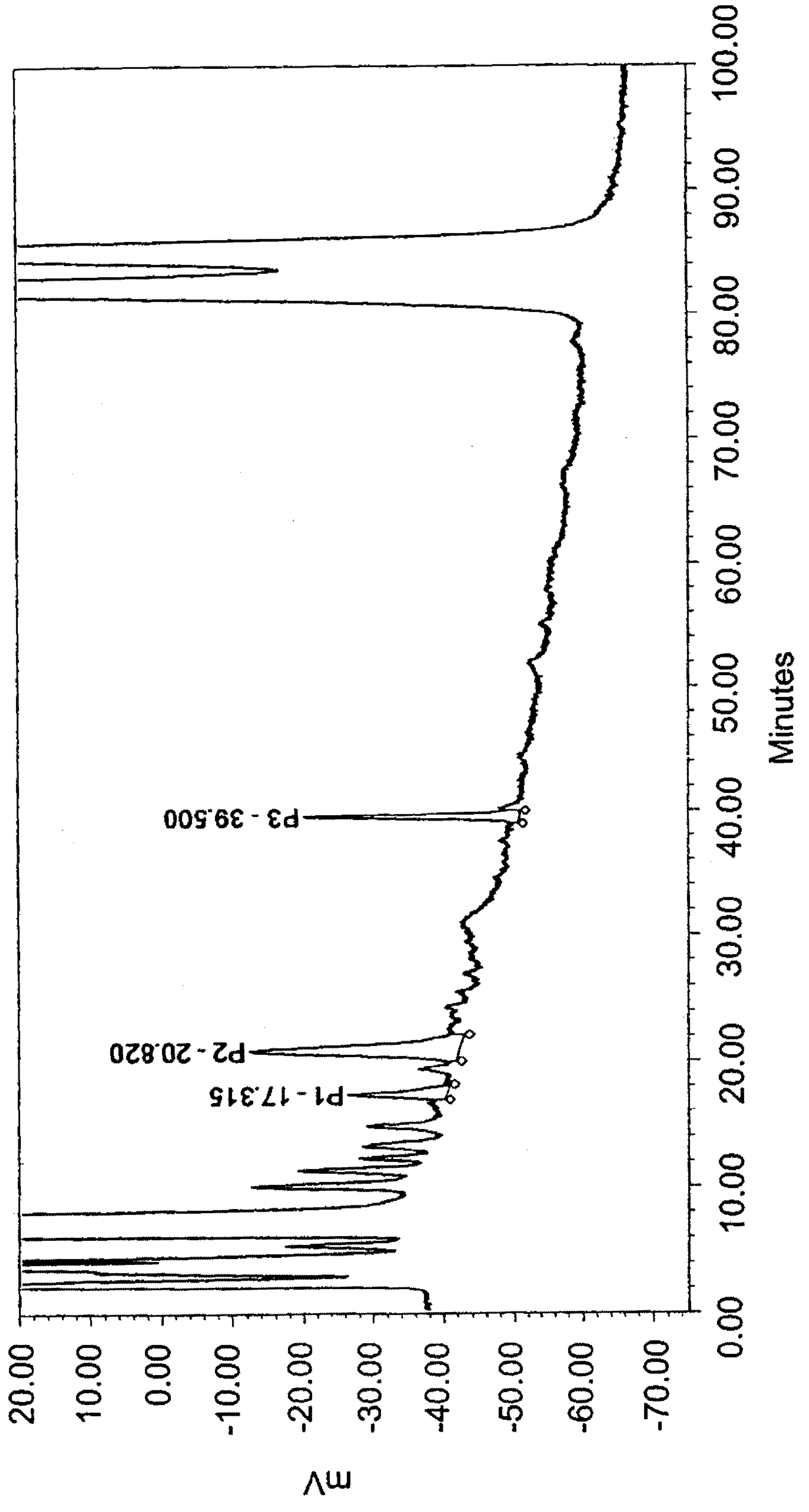
Figure 116C:
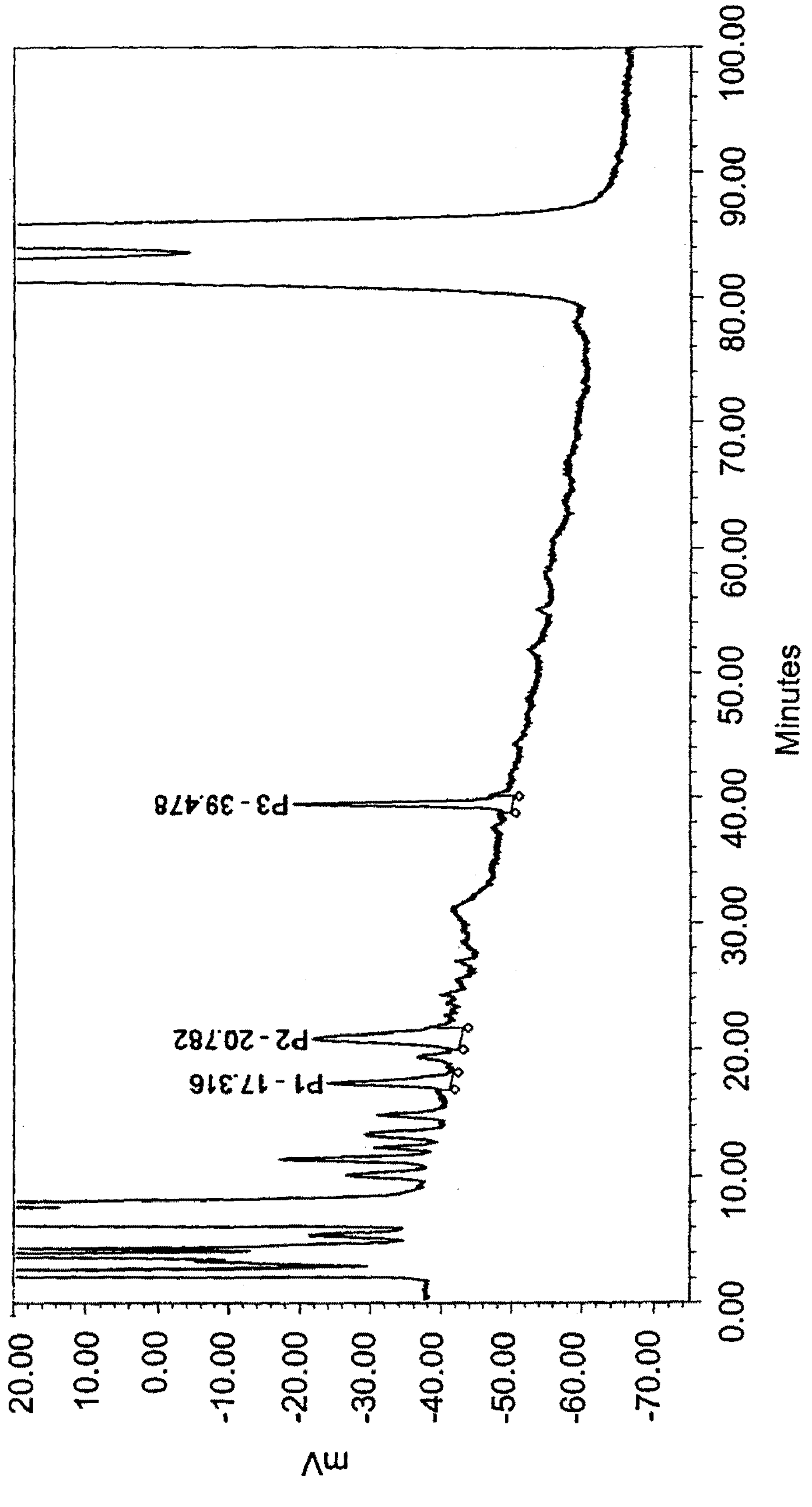

Sialylated (S2G2) glycoforms of Cri-IgG1. The glycoremodeled G2 glycoforms of Cri-IgG1 antibody were further remodeled using both ST3Gal3 and ST6Gal 1. FIG. 113A-113C shows the HPLC profile of the G2 glycoforms remodeled with ST3Gal3. Most of the G2 glycoforms were converted into S2G2 glycoforms (the G2 glycoform with 2 additional terminal sialic acid moieties; ~70%, see, Table 19), and only small amounts were the S1G2 glycoform (the G2 glycoform with 1 additional terminal sialic acid moiety; <25%, see Table 19). These results were further confirmed in the MALDI analysis shown in FIGS. 114A-114C. MALDI data also shows that all the G2 glycoforms were sialylated to either S2G2 or S1 G2 glycoforms.

TABLE 19

Relative amounts of different glycoforms from ST3Gal3 remodeled Cri-IgG1 as determined by HPLC.

| | RT (min.) | DEAE | SPA | Fc |
|---|---|---|---|---|
| S1G2 | 36.7 | 25.6 | 24.83 | 23.39 |
| | 46.9 | 4.12 | 6.83 | |
| S2G2 | 49.4 | 58.93 | 50.68 | 61.88 |
| | 52.19 | 9.1 | 7.56 | 6.07 |

By comparison, ST6Gal1 remodeling of the G0 glycoform did not reach the level of completion found with ST3Gal3 remodeling. FIGS. 115A-115D and FIGS. 116A-116C show the results obtained from CE and HPLC analysis, respectively. No S2G2 glycoforms were seen in any of the glycoremodeled samples. However, all of the G2 glycoforms were converted into S1-G2. Analysis from MALDI-MS also supports these data (FIGS. 117A-117C).

Stability of remodeled glycans of Cri-IgG1. Lastly, the stability of the Cri-IgG1 glycans remodeled by exoglycosidase treatment and glycosylation was investigated. Each glycoremodeled Cri-IgG1 antibody was stored at 4° C., and was checked by SDS-PAGE for degradation at two weeks after remodeling. As shown in FIGS. 118A-118E, the remodeled DEAE and SPA antibodies both retained a molecular weight of about 150 kDa, indicating little to no degradation, regardless of the kind of glycoremodeling performed. The Fc Cri-IgG1 antibody retained a molecular weight of about 38 kDa, also indicating little to no degradation, regardless of the kind of remodeling performed.

Effector Function Bioassay of Remodeled Cri-IgG1 antibodies. The effector function bioassay was derived from the procedure of Mimura et al. (2000, Molecular Immunology 37:697-706). The $IC_{50}$ of the glycoforms of Cri-IgG1 antibody was determined by inhibition of the superoxide response of U937 cells elicited by red blood cells sensitized with native anti-NIP antibody.

Monocytic U937 cells were cultured in the presence of 1000 units/mL interferon gamma for 2 days to induce the differentiation of the cells and their capacity to generate superoxide. The cells were then washed and resuspended at $2\times10^6$ cells/mL in Hanks balanced salt solution without phenol red and containing 20 mM HEPES pH 7.4 and 0.15 mM BSA. The red blood cells were sensitized with anti-NIP (5-iodo-4-hydroxy-3-nitrophenacetyl) antibody, in the absence or presence of the various glycoforms of Cri-IgG1 antibody, with incubation at 37° C. for 30 minutes. The cells were then washed three times with PBS and resuspended at $2.5\times10^7$ cells/mL in HBSS-BSA. The U937 cells (100 μl, $2\times10^6$ cells/mL) were added to plastic tubes and lucigenin (20 μl, 2.5 mM) was added to the tubes. The tubes were warmed in a 37° C. water bath for 5 minutes. The sensitized red blood cells (80 μl, $2.5\times10^7$/mL) were then added to the tubes. Superoxide anion production was measured by lucigenin-enhanced chemiluminescence at 37° C. over a 30 minute period using a Berthold LV953 luminometer (Berthold Australia Pty Ltd, Bundoora, Australia).

The G0 and M3N2 glycoforms Cri-IgG1 antibody had relative inhibitory values of 92% and 85%, respectively, as compared with the native antibody. However, the native CRI-IgG1 antibody lacked core fucose. Shields et al. (2002, J. Biol. Chem. 277:26733-26740) suggests that the lack of core fucose will improve inhibitory values 10 fold. Based on these results, it is anticipated that inhibitory values of the galactosylated-bisecting-G0 glycoform will be greater than the bisecting-G0 glycoform, which in turn will be much greater than the G2 glycoform, which in turn will be approximately equal to the disialylated-G2 glycoform and the monosialylated-G2 glycoform, which in turn will be greater than the native antibody glycoform, which in turn will be greater than the G0 glycoform, which in turn will be greater than the M3N2 glycoform.

Complement Receptor-1

9. Sialylation and Fucosylation of TP10

This example sets forth the preparation of TP10 with sialyl Lewis X moieties and analysis of enhanced biological activity.

Interrupting blood flow to the brain, even for a short time, can trigger inflammatory events within the cerebral microvasculature that can exacerbrate cerebral tissue damage. The tissue damage that accrues is amplified by activation of both inflammation and coagulation cascades. In a murine model of stroke, increased expression of P-selectin and ICAM-1 promotes leukocyte recruitment. sCR1 is recombinant form of the extracellular domain of Complement Receptor-1 (CR-1). sCR-1 is a potent inhibitor of complement activation. $sCR1sLe^X$ (CD20) is an alternately glycosylated form of sCR1 that is alternately glycosylated to display sialylated $Lewis^X$ antigen. Previously, sCR-1sLeX that was expressed and glycosylated in vivo in engineered Lec11 CHO cells was found to correctly localize to ischemic cerebral microvessels and Clq-expressing neurons, thus inhibiting neutrophil and platelet accumulation and reducing cerebral infarct volumes (Huang et al., 1999, Science 285:595-599). In the present example, sCR1sLe$^X$ which was prepared in vitro by remodeling of glycans, exhibited enhanced biological activity similar to that of sCRsLe$^X$ glycosylated in vivo.

The TP10 peptide was expressed in DUK B11 CHO cells. This CHO cell line produces the TP10 peptide with the typical CHO cell glycosylation, with many but not all glycans capped with sialic acid.

Sialylation of 66 mg of TP10. TP10 (2.5 mg/mL), CMPSA (5 mM), and ST3Gal3 (0.1 U/mL) were incubated at 32° C. in 50 mM Tris, 0.15M NaCl, 0.05% sodium azide, pH 7.2 for 48 hours. Radiolabelled CMP sialic acid was added to a small aliquot to monitor incorporation. TP10 was separated from nucleotide sugar by SEC HPLC. Samples analyzed at 24 hours and 48 hours demonstrated that the reaction was completed after 24 hours. The reaction mixture was then frozen. The reaction products were subjected to Fluorophore Assisted Carbohydrate Electrophoresis (FACE®; Glyko, Inc, Novato Calif.) analysis (FIG. 119).

Pharmacokinetic studies. Rats were purchased with a jugular vein cannula. 10 mg/kg of either the pre-sialylation or post-sialylation TP10 peptide was given by tail vein injection to three rats for each treatment (n=3). Fourteen blood samples were taken from 0 to 50 hours. The concentration in the blood of post-sialylation TP10 peptide was higher than that of pre-sialylation TP10 at every time point past 0 hour (FIG. 120). Sialic acid addition doubled the area under the plasma concentration-time curve (AUC) of the pharmacokinetic curve as compared to the starting material (FIG. 121).

Fucosylation of sialylated TP10. 10 mL (25 mg TP10) of the above sialylation mix was thawed, and GDP-fucose was added to 5 mM, $MnCl_2$ to 5 mM, and FTVI (fucosyltransferase VI) to 0.05 U/mL. The reaction was incubated at 32° C. for 48 hours. The reaction products were subjected to Fluorophore Assisted Carbohydrate Electrophoresis (FACE®; Glyko, Inc, Novato Calif.) analysis (FIG. 122). To a small aliquot, radiolabelled GDP-fucose was added to monitor incorporation. TP10 was separated from nucleotide sugar by SEC HPLC. Samples analyzed at 24 hours and 48 hours demonstrated that the reaction was completed at 24 hours. An in vitro assay measuring binding to E-selectin indicate that fucose addition can produce a biologically-active E-selectin ligand (FIG. 123).

Enbrel™

10. GlycoPEGylation of an antibody Enbrel™

This example sets forth the procedures to PEGylate the O-linked glycans of an antibody molecule. Here, Enbrel™ is used as an example, however one of skill in the art will appreciate that this procedure can be used with many antibody molecules.

Preparation of Enbrel™-SA-PEG (10 kDa). Enbrel™ (TNF-receptor-Ig$G_1$-chimera), either with the O-linked glycans sialylated prior to PEGylation or not, is dissolved at 2.5 mg/mL in 50 mM Tris-HCl, 0.15 M NaCl, 5 mM $MnCl_2$, 0.05% $NaN_3$, pH 7.2. The solution is incubated with 5 mM UDP-galactose and 0.1 U/mL of galactosyltransferase at 32° C. for 2 days to cap the undergalactosylated glycans with galactose. To monitor the incorporation of galactose, a small aliquot of the reaction has $^{14}C$-galactose-UDP ligand added; the label incorporated into the peptide is separated from the free label by gel filtration on a Toso Haas G2000SW analytical column in methanol and water. The radioactive label incorporation into the peptide is quantitated using an in-line radiation detector.

When the reaction is complete, the solution is incubated with 1 mM CMP-sialic acid-linker-PEG (10 kDa) and 0.1 U/mL of ST3Gal3 at 32° C. for 2 days. To monitor the incorporation of sialic acid-linker-PEG, the peptide is separated by gel filtration on a Toso Haas G3000SW analytical column using PBS buffer (pH 7.1). When the reaction is complete, the reaction mixture is purified using a Toso Haas TSK-Gel-3000 preparative column using PBS buffer (pH 7.1) and collecting fractions based on UV absorption. The fractions containing product are combined, concentrated, buffer exchanged and then freeze-dried. The product of the reaction is analyzed using SDS-PAGE and IEF analysis according to the procedures and reagents supplied by Invitrogen. Samples are dialyzed against water and analyzed by MALDI-TOF MS.

Erythropoietin (EPO)

11. Addition of GlcNAc to EPO

This example sets forth the addition of a GlcNAc residue on to a tri-mannosyl core. Addition of GlcNAc to EPO. EPO was expressed in SF-9 insect cells and purified (Protein Sciences, Meriden, Conn.). A 100% conversion from the tri-mannosyl glycoform of Epo to the "tri-mannosyl core+2 GlcNAc" (Peak 1, P1 in FIG. 124) was achieved in 24 hours of incubation at 32° C. with 100 mU/ml of GlcNAcT-I and 100 mU/ml of GlcNAcT-II in the following reaction final concentrations:

100 mM MES pH 6.5, or 100 mM Tris pH 7.5
5 mM UDP-GlcNAc
20 mM $MnCl_2$
100 mU/ml GlcNAcT-I
100 mU/ml GlcNAcT-II
1 mg/ml EPO (purified, expressed in Sf9 cells, purchased from Protein Sciences).

Analysis of glycoforms. This assay is a slight modification on K-R Anumula and ST Dhume, Glycobiology 8 (1998) 685-69. N-glycanase (PNGase) released N-glycans were reductively labeled with anthranilic acid. The reductively-aminated N-glycans were injected onto a Shodex Asahipak NH2P-50 4D amino column (4.6 mm×150 mm). Two solvents were used for the separation: A) 5% (v/v) acetic acid, 1% tetrahydrofuran, and 3% triethylamine in water, and B) 2% acetic acid and 1% tetrahydrofuran in acetonitrile. The column was then eluted isocratically with 70% B for 2.5 minutes, followed by a linear gradient over a period of 97.5 minutes going from 70 to 5% B and a final isocratic elution with 5% B for 15 minutes. Eluted peaks were detected using fluorescence detection with an excitation of 230 nm and emission wavelength of 420 nm.

Under these conditions, the trimannosyl core had a retention time of 22.3 minutes, and the product of the GnT reaction has a retention time of 30 minutes. The starting material was exclusively trimannosyl core with core GlcNAc (FIG. 124).

12. Preparation of EPO with Multi-Antennary Complex Glycans

This example sets forth the preparation of PEGylated, biantennary EPO, and triantennary, sialylated EPO from insect cell expressed EPO.

Recombinant human erythropoietin (rhEPO) from the baculovirus/Sf9 expression system (Protein Sciences Corp., Meriden, Conn.) was subjected to glycan analysis and the resulting glycans were shown to be primarily trimannosyl core with core fucose, with a small percentage of glycans also having a single GlcNAc.

Addition of N-acetylglucosamine with GnT-I and GnT-II. Two lots of rhEPO (1 mg/mL) were incubated with GnT-I and GnT-II, 5 mM UDP-glcNAc, 20 mM $MnCl_2$, and 0.02% sodium azide in 100 mM MES pH 6.5 at 32° C. for 24 hr. Lot A contained 20 mg of EPO, and 100 mU/mL GnT-1 and 60 mU/mL GnT-II. Lot B contained 41 mg of EPO, and 41 mU/mL GnT-I+50 mU/mL GnT-II. After the reaction, the sample was desalted by gel filtration (PD10 columns, Pharmacia LKB Biotechnology Inc., Piscataway, N.J.).

EPO glycans analyzed by 2-AA HPLC profiling. This assay is a slight modification on Anumula and Dhume, Glycobiology 8 (1998) 685-69. Reductively-aminated N-glycans were injected onto a Shodex Asahipak NH2P-50 4D amino column (4.6 mm×150 mm). Two solvents were used for the separation, A) 5% (v/v) acetic acid, 1% tetrahydrofuran, and 3% triethylamine in water and B) 2% acetic acid and 1% tetrahydrofuran in acetonitrile. The column was then eluted isocratically with 70% B for 2.5 min, followed by a linear gradient over a period of 100 min going from 70 to 5% B, and a final isocratic elution with 5% B for 20 min. Eluted peaks were detected using fluorescence detection with an excitation of 230 nm and emission wavelength of 420 nm. Non-sialylated N-linked glycans fall in the LC range of 23-34 min, monosialylated from 34-42 min, disialylated from 42-52 min, trisialylated from 55-65 min and tetrasialylated from 68-78 min.

Glycan profiling by 2AA HPLC revealed that lot A was 92% converted to a biantennary structure with two GlcNAcs (the balance having a single GlcNAc. Lot B showed 97% conversion to the desired product (FIGS. 125A and 125B).

Introducing a third antennary branch with GnT-V. EPO (1 mg/mL of lot B) from the product of the GnT-I and GnT-II reactions, after desalting on PD-10 columns and subsequent concentration, was incubated with 10 mU/mL GnT-V and 5 mM UDP-GlcNAc in 100 mM MES pH 6.5 containing 5 mM $MnCl_2$ and 0.02% sodium azide at 32° C. for 24 hrs. 2AA HPLC analysis demonstrated that the conversion occurred with 92% efficiency (FIG. 126).

After desalting (PD-10) and concentration, galactose was added with rGalTI: EPO (1 mg/mL) was incubated with 0.1 U/mL GalT1, 5 mM UDP-galactose, 5 mM $MnCl_2$ at 32° C. for 24 hrs.

MALDI analysis of reductively-aminated N-glycans from EPO. A small aliquot of the PNGase released N-glycans from EPO that had been reductively labeled with anthranilic acid was dialyzed for 45 min on an MF-Millipore membrane filter (0.025 μm pore, 47 mm dia), which was floating on water. The dialyzed aliquot was dried in a speedvac, redissolved in a small amount of water, and mixed with a solution of 2,5-dihydroxybenzoic acid (10 g/L) dissolved in water/acetonitrile (50:50). The mixture was dried onto the target and analyzed using an Applied Biosystems DE-Pro MALDI-TOF mass spectrometer operated in the linear/negative-ion mode. Oligosaccharides were assigned based on the observed mass-to-charge ratio and literature precedence.

Analysis of released glycans by MALDI showed that galactose was added quantitatively to all available sites (FIG. 127). Galactosylated EPO from above was then purified by gel filtration on a Superdex 1.6/60 column in 50 mM Tris, 0.15M NaCl, pH 6. Sialylation. After concentration and desalting (PD-10), 10 mg galactosylated EPO (1 mg/mL) was incubated with ST3Gal3 (0.05 U/mL), and CMP-SA (3 mM) in 50 mM Tris, 150 mM NaCl, pH 7.2 containing 0.02% sodium azide. A separate aliquot contained radiolabelled CMP-SA. The resulting incorporated label and free label was separated by isocratic size exclusion chromatography/HPLC at 0.5 mL/min in 45% MeOH, 0.1% TFA (7.8 mm×30 cm column, particle size 5 μm, TSK G2000SW$_{XL}$, Toso Haas, Ansys Technologies, Lake Forest, Calif.). Using this procedure, 12% of the counts were incorporated (360 micromolar, at 33 micromolar EPO, or about 10.9 moles/mole). Theoretical (3 N-linked sites, tri-antennary) is about 9 moles/mole incorporation. These correspond within the limits of the method. In an identical reaction with ST6Gal1 instead of ST3Gal3, 5.7% of the radiolabel was incorporated into the galactosylated EPO, or about 48% compared with ST3Gal3.

13. GlycoPEGylation of EPO Produced in Insect Cells

This example sets forth the preparation of PEGylated biantennary EPO from insect cell expressed EPO.

Recombinant human erythropoietin (rhEPO) from the baculovirus/Sf9 expression system (Protein Sciences Corp., Meriden, Conn.) was subjected to glycan analysis and the resulting glycans were shown to be primarily trimannosyl core with core fucose, with a small percentage of glycans also having a single GlcNAc (FIG. 128).

Addition of N-acetylglucosamine with GnT-I and GnT-II. Two lots of rhEPO (1 mg/mL) were incubated with GnT-I and GnT-II, 5 mM UDP-glcNAc, 20 mM $MnCl_2$, and 0.02% sodium azide in 100 mM MES pH 6.5 at 32° C. for 24 hr. Lot A contained 20 mg of EPO, and 100 mU/mL GnT-1 and 60 mU/mL GnT-II. Lot B contained 41 mg of EPO, and 41 mU/mL GnT-I+50 mU/mL GnT-II. After the reaction, the sample was desalted by gel filtration (PD10 columns, Pharmacia LKB Biotechnology Inc., Piscataway, N.J.).

Glycan profiling by 2AA HPLC revealed that lot A was 92% converted to a biantennary structure with two GlcNAcs (the balance having a single glcNAc. Lot B showed 97% conversion to the desired product (FIGS. 125A and 125B).

Galactosylation of EPO lot A. EPO (~16 mgs of lot A) was treated with GnT-II to complete the addition of GlcNAc. The reaction was carried out in 50 mM Tris pH 7.2 containing 150 mM NaCl, EPO mg/ml, 1 mM UDP-GlcNAc, 5 mM $MnCl_2$, 0.02% sodium azide and 0.02 U/ml GnT-II at 32 C for 4 hrs. Then galactosylation of EPO was done by adding UDP-galactose to 3 mM and GalT1 to 0.5 μ/ml and the incubation continued at 32° C. for 48 hrs.

Galactosylated EPO was then purified by gel filtration on a Superdex75 1.6/60 column in 50 mM Tris, 0.15M NaCl, pH 6. The EPO containing peak was then analyzed by 2AA HPLC. Based on the HPLC data ~85% of the glycans contains two galactose and ~15% of the glycans did not have any galactose after galactosylation reaction.

Sialylation of galactosylated EPO. Sialylation of galactosylated EPO was carried out in 100 mM Tris pH containing 150 mM NaCl, 0.5 mg/ml EPO, 200 mU/ml of ST3Gal3 and either 0.5 mM CMP-SA or CMP-SA-PEG (1 kDa) or CMP-SA-PEG (10 kDa) for 48 hrs at 32° C. Almost all of the glycans that have two galactose residues were fully sialylated (2 sialic acids/glycan) after sialylation reaction with CMP-SA. MALDI-TOF analysis confirmed the HPLC data.

PEGylation of galactosylated EPO. For PEGylation reactions using CMP-SA-PEG (1 kDa) and CMP-SA-PEG (10 kDa), an aliquot of the reaction mixture was analyzed by SDS-PAGE (FIG. 129). The molecular weight of the EPO peptide increased with the addition of each sugar, and increased more dramatically in molecular weight after the PEGylation reactions.

In vitro bioassay of EPO. In vitro EPO bioassay (adapted from Hammerling et al, 1996, J. Pharm. Biomed. Anal. 14: 1455-1469) is based on the responsiveness of the TF-1 cell line to multiple levels of EPO. TF-1 cells provide a good system for investigating the proliferation and differentiation of myeloid progenitor cells. This cell line was established by T. Kitamura et al. in October 1987 from a heparinized bone marrow aspiration sample from a 35 year old Japanese male with severe pancytopenia. These cells are completely dependent on Interleukin 3 or Granulocyte-macrophage colony-stimulating factor (GM-CSF).

The TF-1 cell line (ATCC, Cat. No. CRL-2003) was grown in RPMI+FBS 10%+GM-CSF (12 ng/ml) and incubated at 37° C. 5% $CO_2$. The cells were in suspension at a concentration of 5000 cells/ml of media, and 200 μl were dispensed in a 96 well plate. The cells were incubated with various concentrations of EPO (0.1 μg/ml to 10 μg/ml) for 48 hours. A MTT Viability Assay was then done by adding 25 μl of MTT at 5 mg/ml (SIGMA M5655), incubating the plate at 37° C. for 20 min to 4 hours, adding 100 μl of isopropanol/HCl solution (100 ml isopropanol+333 μl HCl 6N), reading the OD at 570 nm, and 630 nm or 690 nm, and subtracting the readings at 630 nm or 690 nm from the readings at 570 nm.

FIG. 130 contains the results when sialylated EPO, and EPO glycoPEGylated with 1 kDa or 10 kDa PEG was subjected to an in vitro EPO bioactivity test. The EPO glycoPEGylated with 1 kDa PEG had almost the same activity as the unglycoPEGylated EPO when both were at a concentration of approximately 5 μg/ml. The EPO glycoPEGylated with 10 kDa PEG had approximately half the activity of the unglycoPEGylated EPO when both were at a concentration of approximately 5 μg/ml.

14. GlycoPEGylation of O-Linked Glycans of EPO Produced in CHO Cells

Preparation of O-linked EPO-SA-PEG (10 kDa). Asialo-EPO, originally produced in CHO cells, is dissolved at 2.5 mg/mL in 50 mM Tris-HCl, 0.15 M NaCl, 0.05% $NaN_3$, pH 7.2. The solution is incubated with 5 mM CMP-SA and 0.1 U/mL of ST3Gal3 at 32° C. for 2 days. To monitor the incorporation of sialic acid onto the N-linked glycans, a small aliquot of the reaction had CMP-SA-$^{14}$C added; the peptide is separated by gel filtration on a Toso Haas G2000SW analytical column using methanol, water and the product detected using a radiation detector. When the reaction is complete, the solution is concentrated using a Centricon-20 filter. The remaining solution is buffer exchanged with 0.05 M Tris (pH 7.2), 0.15 M NaCl, 0.05% $NaN_3$ to a final volume of 7.2 mL until the CMP-SA could no longer be detected. The retentate is then resuspended in 0.05 M Tris (pH 7.2), 0.15 M NaCl, 0.05% $NaN_3$ at 2.5 mg/mL protein. The solution is incubated with 1 mM CMP-SA-PEG (10 kDa) and ST3Gal1, to glycosylate the O-linked site, at 32° C. for 2 days. To monitor the incorporation of sialic acid-PEG, a small aliquot of the reaction is separated by gel filtration suing a Toso Haas TSK-gel-3000 analytical column eluting with PBS pH 7.0 and analyzing by UV detection. When the reaction is complete, the reaction mixture is purified using a Toso Haas TSK-gel-3000 preparative column using PBS buffer (pH 7.0) collecting fractions based on UV absorption. The product of the reaction is analyzed using SDS-PAGE and IEF analysis according to the procedures and reagents supplied by Invitrogen. Samples are dialyzed against water and analyzed by MALDI-TOF MS.

15. EPO-Transferrin

This example sets forth the procedures for the glycoconjugation of proteins to O-linked glycans, and in particular, transferrin is glycoconjugated to EPO. The sialic acid residue is removed from O-linked glycan of EPO, and EPO-SA-linker-SA-CMP is prepared. EPO-SA-linker-SA-CMP is glycoconjugated to asialotransferrin with ST3Gal3.

Preparation of O-linked asialo-EPO. EPO (erythropoietin) produced in CHO cells is dissolved at 2.5 mg/mL in 50 mM Tris 50 mM Tris-HCl pH 7.4, 0.15 M NaCl, and is incubated with 300 mU/mL sialidase (*Vibrio cholera*)-agarose conjugate for 16 hours at 32° C. To monitor the reaction a small aliquot of the reaction is diluted with the appropriate buffer and a IEF gel performed according to Invitrogen procedures. The mixture is centrifuged at 10,000 rpm and the supernatant is collected. The supernatant is concentrated to a EPO concentration of about 2.5 mg/mL in 50 mM Tris-HCl, 0.15 M NaCl, 0.05% $NaN_3$, pH 7.2. The solution is incubated with 5 mM CMP-sialic acid and 0.1 U/mL of ST3Gal3 at 32° C. for 2 days. To monitor the incorporation of sialic acid, a small aliquot of the reaction had CMP-SA-fluorescent ligand added; the label incorporated into the peptide is separated from the free label by gel filtration on a Toso Haas G3000SW analytical column using PBS buffer (pH 7.1). When the reaction is complete, the reaction mixture is purified using a Toso Haas G3000SW preparative column using PBS buffer (pH 7.1) and collecting fractions based on UV absorption. The product of the reaction is analyzed using SDS-PAGE and IEF analysis according to the procedures and reagents supplied by Invitrogen. Samples are dialyzed against water and analyzed by MALDI-TOF MS.

Preparation of EPO-SA-linker-SA-CMP. The O-linked asialo-EPO 2.5 mg/mL in 50 mM Tris-HCl, 0.15 M NaCl, 0.05% $NaN_3$, pH 7.2. The solution is incubated with 1 mM CMP-sialic acid-linker-SA-CMP and 0.1 U/mL of ST3Gal1 at 32° C. for 2 days. To monitor the incorporation of sialic acid-linker-SA-CMP, the peptide is separated by gel filtration on a Toso Haas G3000SW analytical column using PBS buffer (pH 7.1).

After 2 days, the reaction mixture is purified using a Toso Haas G3000SW preparative column using PBS buffer (pH 7.1) and collecting fractions based on UV absorption. The product of the reaction is analyzed using SDS-PAGE and IEF analysis according to the procedures and reagents supplied by Invitrogen. Samples are dialyzed against water and analyzed by MALDI-TOF MS.

Preparation of Transferrin-SA-Linker-SA-EPO. EPO-SA-Linker-SA-CMP from above is dissolved at 2.5 mg/mL in 50 mM Tris-HCl, 0.15 M NaCl, 0.05% $NaN_3$, pH 7.2. The solution is incubated with 2.5 mg/mL asialo-transferrin and 0.1 U/mL of ST3Gal3 at 32° C. for 2 days. To monitor the incorporation of transferrin, the peptide is separated by gel filtration on a Toso Haas G3000SW analytical column using PBS buffer (pH 7.1) and the product detected by UV absorption. When the reaction is complete, the solution is incubated with 5 mM CMP-SA and 0.1 U/mL of ST3Gal3 (to cap any unreacted transferrin glycans) at 32° C. for 2 days. The reaction mixture is purified using a Toso Haas G3000SW preparative column using PBS buffer (pH 7.1) collecting fractions based on UV absorption. The product of the reaction is analyzed using SDS-PAGE and IEF analysis according to the procedures and reagents supplied by Invitrogen. Samples are dialyzed against water and analyzed by MALDI-TOF MS.

16. EPO-GDNF

This example sets forth the procedures for the glycoconjugation of proteins, and in particular, the preparation of EPO-SA-Linker-SA-GDNF.

Preparation of EPO-SA-Linker-SA-GDNF. EPO-SA-Linker-SA-CMP from above is dissolved at 2.5 mg/mL in 50 mM Tris-HCl, 0.15 M NaCl, 0.05% $NaN_3$, pH 7.2. The solution is incubated with 2.5 mg/mL GDNF (produced in NSO) and 0.1 U/mL of ST3Gal3 at 32° C. for 2 days. To monitor the incorporation of GDNF, the peptide is separated by gel filtration on a Toso Haas G3000SW analytical column using PBS buffer (pH 7.1) and the product detected by UV absorption. When the reaction is complete, the solution is incubated with 5 mM CMP-SA and 0.1 U/mL of ST3Gal3 (to cap any unreacted GDNF glycans) at 32° C. for 2 days. The reaction mixture is purified using a Toso Haas G3000SW preparative column using PBS buffer (pH 7.1) collecting fractions based on UV absorption. The product of the reaction is analyzed using SDS-PAGE and IEF analysis according to the procedures and reagents supplied by Invitrogen. Samples are dialyzed against water and analyzed by MALDI-TOF MS.

17. Mono-Antennary GlycoPEGylation of EPO

This example sets forth the procedure for the preparation of glycoPEGylated mono-antennary erythropoietin (EPO), and its bioactivity in vitro and in vivo.

When EPO (GenBank Accession No. P01588) is expressed in CHO cells, N-linked glycans are formed at amino acid residues 24, 38 and 83, and an O-linked glycan is formed at amino acid residue 126 (FIG. 131; Lai et al., 1986, J. Biol. Chem. 261:3116-3121). The bioactivity of this glycoprotein is directly correlated with the level of NeuAc content. Increased sialic acid decreases the binding of EPO to its receptor in vitro; however increased sialic acid increases the bioactivity of EPO in vivo. The O-linked glycan has no impact on the in vitro or in vivo activity of EPO, or the pharmacokinetics of the molecule (Wasley et al., 1991, Blood 77:2624-2632).

When EPO is expressed in insect cells, such as is accomplished using a baculovirus/Sf9 expression system (see also, Wojchowshi et al., 1987, Biochem. Biophys. Acta 910:224-232; Quelle et al., 1989, Blood 74:652-657), N-linked glycans are formed at amino acid residues 24, 38 and 83, but an O-linked glycan is not formed at amino acid residue 126 (FIG. 132). This is because the insect cell does not have a glycosyl transferase that recognizes the amino acid sequence around amino acid residue 126 of EPO. The majority of the N-linked glycans are composed of $GlcNAc_2Man_3Fuc$. In the present example, EPO expressed in insect cells was remodeled with high efficiency to achieve the complex glycan $SA_2Gal_2GlcNAc_2Man_3FucGlcNAc_2$ by contacting the protein with, in series, GnT1,2, GalT-1, and ST in the presence of the appropriate donor molecules. These enzymatic reactions were performed on insect cell expressed EPO using reaction conditions disclosed herein, to yield the complex glycans herein with 92% total efficiency (Table 21). Optionally, O-linked glycans can also be added (O'Connell and Tabak, 1993, J. Dent. Res. 72:1554-1558; Wang et al., 1993, J. Biol. Chem. 268:22979-22983).

TABLE 21

Percent of each species of glycan structure in the population of glycan structures on insect cell expressed EPO ("starting material"), and on EPO after each sequential enzymatic remodeling step.

| Glycan | Starting Material | After GnT-I, II | After GalT-I | After ST |
|---|---|---|---|---|
| 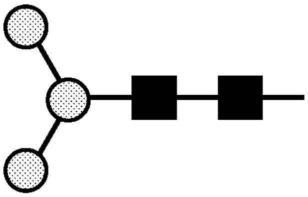 | 0.5% | | | |
| 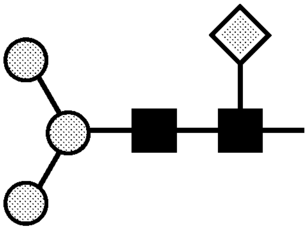 | 98.0% | | | |
| 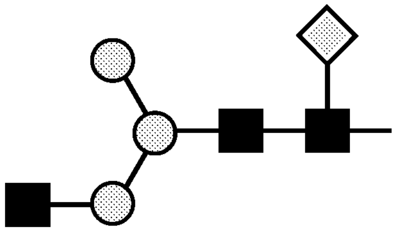 | 1.0% | 0.5% | 0.5% | |
| 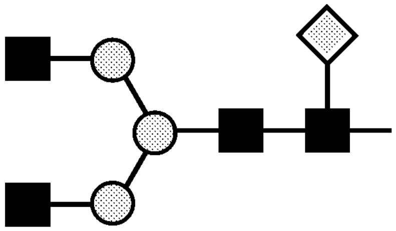 | 0.5% | 99.5% | 4% | 2% |

TABLE 21-continued

Percent of each species of glycan structure in the population of glycan structures on insect cell expressed EPO ("starting material"), and on EPO after each sequential enzymatic remodeling step.

| Glycan | Starting Material | After GnT-I, II | After GalT-I | After ST |
|---|---|---|---|---|
| 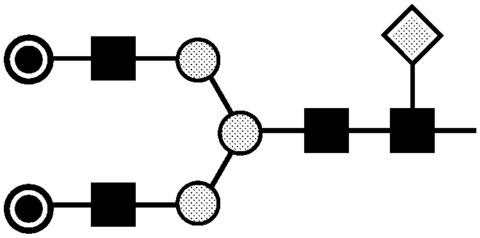 | | | 95.9% | 5% |
| 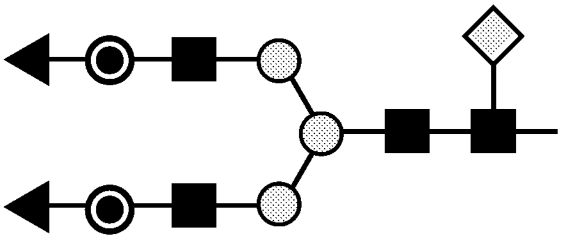 | | | | 92.0% |

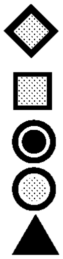

= fucose,

= GlcNAc,

= mannose,

= galactose,

= N-acetylneuraminic acid

Also in the present example, EPO expressed in insect cells was remodeled to form mono-antennary, bi-anntenary and tri-antennary glycans, which were subsequently glycoPEGylated with 1 kDa; 10 kDa and 20 kDa PEG molecules suing procedures described elsewhere herein. The molecular weights of these EPO forms were determined, and were compared to Epoetin™ having 3 N-linked glycans, and NESP (Aranesp™) having 5 N-linked glycans (FIG. 133). Examples of the preparation of bi- and tri-antennary glycan structures are given in Example 7, herein.

EPO having monoantennary PEGylated glycan structures is prepared by expressing EPO peptide in insect cells, then contacting the EPO peptide with GnTI only (or alternatively GnTII only) in the presence of a GlcNAc donor. The EPO peptide is then contacted with GalT-I in the presence of a galactose donor. The EPO peptide is then contacted with ST in the presence of SA-PEG donor molecules (FIG. 134A) to generate an EPO peptide having three N-linked mono-antennary PEGylated glycan structures (FIG. 134B).

The in vitro bioactivity of EPO-SA and EPO-SA-PEG generated from insect cell expressed EPO was accessed by measuring the ability of the molecule to stimulate the proliferation of TF-I erythroleukemia cells. Tri-antennary EPO-SA-PEG 1 kDa exhibited almost all of the bioactivity of tri-antennary EPO-SA, and di-antennary EPO-SA-PEG 10 kDa exhibited almost all of the bioactivity of di-antennary EPO-SA over a range of EPO concentrations (FIG. 135). Remodeled and glycoPEGylated EPO generated in insect cells exhibited up to 94% of the in vitro bioactivity of Epogen™, which is EPO expressed in CHO cells without further glycan remodeling or PEGylation (Table 22).

TABLE 22

In vitro activity of the EPO constructs as compared with Epogen ™ at 2 μg/ml protein and 48 hr.

| Compound (2 μg/ml protein) | Activity (percent of Epogen ™) |
|---|---|
| Biantennary-SA | 146 |
| Biantennary-SA-PEG 1K | 94 |
| Biantennary-SA-PEG 10K | 75 |
| Triantennary-SA 2, 3[1] | 42 |
| Triantennary-SA-PEG 1K | 48 |
| Triantennary-SA-PEG 10K | 34 |

[1]The triantennary - SA 2, 3 construct has the SA molecule bonded in a 2, 3 linkage.

The in vivo pharmacokinetics of glycoPEGylated and non-glycoPEGylated EPO was determined. GlycoPEGylated and non-glycoPEGylated [$I^{125}$]-labeled EPO was bolus injected into rats and the pharmacokinetics of the molecules were determined. As compared with bi-antennary EPO, the AUC of bi-antennary EPO-PEG 1 kDa was 1.8 times greater, and the AUC of bi-antennary EPO-PEG 10 kDa was 11 times greater (FIG. 136). As compared with bi-antennary EPO, the AUC of bi-antennary EPO-PEG 1 kDa was 1.6 times greater, and the AUC of bi-antennary EPO-PEG 10 kDa was 46 times greater (FIG. 136). Therefore, the pharmacokinetics of EPO was greatly improved by glycoPEGylation.

The in vivo bioactivity of glycoPEGylated and non-glycoPEGylated EPO was also determined by measuring the degree to which the EPO construct could stimulate reticulocytosis. Reticulocytosis is a measure of the rate of the maturation of red blood cell precursor cells into mature red blood cells (erythrocyte). Eight mice per treatment group were given a single subcutaneous injection of 10 μg protein/Kg, and the percent reticulocytes was measured at 96 hours (FIG. 137). Tri- and bi-antennary PEGylated EPO exhibited greater in vivo bioactivity than non-PEGylated EPO forms, including Epogen™.

Further determination of in vivo bioactivity of the EPO constructs was assessed by measuring the hematocrit (the percent of whole blood that is comprised of red blood cells) of CD-1 female mice 15 days after intraperitoneal injection three times per week with 2.5 μg peptide/kg body weight of the EPO construct. The hematocrit increment increased with the size of the EPO form, with the 82.7 kDa mono-antennary EPO-PEG 20 kDa having a slightly greater activity than the 35.6 kDa NESP (Aranesp™) and about two times the bioactivity of 28.5 kDa Epogen™ (FIG. 138).

This example illustrates that the generation of a longer-acting glycoPEGylated EPO is feasible. The pharmacokinetic profile of glycoPEGylated EPO can be customized by altering the number of glycoPEGylation sites and the size of the PEG molecule added to alter the half-life of the peptide in the bloodstream. Finally, glycoPEGylated EPO retains both in vitro and in vivo bioactivity.

18. Preparation and Bioactivity of Sialylated and PEGylated Mono-, Bi- and Tri-Antennary EPO This example illustrates the production of glycoPEGylated EPO, in particular PEGylated EPO having mono-antennary and bi-antennary glycans with PEG linked thereto. The following EPO variants were produced: mono-antennary PEG (1 kDa) and PEG (20 kDa); bi-antennary 2,3-sialic acid (SA), bi-antennary SA-PEG (1 kDa), bi-antennary SA-PEG (10 kDa); tri-antennary 2,3-SA and tri-antennary 2,6-SA capped with 2,3-SA.

Recombinant erythropoietin (rEPO) expressed in insect cells was obtained from Protein Sciences (Lot # 060302, Meridan Conn.). The glycan composition of this batch of EPO had approximately 98% trimannosyl core structure. FIG. 139A depicts the HPLC analysis of the released glycans from this EPO, with peak “P2” representing the trimannosyl core glycan. FIG. 139B shows the MALDI analysis of the released glycans with the structures of the released glycans beside the peak they represent.

Mono-Antennary Branching

Several steps were performed to produce the mono-antennary branched structure. In brief, the first step was a GnT-I/GalT-1 reaction followed by purification using Superdex-75 chromatography. This reaction adds a GlcNAc moiety to one branch of the tri-mannosyl core, and a galactose moiety onto the GlcNAc moiety. Branching was extended with the ST3Gal3 reaction to add the SA-PEG (10 kDa) moiety or the SA-PEG (20 kDa) moiety onto the terminal galactose moiety. The final purification was accomplished using Superdex-200 chromatography (Amersham Biosciences, Arlington Heights, Ill.).

GnT-I/GalT-1 Reaction. The GnT-I and GalT-1 reactions were combined and incubated at 32° C. for 36 hours. The reaction contained 1 mg/mL EPO, 100 mM Tris-Cl pH 7.2, 150 mM NaCl, 5 mM $MnCl_2$, 0.02% $NaN_3$, 3 mM UDP-GlcNAc, 50 mU/mg GnT-1,3 mM UDP-Gal, and 200 mU/mg GalT-1. FIG. 140 depicts the MALDI analysis of glycans released from EPO after the GnT-I/GalT-1 reaction. Glycan analysis showed approximately 90% of the glycans had the desired mono-antennary branched structure with a terminal galactose moiety.

Superdex 75 Purification. After the GnT-1/GalT1 reaction, EPO was purified from the enzyme protein contaminants and nucleotide sugars using a 1.6 cm×60 cm Superdex-75 gel filtration chromatography (Amersham Biosciences, Arlington Heights, Ill.) in PBS containing 0.02% Tween 20 (Sigma-Aldrich Corp., St. Louis, Mo.).

ST3Gal3 Reaction. The ST3Gal3 PEGylation reaction was incubated at 32° C. for 24 hours. The reaction contained 1 mg/mL EPO, 100 mM Tris-C1 pH 7.2, 150 mM NaCl, 0.02% $NaN_3$, 200 mU/mg ST3Gal3, and 0.5 mM CMP-SA-PEG (10 kDa) or 0.5 mM CMP-SA-PEG (20 kDa). FIG. 141 depicts the SDS-PAGE analysis of EPO after this reaction. The corresponding molecular weights of the protein bands indicate that the EPO glycans formed by the GnT-I/GalT-1 reaction were completely sialylated with the PEG derivative.

Superdex 200 Purification. EPO then was purified from the contaminants of the ST3Gal3 reaction by a 1.6 cm×60 cm Superdex-200 gel filtration chromatography (Amersham Biosciences, Arlington Heights, Ill.) in PBS containing 0.02% Tween-20.

TF-1 Cell In Vitro Bioassay of Mono-antennary PEGylated EPO. The TF-1 cell line is used to assess the activity of EPO in vitro. The TF-1 cells line is a myeloid progenitor cell line available from the American Type Culture Collection (Catalogue No. CRL-2003, Rockville, Md.). The cell line is completely dependant on Interleukin-3 or Granulocyte-Macrophage Colony-Stimulating Factor for viability. TF-1 cells provide a good system for investigating the effect of EPO on proliferation and differentiation.

The TF-1 cells were grown in RPMI with 10% FBS and 12 ng/ml GM-CSF at 37° C. in 5% $CO_2$. The cells were suspended at a concentration of 10,000 cells/ml of media: 200 μl aliquots of cells were dispensed into a 96-well plate. The cells were incubated with 0.1 to 10 μg/ml EPO for 48 hrs.

The MTT viability assay was then performed by first adding 25 μl of 5 μg/ml MTT (3-[4,5-dimethlythiazol-2-yl]-2,5-diphenyltetrazolium bromide, or thiazolyl blue; Sigma Chemical Co., St. Louis, Mo., Catalogue No. M5655). The plate was incubated for 4 hrs at 37° C. 100 μl of isopropanol/HCl solution (100 ml isopropanol and 333 μl HCl 6N) was added. The absorbency of the plates was read at 570 nm and either 630 or 690 nm, and the reading at either 630 nm or 690 nm was subtracted for the reading at 570 nm.

FIG. 142 depicts the results of the bioassay of EPO activity after PEGylation of it mono-antennary glycans. In this bioassay, the mono-antennary PEGylated EPO is much less active that a non-PEGylated EPO (Epogen).

Bi-Antennary Branching

Several reactions were performed to accomplish the bi-antennary branching of EPO. Briefly, the first reaction combined the GnT-I and GnT-II reactions to add GlcNAc moieties to two of the tri-mannosyl core branches. The second reaction, the GalT-1 reaction, adds a galactose moiety to each GlcNAc moieties. Superdex 75 chromatography (Amersham Biosciences, Arlington Heights, Ill.) was performed prior to the ST3Gal3 reaction. The bi-antennary branching was further extended with the ST3Gal3 reaction to add either a 2,3-SA, or SA-PEG (1 kDa), SA-PEG (10 kDa). Final purification was accomplished using Superdex 200 chromatography (Amersham Biosciences, Arlington Heights, Ill.).

GnT-I/GnT-II Reaction. The GnT-I and GnT-II reactions were combined and incubated at 32° C. for 48 hours. The reaction contained 1 mg/mL EPO, 100 mM MES pH 6.5, 150 mM NaCl, 20 mM $MnCl_2$, 0.02% $NaN_3$, 5 mM UDP- GlcNAc, 100 mU/mg GnT-I, 60 mU/mg GnT-II. The reaction achieved 92% completion of the addition of bi-antennary GlcNAc moieties, with 8% mono-antennary GlcNAc moieties. FIG. 143A shows the HPLC analysis of the released glycans, where peak "P3" represents the bi-antennary GlcNAc glycan. FIG. 143B depicts the MALDI analysis of the released glycans with the structures of the glycans indicated beside the peak that they represent.

In order to further the reaction, an additional 20 mU/mg of GnT-II was added along with 1 mM UDP-GlcNAc, 5 mM $MnCl_2$, 0.02% $NaN_3$, and the mixture was incubated for 4 hours at 32° C. Greater than 99% of this reaction achieved completion of the bi-antennary GlcNAc glycan.

GalT-1 Reaction. The GalT-1 reaction was started immediately after the completion of the second GnT-II reaction. Enzyme and nucleotide sugar were added to the completed GnT-II reaction at concentrations of 0.5 U/mg GalT-1 and 3 mM UDP-Gal.

When the GalT-1 reaction was performed on a small scale, with about 100 µg EPO per reaction, approximately 95% of the reaction produced EPO with bi-antennary terminal galactose moiety. FIG. 144A depicts the HPLC analysis of the released glycans where peak "P2" is the bi-antennary glycan with terminal galactose moieties (85% of the glycans), and peak "P1" is the bi-antennary glycan without the terminal galactose moieties (15% of the glycans).

The GalT-1 reaction was also performed on a large scale with about 16 mg of EPO per reaction. FIG. 144B depicts the HPLC analysis of the release glycans from the large scale GalT-1 reaction, where peak "P2" is the bi-antennary glycan with terminal galactose moieties, and peak "P1" is the bi-antennary glycan without the terminal galactose moieties.

Superdex 75 Purification. EPO was then purified from the enzyme protein contaminants and nucleotide sugars using a 1.6 cm×60 cm Superdex-75 gel filtration chromatography (Amersham Biosciences, Arlington Heights, Ill.) in PBS containing 0.02% Tween 20 after the GnT-1/GalT1 reaction. FIG. 145 depicts the chromatogram of the Superdex 75 gel filtration, where peak 2 is EPO with bi-antennary glycans with terminal galactose moieties. FIG. 146 shows SDS-PAGE analysis of the products of each remodeling step indicating the increase in the molecular weight of EPO with each remodeling step.

ST3Gal3 Reaction. The ST3Gal3 reaction was incubated at 32° C. for 24 hours. The reaction contained 0.5 mg/mL EPO, 100 mM Tris-Cl pH 7.2, 150 mM NaCl, 0.02% $NaN_3$, 100 mU/mg ST3Gal3, and 0.5 mM CMP-SA, 0.5 mM CMP-SA-PEG (1 kDa), or 0.5 mM CMP-SA-PEG (10 kDa). FIG. 147 shows the results of SDS-PAGE analysis of EPO before and after the ST3Gal3 reaction. Based on this SDS-PAGE analysis, bi-antennary EPO containing terminal Gal can no longer be visually detected after each ST3Gal3 reaction. All sialylated EPO variants show an increase in size compared to non-sialylated EPO at the start of the reaction.

Superdex 200 Purification. EPO was purified from the contaminants of the ST3Gal3 reactions by a 1.6 cm×60 cm Superdex-200 gel filtration chromatography (Amersham Biosciences, Arlington Heights, Ill.) in PBS containing 0.02% Tween-20. Table 23 summaries the distribution of glycan structures at each remodeling step.

TABLE 23

Summary of glycan structures on EPO after each remodeling step.

| Glycan | Starting Material | After GnT-I and GnT-II | After 2nd GnT-II | After GalT-I | After ST |
|---|---|---|---|---|---|
| 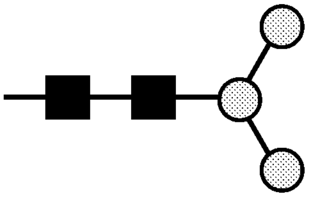 | 0.5% | | | | |
| 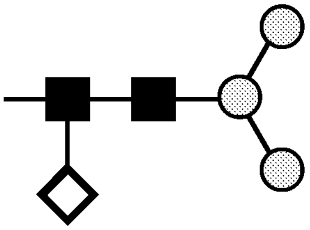 | 98.0% | | | | |
| 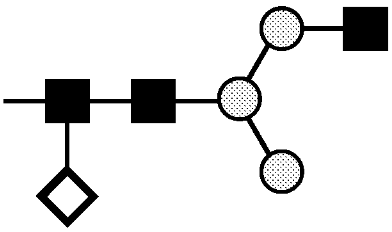 | 1.0% | 8.0% | 0.5% | 0.5% | 0.5% |

TABLE 23-continued

Summary of glycan structures on EPO after each remodeling step.

| Glycan | Starting Material | After GnT-I and GnT-II | After 2nd GnT-II | After GalT-I | After ST |
|---|---|---|---|---|---|
| 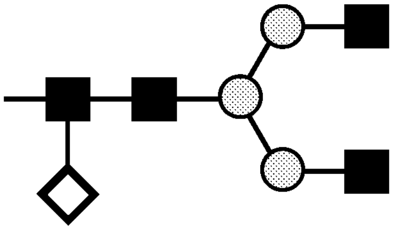 | 0.5% | 92.0% | 99.5% | 15.5% | 15.5% |
| 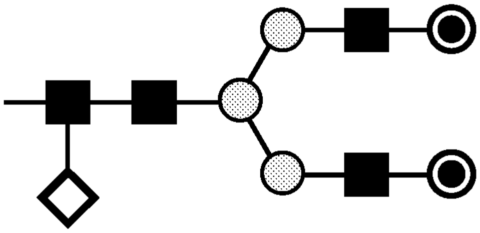 | | | | 84.0% | 2.0% |
| 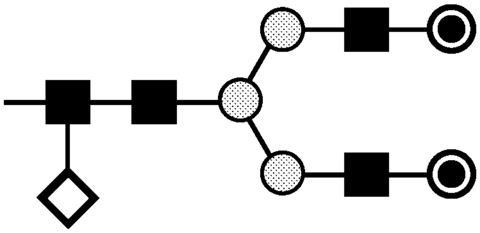 | | | | | 82.0% |

Diamonds represent fucose, and squares represent GlcNAc, circles represent mannose, open circles represent galactose.

Tri-Antennary Branching

Several reactions were performed to accomplish the tri-antennary branching of EPO. Briefly, the first reaction combined the GnT-I and GnT-II reactions to add a GlcNAc moiety to the two outer tri-mannosyl core branches of the glycan. The second reaction, GnT-V reaction, adds a second GlcNAc moiety to one of the two outer trimannosyl core branches so that there are now three GlcNAc moieties. The third reaction, GalT-1 reaction, adds a galactose moiety to each terminal GlcNAc moiety. The EPO products were then separated by Superdex 75 chromatography. The tri-antennary branching was further extended with the ST3Gal3 reaction to add either a 2,3-SA moiety or a 2,6-SA moiety, and capped with a 2,3-SA moiety. Final purification was accomplished using Superdex 75 chromatography.

GnT-1/GnT-II Reaction. The GnT-I and GnT-II reactions were combined and incubated at 32° C. for 24 hours. The reaction contained 1 mg/mL EPO, 100 mM MES pH 6.5, 150 mM NaCl, 20 mM $MnCl_2$, 0.02% $NaN_3$, 5 mM UDP GlcNAc, 50 mU/mg GnT-1 and 41 mU/mg GnT-II. The reaction achieved 97% completion of the addition of the bi-antennary GlcNAc moiety, with 3% tri-mannosyl core remaining. FIG. 148 depicts the HPLC analysis of the glycans released from EPO after the GnT-I/GnT-II reaction.

GnT-V Reaction. The GnT-V reaction containing 100 mM MES pH 6.5, 5 mM UDP-GlcNAc, 5 mM $MnCl_2$, 0.02% $NaN_3$, 10 mU/mg GnT-V and 1 mg/mL EPO, was incubated at 32° C. for 24 hours. This reaction adds a GlcNAc moiety to an outer mannose moiety already containing a GlcNAc moiety. FIG. 149 depicts the HPLC analysis of the glycans released from EPO after the GnT-V reaction. Approximately 92% the glycans released from EPO were the desired product, tri-antennary branched EPO with terminal GlcNAc moieties, based on glycan and MALDI analysis. The remaining 8% of the glycans were bi-antennary branched structures containing terminal GlcNAc moieties.

GalT-1 Reaction. The GalT-1 reaction containing 100 mM Tris pH 7.2, 150 mM NaCl, 5 mM UDP Gal, 100 mU/mg GalT-1, 5 mM $MnCl_2$, 0.02% $NaN_3$ and 1 mg/mL EPO was incubated at 32° C. for 24 hours. FIG. 150 depicts the HPLC analysis of the glycans released from EPO after this reaction. Glycan and MALDI analysis indicates that 97% of the released glycans had terminal galactose moieties on the tri-antennary branched structures. The remaining 3% was a bi-antennary structure containing a terminal galactose.

Superdex 75 Purification. After the GnT-I/GalT1 reaction, EPO was purified from the enzyme protein contaminants and nucleotide sugars using a 1.6 cm×60 cm Superdex-75 gel filtration chromatography (Amersham Biosciences, Arlington Heights, Ill.) in PBS containing 0.02% Tween 20. The purified material was divided into two batches to produce the tri-antennary glycan with terminal 2,6-SA moieties and the tri-antennary glycan with terminal 2,6-SA moieties capped with 2,6-SA moieties.

ST3Gal3 Reaction. The ST3Gal3 reaction was incubated at 32° C. for 24 hours. The reaction contained 1 mg/mL galactosylated EPO, 100 mM Tris-Cl pH 7.2, 150 mM NaCl, 0.02% $NaN_3$, 50 mU/mg ST3Gal3, and 3 mM CMP-SA. FIG. 151 depicts the HPLC analysis of glycans released from EPO after this step. Based on glycan and MALDI analysis, approximately 80% of the released glycans were tri-antennary branched structures with terminal 2,3-SA moieties. The remaining 20% of the released glycans were bi-antennary structures with terminal 2,3-SA moieties.

ST6Gal1 sialylation Reaction following the ST3Gal3 Reaction. The ST6Gal1 reaction was incubated at 32° C. for 24 hours. The reaction contained 1 mg/mL sialylated galactosylated EPO, 100 mM Tris-Cl pH 7.2, 150 mM NaCl, 0.02% $NaN_3$, 50 mU/mg ST6Gal1, and 3 mM CMP-SA. FIG. 152 depicts the results of HPLC analysis of the glycans released from EPO after the ST6Gal1 reaction. Based on glycan and MALDI analysis, approximately 80% of the tri-antennary branched glycans contained terminal 2,3-SA moieties. The remaining 20% of the glycans were bi-antennary with terminal 2,3-SA moieties.

Superdex 75 Purification. EPO was purified from the contaminants of the ST3Gal3 reactions by a 1.6 cm×60 cm Superdex-75 gel filtration chromatography (Amersham Biosciences, Arlington Heights, Ill.) in PBS containing 0.02% Tween-20.

Bioassay of Tri-antennary and Bi-antennary Sialylated or PEGylated EPO. The activity of the tri-antennary and bi-antennary sialylated EPO glycoforms, and the PEG 10 kDa and 1 kDa bi-antennary glycoforms were assayed using the TF-1 cell line and the MTT viability test, as described above. FIG. 153 depicts the results of the MTT cell proliferation assay. At 2 μg/ml EDP, the bi-antennary sialylated EPO had nearly the activity of the control Epogen, while the tri-antennary sialylated EPO had significantly less activity.

Factor IX

19. GlycoPEGylation of Factor IX Produced in CHO Cells

This example sets forth the preparation of asialoFactor IX and its sialylation with CMP-sialic acid-PEG.

Desialylation of rFactor IX. A recombinant form of Coagulation Factor IX (rFactor IX) was made in CHO cells. 6000 IU of rFactor IX were dissolved in a total of 12 mL USP $H_2O$. This solution was transferred to a Centricon Plus 20, PL-10 centrifugal filter with another 6 mL USP $H_2O$. The solution was concentrated to 2 mL and then diluted with 15 mL 50 mM Tris-HCl pH 7.4, 0.15 M NaCl, 5 mM $CaCl_2$, 0.05% $NaN_3$ and then reconcentrated. The dilution/concentration was repeated 4 times to effectively change the buffer to a final volume of 3.0 mL. Of this solution, 2.9 mL (about 29 mg of rFactor IX) was transferred to a small plastic tube and to it was added 530 mU α2-3,6,8-Neuraminidase—agarose conjugate (*Vibrio cholerae*, Calbiochem, 450 μL). The reaction mixture was rotated gently for 26.5 hours at 32° C. The mixture was centrifuged 2 minutes at 10,000 rpm and the supernatant was collected. The agarose beads (containing neuraminidase) were washed 6 times with 0.5 mL 50 mM Tris-HCl pH 7.12, 1 M NaCl, 0.05% $NaN_3$. The pooled washings and supernatants were centrifuged again for 2 minutes at 10,000 rpm to remove any residual agarose resin. The pooled, desialylated protein solution was diluted to 19 mL with the same buffer and concentrated down to ~2 mL in a Centricon Plus 20 PL-10 centrifugal filter. The solution was twice diluted with 15 mL of 50 mM Tris-HCl pH 7.4, 0.15 M NaCl, 0.05% $NaN_3$ and reconcentrated to 2 mL. The final desialyated rFactor IX solution was diluted to 3 mL final volume (~10 mg/mL) with the Tris Buffer. Native and desialylated rFactor IX samples were analyzed by IEF-Electrophoresis. Isoelectric Focusing Gels (pH 3-7) were run using 1.5 μL (15 μg) samples first diluted with 10 μL Tris buffer and mixed with 12 μL sample loading buffer. Gels were loaded, run and fixed using standard procedures. Gels were stained with Colloidal Blue Stain (FIG. 154), showing a band for desialylated Factor IX.

Preparation of PEG (1 kDa and 10 kDa)-SA-Factor IX. Desialylated rFactor-IX (29 mg, 3 mL) was divided into two 1.5 mL (14.5 mg) samples in two 15 mL centrifuge tubes. Each solution was diluted with 12.67 mL 50 mM Tris-HCl pH 7.4, 0.15 M NaCl, 0.05% $NaN_3$ and either CMP-SA-PEG-1k or 10k (7.25 μmol) was added. The tubes were inverted gently to mix and 2.9 U ST3Gal3 (326 μL) was added (total volume 14.5 mL). The tubes were inverted again and rotated gently for 65 hours at 32° C. The reactions were stopped by freezing at −20° C. 10 μg samples of the reactions were analyzed by SDS-PAGE. The PEGylated proteins were purified on a Toso Haas Biosep G3000SW (21.5×30 cm, 13 um) HPLC column with Dulbecco's Phosphate Buffered Saline, pH 7.1 (Gibco), 6 mL/min. The reaction and purification were monitored using SDS Page and IEF gels. Novex Tris-Glycine 4-20% 1 mm gels were loaded with 10 μL (10 μg) of samples after dilution with 2 μL of 50 mM Tris-HCl, pH 7.4, 150 mM NaCl, 0.05% $NaN_3$ buffer and mixing with 12 μL sample loading buffer and 1 μL 0.5 M DTT and heated for 6 minutes at 85° C. Gels were stained with Colloidal Blue Stain (FIG. 155) showing a band for PEG (1 kDa and 10 kDa)-SA-Factor IX.

20. Direct Sialyl-GlycoPEGylation of Factor IX

This example sets forth the preparation of sialyl-PEGylation of Factor IX without prior sialidase treatment.

Sialyl-PEGylation of Factor-IX with CMP-SA-PEG-(10 KDa). Factor IX (1100 IU), which was expressed in CHO cells and was fully sialylated, was dissolved in 5 mL of 20 mM histidine, 520 mM glycine, 2% sucrose, 0.05% $NaN_3$ and 0.01% polysorbate 80, pH 5.0. The CMP-SA-PEG-(10 kDa) (27 mg, 2.5 μmol) was then dissolved in the solution and 1 U of ST3Gal3 was added. The reaction was complete after gently mixing for 28 hours at 32° C. The reaction was analyzed by SDS-PAGE as described by Invitrogen. The product protein was purified on an Amersham Superdex 200 (10×300 mm, 13 μm) HPLC column with phosphate buffered saline, pH 7.0 (PBS), 1 mL/min. $R_t$=9.5 min.

Sialyl-PEGylation of Factor-IX with CMP-SA-PEG-(20 kDa). Factor IX (1100 IU), which was expressed in CHO cells and was fully sialylated, was dissolved in 5 mL of 20 mM histidine, 520 mM glycine, 2% sucrose, 0.05% $NaN_3$ and 0.01% polysorbate 80, pH 5.0. The CMP-SA-PEG-(20 kDa) (50 mg, 2.3 μmol) was then dissolved in the solution and CST-II was added. The reaction mixture was complete after gently mixing for 42 hours at 32° C. The reaction was analyzed by SDS-PAGE as described by Invitrogen.

The product protein was purified on an Amersham Superdex 200 (10×300 mm, 13 μm) HPLC column with phosphate buffered saline, pH 7.0 (Fisher), 1 mL/min. $R_t$=8.6 min.

21. Sialic Acid Capping of GlycoPEGylated Factor IX

This examples sets forth the procedure for sialic acid capping of sialyl-glycoPEGylated peptides. Here, Factor-IX is the exemplary peptide.

Sialic acid capping of N-linked and O-linked Glycans of Factor-IX-SA-PEG (10 kDa). Purified r-Factor-IX-PEG (10 kDa) (2.4 mg) was concentrated in a Centricon® Plus 20 PL-10 (Millipore Corp., Bedford, Mass.) centrifugal filter and the buffer was changed to 50 mM Tris-HCl pH 7.2, 0.15 M NaCl, 0.05% $NaN_3$ to a final volume of 1.85 mL. The protein solution was diluted with 372 μL of the same Tris buffer and 7.4 mg CMP-SA (12 μmol) was added as a solid. The solution was inverted gently to mix and 0.1 U ST3Gal1 and 0.1 U ST3Gal3 were added. The reaction mixture was rotated gently for 42 hours at 32° C. A 10 μg sample of the reaction was analyzed by SDS-PAGE. Novex Tris-Glycine 4-12% 1 mm gels were performed and stained using Colloidal Blue as described by Invitrogen. Briefly, samples, 10 μL (10

μg), were mixed with 12 μL sample loading buffer and 1 μL 0.5 M DTT and heated for 6 minutes at 85° C. (FIG. 156, lane 4).

Factor VIIa

22. GlycoPEGylation of Recombinant Factor VIIa Produced in MK Cells

This example sets forth the PEGylation of recombinant Factor VIIa made in BHK cells.

Preparation of Asialo-Factor VIIa. Recombinant Factor VIIa was Produced in BHK cells (baby hamster kidney cells). Factor VIIa (14.2 mg) was dissolved at 1 mg/ml in buffer solution (pH 7.4, 0.05 M Tris, 0.15 M NaCl, 0.001 M $CaCl_2$, 0.05% $NaN_3$) and was incubated with 300 mU/mL sialidase (*Vibrio cholera*)-agarose conjugate for 3 days at 32° C. To monitor the reaction a small aliquot of the reaction was diluted with the appropriate buffer and an IEF gel performed according to Invitrogen procedures (FIG. 157). The mixture was centrifuged at 3,500 rpm and the supernatant was collected. The resin was washed three times (3×2 mL) with the above buffer solution (pH 7.4, 0.05 M Tris, 0.15 M NaCl, 0.05% $NaN_3$) and the combined washes were concentrated in a Centricon-Plus-20. The remaining solution was buffer exchanged with 0.05 M Tris (pH 7.4), 0.15 M NaCl, 0.05% $NaN_3$ to a final volume of 14.4 mL.

Preparation of Factor VIIa-SA-PEG (1 kDa and 10 kDa). The desialylation rFactor VIIa solution was split into two equal 7.2 ml samples. To each sample was added either CMP-SA-5-PEG(1 kDa) (7.4 mg) or CMP-SA-5-PEG(10 kDa) (7.4 mg). ST3Gal3 (1.58 U) was added to both tubes and the reaction mixtures were incubated at 32° C. for 96 hrs.

The reaction was monitored by SDS-PAGE gel using reagents and conditions described by Invitrogen. When the reaction was complete, the reaction mixture was purified using a Toso Haas TSK-Gel-3000 preparative column using PBS buffer (pH 7.1) and collecting fractions based on UV absorption. The combined fractions containing the product were concentrated at 4° C. in Centricon-Plus-20 centrifugal filters (Millipore, Bedford, Mass.) and the concentrated solution reformulated to yield 1.97 mg (bicinchoninic acid protein assay, BCA assay, Sigma-Aldrich, St. Louis Mo.) of Factor VIIa-PEG. The product of the reaction was analyzed using SDS-PAGE and IEF analysis according to the procedures and reagents supplied by Invitrogen. Samples were dialyzed against water and analyzed by MALDI-TOF. FIG. 158 shows the MALDI results for native Factor VIIa. FIG. 159 contains the MALDI results for Factor VIIa PEGylated with 1 kDa PEG where peak of Factor VIIa PEGylated with 1 KDa PEG is evident. FIG. 160 contains the MALDI results for Factor VIIa PEGylated with 10 kDa PEG where a peak for Factor VIIa PEGylated with 10 kDa PEG is evident. FIG. 161 depicts the SDS-PAGE analysis of all of the reaction products, where a band for Factor VIIa-SA-PEG (10 kDa) is evident.

Follicle Stimulating Hormone (FSH)

23. GlycoPEGylation of Human Pituitary-Derived FSH

This example illustrates the assembly of a conjugate of the invention. Follicle Stimulating Hormone (FSH) is desialylated and then conjugated with CMP-(sialic acid)-PEG.

Desialylation of Follicle Stimulating Hormone. Follicle Stimulating Hormone (FSH) (Human Pituitary, Calbiochem Cat No. 869001), 1 mg, was dissolved in 500 μL 50 mM Tris-HCl pH 7.4, 0.15 M NaCl, 5 mM $CaCl_2$. This solution, 375 was transferred to a small plastic tube and to it was added 263 mU Neuraminidase II (*Vibrio cholerae*). The reaction mixture was shaken gently for 15 hours at 32° C. The reaction mixture was added to N-(p-aminophenyl)oxamic acid-agarose conjugate, 600 μL, pre-equilibrated with 50 mM Tris-HCl pH 7.4, 150 mM NaCl and 0.05% $NaN_3$ and gently rotated 6.5 hours at 4° C. The suspension was centrifuged for 2 minutes at 14,000 rpm and the supernatant was collected. The beads were washed 5 times with 0.5 mL of the buffer and all supernatants were pooled. The enzyme solution was dialyzed (7000 MWCO) for 15 hours at 4° C. with 2 L of a solution containing 50 mM Tris-HCl pH 7.4, 1 M NaCl, 0.05% $NaN_3$, and then twice for 4 hours at 4° C. into 50 mM Tris-HCl pH 7.4, 1 M NaCl, 0.05% $NaN_3$. The solution was concentrated to 2 μg/μL by Speed Vac and stored at −20° C. Reaction samples were analyzed by IEF gels (pH 3-7) (Invitrogen) (FIG. 162).

Preparation of Human Pituitary-Derived Sa-FSH and Peg-Sa-Follicle Stimulating Hormone. Desialylated FSH (100 μg, 50 μL) and CMP-sialic acid or CMP-SA-PEG (1 kDa or 10 kDa) (0.05 umol) were dissolved in 13.5 μL $H_2O$ (adjusted to pH 8 with NaOH) in 0.5 mL plastic tubes. The tubes were vortexed briefly and 40 mU ST3Gal3 (36.5 μL) was added (total volume 100 μL). The tubes were vortexed again and shaken gently for 24 hours at 32° C. The reactions were stopped by freezing at −80° C. Reaction samples of 15 μg were analyzed by SDS-PAGE (FIG. 163), IEF gels (FIG. 164) and MALDI-TOF. Native FSH was also analyzed by SDS-PAGE (FIG. 165)

Analysis of SDS PAGE and IEF Gels of Reaction Products. Novex Tris-Glycine 8-16% 1 mm gels for SDS PAGE analysis were purchased from Invitrogen. 7.5 μL (15 μg) of FSH reaction samples were diluted with 5 μL of 50 mM Tris-HCl, pH 7.4, 150 mM NaCl, 0.05% $NaN_3$ buffer, mixed with 15 μL sample loading buffer and 1 μL 9 M μ-mercaptoethanol and heated for 6 minutes at 85° C. Gels were run as directed by Invitrogen and stained with Colloidal Blue Stain (Invitrogen).

FSH samples (15 μg) were diluted with 5 μL Tris buffer and mixed with 15 μL sample loading buffer (FIG. 162). The samples were then applied to Isoelectric Focusing Gels (pH 3-7) (Invitrogen) (FIG. 165). Gels were run and fixed as directed by Invitrogen and then stained with Colloidal Blue Stain.

24. GlycoPEGylation of Recombinant FSH Produced Recombinantly in CHO Cells

This example illustrates the assembly of a conjugate of the invention. Desialylated FSH was conjugated with CMP-(sialic acid)-PEG.

Preparation of recombinant Asialo-Follicle Stimulation Hormone. Recombinant Follicle Stimulation Hormone (rFSH) produced from CHO was used in these studies. The 7,500 IU of rFSH was dissolved in 8 mL of water. The FSH solution was dialyzed in 50 mM Tris-HCl pH 7.4, 0.15 M NaCl, 5 mM $CaCl_2$ and concentrated to 500 μL in a Centricon Plus 20 centrifugal filter. A portion of this solution (400 μL) (~0.8 mg FSH) was transferred to a small plastic tube and to it was added 275 mU Neuraminidase II (*Vibrio cholerae*). The reaction mixture was mixed for 16 hours at 32° C. The reaction mixture was added to prewashed N-(p-aminophenyl) oxamic acid-agarose conjugate (800 μL) and gently rotated for 24 hours at 4° C. The mixture was centrifuged at 10,000 rpm and the supernatant was collected. The beads were washed 3 times with 0.6 mL Tris-EDTA buffer, once with 0.4 mL Tris-EDTA buffer and once with 0.2 mL of the Tris-EDTA buffer and all supernatants were pooled. The supernatant was dialyzed at 4° C. against 2 L of 50 mM Tris-HCl pH 7.4, 1 M NaCl, 0.05% $NaN_3$ and then twice more against 50 mM Tris-HCl pH 7.4, 1 M NaCl, 0.05% $NaN_3$. The dialyzed solution was then concentrated to 420 μL in a Centricon Plus 20 centrifugal filter and stored at −20° C.

Native and desialylated rFSH samples were analyzed by SDS-PAGE and IEF (FIG. 166). Novex Tris-Glycine 8-16% 1 mm gels were purchased from Invitrogen. Samples (7.5 μL, 15 μg) samples were diluted with 5 μL of 50 mM Tris-HCl, pH 7.4, 150 mM NaCl, 0.05% $NaN_3$ buffer, mixed with 15 μL sample loading buffer and 1 μL 9 M β-mercaptoethanol and heated for 6 minutes at 85° C. Gels were run as directed by Invitrogen and stained with Colloidal Blue Stain (Invitrogen). Isoelectric Focusing Gels (pH 3-7) were purchased from Invitrogen. Samples (7.5 μL, 15 μg) were diluted with 5 μL Tris buffer and mixed with 15 μL sample loading buffer. Gels were loaded, run and fixed as directed by Invitrogen. Gels were stained with Colloidal Blue Stain. Samples of native and desialylated FSH were also dialyzed against water and analyzed by MALDI-TOF.

Sialyl-PEGylation of recombinant Follicle Stimulation Hormone. Desialylated FSH (100 μg, 54 μL) and CMP-SA-PEG (1 kDa or 10 kDa) (0.05 μmol) were dissolved in 28 μL 50 mM Tris-HCl, 0.15 M NaCl, 0.05% $NaN_3$, pH 7.2 in 0.5 mL plastic tubes. The tubes were vortexed briefly and 20 mU of ST3Gal3 was added (total volume 100 μL). The tubes were vortexed again, mixed gently for 24 hours at 32° C. and the reactions stopped by freezing at −80° C. Samples of this reaction were analyzed as described above by SDS-PAGE gels (FIG. 167), IEF gels (FIG. 168) and MALDI-TOF MS.

MALDI was also performed on the PEGylated rFSH. During ionization, SA-PEG is eliminated from the N-glycan structure of the glycoprotein. Native FSH gave a peak at 13928; AS-rFSH (13282); resialylated r-FSH (13332); PEG1000-rFSH (13515; 14960 (1); 16455 (2); 17796 (3); 19321 (4)); and PEG 10000 (23560 (1); 34790 (2); 45670 (3); and 56760 (4)).

25. Pharmacokinetic Study of GlycoPEGylated FSH

This example sets forth the in vivo testing of the pharmacokinetic properties glycoPEGylated Follicle Stimulating Hormone (FSH) prepared according to the methods of the invention as compared to non-PEGylated FSH.

FSH, FSH-SA-PEG (1 kDa) and FSH-SA-PEG (10 kDa) were radioiodinated using standard conditions (Amersham Biosciences, Arlington Heights, Ill.) and formulated in phosphate buffered saline containing 0.1% BSA. After dilution in phosphate buffer to the appropriate concentration, each of the test FSH proteins (0.4 μg, each) was injected intraveneously into female Sprague Dawley rats (250-300 g body weight) and blood drawn at time points from 0 to 80 hours. Radioactivity in blood samples was analyzed using a gamma counter and the pharmacokinetics analyzed using standard methods (FIG. 169). FSH was cleared from the blood much more quickly than FSH-PEG(1 kDa), which in turn was clear somewhat more quickly than FSH-PEG(10 kDa).

26. Sertoli Cell Bioassay for In Vitro Activity of GlycoPEGylated FSH

This example sets forth a bioassay for follicle stimulating hormone (FSH) activity based on cultured Sertoli cells. This assay is useful to determine the bioactivity of FSH after glycan remodeling, including glycoconjugation.

This bioassay is based on the dose-response relationship that exists between the amount of estradiol produced when FSH, but not lutenizing hormone (LH), is added to cultured Sertoli cells obtained from immature old rats. Exogenous testosterone is converted to 17β-estradiol in the presence of FSH.

Seven to 10 days old Sprague-Dawley rats were used to obtain Sertoli cells. After sacrifice, testes were decapsulated and tissue was dispersed by incubation in collagenase (1 mg/ml), trypsin (1 mg/ml), hyaluronidase (1 mg/ml) and DNases (5 μg/ml) for 5 to 10 min. The tubule fragments settled to the bottom of the flask and were washed in PBS (1×). The tubule fragments were reincubated for 20 min with a media containing the same enzymes: collagenase (1 mg/ml), trypsin (1 mg/ml), hyaluronidase (1 mg/ml) and DNases (5 μg/ml).

The tubule fragments were homogenized and plated into a 24 well plate in a serum free media. $5\times10^5$ cells were dispersed per well. After 48 h incubation at 37° C. and 5% $CO_2$, fresh media was added to the cells. Composition of the serum free media: DMEM (1 vol), Ham's F10 nutrient mixture (1 vol), insulin 1 μg/ml, Transferrin 5 μg/ml, EGF 10 ng/ml, T4 20 pg/ml, Hydrocortisone $10^{-8}$M, Retinoic acid $10^{-6}$M.

The stimulation experiment consists of a 24 hour incubation with standard FSH or samples at 37° C. and 5% $CO_2$. The mean intra-assay coefficient of variation is 9% and the mean inter-assay coefficient of variation is 11%.

The 17B-estradiol Elisa Kit DE2000 (R&D Systems, Minneapolis, Minn.) was used to quantify the level of estradiol after incubation with FSH, FSH-SA-PEG (1 kDa) and FSH-SA-PEG (10 kDa).

The procedure was as follows: 100 μl of Estradiol Standard (provided with kit and prepared as per instructions with kit) or sample was pipetted into wells of 17B-estradiol Elisa plate(s); 50 μA of 17B-estradiol Conjugate (provided with kit, prepared as per instructions with kit) was added to each well; 50 μl of 17B-estradiol antibody solution (provided with kit and prepared as per instructions with kit) was added to each well; plates were incubated for 2 hour at room temperature at 200 rpm; the liquid was aspirated from each well; the wells were washed 4 times using the washing solution; all the liquid was removed from the wells; 200 μl of pNPP Substrate (provided with kit and prepared as per instructions with kit) was added to all wells and incubated for 45 min; 50 μl of Stop solution (provided with kit and prepared as per instructions with kit) was added and the plates were read it at 405 nm (FIG. 170). While FSH-PEG(10 kDa) exhibited a modest stimulation of Sertoli cells, at 1 μg/ml, FSH-PEG(1 kDa) stimulated Sertoli cells up to 50% more than unPEGylated FSH.

27. Steelman-Pohley Bioassay of In Vivo Activity of GlycoPEGvlated FSH

In this example, the Steelman-Pohley bioassay (Steelman and Pohley, 1953, Endocrinology 53:604-615) was used to determine the in vivo activity of glycoPEGylated FSH. The Steelman-Pohley assay uses the change in ovary weight of a rat to measure the in vivo activity of FSH that is coinjected with human chorionic gonadotropin.

The Steelman-Pohley bioassay was performed according to the protocol described in Christin-Maitre et al. (2000, Methods 21:51-57). Seventy female Sprague-Dawley Rats (Charles River Laboratories, Wilmington, Mass.), aged 21 to 22 days, were housed in the testing facility for at least 5 days before the beginning the assay procedure. Throughout the procedure, the animal room was climate controlled at 18 to 26° C., 30 to 70% relative humidity, and 12 hr. artificial light/12 hr. dark. All animals were fed Certified Rodent Chow (Harlan Teklad, Madison Wis.) or the equivalent, and water, both ad libitum. Animal procedures were performed at Calvert Preclinical Services, Inc. (Olyphant, Pa.).

Recombinant FSH was expressed in CHO cells, purified by standard techniques and glycoPEGylated with PEG (1 kDa). The rats were divided into seven test groups, with ten animals per group. On days −1 and 0, animals of all groups were subcutaneously injected with 20 I.U. of human chorionic gonadotropin (HCG) in 0.5 ml of 0.9% NaCl. On days 1, 2 and 3, the control animals were subcutaneously injected with a dose of 0.5 ml containing 20 I.U. HCG in 0.9% NaCl, while in the other groups, the HCG dose was augmented with either rFSH or rFSH-SA-PEG (1 kDa) at either 0.14 μg, 0.4 μg or 1.2 μg per dose. On day 4, the animals were euthanized by $CO_2$ inhalation. The ovaries were removed, trimmed and weighted. The average ovary weight was determined for each group.

FIG. 171 presents the average ovary weight of the test groups on day 4. The groups receiving HCG alone (control) or the low dose (0.14 μg) of either rFSH or rFSH-SA-PEG (1 kDa) had ovary weights that were roughly equivalent. The groups receiving the medium (0.4 μg) or high (1.2 μg) doses of rFSH or rFSH-SA-PEG (1 kDa) had ovary weights roughly twice that of the control group. At the medium dose (0.4 μg), the glycoPEGylated rFSH had roughly the same in vivo activity (as determined by ovary weight) as the unPEGylated rFSH. At the high dose (1.2 μg), the glycoPEGylated rFSH had somewhat higher in vivo activity than the unPEGylated rFSH.

G-CSF

28. GlycoPEGylation of G-CSF produced in CHO cells

Preparation of Asialo-Granulocyte-Colony Stimulation Factor (G-CSF). G-CSF produced in CHO cells is dissolved at 2.5 mg/mL in 50 mM Tris 50 mM Tris-HCl pH 7.4, 0.15 M NaCl, 5 mM $CaCl_2$ and concentrated to 500 μL in a Centricon Plus 20 centrifugal filter. The solution is incubated with 300 mU/mL Neuraminidase II (*Vibrio cholerae*) for 16 hours at 32° C. To monitor the reaction a small aliquot of the reaction is diluted with the appropriate buffer and a IEF gel performed. The reaction mixture is then added to prewashed N-(p-aminophenyl)oxamic acid-agarose conjugate (800 μL/mL reaction volume) and the washed beads gently rotated for 24 hours at 4° C. The mixture is centrifuged at 10,000 rpm and the supernatant was collected. The beads are washed 3 times with Tris-EDTA buffer, once with 0.4 mL Tris-EDTA buffer and once with 0.2 mL of the Tris-EDTA buffer and all supernatants are pooled. The supernatant is dialyzed at 4° C. against 50 mM Tris-HCl pH 7.4, 1 M NaCl, 0.05% $NaN_3$ and then twice more against 50 mM Tris-HCl pH 7.4, 1 M NaCl, 0.05% $NaN_3$. The dialyzed solution is then concentrated using a Centricon Plus 20 centrifugal filter and stored at −20° C. The conditions for the IEF gel were run according to the procedures and reagents provided by Invitrogen. Samples of native and desialylated G-CSF are dialyzed against water and analyzed by MALDI-TOF MS.

Preparation of G-CSF-(alpha-2,3)-Sialyl-PEG. Desialylated G-CSF was dissolved at 2.5 mg/mL in 50 mM Tris-HCl, 0.15 M NaCl, 0.05% $NaN_3$, pH 7.2. The solution is incubated with 1 mM CMP-sialic acid-PEG and 0.1 U/mL of ST3Gal1 at 32° C. for 2 days. To monitor the incorporation of sialic acid-PEG, a small aliquot of the reaction had CMP-SA-PEG-fluorescent ligand added; the label incorporated into the peptide is separated from the free label by gel filtration on a Toso Haas G3000SW analytical column using PBS buffer (pH 7.1). The fluorescent label incorporation into the peptide is quantitated using an in-line fluorescent detector. After 2 days, the reaction mixture is purified using a Toso Haas G3000SW preparative column using PBS buffer (pH 7.1) and collecting fractions based on UV absorption. The product of the reaction is analyzed using SDS-PAGE and IEF analysis according to the procedures and reagents supplied by Invitrogen. Samples of native and PEGylated G-CSF are dialyzed against water and analyzed by MALDI-TOF MS.

Preparation of G-CSF-(alpha-2,8)-Sialyl-PEG. G-CSF produced in CHO cells, which contains an alpha-2,3-sialylated O-linked glycan, is dissolved at 2.5 mg/mL in 50 mM Tris-HCl, 0.15 M NaCl, 0.05% $NaN_3$, pH 7.2. The solution is incubated with 1 mM CMP-sialic acid-PEG and 0.1 U/mL of CST-II at 32° C. for 2 days. To monitor the incorporation of sialic acid-PEG, a small aliquot of the reaction has CMP-SA-PEG-fluorescent ligand added; the label incorporated into the peptide is separated from the free label by gel filtration on a Toso Haas G3000SW analytical column using PBS buffer (pH 7.1). The fluorescent label incorporation into the peptide is quantitated using an in-line fluorescent detector. After 2 days, the reaction mixture is purified using a Toso Haas G3000SW preparative column using PBS buffer (pH 7.1) and collecting fractions based on UV absorption. The product of the reaction is analyzed using SDS-PAGE and IEF analysis according to the procedures and reagents supplied by Invitrogen. Samples of native and PEGylated G-CSF are dialyzed against water and analyzed by MALDI-TOF MS.

Preparation of G-CSF-(alpha-2,6)-Sialyl-PEG. G-CSF, containing only O-linked GalNAc, is dissolved at 2.5 mg/mL in 50 mM Tris-HCl, 0.15 M NaCl, 0.05% $NaN_3$, pH 7.2. The solution is incubated with 1 mM CMP-sialic acid-PEG and 0.1 U/mL of ST6GalNAcI or II at 32° C. for 2 days. To monitor the incorporation of sialic acid-PEG, a small aliquot of the reaction has CMP-SA-PEG-fluorescent ligand added; the label incorporated into the peptide is separated from the free label by gel filtration on a Toso Haas G3000SW analytical column using PBS buffer (pH 7.1). The fluorescent label incorporation into the peptide is quantitated using an in-line fluorescent detector. After 2 days, the reaction mixture is purified using a Toso Haas G3000SW preparative column using PBS buffer (pH 7.1) and collecting fractions based on UV absorption. The product of the reaction is analyzed using SDS-PAGE and IEF analysis according to the procedures and reagents supplied by Invitrogen. Samples of native and PEGylated G-CSF are dialyzed against water and analyzed by MALDI-TOF MS.

G-CSF produced in CHO cells was treated with *Arthrobacter* sialidase and was then purified by size exclusion on Superdex75 and was treated with ST3Gal1 or ST3 Gal2 and then with CMP-SA-PEG 20 Kda. The resulting molecule was purified by ion exchange and gel filtration and analysis by SDS PAGE demonstrated that the PEGylation was complete. This is the first demonstration of glycoPEGylation of an O-linked glycan.

Glucocerebrosidase

29. Glucocerebrosidase-Mannose-6-Phosphate Produced in CHO Cells

This example sets forth the procedure to glycoconjugate mannose-6-phosphate to a peptide produced in CHO cells such as glucocerebrosidase.

Preparation of asialo-glucoceramidase. Glucocerebrosidase Produced in Cho Cells is dissolved at 2.5 mg/mL in 50 mM Tris 50 mM Tris-HCl pH 7.4, 0.15 M NaCl, and is incubated with 300 mU/mL sialidase-agarose conjugate for 16 hours at 32° C. To monitor the reaction a small aliquot of the reaction is diluted with the appropriate buffer and a IEF gel and SDS-PAGE performed according to Invitrogen procedures. The mixture is centrifuged at 10,000 rpm and the supernatant is collected. The beads are washed 3 times with Tris-EDTA buffer, once with 0.4 mL Tris-EDTA buffer, and once with 0.2 mL of the Tris-EDTA buffer. All supernatants are pooled. The supernatant is dialyzed at 4° C. against 50 mM Tris-HCl pH 7.4, 1 M NaCl, 0.05% $NaN_3$ and then twice more against 50 mM Tris-HCl pH 7.4, 1 M NaCl, 0.05% $NaN_3$. The dialyzed solution is then concentrated using a Centricon Plus 20 centrifugal filter. The product of the reaction is analyzed using SDS-PAGE and IEF analysis according to the procedures and reagents supplied by Invitrogen. Samples are dialyzed against water and analyzed by MALDI-TOF MS.

Preparation of Glucocerebrosidase-SA-linker-Mannose-6-phosphate (procedure 1). Asialo-glucocerebrosidasefrom above is dissolved at 2.5 mg/mL in 50 mM Tris-HCl, 0.15 M NaCl, 0.05% $NaN_3$, pH 7.2. The solution is incubated with 1 mM CMP-sialic acid-linker-Man-6-phosphate and 0.1 U/mL of ST3Gal3 at 32° C. for 2 days. To monitor the incorporation of sialic acid-linker-Man-6-phosphate, a small aliquot of the reaction had CMP-SA-PEG-fluorescent ligand added; the label incorporated into the peptide is separated from the free label by gel filtration on a Toso Haas TSK-Gel-3000 analytical column using PBS buffer (pH 7.1). The fluorescent label incorporation into the peptide is quantitated using an in-line fluorescent detector. When the reaction is complete, the reaction mixture is purified using a Toso Haas TSK-Gel-3000 preparative column using PBS buffer (pH 7.1) and collecting fractions based on UV absorption. The product of the reaction is analyzed using SDS-PAGE and IEF analysis according to the procedures and reagents supplied by Invitrogen. Samples are dialyzed against water and analyzed by MALDI-TOF MS.

Preparation of Glucocerebrosidase-SA-linker-Mannose-6-phosphate (procedure 2). Glucocerebrosidase, produced in CHO but incompletely sialylated, is dissolved at 2.5 mg/mL in 50 mM Tris-HCl, 0.15 M NaCl, 0.05% $NaN_3$, pH 7.2. The solution is incubated with 1 mM CMP-sialic acid-linker-Man-6-phosphate and 0.1 U/mL of ST3Gal3 at 32° C. for 2 days. To monitor the incorporation of sialic acid-linker-Man-6-phosphate, a small aliquot of the reaction had CMP-SA-PEG-fluorescent ligand added; the label incorporated into the peptide is separated from the free label by gel filtration on a Toso Haas TSK-Gel-3000 analytical column using PBS buffer (pH 7.1). The fluorescent label incorporation into the peptide is quantitated using an in-line fluorescent detector. When the reaction is complete, the reaction mixture is purified using a Toso Haas TSK-Gel-3000 preparative column using PBS buffer (pH 7.1) and collecting fractions based on UV absorption. The product of the reaction is analyzed using SDS-PAGE and IEF analysis according to the procedures and reagents supplied by Invitrogen. Samples are dialyzed against water and analyzed by MALDI-TOF MS.

30. Glucocerebrosidase-Transferrin

This example sets forth the procedures for the glycoconjugation of proteins, and in particular, transferrin is glycoconjugated to glucocerebrosidase. The GlcNAc-ASN structures are created on glucoceraminidase, and Transferrin-SA-Linker-Gal-UDP is conjugated to GNDF GlcNAc-ASN structures using galactosyltransferase.

Preparation of GlcNAc-glucocerebrosidase (Cerezyme™). Cerezyme™ (glucocerebrosidase) produced in CHO cells is dissolved at 2.5 mg/mL in 50 mM Tris 50 mM Tris-HCl pH 7.4, 0.15 M NaCl, and is incubated with 300 mU/mL Endo-H-agarose conjugate for 16 hours at 32° C. To monitor the reaction a small aliquot of the reaction is diluted with the appropriate buffer and a IEF gel and SDS-PAGE performed according to Invitrogen procedures. The mixture is centrifuged at 10,000 rpm and the supernatant is collected. The beads are washed 3 times with Tris-EDTA buffer, once with 0.4 mL Tris-EDTA buffer and once with 0.2 mL of the Tris-EDTA buffer and all supernatants are pooled. The supernatant is dialyzed at 4° C. against 50 mM Tris-HCl pH 7.4, 1 M NaCl, 0.05% $NaN_3$ and then twice more against 50 mM Tris-HCl pH 7.4, 1 M NaCl, 0.05% $NaN_3$. The dialyzed solution is then concentrated using a Centricon Plus 20 centrifugal filter. The product of the reaction is analyzed using SDS-PAGE and IEF analysis according to the procedures and reagents supplied by Invitrogen. Samples are dialyzed against water and analyzed by MALDI-TOF MS.

Preparation of Transferrin-SA-Linker-Gal-glucocerebrosidase. Transferrin-SA-Linker-Gal-UDP from above is dissolved at 2.5 mg/mL in 50 mM Tris-HCl, 0.15 M NaCl, 5 mM $MnCl_2$, 0.05% $NaN_3$, pH 7.2. The solution is incubated with 2.5 mg/mL GlcNAc-glucocerebrosidaseand 0.1 U/mL of galactosyltransferase at 32° C. for 2 days. To monitor the incorporation of glucocerebrosidase, the peptide is separated by gel filtration on a Toso Haas G3000SW analytical column using PBS buffer (pH 7.1) and the product detected by UV absorption. The reaction mixture is then purified using a Toso Haas G3000SW preparative column using PBS buffer (pH 7.1) collecting fractions based on UV absorption. The product of the reaction is analyzed using SDS-PAGE and IEF analysis according to the procedures and reagents supplied by Invitrogen. Samples are dialyzed against water and analyzed by MALDI-TOF MS.

GM-CSF

31. Generation and PEGylation of GlcNAc-ASN Structures: GM-CSF Produced in *Saccharomyces*

This example sets forth the preparation of Tissue-type Activator with PEGylated GlcNAc-Asn structures.

Recombinant GM-CSF expressed in yeast is expected to contain 2 N-linked and 2 O-linked glycans. The N-linked glycans should be of the branched mannan type. This recombinant glycoprotein is treated with an endoglycosidase from the group consisting of endoglycosidase H, endoglycosidase-F1, endoglycosidase-F2, endoglycosidase-F3, endoglycosidase-M either alone or in combination with mannosidases I, II and III to generate GlcNAc nubs on the asparagine (Asn) residues on the peptide/protein backbone.

The GlcNAc-Asn structures on the peptide/protein backbone is then be modified with galactose or galactose-PEG using UDP-galactose or UDP-galactose-6-PEG, respectively, and a galactosyltransferase such as GalT1. In one case the galactose-PEG is the terminal residue. In the second case the galactose is further modified with SA-PEG using a CMP-SA-PEG donor and a sialyltransferase such as ST3GalIII. In another embodiment the GlcNAc-Asn structures on the peptide/protein backbone can be galactosylated and sialylated as described above, and then further sialylated using CMP-SA-PEG and an α2,8-sialyltranferase such as the enzyme encoded by the *Campylobacter jejuni* cst-II gene.

Herceptin™

32. Glycoconjugation of Mithramycin to Herceptin™

This example sets forth the procedures to glycoconjugate a small molecule, such as mithramycin to Fc region glycans of an antibody molecule produced in mammalian cells. Here, the antibody Herceptin™ is used, but one of skill in the art will appreciate that the method can be used with many other antibodies.

Preparation of Herceptin™-Gal-linker-mithramycin. Herceptin™ is dissolved at 2.5 mg/mL in 50 mM Tris-HCl, 0.15 M NaCl, 5 mM $MnCl_2$, 0.05% $NaN_3$, pH 7.2. The solution is incubated with 1 mM UDP-galactose-linker-mithramycin and 0.1 U/mL of galactosyltransferase at 32° C. for 2 days to introduce the mithramycin in the Fc region glycans. To monitor the incorporation of galactose, a small aliquot of the reaction has $^{14}C$-galactose-UDP ligand added; the label incorporated into the peptide is separated from the free label by gel filtration on a Toso Haas G3000SW analytical column using PBS buffer (pH 7.1). The radioactive label incorporation into the peptide is quantitated using an in-line radiation detector.

When the reaction is complete, the reaction mixture is purified using a Toso Haas TSK-Gel-3000 preparative column using PBS buffer (pH 7.1) and collecting fractions based on UV absorption. The fractions containing product are combined, concentrated, buffer exchanged and then freeze-dried. The product of the reaction is analyzed using SDS-PAGE and IEF analysis according to the procedures and reagents supplied by Invitrogen. Samples are dialyzed against water and analyzed by MALDI-TOF MS.

Interferon α and Interferon β

33. GlycoPEGylation of Proteins expressed in Mammalian or Insect Systems: EPO, Interferon α and Interferon β

This example sets forth the preparation of PEGylated peptides that are expressed in mammalian and insect systems.

Preparation of acceptor from mammalian expression systems. The peptides to be glycoPEGylated using CMP-sialic acid PEG need to have glycans terminating in galactose. Most peptides from mammalian expression systems will have terminal sialic acid that first needs to be removed.

Sialidase digestion. The peptide is desialylated using a sialidase. A typical procedure involves incubating a 1 mg/mL solution of the peptide in Tris-buffered saline, pH 7.2, with 5 mM $CaCl_2$ added, with 0.2 U/mL immobilized sialidase from *Vibrio cholera* (Calbiochem) at 32° C. for 24 hours. Microbial growth can be halted either by sterile filtration or the inclusion of 0.02% sodium azide. The resin is then removed by centrifugation or filtration, and then washed to recover entrapped peptide. At this point, EDTA may be added to the solution to inhibit any sialidase that has leached from the resin.

Preparation from insect expression systems. EPO, interferon-alpha, and interferon-beta may also be expressed in non-mammalian systems such as yeast, plants, or insect cells. The peptides to be glycoPEGylated using CMP-sialic acid PEG need to have glycans terminating in galactose. The majority of the N-glycans on peptides expressed in insect cells, for example, are the trimannosyl core. These glycans are first built out to glycans terminating in galactose before they are acceptors for sialyltransferase.

Building acceptor glycans from trimannosyl core. Peptide (1 mg/mL) in Tris-buffered saline, pH 7.2, containing 5 mM $MnCl_2$, 5 mM UDP-glcNAc, 0.05 U/mL GLCNACT I, 0.05 U/mL GLCNACT II, is incubated at 32° C. for 24 hours or until the reaction is substantially complete. Microbial growth can be halted either by sterile filtration or the inclusion of 0.02% sodium azide. After buffer exchange to remove UDP and other small molecules, UDP-galactose and $MnCl_2$ are each added to 5 mM, galactosyltransferase is added to 0.05 U/mL, and is incubated at 32° C. for 24 H or until the reaction is substantially complete. Microbial growth can be halted either by sterile filtration or the inclusion of 0.02% sodium azide. The peptides are then ready for glycoPEGylation.

Building O-linked glycans. A similar strategy may be employed for interferon alpha to produce enzymatically the desired O-glycan Gal-GalNAc. If necessary, GalNAc linked to serine or threonine can be added to the peptide using appropriate peptide GalNAc transferases (e.g. GalNAc T1, GalNAc T2, T3, T4, etc.) and UDP-GalNAc. Also, if needed, galactose can be added using galactosyltransferase and UDP-galactose.

GlycoPEGylation using sialyltransferase. The glycopeptides (1 mg/mL) bearing terminal galactose in Tris buffered saline +0.02% sodium azide are incubated with CMP-SA-PEG (0.75 mM) and 0.4 U/mL sialyltransferase (ST3Gal3 or ST3Gal4 for N-glycans on EPO and interferon beta; ST3Gal4, or ST3Gal1 for O-glycans on interferon alpha) at 32° C. for 24 hours. Other transferases that may work include the 2,6 sialyltransferase from *Photobacterium damsella*. The acceptor peptide concentration is most preferably in the range of 0.1 mg/mL up to the solubility limit of the peptide. The concentration of CMP-SA-PEG should be sufficient for there to be excess over the available sites, but not so high as to cause peptide solubility problems due to the PEG, and may range from 50 μM up to 5 mM, and the temperature may range from 2° C. up to 40° C. The time required for complete reaction will depend on the temperature, the relative amounts of enzyme to acceptor substrate, the donor substrate concentration, and the pH.

34. GlycoPEGylation of Interferon α Produced in CHO Cells

Preparation of Asialo-Interferon α. Interferon Alpha Produced from Cho Cells is dissolved at 2.5 mg/mL in 50 mM Tris 50 mM Tris-HCl pH 7.4, 0.15 M NaCl, 5 mM $CaCl_2$ and concentrated to 5004 in a Centricon Plus 20 centrifugal filter. The solution is incubated with 300 mU/mL Neuraminidase II (*Vibrio cholerae*) for 16 hours at 32° C. To monitor the reaction a small aliquot of the reaction is diluted with the appropriate buffer and a IEF gel performed. The reaction mixture is then added to prewashed N-(p-aminophenyl)oxamic acid-agarose conjugate (800 μL/mL reaction volume) and the washed beads gently rotated for 24 hours at 4° C. The mixture is centrifuged at 10,000 rpm and the supernatant was collected. The beads are washed 3 times with Tris-EDTA buffer, once with 0.4 mL Tris-EDTA buffer and once with 0.2 mL of the Tris-EDTA buffer and all supernatants were pooled. The supernatant is dialyzed at 4° C. against 50 mM Tris-HCl pH 7.4, 1 M NaCl, 0.05% $NaN_3$ and then twice more against 50 mM Tris-HCl pH 7.4, 1 M NaCl, 0.05% $NaN_3$. The dialyzed solution is then concentrated using a Centricon Plus 20 centrifugal filter and stored at −20° C. The conditions for the IEF gel are run according to the procedures and reagents provided by Invitrogen. Samples of native and desialylated G-CSF are dialyzed against water and analyzed by MALDI-TOF MS.

Preparation of Interferon-alpha-(alpha-2,3)-Sialyl-PEG. Desialylated interferon-alpha is dissolved at 2.5 mg/mL in 50 mM Tris-HCl, 0.15 M NaCl, 0.05% $NaN_3$, pH 7.2. The solution is incubated with 1 mM CMP-sialic acid-PEG and 0.1 U/mL of ST3Gal1 at 32° C. for 2 days. To monitor the incorporation of sialic acid-PEG, a small aliquot of the reaction had CMP-SA-PEG-fluorescent ligand added; the label incorporated into the peptide is separated from the free label by gel filtration on a Toso Haas G3000SW analytical column using PBS buffer (pH 7.1). The fluorescent label incorporation into the peptide is quantitated using an in-line fluorescent detector. After 2 days, the reaction mixture is purified using a Toso Haas G3000SW preparative column using PBS buffer (pH 7.1) and collecting fractions based on UV absorption. The product of the reaction is analyzed using SDS-PAGE and IEF analysis according to the procedures and reagents supplied by Invitrogen. Samples of native and desialylated Interferon-alpha are dialyzed against water and analyzed by MALDI-TOF MS.

Preparation of Interferon-alpha-(alpha-2,8)-Sialyl-PEG. Interferon-alpha produced in CHO, which contains an alpha-2,3-sialylated O-linked glycan, is dissolved at 2.5 mg/mL in 50 mM Tris-HCl, 0.15 M NaCl, 0.05% $NaN_3$, pH 7.2. The solution is incubated with 1 mM CMP-sialic acid-PEG and 0.1 U/mL of CST-II at 32° C. for 2 days. To monitor the incorporation of sialic acid-PEG, a small aliquot of the reaction has CMP-SA-PEG-fluorescent ligand added; the label incorporated into the peptide is separated from the free label by gel filtration on a Toso Haas G3000SW analytical column using PBS buffer (pH 7.1). The fluorescent label incorporation into the peptide is quantitated using an in-line fluorescent detector. After 2 days, the reaction mixture is purified using a Toso Haas G3000SW preparative column using PBS buffer (pH 7.1) and collecting fractions based on UV absorption. The product of the reaction is analyzed using SDS-PAGE and IEF analysis according to the procedures and reagents supplied by Invitrogen. Samples of native and PEGylated interferon-alpha are dialyzed against water and analyzed by MALDI-TOF MS.

Preparation of Interferon-alpha-(alpha-2,6)-Sialyl-PEG. Interferon-alpha, containing only O-linked GalNAc, was dissolved at 2.5 mg/mL in 50 mM Tris-HCl, 0.15 M NaCl, 0.05% $NaN_3$, pH 7.2. The solution is incubated with 1 mM CMP-sialic acid-PEG and 0.1 U/mL of ST6GalNAcI or II at 32° C. for 2 days. To monitor the incorporation of sialic acid-PEG, a small aliquot of the reaction had CMP-SA-PEG-fluorescent ligand added; the label incorporated into the peptide is separated from the free label by gel filtration on a Toso Haas G3000SW analytical column using PBS buffer (pH 7.1). The fluorescent label incorporation into the peptide is quantitated using an in-line fluorescent detector. After 2 days, the reaction mixture is purified using a Toso Haas G3000SW preparative column using PBS buffer (pH 7.1) and collecting fractions based on UV absorption. The product of the reaction is analyzed using SDS-PAGE and IEF analysis according to the procedures and reagents supplied by Invitrogen. Samples of native and PEGylated interferon-alpha are dialyzed against water and analyzed by MALDI-TOF MS.

35. GlycoPEGylation of Interferon-β-1a with PEG (10 kDa) and PEG (20 kDa)

This example illustrates a procedure PEGylate Interferon-β with either PEG (10 kDa) or PEG (20 kDa).

Briefly, Interferon-β-1a (INF-β) was obtained from Biogen (Avonex™). The IFN-β was first purified by Superdex-75 chromatography. The IFN-β was then desialylated with *Vibrio cholerae* sialidase. The INF-β was then PEGylated with SA-PEG (10 kDa) or SA-PEG (20 kDa) and purified with Superdex-200 chromatography.

Superdex-75 chromatography purification. INF-β (150 μg) was applied to a Superdex-75 column (Amersham Biosciences, Arlington Heights, Ill.) and eluted with PBS with 0.5 M NaCl, 0.02 Tween-20, 20 mM histidine and 10% glycerol. The eluant was monitored for absorbance at 280 nm (FIGS. 172A and 172B) and fractions were collected. Peaks 4 and 5 were pooled, concentrated in an Amicon Ultra 15 spin filter (Millipore, Billerica, Mass.), and the buffer was exchanged to TBS with 5 mM $CaCl_2$, 0.02% Tween-20, mM histidine and 10% glycerol.

Sialidase Reaction. The INF-β was then desialydated with *Vibrio cholera* salidase (70 mU/ml, CALBIOCHEM®, EMD Biosciences, Inc., San Diego, Calif.) on agarose in TBS with 5 mM $CaCl_2$, 0.02% Tween-20, 20 mM histidine and 10% glycerol. The reaction was carried out at 32° C. for 18 hours. The INF-β was removed from the agarose with a 0.22 μm Spin-X™ filter (Corning Technology, Inc., Norcross, Ga.). FIG. 173A depicts the MALDI analysis of glycans released from native INF-β. The native INF-β has many glycoforms containing terminal sialic acid moieties. FIG. 173B depicts the MALDI analysis of glycans released from desialylated INF-β. The desialylated INF-β has primarily one glycoform which is bi-antennary with terminal galactose moieties.

Lectin Dot-Blot Analysis of Sialylation. Samples of the INF-β from the desialidase reaction were dot-blotted onto nitrocellulose and then blocked with Tris buffered saline (TBS: 0.05M Tris, 0.15M NaCl, pH 7.5) and DIG kit (glycan differentiation kit available from Roche #1 210 238) blocking buffer. Some of the blots were incubated with *Maackia amurensis* agglutinin (MAA) labeled with digoxogenin (DIG) (Roche Applied Science, Indianapolis, Ill.) to detect α2,3-sialylation of INF-β. These blots were washed with TBS then incubated with anti-digitonin antibody labeled with alkaline phosphatase, then washed again with TBS and developed with NBT/X-phosphate solution, wherein NBT is 4-nitro blue tetrazolium chloride and X-phosphate is 5-bromo-4-chloro-3indoyl phosphate. The left side of FIG. 174 depicts the results of the MAA blot of INF-β after the desialylation reaction. The INF-β is partially disialylated, as indicated by the decrease in dot development as compared to native INF-β in the desialylated samples.

Other blots were incubated with *Erthrina cristagalli* lectin (ECL) labeled with biotin (Vector Laboratories, Burlingame, Calif.) to detect exposed galactose residues on INF-β. After incubation with 2.5 μg/ml ECL, the blots were washed in TBS and incubated with streptavidin labeled with alkaline phosphatase. The blots were then washed again and developed. The right side of FIG. 174 depicts the ECL blot after development. The increased intensity of the dot of desialylated INF-β as compared to the native INF-β indicate more exposed galactose moieties and therefore extensive desialylation.

PEGylation of Desialylated INF-β with SA-PEG (10 kDa). Desialylated INF-β (0.05 mg/ml) was PEGylated with ST3Gal3 (50 mU/ml) and CMP-SA-PEG (10 kDa) (250 μM) in an appropriate buffer of TBS+5 mM $CaCl_2$, 0.02% Tween 20, 20 mM histidine, 10% glycerol for 50 hours at 32° C. FIG. 175 depicts the SDS-PAGE analysis of the reaction products showing PEGylated INF-β at approximately 98 kDa.

PEGylation of Desialylated INF-β with SA-PEG (20 kDa). Desialylated INF-β (0.5 mg/ml) was PEGylated with ST3Gal3 (170 mU/ml) and CMP-SA-PEG (20 kDa) in an appropriate buffer of TBS+5 mM $CaCl_2$, 0.02% Tween 20, 20 mM histidine, 10% glycerol for 50 hours at 32° C. FIG. 176 depicts the SDS-PAGE analysis the products of the PEGylation reaction. The PEGylated INF-β has many higher molecular weight bands not found in the unmodified INF-β indicating extensive PEGylation.

Superdex-200 Purification of INF-β PEGylated with PEG (10 kDa). The products of the PEGylation reaction were separated on a Superdex-200 column (Amersham Biosciences, Arlington Heights, Ill.) in PBS with 0.5 NaCl, 0.02 Tween-20, 20 mM histidine and 10% glycerol at 1 ml/min and 30 cm/hr flow. The eluant was monitored for absorbance at 280 nm (FIG. 177) and fractions were collected. Peaks 3 and 4 were pooled and concentrated in an Amicon Ultra 15 spin filter.

Bioassay of INF-β PEGylated with PEG (10 kDa).

The test is inhibition of the proliferation of the lung carcinoma cell line, A549. The A549 cell line are lung carcinoma adherent cells growing in RPMI+10% FBS at 37° C. 5% $CO_2$. They can be obtained from ATCC # CCL-185. Wash the cells with 10 ml of PBS and remove the PBS. Add 5 ml of trypsin, incubate for 5 minutes at room temperature or 2 minutes at 37° C. When the cells are detached resuspend into 25 ml of media and count the cells. Dilute the cells at a concentration of 10000 cells/ml and add 200 ul/well (96 wells plate). Incubate for 4 hours at 37° C. 5% $CO_2$. Prepare 1 ml of IFN B at a concentration of 0.1 ug/ml. Filter it under the hood with a 0.2 um filter. Add 100 ul per well (8 replicates=1 lane). Incubate for 3 days (do not let the cells go to confluence). Remove 200 ul of media (only 100 ul per well left). Add 25 μl of MTT (Sigma) (5 mg/ml filtered 0.22 μm). Incubate for 4 hours at 37° C. and 5% $CO_2$. Aspirate the media gently and add 100 μl of a mixture of isopropanol (100 ml and 6N HCl. Aspirate up and down to homogenize the crystal violet. Read OD 570 nm (remove the background at 630 or 690 nm).

FIG. 178 depicts the results of the bioassay of the peaks containing INF-β PEGylated with PEG (10 kDa) as eluted from the Superdex-200 column.

Superdex-200 Purification of INF-β PEGylated with PEG (20 kDa). The products of the PEG (20 kDa) PEGylation reaction were separated on a Superdex-200 column (Amersham Biosciences, Arlington Heights, Ill.) in PBS with 0.5 NaCl, 0.02 Tween-20, 20 mM histidine and 10% glycerol at 1 ml/min flow. The eluant was monitored for absorbance at 280 nm (FIG. 179) and fractions were collected. Peak 3 contained most of the INF-β PEGylated with PEG (20 kDa).

Endotoxin test of INF-β PEGylated with PEG (20 kDa).

Limulus Lysate Test was performed, BioWhittaker # 50-647 U

TABLE 24

Results of the endotoxin test of INF-β PEGylated with PEG (20 kDa).

| | | Concentration | |
|---|---|---|---|
| INF-β with PEG (20 kDa) | 10 EU/ml | 0.06 mg/ml | 0.16 EU/μg |
| INF-β with PEG (20 kDa) | 1 EU/ml | 0.07 mg/ml | 0.014 EU/μg |
| Native INF-β | 40 EU/ml | 0.1 mg/ml | 0.4 EU/μg |

Remicade™

36. GlycoPEGylation of Remicade™ Antibody

This example sets forth the procedure to glycoPEGylate a recombinant antibody molecule by introducing PEG molecules to the Fc region glycans. Here Remicade™, a TNF-R: IgG Fc region fusion protein, is the exemplary peptide.

Preparation of Remicade™-Gal-PEG (10 kDa). Remicade™ is dissolved at 2.5 mg/mL in 50 mM Tris-HCl, 0.15 M NaCl, 5 mM $MnCl_2$, 0.05% $NaN_3$, pH 7.2. The solution is incubated with 1 mM UDP-galactose-PEG (10 kDa) and 0.1 U/mL of galactosyltransferase at 32° C. for 2 days to introduce the PEG in the Fc region glycans. To monitor the incorporation of galactose, a small aliquot of the reaction has $^{14}C$-galactose-UDP ligand added; the label incorporated into the peptide is separated from the free label by gel filtration on a Toso Haas G3000SW analytical column using PBS buffer (pH 7.1). The radioactive label incorporation into the peptide is quantitated using an in-line radiation detector.

When the reaction is complete, the reaction mixture is purified using a Toso Haas TSK-Gel-3000 preparative column using PBS buffer (pH 7.1) and collecting fractions based on UV absorption. The fractions containing product are combined, concentrated, buffer exchanged and then freeze-dried. The product of the reaction is analyzed using SDS-PAGE and IEF analysis according to the procedures and reagents supplied by Invitrogen. Samples are dialyzed against water and analyzed by MALDI-TOF MS.

Rituxan™

37. Glycoconjugation of Geldanamycin to Rituxan™

This example sets forth the glycoconjugation of a small molecule, such as geldanamycin, to the Fc region glycans of an antibody produced in CHO cells, such as Rituxan™. Here, the antibody Rituxan™ is used, but one of skill in the art will appreciate that the method can be used with many other antibodies.

Preparation of Rituxan™-Gal-linker-geldanamycin. Rituxan™ is dissolved at 2.5 mg/mL in 50 mM Tris-HCl, 0.15 M NaCl, 5 mM $MnCl_2$, 0.05% $NaN_3$, pH 7.2. The solution is incubated with 1 mM UDP-galactose-linker-geldanamycin and 0.1 U/mL of galactosyltransferase at 32° C. for 2 days to introduce the geldanamycin in the Fc region glycans. To monitor the incorporation of galactose, a small aliquot of the reaction has $^{14}C$-galactose-UDP ligand added; the label incorporated into the peptide is separated from the free label by gel filtration on a Toso Haas G3000SW analytical column using PBS buffer (pH 7.1). The radioactive label incorporation into the peptide is quantitated using an in-line radiation detector.

When the reaction is complete, the reaction mixture is purified using a Toso Haas TSK-Gel-3000 preparative column using PBS buffer (pH 7.1) and collecting fractions based on UV absorption. The fractions containing product are combined, concentrated, buffer exchanged and then freeze-dried. The product of the reaction is analyzed using SDS-PAGE and IEF analysis according to the procedures and reagents supplied by Invitrogen. Samples are dialyzed against water and analyzed by MALDI-TOF MS.

Rnase

38. Remodeling High Mannose N-Glycans to Hybrid and Complex N-Glycans: Bovine Pancreatic RNase This example sets forth the preparation of bovine pancreas RNase with hybrid or complex N-glycans. The high mannose N-linked glycans of the RNase are enzymatically digested and elaborated to create hybrid N-linked glycans. Additionally, the high mannose N-linked glycans of the RNase are enzymatically digested and elaborated to create complex N-linked glycans.

High mannose structures of N-linked oligosaccharides in glycopeptides can be modified to hybrid or complex forms using the combination of α-mannosidases and glycosyltransferases.

This example summarizes the results in such efforts using a simple N-Glycan as a model substrate.

Ribonuclease B (RNaseB) purified from bovine pancreas (Sigma) is a glycopeptide consisting of 124 amino acid residues. It has a single potential N-glycosylation site modified with high mannose structures. Due to its simplicity and low molecular weight (13.7 kDa to 15.5 kDa), ribonuclease B is a good candidate to demonstrate the feasibility of the N-Glycan remodeling from high mannose structures to hybrid or complex N-linked oligosaccharides. The MALDI-TOF spectrum of RNaseB (FIG. 180A) and HPLC profile for the oligosaccharides cleaved from RNaseB by N-Glycanase (FIG. 180B) indicated that, other than a small portion of the non-modified peptide, the majority of N-glycosylation sites of the peptide are modified with high mannose oligosaccharides consisting of 5 to 9 mannose residues.

Conversion of high mannose N-Glycans to hybrid N-Glycans. High mannose N-Glycans were converted to hybrid N-Glycans using the combination of α1,2-mannosidase, GlcNAcT-I (β-1,2-N-acetyl glucosaminyl transferase), GalT-I (β1,4-galactosyltransfease) and α2,3-sialyltransferase for α2,6-sialyltransferase as shown in FIG. 181.

As an example, high mannose structures in RNaseB were successfully converted to hybrid structures.

$Man_5GlcNAc_2$-R was obtained from $Man_{5-9}GlcNAc_2$-R catalyzed by a single α1,2-mannosidase cloned from *Trichoderma reesei* (FIG. 182). RNase B (1 g, about 67 μmol) was incubated at 30° C. for 45 hr with 15 mU of the recombinant *T. reesei* α1,2-mannosidase in MES buffer (50 mM, pH 6.5) in a total volume of 10 mL. $Man_{6-9}GlcNAc_2$-protein structures have been successfully converted to $Man_5GlcNAc_2$-protein with high efficiency by the recombinant mannosidase.

Alternately, $Man_5GlcNAc_2$-R was obtained from $Man_{5-9}GlcNAc_2$-R catalyzed by a single α1,2-mannosidase purified from *Aspergillus saitoi* (FIG. 183). RNase B (40 μg, about 2.7 nmol) was incubated at 37° C. for 42.5 hr with 25 μU of the commercial *A. saitoi* α1,2-mannosidase (Glyko or CalBioChem) in NaOAC buffer (100 mM, pH 5.0) in a total volume of 20 μl. $Man_{6-9}GlcNAc_2$-protein structures were successfully converted to $Man_5GlcNAc_2$-protein by the commercially available mannosidase. However, a new peak corresponding to the GlcNAc-protein appears in the spectrum, indicating the possible contamination of endoglycosidase H in the preparation. Although several mammalian alpha-mannosidases were required to achieve this step, the fungal α1,2-mannosidase was very efficient to remove all α1,2-linked mannose residues.

GlcNAcT-I then added a GlcNAc residue to the Man$_5$GlcNAc$_2$-R (FIG. 184). The reaction mixture after the *T. reesei* α1,2-mannosidase reaction containing RNase B (600 µg, about 40 nmol) was incubated with non-purified recombinant GlcNAcT-I (34 mU) in MES buffer (50 mM; pH 6.5) containing MnCl$_2$ (20 mM) and UDP-GlcNAc (5 mM) in a total volume of 400 µl. at 37° C. for 42 hr. A GlcNAc residue was quantitatively added to Man$_5$GlcNAc$_2$-protein by the recombinant GlcNAcT-I.

A Gal residue was then added using GalT1 (FIG. 185). The reaction mixture after the GnT-I reaction containing RNase B (120 µg, about 8 nmol) was incubated at 37° C. for 20 hr with 3.3 mU of the recombinant GalT-1 in Tris-HCl buffer (100 mM, pH 7.3) containing UDP-Gal (7.5 mM) and MnCl$_2$ (20 mM) in a total volume of 100 µl. A Gal residue was added to about 98% of the GlcNAc-Man$_5$GlcNAc$_2$-protein by the recombinant GalT1.

The next step was the addition of a sialic acid using an α2,3-sialyltransferase or an α2,6-sialyltransferase (FIG. 186). As an example, ST3GalIII, an α2,3-sialyltransferase was used. The reaction mixture after the GalT-1 reaction containing RNase B (13 µg, about 0.87 nmol) was incubated at 37° C. for 16 hr with 8.9 mU of recombinant ST3Gal III in Tris-HCl buffer (100 mM, pH 7.3) containing CMP-Sialic acid (5 mM) and MnCl$_2$ (20 mM) in a total volume of 20 µl. A sialic acid residue was added to about 90% of the Gal-GlcNAc-Man$_5$GlcNAc$_2$-protein by recombinant ST3Gal III using CMP-SA as the donor. The yield can be further improved by adjusting the reaction conditions.

For convenience, no purification or dialysis step was required after each reaction described above. More interesting, GalT1 and ST3Gal III can be combined in a one-pot reaction. Similar yields were obtained as compared with the separate reactions. The reaction mixture after the GlcNAcT-I reaction containing RNase B (60 µg, about 4 nmol) was incubated at 37° C. for 20 hr with 1.7 mU of recombinant GalT1, 9.8 mU of recombinant ST3Gal III in Tris-HCl buffer (100 mM, pH 7.3) containing UDP-Gal (7.5 mM), CMP-sialic acid (5 mM) and MnCl$_2$ (20 mM) in a total volume of 60 µl.

As shown in FIG. 187, SA-PEG (10 kDa) was successfully added to the RNaseB. The reaction mixture after the GalT-1 reaction containing RNase B (6.7 µg, about 0.45 nmol) was dialyzed against H$_2$O for 1 hour at room temperature and incubated at 37° C. for 15.5 hours with 55 mU of the recombinant ST3Gal III in Tris-HCl buffer (50 mM, pH 7.3) containing CMP-SA-PEG (10 kDa) (0.25 mM) and MnCl$_2$ (20 mM) in a total volume of 20 µl. PEG-modified sialic acid residues were successfully added to the Gal-GlcNAc-Man$_5$GlcNAc$_2$-peptide by the recombinant ST3Gal III. The yield can be further improved by adjusting the reaction conditions.

Conversion of high mannose N-Glycans to complex N-Glycans. To achieve this conversion, a GlcNAcβ1,2Man$_3$GlcNAc$_2$-peptide intermediate is obtained. As shown in FIG. 188, there are at least four feasible routes to carry out the reaction from Man$_5$GlcNAc$_2$-peptide to this intermediate:

Route I: The Man$_5$GlcNAc$_2$-peptide produced by the fungal α1,2 mannosidase is a substrate of GlcNAc transferase I (GlcNAcT-I, enzyme 2) which adds one GlcNAc. The terminal α1,3- and α1,6-linked mannose residues of GlcNAcMan$_5$GlcNAc$_2$-peptide is removed by Golgi α-mannosidase II (ManII, enzyme 5). This route is a part of the natural pathway for the processing of N-linked oligosaccharides carried out in higher organisms.

Route II: Two mannose residues are first removed by an α-mannosidase (enzyme 6), then a GlcNAc is added by GlcNAcT-I (enzyme 2). Other than its natural acceptor Man$_5$GlcNAc$_2$-R, GlcNAcT-I can also recognize Man$_3$GlcNAc$_2$-R as its substrate and add one GlcNAc to the mannose core structure to form GlcNAcMan$_3$GlcNAc$_2$-peptide.

Route III: The α1,6-linked mannose is removed by an α1,6-mannosidase, followed by the addition of GlcNAc by GlcNAcT-I and removal of the terminal α1,3-linked mannose by an α1,3-mannosidase. From the experimental data obtained, GlcNAcT-I can recognize this Man$_4$GlcNAc$_2$-peptide as acceptor and add one GlcNAc residue to form GlcNAcMan$_a$GlcNAc$_2$-peptide.

Route IV: Similar to Route III, α1,3-linked mannose is removed by an α1,3-mannosidase, followed by GlcNAcT-I reaction. Then the terminal α1,6-linked mannose can be removed by an α1,6-mannosidase.

After the function of GlcNAcT-I (responsible for the addition of the GlcNAc β1,2-linked to the α1,3-mannose on the mannose core) and GlcNAcT-II (responsible for the addition of a second GlcNAc β1,2-linked to the α1,6-mannose on the mannose core), the GlcNAc$_2$Man$_3$GlcNAc$_2$-peptide can be processed by GalT 1 and sialyltransferase to form bi-antennary complex N-Glycans. Other GlcNAc transferases such as GlcNAcT-IV, GlcNAcT-V, and/or GlcNAcT-VI (FIG. 188 and FIG. 189) can also glycosylate the GlcNAc$_2$Man$_3$GlcNAc$_2$-peptide. Additional glycosylation by the GalT 1 and sialyltransferases will form multi-antennary complex N-glycans. The enzyme GlcNAcT-III catalyzes the insertion of a bisecting GlcNAc, thus preventing the actions of ManII and subsequent action of transferases GlcNAcT-II, GlcNAcT-IV and GlcNAcT-V.

Tissue-Type Plasminogen Activator (TPA)

39. Fucosylation of TPA to create Sialyl Lewis X

This example sets forth the preparation of Tissue Tissue-type Plasminogen Activator (TPA) with N-linked sialyl Lewis X antigen.

Sialylation. TPA expressed in mammalian cells will often contain a majority of the glycans terminating in sialic acid, but to ensure complete sialylation, it would be beneficial to first perform an in vitro sialylation. TPA in a suitable buffer (most preferably between pH 5.5 and 9, for example Tris buffered saline, pH 7.2) is incubated with CMP sialic acid and sialyltransferase for a time sufficient to convert any glycans lacking sialic acid to sialylated species. Typical conditions would be 1 mg/mL TPA, 3 mM CMP sialic acid, 0.02 U/mL ST3Gal3, 32° C. for 24 hours. Microbial growth can be halted either by sterile filtration or the inclusion of 0.02% sodium azide. The TPA concentration is most preferably in the range 0.1 mg/mL up to the solubility limit of the peptide. The concentration of CMP-SA should be sufficient for there to be excess over the available sites, and might range from 50 µM up to 50 mM, and the temperature from 2° C. up to 40° C. The time required for complete reaction will depend on the temperature, the relative amounts of enzyme to acceptor substrate, the donor substrate concentration, and the pH. Other sialyltransferases that may be capable of adding sialic acid in 2,3 linkage include ST3Gal4; microbial transferases could also be used.

Fucosylation. Typical conditions for fucosylation would be 1 mg/mL TPA, 3 mM GDP-fucose, 0.02 U/mL FTVI, 5 mM MnCl$_2$, 32° C. for 24 H in Tris buffered saline. Microbial growth can be halted either by sterile filtration or the inclusion of 0.02% sodium azide. The TPA concentration is most preferably in the range 0.1 mg/mL up to the solubility limit of the peptide. The concentration of GDP-fucose should be sufficient for there to be excess over the available sites, and might range from 50 µM up to 50 mM, and the temperature from 2°

C. up to 40° C. The time required for complete reaction will depend on the temperature, the relative amounts of enzyme to acceptor substrate, the donor substrate concentration, and the pH. Other fucosyltransferases that may be capable of making sialyl Lewis x include FTVII, FTV, FTIII, as well as microbial transferases could also be used.

40. Trimming of High Mannose to Tri-Mannose Core Structure: Tissue-Type Plasminogen Activator Produced in CHO This example sets forth the preparation of Tissue-type Plasminogen Activator with a trimannose core by trimming back from a high mannose glycan.

Tissue-type plasminogen activator (TPA) is currently produced in Chinese Hamster Ovary (CHO) cells and contains a low amount of high mannose N-linked oligosaccharide. The mannoses can be trimmed down using a variety of the specific mannosidases. The first step is to generate Man5GlcNAc2 (Fuc0-1) from Man9GlcNAc2(Fuc0-1). This can be done using mannosidase I. Then either GlcNAcT1 (GlcNAc transferase I) is used to make GlcNAc1Man5GlcNAc2(Fuc0-1) or Mannosidase III is used to make Man3GlcNAc2(Fuc0-1). From Man3GlcNAc2(Fuc0-1), GlcNAc1Man3GlcNAc2 (Fuc0-1) can be produced using GlcNAcT1 or from GlcNAc1Man5GlcNAc2(Fuc0-1), GlcNAc1Man3GlcNAc2 (Fuc0-1) can be produced using Mannosidase II. GlcNAc1Man3GlcNAc2(Fuc0-1) is then converted into GlcNAc2Man3GlcNAc2(Fuc0-1) using GlcNAcTransferase II (GlcNAcTII). The two terminal GlcNAc residues are then galactosylated using GalTI and then sialylated with SA-PEG using ST3GalIII.

Conversely, TPA can be produce in yeast or fungal systems. Similar processing would be required for fungal derived material.

41. Generation and PEGylation of GlcNAc-Asn Structures: TPA Produced in Yeast

This example sets forth the preparation of PEGylated GlcNAc-Asn structures on a peptide such as TPA expressed in yeast.

Yeast expression is expected to result in a TPA which contains a single N-linked mannan-type structure. This recombinant glycoprotein is first treated with endoglycosidase H to generate GlcNAc structures on the asparagine (Asn) residues on the peptide.

The GlcNAc-Asn structures on the peptide/protein backbone are then be modified with galactose or galactose-PEG using UDP-galactose or UDP-galactose-6-PEG, respectively, and a galactosyltransferase such as GalT1. In one case, the galactose-PEG is the terminal residue. In the second case, the galactose is further modified with SA-PEG using a CMP-SA-PEG donor and a sialyltransferase such as ST3GalIII. In another embodiment, the GlcNAc-Asn structures on the peptide/protein backbone may be galactosylated and sialylated as described above, and then further sialylated using CMP-SA-PEG and an α2,8-sialyltransferase such as the enzyme encoded by the *Campylobacter jejuni* cst-II gene.

Transferrin

42. GlycoPEGylation of Transferrin

This example sets forth the preparation of asialotransferrin and its sialylation with PEG-CMP-sialic acid.

Preparation of Asialo-transferrin. Human-derived holo-Transferrin, (10 mg) was dissolved in 500 μL of 50 mM NaOAc, 5 mM $CaCl_2$, pH 5.5. To this solution was added 500 mU Neuraminidase II (*Vibrio cholerae*) and the reaction mixture was shaken gently for 20.5 hours at 37° C. The reaction mixture was added to the prewashed N-(p-aminophenyl)oxamic acid-agarose conjugate (600 μL) and the washed beads gently rotated for 24 hours at 4° C. The mixture was centrifuged at 10,000 rpm and the supernatant was collected. The reaction mixture was adjusted to 5 mM EDTA by addition of 100 μL of 30 mM EDTA to the washed beads, which were gently rotated for 20 hours at 4° C. The suspension was centrifuged for 2 minutes at 10,000 rpm and the supernatant was collected. The beads were washed 5 times with 0.35 mL of 50 mM NaOAc, 5 mM $CaCl_2$, 5 mM EDTA, pH 5.5 and all supernatants were pooled. The enzyme solution was dialyzed twice at 4° C. into 15 mM Tris-HCl, 1 M NaCl, pH 7.4. 0.3 mL of the transferrin solution (3.3 mL total) was removed and dialyzed twice against water. The remainder was dialyzed twice more at 4° C. against phosphate buffered saline. The dialyzed solution was stored at −20° C. Protein samples were analyzed by IEF Electrophoresis. Samples (9 μL, 25 μg) were diluted with 16 μL Tris buffer and mixed with 25 μl, of the sample loading buffer and applied to Isoelectric Focusing Gels (pH 3-7). Gels were run and fixed using standard procedures. Gels were stained with Colloidal Blue Stain.

Sialyl-PEGylation of asialo-Transferrin. Desialylated transferrin (250 μg) and CMP-sialic acid or CMP-SA-PEG (1 kDa or 10 kDa)(0.05 μmol) were dissolved in 69 μL 50 mM Tris-HCl, 0.15 M NaCl, 0.05% $NaN_3$, pH 7.2 in 1.5 mL plastic tubes. The tubes were vortexed briefly and 100 mU ST3Gal3 (90 μL) were added (total volume 250 μL). The tubes were vortexed again and mixed gently for 24 hours at 32° C. The reactions were stopped by freezing at −80° C. Novex Tris-Glycine 8-16% 1 mm gels were used for SDS PAGE analysis (FIG. 190). Samples (25 μL, 25 μg) were mixed with 25 μL of sample loading buffer and 0.4 μL of β-mercaptoethanol and heated for 6 minutes at 85° C. Gels were run using standard conditions and stained with Colloidal Blue Stain. IEF gels were also performed as described above FIG. 191). Samples were also dialyzed against water analyzed by MALDI-TOF.

Results. MALDI was also performed. Native transferrin (78729); asialotransferrin (78197); resialylated transferrin (79626/80703); with SA-PEG 1k (79037 (1); 80961 (2); 82535 (3); 84778 (4)); with SA-PEG 5k (90003 (2); 96117 (3); 96117 (4)); with SA-PEG 10k (100336 (2); 111421 (3); 122510 (4)).

43. Transferrin-GDNF

This example sets forth the procedures for the glycoconjugation of proteins, and in particular, transferrin is glycoconjugated to GDNF. Transferrin-SA-Linker-Gal-UDP is prepared from transferrin. The galactose residue is removed from GNDF glycans, and Transferrin-SA-Linker-Gal-UDP is conjugated to GNDF glycans using a galactosyltransferase.

Preparation of agalacto-GDNF. GDNF Produced in NSO Cells (NSO Murine myeloma cells) is dissolved at 2.5 mg/mL in 50 mM Tris 50 mM Tris-HCl pH 7.4, 0.15 M NaCl, and is incubated with 300 mU/mL beta-galactosidase-agarose conjugate for 16 hours at 32° C. To monitor the reaction a small aliquot of the reaction is diluted with the appropriate buffer and a IEF gel performed according to Invitrogen procedures. The mixture is centrifuged at 10,000 rpm and the supernatant is collected. The supernatant is dialyzed at 4° C. against 50 mM Tris-HCl pH 7.4, 1 M NaCl, 0.05% $NaN_3$ and then twice more against 50 mM Tris-HCl pH 7.4, 1 M NaCl, 0.05% $NaN_3$. The dialyzed solution is then concentrated using a Centricon Plus 20 centrifugal filter and stored at −20° C. The conditions for the IEF gel are run according to the procedures and reagents provided by Invitrogen. Samples are dialyzed against water and analyzed by MALDI-TOF MS.

Preparation of Transferrin-Sa-Linker-Gal-UDP. Asialo-Transferrin is Dissolved at 2.5 mg/mL in 50 mM Tris-HCl, 0.15 M NaCl, 0.05% $NaN_3$, pH 7.2. The solution is incubated with CMP-sialic acid-linker-Gal-UDP (molar amount to add 1 molar equivalent of nucleotide sugar to transferrin) and 0.1 U/mL of ST3Gal3 at 32° C. for 2 days. To monitor the incorporation of sialic acid, a small aliquot of the reaction has $^{14}$C-SA-UDP ligand added; the label incorporated into the peptide is separated from the free label by gel filtration on a Toso Haas G3000SW analytical column using PBS buffer (pH 7.1). The radioactive label incorporation into the peptide is quantitated using an in-line radiation detector. The solution is incubated with 5 mM CMP-sialic acid and 0.1 U/mL of ST3Gal3 (to cap any unreacted transferrin glycans) at 32° C. for 2 days. The incorporation into the peptide is quantitated using an in-line UV detector. After 2 days, the reaction mixture is purified using a Toso Haas G3000SW preparative column using PBS buffer (pH 7.1) and collecting fractions based on UV absorption. The product of the reaction is analyzed using SDS-PAGE and IEF analysis according to the procedures and reagents supplied by Invitrogen. Samples are dialyzed against water and analyzed by MALDI-TOF MS.

Preparation of Transferrin-SA-Linker-Gal-GDNF. The transferrin-SA-Linker-Gal-UDP prepared as described above is dissolved at 2.5 mg/mL in 50 mM Tris-HCl, 0.15 M NaCl, 5 mM MnCl$_2$, 0.05% NaN$_3$, pH 7.2. The solution is incubated with 2.5 mg/mL agalacto-GDNF and 0.1 U/mL of galactosyltransferase at 32° C. for 2 days. To monitor the incorporation of galactose, a small aliquot of the reaction has $^{14}$C-galactose-UDP ligand added; the label incorporated into the peptide is separated from the free label by gel filtration on a Toso Haas G3000SW analytical column using PBS buffer (pH 7.1). The radioactive label incorporation into the peptide is quantitated using an in-line radiation detector. When the reaction is complete, the solution is incubated with 5 mM UDP-Gal and 0.1 U/mL of galactosyltransferase (to cap any unreacted transferrin glycans) at 32° C. for 2 days followed by addition of 5 mM CMP-SA and 0.1 U/mL of ST3Gal3. After 2 additional days, the reaction mixture is purified using a Toso Haas G3000SW preparative column using PBS buffer (pH 7.1) collecting fractions based on UV absorption. The product of the reaction is analyzed using SDS-PAGE and IEF analysis according to the procedures and reagents supplied by Invitrogen. Samples are dialyzed against water and analyzed by MALDI-TOF MS.

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A covalent conjugate between a peptide and a water-soluble polymer, wherein said water-soluble polymer is not a naturally occurring sugar and is covalently attached to said peptide through an intact glycosyl linking group, and wherein said covalent conjugate is formed via reaction with *Campylobacter* sialyltransferase I (CST-I).

2. The covalent conjugate according to claim 1, wherein said water-soluble polymer is a poly(ether).

3. The covalent conjugate according to claim 2, wherein said poly(ether) is a poly(alkylene oxide).

4. The covalent conjugate according to claim 3, wherein said poly(alkylene oxide) is a poly(ethylene glycol).

5. The covalent conjugate according to claim 4, wherein said poly(ethylene glycol) is a member selected from linear poly(ethylene glycol) and branched poly(ethylene glycol).

6. The covalent conjugate according to claim 4, wherein said poly(ethylene glycol) has a degree of polymerisation of from about 1 to about 5,000.

7. The covalent conjugate according to claim 6, wherein said poly(ethylene glycol) has a degree of polymerisation of from about 1 to about 1,000.

8. The covalent conjugate according to claim 1, wherein said intact glycosyl linking group is attached to a member selected from a carbohydrate moiety, an amino acid moiety and combinations thereof.

9. The covalent conjugate according to claim 8, wherein said intact glycosyl linking group is attached to said carbohydrate moiety which is a member selected from an O- or N-linked glycan and combinations thereof.

10. The covalent conjugate according to claim 8, wherein said intact glycosyl linking group is attached to hydroxyl or amino groups or combinations thereof of said amino acid moiety.

11. The covalent conjugate according to claim 8, wherein said intact glycosyl linking group comprises sialic acid, galactose, N-acetylglucosamine or N-acetylgalactosamine residue.

12. The covalent conjugate according to claim 1, wherein said water-soluble polymer is attached to a sialic acid residue at a position which is a member selected from the 5-, and the 9-position of said sialic acid.

13. The covalent conjugate according to claim 1, wherein said peptide is a therapeutic agent.

14. The covalent conjugate according to claim 1, wherein said peptide is selected from the group consisting of granulocyte colony stimulating factor, interferon-alpha, interferon-beta, Factor VIIa, Factor VIII, Factor IX, follicle stimulating hormone, erythropoietin, granulocyte macrophage colony stimulating factor, interferon-gamma, alpha-1-protease inhibitor, beta-glucosidase, tissue plasminogen activator protein, interleukin-2, chimeric tumor necrosis factor receptor, urokinase, chimeric anti-glycoprotein IIb/IIIa antibody, chimeric anti-HER2 antibody, chimeric anti-respiratory syncytial virus antibody, chimeric anti-CD20 antibody, DNase, chimeric anti-tumor necrosis factor antibody, human insulin, hepatitis B sAg, and human growth hormone.

15. A pharmaceutical composition comprising the covalent conjugate according to claim 1 and a pharmaceutically acceptable diluent.

16. A cell-free, in vitro method of forming a covalent conjugate between a peptide and a water-soluble polymer, wherein said water-soluble polymer is covalently attached to said peptide through an intact glycosyl linking group, said method comprising:

contacting said peptide with a mixture comprising at least one nucleotide sugar covalently linked to said water soluble polymer and at least one glycosyltransferase for which said nucleotide sugar is a substrate, wherein said glycosyltransferase is *Campylobacter* sialyltransferase I (CST-I), thereby forming said covalent conjugate of said peptide.

17. The method according to claim 16, wherein said water-soluble polymer is a poly(ether).

18. The method according to claim 17, wherein said poly (ether) is a poly(ethylene glycol).

19. The method of claim 16, wherein said peptide is selected from the group consisting of granulocyte colony stimulating factor, interferon-alpha, interferon-beta, Factor VIIa, Factor VIII, Factor IX, follicle stimulating hormone, erythropoietin, granulocyte macrophage colony stimulating factor, interferon-gamma, alpha-1-protease inhibitor, beta-glucosidase, tissue plasminogen activator protein, interleukin-2, chimeric tumor necrosis factor receptor, urokinase, chimeric anti-glycoprotein IIb/IIIa antibody, chimeric anti-HER2 antibody, chimeric anti-respiratory syncytial virus antibody, chimeric anti-CD20 antibody, DNase, chimeric anti-tumor necrosis factor antibody, human insulin, hepatitis B sAg, and human growth hormone.

* * * * *

UNITED STATES PATENT AND TRADEMARK OFFICE

CERTIFICATE OF CORRECTION

PATENT NO. : 8,063,015 B2
APPLICATION NO. : 12/496595
DATED : November 22, 2011
INVENTOR(S) : DeFrees et al.

It is certified that error appears in the above-identified patent and that said Letters Patent is hereby corrected as shown below:

Title page, Item (63) should read

Related U.S. Application Data

Continuation of application No. 10/552,896, filed as application No. PCT/US2004/011494 on April 9, 2004, now abandoned, which claims priority to application No. 10/411,012 filed April 9, 2003, now Pat. No. 7,265,084, application No. 10/411,026 filed April 9, 2003, now Pat. No. 7,795,210, application No. 10/410,962 filed April 9, 2003, now Pat. No. 7,173,003, application No. 10/411,049 filed April 9, 2003, now Pat. No. 7,297,511, application No. 10/410,930 filed April 9, 2003, now Pat. No. 7,226,903, application No. 10/410,897 filed April 9, 2003, now Pat. No. 7,179,617, application No. 10/410,997 filed April 9, 2003, now Pat. No. 7,157,277, application No. 10/411,044 filed April 9, 2003, now Pat. No. 8,008,252, application No. 10/410,980 filed April 9, 2003, now Pat. No. 7,399,613, application No. 10/410,945 filed April 9, 2003, now Pat. No. 7,214,660, application No. 10/410,913 filed April 9, 2003, now Pat. No. 7,265,085, application No. 10/411,037 filed April 9, 2003, now Pat. No. 7,125,843, and application No. 10/411,043 filed April 9, 2003, now Pat. No. 7,439,043.

Signed and Sealed this
Thirteenth Day of March, 2012

David J. Kappos
*Director of the United States Patent and Trademark Office*

SEQUENCE LISTING

```
<160> NUMBER OF SEQ ID NOS: 75

<210> SEQ ID NO 1
<211> LENGTH: 525
<212> TYPE: DNA
<213> ORGANISM: Homo sapiens

<400> SEQUENCE: 1

acccccctgg gccctgccag ctccctgccc cagagcttcc tgctcaagtg cttagagcaa      60

gtgaggaaga tccagggcga tggcgcagcg ctccaggaga agctgtgtgc cacctacaag     120

ctgtgccacc ccgaggagct ggtgctgctc ggacactctc tgggcatccc ctgggctccc     180

ctgagcagct gccccagcca ggccctgcag ctggcaggct gcttgagcca actccatagc     240

ggccttttcc tctaccaggg gctcctgcag gccctggaag ggatctcccc cgagttgggt     300

cccaccttgg acacactgca gctggacgtc gccgactttg ccaccaccat ctggcagcag     360

atggaagaac tgggaatggc ccctgccctg cagcccaccc agggtgccat gccggccttc     420

gcctctgctt tccagcgccg ggcaggaggg gtcctggttg cctcccatct gcagagcttc     480

ctggaggtgt cgtaccgcgt tctacgccac cttgcccagc cctga                    525

<210> SEQ ID NO 2
<211> LENGTH: 174
<212> TYPE: PRT
<213> ORGANISM: Homo sapiens

<400> SEQUENCE: 2

Thr Pro Leu Gly Pro Ala Ser Ser Leu Pro Gln Ser Phe Leu Leu Lys
1               5                   10                  15

Cys Leu Glu Gln Val Arg Lys Ile Gln Gly Asp Gly Ala Ala Leu Gln
            20                  25                  30

Glu Lys Leu Cys Ala Thr Tyr Lys Leu Cys His Pro Glu Glu Leu Val
        35                  40                  45
```

```
Leu Leu Gly His Ser Leu Gly Ile Pro Trp Ala Pro Leu Ser Ser Cys
    50                  55                  60

Pro Ser Gln Ala Leu Gln Leu Ala Gly Cys Leu Ser Gln Leu His Ser
65                  70                  75                  80

Gly Leu Phe Leu Tyr Gln Gly Leu Leu Gln Ala Leu Glu Gly Ile Ser
                85                  90                  95

Pro Glu Leu Gly Pro Thr Leu Asp Thr Leu Gln Leu Asp Val Ala Asp
            100                 105                 110

Phe Ala Thr Thr Ile Trp Gln Gln Met Glu Glu Leu Gly Met Ala Pro
        115                 120                 125

Ala Leu Gln Pro Thr Gln Gly Ala Met Pro Ala Phe Ala Ser Ala Phe
    130                 135                 140

Gln Arg Arg Ala Gly Gly Val Leu Val Ala Ser His Leu Gln Ser Phe
145                 150                 155                 160

Leu Glu Val Ser Tyr Arg Val Leu Arg His Leu Ala Gln Pro
                165                 170


<210> SEQ ID NO 3
<211> LENGTH: 1733
<212> TYPE: DNA
<213> ORGANISM: Homo sapiens

<400> SEQUENCE: 3

gcgcctctta tgtacccaca aaaatctatt ttcaaaaaag ttgctctaag aatatagtta      60

tcaagttaag taaaatgtca atagcctttt aatttaattt ttaattgttt tatcattctt     120

tgcaataata aaacattaac tttatacttt ttaatttaat gtatagaata gagatataca     180

taggatatgt aaatagatac acagtgtata tgtgattaaa atataatggg agattcaatc     240

agaaaaaagt ttctaaaaag gctctggggt aaaagaggaa ggaaacaata atgaaaaaaa     300

tgtggtgaga aaaacagctg aaaacccatg taaagagtgt ataaagaaag caaaaagaga     360

agtagaaagt aacacagggg catttggaaa atgtaaacga gtatgttccc tatttaaggc     420

taggcacaaa gcaaggtctt cagagaacct ggagcctaag gtttaggctc acccatttca     480

accagtctag cagcatctgc aacatctaca atggccttga cctttgcttt actggtggcc     540

ctcctggtgc tcagctgcaa gtcaagctgc tctgtgggct gtgatctgcc tcaaacccac     600

agcctgggta gcaggaggac cttgatgctc ctggcacaga tgaggagaat ctctcttttc     660

tcctgcttga aggacagaca tgactttgga tttccccagg aggagtttgg caaccagttc     720

caaaaggctg aaaccatccc tgtcctccat gagatgatcc agcagatctt caatctcttc     780

agcacaaagg actcatctgc tgcttgggat gagaccctcc tagacaaatt ctacactgaa     840

ctctaccagc agctgaatga cctggaagcc tgtgtgatac agggggtggg ggtgacagag     900

actcccctga tgaaggagga ctccattctg gctgtgagga aatacttcca aagaatcact     960

ctctatctga aagagaagaa atacagccct tgtgcctggg aggttgtcag agcagaaatc    1020

atgagatctt tttctttgtc aacaaacttg caagaaagtt taagaagtaa ggaatgaaaa    1080

ctggttcaac atggaaatga ttttcattga ttcgtatgcc agctcacctt tttatgatct    1140

gccatttcaa agactcatgt ttctgctatg accatgacac gatttaaatc ttttcaaatg    1200

tttttaggag tattaatcaa cattgtattc agctcttaag gcactagtcc cttacagagg    1260

accatgctga ctgatccatt atctatttaa atatttttaa aatattattt atttaactat    1320

ttataaaaca acttattttt gttcatatta tgtcatgtgc acctttgcac agtggttaat    1380

gtaataaaat gtgttctttg tatttggtaa atttattttg tgttgttcat tgaacttttg    1440
```

ctatggaact tttgtacttg tttattcttt aaaatgaaat tccaagccta attgtgcaac 1500
ctgattacag aataactggt acacttcatt tgtccatcaa tattatattc aagatataag 1560
taaaaataaa ctttctgtaa accaagttgt atgttgtact caagataaca gggtgaacct 1620
aacaaataca attctgctct cttgtgtatt tgatttttgt atgaaaaaaa ctaaaaatgg 1680
taatcatact taattatcag ttatggtaaa tggtatgaag agaagaagga acg 1733

<210> SEQ ID NO 4
<211> LENGTH: 188
<212> TYPE: PRT
<213> ORGANISM: Homo sapiens

<400> SEQUENCE: 4

Met Ala Leu Thr Phe Ala Leu Leu Val Ala Leu Leu Val Leu Ser Cys
1 5 10 15

Lys Ser Ser Cys Ser Val Gly Cys Asp Leu Pro Gln Thr His Ser Leu
20 25 30

Gly Ser Arg Arg Thr Leu Met Leu Leu Ala Gln Met Arg Arg Ile Ser
35 40 45

Leu Phe Ser Cys Leu Lys Asp Arg His Asp Phe Gly Phe Pro Gln Glu
50 55 60

Glu Phe Gly Asn Gln Phe Gln Lys Ala Glu Thr Ile Pro Val Leu His
65 70 75 80

Glu Met Ile Gln Gln Ile Phe Asn Leu Phe Ser Thr Lys Asp Ser Ser
85 90 95

Ala Ala Trp Asp Glu Thr Leu Leu Asp Lys Phe Tyr Thr Glu Leu Tyr
100 105 110

Gln Gln Leu Asn Asp Leu Glu Ala Cys Val Ile Gln Gly Val Gly Val
115 120 125

Thr Glu Thr Pro Leu Met Lys Glu Asp Ser Ile Leu Ala Val Arg Lys
130 135 140

Tyr Phe Gln Arg Ile Thr Leu Tyr Leu Lys Glu Lys Lys Tyr Ser Pro
145 150 155 160

Cys Ala Trp Glu Val Val Arg Ala Glu Ile Met Arg Ser Phe Ser Leu
165 170 175

Ser Thr Asn Leu Gln Glu Ser Leu Arg Ser Lys Glu
180 185

<210> SEQ ID NO 5
<211> LENGTH: 757
<212> TYPE: DNA
<213> ORGANISM: Homo sapiens

<400> SEQUENCE: 5
atgaccaaca agtgtctcct ccaaattgct ctcctgttgt gcttctccac tacagctctt 60
tccatgagct acaacttgct tggattccta caaagaagca gcaattttca gtgtcagaag 120
ctcctgtggc aattgaatgg gaggcttgaa tattgcctca aggacaggat gaactttgac 180
atccctgagg agattaagca gctgcagcag ttccagaagg aggacgccgc attgaccatc 240
tatgagatgc tccagaacat ctttgctatt ttcagacaag attcatctag cactggctgg 300
aatgagacta ttgttgagaa cctcctggct aatgtctatc atcagataaa ccatctgaag 360
acagtcctgg aagaaaaact ggagaaagaa gattttacca ggggaaaact catgagcagt 420
ctgcacctga aaagatatta tgggaggatt ctgcattacc tgaaggccaa ggagtacagt 480
cactgtgcct ggaccatagt cagagtggaa atcctaagga acttttactt cattaacaga 540
cttacaggtt acctccgaaa ctgaagatct cctagcctgt ccctctggga ctggacaatt 600
gcttcaagca ttcttcaacc agcagatgct gtttaagtga ctgatggcta atgtactgca 660
aatgaaagga cactagaaga ttttgaaatt tttattaaat tatgagttat ttttatttat 720
ttaaatttta ttttggaaaa taaattattt ttggtgc 757

<210> SEQ ID NO 6
<211> LENGTH: 187
<212> TYPE: PRT
<213> ORGANISM: Homo sapiens

<400> SEQUENCE: 6

Met Thr Asn Lys Cys Leu Leu Gln Ile Ala Leu Leu Leu Cys Phe Ser
1               5                   10                  15

Thr Thr Ala Leu Ser Met Ser Tyr Asn Leu Leu Gly Phe Leu Gln Arg
            20                  25                  30

Ser Ser Asn Phe Gln Cys Gln Lys Leu Leu Trp Gln Leu Asn Gly Arg
        35                  40                  45

Leu Glu Tyr Cys Leu Lys Asp Arg Met Asn Phe Asp Ile Pro Glu Glu
    50                  55                  60

Ile Lys Gln Leu Gln Gln Phe Gln Lys Glu Asp Ala Ala Leu Thr Ile
65                  70                  75                  80

Tyr Glu Met Leu Gln Asn Ile Phe Ala Ile Phe Arg Gln Asp Ser Ser
                85                  90                  95

Ser Thr Gly Trp Asn Glu Thr Ile Val Glu Asn Leu Leu Ala Asn Val
            100                 105                 110

Tyr His Gln Ile Asn His Leu Lys Thr Val Leu Glu Glu Lys Leu Glu
        115                 120                 125

Lys Glu Asp Phe Thr Arg Gly Lys Leu Met Ser Ser Leu His Leu Lys
    130                 135                 140

Arg Tyr Tyr Gly Arg Ile Leu His Tyr Leu Lys Ala Lys Glu Tyr Ser
145                 150                 155                 160

His Cys Ala Trp Thr Ile Val Arg Val Glu Ile Leu Arg Asn Phe Tyr
                165                 170                 175

Phe Ile Asn Arg Leu Thr Gly Tyr Leu Arg Asn
            180                 185

<210> SEQ ID NO 7
<211> LENGTH: 1332
<212> TYPE: DNA
<213> ORGANISM: Homo sapiens

<400> SEQUENCE: 7
atggtctccc aggccctcag gctcctctgc cttctgcttg ggcttcaggg ctgcctggct 60
gcagtcttcg taacccagga ggaagcccac ggcgtcctgc accggcgccg gcgcgccaac 120
gcgttcctgg aggagctgcg gccgggctcc ctggagaggg agtgcaagga ggagcagtgc 180
tccttcgagg aggcccggga gatcttcaag gacgcggaga ggacgaagct gttctggatt 240
tcttacagtg atggggacca gtgtgcctca agtccatgcc agaatggggg ctcctgcaag 300
gaccagctcc agtcctatat ctgcttctgc ctccctgcct tcgagggccg gaactgtgag 360
acgcacaagg atgaccagct gatctgtgtg aacgagaacg gcggctgtga gcagtactgc 420
agtgaccaca cgggcaccaa gcgctcctgt cggtgccacg aggggtactc tctgctggca 480
gacggggtgt cctgcacacc cacagttgaa tatccatgtg gaaaaatacc tattctagaa 540
aaaagaaatg ccagcaaacc ccaaggccga attgtggggg gcaaggtgtg ccccaaaggg 600

```
gagtgtccat ggcaggtcct gttgttggtg aatggagctc agttgtgtgg ggggaccctg    660

atcaacacca tctgggtggt ctccgcggcc cactgtttcg acaaaatcaa gaactggagg    720

aacctgatcg cggtgctggg cgagcacgac ctcagcgagc acgacgggga tgagcagagc    780

cggcgggtgg cgcaggtcat catccccagc acgtacgtcc cgggcaccac caaccacgac    840

atcgcgctgc tccgcctgca ccagcccgtg gtcctcactg accatgtggt gcccctctgc    900

ctgcccgaac ggacgttctc tgagaggacg ctggccttcg tgcgcttctc attggtcagc    960

ggctggggcc agctgctgga ccgtggcgcc acggccctgg agctcatggt gctcaacgtg   1020

ccccggctga tgacccagga ctgcctgcag cagtcacgga aggtgggaga ctccccaaat   1080

atcacggagt acatgttctg tgccggctac tcggatggca gcaaggactc ctgcaagggg   1140

gacagtggag gcccacatgc cacccactac cggggcacgt ggtacctgac gggcatcgtc   1200

agctggggcc agggctgcgc aaccgtgggc cactttgggg tgtacaccag ggtctcccag   1260

tacatcgagt ggctgcaaaa gctcatgcgc tcagagccac gcccaggagt cctcctgcga   1320

gccccatttc cc                                                         1332
```

<210> SEQ ID NO 8
<211> LENGTH: 444
<212> TYPE: PRT
<213> ORGANISM: Homo sapiens

<400> SEQUENCE: 8

```
Met Val Ser Gln Ala Leu Arg Leu Leu Cys Leu Leu Leu Gly Leu Gln
1               5                   10                  15

Gly Cys Leu Ala Ala Val Phe Val Thr Gln Glu Glu Ala His Gly Val
            20                  25                  30

Leu His Arg Arg Arg Arg Ala Asn Ala Phe Leu Glu Glu Leu Arg Pro
        35                  40                  45

Gly Ser Leu Glu Arg Glu Cys Lys Glu Glu Gln Cys Ser Phe Glu Glu
    50                  55                  60

Ala Arg Glu Ile Phe Lys Asp Ala Glu Arg Thr Lys Leu Phe Trp Ile
65                  70                  75                  80

Ser Tyr Ser Asp Gly Asp Gln Cys Ala Ser Ser Pro Cys Gln Asn Gly
                85                  90                  95

Gly Ser Cys Lys Asp Gln Leu Gln Ser Tyr Ile Cys Phe Cys Leu Pro
            100                 105                 110

Ala Phe Glu Gly Arg Asn Cys Glu Thr His Lys Asp Asp Gln Leu Ile
        115                 120                 125

Cys Val Asn Glu Asn Gly Gly Cys Glu Gln Tyr Cys Ser Asp His Thr
    130                 135                 140

Gly Thr Lys Arg Ser Cys Arg Cys His Glu Gly Tyr Ser Leu Leu Ala
145                 150                 155                 160

Asp Gly Val Ser Cys Thr Pro Thr Val Glu Tyr Pro Cys Gly Lys Ile
                165                 170                 175

Pro Ile Leu Glu Lys Arg Asn Ala Ser Lys Pro Gln Gly Arg Ile Val
            180                 185                 190

Gly Gly Lys Val Cys Pro Lys Gly Glu Cys Pro Trp Gln Val Leu Leu
        195                 200                 205

Leu Val Asn Gly Ala Gln Leu Cys Gly Gly Thr Leu Ile Asn Thr Ile
    210                 215                 220

Trp Val Val Ser Ala Ala His Cys Phe Asp Lys Ile Lys Asn Trp Arg
225                 230                 235                 240

Asn Leu Ile Ala Val Leu Gly Glu His Asp Leu Ser Glu His Asp Gly
```

```
                245                 250                 255

Asp Glu Gln Ser Arg Arg Val Ala Gln Val Ile Ile Pro Ser Thr Tyr
            260                 265                 270

Val Pro Gly Thr Thr Asn His Asp Ile Ala Leu Leu Arg Leu His Gln
        275                 280                 285

Pro Val Val Leu Thr Asp His Val Val Pro Leu Cys Leu Pro Glu Arg
    290                 295                 300

Thr Phe Ser Glu Arg Thr Leu Ala Phe Val Arg Phe Ser Leu Val Ser
305                 310                 315                 320

Gly Trp Gly Gln Leu Leu Asp Arg Gly Ala Thr Ala Leu Glu Leu Met
                325                 330                 335

Val Leu Asn Val Pro Arg Leu Met Thr Gln Asp Cys Leu Gln Gln Ser
            340                 345                 350

Arg Lys Val Gly Asp Ser Pro Asn Ile Thr Glu Tyr Met Phe Cys Ala
        355                 360                 365

Gly Tyr Ser Asp Gly Ser Lys Asp Ser Cys Lys Gly Asp Ser Gly Gly
    370                 375                 380

Pro His Ala Thr His Tyr Arg Gly Thr Trp Tyr Leu Thr Gly Ile Val
385                 390                 395                 400

Ser Trp Gly Gln Gly Cys Ala Thr Val Gly His Phe Gly Val Tyr Thr
                405                 410                 415

Arg Val Ser Gln Tyr Ile Glu Trp Leu Gln Lys Leu Met Arg Ser Glu
            420                 425                 430

Pro Arg Pro Gly Val Leu Leu Arg Ala Pro Phe Pro
        435                 440


<210> SEQ ID NO 9
<211> LENGTH: 1437
<212> TYPE: DNA
<213> ORGANISM: Homo sapiens

<400> SEQUENCE: 9

atgcagcgcg tgaacatgat catggcagaa tcaccaagcc tcatcaccat ctgcctttta      60

ggatatctac tcagtgctga atgtacagtt tttcttgatc atgaaaacgc caacaaaatt     120

ctgaatcggc caaagaggta taattcaggt aaattggaag agtttgttca agggaacctt     180

gagagagaat gtatggaaga aaagtgtagt tttgaagaac cacgagaagt ttttgaaaac     240

actgaaaaga caactgaatt ttggaagcag tatgttgatg gagatcagtg tgagtccaat     300

ccatgtttaa atggcggcag ttgcaaggat gacattaatt cctatgaatg ttggtgtccc     360

tttggatttg aaggaaagaa ctgtgaatta gatgtaacat gtaacattaa gaatggcaga     420

tgcgagcagt tttgtaaaaa tagtgctgat aacaaggtgg tttgctcctg tactgaggga     480

tatcgacttg cagaaaacca gaagtcctgt gaaccagcag tgccatttcc atgtggaaga     540

gtttctgttt cacaaacttc taagctcacc cgtgctgagg ctgtttttcc tgatgtggac     600

tatgtaaatc ctactgaagc tgaaaccatt ttggataaca tcactcaagg cacccaatca     660

tttaatgact tcactcgggt tgttggtgga gaagatgcca aaccaggtca attcccttgg     720

caggttgttt tgaatggtaa agttgatgca ttctgtggag gctctatcgt taatgaaaaa     780

tggattgtaa ctgctgccca ctgtgttgaa actggtgtta aaattacagt tgtcgcaggt     840

gaacataata ttgaggagac agaacataca gagcaaaagc gaaatgtgat tcgagcaatt     900

attcctcacc acaactacaa tgcagctatt aataagtaca accatgacat tgcccttctg     960

gaactggacg aacccttagt gctaaacagc tacgttacac ctatttgcat tgctgacaag    1020
```

gaatacacga acatcttcct caaatttgga tctggctatg taagtggctg ggcaagagtc 1080
ttccacaaag ggagatcagc tttagttctt cagtacctta gagttccact tgttgaccga 1140
gccacatgtc ttcgatctac aaagttcacc atctataaca acatgttctg tgctggcttc 1200
catgaaggag gtagagattc atgtcaagga gatagtgggg gaccccatgt tactgaagtg 1260
gaagggacca gtttcttaac tggaattatt agctggggtg aagagtgtgc aatgaaaggc 1320
aaatatggaa tatataccaa ggtatcccgg tatgtcaact ggattaagga aaaaacaaag 1380
ctcacttaat gaaagatgga tttccaaggt taattcattg gaattgaaaa ttaacag 1437

<210> SEQ ID NO 10
<211> LENGTH: 462
<212> TYPE: PRT
<213> ORGANISM: Homo sapiens

<400> SEQUENCE: 10

Met Gln Arg Val Asn Met Ile Met Ala Glu Ser Pro Ser Leu Ile Thr
1 5 10 15

Ile Cys Leu Leu Gly Tyr Leu Leu Ser Ala Glu Cys Thr Val Phe Leu
20 25 30

Asp His Glu Asn Ala Asn Lys Ile Leu Asn Arg Pro Lys Arg Tyr Asn
35 40 45

Ser Gly Lys Leu Glu Glu Phe Val Gln Gly Asn Leu Glu Arg Glu Cys
50 55 60

Met Glu Glu Lys Cys Ser Phe Glu Glu Pro Arg Glu Val Phe Glu Asn
65 70 75 80

Thr Glu Lys Thr Thr Glu Phe Trp Lys Gln Tyr Val Asp Gly Asp Gln
85 90 95

Cys Glu Ser Asn Pro Cys Leu Asn Gly Gly Ser Cys Lys Asp Asp Ile
100 105 110

Asn Ser Tyr Glu Cys Trp Cys Pro Phe Gly Phe Glu Gly Lys Asn Cys
115 120 125

Glu Leu Asp Val Thr Cys Asn Ile Lys Asn Gly Arg Cys Glu Gln Phe
130 135 140

Cys Lys Asn Ser Ala Asp Asn Lys Val Val Cys Ser Cys Thr Glu Gly
145 150 155 160

Tyr Arg Leu Ala Glu Asn Gln Lys Ser Cys Glu Pro Ala Val Pro Phe
165 170 175

Pro Cys Gly Arg Val Ser Val Ser Gln Thr Ser Lys Leu Thr Arg Ala
180 185 190

Glu Ala Val Phe Pro Asp Val Asp Tyr Val Asn Pro Thr Glu Ala Glu
195 200 205

Thr Ile Leu Asp Asn Ile Thr Gln Gly Thr Gln Ser Phe Asn Asp Phe
210 215 220

Thr Arg Val Val Gly Gly Glu Asp Ala Lys Pro Gly Gln Phe Pro Trp
225 230 235 240

Gln Val Val Leu Asn Gly Lys Val Asp Ala Phe Cys Gly Gly Ser Ile
245 250 255

Val Asn Glu Lys Trp Ile Val Thr Ala Ala His Cys Val Glu Thr Gly
260 265 270

Val Lys Ile Thr Val Val Ala Gly Glu His Asn Ile Glu Glu Thr Glu
275 280 285

His Thr Glu Gln Lys Arg Asn Val Ile Arg Ala Ile Ile Pro His His
290 295 300

Asn Tyr Asn Ala Ala Ile Asn Lys Tyr Asn His Asp Ile Ala Leu Leu

```
305                 310                 315                 320

Glu Leu Asp Glu Pro Leu Val Leu Asn Ser Tyr Val Thr Pro Ile Cys
                325                 330                 335

Ile Ala Asp Lys Glu Tyr Thr Asn Ile Phe Leu Lys Phe Gly Ser Gly
            340                 345                 350

Tyr Val Ser Gly Trp Ala Arg Val Phe His Lys Gly Arg Ser Ala Leu
        355                 360                 365

Val Leu Gln Tyr Leu Arg Val Pro Leu Val Asp Arg Ala Thr Cys Leu
    370                 375                 380

Arg Ser Thr Lys Phe Thr Ile Tyr Asn Asn Met Phe Cys Ala Gly Phe
385                 390                 395                 400

His Glu Gly Gly Arg Asp Ser Cys Gln Gly Asp Ser Gly Gly Pro His
                405                 410                 415

Val Thr Glu Val Glu Gly Thr Ser Phe Leu Thr Gly Ile Ile Ser Trp
            420                 425                 430

Gly Glu Glu Cys Ala Met Lys Gly Lys Tyr Gly Ile Tyr Thr Lys Val
        435                 440                 445

Ser Arg Tyr Val Asn Trp Ile Lys Glu Lys Thr Lys Leu Thr
    450                 455                 460


<210> SEQ ID NO 11
<211> LENGTH: 603
<212> TYPE: DNA
<213> ORGANISM: Homo sapiens

<400> SEQUENCE: 11

atggattact acagaaaata tgcagctatc tttctggtca cattgtcggt gtttctgcat      60

gttctccatt ccgctcctga tgtgcaggat tgcccagaat gcacgctaca ggaaaaccca     120

ttcttctccc agccgggtgc cccaatactt cagtgcatgg gctgctgctt ctctagagca     180

tatcccactc cactaaggtc caagaagacg atgttggtcc aaaagaacgt cacctcagag     240

tccacttgct gtgtagctaa atcatataac agggtcacag taatgggggg tttcaaagtg     300

gagaaccaca cggcgtgcca ctgcagtact tgttattatc acaaatctta aatgttttac     360

caagtgctgt cttgatgact gctgattttc tggaatggaa aattaagttg tttagtgttt     420

atggctttgt gagataaaac tctccttttc cttaccatac cactttgaca cgcttcaagg     480

atatactgca gctttactgc cttcctcctt atcctacagt acaatcagca gtctagttct     540

tttcatttgg aatgaataca gcattaagct tgttccactg caaataaagc cttttaaatc     600

atc                                                                   603


<210> SEQ ID NO 12
<211> LENGTH: 116
<212> TYPE: PRT
<213> ORGANISM: Homo sapiens

<400> SEQUENCE: 12

Met Asp Tyr Tyr Arg Lys Tyr Ala Ala Ile Phe Leu Val Thr Leu Ser
1               5                   10                  15

Val Phe Leu His Val Leu His Ser Ala Pro Asp Val Gln Asp Cys Pro
            20                  25                  30

Glu Cys Thr Leu Gln Glu Asn Pro Phe Phe Ser Gln Pro Gly Ala Pro
        35                  40                  45

Ile Leu Gln Cys Met Gly Cys Cys Phe Ser Arg Ala Tyr Pro Thr Pro
    50                  55                  60

Leu Arg Ser Lys Lys Thr Met Leu Val Gln Lys Asn Val Thr Ser Glu
```

65 70 75 80

Ser Thr Cys Cys Val Ala Lys Ser Tyr Asn Arg Val Thr Val Met Gly
85 90 95

Gly Phe Lys Val Glu Asn His Thr Ala Cys His Cys Ser Thr Cys Tyr
100 105 110

Tyr His Lys Ser
115

<210> SEQ ID NO 13
<211> LENGTH: 390
<212> TYPE: DNA
<213> ORGANISM: Homo sapiens

<400> SEQUENCE: 13
atgaagacac tccagttttt cttccttttc tgttgctgga aagcaatctg ctgcaatagc 60
tgtgagctga ccaacatcac cattgcaata gagaaagaag aatgtcgttt ctgcataagc 120
atcaacacca cttggtgtgc tggctactgc tacaccaggg atctggtgta taaggaccca 180
gccaggccca aaatccagaa aacatgtacc ttcaaggaac tggtatatga aacagtgaga 240
gtgcccggct gtgctcacca tgcagattcc ttgtatacat acccagtggc cacccagtgt 300
cactgtggca agtgtgacag cgacagcact gattgtactg tgcgaggcct ggggcccagc 360
tactgctcct ttggtgaaat gaaagaataa 390

<210> SEQ ID NO 14
<211> LENGTH: 129
<212> TYPE: PRT
<213> ORGANISM: Homo sapiens

<400> SEQUENCE: 14

Met Lys Thr Leu Gln Phe Phe Phe Leu Phe Cys Cys Trp Lys Ala Ile
1 5 10 15

Cys Cys Asn Ser Cys Glu Leu Thr Asn Ile Thr Ile Ala Ile Glu Lys
20 25 30

Glu Glu Cys Arg Phe Cys Ile Ser Ile Asn Thr Thr Trp Cys Ala Gly
35 40 45

Tyr Cys Tyr Thr Arg Asp Leu Val Tyr Lys Asp Pro Ala Arg Pro Lys
50 55 60

Ile Gln Lys Thr Cys Thr Phe Lys Glu Leu Val Tyr Glu Thr Val Arg
65 70 75 80

Val Pro Gly Cys Ala His His Ala Asp Ser Leu Tyr Thr Tyr Pro Val
85 90 95

Ala Thr Gln Cys His Cys Gly Lys Cys Asp Ser Asp Ser Thr Asp Cys
100 105 110

Thr Val Arg Gly Leu Gly Pro Ser Tyr Cys Ser Phe Gly Glu Met Lys
115 120 125

Glu

<210> SEQ ID NO 15
<211> LENGTH: 1342
<212> TYPE: DNA
<213> ORGANISM: Homo sapiens

<400> SEQUENCE: 15
cccggagccg gaccggggcc accgcgcccg ctctgctccg acaccgcgcc ccctggacag 60
ccgccctctc ctccaggccc gtggggctgg ccctgcaccg ccgagcttcc cgggatgagg 120
gcccccggtg tggtcacccg gcgcgcccca ggtcgctgag ggaccccggc caggcgcgga 180

```
gatgggggtg cacgaatgtc ctgcctggct gtggcttctc ctgtccctgc tgtcgctccc    240

tctgggcctc ccagtcctgg gcgccccacc acgcctcatc tgtgacagcc gagtcctgga    300

gaggtacctc ttggaggcca aggaggccga gaatatcacg acgggctgtg ctgaacactg    360

cagcttgaat gagaatatca ctgtcccaga caccaaagtt aatttctatg cctggaagag    420

gatggaggtc gggcagcagg ccgtagaagt ctggcagggc ctggccctgc tgtcggaagc    480

tgtcctgcgg ggccaggccc tgttggtcaa ctcttcccag ccgtgggagc ccctgcagct    540

gcatgtggat aaagccgtca gtggccttcg cagcctcacc actctgcttc gggctctgcg    600

agcccagaag gaagccatct cccctccaga tgcggcctca gctgctccac tccgaacaat    660

cactgctgac actttccgca aactcttccg agtctactcc aatttcctcc ggggaaagct    720

gaagctgtac acaggggagg cctgcaggac aggggacaga tgaccaggtg tgtccacctg    780

ggcatatcca ccacctccct caccaacatt gcttgtgcca caccctcccc cgccactcct    840

gaaccccgtc gaggggctct cagctcagcg ccagcctgtc ccatggacac tccagtgcca    900

gcaatgacat ctcaggggcc agaggaactg tccagagagc aactctgaga tctaaggatg    960

tcacagggcc aacttgaggg cccagagcag gaagcattca gagagcagct ttaaactcag   1020

ggacagagcc atgctgggaa gacgcctgag ctcactcggc accctgcaaa atttgatgcc   1080

aggacacgct ttggaggcga tttacctgtt ttcgcaccta ccatcaggga caggatgacc   1140

tggagaactt aggtggcaag ctgtgacttc tccaggtctc acgggcatgg gcactccctt   1200

ggtggcaaga gcccccttga caccggggtg gtgggaacca tgaagacagg atgggggctg   1260

gcctctggct ctcatggggt ccaagttttg tgtattcttc aacctcattg acaagaactg   1320

aaaccaccaa aaaaaaaaaa aa                                            1342
```

<210> SEQ ID NO 16
<211> LENGTH: 193
<212> TYPE: PRT
<213> ORGANISM: Homo sapiens

<400> SEQUENCE: 16

```
Met Gly Val His Glu Cys Pro Ala Trp Leu Trp Leu Leu Leu Ser Leu
1               5                   10                  15

Leu Ser Leu Pro Leu Gly Leu Pro Val Leu Gly Ala Pro Pro Arg Leu
            20                  25                  30

Ile Cys Asp Ser Arg Val Leu Glu Arg Tyr Leu Leu Glu Ala Lys Glu
        35                  40                  45

Ala Glu Asn Ile Thr Thr Gly Cys Ala Glu His Cys Ser Leu Asn Glu
    50                  55                  60

Asn Ile Thr Val Pro Asp Thr Lys Val Asn Phe Tyr Ala Trp Lys Arg
65                  70                  75                  80

Met Glu Val Gly Gln Gln Ala Val Glu Val Trp Gln Gly Leu Ala Leu
                85                  90                  95

Leu Ser Glu Ala Val Leu Arg Gly Gln Ala Leu Leu Val Asn Ser Ser
            100                 105                 110

Gln Pro Trp Glu Pro Leu Gln Leu His Val Asp Lys Ala Val Ser Gly
        115                 120                 125

Leu Arg Ser Leu Thr Thr Leu Leu Arg Ala Leu Arg Ala Gln Lys Glu
    130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
```

-continued

```
                165                 170                 175

Arg Gly Lys Leu Lys Leu Tyr Thr Gly Glu Ala Cys Arg Thr Gly Asp
            180                 185                 190

Arg
```

<210> SEQ ID NO 17
<211> LENGTH: 435
<212> TYPE: DNA
<213> ORGANISM: Homo sapiens

<400> SEQUENCE: 17

```
atgtggctgc agagcctgct gctcttgggc actgtggcct gcagcatctc tgcacccgcc     60

cgctcgccca gccccagcac gcagccctgg gagcatgtga atgccatcca ggaggcccgg    120

cgtctcctga acctgagtag agacactgct gctgagatga atgaaacagt agaagtcatc    180

tcagaaatgt ttgacctcca ggagccgacc tgcctacaga cccgcctgga gctgtacaag    240

cagggcctgc ggggcagcct caccaagctc aagggcccct tgaccatgat ggccagccac    300

tacaagcagc actgccctcc aaccccggaa acttcctgtg caacccagat tatcaccttt    360

gaaagtttca aagagaacct gaaggacttt ctgcttgtca tcccctttga ctgctgggag    420

ccagtccagg agtga                                                      435
```

<210> SEQ ID NO 18
<211> LENGTH: 144
<212> TYPE: PRT
<213> ORGANISM: Homo sapiens

<400> SEQUENCE: 18

```
Met Trp Leu Gln Ser Leu Leu Leu Leu Gly Thr Val Ala Cys Ser Ile
1               5                   10                  15

Ser Ala Pro Ala Arg Ser Pro Ser Pro Ser Thr Gln Pro Trp Glu His
            20                  25                  30

Val Asn Ala Ile Gln Glu Ala Arg Arg Leu Leu Asn Leu Ser Arg Asp
        35                  40                  45

Thr Ala Ala Glu Met Asn Glu Thr Val Glu Val Ile Ser Glu Met Phe
    50                  55                  60

Asp Leu Gln Glu Pro Thr Cys Leu Gln Thr Arg Leu Glu Leu Tyr Lys
65                  70                  75                  80

Gln Gly Leu Arg Gly Ser Leu Thr Lys Leu Lys Gly Pro Leu Thr Met
                85                  90                  95

Met Ala Ser His Tyr Lys Gln His Cys Pro Pro Thr Pro Glu Thr Ser
            100                 105                 110

Cys Ala Thr Gln Ile Ile Thr Phe Glu Ser Phe Lys Glu Asn Leu Lys
        115                 120                 125

Asp Phe Leu Leu Val Ile Pro Phe Asp Cys Trp Glu Pro Val Gln Glu
    130                 135                 140
```

<210> SEQ ID NO 19
<211> LENGTH: 501
<212> TYPE: DNA
<213> ORGANISM: Homo sapiens

<400> SEQUENCE: 19

```
atgaaatata caagttatat cttggctttt cagctctgca tcgttttggg ttctcttggc     60

tgttactgcc aggacccata tgtaaaagaa gcagaaaacc ttaagaaata ttttaatgca    120

ggtcattcag atgtagcgga taatggaact cttttcttag gcattttgaa gaattggaaa    180
```

gaggagagtg acagaaaaat aatgcagagc caaattgtct ccttttactt caaacttttt 240
aaaaacttta aagatgacca gagcatccaa aagagtgtgg agaccatcaa ggaagacatg 300
aatgtcaagt ttttcaatag caacaaaaag aaacgagatg acttcgaaaa gctgactaat 360
tattcggtaa ctgacttgaa tgtccaacgc aaagcaatac atgaactcat ccaagtgatg 420
gctgaactgt cgccagcagc taaaacaggg aagcgaaaaa ggagtcagat gctgtttcga 480
ggtcgaagag catcccagta a 501

<210> SEQ ID NO 20
<211> LENGTH: 166
<212> TYPE: PRT
<213> ORGANISM: Homo sapiens

<400> SEQUENCE: 20

```
Met Lys Tyr Thr Ser Tyr Ile Leu Ala Phe Gln Leu Cys Ile Val Leu
1               5                   10                  15

Gly Ser Leu Gly Cys Tyr Cys Gln Asp Pro Tyr Val Lys Glu Ala Glu
            20                  25                  30

Asn Leu Lys Lys Tyr Phe Asn Ala Gly His Ser Asp Val Ala Asp Asn
        35                  40                  45

Gly Thr Leu Phe Leu Gly Ile Leu Lys Asn Trp Lys Glu Glu Ser Asp
    50                  55                  60

Arg Lys Ile Met Gln Ser Gln Ile Val Ser Phe Tyr Phe Lys Leu Phe
65                  70                  75                  80

Lys Asn Phe Lys Asp Asp Gln Ser Ile Gln Lys Ser Val Glu Thr Ile
                85                  90                  95

Lys Glu Asp Met Asn Val Lys Phe Phe Asn Ser Asn Lys Lys Lys Arg
            100                 105                 110

Asp Asp Phe Glu Lys Leu Thr Asn Tyr Ser Val Thr Asp Leu Asn Val
        115                 120                 125

Gln Arg Lys Ala Ile His Glu Leu Ile Gln Val Met Ala Glu Leu Ser
    130                 135                 140

Pro Ala Ala Lys Thr Gly Lys Arg Lys Arg Ser Gln Met Leu Phe Arg
145                 150                 155                 160

Gly Arg Arg Ala Ser Gln
                165
```

<210> SEQ ID NO 21
<211> LENGTH: 1352
<212> TYPE: DNA
<213> ORGANISM: Homo sapiens

<400> SEQUENCE: 21
ctgggacagt gaatcgacaa tgccgtcttc tgtctcgtgg ggcatcctcc tgctggcagg 60
cctgtgctgc ctggtccctg tctccctggc tgaggatccc cagggagatg ctgcccagaa 120
gacagataca tcccaccatg atcaggatca cccaaccttc aacaagatca cccccaacct 180
ggctgagttc gccttcagcc tataccgcca gctggcacac cagtccaaca gcaccaatat 240
cttcttctcc ccagtgagca tcgctacagc ctttgcaatg ctctccctgg ggaccaaggc 300
tgacactcac gatgaaatcc tggagggcct gaatttcaac ctcacggaga ttccggaggc 360
tcagatccat gaaggcttcc aggaactcct ccgtaccctc aaccagccag acagccagct 420
ccagctgacc accggcaatg gcctgttcct cagcgagggc ctgaagctag tggataagtt 480
tttggaggat gttaaaaagt tgtaccactc agaagccttc actgtcaact tcggggacac 540
cgaagaggcc aagaaacaga tcaacgatta cgtggagaag ggtactcaag ggaaaattgt 600

```
ggatttggtc aaggagcttg acagagacac agtttttgct ctggtgaatt acatcttctt    660

taaaggcaaa tgggagagac cctttgaagt caaggacacc gaggaagagg acttccacgt    720

ggaccaggtg accaccgtga aggtgcctat gatgaagcgt ttaggcatgt ttaacatcca    780

gcactgtaag aagctgtcca gctgggtgct gctgatgaaa tacctgggca atgccaccgc    840

catcttcttc ctgcctgatg aggggaaact acagcacctg gaaaatgaac tcacccacga    900

tatcatcacc aagttcctgg aaaatgaaga cagaaggtct gccagcttac atttacccaa    960

actgtccatt actggaacct atgatctgaa gagcgtcctg ggtcaactgg gcatcactaa   1020

ggtcttcagc aatggggctg acctctccgg ggtcacagag gaggcacccc tgaagctctc   1080

caaggccgtg cataaggctg tgctgaccat cgacgagaaa gggactgaag ctgctggggc   1140

catgttttta gaggccatac ccatgtctat cccccccgag gtcaagttca acaaaccctt   1200

tgtcttctta atgattgaac aaaataccaa gtctcccctc ttcatgggaa aagtggtgaa   1260

tcccacccaa aaataactgc ctctcgctcc tcaacccctc ccctccatcc ctggcccccct   1320

ccctggatga cattaaagaa gggttgagct gg                                 1352
```

<210> SEQ ID NO 22
<211> LENGTH: 418
<212> TYPE: PRT
<213> ORGANISM: Homo sapiens

<400> SEQUENCE: 22

```
Met Pro Ser Ser Val Ser Trp Gly Ile Leu Leu Leu Ala Gly Leu Cys
1               5                   10                  15

Cys Leu Val Pro Val Ser Leu Ala Glu Asp Pro Gln Gly Asp Ala Ala
            20                  25                  30

Gln Lys Thr Asp Thr Ser His His Asp Gln Asp His Pro Thr Phe Asn
        35                  40                  45

Lys Ile Thr Pro Asn Leu Ala Glu Phe Ala Phe Ser Leu Tyr Arg Gln
    50                  55                  60

Leu Ala His Gln Ser Asn Ser Thr Asn Ile Phe Phe Ser Pro Val Ser
65                  70                  75                  80

Ile Ala Thr Ala Phe Ala Met Leu Ser Leu Gly Thr Lys Ala Asp Thr
                85                  90                  95

His Asp Glu Ile Leu Glu Gly Leu Asn Phe Asn Leu Thr Glu Ile Pro
            100                 105                 110

Glu Ala Gln Ile His Glu Gly Phe Gln Glu Leu Leu Arg Thr Leu Asn
        115                 120                 125

Gln Pro Asp Ser Gln Leu Gln Leu Thr Thr Gly Asn Gly Leu Phe Leu
    130                 135                 140

Ser Glu Gly Leu Lys Leu Val Asp Lys Phe Leu Glu Asp Val Lys Lys
145                 150                 155                 160

Leu Tyr His Ser Glu Ala Phe Thr Val Asn Phe Gly Asp Thr Glu Glu
                165                 170                 175

Ala Lys Lys Gln Ile Asn Asp Tyr Val Glu Lys Gly Thr Gln Gly Lys
            180                 185                 190

Ile Val Asp Leu Val Lys Glu Leu Asp Arg Asp Thr Val Phe Ala Leu
        195                 200                 205

Val Asn Tyr Ile Phe Phe Lys Gly Lys Trp Glu Arg Pro Phe Glu Val
    210                 215                 220

Lys Asp Thr Glu Glu Glu Asp Phe His Val Asp Gln Val Thr Thr Val
225                 230                 235                 240
```

```
Lys Val Pro Met Met Lys Arg Leu Gly Met Phe Asn Ile Gln His Cys
                245                 250                 255

Lys Lys Leu Ser Ser Trp Val Leu Leu Met Lys Tyr Leu Gly Asn Ala
            260                 265                 270

Thr Ala Ile Phe Phe Leu Pro Asp Glu Gly Lys Leu Gln His Leu Glu
        275                 280                 285

Asn Glu Leu Thr His Asp Ile Ile Thr Lys Phe Leu Glu Asn Glu Asp
    290                 295                 300

Arg Arg Ser Ala Ser Leu His Leu Pro Lys Leu Ser Ile Thr Gly Thr
305                 310                 315                 320

Tyr Asp Leu Lys Ser Val Leu Gly Gln Leu Gly Ile Thr Lys Val Phe
                325                 330                 335

Ser Asn Gly Ala Asp Leu Ser Gly Val Thr Glu Glu Ala Pro Leu Lys
            340                 345                 350

Leu Ser Lys Ala Val His Lys Ala Val Leu Thr Ile Asp Glu Lys Gly
        355                 360                 365

Thr Glu Ala Ala Gly Ala Met Phe Leu Glu Ala Ile Pro Met Ser Ile
    370                 375                 380

Pro Pro Glu Val Lys Phe Asn Lys Pro Phe Val Phe Leu Met Ile Glu
385                 390                 395                 400

Gln Asn Thr Lys Ser Pro Leu Phe Met Gly Lys Val Val Asn Pro Thr
                405                 410                 415

Gln Lys


<210> SEQ ID NO 23
<211> LENGTH: 2004
<212> TYPE: DNA
<213> ORGANISM: Homo sapiens

<400> SEQUENCE: 23

gctaacctag tgcctatagc taaggcaggt acctgcatcc ttgtttttgt ttagtggatc     60

ctctatcctt cagagactct ggaacccctg tggtcttctc ttcatctaat gaccctgagg    120

ggatggagtt ttcaagtcct tccagagagg aatgtcccaa gcctttgagt agggtaagca    180

tcatggctgg cagcctcaca ggtttgcttc tacttcaggc agtgtcgtgg gcatcaggtg    240

cccgccccctg catccctaaa agcttcggct acagctcggt ggtgtgtgtc tgcaatgcca    300

catactgtga ctcctttgac cccccgacct ttcctgccct tggtaccttc agccgctatg    360

agagtacacg cagtgggcga cggatggagc tgagtatggg gcccatccag gctaatcaca    420

cgggcacagg cctgctactg accctgcagc cagaacagaa gttccagaaa gtgaagggat    480

ttggaggggc catgacagat gctgctgctc tcaacatcct tgccctgtca ccccctgccc    540

aaaatttgct acttaaatcg tacttctctg aagaaggaat cggatataac atcatccggg    600

tacccatggc cagctgtgac ttctccatcc gcacctacac ctatgcagac acccctgatg    660

atttccagtt gcacaacttc agcctcccag aggaagatac caagctcaag ataccccctga    720

ttcaccgagc cctgcagttg gcccagcgtc ccgtttcact ccttgccagc ccctggacat    780

cacccacttg gctcaagacc aatggagcgg tgaatgggaa ggggtcactc aagggacagc    840

ccggagacat ctaccaccag acctgggcca gatactttgt gaagttcctg gatgcctatg    900

ctgagcacaa gttacagttc tgggcagtga cagctgaaaa tgagccttct gctgggctgt    960

tgagtggata ccccttccag tgcctgggct tcacccctga acatcagcga gacttcattg   1020

cccgtgacct aggtcctacc ctcgccaaca gtactcacca caatgtccgc ctactcatgc   1080

tggatgacca acgcttgctg ctgccccact gggcaaaggt ggtactgaca gacccagaag   1140
```

cagctaaata tgttcatggc attgctgtac attggtacct ggactttctg gctccagcca 1200
aagccaccct aggggagaca caccgcctgt tccccaacac catgctcttt gcctcagagg 1260
cctgtgtggg ctccaagttc tgggagcaga gtgtgcggct aggctcctgg gatcgaggga 1320
tgcagtacag ccacagcatc atcacgaacc tcctgtacca tgtggtcggc tggaccgact 1380
ggaaccttgc cctgaacccc gaaggaggac ccaattgggt gcgtaacttt gtcgacagtc 1440
ccatcattgt agacatcacc aaggacacgt tttacaaaca gcccatgttc taccaccttg 1500
gccacttcag caagttcatt cctgagggct cccagagagt ggggctggtt gccagtcaga 1560
agaacgacct ggacgcagtg gcactgatgc atcccgatgg ctctgctgtt gtggtcgtgc 1620
taaaccgctc ctctaaggat gtgcctctta ccatcaagga tcctgctgtg ggcttcctgg 1680
agacaatctc acctggctac tccattcaca cctacctgtg gcatcgccag tgatggagca 1740
gatactcaag gaggcactgg gctcagcctg ggcattaaag ggacagagtc agctcacacg 1800
ctgtctgtga ctaaagaggg cacagcaggg ccagtgtgag cttacagcga cgtaagccca 1860
ggggcaatgg tttgggtgac tcactttccc ctctaggtgg tgcccagggc tggaggcccc 1920
tagaaaaaga tcagtaagcc ccagtgtccc cccagccccc atgcttatgt gaacatgcgc 1980
tgtgtgctgc ttgctttgga aact 2004

<210> SEQ ID NO 24
<211> LENGTH: 536
<212> TYPE: PRT
<213> ORGANISM: Homo sapiens

<400> SEQUENCE: 24

Met Glu Phe Ser Ser Pro Ser Arg Glu Glu Cys Pro Lys Pro Leu Ser
1 5 10 15

Arg Val Ser Ile Met Ala Gly Ser Leu Thr Gly Leu Leu Leu Leu Gln
20 25 30

Ala Val Ser Trp Ala Ser Gly Ala Arg Pro Cys Ile Pro Lys Ser Phe
35 40 45

Gly Tyr Ser Ser Val Val Cys Val Cys Asn Ala Thr Tyr Cys Asp Ser
50 55 60

Phe Asp Pro Pro Thr Phe Pro Ala Leu Gly Thr Phe Ser Arg Tyr Glu
65 70 75 80

Ser Thr Arg Ser Gly Arg Arg Met Glu Leu Ser Met Gly Pro Ile Gln
85 90 95

Ala Asn His Thr Gly Thr Gly Leu Leu Leu Thr Leu Gln Pro Glu Gln
100 105 110

Lys Phe Gln Lys Val Lys Gly Phe Gly Gly Ala Met Thr Asp Ala Ala
115 120 125

Ala Leu Asn Ile Leu Ala Leu Ser Pro Pro Ala Gln Asn Leu Leu Leu
130 135 140

Lys Ser Tyr Phe Ser Glu Glu Gly Ile Gly Tyr Asn Ile Ile Arg Val
145 150 155 160

Pro Met Ala Ser Cys Asp Phe Ser Ile Arg Thr Tyr Thr Tyr Ala Asp
165 170 175

Thr Pro Asp Asp Phe Gln Leu His Asn Phe Ser Leu Pro Glu Glu Asp
180 185 190

Thr Lys Leu Lys Ile Pro Leu Ile His Arg Ala Leu Gln Leu Ala Gln
195 200 205

Arg Pro Val Ser Leu Leu Ala Ser Pro Trp Thr Ser Pro Thr Trp Leu
210 215 220

```
Lys Thr Asn Gly Ala Val Asn Gly Lys Gly Ser Leu Lys Gly Gln Pro
225                 230                 235                 240

Gly Asp Ile Tyr His Gln Thr Trp Ala Arg Tyr Phe Val Lys Phe Leu
                245                 250                 255

Asp Ala Tyr Ala Glu His Lys Leu Gln Phe Trp Ala Val Thr Ala Glu
            260                 265                 270

Asn Glu Pro Ser Ala Gly Leu Leu Ser Gly Tyr Pro Phe Gln Cys Leu
        275                 280                 285

Gly Phe Thr Pro Glu His Gln Arg Asp Phe Ile Ala Arg Asp Leu Gly
    290                 295                 300

Pro Thr Leu Ala Asn Ser Thr His His Asn Val Arg Leu Leu Met Leu
305                 310                 315                 320

Asp Asp Gln Arg Leu Leu Leu Pro His Trp Ala Lys Val Val Leu Thr
                325                 330                 335

Asp Pro Glu Ala Ala Lys Tyr Val His Gly Ile Ala Val His Trp Tyr
            340                 345                 350

Leu Asp Phe Leu Ala Pro Ala Lys Ala Thr Leu Gly Glu Thr His Arg
        355                 360                 365

Leu Phe Pro Asn Thr Met Leu Phe Ala Ser Glu Ala Cys Val Gly Ser
    370                 375                 380

Lys Phe Trp Glu Gln Ser Val Arg Leu Gly Ser Trp Asp Arg Gly Met
385                 390                 395                 400

Gln Tyr Ser His Ser Ile Ile Thr Asn Leu Leu Tyr His Val Val Gly
                405                 410                 415

Trp Thr Asp Trp Asn Leu Ala Leu Asn Pro Glu Gly Gly Pro Asn Trp
            420                 425                 430

Val Arg Asn Phe Val Asp Ser Pro Ile Ile Val Asp Ile Thr Lys Asp
        435                 440                 445

Thr Phe Tyr Lys Gln Pro Met Phe Tyr His Leu Gly His Phe Ser Lys
    450                 455                 460

Phe Ile Pro Glu Gly Ser Gln Arg Val Gly Leu Val Ala Ser Gln Lys
465                 470                 475                 480

Asn Asp Leu Asp Ala Val Ala Leu Met His Pro Asp Gly Ser Ala Val
                485                 490                 495

Val Val Val Leu Asn Arg Ser Ser Lys Asp Val Pro Leu Thr Ile Lys
            500                 505                 510

Asp Pro Ala Val Gly Phe Leu Glu Thr Ile Ser Pro Gly Tyr Ser Ile
        515                 520                 525

His Thr Tyr Leu Trp His Arg Gln
    530                 535
```

<210> SEQ ID NO 25
<211> LENGTH: 1726
<212> TYPE: DNA
<213> ORGANISM: Homo sapiens

<400> SEQUENCE: 25

```
atggatgcaa tgaagagagg gctctgctgt gtgctgctgc tgtgtggagc agtcttcgtt      60

tcgcccagcc aggaaatcca tgcccgattc agaagaggag ccagatctta ccaagtgatc     120

tgcagagatg aaaaaacgca gatgatatac cagcaacatc agtcatggct gcgccctgtg     180

ctcagaagca accgggtgga atattgctgg tgcaacagtg gcagggcaca gtgccactca     240

gtgcctgtca aaagttgcag cgagccaagg tgtttcaacg ggggcacctg ccagcaggcc     300

ctgtacttct cagatttcgt gtgccagtgc cccgaaggat ttgctgggaa gtgctgtgaa     360
```

```
atagatacca gggccacgtg ctacgaggac cagggcatca gctacagggg cacgtggagc    420

acagcggaga gtggcgccga gtgcaccaac tggaacagca gcgcgttggc ccagaagccc    480

tacagcgggc ggaggccaga cgccatcagg ctgggcctgg ggaaccacaa ctactgcaga    540

aacccagatc gagactcaaa gccctggtgc tacgtcttta aggcggggaa gtacagctca    600

gagttctgca gcacccctgc ctgctctgag ggaaacagtg actgctactt tgggaatggg    660

tcagcctacc gtggcacgca cagcctcacc gagtcgggtg cctcctgcct cccgtggaat    720

tccatgatcc tgataggcaa ggtttacaca gcacagaacc ccagtgccca ggcactgggc    780

ctgggcaaac ataattactg ccggaatcct gatggggatg ccaagccctg gtgccacgtg    840

ctgaagaacc gcaggctgac gtgggagtac tgtgatgtgc cctcctgctc cacctgcggc    900

ctgagacagt acagccagcc tcagtttcgc atcaaaggag ggctcttcgc cgacatcgcc    960

tcccacccct ggcaggctgc catctttgcc aagcacagga ggtcgccggg agagcggttc   1020

ctgtgcgggg gcatactcat cagctcctgc tggattctct ctgccgccca ctgcttccag   1080

gagaggtttc cgccccacca cctgacggtg atcttgggca gaacataccg ggtggtccct   1140

ggcgaggagg agcagaaatt tgaagtcgaa aaatacattg tccataagga attcgatgat   1200

gacacttacg acaatgacat tgcgctgctg cagctgaaat cggattcgtc ccgctgtgcc   1260

caggagagca gcgtggtccg cactgtgtgc cttcccccgg cggacctgca gctgccggac   1320

tggacggagt gtgagctctc cggctacggc aagcatgagg ccttgtctcc tttctattcg   1380

gagcggctga aggaggctca tgtcagactg tacccatcca gccgctgcac atcacaacat   1440

ttacttaaca gaacagtcac cgacaacatg ctgtgtgctg gagacactcg gagcggcggg   1500

ccccaggcaa acttgcacga cgcctgccag ggcgattcgg gaggccccct ggtgtgtctg   1560

aacgatggcc gcatgacttt ggtgggcatc atcagctggg gcctgggctg tggacagaag   1620

gatgtcccgg gtgtgtacac caaggttacc aactacctag actggattcg tgacaacatg   1680

cgaccgtgac caggaacacc cgactcctca aaagcaaatg agatcc                  1726
```

<210> SEQ ID NO 26
<211> LENGTH: 562
<212> TYPE: PRT
<213> ORGANISM: Homo sapiens

<400> SEQUENCE: 26

```
Met Asp Ala Met Lys Arg Gly Leu Cys Cys Val Leu Leu Leu Cys Gly
1               5                   10                  15

Ala Val Phe Val Ser Pro Ser Gln Glu Ile His Ala Arg Phe Arg Arg
            20                  25                  30

Gly Ala Arg Ser Tyr Gln Val Ile Cys Arg Asp Glu Lys Thr Gln Met
        35                  40                  45

Ile Tyr Gln Gln His Gln Ser Trp Leu Arg Pro Val Leu Arg Ser Asn
    50                  55                  60

Arg Val Glu Tyr Cys Trp Cys Asn Ser Gly Arg Ala Gln Cys His Ser
65                  70                  75                  80

Val Pro Val Lys Ser Cys Ser Glu Pro Arg Cys Phe Asn Gly Gly Thr
                85                  90                  95

Cys Gln Gln Ala Leu Tyr Phe Ser Asp Phe Val Cys Gln Cys Pro Glu
            100                 105                 110

Gly Phe Ala Gly Lys Cys Cys Glu Ile Asp Thr Arg Ala Thr Cys Tyr
        115                 120                 125

Glu Asp Gln Gly Ile Ser Tyr Arg Gly Thr Trp Ser Thr Ala Glu Ser
```

-continued

```
    130                 135                 140

Gly Ala Glu Cys Thr Asn Trp Asn Ser Ser Ala Leu Ala Gln Lys Pro
145                 150                 155                 160

Tyr Ser Gly Arg Arg Pro Asp Ala Ile Arg Leu Gly Leu Gly Asn His
                165                 170                 175

Asn Tyr Cys Arg Asn Pro Asp Arg Asp Ser Lys Pro Trp Cys Tyr Val
            180                 185                 190

Phe Lys Ala Gly Lys Tyr Ser Ser Glu Phe Cys Ser Thr Pro Ala Cys
        195                 200                 205

Ser Glu Gly Asn Ser Asp Cys Tyr Phe Gly Asn Gly Ser Ala Tyr Arg
    210                 215                 220

Gly Thr His Ser Leu Thr Glu Ser Gly Ala Ser Cys Leu Pro Trp Asn
225                 230                 235                 240

Ser Met Ile Leu Ile Gly Lys Val Tyr Thr Ala Gln Asn Pro Ser Ala
                245                 250                 255

Gln Ala Leu Gly Leu Gly Lys His Asn Tyr Cys Arg Asn Pro Asp Gly
            260                 265                 270

Asp Ala Lys Pro Trp Cys His Val Leu Lys Asn Arg Arg Leu Thr Trp
        275                 280                 285

Glu Tyr Cys Asp Val Pro Ser Cys Ser Thr Cys Gly Leu Arg Gln Tyr
    290                 295                 300

Ser Gln Pro Gln Phe Arg Ile Lys Gly Gly Leu Phe Ala Asp Ile Ala
305                 310                 315                 320

Ser His Pro Trp Gln Ala Ala Ile Phe Ala Lys His Arg Arg Ser Pro
                325                 330                 335

Gly Glu Arg Phe Leu Cys Gly Gly Ile Leu Ile Ser Ser Cys Trp Ile
            340                 345                 350

Leu Ser Ala Ala His Cys Phe Gln Glu Arg Phe Pro Pro His His Leu
        355                 360                 365

Thr Val Ile Leu Gly Arg Thr Tyr Arg Val Val Pro Gly Glu Glu Glu
    370                 375                 380

Gln Lys Phe Glu Val Glu Lys Tyr Ile Val His Lys Glu Phe Asp Asp
385                 390                 395                 400

Asp Thr Tyr Asp Asn Asp Ile Ala Leu Leu Gln Leu Lys Ser Asp Ser
                405                 410                 415

Ser Arg Cys Ala Gln Glu Ser Ser Val Val Arg Thr Val Cys Leu Pro
            420                 425                 430

Pro Ala Asp Leu Gln Leu Pro Asp Trp Thr Glu Cys Glu Leu Ser Gly
        435                 440                 445

Tyr Gly Lys His Glu Ala Leu Ser Pro Phe Tyr Ser Glu Arg Leu Lys
    450                 455                 460

Glu Ala His Val Arg Leu Tyr Pro Ser Ser Arg Cys Thr Ser Gln His
465                 470                 475                 480

Leu Leu Asn Arg Thr Val Thr Asp Asn Met Leu Cys Ala Gly Asp Thr
                485                 490                 495

Arg Ser Gly Gly Pro Gln Ala Asn Leu His Asp Ala Cys Gln Gly Asp
            500                 505                 510

Ser Gly Gly Pro Leu Val Cys Leu Asn Asp Gly Arg Met Thr Leu Val
        515                 520                 525

Gly Ile Ile Ser Trp Gly Leu Gly Cys Gly Gln Lys Asp Val Pro Gly
    530                 535                 540

Val Tyr Thr Lys Val Thr Asn Tyr Leu Asp Trp Ile Arg Asp Asn Met
545                 550                 555                 560
```

Arg Pro

<210> SEQ ID NO 27
<211> LENGTH: 825
<212> TYPE: DNA
<213> ORGANISM: Homo sapiens

<400> SEQUENCE: 27
atcactctct ttaatcacta ctcacattaa cctcaactcc tgccacaatg tacaggatgc 60
aactcctgtc ttgcattgca ctaattcttg cacttgtcac aaacagtgca cctacttcaa 120
gttcgacaaa gaaaacaaag aaaacacagc tacaactgga gcatttactg ctggatttac 180
agatgatttt gaatggaatt aataattaca agaatcccaa actcaccagg atgctcacat 240
ttaagtttta catgcccaag aaggccacag aactgaaaca gcttcagtgt ctagaagaag 300
aactcaaacc tctggaggaa gtgctgaatt tagctcaaag caaaaacttt cacttaagac 360
ccagggactt aatcagcaat atcaacgtaa tagttctgga actaaaggga tctgaaacaa 420
cattcatgtg tgaatatgca gatgagacag caaccattgt agaatttctg aacagatgga 480
ttaccttttg tcaaagcatc atctcaacac taacttgata attaagtgct tcccacttaa 540
aacatatcag gccttctatt tatttattta aatatttaaa ttttatattt attgttgaat 600
gtatggttgc tacctattgt aactattatt cttaatctta aaactataaa tatggatctt 660
ttatgattct ttttgtaagc cctaggggct ctaaaatggt ttaccttatt tatcccaaaa 720
atatttatta ttatgttgaa tgttaaatat agtatctatg tagattggtt agtaaaacta 780
tttaataaat ttgataaata taaaaaaaaa aaacaaaaaa aaaaa 825

<210> SEQ ID NO 28
<211> LENGTH: 156
<212> TYPE: PRT
<213> ORGANISM: Homo sapiens

<400> SEQUENCE: 28

Met Tyr Arg Met Gln Leu Leu Ser Cys Ile Ala Leu Ile Leu Ala Leu
1 5 10 15

Val Thr Asn Ser Ala Pro Thr Ser Ser Ser Thr Lys Lys Thr Lys Lys
20 25 30

Thr Gln Leu Gln Leu Glu His Leu Leu Leu Asp Leu Gln Met Ile Leu
35 40 45

Asn Gly Ile Asn Asn Tyr Lys Asn Pro Lys Leu Thr Arg Met Leu Thr
50 55 60

Phe Lys Phe Tyr Met Pro Lys Lys Ala Thr Glu Leu Lys Gln Leu Gln
65 70 75 80

Cys Leu Glu Glu Glu Leu Lys Pro Leu Glu Glu Val Leu Asn Leu Ala
85 90 95

Gln Ser Lys Asn Phe His Leu Arg Pro Arg Asp Leu Ile Ser Asn Ile
100 105 110

Asn Val Ile Val Leu Glu Leu Lys Gly Ser Glu Thr Thr Phe Met Cys
115 120 125

Glu Tyr Ala Asp Glu Thr Ala Thr Ile Val Glu Phe Leu Asn Arg Trp
130 135 140

Ile Thr Phe Cys Gln Ser Ile Ile Ser Thr Leu Thr
145 150 155

<210> SEQ ID NO 29
<211> LENGTH: 7931
<212> TYPE: DNA

<213> ORGANISM: Homo sapiens

<400> SEQUENCE: 29

```
atgcaaatag agctctccac ctgcttcttt ctgtgccttt tgcgattctg ctttagtgcc     60
accagaagat actacctggg tgcagtggaa ctgtcatggg actatatgca aagtgatctc    120
ggtgagctgc ctgtggacgc aagatttcct cctagagtgc caaaatcttt tccattcaac    180
acctcagtcg tgtacaaaaa gactctgttt gtagaattca cggatcacct tttcaacatc    240
gctaagccaa ggccaccctg gatgggtctg ctaggtccta ccatccaggc tgaggtttat    300
gatacagtgg tcattacact taagaacatg gcttcccatc ctgtcagtct tcatgctgtt    360
ggtgtatcct actggaaagc ttctgaggga gctgaatatg atgatcagac cagtcaaagg    420
gagaaagaag atgataaagt cttccctggt ggaagccata catatgtctg gcaggtcctg    480
aaagagaatg gtccaatggc ctctgaccca ctgtgcctta cctactcata tctttctcat    540
gtggacctgg taaaagactt gaattcaggc ctcattggag ccctactagt atgtagagaa    600
gggagtctgg ccaaggaaaa gacacagacc ttgcacaaat ttatactact ttttgctgta    660
tttgatgaag ggaaaagttg gcactcagaa acaaagaact ccttgatgca ggatagggat    720
gctgcatctg ctcgggcctg gcctaaaatg cacacagtca atggttatgt aaacaggtct    780
ctgccaggtc tgattggatg ccacaggaaa tcagtctatt ggcatgtgat tggaatgggc    840
accactcctg aagtgcactc aatattcctc gaaggtcaca catttcttgt gaggaaccat    900
cgccaggcgt ccttggaaat ctcgccaata actttcctta ctgctcaaac actcttgatg    960
gaccttggac agtttctact gttttgtcat atctcttccc accaacatga tggcatggaa   1020
gcttatgtca aagtagacag ctgtccagag gaaccccaac tacgaatgaa aaataatgaa   1080
gaagcggaag actatgatga tgatcttact gattctgaaa tggatgtggt caggtttgat   1140
gatgacaact ctccttcctt tatccaaatt cgctcagttg ccaagaagca tcctaaaact   1200
tgggtacatt acattgctgc tgaagaggag gactgggact atgctccctt agtcctcgcc   1260
cccgatgaca gaagttataa aagtcaatat ttgaacaatg gccctcagcg gattggtagg   1320
aagtacaaaa aagtccgatt tatggcatac acagatgaaa cctttaagac tcgtgaagct   1380
attcagcatg aatcaggaat cttgggacct ttactttatg gggaagttgg agacacactg   1440
ttgattatat ttaagaatca agcaagcaga ccatataaca tctaccctca cggaatcact   1500
gatgtccgtc ctttgtattc aaggagatta ccaaaaggtg taaaacattt gaaggatttt   1560
ccaattctgc caggagaaat attcaaatat aaatggacag tgactgtaga agatgggcca   1620
actaaatcag atcctcggtg cctgacccgc tattactcta gtttcgttaa tatggagaga   1680
gatctagctt caggactcat tggccctctc ctcatctgct acaaagaatc tgtagatcaa   1740
agaggaaacc agataatgtc agacaagagg aatgtcatcc tgttttctgt atttgatgag   1800
aaccgaagct ggtacctcac agagaatata caacgctttc tccccaatcc agctggagtg   1860
cagcttgagg atccagagtt ccaagcctcc aacatcatgc acagcatcaa tggctatgtt   1920
tttgatagtt tgcagttgtc agtttgtttg catgaggtgg catactggta cattctaagc   1980
attggagcac agactgactt cctttctgtc ttcttctctg gatatacctt caaacacaaa   2040
atggtctatg aagacacact caccctattc ccattctcag gagaaactgt cttcatgtcg   2100
atggaaaacc caggtctatg gattctgggg tgccacaact cagactttcg gaacagaggc   2160
atgaccgcct tactgaaggt ttctagttgt gacaagaaca ctggtgatta ttacgaggac   2220
agttatgaag atatttcagc atacttgctg agtaaaaaca atgccattga accaagaagc   2280
```

-continued

```
ttctcccaga attcaagaca ccgtagcact aggcaaaagc aatttaatgc caccacaatt   2340
ccagaaaatg acatagagaa gactgaccct tggtttgcac acagaacacc tatgcctaaa   2400
atacaaaatg tctcctctag tgatttgttg atgctcttgc gacagagtcc tactccacat   2460
gggctatcct tatctgatct ccaagaagcc aaatatgaga ctttttctga tgatccatca   2520
cctggagcaa tagacagtaa taacagcctg tctgaaatga cacacttcag gccacagctc   2580
catcacagtg gggacatggt atttacccct gagtcaggcc tccaattaag attaaatgag   2640
aaactgggga caactgcagc aacagagttg aagaaacttg atttcaaagt ttctagtaca   2700
tcaaataatc tgatttcaac aattccatca gacaatttgg cagcaggtac tgataataca   2760
agttccttag gacccccaag tatgccagtt cattatgata gtcaattaga taccactcta   2820
tttggcaaaa agtcatctcc ccttactgag tctggtggac ctctgagctt gagtgaagaa   2880
aataatgatt caaagttgtt agaatcaggt ttaatgaata gccaagaaag ttcatgggga   2940
aaaaatgtat cgtcaacaga gagtggtagg ttatttaaag ggaaaagagc tcatggacct   3000
gctttgttga ctaaagataa tgccttattc aaagttagca tctctttgtt aaagacaaac   3060
aaaacttcca ataattcagc aactaataga aagactcaca ttgatggccc atcattatta   3120
attgagaata gtccatcagt ctggcaaaat atattagaaa gtgacactga gtttaaaaaa   3180
gtgacacctt tgattcatga cagaatgctt atggacaaaa atgctacagc tttgaggcta   3240
aatcatatgt caaataaaac tacttcatca aaaaacatgg aaatggtcca acagaaaaaa   3300
gagggcccca ttccaccaga tgcacaaaat ccagatatgt cgttctttaa gatgctattc   3360
ttgccagaat cagcaaggtg gatacaaagg actcatggaa agaactctct gaactctggg   3420
caaggcccca gtccaaagca attagtatcc ttaggaccag aaaaatctgt ggaaggtcag   3480
aatttcttgt ctgagaaaaa caaagtggta gtaggaaagg gtgaatttac aaaggacgta   3540
ggactcaaag agatggtttt tccaagcagc agaaacctat ttcttactaa cttggataat   3600
ttacatgaaa ataatacaca caatcaagaa aaaaaaattc aggaagaaat agaaaagaag   3660
gaaacattaa tccaagagaa tgtagttttg cctcagatac atacagtgac tggcactaag   3720
aatttcatga agaacctttt cttactgagc actaggcaaa atgtagaagg ttcatatgac   3780
ggggcatatg ctccagtact tcaagatttt aggtcattaa atgattcaac aaatagaaca   3840
aagaaacaca cagctcattt ctcaaaaaaa ggggaggaag aaaacttgga aggcttggga   3900
aatcaaacca agcaaattgt agagaaatat gcatgcacca caaggatatc tcctaataca   3960
agccagcaga attttgtcac gcaacgtagt aagagagctt tgaaacaatt cagactccca   4020
ctagaagaaa cagaacttga aaaaaggata attgtggatg acacctcaac ccagtggtcc   4080
aaaaacatga aacatttgac cccgagcacc ctcacacaga tagactacaa tgagaaggag   4140
aaaggggcca ttactcagtc tcccttatca gattgcctta cgaggagtca tagcatccct   4200
caagcaaata gatctccatt acccattgca aaggtatcat catttccatc tattagacct   4260
atatatctga ccagggtcct attccaagac aactcttctc atcttccagc agcatcttat   4320
agaaagaaag attctggggt ccaagaaagc agtcatttct tacaaggagc caaaaaaaat   4380
aacctttctt tagccattct aaccttggag atgactggtg atcaaagaga ggttggctcc   4440
ctggggacaa gtgccacaaa ttcagtcaca tacaagaaag ttgagaacac tgttctcccg   4500
aaaccagact tgcccaaaac atctggcaaa gttgaattgc ttccaaaagt tcacatttat   4560
cagaaggacc tattccctac ggaaactagc aatgggtctc ctggccatct ggatctcgtg   4620
gaagggagcc ttcttcaggg aacagaggga gcgattaagt ggaatgaagc aaacagacct   4680
```

-continued

```
ggaaaagttc cctttctgag agtagcaaca gaaagctctg caaagactcc ctccaagcta   4740
ttggatcctc ttgcttggga taaccactat ggtactcaga taccaaaaga agagtggaaa   4800
tcccaagaga agtcaccaga aaaaacagct tttaagaaaa aggataccat tttgtccctg   4860
aacgcttgtg aaagcaatca tgcaatagca gcaataaatg agggacaaaa taagcccgaa   4920
atagaagtca cctgggcaaa gcaaggtagg actgaaaggc tgtgctctca aaacccacca   4980
gtcttgaaac gccatcaacg ggaaataact cgtactactc ttcagtcaga tcaagaggaa   5040
attgactatg atgataccat atcagttgaa atgaagaagg aagattttga catttatgat   5100
gaggatgaaa atcagagccc ccgcagcttt caaaagaaaa cacgacacta ttttattgct   5160
gcagtggaga ggctctggga ttatgggatg agtagctccc cacatgttct aagaaacagg   5220
gctcagagtg gcagtgtccc tcagttcaag aaagttgttt tccaggaatt tactgatggc   5280
tcctttactc agcccttata ccgtggagaa ctaaatgaac atttgggact cctggggcca   5340
tatataagag cagaagttga agataaatatc atggtaactt tcagaaatca ggcctctcgt   5400
ccctattcct tctattctag ccttatttct tatgaggaag atcagaggca aggagcagaa   5460
cctagaaaaa actttgtcaa gcctaatgaa accaaaactt acttttggaa agtgcaacat   5520
catatggcac ccactaaaga tgagtttgac tgcaaagcct gggcttattt ctctgatgtt   5580
gacctggaaa aagatgtgca ctcaggcctg attggacccc ttctggtctg ccacactaac   5640
acactgaacc ctgctcatgg gagacaagtg acagtacagg aatttgctct gtttttcacc   5700
atctttgatg agaccaaaag ctggtacttc actgaaaata tggaaagaaa ctgcagggct   5760
ccctgcaata tccagatgga agatcccact tttaaagaga attatcgctt ccatgcaatc   5820
aatggctaca taatggatac actacctggc ttagtaatgg ctcaggatca aaggattcga   5880
tggtatctgc tcagcatggg cagcaatgaa aacatccatt ctattcattt cagtggacat   5940
gtgttcactg tacgaaaaaa agaggagtat aaaatggcac tgtacaatct ctatccaggt   6000
gtttttgaga cagtggaaat gttaccatcc aaagctggaa tttggcgggt ggaatgcctt   6060
attggcgagc atctacatgc tgggatgagc acactttttc tggtgtacag caataagtgt   6120
cagactcccc tgggaatggc ttctggacac attagagatt ttcagattac agcttcagga   6180
caatatggac agtgggcccc aaagctggcc agacttcatt attccggatc aatcaatgcc   6240
tggagcacca aggagccctt ttcttggatc aaggtggatc tgttggcacc aatgattatt   6300
cacggcatca agacccaggg tgcccgtcag aagttctcca gcctctacat ctctcagttt   6360
atcatcatgt atagtcttga tgggaagaag tggcagactt atcgaggaaa ttccactgga   6420
accttaatgg tcttctttgg caatgtggat tcatctggga taaaacacaa tatttttaac   6480
cctccaatta ttgctcgata catccgtttg cacccaactc attatagcat tcgcagcact   6540
cttcgcatgg agttgatggg ctgtgattta aatagttgca gcatgccatt gggaatggag   6600
agtaaagcaa tatcagatgc acagattact gcttcatcct actttaccaa tatgtttgcc   6660
acctggtctc cttcaaaagc tcgacttcac ctccaaggga ggagtaatgc ctggagacct   6720
caggtgaata atccaaaaga gtggctgcaa gtggacttcc agaagacaat gaaagtcaca   6780
ggagtaacta ctcagggagt aaaatctctg cttaccagca tgtatgtgaa ggagttcctc   6840
atctccagca gtcaagatgg ccatcagtgg actctctttt ttcagaatgg caaagtaaag   6900
gtttttcagg gaaatcaaga ctccttcaca cctgtggtga actctctaga cccaccgtta   6960
ctgactcgct accttcgaat tcacccccag agttgggtgc accagattgc cctgaggatg   7020
gaggttctgg gctgcgaggc acaggacctc tactgagggt ggccactgca gcacctgcca   7080
```

ctgccgtcac ctctccctcc tcagctccag ggcagtgtcc ctccctggct tgccttctac 7140
ctttgtgcta aatcctagca gacactgcct tgaagcctcc tgaattaact atcatcagtc 7200
ctgcatttct ttggtggggg gccaggaggg tgcatccaat ttaacttaac tcttacctat 7260
tttctgcagc tgctcccaga ttactccttc cttccaatat aactaggcaa aaagaagtga 7320
ggagaaacct gcatgaaagc attcttccct gaaaagttag gcctctcaga gtcaccactt 7380
cctctgttgt agaaaaacta tgtgatgaaa ctttgaaaaa gatatttatg atgttaacat 7440
ttcaggttaa gcctcatacg tttaaaataa aactctcagt tgtttattat cctgatcaag 7500
catggaacaa agcatgtttc aggatcagat caatacaatc ttggagtcaa aaggcaaatc 7560
atttggacaa tctgcaaaat ggagagaata caataactac tacagtaaag tctgtttctg 7620
cttccttaca catagatata attatgttat ttagtcatta tgaggggcac attcttatct 7680
ccaaaactag cattcttaaa ctgagaatta tagatggggt tcaagaatcc ctaagtcccc 7740
tgaaattata taaggcattc tgtataaatg caaatgtgca tttttctgac gagtgtccat 7800
agatataaag ccatttggtc ttaattctga ccaataaaaa aataagtcag gaggatgcaa 7860
ttgttgaaag ctttgaaata aaataacaat gtcttcttga aatttgtgat ggccaagaaa 7920
gaaaatgatg a 7931

<210> SEQ ID NO 30
<211> LENGTH: 2351
<212> TYPE: PRT
<213> ORGANISM: Homo sapiens

<400> SEQUENCE: 30

Met Gln Ile Glu Leu Ser Thr Cys Phe Phe Leu Cys Leu Leu Arg Phe
1 5 10 15

Cys Phe Ser Ala Thr Arg Arg Tyr Tyr Leu Gly Ala Val Glu Leu Ser
20 25 30

Trp Asp Tyr Met Gln Ser Asp Leu Gly Glu Leu Pro Val Asp Ala Arg
35 40 45

Phe Pro Pro Arg Val Pro Lys Ser Phe Pro Phe Asn Thr Ser Val Val
50 55 60

Tyr Lys Lys Thr Leu Phe Val Glu Phe Thr Asp His Leu Phe Asn Ile
65 70 75 80

Ala Lys Pro Arg Pro Pro Trp Met Gly Leu Leu Gly Pro Thr Ile Gln
85 90 95

Ala Glu Val Tyr Asp Thr Val Val Ile Thr Leu Lys Asn Met Ala Ser
100 105 110

His Pro Val Ser Leu His Ala Val Gly Val Ser Tyr Trp Lys Ala Ser
115 120 125

Glu Gly Ala Glu Tyr Asp Asp Gln Thr Ser Gln Arg Glu Lys Glu Asp
130 135 140

Asp Lys Val Phe Pro Gly Gly Ser His Thr Tyr Val Trp Gln Val Leu
145 150 155 160

Lys Glu Asn Gly Pro Met Ala Ser Asp Pro Leu Cys Leu Thr Tyr Ser
165 170 175

Tyr Leu Ser His Val Asp Leu Val Lys Asp Leu Asn Ser Gly Leu Ile
180 185 190

Gly Ala Leu Leu Val Cys Arg Glu Gly Ser Leu Ala Lys Glu Lys Thr
195 200 205

Gln Thr Leu His Lys Phe Ile Leu Leu Phe Ala Val Phe Asp Glu Gly
210 215 220

```
Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Lys Ser Val
            260                 265                 270

Tyr Trp His Val Ile Gly Met Gly Thr Thr Pro Glu Val His Ser Ile
        275                 280                 285

Phe Leu Glu Gly His Thr Phe Leu Val Arg Asn His Arg Gln Ala Ser
    290                 295                 300

Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                325                 330                 335

Asp Gly Met Glu Ala Tyr Val Lys Val Asp Ser Cys Pro Glu Glu Pro
            340                 345                 350

Gln Leu Arg Met Lys Asn Asn Glu Glu Ala Glu Asp Tyr Asp Asp Asp
        355                 360                 365

Leu Thr Asp Ser Glu Met Asp Val Val Arg Phe Asp Asp Asp Asn Ser
    370                 375                 380

Pro Ser Phe Ile Gln Ile Arg Ser Val Ala Lys Lys His Pro Lys Thr
385                 390                 395                 400

Trp Val His Tyr Ile Ala Ala Glu Glu Glu Asp Trp Asp Tyr Ala Pro
                405                 410                 415

Leu Val Leu Ala Pro Asp Asp Arg Ser Tyr Lys Ser Gln Tyr Leu Asn
            420                 425                 430

Asn Gly Pro Gln Arg Ile Gly Arg Lys Tyr Lys Lys Val Arg Phe Met
        435                 440                 445

Ala Tyr Thr Asp Glu Thr Phe Lys Thr Arg Glu Ala Ile Gln His Glu
    450                 455                 460

Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
                485                 490                 495

His Gly Ile Thr Asp Val Arg Pro Leu Tyr Ser Arg Arg Leu Pro Lys
            500                 505                 510

Gly Val Lys His Leu Lys Asp Phe Pro Ile Leu Pro Gly Glu Ile Phe
        515                 520                 525

Lys Tyr Lys Trp Thr Val Thr Val Glu Asp Gly Pro Thr Lys Ser Asp
    530                 535                 540

Pro Arg Cys Leu Thr Arg Tyr Tyr Ser Ser Phe Val Asn Met Glu Arg
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Ile Met Ser Asp Lys Arg Asn Val
            580                 585                 590

Ile Leu Phe Ser Val Phe Asp Glu Asn Arg Ser Trp Tyr Leu Thr Glu
        595                 600                 605

Asn Ile Gln Arg Phe Leu Pro Asn Pro Ala Gly Val Gln Leu Glu Asp
    610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
                645                 650                 655
```

```
Tyr Ile Leu Ser Ile Gly Ala Gln Thr Asp Phe Leu Ser Val Phe Phe
            660                 665                 670

Ser Gly Tyr Thr Phe Lys His Lys Met Val Tyr Glu Asp Thr Leu Thr
        675                 680                 685

Leu Phe Pro Phe Ser Gly Glu Thr Val Phe Met Ser Met Glu Asn Pro
    690                 695                 700

Gly Leu Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
                725                 730                 735

Tyr Tyr Glu Asp Ser Tyr Glu Asp Ile Ser Ala Tyr Leu Leu Ser Lys
            740                 745                 750

Asn Asn Ala Ile Glu Pro Arg Ser Phe Ser Gln Asn Ser Arg His Arg
        755                 760                 765

Ser Thr Arg Gln Lys Gln Phe Asn Ala Thr Thr Ile Pro Glu Asn Asp
    770                 775                 780

Ile Glu Lys Thr Asp Pro Trp Phe Ala His Arg Thr Pro Met Pro Lys
785                 790                 795                 800

Ile Gln Asn Val Ser Ser Ser Asp Leu Leu Met Leu Leu Arg Gln Ser
                805                 810                 815

Pro Thr Pro His Gly Leu Ser Leu Ser Asp Leu Gln Glu Ala Lys Tyr
            820                 825                 830

Glu Thr Phe Ser Asp Asp Pro Ser Pro Gly Ala Ile Asp Ser Asn Asn
        835                 840                 845

Ser Leu Ser Glu Met Thr His Phe Arg Pro Gln Leu His His Ser Gly
    850                 855                 860

Asp Met Val Phe Thr Pro Glu Ser Gly Leu Gln Leu Arg Leu Asn Glu
865                 870                 875                 880

Lys Leu Gly Thr Thr Ala Ala Thr Glu Leu Lys Lys Leu Asp Phe Lys
                885                 890                 895

Val Ser Ser Thr Ser Asn Asn Leu Ile Ser Thr Ile Pro Ser Asp Asn
            900                 905                 910

Leu Ala Ala Gly Thr Asp Asn Thr Ser Ser Leu Gly Pro Pro Ser Met
        915                 920                 925

Pro Val His Tyr Asp Ser Gln Leu Asp Thr Thr Leu Phe Gly Lys Lys
    930                 935                 940

Ser Ser Pro Leu Thr Glu Ser Gly Gly Pro Leu Ser Leu Ser Glu Glu
945                 950                 955                 960

Asn Asn Asp Ser Lys Leu Leu Glu Ser Gly Leu Met Asn Ser Gln Glu
                965                 970                 975

Ser Ser Trp Gly Lys Asn Val Ser Ser Thr Glu Ser Gly Arg Leu Phe
            980                 985                 990

Lys Gly Lys Arg Ala His Gly Pro  Ala Leu Leu Thr Lys  Asp Asn Ala
        995                 1000                1005

Leu Phe  Lys Val Ser Ile Ser  Leu Leu Lys Thr Asn  Lys Thr Ser
    1010                1015                1020

Asn Asn  Ser Ala Thr Asn Arg  Lys Thr His Ile Asp  Gly Pro Ser
    1025                1030                1035

Leu Leu  Ile Glu Asn Ser Pro  Ser Val Trp Gln Asn  Ile Leu Glu
    1040                1045                1050

Ser Asp  Thr Glu Phe Lys Lys  Val Thr Pro Leu Ile  His Asp Arg
    1055                1060                1065

Met Leu  Met Asp Lys Asn Ala  Thr Ala Leu Arg Leu  Asn His Met
```

1070 1075 1080

Ser Asn Lys Thr Thr Ser Ser Lys Asn Met Glu Met Val Gln Gln
1085 1090 1095

Lys Lys Glu Gly Pro Ile Pro Pro Asp Ala Gln Asn Pro Asp Met
1100 1105 1110

Ser Phe Phe Lys Met Leu Phe Leu Pro Glu Ser Ala Arg Trp Ile
1115 1120 1125

Gln Arg Thr His Gly Lys Asn Ser Leu Asn Ser Gly Gln Gly Pro
1130 1135 1140

Ser Pro Lys Gln Leu Val Ser Leu Gly Pro Glu Lys Ser Val Glu
1145 1150 1155

Gly Gln Asn Phe Leu Ser Glu Lys Asn Lys Val Val Val Gly Lys
1160 1165 1170

Gly Glu Phe Thr Lys Asp Val Gly Leu Lys Glu Met Val Phe Pro
1175 1180 1185

Ser Ser Arg Asn Leu Phe Leu Thr Asn Leu Asp Asn Leu His Glu
1190 1195 1200

Asn Asn Thr His Asn Gln Glu Lys Lys Ile Gln Glu Glu Ile Glu
1205 1210 1215

Lys Lys Glu Thr Leu Ile Gln Glu Asn Val Val Leu Pro Gln Ile
1220 1225 1230

His Thr Val Thr Gly Thr Lys Asn Phe Met Lys Asn Leu Phe Leu
1235 1240 1245

Leu Ser Thr Arg Gln Asn Val Glu Gly Ser Tyr Asp Gly Ala Tyr
1250 1255 1260

Ala Pro Val Leu Gln Asp Phe Arg Ser Leu Asn Asp Ser Thr Asn
1265 1270 1275

Arg Thr Lys Lys His Thr Ala His Phe Ser Lys Lys Gly Glu Glu
1280 1285 1290

Glu Asn Leu Glu Gly Leu Gly Asn Gln Thr Lys Gln Ile Val Glu
1295 1300 1305

Lys Tyr Ala Cys Thr Thr Arg Ile Ser Pro Asn Thr Ser Gln Gln
1310 1315 1320

Asn Phe Val Thr Gln Arg Ser Lys Arg Ala Leu Lys Gln Phe Arg
1325 1330 1335

Leu Pro Leu Glu Glu Thr Glu Leu Glu Lys Arg Ile Ile Val Asp
1340 1345 1350

Asp Thr Ser Thr Gln Trp Ser Lys Asn Met Lys His Leu Thr Pro
1355 1360 1365

Ser Thr Leu Thr Gln Ile Asp Tyr Asn Glu Lys Glu Lys Gly Ala
1370 1375 1380

Ile Thr Gln Ser Pro Leu Ser Asp Cys Leu Thr Arg Ser His Ser
1385 1390 1395

Ile Pro Gln Ala Asn Arg Ser Pro Leu Pro Ile Ala Lys Val Ser
1400 1405 1410

Ser Phe Pro Ser Ile Arg Pro Ile Tyr Leu Thr Arg Val Leu Phe
1415 1420 1425

Gln Asp Asn Ser Ser His Leu Pro Ala Ala Ser Tyr Arg Lys Lys
1430 1435 1440

Asp Ser Gly Val Gln Glu Ser Ser His Phe Leu Gln Gly Ala Lys
1445 1450 1455

Lys Asn Asn Leu Ser Leu Ala Ile Leu Thr Leu Glu Met Thr Gly
1460 1465 1470

-continued

```
Asp Gln Arg Glu Val Gly Ser Leu Gly Thr Ser Ala Thr Asn Ser
    1475                1480                1485

Val Thr Tyr Lys Lys Val Glu Asn Thr Val Leu Pro Lys Pro Asp
    1490                1495                1500

Leu Pro Lys Thr Ser Gly Lys Val Glu Leu Leu Pro Lys Val His
    1505                1510                1515

Ile Tyr Gln Lys Asp Leu Phe Pro Thr Glu Thr Ser Asn Gly Ser
    1520                1525                1530

Pro Gly His Leu Asp Leu Val Glu Gly Ser Leu Leu Gln Gly Thr
    1535                1540                1545

Glu Gly Ala Ile Lys Trp Asn Glu Ala Asn Arg Pro Gly Lys Val
    1550                1555                1560

Pro Phe Leu Arg Val Ala Thr Glu Ser Ser Ala Lys Thr Pro Ser
    1565                1570                1575

Lys Leu Leu Asp Pro Leu Ala Trp Asp Asn His Tyr Gly Thr Gln
    1580                1585                1590

Ile Pro Lys Glu Glu Trp Lys Ser Gln Glu Lys Ser Pro Glu Lys
    1595                1600                1605

Thr Ala Phe Lys Lys Lys Asp Thr Ile Leu Ser Leu Asn Ala Cys
    1610                1615                1620

Glu Ser Asn His Ala Ile Ala Ala Ile Asn Glu Gly Gln Asn Lys
    1625                1630                1635

Pro Glu Ile Glu Val Thr Trp Ala Lys Gln Gly Arg Thr Glu Arg
    1640                1645                1650

Leu Cys Ser Gln Asn Pro Pro Val Leu Lys Arg His Gln Arg Glu
    1655                1660                1665

Ile Thr Arg Thr Thr Leu Gln Ser Asp Gln Glu Glu Ile Asp Tyr
    1670                1675                1680

Asp Asp Thr Ile Ser Val Glu Met Lys Lys Glu Asp Phe Asp Ile
    1685                1690                1695

Tyr Asp Glu Asp Glu Asn Gln Ser Pro Arg Ser Phe Gln Lys Lys
    1700                1705                1710

Thr Arg His Tyr Phe Ile Ala Ala Val Glu Arg Leu Trp Asp Tyr
    1715                1720                1725

Gly Met Ser Ser Ser Pro His Val Leu Arg Asn Arg Ala Gln Ser
    1730                1735                1740

Gly Ser Val Pro Gln Phe Lys Lys Val Val Phe Gln Glu Phe Thr
    1745                1750                1755

Asp Gly Ser Phe Thr Gln Pro Leu Tyr Arg Gly Glu Leu Asn Glu
    1760                1765                1770

His Leu Gly Leu Leu Gly Pro Tyr Ile Arg Ala Glu Val Glu Asp
    1775                1780                1785

Asn Ile Met Val Thr Phe Arg Asn Gln Ala Ser Arg Pro Tyr Ser
    1790                1795                1800

Phe Tyr Ser Ser Leu Ile Ser Tyr Glu Glu Asp Gln Arg Gln Gly
    1805                1810                1815

Ala Glu Pro Arg Lys Asn Phe Val Lys Pro Asn Glu Thr Lys Thr
    1820                1825                1830

Tyr Phe Trp Lys Val Gln His His Met Ala Pro Thr Lys Asp Glu
    1835                1840                1845

Phe Asp Cys Lys Ala Trp Ala Tyr Phe Ser Asp Val Asp Leu Glu
    1850                1855                1860

Lys Asp Val His Ser Gly Leu Ile Gly Pro Leu Leu Val Cys His
    1865                1870                1875
```

Thr Asn Thr Leu Asn Pro Ala His Gly Arg Gln Val Thr Val Gln
1880 1885 1890

Glu Phe Ala Leu Phe Phe Thr Ile Phe Asp Glu Thr Lys Ser Trp
1895 1900 1905

Tyr Phe Thr Glu Asn Met Glu Arg Asn Cys Arg Ala Pro Cys Asn
1910 1915 1920

Ile Gln Met Glu Asp Pro Thr Phe Lys Glu Asn Tyr Arg Phe His
1925 1930 1935

Ala Ile Asn Gly Tyr Ile Met Asp Thr Leu Pro Gly Leu Val Met
1940 1945 1950

Ala Gln Asp Gln Arg Ile Arg Trp Tyr Leu Leu Ser Met Gly Ser
1955 1960 1965

Asn Glu Asn Ile His Ser Ile His Phe Ser Gly His Val Phe Thr
1970 1975 1980

Val Arg Lys Lys Glu Glu Tyr Lys Met Ala Leu Tyr Asn Leu Tyr
1985 1990 1995

Pro Gly Val Phe Glu Thr Val Glu Met Leu Pro Ser Lys Ala Gly
2000 2005 2010

Ile Trp Arg Val Glu Cys Leu Ile Gly Glu His Leu His Ala Gly
2015 2020 2025

Met Ser Thr Leu Phe Leu Val Tyr Ser Asn Lys Cys Gln Thr Pro
2030 2035 2040

Leu Gly Met Ala Ser Gly His Ile Arg Asp Phe Gln Ile Thr Ala
2045 2050 2055

Ser Gly Gln Tyr Gly Gln Trp Ala Pro Lys Leu Ala Arg Leu His
2060 2065 2070

Tyr Ser Gly Ser Ile Asn Ala Trp Ser Thr Lys Glu Pro Phe Ser
2075 2080 2085

Trp Ile Lys Val Asp Leu Leu Ala Pro Met Ile Ile His Gly Ile
2090 2095 2100

Lys Thr Gln Gly Ala Arg Gln Lys Phe Ser Ser Leu Tyr Ile Ser
2105 2110 2115

Gln Phe Ile Ile Met Tyr Ser Leu Asp Gly Lys Lys Trp Gln Thr
2120 2125 2130

Tyr Arg Gly Asn Ser Thr Gly Thr Leu Met Val Phe Phe Gly Asn
2135 2140 2145

Val Asp Ser Ser Gly Ile Lys His Asn Ile Phe Asn Pro Pro Ile
2150 2155 2160

Ile Ala Arg Tyr Ile Arg Leu His Pro Thr His Tyr Ser Ile Arg
2165 2170 2175

Ser Thr Leu Arg Met Glu Leu Met Gly Cys Asp Leu Asn Ser Cys
2180 2185 2190

Ser Met Pro Leu Gly Met Glu Ser Lys Ala Ile Ser Asp Ala Gln
2195 2200 2205

Ile Thr Ala Ser Ser Tyr Phe Thr Asn Met Phe Ala Thr Trp Ser
2210 2215 2220

Pro Ser Lys Ala Arg Leu His Leu Gln Gly Arg Ser Asn Ala Trp
2225 2230 2235

Arg Pro Gln Val Asn Asn Pro Lys Glu Trp Leu Gln Val Asp Phe
2240 2245 2250

Gln Lys Thr Met Lys Val Thr Gly Val Thr Thr Gln Gly Val Lys
2255 2260 2265

Ser Leu Leu Thr Ser Met Tyr Val Lys Glu Phe Leu Ile Ser Ser 2270 2275 2280

Ser Gln Asp Gly His Gln Trp Thr Leu Phe Phe Gln Asn Gly Lys
2285 2290 2295

Val Lys Val Phe Gln Gly Asn Gln Asp Ser Phe Thr Pro Val Val
2300 2305 2310

Asn Ser Leu Asp Pro Pro Leu Leu Thr Arg Tyr Leu Arg Ile His
2315 2320 2325

Pro Gln Ser Trp Val His Gln Ile Ala Leu Arg Met Glu Val Leu
2330 2335 2340

Gly Cys Glu Ala Gln Asp Leu Tyr
2345 2350

<210> SEQ ID NO 31
<211> LENGTH: 1471
<212> TYPE: DNA
<213> ORGANISM: Homo sapiens

<400> SEQUENCE: 31
atggcgcccg tcgccgtctg ggccgcgctg gccgtcggac tggagctctg ggctgcggcg 60
cacgccttgc ccgcccaggt ggcatttaca ccctacgccc cggagcccgg gagcacatgc 120
cggctcagag aatactatga ccagacagct cagatgtgct gcagcaaatg ctcgccgggc 180
caacatgcaa aagtcttctg taccaagacc tcggacaccg tgtgtgactc ctgtgaggac 240
agcacataca cccagctctg gaactgggtt cccgagtgct tgagctgtgg ctcccgctgt 300
agctctgacc aggtggaaac tcaagcctgc actcgggaac agaaccgcat ctgcacctgc 360
aggcccggct ggtactgcgc gctgagcaag caggaggggt gccggctgtg cgcgccgctg 420
cgcaagtgcc gcccgggctt cggcgtggcc agaccaggaa ctgaaacatc agacgtggtg 480
tgcaagccct gtgccccggg gacgttctcc aacacgactt catccacgga tatttgcagg 540
ccccaccaga tctgtaacgt ggtggccatc cctgggaatg caagcatgga tgcagtctgc 600
acgtccacgt cccccacccg gagtatggcc ccaggggcag tacacttacc ccagccagtg 660
tccacacgat cccaacacac gcagccaact ccagaaccca gcactgctcc aagcacctcc 720
ttcctgctcc caatgggccc cagcccccca gctgaaggga gcactggcga cttcgctctt 780
ccagttggac tgattgtggg tgtgacagcc ttgggtctac taataatagg agtggtgaac 840
tgtgtcatca tgacccaggt gaaaaagaag cccttgtgcc tgcagagaga agccaaggtg 900
cctcacttgc ctgccgataa ggcccggggt acacagggcc ccgagcagca gcacctgctg 960
atcacagcgc cgagctccag cagcagctcc ctggagagct cggccagtgc gttggacaga 1020
agggcgccca ctcggaacca gccacaggca ccaggcgtgg aggccagtgg ggccggggag 1080
gcccgggcca gcaccgggag ctcagattct tcccctggtg gccatgggac ccaggtcaat 1140
gtcacctgca tcgtgaacgt ctgtagcagc tctgaccaca gctcacagtg ctcctcccaa 1200
gccagctcca caatgggaga cacagattcc agcccctcgg agtccccgaa ggacgagcag 1260
gtccccttct ccaaggagga atgtgccttt cggtcacagc tggagacgcc agagaccctg 1320
ctggggagca ccgaagagaa gcccctgccc cttggagtgc ctgatgctgg gatgaagccc 1380
agttaaccag gccggtgtgg gctgtgtcgt agccaaggtg ggctgagccc tggcaggatg 1440
accctgcgaa ggggccctgg tccttccagg c 1471

<210> SEQ ID NO 32
<211> LENGTH: 461
<212> TYPE: PRT
<213> ORGANISM: Homo sapiens

<400> SEQUENCE: 32

```
Met Ala Pro Val Ala Val Trp Ala Ala Leu Ala Val Gly Leu Glu Leu
1               5                   10                  15

Trp Ala Ala Ala His Ala Leu Pro Ala Gln Val Ala Phe Thr Pro Tyr
            20                  25                  30

Ala Pro Glu Pro Gly Ser Thr Cys Arg Leu Arg Glu Tyr Tyr Asp Gln
        35                  40                  45

Thr Ala Gln Met Cys Cys Ser Lys Cys Ser Pro Gly Gln His Ala Lys
    50                  55                  60

Val Phe Cys Thr Lys Thr Ser Asp Thr Val Cys Asp Ser Cys Glu Asp
65                  70                  75                  80

Ser Thr Tyr Thr Gln Leu Trp Asn Trp Val Pro Glu Cys Leu Ser Cys
                85                  90                  95

Gly Ser Arg Cys Ser Ser Asp Gln Val Glu Thr Gln Ala Cys Thr Arg
            100                 105                 110

Glu Gln Asn Arg Ile Cys Thr Cys Arg Pro Gly Trp Tyr Cys Ala Leu
        115                 120                 125

Ser Lys Gln Glu Gly Cys Arg Leu Cys Ala Pro Leu Arg Lys Cys Arg
    130                 135                 140

Pro Gly Phe Gly Val Ala Arg Pro Gly Thr Glu Thr Ser Asp Val Val
145                 150                 155                 160

Cys Lys Pro Cys Ala Pro Gly Thr Phe Ser Asn Thr Thr Ser Ser Thr
                165                 170                 175

Asp Ile Cys Arg Pro His Gln Ile Cys Asn Val Val Ala Ile Pro Gly
            180                 185                 190

Asn Ala Ser Met Asp Ala Val Cys Thr Ser Thr Ser Pro Thr Arg Ser
        195                 200                 205

Met Ala Pro Gly Ala Val His Leu Pro Gln Pro Val Ser Thr Arg Ser
    210                 215                 220

Gln His Thr Gln Pro Thr Pro Glu Pro Ser Thr Ala Pro Ser Thr Ser
225                 230                 235                 240

Phe Leu Leu Pro Met Gly Pro Ser Pro Pro Ala Glu Gly Ser Thr Gly
                245                 250                 255

Asp Phe Ala Leu Pro Val Gly Leu Ile Val Gly Val Thr Ala Leu Gly
            260                 265                 270

Leu Leu Ile Ile Gly Val Val Asn Cys Val Ile Met Thr Gln Val Lys
        275                 280                 285

Lys Lys Pro Leu Cys Leu Gln Arg Glu Ala Lys Val Pro His Leu Pro
    290                 295                 300

Ala Asp Lys Ala Arg Gly Thr Gln Gly Pro Glu Gln Gln His Leu Leu
305                 310                 315                 320

Ile Thr Ala Pro Ser Ser Ser Ser Ser Ser Leu Glu Ser Ser Ala Ser
                325                 330                 335

Ala Leu Asp Arg Arg Ala Pro Thr Arg Asn Gln Pro Gln Ala Pro Gly
            340                 345                 350

Val Glu Ala Ser Gly Ala Gly Glu Ala Arg Ala Ser Thr Gly Ser Ser
        355                 360                 365

Asp Ser Ser Pro Gly Gly His Gly Thr Gln Val Asn Val Thr Cys Ile
    370                 375                 380

Val Asn Val Cys Ser Ser Ser Asp His Ser Ser Gln Cys Ser Ser Gln
385                 390                 395                 400

Ala Ser Ser Thr Met Gly Asp Thr Asp Ser Ser Pro Ser Glu Ser Pro
                405                 410                 415
```

```
Lys Asp Glu Gln Val Pro Phe Ser Lys Glu Glu Cys Ala Phe Arg Ser
            420                 425                 430

Gln Leu Glu Thr Pro Glu Thr Leu Leu Gly Ser Thr Glu Glu Lys Pro
        435                 440                 445

Leu Pro Leu Gly Val Pro Asp Ala Gly Met Lys Pro Ser
    450                 455                 460


<210> SEQ ID NO 33
<211> LENGTH: 1475
<212> TYPE: DNA
<213> ORGANISM: Homo sapiens

<400> SEQUENCE: 33

tccacctgtc cccgcagcgc cggctcgcgc cctcctgccg cagccaccga gccgccgtct      60

agcgccccga cctcgccacc atgagagccc tgctggcgcg cctgcttctc tgcgtcctgg     120

tcgtgagcga ctccaaaggc agcaatgaac ttcatcaagt tccatcgaac tgtgactgtc     180

taaatggagg aacatgtgtg tccaacaagt acttctccaa cattcactgg tgcaactgcc     240

caaagaaatt cggagggcag cactgtgaaa tagataagtc aaaaacctgc tatgagggga     300

atggtcactt ttaccgagga aaggccagca ctgacaccat gggccggccc tgcctgccct     360

ggaactctgc cactgtcctt cagcaaacgt accatgccca cagatctgat gctcttcagc     420

tgggcctggg gaaacataat tactgcagga acccagacaa ccggaggcga ccctggtgct     480

atgtgcaggt gggcctaaag ccgcttgtcc aagagtgcat ggtgcatgac tgcgcagatg     540

gaaaaaagcc ctcctctcct ccagaagaat taaaatttca gtgtggccaa aagactctga     600

ggccccgctt taagattatt gggggagaat tcaccaccat cgagaaccag ccctggtttg     660

cggccatcta caggaggcac cggggggct ctgtcaccta cgtgtgtgga ggcagcctca      720

tcagcccttg ctgggtgatc agcgccacac actgcttcat tgattaccca aagaaggagg     780

actacatcgt ctacctgggt cgctcaaggc ttaactccaa cacgcaaggg gagatgaagt     840

ttgaggtgga aaacctcatc ctacacaagg actacagcgc tgacacgctt gctcaccaca     900

acgacattgc cttgctgaag atccgttcca aggagggcag gtgtgcgcag ccatcccgga     960

ctatacagac catctgcctg ccctcgatgt ataacgatcc ccagtttggc acaagctgtg    1020

agatcactgg ctttggaaaa gagaattcta ccgactatct ctatccggag cagctgaaga    1080

tgactgttgt gaagctgatt tcccaccggg agtgtcagca gccccactac tacggctctg    1140

aagtcaccac caaaatgctg tgtgctgctg acccacagtg gaaaacagat tcctgccagg    1200

gagactcagg gggacccctc gtctgttccc tccaaggccg catgactttg actggaattg    1260

tgagctgggg ccgtggatgt gccctgaagg acaagccagg cgtctacacg agagtctcac    1320

acttcttacc ctggatccgc agtcacacca aggaagagaa tggcctggcc ctctgagggt    1380

ccccagggag gaaacgggca ccacccgctt tcttgctggt tgtcattttt gcagtagagt    1440

catctccatc agctgtaaga agagactggg aagat                               1475


<210> SEQ ID NO 34
<211> LENGTH: 431
<212> TYPE: PRT
<213> ORGANISM: Homo sapiens

<400> SEQUENCE: 34

Met Arg Ala Leu Leu Ala Arg Leu Leu Leu Cys Val Leu Val Val Ser
1               5                   10                  15

Asp Ser Lys Gly Ser Asn Glu Leu His Gln Val Pro Ser Asn Cys Asp
```

-continued

```
            20                  25                  30

Cys Leu Asn Gly Gly Thr Cys Val Ser Asn Lys Tyr Phe Ser Asn Ile
        35                  40                  45

His Trp Cys Asn Cys Pro Lys Lys Phe Gly Gly Gln His Cys Glu Ile
    50                  55                  60

Asp Lys Ser Lys Thr Cys Tyr Glu Gly Asn Gly His Phe Tyr Arg Gly
65                  70                  75                  80

Lys Ala Ser Thr Asp Thr Met Gly Arg Pro Cys Leu Pro Trp Asn Ser
                85                  90                  95

Ala Thr Val Leu Gln Gln Thr Tyr His Ala His Arg Ser Asp Ala Leu
            100                 105                 110

Gln Leu Gly Leu Gly Lys His Asn Tyr Cys Arg Asn Pro Asp Asn Arg
        115                 120                 125

Arg Arg Pro Trp Cys Tyr Val Gln Val Gly Leu Lys Pro Leu Val Gln
    130                 135                 140

Glu Cys Met Val His Asp Cys Ala Asp Gly Lys Lys Pro Ser Ser Pro
145                 150                 155                 160

Pro Glu Glu Leu Lys Phe Gln Cys Gly Gln Lys Thr Leu Arg Pro Arg
                165                 170                 175

Phe Lys Ile Ile Gly Gly Glu Phe Thr Thr Ile Glu Asn Gln Pro Trp
            180                 185                 190

Phe Ala Ala Ile Tyr Arg Arg His Arg Gly Gly Ser Val Thr Tyr Val
        195                 200                 205

Cys Gly Gly Ser Leu Ile Ser Pro Cys Trp Val Ile Ser Ala Thr His
    210                 215                 220

Cys Phe Ile Asp Tyr Pro Lys Lys Glu Asp Tyr Ile Val Tyr Leu Gly
225                 230                 235                 240

Arg Ser Arg Leu Asn Ser Asn Thr Gln Gly Glu Met Lys Phe Glu Val
                245                 250                 255

Glu Asn Leu Ile Leu His Lys Asp Tyr Ser Ala Asp Thr Leu Ala His
            260                 265                 270

His Asn Asp Ile Ala Leu Leu Lys Ile Arg Ser Lys Glu Gly Arg Cys
        275                 280                 285

Ala Gln Pro Ser Arg Thr Ile Gln Thr Ile Cys Leu Pro Ser Met Tyr
    290                 295                 300

Asn Asp Pro Gln Phe Gly Thr Ser Cys Glu Ile Thr Gly Phe Gly Lys
305                 310                 315                 320

Glu Asn Ser Thr Asp Tyr Leu Tyr Pro Glu Gln Leu Lys Met Thr Val
                325                 330                 335

Val Lys Leu Ile Ser His Arg Glu Cys Gln Gln Pro His Tyr Tyr Gly
            340                 345                 350

Ser Glu Val Thr Thr Lys Met Leu Cys Ala Ala Asp Pro Gln Trp Lys
        355                 360                 365

Thr Asp Ser Cys Gln Gly Asp Ser Gly Gly Pro Leu Val Cys Ser Leu
    370                 375                 380

Gln Gly Arg Met Thr Leu Thr Gly Ile Val Ser Trp Gly Arg Gly Cys
385                 390                 395                 400

Ala Leu Lys Asp Lys Pro Gly Val Tyr Thr Arg Val Ser His Phe Leu
                405                 410                 415

Pro Trp Ile Arg Ser His Thr Lys Glu Glu Asn Gly Leu Ala Leu
            420                 425                 430
```

<210> SEQ ID NO 35
<211> LENGTH: 107

<212> TYPE: PRT
<213> ORGANISM: Mus musculus

<400> SEQUENCE: 35

Asp Ile Gln Met Thr Gln Ser Pro Ser Ser Leu Ser Ala Ser Val Gly
1 5 10 15

Asp Arg Val Thr Ile Thr Cys Arg Ala Ser Gln Asp Val Asn Thr Ala
20 25 30

Val Ala Trp Tyr Gln Gln Lys Pro Gly Lys Ala Pro Lys Leu Leu Ile
35 40 45

Tyr Ser Ala Ser Phe Leu Tyr Ser Gly Val Pro Ser Arg Phe Ser Gly
50 55 60

Ser Arg Ser Gly Thr Asp Phe Thr Leu Thr Ile Ser Ser Leu Gln Pro
65 70 75 80

Glu Asp Phe Ala Thr Tyr Tyr Cys Gln Gln His Tyr Thr Thr Pro Pro
85 90 95

Thr Phe Gly Gln Gly Thr Lys Val Glu Ile Lys
100 105

<210> SEQ ID NO 36
<211> LENGTH: 120
<212> TYPE: PRT
<213> ORGANISM: Mus musculus

<400> SEQUENCE: 36

Glu Val Gln Leu Val Glu Ser Gly Gly Gly Leu Val Gln Pro Gly Gly
1 5 10 15

Ser Leu Arg Leu Ser Cys Ala Ala Ser Gly Phe Asn Ile Lys Asp Thr
20 25 30

Tyr Ile His Trp Val Arg Gln Ala Pro Gly Lys Gly Leu Glu Trp Val
35 40 45

Ala Arg Ile Tyr Pro Thr Asn Gly Tyr Thr Arg Tyr Ala Asp Ser Val
50 55 60

Lys Gly Arg Phe Thr Ile Ser Ala Asp Thr Ser Lys Asn Thr Ala Tyr
65 70 75 80

Leu Gln Met Asn Ser Leu Arg Ala Glu Asp Thr Ala Val Tyr Tyr Cys
85 90 95

Ser Arg Trp Gly Gly Asp Gly Phe Tyr Ala Met Asp Tyr Trp Gly Gln
100 105 110

Gly Thr Leu Val Thr Val Ser Ser
115 120

<210> SEQ ID NO 37
<211> LENGTH: 120
<212> TYPE: PRT
<213> ORGANISM: Mus musculus

<400> SEQUENCE: 37

Gln Val Thr Leu Arg Glu Ser Gly Pro Ala Leu Val Lys Pro Thr Gln
1 5 10 15

Thr Leu Thr Leu Thr Cys Thr Phe Ser Gly Phe Ser Leu Ser Thr Ser
20 25 30

Gly Met Ser Val Gly Trp Ile Arg Gln Pro Ser Gly Lys Ala Leu Glu
35 40 45

Trp Leu Ala Asp Ile Trp Trp Asp Asp Lys Lys Asp Tyr Asn Pro Ser
50 55 60

Leu Lys Ser Arg Leu Thr Ile Ser Lys Asp Thr Ser Lys Asn Gln Val
65 70 75 80

Val Leu Lys Val Thr Asn Met Asp Pro Ala Asp Thr Ala Thr Tyr Tyr
85 90 95

Cys Ala Arg Ser Met Ile Thr Asn Trp Tyr Phe Asp Val Trp Gly Ala
100 105 110

Gly Thr Thr Val Thr Val Ser Ser
115 120

<210> SEQ ID NO 38
<211> LENGTH: 106
<212> TYPE: PRT
<213> ORGANISM: Mus musculus

<400> SEQUENCE: 38

Asp Ile Gln Met Thr Gln Ser Pro Ser Thr Leu Ser Ala Ser Val Gly
1 5 10 15

Asp Arg Val Thr Ile Thr Cys Lys Cys Gln Leu Ser Val Gly Tyr Met
20 25 30

His Trp Tyr Gln Gln Lys Pro Gly Lys Ala Pro Lys Leu Trp Ile Tyr
35 40 45

Asp Thr Ser Lys Leu Ala Ser Gly Val Pro Ser Arg Phe Ser Gly Ser
50 55 60

Gly Ser Gly Thr Glu Phe Thr Leu Thr Ile Ser Ser Leu Gln Pro Asp
65 70 75 80

Asp Phe Ala Thr Tyr Tyr Cys Phe Gln Gly Ser Gly Tyr Pro Phe Thr
85 90 95

Phe Gly Gly Gly Thr Lys Leu Glu Ile Lys
100 105

<210> SEQ ID NO 39
<211> LENGTH: 1039
<212> TYPE: DNA
<213> ORGANISM: Homo sapiens

<400> SEQUENCE: 39
tcctgcacag gcagtgcctt gaagtgcttc ttcagagacc tttcttcata gactactttt 60
ttttctttaa gcagcaaaag gagaaaattg tcatcaaagg atattccaga ttcttgacag 120
cattctcgtc atctctgagg acatcaccat catctcagga tgaggggcat gaagctgctg 180
ggggcgctgc tggcactggc ggccctactg caggggggccg tgtccctgaa gatcgcagcc 240
ttcaacatcc agacatttgg ggagaccaag atgtccaatg ccaccctcgt cagctacatt 300
gtgcagatcc tgagccgcta tgacatcgcc ctggtccagg aggtcagaga cagccacctg 360
actgccgtgg ggaagctgct ggacaacctc aatcaggatg caccagacac ctatcactac 420
gtggtcagtg agccactggg acggaacagc tataaggagc gctacctgtt cgtgtacagg 480
cctgaccagg tgtctgcggt ggacagctac tactacgatg atggctgcga gccctgcggg 540
aacgacacct tcaaccgaga gccagccatt gtcaggttct tctcccggtt cacagaggtc 600
agggagtttg ccattgttcc cctgcatgcg gccccggggg acgcagtagc cgagatcgac 660
gctctctatg acgtctacct ggatgtccaa gagaaatggg gcttggagga cgtcatgttg 720
atgggcgact tcaatgcggg ctgcagctat gtgagaccct cccagtggtc atccatccgc 780
ctgtggacaa gccccacctt ccagtggctg atccccgaca gcgctgacac cacagctaca 840
cccacgcact gtgcctatga caggatcgtg gttgcaggga tgctgctccg aggcgccgtt 900
gttcccgact cggctcttcc ctttaacttc caggctgcct atggcctgag tgaccaactg 960
gcccaagcca tcagtgacca ctatccagtg gaggtgatgc tgaagtgagc agcccctccc 1020
cacaccagtt gaactgcag 1039

<210> SEQ ID NO 40
<211> LENGTH: 282
<212> TYPE: PRT
<213> ORGANISM: Homo sapiens

<400> SEQUENCE: 40

Met Arg Gly Met Lys Leu Leu Gly Ala Leu Leu Ala Leu Ala Ala Leu
1 5 10 15

Leu Gln Gly Ala Val Ser Leu Lys Ile Ala Ala Phe Asn Ile Gln Thr
20 25 30

Phe Gly Glu Thr Lys Met Ser Asn Ala Thr Leu Val Ser Tyr Ile Val
35 40 45

Gln Ile Leu Ser Arg Tyr Asp Ile Ala Leu Val Gln Glu Val Arg Asp
50 55 60

Ser His Leu Thr Ala Val Gly Lys Leu Leu Asp Asn Leu Asn Gln Asp
65 70 75 80

Ala Pro Asp Thr Tyr His Tyr Val Val Ser Glu Pro Leu Gly Arg Asn
85 90 95

Ser Tyr Lys Glu Arg Tyr Leu Phe Val Tyr Arg Pro Asp Gln Val Ser
100 105 110

Ala Val Asp Ser Tyr Tyr Tyr Asp Asp Gly Cys Glu Pro Cys Gly Asn
115 120 125

Asp Thr Phe Asn Arg Glu Pro Ala Ile Val Arg Phe Phe Ser Arg Phe
130 135 140

Thr Glu Val Arg Glu Phe Ala Ile Val Pro Leu His Ala Ala Pro Gly
145 150 155 160

Asp Ala Val Ala Glu Ile Asp Ala Leu Tyr Asp Val Tyr Leu Asp Val
165 170 175

Gln Glu Lys Trp Gly Leu Glu Asp Val Met Leu Met Gly Asp Phe Asn
180 185 190

Ala Gly Cys Ser Tyr Val Arg Pro Ser Gln Trp Ser Ser Ile Arg Leu
195 200 205

Trp Thr Ser Pro Thr Phe Gln Trp Leu Ile Pro Asp Ser Ala Asp Thr
210 215 220

Thr Ala Thr Pro Thr His Cys Ala Tyr Asp Arg Ile Val Val Ala Gly
225 230 235 240

Met Leu Leu Arg Gly Ala Val Val Pro Asp Ser Ala Leu Pro Phe Asn
245 250 255

Phe Gln Ala Ala Tyr Gly Leu Ser Asp Gln Leu Ala Gln Ala Ile Ser
260 265 270

Asp His Tyr Pro Val Glu Val Met Leu Lys
275 280

<210> SEQ ID NO 41
<211> LENGTH: 678
<212> TYPE: DNA
<213> ORGANISM: Mus musculus

<400> SEQUENCE: 41
gacatcttgc tgactcagtc tccagccatc ctgtctgtga gtccaggaga aagagtcagt 60
ttctcctgca gggccagtca gttcgttggc tcaagcatcc actggtatca gcaaagaaca 120
aatggttctc caaggcttct cataaagtat gcttctgagt ctatgtctgg gatcccttcc 180
aggtttagtg gcagtggatc agggacagat tttactctta gcatcaacac tgtggagtct 240

```
gaagatattg cagattatta ctgtcaacaa agtcatagct ggccattcac gttcggctcg      300

gggacaaatt tggaagtaaa agaagtgaag cttgaggagt ctggaggagg cttggtgcaa      360

cctggaggat ccatgaaact ctcctgtgtt gcctctggat tcattttcag taaccactgg      420

atgaactggg tccgccagtc tccagagaag gggcttgagt gggttgctga aattagatca      480

aaatctatta attctgcaac acattatgcg gagtctgtga aagggaggtt caccatctca      540

agagatgatt ccaaaagtgc tgtctacctg caaatgaccg acttaagaac tgaagacact      600

ggcgtttatt actgttccag gaattactac ggtagtacct acgactactg gggccaaggc      660

accactctca cagtctcc                                                    678
```

```
<210> SEQ ID NO 42
<211> LENGTH: 226
<212> TYPE: PRT
<213> ORGANISM: Mus musculus

<400> SEQUENCE: 42
```

```
Asp Ile Leu Leu Thr Gln Ser Pro Ala Ile Leu Ser Val Ser Pro Gly
1               5                   10                  15

Glu Arg Val Ser Phe Ser Cys Arg Ala Ser Gln Phe Val Gly Ser Ser
            20                  25                  30

Ile His Trp Tyr Gln Gln Arg Thr Asn Gly Ser Pro Arg Leu Leu Ile
        35                  40                  45

Lys Tyr Ala Ser Glu Ser Met Ser Gly Ile Pro Ser Arg Phe Ser Gly
    50                  55                  60

Ser Gly Ser Gly Thr Asp Phe Thr Leu Ser Ile Asn Thr Val Glu Ser
65                  70                  75                  80

Glu Asp Ile Ala Asp Tyr Tyr Cys Gln Gln Ser His Ser Trp Pro Phe
                85                  90                  95

Thr Phe Gly Ser Gly Thr Asn Leu Glu Val Lys Glu Val Lys Leu Glu
            100                 105                 110

Glu Ser Gly Gly Gly Leu Val Gln Pro Gly Gly Ser Met Lys Leu Ser
        115                 120                 125

Cys Val Ala Ser Gly Phe Ile Phe Ser Asn His Trp Met Asn Trp Val
    130                 135                 140

Arg Gln Ser Pro Glu Lys Gly Leu Glu Trp Val Ala Glu Ile Arg Ser
145                 150                 155                 160

Lys Ser Ile Asn Ser Ala Thr His Tyr Ala Glu Ser Val Lys Gly Arg
                165                 170                 175

Phe Thr Ile Ser Arg Asp Asp Ser Lys Ser Ala Val Tyr Leu Gln Met
            180                 185                 190

Thr Asp Leu Arg Thr Glu Asp Thr Gly Val Tyr Tyr Cys Ser Arg Asn
        195                 200                 205

Tyr Tyr Gly Ser Thr Tyr Asp Tyr Trp Gly Gln Gly Thr Thr Leu Thr
    210                 215                 220

Val Ser
225
```

```
<210> SEQ ID NO 43
<211> LENGTH: 450
<212> TYPE: DNA
<213> ORGANISM: Homo sapiens

<400> SEQUENCE: 43
```

```
gctgcatcag aagaggccat caagcacatc actgtccttc tgccatggcc ctgtggatgc       60
```

-continued gcctcctgcc cctgctggcg ctgctggccc tctggggacc tgacccagcc gcagcctttg 120
tgaaccaaca cctgtgcggc tcacacctgg tggaagctct ctacctagtg tgcggggaac 180
gaggcttctt ctacacaccc aagacccgcc gggaggcaga ggacctgcag gtggggcagg 240
tggagctggg cgggggccct ggtgcaggca gcctgcagcc cttggccctg gaggggtccc 300
tgcagaagcg tggcattgtg gaacaatgct gtaccagcat ctgctccctc taccagctgg 360
agaactactg caactagacg cagcccgcag gcagcccccc acccgccgcc tcctgcaccg 420
agagagatgg aataaagccc ttgaaccagc 450

<210> SEQ ID NO 44
<211> LENGTH: 110
<212> TYPE: PRT
<213> ORGANISM: Homo sapiens

<400> SEQUENCE: 44

Met Ala Leu Trp Met Arg Leu Leu Pro Leu Leu Ala Leu Leu Ala Leu
1 5 10 15

Trp Gly Pro Asp Pro Ala Ala Ala Phe Val Asn Gln His Leu Cys Gly
20 25 30

Ser His Leu Val Glu Ala Leu Tyr Leu Val Cys Gly Glu Arg Gly Phe
35 40 45

Phe Tyr Thr Pro Lys Thr Arg Arg Glu Ala Glu Asp Leu Gln Val Gly
50 55 60

Gln Val Glu Leu Gly Gly Gly Pro Gly Ala Gly Ser Leu Gln Pro Leu
65 70 75 80

Ala Leu Glu Gly Ser Leu Gln Lys Arg Gly Ile Val Glu Gln Cys Cys
85 90 95

Thr Ser Ile Cys Ser Leu Tyr Gln Leu Glu Asn Tyr Cys Asn
100 105 110

<210> SEQ ID NO 45
<211> LENGTH: 1203
<212> TYPE: DNA
<213> ORGANISM: Hepatitis B virus

<400> SEQUENCE: 45
atgggaggtt ggtcttccaa acctcgacaa ggcatgggga cgaatctttc tgttcccaat 60
cctctgggat tctttcccga tcaccagttg gaccctgcgt tcggagccaa ctcaaacaat 120
ccagattggg acttcaaccc caacaaggat cactggccag aggcaatcaa ggtaggagcg 180
ggagacttcg ggccagggtt caccccacca cacggcggtc ttttggggtg gagccctcag 240
gctcagggca tattgacaac agtgccagca gcgcctcctc ctgtttccac caatcggcag 300
tcaggaagac agcctactcc catctctcca cctctaagag acagtcatcc tcaggccatg 360
cagtggaact ccacaacatt ccaccaagct ctgctagatc ccagagtgag ggcctatat 420 tttcctgctg gtggctccag ttccggaaca gtaaaccctg ttccgactac tgtctcaccc 480
atatcgtcaa tcttctcgag gactggggac cctgcaccga acatggagag cacaacatca 540
ggattcctag gacccctgct cgtgttacag gcggggtttt tcttgttgac aagaatcctc 600
acaataccac agagtctaga ctcgtggtgg acttctctca attttctagg gggagcaccc 660
acgtgtcctg gccaaaattc gcagtcccca acctccaatc actcaccaac ctcttgtcct 720
ccaatttgtc ctggttatcg ctggatgtgt ctgcggcgtt ttatcatatt cctcttcatc 780
ctgctgctat gcctcatctt cttgttggtt cttctggact accaaggtat gttgcccgtt 840
tgtcctctac ttccaggaac atcaactacc agcacgggac catgcaagac ctgcacgatt 900

```
cctgctcaag gaacctctat gtttccctct tgttgctgta caaaaccttc ggacggaaac    960

tgcacttgta ttcccatccc atcatcctgg gctttcgcaa gattcctatg ggagtgggcc   1020

tcagtccgtt tctcctggct cagtttacta gtgccatttg ttcagtggtt cgcagggctt   1080

tcccccactg tttggctttc agttatatgg atgatgtggt attgggggcc aagtctgtac   1140

aacatcttga gtcccttttt acctctatta ccaattttct tttgtctttg ggtatacatt   1200

tga                                                                 1203


<210> SEQ ID NO 46
<211> LENGTH: 400
<212> TYPE: PRT
<213> ORGANISM: Hepatitis B virus

<400> SEQUENCE: 46

Met Gly Gly Trp Ser Ser Lys Pro Arg Gln Gly Met Gly Thr Asn Leu
1               5                   10                  15

Ser Val Pro Asn Pro Leu Gly Phe Phe Pro Asp His Gln Leu Asp Pro
            20                  25                  30

Ala Phe Gly Ala Asn Ser Asn Asn Pro Asp Trp Asp Phe Asn Pro Asn
        35                  40                  45

Lys Asp His Trp Pro Glu Ala Ile Lys Val Gly Ala Gly Asp Phe Gly
    50                  55                  60

Pro Gly Phe Thr Pro Pro His Gly Gly Leu Leu Gly Trp Ser Pro Gln
65                  70                  75                  80

Ala Gln Gly Ile Leu Thr Thr Val Pro Ala Ala Pro Pro Pro Val Ser
                85                  90                  95

Thr Asn Arg Gln Ser Gly Arg Gln Pro Thr Pro Ile Ser Pro Pro Leu
            100                 105                 110

Arg Asp Ser His Pro Gln Ala Met Gln Trp Asn Ser Thr Thr Phe His
        115                 120                 125

Gln Ala Leu Leu Asp Pro Arg Val Arg Gly Leu Tyr Phe Pro Ala Gly
    130                 135                 140

Gly Ser Ser Ser Gly Thr Val Asn Pro Val Pro Thr Thr Val Ser Pro
145                 150                 155                 160

Ile Ser Ser Ile Phe Ser Arg Thr Gly Asp Pro Ala Pro Asn Met Glu
                165                 170                 175

Ser Thr Thr Ser Gly Phe Leu Gly Pro Leu Leu Val Leu Gln Ala Gly
            180                 185                 190

Phe Phe Leu Leu Thr Arg Ile Leu Thr Ile Pro Gln Ser Leu Asp Ser
        195                 200                 205

Trp Trp Thr Ser Leu Asn Phe Leu Gly Gly Ala Pro Thr Cys Pro Gly
    210                 215                 220

Gln Asn Ser Gln Ser Pro Thr Ser Asn His Ser Pro Thr Ser Cys Pro
225                 230                 235                 240

Pro Ile Cys Pro Gly Tyr Arg Trp Met Cys Leu Arg Arg Phe Ile Ile
                245                 250                 255

Phe Leu Phe Ile Leu Leu Leu Cys Leu Ile Phe Leu Leu Val Leu Leu
            260                 265                 270

Asp Tyr Gln Gly Met Leu Pro Val Cys Pro Leu Leu Pro Gly Thr Ser
        275                 280                 285

Thr Thr Ser Thr Gly Pro Cys Lys Thr Cys Thr Ile Pro Ala Gln Gly
    290                 295                 300

Thr Ser Met Phe Pro Ser Cys Cys Cys Thr Lys Pro Ser Asp Gly Asn
305                 310                 315                 320
```

```
Cys Thr Cys Ile Pro Ile Pro Ser Ser Trp Ala Phe Ala Arg Phe Leu
                325                 330                 335

Trp Glu Trp Ala Ser Val Arg Phe Ser Trp Leu Ser Leu Leu Val Pro
            340                 345                 350

Phe Val Gln Trp Phe Ala Gly Leu Ser Pro Thr Val Trp Leu Ser Val
        355                 360                 365

Ile Trp Met Met Trp Tyr Trp Gly Pro Ser Leu Tyr Asn Ile Leu Ser
    370                 375                 380

Pro Phe Leu Pro Leu Leu Pro Ile Phe Phe Cys Leu Trp Val Tyr Ile
385                 390                 395                 400
```

```
<210> SEQ ID NO 47
<211> LENGTH: 799
<212> TYPE: DNA
<213> ORGANISM: Homo sapiens

<400> SEQUENCE: 47

cgaaccactc agggtcctgt ggacagctca cctagctgca atggctacag gctcccggac      60

gtccctgctc ctggcttttg gcctgctctg cctgccctgg cttcaagagg gcagtgcctt     120

cccaaccatt cccttatcca ggccttttga caacgctatg ctccgcgccc atcgtctgca     180

ccagctggcc tttgacacct accaggagtt tgaagaagcc tatatcccaa aggaacagaa     240

gtattcattc ctgcagaacc cccagacctc cctctgtttc tcagagtcta ttccgacacc     300

ctccaacagg gaggaaacac aacagaaatc caacctagag ctgctccgca tctccctgct     360

gctcatccag tcgtggctgg agcccgtgca gttcctcagg agtgtcttcg ccaacagcct     420

ggtgtacggc gcctctgaca gcaacgtcta tgacctccta aaggacctag aggaaggcat     480

ccaaacgctg atggggaggc tggaagatgg cagcccccgg actgggcaga tcttcaagca     540

gacctacagc aagttcgaca caaactcaca caacgatgac gcactactca agaactacgg     600

gctgctctac tgcttcagga aggacatgga caaggtcgag acattcctgc gcatcgtgca     660

gtgccgctct gtggagggca gctgtggctt ctagctgccc gggtggcatc cctgtgaccc     720

ctccccagtg cctctcctgg ccctggaagt tgccactcca gtgcccacca gccttgtcct     780

aataaaatta agttgcatc                                                  799
```

```
<210> SEQ ID NO 48
<211> LENGTH: 217
<212> TYPE: PRT
<213> ORGANISM: Homo sapiens

<400> SEQUENCE: 48

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Phe Pro Thr Ile Pro Leu
            20                  25                  30

Ser Arg Pro Phe Asp Asn Ala Met Leu Arg Ala His Arg Leu His Gln
        35                  40                  45

Leu Ala Phe Asp Thr Tyr Gln Glu Phe Glu Glu Ala Tyr Ile Pro Lys
    50                  55                  60

Glu Gln Lys Tyr Ser Phe Leu Gln Asn Pro Gln Thr Ser Leu Cys Phe
65                  70                  75                  80

Ser Glu Ser Ile Pro Thr Pro Ser Asn Arg Glu Glu Thr Gln Gln Lys
                85                  90                  95

Ser Asn Leu Glu Leu Leu Arg Ile Ser Leu Leu Leu Ile Gln Ser Trp
            100                 105                 110
```

```
Leu Glu Pro Val Gln Phe Leu Arg Ser Val Phe Ala Asn Ser Leu Val
        115                 120                 125

Tyr Gly Ala Ser Asp Ser Asn Val Tyr Asp Leu Leu Lys Asp Leu Glu
    130                 135                 140

Glu Gly Ile Gln Thr Leu Met Gly Arg Leu Glu Asp Gly Ser Pro Arg
145                 150                 155                 160

Thr Gly Gln Ile Phe Lys Gln Thr Tyr Ser Lys Phe Asp Thr Asn Ser
                165                 170                 175

His Asn Asp Asp Ala Leu Leu Lys Asn Tyr Gly Leu Leu Tyr Cys Phe
            180                 185                 190

Arg Lys Asp Met Asp Lys Val Glu Thr Phe Leu Arg Ile Val Gln Cys
        195                 200                 205

Arg Ser Val Glu Gly Ser Cys Gly Phe
    210                 215


<210> SEQ ID NO 49
<211> LENGTH: 963
<212> TYPE: DNA
<213> ORGANISM: Homo sapiens

<400> SEQUENCE: 49

atggagacag acacactcct gttatgggtg ctgctgctct gggttccagg ttccactggt      60

gacgtcaggc gagggccccg gagcctgcgg ggcagggacg cgccagcccc cacgccctgc     120

gtcccggccg agtgcttcga cctgctggtc cgccactgcg tggcctgcgg gctcctgcgc     180

acgccgcggc cgaaaccggc cggggccagc agccctgcgc ccaggacggc gctgcagccg     240

caggagtcgg tgggcgcggg ggccggcgag gcggcggtcg acaaaactca cacatgccca     300

ccgtgcccag cacctgaact cctgggggga ccgtcagtct tcctcttccc cccaaaaccc     360

aaggacaccc tcatgatctc ccggacccct gaggtcacat gcgtggtggt ggacgtgagc     420

cacgaagacc ctgaggtcaa gttcaactgg tacgtggacg gcgtggaggt gcataatgcc     480

aagacaaagc cgcgggagga gcagtacaac agcacgtacc gtgtggtcag cgtcctcacc     540

gtcctgcacc aggactggct gaatggcaag gagtacaagt gcaaggtctc caacaaagcc     600

ctcccagccc ccatcgagaa aaccatctcc aaagccaaag ggcagccccg agaaccacag     660

gtgtacaccc tgcccccatc ccgggatgag ctgaccaaga accaggtcag cctgacctgc     720

ctggtcaaag gcttctatcc cagcgacatc gccgtggagt gggagagcaa tgggcagccg     780

gagaacaact acaagaccac gcctcccgtg ttggactccg acggctcctt cttcctctac     840

agcaagctca ccgtggacaa gagcaggtgg cagcagggga acgtcttctc atgctccgtg     900

atgcatgagg ctctgcacaa ccactacacg cagaagagcc tctccctgtc tcccgggaaa     960

tga                                                                   963


<210> SEQ ID NO 50
<211> LENGTH: 320
<212> TYPE: PRT
<213> ORGANISM: Homo sapiens

<400> SEQUENCE: 50

Met Glu Thr Asp Thr Leu Leu Leu Trp Val Leu Leu Leu Trp Val Pro
1               5                   10                  15

Gly Ser Thr Gly Asp Val Arg Arg Gly Pro Arg Ser Leu Arg Gly Arg
            20                  25                  30

Asp Ala Pro Ala Pro Thr Pro Cys Val Pro Ala Glu Cys Phe Asp Leu
        35                  40                  45
```

```
Leu Val Arg His Cys Val Ala Cys Gly Leu Leu Arg Thr Pro Arg Pro
    50                  55                  60

Lys Pro Ala Gly Ala Ser Ser Pro Ala Pro Arg Thr Ala Leu Gln Pro
65                  70                  75                  80

Gln Glu Ser Val Gly Ala Gly Ala Gly Glu Ala Ala Val Asp Lys Thr
                85                  90                  95

His Thr Cys Pro Pro Cys Pro Ala Pro Glu Leu Leu Gly Gly Pro Ser
            100                 105                 110

Val Phe Leu Phe Pro Pro Lys Pro Lys Asp Thr Leu Met Ile Ser Arg
        115                 120                 125

Thr Pro Glu Val Thr Cys Val Val Val Asp Val Ser His Glu Asp Pro
    130                 135                 140

Glu Val Lys Phe Asn Trp Tyr Val Asp Gly Val Glu Val His Asn Ala
145                 150                 155                 160

Lys Thr Lys Pro Arg Glu Glu Gln Tyr Asn Ser Thr Tyr Arg Val Val
                165                 170                 175

Ser Val Leu Thr Val Leu His Gln Asp Trp Leu Asn Gly Lys Glu Tyr
            180                 185                 190

Lys Cys Lys Val Ser Asn Lys Ala Leu Pro Ala Pro Ile Glu Lys Thr
        195                 200                 205

Ile Ser Lys Ala Lys Gly Gln Pro Arg Glu Pro Gln Val Tyr Thr Leu
    210                 215                 220

Pro Pro Ser Arg Asp Glu Leu Thr Lys Asn Gln Val Ser Leu Thr Cys
225                 230                 235                 240

Leu Val Lys Gly Phe Tyr Pro Ser Asp Ile Ala Val Glu Trp Glu Ser
                245                 250                 255

Asn Gly Gln Pro Glu Asn Asn Tyr Lys Thr Thr Pro Pro Val Leu Asp
            260                 265                 270

Ser Asp Gly Ser Phe Phe Leu Tyr Ser Lys Leu Thr Val Asp Lys Ser
        275                 280                 285

Arg Trp Gln Gln Gly Asn Val Phe Ser Cys Ser Val Met His Glu Ala
    290                 295                 300

Leu His Asn His Tyr Thr Gln Lys Ser Leu Ser Leu Ser Pro Gly Lys
305                 310                 315                 320


<210> SEQ ID NO 51
<211> LENGTH: 107
<212> TYPE: PRT
<213> ORGANISM: Homo sapiens

<400> SEQUENCE: 51

Asp Ile Gln Met Thr Gln Thr Pro Ser Thr Leu Ser Ala Ser Val Gly
1               5                   10                  15

Asp Arg Val Thr Ile Ser Cys Arg Ala Ser Gln Asp Ile Asn Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Thr Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Asp Asp Phe Ala Thr Tyr Phe Cys Gln Gln Gly Asn Thr Leu Pro Trp
                85                  90                  95

Thr Phe Gly Gln Gly Thr Lys Val Glu Val Lys
            100                 105
```

<210> SEQ ID NO 52
<211> LENGTH: 107
<212> TYPE: PRT
<213> ORGANISM: Mus musculus

<400> SEQUENCE: 52

Asp Ile Gln Met Thr Gln Thr Thr Ser Ser Leu Ser Ala Ser Leu Gly
1 5 10 15

Asp Arg Val Thr Ile Ser Cys Arg Ala Ser Gln Asp Ile Asn Asn Tyr
20 25 30

Leu Asn Trp Tyr Gln Gln Lys Pro Asp Gly Ile Val Lys Leu Leu Ile
35 40 45

Tyr Tyr Thr Ser Thr Leu His Ser Gly Val Pro Ser Arg Phe Ser Gly
50 55 60

Ser Gly Ser Gly Thr Asp Tyr Ser Leu Thr Ile Ser Asn Leu Glu Gln
65 70 75 80

Glu Asp Ile Ala Thr Tyr Phe Cys Gln Gln Gly Asn Thr Leu Pro Trp
85 90 95

Thr Phe Gly Gly Gly Thr Lys Leu Glu Ile Lys
100 105

<210> SEQ ID NO 53
<211> LENGTH: 119
<212> TYPE: PRT
<213> ORGANISM: Homo sapiens

<400> SEQUENCE: 53

Gln Val Gln Leu Val Gln Ser Gly Ala Glu Val Lys Lys Pro Gly Ser
1 5 10 15

Ser Val Lys Val Ser Cys Lys Ala Ser Gly Tyr Ala Phe Thr Asn Tyr
20 25 30

Leu Ile Glu Trp Val Arg Gln Ala Pro Gly Gln Gly Leu Glu Trp Ile
35 40 45

Gly Val Ile Tyr Pro Gly Ser Gly Gly Thr Asn Tyr Asn Glu Lys Phe
50 55 60

Lys Gly Arg Val Thr Leu Thr Val Asp Glu Ser Thr Asn Thr Ala Tyr
65 70 75 80

Met Glu Leu Ser Ser Leu Arg Ser Glu Asp Thr Ala Val Tyr Phe Cys
85 90 95

Ala Arg Arg Asp Gly Asn Tyr Gly Trp Phe Ala Tyr Trp Gly Gln Gly
100 105 110

Thr Leu Val Thr Val Ser Ser
115

<210> SEQ ID NO 54
<211> LENGTH: 119
<212> TYPE: PRT
<213> ORGANISM: Mus musculus

<400> SEQUENCE: 54

Gln Val Gln Leu Gln Gln Ser Gly Ala Glu Leu Val Gly Pro Gly Thr
1 5 10 15

Ser Val Arg Val Ser Cys Lys Ala Ser Gly Tyr Ala Phe Thr Asn Tyr
20 25 30

Leu Ile Glu Trp Val Lys Gln Arg Pro Gly Gln Gly Leu Glu Trp Ile
35 40 45

Gly Val Ile Tyr Pro Gly Ser Gly Gly Thr Asn Tyr Asn Glu Lys Phe

```
    50                  55                  60

Lys Gly Lys Ala Thr Leu Thr Val Asp Lys Ser Ser Thr Thr Ala Tyr
65                  70                  75                  80

Met Gln Leu Ser Ser Leu Thr Ser Asp Asp Ser Ala Val Tyr Phe Cys
                85                  90                  95

Ala Arg Arg Asp Gly Asn Tyr Gly Trp Phe Ala Tyr Trp Gly Arg Gly
            100                 105                 110

Thr Leu Val Thr Val Ser Ala
        115


<210> SEQ ID NO 55
<211> LENGTH: 214
<212> TYPE: PRT
<213> ORGANISM: Homo sapiens

<400> SEQUENCE: 55

Asp Ile Gln Met Thr Gln Thr Pro Ser Thr Leu Ser Ala Ser Val Gly
1               5                   10                  15

Asp Arg Val Thr Ile Ser Cys Arg Ala Ser Gln Asp Ile Asn Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Thr Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Asp Asp Phe Ala Thr Tyr Phe Cys Gln Gln Gly Asn Thr Leu Pro Trp
                85                  90                  95

Thr Phe Gly Gln Gly Thr Lys Val Glu Val Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 56
<211> LENGTH: 448
<212> TYPE: PRT
<213> ORGANISM: Homo sapiens

<400> SEQUENCE: 56

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Thr Asn Tyr
            20                  25                  30

Leu Ile Glu Trp Val Arg Gln Ala Pro Gly Gln Gly Leu Glu Trp Ile
        35                  40                  45
```

```
Gly Val Ile Tyr Pro Gly Ser Gly Gly Thr Asn Tyr Asn Glu Lys Phe
    50                  55                  60

Lys Gly Arg Val Thr Leu Thr Val Asp Glu Ser Thr Asn Thr Ala Tyr
65                  70                  75                  80

Met Glu Leu Ser Ser Leu Arg Ser Glu Asp Thr Ala Val Tyr Phe Cys
                85                  90                  95

Ala Arg Arg Asp Gly Asn Tyr Gly Trp Phe Ala Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445
```

<210> SEQ ID NO 57
<211> LENGTH: 8540
<212> TYPE: DNA

<213> ORGANISM: Homo sapiens

<400> SEQUENCE: 57
gacgtcgcgg ccgctctagg cctccaaaaa agcctcctca ctacttctgg aatagctcag 60
aggccgaggc ggcctcggcc tctgcataaa taaaaaaaat tagtcagcca tgcatggggc 120
ggagaatggg cggaactggg cggagttagg ggcgggatgg gcggagttag gggcgggact 180
atggttgctg actaattgag atgcatgctt tgcatacttc tgcctgctgg ggagcctggg 240
gactttccac acctggttgc tgactaattg agatgcatgc tttgcatact tctgcctgct 300
ggggagcctg ggactttcc acaccctaac tgacacacat tccacagaat taattcccct 360
agttattaat agtaatcaat tacggggtca ttagttcata gcccatatat ggagttccgc 420
gttacataac ttacggtaaa tggcccgcct ggctgaccgc ccaacgaccc ccgcccattg 480
acgtcaataa tgacgtatgt tcccatagta acgccaatag ggactttcca ttgacgtcaa 540
tgggtggact atttacggta aactgcccac ttggcagtac atcaagtgta tcatatgcca 600
agtacgcccc ctattgacgt caatgacggt aaatggcccg cctggcatta tgcccagtac 660
atgaccttat gggactttcc tacttggcag tacatctacg tattagtcat cgctattacc 720
atggtgatgc ggttttggca gtacatcaat gggcgtggat agcggtttga ctcacgggga 780
tttccaagtc tccaccccat tgacgtcaat gggagtttgt tttggcacca aaatcaacgg 840
gactttccaa aatgtcgtaa caactccgcc ccattgacgc aaatgggcgg taggcgtgta 900
cggtgggagg tctatataag cagagctggg tacgtgaacc gtcagatcgc ctggagacgc 960
catcacagat ctctcaccat gagggtcccc gctcagctcc tggggctcct gctgctctgg 1020
ctcccaggtg cacgatgtga tggtaccaag gtggaaatca aacgtacggt ggctgcacca 1080
tctgtcttca tcttcccgcc atctgatgag cagttgaaat ctggaactgc ctctgttgtg 1140
tgcctgctga ataacttcta tcccagagag gccaaagtac agtggaaggt ggataacgcc 1200
ctccaatcgg gtaactccca ggagagtgtc acagagcagg acagcaagga cagcacctac 1260
agcctcagca gcaccctgac gctgagcaaa gcagactacg agaaacacaa agtctacgcc 1320
tgcgaagtca cccatcaggg cctgagctcg cccgtcacaa agagcttcaa caggggagag 1380
tgttgaattc agatccgtta acggttacca actacctaga ctggattcgt gacaacatgc 1440
ggccgtgata tctacgtatg atcagcctcg actgtgcctt ctagttgcca gccatctgtt 1500
gtttgcccct cccccgtgcc ttccttgacc ctggaaggtg ccactcccac tgtcctttcc 1560
taataaaatg aggaaattgc atcgcattgt ctgagtaggt gtcattctat tctggggggt 1620
ggggtggggc aggacagcaa gggggaggat tgggaagaca atagcaggca tgctggggat 1680
gcggtgggct ctatggaacc agctggggct cgacagctat gccaagtacg ccccctattg 1740
acgtcaatga cggtaaatgg cccgcctggc attatgccca gtacatgacc ttatgggact 1800
ttcctacttg gcagtacatc tacgtattag tcatcgctat taccatggtg atgcggtttt 1860
ggcagtacat caatgggcgt ggatagcggt ttgactcacg gggatttcca agtctccacc 1920
ccattgacgt caatgggagt ttgttttggc accaaaatca acgggacttt ccaaaatgtc 1980
gtaacaactc cgccccattg acgcaaatgg gcggtaggcg tgtacggtgg gaggtctata 2040
taagcagagc tgggtacgtc ctcacattca gtgatcagca ctgaacacag acccgtcgac 2100
atgggttgga gcctcatctt gctcttcctt gtcgctgttg ctacgcgtgt cgctagcacc 2160
aagggcccat cggtcttccc cctggcaccc tcctccaaga gcacctctgg gggcacagcg 2220
gccctgggct gcctggtcaa ggactacttc cccgaaccgg tgacggtgtc gtggaactca 2280

-continued

```
ggcgccctga ccagcggcgt gcacaccttc ccggctgtcc tacagtcctc aggactctac   2340

tccctcagca gcgtggtgac cgtgccctcc agcagcttgg gcacccagac ctacatctgc   2400

aacgtgaatc acaagcccag caacaccaag gtggacaaga aagcagagcc caaatcttgt   2460

gacaaaactc acacatgccc accgtgccca gcacctgaac tcctgggggg accgtcagtc   2520

ttcctcttcc ccccaaaacc caaggacacc ctcatgatct cccggacccc tgaggtcaca   2580

tgcgtggtgg tggacgtgag ccacgaagac cctgaggtca agttcaactg gtacgtggac   2640

ggcgtggagg tgcataatgc caagacaaag ccgcgggagg agcagtacaa cagcacgtac   2700

cgtgtggtca gcgtcctcac cgtcctgcac caggactggc tgaatggcaa ggactacaag   2760

tgcaaggtct ccaacaaagc cctcccagcc cccatcgaga aaaccatctc caaagccaaa   2820

gggcagcccc gagaaccaca ggtgtacacc ctgcccccat cccgggatga gctgaccagg   2880

aaccaggtca gcctgacctg cctggtcaaa ggcttctatc ccagcgacat cgccgtggag   2940

tgggagagca atgggcagcc ggagaacaac tacaagacca cgcctcccgt gctggactcc   3000

gacggctcct tcttcctcta cagcaagctc accgtggaca agagcaggtg gcagcagggg   3060

aacgtcttct catgctccgt gatgcatgag gctctgcaca accactacac gcagaagagc   3120

ctctccctgt ctccgggtaa atgaggatcc gttaacggtt accaactacc tagactggat   3180

tcgtgacaac atgcggccgt gatatctacg tatgatcagc ctcgactgtg ccttctagtt   3240

gccagccatc tgttgtttgc ccctcccccg tgccttcctt gaccctggaa ggtgccactc   3300

ccactgtcct ttcctaataa aatgaggaaa ttgcatcgca ttgtctgagt aggtgtcatt   3360

ctattctggg gggtggggtg gggcaggaca gcaaggggga ggattgggaa gacaatagca   3420

ggcatgctgg ggatgcggtg ggctctatgg aaccagctgg ggctcgacag cgctggatct   3480

cccgatcccc agctttgctt ctcaatttct tatttgcata atgagaaaaa aaggaaaatt   3540

aattttaaca ccaattcagt agttgattga gcaaatgcgt tgccaaaaag gatgctttag   3600

agacagtgtt ctctgcacag ataaggacaa acattattca gagggagtac ccagagctga   3660

gactcctaag ccagtgagtg gcacagcatt ctagggagaa atatgcttgt catcaccgaa   3720

gcctgattcc gtagagccac accttggtaa gggccaatct gctcacacag gatagagagg   3780

gcaggagcca gggcagagca tataaggtga ggtaggatca gttgctcctc acatttgctt   3840

ctgacatagt tgtgttggga gcttggatag cttggacagc tcagggctgc gatttcgcgc   3900

caaacttgac ggcaatccta gcgtgaaggc tggtaggatt ttatccccgc tgccatcatg   3960

gttcgaccat tgaactgcat cgtcgccgtg tcccaaaata tggggattgg caagaacgga   4020

gacctaccct ggcctccgct caggaacgag ttcaagtact tccaaagaat gaccacaacc   4080

tcttcagtgg aaggtaaaca gaatctggtg attatgggta ggaaaacctg gttctccatt   4140

cctgagaaca atcgaccttt aaaggacaga attaatatag ttctcagtag agaactcaaa   4200

gaaccaccac gaggagctca ttttcttgcc aaaagtttgg atgatgcctt aagacttatt   4260

gaacaaccgg aattggcaag taaagtagac atggtttgga tagtcggagg cagttctgtt   4320

taccaggaag ccatgaatca accaggccac cttagactct ttgtgacaag gatcatgcag   4380

gaatttgaaa gtgacacgtt tttcccagaa attgatttgg ggaaatataa acttctccca   4440

gaatacccag gcgtcctctc tgaggtccag gaggaaaaag gcatcaagta taagtttgaa   4500

gtctacgaga agaaagacta acaggaagat gctttcaagt tctctgctcc cctcctaaag   4560

tcatgcattt ttataagacc atgggacttt tgctggcttt agatcagcct cgactgtgcc   4620

ttctagttgc cagccatctg ttgtttgccc ctcccccgtg ccttccttga ccctggaagg   4680
```

-continued

```
tgccactccc actgtccttt cctaataaaa tgaggaaatt gcatcgcatt gtctgagtag   4740
gtgtcattct attctggggg gtggggtggg gcaggacagc aagggggagg attgggaaga   4800
caatagcagg catgctgggg atgcggtggg ctctatggaa ccagctgggg ctcgagctac   4860
tagctttgct tctcaatttc ttatttgcat aatgagaaaa aaaggaaaat taattttaac   4920
accaattcag tagttgattg agcaaatgcg ttgccaaaaa ggatgcttta gagacagtgt   4980
tctctgcaca gataaggaca aacattattc agagggagta cccagagctg agactcctaa   5040
gccagtgagt ggcacagcat tctagggaga aatatgcttg tcatcaccga agcctgattc   5100
cgtagagcca caccttggta agggccaatc tgctcacaca ggatagagag ggcaggagcc   5160
agggcagagc atataaggtg aggtaggatc agttgctcct cacatttgct tctgacatag   5220
ttgtgttggg agcttggatc gatcctctat ggttgaacaa gatggattgc acgcaggttc   5280
tccggccgct tgggtggaga ggctattcgg ctatgactgg gcacaacaga caatcggctg   5340
ctctgatgcc gccgtgttcc ggctgtcagc gcaggggcgc ccggttcttt ttgtcaagac   5400
cgacctgtcc ggtgccctga atgaactgca ggacgaggca gcgcggctat cgtggctggc   5460
cacgacgggc gttccttgcg cagctgtgct cgacgttgtc actgaagcgg gaagggactg   5520
gctgctattg ggcgaagtgc cggggcagga tctcctgtca tctcaccttg ctcctgccga   5580
gaaagtatcc atcatggctg atgcaatgcg gcggctgcat acgcttgatc cggctacctg   5640
cccattcgac caccaagcga aacatcgcat cgagcgagca cgtactcgga tggaagccgg   5700
tcttgtcgat caggatgatc tggacgaaga gcatcagggg ctcgcgccag ccgaactgtt   5760
cgccaggctc aaggcgcgca tgcccgacgg cgaggatctc gtcgtgaccc atggcgatgc   5820
ctgcttgccg aatatcatgg tggaaaatgg ccgcttttct ggattcatcg actgtggccg   5880
gctgggtgtg gcggaccgct atcaggacat agcgttggct acccgtgata ttgctgaaga   5940
gcttggcggc gaatgggctg accgcttcct cgtgctttac ggtatcgccg cttcccgatt   6000
cgcagcgcat cgccttctat cgccttcttg acgagttctt ctgagcggga ctctggggtt   6060
cgaaatgacc gaccaagcga cgcccaacct gccatcacga gatttcgatt ccaccgccgc   6120
cttctatgaa aggttgggct tcggaatcgt tttccgggac gccggctgga tgatcctcca   6180
gcgcggggat ctcatgctgg agttcttcgc ccaccccaac ttgtttattg cagcttataa   6240
tggttacaaa taaagcaata gcatcacaaa tttcacaaat aaagcatttt tttcactgca   6300
ttctagttgt ggtttgtcca aactcatcaa tctatcttat catgtctgga tcgcggccgc   6360
gatcccgtcg agagcttggc gtaatcatgg tcatagctgt ttcctgtgtg aaattgttat   6420
ccgctcacaa ttccacacaa catacgagcc ggagcataaa gtgtaaagcc tggggtgcct   6480
aatgagtgag ctaactcaca ttaattgcgt tgcgctcact gcccgctttc cagtcgggaa   6540
acctgtcgtg ccagctgcat taatgaatcg gccaacgcgc ggggagaggc ggtttgcgta   6600
ttgggcgctc ttccgcttcc tcgctcactg actcgctgcg ctcggtcgtt cggctgcggc   6660
gagcggtatc agctcactca aaggcggtaa tacggttatc cacagaatca ggggataacg   6720
caggaaagaa catgtgagca aaaggccagc aaaaggccag gaaccgtaaa aaggccgcgt   6780
tgctggcgtt tttccatagg ctccgccccc ctgacgagca tcacaaaaat cgacgctcaa   6840
gtcagaggtg gcgaaacccg acaggactat aaagatacca ggcgtttccc cctggaagct   6900
ccctcgtgcg ctctcctgtt ccgaccctgc cgcttaccgg atacctgtcc gcctttctcc   6960
cttcgggaag cgtggcgctt tctcaatgct cacgctgtag gtatctcagt tcggtgtagg   7020
tcgttcgctc caagctgggc tgtgtgcacg aaccccccgt tcagcccgac cgctgcgcct   7080
```

```
tatccggtaa ctatcgtctt gagtccaacc cggtaagaca cgacttatcg ccactggcag   7140

cagccactgg taacaggatt agcagagcga ggtatgtagg cggtgctaca gagttcttga   7200

agtggtggcc taactacggc tacactagaa ggacagtatt tggtatctgc gctctgctga   7260

agccagttac cttcggaaaa agagttggta gctcttgatc cggcaaacaa accaccgctg   7320

gtagcggtgg tttttttgtt tgcaagcagc agattacgcg cagaaaaaaa ggatctcaag   7380

aagatccttt gatcttttct acggggtctg acgctcagtg gaacgaaaac tcacgttaag   7440

ggattttggt catgagatta tcaaaaagga tcttcaccta gatcctttta aattaaaaat   7500

gaagttttaa atcaatctaa agtatatatg agtaaacttg gtctgacagt taccaatgct   7560

taatcagtga ggcacctatc tcagcgatct gtctatttcg ttcatccata gttgcctgac   7620

tccccgtcgt gtagataact acgatacggg agggcttacc atctggcccc agtgctgcaa   7680

tgataccgcg agacccacgc tcaccggctc cagatttatc agcaataaac cagccagccg   7740

gaagggccga gcgcagaagt ggtcctgcaa ctttatccgc ctccatccag tctattaatt   7800

gttgccggga agctagagta agtagttcgc cagttaatag tttgcgcaac gttgttgcca   7860

ttgctacagg catcgtggtg tcacgctcgt cgtttggtat ggcttcattc agctccggtt   7920

cccaacgatc aaggcgagtt acatgatccc ccatgttgtg caaaaaagcg gttagctcct   7980

tcggtcctcc gatcgttgtc agaagtaagt tggccgcagt gttatcactc atggttatgg   8040

cagcactgca taattctctt actgtcatgc catccgtaag atgcttttct gtgactggtg   8100

agtactcaac caagtcattc tgagaatagt gtatgcggcg accgagttgc tcttgcccgg   8160

cgtcaatacg ggataatacc gcgccacata gcagaacttt aaaagtgctc atcattggaa   8220

aacgttcttc ggggcgaaaa ctctcaagga tcttaccgct gttgagatcc agttcgatgt   8280

aacccactcg tgcacccaac tgatcttcag catcttttac tttcaccagc gtttctgggt   8340

gagcaaaaac aggaaggcaa aatgccgcaa aaaagggaat aagggcgaca cggaaatgtt   8400

gaatactcat actcttcctt tttcaatatt attgaagcat ttatcagggt tattgtctca   8460

tgagcggata catatttgaa tgtatttaga aaaataaaca aataggggtt ccgcgcacat   8520

ttccccgaaa agtgccacct                                               8540
```

<210> SEQ ID NO 58
<211> LENGTH: 9209
<212> TYPE: DNA
<213> ORGANISM: Mus musculus

<400> SEQUENCE: 58

```
gacgtcgcgg ccgctctagg cctccaaaaa agcctcctca ctacttctgg aatagctcag     60

aggccgaggc ggcctcggcc tctgcataaa taaaaaaaat tagtcagcca tgcatggggc    120

ggagaatggg cggaactggg cggagttagg ggcgggatgg gcggagttag gggcgggact    180

atggttgctg actaattgag atgcatgctt tgcatacttc tgcctgctgg ggagcctggg    240

gactttccac acctggttgc tgactaattg agatgcatgc tttgcatact tctgcctgct    300

ggggagcctg gggactttcc acaccctaac tgacacacat tccacagaat taattcccct    360

agttattaat agtaatcaat tacggggtca ttagttcata gcccatatat ggagttccgc    420

gttacataac ttacggtaaa tggcccgcct ggctgaccgc ccaacgaccc ccgcccattg    480

acgtcaataa tgacgtatgt tcccatagta acgccaatag ggactttcca ttgacgtcaa    540

tgggtggact atttacggta aactgcccac ttggcagtac atcaagtgta tcatatgcca    600

agtacgcccc ctattgacgt caatgacggt aaatggcccg cctggcatta tgcccagtac    660
```

-continued

```
atgaccttat gggactttcc tacttggcag tacatctacg tattagtcat cgctattacc    720
atggtgatgc ggttttggca gtacatcaat gggcgtggat accggtttga ctcacgcgga    780
tttccaagtc tccaccccat tgacgtcaat gggagtttgt tttggcacca aaatcaacgg    840
gactttccaa aatgtcgtaa caactccgcc ccattgacgc aaatgggcgg taggcgtgta    900
cggtgggagg tctatataag cagagctggg tacgtgaacc gtcagatcgc ctggagacgc    960
catcacagat ctctcactat ggattttcag gtgcagatta tcagcttcct gctaatcagt   1020
gcttcagtca taatgtccag aggacaaatt gttctctccc agtctccagc aatcctgtct   1080
gcatctccag gggagaaggt cacaatgact tgcagggcca gctcaagtgt aagttacatc   1140
cactggttcc agcagaagcc aggatcctcc cccaaaccct ggatttatgc cacatccaac   1200
ctggcttctg gagtccctgt tcgcttcagt ggcagtgggt ctgggacttc ttactctctc   1260
acaatcagca gagtggaggc tgaagatgct gccacttatt actgccagca gtggactagt   1320
aacccaccca cgttcggagg ggggaccaag ctggaaatca aacgtacggt ggctgcacca   1380
tctgtcttca tcttcccgcc atctgatgag cagttgaaat ctggaactgc ctctgttgtg   1440
tgcctgctga ataacttcta tcccagagag gccaaagtac agtggaaggt ggataacgcc   1500
ctccaatcgg gtaactccca ggagagtgtc acagagcagg acagcaagga cagcacctac   1560
agcctcagca gcaccctgac gctgagcaaa gcagactacg agaaacacaa agtctacgcc   1620
tgcgaagtca cccatcaggg cctgagctcg cccgtcacaa agagcttcaa caggggagag   1680
tgttgaattc agatccgtta acggttacca actacctaga ctggattcgt gacaacatgc   1740
ggccgtgata tctacgtatg atcagcctcg actgtgcctt ctagttgcca gccatctgtt   1800
gtttgcccct cccccgtgcc ttccttgacc ctggaaggtg ccactcccac tgtcctttcc   1860
taataaaatg aggaaattgc atcgcattgt ctgagtaggt gtcattctat tctggggggt   1920
ggggtggggc aggacagcaa gggggaggat tgggaagaca atagcaggca tgctggggat   1980
gcggtgggct ctatggaacc agctggggct cgacagctat gccaagtacg ccccctattg   2040
acgtcaatga cggtaaatgg cccgcctggc attatgccca gtacatgacc ttatgggact   2100
ttcctacttg gcagtacatc tacgtattag tcatcgctat taccatggtg atgcggtttt   2160
ggcagtacat caatgggcgt ggatagcggt ttgactcacg gggatttcca agtctccacc   2220
ccattgacgt caatgggagt ttgttttggc accaaaatca acgggacttt ccaaaatgtc   2280
gtaacaactc cgccccattg acgcaaatgg gcggtaggcg tgtacggtgg gaggtctata   2340
taagcagagc tgggtacgtc ctcacattca gtgatcagca ctgaacacag acccgtcgac   2400
atgggttgga gcctcatctt gctcttcctt gtcgctgttg ctacgcgtgt cctgtcccag   2460
gtacaactgc agcagcctgg ggctgagctg gtgaagcctg gggcctcagt gaagatgtcc   2520
tgcaaggctt ctggctacac atttaccagt tacaatatgc actgggtaaa acagacacct   2580
ggtcggggcc tggaatggat tggagctatt tatcccggaa atggtgatac ttcctacaat   2640
cagaagttca aaggcaaggc cacattgact gcagacaaat cctccagcac agcctacatg   2700
cagctcagca gcctgacatc tgaggactct gcggtctatt actgtgcaag atcgacttac   2760
tacggcggtg actggtactt caatgtctgg ggcgcaggga ccacggtcac cgtctctgca   2820
gctagcacca agggcccatc ggtcttcccc ctggcaccct cctccaagag cacctctggg   2880
ggcacagcgg ccctgggctg cctggtcaag gactacttcc ccgaaccggt gacggtgtcg   2940
tggaactcag gcgccctgac cagcggcgtg cacaccttcc cggctgtcct acagtcctca   3000
ggactctact ccctcagcag cgtggtgacc gtgccctcca gcagcttggg cacccagacc   3060
```

```
tacatctgca acgtgaatca caagcccagc aacaccaagg tggacaagaa agcagagccc   3120
aaatcttgtg acaaaactca cacatgccca ccgtgcccag cacctgaact cctgggggga   3180
ccgtcagtct tcctcttccc cccaaaaccc aaggacaccc tcatgatctc ccggacccct   3240
gaggtcacat gcgtggtggt ggacgtgagc cacgaagacc ctgaggtcaa gttcaactgg   3300
tacgtggacg gcgtggaggt gcataatgcc aagacaaagc cgcgggagga gcagtacaac   3360
agcacgtacc gtgtggtcag cgtcctcacc gtcctgcacc aggactggct gaatggcaag   3420
gagtacaagt gcaaggtctc caacaaagcc ctcccagccc ccatcgagaa aaccatctcc   3480
aaagccaaag ggcagccccg agaaccacag gtgtacaccc tgcccccatc ccgggatgag   3540
ctgaccaaga accaggtcag cctgacctgc ctggtcaaag gcttctatcc cagcgacatc   3600
gccgtggagt gggagagcaa tgggcagccg gagaacaact acaagaccac gcctcccgtg   3660
ctggactccg acggctcctt cttcctctac agcaagctca ccgtggacaa gagcaggtgg   3720
cagcagggga acgtcttctc atgctccgtg atgcatgagg ctctgcacaa ccactacacg   3780
cagaagagcc tctccctgtc tccgggtaaa tgaggatccg ttaacggtta ccaactacct   3840
agactggatt cgtgacaaca tgcggccgtg atatctacgt atgatcagcc tcgactgtgc   3900
cttctagttg ccagccatct gttgtttgcc cctcccccgt gccttccttg accctggaag   3960
gtgccactcc cactgtcctt tcctaataaa atgaggaaat tgcatcgcat tgtctgagta   4020
ggtgtcattc tattctgggg ggtggggtgg ggcaggacag caagggggag gattgggaag   4080
acaatagcag gcatgctggg gatgcggtgg gctctatgga accagctggg gctcgacagc   4140
gctggatctc ccgatcccca gctttgcttc tcaatttctt atttgcataa tgagaaaaaa   4200
aggaaaatta attttaacac caattcagta gttgattgag caaatgcgtt gccaaaaagg   4260
atgctttaga gacagtgttc tctgcacaga taaggacaaa cattattcag agggagtacc   4320
cagagctgag actcctaagc cagtgagtgg cacagcattc tagggagaaa tatgcttgtc   4380
atcaccgaag cctgattccg tagagccaca ccttggtaag ggccaatctg ctcacacagg   4440
atagagaggg caggagccag ggcagagcat ataaggtgag gtaggatcag ttgctcctca   4500
catttgcttc tgacatagtt gtgttgggag cttggatagc ttggacagct cagggctgcg   4560
atttcgcgcc aaacttgacg gcaatcctag cgtgaaggct ggtaggattt tatccccgct   4620
gccatcatgg ttcgaccatt gaactgcatc gtcgccgtgt cccaaaatat ggggattggc   4680
aagaacggag acctaccctg gcctccgctc aggaacgagt tcaagtactt ccaaagaatg   4740
accacaacct cttcagtgga aggtaaacag aatctggtga ttatgggtag gaaaacctgg   4800
ttctccattc ctgagaagaa tcgaccttta aaggacagaa ttaatatagt tctcagtaga   4860
gaactcaaag aaccaccacg aggagctcat tttcttgcca aaagtttgga tgatgcctta   4920
agacttattg aacaaccgga attggcaagt aaagtagaca tggtttggat agtcggaggc   4980
agttctgttt accaggaagc catgaatcaa ccaggccacc ttagactctt tgtgacaagg   5040
atcatgcagg aatttgaaag tgacacgttt ttcccagaaa ttgatttggg gaaatataaa   5100
cttctcccag aatacccagg cgtcctctct gaggtccagg aggaaaaagg catcaagtat   5160
aagtttgaag tctacgagaa gaaagactaa caggaagatg ctttcaagtt ctctgctccc   5220
ctcctaaagc tatgcatttt tataagacca tgggactttt gctggcttta gatcagcctc   5280
gactgtgcct tctagttgcc agccatctgt tgtttgcccc tcccccgtgc cttccttgac   5340
cctggaaggt gccactccca ctgtcctttc ctaataaaat gaggaaattg catcgcattg   5400
tctgagtagg tgtcattcta ttctgggggg tggggtgggg caggacagca agggggagga   5460
```

-continued

```
ttgggaagac aatagcaggc atgctgggga tgcggtgggc tctatggaac cagctggggc   5520
tcgagctact agctttgctt ctcaatttct tatttgcata atgagaaaaa aaggaaaatt   5580
aattttaaca ccaattcagt agttgattga gcaaatgcgt tgccaaaaag gatgctttag   5640
agacagtgtt ctctgcacag ataaggacaa acattattca gagggagtac ccagagctga   5700
gactcctaag ccagtgagtg gcacagcatt ctagggagaa atatgcttgt catcaccgaa   5760
gcctgattcc gtagagccac accttggtaa gggccaatct gctcacacag gatagagagg   5820
gcaggagcca gggcagagca tataaggtga ggtaggatca gttgctcctc acatttgctt   5880
ctgacatagt tgtgttggga gcttggatcg atcctctatg gttgaacaag atggattgca   5940
cgcaggttct ccggccgctt gggtggagag gctattcggc tatgactggg cacaacagac   6000
aatcggctgc tctgatgccg ccgtgttccg gctgtcagcg caggggcgcc cggttctttt   6060
tgtcaagacc gacctgtccg gtgccctgaa tgaactgcag gacgaggcag cgcggctatc   6120
gtggctggcc acgacgggcg ttccttgcgc agctgtgctc gacgttgtca ctgaagcggg   6180
aagggactgg ctgctattgg gcgaagtgcc ggggcaggat ctcctgtcat ctcaccttgc   6240
tcctgccgag aaagtatcca tcatggctga tgcaatgcgg cggctgcata cgcttgatcc   6300
ggctacctgc ccattcgacc accaagcgaa acatcgcatc gagcgagcac gtactcggat   6360
ggaagccggt cttgtcgatc aggatgatct ggacgaagag catcaggggc tcgcgccagc   6420
cgaactgttc gccaggctca aggcgcgcat gcccgacggc gaggatctcg tcgtgaccca   6480
tggcgatgcc tgcttgccga atatcatggt ggaaaatggc cgcttttctg gattcatcga   6540
ctgtggccgg ctgggtgtgg cggaccgcta tcaggacata gcgttggcta cccgtgatat   6600
tgctgaagag cttggcggcg aatgggctga ccgcttcctc gtgctttacg gtatcgccgc   6660
tcccgattcg cagcgcatcg ccttctatcg ccttcttgac gagttcttct gagcgggact   6720
ctggggttcg aaatgaccga ccaagcgacg cccaacctgc catcacgaga tttcgattcc   6780
accgccgcct tctatgaaag gttgggcttc ggaatcgttt tccgggacgc cggctggatg   6840
atcctccagc gcggggatct catgctggag ttcttcgccc accccaactt gtttattgca   6900
gcttataatg gttacaaata aagcaatagc atcacaaatt tcacaaataa agcatttttt   6960
tcactgcatt ctagttgtgg tttgtccaaa ctcatcaatc tatcttatca tgtctggatc   7020
gcggccgcga tcccgtcgag agcttggcgt aatcatggtc atagctgttt cctgtgtgaa   7080
attgttatcc gctcacaatt ccacacaaca tacgagccgg aagcataaag tgtaaagcct   7140
ggggtgccta atgagtgagc taactcacat taattgcgtt gcgctcactg cccgctttcc   7200
agtcgggaaa cctgtcgtgc cagctgcatt aatgaatcgg ccaacgcgcg gggagaggcg   7260
gtttgcgtat tgggcgctct tccgcttcct cgctcactga ctcgctgcgc tcggtcgttc   7320
ggctgcggcg agcggtatca gctcactcaa aggcggtaat acggttatcc acagaatcag   7380
gggataacgc aggaaagaac atgtgagcaa aaggccagca aaaggccagg aaccgtaaaa   7440
aggccgcgtt gctggcgttt ttccataggc tccgcccccc tgacgagcat cacaaaaatc   7500
gacgctcaag tcagaggtgg cgaaacccga caggactata aagataccag gcgtttcccc   7560
ctggaagctc cctcgtgcgc tctcctgttc cgaccctgcc gcttaccgga tacctgtccg   7620
cctttctccc ttcgggaagc gtggcgcttt ctcaatgctc acgctgtagg tatctcagtt   7680
cggtgtaggt cgttcgctcc aagctgggct gtgtgcacga accccccgtt cagcccgacc   7740
gctgcgcctt atccggtaac tatcgtcttg agtccaaccc ggtaagacac gacttatcgc   7800
cactggcagc agccactggt aacaggatta gcagagcgag gtatgtaggc ggtgctacag   7860
```

agttcttgaa gtggtggcct aactacggct acactagaag gacagtattt ggtatctgcg 7920
ctctgctgaa gccagttacc ttcggaaaaa gagttggtag ctcttgatcc ggcaaacaaa 7980
ccaccgctgg tagcggtggt ttttttgttt gcaagcagca gattacgcgc agaaaaaaag 8040
gatctcaaga agatcctttg atcttttcta cggggtctga cgctcagtgg aacgaaaact 8100
cacgttaagg gattttggtc atgagattat caaaaaggat cttcacctag atccttttaa 8160
attaaaaatg aagttttaaa tcaatctaaa gtatatatga gtaaacttgg tctgacagtt 8220
accaatgctt aatcagtgag gcacctatct cagcgatctg tctatttcgt tcatccatag 8280
ttgcctgact ccccgtcgtg tagataacta cgatacggga gggcttacca tctggcccca 8340
gtgctgcaat gataccgcga gacccacgct caccggctcc agatttatca gcaataaacc 8400
agccagccgg aagggccgag cgcagaagtg gtcctgcaac tttatccgcc tccatccagt 8460
ctattaattg ttgccgggaa gctagagtaa gtagttcgcc agttaatagt ttgcgcaacg 8520
ttgttgccat tgctacaggc atcgtggtgt cacgctcgtc gtttggtatg gcttcattca 8580
gctccggttc ccaacgatca aggcgagtta catgatcccc catgttgtgc aaaaaagcgg 8640
ttagctcctt cggtcctccg atcgttgtca gaagtaagtt ggccgcagtg ttatcactca 8700
tggttatggc agcactgcat aattctctta ctgtcatgcc atccgtaaga tgcttttctg 8760
tgactggtga gtactcaacc aagtcattct gagaatagtg tatgcggcga ccgagttgct 8820
cttgcccggc gtcaatacgg gataataccg cgccacatag cagaacttta aaagtgctca 8880
tcattggaaa acgttcttcg gggcgaaaac tctcaaggat cttaccgctg ttgagatcca 8940
gttcgatgta acccactcgt gcacccaact gatcttcagc atcttttact ttcaccagcg 9000
tttctgggtg agcaaaaaca ggaaggcaaa atgccgcaaa aaagggaata agggcgacac 9060
ggaaatgttg aatactcata ctcttccttt ttcaatatta ttgaagcatt tatcagggtt 9120
attgtctcat gagcggatac atatttgaat gtatttagaa aaataaacaa ataggggttc 9180
cgcgcacatt tccccgaaaa gtgccacct 9209

<210> SEQ ID NO 59
<211> LENGTH: 384
<212> TYPE: DNA
<213> ORGANISM: Mus musculus

<400> SEQUENCE: 59
atggattttc aggtgcagat tatcagcttc ctgctaatca gtgcttcagt cataatgtcc 60
agagggcaaa ttgttctctc ccagtctcca gcaatcctgt ctgcatctcc aggggagaag 120
gtcacaatga cttgcagggc cagctcaagt gtaagttaca tccactggtt ccagcagaag 180
ccaggatcct cccccaaacc ctggatttat gccacatcca acctggcttc tggagtccct 240
gttcgcttca gtggcagtgg gtctgggact tcttactctc tcacaatcag cagagtggag 300
gctgaagatg ctgccactta ttactgccag cagtggacta gtaacccacc cacgttcgga 360
ggggggacca agctggaaat caaa 384

<210> SEQ ID NO 60
<211> LENGTH: 128
<212> TYPE: PRT
<213> ORGANISM: Mus musculus

<400> SEQUENCE: 60

Met Asp Phe Gln Val Gln Ile Ile Ser Phe Leu Leu Ile Ser Ala Ser
1 5 10 15

Val Ile Met Ser Arg Gly Gln Ile Val Leu Ser Gln Ser Pro Ala Ile

```
            20                  25                  30

Leu Ser Ala Ser Pro Gly Glu Lys Val Thr Met Thr Cys Arg Ala Ser
        35                  40                  45

Ser Ser Val Ser Tyr Ile His Trp Phe Gln Gln Lys Pro Gly Ser Ser
    50                  55                  60

Pro Lys Pro Trp Ile Tyr Ala Thr Ser Asn Leu Ala Ser Gly Val Pro
65                  70                  75                  80

Val Arg Phe Ser Gly Ser Gly Ser Gly Thr Ser Tyr Ser Leu Thr Ile
                85                  90                  95

Ser Arg Val Glu Ala Glu Asp Ala Ala Thr Tyr Tyr Cys Gln Gln Trp
            100                 105                 110

Thr Ser Asn Pro Pro Thr Phe Gly Gly Gly Thr Lys Leu Glu Ile Lys
        115                 120                 125


<210> SEQ ID NO 61
<211> LENGTH: 420
<212> TYPE: DNA
<213> ORGANISM: Mus musculus

<400> SEQUENCE: 61

atgggttgga gcctcatctt gctcttcctt gtcgctgttg ctacgcgtgt cctgtcccag      60

gtacaactgc agcagcctgg ggctgagctg gtgaagcctg gggcctcagt gaagatgtcc     120

tgcaaggctt ctggctacac atttaccagt tacaatatgc actgggtaaa acagacacct     180

ggtcggggcc tggaatggat tggagctatt tatcccggaa atggtgatac ttcctacaat     240

cagaagttca aaggcaaggc cacattgact gcagacaaat cctccagcac agcctacatg     300

cagctcagca gcctgacatc tgaggactct gcggtctatt actgtgcaag atcgacttac     360

tacggcggtg actggtactt caatgtctgg ggcgcaggga ccacggtcac cgtctctgca     420


<210> SEQ ID NO 62
<211> LENGTH: 140
<212> TYPE: PRT
<213> ORGANISM: Mus musculus

<400> SEQUENCE: 62

Met Gly Trp Ser Leu Ile Leu Leu Phe Leu Val Ala Val Ala Thr Arg
1               5                   10                  15

Val Leu Ser Gln Val Gln Leu Gln Gln Pro Gly Ala Glu Leu Val Lys
            20                  25                  30

Pro Gly Ala Ser Val Lys Met Ser Cys Lys Ala Ser Gly Tyr Thr Phe
        35                  40                  45

Thr Ser Tyr Asn Met His Trp Val Lys Gln Thr Pro Gly Arg Gly Leu
    50                  55                  60

Glu Trp Ile Gly Ala Ile Tyr Pro Gly Asn Gly Asp Thr Ser Tyr Asn
65                  70                  75                  80

Gln Lys Phe Lys Gly Lys Ala Thr Leu Thr Ala Asp Lys Ser Ser Ser
                85                  90                  95

Thr Ala Tyr Met Gln Leu Ser Ser Leu Thr Ser Glu Asp Ser Ala Val
            100                 105                 110

Tyr Tyr Cys Ala Arg Ser Thr Tyr Tyr Gly Gly Asp Trp Tyr Phe Asn
        115                 120                 125

Val Trp Gly Ala Gly Thr Thr Val Thr Val Ser Ala
    130                 135                 140


<210> SEQ ID NO 63
<211> LENGTH: 1395
```

<212> TYPE: DNA
<213> ORGANISM: Homo sapiens

<400> SEQUENCE: 63

```
atgtattcca atgtgatagg aactgtaacc tctggaaaaa ggaaggttta tcttttgtcc      60
ttgctgctca ttggcttctg ggactgcgtg acctgtcacg ggagccctgt ggacatctgc     120
acagccaagc cgcgggacat tcccatgaat cccatgtgca tttaccgctc cccggagaag     180
aaggcaactg aggatgaggg ctcagaacag aagatcccgg aggccaccaa ccggcgtgtc     240
tgggaactgt ccaaggccaa ttcccgcttt gctaccactt tctatcagca cctggcagat     300
tccaagaatg acaatgataa cattttcctg tcacccctga gtatctccac ggcttttgct     360
atgaccaagc tgggtgcctg taatgacacc ctccagcaac tgatggaggt atttaagttt     420
gacaccatat ctgagaaaac atctgatcag atccacttct tctttgccaa actgaactgc     480
cgactctatc gaaaagccaa caaatcctcc aagttagtat cagccaatcg ccttttttgga    540
gacaaatccc ttaccttcaa tgagacctac caggacatca gtgagttggt atatggagcc     600
aagctccagc ccctggactt caaggaaaat gcagagcaat ccagagcggc catcaacaaa     660
tgggtgtcca ataagaccga aggccgaatc accgatgtca ttccctcgga agccatcaat     720
gagctcactg ttctggtgct ggttaacacc atttacttca agggcctgtg gaagtcaaag     780
ttcagccctg agaacacaag gaaggaactg ttctacaagg ctgatggaga gtcgtgttca     840
gcatctatga tgtaccagga aggcaagttc cgttatcggc gcgtggctga aggcacccag     900
gtgcttgagt tgcccttcaa aggtgatgac atcaccatgg tcctcatctt gcccaagcct     960
gagaagagcc tggccaaggt ggagaaggaa ctcaccccag aggtgctgca ggagtggctg    1020
gatgaattgg aggagatgat gctggtggtc cacatgcccc gcttccgcat tgaggacggc    1080
ttcagtttga aggagcagct gcaagacatg ggccttgtcg atctgttcag ccctgaaaag    1140
tccaaactcc caggtattgt tgcagaaggc cgagatgacc tctatgtctc agatgcattc    1200
cataaggcat ttcttgaggt aaatgaagaa ggcagtgaag cagctgcaag taccgctgtt    1260
gtgattgctg gccgttcgct aaaccccaac agggtgactt tcaaggccaa caggcctttc    1320
ctggttttta taagagaagt tcctctgaac actattatct tcatgggcag agtagccaac    1380
ccttgtgtta agtaa                                                     1395
```

<210> SEQ ID NO 64
<211> LENGTH: 464
<212> TYPE: PRT
<213> ORGANISM: Homo sapiens

<400> SEQUENCE: 64

```
Met Tyr Ser Asn Val Ile Gly Thr Val Thr Ser Gly Lys Arg Lys Val
1               5                   10                  15

Tyr Leu Leu Ser Leu Leu Leu Ile Gly Phe Trp Asp Cys Val Thr Cys
            20                  25                  30

His Gly Ser Pro Val Asp Ile Cys Thr Ala Lys Pro Arg Asp Ile Pro
        35                  40                  45

Met Asn Pro Met Cys Ile Tyr Arg Ser Pro Glu Lys Lys Ala Thr Glu
    50                  55                  60

Asp Glu Gly Ser Glu Gln Lys Ile Pro Glu Ala Thr Asn Arg Arg Val
65                  70                  75                  80

Trp Glu Leu Ser Lys Ala Asn Ser Arg Phe Ala Thr Thr Phe Tyr Gln
                85                  90                  95

His Leu Ala Asp Ser Lys Asn Asp Asn Asp Asn Ile Phe Leu Ser Pro
```

```
            100                 105                 110

Leu Ser Ile Ser Thr Ala Phe Ala Met Thr Lys Leu Gly Ala Cys Asn
        115                 120                 125

Asp Thr Leu Gln Gln Leu Met Glu Val Phe Lys Phe Asp Thr Ile Ser
    130                 135                 140

Glu Lys Thr Ser Asp Gln Ile His Phe Phe Phe Ala Lys Leu Asn Cys
145                 150                 155                 160

Arg Leu Tyr Arg Lys Ala Asn Lys Ser Ser Lys Leu Val Ser Ala Asn
                165                 170                 175

Arg Leu Phe Gly Asp Lys Ser Leu Thr Phe Asn Glu Thr Tyr Gln Asp
            180                 185                 190

Ile Ser Glu Leu Val Tyr Gly Ala Lys Leu Gln Pro Leu Asp Phe Lys
        195                 200                 205

Glu Asn Ala Glu Gln Ser Arg Ala Ala Ile Asn Lys Trp Val Ser Asn
    210                 215                 220

Lys Thr Glu Gly Arg Ile Thr Asp Val Ile Pro Ser Glu Ala Ile Asn
225                 230                 235                 240

Glu Leu Thr Val Leu Val Leu Val Asn Thr Ile Tyr Phe Lys Gly Leu
                245                 250                 255

Trp Lys Ser Lys Phe Ser Pro Glu Asn Thr Arg Lys Glu Leu Phe Tyr
            260                 265                 270

Lys Ala Asp Gly Glu Ser Cys Ser Ala Ser Met Met Tyr Gln Glu Gly
        275                 280                 285

Lys Phe Arg Tyr Arg Arg Val Ala Glu Gly Thr Gln Val Leu Glu Leu
    290                 295                 300

Pro Phe Lys Gly Asp Asp Ile Thr Met Val Leu Ile Leu Pro Lys Pro
305                 310                 315                 320

Glu Lys Ser Leu Ala Lys Val Glu Lys Glu Leu Thr Pro Glu Val Leu
                325                 330                 335

Gln Glu Trp Leu Asp Glu Leu Glu Glu Met Met Leu Val Val His Met
            340                 345                 350

Pro Arg Phe Arg Ile Glu Asp Gly Phe Ser Leu Lys Glu Gln Leu Gln
        355                 360                 365

Asp Met Gly Leu Val Asp Leu Phe Ser Pro Glu Lys Ser Lys Leu Pro
    370                 375                 380

Gly Ile Val Ala Glu Gly Arg Asp Asp Leu Tyr Val Ser Asp Ala Phe
385                 390                 395                 400

His Lys Ala Phe Leu Glu Val Asn Glu Glu Gly Ser Glu Ala Ala Ala
                405                 410                 415

Ser Thr Ala Val Val Ile Ala Gly Arg Ser Leu Asn Pro Asn Arg Val
            420                 425                 430

Thr Phe Lys Ala Asn Arg Pro Phe Leu Val Phe Ile Arg Glu Val Pro
        435                 440                 445

Leu Asn Thr Ile Ile Phe Met Gly Arg Val Ala Asn Pro Cys Val Lys
    450                 455                 460
```

<210> SEQ ID NO 65
<211> LENGTH: 1962
<212> TYPE: DNA
<213> ORGANISM: Homo sapiens

<400> SEQUENCE: 65

```
atgcgtcccc tgcgcccccg cgccgcgctg ctggcgctcc tggcctcgct cctggccgcg      60

cccccggtgg ccccggccga ggccccgcac ctggtgcagg tggacgcggc ccgcgcgctg     120
```

-continued

```
tggcccctgc ggcgcttctg gaggagcaca ggcttctgcc ccccgctgcc acacagccag    180
gctgaccagt acgtcctcag ctgggaccag cagctcaacc tcgcctatgt gggcgccgtc    240
cctcaccgcg gcatcaagca ggtccggacc cactggctgc tggagcttgt caccaccagg    300
gggtccactg gacggggcct gagctacaac ttcacccacc tggacgggta cttggacctt    360
ctcagggaga accagctcct cccagggttt gagctgatgg gcagcgcctc gggccacttc    420
actgactttg aggacaagca gcaggtgttt gagtggaagg acttggtctc cagcctggcc    480
aggagataca tcggtaggta cggactggcg catgtttcca agtggaactt cgagacgtgg    540
aatgagccag accaccacga ctttgacaac gtctccatga ccatgcaagg cttcctgaac    600
tactacgatg cctgctcgga gggtctgcgc gccgccagcc ccgccctgcg gctgggaggc    660
cccggcgact ccttccacac cccaccgcga tccccgctga gctggggcct cctgcgccac    720
tgccacgacg gtaccaactt cttcactggg gaggcgggcg tgcggctgga ctacatctcc    780
ctccacagga agggtgcgcg cagctccatc tccatcctgg agcaggagaa ggtcgtcgcg    840
cagcagatcc ggcagctctt ccccaagttc gcggacaccc ccatttacaa cgacgaggcg    900
gacccgctgg tgggctggtc cctgccacag ccgtggaggg cggacgtgac ctacgcggcc    960
atggtggtga aggtcatcgc gcagcatcag aacctgctac tggccaacac cacctccgcc   1020
ttcccctacg cgctcctgag caacgacaat gccttcctga gctaccaccc gcaccccttc   1080
gcgcagcgca cgctcaccgc gcgcttccag gtcaacaaca cccgcccgcc gcacgtgcag   1140
ctgttgcgca agccggtgct cacggccatg gggctgctgg cgctgctgga tgaggagcag   1200
ctctgggccg aagtgtcgca ggccgggacc gtcctggaca gcaaccacac ggtgggcgtc   1260
ctggccagcg cccaccgccc ccagggcccg gccgacgcct ggcgcgccgc ggtgctgatc   1320
tacgcgagcg acgacacccg cgcccacccc aaccgcagcg tcgcggtgac cctgcggctg   1380
cgcggggtgc ccccggccc gggcctggtc tacgtcacgc gctacctgga caacgggctc   1440
tgcagccccg acggcgagtg gcggcgcctg ggccggcccg tcttccccac ggcagagcag   1500
ttccggcgca tgcgcgcggc tgaggacccg gtggccgcgg cgccccgccc cttacccgcc   1560
ggcggccgcc tgaccctgcg ccccgcgctg cggctgccgt cgcttttgct ggtgcacgtg   1620
tgtgcgcgcc ccgagaagcc gcccgggcag gtcacgcggc tccgcgccct gcccctgacc   1680
caagggcagc tggttctggt ctggtcggat gaacacgtgg gctccaagtg cctgtggaca   1740
tacgagatcc agttctctca ggacggtaag gcgtacaccc cggtcagcag gaagccatcg   1800
accttcaacc tctttgtgtt cagcccagac acaggtgctg tctctggctc ctaccgagtt   1860
cgagccctgg actactgggc ccgaccaggc cccttctcgg accctgtgcc gtacctggag   1920
gtccctgtgc caagagggcc cccatccccg ggcaatccat ga                      1962
```

<210> SEQ ID NO 66
<211> LENGTH: 653
<212> TYPE: PRT
<213> ORGANISM: Homo sapiens

<400> SEQUENCE: 66

```
Met Arg Pro Leu Arg Pro Arg Ala Ala Leu Leu Ala Leu Leu Ala Ser
1               5                   10                  15

Leu Leu Ala Ala Pro Pro Val Ala Pro Ala Glu Ala Pro His Leu Val
            20                  25                  30

Gln Val Asp Ala Ala Arg Ala Leu Trp Pro Leu Arg Arg Phe Trp Arg
        35                  40                  45

Ser Thr Gly Phe Cys Pro Pro Leu Pro His Ser Gln Ala Asp Gln Tyr
```

-continued

```
    50                  55                  60

Val Leu Ser Trp Asp Gln Gln Leu Asn Leu Ala Tyr Val Gly Ala Val
65                  70                  75                  80

Pro His Arg Gly Ile Lys Gln Val Arg Thr His Trp Leu Leu Glu Leu
                85                  90                  95

Val Thr Thr Arg Gly Ser Thr Gly Arg Gly Leu Ser Tyr Asn Phe Thr
            100                 105                 110

His Leu Asp Gly Tyr Leu Asp Leu Leu Arg Glu Asn Gln Leu Leu Pro
        115                 120                 125

Gly Phe Glu Leu Met Gly Ser Ala Ser Gly His Phe Thr Asp Phe Glu
    130                 135                 140

Asp Lys Gln Gln Val Phe Glu Trp Lys Asp Leu Val Ser Ser Leu Ala
145                 150                 155                 160

Arg Arg Tyr Ile Gly Arg Tyr Gly Leu Ala His Val Ser Lys Trp Asn
                165                 170                 175

Phe Glu Thr Trp Asn Glu Pro Asp His His Asp Phe Asp Asn Val Ser
            180                 185                 190

Met Thr Met Gln Gly Phe Leu Asn Tyr Tyr Asp Ala Cys Ser Glu Gly
        195                 200                 205

Leu Arg Ala Ala Ser Pro Ala Leu Arg Leu Gly Gly Pro Gly Asp Ser
    210                 215                 220

Phe His Thr Pro Pro Arg Ser Pro Leu Ser Trp Gly Leu Leu Arg His
225                 230                 235                 240

Cys His Asp Gly Thr Asn Phe Phe Thr Gly Glu Ala Gly Val Arg Leu
                245                 250                 255

Asp Tyr Ile Ser Leu His Arg Lys Gly Ala Arg Ser Ser Ile Ser Ile
            260                 265                 270

Leu Glu Gln Glu Lys Val Val Ala Gln Gln Ile Arg Gln Leu Phe Pro
        275                 280                 285

Lys Phe Ala Asp Thr Pro Ile Tyr Asn Asp Glu Ala Asp Pro Leu Val
    290                 295                 300

Gly Trp Ser Leu Pro Gln Pro Trp Arg Ala Asp Val Thr Tyr Ala Ala
305                 310                 315                 320

Met Val Val Lys Val Ile Ala Gln His Gln Asn Leu Leu Leu Ala Asn
                325                 330                 335

Thr Thr Ser Ala Phe Pro Tyr Ala Leu Leu Ser Asn Asp Asn Ala Phe
            340                 345                 350

Leu Ser Tyr His Pro His Pro Phe Ala Gln Arg Thr Leu Thr Ala Arg
        355                 360                 365

Phe Gln Val Asn Asn Thr Arg Pro Pro His Val Gln Leu Leu Arg Lys
    370                 375                 380

Pro Val Leu Thr Ala Met Gly Leu Leu Ala Leu Leu Asp Glu Glu Gln
385                 390                 395                 400

Leu Trp Ala Glu Val Ser Gln Ala Gly Thr Val Leu Asp Ser Asn His
                405                 410                 415

Thr Val Gly Val Leu Ala Ser Ala His Arg Pro Gln Gly Pro Ala Asp
            420                 425                 430

Ala Trp Arg Ala Ala Val Leu Ile Tyr Ala Ser Asp Asp Thr Arg Ala
        435                 440                 445

His Pro Asn Arg Ser Val Ala Val Thr Leu Arg Leu Arg Gly Val Pro
    450                 455                 460

Pro Gly Pro Gly Leu Val Tyr Val Thr Arg Tyr Leu Asp Asn Gly Leu
465                 470                 475                 480
```

```
Cys Ser Pro Asp Gly Glu Trp Arg Arg Leu Gly Arg Pro Val Phe Pro
                485                 490                 495

Thr Ala Glu Gln Phe Arg Arg Met Arg Ala Ala Glu Asp Pro Val Ala
            500                 505                 510

Ala Ala Pro Arg Pro Leu Pro Ala Gly Gly Arg Leu Thr Leu Arg Pro
        515                 520                 525

Ala Leu Arg Leu Pro Ser Leu Leu Leu Val His Val Cys Ala Arg Pro
    530                 535                 540

Glu Lys Pro Pro Gly Gln Val Thr Arg Leu Arg Ala Leu Pro Leu Thr
545                 550                 555                 560

Gln Gly Gln Leu Val Leu Val Trp Ser Asp Glu His Val Gly Ser Lys
                565                 570                 575

Cys Leu Trp Thr Tyr Glu Ile Gln Phe Ser Gln Asp Gly Lys Ala Tyr
            580                 585                 590

Thr Pro Val Ser Arg Lys Pro Ser Thr Phe Asn Leu Phe Val Phe Ser
        595                 600                 605

Pro Asp Thr Gly Ala Val Ser Gly Ser Tyr Arg Val Arg Ala Leu Asp
    610                 615                 620

Tyr Trp Ala Arg Pro Gly Pro Phe Ser Asp Pro Val Pro Tyr Leu Glu
625                 630                 635                 640

Val Pro Val Pro Arg Gly Pro Pro Ser Pro Gly Asn Pro
                645                 650


<210> SEQ ID NO 67
<211> LENGTH: 1290
<212> TYPE: DNA
<213> ORGANISM: Homo sapiens

<400> SEQUENCE: 67

atgcagctga ggaacccaga actacatctg ggctgcgcgc ttgcgcttcg cttcctggcc     60

ctcgtttcct gggacatccc tggggctaga gcactggaca atggattggc aaggacgcct    120

accatgggct ggctgcactg ggagcgcttc atgtgcaacc ttgactgcca ggaagagcca    180

gattcctgca tcagtgagaa gctcttcatg gagatggcag agctcatggt ctcagaaggc    240

tggaaggatg caggttatga gtacctctgc attgatgact gttggatggc tccccaaaga    300

gattcagaag gcagacttca ggcagaccct cagcgctttc ctcatgggat tcgccagcta    360

gctaattatg ttcacagcaa aggactgaag ctagggattt atgcagatgt tggaaataaa    420

acctgcgcag gcttccctgg gagttttgga tactacgaca ttgatgccca gacctttgct    480

gactggggag tagatctgct aaaatttgat ggttgttact gtgacagttt ggaaaatttg    540

gcagatggtt ataagcacat gtccttggcc ctgaatagga ctggcagaag cattgtgtac    600

tcctgtgagt ggcctcttta tatgtggccc tttcaaaagc ccaattatac agaaatccga    660

cagtactgca atcactggcg aaattttgct gacattgatg attcctggaa aagtataaag    720

agtatcttgg actggacatc ttttaaccag gagagaattg ttgatgttgc tggaccaggg    780

ggttggaatg acccagatat gttagtgatt ggcaactttg gcctcagctg gaatcagcaa    840

gtaactcaga tggccctctg ggctatcatg gctgctcctt tattcatgtc taatgacctc    900

cgacacatca gccctcaagc caaagctctc cttcaggata aggacgtaat tgccatcaat    960

caggacccct tgggcaagca agggtaccag cttagacagg gagacaactt tgaagtgtgg   1020

gaacgacctc tctcaggctt agcctgggct gtagctatga taaaccggca ggagattggt   1080

ggacctcgct cttataccat cgcagttgct tccctgggta aaggagtggc ctgtaatcct   1140

gcctgcttca tcacacagct cctccctgtg aaaaggaagc tagggttcta tgaatggact   1200
```

tcaaggttaa gaagtcacat aaatcccaca ggcactgttt tgcttcagct agaaaataca 1260
atgcagatgt cattaaaaga cttactttaa 1290

<210> SEQ ID NO 68
<211> LENGTH: 429
<212> TYPE: PRT
<213> ORGANISM: Homo sapiens

<400> SEQUENCE: 68

Met Gln Leu Arg Asn Pro Glu Leu His Leu Gly Cys Ala Leu Ala Leu
1 5 10 15

Arg Phe Leu Ala Leu Val Ser Trp Asp Ile Pro Gly Ala Arg Ala Leu
20 25 30

Asp Asn Gly Leu Ala Arg Thr Pro Thr Met Gly Trp Leu His Trp Glu
35 40 45

Arg Phe Met Cys Asn Leu Asp Cys Gln Glu Glu Pro Asp Ser Cys Ile
50 55 60

Ser Glu Lys Leu Phe Met Glu Met Ala Glu Leu Met Val Ser Glu Gly
65 70 75 80

Trp Lys Asp Ala Gly Tyr Glu Tyr Leu Cys Ile Asp Asp Cys Trp Met
85 90 95

Ala Pro Gln Arg Asp Ser Glu Gly Arg Leu Gln Ala Asp Pro Gln Arg
100 105 110

Phe Pro His Gly Ile Arg Gln Leu Ala Asn Tyr Val His Ser Lys Gly
115 120 125

Leu Lys Leu Gly Ile Tyr Ala Asp Val Gly Asn Lys Thr Cys Ala Gly
130 135 140

Phe Pro Gly Ser Phe Gly Tyr Tyr Asp Ile Asp Ala Gln Thr Phe Ala
145 150 155 160

Asp Trp Gly Val Asp Leu Leu Lys Phe Asp Gly Cys Tyr Cys Asp Ser
165 170 175

Leu Glu Asn Leu Ala Asp Gly Tyr Lys His Met Ser Leu Ala Leu Asn
180 185 190

Arg Thr Gly Arg Ser Ile Val Tyr Ser Cys Glu Trp Pro Leu Tyr Met
195 200 205

Trp Pro Phe Gln Lys Pro Asn Tyr Thr Glu Ile Arg Gln Tyr Cys Asn
210 215 220

His Trp Arg Asn Phe Ala Asp Ile Asp Asp Ser Trp Lys Ser Ile Lys
225 230 235 240

Ser Ile Leu Asp Trp Thr Ser Phe Asn Gln Glu Arg Ile Val Asp Val
245 250 255

Ala Gly Pro Gly Gly Trp Asn Asp Pro Asp Met Leu Val Ile Gly Asn
260 265 270

Phe Gly Leu Ser Trp Asn Gln Gln Val Thr Gln Met Ala Leu Trp Ala
275 280 285

Ile Met Ala Ala Pro Leu Phe Met Ser Asn Asp Leu Arg His Ile Ser
290 295 300

Pro Gln Ala Lys Ala Leu Leu Gln Asp Lys Asp Val Ile Ala Ile Asn
305 310 315 320

Gln Asp Pro Leu Gly Lys Gln Gly Tyr Gln Leu Arg Gln Gly Asp Asn
325 330 335

Phe Glu Val Trp Glu Arg Pro Leu Ser Gly Leu Ala Trp Ala Val Ala
340 345 350

Met Ile Asn Arg Gln Glu Ile Gly Gly Pro Arg Ser Tyr Thr Ile Ala

```
        355                 360                 365

Val Ala Ser Leu Gly Lys Gly Val Ala Cys Asn Pro Ala Cys Phe Ile
    370                 375                 380

Thr Gln Leu Leu Pro Val Lys Arg Lys Leu Gly Phe Tyr Glu Trp Thr
385                 390                 395                 400

Ser Arg Leu Arg Ser His Ile Asn Pro Thr Gly Thr Val Leu Leu Gln
                405                 410                 415

Leu Glu Asn Thr Met Gln Met Ser Leu Lys Asp Leu Leu
            420                 425


<210> SEQ ID NO 69
<211> LENGTH: 351
<212> TYPE: DNA
<213> ORGANISM: Homo sapiens

<400> SEQUENCE: 69

atggattact acagaaaata tgcagctatc tttctggtca cattgtcggt gtttctgcat      60

gttctccatt ccgctcctga tgtgcaggat tgcccagaat gcacgctaca ggaaaaccca     120

ttcttctccc agccgggtgc cccaatactt cagtgcatgg gctgctgctt ctctagagca     180

tatcccactc cactaaggtc caagaagacg atgttggtcc aaaagaacgt cacctcagag     240

tccacttgct gtgtagctaa atcatataac agggtcacag taatgggggg tttcaaagtg     300

gagaaccaca cggcgtgcca ctgcagtact tgttattatc acaaatctta a              351


<210> SEQ ID NO 70
<211> LENGTH: 116
<212> TYPE: PRT
<213> ORGANISM: Homo sapiens

<400> SEQUENCE: 70

Met Asp Tyr Tyr Arg Lys Tyr Ala Ala Ile Phe Leu Val Thr Leu Ser
1               5                   10                  15

Val Phe Leu His Val Leu His Ser Ala Pro Asp Val Gln Asp Cys Pro
            20                  25                  30

Glu Cys Thr Leu Gln Glu Asn Pro Phe Phe Ser Gln Pro Gly Ala Pro
        35                  40                  45

Ile Leu Gln Cys Met Gly Cys Cys Phe Ser Arg Ala Tyr Pro Thr Pro
    50                  55                  60

Leu Arg Ser Lys Lys Thr Met Leu Val Gln Lys Asn Val Thr Ser Glu
65                  70                  75                  80

Ser Thr Cys Cys Val Ala Lys Ser Tyr Asn Arg Val Thr Val Met Gly
                85                  90                  95

Gly Phe Lys Val Glu Asn His Thr Ala Cys His Cys Ser Thr Cys Tyr
            100                 105                 110

Tyr His Lys Ser
        115


<210> SEQ ID NO 71
<211> LENGTH: 498
<212> TYPE: DNA
<213> ORGANISM: Homo sapiens

<400> SEQUENCE: 71

atggagatgt tccaggggct gctgctgttg ctgctgctga gcatgggcgg gacatgggca      60

tccaaggagc cgcttcggcc acggtgccgc cccatcaatg ccaccctggc tgtggagaag     120

gagggctgcc ccgtgtgcat caccgtcaac accaccatct gtgccggcta ctgccccacc     180
```

-continued atgacccgcg tgctgcaggg ggtcctgccg gccctgcctc aggtggtgtg caactaccgc 240
gatgtgcgct tcgagtccat ccggctccct ggctgcccgc gcggcgtgaa ccccgtggtc 300
tcctacgccg tggctctcag ctgtcaatgt gcactctgcc gccgcagcac cactgactgc 360
gggggtccca aggaccaccc cttgacctgt gatgaccccc gcttccagga ctcctcttcc 420
tcaaaggccc ctcccccccag ccttccaagc ccatcccgac tcccggggcc ctcggacacc 480
ccgatcctcc cacaataa 498

<210> SEQ ID NO 72
<211> LENGTH: 165
<212> TYPE: PRT
<213> ORGANISM: Homo sapiens

<400> SEQUENCE: 72

Met Glu Met Phe Gln Gly Leu Leu Leu Leu Leu Leu Leu Ser Met Gly
1 5 10 15

Gly Thr Trp Ala Ser Lys Glu Pro Leu Arg Pro Arg Cys Arg Pro Ile
20 25 30

Asn Ala Thr Leu Ala Val Glu Lys Glu Gly Cys Pro Val Cys Ile Thr
35 40 45

Val Asn Thr Thr Ile Cys Ala Gly Tyr Cys Pro Thr Met Thr Arg Val
50 55 60

Leu Gln Gly Val Leu Pro Ala Leu Pro Gln Val Val Cys Asn Tyr Arg
65 70 75 80

Asp Val Arg Phe Glu Ser Ile Arg Leu Pro Gly Cys Pro Arg Gly Val
85 90 95

Asn Pro Val Val Ser Tyr Ala Val Ala Leu Ser Cys Gln Cys Ala Leu
100 105 110

Cys Arg Arg Ser Thr Thr Asp Cys Gly Gly Pro Lys Asp His Pro Leu
115 120 125

Thr Cys Asp Asp Pro Arg Phe Gln Asp Ser Ser Ser Ser Lys Ala Pro
130 135 140

Pro Pro Ser Leu Pro Ser Pro Ser Arg Leu Pro Gly Pro Ser Asp Thr
145 150 155 160

Pro Ile Leu Pro Gln
165

<210> SEQ ID NO 73
<211> LENGTH: 165
<212> TYPE: PRT
<213> ORGANISM: Homo sapiens

<400> SEQUENCE: 73

Ala Pro Pro Arg Leu Ile Cys Asp Ser Arg Val Leu Glu Arg Tyr Leu
1 5 10 15

Leu Glu Ala Lys Glu Ala Glu Asn Ile Thr Thr Gly Cys Ala Glu His
20 25 30

Cys Ser Leu Asn Glu Asn Ile Thr Val Pro Asp Thr Lys Val Asn Phe
35 40 45

Tyr Ala Trp Lys Arg Met Glu Val Gly Gln Gln Ala Val Glu Val Trp
50 55 60

Gln Gly Leu Ala Leu Leu Ser Glu Ala Val Leu Arg Gly Gln Ala Leu
65 70 75 80

Leu Val Asn Ser Ser Gln Pro Trp Glu Pro Leu Gln Leu His Val Asp
85 90 95

Lys Ala Val Ser Gly Leu Arg Ser Leu Thr Thr Leu Leu Arg Ala Leu

```
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Gly Glu Ala
145                 150                 155                 160

Cys Arg Thr Gly Asp
                165


<210> SEQ ID NO 74
<211> LENGTH: 588
<212> TYPE: DNA
<213> ORGANISM: Homo sapiens

<400> SEQUENCE: 74

atggccctcc tgttccctct actggcagcc ctagtgatga ccagctatag ccctgttgga      60

tctctgggct gtgatctgcc tcagaaccat ggcctactta gcaggaacac cttggtgctt     120

ctgcaccaaa tgaggagaat ctcccctttc ttgtgtctca aggacagaag agacttcagg     180

ttcccccagg agatggtaaa agggagccag ttgcagaagg cccatgtcat gtctgtcctc     240

catgagatgc tgcagcagat cttcagcctc ttccacacag agcgctcctc tgctgcctgg     300

aacatgaccc tcctagacca actccacact ggacttcatc agcaactgca acacctggag     360

acctgcttgc tgcaggtagt gggagaagga gaatctgctg gggcaattag cagccctgca     420

ctgaccttga ggaggtactt ccagggaatc cgtgtctacc tgaaagagaa gaaatacagc     480

gactgtgcct gggaagttgt cagaatggaa atcatgaaat ccttgttctt atcaacaaac     540

atgcaagaaa gactgagaag taaagataga gacctgggct catcttga                 588


<210> SEQ ID NO 75
<211> LENGTH: 195
<212> TYPE: PRT
<213> ORGANISM: Homo sapiens

<400> SEQUENCE: 75

Met Ala Leu Leu Phe Pro Leu Leu Ala Ala Leu Val Met Thr Ser Tyr
1               5                   10                  15

Ser Pro Val Gly Ser Leu Gly Cys Asp Leu Pro Gln Asn His Gly Leu
            20                  25                  30

Leu Ser Arg Asn Thr Leu Val Leu Leu His Gln Met Arg Arg Ile Ser
        35                  40                  45

Pro Phe Leu Cys Leu Lys Asp Arg Arg Asp Phe Arg Phe Pro Gln Glu
    50                  55                  60

Met Val Lys Gly Ser Gln Leu Gln Lys Ala His Val Met Ser Val Leu
65                  70                  75                  80

His Glu Met Leu Gln Gln Ile Phe Ser Leu Phe His Thr Glu Arg Ser
                85                  90                  95

Ser Ala Ala Trp Asn Met Thr Leu Leu Asp Gln Leu His Thr Gly Leu
            100                 105                 110

His Gln Gln Leu Gln His Leu Glu Thr Cys Leu Leu Gln Val Val Gly
        115                 120                 125

Glu Gly Glu Ser Ala Gly Ala Ile Ser Ser Pro Ala Leu Thr Leu Arg
    130                 135                 140

Arg Tyr Phe Gln Gly Ile Arg Val Tyr Leu Lys Glu Lys Lys Tyr Ser
145                 150                 155                 160
```

-continued

```
Asp Cys Ala Trp Glu Val Val Arg Met Glu Ile Met Lys Ser Leu Phe
                165                 170                 175

Leu Ser Thr Asn Met Gln Glu Arg Leu Arg Ser Lys Asp Arg Asp Leu
            180                 185                 190

Gly Ser Ser
        195
```